US012568972B2

(12) United States Patent
Lian et al.

(10) Patent No.: US 12,568,972 B2
(45) **Date of Patent: *Mar. 10, 2026**

(54) PYRIDAZINOL COMPOUNDS AND DERIVATIVES, PREPARATION METHODS, HERBICIDAL COMPOSITIONS AND APPLICATIONS THEREOF

(71) Applicant: Qingdao Kingagroot Chemical Compound Co., Ltd., Qingdao (CN)

(72) Inventors: Lei Lian, Qingdao (CN); Yurong Zheng, Qingdao (CN); Rongbao Hua, Qingdao (CN); Jianfeng Wang, Qingdao (CN); Xuegang Peng, Qingdao (CN); Qi Cui, Qingdao (CN)

(73) Assignee: Qingdao Kingagroot Chemical Compound Co., Ltd., Qingdao (CN)

( * ) Notice: Subject to any disclaimer, the term of this patent is extended or adjusted under 35 U.S.C. 154(b) by 1192 days.

This patent is subject to a terminal disclaimer.

(21) Appl. No.: 16/966,667

(22) PCT Filed: Feb. 1, 2019

(86) PCT No.: PCT/CN2019/074315

§ 371 (c)(1),
(2) Date: Jul. 31, 2020

(87) PCT Pub. No.: WO2019/149260

PCT Pub. Date: Aug. 8, 2019

(65) Prior Publication Data

US 2022/0312770 A1 Oct. 6, 2022

(30) Foreign Application Priority Data

Feb. 2, 2018 (CN) ......................... 201810104963.4
Sep. 6, 2018 (CN) ......................... 201811035352.5

(51) Int. Cl.

| | |
|---|---|
| *A01N 57/32* | (2006.01) |
| *A01N 43/58* | (2006.01) |
| *A01N 43/60* | (2006.01) |
| *A01N 43/647* | (2006.01) |
| *A01N 43/82* | (2006.01) |
| *A01N 43/84* | (2006.01) |
| *A01N 43/90* | (2006.01) |
| *C07D 237/14* | (2006.01) |
| *C07D 401/04* | (2006.01) |
| *C07D 401/10* | (2006.01) |
| *C07D 401/14* | (2006.01) |
| *C07D 403/10* | (2006.01) |
| *C07D 405/10* | (2006.01) |
| *C07D 409/10* | (2006.01) |
| *C07D 409/14* | (2006.01) |
| *C07D 413/12* | (2006.01) |
| *C07D 417/10* | (2006.01) |

(Continued)

(52) U.S. Cl.

CPC ............ *A01N 57/32* (2013.01); *A01N 43/58* (2013.01); *A01N 43/60* (2013.01); *A01N 43/647* (2013.01); *A01N 43/82* (2013.01); *A01N 43/84* (2013.01); *A01N 43/90* (2013.01); *C07D 237/14* (2013.01); *C07D 401/04* (2013.01); *C07D 401/10* (2013.01); *C07D 401/14* (2013.01); *C07D 403/10* (2013.01); *C07D 405/10* (2013.01); *C07D 409/10* (2013.01); *C07D 409/14* (2013.01); *C07D 413/12* (2013.01); *C07D 417/10* (2013.01); *C07D 417/12* (2013.01); *C07D 487/04* (2013.01); *C07F 9/65583* (2013.01)

(58) Field of Classification Search

None

See application file for complete search history.

(56) References Cited

U.S. PATENT DOCUMENTS 4,058,390 A 11/1977 Schonbeck et al.
5,013,659 A 5/1991 Bedbrook et al.

(Continued)

FOREIGN PATENT DOCUMENTS

AT 375071 B 6/1984
CN 1075477 A 8/1993

(Continued)

OTHER PUBLICATIONS

Feraldi-Xypolia et al., Synthesis of Functionalized 4-Fluoropyridazines, Asian J. Org. Chem., 6:927-935 (Year: 2017).*

(Continued)

*Primary Examiner* — Anna R Falkowitz
*Assistant Examiner* — Edwin Coleman Mitchell
(74) *Attorney, Agent, or Firm* — FINNEGAN, HENDERSON, FARABOW, GARRETT & DUNNER LLP

(57) ABSTRACT

The invention belongs to the technical field of agricultural chemicals, and in particular relates to a pyridazinol compound represented by the Formula I, a derivative, preparation method, herbicidal composition and use thereof. The compound, derivative and herbicidal composition thereof have very high herbicidal activity and selectivity, and are safe for crops,

I

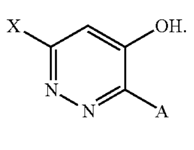

24 Claims, No Drawings

(51) Int. Cl.

| | |
|---|---|
| *C07D 417/12* | (2006.01) |
| *C07D 487/04* | (2006.01) |
| *C07F 9/6558* | (2006.01) |

(56) References Cited

U.S. PATENT DOCUMENTS

| | | | | |
|---|---|---|---|---|
| 5,362,708 A | | 11/1994 | Kores et al. | |
| 5,462,914 A | * | 10/1995 | Leitner ................ | C07D 237/16 544/239 |
| 5,616,789 A | | 4/1997 | South et al. | |

FOREIGN PATENT DOCUMENTS

| | | | |
|---|---|---|---|
| CN | 1543455 | A | 11/2004 |
| CN | 101648914 | A | 2/2010 |
| CN | 106316962 | A | 1/2017 |
| EP | 0131624 | A | 1/1985 |
| EP | 0142924 | A | 5/1985 |
| EP | 0193259 | A | 9/1986 |
| EP | 0221044 | A | 5/1987 |
| EP | 0242236 | A | 10/1987 |
| EP | 0242246 | A | 10/1987 |
| EP | 0257993 | | 3/1988 |
| EP | 0556647 | A1 | 8/1993 |
| EP | 1 426 365 | A1 | 6/2004 |
| JP | 2004284970 | A | 10/2014 |
| RU | 2440992 | C2 | 1/2012 |
| WO | WO91/13972 | | 9/1991 |
| WO | WO91/19806 | | 12/1991 |
| WO | WO92/00377 | | 1/1992 |
| WO | WO92/11376 | | 7/1992 |
| WO | WO92/14827 | | 9/1992 |
| WO | WO 2017/036266 | A1 | 3/2017 |

OTHER PUBLICATIONS

Liu et al., Associations of maternal exposure to 2,4-dichlorophenoxyacetic acid during early pregnancy with steroid hormones among one-month-old infants, Science of the Total Environment 912 (2024) 169414 (Year: 2014).*

Safrygin et al, Synthesis of 5-aryl-2-hydroxy-2-(trifluoromethyl) furan-3(2H)—ones and their reactions with aromatic 1,2-diamines, hydrazine and hydroxylamine, *Tetrahedron*, Sep. 15, 2015, pp. 8535-8543, vol. 71, No. 45.

Roffey et al, Some Reactions of 3,6-Disubstituted-s-Tetrazines; A New Synthesis of the 1,2,4-Triazine Ring System, *Journal of Heterocyclic Chemistry*, Aug. 1, 1969, pp. 497-502, vol. 6, No. 4.

Irgashev et al, Methyl 2-methoxytetrafluoropropionate as a synthetic equivalent of methyl trifluoropyruvate in the Claisen condensation. The first synthesis of 2—(trifluoroacetyl) chromones and 5-aryl-2-hydroxy-2-(trifluoromethyl) furan-3 (2H)—ones, *Tetrahedron Letters*, Elsevier, Amsterdam, NL, Aug. 26, 2009, pp. 4903-4095, vol. 50, No. 34.

Extended European Search Report for EP19747228, dated Sep. 24, 2021.

Christou P, Transformation Technology, *Trends in Plant Science*, 1:423-431 (1996).

Braun et al., The General Mitochondrial Processing Peptidase from Potato Is an Integral Part of Cytochrome C Reductase of the Respiratory Chain, *EMBO J.* 11:3219-3227 (1992).

Sonnewald et al., Transgenic Tobacco Plants Expressing Yeast-Derived Invertase in Either the Cytosol, Vacuole or Apoplast: A Powerful Tool for Studying Sucrose Metabolism and Sink/Source Interactions, *Plant J.* 1:95-106 (1991).

International Search Report and Written Opinion of International Patent Application No. PCT/CN2019/074315, mailed May 6, 2019.

Feraldi-Xypolia et al., Synthesis of Functionalized 4-Fluoropyridazines, *Asian J. Org. Chem.*, 6:927-935 (2017).

Wolter et al., Rbcs Genes in Solanum Tuberosum: Conservation of Transit Peptide and Exon Shuffling During Evolution, Proc. Natl. Acad. Sci. USA, 85:846-850 (1988).

Sako, Syntheses of Pyridazine Derivatives, III. 4OR 5-Chloro-3, 6-dimethylpyridazine 1-Oxide, Chemical and Pharmaceutical Bulletin, Jan. 1, 1963, pp. 337-341, vol. 11, No. 3.

T. Kappe et al., Synthesis of aminopyridazines from Azidopyridazines and tetrazolo[1,5-b]pyridazines, Synthesis, vol. 9, pp. 666-671 (1989).

L. Henning et al., New Aspects in the Reaction of Azomethines with Cyclic CH-Acidic Compounds, Monatshefte Fur Chemie—Chemical Monthly, vol. 123, pp. 517-579 (1992).

V. Becker et al., Neue Derivate des Pyridazins, Journal fur praktische Chemi: practical applications and applied chemistry: covering all aspects of applied chemistry, vol. 311, No. 2, pp. 286-295 (1968).

European Examination Report of European patent application No. 19747728.4, dated Jul. 31, 2025.

* cited by examiner

PYRIDAZINOL COMPOUNDS AND DERIVATIVES, PREPARATION METHODS, HERBICIDAL COMPOSITIONS AND APPLICATIONS THEREOF

This application is a national stage filing under 35 U.S.C. § 371 of International Application No. PCT/CN2019/074315, filed Feb. 1, 2019, and claims the priority to and benefits of Chinese Patent Application No. 201810104963.4, filed Feb. 2, 2018, and Chinese Patent Application No. 201811035352.5, filed Sep. 6, 2018, which are incorporated herein by reference in their entireties.

TECHNICAL FIELD

The invention belongs to the technical field of agricultural chemicals, and in particular relates to a pyridazinol compound and a derivative thereof, preparation method, herbicidal composition and application thereof.

BACKGROUND ART

Weed control is a vital part in achieving high-efficiency agriculture. At present, various herbicides are available in the market, such as protoporphyrinogen oxidase inhibitors and photosystem II inhibitors. CN106316962A discloses 3-arylpyridazinone compounds as protoporphyrinogen oxidase inhibitors, which have the structure of

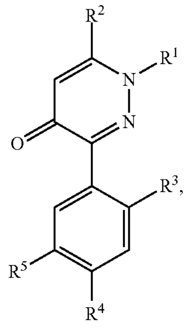

and have inhibitory effect on broad-leaved weeds, gramineous weeds and sedgy weeds. In addition, pyridazine herbicides such as Pyridate

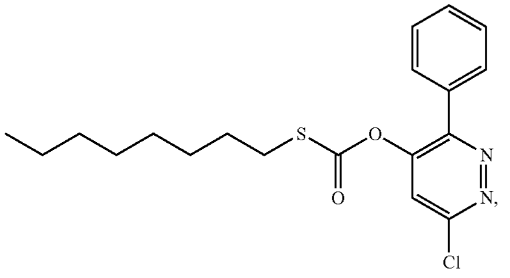 [SMILES: CCCCCCCCSC(=O)Oc1cc(Cl)nnc1-c1ccccc1]

pyridazinol

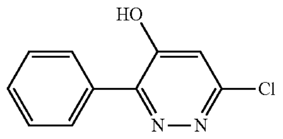 [SMILES: Oc1cc(Cl)nnc1-c1ccccc1]

and the like are photosystem II inhibitors that inhibit photosynthesis by blocking electron transport and conversion of light energy.

Since the continuous expansion of the market, the resistance of weeds, the service life of herbicides and the economical efficiency of herbicides as well as the increasing attention on environmental protection, it is in great demand of constantly research of scientists for developing new herbicides with high-efficiency, safety, economical efficiency and different mechanism of action.

CONTENTS OF THE INVENTION

In order to solve the above problems in the prior art, the present invention provides a pyridazinol compound and a derivative, preparation method, herbicidal composition and use thereof. The compound and the derivative, as well as the composition thereof have very high herbicidal activity and good selectivity, and are safe for crops.

The technical solution adopted by the present invention is as follows:

A pyridazinol compound of Formula I or a derivative thereof:

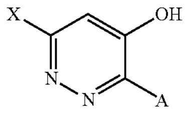

I wherein, X is halogenated alkyl, cyano, alkyl, alkoxy, halogenated alkoxy, $R_1R_2N$—(C═O)—, $R_1R_2N$—, hydroxy, or unsubstituted or substituted aryl;

A is selected from the group consisting of alkyl, alkenyl, alkynyl, cycloalkyl, cycloalkenyl, cycloalkylalkyl, aryl, heteroaryl, and aliphatic heterocyclyl, each of which is unsubstituted or substituted; wherein, when being substituted, each of the alkyl, alkenyl, alkynyl, cycloalkyl, cycloalkenyl, or cycloalkylalkyl is independently substituted with one or more substituents selected from the group consisting of halogen, cyano, nitro, azido, unsubstituted or substituted aryl, unsubstituted or substituted heteroaryl, —$(CH_2)_n$—O—$(CH_2)_p$—, —$(CH_2)_n$—S—$(CH_2)_p$—, —$(CH_2)_n$—$NR_3$—$(CH_2)_p$—, R—O—, R—O—$(CH_2)_p$—O—, R—O—$(CH_2)_p$—S—, R—S—, R—S—$(CH_2)_p$—O—, R—S—$(CH_2)_p$—S—, R—O—$(CH_2)_n$—(C═O)—$(CH_2)_q$—$(O)_m$—, R—S—$(CH_2)_n$—(C═S)—$(CH_2)_q$—$(S)_m$—, R—O—$(CH_2)_n$—(C═O)—$(CH_2)_q$—$(S)_m$—, R—O—$(CH_2)_n$—(C═S)—$(CH_2)_q$—$(O)_m$—, R—S—$(CH_2)_n$—(C═O)—$(CH_2)_q$—$(O)_m$—, R—O—$(CH_2)_n$—(C═S)—$(CH_2)_q$—$(S)_m$—, R—S—$(CH_2)_n$—(C═O)—$(CH_2)_q$—$(S)_m$—, R—S—$(CH_2)_n$—(C═S)—$(CH_2)_q$—$(O)_m$—, R—(C═O)—, R—(C═S)—, R—(C═O)—$(CH_2)_n$—O—, R—(C═S)—$(CH_2)_n$—

S—, R—(C═O)—$(CH_2)_n$—S—, R—(C═S)—$(CH_2)_n$—O—, R—SO—$(CH_2)_n$—$(O)_m$—, R—SO—$(CH_2)_n$—$(S)_m$—, R—SO—$(CH_2)_n$—$(NR_3)_m$—, R—$SO_2$—$(CH_2)_n$—$(O)_m$—, R—$SO_2$—$(CH_2)_n$—$(S)_m$—, R—$SO_2$—$(CH_2)_n$—$(NR_3)_m$—, $R_1R_2N$—, $R_1R_2N$—$(CH_2)_n$—O—$(CH_2)_q$—$(O)_m$—, $R_1R_2N$—$(CH_2)_n$—O—$(CH_2)_q$—$(S)_m$—, $R_1R_2N$—$(CH_2)_n$—O—$(CH_2)_q$—$(NR_3)_m$—, $R_1R_2N$—$(CH_2)_n$—(C═O)—$(CH_2)_q$—$(O)_m$—, $R_1R_2N$—$(CH_2)_n$—(C═O)—$(CH_2)_q$—$(S)_m$—, $R_1R_2N$—$(CH_2)_n$—(C═O)—$(CH_2)_q$—$(NR_3)_m$—, $R_1R_2N$—$(CH_2)_n$—$SO_2$—$(CH_2)_q$—$(O)_m$—, $R_1R_2N$—$(CH_2)_n$—$SO_2$—$(CH_2)_q$—$(S)_m$—, $R_1R_2N$—$(CH_2)_n$—$SO_2$—$(CH_2)_q$—$(NR_3)_m$—, $R_1R_2P(O)$—$(O)_m$—, $R_1R_2R_3SiO$—, $R_1R_2R_3Si$—(CH═CH)$_m$—, $R_1R_2C$═N—$(O)_m$—, and $R_1R_2C$═N—NH—;

when being substituted, each of the aryl, heteroaryl, or aliphatic heterocyclyl is substituted with one or more substituents selected from the group consisting of halogen, cyano, nitro, azido, a halogen-containing or not containing group selected from alkyl, alkenyl, alkynyl, cycloalkyl, cycloalkenyl, and cycloalkylalkyl, a group selected from aryl, arylalkyl, heteroaryl, heteroarylalkyl, aliphatic heterocyclyl, and aliphatic heterocyclylalkyl, which is unsubstituted or substituted, R—O—$(CH_2)_n$—, R—O—$(CH_2)_p$—O—$(CH_2)_q$—, R—O—$(CH_2)_p$—S—$(CH_2)_q$—, R—S—$(CH_2)_n$—, R—S—$(CH_2)_p$—O—$(CH_2)_q$—, R—S—$(CH_2)_p$—S—$(CH_2)_q$—, R—O—$(CH_2)_n$—(C═O)—$(CH_2)_q$—$(O)_m$—, R—S—$(CH_2)_n$—(C═S)—$(CH_2)_q$—$(S)_m$—, R—O—$(CH_2)_n$—(C═O)—$(CH_2)_q$—$(S)_m$—, R—O—$(CH_2)_n$—(C═S)—$(CH_2)_q$—$(O)_m$—, R—S—$(CH_2)_n$—(C═O)—$(CH_2)_q$—$(O)_m$—, R—O—$(CH_2)_n$—(C═S)—$(CH_2)_q$—$(S)_m$—, R—S—$(CH_2)_n$—(C═O)—$(CH_2)_q$—$(S)_m$—, R—S—$(CH_2)_n$—(C═S)—$(CH_2)_q$—$(O)_m$—, R—(C═O)—$(CH_2)_n$—, R—(C═S)—$(CH_2)_n$—, R—(C═O)—$(CH_2)_n$—O—$(CH_2)_q$—, R—(C═S)—$(CH_2)_n$—S—$(CH_2)_q$—, R—(C═O)—$(CH_2)_n$—S—$(CH_2)_q$—, R—(C═S)—$(CH_2)_n$—O—$(CH_2)_q$—, R—SO—$(CH_2)_n$—$(O)_m$—, R—SO—$(CH_2)_n$—$(S)_m$—, R—SO—$(CH_2)_n$—$(NR_3)_m$—, R—$SO_2$—$(CH_2)_n$—$(O)_m$—, R—$SO_2$—$(CH_2)_n$—$(S)_m$—, R—$SO_2$—$(CH_2)_n$—$(NR_3)_m$—, $R_1R_2N$—$(CH_2)_n$—, $R_1R_2N$—$(CH_2)_n$—O—$(CH_2)_q$—$(O)_m$—, $R_1R_2N$—$(CH_2)_n$—O—$(CH_2)_q$—$(S)_m$—, $R_1R_2N$—$(CH_2)_n$—O—$(CH_2)_q$—$(NR_3)_m$—, $R_1R_2N$—$(CH_2)_n$—(C═O)—$(CH_2)_q$—$(O)_m$—, $R_1R_2N$—$(CH_2)_n$—(C═O)—$(CH_2)_q$—$(S)_m$—, $R_1R_2N$—$(CH_2)_n$—(C═O)—$(CH_2)_q$—$(NR_3)_m$—, $R_1R_2N$—$(CH_2)_n$—$SO_2$—$(CH_2)_q$—$(O)_m$—, $R_1R_2N$—$(CH_2)_n$—$SO_2$—$(CH_2)_q$—$(S)_m$—, $R_1R_2N$—$(CH_2)_n$—$SO_2$—$(CH_2)_q$—$(NR_3)_m$—, $R_1R_2PO_3$—$(O)_m$—$(CH_2)_q$—, $R_1R_2R_3SiO$—$(CH_2)_q$—, $R_1R_2R_3Si$—(CH═CH)$_m$—$(CH_2)_q$—, $R_1R_2C$═N—$(O)_m$—$(CH_2)_n$—, and $R_1R_2C$═N—NH—$(CH_2)_n$—;

m is 0 or 1, n and q are independently an integer from 0 to 8, p is an integer from 1 to 8;

R is hydrogen, a halogen-containing or not containing group selected from alkyl, alkenyl, alkynyl, cycloalkyl, cycloalkenyl, and cycloalkylalkyl, or a group selected from aryl, arylalkyl, heteroaryl, and heteroarylalkyl, which is unsubstituted or substituted;

$R_1$, $R_2$, $R_3$ are each independently hydrogen, nitro, hydroxy, amino, a halogen-containing or not containing group selected from alkyl, alkenyl, alkynyl, cycloalkyl, cycloalkenyl, cycloalkylalkyl, alkoxy, alkenyloxy, alkynyloxy, cycloalkyloxy, alkoxyalkyl, alkoxycarbonyl, alkylsulfanylcarbonyl, alkylsulfonyl, alkylsulfonylalkyl, alkylcarbonyl, alkylcarbonylalkyl, alkylcarbonyloxy, alkylamino, alkylaminocarbonyl, alkoxyaminocarbonyl, alkoxycarbonylalkyl, alkylaminocarbonylalkyl, trialkylsilyl, and dialkylphosphonyl, or a group selected from aryl, arylalkyl, aryloxy, arylalkyloxy, aryloxyalkyl, arylcarbonyl, arylsulfonyl, heteroaryl, heteroarylalkyl, heteroaryloxy, heteroarylalkyloxy, heteroaryloxyalkyl, heteroarylcarbonyl, heteroarylsulfonyl, aliphatic heterocyclyl, aliphatic heterocyclylalkyl, aliphatic heterocyclyloxy, aliphatic heterocyclylalkoxy, aliphatic heterocyclyloxyalkyl, aliphatic heterocyclylcarbonyl, and aliphatic heterocyclylsulfonyl, which is unsubstituted or substituted; or $R_1R_2N$— forms a 5- to 6-membered heterocyclyl.

As used in the present application, the term "heteroaryl" refers to an aromatic group, wherein one or more ring atoms, preferable 1, 2, 3 or 4 ring atom, are hetero atoms selected from N, O and S, for example, 5-14 membered heteroaryl, 5-10 membered heteroaryl, 5-9 membered heteroaryl, or 5-6 membered heteroaryl. And when the ring member of the heteroaryl includes a N atom, the heteroaryl substituted with a substituent at the N atom is also included in the scope of the heteroaryl. In a preferred embodiment, the substituent is selected from hydrogen, nitro, hydroxy, amino, a fluoro-, chloro-, or bromo-containing or not containing group selected from C1~C6 alkyl, C2~C6 alkenyl, C2~C6 alkynyl, C3~C6 cycloalkyl, C3~C6 cycloalkenyl, C3~C6 cycloalkyl-C1~C6 alkyl, C1~C6 alkoxy, C2~C6 alkenyloxy, C2~C6 alkynyloxy, C3~C6 cycloalkyloxy, C1~C6 alkoxy-C1~C6 alkyl, C1~C6 alkoxycarbonyl, C1~C6 alkylsulfanylcarbonyl, C1~C6 alkylsulfonyl, C1~C6 alkylsulfonyl-C1~C6 alkyl, C1~C6 alkylcarbonyl, C1~C6 alkylcarbonyl-C1~C6 alkyl, C1~C6 alkylcarbonyloxy, C1~C6 alkylamino, C1~C6 alkylaminocarbonyl, C1~C6 alkoxyaminocarbonyl, C1~C6 alkoxycarbonyl-C1~C6 alkyl, C1~C6 alkylaminocarbonyl-C1~C6 alkyl, triC1~C6 alkylsilyl, and diC1~C6 alkylphosphonyl, aryl, aryl-C1~C6 alkyl, aryloxy, aryl-C1~C6 alkyloxy, aryloxy-C1~C6 alkyl, arylcarbonyl, arylsulfonyl, heteroaryl, heteroaryl-C1~C6 alkyl, heteroaryloxy, heteroaryl-C1~C6 alkyloxy, heteroaryloxy-C1~C6 alkyl, heteroarylcarbonyl, heteroarylsulfonyl, aliphatic heterocyclyl, aliphatic heterocyclyl-C1~C6 alkyl, aliphatic heterocyclyloxy, aliphatic heterocyclyl-C1~C6 alkyloxy, aliphatic heterocyclyloxy-C1~C6 alkyl, aliphatic heterocyclylcarbonyl, and aliphatic heterocyclylsulfonyl, each of the aryl, aryl-C1~C6 alkyl, aryloxy, aryl-C1~C6 alkyloxy, aryloxy-C1~C6 alkyl, arylcarbonyl, arylsulfonyl, heteroaryl, heteroaryl-C1~C6 alkyl, heteroaryloxy, heteroaryl-C1~C6 alkyloxy, heteroaryloxy-C1~C6 alkyl, heteroarylcarbonyl, heteroarylsulfonyl, aliphatic heterocyclyl, aliphatic heterocyclyl-C1~C6 alkyl, aliphatic heterocyclyloxy, aliphatic heterocyclyl-C1~C6 alkyloxy, aliphatic heterocyclyloxy-C1~C6 alkyl, aliphatic heterocyclylcarbonyl, or aliphatic heterocyclylsulfonyl is unsubstituted or substituted with 1-3 groups independently selected from fluorine, chlorine, bromine, cyano, nitro, hydroxy, carboxyl, sulfhydryl, amino, and a fluoro-, chloro-, bromo-containing or not containing group selected from C1~C6 alkyl, C3~C6 cycloalkyl, C3~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy.

In a preferred embodiment, X is halogenated C1~C8 alkyl, cyano, C1~C8 alkyl, C1~C8 alkoxy, halogenated C1~C8 alkoxy, $R_1R_2N$—(C═O)—, $R_1R_2N$—, hydroxy, or aryl, the aryl is unsubstituted or substituted with 1-5 substituents independently selected from the group consisting of halogen, cyano, nitro, hydroxy, carboxyl, sulfhydryl, amino, and a halogen-containing or not containing group selected from C1~C8 alkyl, C3~C8 cycloalkyl, C3~C8 cycloalkyl-C1~C8 alkyl, C2~C8 alkenyl, C2~C8 alkynyl, C1~C8 alkoxy, C1~C8 alkylcarbonyl, C1~C8 alkoxycarbonyl, C1~C8 alkylsulfonyl, C1~C8 alkylamino, and C1~C8 alkylcarbonyloxy; A is selected from the group consisting of C1~C8 alkyl, C2~C8 alkenyl, C2~C8 alkynyl, C3~C8 cycloalkyl, C3~C8 cycloalkenyl, C3~C8 cycloalkyl-C1~C8 alkyl, 5- to 14-membered aryl, 5- to 14-membered heteroaryl, and 5- to 14-membered aliphatic heterocyclyl, each of which is unsubstituted or substituted; wherein,

- when being substituted, the C1~C8 alkyl, C2~C8 alkenyl, C2~C8 alkynyl, C3~C8 cycloalkyl, C3~C8 cycloalkenyl, or C3~C8 cycloalkyl-C1~C8 alkyl is substituted with one or more substituents independently selected from the group consisting of halogen, cyano, nitro, azido, aryl, heteroaryl, the aryl or heteroaryl is unsubstituted or independently substituted with 1-5 groups selected from halogen, cyano, nitro, hydroxy, carboxyl, sulfhydryl, amino, and a halogen-containing or not containing group selected from C1~C8 alkyl, C3~C8 cycloalkyl, C3~C8 cycloalkenyl, C3~C8 cycloalkyl-C1~C8 alkyl, C2~C8 alkenyl, C2~C8 alkynyl, C1~C8 alkoxy, C1~C8 alkylcarbonyl, C1~C8 alkoxycarbonyl, C1~C8 alkylsulfonyl, C1~C8 alkylamino, and C1~C8 alkylcarbonyloxy, $-(CH_2)_n-O-(CH_2)_p-$, $-(CH_2)_n-S-(CH_2)_p-$, $-(CH_2)_n-NR_3-(CH_2)_p-$, $R-O-$, $R-O-(CH_2)_p-O-$, $R-O-(CH_2)_p-S-$, $R-S-$, $R-S-(CH_2)_p-O-$, $R-S-(CH_2)_p-S-$, $R-O-(C=O)-(CH_2)_q-(O)_m-$, $R-O-(CH_2)_n-(C=O)-(O)_m-$, $R-O-(CH_2)_n-(C=O)-$, $R-S-(C=S)-(CH_2)_q-(S)_m-$, $R-S-(CH_2)_n-(C=S)-(S)_m-$, $R-S-(CH_2)_n-(C=S)-$, $R-O-(C=O)-(CH_2)_q-(S)_m-$, $R-O-(CH_2)_n-(C=O)-(S)_m-$, $R-O-(C=S)-(CH_2)_q-(O)_m-$, $R-O-(CH_2)_n-(C=S)-(O)_m-$, $R-O-(CH_2)_n-(C=S)-$, $R-S-(C=O)-(CH_2)_q-(O)_m-$, $R-S-(CH_2)_n-(C=O)-(O)_m-$, $R-S-(CH_2)_n-(C=O)-$, $R-O-(C=S)-(CH_2)_q-(S)_m-$, $R-O-(CH_2)_n-(C=S)-(S)_m-$, $R-S-(C=O)-(CH_2)_q-(S)_m-$, $R-S-(CH_2)_n-(C=O)-(S)_m-$, $R-S-(C=S)-(CH_2)_q-(O)_m-$, $R-S-(CH_2)_n-(C=S)-(O)_m-$, $R-(C=O)-$, $R-(C=S)-$, $R-(C=O)-O-$, $R-(C=S)-S-$, $R-(C=O)-S-$, $R-(C=S)-O-$, $R-SO-(O)_m-$, $R-SO-(S)_m-$, $R-SO-(NR_3)_m-$, $R-SO_2-(O)_m-$, $R-SO_2-(S)_m-$, $R-SO_2(NR_3)_m-$, $R_1R_2N-$, $R_1R_2N-O-(CH_2)_q-(O)_m-$, $R_1R_2N-(CH_2)_n-O-$, $R_1R_2N-O-(CH_2)_q-(S)_m-$, $R_1R_2N-O-(CH_2)_q-(NR_3)_m-$, $R_1R_2N-(C=O)-(CH_2)_q-(O)_m-$, $R_1R_2N-(CH_2)_n-(C=O)-(O)_m-$, $R_1R_2N-(CH_2)_n-(C=O)-$, $R_1R_2N-(C=O)-(CH_2)_q-(S)_m-$, $R_1R_2N-(CH_2)_n-(C=O)-(S)_m-$, $R_1R_2N-(C=O)-(CH_2)_q-(NR_3)_m-$, $R_1R_2N-(CH_2)_n-(C=O)-(NR_3)_m-$, $R_1R_2N-SO_2-(CH_2)_q-(O)_m-$, $R_1R_2N-(CH_2)_n-SO_2-(O)_m-$, $R_1R_2N-(CH_2)_n-SO_2-$, $R_1R_2N-SO_2-(CH_2)_q-(S)_m-$, $R_1R_2N-(CH_2)_n-SO_2-(S)_m-$, $R_1R_2N-SO_2-(CH_2)_q-(NR_3)_m-$, $R_1R_2N-(CH_2)_n-SO_2-(NR_3)_m-$, $R_1R_2P(O)-$, $R_1R_2R_3SiO-$, $R_1R_2R_3Si-(CH=CH)_m-$, $R_1R_2C=N-(O)_m-$, and $R_1R_2C=N-NH-$;
- when being substituted, each of the 5- to 14-membered aryl, 5- to 14-membered heteroaryl or 5- to 14-membered aliphatic heterocyclyl is independently substituted with one or more substituents selected from the group consisting of halogen, cyano, nitro, azido, a halogen-containing or not containing group selected from C1~C8 alkyl, C2~C8 alkenyl, C2~C8 alkynyl, C3~C8 cycloalkyl, C3~C8 cycloalkenyl, and C3~C8 cycloalkyl-C1~C8 alkyl, aryl, aryl-C1~C8 alkyl, heteroaryl, heteroaryl-C1~C8 alkyl, aliphatic heterocyclyl, aliphatic heterocyclyl-C1~C8 alkyl, each of the aryl, aryl-C1~C8 alkyl, heteroaryl, heteroaryl-C1~C8 alkyl, aliphatic heterocyclyl, or aliphatic heterocyclyl-C1~C8 alkyl is unsubstituted or substituted with 1-5 groups independently selected from halogen, cyano, nitro, hydroxy, carboxyl, sulfhydryl, amino, and a halogen-containing or not containing group selected from C1~C8 alkyl, C3~C8 cycloalkyl, C3~C8 cycloalkenyl, C3~C8 cycloalkyl-C1~C8 alkyl, C2~C8 alkenyl, C2~C8 alkynyl, C1~C8 alkoxy, C1~C8 alkylcarbonyl, C1~C8 alkoxycarbonyl, C1~C8 alkylsulfonyl, C1~C8 alkylamino, and C1~C8 alkylcarbonyloxy, $R-O-(CH_2)_n-$, $R-O-(CH_2)_p-O-(CH_2)_q-$, $R-O-(CH_2)_p-S-(CH_2)_q-$, $R-S-(CH_2)_n-$, $R-S-(CH_2)_p-O-(CH_2)_q-$, $R-S-(CH_2)_p-S-(CH_2)_q-$, $R-O-(CH_2)_n-(C=O)-(CH_2)_q-(O)_m-$, $R-S-(CH_2)_n-(C=S)-(CH_2)_q-$, $R-O-(CH_2)_n-(C=S)-(CH_2)_q-$, $R-S-(CH_2)_n-(C=O)-(CH_2)_q-$, $R-S-(C=S)-(CH_2)_g-(S)_m-$, $R-O-(CH_2)_n-(C=O)-(CH_2)_q-(S)_m-$, $R-O-(C=S)-(CH_2)_q-(O)_m-$, $R-S-(C=O)-(CH_2)_q-(O)_m-$, $R-O-(C=S)-(CH_2)_q-(S)_m-$, $R-S-(C=O)-(CH_2)_q-(S)_m-$, $R-S-(C=S)-(CH_2)_q-(O)_m-$, $R-S-(CH_2)_n-(C=S)-(S)_m-$, $R-O-(CH_2)_n-(C=S)-(O)_m-$, $R-S-(CH_2)_n-(C=O)-(O)_m-$, $R-O-(CH_2)_n-(C=S)-(S)_m-$, $R-S-(CH_2)_n-(C=O)-(S)_m-$, $R-S-(CH_2)_n-(C=S)-(O)_m-$, $R-(C=O)-(CH_2)_n-$, $R-(C=S)-$, $R-(C=O)-(CH_2)_n-O-(CH_2)_q-$, $R-(C=S)-(CH_2)_n-S-$, $R-(C=O)-(CH_2)_n-S-$, $R-(C=S)-(CH_2)_n-O-$, $R-(C=S)-S-(CH_2)_q-$, $R-(C=O)-S-(CH_2)_q-$, $R-(C=S)-O-(CH_2)_q-$, $R-SO-(O)_m-$, $R-SO-(S)_m-$, $R-SO-(NR_3)_m-$, $R-SO_2-(CH_2)_n-(O)_m-$, $R-SO_2-(S)_m-$, $R-SO_2-(CH_2)_n-(NR_3)_m-$, $R-SO-(CH_2)_n-$, $R_1R_2N-(CH_2)_n-$, $R_1R_2N-(CH_2)_n-O-(CH_2)_q-$, $R_1R_2N-(C=O)-(CH_2)_q-(O)_m-$, $R_1R_2N-(CH_2)_n-(C=O)-(CH_2)_q-$, $R_1R_2N-(CH_2)_n-(C=O)-(O)_m-$, $R_1R_2N-(CH_2)_n-(C=O)-(S)_m-$, $R_1R_2N-(CH_2)_n-(C=O)-(NR_3)_m-$, $R_1R_2N-(CH_2)_n-SO_2-(CH_2)_q-(O)_m-$, $R_1R_2N-(CH_2)_n-SO_2-(S)_m-$, $R_1R_2N-(CH_2)_n-SO_2-(NR_3)_m-$, $R_1R_2N-(C=O)-(CH_2)_n-(O)_m-$, $R_1R_2N-(C=O)-(CH_2)_n-(S)_m-$, $R_1R_2N-(C=O)-(CH_2)_n-(NR_3)_m-$, $R_1R_2N-SO_2-(CH_2)_q-(S)_m-$, $R_1R_2N-SO_2-(CH_2)_q-(NR_3)_m-$, $R_1R_2N-(CH_2)_n-O-$, $R_1R_2N-O-(CH_2)_q-$, $R_1R_2P(O)-(O)_m-$, $R_1R_2R_3SiO-$, $R_1R_2R_3Si-(CH=CH)_m-$, $R_1R_2C=N-(O)_m-$, and $R_1R_2C=N-NH-$;

m is 0 or 1, n and q are independently an integer from 0 to 6, p is an integer from 1 and 6;

R is hydrogen, a halogen-containing or not containing group selected from C1~C8 alkyl, C2~C8 alkenyl, C2~C8 alkynyl, C3~C8 cycloalkyl, C3~C8 cycloalkenyl, and C3~C8 cycloalkyl-C1~C8 alkyl, aryl, aryl-C1~C8 alkyl, heteroaryl, or heteroaryl-C1~C8 alkyl, each of the aryl, aryl-C1~C8 alkyl, heteroaryl, or heteroaryl-C1~C8 alkyl is unsubstituted or substituted with 1-5 groups substituents independently selected from halogen, cyano, nitro, hydroxy, carboxyl, sulfhydryl, amino, and a halogen-containing or not containing group selected from C1~C8 alkyl, C3~C8 cycloalkyl, C3~C8 cycloalkenyl, C3~C8 cycloalkyl-C1~C8 alkyl, C2~C8 alkenyl, C2~C8 alkynyl, C1~C8 alkoxy, C1~C8 alkylcarbonyl, C1~C8 alkoxycarbonyl, C1~C8 alkylsulfonyl, C1~C8 alkylamino, and C1~C8 alkylcarbonyloxy;

$R_1$, $R_2$, $R_3$ are each independently hydrogen, nitro, hydroxy, amino, a halogen-containing or not containing group selected from C1~C8 alkyl, C2~C8 alkenyl, C2~C8 alkynyl, C3~C8 cycloalkyl, C3~C8 cycloalkenyl, C3~C8 cycloalkyl-C1~C8 alkyl, C1~C8 alkoxy, C2~C8 alkenyloxy, C2~C8 alkynyloxy, C3~C8 cycloalkyloxy, C1~C8 alkoxy-C1~C8 alkyl, C1~C8 alkoxycarbonyl, C1~C8 alkylcarbonyl-C1~C8 alkyl, C1~C8 alkylsulfanylcarbonyl, C1~C8 alkylsulfonyl, C1~C8 alkylsulfonyl-C1~C8 alkyl, C1~C8 alkylcarbonyl, C1~C8 alkylcarbonyloxy, C1~C8 alkylamino, C1~C8 alkylaminocarbonyl, C1~C8 alkoxyaminocarbonyl, C1~C8 alkoxycarbonyl-C1~C8 alkyl, C1~C8 alkylaminocarbonyl-C1~C8 alkyl, triC1~C8 alkylsilyl, and diC1~C8 alkylphosphonyl, aryl, aryl-C1~C8 alkyl, aryloxy, aryl-C1~C8 alkyloxy, aryloxy-C1~C8 alkyl, arylcarbonyl, arylsulfonyl, heteroaryl, heteroaryl-C1~C8 alkyl, heteroaryloxy, heteroaryl-C1~C8 alkyloxy, heteroaryloxy-C1~C8 alkyl, heteroarylcarbonyl, heteroarylsulfonyl, aliphatic heterocyclyl, aliphatic heterocyclyl-C1~C8 alkyl, aliphatic heterocyclyloxy, aliphatic heterocyclyl-C1~C8 alkyloxy, aliphatic heterocyclyloxy-C1~C8 alkyl, aliphatic heterocyclylcarbonyl, or aliphatic heterocyclylsulfonyl, each of the aryl, aryl-C1~C8 alkyl, aryloxy, aryl-C1~C8 alkyloxy, aryloxy-C1~C8 alkyl, arylcarbonyl, arylsulfonyl, heteroaryl, heteroaryl-C1~C8 alkyl, heteroaryloxy, heteroaryl-C1~C8 alkyloxy, heteroaryloxy-C1~C8 alkyl, heteroarylcarbonyl, heteroarylsulfonyl, aliphatic heterocyclyl, aliphatic heterocyclyl-C1~C8 alkyl, aliphatic heterocyclyloxy, aliphatic heterocyclyl-C1~C8 alkyloxy, aliphatic heterocyclyloxy-C1~C8 alkyl, aliphatic heterocyclylcarbonyl, or aliphatic heterocyclylsulfonyl is unsubstituted or substituted with 1-5 groups independently selected from halogen, cyano, nitro, hydroxy, carboxyl, sulfhydryl, amino, and a halogen-containing or not containing group selected from C1~C8 alkyl, C3~C8 cycloalkyl, C3~C8 cycloalkenyl, C3~C8 cycloalkyl-C1~C8 alkyl, C2~C8 alkenyl, C2~C8 alkynyl, C1~C8 alkoxy, C1~C8 alkylcarbonyl, C1~C8 alkoxycarbonyl, C1~C8 alkylsulfonyl, C1~C8 alkylamino, and C1~C8 alkylcarbonyloxy; or $R_1R_2N$— forms a 5- to 6-membered heterocyclyl;

the derivative is an agriculturally acceptable salt or a compound derivatized from the 4-hydroxy of the pyridazine ring of the Formula I.

In a preferred embodiment, X is halogenated C1~C6 alkyl;

A is selected from the group consisting of C1~C6 alkyl, C2~C6 alkenyl, C2~C6 alkynyl, C3~C6 cycloalkyl, C3~C6 cycloalkenyl, C3~C6 cycloalkyl-C1~C6 alkyl, 5- to 14-membered aryl, 5- to 14-membered heteroaryl, and 5- to 14-membered aliphatic heterocyclyl, each of which is unsubstituted or substituted; wherein, when being substituted, each of the C1~C6 alkyl, C2~C6 alkenyl, C2~C6 alkynyl, C3~C6 cycloalkyl, C3~C6 cycloalkenyl, or C3~C6 cycloalkyl-C1~C6 alkyl is substituted with one or more substituents independently selected from the group consisting of halogen, cyano, nitro, azido, aryl, heteroaryl, the aryl or heteroaryl is unsubstituted or substituted with 1-3 groups independently selected from halogen, cyano, nitro, hydroxy, carboxyl, sulfhydryl, amino, and a halogen-containing or not containing group selected from C1~C6 alkyl, C3~C6 cycloalkyl, C3~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy, $—(CH_2)_n—O—$, $—(CH_2)_n—S—$, $—(CH_2)_n—NR_3—$, R—O—, $R—O—(CH_2)_p—O—$, $R—O—(CH_2)_p—S—$, R—S—, $R—S—(CH_2)_p—O—$, $R—S—(CH_2)_p—S—$, $R—O—(CH_2)_n—(C{=}O)—$, $R—S—(C{=}S)—$, $R—O—(C{=}S)—$, $R—S—(C{=}O)—$, $R—(C{=}O)—$, $R—(C{=}S)—$, $R—(C{=}O)—O—$, $R—(C{=}S)—S—$, $R—(C{=}O)—S—$, $R—(C{=}S)—O—$, R—SO—, $R—SO_2—$, $R_1R_2N—$, $R_1R_2N—O—$, $R_1R_2N—(C{=}O)—$, $R_1R_2N—SO_2—$, $R_1R_2P(O)—$, $R_1R_2R_3SiO—$, $R_1R_2R_3Si—(CH{=}CH)—$, $R_1R_2R_3Si—$, $R_1R_2C{=}N—(O)—$, $R_1R_2C{=}N—$, and $R_1R_2C{=}N—NH—$;

when being substituted, each of the 5- to 14-membered aryl, 5- to 14-membered heteroaryl or 5- to 14-membered aliphatic heterocyclyl is substituted with one or more substituents independently selected from the group consisting of halogen, cyano, nitro, azido, a halogen-containing or not containing group selected from C1~C6 alkyl, C2~C6 alkenyl, C2~C6 alkynyl, C3~C6 cycloalkyl, C3~C6 cycloalkenyl, and C3~C6 cycloalkyl-C1~C6 alkyl, aryl, aryl-C1~C6 alkyl, heteroaryl, heteroaryl-C1~C6 alkyl, aliphatic heterocyclyl, aliphatic heterocyclyl-C1~C6 alkyl, each of the aryl, aryl-C1~C6 alkyl, heteroaryl, heteroaryl-C1~C6 alkyl, aliphatic heterocyclyl, or aliphatic heterocyclyl-C1~C6 alkyl is unsubstituted or substituted with 1~5 groups independently selected from halogen, cyano, nitro, hydroxy, carboxyl, sulfhydryl, amino, and a halogen-containing or not containing group selected from C1~C6 alkyl, C3~C6 cycloalkyl, C3~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy, $R—O—(CH_2)_n—$, $R—O—(CH_2)_p—O—$, $R—O—(CH_2)_p—S—$, $R—S—(CH_2)_n—$, $R—O—(CH_2)_n—(C{=}O)—(CH_2)_q—(O)_m—$, $R—O—(CH_2)_n—(C{=}O)—(CH_2)_q—(S)_m—$, $R—S—(CH_2)_p—O—$, $R—S—(CH_2)_p—S—$, $R—S—(C{=}S)—(S)_m—$, $R—O—(C{=}S)—(O)_m—$, $R—S—(CH_2)_n—(C{=}O)—(O)_m—$, $R—O—(C{=}S)—(S)_m—$, $R—S—(C{=}O)—(S)_m—$, $R—S—(C{=}S)—(O)_m—$, $R—S—(C{=}S)—(CH_2)_q—$, $R—O—(C{=}S)—(CH_2)_q—$, $R—S—(C{=}O)—(CH_2)_q—$, $R—S—(CH_2)_n—(C{=}S)—$, $R—O—(CH_2)_n—(C{=}S)—$, $R—S—(CH_2)_n—(C{=}O)—$, $R—(C{=}O)—(CH_2)_n—$, $R—(C{=}S)—$, $R—(C{=}O)—(CH_2)_n—O—(CH_2)_q—$, $R—(C{=}S)—S—$, $R—(C{=}O)—S—$, $R—(C{=}S)—O—$, $R—SO—(CH_2)_n—$, $R—SO_2—(CH_2)_n—(O)_m—$, $R—SO_2—(CH_2)_n—(NR_3)_m—$, $R_1R_2N—(CH_2)_n—$, $R_1R_2N—O—$, $R_1R_2N—(C{=}O)—(CH_2)_q—(O)_m—$, $R_1R_2N—(C{=}O)—(S)_m—$, $R_1R_2N—(C{=}O)—(NR_3)_m—$, $R_1R_2N—(CH_2)_n—SO_2—(CH_2)_q—(O)_m—$, $R_1R_2N—(CH_2)_p—(C{=}O)—$, $R_1R_2N—(CH_2)_p—O—$, $R_1R_2N—O—(CH_2)_p—$, $R_1R_2P(O)—$, $R_1R_2R_3SiO—$, $R_1R_2R_3Si—$, $R_1R_2R_3Si—CH{=}CH—$, $R_1R_2C{=}N—$, $R_1R_2C{=}N—O—$, and $R_1R_2C{=}N—NH—$;

m is 0 or 1, n and q are each independently an integer from 0 to 4, p is an integer from 1 to 4;

R is hydrogen, a halogen-containing or not containing group selected from C1~C6 alkyl, C2~C6 alkenyl, C2~C6 alkynyl, C3~C6 cycloalkyl, C3~C6 cycloalkenyl, and C3~C6 cycloalkyl-C1~C6 alkyl, aryl, aryl-C1~C6 alkyl, heteroaryl, or heteroaryl-C1~C6 alkyl, each of the aryl, aryl-C1~C6 alkyl, heteroaryl, or heteroaryl-C1~C6 alkyl is unsubstituted or substituted with 1-3 groups independently selected from halogen, cyano, nitro, hydroxy, carboxyl, sulfhydryl, amino, and a halogen-containing or not containing group selected from C1~C6 alkyl, C3~C6 cycloalkyl, C3~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy;

$R_1$, $R_2$, $R_3$ are each independently is hydrogen, nitro, hydroxy, amino, a halogen-containing or not containing group selected from C1~C6 alkyl, C2~C6 alkenyl, C2~C6 alkynyl, C3~C6 cycloalkyl, C3~C6 cycloalkenyl, C3~C6 cycloalkyl-C1~C6 alkyl, C1~C6 alkoxy, C2~C6 alkenyloxy, C2~C6 alkynyloxy, C3~C6 cycloalkyloxy, C1~C6 alkoxy-C1~C6 alkyl, C1~C6 alkoxycarbonyl, C1~C6 alkylsulfanylcarbonyl, C1~C6 alkylsulfonyl, C1~C6 alkylsulfonyl-C1~C6 alkyl, C1~C6 alkylcarbonyl, C1~C6 alkylcarbonyl-C1~C6 alkyl, C1~C6 alkylcarbonyloxy, C1~C6 alkylamino, C1~C6 alkylaminocarbonyl, C1~C6 alkoxyaminocarbonyl, C1~C6 alkoxycarbonyl-C1~C6 alkyl, C1~C6 alkylaminocarbonyl-C1~C6 alkyl, triC1~C6 alkylsilyl, and diC1~C6 alkylphosphonyl, aryl, aryl-C1~C6 alkyl, aryloxy, aryl-C1~C6 alkyloxy, aryloxy-C1~C6 alkyl, arylcarbonyl, arylsulfonyl, heteroaryl, heteroaryl-C1~C6 alkyl, heteroaryloxy, heteroaryl-C1~C6 alkyloxy, heteroaryloxy-C1~C6 alkyl, heteroarylcarbonyl, heteroarylsulfonyl, aliphatic heterocyclyl, aliphatic heterocyclyl-C1~C6 alkyl, aliphatic heterocyclyloxy, aliphatic heterocyclyl-C1~C6 alkyloxy, aliphatic heterocyclyloxy-C1~C6 alkyl, aliphatic heterocyclylcarbonyl, or aliphatic heterocyclylsulfonyl, each of the aryl, aryl-C1~C6 alkyl, aryloxy, aryl-C1~C6 alkyloxy, aryloxy-C1~C6 alkyl, arylcarbonyl, arylsulfonyl, heteroaryl, heteroaryl-C1~C6 alkyl, heteroaryloxy, heteroaryl-C1~C6 alkyloxy, heteroaryloxy-C1~C6 alkyl, heteroarylcarbonyl, heteroarylsulfonyl, aliphatic heterocyclyl, aliphatic heterocyclyl-C1~C6 alkyl, aliphatic heterocyclyloxy, aliphatic heterocyclyl-C1~C6 alkyloxy, aliphatic heterocyclyloxy-C1~C6 alkyl, aliphatic heterocyclylcarbonyl, or aliphatic heterocyclylsulfonyl is unsubstituted or substituted with 1-3 groups independently selected from halogen, cyano, nitro, hydroxy, carboxyl, sulfhydryl, amino, and a halogen-containing or not containing group selected from C1~C6 alkyl, C3~C6 cycloalkyl, C3~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy; or $R_1R_2N$— is

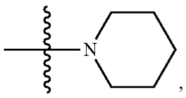,
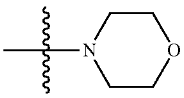
or

-continued

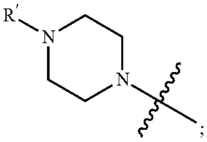

the aryl is selected from

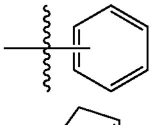,
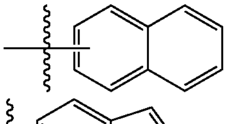,
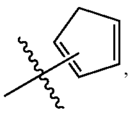,
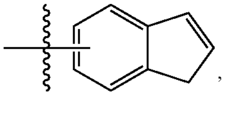,
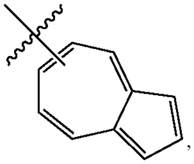,
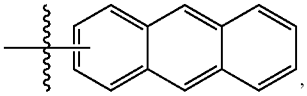,
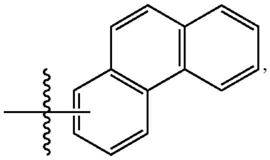, and
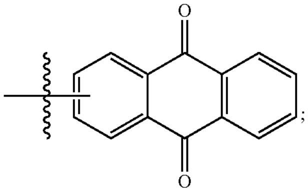;

the heteroaryl is selected from

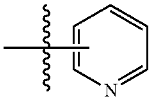,
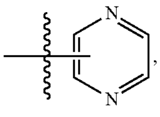,
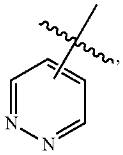,
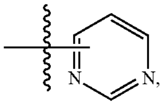,
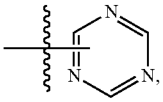,
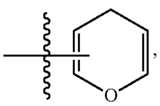,
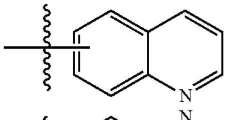,
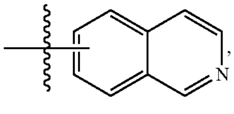,
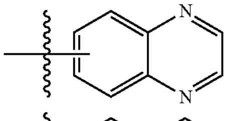,
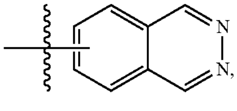,
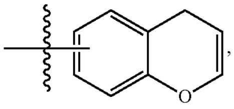,
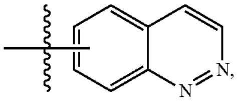

-continued

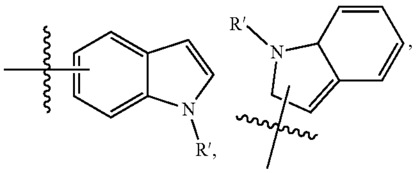

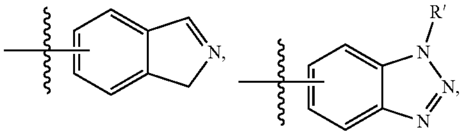

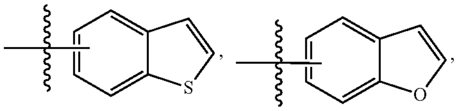

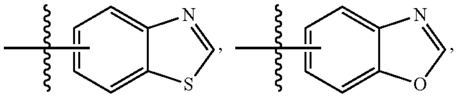

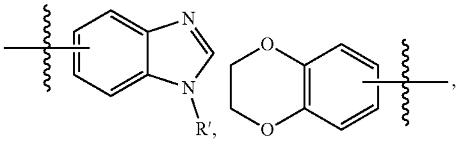

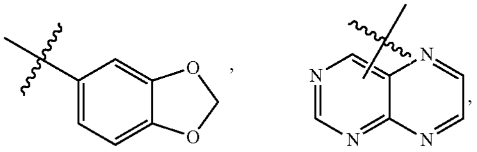

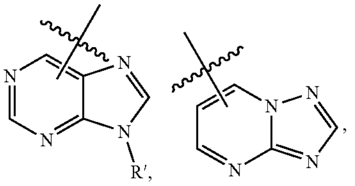

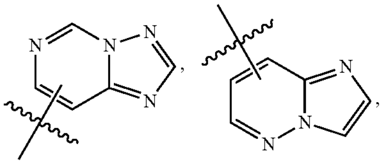

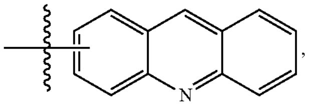

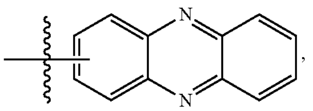

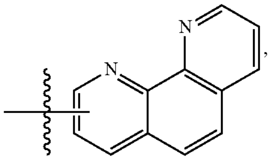

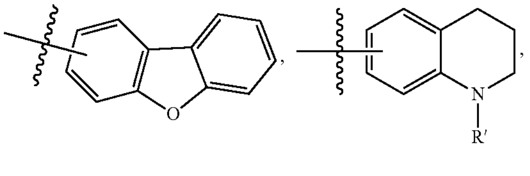

-continued

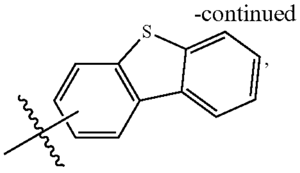

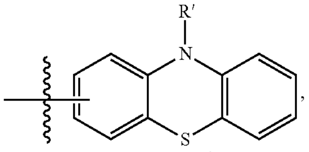

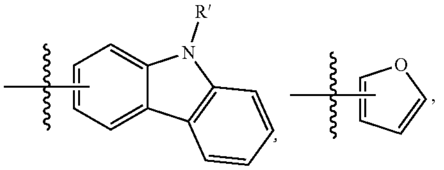

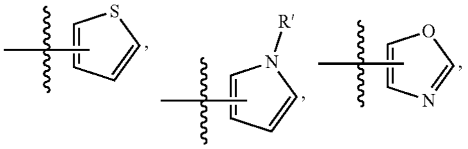

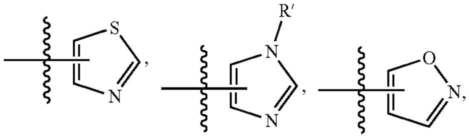

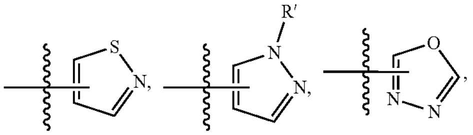

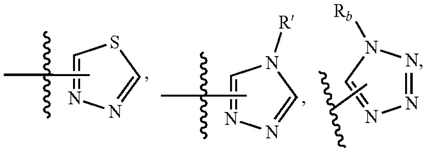

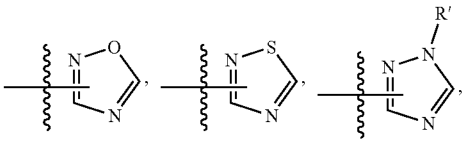

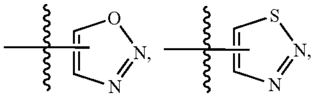

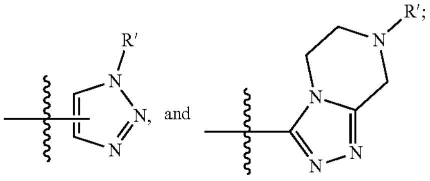

R' is hydrogen, nitro, hydroxy, amino, a fluoro-, chloro-, or bromo-containing or not containing group selected from C1~C6 alkyl, C2~C6 alkenyl, C2~C6 alkynyl, C3~C6 cycloalkyl, C3~C6 cycloalkenyl, C3~C6 cycloalkyl-C1~C6 alkyl, C1~C6 alkoxy, C2~C6 alkenyloxy, C2~C6 alkynyloxy, C3~C6 cycloalkyloxy, C1~C6 alkoxy-C1~C6 alkyl, C1~C6 alkoxycarbonyl, C1~C6 alkylsulfanylcarbonyl, C1~C6 alkylsulfonyl, C1~C6 alkylsulfonyl-C1~C6 alkyl, C1~C6 alkylcarbonyl, C1~C6 alkylcarbonyl-C1~C6 alkyl, C1~C6 alkylcarbonyloxy, C1~C6 alkylamino, C1~C6 alkylaminocarbonyl, C1~C6 alkoxyaminocarbonyl, C1~C6 alkoxycarbonyl-C1~C6 alkyl, C1~C6 alkylaminocarbonyl-C1~C6 alkyl, triC1~C6 alkylsilyl, and diC1~C6 alkylphosphonyl, aryl, aryl-C1~C6 alkyl, aryloxy, aryl-C1~C6 alkyloxy, aryloxy-C1~C6 alkyl, arylcarbonyl, arylsulfonyl, heteroaryl, heteroaryl-C1~C6 alkyl, heteroaryloxy, heteroaryl-C1~C6 alkyloxy, heteroaryloxy-C1~C6 alkyl, heteroarylcarbonyl, heteroarylsulfonyl, aliphatic heterocyclyl, aliphatic heterocyclyl-C1~C6 alkyl, aliphatic heterocyclyloxy, aliphatic heterocyclyl-C1~C6 alkyloxy, aliphatic heterocyclyloxy-C1~C6 alkyl, aliphatic heterocyclylcarbonyl, or aliphatic heterocyclylsulfonyl, each of the aryl, aryl-C1~C6 alkyl, aryloxy, aryl-C1~C6 alkyloxy, aryloxy-C1~C6 alkyl, arylcarbonyl, arylsulfonyl, heteroaryl, heteroaryl-C1~C6 alkyl, heteroaryloxy, heteroaryl-C1~C6 alkyloxy, heteroaryloxy-C1~C6 alkyl, heteroarylcarbonyl, heteroarylsulfonyl, aliphatic heterocyclyl, aliphatic heterocyclyl-C1~C6 alkyl, aliphatic heterocyclyloxy, aliphatic heterocyclyl-C1~C6 alkyloxy, aliphatic heterocyclyloxy-C1~C6 alkyl, aliphatic heterocyclylcarbonyl, or aliphatic heterocyclylsulfonyl is unsubstituted or substituted with 1-3 groups independently selected from fluorine, chlorine, bromine, cyano, nitro, hydroxy, carboxyl, sulfhydryl, amino, and a fluoro-, chloro-, bromo-containing or not containing group selected from C1~C6 alkyl, C3~C6 cycloalkyl, C3~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy;

the aliphatic heterocyclyl is selected from

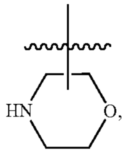 , 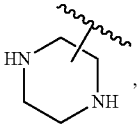 , 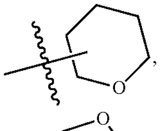 ,

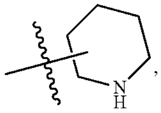 , 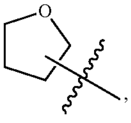 , 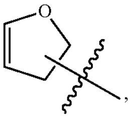 , and

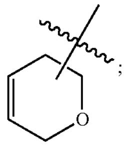 ;

the derivative is an agriculturally acceptable salt or a compound derivatized from 4-hydroxy of the pyridazine ring of the Formula I, including an ester, an oxime, a hydroxylamine and an ether thereof.

In a preferred embodiment, X is halogenated C1~C6 alkyl;

A is selected from the group consisting of C1~C6 alkyl, C2~C6 alkenyl, C3~C6 cycloalkyl, C3~C6 cycloalkenyl, 5- to 14-membered aryl, 5- to 14-membered heteroaryl, and 5- to 14-membered aliphatic heterocyclyl, each of which is unsubstituted or substituted; wherein, when being substituted, the C1~C6 alkyl, C2~C6 alkenyl, C3~C6 cycloalkyl, or C3~C6 cycloalkenyl is substituted with one or more substituents independently selected from R—O—$(CH_2)_n$—(C═O)— and $R_1R_2R_3SiO$—;

when being substituted, the 5- to 14-membered aryl, 5- to 14-membered heteroaryl or 5- to 14-membered aliphatic heterocyclyl is substituted with one or more substituents independently selected from the group consisting of halogen, cyano, nitro, azido, a halogen-containing or not containing group selected from C1~C6 alkyl, C2~C6 alkenyl, C2~C6 alkynyl, C3~C6 cycloalkyl, and C3~C6 cycloalkyl-C1~C6 alkyl, aryl, aryl-C1~C6 alkyl, heteroaryl, heteroaryl-C1~C6 alkyl, aliphatic heterocyclyl, aliphatic heterocyclyl-C1~C6 alkyl, each of the aryl, aryl-C1~C6 alkyl, heteroaryl, heteroaryl-C1~C6 alkyl, aliphatic heterocyclyl, or aliphatic heterocyclyl-C1~C6 alkyl is unsubstituted or substituted with 1-5 groups independently selected from halogen, cyano, nitro, hydroxy, carboxyl, sulfhydryl, amino, and a halogen-containing or not containing group selected from C1~C6 alkyl, C3~C6 cycloalkyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy, R—O—$(CH_2)_n$—, R—O—$(CH_2)_p$—O—, R—S—$(CH_2)_n$—, R—O—$(CH_2)_n$—(C═O)—$(CH_2)_q$—$(O)_m$—, R—O—$(CH_2)_n$—(C═O)—$(CH_2)_q$—$(S)_m$—, R—S—$(CH_2)_n$—(C═O)—, R—(C═O)—$(CH_2)_n$—, R—(C═O)—$(CH_2)_n$—O—$(CH_2)_q$—, R—SO—$(CH_2)_n$—, R—$SO_2$—$(CH_2)_n$—$(O)_m$—, R—$SO_2$—$(CH_2)_n$—$(NR_3)_m$—, $R_1R_2N$—(C═O)—$(CH_2)_q$—$(O)_m$—, $R_1R_2N$—(C═O)—$(NR_3)_m$—, $R_1R_2N$—$(CH_2)_n$—, $R_1R_2N$—$(CH_2)_n$—$SO_2$—$(CH_2)_q$—, $R_1R_2P(O)$—, and $R_1R_2R_3Si$—;

m is 0 or 1, n and q are each independently an integer from 0 to 4, p is an integer from 1 to 4;

R is hydrogen, a halogen-containing or not containing group selected from C1~C6 alkyl, C2~C6 alkenyl, C2~C6 alkynyl, C3~C6 cycloalkyl, and C3~C6 cycloalkyl-C1~C6 alkyl, 5- to 14-membered aryl, 5- to 14-membered aryl-C1-~C4 alkyl, or 5- to 14-membered heteroaryl, each of the 5- to 14-membered aryl, 5- to 14-membered aryl-C1~C4 alkyl, or 5- to 14-membered heteroaryl is unsubstituted or substituted with 1-3 groups independently selected from halogens;

$R_1$, $R_2$, $R_3$ are each independently hydrogen, nitro, hydroxy, amino, a halogen-containing or not containing group selected from C1~C6 alkyl, C2~C6 alkenyl, C2~C6 alkynyl, C3~C6 cycloalkyl, C1~C6 alkoxy, C1~C6 alkoxy-C1~C6 alkyl, C1~C6 alkoxycarbonyl, C1~C6 alkylcarbonyl, C1~C6 alkylcarbonyl-C1~C6 alkyl, and C1~C6 alkylcarbonyloxy, 5- to 14-membered aryl, 5- to 14-membered aryl-C1~C6 alkyl, 5- to 14-membered aryloxy, 5- to 14-membered arylcarbonyl, 5- to 14-membered heteroaryl, 5- to 14-membered heteroaryl-C1~C6 alkyl, 5- to 14-membered heteroaryloxy, 5- to 14-membered heteroarylcarbonyl, or 5- to 14-membered aliphatic heterocyclylcarbonyl, each of the 5- to 14-membered aryl, 5- to 14-membered aryl-C1~C6 alkyl, 5- to 14-membered aryloxy, 5- to 14-membered arylcarbonyl, 5- to 14-membered heteroaryl, 5- to 14-membered heteroaryl-C1~C6 alkyl, 5- to 14-membered heteroaryloxy, 5- to 14-membered heteroarylcarbonyl, or 5- to 14-membered aliphatic heterocyclylcarbonyl is unsubstituted or substituted with 1-3 groups independently selected from halogen, cyano, nitro, hydroxy, carboxyl, sulfhydryl, amino, and a halogen-containing or not containing group selected from C1~C6 alkyl, C3~C6 cycloalkyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1-~C6 alkylcarbonyloxy; or $R_1R_2N$— is

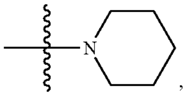,
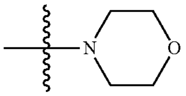
or
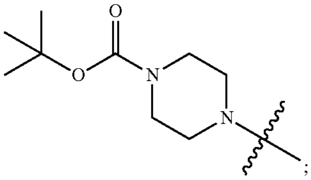;

the aryl is selected from

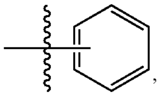,
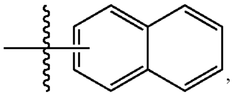,
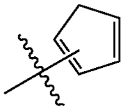,
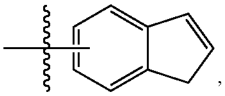,
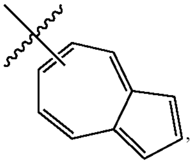,
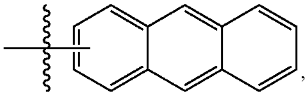,
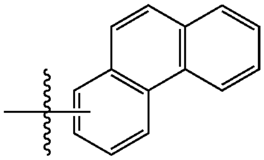
and
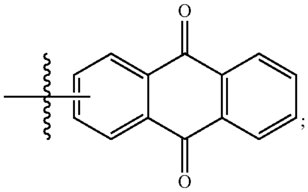;

the heteroaryl is selected from

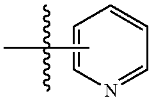,
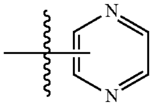,
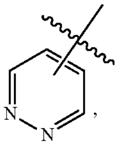,
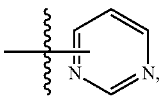,
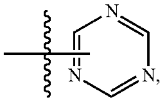,
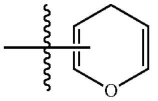,

-continued

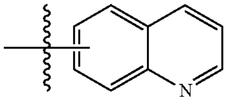,
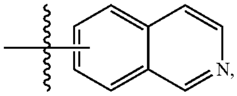,
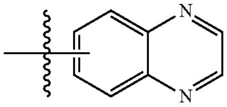,
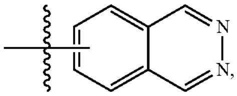,
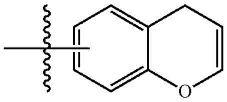,
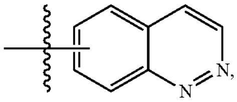,
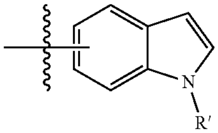,
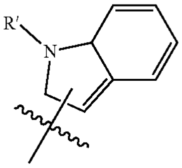,
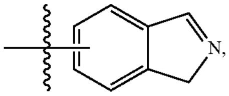,
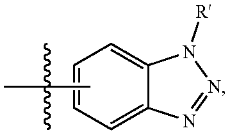,
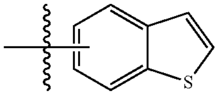,
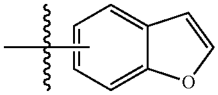,
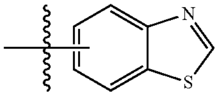,
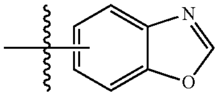,
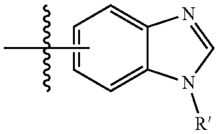,
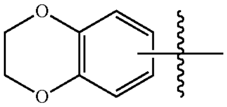,
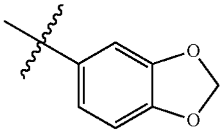,
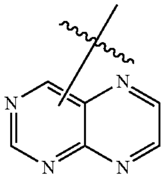,
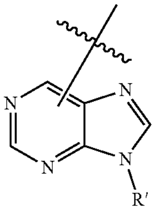,
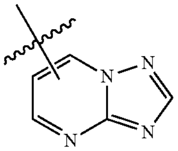,
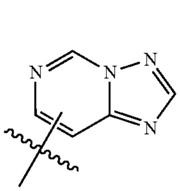,
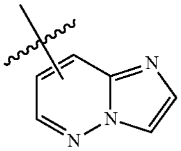,
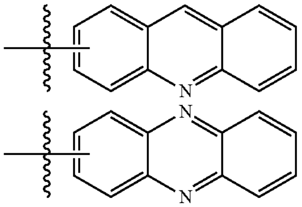, -continued

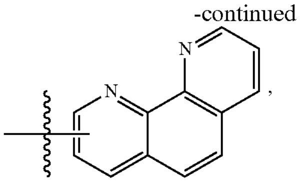,

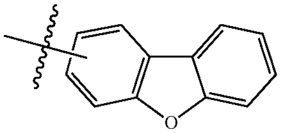,

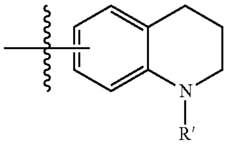,

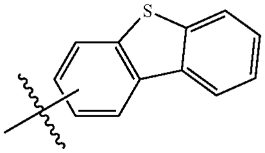,

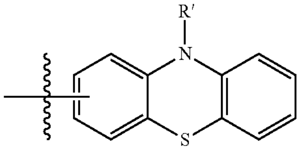,

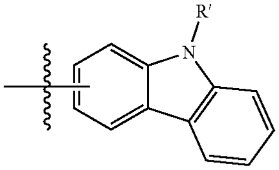,

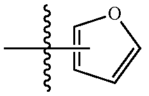, 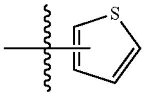, 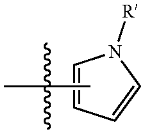,

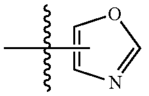, 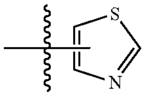, 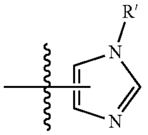,

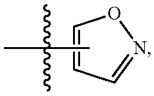, 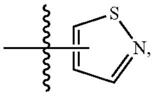, 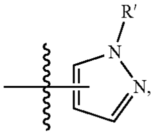

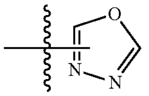, 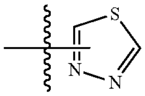, 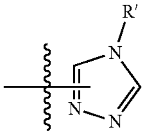,

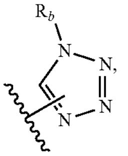 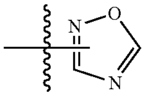, 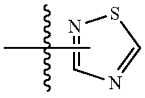,

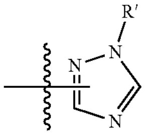, 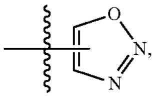 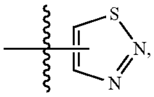

-continued

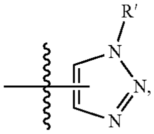 and 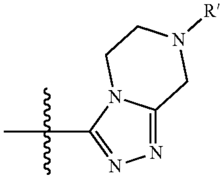 ;

R' is hydrogen, a fluoro-, chloro-, or bromo-containing or not containing group selected from C1~C6 alkyl, C1~C6 alkoxy-C1~C6 alkyl, C1~C6 alkoxycarbonyl, and C1~C6 alkylcarbonyl, the aliphatic heterocyclyl is selected from

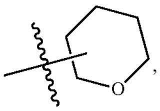, 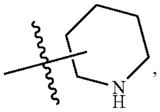,

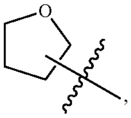, 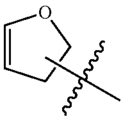 and 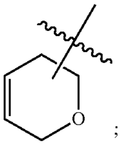 ;

the derivative is an agriculturally acceptable salt or a compound derivatized from 4-hydroxy of the pyridazine ring of the Formula I, including an ester, an oxime, a hydroxylamine and an ether thereof.

In a preferred embodiment, X is halogenated C1~C4 alkyl;

A is selected from the group consisting of C1~C4 alkyl, C2~C4 alkenyl, C3~C6 cycloalkyl, C3~C6 cycloalkenyl, 5- to 14-membered aryl, 5- to 14-membered heteroaryl and 5- to 14-membered aliphatic heterocyclyl, each of which is unsubstituted or substituted; wherein, when being substituted, the C1~C4 alkyl, C2~C4 alkenyl, C3~C6 cycloalkyl, or C3~C6 cycloalkenyl is substituted with one or more substituents independently selected from R—O—(C═O)— and $R_1R_2R_3SiO$—;

when being substituted, the 5- to 14-membered aryl, 5- to 14-membered heteroaryl or 5- to 14-membered aliphatic heterocyclyl is substituted with one or more substituents independently selected from the group consisting of fluorine, chlorine, bromine, iodine, cyano, nitro, azido, a fluoro-, chloro- or bromo-containing or not containing group selected from C1~C4 alkyl, C2~C4 alkenyl, C2~C4 alkynyl, C3~C6 cycloalkyl, and C3~C6 cycloalkyl-C1~C4 alkyl, aryl, aryl-C1~C4 alkyl, heteroaryl, heteroaryl-C1~C4 alkyl, aliphatic heterocyclyl, each of said aryl, aryl-C1~C4 alkyl, heteroaryl, heteroaryl-C1~C4 alkyl, or aliphatic heterocyclyl is unsubstituted or substituted with 1-3 groups independently selected from fluorine, chlorine, bromine, cyano, hydroxy, and a fluoro-, chloro- or bromo-containing or not containing group selected from C1~C4 alkyl, C1~C4 alkoxy, C1~C4 alkoxycarbonyl, C1~C4 alkylsulfonyl, and C1~C4 alkylamino, R—O—$(CH_2)_n$—, R—O—$CH_2$—O—, R—S—$(CH_2)_n$—, R—O—$(CH_2)_n$—(C═O)—, R—O—$(CH_2)_n$—(C═O)—O—, R—O—(C═O)—$(CH_2)_q$—O—, R—O—$(CH_2)_n$—(C═O)—$(CH_2)_q$—S—, R—S—$(CH_2)_n$—(C═O)—, R—(C═O)—$(CH_2)_n$—, R—(C═O)—O—$(CH_2)_q$—, R—(C═O)—$(CH_2)_n$—O—, R—SO—$(CH_2)_n$—, R—$SO_2$—$(CH_2)_n$—$(O)_m$—, R—$SO_2$—$(CH_2)_n$—$NR_3$—, $R_1R_2N$—(C═O)—$(CH_2)_q$—, $R_1R_2N$—(C═O)—$(CH_2)_q$—O—, $R_1R_2N$—(C═O)—$(NR_3)_m$—, $R_1R_2N$—$(CH_2)_n$—, $R_1R_2N$—$(CH_2)_n$—$SO_2$—$(CH_2)_q$—, $R_1R_2P(O)$—, and $R_1R_2R_3Si$—;

m is 0 or 1, n and q are each independently an integer from 0, 1, 2 and 3, p is an integer from 1, 2 and 3;

R is hydrogen, a halogen-containing or not containing group selected from C1~C4 alkyl, C2~C4 alkenyl, C2~C6 alkynyl, C3~C6 cycloalkyl, and C3~C6 cycloalkyl-C1~C4 alkyl, 5- to 14-membered aryl, 5- to 14-membered aryl-C1~C2 alkyl, or 5- to 6-membered heteroaryl, each of the 5- to 14-membered aryl, 5- to 14-membered aryl-C1~C2 alkyl, or 5- to 6-membered heteroaryl is unsubstituted or substituted with 1-3 groups independently selected from fluorine, chlorine, and bromine;

$R_1$, $R_2$, $R_3$ are each independently hydrogen, a fluoro-, chloro- or bromo-containing or not containing group selected from C1~C4 alkyl, C2~C4 alkenyl, C2~C4 alkynyl, C3~C6 cycloalkyl, C1~C4 alkoxy, C1~C4 alkoxyC1~C4 alkyl, C1~C4 alkoxycarbonyl, C1~C4 alkylcarbonyl, C1~C4 alkylcarbonyl-C1~C4 alkyl, and C1~C4 alkylcarbonyloxy, 5- to 14-membered aryl, 5- to 14-membered aryloxy, 5- to 14-membered arylcarbonyl, 5- to 6-membered heteroaryl, 5- to 6-membered heteroaryl-C1~C4 alkyl, or 5- to 6-membered heteroarylcarbonyl, each of the 5- to 14-membered aryl, 5- to 14-membered aryloxy, 5- to 14-membered arylcarbonyl, 5- to 6-membered heteroaryl, 5- to 6-membered heteroaryl-C1~C4 alkyl, or 5- to 6-membered heteroarylcarbonyl is unsubstituted or substituted with 1-3 groups independently selected from fluorine, chlorine, bromine, C1~C4 alkyl, C1~C4 alkoxy, C1~C4 alkylamino, and C3~C6 cycloalkyl; or $R_1R_2N$— is

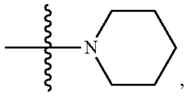,
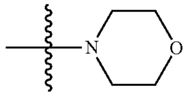
or
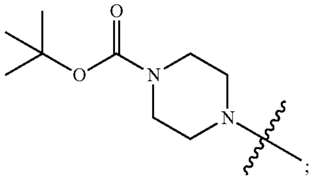;

the aryl is selected from

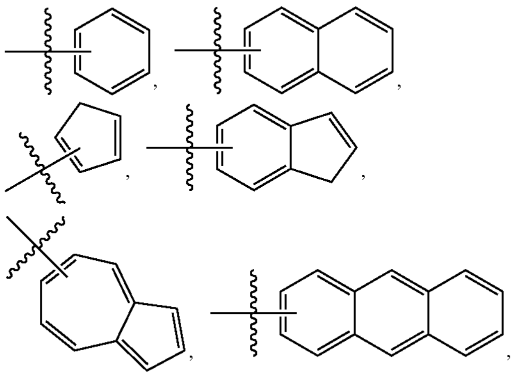

-continued

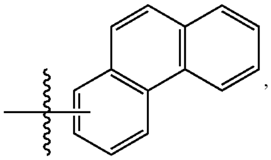, and

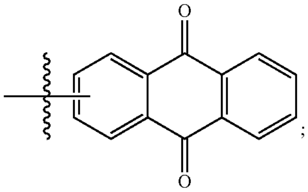;

the heteroaryl is selected from

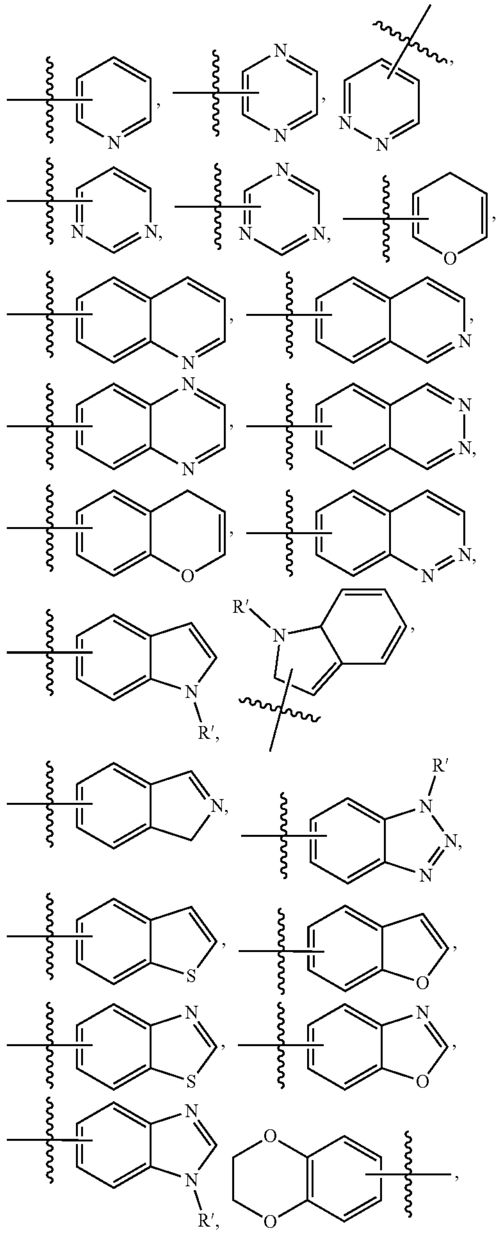

-continued

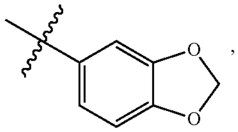

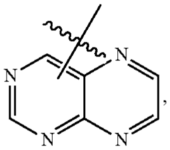

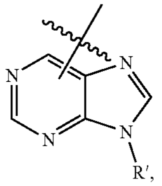

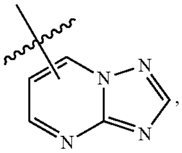

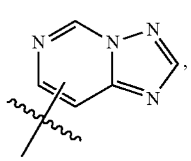

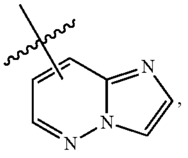

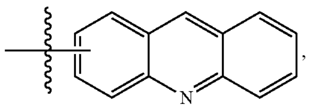

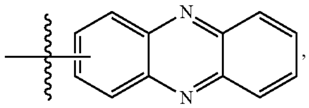

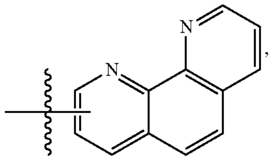

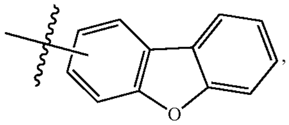

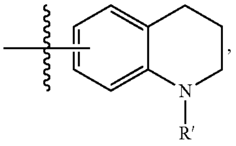

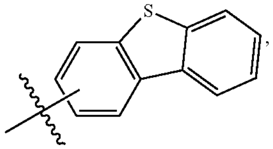

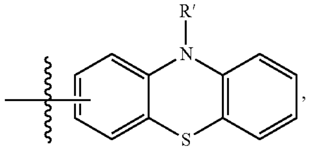

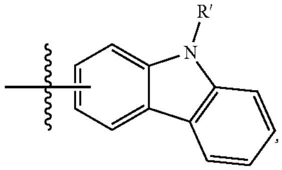

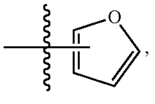

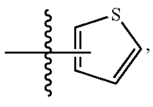

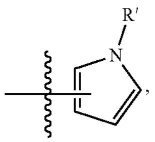

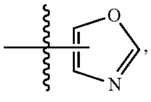

-continued

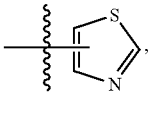

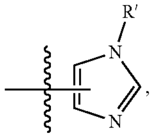

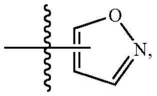

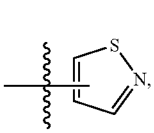

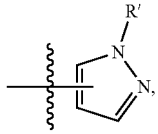

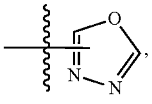

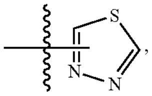

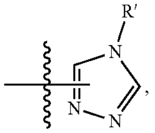

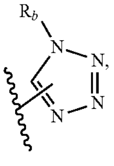

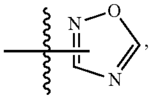

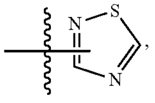

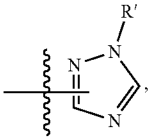

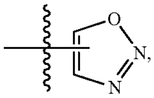

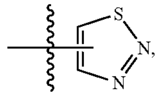

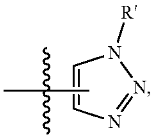

and

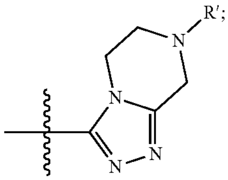

R' is hydrogen, a fluoro-, chloro-, or bromo-containing or not containing group selected from C1~C4 alkyl, C1~C4 alkoxy-C1~C4 alkyl, C1~C4 alkoxycarbonyl, and C1~C4 alkylcarbonyl,

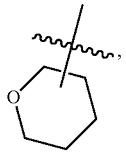

phenyl, or benzyl;

the aliphatic heterocyclyl is selected from

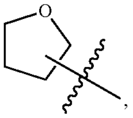

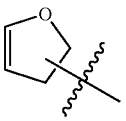

and

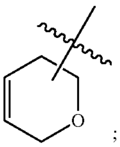

;

The derivative is an agriculturally acceptable salt or a compound derivatized from 4-hydroxy of the pyridazine ring of the Formula I, including an ester, an oxime, a hydroxylamine and an ether thereof.

In a preferred embodiment, X is $CH_2F$, $CHF_2$, $CF_3$, or $CF_2CF_3$;

A is methyl, ethyl,

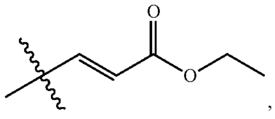
,
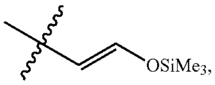
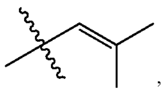
,
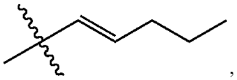
,
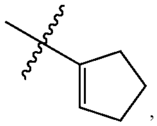
,
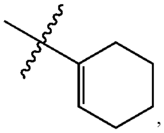
, unsubstituted or substituted 5- to 14-membered aryl, unsubstituted or substituted 5- to 14-membered heteroaryl, or unsubstituted or substituted 5- to 14-membered aliphatic heterocyclyl; wherein, said substituted 5- to 14-membered aryl, substituted 5- to 14-membered heteroaryl or substituted 5- to 14-membered aliphatic heterocyclyl is the 5- to 14-membered aryl, 5- to 14-membered heteroaryl, or 5- to 14-membered aliphatic heterocyclyl, which is substituted with one or more substituents independently selected from the group consisting of fluorine, chlorine, bromine, iodine, cyano, nitro, azido, a fluoro-, chloro-, or bromo-containing or not containing group selected from C1~C4 alkyl, C2~C4 alkenyl, C2~C4 alkynyl, C3~C6 cycloalkyl, and C3~C6 cycloalkyl-C1~C2 alkyl, phenyl, pyrrolyl, furyl, imidazolyl, pyrazolyl, oxazolyl, isoxazolyl, thiazolyl, oxadiazolyl, thiadiazolyl, triazolyl, pyridyl, pyrazinyl, pyrimidinyl, benzyl, tetrahydropyranyl, thienylmethyl, each of the phenyl, pyrrolyl, furyl, imidazolyl, pyrazolyl, oxazolyl, isoxazolyl, thiazolyl, oxadiazolyl, thiadiazolyl, triazolyl, pyridyl, pyrazinyl, pyrimidinyl, benzyl, tetrahydropyranyl, thienylmethyl is unsubstituted or substituted with 1-3 groups independently selected from fluorine, chlorine, bromine, cyano, hydroxy, and a fluoro-, chloro-, or bromo-containing or not containing group selected from C1~C4 alkyl, C1~C4 alkoxy, C1~C4 alkoxycarbonyl, C1~C4 alkylsulfonyl, and C1~C4 alkylamino, R—O—, R—O—$CH_2$—, R—O—$CH_2CH_2$—, R—O—$CH_2$—O—, R—O—(C═O)—, R—O—$CH_2$—(C═O)—, R—O—$CH_2$—(C═O)—O—, R—O—(C═O)—$CH_2$—O—, R—O—(C═O)—$CH_2CH_2$—O—, R—O—(C═O)—$CH_2$—S—, R—O—$CH_2$—(C═O)—S—, R—O—$CH_2$—(C═O)—$CH_2$—S—, R—S—$CH_2$—, R—S—, R—S—(C═O)—, R—S—$CH_2$—(C═O)—, R—(C═O)—$CH_2$—, R—(C═O)—, R—(C═O)—O—$CH_2$—, R—(C═O)—$CH_2$—O—, R—(C═O)—$CH_2CH_2$—O—, R—(C═O)—O—, R—SO—$CH_2$—, R—SO—, R—$SO_2$—$CH_2$—O—, R—$SO_2$—$CH_2$—, R—$SO_2$—O—, R—$SO_2$—, R—$SO_2$—$CH_2$—$NR_3$—, R—$SO_2$—$NR_3$—, $R_1R_2N$—$CH_2$—, $R_1R_2N$—, $R_1R_2N$—(C═O)—$CH_2$—, $R_1R_2N$—(C═O)—$CH_2$—O—, $R_1R_2N$—(C═O)—, $R_1R_2N$—(C═O)—$NR_3$—, $R_1R_2N$—$CH_2$—$SO_2$—, $R_1R_2N$—$CH_2$—$SO_2$—$CH_2$—, $R_1R_2N$—$SO_2$—$CH_2$—, $R_1R_2N$—$SO_2$—, $R_1R_2P(O)$—, and $R_1R_2R_3Si$—;

R is hydrogen, a fluoro-, chloro-, or bromo-containing or not containing group selected from C1~C4 alkyl, C2~C4 alkenyl, C2~C4 alkynyl, C3~C6 cycloalkyl, and C3~C6 cycloalkyl-C1~C2 alkyl, phenyl, benzyl, or thienyl, each of the phenyl, benzyl, or thienyl is unsubstituted or substituted with 1-3 groups independently selected from fluorine, chlorine, and bromine;

$R_1$, $R_2$, $R_3$ are each independently is hydrogen, a fluoro-, chloro-, or bromo-containing or not containing group selected from C1~C4 alkyl, C2~C4 alkenyl, C2~C4 alkynyl, C3~C6 cycloalkyl, C1~C4 alkoxy, C1~C4 alkoxy-C1-~C2 alkyl, C1~C4 alkoxycarbonyl, C1-~C4 alkylcarbonyl, C1~C4 alkylcarbonyl-C1~C2 alkyl, and C1~C4 alkylcarbonyloxy, phenyl, naphthyl, phenoxy, furyl, thienyl, thiadiazolyl, thienylmethyl, pyrazolylmethyl, benzoyl, or pyridinylformyl, each of the phenyl, naphthyl, phenoxy, furyl, thienyl, thiadiazolyl, thienylmethyl, pyrazolylmethyl, benzoyl, or pyridinylformyl is unsubstituted or substituted with 1-3 groups independently selected from fluorine, chlorine, bromine, C1~C4 alkyl, C3~C6 cycloalkyl, C1~C4 alkoxy, and C1~C4 alkylamino; or $R_1R_2N$— is

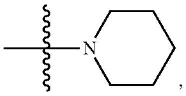
,
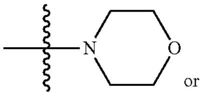
or
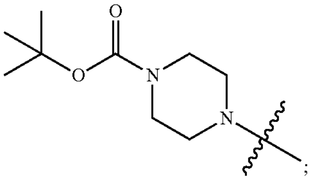
;

the 5- to 14-membered aryl is selected from

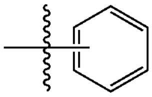
,
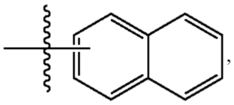
,
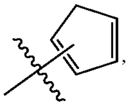
,
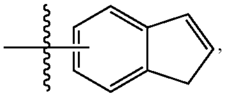
,
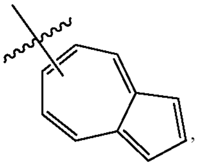
,
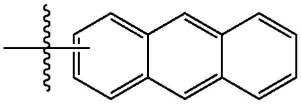
,
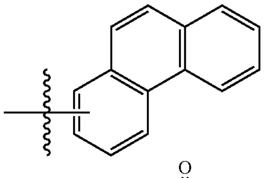
, and
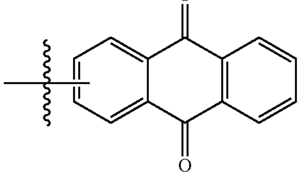
;

the heteroaryl is selected from
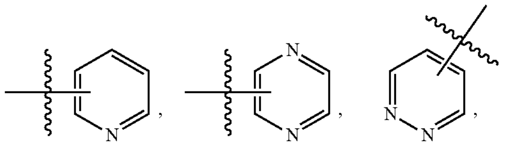
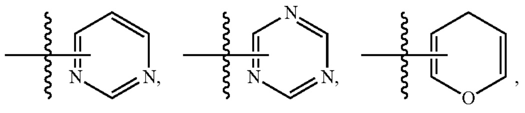
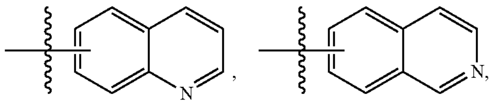
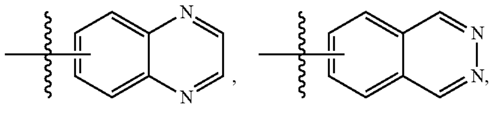
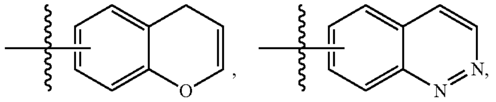
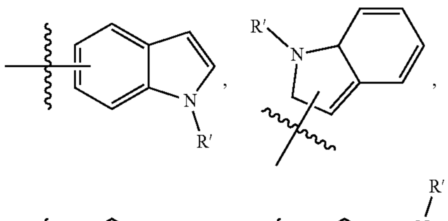
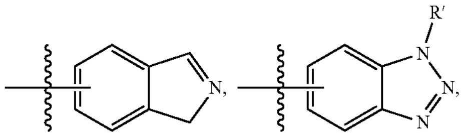
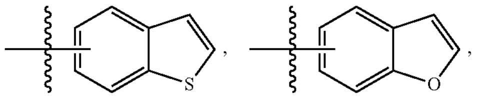
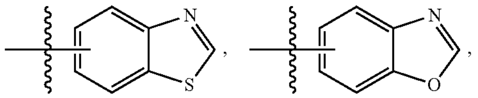
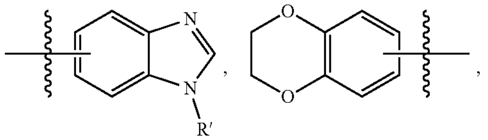
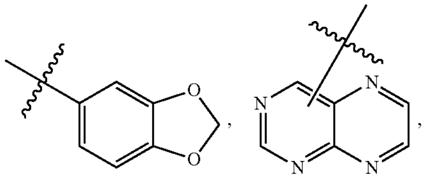
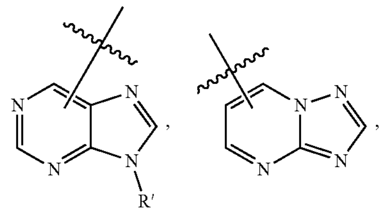
-continued
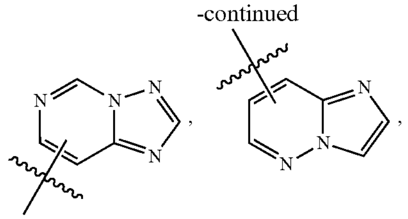
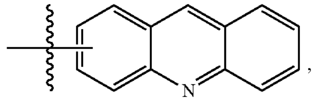
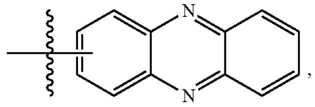
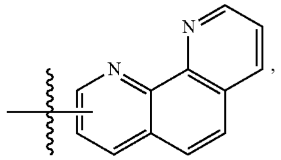
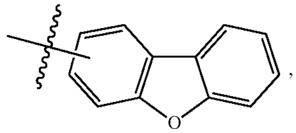
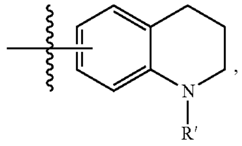
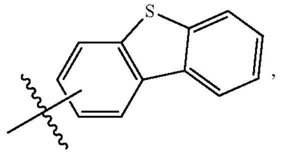
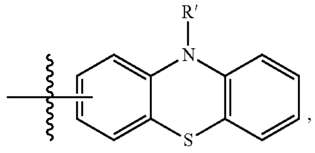
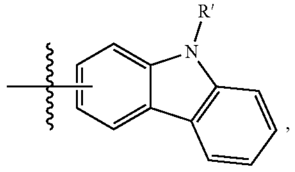
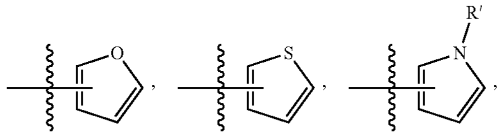
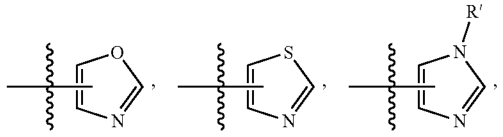
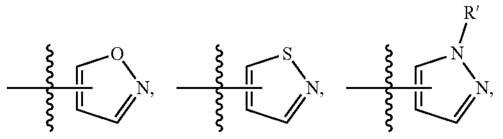

-continued

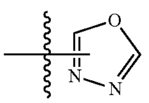, 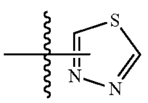, 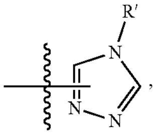,

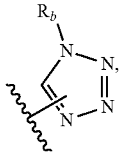 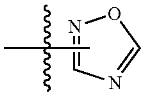, 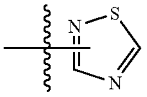,

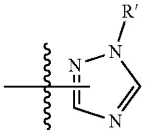, 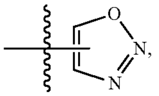 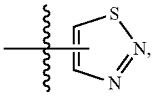

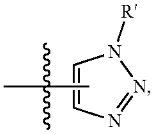 and 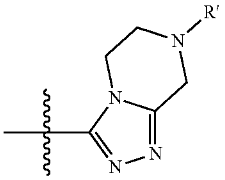 ;

R' is hydrogen, a fluoro-, chloro-, or bromo-containing or not containing group selected from C1~C4 alkyl, C1~C4 alkoxy-C1~C2 alkyl, C1~C4 alkoxycarbonyl, and C1~C4 alkylcarbonyl,

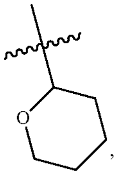 [SMILES: *C1CCCCO1], phenyl, or benzyl;

the aliphatic heterocyclyl is

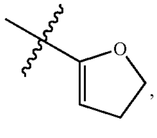, or 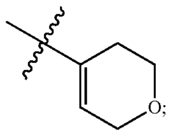;

the derivative is an agriculturally acceptable salt or a compound derivatized from 4-hydroxy of the pyridazine ring of the Formula I, including an ester, an oxime, a hydroxylamine and an ether thereof.

In a preferred embodiment, X is halogenated alkyl, cyano, alkyl, alkoxy, halogenated alkoxy, $R_1R_2N$—(C═O)—, $R_1R_2N$—, hydroxy, or unsubstituted or substituted aryl;

A is selected from the group consisting of alkyl, alkenyl, alkynyl, cycloalkyl, cycloalkenyl, cycloalkylalkyl, aryl, and heteroaryl, each of which is unsubstituted or substituted; wherein, when being substituted, each of the alkyl, alkenyl, alkynyl, cycloalkyl, cycloalkenyl, or cycloalkylalkyl is substituted with one or more substituents selected from the group consisting of halogen, cyano, nitro, azido, unsubstituted or substituted aryl, unsubstituted or substituted heteroaryl, —$(CH_2)_n$—O—$(CH_2)_p$—, —$(CH_2)_n$—S—$(CH_2)_p$—, —$(CH_2)_n$—$NR_3$—$(CH_2)_p$—, R—O—, R—O—$(CH_2)_p$—O—, R—O—$(CH_2)_p$—S—, R—S—, R—S—$(CH_2)_p$—O—, R—S—$(CH_2)_p$—S—, R—O—$(CH_2)_n$—(C═O)—$(CH_2)_q$—$(O)_m$—, R—S—$(CH_2)_n$—(C═S)—$(CH_2)_q$—$(S)_m$—, R—O—$(CH_2)_n$—(C═O)—$(CH_2)_q$—$(S)_m$—, R—O—$(CH_2)_n$—(C═S)—$(CH_2)_q$—$(O)_m$—, R—S—$(CH_2)_n$—(C═O)—$(CH_2)_q$—$(O)_m$—, R—O—$(CH_2)_n$—(C═S)—$(CH_2)_q$—$(S)_m$—, R—S—$(CH_2)_n$—(C═O)—$(CH_2)_q$—$(S)_m$—, R—S—$(CH_2)_n$—(C═S)—$(CH_2)_q$—$(O)_m$—, R—(C═O)—, R—(C═S)—, R—(C═O)—$(CH_2)_n$—O—, R—(C═S)—$(CH_2)_n$—S—, R—(C═O)—$(CH_2)_n$—S—, R—(C═S)—$(CH_2)_n$—O—, R—SO—$(CH_2)_n$—$(O)_m$—, R—SO—$(CH_2)_n$—$(S)_m$—, R—SO—$(CH_2)_n$—$(NR_3)_m$—, R—$SO_2$—$(CH_2)_n$—$(O)_m$—, R—$SO_2$—$(CH_2)_n$—$(S)_m$—, R—$SO_2$—$(CH_2)_n$—$(NR_3)_m$—, $R_1R_2N$—, $R_1R_2N$—$(CH_2)_n$—O—$(CH_2)_q$—$(O)_m$—, $R_1R_2N$—$(CH_2)_n$—O—$(CH_2)_q$—$(S)_m$—, $R_1R_2N$—$(CH_2)_n$—O—$(CH_2)_q$—$(NR_3)_m$—, $R_1R_2N$—$(CH_2)_n$—(C═O)—$(CH_2)_q$—$(O)_m$—, $R_1R_2N$—$(CH_2)_n$—(C═O)—$(CH_2)_q$—$(S)_m$—, $R_1R_2N$—$(CH_2)_n$—(C═O)—$(CH_2)_q$—$(NR_3)_m$—, $R_1R_2N$—$(CH_2)_n$—$SO_2$—$(CH_2)_q$—$(O)_m$—, $R_1R_2N$—$(CH_2)_n$—$SO_2$—$(CH_2)_q$—$(S)_m$—, $R_1R_2N$—$(CH_2)_n$—$SO_2$—$(CH_2)_q$—$(NR_3)_m$—, $R_1R_2PO_3$—$(O)_m$—, $R_1R_2R_3SiO$—, $R_1R_2R_3Si$—(CH═CH)$_m$—, $R_1R_2C$═N—$(O)_m$—, and $R_1R_2C$═N—NH—;

when being substituted, each of the aryl or heteroaryl is substituted with one or more substituents selected from the group consisting of halogen, cyano, nitro, azido, a halogen-containing or not containing group selected from alkyl, alkenyl, alkynyl, cycloalkyl, cycloalkenyl, and cycloalkylalkyl, a group selected from aryl, arylalkyl, heteroaryl, heteroarylalkyl, which is unsubstituted or substituted, R—O—$(CH_2)_n$—, R—O—$(CH_2)_p$—O—$(CH_2)_q$—, R—O—$(CH_2)_p$—S—$(CH_2)_q$—, R—S—$(CH_2)_n$—, R—S—$(CH_2)_p$—O—$(CH_2)_q$—, R—S—$(CH_2)_p$—S—$(CH_2)_q$—, R—O—$(CH_2)_n$—(C═O)—$(CH_2)_q$—$(O)_m$—, R—S—$(CH_2)_n$—(C═S)—$(CH_2)_q$—$(S)_m$—, R—O—$(CH_2)_n$—(C═O)—$(CH_2)_q$—$(S)_m$—, R—O—$(CH_2)_n$—(C═S)—$(CH_2)_q$—$(O)_m$—, R—S—$(CH_2)_n$—(C═O)—$(CH_2)_q$—$(O)_m$—, R—O—$(CH_2)_n$—(C═S)—$(CH_2)_q$—$(S)_m$—, R—S—$(CH_2)_n$—(C═O)—$(CH_2)_q$—$(S)_m$—, R—S—$(CH_2)_n$—(C═S)—$(CH_2)_q$—$(O)_m$—, R—(C═O)—$(CH_2)_n$—, R—(C═S)—$(CH_2)_n$—, R—(C═O)—$(CH_2)_n$—O—$(CH_2)_q$—, R—(C═S)—$(CH_2)_n$—S—$(CH_2)_q$—, R—(C═O)—$(CH_2)_n$—S—$(CH_2)_q$—, R—(C═S)—$(CH_2)_n$—O—$(CH_2)_q$—, R—SO—$(CH_2)_n$—$(O)_m$—, R—SO—$(CH_2)_n$—$(S)_m$—, R—SO—$(CH_2)_n$—$(NR_3)_m$—, R—$SO_2$—$(CH_2)_n$—$(O)_m$—, R—$SO_2$—$(CH_2)_n$—$(S)_m$—, R—$SO_2$—$(CH_2)_n$—$(NR_3)_m$—, $R_1R_2N$—$(CH_2)_n$—, $R_1R_2N$—$(CH_2)_n$—O—$(CH_2)_q$—$(O)_m$—, $R_1R_2N$—$(CH_2)_n$—O—$(CH_2)_q$—$(S)_m$—, $R_1R_2N$—$(CH_2)_n$—O—$(CH_2)_q$—$(NR_3)_m$—, $R_1R_2N$—$(CH_2)_n$—(C═O)—$(CH_2)_q$—$(O)_m$—, $R_1R_2N$—$(CH_2)_n$—(C═O)—$(CH_2)_q$—$(S)_m$—, $R_1R_2N$—$(CH_2)_n$—(C═O)—$(CH_2)_q$—$(NR_3)_m$—, $R_1R_2N$—$(CH_2)_n$—$SO_2$—$(CH_2)_q$—$(O)_m$—, $R_1R_2N$—$(CH_2)_n$—$SO_2$—$(CH_2)_q$—$(S)_m$—, $R_1R_2N$—$(CH_2)_n$—$SO_2$—$(CH_2)_q$—$(NR_3)_m$—, $R_1R_2PO_3$—$(O)_m$—$(CH_2)_q$—, $R_1R_2R_3SiO$—$(CH_2)_q$—, $R_1R_2R_3Si$—(CH═CH)$_m$—$(CH_2)_q$—, $R_1R_2C$═N—$(O)_m$—$(CH_2)_n$—, and $R_1R_2C$═N—NH—$(CH_2)_n$—;

m is 0 or 1, n and q are independently an integer from 0 to 8, p is an integer from 1 to 8; wherein, m, n, q, p in the above substituents are valued independently, and these values render the substituents different from each other;

R is hydrogen, a halogen-containing or not containing group selected from alkyl, alkenyl, alkynyl, cycloalkyl, cycloalkenyl, and cycloalkylalkyl, or a group selected from aryl, arylalkyl, heteroaryl, and heteroarylalkyl, which is unsubstituted or substituted;

$R_1$, $R_2$, $R_3$ are each independently hydrogen, nitro, hydroxy, amino, a halogen-containing or not containing group selected from alkyl, alkenyl, alkynyl, cycloalkyl, cycloalkenyl, cycloalkylalkyl, alkoxy, alkenyloxy, alkynyloxy, cycloalkyloxy, alkoxyalkyl, alkoxycarbonyl, alkylsulfanylcarbonyl, alkylsulfonyl, alkylsulfonylalkyl, alkylcarbonyl, alkylcarbonylalkyl, alkylcarbonyloxy, alkylamino, alkylaminocarbonyl, alkoxyaminocarbonyl, alkoxycarbonylalkyl, alkylaminocarbonylalkyl, trialkylsilyl, and dialkylphosphonyl, or a group selected from 6-membered heterocyclyl, aryl, arylalkyl, aryloxy, arylalkyloxy, aryloxyalkyl, arylcarbonyl, arylsulfonyl, heteroaryl, heteroarylalkyl, heteroaryloxy, heteroarylalkyloxy, heteroaryloxyalkyl, heteroarylcarbonyl, and heteroarylsulfonyl, which is unsubstituted or substituted; or $R_1R_2N$— forms a 6-membered heterocyclyl.

In a preferred embodiment, X is halogenated C1~C8 alkyl, cyano, C1~C8 alkyl, C1~C8 alkoxy, halogenated C1~C8 alkoxy, $R_1R_2N$—(C═O)—, $R_1R_2N$—, hydroxy, or aryl, the aryl is unsubstituted or substituted with 1-5 substituents independently selected from the group consisting of halogen, cyano, nitro, hydroxy, carboxyl, sulfhydryl, amino, and a halogen-containing or not containing group selected from C1~C8 alkyl, C3~C8 cycloalkyl, C3~C8 cycloalkyl-C1~C8 alkyl, C2~C8 alkenyl, C2~C8 alkynyl, C1~C8 alkoxy, C1~C8 alkylcarbonyl, C1~C8 alkoxycarbonyl, C1~C8 alkylsulfonyl, C1~C8 alkylamino, and C1~C8 alkylcarbonyloxy;

A is selected from the group consisting of C1~C8 alkyl, C2~C8 alkenyl, C2~C8 alkynyl, C3~C8 cycloalkyl, C5~C8 cycloalkenyl, C3~C8 cycloalkyl-C1~C8 alkyl, 5- to 14-membered aryl, and 5- to 14-membered heteroaryl, each of which is unsubstituted or substituted; wherein, when being substituted, the C1~C8 alkyl, C2~C8 alkenyl, C2~C8 alkynyl, C3~C8 cycloalkyl, C5~C8 cycloalkenyl, or C3~C8 cycloalkyl-C1~C8 alkyl is substituted with one or more substituents independently selected from the group consisting of halogen, cyano, nitro, azido, aryl, heteroaryl, the aryl or heteroaryl is unsubstituted or independently substituted with 1-5 groups selected from halogen, cyano, nitro, hydroxy, carboxyl, sulfhydryl, amino, and a halogen-containing or not containing group selected from C1~C8 alkyl, C3~C8 cycloalkyl, C5~C8 cycloalkenyl, C3~C8 cycloalkyl-C1~C8 alkyl, C2~C8 alkenyl, C2~C8 alkynyl, C1~C8 alkoxy, C1~C8 alkylcarbonyl, C1~C8 alkoxycarbonyl, C1~C8 alkylsulfonyl, C1~C8 alkylamino, and C1~C8 alkylcarbonyloxy, —$(CH_2)_n$—O—$(CH_2)_p$—, —$(CH_2)_n$—S—$(CH_2)_p$—, —$(CH_2)_n$—$NR_3$—$(CH_2)_p$—, R—O—, R—O—$(CH_2)_p$—O—, R—O—$(CH_2)_p$—S—, R—S—, R—S—$(CH_2)_p$—O—, R—S—$(CH_2)_p$—S—, R—O—(C═O)—$(CH_2)_q$—$(O)_m$—, R—O—$(CH_2)_n$—(C═O)—$(O)_m$—, R—O—$(CH_2)_n$—(C═O)—, R—S—(C═S)—$(CH_2)_q$—$(S)_m$—, R—S—$(CH_2)_n$—(C═S)—$(S)_m$—, R—S—$(CH_2)_n$—(C═S)—, R—O—(C═O)—$(CH_2)_q$—$(S)_m$—, R—O—$(CH_2)_n$—(C═O)—$(S)_m$—, R—O—(C═S)—$(CH_2)_q$—$(O)_m$—, R—O—$(CH_2)_n$—(C═S)—$(O)_m$—, R—O—$(CH_2)_n$—(C═S)—, R—S—(C═O)—$(CH_2)_q$—$(O)_m$—, R—S—$(CH_2)_n$—(C═OO)—( )$_m$—, R—S—$(CH_2)_n$—(C═O)—, R—O—(C═S)—$(CH_2)_q$—$(S)_m$—, R—O—$(CH_2)_n$—(C═S)—$(S)_m$—, R—S—(C═O)—$(CH_2)_q$—$(S)_m$—, R—S—$(CH_2)_n$—(C═O)—$(S)_m$—, R—S—(C═S)—$(CH_2)_q$—$(O)_m$—, R—S—$(CH_2)_n$—(C═S)—$(O)_m$—, R—(C═O)—, R—(C═S)—, R—(C═O)—O—, R—(C═S)—S—, R—(C═O)—S—, R—(C═S)—O—, R—SO—$(O)_m$—, R—SO—$(S)_m$—, R—SO—$(NR_3)_m$—, R—$SO_2$—$(O)_m$—, R—$SO_2$—$(S)_m$—, R—$SO_2(NR_3)_m$—, $R_1R_2N$—, $R_1R_2N$—O—$(CH_2)_q$—$(O)_m$—, $R_1R_2N$—$(CH_2)_n$—O—, $R_1R_2N$—O—$(CH_2)_q$—$(S)_m$—, $R_1R_2N$—O—$(CH_2)_q$—$(NR_3)_m$—, $R_1R_2N$—(C═O)—$(CH_2)_q$—$(O)_m$—, $R_1R_2N$—$(CH_2)_n$—(C═O)—$(O)_m$—, $R_1R_2N$—$(CH_2)_n$—(C═O)—, $R_1R_2N$—(C═O)—$(CH_2)_q$—$(S)_m$—, $R_1R_2N$—$(CH_2)_n$—(C═O)—$(S)_m$—, $R_1R_2N$—(C═O)—$(CH_2)_q$—$(NR_3)_m$—, $R_1R_2N$—$(CH_2)_n$—(C═O)—$(NR_3)_m$—, $R_1R_2N$—$SO_2$—$(CH_2)_q$—$(O)_m$—, $R_1R_2N$—$(CH_2)_n$—$SO_2$—$(O)_m$—, $R_1R_2N$—$(CH_2)_n$—$SO_2$—, $R_1R_2N$—$SO_2$—$(CH_2)_q$—$(S)_m$—, $R_1R_2N$—$(CH_2)_n$—$SO_2$—$(S)_m$—, $R_1R_2N$—$SO_2$—$(CH_2)_q$—$(NR_3)_m$—, $R_1R_2N$—$(CH_2)_n$—$SO_2$—$(NR_3)_m$—, $R_1R_2PO_3$—, $R_1R_2R_3SiO$—, $R_1R_2R_3Si$—$(CH{=}CH)_m$—, $R_1R_2C$═N—$(O)_m$—, and $R_1R_2C$═N—NH—;

when being substituted, each of the 5- to 14-membered aryl or 5- to 14-membered heteroaryl is independently substituted with one or more substituents selected from the group consisting of halogen, cyano, nitro, azido, a halogen-containing or not containing group selected from C1~C8 alkyl, C2~C8 alkenyl, C2~C8 alkynyl, C3~C8 cycloalkyl, C5~C8 cycloalkenyl, and C3~C8 cycloalkyl-C1~C8 alkyl, aryl, aryl-C1~C8 alkyl, heteroaryl, heteroaryl-C1~C8 alkyl, each of the aryl, aryl-C1-~C8 alkyl, heteroaryl, or heteroaryl-C1~C8 alkyl is unsubstituted or substituted with 1-5 groups independently selected from halogen, cyano, nitro, hydroxy, carboxyl, sulfhydryl, amino, and a halogen-containing or not containing group selected from C1~C8 alkyl, C3~C8 cycloalkyl, C5~C8 cycloalkenyl, C3~C8 cycloalkyl-C1~C8 alkyl, C2~C8 alkenyl, C2~C8 alkynyl, C1~C8 alkoxy, C1~C8 alkylcarbonyl, C1~C8 alkoxycarbonyl, C1~C8 alkylsulfonyl, C1~C8 alkylamino, and C1~C8 alkylcarbonyloxy, R—O—$(CH_2)_n$—, R—O—$(CH_2)_p$—O—$(CH_2)_q$—, R—O—$(CH_2)_p$—S—$(CH_2)_q$—, R—S—$(CH_2)_n$—, R—S—$(CH_2)_p$—O—$(CH_2)_q$—, R—S—$(CH_2)_p$—S—$(CH_2)_q$—, R—O—$(CH_2)_n$—(C═O)—$(CH_2)_q$—, R—S—$(CH_2)_n$—(C═S)—$(CH_2)_q$—, R—O—$(CH_2)_n$—(C═S)—$(CH_2)_q$—, R—S—$(CH_2)_n$—(C═O)—$(CH_2)_q$—, R—O—(C═O)—$(CH_2)_q$—$(O)_m$—, R—S—(C═S)—$(CH_2)_q$—$(S)_m$—, R—O—(C═O)—$(CH_2)_q$—$(S)_m$—, R—O—(C═S)—$(CH_2)_q$—$(O)_m$—, R—S—(C═O)—$(CH_2)_q$—$(O)_m$—, R—O—(C═S)—$(CH_2)_q$—$(S)_m$—, R—S—(C═O)—$(CH_2)_q$—$(S)_m$—, R—S—(C═S)—$(CH_2)_q$—$(O)_m$—, R—O—$(CH_2)_n$—(C═O)—$(O)_m$—, R—S—$(CH_2)_n$—(C═S)—$(S)_m$—, R—O—$(CH_2)_n$—(C═O)—$(S)_m$—, R—O—$(CH_2)_n$—(C═S)—$(O)_m$—, R—S—$(CH_2)_n$—(C═O)—$(O)_m$—, R—O—$(CH_2)_n$—(C═S)—$(S)_m$—, R—S—$(CH_2)_n$—(C═O)—$(S)_m$—, R—S—$(CH_2)_n$—(C═S)—$(O)_m$—, R—(C═O)—, R—(C═S)—, R—(C═O)—$(CH_2)_n$—O—, R—(C═S)—$(CH_2)_n$—S—, R—(C═O)—$(CH_2)_n$—S—, R—(C═S)—$(CH_2)_n$—O—, R—(C═O)—O—$(CH_2)_q$—, R—(C═S)—S—$(CH_2)_q$—, R—(C═O)—S—$(CH_2)_g$—, R—(C═S)—O—$(CH_2)_q$—, R—SO—$(O)_m$—, R—SO—$(S)_m$—, R—SO—$(NR_3)_m$—, R—$SO_2$—$(O)_m$—, R—$SO_2$—$(S)_m$—, R—$SO_2$—$(NR_3)_m$—, R—SO—$(CH_2)_n$—, R—$SO_2$—$(CH_2)_n$—, $R_1R_2N$—, $R_1R_2N$—$(CH_2)_n$—O—$(CH_2)_q$—, $R_1R_2N$—$(CH_2)_n$—(C═O)—$(CH_2)_q$—, $R_1R_2N$—$(CH_2)_n$—$SO_2$—$(CH_2)_q$—, $R_1R_2N$—$(CH_2)_n$—(C═O)—$(O)_m$—, $R_1R_2N$—$(CH_2)_n$—(C═O)—$(S)_m$—, $R_1R_2N$—$(CH_2)_n$—(C═O)—$(NR_3)_m$—, $R_1R_2N$—$(CH_2)_n$—$SO_2$—$(O)_m$—, $R_1R_2N$—$(CH_2)_n$—$SO_2$—$(S)_m$—, $R_1R_2N$—$(CH_2)_n$—$SO_2$—$(NR_3)_m$—, $R_1R_2N$—(C═O)—$(CH_2)_n$—$(O)_m$—, $R_1R_2N$—(C═O)—$(CH_2)_n$—$(S)_m$—, $R_1R_2N$—(C═O)—$(CH_2)_n$—$(NR_3)_m$—, $R_1R_2N$—$SO_2$—$(CH_2)_q$—$(O)_m$—, $R_1R_2N$—$SO_2$—$(CH_2)_q$—$(S)_m$—, $R_1R_2N$—$SO_2$—$(CH_2)_q$—$(NR_3)_m$—, $R_1R_2N$—$(CH_2)_n$—O—, $R_1R_2N$—O—$(CH_2)_q$—, $R_1R_2PO_3$—$(O)_m$—, $R_1R_2R_3SiO$—, $R_1R_2R_3Si$—$(CH═CH)_m$—, $R_1R_2C$═N—$(O)_m$—, and $R_1R_2C$═N—NH—;

m is 0 or 1, n and q are independently an integer from 0 to 6, p is an integer from 1 to 6; wherein, m, n, q, p in the above substituents are valued independently, and these values render the substituents different from each other;

R is hydrogen, a halogen-containing or not containing group selected from C1~C8 alkyl, C2~C8 alkenyl, C2~C8 alkynyl, C3~C8 cycloalkyl, C5~C8 cycloalkenyl, and C3~C8 cycloalkyl-C1~C8 alkyl, aryl, aryl-C1~C8 alkyl, heteroaryl, or heteroaryl-C1~C8 alkyl, each of the aryl, aryl-C1~C8 alkyl, heteroaryl, or heteroaryl-C1~C8 alkyl is unsubstituted or substituted with 1-5 groups substituents independently selected from halogen, cyano, nitro, hydroxy, carboxyl, sulfhydryl, amino, and a halogen-containing or not containing group selected from C1~C8 alkyl, C3~C8 cycloalkyl, C5~C8 cycloalkenyl, C3~C8 cycloalkyl-C1~C8 alkyl, C2~C8 alkenyl, C2~C8 alkynyl, C1~C8 alkoxy, C1~C8 alkylcarbonyl, C1~C8 alkoxycarbonyl, C1~C8 alkylsulfonyl, C1~C8 alkylamino, and C1~C8 alkylcarbonyloxy;

$R_1$, $R_2$, $R_3$ are each independently hydrogen, nitro, hydroxy, amino, a halogen-containing or not containing group selected from C1~C8 alkyl, C2~C8 alkenyl, C2~C8 alkynyl, C3~C8 cycloalkyl, C5~C8 cycloalkenyl, C3~C8 cycloalkyl-C1~C8 alkyl, C1~C8 alkoxy, C2~C8 alkenyloxy, C2~C8 alkynyloxy, C3~C8 cycloalkyloxy, C1~C8 alkoxy-C1~C8 alkyl, C1~C8 alkoxycarbonyl, C1~C8 alkylcarbonyl-C1~C8 alkyl, C1~C8 alkylsulfanylcarbonyl, C1~C8 alkylsulfonyl, C1~C8 alkylsulfonyl-C1~C8 alkyl, C1~C8 alkylcarbonyl, C1~C8 alkylcarbonyloxy, C1~C8 alkylamino, C1~C8 alkylaminocarbonyl, C1~C8 alkoxyaminocarbonyl, C1~C8 alkoxycarbonyl-C1~C8 alkyl, C1~C8 alkylaminocarbonyl-C1~C8 alkyl, triC1~C8 alkylsilyl, and diC1~C8 alkylphosphonyl, 6-membered heterocyclyl, aryl, aryl-C1~C8 alkyl, aryloxy, aryl-C1~C8 alkyloxy, aryloxy-C1~C8 alkyl, arylcarbonyl, arylsulfonyl, heteroaryl, heteroaryl-C1~C8 alkyl, heteroaryloxy, heteroaryl-C1~C8 alkyloxy, heteroaryloxy-C1~C8 alkyl, heteroarylcarbonyl, or heteroarylsulfonyl, each of the 6-membered herterocyclyl, aryl, aryl-C1~C8 alkyl, aryloxy, aryl-C1~C8 alkyloxy, aryloxy-C1~C8 alkyl, arylcarbonyl, arylsulfonyl, heteroaryl, heteroaryl-C1~C8 alkyl, heteroaryloxy, heteroaryl-C1~C8 alkyloxy, heteroaryloxy-C1~C8 alkyl, heteroarylcarbonyl, or heteroarylsulfonyl is unsubstituted or substituted with 1-5 groups independently selected from halogen, cyano, nitro, hydroxy, carboxyl, sulfhydryl, amino, and a halogen-containing or not containing group selected from C1~C8 alkyl, C3~C8 cycloalkyl, C5~C8 cycloalkenyl, C3~C8 cycloalkyl-C1~C8 alkyl, C2~C8 alkenyl, C2~C8 alkynyl, C1~C8 alkoxy, C1~C8 alkylcarbonyl, C1~C8 alkoxycarbonyl, C1~C8 alkylsulfonyl, C1~C8 alkylamino, and C1~C8 alkylcarbonyloxy; or $R_1R_2N$— forms a 6-membered heterocyclyl containing or not containing other hetero atoms.

In a preferred embodiment, X is halogenated C1~C6 alkyl;

A is selected from the group consisting of C1~C6 alkyl, C2~C6 alkenyl, C2~C6 alkynyl, C3~C6 cycloalkyl, C5~C6 cycloalkenyl, C3~C6 cycloalkyl-C1~C6 alkyl, 5- to 14-membered aryl, and 5- to 14-membered heteroaryl, each of which is unsubstituted or substituted; wherein, when being substituted, each of the C1~C6 alkyl, C2~C6 alkenyl, C2~C6 alkynyl, C3~C6 cycloalkyl, C5~C6 cycloalkenyl, or C3~C6 cycloalkyl-C1~C6 alkyl is substituted with one or more substituents independently selected from the group consisting of fluorine, chlorine, bromine, cyano, nitro, azido, aryl, heteroaryl, the aryl or heteroaryl is unsubstituted or substituted with 1-3 groups independently selected from fluorine, chlorine, bromine, cyano, nitro, hydroxy, carboxyl, sulfhydryl, amino, and a fluoro-, chloro-, or bromo-containing or not containing group selected from C1~C6 alkyl, C3~C6 cycloalkyl, C5~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy, —$(CH_2)_n$—O—, —$(CH_2)_n$—S—, —$(CH_2)_n$—$NR_3$—, R—O—, R—O—$(CH_2)_p$—O—, R—O—$(CH_2)_p$—S—, R—S—, R—S—$(CH_2)_p$—O—, R—S—$(CH_2)_p$—S—, R—O—(C═O)—, R—S—(C═S)—, R—O—(C═S)—, R—S—(C═O)—, R—(C═O)—, R—(C═S)—, R—(C═O)—O—, R—(C═S)—S—, R—(C═O)—S—, R—(C═S)—O—, R—SO—, R—$SO_2$—, $R_1R_2N$—, $R_1R_2N$—O—, $R_1R_2N$—(C═O)—, $R_1R_2N$—$SO_2$—, $R_1R_2PO_3$—, $R_1R_2R_3SiO$—, $R_1R_2R_3Si$—(CH═CH)—, $R_1R_2R_3Si$—, $R_1R_2C$═N—(O)—, $R_1R_2C$═N—, and $R_1R_2C$═N—NH—;

when being substituted, each of the 5- to 14-membered aryl or 5- to 14-membered heteroaryl is substituted with one or more substituents independently selected from the group consisting of fluorine, chlorine, bromine, cyano, nitro, azido, a fluoro-, chloro-, or bromo-containing or not containing group selected from C1~C6 alkyl, C2~C6 alkenyl, C2~C6 alkynyl, C3~C6 cycloalkyl, C5~C6 cycloalkenyl, and C3~C6 cycloalkyl-C1~C6 alkyl, aryl, aryl-C1~C6 alkyl, heteroaryl, heteroaryl-C1~C6 alkyl, each of the aryl, aryl-C1~C6 alkyl, heteroaryl, or heteroaryl-C1~C6 alkyl is unsubstituted or substituted with 1-3 groups independently selected from fluorine, chlorine, bromine, cyano, nitro, hydroxy, carboxyl, sulfhydryl, amino, and a fluoro-, chloro-, or bromo-containing or not containing group selected from C1~C6 alkyl, C3~C6 cycloalkyl, C5~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy, R—O—, R—O—$(CH_2)_p$—O—, R—O—$(CH_2)_p$—S—, R—S—, R—S—$(CH_2)_p$—O—, R—S—$(CH_2)_p$—S—, R—O—(C═O)—$(O)_m$—, R—S—(C═S)—$(S)_m$—, R—O—(C═O)—$(S)_m$—, R—O—(C═S)—$(O)_m$—, R—S—(C═O)—$(O)_m$—, R—O—(C═S)—$(S)_m$—, R—S—(C═O)—$(S)_m$—, R—S—(C═S)—$(O)_m$—, R—O—(C═O)—$(CH_2)_g$—, R—S—(C═S)—$(CH_2)_q$—, R—O—(C═S)—$(CH_2)_q$—, R—S—(C═O)—$(CH_2)_q$—, R—O—$(CH_2)_n$—(C═O)—, R—S—$(CH_2)_n$—(C═S)—, R—O—$(CH_2)_n$—(C═S)—, R—S—$(CH_2)_n$—(C═O)—, R—(C═O)—, R—(C═S)—, R—(C═O)—O—, R—(C═S)—S—, R—(C═O)—S—, R—(C═S)—O—, R—SO—, R—$SO_2$—, $R_1R_2N$—, $R_1R_2N$—O—, $R_1R_2N$—(C═O)—$(CH_2)_p$—, $R_1R_2N$—(C═O)—$(O)_m$—, $R_1R_2N$—(C═O)—$(S)_m$—, $R_1R_2N$—(C═O)—$(NR_3)_m$—, $R_1R_2N$—$SO_2$—$(CH_2)_p$—, $R_1R_2N$—$SO_2$—, $R_1R_2N$—$(CH_2)_p$—(C═O)—, $R_1R_2N$—$(CH_2)_p$—$SO_2$—, $R_1R_2N$—$(CH_2)_p$—O—, $R_1R_2N$—O—$(CH_2)_p$—, $R_1R_2PO_3$—, $R_1R_2R_3SiO$—, $R_1R_2R_3Si$—, $R_1R_2R_3Si$—CH═CH—, $R_1R_2C$═N—, $R_1R_2C$═N—O—, and $R_1R_2C$═N—NH—;

m is 0 or 1, n and q are each independently an integer from 0 to 4, p is an integer from 1 to 4; wherein, m, n, q, p in the above substituents are valued independently, and these values render the substituents different from each other;

R is hydrogen, a halogen-containing or not containing group selected from C1~C6 alkyl, C2~C6 alkenyl, C2~C6 alkynyl, C3~C6 cycloalkyl, C5~C6 cycloalkenyl, and C3~C6 cycloalkyl-C1~C6 alkyl, aryl, aryl-CI—C6 alkyl, heteroaryl, or heteroaryl-C1~C6 alkyl, each of the aryl, aryl-C1~C6 alkyl, heteroaryl, or heteroaryl-C1~C6 alkyl is unsubstituted or substituted with 1-3 groups independently selected from halogen, cyano, nitro, hydroxy, carboxyl, sulfhydryl, amino, and a halogen-containing or not containing group selected from C1~C6 alkyl, C3~C6 cycloalkyl, C5~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy;

$R_1$, $R_2$, $R_3$ are each independently is hydrogen, nitro, hydroxy, amino, a fluoro-, chloro-, or bromo-containing or not containing group selected from C1~C6 alkyl, C2~C6 alkenyl, C2~C6 alkynyl, C3~C6 cycloalkyl, C5~C6 cycloalkenyl, C3~C6 cycloalkyl-C1~C6 alkyl, C1~C6 alkoxy, C2~C6 alkenyloxy, C2~C6 alkynyloxy, C3~C6 cycloalkyloxy, C1~C6 alkoxy-C1~C6 alkyl, C1~C6 alkoxycarbonyl, C1~C6 alkylsulfanylcarbonyl, C1~C6 alkylsulfonyl, C1~C6 alkylsulfonyl-C1~C6 alkyl, C1~C6 alkylcarbonyl, C1~C6 alkylcarbonyl-C1~C6 alkyl, C1~C6 alkylcarbonyloxy, C1~C6 alkylamino, C1~C6 alkylaminocarbonyl, C1~C6 alkoxyaminocarbonyl, C1~C6 alkoxycarbonyl-C1~C6 alkyl, C1~C6 alkylaminocarbonyl-C1~C6 alkyl, triC1~C6 alkylsilyl, and diC1~C6 alkylphosphonyl,

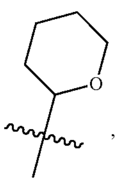 , 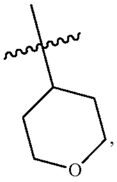 , 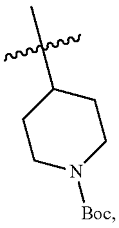

aryl, aryl-C1~C6 alkyl, aryloxy, aryl-C1~C6 alkyloxy, aryloxy-C1~C6 alkyl, arylcarbonyl, arylsulfonyl, heteroaryl, heteroaryl-C1~C6 alkyl, heteroaryloxy, heteroaryl-C1~C6 alkyloxy, heteroaryloxy-C1~C6 alkyl, heteroarylcarbonyl, or heteroarylsulfonyl, each of the

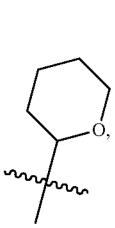 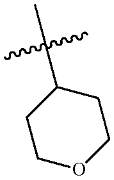 , 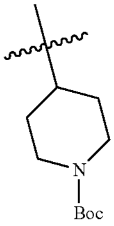 , aryl, aryl-C1~C6 alkyl, aryloxy, aryl-C1~C6 alkyloxy, aryloxy-C1~C6 alkyl, arylcarbonyl, arylsulfonyl, heteroaryl, heteroaryl-C1~C6 alkyl, heteroaryloxy, heteroaryl-C1~C6 alkyloxy, heteroaryloxy-C1~C6 alkyl, heteroarylcarbonyl, or heteroarylsulfonyl is unsubstituted or substituted with 1-3 groups independently selected from fluorine, chlorine, bromine, cyano, nitro, hydroxy, carboxyl, sulfhydryl, amino, and a fluoro-, chloro-, or bromo-containing or not containing group selected from C1~C6 alkyl, C3~C6 cycloalkyl, C5~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy; or $R_1R_2N$— is

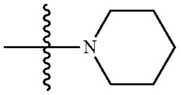 , 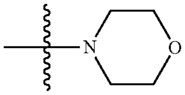 or

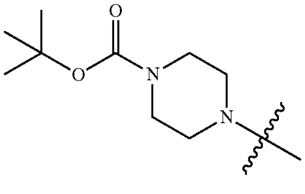 ;

the aryl is selected from

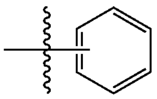 , 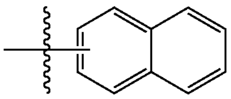 ,

-continued
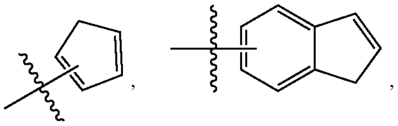
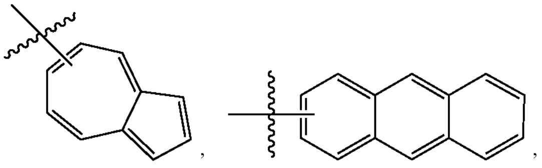
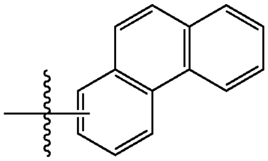
, and
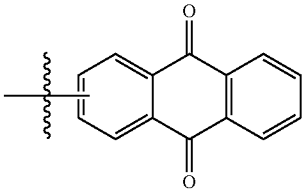
;
the heteroaryl is selected from
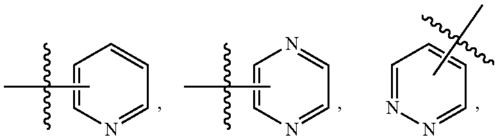
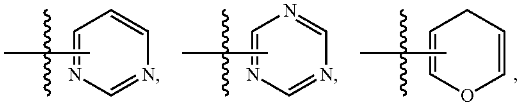
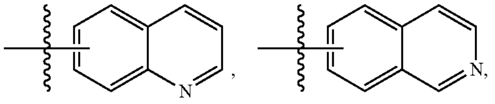
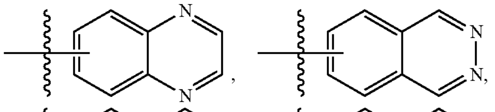
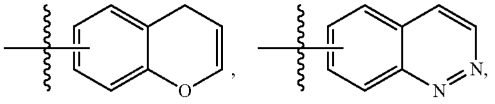
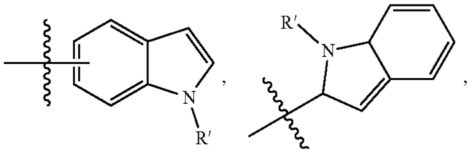
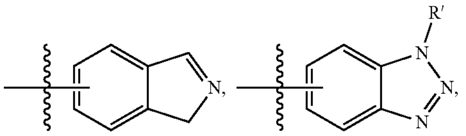
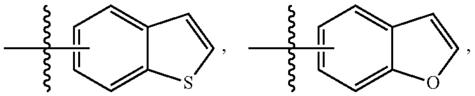
-continued
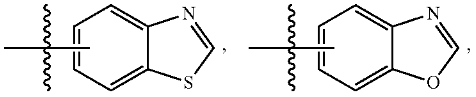
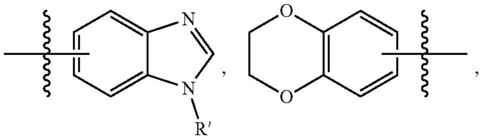
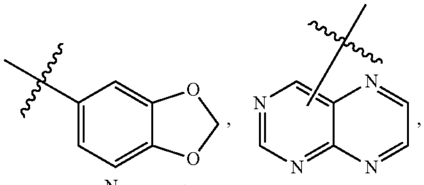
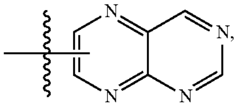
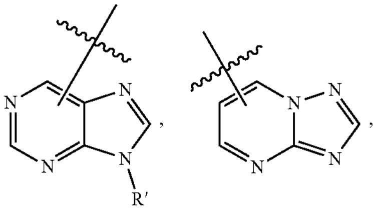
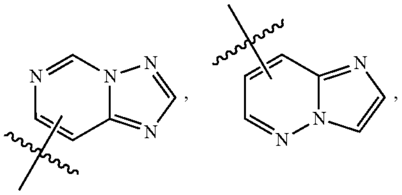
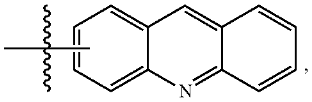
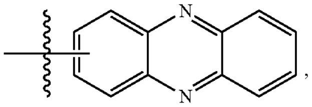
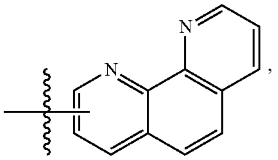
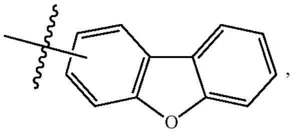
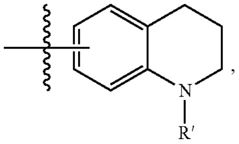
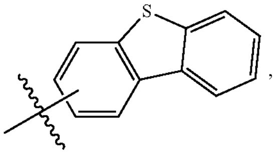

-continued

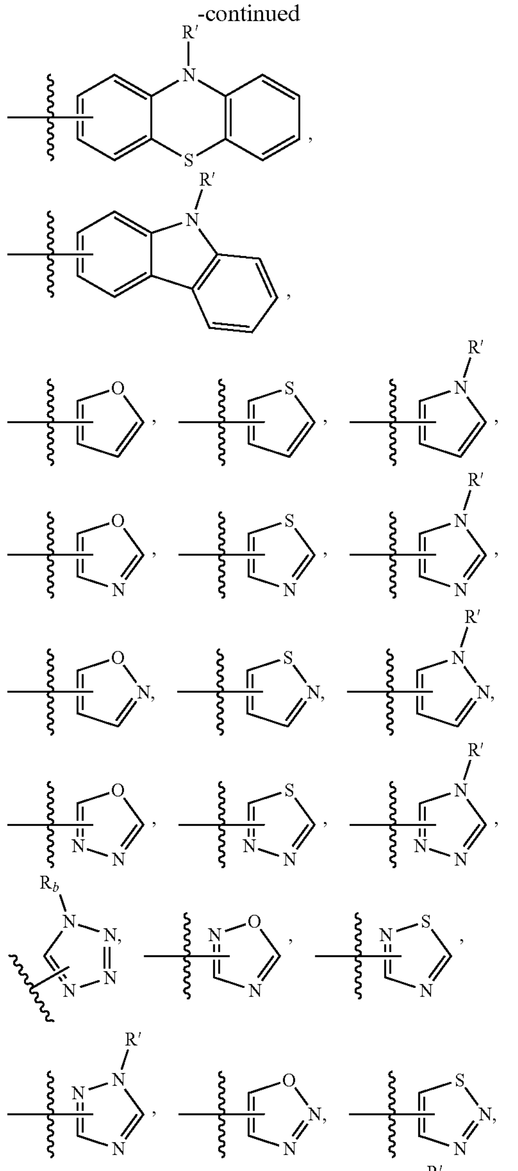

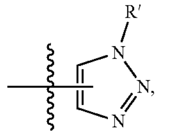

and

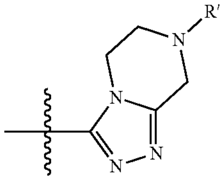

;

R' is hydrogen, nitro, hydroxy, amino, a fluoro-, chloro-, or bromo-containing or not containing group selected from C1~C6 alkyl, C2~C6 alkenyl, C2~C6 alkynyl, C3~C6 cycloalkyl, C5~C6 cycloalkenyl, C3~C6 cycloalkyl-C1~C6 alkyl, C1~C6 alkoxy, C2~C6 alkenyloxy, C2~C6 alkynyloxy, C3~C6 cycloalkyloxy, C1~C6 alkoxy-C1~C6 alkyl, C1~C6 alkoxycarbonyl, C1~C6 alkylsulfanylcarbonyl, C1~C6 alkylsulfonyl, C1~C6 alkylsulfonyl-C1~C6 alkyl, C1~C6 alkylcarbonyl, C1~C6 alkylcarbonyl-C1~C6 alkyl, C1~C6 alkylcarbonyloxy, C1~C6 alkylamino, C1~C6 alkylaminocarbonyl, C1~C6 alkoxyaminocarbonyl, C1~C6 alkoxycarbonyl-C1~C6 alkyl, C1~C6 alkylaminocarbonyl-C1~C6 alkyl, triC1~C6 alkylsilyl, and diC1~C6 alkylphosphonyl,

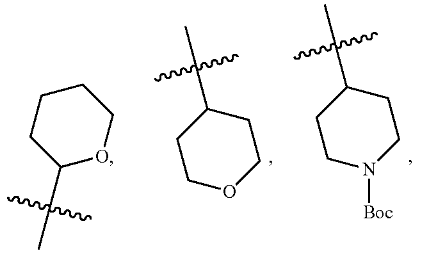 [SMILES: *C1CCCCO1 ; *C1CCOCC1 ; *C1CCN(C(=O)OC(C)(C)C)CC1]

aryl, aryl-C1~C6 alkyl, aryloxy, aryl-C1~C6 alkyloxy, aryloxy-C1~C6 alkyl, arylcarbonyl, arylsulfonyl, heteroaryl, heteroaryl-C1~C6 alkyl, heteroaryloxy, heteroaryl-C1~C6 alkyloxy, heteroaryloxy-C1~C6 alkyl, heteroarylcarbonyl, or heteroarylsulfonyl, each of the

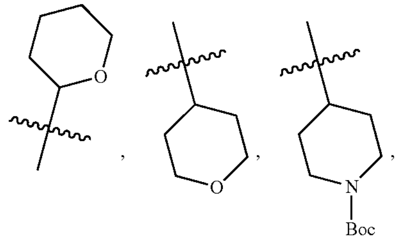

aryl, aryl-C1~C6 alkyl, aryloxy, aryl-C1~C6 alkyloxy, aryloxy-C1~C6 alkyl, arylcarbonyl, arylsulfonyl, heteroaryl, heteroaryl-C1~C6 alkyl, heteroaryloxy, heteroaryl-C1~C6 alkyloxy, heteroaryloxy-C1~C6 alkyl, heteroarylcarbonyl, or heteroarylsulfonyl is unsubstituted or substituted with 1~3 groups independently selected from fluorine, chlorine, bromine, cyano, nitro, hydroxy, carboxyl, sulfhydryl, amino, and a fluoro-, chloro-, bromo-containing or not containing group selected from C1~C6 alkyl, C3~C6 cycloalkyl, C5~C6 cycloalkenyl, C3~C6 cycloalkyl-C1~C6 alkyl, C2~C6 alkenyl, C2~C6 alkynyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy;

wherein,

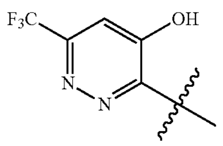 [SMILES: *c1nnc(C(F)(F)F)cc1O]

may bond to any site (e.g. C atom) of the above mentioned aryl or heteroaryl, and when R' is H, it may bond to N atom.

In a preferred embodiment, X is $CH_2F$, $CHF_2$, $CF_3$, or $CF_2CF_3$;

A is

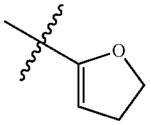, 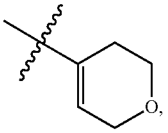

or a unsubstituted or substituted group, wherein the group is selected from methyl, ethyl, vinyl, propenyl,

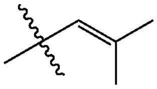, 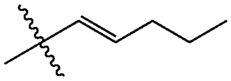,

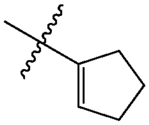, 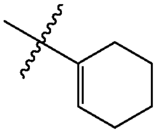,

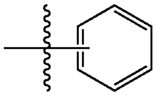, 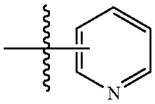, and

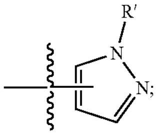

wherein, the substituted methyl, ethyl, vinyl, propenyl,

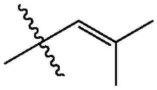, 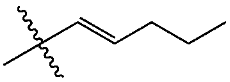,

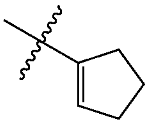, or 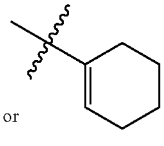

refers to being substituted with one or more substituents independently selected from the group consisting of fluorine, chlorine, bromine, cyano, R—O—, R—O—(C═O)—, R—(C═O)—, R—(C═O)—O—, R—$SO_2$—, $R_1R_2N$—, $R_1R_2N$—(C═O)—, $R_1R_2N$—$SO_2$—, $R_1R_2PO_3$—, $R_1R_2R_3SiO$—, $R_1R_2R_3Si$—(CH═CH)—, $R_1R_2R_3Si$—, $R_1R_2C$═N—(O)—, $R_1R_2C$═N—, and $R_1R_2C$═N—NH—;

R is the substituted

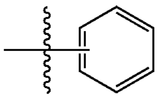, 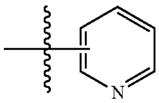, or

-continued

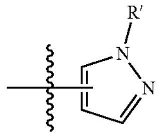

refers to being substituted with one or more substituents selected from the group consisting of fluorine, chlorine, bromine, cyano, nitro, azido, a fluoro-, chloro-, or bromo-containing or not containing group selected from C1~C6alkyl, and C3~C6 cycloalkyl, phenyl, benzyl, the phenyl or benzyl is unsubstituted or substituted from 1-3 substituents selected from fluorine, chlorine, bromine, cyano, nitro, amino, and a fluoro-, chloro-, or bromo-containing or not containing group selected from C1~C6 alkyl, C3~C6 cycloalkyl, C1~C6 alkoxyl, C1~C6 alkylcarbonyl, C1~C6 alkoxycarbonyl, C1~C6 alkylsulfonyl, C1~C6 alkylamino, and C1~C6 alkylcarbonyloxy, R—O—, R—O—(C═O)—, R—(C═O)—, R—(C═O)—O—, R—$SO_2$—, $R_1R_2N$—, $R_1R_2N$—(C═O)—, $R_1R_2N$—$SO_2$—, $R_1R_2PO_3$—, $R_1R_2R_3SiO$—, $R_1R_2R_3Si$—, $R_1R_2R_3Si$—CH═CH—, $R_1R_2C$═N—, $R_1R_2C$═N—O—, and $R_1R_2C$═N—NH—;

m is 0 or 1, n and q are independently 0, 1, or 2, p is 1 or 2;

R is hydrogen, a fluoro-, chloro-, or bromo-containing or not containing group selected from C1~C6 alkyl, and C3~C6 cycloalkyl, phenyl, or benzyl, each of the phenyl or benzyl is unsubstituted or substituted with 1~3 groups independently selected from fluorine, chlorine, bromine, cyano, nitro, amino, and a fluoro-, chloro-, or bromo-containing or not containing group selected from C1~C6 alkyl, C3~C6 cycloalkyl, C1~C6 alkoxy, C1~C6 alkylcarbonyl, C1~C6 alkoxycarbonyl, C1~C6 alkylsulfonyl, C1~C6 alkylamino, and C1~C6 alkylcarbonyloxy;

$R_1$, $R_2$, $R_3$ are each independently is hydrogen, a fluoro-, chloro-, or bromo-containing or not containing group selected from C1~C6 alkyl, C3~C6 cycloalkyl, C1~C6 alkoxy, C1~C6 alkoxy-C1~C6 alkyl, C1~C6 alkoxycarbonyl, C1~C6 alkylsulfonyl, C1~C6 alkylsulfonyl-C1~C6 alkyl, C1~C6 alkylcarbonyl, C1~C6 alkylcarbonyl-C1~C6 alkyl, C1~C6 alkylcarbonyloxy, C1~C6 alkylamino, C1~C6 alkylaminocarbonyl, C1~C6 alkoxylaminocarbonyl, C1~C6 alkoxylcarbonyl-C1~C6 alkyl, and C1~C6 alkylaminocarbonyl-C1~C6 alkyl, phenyl, benzyl,

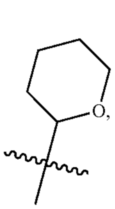, 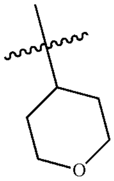, or 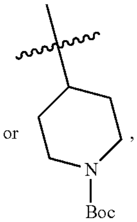, the phenyl, benzyl,

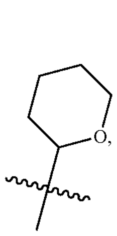

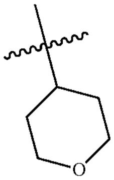

, or

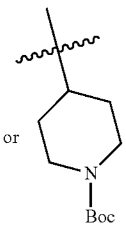

is unsubstituted or substituted with 1-3 groups independently selected from fluorine, chlorine, bromine, cyano, nitro, amino, and a fluoro-, chloro-, or bromo-containing or not containing group selected from C1~C6 alkyl, C3~C6 cycloalkyl, C1~C6 alkoxy, C1~C6 alkylcarbonyl, C1~C6 alkoxylcarbonyl, C1~C6 alkylsulfonyl, C1~C6 alkylamino, and C1~C6 alkylcarbonyloxy; or $R_1R_2N$— is

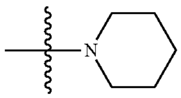

,

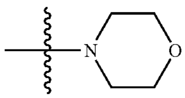

or

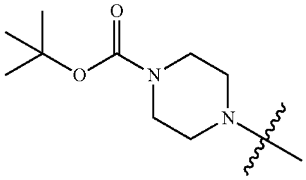

;

R' is hydrogen or C1-6alkyl.

In addition, when X represents —$CH_2Cl$ in Formula I, A is not —$CH_2Cl$.

In the present invention, the derivative

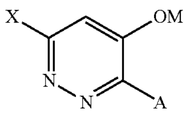

I-1 is an agriculturally acceptable salt or a compound derivatized from the 4-hydroxy of the pyridazine ring of Formula I, including derivatives such as an ester, a hydrazine, a hydroxylamine and an ether thereof.

The agriculturally acceptable salt is a salt commonly used in agricultural chemicals, for example, the pyridazaine compound or the derivative may be processed into an alkali metal salt, an alkaline earth metal salt or an amine salt, or, when a basic moiety is present in the molecule, it can be processed into, for example, a sulfate, a hydrochloride, a nitrate, a phosphate, etc. When these salts are used as herbicides in agriculture or horticulture, they are also included in the present invention. In the present invention, the "alkali metal salt" may be, for example, a sodium salt, a potassium salt or a lithium salt, preferably a sodium salt or a potassium salt. In the present invention, the "alkaline earth metal salt" may be, for example, a calcium salt or a magnesium salt, preferably a calcium salt. In the present invention, the "amine salt" may be, for example, a secondary alkylamine salt, a tertiary alkylamine salt or a quaternary alkylammonium salt; a primary alkanolamine salt, a secondary alkanolamine salt, a tertiary alkanolamine salt or a quaternary alkanoammonium salt; a primary alkylalkanolamine salt, a secondary alkylalkanolamine salt, a tertiary alkylalkanolamine salt or a quaternary alkylalkanolammonium salt; or a primary alkoxyalkanolamine salt, a secondary alkoxyalkanolamine salt, a tertiary alkoxyalkanolamine salt or a quaternary alkoxyalkanolammonium salt, preferably, wherein the alkyl, alkanol and alkoxy are independently saturated and independently contain 1-4 carbon atoms, more preferably, ethanolamine salt, dimethylethanolamine salt, triethanolamine salt, dimethylamine salt, triethylamine salt, isopropylamine salt, choline salt or diglycolamine salt.

Solvates of the compounds of the invention are also included in the invention.

The compound of the present invention may also have a chiral carbon atom. In this case, the present invention also includes an optical isomer and a mixture of optical isomers in any ratio.

The ester derivative refers to a compound having an ester moiety formed by derivatization of the 4-hydroxy of the pyridazine ring, that is, the M group in Formula I-1 may be acyl, thioacyl, sulfoxide, sulfonyl, phosphoryl, thiophosphoryl, etc., and other groups are as defined above in Formula I.

For example, the M group in Formula I-1 may be (thio)formyl, C1~C18 alkyl(thio)carbonyl, wherein the (thio)formyl, or C1~C18 alkyl(thio)carbonyl is optionally substituted by a substituent [the substituent is one or more same or different substituents selected from halogen, amino, C3~C8 cycloalkyl, C1~C8 alkoxy, C1~C8 alkylsulfanyl, C1~C8 alkoxycarbonyl, C1~C8 alkylcarbonyloxy, C1~C8 alkylcarbonyl, and C2~C8 alkenyloxycarbonyl optionally substituted by a substituent {the substituent is 1-3 same or different substituents selected from C3~C8 cycloalkyl, cyano, and benzoyl optionally substituted by a substituent (the substituent is 1-3 same or different substituents selected from halogen, C1~C8 alkyl, C1~C8 halogenated alkyl, C1~C8 alkoxycarbonyl, nitro and C1~C8 alkylsulfonyl)}, hydroxy(methyl)phosphinyl, C3~C8 cycloalkenyloxycarbonyl optionally substituted by a substituent {the substituent is 1-2 same or different substituents selected from oxo and benzoyl optionally substituted by a substituent (the substituent is 1-3 same or different substituents selected from halogen atom, C1~C8 alkyl, C1~C8 halogenated alkyl, C1~C8 alkoxycarbonyl, nitro and C1~C8 alkylsulfonyl)), 5- or 6-membered heterocyclyloxycarbonyl optionally substituted by a substituent {the ring of the heterocyclyl contains one nitrogen atom, oxygen atom or sulfur atom, and may further contain one or two nitrogen atoms, the substituent is 1-3 same or different substituents selected from halogen, a C1~C8 alkyl, phenoxy optionally substituted by a substituent (the substituent is 1-3 same or different substituents selected from halogen, C1~C8 alkyl, C1~C8 halogenated alkyl, C3~C8 cycloalkyl and C1~C8 alkoxycarbonyl), 2,3-dihydro-1H-indenyloxy, and benzoyl optionally substituted by a substituent (the substituent is 1-3 same or different substituents selected from halogen, C1~C8 alkyl, C1~C8 halogenated alkyl, C1~C8 alkoxycarbonyl, nitro and C1~C8 alkylsulfonyl)}, phenyl, phenoxy, benzyloxy, phenylsulfanyl, benzylsulfanyl, wherein the phenyl, phenoxy, benzyloxy, phenylsulfanyl, or benzylsulfanyl is optionally substituted by a substituent (the substituent is 1~3 same or different substituents selected from halogen, C1~C8 alkyl, C1~C8 alkoxy, C1~C8 halogenated alkyl, and C1~C8 alkoxycarbonyl), and C1~C8 alkylsulfanyl], C3~C8cycloalkyl(thio)carbonyl, adamantyl(thio)carbonyl, C2~C8 alkenyl(thio)carbonyl optionally substituted by a substituent {the substituent is one or more same or different substituents selected from halogen, C1~C8 alkoxy, phenyl, phenylsulfanyl, and phenoxy optionally substituted by a substituent (the substituent is 1-3 same or different substituents selected from halogen, C1~C8 alkyl, C1~C8 alkoxy, C1~C8 halogenated alkyl, and C1~C8 alkoxycarbonyl)}, C2~C8 alkynyl(thio)carbonyl, (thio)benzoyl, (thio)naphthoyl, wherein the (thio)benzoyl or (thio)naphthoyl is optionally substituted by a substitutent [the substituent is 1-3 same or different substituents selected from halogen atom, C1~C8 alkyl optionally substituted by a substituent (the substituent is one or more same or different substituents selected from halogen and phenyl), cyano, hydroxy, C1~C8 alkylcarbonyl, C1~C8 alkoxycarbonyl, C1~C8 alkylcarbonyloxy, C1~C8 alkylcarbonylamino, amino optionally substituted by a substituent (the substituent is 1-3 same or different substituents selected from C1~C8 alkyl, C1~C8 alkoxy, C1~C8 alkylcarbonyl, halogenated C1~C8 alkyl and phenyl), C2~C8 alkenyloxycarbonyl optionally substituted by a substituent {the substituent is 1-3 same or different substituents selected from C3~C8 cycloalkyl, cyano, and benzoyl optionally substituted by a substituent (the substituent is 1-3 same or different substituents selected from halogen, C1~C8 alkyl, C1~C8 halogenated alkyl, C1~C8 alkoxycarbonyl, nitro, and C1~C8 alkylsulfonyl)}, C3~C8 cycloalkenyloxycarbonyl optionally substituted by a substituent (the substituent is 1-2 same or different substituents selected from oxo, and benzoyl optionally substituted by a substituent (the substituent is 1-3 same or different substituents selected from halogen, C1~C8 alkyl, halogenated C1~C8 alkyl, C1~C8 alkoxycarbonyl, nitro, and C1~C8 alkylsulfonyl)}, phenyl, nitro, C1~C8 alkoxy optionally substituted by a substituent (the substituent is 1-3 same or different substituents selected from halogen and phenyl), phenoxy, 5- or 6-membered heterocyclyloxycarbonyl optionally substituted by a substituent {the ring of the heterocyclyl contains 1 nitrogen atom, oxygen atom or sulfur atom, and may further contain 1 to 2 nitrogen atoms, the substituent is 1-3 same or different substituents selected from halogen atom, C1~C8 alkyl, phenoxy optionally substituted by a substituent (the substituent is 1-3 same or different substituents selected from halogen, C1~C8 alkyl, halogenated C1~C8 alkyl, C3~C8 cycloalkyl, and C1~C8 alkoxycarbonyl), 2,3-dihydro-1H-indenyloxy, and benzoyl optionally substituted by a substituent (the substituent is 1-3 same or different substituents selected from halogen, C1~C8 alkyl, halogenated C1~C8 alkyl, C1~C8 alkoxycarbonyl, nitro, and C1~C8 alkylsulfonyl)}, and 5- or 6-membered heterocyclyloxysulfonyl optionally substituted by a substituent {the ring of the heterocyclyl contains 1 nitrogen atom, oxygen atom or sulfur atom, and may further contain 1 to 2 nitrogen atoms, the substituent is 1-3 same or different substituents selected from halogen, C1~C8 alkyl, phenoxy optionally substituted by a substituent (the substituent is 1-3 same or different substituents selected from halogen, C1~C8 alkyl, halogenated C1~C8 alkyl, C3~C8cycloalkyl, and C1~C8 alkoxycarbonyl), 2,3-dihydro-1H-indenyloxy, and benzoyl optionally substituted by a substituent (the substituent is 1-3 same or different substituents selected from halogen, C1~C8 alkyl, C1~C8 halogenated alkyl, C1~C8 alkoxycarbonyl, nitro, and C1~C8 alkylsulfonyl)}], halogen-substituted sulfhydryl formyl, 3- to 8-membered heterocyclyl(thio)carbonyl optionally substituted by a substituent {the ring of the heterocyclyl contains 1 nitrogen atom, oxygen atom or sulfur atom, and may further contain 1 to 2 nitrogen atoms, or may form a 5- to 6-membered spiro ring having 1 to 2 oxygen atoms in the heterocyclyl, the substituent is 1-3 same or different substituents selected from halogen, C1~~C8 alkyl optionally substituted by a substituent (the substituent is one or more same or different substituents selected from halogen and phenyl), C1~C8 alkylcarbonyl, C1~C8 alkoxycarbonyl, phenyl optionally substituted by a substituent (the substituent is 1-3 same or different halogen), nitro, hydroxy, C1~C8 alkoxy, phenoxy, C1~C8 alkylsulfanyl, C2~C8 alkenylsulfanyl, and phenylsulfanyl}, fused 5- to 14-membered bicyclic or tricyclic heterocyclyl(thio)carbonyl optionally substituted by a substituent (the ring of the heterocyclyl contains 1 nitrogen atom, oxygen atom or sulfur atom, and may further contain 1 to 2 nitrogen atoms or oxygen atoms; the substituent is 1-3 same or different substituents selected from halogen atom and C1~C8 alkyl), 5- or 6-membered heterocyclyl(thio)carbonyl(thio)carbonyl (the ring of the heterocyclyl contains one nitrogen atom, oxygen atom or sulfur atom, and may further contain one or two nitrogen atoms), C1~C18 alkoxy(thio)carbonyl, C1~~C18 alkylthio(thio)carbonyl, wherein the C1~C18 alkoxy(thio)carbonyl or C1~C18 alkylthio(thio)carbonyl is optionally substituted by a substituent (the substituent is one or more same or different substituents selected from halogen atom, C1~~C8 alkoxy and phenyl), C2~C8 alkenyloxy(thio)carbonyl, C2~C8 alkenylsulfanyl(thio)carbonyl, C2~C8 chain alkynyloxy(thio)carbonyl, C2~C8 chain alkynylsulfanyl(thio)carbonyl, C3~C8 cycloalkyloxy(thio)carbonyl, C3~C8 cycloalkylsulfanyl(thio)carbonyl, phenoxy(thio)carbonyl, phenylsulfanyl(thio)carbonyl, phenyl C1~C8 alkyloxy(thio)carbonyl, phenyl C1~C8 alkylthio(thio)carbonyl, wherein the phenoxy(thio)carbonyl, phenylsulfanyl(thio)carbonyl, phenyl C1~C8 alkyloxy(thio)carbonyl or phenyl C1~C8 alkylthio(thio)carbonyl is optionally substituted by a substituent (the substituent is 1-3 same or different substituents selected from halogen, C1-C8 alkyl, cyano, C1~C8 alkylcarbonyl, C1~C8 alkoxycarbonyl, nitro, and C1~C8 alkoxy), fused polycyclicoxy(thio)carbonyl, fused polycyclicsulfanyl(thio)carbonyl, a group selected from 5- or 6-membered heterocyclyloxy(thio)carbonyl and 5- or 6-membered heterocyclylsulfanyl(thio)carbonyl, which is optionally substituted by a substituent {the ring of the heterocyclyl contains 1 nitrogen atom, oxygen atom or sulfur atom, and may further contain 1 to 2 nitrogen atoms, the substituent is 1-3 same or different substituents selected from halogen atom, C1~C8 alkyl, phenoxy optionally substituted by a substituent (the substituent is 1-3 same or different substituents selected from halogen, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituted by a substituent (the substituent is 1-3 same or different substituents selected from halogen, C1~C8 alkyl, C1~C8 halogenated alkyl, C1~C8 alkoxycarbonyl, nitro, and C1~C8 alkylsulfonyl)}, amino(thio)formyl optionally substituted by a substituent {the substituent is 1-3 same or different substituents selected from C1~C8 alkyl optionally substituted by a substituent (the substituent is one or more same or different substituents selected from halogen, C1~C8 alkoxycarbonyl, cyano, phenyl, and C1~C8 alkoxy), C2~C8 alkenyl, phenyl, C1~C8 alkylcarbonyl, C1~C8 alkoxycarbonyl, and C1~C8 alkoxy},

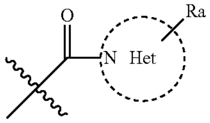

(Het is a 5- to 6-membered heterocyclyl, the heterocyclyl contains, besides C atoms and the 1-N, 0 to 3 atoms or radicals follows to form the ring: O, $NR_b$, C═O, $R_a$ and $R_b$ independently are hydrogen or C1~C8 alkyl), C1~C8 alkylsulfoxide, C1~C8 alkylsulfonyl, C2~C8 alkenylsulfonyl, C3~C8 cycloalkylsulfonyl, wherein the C1~C8 alkylsulfoxide, C1~C8 alkylsulfonyl, C2~C8 alkenylsulfonyl, or C3~C8 cycloalkylsulfonyl is optionally substituted by a substituent (the substituent is one or more same or different substituents selected from halogen and C1~C8 alkylsulfonyl), phenylsulfonyl, benzylsulfonyl, naphthylsulfonyl, wherein the phenylsulfonyl, benzylsulfonyl, or naphthylsulfonyl is optionally substituted by a substituent [the substituent is 1~3 same or different substituents selected from halogen, C1~C8 alkyl, halogenated C1~C8 alkyl, cyano, C1~C8 alkylcarbonyl, C1~C8 alkoxycarbonyl, nitro, C1~C8 alkoxy, halogenated C1~C8 alkoxy, C1~C8 alkylsulfonyl, aminoformyl optionally substituted by a substituent (the substituent is C1~C8 alkyl), phenoxy optionally substituted by a substituent (the substituent is 1~3 same or different substituents selected from halogen, C1~C8 alkyl, C1~C8 halogenated alkyl, C3~C8 cycloalkyl, and C1~C8 alkoxycarbonyl), C2~C8 alkenyloxysulfonyl optionally substituted by a substituent {the substituent is 1~3 same or different substituents selected from C3~C8 cycloalkyl, cyano, and benzoyl optionally substituted by a substituent (the substituent is 1~3 same or different substituents selected from halogen, C1~C8 alkyl, C1~C8 halogenated alkyl, C1~C8 alkoxycarbonyl, nitro, and C1~C8 alkylsulfonyl)}, C3~C8 cycloalkenyloxysulfonyl optionally substituted by a substituent {the substituent is 1-2 same or different substituents selected from oxo, and benzoyl optionally substituted by a substituent (the substituent is 1~3 same or different substituents selected from halogen, C1~C8 alkyl, C1~C8 halogenated alkyl, C1~C8 alkoxycarbonyl, nitro, and C1~C8 alkylsulfonyl)}, and 5- or 6-membered heterocyclyloxysulfonyl optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen atom, C1~C8 alkyl, phenoxy optionally substituted by a substituent (the substituent is 1~3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituted by a substituent (the substituent is 1~3 same or different substituents selected from halogen atom, C1~C8 alkyl, C1~C8 halogenated alkyl, C1~C8 alkoxycarbonyl, nitro, and C1~C8 alkylsulfonyl)}], 5- to 10-membered heteroarylsulfonyl, 5- to 10-membered heterocyclyloxysulfonyl, wherein the 5- to 10-membered heteroarylsulfonyl or 5- to 10-membered heterocyclyloxysulfonyl is optionally substituted by a substituent {the ring of the heterocyclyl contains 1 nitrogen atom, oxygen atom or sulfur atom, and may further contain 1 to 2 nitrogen atoms, the substituent is 1~3 same or different substituents selected from halogen atom, C1~C8 alkyl, phenoxy optionally substituted by a substituent (the substituent is 1~3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituted by a substituent (the substituent is 1~3 same or different substituents selected from halogen atom, C1~C8 alkyl, C1~C8 halogenated alkyl, C1~C8 alkoxycarbonyl, nitro, and C1~C8 alkylsulfonyl)}, C1~C8 alkoxysulfonyl, C1~C8 alkylaminosulfonyl optionally substituted by a substituent (the substituent is one or more same or different substituents selected from halogen atom),

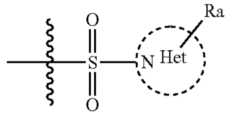

(Het is a 5- to 6-membered heterocyclyl, and contains, besides C atoms and the 1-N, 0 to 3 atoms or radicals as follows to form the ring: O, $NR_b$, and C═O, $R_a$ and $R_b$ independently are hydrogen or C1~C8 alkyl), di(C1~C8 alkyl)phosphoryl, or di(C1~C8 alkyl)thiophosphoryl.

In a preferred embodiment, the M group may be C1~C10 alkyl(thio)carbonyl optionally substituted by a substituent {the substituent is one or more same or different substituents selected from fluorine, chlorine, bromine, C3~C6 cycloalkyl, C1~C6 alkoxy, C1~C6 alkylsulfanyl, C1~C6 alkoxycarbonyl, C1~C6 alkylcarbonyl, C1~C6 alkylcarbonyloxy, phenyl, phenylsulfanyl, phenoxy, and benzyloxy, wherein the phenyl, phenylsulfanyl, phenoxy or benzyloxy is optionally substituted by a substituent (the substituent is 1~3 same or different substituents selected from fluorine, chlorine, bromine, C1~C6 alkyl, and C1~C6 alkoxy)}, C3~C6 cycloalkyl(thio)carbonyl, C2~C6 alkenyl(thio)carbonyl optionally substituted by a substituent {the substituent is one or more same or different substituents selected from fluorine, chlorine, bromine, C1~C6 alkoxy, phenyl, phenylthio, and phenoxy, wherein the phenyl, phenylthio or phenoxy is optionally substituted by a substituent (the substituent is 1~3 same or different substituents selected from fluoride, chlorine, bromine, C1~C6 alkyl, and C1~C6 alkoxy)}, (thio) benzoyl, (thio)naphthoyl, wherein the (thio)benzoyl or (thio) naphthoyl is optionally substituted by a substituent {the substituent is 1~3 same or different substituents selected from fluorine, chlorine, bromine, C1~C6 alkyl, C1~C6 alkoxy, wherein the C1~C6 alkyl or C1~C6 alkoxy is optionally substituted by a substituent (the substituent is 1~3 same or different substituents selected from fluorine, chlorine, bromine, and phenyl), cyano, hydroxy, C1~C6 alkylcarbonyl, C1~C6 alkoxycarbonyl, C1~C6 alkylcarbonyloxy, C1~C6 alkylcarbonylamino, amino optionally substituted by a substituent (the substituent is 1~3 same or different substituents selected from C1~C6 alkyl, C1~C6 alkoxy, C1~C6 alkylcarbonyl, halogenated C1~C6 alkyl, and phenyl), phenyl, nitro, and phenoxy}, 3- to 8-membered heterocyclyl(thio)carbonyl optionally substituted by a substituent the heterocyclyl is

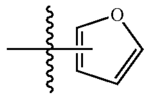, 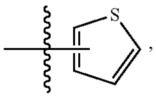, 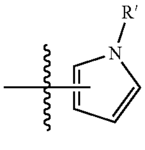,

-continued

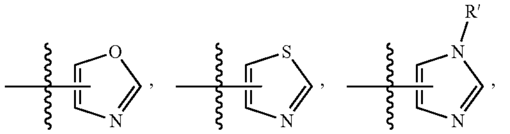

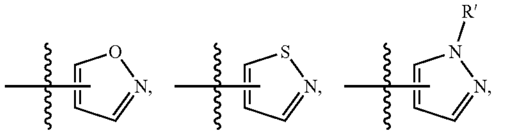

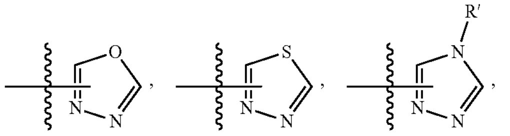

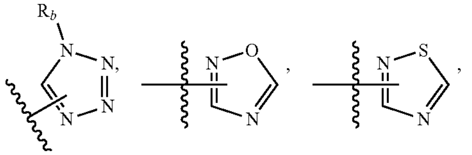

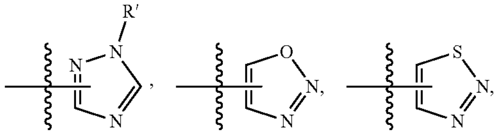

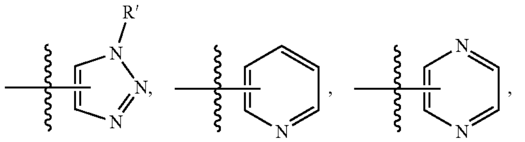

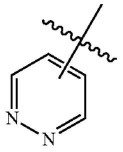

or

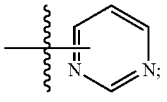

the substituent is 1~3 same or different substituents selected from fluorine, chlorine, bromine, C1~C6 alkyl optionally substituted by a substituent (the substituent is one or more same or different substituents selected from fluorine, chlorine, bromine, and phenyl), C1~C6 alkylcarbonyl, C1~C6 alkoxycarbonyl, phenyl optionally substituted by a substituent (the substituent is 1~3 same or different substituents selected from fluorine, chlorine, and bromine), nitro, hydroxy, C1~C6 alkoxy, phenoxy, C1~C6 alkylsulfanyl, C2~C6 alkenylsulfanyl, and phenylsulfanyl}, fused 5- to 14-membered bicyclic or tricyclic heterocyclyl(thio)carbonyl optionally substituted by a substituent (the heterocyclyl is

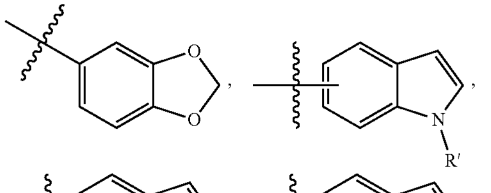

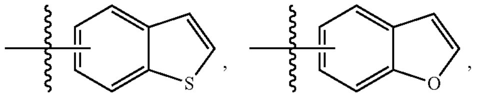

-continued

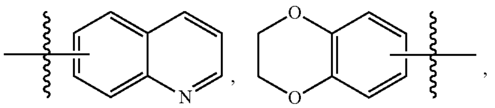

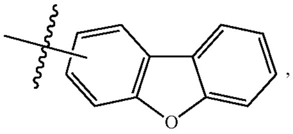

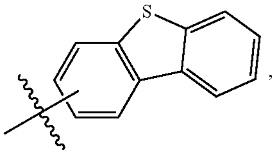

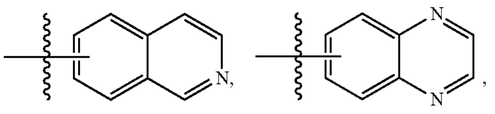

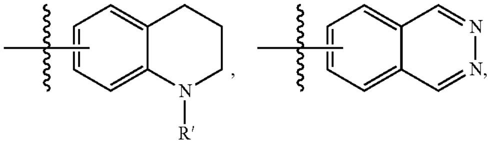

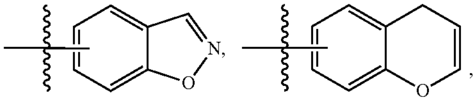

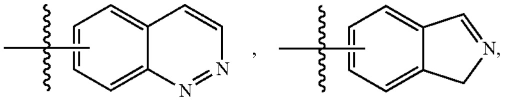

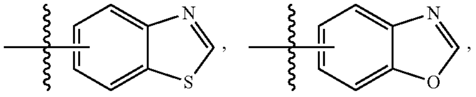

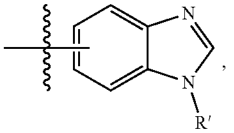

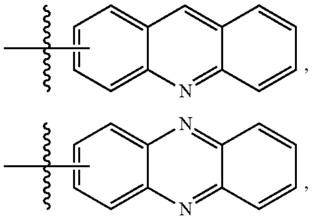

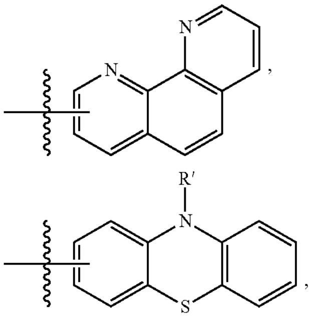

or

-continued

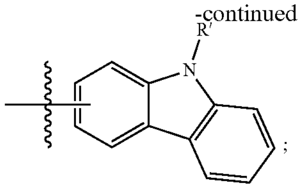
;

the substituent is 1-3 same or different substituents selected from fluorine, chlorine, bromine, and C1~C6 alkyl), C1~C10 alkoxy(thio)carbonyl, C1~C10 alkylsulfanyl(thio) carbonyl, wherein the C1~C10 alkoxy(thio)carbonyl or C1~C10 alkylsulfanyl(thio)carbonyl is optionally substituted by a substituent (the substituent is one or more same or different substituents selected from fluorine, chlorine, bromine, C1~C6 alkoxy, and phenyl), C3~C6 cycloalkyloxy (thio)carbonyl, C3~C6 cycloalkylsulfanyl(thio)carbonyl, phenoxy(thio)carbonyl, phenylsulfanyl(thio)carbonyl, phenyl-C1~C6 alkyloxy(thio)carbonyl, phenyl-C1~C6 alkylthio(thio)carbonyl, wherein the phenoxy(thio)carbonyl, phenylsulfanyl(thio)carbonyl, phenyl-C1~C6 alkyloxy(thio) carbonyl or phenyl-C1~C6 alkylthio(thio)carbonyl is optionally substituted by a substituent (the substituent is 1-3 same or different substituents selected from fluorine, chlorine, bromine, C1~C6 alkyl, cyano, C1~C6 alkylcarbonyl, C1~C6 alkoxycarbonyl, nitro, and C1~C6 alkoxy), amino (thio)formyl optionally substituted by a substituent {the substituent is 1-3 same or different substituents selected from C1~C6 alkyl optionally substituted by a substituent (the substituent is one or more same or different substituents selected from fluorine, chlorine, and bromine), C2~C6 alkenyl, phenyl, C1~C6 alkylcarbonyl, C1~C6 alkoxycarbonyl, and C1~C6 alkoxy)},

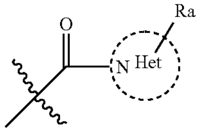

(Het is

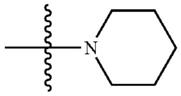
,
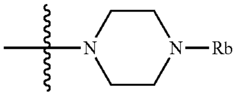
,
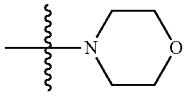
or
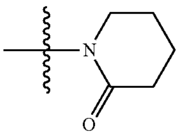
, $R_a$ and $R_b$ independently are hydrogen or C1~C6 alkyl), C1~C6 alkylsulfoxide, C1~C6 alkylsulfonyl, C2~C6 alkenylsulfonyl, C3~C6 cycloalkylsulfonyl, wherein the C1~C6 alkylsulfoxide, C1~C6 alkylsulfonyl, C2~C6 alkenylsulfonyl or C3~C6 cycloalkylsulfonyl is optionally substituted by a substituent (the substituent is one or more same or different substituents selected from fluorine, chlorine, bromine, and C1~C6 alkylsulfonyl), phenylsulfonyl, benzylsulfonyl, naphthylsulfonyl, wherein the phenylsulfonyl, benzylsulfonyl or naphthylsulfonyl is optionally substituted by a substituent {the substituent is 1-3 same or different substituents selected from fluorine, chlorine, bromine, C1~C6 alkyl, halogenated C1~C6 alkyl, cyano, C1~C6 alkanocarbonyl, C1~C6 alkoxycarbonyl, nitro, C1~C6 alkoxy, halogenated C1~C6 alkoxy, C1~C6 alkylsulfonyl, aminoformyl optionally substituted by a substituent (the substituent is C1~C6 alkyl), and phenoxy optionally substituted by a substituent (the substituent is 1-3 same or different substituents selected from fluorine, chlorine, bromine, C1~C6 alkyl, C1~C8 halogenated alkyl, C3~C6 cycloalkyl, and C1~C6 alkoxycarbonyl)}, 5- to 10-membered heteroarylsulfonyl optionally substituted by a substituent {the heterocyclyl is

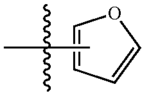
,
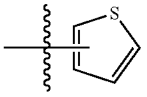
,
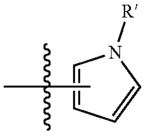
,
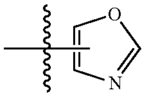
,
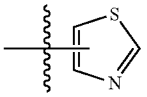
,
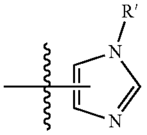
,
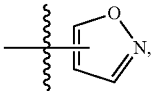
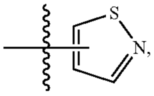
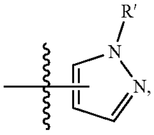
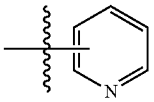
,
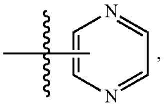
,
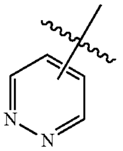
,
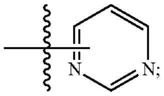
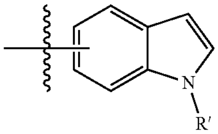
,
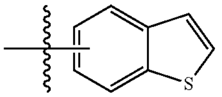
,
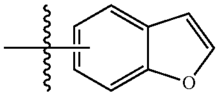
,
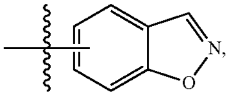
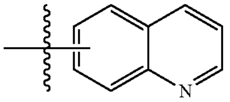
,
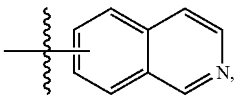
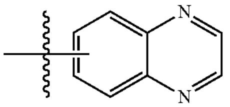
,
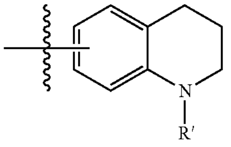
,
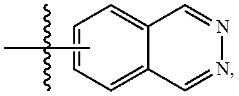
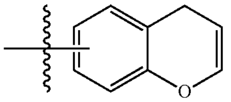
,
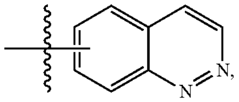
,
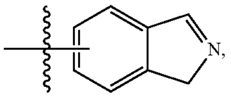
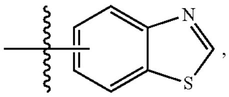
, -continued

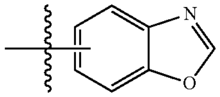
, or
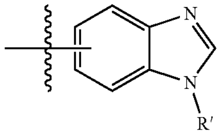
;

the substituent is 1~3 same or different substituents selected from fluorine, chlorine, bromine, C1~C6 alkyl, and phenoxy optionally substituted by a substituent (the substituent is 1-3 same or different substituents selected from fluorine, chlorine, bromine, C1~C6 alkyl, C1~C6 halogenated alkyl, C3~C6 cycloalkyl, and C1~C6 alkoxycarbonyl)}, C1~C6 alkylaminosulfonyl optionally substituted by a substituent (the substituent is one or more same or different substituents selected from fluorine, chlorine, and bromine),

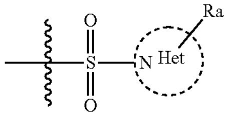

(Het is

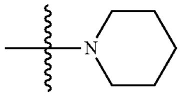
,
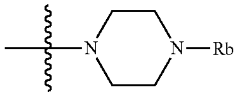
,
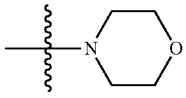
or
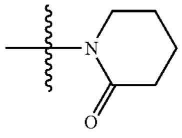
, $R_a$ and $R_b$ independently are hydrogen or C1~C6 alkyl), di(C1~C6 alkyl)phosphoryl, or di(C1~C6 alkyl)thiophosphoryl.

In a preferred embodiment, M is (thio)formyl, C1~C18 alkyl(thio)carbonyl, wherein the (thio)formyl or C1~C18 alkyl(thio)carbonyl is unsubstituted or substituted with a substituent independently selected from the group consisting of: halogen, amino, C3~C8 cycloalkyl, C1~C8 alkoxycarbonyl, C1~C8 alkylcarbonyloxy, C1~C8 alkylcarbonyl, hydroxy(methyl)phosphinyl, and an unsubstituted or halogenated or C1~C8 alkoxy substituted group selected from phenyl, phenylsulfanyl, phenyloxy, and benzyloxy; an unsubstituted or phenyl substituted group of C1~C18 alkoxy (thio)carbonyl or C1~C18 alkylsulfanyl(thio)carbonyl; C3~C8 cycloalkylsulfanyl(thio)carbonyl; phenyl-C1~C8 alkylsulfanyl(thio)carbonyl; C2~C8 alkenyl(thio)carbonyl, wherein the C2~C8 alkenyl(thio)carbonyl unsubstituted or substituted with a substituent selected from the group consisting of: C1~C8 alkoxy, phenyl and halogenated phenyl; (thio)benzoyl, wherein the (thio)benzoyl is unsubstituted or substituted with a substituent selected from the group consisting of: halogen, hydroxy, C1~C8 alkyl, C1~C8 alkoxy, cyano, halogenated C1~C8 alkoxy, C1~C8 alkylcarbonyloxy, C1~C8 alkylcarbonylamino, amino and amino substituted with 1 or 2 C1~C8 alkyl; halogenated sulfhydryl formyl; 3- to 8-membered heterocyclyl(thio)carbonyl, wherein the 3- to 8-membered heterocyclyl(thio)carbonyl is unsubstituted or substituted with a substituent selected from C1~C8 alkyl, halogen, and C1~C8 alkylsulfanyl; fused 5- to 14-membered bicyclic or tricyclic heterocyclyl(thio)carbonyl; amino(thio)formyl, wherein the amino(thio)formyl is unsubstituted or substituted with a substituent selected from C1~C8 alkyl and C1~C8 alkoxy; an unsubstituted or halogen or C1~C8 alkylsulfonyl substituted group selected from C1~C8 alkylsulfoxide, C1~C8 alkylsulfonyl, and C3~C8 cycloalkylsulfonyl; phenylsulfonyl, benzylsulfonyl or naphthylsulfonyl, wherein each of the phenylsulfonyl, benzylsulfonyl or naphthylsulfonyl is unsubstituted or substituted with a substituent independently selected from the group consisting of: halogen, nitro, C1~C8 alkyl, halogenated C1~C8 alkyl, halogenated C1~C8 alkoxy, C1~C8 alkylcarbonyl, C1~C8 alkylsulfonyl, aminoformyl, phenoxy and halogenated phenoxy; 5- to 10-membered heteroarylsulfonyl, wherein the 5- to 10-membered heteroarylsulfonyl is unsubstituted or substituted with C1~C8 alkyl or phenoxy; C1~C8 alkylaminosulfonyl that is unsubstituted or substituted with halogen; di(C1~C8 alkyl)phosphoryl;

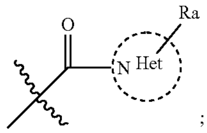
; or
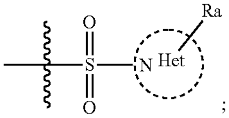
;

wherein, Het is selected from

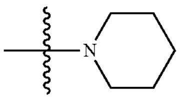
,
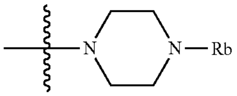
,
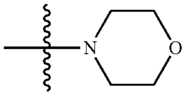
and
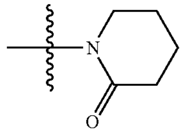
,

Ra and Rb independently are hydrogen or C1~C6 alkyl.

The oxime derivative refers to a compound having an oxime moiety formed by derivatization of the 4-hydroxy of the pyridazine ring of Formula I. In a preferred embodiment, the oxime group is selected from

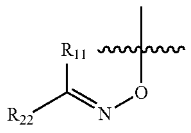
, wherein, $R_{11}$, $R_{22}$ separately and independently are hydrogen, C1~C18 alkyl, C2~C18 alkenyl, wherein the C1~C18 alkyl or C2~C18 alkenyl is optionally substituted with a substituent (the substituent is one or more same or different substituents selected from halogen atom, C1~C8 alkoxy, C1~C8 alkylsulfanyl, and C1~C8 alkylamino), phenyl, phenylcarbonyl, 5- to 6-membered heteroaryl, wherein the phenyl, phenylcarbonyl or 5- to 6-membered heteroaryl is optionally substituted with a substituent (the substituent is 1-3 same or different substituents selected from halogen atom, C1~C8 alkyl, C2~C8 alkenyl, C2~C8 alkynyl, C3~C8 cycloalkyl, C1~C8 halogenated alkyl, C1~C8 alkylcarbonyl, C1~C8 alkoxy, C1~C8 alkoxycarbonyl, C1~C8 alkylamino, hydroxy, carboxyl, sulfhydryl, amino, cyano, nitro, and C1~C8 alkylsulfonyl, the heteroaryl contains at least one oxygen, sulfur, or nitrogen, or other heteroatoms), or $R_{11}$, $R_{22}$ form a 5- to 6-membered saturated carbocyclic ring or 5- to 6-membered heterocyclic ring (containing at least one heteroatom such as oxygen, sulfur, nitrogen, etc.).

In a preferred embodiment, $R_{11}$, $R_{22}$ independently are hydrogen, C1~C10 alkyl, C2~C10 alkenyl, the C1~C10 alkyl or C2~C10 alkenyl is optionally substituted with a substituent (the substituent is one or more same or different substituents selected from fluorine, chlorine, bromine, C1~C6 alkoxy, C1~C6 alkylsulfanyl, and C1~C6 alkylamino), phenyl, benzoyl, 5- to 6-membered heteroaryl, wherein the phenyl, benzoyl or 5- to 6-membered heteroaryl is optionally substituted with a substituent (the heteroaryl is

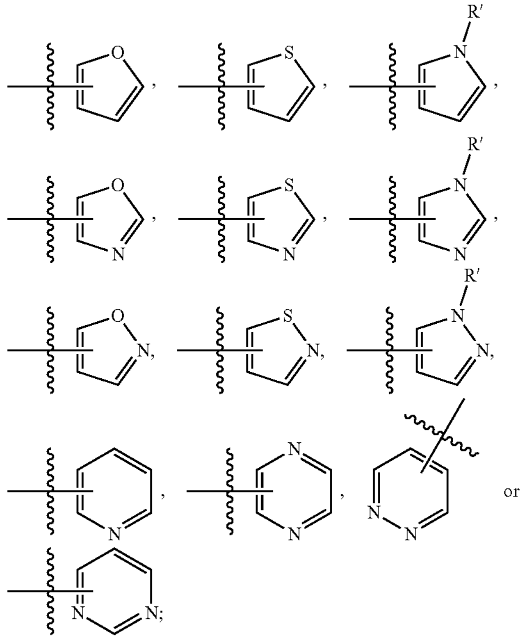

the substituent is 1~3 same or different substituents selected from fluorine, chlorine, bromine, C1~C6 alkyl, C3~C6 cycloalkyl, C1~C6 halogenated alkyl, C1~C6 alkylcarbonyl, C1~C6 alkoxy, C1~C6 alkoxycarbonyl, C1~C6 alkylamino, hydroxy, carboxyl, sulfhydryl, amino, cyano, nitro, and C1~C6 alkylsulfonyl), or $R_{11}$ and $R_{22}$ form a 5- to 6-membered saturated carbocyclic ring or a 5- to 6-membered heterocyclic ring (containing at least one heteroatom such as oxygen, sulfur, nitrogen, etc.).

In a preferred embodiment, $R_{11}$ and $R_{22}$ are independently selected from hydrogen, C1~C18 alkyl, wherein the C1~C18 alkyl is unsubstituted or substituted with a substituent selected from C1~C8 alkoxy, C1~C8 alkylsulfanyl, and an unsubstituted or halogenated C1~C8 alkyl substituted group selected from phenyl and 5- to 6-membered heteroaryl; or $R_1$ and $R_{12}$ forms a 5- to 6-membered saturated carbocyclic ring or a 5- to 6-membered saturated heterocyclic ring.

The hydroxylamine derivative refers to a compound having a hydroxylamine moiety formed by derivatization of the 4-hydroxyl of the pyridazine ring of Formula I. In a preferred embodiment, the hydroxylamine group is selected from

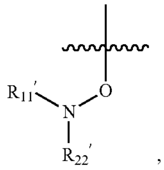

, wherein, $R_{11}'$, $R_{22}'$ are independently hydrogen, C1-C18 alkyl, C2~C18 alkenyl, wherein the C1~C18 alkyl or C2~C18 alkenyl is optionally substituent with a substituent (the substituent is one or more same or different substituents selected from halogen atom, C1~C8 alkoxy, C1~C8 alkylsulfanyl, and C1~C8 alkylamino), phenyl optionally substituent with a substituent (the substituent is 1-3 same or different substituents selected from halogen atom, C1~C8 alkyl, C2~C8 alkenyl, C2~C8 alkynyl, C3~C8 cycloalkyl, C1~C8 halogenated alkyl, C1~C8 alkylcarbonyl, C1~C8 alkoxy, C1~C8 alkoxycarbonyl, C1~C8 alkylamino, hydroxy, carboxyl, sulfhydryl, amino, cyano, nitro, and C1~C8 alkylsulfonyl), C1~C18 alkoxycarbonyl, or benzoyl optionally substituent with a substituent [the substituent is 1-3 same or different substituents selected from halogen atom, C1~C8 alkyl, C2~C8 alkenyl, C2~C8 alkynyl, C3~C8 cycloalkyl, wherein the C1~C8 alkyl, C2~C8 alkenyl, C2~C8 alkynyl or C3~C8 cycloalkyl is optionally substituent with a substituent (the substituent is 1-3 same or different substituents selected from halogen and phenyl), cyano, C1~C8 alkylcarbonyl, C1~C8 alkoxycarbonyl, C1~C8 alkylsulfonyl, C2~C8 alkenyloxycarbonyl optionally substituent with a substituent {the substituent is 1-3 same or different substituents selected from C3~C8 cycloalkyl, cyano, and benzoyl optionally substituent with a substituent (the substituent is 1-3 same or different substituents selected from halogen atom, C1~C8 alkyl, C1~C8 halogenated alkyl, C1~C8 alkoxycarbonyl, nitro, and C1~C8 alkylsulfonyl)}, C3~C8 cycloalkenyloxycarbonyl optionally substituent with a substituent {the substituent is 1-2 same or different substituents selected from oxo, and benzoyl optionally substituent with a substituent (the substituent is 1-3 same or different substituents selected from halogen atom, C1~C8 alkyl, C1~C8 halogenated alkyl, C1~C8 alkoxycarbonyl, nitro, and C1~C8 alkylsulfonyl)}, hydroxy, carboxyl, sulfhydryl, amino, phenyl, nitro, C1-~C8 alkoxy, C1~C8 alkylamino, C1~C8 alkylsulfanyl, wherein the C1~C8 alkoxy, C1~C8 alkylamino or C1~C8 alkylsulfanyl is optionally substituent with a substituent (the substituent is 1-3 same or different substituents selected from halogen and phenyl), phenoxy, 5- or 6-membered heterocyclyloxycarbonyl optionally substituent with a substituent {the ring of the heterocyclyl contains one nitrogen atom, oxygen atom or sulfur atom, may further contain 1 to 2 nitrogen atoms; the substituent is 1-3 same or different substituents selected from halogen atom, C1~C8 alkyl, phenoxy optionally substituent with a substituent (the substituent is 1-3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituent with a substituent (the substituent is 1-3 same or different substituents selected from halogen atom, C1~C8 alkyl, C1~C8 halogenated alkyl, C1~C8 alkoxycarbonyl, nitro, and C1~C8 alkylsulfonyl)}, and 5- or 6-membered heterocyclyloxysulfonyl optionally substituent with a substituent {the ring in the heterocyclyl contains one nitrogen atom, oxygen atom or sulfur atom, and may further contain 1 or 2 nitrogen atoms; the substituent is 1-3 same or different substituents selected from halogen atom, C1~C8 alkyl, phenoxy optionally substituent with a substituent (the substituent is 1-3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxyl, and benzoyl optionally substituent with a substituent (the substituent is 1-3 same or different substitutions selected from halogen atom, C1~C8 alkyl, C1~C8 halogenated alkyl, C1~C8 alkoxycarbonyl, nitro, and C1~C8 alkylsulfonyl)}].

In a preferred embodiment, $R_{11}$', $R_{22}$' are independently hydrogen, C1~C10 alkyl, C2~C10 alkenyl, wherein the C1~C10 alkyl or C2~C10 alkenyl is optionally substituent with a substituent (the substituent is one or more same or different substituents selected from fluorine, chlorine, bromine), C1~C10 alkoxycarbonyl, phenyl, or benzoyl, wherein the phenyl or benzoyl optionally substituent with a substituent (the substituent is 1-3 same or different substituents selected from fluorine, chlorine, bromine, C1~C6 alkyl, C2~C6 alkenyl, C2~C6 alkynyl, C3~C6 cycloalkyl, C1~C6 halogenated alkyl, C1~C6 alkylcarbonyl, C1~C6 alkoxy, C1~C6 alkoxycarbonyl, C1~C6 alkylamino, hydroxy, carboxyl, sulfhydryl, amino, cyano, nitro, and C1~C6 alkylsulfonyl).

In a preferred embodiment, $R_{11}$' and $R_{22}$' independently is C1~C18 alkyl.

The ether derivative refers to a compound formed by bonding the oxygen atom of the 4-hydroxy of the pyridazine ring with a group as follows: cyano, C1~C18 alkyl, C2~C18 alkenyl, wherein the C1~C18 alkyl or C2~C18 alkenyl is optionally substituted with a substituent (the substituent is one or more same or different substituents selected from halogen atom, C1~C8 alkoxy, C1~C8 alkylsulfanyl, C1~C8 alkylamino, di(C1~C8 alkyl)amino, C1~C8 alkoxycarbonyl, C1~C8 alkoxycarbonyloxy, C3~C8 cycloalkyloxy, C3~C8 cycloalkylsulfanyl, C3~C8 cycloalkylamino, di(C3~C8cycloalkyl)amino, C3~C8 cycloalkoxycarbonyl, and C3~C8 cycloalkoxycarbonyloxy), phenyl, benzyl, or benzoyl-C1~C8 alkyl, wherein the phenyl, benzyl or benzoyl-C1~C8 alkyl is optionally substituent with a substituent [the substituent is 1-3 same or different substituents selected from halogen atom, C1~C8 alkyl, C2~C8 alkenyl, C2~C8 alkynyl, C3~C8 cycloalkyl, wherein the C1~C8 alkyl, C2~C8 alkenyl, C2~C8 alkynyl or C3~C8 cycloalkyl is optionally substituent with a substituent (the substituent is 1-3 same or different substituents selected from halogen and phenyl), cyano, C1~C8 alkylcarbonyl, C1~C8 alkoxycarbonyl, C1~C8 alkylsulfonyl, C2~C8 alkenyloxycarbonyl optionally substituent with a substituent {the substituent is 1-3 same or different substituents selected from C3~C8 cycloalkyl, cyano, and benzoyl optionally substituent with a substituent (the substituent is 1~3 same or different substitutions selected from halogen atom, C1~C8 alkyl, C1~C8 halogenated alkyl, C1~C8 alkoxycarbonyl, nitro, and C1~C8 alkylsulfonyl)}, C3~C8 cycloalkenyloxycarbonyl optionally substituent with a substituent {the substituent is 1~2 same or different substituents selected from oxo, and benzoyl optionally substituent with a substituent (the substituent is 1-3 same or different substituents selected from halogen atom, C1~C8 alkyl, C1~C8 halogenated alkyl, C1~C8 alkoxycarbonyl, nitro, and C1~C8 alkylsulfonyl)}, hydroxy, carboxyl, sulfhydryl, amino, phenyl, nitro, C1~C8 alkoxy, C1~C8 alkylamino, C1~C8 alkylsufanyl, wherein the C1~C8 alkoxy, C1~C8 alkylamino or C1~C8 alkylsufanyl is optionally substituent with a substituent (the substituent is 1-3 same or different substituents selected from halogen and phenyl), phenoxy, 5- or 6-membered heterocyclyloxycarbonyl optionally substituent with a substituent {the ring of the heterocyclyl contains one nitrogen atom, oxygen atom or sulfur atom, and may further contain 1 to 2 nitrogen atoms; the substituent is 1-3 same or different substituents selected from halogen atom, C1~C8 alkyl, phenoxy optionally substituent with a substituent (the substituent is 1-3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituent with a substituent (the substituent is 1-3 same or different substituents selected from halogen atom, C1~C8 alkyl, C1~C8 halogenated alkyl, C1~C8 alkoxycarbonyl, nitro, and C1~C8 alkylsulfonyl)}, and 5- or 6-membered heterocyclyloxysulfonyl optionally substituent with a substituent {the ring of the heterocyclyl contains one nitrogen atom, oxygen atom or sulfur atom, and may further contain 1 to 2 nitrogen atoms; the substituent is 1-3 same or different substituents selected from halogen atom, C1~C8 alkyl, phenoxy optionally substituent with a substituent (the substituent is 1-3 same or different substituents selected from halogen atom, C1~C8 alkyl, C1~C8 halogenated alkyl, C3~C8 cycloalkyl, and C1~C8 alkoxycarbonyl), 2,3-dihydro-1H-indenyloxy, and benzoyl optionally substituent with a substituent (the substituent is 1-3 same or different substituents selected from halogen atom, C1~C8 alkyl, C1~C8 halogenated alkyl, C1~C8 alkoxycarbonyl, nitro, and C1~C8 alkylsulfonyl)}]; wherein, in Formula I-1, when X is $—CF_3$ and A is phenyl in Formula I-1, the M group is not methyl or allyl; when X is $—CHFCF_3$ and A is $—CHFCF_3$, the M group is not

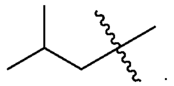

In a preferred embodiment, the ether derivative refers to a compound formed by bonding the oxygen of the 4-hydroxy of the pyridazine ring with a group as follows: C8~C18 alkyl, C8~C18 alkenyl, C1~C10 alkyl, C2~C10 alkenyl, wherein the C1~C10 alkyl or C2~C10 alkenyl is substituent with a substituent {the substituent is one or more same or different substituents selected from fluorine, chlorine, bromine, C1~C6 alkoxy, C1~C6 alkylsulfanyl, C1~C6 alkylamino, C1~C6 alkoxycarbonyl, C1~C6 alkoxycarbonyloxy, and C3~C6 cycloalkoxycarbonyloxy}, phenyl, benzyl, or benzoyl-C1~C6 alkyl, wherein the phenyl, benzyl or benzoyl-C1~C6 alkyl is optionally substituent with a substituent (the substituent is 1-3 same or different substituents selected from fluorine, chlorine, bromine, C1~C6 alkyl, C2~C6 alkenyl, C2~C6 alkynyl, C3~C6 cycloalkyl, C1~C6 halogenated alkyl, C1~C6 alkylcarbonyl, C1~C6 alkoxy, C1~C6 alkoxycarbonyl, C1~C6 alkylamino, hydroxy, carboxyl, sulfhydryl, amino, cyano, nitro, and C1~C6 alkylsulfonyl).

In a preferred embodiment, the group is selected from $C_{1-18}$ alkyl, which is unsubstituted or substituted with a substituent selected from C1~C8 alkoxycarbonyl and C1~C8 alkoxycarbonyloxy; and phenyl, benzyl or benzoyl-C1~C8 alkyl, each of which is unsubstituted or substituted with a substituent selected from halogen and C1~C8 alkoxy.

A method for preparing the pyridazinol compound, comprising the steps of:

(1) subjecting a compound of Formula II and a compound of Formula III to Suzuki reaction to obtain a compound of Formula IV;

(2) hydrolyzing the compound of Formula IV to obtain a compound of Formula I;

wherein the reaction route is as follows:

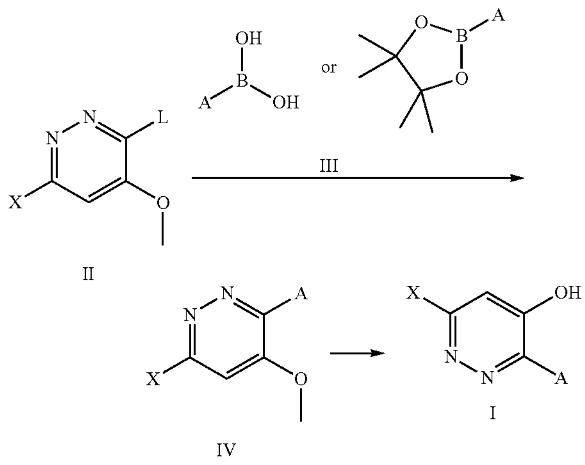

II

IV

I or comprising:

(a) hydrolyzing a compound of Formula II to give a compound of Formula V;

(b) subjecting the compound of Formula V and a compound of Formula III to Suzuki reaction to obtain a compound of Formula I;

the reaction route is as follows:

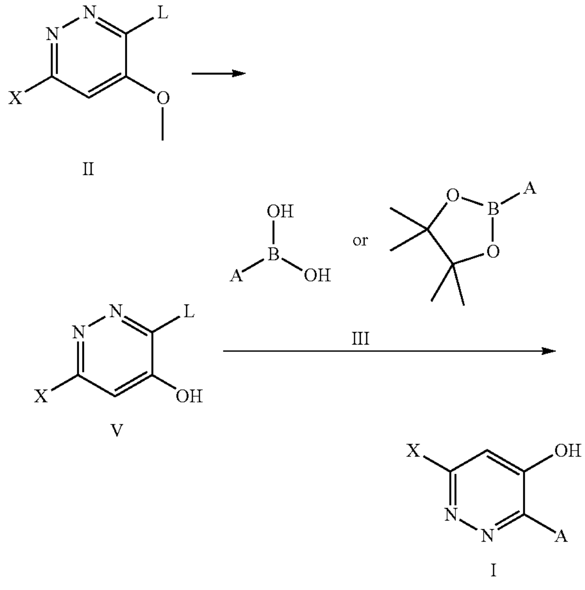

II

V

I

L is halogen, preferably bromine, other groups are as defined above.

In a preferred embodiment, each of the steps independently is carried out in the range of 20 to 150° C., preferably 50 to 130° C.;

steps (1) and (b) are carried out in the presence of a catalyst, a base and a solvent, wherein the catalyst is $Pd(dppf)Cl_2CH_2Cl_2$, $Pd(dba)_2$, $Pd_2(dba)_3$, $Pd(PPh_3)_4$, $PdCl_2$, $Pd(OAc)_2$, $Pd(dppf)Cl_2$, $Pd(PPh_3)_2Cl_2$, or $Ni(dppf)Cl_2$, the base is one or more selected from $Et_3N$, $NaHCO_3$, KOAc, $K_2CO_3$, $K_3PO_4$, $Na_2CO_3$, CsF, $Cs_2CO_3$, t-BuONa, EtONa, KOH, and NaOH, the solvent is THE/water, toluene/water, DMF/water, 1,4-dioxane/water, toluene/ethanol/water, acetonitrile/water, THF, toluene, 1,4-dioxane, acetonitrile, or DMF system;

steps (2) and (a) are carried out in the presence of a base and a solvent or in the presence of a solution of boron tribromide, a solution of hydrobromic acid in acetic acid, a solution of hydrochloric acid in methanol or a solution of hydrochloric acid in ethyl acetate, the base is preferably selected from NaOH, KOH, potassium acetate, and sodium acetate, the solvent is preferably water or DMSO.

When the derivative is an ester or ether derivative, the reaction route is as follows:

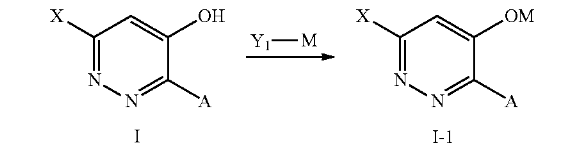

I

I-1 wherein, $Y_1$ is a halogen, preferably chlorine or bromine; other groups are as defined above.

When the derivative is an oxime or hydroxylamine derivative, the reaction route is as follows:

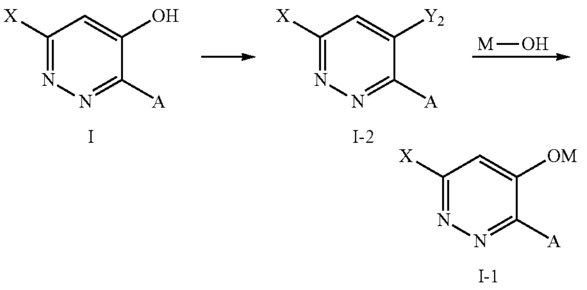

I

I-2

I-1 wherein, $Y_2$ is a halogen, preferably chlorine or fluorine; other groups are as defined above.

In a preferred embodiment, reactions for preparing the ester and ether derivatives and the second step for preparing the oxime and hydroxylamine derivatives are carried out in the presence of a base and a solvent, the base is one or more selected from the group consisting of sodium hydroxide, potassium hydroxide, sodium carbonate, potassium carbonate, sodium hydrogen carbonate, cesium carbonate, triethylamine and diisopropylethylamine; the solvent is THF, 1,4-dioxane, toluene, 1,2-dichloroethane, ethyl acetate, acetonitrile, DMF, acetone, dichloromethane, or chloroform.

In a preferred embodiment, the first step for preparing the oxime and hydroxylamine derivative is carried out in the presence of a halogenation reagent and a solvent, wherein the halogenation reagent is Phenofluor™/cesium fluoride or $POCl_3$, and the solvent is one or more selected from the group consisting of toluene, 1,2-dichloroethane, and DMF; the reaction temperature is in the range of 0 to 120° C., preferably 20 to 80° C.

Unless otherwise stated, the terms used in the text have the meanings commonly understood by those skilled in the art. When the terms used are different from those commonly understood in the art, the definitions herein prevail.

In the definitions of the compounds represented by the above formulas, and in all the aftermentioned compounds, the term "alkyl" or "$-(CH_2)_n-$" for the definition of a corresponding radical having more than two carbon atoms, whether used alone or in a compound word, may be a straight or branched chain. For example, alkyl in the compound word "heteroarylalkyl" and $-(CH_2)_n-$ in "R—O—$(CH_2)_n-$" all may be straight or branched. In a preferred embodiment, $-(CH_2)_n-$ may be $-CH_2-$, $-CH_2CH_2-$, $-CH(CH_3)-$, $-C(CH_3)_2-$, and the like.

The alkyl is, for example, methyl; ethyl; n-propyl or isopropyl; n-butyl, isobutyl, tert-butyl or 2-butyl; pentyl; hexyl, for example, n-hexyl, isohexyl or 1,3-dimethylbutyl. Similarly, alkenyl is, for example, allyl, 1-methyl-allyl, 2-methyl-allyl, but-2-enyl, but-3-enyl, 1-methyl-but-3-enyl or 1-methyl-but-2-enyl. Alkynyl is, for example, propargyl, but-2-ynyl, but-3-ynyl, or 1-methyl-but-3-ynyl. Multiple bonds can be at any site of an unsaturated group. Cycloalkyl preferably is a saturated carbocyclic ring having 3 to 8 carbon atoms, such as cyclopropyl, cyclobutyl, cyclopentyl or cyclohexyl. Similarly, cycloalkenyl preferably is a monocyclic ring having 3 to 8 carbocyclic ring members and at least one carbon-carbon double bond, such as cyclopropenyl, cyclobutenyl, cyclopentenyl or cyclohexenyl, wherein the double bond may be at any site of the ring. Halogen is fluorine, chlorine, bromine or iodine.

Unless specifically limited, heterocyclyl includes aliphatic heterocyclyl and heteroaryl.

If a group is substituted by a substituent, it should be understood that the group is substituted by one or more same or different substituents selected from those mentioned. In addition, the identical or different variables in identical or different substituents should be independently selected, i.e., could be same or different. This also applicable to a ring systems formed with different atoms and units. Meanwhile, the scope of the claims will exclude those compounds chemically unstable under standard conditions known to those skilled in the art.

In addition, unless specifically defined, a group without being specified a linking site may be attached at any site, including a C or N site; if it is substituted, the substituent may be substituted at any site as long as it comply with the valence bond theory. For example, if

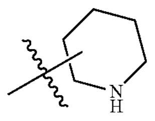

is substituted with one methyl, it can be

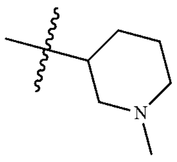

,

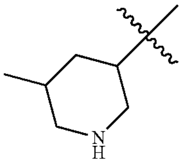

,

-continued

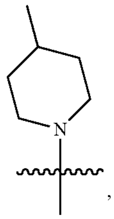

, etc.

The compound of the present invention may exist in the form of one or more stereoisomers. The various isomers include enantiomers, diastereomers, and geometric isomers. These isomers and mixtures thereof are all within the scope of the invention.

A herbicidal composition, comprising component (i) the pyridazinol compound of Formula I or the derivative thereof as shown in Formula I-1.

Preferably, further comprises component (ii) one or more additional herbicides and/or safeners.

More preferably, also comprises component (iii) an agriculturally acceptable formulation auxiliary.

Usable combination partners for the inventive compounds in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 15th edition, The British Crop Protection Council and the Royal Soc. of Chemistry, 2009 and literature cited therein. Examples of known herbicides or plant growth regulators which can be combined with the inventive compounds include the active ingredients which follow (the compounds are designated by the common name according to the International Organization for Standardization (ISO) or by the chemical name or by the code number) and always encompass all use forms, such as acids, salts, esters and isomers, such as stereoisomers and optical isomers. In this list, one or else, in some cases, more than one application forms is mentioned:

Acetochlor, Acibenzolar, Acibenzolar-S-methyl, Acifluorfen, Acifluorfen-sodium, Aclonifen, Alachlor, Allidochlor, Alloxydim, Alloxydim-sodium, Ametryn, Amicarbazone, Amidochlor, Amidosulfuron, Aminocyclopyrachlor, Aminopyralid, Amitrole, Ammoniumsulfamat, Ancymidol, Anilofos, Asulam, Atrazine, Azafenidin, Azimsulfuron, Aziprotryn, Beflubutamid, Benazolin, Benazolin-ethyl, Bencarbazone, Benfluralin, Benfuresate, Bensulide, Bensulfuron, Bensulfuron-methyl, Bentazone, Benzfendizone, Benzobicyclon, Benzofenap, Benzofluor, Benzoylprop, Bicyclopyrone, Bifenox, Bilanafos, Bilanafos-natrium, Bispyribac, Bispyribac-natrium, Bromacil, Bromobutide, Bromofenoxim, Bromoxynil, Bromuron, Buminafos, Busoxinone, Butachlor, Butafenacil, Butamifos, Butenachlor, Butralin, Butroxydim, Butylate, Cafenstrole, Carbetamide, Carfentrazone, Carfentrazone-ethyl, Chlomethoxyfen, Chloramben, Chlorazifop, Chlorazifop-butyl, Chlorbromuron, Chlorbufam, Chlorfenac, Chlorfenac-natrium, Chlorfenprop, Chlorflurenol, Chlorflurenol-methyl, Chloridazon, Chlorimuron (acid), Chlorimuron-ethyl, Chlormequat-chloride, Chlornitrofen, Chlorophthalim, Chlorthal-dimethyl, Chlorotoluron, Chlorsulfuron, Cinidon, Cinidon-ethyl, Cinmethylin, Cinosulfuron, Clethodim, Clodinafop, Clodinafop-propargyl, Clofencet, Clomazone, Clomeprop, Cloprop, Clopyralid, Cloransulam, Cloransulam-methyl, Cumyluron, Cyanamide, Cyanazine, Cyclanilide, Cycloate, Cyclosulfamuron, Cycloxydim, Cycluron, Cyhalofop, Cyhalofop-butyl, Cyperquat, Cyprazine, Cyprazole, 2,4-D, 2,4-DB, Daimuron/dymron, Dalapon, Daminozide, Dazomet, n-decanol, Desmedipham, Desmetryn, Detosyl-Pyrazolate (DTP), Diallate, Dicamba, Dichlobenil, Dichlorprop, Dichlorprop-P, Diclofop, Diclofop-methyl, Diclofop-P-methyl, Diclosulam, Acetyl Alachlor acid (Diethatyl), Acetyl Alachlor (Diethatyl-ethyl), Difenoxuron, Difenzoquat, Diflufenican, Diflufenzopyr, Diflufenzopyr-natrium, Dimefuron, Dikegulac-sodium, Dimepiperate, Dimethachlor, Dimethametryn, Dimethenamid, Dimethenamid-P, Dimethipin, Dimetrasulfuron, Dinitramine, Dinoseb, Dinoterb, Diphenamid, Dipropetryn, Diquat, Diquat dibromide, Dithiopyr, Diuron, DNOC, Eglinazine-ethyl, Endothal, EPTC, Esprocarb, Ethalfluralin, Ethametsulfuron, Ethametsulfuron-methyl, Ethephon, Ethidimuron, Ethiozin, Ethofumesate, Ethoxyfen, Ethoxyfen-ethyl, Ethoxysulfuron, Etobenzanid, F-5331, i.e., N-[2-chloro-4-fluoro-5-[4-(3-fluoropropyl)-4,5-dihydro-5-oxo-1H-tetrazol-1-yl]-phenyl] ethylsulfonamide, F-7967, i.e., 3-[7-chloro-5-fluoro-2-(trifluoromethyl)-1H-benzimidazol-4-yl]-1-methyl-6-(trifluoromethyl) pyrimidine-2,4(1H,3H)-dione, Fenoprop, Fenoxaprop, Fenoxaprop-P, Fenoxaprop-ethyl, Fenoxaprop-P-ethyl, Fenoxasulfone, Fentrazamide, Fenuron, Flamprop, Flamprop-M-isopropyl, Flamprop-M-methyl, Flazasulfuron, Florasulam, Fluazifop, Fluazifop-P, Fluazifop-butyl, Fluazifop-P-butyl, Fluazolate, Flucarbazone, Flucarbazone-sodium, Flucetosulfuron, Fluchloralin, Flufenacet(Thiafluamide)), Flufenpyr, Flufenpyr-ethyl, Flumetralin, Flumetsulam, Flumiclorac, Flumiclorac-pentyl, Flumioxazin, Flumipropyn, Fluometuron, Fluorodifen, Fluoroglycofen, Fluoroglycofen-ethyl, Flupoxam, Flupropacil, Flupropanate, Flupyrsulfuron, Flupyrsulfuron-methyl-sodium, Flurenol, Flurenol-butyl, Fluridone, Flurochloridone, Fluroxypyr, Fluroxypyr-meptyl, Flurprimidol, Flurtamone, Fluthiacet, Fluthiacet-methyl, Fluthiamide, Fomesafen, Foramsulfuron, Forchlorfenuron, Fosamine, Furyloxyfen, Gibberellinsiure, Glufosinate, Glufosinate-ammonium, Glufosinate-P, Glufosinate-P-ammonium, Glufosinate-P-natrium, Glyphosate, Glyphosate-isopropylammonium, H-9201, i.e., O-(2,4-dimethyl-6-nitrophenyl)-O-ethyl-isopropylthiophosphoramide, Halosafen, Halosulfuron, Halosulfuron-methyl, Haloxyfop, Haloxyfop-P, Haloxyfop-ethoxyethyl, Haloxyfop-P-ethoxyethyl, Haloxyfop-methyl, Haloxyfop-P-methyl, Hexazinone, HW-02, i.e., 1-(dimethyloxyphosphoryl)ethyl (2,4-dichlorophenoxy) acetate, Imazamethabenz, Imazamethabenz-methyl, Imazamox, Imazamox-ammonium, Imazapic, Imazapyr, imazapyr-isopropylammonium, Imazaquin, Imazaquin-ammonium, Imazethapyr, Imazethapyr-ammonium, Imazosulfuron, Inabenfide, Indanofan, Indaziflam, Indoleacetic acid (IAA), 4-indol-3-ylbutyric acid (IBA), Iodosulfuron, Iodosulfuron-methyl-natrium, Ioxynil, Ipfencarbazone, Isocarbamid, Isopropalin, Isoproturon, Isouron, Isoxaben, Isoxachlortole, Isoxaflutole, Isoxapyrifop, KUH-043, i.e., 3-({[5-(difluoromethyl)-1-methyl-3-(trifluoromethyl)-1H-pyrazol-4-yl] methyl}sulfonyl)-5,5-dimethyl-4,5-dihydro-1,2-oxazole, Karbutilate, Ketospiradox, Lactofen, Lenacil, Linuron, Maleinsiure-hydrazid, MCPA, MCPB, MCPAB-methyl, -ethyl and -sodium salt, 2-methyl-4-chlorophenoxypropionic acid (Mecoprop), sodium 2-methyl-4-chlorophenoxypropionate, butyloxyethyl 2-methyl-4-chlorophenoxypropionate (Mecoprop-butotyl), Mecoprop-P-butotyl, Mecoprop-P-dimethylammonium, Mecoprop-P-2-ethylhexyl, Mecoprop-P-kalium, Mefenacet, Mefluidide, Mepiquatchlorid, Mesosulfuron, Mesosulfuron-methyl, Mesotrione, Methabenzthiazuron, Metam, Metamifop, Metamitron, Metazachlor, Metazosulfuron, Methazole, Methiopyrsulfuron, Methiozolin, Methoxyphenone, Methyldymron, 1-methylcyclopropene, methyl isothiocyanate, Metobenzuron, Metobromuron, Metolachlor, S-Metolachlor, Metosulam, Metoxuron, Metribuzin, Metsulfuron, Metsulfuron-methyl, Molinate, Monalide, Monocarbamide, Monocarbamide-dihydrogensulfat, Monolinuron, Monosulfuron, Monosulfuron-ester, Monuron, MT-128, i.e., 6-chloro-N-[(2E)-3-chloroprop-2-en-1-yl]-5-methyl-N-phenylpyridazin-3-amine, MT-5950, i.e., N-[3-chloro-4-(1-methylethyl)phenyl]-2-methylpentanamide, NGGC-011, Naproanilide, Napropamide, Naptalam, NC-310, i.e., 4-(2,4-dichlorobenzoyl)-1-methyl-5-benzyloxypyrazole, Neburon, Nicosulfuron, Nipyraclofen, Nitralin, Nitrofen, Nitrophenolate-natrium (mixture of isomers), Nitrofluorfen, nonylic acid, Norflurazon, Orbencarb, Orthosulfamuron, Oryzalin, Oxadiargyl, Oxadiazon, Oxasulfuron, Oxaziclomefone, Oxyfluorfen, Paclobutrazol, Paraquat, Paraquat dichloride, n-nonylic acid (Pelargonsiure), Pendimethalin, Pendralin, Penoxsulam, Pentanochlor, Pentoxazone, Perfluidone, Pethoxamid, Phenisopham, Phenmedipham, Phenmedipham-ethyl, Picloram, Picolinafen, Pinoxaden, Piperophos, Pirifenop, Pirifenop-butyl, Pretilachlor, Primisulfuron, Primisulfuron-methyl, Probenazole, Profluazol, Procyazine, Prodiamine, Prifluraline, Profoxydim, Prohexadione, Prohexadione-calcium, Prohydrojasmone, Prometon, Prometryn, Propachlor, Propanil, Propaquizafop, Propazine, Propham, Propisochlor, Propoxycarbazone, Propoxycarbazone-natrium, Propyrisulfuron, Propyzamide, Prosulfalin, Prosulfocarb, Prosulfuron, Prynachlor, Pyraclonil, Pyraflufen, Pyraflufen-ethyl, Pyrasulfotole, Pyrazolynate (Pyrazolate), Pyrazosulfuron, Pyrazosulfuron-ethyl, Pyrazoxyfen, Pyribambenz, Pyribambenz-isopropyl, Pyribambenz-propyl, Pyribenzoxim, Pyributicarb, Pyridafol, Pyridate, Pyriferalid, Pyriminobac, Pyriminobac-methyl, Pyrimisulfan, Pyrithiobac, Pyrithiobac-natrium, Pyroxasulfone, Pyroxsulam, Quinclorac, Quinmerac, Quinoclamine, Quizalofop, Quizalofop-ethyl, Quizalofop-P, Quizalofop-P-ethyl, Quizalofop-P-tefuryl, Rimsulfuron, Saflufenacil, Secbumeton, Sethoxydim, Siduron, Simazine, Simetryn, SN-106279, i.e., methyl-(2R)-2-{7-[2-chloro-4-(trifluoromethyl)phenoxy]-2-naphthyl}oxy)propionate, Sulcotrione, Sulfallate(CDEC), Sulfentrazone, Sulfometuron, Sulfometuron-methyl, Sulfosate(Glyphosate-trimesium), Sulfosulfuron, SYN-523, SYP-249, i.e., 1-ethyloxy-3-methyl-1-oxobut-3-en-2-yl-5-[2-chloro-4-(trifluoromethyl)phenoxy)-2-nitrobenzoic acid ester, SYP-300, i.e., 1-[7-fluoro-3-oxo-4-(prop-2-yn-1-yl)-3,4-dihydro-2H-1,4-benzoxazine-6-yl]-3-propyl-2-thioimidazolidine-4,5-dione, Tebutam, Tebuthiuron, Teenazene, Tefuryltrione, Tembotrione, Tepraloxydim, Terbacil, Terbucarb, Terbuchlor, Terbumeton, Terbuthylazine, Terbutryn, Thenylchlor, Thiafluamide, Thiazafluron, Thiazopyr, Thidiazimin, Thidiazuron, Thiencarbazone, Thiencarbazone-methyl, Thifensulfuron, Thifensulfuron-methyl, Thiobencarb, Tiocarbazil, Topramezone, Tralkoxydim, Triafamone, Triallate, Triasulfuron, Triaziflam, Triazofenamide, Tribenuron, Tribenuron-methyl, trichloroacetic acid (TCA), Triclopyr, Tridiphane, Trietazine, Trifloxysulfuron, Trifloxysulfuron-natrium, Trifluralin, Triflusulfuron, Triflusulfuron-methyl, Trimeturon, Trinexapac, Trinexapac-ethyl, Tritosulfuron, Tsitodef, Uniconazole, Uniconazole-P, Vernolate, ZJ-0862, i.e., 3,4-dichloro-N-{2-[(4,6-dimethoxy-pyrimidin-2-yl)oxy]benzyl}aniline, and the following compounds:

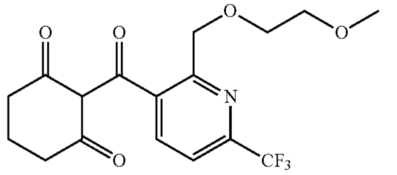

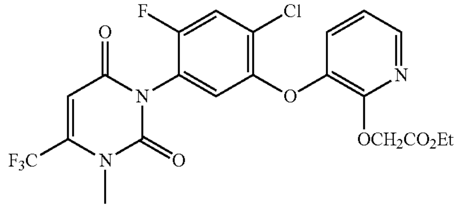

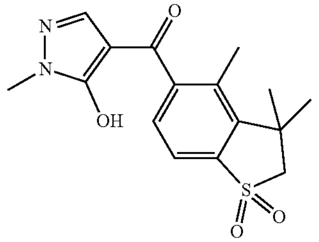

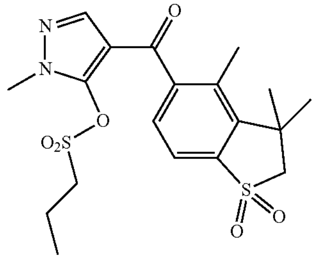

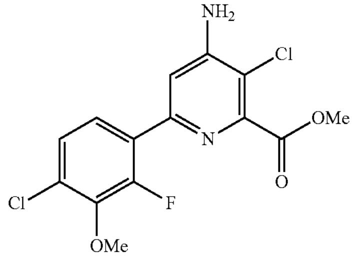

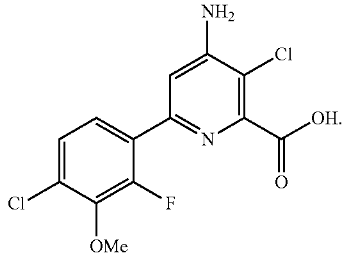

The additional herbicide is one selected from a HPPD inhibitor, a hormones and a PDS inhibitor; preferably, the HPPD inhibitor is selected from the group consisting of Sulcotrione (CAS NO.: 99105-77-8), Mesotrione (CAS NO.: 104206-82-8), Topramezone (CAS NO.: 210631-68-8), Tembotrione (CAS NO.: 335104-84-2), Bicyclopyrone (CAS NO.: 352010-68-5), Tefuryltrione (CAS NO.: 473278-76-1), Benzobicyclon (CAS NO.: 156963-66-5), Lancotrione (CAS NO.: 1486617-21-3), Shuangzuocaotong (CAS NO.: 1622908-18-2), Huanbifucaotong (CAS NO.: 1855929-45-1), Sanzuohuangcaotong (CAS NO.: 1911613-97-2), Benzuofucaotong (CAS NO.: 1992017-55-6), Pyrasulfotole (CAS NO.: 365400-11-9), Pyrazolate (CAS NO.: 58011-68-0), Benzofenap (CAS NO.: 82692-44-2), Tolpyralate (CAS NO.: 1101132-67-5), Fenquinotrione (CAS NO.: 1342891-70-6), and Isoxaflutole (CAS NO.: 141112-29-0); the hormone is selected from the group consisting of Fluroxypyr (CAS NO.: 69377-81-7) or a derivative thereof, Halauxifen-methyl (CAS NO.: 943831-98-9), Florpyrauxifen-benzyl (CAS NO.: 1390661-72-9), Quinclorac (CAS NO.: 84087-01-4), Quinmerac (CAS NO.: 90717-03-6), Chipton (CAS NO.: 94-74-6), 2-methyl-4-chlorophenoxypropionic acid (CAS NO.: 93-65-2), MCPB (CAS NO.: 94-81-5), 2,4-D (CAS NO.: 94-75-7), Dichlorprop (CAS NO.: 120-36-5), 2,4-DB (CAS NO.: 94-82-6), Dicamba (CAS NO.: 1918-00-9), Picloram (CAS NO.: 1918-02-1), Trichlopyr (CAS NO.: 55335-06-3), Clopyralid (CAS NO.: 1702-17-6), and Triclopyr (CAS NO.: 55335-06-3) and derivatives thereof, the PDS inhibitor is selected from the group consisting of Flurochloridone (CAS NO.: 61213-25-0), Flurtamone (CAS NO.: 96525-23-4), Diflufenican (CAS NO.: 83164-33-4), Picolinafen (CAS NO.: 137641-05-5), Beflubutamid (CAS NO.: 113614-08-7), Norflurazon (CAS NO.: 27314-13-2), and Fluridone (CAS NO.: 59756-60-4).

wherein, the Fluroxypyr derivative include, but are not limited to: Fluroxypyr-methyl; the derivatives of Chipton, 2-methyl 4-chlorophenoxypropionic acid, MCPB include but are not limited to: sodium salts, potassium salts, dimethylammonium salts, isopropylamine salts, etc., and methyl esters, ethyl esters, isooctyl esters, ethylthio esters, etc.; the derivatives of 2,4-D, Dichlorprop and 2,4-DB include but are not limited to: salts such as sodium salts, potassium salts, dimethylammonium salts, triethanolammonium salts, isopropylamine salts, cholines, etc., and esters such as methyl esters, ethyl esters, butyl esters, isooctyl esters, etc.

In a preferred embodiment, the component (i) is

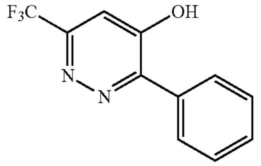

or

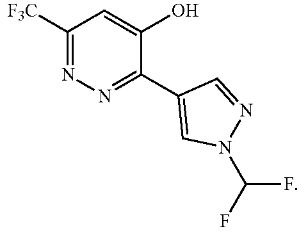

In a preferred embodiment, the additional herbicide is one or more selected from the group consisting of Sulcotrione, Mesotrione, Topramezone, Tembotrione, Bicyclopyrone, Tefuryltrione, Benzobicyclon, Lancotrione, Shuangzuocaotong, Huanbifucaotong, Sanzuohuangcaotong, Benzuofucaotong, Pyrasulfotole, Benzofenap, Tolpyralate, Isoxaflutole, Fluroxypyr or esters thereof, Halauxifen-methyl, Florpyrauxifen-benzyl, Quinclorac, Chipton or salts/esters thereof, 2-methyl 4-chlorophenoxypropionic acid or salts/esters thereof, MCPB or salts/esters thereof, 2,4-D or salts/ esters thereof, Dichlorprop or salts/esters thereof, 2,4-DB or salts/esters thereof, Dicamba, Picloram, Trichlopyr, Clopyralid, Triclopyr, Flurochloridone, Flurtamone, Diflufenican, Picolinafen, Beflubutamid, Norflurazon and Fluridone.

A method for controlling a harmful plant, comprising applying a herbicidally effective amount of at least one of the above mentioned pyridazinol compound or derivative thereof, or the herbicidal composition to the harmful plant or an area with the harmful plant.

Use of the above mentioned pyridazinol compound or derivative thereof, or the herbicidal composition for controlling a harmful plant;

Preferably, the pyridazinol compound or derivative thereof or the herbicidal composition is used to control a harmful plant in a useful crop.

More preferably, the useful crop is a genetically modified crop or a crop treated by genome editing technique. In a preferred embodiment, the useful crop is selected from the group consisting of wheat, corn, rice, soybean, cotton, rape, millet and sorghum.

The compounds of Formula I according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and *Sorghum*, and also perennial *Cyperus* species.

In the case of the dicotyledonous weed species, the spectrum of action extends to species such as, for example, *galium, viola, veronica, lamium, stellaria, amaranthus, sinapis, ipomoea, sida, matricaria* and *abutilon* from amongst the annuals, and *convolvulus, cirsium, rumex* and *artemisia* in the case of the perennial weeds. The active compounds according to the invention also effect outstanding control of harmful plants which occur under the specific conditions of rice growing such as, for example, *echinochloa, sagittaria, alisma, eleocharis, scirpus* and *cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti, Chenopodium album, Lamium purpureum, Polygonum convulvulus, Stellaria media, Veronica hederifolia, Veronica persica, Viola tricolor* and against *Amaranthus, Galium* and *Kochia* species.

In a preferred embodiment, the compounds described herein exhibit excellent inhibitory activity against the following harmful plants: *Amaranthus retroflexus, Rorippa indica, Veronica polita, Chenopodiaceae, Echinochloa crus-galli, Setaria viridis, Galium aparine, Abutilon mill, Sisymbrium sophia* and *Galinsoga parviflora*.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of Formula I according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of Formula I can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases:

- genetically engineered changes in crop plants in order to modify the starch synthesized in the plants (for example WO 92/11376, WO 92/14827, WO 91/19806);
- transgenic crop plants which are resistant to certain herbicides, for example, glufosinate (EP-A 0 242 236, EP-A 0 242 246), glyphosate-type (WO 92/00377), or sulfonylurea-type (EP-A 0 257 993, U.S. Pat. No. 5,013,659);
- transgenic crop plants, for example cotton, having the ability to produce *Bacillus thuringiensis* toxins (Bt toxins) which impart resistance to certain pests to the plants (EP-A 0 142 924, EP-A 0 193 259);
- transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker “Gene und Klone” [Genes and Clones], VCH Weinheim, 2nd edition 1996, or Christou, “Trends in Plant Science” 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of Formula I. The compounds of Formula I can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Kuhler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflchenaktive thylenoxidaddukte" [Surface-active ethylene oxide adducts], Wiss. Verlagsgesell., Stuttgart 1976; Winnacker-Kuchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with Formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of Formula I. In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, the formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

For use, Formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of Formula I required varies with the external conditions, such as temperature, humidity, the nature of the herbicide used and the like. It can vary within wide limits, for example between 0.001 and 1.0 kg/ha or more of active substance, but it is preferably between 0.005 and 750 g/ha, in particular between 0.005 and 250 g/ha.

SPECIFIC MODE FOR CARRYING OUT THE INVENTION

The following embodiments are used to illustrate the present invention in detail and should not be taken as any limit to the present invention. The scope of the invention would be explained through the Claims.

In view of economics, variety and biological activity of a compound, we preferably synthesized several compounds, part of which are listed in the following table 1-2. The structure and information of a certain compound are shown in Table 1-2. The compounds in Table 1-2 are listed for further explication of the present invention, other than any limit therefor. The subject of the present invention should not be interpreted by those skilled in the art as being limited to the following compounds.

TABLE 1

Structure and $^1$HNMR data of Compound I

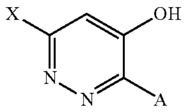

I

| No. | X | A | $^1$H NMR |
|---|---|---|---|
| 1 | $CF_3$ | 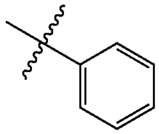 [SMILES: *c1ccccc1] | (500 MHz, Chloroform-d) δ 7.55-7.47 (m, 2H), 7.41-7.27 (m, 3H), 7.06 (s, 1H), 5.58 (s, 1H). |
| 2 | $CF_3$ | 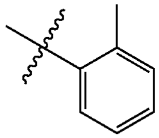 [SMILES: *c1ccccc1C] | (500 MHz, Chloroform-d) δ 7.46-7.40 (m, 1H), 7.39-7.30 (m, 2H), 7.32-7.26 (m, 1H), 7.03 (s, 1H), 5.68 (s, 1H), 2.50 (s, 3H). |
| 3 | $CF_3$ | 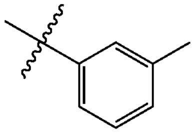 [SMILES: *c1cccc(C)c1] | (500 MHz, Chloroform-d) δ 7.45-7.41 (m, 1H), 7.40-7.30 (m, 2H), 7.29-7.23 (m, 1H), 7.06 (s, 1H), 5.58 (s, 1H), 2.50 (s, 3H). |
| 4 | $CF_3$ | 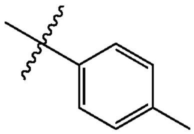 [SMILES: *c1ccc(C)cc1] | (500 MHz, Chloroform-d) δ 7.44 (d, J = 7.5 Hz, 2H), 7.22 (d, J = 7.5 Hz, 2H), 7.06 (s, 1H), 5.57 (s, 1H), 2.33 (s, 3H). |
| 5 | $CF_3$ | 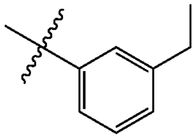 [SMILES: *c1cccc(CC)c1] | (500 MHz, Chloroform-d) δ 7.47-7.44 (m, 1H), 7.43-7.34 (m, 2H), 7.34-7.27 (m, 1H), 7.06 (s, 1H), 5.60 (s, 1H), 2.61 (q, J = 8.0 Hz, 2H), 1.21 (t, J = 8.0 Hz, 3H). |
| 6 | $CF_3$ | 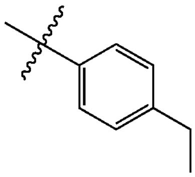 [SMILES: *c1ccc(CC)cc1] | (500 MHz, Chloroform-d) δ 7.46 (d, J = 7.5 Hz, 2H), 7.11 (d, J = 7.5 Hz, 2H), 7.06 (s, 1H), 5.57 (s, 1H), 2.67 (q, J = 8.0 Hz, 2H), 1.19 (t, J = 8.0 Hz, 3H). |
| 7 | $CF_3$ | 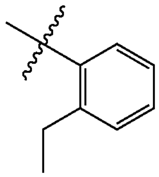 [SMILES: *c1ccccc1CC] | (500 MHz, Chloroform-d) δ 7.50-7.42 (m, 1H), 7.45-7.34 (m, 3H), 7.01 (s, 1H), 5.60 (s, 1H), 2.66 (q, J = 8.0, Hz, 2H), 1.20 (t, J = 8.0 Hz, 3H). |
| 8 | $CF_3$ | 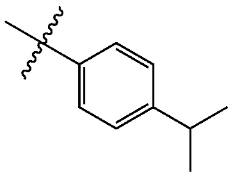 [SMILES: *c1ccc(C(C)C)cc1] | (500 MHz, Chloroform-d) δ 7.56 (d, J = 7.5 Hz, 2H), 7.43 (d, J = 7.5 Hz, 2H), 7.00 (s, 1H), 5.77 (s, 1H), 2.94 (hept, J = 8.0 Hz, 1H), 1.20 (d, J = 8.0 Hz, 6H). |

TABLE 1-continued

Structure and $^{1}$HNMR data of Compound I

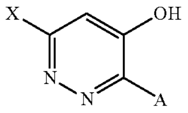

I

| No. | X | A | $^{1}$H NMR |
| --- | --- | --- | --- |
| 9 | $CF_3$ | 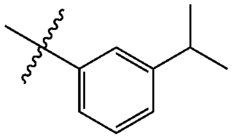 [SMILES: *c1cccc(C(C)C)c1] | (500 MHz, Chloroform-d) δ 7.55-7.50 (m, 1H), 7.45-7.33 (m, 3H), 7.06 (s, 1H), 5.61 (s, 1H), 2.90 (hept, J = 8.0 Hz, 1H), 1.24 (d, J = 8.0 Hz, 6H). |
| 10 | $CF_3$ | 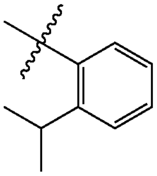 [SMILES: *c1ccccc1C(C)C] | (500 MHz, Chloroform-d) δ 7.50-7.40 (m, 2H), 7.37-7.30 (m, 2H), 7.01 (s, 1H), 5.58 (s, 1H), 3.12 (hept, J = 8.0 Hz, 1H), 1.27 (d, J = 8.0 Hz, 6H). |
| 11 | $CF_3$ | 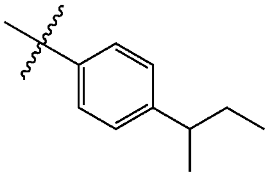 [SMILES: *c1ccc(C(C)CC)cc1] | (500 MHz, Chloroform-d) δ 7.56 (d, J = 7.5 Hz, 2H), 7.43 (d, J = 7.5 Hz, 2H), 7.00 (s, 1H), 5.77 (s, 1H), 2.61-2.46 (m, 1H), 1.80-1.61 (m, 2H), 1.16 (d, J = 7.0 Hz, 3H), 0.76 (t, J = 8.0 Hz, 3H). |
| 12 | $CF_3$ | 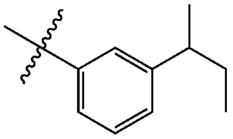 [SMILES: *c1cccc(C(C)CC)c1] | (500 MHz, Chloroform-d) δ 7.57-7.39 (m, 2H), 7.42-7.33 (m, 2H), 7.06 (s, 1H), 5.58 (s, 1H), 2.65-2.49 (m, 1H), 1.84-1.65 (m, 2H), 1.18 (d, J = 7.0 Hz, 3H), 0.79 (t, J = 8.0 Hz, 3H). |
| 13 | $CF_3$ | 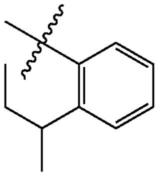 | (500 MHz, Chloroform-d) δ 7.50-7.35 (m, 4H), 7.04 (s, 1H), 5.67 (s, 1H), 2.79-2.68 (m, 1H), 1.94-1.75 (m, 2H), 1.28 (d, J = 7.0 Hz, 3H), 0.83 (t, J = 8.0 Hz, 3H). |
| 14 | $CF_3$ | 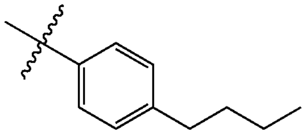 [SMILES: *c1ccc(CCCC)cc1] | (500 MHz, Chloroform-d) δ 7.46 (d, J = 7.5 Hz, 2H), 7.12 (d, J = 7.5 Hz, 2H), 7.06 (s, 1H), 5.56 (s, 1H), 2.59 (t, J = 7.5 Hz, 2H), 1.56-1.32 (m, 4H), 0.89 (t, J = 8.0 Hz, 3H). |
| 15 | $CF_3$ | 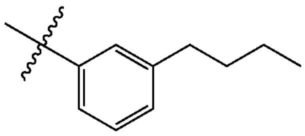 [SMILES: *c1cccc(CCCC)c1] | (500 MHz, Chloroform-d) δ 7.47-7.33 (m, 3H), 7.34-7.28 (m, 1H), 7.06 (s, 1H), 5.59 (s, 1H), 2.61 (t, J = 7.5 Hz, 2H), 1.59-1.37 (m, 4H), 0.95 (t, J = 8.0 Hz, 3H). |
| 16 | $CF_3$ | 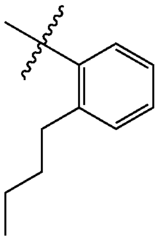 [SMILES: *c1ccccc1CCCC] | (500 MHz, Chloroform-d) δ 7.49-7.37 (m, 4H), 7.01 (s, 1H), 5.62 (s, 1H), 2.58 (t, J = 7.5 Hz, 2H), 1.53-1.33 (m, 4H), 0.85 (t, J = 8.0 Hz, 3H). |

TABLE 1-continued

Structure and $^{1}$HNMR data of Compound I

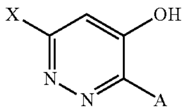

I

| No. | X | A | $^{1}$H NMR |
|---|---|---|---|
| 17 | $CF_3$ | 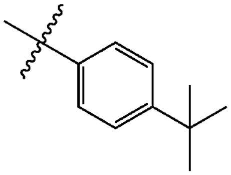 [SMILES: *c1ccc(C(C)(C)C)cc1] | (500 MHz, Chloroform-d) δ 7.54 (d, J = 7.5 Hz, 2H), 7.43 (d, J = 7.5 Hz, 2H), 7.06 (s, 1H), 5.56 (s, 1H), 1.28 (s, 9H). |
| 18 | $CF_3$ | 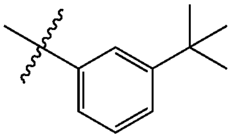 [SMILES: *c1cccc(C(C)(C)C)c1] | (500 MHz, Chloroform-d) δ 7.60 (dd, J = 2.0, 1.5 Hz, 1H), 7.53-7.45 (m, 1H), 7.39-7.30 (m, 2H), 7.06 (s, 1H), 5.60 (s, 1H), 1.33 (s, 9H). |
| 19 | $CF_3$ | 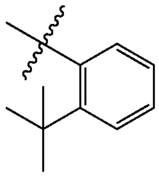 [SMILES: *c1ccccc1C(C)(C)C] | (500 MHz, Chloroform-d) δ 7.47 (dd, J = 7.0, 2.5 Hz, 1H), 7.40-7.31 (m, 2H), 7.29 (dd, J = 6.5, 3.0 Hz, 1H), 7.03 (s, 1H), 5.64 (s, 1H), 1.24 (s, 9H). |
| 20 | $CF_3$ | 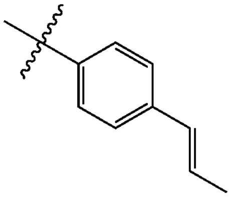 [SMILES: *c1ccc(/C=C/C)cc1] | (500 MHz, Chloroform-d) δ 7.58-7.52 (m, 2H), 7.45-7.38 (m, 2H), 7.01 (s, 1H), 6.40-6.33 (m, 1H), 6.15-6.01 (m, 1H), 5.78 (s, 1H), 1.72 (d, J = 6.5 Hz, 3H). |
| 21 | $CF_3$ | 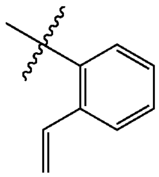 [SMILES: *c1ccccc1C=C] | (500 MHz, Chloroform-d) δ 7.82-7.42 (m, 4H), 7.02 (s, 1H), 6.91-6.70 (m, 1H), 5.92 (s, 1H), 5.70-5.49 (m, 2H). |
| 22 | $CF_3$ | 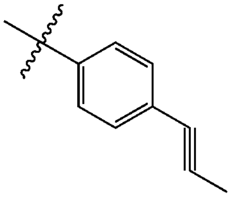 [SMILES: *c1ccc(C#CC)cc1] | (500 MHz, Chloroform-d) δ 7.73 (d, J = 7.5 Hz, 2H), 7.67 (d, J = 7.5 Hz, 2H), 7.05 (s, 1H), 5.51 (s, 1H), 1.86 (s, 3H). |
| 23 | $CF_3$ | 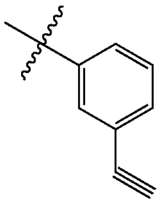 [SMILES: *c1cccc(C#C)c1] | (500 MHz, Chloroform-d) δ 7.79 (dd, J = 2.0, 1.5 Hz, 1H), 7.57-7.35 (m, 3H), 7.06 (s, 1H), 5.53 (s, 1H), 3.14 (s, 1H). |

TABLE 1-continued

Structure and $^1$HNMR data of Compound I

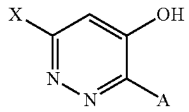

I

| No. | X | A | $^{1}$H NMR |
| --- | --- | --- | --- |
| 24 | $CF_3$ | 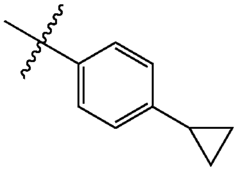 [SMILES: *c1ccc(C2CC2)cc1] | (500 MHz, Chloroform-d) δ 7.47 (d, J = 7.5 Hz, 2H), 7.34 (d, J = 7.5 Hz, 2H), 7.06 (s, 1H), 5.53 (s, 1H), 1.93-1.84 (m, 1H), 1.20-1.11 (m, 2H), 0.92-0.83 (m, 2H). |
| 25 | $CF_3$ | 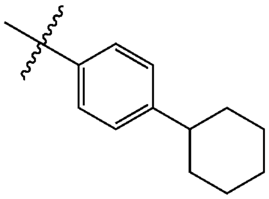 [SMILES: *c1ccc(C2CCCCC2)cc1] | (500 MHz, Chloroform-d) δ 7.56 (d, J = 7.5 Hz, 2H), 7.44 (d, J = 7.5 Hz, 2H), 7.00 (s, 1H), 5.76 (s, 1H), 2.60-2.51 (m, 1H), 1.94-1.81 (m, 8H), 1.81-1.71 (m, 2H). |
| 26 | $CF_3$ | 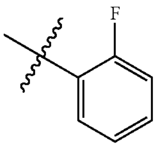 | (500 MHz, Chloroform-d) δ 7.60-7.51 (m, 1H), 7.39-7.16 m, 3H), 7.09 (s, 1H), 5.81 (s, 1H). |
| 27 | $CF_3$ | 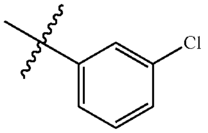 [SMILES: *c1cccc(Cl)c1] | (500 MHz, Chloroform-d) δ 7.82-7.68 (m, 1H), 7.73 (dd, J = 2.0, 1.5 Hz, 1H), 7.42-7.37 (m, 2H), 7.07 (s, 1H), 5.51 (s, 1H). |
| 28 | $CF_3$ | 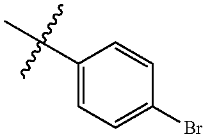 [SMILES: *c1ccc(Br)cc1] | (500 MHz, Chloroform-d) δ 7.70 (d, J = 7.5 Hz, 2H), 7.57 (d, J = 7.5 Hz, 2H), 7.00 (s, 1H), 5.78 (s, 1H). |
| 29 | $CF_3$ | 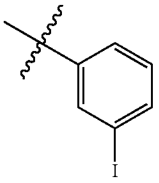 [SMILES: *c1cccc(I)c1] | (500 MHz, Chloroform-d) δ 7.99 (dd, J = 2.0, 1.5 Hz, 1H), 7.83-7.47 (m, 2H), 7.16-7.03 (m, 1H), 7.06 (s, 1H), 5.49 (s, 1H). |
| 30 | $CF_3$ | 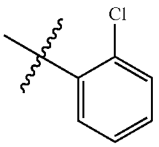 [SMILES: *c1ccccc1Cl] | (500 MHz, Chloroform-d) δ 7.49-7.39 (m, 3H), 7.29-7.17 (m, 1H), 7.04 (s, 1H), 5.94 (s, 1H). |
| 31 | $CF_3$ | 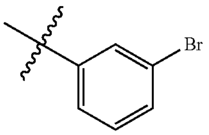 [SMILES: *c1cccc(Br)c1] | (500 MHz, Chloroform-d) δ 7.84 (dd, J = 2.0, 1.5 Hz, 1H), 7.64-7.31 (m, 1H), 7.01 (s, 1H), 5.80 (s, 1H). |

TABLE 1-continued

Structure and $^{1}$HNMR data of Compound I

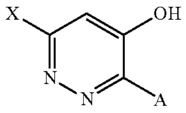

I

| No. | X | A | $^{1}$H NMR |
|---|---|---|---|
| 32 | $CF_3$ | 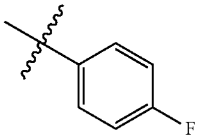 [SMILES: *c1ccc(F)cc1] | (500 MHz, Chloroform-d) δ 7.44-7.16 (m, 2H), 7.11-6.95 (m, 2H), 7.07 (s, 2H), 5.48 (s, 1H). |
| 33 | $CF_3$ | 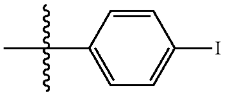 [SMILES: *c1ccc(I)cc1] | (500 MHz, Chloroform-d) δ 7.89 (d, J = 7.5 Hz, 2H), 7.34 (d, J = 7.5 Hz, 2H), 7.06 (s, 1H), 5.47 (s, 1H). |
| 34 | $CF_3$ | 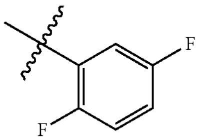 [SMILES: *c1cc(F)ccc1F] | (500 MHz, Chloroform-d) δ 7.45-7.38 (m, 2H), 7.30-7.14 (m, 1H), 7.01 (s, 1H), 5.68 (s, 1H). |
| 35 | $CF_3$ | 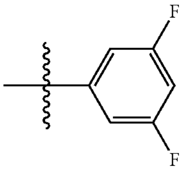 [SMILES: *c1cc(F)cc(F)c1] | (500 MHz, Chloroform-d) δ 7.41-7.35 (m, 2H), 7.02 (s, 1H), 6.95-6.76 (m, 1H), 5.82 (s, 1H). |
| 36 | $CF_3$ | 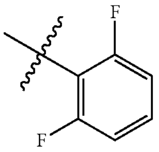 [SMILES: *c1c(F)cccc1F] | (500 MHz, Chloroform-d) δ 7.71-7.57 (m, 1H), 7.22-7.06 (m, 2H), 7.11 (s, 1H), 5.20 (s, 1H). |
| 37 | $CF_3$ | 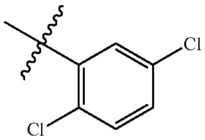 [SMILES: *c1cc(Cl)ccc1Cl] | (500 MHz, Chloroform-d) δ 7.52-7.44 (m, 3H), 7.04 (s, 1H), 5.94 (s, 1H). |
| 38 | $CF_3$ | 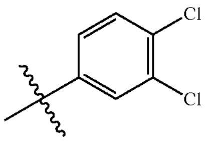 [SMILES: *c1ccc(Cl)c(Cl)c1] | (500 MHz, Chloroform-d) δ 7.69 (d, J = 2.0 Hz, 1H), 7.35 (dd, J = 7.5, 2.0 Hz, 1H), 7.26 (d, J = 7.5 Hz, 1H), 7.01 (s, 1H), 5.79 (s, 1H). |
| 39 | $CF_3$ | 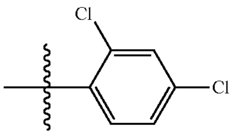 [SMILES: *c1ccc(Cl)cc1Cl] | (500 MHz, Chloroform-d) δ 7.53 (d, J = 2.0 Hz, 1H), 7.48 (d, J = 7.5 Hz, 1H), 7.33 (dd, J = 7.5, 2.0 Hz, 1H), 7.04 (s, 1H), 5.93 (s, 1H). |
| 40 | $CF_3$ | 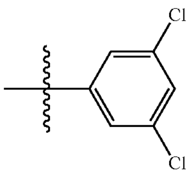 [SMILES: *c1cc(Cl)cc(Cl)c1] | (500 MHz, Chloroform-d) δ 7.71-7.45 (m, 3H), 7.01 (s, 1H), 5.81 (s, 1H). |

TABLE 1-continued
Structure and ¹HNMR data of Compound I
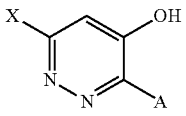
I
| No. | X | A | ¹H NMR |
|---|---|---|---|
| 41 | $CF_3$ | 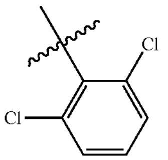 [SMILES: *c1c(Cl)cccc1Cl] | (500 MHz, Chloroform-d) δ 7.48-7.41 (m, 3H), 7.03 (s, 1H), 5.58 (s, 1H). |
| 42 | $CF_3$ | 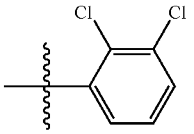 [SMILES: *c1cccc(Cl)c1Cl] | (500 MHz, Chloroform-d) δ 7.70 (dd, J = 7.5, 2.0 Hz, 1H), 7.36 (dd, J = 8.0, 2.0 Hz, 1H), 7.28 (dd, J = 8.0, 7.5 Hz, 1H), 7.04 (s, 1H), 5.92 (s, 1H). |
| 43 | $CF_3$ | 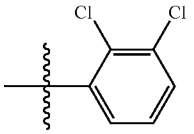 [SMILES: *c1cccc(Cl)c1Cl] | (500 MHz, Chloroform-d) δ 7.54-7.40 (m, 2H), 7.15-7.09 (m, 1H), 7.11 (s, 1H), 5.61 (s, 1H). |
| 44 | $CF_3$ | 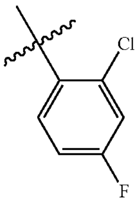 [SMILES: *c1ccc(F)cc1Cl] | (500 MHz, Chloroform-d) δ 7.48-7.40 (m, 2H), 7.06-6.99 (m, 2H), 5.92 (s, 1H). |
| 45 | $CF_3$ | 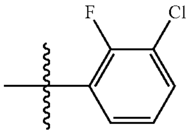 [SMILES: *c1cccc(Cl)c1F] | (500 MHz, Chloroform-d) δ 7.49-7.43 (m, 2H), 7.14-7.02 (m, 1H), 7.02 (s, 1H), 5.47 (s, 1H). |
| 46 | $CF_3$ | 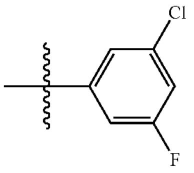 [SMILES: *c1cc(F)cc(Cl)c1] | (500 MHz, Chloroform-d) δ 7.59-7.49 (m, 1H), 7.36-7.21 (m, 1H), 7.02 (s, 1H), 5.82 (s, 1H). |
| 47 | $CF_3$ | 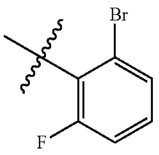 [SMILES: *c1c(F)cccc1Br] | (500 MHz, Chloroform-d) δ 7.41-7.18 (m, 3H), 7.04 (s, 1H), 5.51 (s, 1H). |
| 48 | $CF_3$ | 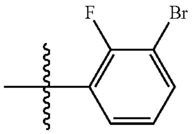 [SMILES: *c1cccc(Br)c1F] | (500 MHz, Chloroform-d) δ 7.57-7.41 (m, 2H), 7.12 (s, 1H), 7.07-6.93 (m, 1H), 5.48 (s, 1H). |

TABLE 1-continued
Structure and $^1$HNMR data of Compound I
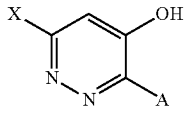
I
| No. | X | A | $^1$H NMR |
|---|---|---|---|
| 49 | $CF_3$ | 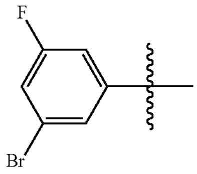 [SMILES: *c1cc(F)cc(Br)c1] | (500 MHz, Chloroform-d) δ 7.62-7.53 (m, 2H), 7.40-7.22 (m, 1H), 7.01 (s, 1H), 5.81 (s, 1H). |
| 50 | $CF_3$ | 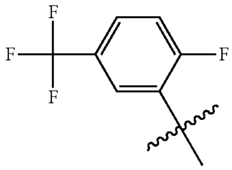 [SMILES: *c1cc(C(F)(F)F)ccc1F] | (500 MHz, Chloroform-d) δ 7.83-7.58 (m, 2H), 7.25-7.11 (m, 1H), 7.02 (s, 1H), 5.52 (s, 1H). |
| 51 | $CF_3$ | 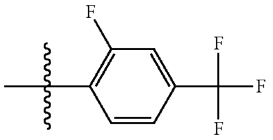 [SMILES: *c1ccc(C(F)(F)F)cc1F] | (500 MHz, Chloroform-d) δ 7.59-7.46 (m, 2H), 7.41-7.35 (m, 1H), 7.01 (s, 1H), 5.68 (s, 1H). |
| 52 | $CF_3$ | 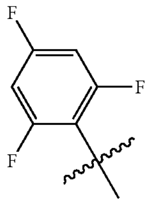 [SMILES: *c1c(F)cc(F)cc1F] | (500 MHz, Chloroform-d) δ 7.00 (s, 1H), 6.75-6.52 (m, 2H), 5.64 (s, 1H). |
| 53 | $CF_3$ | 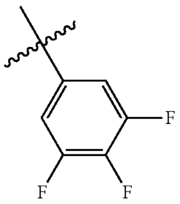 [SMILES: *c1cc(F)c(F)c(F)c1] | (500 MHz, Chloroform-d) δ 7.28-7.20 (m, 2H), 7.02 (s, 1H), 5.84 (s, 1H). |
| 54 | $CF_3$ | 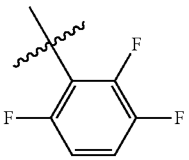 [SMILES: *c1c(F)ccc(F)c1F] | (500 MHz, Chloroform-d) δ 7.17-7.03 (m, 3H), 6.98-6.77 (m, 1H), 4.92 (s, 1H). |
| 55 | $CF_3$ | 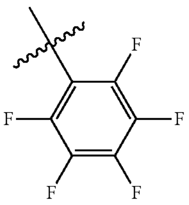 [SMILES: *c1c(F)c(F)c(F)c(F)c1F] | (500 MHz, Chloroform-d) δ 7.03 (s, 1H), 5.57 (s, 1H). |

TABLE 1-continued

Structure and $^1$HNMR data of Compound I

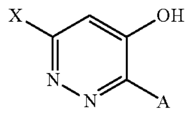

I

| No. | X | A | $^1$H NMR |
|---|---|---|---|
| 56 | $CF_3$ | 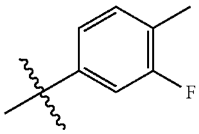 [SMILES: *c1ccc(C)c(F)c1] | (500 MHz, Chloroform-d) δ 7.34 (dd, J = 9.0, 1.5 Hz, 1H), 7.24-7.07 (m, 1H), 7.17 (dd, J = 7.5, 2.5 Hz, 1H), 7.07 (s, 1H), 5.45 (s, 1H), 2.31 (s, 3H). |
| 57 | $CF_3$ | 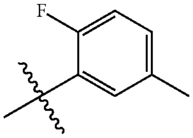 [SMILES: *c1cc(C)ccc1F] | (500 MHz, Chloroform-d) δ 7.48-7.42 (m, 1H), 7.25-7.10 (m, 2H), 7.02 (s, 1H), 5.46 (s, 1H), 2.50 (s, 3H). |
| 58 | $CF_3$ | 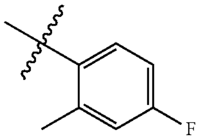 [SMILES: *c1ccc(F)cc1C] | (500 MHz, Chloroform-d) δ 7.22-7.08 (m, 3H), 7.01 (s, 1H), 5.66 (s, 1H), 2.44 (s, 3H). |
| 59 | $CF_3$ | 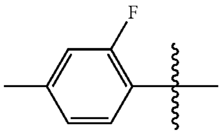 [SMILES: *c1ccc(C)cc1F] | (500 MHz, Chloroform-d) δ 7.55-7.40 (m, 1H), 7.09 (s, 1H), 7.03-6.95 (m, 2H), 5.79 (s, 1H), 2.35 (s, 3H). |
| 60 | $CF_3$ | 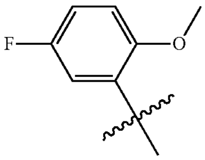 [SMILES: *c1cc(F)ccc1OC] | (500 MHz, Chloroform-d) δ 8.74-8.55 (m, 1H), 7.44-7.17 (m, 2H), 7.09 (s, 1H), 5.89 (s, 1H), 3.90 (s, 3H). |
| 61 | $CF_3$ | 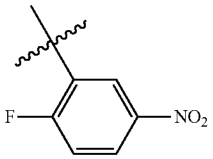 [SMILES: *c1cc([N+](=O)[O-])ccc1F] | (500 MHz, Chloroform-d) δ 8.54 (dd, J = 5.5, 2.0 Hz, 1H), 8.27-8.03 (m, 1H), 7.44 (dd, J = 10.5, 7.5 Hz, 1H), 7.13 (s, 1H), 5.37 (s, 1H). |
| 62 | $CF_3$ | 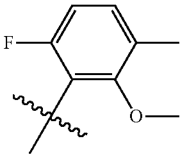 [SMILES: *c1c(F)ccc(C)c1OC] | (500 MHz, Chloroform-d) δ 7.46-7.22 (m, 1H), 7.09-6.96 (m, 2H), 6.92-6.76 (m, 1H), 5.58 (s, 1H), 3.90 (s, 3H). |
| 63 | $CF_3$ | 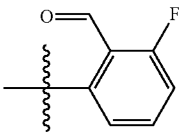 [SMILES: *c1cccc(F)c1C=O] | (500 MHz, Chloroform-d) δ 7.74-7.64 (m, 2H), 7.39-7.22 (m, 2H), 6.51 (s, 1H). |
| 64 | $CF_3$ | 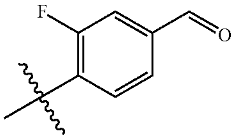 [SMILES: *c1ccc(C=O)cc1F] | (500 MHz, Chloroform-d) δ 7.71-7.64 (m, 2H), 7.61-7.46 (m, 1H), 7.11 (s, 1H), 5.86 (s, 1H), 5.60 (s, 1H). |

TABLE 1-continued

Structure and $^1$HNMR data of Compound I

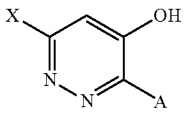

I

| No. | X | A | $^1$H NMR |
|---|---|---|---|
| 65 | $CF_3$ | 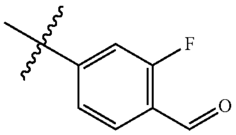 [SMILES: *c1ccc(C=O)c(F)c1] | (500 MHz, Chloroform-d) δ 7.93-7.78 (m, 1H), 7.60-7.39 (m, 2H), 7.07 (s, 1H), 5.84 (s, 1H), 5.41 (s, 1H). |
| 66 | $CF_3$ | 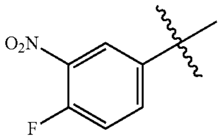 [SMILES: *c1ccc(F)c([N+](=O)[O-])c1] | (500 MHz, Chloroform-d) δ 8.27 (dd, J = 5.5, 2.0 Hz, 1H), 7.76-7.61 (m, 1H), 7.42 (dd, J = 10.5, 7.5 Hz, 1H), 7.06 (s, 1H), 5.47 (s, 1H). |
| 67 | $CF_3$ | 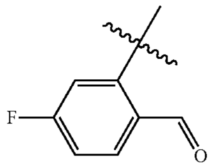 [SMILES: *c1cc(F)ccc1C=O] | (500 MHz, Chloroform-d) δ 7.73-7.56 (m, 1H), 7.51 (dd, J = 11.0, 2.0 Hz, 1H), 7.31 (s, 1H), 7.25-7.10 (m, 1H), 6.57 (s, 1H). |
| 68 | $CF_3$ | 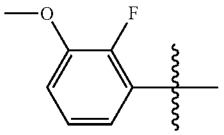 [SMILES: *c1cccc(OC)c1F] | (500 MHz, Chloroform-d) δ 7.30-7.22 (m, 1H), 7.11-7.00 (m, 3H), 5.74 (s, 1H), 3.90 (s, 3H). |
| 69 | $CF_3$ | 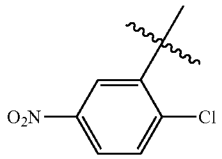 [SMILES: *c1cc([N+](=O)[O-])ccc1Cl] | (500 MHz, Chloroform-d) δ 8.42 (d, J = 2.0 Hz, 1H), 8.19 (dd, J = 7.5, 2.0 Hz, 1H), 7.76 (d, J = 7.5 Hz, 1H), 7.06 (s, 1H), 5.75 (s, 1H). |
| 70 | $CF_3$ | 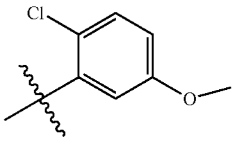 [SMILES: *c1cc(OC)ccc1Cl] | (500 MHz, Chloroform-d) δ 7.54 (d, J = 7.5 Hz, 1H), 7.15 (d, J = 2.0 Hz, 1H), 7.00 (s, 1H), 6.90 (dd, J = 7.5, 2.0 Hz, 1H), 5.62 (s, 1H), 3.87 (s, 3H). |
| 71 | $CF_3$ | 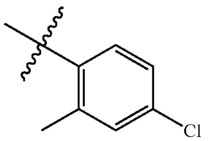 [SMILES: *c1ccc(Cl)cc1C] | (500 MHz, Chloroform-d) δ 7.39-7.32 (m, 2H), 7.21 (dd, J = 7.5, 2.0 Hz, 1H), 7.04 (s, 1H), 5.66 (s, 1H), 2.34 (s, 3H). |
| 72 | $CF_3$ | 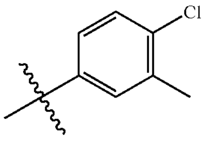 | (500 MHz, Chloroform-d) δ 7.48-7.42 (m, 2H), 7.25 (dd, J = 7.5, 2.0 Hz, 1H), 7.07 (s, 1H), 5.47 (s, 1H), 2.32 (s, 3H). |
| 73 | $CF_3$ | 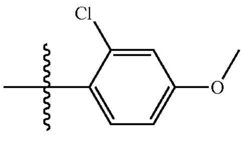 [SMILES: *c1ccc(OC)cc1Cl] | (500 MHz, Chloroform-d) δ 7.60 (d, J = 7.5 Hz, 1H), 7.07 (d, J = 2.0 Hz, 1H), 7.00 (s, 1H), 6.84 (dd, J = 7.5, 2.0 Hz, 1H), 5.63 (s, 1H), 3.81 (s, 3H). |

TABLE 1-continued

Structure and $^1$HNMR data of Compound I

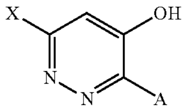

I

| No. | X | A | $^1$H NMR |
|---|---|---|---|
| 74 | $CF_3$ | 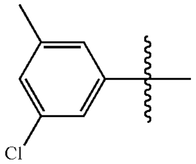 [SMILES: *c1cc(C)cc(Cl)c1] | (500 MHz, Chloroform-d) δ 7.60 (dd, J = 2.0, 1.5 Hz, 1H), 7.38-7.28 (m, 2H), 7.07 (s, 1H), 5.47 (s, 1H), 2.34 (s, 3H). |
| 75 | $CF_3$ | 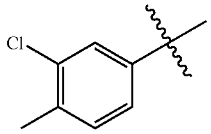 [SMILES: *c1ccc(C)c(Cl)c1] | (500 MHz, Chloroform-d) δ 7.50 (d, J = 2.0 Hz, 1H), 7.29 (dd, J = 7.5, 2.0 Hz, 1H), 7.23 (d, J = 7.5 Hz, 1H), 7.07 (s, 1H), 5.48 (s, 1H), 2.28 (s, 3H). |
| 76 | $CF_3$ | 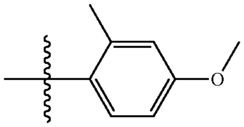 [SMILES: *c1ccc(OC)cc1C] | (500 MHz, Chloroform-d) δ 7.38 (d, J = 7.5 Hz, 1H), 7.00 (s, 1H), 6.88-6.80 (m, 2H), 5.61 (s, 1H), 3.71 (s, 3H), 2.34 (s, 3H). |
| 77 | $CF_3$ | 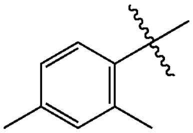 | (500 MHz, Chloroform-d) δ 7.37 (d, J = 7.5 Hz, 1H), 7.10-7.02 (m, 2H), 7.04 (s, 1H), 5.68 (s, 1H), 2.36-2.29 (m, 6H). |
| 78 | $CF_3$ | 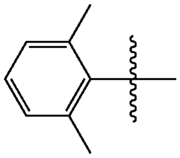 [SMILES: *c1c(C)cccc1C] | (500 MHz, Chloroform-d) δ 7.33-7.16 (m, 3H), 7.03 (s, 1H), 5.60 (s, 1H), 2.30 (s, 6H). |
| 79 | $CF_3$ | 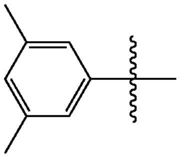 [SMILES: *c1cc(C)cc(C)c1] | (500 MHz, Chloroform-d) δ 7.52-7.38 (m, 3H), 7.01 (s, 1H), 5.78 (s, 1H), 1.33 (s, 6H). |
| 80 | $CF_3$ | 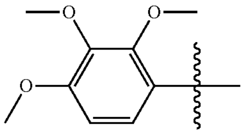 | (500 MHz, Chloroform-d) δ 8.97 (s, 1H), 7.09 (s, 1H), 7.03-6.95 (m, 2H), 3.82 (s, 3H), 3.76 (s, 3H), 3.72 (s, 3H). |
| 81 | $CF_3$ | 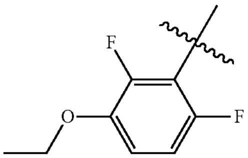 [SMILES: *c1c(F)ccc(OCC)c1F] | (500 MHz, Chloroform-d) δ 7.02-6.91 (m, 3H), 5.63 (s, 1H), 4.34 (q, J = 8.0 Hz, 2H), 1.61 (t, J = 8.0 Hz, 3H). |

TABLE 1-continued

Structure and $^{1}$HNMR data of Compound I

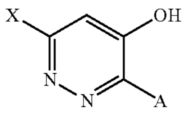

I

| No. | X | A | $^{1}$H NMR |
| --- | --- | --- | --- |
| 82 | $CF_3$ | 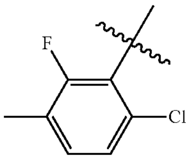 [SMILES: *c1c(Cl)ccc(C)c1F] | (500 MHz, Chloroform-d) δ 7.25 (d, J = 7.5 Hz, 1H), 7.20-7.13 (m, 1H), 7.00 (s, 1H), 5.60 (s, 1H), 2.30 (s, 3H). |
| 83 | $CF_3$ | 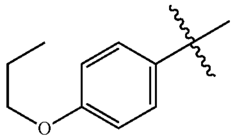 [SMILES: *c1ccc(OCCC)cc1] | (500 MHz, Chloroform-d) δ 7.57 (d, J = 7.5 Hz, 2H), 7.09 (d, J = 7.5 Hz, 2H), 7.00 (s, 1H), 5.76 (s, 1H), 3.99 (t, J = 7.5 Hz, 2H), 1.75-1.61 (m, 2H), 1.14 (t, J = 8.0 Hz, 3H). |
| 84 | $CF_3$ | 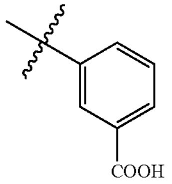 [SMILES: *c1cccc(C(=O)O)c1] | (500 MHz, Chloroform-d) δ 7.57-7.50 (m, 2H), 7.09-7.03 (m, 2H), 7.00 (s, 1H), 5.76 (s, 1H). |
| 85 | $CF_3$ | 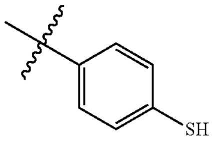 [SMILES: *c1ccc(S)cc1] | (500 MHz, Chloroform-d) δ 7.47-7.41 (m, 2H), 7.41-7.35 (m, 2H), 7.06 (s, 1H). |
| 86 | $CF_3$ | 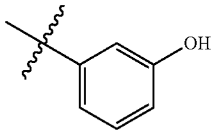 [SMILES: *c1cccc(O)c1] | (500 MHz, Chloroform-d) δ 7.19 (dd, J = 8.0, 7.5 Hz, 1H), 7.13-7.02 (m, 3H), 6.93-6.78 (m, 1H). |
| 87 | $CF_3$ | 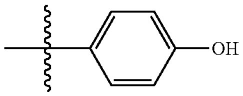 [SMILES: *c1ccc(O)cc1] | (500 MHz, Chloroform-d) δ 7.38 (d, J = 7.5 Hz, 2H), 7.06 (s, 1H), 6.84 (d, J = 7.5 Hz, 2H), 5.57 (s, 1H), 4.92 (s, 1H). |
| 88 | $CF_3$ | 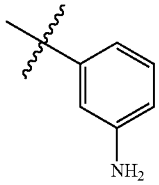 [SMILES: *c1cccc(N)c1] | (500 MHz, Chloroform-d) δ 7.15-7.01 (m, 2H), 7.03-6.97 (m, 1H), 6.72-6.57 (m, 2H), 5.77 (s, 1H), 4.14 (s, 2H). |
| 89 | $CF_3$ | 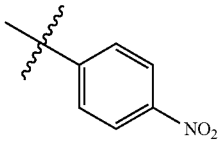 [SMILES: *c1ccc([N+](=O)[O-])cc1] | (500 MHz, Chloroform-d) δ 8.28 (d, J = 7.5 Hz, 2H), 7.87 (d, J = 7.5 Hz, 2H), 7.02 (s, 1H), 5.84 (s, 1H). |

TABLE 1-continued

Structure and $^1$HNMR data of Compound I

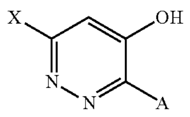

I

| No. | X | A | $^1$H NMR |
| --- | --- | --- | --- |
| 90 | $CF_3$ | 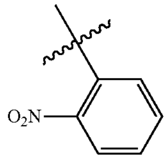 [SMILES: *c1ccccc1[N+](=O)[O-]] | (500 MHz, Chloroform-d) δ 8.28-8.22 (m, 2H), 7.87-7.80 (m, 2H), 7.02 (s, 1H), 5.84 (s, 1H). |
| 91 | $CF_3$ | 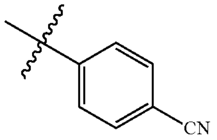 [SMILES: *c1ccc(C#N)cc1] | (500 MHz, Chloroform-d) δ 8.02 (d, J = 7.5 Hz, 2H), 7.77 (d, J = 7.5 Hz, 2H), 7.02 (s, 1H), 5.82 (s, 1H). |
| 92 | $CF_3$ | 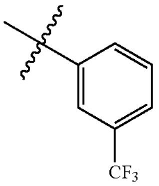 [SMILES: *c1cccc(C(F)(F)F)c1] | (500 MHz, Chloroform-d) δ 7.99-7.91 (m, 2H), 7.75-7.60 (m, 2H), 7.07 (s, 1H), 5.52 (s, 1H). |
| 93 | $CF_3$ | 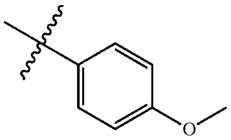 [SMILES: *c1ccc(OC)cc1] | (500 MHz, Chloroform-d) δ 7.48 (d, J = 7.5 Hz, 2H), 7.06 (s, 1H), 6.80 (d, J = 7.5 Hz, 2H), 5.56 (s, 1H), 3.80 (s, 3H). |
| 94 | $CF_3$ | 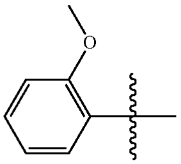 [SMILES: *c1ccccc1OC] | (500 MHz, Chloroform-d) δ 7.66-7.40 (m, 4H), 7.08 (s, 1H), 5.87 (s, 1H), 3.90 (s, 3H). |
| 95 | $CF_3$ | 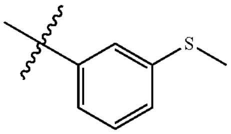 [SMILES: *c1cccc(SC)c1] | (500 MHz, Chloroform-d) δ 7.68 (dd, J = 2.0, 1.5 Hz, 1H), 7.46-7.35 (m, 3H), 7.01 (s, 1H), 5.80 (s, 1H), 2.50 (s, 3H). |
| 96 | $CF_3$ | 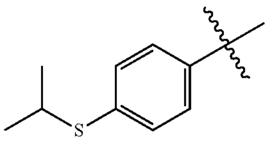 [SMILES: *c1ccc(SC(C)C)cc1] | (500 MHz, Chloroform-d) δ 7.61 (d, J = 7.5 Hz, 2H), 7.44 (d, J = 7.5 Hz, 2H), 7.01 (s, 1H), 5.77 (s, 1H), 3.25 (hept, J = 7.0 Hz, 1H), 1.40 (d, J = 7.0 Hz, 6H). |
| 97 | $CF_3$ | 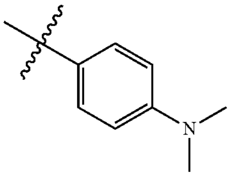 [SMILES: *c1ccc(N(C)C)cc1] | (500 MHz, Chloroform-d) δ 7.59 (d, J = 7.5 Hz, 2H), 7.05 (s, 1H), 6.70 (d, J = 7.5 Hz, 2H), 5.56 (s, 1H), 3.02 (s, 6H). |

TABLE 1-continued

Structure and $^1$HNMR data of Compound I

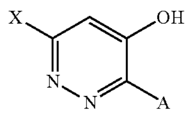

I

| No. | X | A | $^1$H NMR |
|---|---|---|---|
| 98 | $CF_3$ | 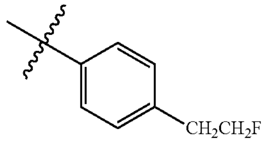 | (500 MHz, Chloroform-d) δ 7.49 (d, J = 7.5 Hz, 2H), 7.16 (d, J = 7.5 Hz, 2H), 7.07 (s, 1H), 5.53 (s, 1H), 4.47-4.37 (m, 2H), 2.76-2.69 (m, 2H). |
| 99 | $CF_3$ | 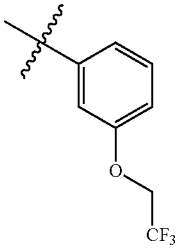 [SMILES: *c1cccc(OCC(F)(F)F)c1] | (500 MHz, Chloroform-d) δ 7.33-7.25 (m, 2H), 7.20-6.96 (m, 2H), 5.61 (s, 1H), 4.46 (q, J = 9.5 Hz, 2H). |
| 100 | $CF_3$ | 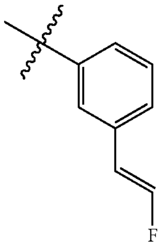 [SMILES: *c1cccc(/C=C/F)c1] | |
| 101 | $CF_3$ | 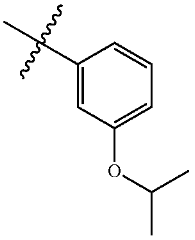 [SMILES: *c1cccc(OC(C)C)c1] | (500 MHz, Chloroform-d) δ 7.35-7.23 (m, 3H), 7.02-6.94 (m, 2H), 5.76 (s, 1H), 4.41 (hept, J = 7.0 Hz, 1H), 1.29 (d, J = 7.0 Hz, 6H). |
| 102 | $CF_3$ | 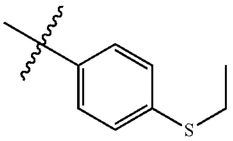 [SMILES: *c1ccc(SCC)cc1] | (500 MHz, Chloroform-d) δ 7.53 (d, J = 7.0 Hz, 2H), 7.41 (d, J = 7.0 Hz, 2H), 7.06 (s, 1H), 5.54 (s, 1H), 2.83 (q, J = 8.0 Hz, 2H), 1.38 (t, J = 8.0 Hz, 3H). |
| 103 | $CF_3$ | 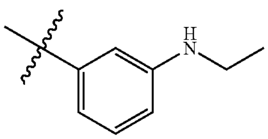 [SMILES: *c1cccc(NCC)c1] | (500 MHz, Chloroform-d) δ 7.19 (dd, J = 7.5, 7.0 Hz, 1H), 7.06 (s, 1H), 6.92-6.70 (m, 2H), 6.63 (dd, J = 2.0, 1.5 Hz, 1H), 5.62 (s, 1H), 4.09 (s, 1H), 3.36 (q, J = 8.0 Hz, 2H), 1.23 (t, J = 8.0 Hz, 3H). |
| 104 | $CF_3$ | 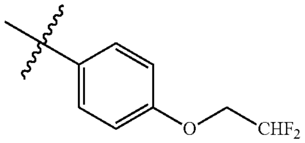 [SMILES: *c1ccc(OCC(F)F)cc1] | (500 MHz, Chloroform-d) δ 7.49 (d, J = 7.0 Hz, 2H), 7.19-7.03 (m, 3H), 5.47 (s, 1H), 5.14-4.91 (m, 1H), 4.04-3.91 (m, 2H). |

TABLE 1-continued

Structure and $^1$HNMR data of Compound I

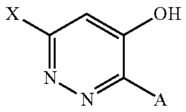

I

| No. | X | A | $^1$H NMR |
|---|---|---|---|
| 105 | $CF_3$ | 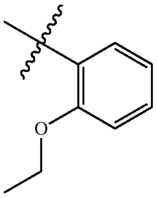 [SMILES: *c1ccccc1OCC] | (500 MHz, Chloroform-d) δ 8.85 (s, 1H), 7.58 (dd, J = 7.5, 2.0 Hz, 1H), 7.40-7.18 (m, 2H), 7.11 (dd, J = 7.0, 2.0 Hz, 1H), 7.08 (s, 1H), 4.38 (q, J = 8.0 Hz, 2H), 1.45 (t, J = 8.0 Hz, 3H). |
| 106 | $CF_3$ | 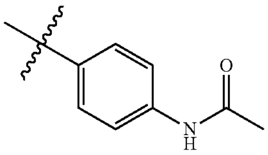 [SMILES: *c1ccc(NC(C)=O)cc1] | (500 MHz, Chloroform-d) δ 7.96 (d, J = 8.0 Hz, 2H), 7.73 (s, 1H), 7.69 (d, J = 8.0 Hz, 2H), 7.01 (s, 1H), 5.78 (s, 1H), 2.10 (s, 3H). |
| 107 | $CF_3$ | 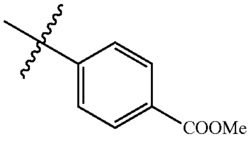 [SMILES: *c1ccc(C(=O)OC)cc1] | (500 MHz, Chloroform-d) δ 8.08 (d, J = 7.0 Hz, 2H), 7.61 (d, J = 7.0 Hz, 2H), 7.07 (s, 1H), 5.49 (s, 1H), 3.95 (s, 3H). |
| 108 | $CF_3$ | 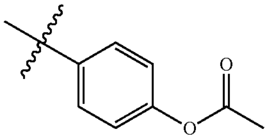 [SMILES: *c1ccc(OC(C)=O)cc1] | (500 MHz, Chloroform-d) δ 7.51 (d, J = 7.5 Hz, 2H), 7.06 (d, J = 7.5 Hz, 2H), 7.00 (s, 1H), 5.61 (s, 1H), 2.29 (s, 3H). |
| 109 | $CF_3$ | 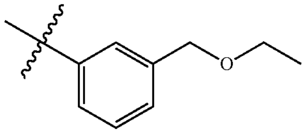 [SMILES: *c1cccc(COCC)c1] | (500 MHz, Chloroform-d) δ 7.71 (dd, J = 2.0, 1.5 Hz, 1H), 7.62-7.55 (m, 2H), 7.43 (dd, J = 8.0, 7.5 Hz, 1H), 7.01 (s, 1H), 5.77 (s, 1H), 4.47 (s, 2H), 3.58 (q, J = 8.0 Hz, 2H), 1.18 (t, J = 8.0 Hz, 3H). |
| 110 | $CF_3$ | 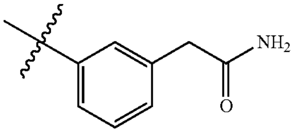 [SMILES: *c1cccc(CC(N)=O)c1] | (500 MHz, Chloroform-d) δ 7.84 (dd, J = 2.5, 1.5 Hz, 1H), 7.47-7.38 (m, 3H), 7.01 (s, 1H), 5.84 (s, 1H), 5.69 (s, 2H), 3.52 (s, 2H). |
| 111 | $CF_3$ | 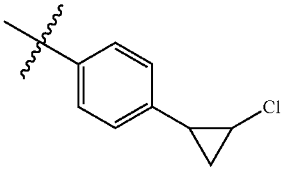 [SMILES: *c1ccc(C2CC2Cl)cc1] | (500 MHz, Chloroform-d) δ 7.49 (d, J = 7.5 Hz, 2H), 7.39 (d, J = 7.5 Hz, 2H), 7.06 (s, 1H), 5.54 (s, 1H), 3.48-3.33 (m, 1H), 2.43-2.29 (m, 1H), 1.51-1.33 (m, 1H). |
| 112 | $CF_3$ | 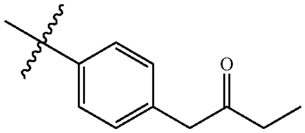 [SMILES: *c1ccc(CC(=O)CC)cc1] | (500 MHz, Chloroform-d) δ 7.58 (d, J = 7.5 Hz, 2H), 7.51 (d, J = 7.5 Hz, 2H), 7.06 (s, 1H), 5.53 (s, 1H), 3.71 (s, 2H), 2.47 (q, J = 8.0 Hz, 2H), 1.16 (t, J = 8.0 Hz, 3H). |

TABLE 1-continued

Structure and $^1$HNMR data of Compound I

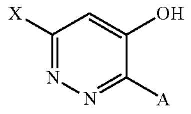

I

| No. | X | A | $^{1}$H NMR |
|---|---|---|---|
| 113 | $CF_3$ | 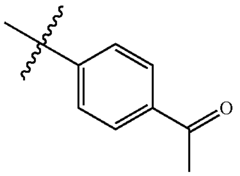 [SMILES: *c1ccc(C(C)=O)cc1] | (500 MHz, Chloroform-d) δ 7.99 (d, J = 7.5 Hz, 2H), 7.61 (d, J = 7.5 Hz, 2H), 7.07 (s, 1H), 5.58 (s, 1H), 2.51 (s, 3H). |
| 114 | $CF_3$ | 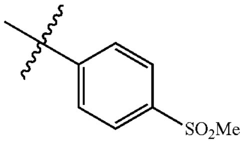 [SMILES: *c1ccc(S(C)(=O)=O)cc1] | (500 MHz, Chloroform-d) δ 7.98 (d, J = 7.5 Hz, 2H), 7.85 (d, J = 7.5 Hz, 2H), 7.07 (s, 1H), 5.53 (s, 1H), 3.30 (s, 3H). |
| 115 | $CF_3$ | 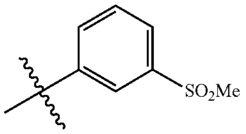 [SMILES: *c1cccc(S(C)(=O)=O)c1] | (500 MHz, Chloroform-d) δ 8.19 (dd, J = 2.0, 1.5 Hz, 1H), 8.04-7.80 (m, 2H), 7.66 (dd, J = 8.0, 7.5 Hz, 1H), 7.07 (s, 1H), 5.43 (s, 1H), 3.25 (s, 3H). |
| 116 | $CF_3$ | 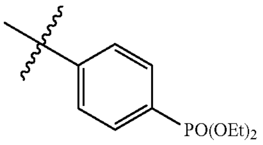 | (500 MHz, Chloroform-d) δ 7.95 (d, J = 7.5 Hz, 2H), 7.71 (d, J = 7.5 Hz, 2H), 7.07 (s, 1H), 5.53 (s, 1H), 4.07 (q, J = 6.5 Hz, 4H), 1.17 (t, J = 6.5 Hz, 6H). |
| 117 | $CF_3$ | 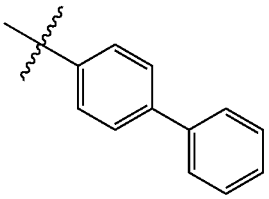 [SMILES: *c1ccc(-c2ccccc2)cc1] | (500 MHz, Chloroform-d) δ 7.86-7.79 (m, 4H), 7.62-7.56 (m, 2H), 7.37-7.29 (m, 3H), 7.07 (s, 1H), 5.62 (s, 1H). |
| 118 | $CF_3$ | 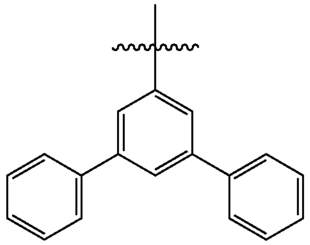 [SMILES: *c1cc(-c2ccccc2)cc(-c2ccccc2)c1] | (500 MHz, Chloroform-d) δ 8.09-7.96 (m, 3H), 7.62-7.56 (m, 4H), 7.44-7.28 (m, 4H), 7.37-7.29 (m, 2H), 7.02 (s, 1H), 5.84 (s, 1H). |
| 119 | $CF_3$ | 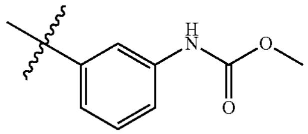 [SMILES: *c1cccc(NC(=O)OC)c1] | (500 MHz, Chloroform-d) δ 7.49-7.38 (m, 3H), 7.28 (dd, J = 2.0, 1.5 Hz, 1H), 7.02 (s, 1H), 6.56 (s, 1H), 5.87 (s, 1H), 3.67 (s, 3H). |

TABLE 1-continued

Structure and $^1$HNMR data of Compound I

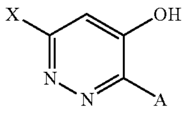

I

| No. | X | A | $^1H$ NMR |
| --- | --- | --- | --- |
| 120 | $CF_3$ | 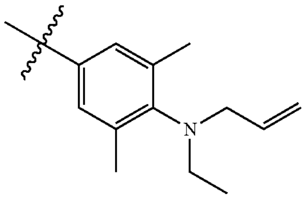 [SMILES: *c1cc(C)c(N(CC)CC=C)c(C)c1] | (500 MHz, Chloroform-d) δ 7.29 (s, 2H), 7.00 (s, 1H), 6.00-5.88 (m, 1H), 5.77 (s, 1H), 5.30-5.21 (m, 1H), 5.15-5.04 (m, 1H), 4.05-3.99 (m, 2H), 3.29 (q, J = 8.0 Hz, 2H), 2.27 (s, 6H), 1.09 (t, J = 8.0 Hz, 3H). |
| 121 | $CF_3$ | 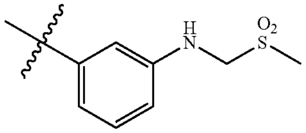 [SMILES: *c1cccc(NCS(C)(=O)=O)c1] | (500 MHz, Chloroform-d) δ 7.23 (dd, J = 7.5, 7.0 Hz, 1H), 7.17-7.11 (m, 1H), 7.07 (s, 1H), 6.92-6.81 (m, 1H), 6.69 (dd, J = 2.0, 1.5 Hz, 1H), 5.54 (s, 1H), 5.18 (s, 2H), 4.22 (s, 1H), 2.97 (s, 3H). |
| 122 | $CF_3$ | 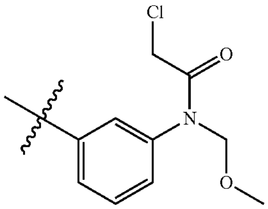 [SMILES: *c1cccc(N(COC)C(=O)CCl)c1] | (500 MHz, Chloroform-d) δ 7.56-7.37 (m, 3H), 7.20 (dd, J = 2.0, 1.5 Hz, 1H), 7.02 (s, 1H), 5.84 (s, 1H), 5.46 (s, 2H), 3.68 (s, 2H), 3.20 (s, 3H). |
| 123 | $CF_3$ | 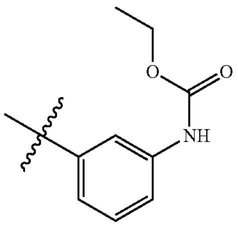 [SMILES: *c1cccc(NC(=O)OCC)c1] | (500 MHz, Chloroform-d) δ 7.42-7.14 (m, 4H), 7.06 (s, 1H), 6.56 (s, 1H), 5.97 (s, 1H), 4.15 (q, J = 8.0 Hz, 2H), 1.26 (t, J = 8.1 Hz, 3H). |
| 124 | $CF_3$ | 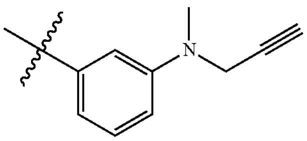 [SMILES: *c1cccc(N(C)CC#C)c1] | (500 MHz, Chloroform-d) δ 7.17 (dd, J = 7.5, 7.0 Hz, 1H), 7.05 (s, 1H), 6.94-6.88 (m, 2H), 6.63 (dd, J = 2.0, 1.5 Hz, 1H), 5.61 (s, 1H), 4.09 (s, 2H), 3.00 (s, 3H), 2.76 (s, 1H). |
| 125 | $CF_3$ | 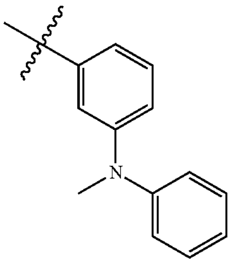 [SMILES: *c1cccc(N(C)c2ccccc2)c1] | (500 MHz, Chloroform-d) δ 7.36-7.29 (m, 1H), 7.25-7.17 (m, 5H), 7.10-7.03 (m, 1H), 7.00 (s, 1H), 6.87-6.80 (m, 2H), 5.74 (s, 1H), 3.35 (s, 3H). |
| 126 | $CF_3$ | 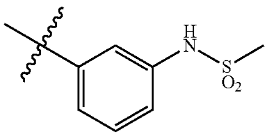 [SMILES: *c1cccc(NS(C)(=O)=O)c1] | (500 MHz, Chloroform-d) δ 7.40-7.23 (m, 3H), 7.05 (s, 1H), 6.52 (dd, J = 2.0, 1.5 Hz, 1H), 6.39 (s, 1H), 6.01 (s, 1H), 2.99 (s, 3H). |

TABLE 1-continued

Structure and $^1$HNMR data of Compound I

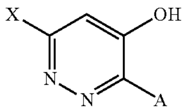
I

| No. | X | A | $^1$H NMR |
|---|---|---|---|
| 127 | $CF_3$ | 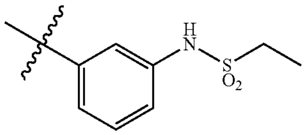 [SMILES: *c1cccc(NS(=O)(=O)CC)c1] | (500 MHz, Chloroform-d) δ 7.20-7.21 (m, 3H), 7.08 (s, 1H), 6.55 (dd, J = 2.0, 1.5 Hz, 1H), 6.38 (s, 1H), 6.05 (s, 1H), 3.45 (q, J = 8.0 Hz, 2H), 1.59 (t, J = 8.0 Hz, 3H). |
| 128 | $CF_3$ | 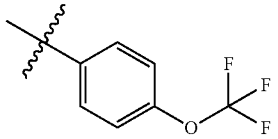 [SMILES: *c1ccc(OC(F)(F)F)cc1] | (500 MHz, Chloroform-d) δ 7.59 (d, J = 7.5 Hz, 2H), 7.27 (d, J = 7.5 Hz, 2H), 7.00 (s, 1H), 5.78 (s, 1H). |
| 129 | $CF_3$ | 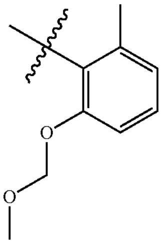 [SMILES: *c1c(C)cccc1OCOC] | (500 MHz, Chloroform-d) δ 7.38 (dd, J = 7.5, 7.0 Hz, 1H), 7.13 (dd, J = 7.5, 2.0 Hz, 1H), 7.09 (s, 1H), 7.07 (dd, J = 7.0, 2.0 Hz, 1H), 6.02 (s, 1H), 5.77 (s, 2H), 3.13 (s, 3H), 2.33 (s, 3H). |
| 130 | $CF_3$ | 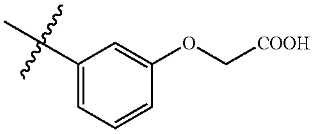 [SMILES: *c1cccc(OCC(=O)O)c1] | (500 MHz, Chloroform-d) δ 7.42-7.37 (m, 1H), 7.33-7.24 (m, 2H), 7.01 (s, 1H), 7.04-6.97 (m, 1H), 5.81 (s, 1H), 4.71 (s, 2H). |
| 131 | $CF_3$ | 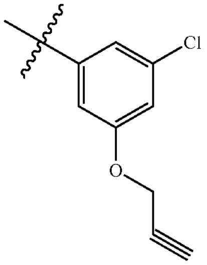 [SMILES: *c1cc(Cl)cc(OCC#C)c1] | (500 MHz, Chloroform-d) δ 7.41 (dd, J = 2.0, 1.5 Hz, 1H), 7.11 (dd, J = 2.5, 2.0 Hz, 1H), 7.06 (d, J = 2.5, 1.5 Hz, 1H), 7.00 (s, 1H), 5.48 (s, 1H), 4.68 (s, 2H), 3.00 (s, 1H). |
| 132 | $CF_3$ | 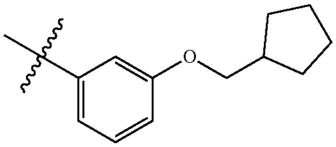 [SMILES: *c1cccc(OCC2CCCC2)c1] | (500 MHz, Chloroform-d) δ 7.33-7.23 (m, 3H), 7.03-6.96 (m, 2H), 5.77 (s, 1H), 3.92 (d, J = 6.5 Hz, 2H), 1.84-1.73 (m, 2H), 1.77-1.61 (m, 3H), 1.65-1.51 (m, 2H), 1.25-1.14 (m, 2H). |
| 133 | $CF_3$ | 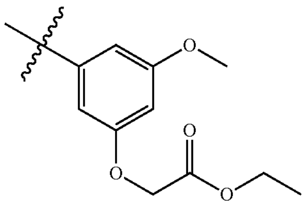 [SMILES: *c1cc(OC)cc(OCC(=O)OCC)c1] | (500 MHz, Chloroform-d) δ 7.07-6.99 (m, 4H), 6.47 (dd, J = 2.0, 1.5 Hz, 1H), 5.77 (s, 1H), 4.99 (s, 2H), 4.21 (q, J = 8.0 Hz, 2H), 3.85 (s, 3H), 1.22 (t, J = 8.0 Hz, 3H). |

TABLE 1-continued
Structure and ¹HNMR data of Compound I
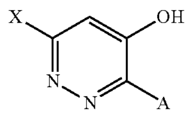
I
| No. | X | A | $^1$H NMR |
| --- | --- | --- | --- |
| 134 | $CF_3$ | 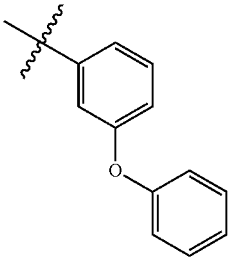 [SMILES: *c1cccc(Oc2ccccc2)c1] | (500 MHz, Chloroform-d) δ 7.38-7.30 (m, 4H), 7.20-7.08 (m, 3H), 7.05-6.96 (m, 3H), 5.54 (s, 1H). |
| 135 | $CF_3$ | 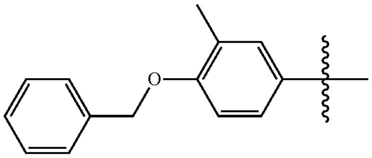 [SMILES: *c1ccc(OCc2ccccc2)c(C)c1] | (500 MHz, Chloroform-d) δ 7.44-7.27 (m, 8H), 7.07 (s, 1H), 5.54 (s, 1H), 5.12 (s, 2H), 2.24 (s, 3H). |
| 136 | $CF_3$ | 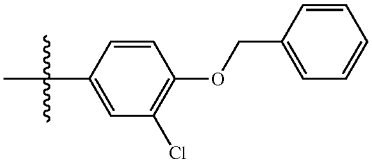 [SMILES: *c1ccc(OCc2ccccc2)c(Cl)c1] | (500 MHz, Chloroform-d) δ 7.66 (d, J = 2.0 Hz, 1H), 7.49-7.27 (m, 6H), 7.17 (d, J = 7.5 Hz, 1H), 7.01 (s, 1H), 5.81 (s, 1H), 5.11 (s, 2H). |
| 137 | $CF_3$ | 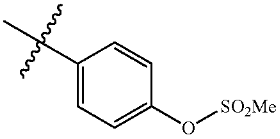 [SMILES: *c1ccc(OS(C)(=O)=O)cc1] | (500 MHz, Chloroform-d) δ 7.56 (d, J = 7.0 Hz, 2H), 7.50 (d, J = 7.0 Hz, 2H), 7.06 (s, 1H), 5.56 (s, 1H), 3.53 (s, 3H). |
| 138 | $CF_3$ | 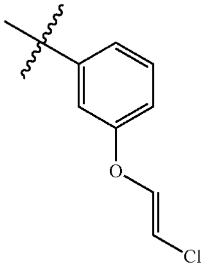 [SMILES: *c1cccc(O/C=C/Cl)c1] | |
| 139 | $CF_3$ | 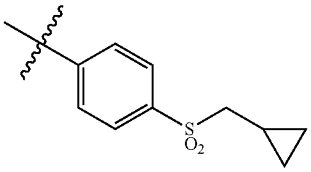 | (500 MHz, Chloroform-d) δ 8.03 (d, J = 7.5 Hz, 2H), 7.91 (d, J = 7.5 Hz, 2H), 7.01 (s, 1H), 5.79 (s, 1H), 3.51 (d, J = 7.0 Hz, 2H), 1.41-1.31 (m, 1H), 0.51-0.39 (m, 2H), 0.36-0.26 (m, 2H). |
| 140 | $CF_3$ | 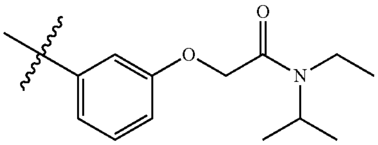 [SMILES: *c1cccc(OCC(=O)N(CC)C(C)C)c1] | (500 MHz, Chloroform-d) δ 7.33-7.23 (m, 3H), 7.08-7.00 (m, 2H), 5.60 (s, 1H), 4.88 (s, 2H), 4.02 (hept, J = 7.0 Hz, 1H), 3.72 (q, J = 8.0 Hz, 2H), 1.29 (d, J = 7.0 Hz, 6H), 1.23 (t, J = 8.0 Hz, 3H). |

TABLE 1-continued

Structure and $^1$HNMR data of Compound I

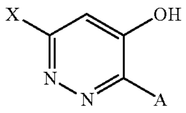

I

| No. | X | A | $^1$H NMR |
|---|---|---|---|
| 141 | $CF_3$ | 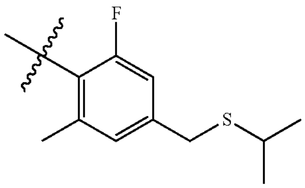 [SMILES: *c1c(C)cc(CSC(C)C)cc1F] | (500 MHz, Chloroform-d) δ 7.04 (s, 1H), 6.97-6.88 (m, 2H), 5.73 (s, 1H), 3.70 (s, 2H), 2.87 (hept, J = 6.5 Hz, 1H), 2.36 (s, 3H), 1.39 (d, J = 6.5 Hz, 6H). |
| 142 | $CF_3$ | 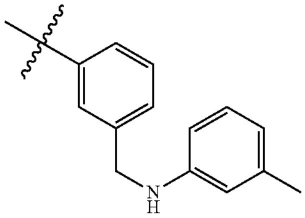 [SMILES: *c1cccc(CNc2cccc(C)c2)c1] | (500 MHz, Chloroform-d) δ 7.52-7.44 (m, 2H), 7.48-7.40 (m, 2H), 7.07 (s, 1H), 6.57-6.48 (m, 2H), 6.40-6.34 (m, 2H), 5.63 (s, 1H), 4.43 (s, 1H), 4.32 (s, 2H), 2.19 (s, 3H). |
| 143 | $CF_3$ | 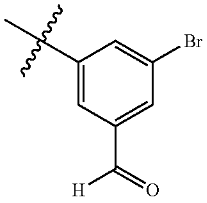 [SMILES: *c1cc(Br)cc(C=O)c1] | (500 MHz, Chloroform-d) δ 8.12-8.04 (m, 3H), 7.02 (s, 1H), 5.83 (s, 1H). |
| 144 | $CF_3$ | 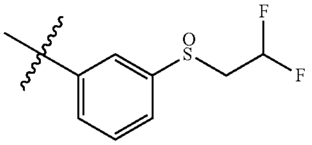 | (500 MHz, Chloroform-d) δ 8.04 (dd, J = 2.0, 1.5 Hz, 1H), 7.60-7.49 (m, 3H), 7.04 (s, 1H), 6.49-6.21 (m, 1H), 5.73 (s, 1H), 3.14-3.05 (m, 2H). |
| 145 | $CF_3$ | 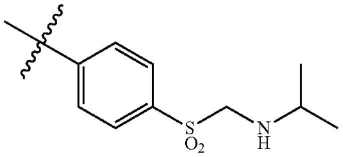 [SMILES: *c1ccc(S(=O)(=O)CNC(C)C)cc1] | (500 MHz, Chloroform-d) δ 7.99 (d, J = 7.5 Hz, 2H), 7.91 (d, J = 7.5 Hz, 2H), 7.01 (s, 1H), 5.80 (s, 1H), 4.67 (s, 2H), 2.92 (hept, J = 6.5 Hz, 1H), 1.20-1.15 (m, 7H). |
| 146 | $CF_3$ | 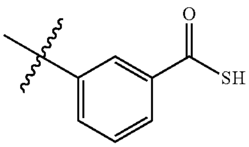 [SMILES: *c1cccc(C(=O)S)c1] | |
| 147 | $CF_3$ | 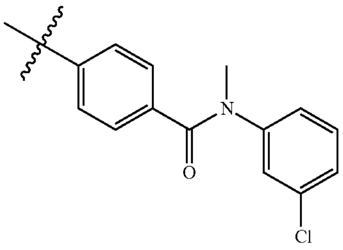 [SMILES: *c1ccc(C(=O)N(C)c2cccc(Cl)c2)cc1] | (500 MHz, Chloroform-d) δ 8.20-8.08 (m, 1H), 7.89 (d, J = 7.5 Hz, 2H), 7.76 (d, J = 7.5 Hz, 2H), 7.49 (dd, J = 7.5, 7.0 Hz, 1H), 7.25-7.14 (m, 2H), 7.05 (s, 1H), 5.63 (s, 1H), 3.40 (s, 3H). |

TABLE 1-continued

Structure and $^1$HNMR data of Compound I

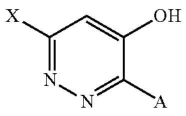

I

| No. | X | A | $^1$H NMR |
|---|---|---|---|
| 148 | $CF_3$ | 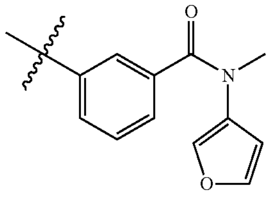 [SMILES: *c1cccc(C(=O)N(C)c2ccoc2)c1] | (500 MHz, Chloroform-d) δ 8.18 (dd, J = 2.0, 1.5 Hz, 1H), 7.82-7.77 (m, 2H), 7.65-7.54 (m, 2H), 7.01 (s, 1H), 6.87 (d, J = 1.5 Hz, 1H), 6.48 (d, J = 1.5 Hz, 1H), 5.82 (s, 1H), 3.25 (s, 3H). |
| 149 | $CF_3$ | 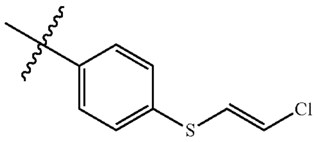 [SMILES: *c1ccc(S/C=C/Cl)cc1] | |
| 150 | $CF_3$ | 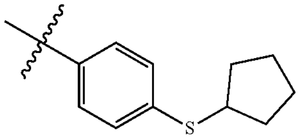 [SMILES: *c1ccc(SC2CCCC2)cc1] | (500 MHz, Chloroform-d) δ 7.52 (d, J = 7.5 Hz, 2H), 7.46 (d, J = 7.5 Hz, 2H), 7.06 (s, 1H), 5.52 (s, 1H), 3.24-3.16 (m, 1H), 2.13-2.01 (m, 2H), 1.75-1.63 (m, 4H), 1.55-1.38 (m, 2H). |
| 151 | $CF_3$ | 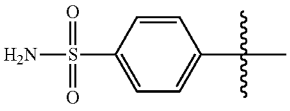 [SMILES: *c1ccc(S(N)(=O)=O)cc1] | (500 MHz, Chloroform-d) δ 8.06 (d, J = 7.5 Hz, 2H), 7.79 (d, J = 7.5 Hz, 2H), 7.07 (s, 1H), 5.46 (s, 1H), 4.40 (s, 2H). |
| 152 | $CF_3$ | 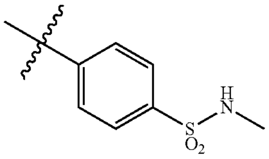 [SMILES: *c1ccc(S(=O)(=O)NC)cc1] | (500 MHz, Chloroform-d) δ 8.06 (d, J = 7.5 Hz, 2H), 7.87 (d, J = 7.5 Hz, 2H), 7.01 (s, 1H), 5.80 (s, 1H), 4.45 (s, 1H), 2.53 (s, 3H). |
| 153 | $CF_3$ | 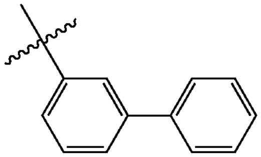 [SMILES: *c1cccc(-c2ccccc2)c1] | (500 MHz, Chloroform-d) δ 7.90-7.78 (m, 2H), 7.67-7.56 (m, 4H), 7.37-7.29 (m, 3H), 7.06 (s, 1H), 5.66 (s, 1H). |
| 154 | $CF_3$ | 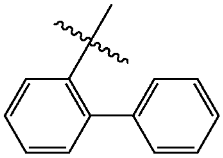 [SMILES: *c1ccccc1-c1ccccc1] | (500 MHz, Chloroform-d) δ 7.68-7.50 (m, 6H), 7.37-7.29 (m, 3H), 6.94 (s, 1H), 5.70 (s, 1H). |
| 155 | $CF_3$ | 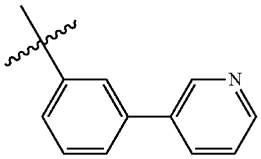 [SMILES: *c1cccc(-c2cccnc2)c1] | (500 MHz, Chloroform-d) δ 8.73 (d, J = 1.5 Hz, 1H), 8.63 (dd, J = 5.0, 1.0 Hz, 1H), 7.94-7.81 (m, 2H), 7.65-7.56 (m, 3H), 7.38-7.29 (m, 1H), 7.07 (s, 1H), 5.62 (s, 1H). |

TABLE 1-continued
Structure and $^1$HNMR data of Compound I
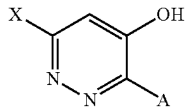
I
| No. | X | A | $^1$H NMR |
|---|---|---|---|
| 156 | $CF_3$ | 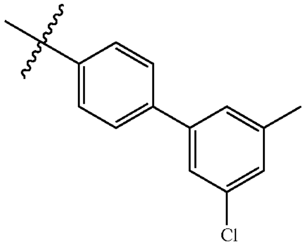 [SMILES: *c1ccc(-c2cc(C)cc(Cl)c2)cc1] | (500 MHz, Chloroform-d) δ 7.87-7.55 (m, 5H), 7.42-7.37 (m, 2H), 7.08 (s, 1H), 5.60 (s, 1H), 2.35 (s, 3H). |
| 157 | $CF_3$ | 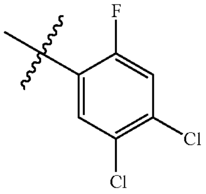 [SMILES: *c1cc(Cl)c(Cl)cc1F] | |
| 158 | $CF_3$ | 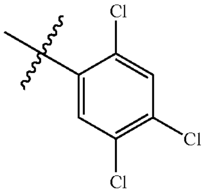 | |
| 159 | $CF_3$ | 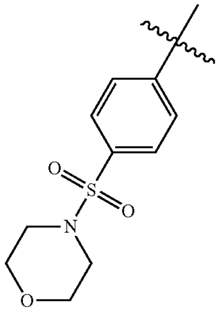 [SMILES: *c1ccc(S(=O)(=O)N2CCOCC2)cc1] | (500 MHz, Chloroform-d) δ 8.09 (d, J = 7.5 Hz, 2H), 7.87 (d, J = 7.5 Hz, 2H), 7.01 (s, 1H), 5.80 (s, 1H), 3.64-3.51 (m, 4H), 2.96-2.83 (m, 4H). |
| 160 | $CF_3$ | 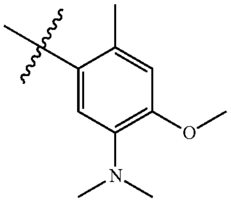 [SMILES: *c1cc(N(C)C)c(OC)cc1C] | (500 MHz, Chloroform-d) δ 7.04 (s, 1H), 6.84 (s, 1H), 6.68 (s, 1H), 5.70 (s, 1H), 3.94 (s, 3H), 2.94 (s, 6H), 2.30 (s, 3H). |
| 161 | $CF_3$ | 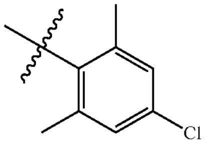 [SMILES: *c1c(C)cc(Cl)cc1C] | (500 MHz, Chloroform-d) δ 7.20 (s, 2H), 7.01 (s, 1H), 5.56 (s, 1H), 2.32 (s, 6H). |

TABLE 1-continued
Structure and $^1$HNMR data of Compound I
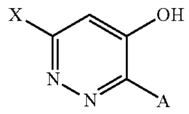
I
| No. | X | A | $^1$H NMR |
|---|---|---|---|
| 162 | $CF_3$ | 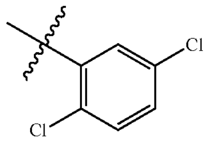 [SMILES: *c1cc(Cl)ccc1Cl] | (500 MHz, Chloroform-d) δ 7.42 (d, J = 7.5 Hz, 1H), 7.36 (d, J = 7.5 Hz, 1H), 7.01 (s, 1H), 5.62 (s, 1H), 2.32 (s, 3H). |
| 163 | $CF_3$ | 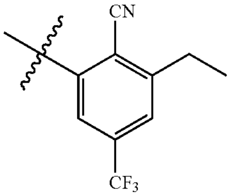 [SMILES: *c1cc(C(F)(F)F)cc(CC)c1C#N] | (500 MHz, Chloroform-d) δ 7.83 (d, J = 2.5 Hz, 1H), 7.66 (d, J = 2.5 Hz, 1H), 7.06 (s, 1H), 5.38 (s, 1H), 2.88 (q, J = 8.0 Hz, 2H), 1.27 (t, J = 8.0 Hz, 3H). |
| 164 | $CF_3$ | 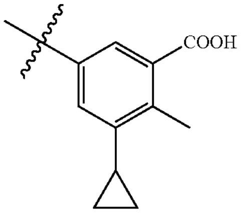 [SMILES: *c1cc(C(=O)O)c(C)c(C2CC2)c1] | (500 MHz, Chloroform-d) δ 8.12 (d, J = 2.0 Hz, 1H), 7.63 (d, J = 2.0 Hz, 1H), 7.07 (s, 1H), 5.65 (s, 1H), 2.51 (s, 3H), 1.92-1.83 (m, 1H), 1.20-1.11 (m, 2H), 0.93-0.81 (m, 2H). |
| 165 | $CF_3$ | 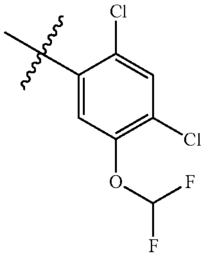 [SMILES: *c1cc(OC(F)F)c(Cl)cc1Cl] | (500 MHz, Chloroform-d) δ 7.49 (s, 1H), 7.19 (t, J = 73.5 Hz, 1H), 7.07 (s, 1H), 7.01 (s, 1H), 5.64 (s, 1H). |
| 166 | $CF_3$ | 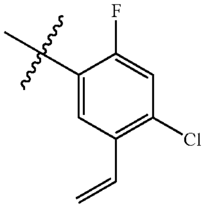 [SMILES: *c1cc(C=C)c(Cl)cc1F] | (500 MHz, Chloroform-d) δ 7.68 (d, J = 10.5 Hz, 1H), 7.41 (d, J = 6.0 Hz, 1H), 7.13-7.09 (m, 2H), 5.58-5.29 (m, 3H). |
| 167 | $CF_3$ | 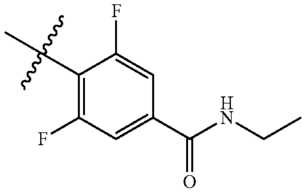 [SMILES: *c1c(F)cc(C(=O)NCC)cc1F] | (500 MHz, Chloroform-d) δ 7.45-7.33 (m, 2H), 7.13 (s, 1H), 6.75 (s, 1H), 5.07 (s, 1H), 3.24 (q, J = 8.0 Hz, 2H), 1.09 (t, J = 8.0 Hz, 3H). |

TABLE 1-continued

Structure and $^1$HNMR data of Compound I

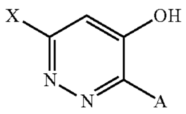

I

| No. | X | A | $^1$H NMR |
|---|---|---|---|
| 168 | $CF_3$ | 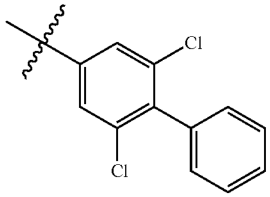 [SMILES: *c1cc(Cl)c(-c2ccccc2)c(Cl)c1] | (500 MHz, Chloroform-d) δ 7.62 (s, 2H), 7.54-7.48 (m, 2H), 7.44-7.36 (m, 3H), 7.08 (s, 1H), 5.54 (s, 1H). |
| 169 | $CF_3$ | 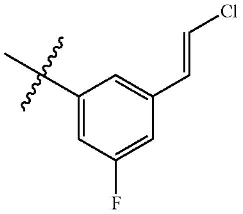 [SMILES: *c1cc(F)cc(/C=C/Cl)c1] | $^1$H NMR (500 MHz, Chloroform-d) δ 7.48-7.38 (m, 1H), 7.22-7.16 (m, 2H), 7.08 (s, 1H), 6.79-6.74 (m, 2H), 5.42 (s, 1H). |
| 170 | $CF_3$ | 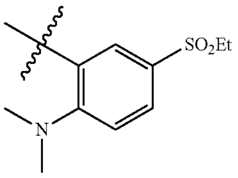 | (500 MHz, Chloroform-d) δ 8.28 (d, J = 2.0 Hz, 1H), 7.93 (s, 1H), 7.79 (dd, J = 7.5, 2.0 Hz, 1H), 7.20-7.10 (m, 2H), 3.45 (q, J = 6.8 Hz, 2H), 2.83 (s, 6H), 1.40 (t, J = 6.8 Hz, 3H). |
| 171 | $CF_3$ | 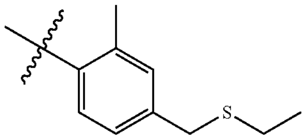 [SMILES: *c1ccc(CSCC)cc1C] | (500 MHz, Chloroform-d) δ 7.39 (d, J = 7.5 Hz, 1H), 7.22-7.15 (m, 2H), 7.03 (s, 1H), 5.67 (s, 1H), 3.70 (s, 2H), 2.48 (q, J = 8.0 Hz, 2H), 2.30 (s, 3H), 1.24 (t, J = 8.0 Hz, 3H). |
| 172 | $CF_3$ | 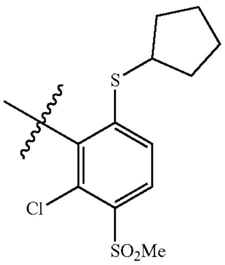 [SMILES: *c1c(SC2CCCC2)ccc(S(C)(=O)=O)c1Cl] | (500 MHz, Chloroform-d) δ 8.01 (d, J = 7.5 Hz, 1H), 7.58 (d, J = 7.5 Hz, 1H), 7.00 (s, 1H), 5.69 (s, 1H), 3.24-3.17 (m, 1H), 3.14 (s, 3H), 2.11-2.00 (m, 2H), 1.77-1.64 (m, 2H), 1.59-1.48 (m, 4H). |
| 173 | $CF_3$ | 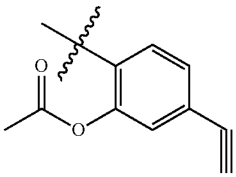 [SMILES: *c1ccc(C#C)cc1OC(C)=O] | (500 MHz, Chloroform-d) δ 7.60 (dd, J = 7.5, 2.0 Hz, 1H), 7.54 (d, J = 7.5 Hz, 1H), 7.36 (d, J = 2.0 Hz, 1H), 6.99 (s, 1H), 5.68 (s, 1H), 3.07 (s, 1H), 2.67 (s, 1H). |

TABLE 1-continued

Structure and $^1$HNMR data of Compound I

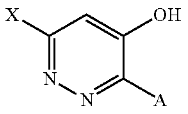

I

| No. | X | A | $^1$H NMR |
|---|---|---|---|
| 174 | $CF_3$ | 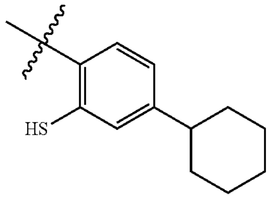 [SMILES: *c1ccc(C2CCCCC2)cc1S] | (500 MHz, Chloroform-d) δ 7.50-7.40 (m, 2H), 7.26-7.11 (m, 1H), 7.03 (s, 1H), 5.66 (s, 1H), 5.34 (s, 1H), 2.61-2.51 (m, 1H), 2.19-2.10 (m, 2H), 1.82-1.71 (m, 4H), 1.54-1.34 (m, 4H). |
| 175 | $CF_3$ | 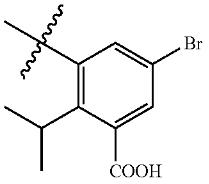 [SMILES: *c1cc(Br)cc(C(=O)O)c1C(C)C] | (500 MHz, Chloroform-d) δ 8.25 (d, J = 2.0 Hz, 1H), 7.92 (d, J = 2.0 Hz, 1H), 7.02 (s, 1H), 5.64 (s, 1H), 3.12 (hept, J = 6.5 Hz, 1H), 1.30 (d, J = 6.5 Hz, 6H). |
| 176 | $CF_3$ | 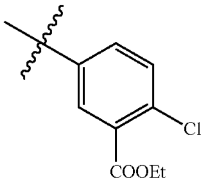 [SMILES: *c1ccc(Cl)c(C(=O)OCC)c1] | (500 MHz, Chloroform-d) δ 7.99 (d, J = 1.5 Hz, 1H), 7.66-7.43 (m, 2H), 7.01 (s, 1H), 5.80 (s, 1H), 4.19 (q, J = 8.0 Hz, 2H), 1.34 (t, J = 8.0 Hz, 3H). |
| 177 | $CF_3$ | 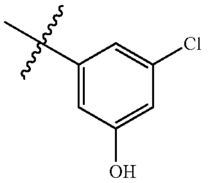 [SMILES: *c1cc(O)cc(Cl)c1] | (500 MHz, Chloroform-d) δ 7.35-7.29 (m, 2H), 7.06 (s, 1H), 6.96-6.89 (m, 1H), 6.57 (s, 1H), 5.62 (s, 1H). |
| 178 | $CF_3$ | 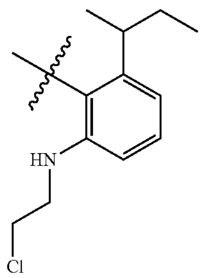 [SMILES: *c1c(NCCCl)cccc1C(C)CC] | (500 MHz, Chloroform-d) δ 7.21-7.10 (m, 1H), 7.06 (s, 1H), 6.81-6.62 (m, 2H), 5.39 (s, 1H), 4.39 (s, 1H), 3.87-3.77 (m, 2H), 3.51-3.34 (m, 2H), 2.99-2.89 (m, 1H), 1.92-1.71 (m, 2H), 1.27 (d, J = 6.5 Hz, 3H), 0.91 (t, J = 8.0 Hz, 3H). |
| 179 | $CF_3$ | 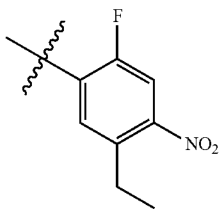 [SMILES: *c1cc(CC)c([N+](=O)[O-])cc1F] | (500 MHz, Chloroform-d) δ 8.78 (d, J = 11.0 Hz, 1H), 8.08 (d, J = 6.5 Hz, 1H), 7.12 (s, 1H), 5.49 (s, 1H), 2.66 (q, J = 8.0, Hz, 2H), 1.17 (t, J = 8.0 Hz, 3H). |

TABLE 1-continued

Structure and $^1$HNMR data of Compound I

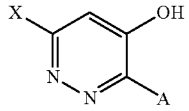

I

| No. | X | A | $^1$H NMR |
|---|---|---|---|
| 180 | $CF_3$ | 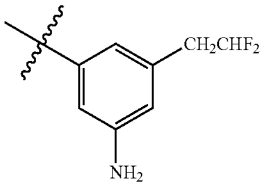 | (500 MHz, Chloroform-d) δ 7.10-7.01 (m, 3H), 6.64-6.56 (m, 3H), 5.83-5.76 (m, 1H), 5.79 (s, 1H), 2.91-2.76 (m, 2H). |
| 181 | $CF_3$ | 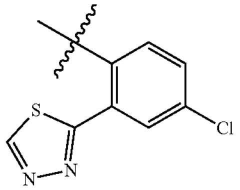 [SMILES: *c1ccc(Cl)cc1-c1nncs1] | (500 MHz, Chloroform-d) δ 7.65 (s, 1H), 7.59 (d, J = 2.0 Hz, 1H), 7.53 (d, J = 7.5 Hz, 1H), 7.45 (dd, J = 7.5, 2.0 Hz, 1H), 7.29 (s, 1H), 6.15 (s, 1H). |
| 182 | $CF_3$ | 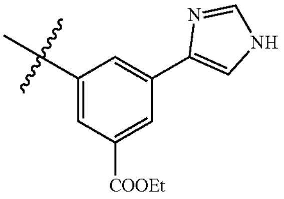 [SMILES: *c1cc(C(=O)OCC)cc(-c2c[nH]cn2)c1] | (500 MHz, Chloroform-d) δ 8.25-8.17 (m, 3H), 7.33 (s, 1H), 7.10 (s, 1H), 5.54-5.31 (m, 3H), 4.31 (q, J = 7.5 Hz, 2H), 1.34 (t, J = 7.5 Hz, 3H). |
| 183 | $CF_3$ | 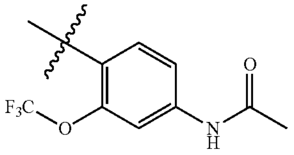 [SMILES: *c1ccc(NC(C)=O)cc1OC(F)(F)F] | (500 MHz, Chloroform-d) δ 8.27 (s, 1H), 7.85 (dd, J = 7.5, 2.0 Hz, 1H), 7.62 (d, J = 7.5 Hz, 1H), 7.24 (d, J = 2.0 Hz, 1H), 7.02 (s, 1H), 5.72 (s, 1H), 2.10 (s, 3H). |
| 184 | $CF_3$ | 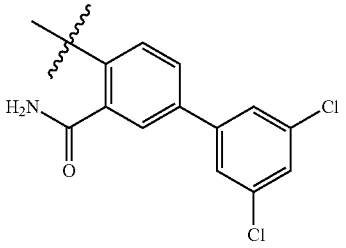 [SMILES: *c1ccc(-c2cc(Cl)cc(Cl)c2)cc1C(N)=O] | (500 MHz, Chloroform-d) δ 8.33 (d, J = 2.0 Hz, 1H), 7.88 (dd, J = 7.5, 2.0 Hz, 1H), 7.80 (d, J = 7.5 Hz, 1H), 7.57 (d, J = 2.0 Hz, 2H), 7.45-7.37 (m, 1H), 7.08 (s, 1H), 6.46 (s, 2H), 5.62 (s, 1H). |
| 185 | $CF_3$ | 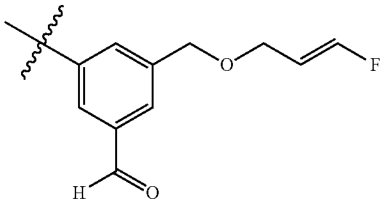 [SMILES: *c1cc(C=O)cc(COC/C=C/F)c1] | |
| 186 | $CF_3$ | 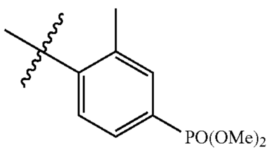 | (500 MHz, Chloroform-d) δ 7.84-7.74 (m, 2H), 7.56 (d, J = 7.5 Hz, 1H), 7.04 (s, 1H), 5.63 (s, 1H), 3.39 (s, 6H), 2.34 (s, 3H). |

TABLE 1-continued
Structure and $^1$HNMR data of Compound I
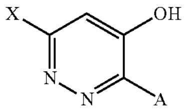
I
| No. | X | A | $^1$H NMR |
|---|---|---|---|
| 187 | $CF_3$ | 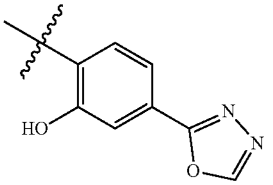 [SMILES: *c1ccc(-c2nnco2)cc1O] | (500 MHz, Chloroform-d) δ 8.67 (s, 1H), 7.87 (s, 1H), 7.63 (d, J = 7.5 Hz, 1H), 7.42 (dd, J = 7.5, 2.0 Hz, 1H), 7.16 (d, J = 2.0 Hz, 1H), 7.00 (s, 1H), 5.80 (s, 1H). |
| 188 | $CF_3$ | 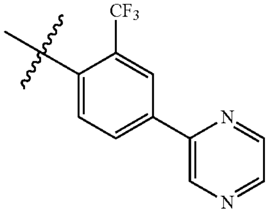 [SMILES: *c1ccc(-c2cnccn2)cc1C(F)(F)F] | (500 MHz, Chloroform-d) δ 9.31 (s, 1H), 8.85 (d, J = 5.5 Hz, 1H), 8.75 (d, J = 5.5 Hz, 1H), 8.42-8.38 (m, 1H), 8.32 (dd, J = 7.5, 2.0 Hz, 1H), 7.72 (d, J = 7.5 Hz, 1H), 7.06 (s, 1H), 5.55 (s, 1H). |
| 189 | $CF_3$ | 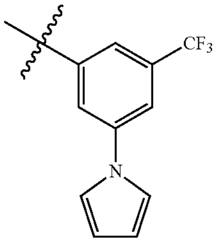 [SMILES: *c1cc(-n2cccc2)cc(C(F)(F)F)c1] | (500 MHz, Chloroform-d) δ 8.15-8.09 (m, 2H), 7.97-7.81 (m, 1H), 7.35-7.21 (m, 2H), 7.03 (s, 1H), 6.34-6.20 (m, 2H), 5.84 (s, 1H). |
| 190 | $CF_3$ | 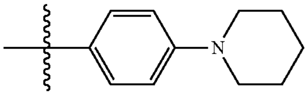 | (500 MHz, Chloroform-d) δ 7.63 (d, J = 7.5 Hz, 2H), 7.06 (s, 1H), 6.94 (d, J = 7.5 Hz, 2H), 5.58 (s, 1H), 3.49-3.43 (m, 4H), 1.67-1.57 (m, 6H). |
| 191 | $CF_3$ | 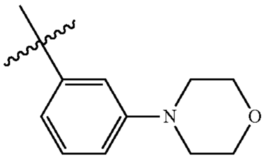 [SMILES: *c1cccc(N2CCOCC2)c1] | (500 MHz, Chloroform-d) δ 7.23-7.06 (m, 2H), 6.95-6.72 (m, 3H), 5.51 (s, 1H), 3.74-3.55 (m, 4H), 3.33-3, 16 (m, 4H). |
| 192 | $CF_3$ | 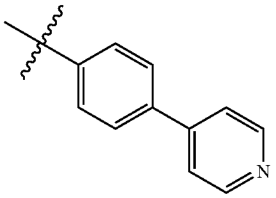 [SMILES: *c1ccc(-c2ccncc2)cc1] | (500 MHz, Chloroform-d) δ 8.69 (d, J = 5.0 Hz, 2H), 7.96 (d, J = 5.0 Hz, 2H), 7.86-7.74 (m, 4H), 7.02 (s, 1H), 5.82 (s, 1H). |

TABLE 1-continued
Structure and $^1$HNMR data of Compound I
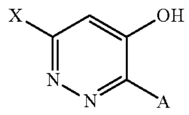
I
| No. | X | A | $^1$H NMR |
| --- | --- | --- | --- |
| 193 | $CF_3$ | 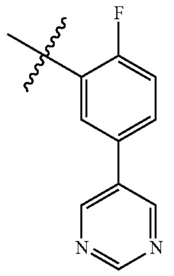 [SMILES: *c1cc(-c2cncnc2)ccc1F] | (500 MHz, Chloroform-d) δ 9.17 (s, 1H), 9.08 (s, 2H), 7.98-7.82 (m, 1H), 7.65-7.38 (m, 3H), 7.12 (s, 1H), 5.67 (s, 1H). |
| 194 | $CF_3$ | 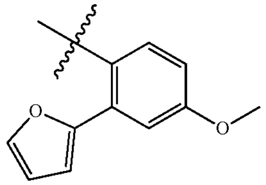 [SMILES: *c1ccc(OC)cc1-c1ccco1] | (500 MHz, Chloroform-d) δ 7.64-7.57 (m, 2H), 7.37 (d, J = 2.0 Hz, 1H), 7.06-7.00 (m, 2H), 6.68-6.54 (m, 2H), 6.14 (s, 1H), 3.87 (s, 3H). |
| 195 | $CF_3$ | 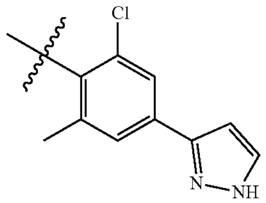 [SMILES: *c1c(C)cc(-c2cc[nH]n2)cc1Cl] | (500 MHz, Chloroform-d) δ 7.61 (d, J = 2.0 Hz, 1H), 7.50 (d, J = 2.0 Hz, 1H), 7.30 (d, J = 2.5 Hz, 1H), 7.05 (s, 1H), 6.71 (d, J = 2.5 Hz, 1H), 2.36 (s, 3H). |
| 196 | $CF_3$ | 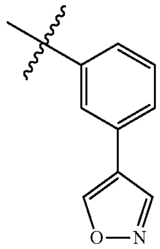 [SMILES: *c1cccc(-c2cnoc2)c1] | (500 MHz, Chloroform-d) δ 7.78 (s, 1H), 7.47-7.41 (m, 2H), 7.32-7.25 (m, 2H), 7.09 (s, 1H), 6.34-6.23 (m, 1H), 5.60 (s, 1H). |
| 197 | $CF_3$ | 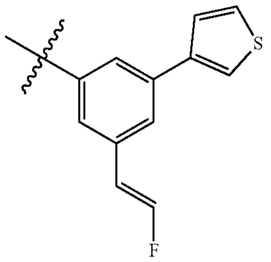 [SMILES: *c1cc(/C=C/F)cc(-c2ccsc2)c1] | |
| 198 | $CF_3$ | 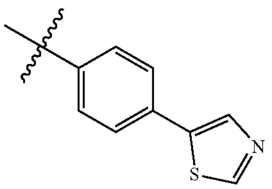 [SMILES: *c1ccc(-c2cncs2)cc1] | (500 MHz, Chloroform-d) δ 8.97 (s, 1H), 7.96 (d, J = 7.5 Hz, 2H), 7.85 (s, 1H), 7.83 (d, J = 7.5 Hz, 2H), 7.02 (s, 1H), 5.82 (s, 1H). |

TABLE 1-continued

Structure and $^1$HNMR data of Compound I

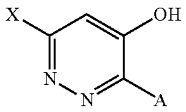

I

| No. | X | A | $^1H$ NMR |
| --- | --- | --- | --- |
| 199 | $CF_3$ | 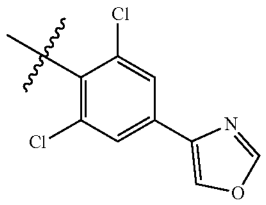 [SMILES: *c1c(Cl)cc(-c2cocn2)cc1Cl] | (500 MHz, Chloroform-d) δ 8.53 (s, 1H), 8.43 (s, 1H), 7.64 (s, 2H), 7.04 (s, 1H), 5.64 (s, 1H). |
| 200 | $CF_3$ | 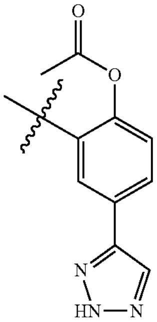 [SMILES: *c1cc(-c2cn[nH]n2)ccc1OC(C)=O] | (500 MHz, Chloroform-d) δ 8.32 (s, 1H), 7.89 (d, J = 2.0 Hz, 1H), 7.64 (dd, J = 7.5, 2.0 Hz, 1H), 7.31 (d, J = 7.5 Hz, 1H), 7.04 (s, 1H), 2.67 (s, 3H). |
| 201 | $CF_3$ | 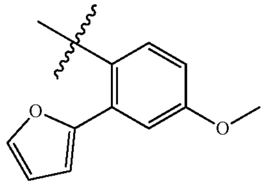 [SMILES: *c1ccc(OC)cc1-c1ccco1] | (500 MHz, Chloroform-d) δ 7.64-7.57 (m, 2H), 7.37 (d, J = 2.0 Hz, 1H), 7.06-6.99 (m, 2H), 6.69-6.54 (m, 2H), 6.14 (s, 1H), 3.87 (s, 3H). |
| 202 | $CF_3$ | 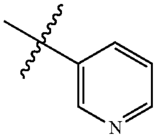 [SMILES: *c1cccnc1] | $^1H$ NMR (500 MHz, DMSO-$d_6$) δ 12.37 (s, 1H), 9.18 (d, J = 2.5 Hz, 1H), 8.68-8.56 (m, 2H), 7.56-7.41 (m, 1H), 7.28 (s, 1H). |
| 203 | $CF_3$ | 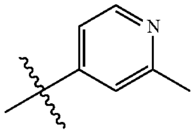 [SMILES: *c1ccnc(C)c1] | (500 MHz, Chloroform-d) δ 8.68 (d, J = 5.0 Hz, 1H), 7.56-7.50 (m, 2H), 7.24 (s, 1H), 5.80 (s, 1H), 2.69 (s, 3H). |
| 204 | $CF_3$ | 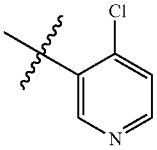 | $^1H$ NMR (500 MHz, DMSO-d6) δ 12.66 (s, 1H), 8.79 (s, 1H), 8.55 (d, J = 5.0 Hz, 1H), 7.46 (dd, J = 5.0 Hz, 1H), 7.26 (s, 1H). |
| 205 | $CF_3$ | 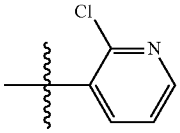 [SMILES: *c1cccnc1Cl] | $^1H$ NMR (500 MHz, DMSO-$d_6$) δ 13.09 (s, 1H), 8.55-8.43 (m 1H), 8.02-7.89 (m, 1H), 7.59-7.40 (m, 1H), 7.36 (s, 1H). |

TABLE 1-continued

Structure and $^1$HNMR data of Compound I

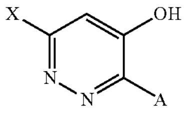

I

| No. | X | A | $^1$H NMR |
|---|---|---|---|
| 206 | $CF_3$ | 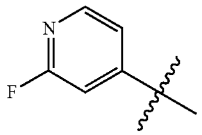 [SMILES: *c1ccnc(F)c1] | (500 MHz, Chloroform-d) δ 8.45 (dd, J = 5.5, 5.0 Hz, 1H), 7.63-7.52 (m, 1H), 7.42 (dd, J = 8.0, 1.0 Hz, 1H), 7.30 (s, 1H), 5.34 (s, 1H). |
| 207 | $CF_3$ | 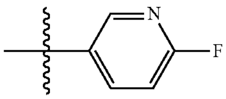 [SMILES: *c1ccc(F)nc1] | $^1$H NMR (500 MHz, DMSO-$d_6$) δ 13.65 (s, 1H), 8.80-8.57 (m, 2H), 7.36-7.34 (m, 2H). |
| 208 | $CF_3$ | 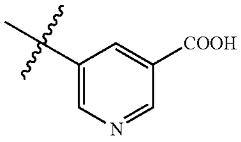 [SMILES: *c1cncc(C(=O)O)c1] | (500 MHz, Chloroform-d) δ 9.20 (d, J = 1.5 Hz, 1H), 9.07 (d, J = 2.0 Hz, 1H), 8.40 (dd, J = 2.0, 1.5 Hz, 1H), 8.40 (s, 1H), 7.31 (s, 1H), 5.41 (s, 1H). |
| 209 | $CF_3$ | 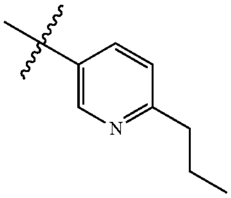 [SMILES: *c1ccc(CCC)nc1] | (500 MHz, Chloroform-d) δ 9.09 (d, J = 1.5 Hz, 1H), 8.02 (dd, J = 8.0, 1.5 Hz, 1H), 7.47 (d, J = 8.0 Hz, 1H), 7.30 (s, 1H), 5.34 (s, 1H), 3.26 (t, J = 8.0 Hz, 2H), 1.86-1.67 (m, 2H), 1.01 (t, J = 8.0 Hz, 3H). |
| 210 | $CF_3$ | 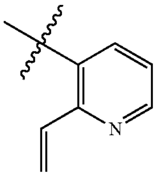 [SMILES: *c1cccnc1C=C] | (500 MHz, Chloroform-d) δ 8.61 (dd, J = 5.0, 1.5 Hz, 1H), 7.85 (dd, J = 8.0, 1.5 Hz, 1H), 7.49 (dd, J = 8.0, 5.0 Hz, 1H), 7.25 (s, 1H), 6.72 (dd, J = 16.5, 10.0 Hz, 1H), 6.19 (dd, J = 13.5, 10.0 Hz, 1H), 5.67 (dd, J = 16.5, 13.5 Hz, 1H), 5.60 (s, 1H). |
| 211 | $CF_3$ | 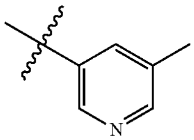 [SMILES: *c1cncc(C)c1] | $^1$H NMR (500 MHz, DMSO-$d_6$) δ 13.41 (s, 1H), 8.97 (s, 1H), 8.52 (s, 1H), 8.20 (s, 1H), 7.29 (s, 1H), 2.38 (s, 3H). |
| 212 | $CF_3$ | 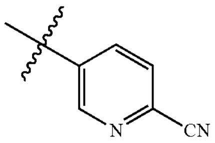 [SMILES: *c1ccc(C#N)nc1] | (500 MHz, Chloroform-d) δ 9.18 (d, J = 1.5 Hz, 1H), 8.24 (dd, J = 8.0, 1.5 Hz, 1H), 8.02 (d, J = 8.0 Hz, 1H), 7.32 (s, 1H), 5.20 (s, 1H). |
| 213 | $CF_3$ | 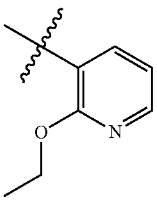 [SMILES: *c1cccnc1OCC] | $^1$H NMR (500 MHz, DMSO-$d_6$) δ 12.45 (s, 1H), 8.32 (dd, J = 5.0, 1.5 Hz, 1H), 7.79 (dd, J = 6.5, 1.5 Hz, 1H), 7.36 (s, 1H), 7.11 (dd, J = 6.5, 5.0 Hz, 1H), 4.32 (q, J = 7.0 Hz, 2H), 1.19 (t, J = 7.0 Hz, 3H). |

TABLE 1-continued

Structure and $^1$HNMR data of Compound I

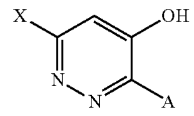

I

| No. | X | A | $^1$H NMR |
|---|---|---|---|
| 214 | $CF_3$ | 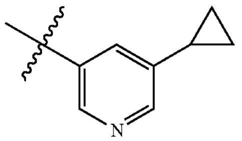 [SMILES: *c1cncc(C2CC2)c1] | (500 MHz, Chloroform-d) δ 8.91 (s, 1H), 8.53 (s, 1H), 7.80 (s, 1H), 7.24 (s, 1H), 5.81 (s, 1H), 1.71-1.60 (m, 1H), 1.07-0.98 (m, 2H), 0.79-0.70 (m, 2H). |
| 215 | $CF_3$ | 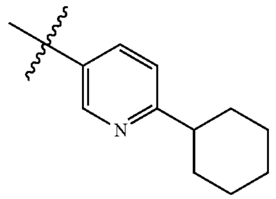 [SMILES: *c1ccc(C2CCCCC2)nc1] | (500 MHz, Chloroform-d) δ 9.19 (d, J = 1.5 Hz, 1H), 8.11 (dd, J = 7.0, 1.5 Hz, 1H), 7.52 (d, J = 7.0 Hz, 1H), 7.30 (s, 1H), 5.36 (s, 1H), 2.61-2.42 (m, 2H), 1.85-1.73 (m, 7H), 1.28-1.20 (m, 2H). |
| 216 | $CF_3$ | 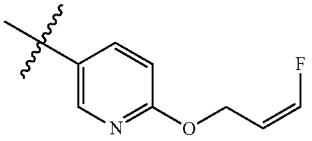 [SMILES: *c1ccc(OC/C=C\F)nc1] | |
| 217 | $CF_3$ | 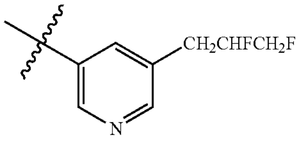 | (500 MHz, Chloroform-d) δ 8.80 (d, J = 1.5 Hz, 1H), 8.48 (d, J = 2.0 Hz, 1H), 7.87 (dd, J = 2.0, 1.5 Hz, 1H), 7.28 (s, 1H), 5.51 (s, 1H), 4.72-4.16 (m, 3H), 3.00-2.76 (m, 2H). |
| 218 | $CF_3$ | 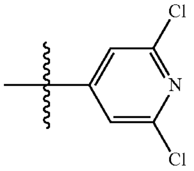 | (500 MHz, Chloroform-d) δ 7.93 (s, 2H), 7.26 (s, 1H), 5.74 (s, 1H). |
| 219 | $CF_3$ | 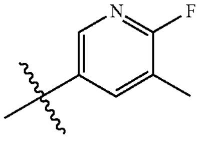 [SMILES: *c1cnc(F)c(C)c1] | (500 MHz, Chloroform-d) δ 8.75 (dd, J = 4.5, 1.5 Hz, 1H), 7.76 (dd, J = 6.0, 1.5 Hz, 1H), 7.24 (s, 1H), 5.81 (s, 1H), 2.33 (s, 3H). |
| 220 | $CF_3$ | 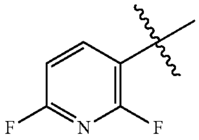 [SMILES: *c1ccc(F)nc1F] | $^1$H NMR (500 MHz, DMSO-$d_6$) δ 13.36 (s, 1H), 7.52 (s, 1H), 7.45-7.25 (m, 2H). |
| 221 | $CF_3$ | 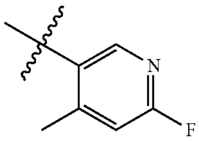 [SMILES: *c1cnc(F)cc1C] | $^1$H NMR (500 MHz, DMSO-$d_6$) δ 13.40 (s, 1H), 8.20 (d, J = 4.5 Hz, 1H), 7.34 (d, J = 10.5 Hz, 1H), 7.22 (s, 1H), 2.22 (s, 3H). |

TABLE 1-continued

Structure and $^1$HNMR data of Compound I

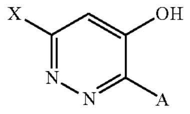

I

| No. | X | A | $^1$H NMR |
|---|---|---|---|
| 222 | $CF_3$ | 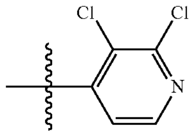 [SMILES: *c1ccnc(Cl)c1Cl] | (500 MHz, Chloroform-d) δ 8.48 (d, J = 5.0 Hz, 1H), 7.74 (d, J = 5.0 Hz, 1H), 7.24 (s, 1H), 5.68 (s, 1H). |
| 223 | $CF_3$ | 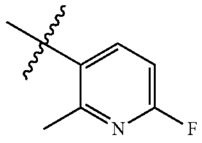 | (500 MHz, Chloroform-d) δ 8.11 (dd, J = 8.0, 5.0 Hz, 1H), 7.24 (s, 1H), 6.84 (dd, J = 8.0, 7.5 Hz, 1H), 5.67 (s, 1H), 2.83 (s, 3H). |
| 224 | $CF_3$ | 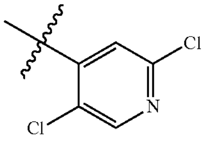 [SMILES: *c1cc(Cl)ncc1Cl] | (500 MHz, Chloroform-d) δ 8.11 (s, 1H), 7.24 (s, 1H), 6.84 (s, 1H), 5.67 (s, 1H). |
| 225 | $CF_3$ | 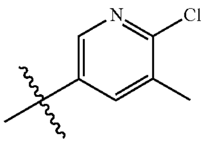 [SMILES: *c1cnc(Cl)c(C)c1] | $^1$H NMR (500 MHz, DMSO-$d_6$) δ 13.59 (s, 1H), 8.87 (s, 1H), 8.42 (s, 1H), 7.33 (s, 1H), 2.43 (s, 3H). |
| 226 | $CF_3$ | 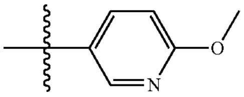 | $^1$H NMR (500 MHz, DMSO-$d_6$) δ 13.16 (s, 1H), 8.88 (d, J = 2.5 Hz, 1H), 8.35 (dd, J = 8.5, 2.5 Hz, 1H), 7.29 (s, 1H), 6.98 (d, J = 8.5 Hz, 1H), 3.93 (s, 3H). |
| 227 | $CF_3$ | 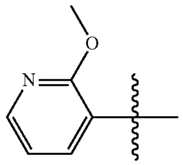 [SMILES: *c1cccnc1OC] | $^1$H NMR (500 MHz, DMSO-$d_6$) δ 12.61 (s, 1H), 8.33 (d, J = 5.0 Hz, 1H), 7.82 (d, J = 7.5 Hz, 1H), 7.33 (s, 1H), 7.16 (dd, J = 7.5, 5.0 Hz, 1H), 3.84 (s, 3H). |
| 228 | $CF_3$ | 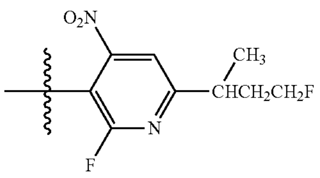 | (500 MHz, Chloroform-d) δ 8.02 (s, 1H), 7.30 (s, 1H), 5.42 (s, 1H), 4.76-4.38 (m, 2H), 3.19-3.02 (m, 1H), 2.08-1.94 (m, 2H), 1.39 (d, J = 7.0 Hz, 3H). |
| 229 | $CF_3$ | 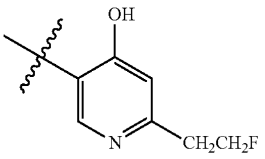 | (500 MHz, Chloroform-d) δ 8.96 (s, 1H), 7.53 (s, 1H), 7.23 (s, 1H), 6.89 (s, 1H), 5.80 (s, 1H), 4.47-4.37 (m, 2H), 3.08-2.91 (m, 2H). |

TABLE 1-continued

Structure and $^1$HNMR data of Compound I

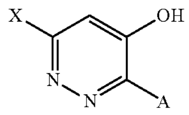

I

| No. | X | A | $^1$H NMR |
|---|---|---|---|
| 230 | $CF_3$ | 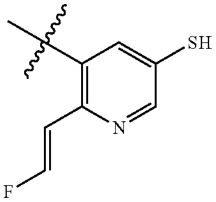 [SMILES: *c1cc(S)cnc1/C=C/F] | |
| 231 | $CF_3$ | 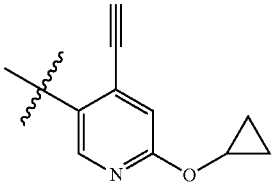 [SMILES: *c1cnc(OC2CC2)cc1C#C] | (500 MHz, Chloroform-d) δ 8.56 (s, 1H), 7.41 (s, 1H), 7.35 (s, 1H), 4.45 (s, 1H), 3.50 (s, 1H), 3.11-3.01 (m, 1H), 0.65-0.55 (m, 2H), 0.43-0.31 (m, 2H). |
| 232 | $CF_3$ | 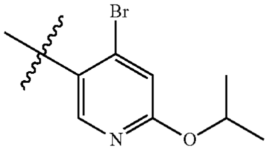 [SMILES: *c1cnc(OC(C)C)cc1Br] | (500 MHz, Chloroform-d) δ 8.42 (s, 1H), 7.25 (s, 1H), 7.11 (s, 1H), 5.68 (s, 1H), 4.90 (hept, J = 7.0 Hz, 1H), 1.29 (d, J = 7.0 Hz, 6H). |
| 233 | $CF_3$ | 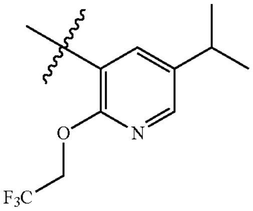 [SMILES: *c1cc(C(C)C)cnc1OCC(F)(F)F] | (500 MHz, Chloroform-d) δ 8.00 (d, J = 1.5 Hz, 1H), 7.52 (d, J = 1.5 Hz, 1H), 7.29 (s, 1H), 5.17 (s, 1H), 5.03 (q, J = 7.0 Hz, 2H), 2.98 (hept, J = 7.5 Hz, 1H), 1.30 (d, J = 7.5 Hz, 6H). |
| 234 | $CF_3$ | 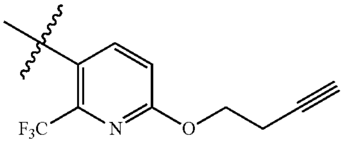 [SMILES: *c1ccc(OCCC#C)nc1C(F)(F)F] | (500 MHz, Chloroform-d) δ 7.92 (d, J = 8.0 Hz, 1H), 7.24 (s, 1H), 6.92 (d, J = 8.0 Hz, 1H), 5.68 (s, 1H), 4.68 (s, 2H), 2.99 (s, 1H). |
| 235 | $CF_3$ | 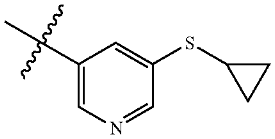 [SMILES: *c1cncc(SC2CC2)c1] | (500 MHz, Chloroform-d) δ 8.66 (d, J = 1.0 Hz, 1H), 8.61 (d, J = 1.5 Hz, 1H), 7.90 (dd, J = 1.5, 1.0 Hz, 1H), 7.32 (s, 1H), 5.20 (s, 1H), 2.39-2.26 (m, 1H), 1.05-0.95 (m, 2H), 0.53-0.44 (m, 2H). |
| 236 | $CF_3$ | 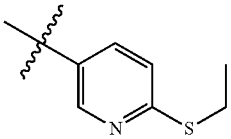 [SMILES: *c1ccc(SCC)nc1] | (500 MHz, Chloroform-d) δ 8.88 (d, J = 1.5 Hz, 1H), 7.94 (dd, J = 8.0, 1.5 Hz, 1H), 7.38 (d, J = 8.0 Hz, 1H), 7.23 (s, 1H), 5.78 (s, 1H), 2.97 (q, J = 8.0 Hz, 2H), 1.36 (t, J = 8.0 Hz, 3H). |
| 237 | $CF_3$ | 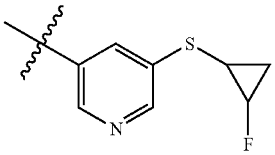 [SMILES: *c1cncc(SC2CC2F)c1] | |

TABLE 1-continued

Structure and $^{1}$HNMR data of Compound I

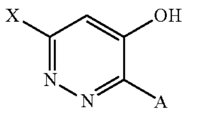

I

| No. | X | A | $^{1}$H NMR |
|---|---|---|---|
| 238 | $CF_3$ | 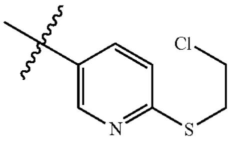 [SMILES: *c1ccc(SCCCl)nc1] | (500 MHz, Chloroform-d) δ 8.89 (d, J = 1.0 Hz, 1H), 7.94 (dd, J = 8.0, 1.0 Hz, 1H), 7.39 (d, J = 8.0 Hz, 1H), 7.23 (s, 1H), 5.79 (s, 1H), 3.78 (t, J = 7.5 Hz, 2H), 3.21 (t, J = 7.5 Hz, 2H). |
| 239 | $CF_3$ | 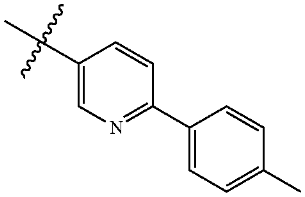 [SMILES: *c1ccc(-c2ccc(C)cc2)nc1] | (500 MHz, Chloroform-d) δ 9.14 (d, J = 1.0 Hz, 1H), 8.04-7.96 (m, 2H), 7.77-7.71 (m, 2H), 7.31-7.22 (m, 3H), 5.59 (s, 1H), 2.33 (s, 3H). |
| 240 | $CF_3$ | 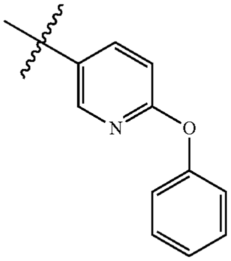 [SMILES: *c1ccc(Oc2ccccc2)nc1] | (500 MHz, Chloroform-d) δ 8.66 (d, J = 1.0 Hz, 1H), 7.87 (dd, J = 8.0, 1.0 Hz, 1H), 7.47-7.39 (m, 2H), 7.31 (s, 1H), 7.18-7.12 (m, 2H), 7.09 (d, J = 8.0 Hz, 1H), 6.96-6.83 (m, 1H), 5.37 (s, 1H). |
| 241 | $CF_3$ | 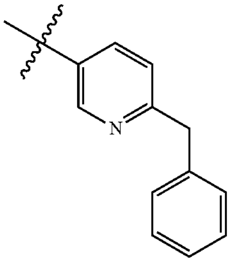 [SMILES: *c1ccc(Cc2ccccc2)nc1] | (500 MHz, Chloroform-d) δ 9.22 (d, J = 1.0 Hz, 1H), 8.11 (dd, J = 8.0, 1.0 Hz, 1H), 7.54 (d, J = 8.0 Hz, 1H), 7.32-7.23 (m, 3H), 7.19-7.11 (m, 1H), 7.14-7.06 (m, 2H), 5.32 (s, 1H), 4.21 (s, 2H). |
| 242 | $CF_3$ | 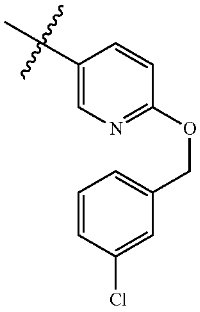 [SMILES: *c1ccc(OCc2cccc(Cl)c2)nc1] | (500 MHz, Chloroform-d) δ 8.69 (d, J = 1.0 Hz, 1H), 7.85 (dd, J = 8.0, 1.0 Hz, 1H), 7.48-7.40 (m, 3H), 7.33-7.27 (m, 2H), 6.97 (d, J = 8.0 Hz, 1H), 5.31 (s, 1H). |
| 243 | $CF_3$ | 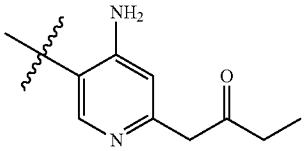 | (500 MHz, Chloroform-d) δ 9.07 (s, 1H), 7.23 (s, 1H), 7.06 (s, 1H), 5.75 (s, 1H), 4.04 (s, 2H), 3.50 (s, 2H), 2.47 (q, J = 8.0 Hz, 2H), 1.22 (t, J = 8.0 Hz, 3H). |

TABLE 1-continued

Structure and ¹HNMR data of Compound I

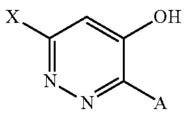

I

| No. | X | A | ¹H NMR |
| --- | --- | --- | --- |
| 244 | $CF_3$ | 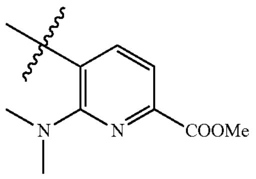 [SMILES: *c1ccc(C(=O)OC)nc1N(C)C] | (500 MHz, Chloroform-d) δ 8.23 (d, J = 8.0 Hz, 1H), 7.71 (d, J = 8.0 Hz, 1H), 7.36 (s, 1H), 6.70 (s, 1H), 3.98 (s, 3H), 3.28 (s, 6H). |
| 245 | $CF_3$ | 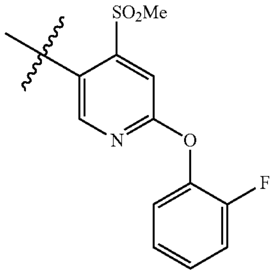 [SMILES: *c1cnc(Oc2ccccc2F)cc1S(C)(=O)=O] | (500 MHz, Chloroform-d) δ 9.26 (s, 1H), 8.62 (s, 1H), 7.54 (s, 1H), 7.42 (s, 1H), 7.36-7.25 (m, 2H), 7.22-7.11 (m, 2H), 3.18 (s, 3H). |
| 246 | $CF_3$ | 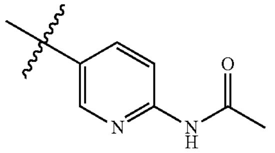 [SMILES: *c1ccc(NC(C)=O)nc1] | (500 MHz, Chloroform-d) δ 9.13 (d, J = 1.0 Hz, 1H), 8.44 (d, J = 8.0 Hz, 1H), 8.15 (dd, J = 8.0, 1.0 Hz, 1H), 7.83 (s, 1H), 7.30 (s, 1H), 5.42 (s, 1H), 2.16 (s, 3H). |
| 247 | $CF_3$ | 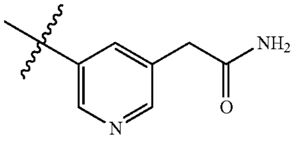 [SMILES: *c1cncc(CC(N)=O)c1] | (500 MHz, Chloroform-d) δ 8.92 (d, J = 1.0 Hz, 1H), 8.61 (d, J = 1.5 Hz, 1H), 7.98 (dd, J = 1.5, 1.0 Hz, 1H), 7.24 (s, 1H), 5.83 (s, 1H), 5.72 (s, 2H), 3.52 (s, 2H). |
| 248 | $CF_3$ | 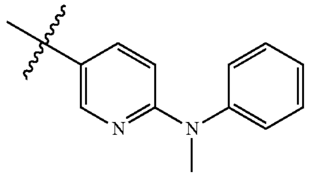 [SMILES: *c1ccc(N(C)c2ccccc2)nc1] | (500 MHz, Chloroform-d) δ 9.08 (d, J = 1.0 Hz, 1H), 8.05 (dd, J = 8.0, 1.0 Hz, 1H), 7.37-7.18 (m, 5H), 7.03-6.92 (m, 1H), 6.78 (d, J = 8.0 Hz, 1H), 5.83 (s, 1H), 3.70 (s, 3H). |
| 249 | $CF_3$ | 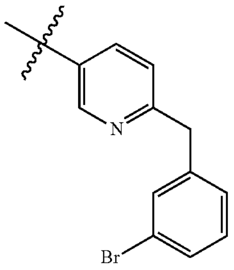 [SMILES: *c1ccc(Cc2cccc(Br)c2)nc1] | (500 MHz, Chloroform-d) δ 9.29 (d, J = 1.0 Hz, 1H), 8.22 (dd, J = 8.0, 1.0 Hz, 1H), 7.56-7.46 (m, 3H), 7.33-7.20 (m, 1H), 7.24 (s, 2H), 5.79 (s, 1H), 4.21 (s, 2H). |

TABLE 1-continued

Structure and $^{1}$HNMR data of Compound I

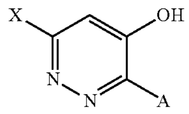

I

| No. | X | A | $^{1}$H NMR |
| --- | --- | --- | --- |
| 250 | $CF_3$ | 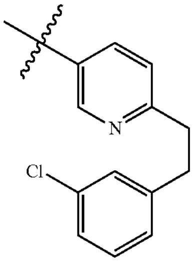 [SMILES: *c1ccc(CCc2cccc(Cl)c2)nc1] | (500 MHz, Chloroform-d) δ 8.71 (d, J = 1.0 Hz, 1H), 7.84 (dd, J = 8.0, 1.0 Hz, 1H), 7.48-7.40 (m, 4H), 7.31 (s, 1H), 6.98 (d, J = 8.0 Hz, 1H), 5.38 (s, 1H), 5.31 (s, 2H). |
| 251 | $CF_3$ | 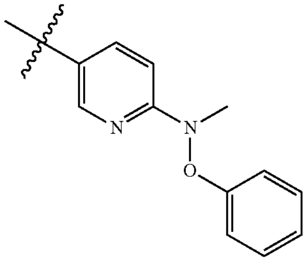 [SMILES: *c1ccc(N(C)Oc2ccccc2)nc1] | (500 MHz, Chloroform-d) δ 9.15 (d, J = 1.0 Hz, 1H), 8.10 (dd, J = 8.0, 1.0 Hz, 1H), 7.24 (s, 1H), 7.23-7.15 (m, 2H), 6.95-6.88 (m, 2H), 6.82-6.74 (m, 2H), 5.89 (s, 1H), 2.86 (s, 3H). |
| 252 | $CF_3$ | 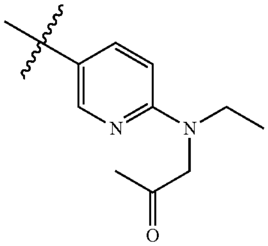 [SMILES: *c1ccc(N(CC)CC(C)=O)nc1] | (500 MHz, Chloroform-d) δ 8.94 (d, J = 1.0 Hz, 1H), 7.90 (dd, J = 8.0, 1.0 Hz, 1H), 7.28 (s, 1H), 6.58 (d, J = 8.0 Hz, 1H), 5.51 (s, 1H), 4.48 (s, 2H), 3.26 (q, J = 8.0 Hz, 2H), 2.13 (s, 3H), 0.93 (t, J = 8.0 Hz, 3H). |
| 253 | $CF_3$ | 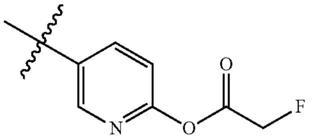 [SMILES: *c1ccc(OC(=O)CF)nc1] | (500 MHz, Chloroform-d) δ 8.61 (d, J = 1.0 Hz, 1H), 7.88 (dd, J = 8.0, 1.0 Hz, 1H), 7.23 (s, 1H), 6.92 (d, J = 8.0 Hz, 1H), 5.78 (s, 1H), 5.08 (d, J = 63.5 Hz, 2H). |
| 254 | $CF_3$ | 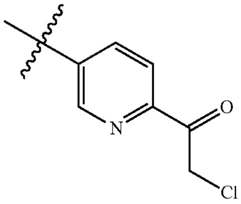 [SMILES: *c1ccc(C(=O)CCl)nc1] | (500 MHz, Chloroform-d) δ 9.23 (d, J = 1.0 Hz, 1H), 8.25 (dd, J = 8.0, 1.0 Hz, 1H), 8.19 (d, J = 8.0 Hz, 1H), 7.26 (s, 1H), 5.70 (s, 1H), 4.65 (s, 2H). |
| 255 | $CF_3$ | 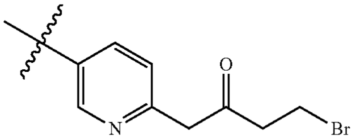 [SMILES: *c1ccc(CC(=O)CCBr)nc1] | (500 MHz, Chloroform-d) δ 9.23 (d, J = 1.0 Hz, 1H), 8.18 (dd, J = 8.0, 1.0 Hz, 1H), 7.31 (d, J = 8.0 Hz, 1H), 7.23 (s, 1H), 5.78 (s, 1H), 4.04 (s, 2H), 3.58 (t, J = 8.0 Hz, 2H), 2.95 (t, J = 8.0 Hz, 2H). |

TABLE 1-continued
Structure and $^1$HNMR data of Compound I
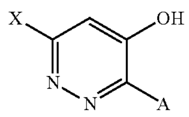
I
| No. | X | A | $^1$H NMR |
|---|---|---|---|
| 256 | $CF_3$ | 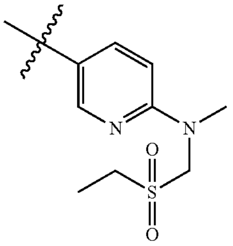 [SMILES: *c1ccc(N(C)CS(=O)(=O)CC)nc1] | (500 MHz, Chloroform-d) δ 8.96 (d, J = 1.5 Hz, 1H), 7.97 (dd, J = 8.0, 1.5 Hz, 1H), 7.24 (s, 1H), 6.58 (d, J = 8.0 Hz, 1H), 5.80 (s, 1H), 5.44 (s, 2H), 3.45 (q, J = 8.0 Hz, 2H), 3.24 (s, 3H), 1.33 (t, J = 8.0 Hz, 3H). |
| 257 | $CF_3$ | 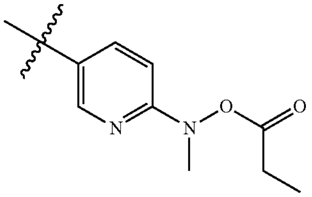 [SMILES: *c1ccc(N(C)OC(=O)CC)nc1] | (500 MHz, Chloroform-d) δ 8.91 (d, J = 1.0 Hz, 1H), 7.89 (dd, J = 7.5, 1.0 Hz, 1H), 7.23 (s, 1H), 6.78 (d, J = 7.5 Hz, 1H), 5.66 (s, 1H), 2.86 (s, 3H), 2.27 (q, J = 8.0 Hz, 2H), 1.07 (t, J = 8.0 Hz, 3H). |
| 258 | $CF_3$ | 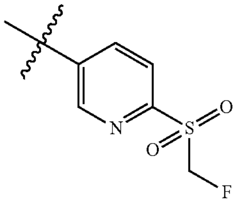 [SMILES: *c1ccc(S(=O)(=O)CF)nc1] | |
| 259 | $CF_3$ | 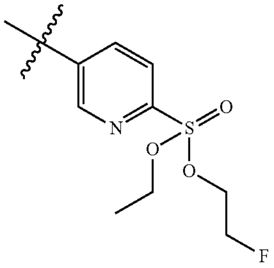 | |
| 260 | $CF_3$ | 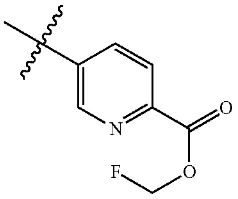 [SMILES: *c1ccc(C(=O)OCF)nc1] | |
| 261 | $CF_3$ | 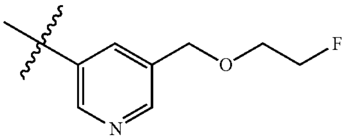 [SMILES: *c1cncc(COCCF)c1] | (500 MHz, Chloroform-d) δ 8.86 (d, J = 1.0 Hz, 1H), 8.63 (d, J = 1.5 Hz, 1H), 8.00 (dd, J = 1.5, 1.0 Hz, 1H), 7.31 (s, 1H), 5.22 (s, 1H), 4.54 (s, 2H), 4.31-3.54 (m, 4H). |

TABLE 1-continued

Structure and $^1$HNMR data of Compound I

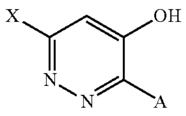

I

| No. | X | A | $^1$H NMR |
|---|---|---|---|
| 262 | $CF_3$ | 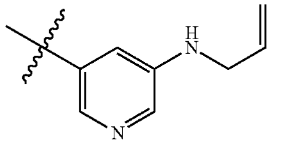 [SMILES: *c1cncc(NCC=C)c1] | (500 MHz, Chloroform-d) δ 8.41 (d, J = 1.0 Hz, 1H), 8.09 (d, J = 1.5 Hz, 1H), 7.29-7.21 (m, 2H), 6.00-5.78 (m, 1H), 5.29-5.10 (m, 2H), 4.26 (s, 1H), 3.99-3.77 (m, 2H). |
| 263 | $CF_3$ | 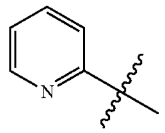 [SMILES: *c1ccccn1] | (500 MHz, Chloroform-d) δ 8.41 (dd, J = 5.5, 1.0 Hz, 1H), 8.09-8.00 (m, 2H), 7.29-7.21 (m, 2H), 5.78 (s, 1H). |
| 264 | $CF_3$ | 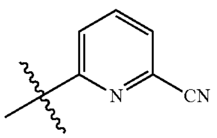 [SMILES: *c1cccc(C#N)n1] | (500 MHz, Chloroform-d) δ 8.26 (dd, J = 8.0, 1.0 Hz, 1H), 8.04 (dd, J = 7.5, 1.0 Hz, 1H), 7.92 (dd, J = 8.0, 7.5 Hz, 1H), 7.14 (s, 1H), 5.76 (s, 1H). |
| 265 | $CF_3$ | 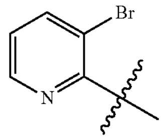 [SMILES: *c1ncccc1Br] | (500 MHz, Chloroform-d) δ 8.75 (dd, J = 5.0, 1.0 Hz, 1H), 7.85 (dd, J = 8.0, 1.0 Hz, 1H), 7.49 (dd, J = 8.0, 5.0 Hz, 1H), 7.14 (s, 1H), 5.46 (s, 1H). |
| 266 | $CF_3$ | 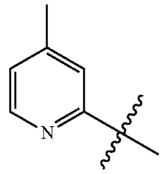 [SMILES: *c1cc(C)ccn1] | (500 MHz, Chloroform-d) δ 8.67 (d, J = 5.0 Hz, 1H), 7.45 (dd, J = 5.0, 1.0 Hz, 1H), 7.28 (d, J = 1.0 Hz, 1H), 7.12 (s, 1H), 5.66 (s, 1H), 2.38 (s, 3H). |
| 267 | $CF_3$ | 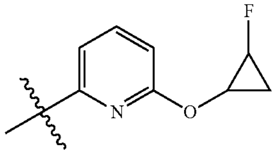 [SMILES: *c1cccc(OC2CC2F)n1] | |
| 268 | $CF_3$ | 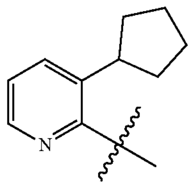 [SMILES: *c1ncccc1C1CCCC1] | (500 MHz, Chloroform-d) δ 8.60 (dd, J = 5.0, 1.0 Hz, 1H), 7.54 (dd, J = 8.0, 1.0 Hz, 1H), 7.37 (dd, J = 8.0, 5.0 Hz, 1H), 7.14 (s, 1H), 5.36 (s, 1H), 3.38-3.29 (m, 1H), 2.04-1.92 (m, 4H), 1.74-1.57 (m, 4H). |
| 269 | $CF_3$ | 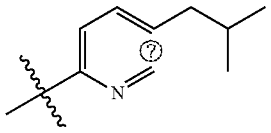 [SMILES: */C(=C/C=C/CC(C)C)N=C] | (500 MHz, Chloroform-d) δ 8.52 (d, J = 1.0 Hz, 1H), 7.82 (d, J = 8.0 Hz, 1H), 7.56 (dd, J = 8.0, 1.0 Hz, 1H), 7.08 (s, 1H), 5.73 (s, 1H), 2.47 (d, J = 7.5 Hz, 2H), 1.94-1.82 (m, 1H), 0.92 (d, J = 7.0 Hz, 6H). |

TABLE 1-continued

Structure and $^1$HNMR data of Compound I

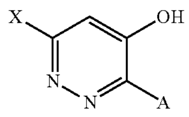

I

| No. | X | A | $^1$H NMR |
|---|---|---|---|
| 270 | $CF_3$ | 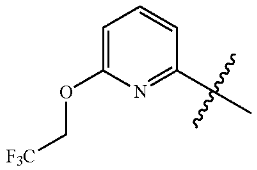 [SMILES: *c1cccc(OCC(F)(F)F)n1] | (500 MHz, Chloroform-d) δ 7.61 (dd, J = 8.0, 7.5 Hz, 1H), 7.23 (dd, J = 8.0, 1.0 Hz, 1H), 7.13 (s, 1H), 6.87 (dd, J = 8.0, 1.0 Hz, 1H), 5.75 (s, 1H), 5.03 (q, J = 9.0 Hz, 2H). |
| 271 | $CF_3$ | 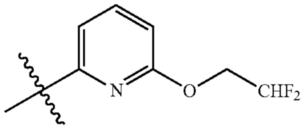 [SMILES: *c1cccc(OCC(F)F)n1] | (500 MHz, Chloroform-d) δ 7.65 (dd, J = 8.0, 7.5 Hz, 1H), 7.26 (dd, J = 8.0, 1.0 Hz, 1H), 7.17 (s, 1H), 6.89 (dd, J = 8.0, 1.0 Hz, 1H), 5.98 (s, 1H), 5.86-5.66 (m, 1H), 4.32-4.26 (m, 2H). |
| 272 | $CF_3$ | 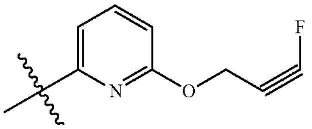 [SMILES: *c1cccc(OCC#CF)n1] | |
| 273 | $CF_3$ | 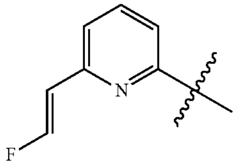 [SMILES: *c1cccc(/C=C/F)n1] | |
| 274 | $CF_3$ | 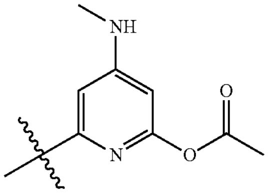 [SMILES: *c1cc(NC)cc(OC(C)=O)n1] | (500 MHz, Chloroform-d) δ 7.11 (s, 1H), 6.58 (s, 1H), 6.15 (s, 1H), 4.71 (s, 1H), 2.84 (s, 3H), 2.28 (s, 3H). |
| 275 | $CF_3$ | 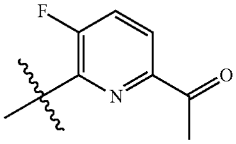 [SMILES: *c1nc(C(C)=O)ccc1F] | (500 MHz, Chloroform-d) δ 7.11 (s, 1H), 6.58 (dd, J = 10.5, 7.5 Hz, 1H), 6.15 (dd, J = 7.5, 5.5 Hz, 1H), 5.71 (s, 1H), 2.28 (s, 3H). |
| 276 | $CF_3$ | 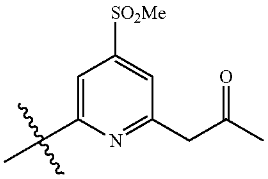 [SMILES: *c1cc(S(C)(=O)=O)cc(CC(C)=O)n1] | (500 MHz, Chloroform-d) δ 8.23 (d, J = 1.0 Hz, 1H), 8.05 (d, J = 1.0 Hz, 1H), 7.10 (s, 1H), 5.82 (s, 1H), 4.04 (s, 2H), 3.12 (s, 3H), 2.47 (q, J = 8.0 Hz, 2H), 1.24 (t, J = 8.0 Hz, 3H). |
| 277 | $CF_3$ | 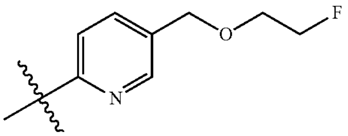 [SMILES: *c1ccc(COCCF)cn1] | (500 MHz, Chloroform-d) δ 8.72 (d, J = 1.0 Hz, 1H), 8.01 (d, J = 8.0 Hz, 1H), 7.81 (dd, J = 8.0, 1.0 Hz, 1H), 7.12 (s, 1H), 5.62 (s, 1H), 4.54 (s, 2H), 4.31-4.21 (m, 2H), 3.60-3.54 (m, 2H). |

TABLE 1-continued

Structure and $^1$HNMR data of Compound I

I

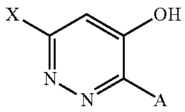

| No. | X | A | $^1$H NMR |
|---|---|---|---|
| 278 | $CF_3$ | 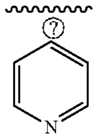 | (500 MHz, Chloroform-d) δ 8.54 (d, J = 5.1 Hz, 2H), 7.68 (d, J = 5.1 Hz, 2H), 7.31 (s, 1H), 5.31 (s, 1H). |
| 279 | $CF_3$ | 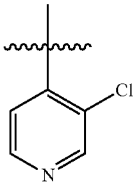 [SMILES: *c1ccncc1Cl] | (500 MHz, Chloroform-d) δ 8.58-8.49 (m, 2H), 7.61 (d, J = 5.0 Hz, 1H), 7.27 (s, 1H), 5.82 (s, 1H). |
| 280 | $CF_3$ | 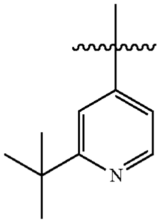 [SMILES: *c1ccnc(C(C)(C)C)c1] | (500 MHz, Chloroform-d) δ 8.65 (d, J = 5.0 Hz, 1H), 7.58 (d, J = 1.0 Hz, 1H), 7.46 (dd, J = 5.0, 1.0 Hz, 1H), 7.30 (s, 1H), 5.35 (s, 1H), 1.33 (s, 9H). |
| 281 | $CF_3$ | 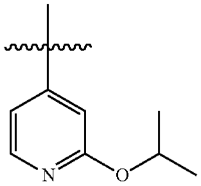 [SMILES: *c1ccnc(OC(C)C)c1] | (500 MHz, Chloroform-d) δ 8.12 (d, J = 5.0 Hz, 1H), 7.24 (s, 1H), 7.13 (d, J = 1.0 Hz, 1H), 7.01 (dd, J = 5.0, 1.0 Hz, 1H), 5.81 (s, 1H), 4.90 (hept, J = 7.0 Hz, 1H), 1.29 (d, J = 7.0 Hz, 6H). |
| 282 | $CF_3$ | 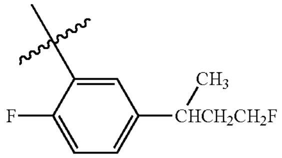 | (500 MHz, Chloroform-d) δ 8.67 (d, J = 8.0 Hz, 1H), 7.41 (d, J = 5.0 Hz, 1H), 7.26 (s, 1H), 6.31 (s, 1H), 4.12-4.02 (m, 2H), 3.43-3.31 (m, 1H), 1.79-1.73 (m, 2H), 1.33 (d, J = 7.0 Hz, 3H). |
| 283 | $CF_3$ | 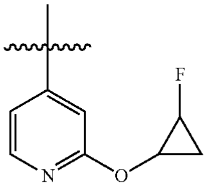 [SMILES: *c1ccnc(OC2CC2F)c1] | |
| 284 | $CF_3$ | 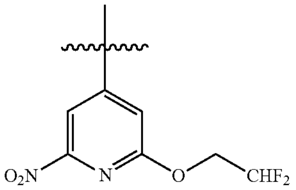 [SMILES: *c1cc(OCC(F)F)nc([N+](=O)[O-])c1] | (500 MHz, Chloroform-d) δ 8.05 (d, J = 1.0 Hz, 1H), 7.67 (d, J = 1.0 Hz, 1H), 7.26 (s, 1H), 5.96-5.86 (m, 1H), 5.84 (s, 1H), 4.30-4.20 (m, 2H). |

TABLE 1-continued

Structure and $^{1}$HNMR data of Compound I

I

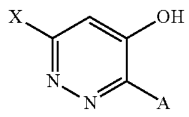

| No. | X | A | $^{1}$H NMR |
| --- | --- | --- | --- |
| 285 | $CF_3$ | 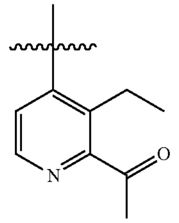 [SMILES: *c1ccnc(C(C)=O)c1CC] | (500 MHz, Chloroform-d) δ 8.73 (d, J = 5.0 Hz, 1H), 7.76 (d, J = 5.0 Hz, 1H), 7.24 (s, 1H), 5.62 (s, 1H), 2.66 (q, J = 8.0 Hz, 2H), 2.45 (s, 3H), 1.22 (t, J = 8.0 Hz, 3H). |
| 286 | $CF_3$ | 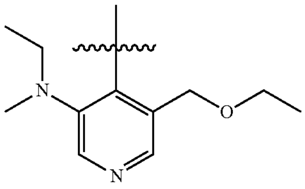 [SMILES: *c1c(COCC)cncc1N(C)CC] | (500 MHz, Chloroform-d) δ 8.61 (s, 1H), 8.34 (s, 1H), 7.36 (s, 1H), 6.36 (s, 1H), 4.52 (s, 2H), 3.58 (q, J = 8.0 Hz, 2H), 3.26 (q, J = 8.0 Hz, 2H), 2.95 (s, 3H), 1.15 (d, J = 8.0 Hz, 3H), 1.10 (d, J = 8.0 Hz, 3H). |
| 287 | $CF_3$ | 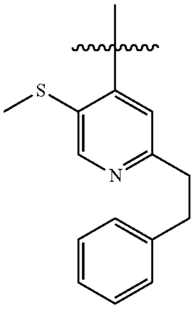 [SMILES: *c1cc(CCc2ccccc2)ncc1SC] | (500 MHz, Chloroform-d) δ 8.37 (s, 1H), 7.46-7.40 (m, 2H), 7.44-7.34 (m, 2H), 7.37-7.27 (m, 1H), 7.31 (s, 1H), 7.18 (s, 1H), 5.66 (s, 1H), 5.28 (s, 2H), 2.32 (s, 3H). |
| 288 | $CF_3$ | 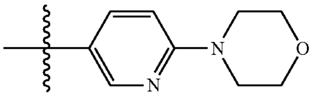 [SMILES: *c1ccc(N2CCOCC2)nc1] | $^{1}$H NMR (500 MHz, DMSO-$d_6$) δ 13.15 (s, 1H), 8.89 (d, J = 2.0 Hz, 1H), 8.25 (dd, J = 7.0, 2.0 Hz, 1H), 7.19 (s, 1H), 6.94 (d, J = 7.0 Hz, 1H), 3.69-3.57 (m, 4H), 3.55-3.38 (m, 4H). |
| 289 | $CF_3$ | 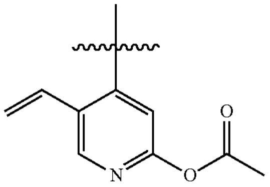 [SMILES: *c1cc(OC(C)=O)ncc1C=C] | (500 MHz, Chloroform-d) δ 8.31 (s, 1H), 7.26 (s, 1H), 6.96 (s, 1H), 6.80-6.61 (m, 1H), 5.85 (s, 1H), 5.72-5.43 (m, 2H), 2.32 (s, 3H). |
| 290 | $CF_3$ | 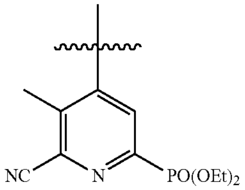 | (500 MHz, Chloroform-d) δ 8.29 (s, 1H), 7.25 (s, 1H), 5.75 (s, 1H), 4.07 (q, J = 8.0 Hz, 4H), 2.48 (s, 3H), 1.20 (t, J = 8.0 Hz, 6H). |

TABLE 1-continued
Structure and $^1$HNMR data of Compound I
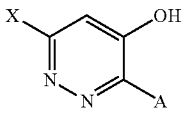
I
| No. | X | A | $^1$H NMR |
|---|---|---|---|
| 291 | $CF_3$ | 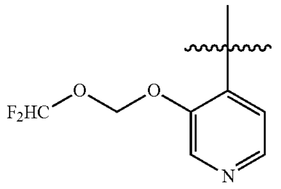 [SMILES: *c1ccncc1OCOC(F)F] | (500 MHz, Chloroform-d) δ 8.38 (d, J = 5.0 Hz, 1H), 8.31 (s, 1H), 7.62 (d, J = 5.0 Hz, 1H), 7.29 (t, J = 73.5 Hz, 1H), 7.25 (s, 2H), 7.02 (s, 1H), 5.70 (s, 1H). |
| 292 | $CF_3$ | 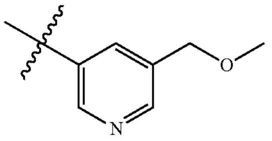 [SMILES: *c1cncc(COC)c1] | (500 MHz, Chloroform-d) δ 8.87 (d, J = 1.0 Hz, 1H), 8.55 (d, J = 1.5 Hz, 1H), 7.98 (dd, J = 1.5, 1.0 Hz, 1H), 7.28 (s, 1H), 5.72 (s, 1H), 4.52 (s, 2H), 3.36 (s, 3H). |
| 293 | $CF_3$ | 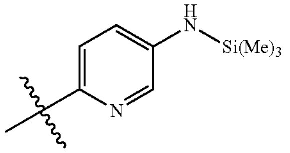 | |
| 294 | $CF_3$ | 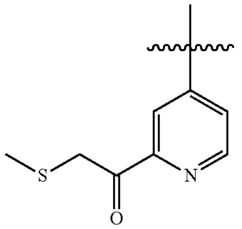 [SMILES: *c1ccnc(C(=O)CSC)c1] | (500 MHz, Chloroform-d) δ 8.83 (d, J = 5.0 Hz, 1H), 8.42 (d, J = 1.0 Hz, 1H), 7.98 (dd, J = 5.0, 1.0 Hz, 1H), 7.24 (s, 1H), 5.79 (s, 1H), 3.55 (s, 2H), 2.20 (s, 3H). |
| 295 | $CF_3$ | 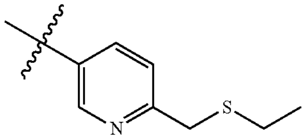 [SMILES: *c1ccc(CSCC)nc1] | (500 MHz, Chloroform-d) δ 9.11 (d, J = 1.0 Hz, 1H), 8.05 (dd, J = 8.0, 1.0 Hz, 1H), 7.32-7.23 (m, 2H), 5.38 (s, 1H), 4.03 (s, 2H), 2.48 (q, J = 8.0 Hz, 2H), 1.27 (t, J = 8.0 Hz, 3H). |
| 296 | $CF_3$ | 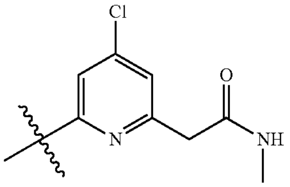 [SMILES: *c1cc(Cl)cc(CC(=O)NC)n1] | (500 MHz, Chloroform-d) δ 7.73 (d, J = 1.0 Hz, 1H), 7.53 (d, J = 1.0 Hz, 1H), 7.11 (s, 1H), 3.77 (s, 2H), 2.91 (s, 3H). |
| 297 | $CF_3$ | 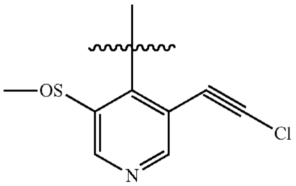 | |

TABLE 1-continued
Structure and $^1$HNMR data of Compound I
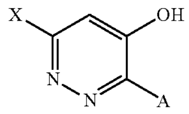
I
| No. | X | A | $^1H$ NMR |
|---|---|---|---|
| 298 | $CF_3$ | 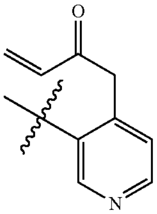 [SMILES: *c1cnccc1CC(=O)C=C] | |
| 299 | $CF_3$ | 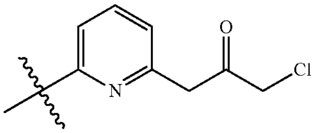 [SMILES: *c1cccc(CC(=O)CCl)n1] | |
| 300 | $CF_3$ | 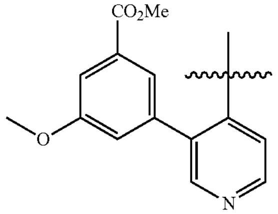 [SMILES: *c1ccncc1-c1cc(OC)cc(C(=O)OC)c1] | (500 MHz, Chloroform-d) δ 9.06 (s, 1H), 8.82 (d, J = 5.0 Hz, 1H), 7.94 (dd, J = 2.0, 1.5 Hz, 1H), 7.75 (d, J = 5.0 Hz, 1H), 7.55 (dd, J = 2.5, 1.5 Hz, 1H), 7.44 (dd, J = 2.5, 2.0 Hz, 1H), 7.28 (s, 1H), 5.63 (s, 1H), 3.81 (s, 3H), 3.12 (s, 3H). |
| 301 | $CF_3$ | 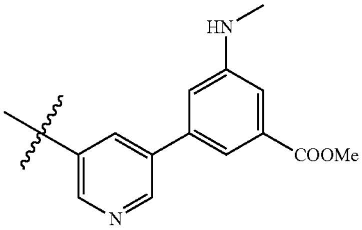 [SMILES: *c1cncc(-c2cc(NC)cc(C(=O)OC)c2)c1] | (500 MHz, Chloroform-d) δ 9.11 (d, J = 1.0 Hz, 1H), 8.96 (d, J = 1.5 Hz, 1H), 8.36 (dd, J = 1.5, 1.0 Hz, 1H), 7.68-7.63 (m, 1H), 7.25 (s, 1H), 7.09-6.92 (m, 2H), 5.89 (s, 1H), 4.33 (s, 1H), 3.95 (s, 3H), 2.83 (s, 3H). |
| 302 | $CF_3$ | 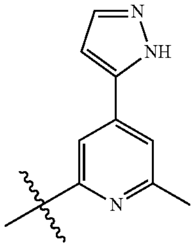 [SMILES: *c1cc(-c2ccn[nH]2)cc(C)n1] | (500 MHz, Chloroform-d) δ 7.90 (d, J = 1.0 Hz, 1H), 7.76 (d, J = 2.5 Hz, 1H), 7.48 (d, J = 1.0 Hz, 1H), 7.13 (s, 1H), 6.75 (d, J = 2.5 Hz, 1H), 2.69 (s, 3H). |
| 303 | $CF_3$ | 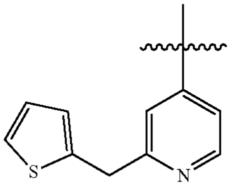 [SMILES: *c1ccnc(Cc2cccs2)c1] | (500 MHz, Chloroform-d) δ 8.76 (d, J = 5.0 Hz, 1H), 7.77 (d, J = 1.0 Hz, 1H), 7.64 (dd, J = 5.0, 1.0 Hz, 1H), 7.27 (d, J = 2.5 Hz, 1H), 7.24 (s, 1H), 7.00 (dd, J = 2.5, 2.0 Hz, 1H), 6.88 (d, J = 2.0 Hz, 1H), 5.80 (s, 1H), 4.41 (s, 2H). |

TABLE 1-continued

Structure and $^1$HNMR data of Compound I

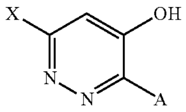

I

| No. | X | A | $^1$H NMR |
|---|---|---|---|
| 304 | $CF_3$ | 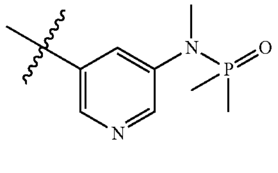 [SMILES: *c1cncc(N(C)P(C)(C)=O)c1] | |
| 305 | $CF_3$ | 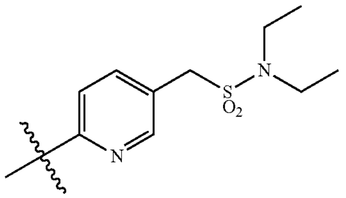 [SMILES: *c1ccc(CS(=O)(=O)N(CC)CC)cn1] | (500 MHz, Chloroform-d) δ 8.66 (d, J = 1.5 Hz, 1H), 7.83 (d, J = 8.0 Hz, 1H), 7.66 (dd, J = 8.0, 1.5 Hz, 1H), 7.10 (s, 1H), 5.44 (s, 1H), 4.67 (s, 2H), 2.59 (q, J = 8.0 Hz, 4H), 1.17 (t, J = 8.0 Hz, 6H). |
| 306 | $CF_3$ | 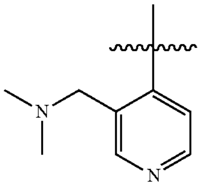 [SMILES: *c1ccncc1CN(C)C] | (500 MHz, Chloroform-d) δ 8.66 (s, 1H), 8.51 (d, J = 5.0 Hz, 1H), 7.48 (d, J = 5.0 Hz, 1H), 7.42 (s, 1H), 6.07 (s, 1H), 3.28 (s, 2H), 2.34 (s, 6H). |
| 307 | $CF_3$ | 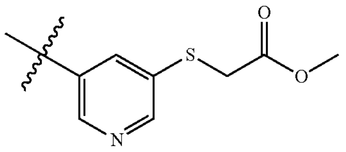 [SMILES: *c1cncc(SCC(=O)OC)c1] | (500 MHz, Chloroform-d) δ 8.72 (d, J = 1.5 Hz, 1H), 8.66 (d, J = 1.0 Hz, 1H), 8.12 (dd, J = 1.5, 1.0 Hz, 1H), 7.29 (s, 1H), 5.54 (s, 1H), 3.84 (s, 3H), 3.70 (s, 2H). |
| 308 | $CF_3$ | 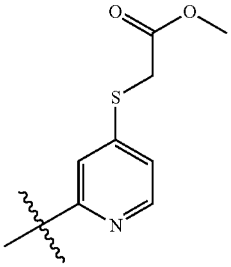 [SMILES: *c1cc(SCC(=O)OC)ccn1] | (500 MHz, Chloroform-d) δ 8.63 (d, J = 5.0 Hz, 1H), 7.79 (d, J = 1.0 Hz, 1H), 7.38 (dd, J = 5.0, 1.0 Hz, 1H), 7.12 (s, 1H), 3.69 (s, 3H), 3.59 (s, 2H). |
| 309 | $CF_3$ | 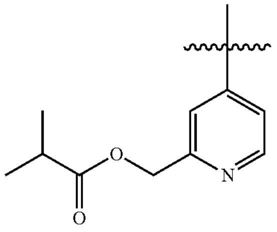 [SMILES: *c1ccnc(COC(=O)C(C)C)c1] | (500 MHz, Chloroform-d) δ 8.67 (d, J = 5.0 Hz, 1H), 7.88 (d, J = 1.0 Hz, 1H), 7.64 (dd, J = 5.0, 1.0 Hz, 1H), 7.30 (s, 1H), 5.67 (s, 2H), 5.33 (s, 1H), 2.69 (hept, J = 6.5 Hz, 1H), 1.24 (d, J = 6.5 Hz, 6H). |

TABLE 1-continued
Structure and ¹HNMR data of Compound I
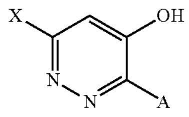
I
| No. | X | A | ¹H NMR |
|---|---|---|---|
| 310 | $CF_3$ | 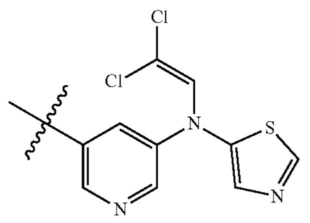 [SMILES: *c1cncc(N(C=C(Cl)Cl)c2cncs2)c1] | |
| 311 | $CF_3$ | 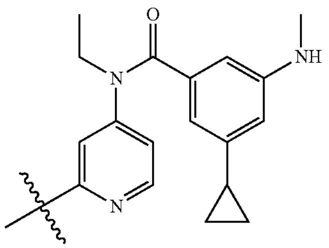 [SMILES: *c1cc(N(CC)C(=O)c2cc(NC)cc(C3CC3)c2)ccn1] | (500 MHz, Chloroform-d) δ 8.60 (d, J = 5.0 Hz, 1H), 7.99 (d, J = 1.0 Hz, 1H), 7.28 (dd, J = 5.0, 1.0 Hz, 1H), 7.14 (s, 1H), 6.87 (dd, J = 2.0, 1.0 Hz, 1H), 6.72-6.56 (m, 3H), 4.48 (s, 1H), 3.95 (q, J = 8.0 Hz, 2H), 2.78 (s, 3H), 1.91-1.81 (m, 1H), 1.20 (t, J = 8.0 Hz, 3H), 1.14-1.05 (m, 2H), 0.78-0.69 (m, 2H). |
| 312 | $CF_3$ | 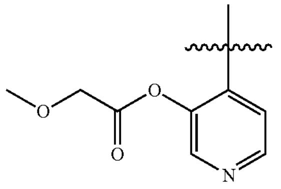 [SMILES: *c1ccncc1OC(=O)COC] | (500 MHz, Chloroform-d) δ 8.41 (d, J = 5.0 Hz, 1H), 8.23 (s, 1H), 7.59 (d, J = 5.0 Hz, 1H), 7.29 (s, 1H), 6.11 (s, 1H), 4.31 (s, 2H), 3.39 (s, 3H). |
| 313 | $CF_3$ | 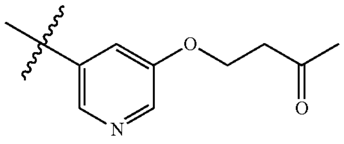 [SMILES: *c1cncc(OCCC(C)=O)c1] | (500 MHz, Chloroform-d) δ 8.60 (d, J = 1.5 Hz, 1H), 8.12 (d, J = 1.0 Hz, 1H), 7.53 (dd, J = 1.5, 1.0 Hz, 1H), 7.24 (s, 1H), 5.81 (s, 1H), 4.22 (t, J = 6.5 Hz, 2H), 2.87 (t, J = 6.5 Hz, 2H), 2.12 (s, 3H). |
| 314 | $CF_3$ | 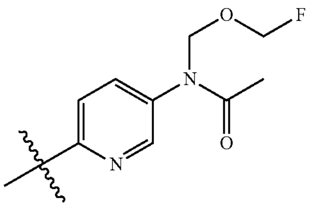 [SMILES: *c1ccc(N(COCF)C(C)=O)cn1] | |
| 315 | $CF_3$ | 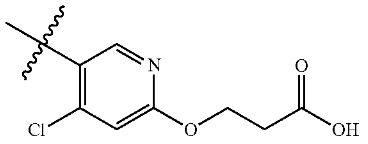 [SMILES: *c1cnc(OCCC(=O)O)cc1Cl] | (500 MHz, Chloroform-d) δ 8.42 (s, 1H), 7.29 (s, 1H), 6.94 (s, 1H), 5.78 (s, 1H), 4.21 (t, J = 7.0 Hz, 2H), 2.65 (t, J = 7.0 Hz, 2H). |

TABLE 1-continued
Structure and $^{1}$HNMR data of Compound I
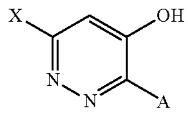
I
| No. | X | A | $^{1}$H NMR |
|---|---|---|---|
| 316 | $CF_3$ | 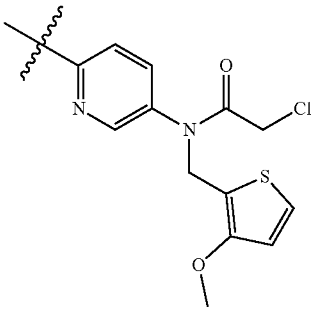 [SMILES: *c1ccc(N(Cc2sccc2OC)C(=O)CCl)cn1] | (500 MHz, Chloroform-d) δ 9.74 (d, J = 1.0 Hz, 1H), 7.93-7.84 (m, 2H), 7.22 (d, J = 2.5 Hz, 1H), 7.13 (s, 1H), 6.63 (d, J = 2.5 Hz, 1H), 4.91 (s, 2H), 3.85 (s, 3H), 3.63 (s, 2H). |
| 317 | $CF_3$ | 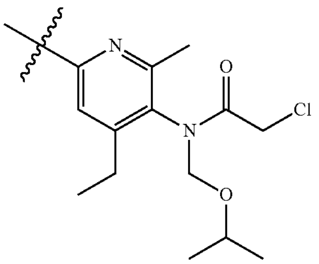 [SMILES: *c1cc(CC)c(N(COC(C)C)C(=O)CCl)c(C)n1] | (500 MHz, Chloroform-d) δ 7.25 (s, 1H), 7.13 (s, 1H), 5.46 (s, 2H), 3.89 (hept, J = 6.5 Hz, 1H), 3.63 (s, 2H), 3.42 (q, J = 8.0 Hz, 2H), 2.66 (s, 3H), 1.20 (t, J = 8.0 Hz, 3H), 1.15 (d, J = 6.5 Hz, 6H). |
| 318 | $CF_3$ | 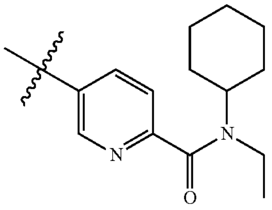 [SMILES: *c1ccc(C(=O)N(CC)C2CCCCC2)nc1] | (500 MHz, Chloroform-d) δ 9.26 (s, 1H), 8.37 (d, J = 8.0 Hz, 1H), 8.12 (d, J = 8.0 Hz, 1H), 7.31 (s, 1H), 5.33 (s, 1H), 3.48 (q, J = 8.0 Hz, 2H), 3.21-3.13 (m, 1H), 1.97-1.87 (m, 2H), 1.84-1.72 (m, 1H), 1.75-1.57 (m, 4H), 1.54-1.42 (m, 2H), 1.45-1.37 (m, 1H), 1.23 (t, J = 8.0 Hz, 3H). |
| 319 | $CF_3$ | 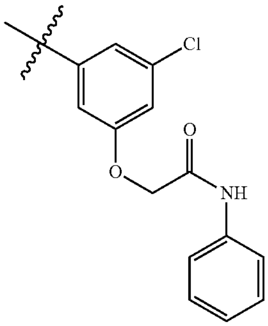 [SMILES: *c1cc(Cl)cc(OCC(=O)Nc2ccccc2)c1] | (500 MHz, Chloroform-d) δ 8.01 (s, 1H), 7.33 (s, 1H), 7.34-7.23 (m, 6H), 7.07 (s, 1H), 5.83 (s, 1H), 4.88 (s, 2H). |
| 320 | $CF_3$ | 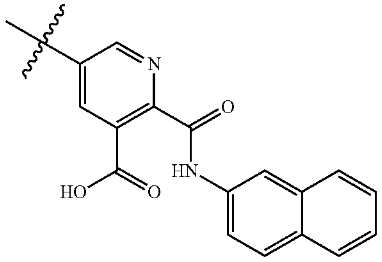 [SMILES: *c1cnc(C(=O)Nc2ccc3ccccc3c2)c(C(=O)O)c1] | (500 MHz, Chloroform-d) δ 9.45 (d, J = 1.5 Hz, 1H), 8.59 (s, 1H), 8.52 (d, J = 1.5 Hz, 1H), 7.96-7.80 (m, 2H), 7.41-7.34 (m, 4H), 7.31-7.26 (m, 2H), 4.59 (s, 1H). |

TABLE 1-continued

Structure and $^1$HNMR data of Compound I

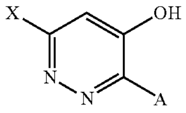

I

| No. | X | A | $^1$H NMR |
|---|---|---|---|
| 321 | $CF_3$ | 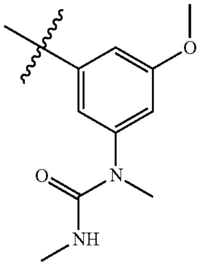 [SMILES: *c1cc(OC)cc(N(C)C(=O)NC)c1] | (500 MHz, Chloroform-d) δ 7.68 (dd, J = 2.0, 1.5 Hz, 1H), 7.17 (s, 1H), 7.07 (s, 1H), 7.01 (dd, J = 1.5, 1.0 Hz, 1H), 6.94 (dd, J = 2.0, 1.0 Hz, 1H), 4.67 (s, 1H), 3.81 (s, 3H), 3.74 (s, 3H), 2.84 (s, 3H). |
| 322 | $CF_3$ | 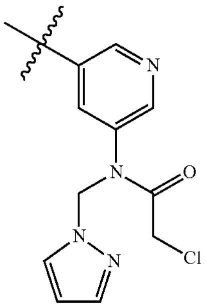 [SMILES: *c1cncc(N(Cn2cccn2)C(=O)CCl)c1] | (500 MHz, Chloroform-d) δ 9.41 (d, J = 1.0 Hz, 1H), 8.68 (d, J = 1.0 Hz, 1H), 8.03 (s, 1H), 7.44 (d, J = 2.5 Hz, 1H), 7.36-7.30 (m, 2H), 6.61 (dd, J = 2.5, 2.0 Hz, 1H), 5.82 (s, 2H), 5.17 (s, 1H), 3.63 (s, 2H). |
| 323 | $CF_3$ | 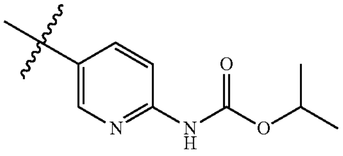 [SMILES: *c1ccc(NC(=O)OC(C)C)nc1] | (500 MHz, Chloroform-d) δ 9.07 (d, J = 1.5 Hz, 1H), 8.38 (d, J = 8.0 Hz, 1H), 8.16 (dd, J = 8.0, 1.5 Hz, 1H), 7.30 (s, 1H), 6.64 (s, 1H), 5.29 (s, 1H), 5.32-5.20 (hept, J = 6.5 Hz, 1H), 1.29 (d, J = 6.5 Hz, 6H). |
| 324 | $CF_3$ | 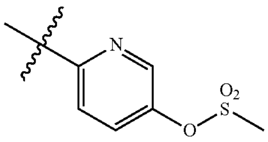 [SMILES: *c1ccc(OS(C)(=O)=O)cn1] | (500 MHz, Chloroform-d) δ 8.74 (d, J = 1.0 Hz, 1H), 8.00 (d, J = 8.0 Hz, 1H), 7.92 (dd, J = 8.0, 1.0 Hz, 1H), 7.12 (s, 1H), 5.39 (s, 1H), 3.53 (s, 3H). |
| 325 | $CF_3$ | 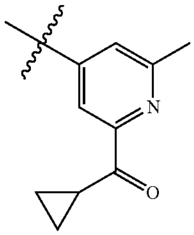 [SMILES: *c1cc(C)nc(C(=O)C2CC2)c1] | (500 MHz, Chloroform-d) δ 8.27 (d, J = 1.0 Hz, 1H), 7.87 (d, J = 1.0 Hz, 1H), 7.31 (s, 1H), 5.43 (s, 1H), 2.68 (s, 3H), 2.32-2.21 (m, 1H), 1.37-1.27 (m, 2H), 1.08-0.99 (m, 2H). |

TABLE 1-continued
Structure and $^1$HNMR data of Compound I
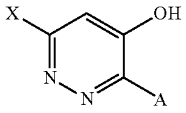
I
| No. | X | A | $^1$H NMR |
| --- | --- | --- | --- |
| 326 | $CF_3$ | 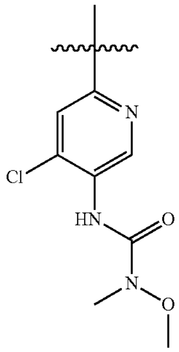 [SMILES: *c1cc(Cl)c(NC(=O)N(C)OC)cn1] | (500 MHz, Chloroform-d) δ 8.07 (s, 1H), 7.84 (s, 1H), 7.13 (s, 1H), 5.33 (s, 1H), 3.58 (s, 3H), 2.70 (s, 3H). |
| 327 | $CF_3$ | 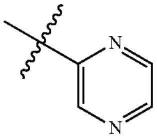 [SMILES: *c1cnccn1] | (500 MHz, Chloroform-d) δ 9.32 (s, 1H), 8.82 (d, J = 5.5 Hz, 1H), 8.76 (d, J = 5.5 Hz, 1H), 7.10 (s, 1H), 5.13 (s, 1H). |
| 328 | $CF_3$ | 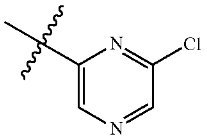 [SMILES: *c1cncc(Cl)n1] | (500 MHz, Chloroform-d) δ 9.24 (s, 1H), 8.72 (s, 1H), 7.29 (s, 1H), 5.18 (s, 1H). |
| 329 | $CF_3$ | 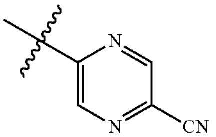 [SMILES: *c1cnc(C#N)cn1] | (500 MHz, Chloroform-d) δ 9.42 (s, 1H), 9.11 (s, 1H), 7.30 (s, 1H), 5.23 (s, 1H). |
| 330 | $CF_3$ | 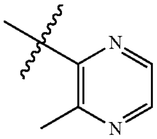 [SMILES: *c1nccnc1C] | (500 MHz, Chloroform-d) δ 8.62 (d, J = 5.5 Hz, 1H), 8.34 (d, J = 5.5 Hz, 1H), 7.28 (s, 1H), 5.19 (s, 1H), 2.80 (s, 3H). |
| 331 | $CF_3$ | 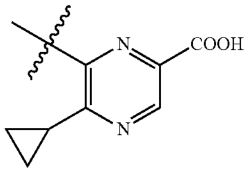 [SMILES: *c1nc(C(=O)O)cnc1C1CC1] | (500 MHz, Chloroform-d) δ 9.18 (s, 1H), 7.31 (s, 1H), 6.93 (s, 1H), 5.43 (s, 1H), 1.99-1.83 (m, 1H), 0.91-0.81 (m, 2H), 0.70-0.60 (m, 2H). |
| 332 | $CF_3$ | 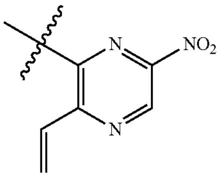 [SMILES: *c1nc([N+](=O)[O-])cnc1C=C] | (500 MHz, Chloroform-d) δ 9.91 (s, 1H), 7.35 (s, 1H), 6.96-6.82 (m, 1H), 6.01-5.83 (m, 1H), 5.35 (s, 1H). |

TABLE 1-continued
Structure and $^1$HNMR data of Compound I
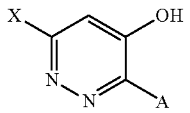
I
| No. | X | A | $^1$H NMR |
|---|---|---|---|
| 333 | $CF_3$ | 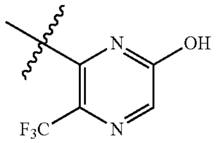 [SMILES: *c1nc(O)cnc1C(F)(F)F] | (500 MHz, Chloroform-d) δ 8.12 (s, 1H), 7.99 (s, 1H), 7.28 (s, 1H), 5.29 (s, 1H). |
| 334 | $CF_3$ | 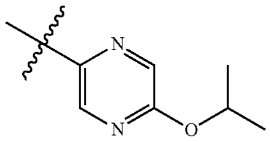 [SMILES: *c1cnc(OC(C)C)cn1] | (500 MHz, Chloroform-d) δ 9.13 (s, 1H), 8.40 (s, 1H), 7.28 (s, 1H), 5.39 (s, 1H), 4.89 (hept, J = 6.5 Hz, 1H), 1.30 (d, J = 6.5 Hz, 6H). |
| 335 | $CF_3$ | 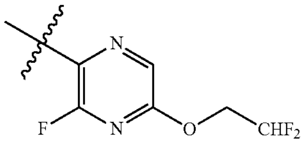 [SMILES: *c1ncc(OCC(F)F)nc1F] | (500 MHz, Chloroform-d) δ 8.35 (s, 1H), 7.25 (s, 1H), 5.91-5.80 (m, 1H), 5.70 (s, 1H), 4.34-4.28 (m, 2H). |
| 336 | $CF_3$ | 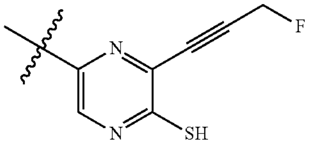 [SMILES: *c1cnc(S)c(C#CCF)n1] | |
| 337 | $CF_3$ | 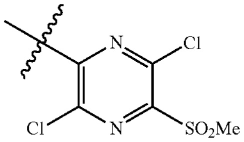 [SMILES: *c1nc(Cl)c(S(C)(=O)=O)nc1Cl] | (500 MHz, Chloroform-d) δ 7.26 (s, 1H), 5.71 (s, 1H), 3.35 (s, 3H). |
| 338 | $CF_3$ | 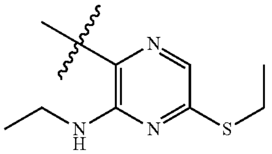 [SMILES: *c1ncc(SCC)nc1NCC] | (500 MHz, Chloroform-d) δ 9.21 (s, 1H), 8.55 (s, 1H), 7.33 (s, 1H), 5.07 (s, 1H), 3.53 (q, J = 8.0 Hz, 2H), 2.97 (q, J = 8.0 Hz, 2H), 1.37 (t, J = 8.0 Hz, 3H), 1.20 (t, J = 8.0 Hz, 3H). |
| 339 | $CF_3$ | 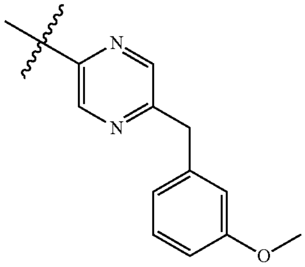 [SMILES: *c1cnc(Cc2cccc(OC)c2)cn1] | (500 MHz, Chloroform-d) δ 9.34 (s, 1H), 8.75 (s, 1H), 7.30-7.23 (m, 2H), 7.02-6.96 (m, 3H), 5.41 (s, 1H), 3.88 (s, 2H), 3.71 (s, 3H). |
| 340 | $CF_3$ | 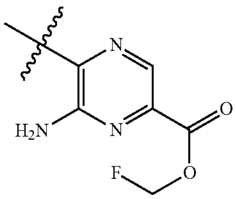 [SMILES: *c1ncc(C(=O)OCF)nc1N] | |

TABLE 1-continued

Structure and $^1$HNMR data of Compound I

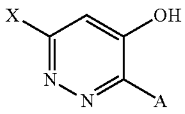

I

| No. | X | A | $^1$H NMR |
|---|---|---|---|
| 341 | $CF_3$ | 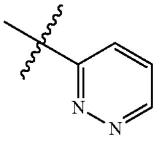 [SMILES: *c1cccnn1] | (500 MHz, Chloroform-d) δ 9.50 (dd, J = 5.5, 1.5 Hz, 1H), 8.01 (dd, J = 7.5, 1.5 Hz, 1H), 7.82 (dd, J = 7.5, 5.5 Hz, 1H), 7.23 (s, 1H), 5.77 (s, 1H). |
| 342 | $CF_3$ | 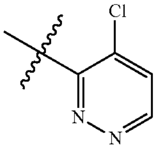 [SMILES: *c1nnccc1Cl] | (500 MHz, Chloroform-d) δ 9.49 (d, J = 5.5 Hz, 1H), 7.88 (d, J = 5.5 Hz, 1H), 7.29 (s, 1H), 5.37 (s, 1H). |
| 343 | $CF_3$ | 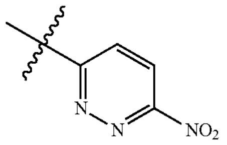 [SMILES: *c1ccc([N+](=O)[O-])nn1] | (500 MHz, Chloroform-d) δ 8.78 (d, J = 7.5 Hz, 1H), 8.38 (d, J = 7.5 Hz, 1H), 7.24 (s, 1H), 5.82 (s, 1H). |
| 344 | $CF_3$ | 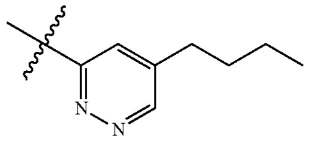 [SMILES: *c1cc(CCCC)cnn1] | (500 MHz, Chloroform-d) δ 9.40 (d, J = 1.5 Hz, 1H), 7.94 (d, J = 1.5 Hz, 1H), 7.27 (s, 1H), 5.62 (s, 1H), 2.60 (t, J = 8.0 Hz, 2H), 1.54-1.31 (m, 4H), 0.89 (t, J = 7.5 Hz, 3H). |
| 345 | $CF_3$ | 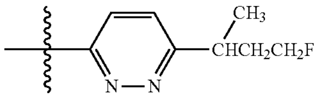 | (500 MHz, Chloroform-d) δ 7.96 (d, J = 7.5 Hz, 1H), 7.77 (d, J = 7.5 Hz, 1H), 7.23 (s, 1H), 5.79 (s, 1H), 4.33-4.12 (m, 2H), 3.17-3.01 (m, 1H), 2.12-1.88 (m, 2H), 1.39 (d, J = 6.5 Hz, 3H). |
| 346 | $CF_3$ | 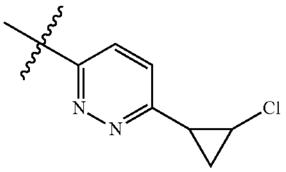 [SMILES: *c1ccc(C2CC2Cl)nn1] | (500 MHz, Chloroform-d) δ 8.02 (d, J = 7.5 Hz, 1H), 7.69 (d, J = 7.5 Hz, 1H), 7.27 (s, 1H), 5.39 (s, 1H), 4.46-4.23 (m, 1H), 2.53-2.34 (m, 1H), 1.53-1.29 (m, 1H). |
| 347 | $CF_3$ | 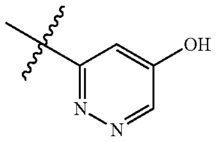 [SMILES: *c1cc(O)cnn1] | (500 MHz, Chloroform-d) δ 9.31 (d, J = 1.5 Hz, 1H), 7.46 (d, J = 1.5 Hz, 1H), 7.25 (s, 1H), 5.93 (s, 1H), 5.49 (s, 1H). |
| 348 | $CF_3$ | 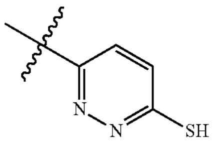 [SMILES: *c1ccc(S)nn1] | (500 MHz, Chloroform-d) δ 7.99 (d, J = 7.5 Hz, 1H), 7.86 (d, J = 7.5 Hz, 1H), 7.27 (s, 1H), 5.63 (s, 1H), 5.17 (s, 1H). |

TABLE 1-continued
Structure and $^1$HNMR data of Compound I
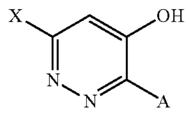
I
| No. | X | A | $^1$H NMR |
| --- | --- | --- | --- |
| 349 | $CF_3$ | 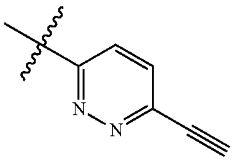 [SMILES: *c1ccc(C#C)nn1] | (500 MHz, Chloroform-d) δ 8.04 (d, J = 7.5 Hz, 1H), 7.98 (d, J = 7.3 Hz, 1H), 7.26 (s, 1H), 5.44 (s, 1H), 3.35 (s, 1H). |
| 350 | $CF_3$ | 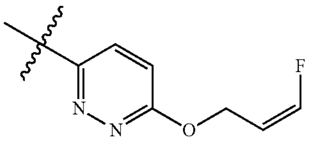 | |
| 351 | $CF_3$ | 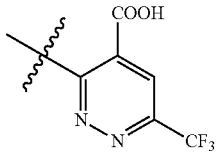 [SMILES: *c1nnc(C(F)(F)F)cc1C(=O)O] | (500 MHz, Chloroform-d) δ 8.30 (s, 1H), 7.84 (s, 1H), 7.31 (s, 1H), 5.53 (s, 1H). |
| 352 | $CF_3$ | 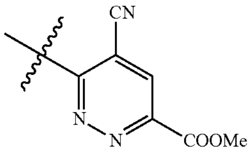 [SMILES: *c1nnc(C(=O)OC)cc1C#N] | (500 MHz, Chloroform-d) δ 9.58 (s, 1H), 7.07 (s, 1H), 5.31 (s, 1H), 3.73 (s, 3H). |
| 353 | $CF_3$ | 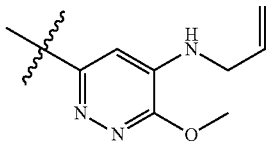 [SMILES: *c1cc(NCC=C)c(OC)nn1] | (500 MHz, Chloroform-d) δ 7.23 (s, 1H), 7.07 (s, 1H), 5.98-5.81 (m, 1H), 5.77 (s, 1H), 5.29-5.20 (m, 1H), 5.14-5.03 (m, 1H), 4.90 (s, 1H), 3.99-3.83 (m, 2H), 3.76 (s, 3H). |
| 354 | $CF_3$ | 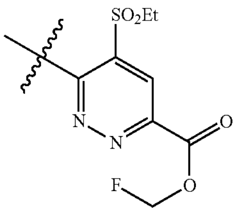 | |
| 355 | $CF_3$ | 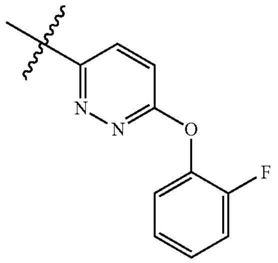 [SMILES: *c1ccc(Oc2ccccc2F)nn1] | (500 MHz, Chloroform-d) δ 8.12 (d, J = 7.5 Hz, 1H), 7.48 (d, J = 7.5 Hz, 1H), 7.30-7.17 (m, 4H), 7.33 (s, 1H), 5.41 (s, 1H). |

TABLE 1-continued

Structure and $^1$HNMR data of Compound I

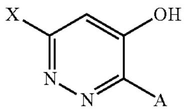

I

| No. | X | A | $^1$H NMR |
|---|---|---|---|
| 356 | $CF_3$ | 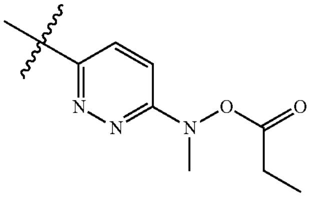 [SMILES: *c1ccc(N(C)OC(=O)CC)nn1] | (500 MHz, Chloroform-d) δ 7.86 (d, J = 7.5 Hz, 1H), 7.28 (s, 1H), 7.06 (d, J = 7.5 Hz, 1H), 5.21 (s, 1H), 2.86 (s, 3H), 2.27 (q, J = 8.0 Hz, 2H), 1.12 (t, J = 8.0 Hz, 3H). |
| 357 | $CF_3$ | 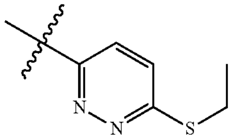 [SMILES: *c1ccc(SCC)nn1] | (500 MHz, Chloroform-d) δ 8.02 (d, J = 7.5 Hz, 1H), 7.85 (d, J = 7.5 Hz, 1H), 7.27 (s, 1H), 5.46 (s, 1H), 2.97 (q, J = 8.1 Hz, 2H), 1.37 (t, J = 8.0 Hz, 3H). |
| 358 | $CF_3$ | 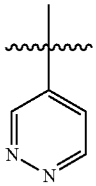 | (500 MHz, Chloroform-d) δ 9.72 (d, J = 1.5 Hz, 1H), 9.43 (d, J = 5.5 Hz, 1H), 8.04 (dd, J = 5.5, 1.5 Hz, 1H), 7.24 (s, 1H), 5.86 (s, 1H). |
| 359 | $CF_3$ | 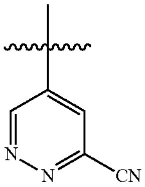 [SMILES: *c1cnnc(C#N)c1] | (500 MHz, Chloroform-d) δ 8.61 (d, J = 1.5 Hz, 1H), 8.21 (d, J = 1.5 Hz, 1H), 7.26 (s, 1H), 5.87 (s, 1H). |
| 360 | $CF_3$ | 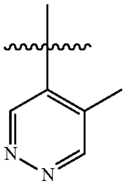 [SMILES: *c1cnncc1C] | (500 MHz, Chloroform-d) δ 9.48 (s, 1H), 9.42 (s, 1H), 7.27 (s, 1H), 5.60 (s, 1H), 2.36 (s, 3H). |
| 361 | $CF_3$ | 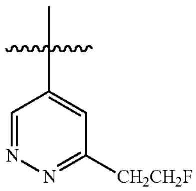 | (500 MHz, Chloroform-d) δ 9.58 (d, J = 1.5 Hz, 1H), 7.94 (d, J = 1.5 Hz, 1H), 7.28 (s, 1H), 5.54 (s, 1H), 4.47-4.37 (m, 2H), 2.75-2.34 (m, 2H). |
| 362 | $CF_3$ | 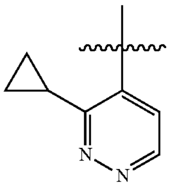 [SMILES: *c1ccnnc1C1CC1] | (500 MHz, Chloroform-d) δ 9.35 (d, J = 6.0 Hz, 1H), 7.84 (d, J = 6.0 Hz, 1H), 7.27 (s, 1H), 5.73 (s, 1H), 2.38-2.22 (m, 1H), 0.85-0.74 (m, 2H), 0.73-0.61 (m, 2H). |

TABLE 1-continued
Structure and $^1$HNMR data of Compound I
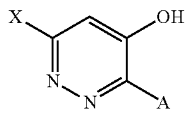
I
| No. | X | A | $^1$H NMR |
| --- | --- | --- | --- |
| 363 | $CF_3$ | 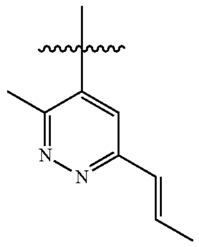 [SMILES: *c1cc(/C=C/C)nnc1C] | (500 MHz, Chloroform-d) δ 7.90 (s, 1H), 7.27 (s, 1H), 6.39-6.29 (m, 2H), 5.61 (s, 1H), 2.76 (s, 3H), 2.16 (d, J = 6.0 Hz, 3H). |
| 364 | $CF_3$ | 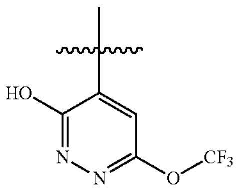 [SMILES: *c1cc(OC(F)(F)F)nnc1O] | (500 MHz, Chloroform-d) δ 7.99 (s, 1H), 7.72 (s, 1H), 7.37 (s, 1H), 5.37 (s, 1H). |
| 365 | $CF_3$ | 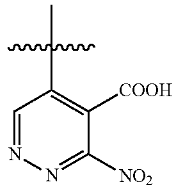 [SMILES: *c1cnnc([N+](=O)[O-])c1C(=O)O] | (500 MHz, Chloroform-d) δ 7.57 (s, 1H), 6.95 (s, 1H). |
| 366 | $CF_3$ | 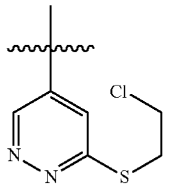 [SMILES: *c1cnnc(SCCCl)c1] | (500 MHz, Chloroform-d) δ 9.53 (d, J = 1.5 Hz, 1H), 8.08 (d, J = 1.5 Hz, 1H), 7.24 (s, 1H), 5.86 (s, 1H), 3.78 (t, J = 7.5 Hz, 2H), 3.21 (t, J = 7.5 Hz, 2H). |
| 367 | $CF_3$ | 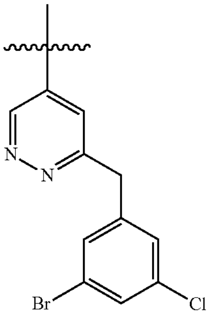 [SMILES: *c1cnnc(Cc2cc(Cl)cc(Br)c2)c1] | (500 MHz, Chloroform-d) δ 9.63 (d, J = 1.5 Hz, 1H), 8.02 (d, J = 1.5 Hz, 1H), 7.46-7.29 (m, 3H), 7.23 (s, 1H), 5.80 (s, 1H), 3.88 (s, 2H). |
| 368 | $CF_3$ | 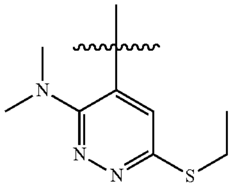 [SMILES: *c1cc(SCC)nnc1N(C)C] | (500 MHz, Chloroform-d) δ 8.03 (s, 1H), 7.37 (s, 1H), 6.50 (s, 1H), 3.27 (s, 6H), 2.97 (q, J = 8.0 Hz, 2H), 1.36 (t, J = 8.0 Hz, 3H). |

TABLE 1-continued

Structure and $^1$HNMR data of Compound I

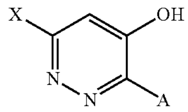

I

| No. | X | A | $^1$H NMR |
| --- | --- | --- | --- |
| 369 | $CF_3$ | 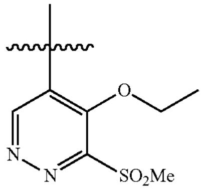 [SMILES: *c1cnnc(S(C)(=O)=O)c1OCC] | (500 MHz, Chloroform-d) δ 9.95 (s, 1H), 7.26 (s, 1H), 5.43 (s, 1H), 4.34 (q, J = 8.0 Hz, 2H), 3.39 (s, 3H), 1.61 (t, J = 8.0 Hz, 3H). |
| 370 | $CF_3$ | 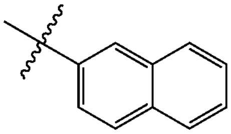 [SMILES: *c1ccc2ccccc2c1] | (500 MHz, Chloroform-d) δ 8.27-8.06 (m, 2H), 8.04-7.94 (m, 2H), 7.84-7.70 (m, 1H), 7.55-7.50 (m, 2H), 7.09 (s, 1H), 5.52 (s, 1H). |
| 371 | $CF_3$ | 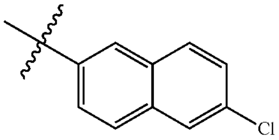 [SMILES: *c1ccc2cc(Cl)ccc2c1] | (500 MHz, Chloroform-d) δ 8.23-7.96 (m, 2H), 7.82-7.71 (m, 3H), 7.62-6.51 (m, 1H), 7.09 (s, 1H), 5.47 (s, 1H). |
| 372 | $CF_3$ | 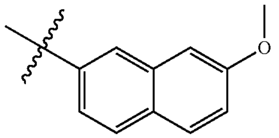 [SMILES: *c1ccc2ccc(OC)cc2c1] | (500 MHz, Chloroform-d) δ 8.18-7.93 (m, 2H), 7.69-7.55 (m, 2H), 7.23-7.16 (m, 1H), 7.10 (s, 1H), 6.98-6.91 (m, 1H), 5.47 (s, 1H), 3.87 (s, 3H). |
| 373 | $CF_3$ | 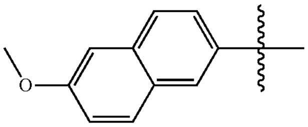 [SMILES: *c1ccc2cc(OC)ccc2c1] | (500 MHz, Chloroform-d) δ 8.04-7.80 (m, 2H), 7.64-7.55 (m, 1H), 7.31-7.26 (m, 2H), 7.14-7.09 (m, 2H), 5.52 (s, 1H), 3.87 (s, 3H). |
| 374 | $CF_3$ | 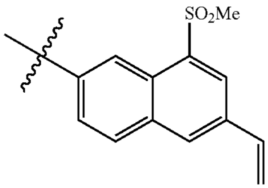 [SMILES: *c1ccc2cc(C=C)cc(S(C)(=O)=O)c2c1] | (500 MHz, Chloroform-d) δ 8.76 (d, J = 1.5 Hz, 1H), 8.34-8.25 (m, 2H), 8.10-7.90 (m, 2H), 7.05 (s, 1H), 6.77-6.51 (m, 1H), 5.76-5.65 (m, 2H), 5.25-5.11 (m, 1H), 3.16 (s, 3H). |
| 375 | $CF_3$ | 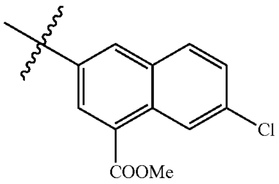 [SMILES: *c1cc(C(=O)OC)c2cc(Cl)ccc2c1] | (500 MHz, Chloroform-d) δ 8.24-8.19 (m, 2H), 8.12 (d, J = 1.5 Hz, 1H), 7.87-7.63 (m, 2H), 7.11 (s, 1H), 5.33 (s, 1H), 3.95 (s, 3H). |
| 376 | $CF_3$ | 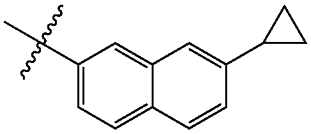 [SMILES: *c1ccc2ccc(C3CC3)cc2c1] | (500 MHz, Chloroform-d) δ 8.21-8.16 (m, 1H), 7.94-7.85 (m, 1H), 7.77-7.55 (m, 2H), 7.42-7.31 (m, 2H), 7.09 (s, 1H), 5.52 (s, 1H), 1.94-1.82 (m, 1H), 1.23-1.14 (m, 2H), 0.96-0.87 (m, 2H). |

TABLE 1-continued
Structure and $^1$HNMR data of Compound I
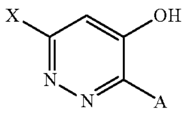
I
| No. | X | A | $^1$H NMR |
|---|---|---|---|
| 377 | $CF_3$ | 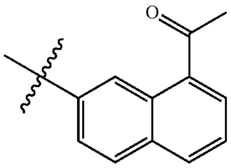 [SMILES: *c1ccc2cccc(C(C)=O)c2c1] | (500 MHz, Chloroform-d) δ 8.63-8.51 (m, 1H), 8.06-7.99 (m, 2H), 7.90-7.84 (m, 1H), 7.81-7.76 (m, 2H), 7.07 (s, 1H), 6.11 (s, 1H), 2.65 (s, 3H). |
| 378 | $CF_3$ | 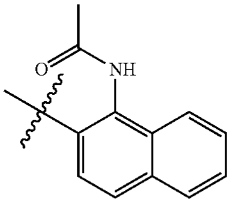 [SMILES: *c1ccc2ccccc2c1NC(C)=O] | (500 MHz, Chloroform-d) δ 9.50 (s, 1H), 7.99-7.90 (m, 2H), 7.89-7.81 (m, 1H), 7.67-7.47 (m, 3H), 7.03 (s, 1H), 5.43 (s, 1H), 2.22 (s, 3H). |
| 379 | $CF_3$ | 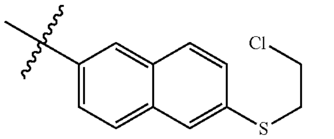 [SMILES: *c1ccc2cc(SCCCl)ccc2c1] | (500 MHz, Chloroform-d) δ 8.20-7.95 (m, 2H), 7.87-7.81 (m, 1H), 7.78-7.64 (m, 3H), 7.10 (s, 1H), 5.48 (s, 1H), 3.78 (t, J = 7.5 Hz, 2H), 3.07 (t, J = 7.5 Hz, 2H). |
| 380 | $CF_3$ | 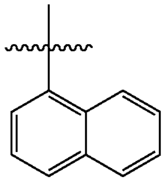 [SMILES: *c1cccc2ccccc12] | (500 MHz, Chloroform-d) δ 8.11-8.01 (m, 2H), 7.99-7.87 (m, 1H), 7.92-7.78 (m, 2H), 7.53-7.47 (m, 2H), 7.09 (s, 1H), 5.63 (s, 1H). |
| 381 | $CF_3$ | 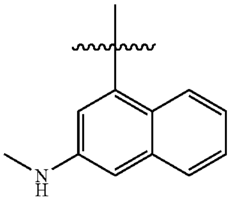 [SMILES: *c1cc(NC)cc2ccccc12] | (500 MHz, Chloroform-d) δ 7.79-7.57 (m, 3H), 7.56 (d, J = 1.5 Hz, 1H), 7.20-7.13 (m, 2H), 7.08 (s, 1H), 5.55 (s, 1H), 5.00 (s, 1H), 2.82 (s, 3H). |
| 382 | $CF_3$ | 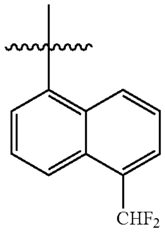 [SMILES: *c1cccc2c(C(F)F)cccc12] | (500 MHz, Chloroform-d) δ 8.11-8.02 (m, 2H), 8.00-7.90 (m, 2H), 7.78-7.65 (m, 2H), 7.50 (t, J = 73.5 Hz, 2H), 7.09 (s, 1H), 5.55 (s, 1H). |
| 383 | $CF_3$ | 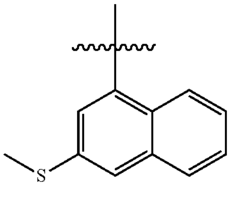 [SMILES: *c1cc(SC)cc2ccccc12] | (500 MHz, Chloroform-d) δ 8.03-7.93 (m, 2H), 7.92-7.83 (m, 2H), 7.46-7.38 (m, 2H), 7.09 (s, 1H), 5.61 (s, 1H), 2.50 (s, 3H). |

TABLE 1-continued
Structure and $^1$HNMR data of Compound I
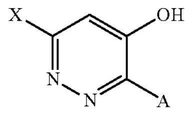
I
| No. | X | A | $^1$H NMR |
| --- | --- | --- | --- |
| 384 | $CF_3$ | 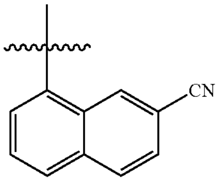 [SMILES: *c1cccc2ccc(C#N)cc12] | (500 MHz, Chloroform-d) δ 8.13-8.02 (m, 2H), 7.89-7.77 (m, 2H), 7.65-7.52 (m, 2H), 7.10 (s, 1H), 5.51 (s, 1H). |
| 385 | $CF_3$ | 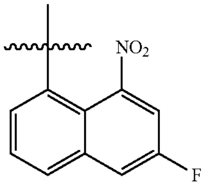 [SMILES: *c1cccc2cc(F)cc([N+](=O)[O-])c12] | (500 MHz, Chloroform-d) δ 8.12-8.04 (m, 2H), 7.87-7.62 (d, J = 8.0 Hz, 4H), 7.07 (s, 1H), 5.26 (s, 1H). |
| 386 | $CF_3$ | 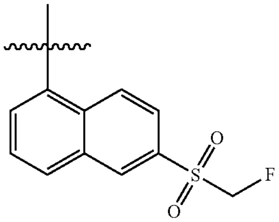 [SMILES: *c1cccc2cc(S(=O)(=O)CF)ccc12] | (500 MHz, Chloroform-d) δ 8.57 (d, J = 1.5 Hz, 1H), 8.10-8.02 (m, 3H), 7.99-7.81 (m, 2H), 7.09 (s, 1H), 6.26 (d, J = 72.5 Hz 1H), 5.53 (s, 1H). |
| 387 | $CF_3$ | 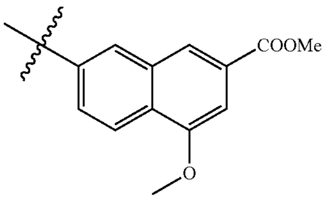 [SMILES: *c1ccc2c(OC)cc(C(=O)OC)cc2c1] | (500 MHz, Chloroform-d) δ 8.33-8.23 (m, 2H), 8.09-7.98 (m, 2H), 7.10 (s, 1H), 6.34-6.22 (m, 1H), 5.50 (s, 1H), 3.95 (s, 3H), 3.90 (s, 3H). |
| 388 | $CF_3$ | 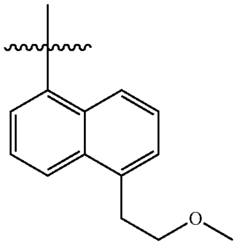 [SMILES: *c1cccc2c(CCOC)cccc12] | (500 MHz, Chloroform-d) δ 8.11-8.00 (m, 2H), 7.91-7.78 (m, 2H), 7.47-7.37 (m, 2H), 7.05 (s, 1H), 5.51 (s, 1H), 3.51 (t, J = 7.5 Hz, 2H), 3.23 (s, 3H), 2.43 (t, J = 7.5 Hz, 2H). |
| 389 | $CF_3$ | 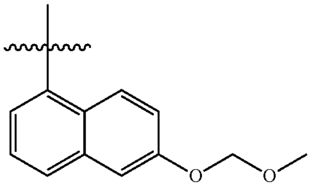 [SMILES: *c1cccc2cc(OCOC)ccc12] | (500 MHz, Chloroform-d) δ 8.15-8.03 (m, 1H), 7.87-7.78 (m, 2H), 7.61-7.44 (m, 2H), 7.10-7.01 (m, 2H), 6.12 (s, 2H), 5.52 (s, 1H), 3.29 (s, 3H). |

TABLE 1-continued
Structure and $^1$HNMR data of Compound I
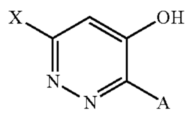
I
| No. | X | A | $^1$H NMR |
|---|---|---|---|
| 390 | $CF_3$ | 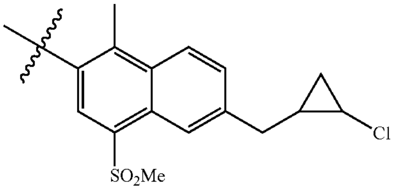 [SMILES: *c1cc(S(C)(=O)=O)c2cc(CC3CC3Cl)ccc2c1C] | (500 MHz, Chloroform-d) δ 8.42 (s, 1H), 8.27 (d, J = 1.5 Hz, 1H), 7.92 (d, J = 7.5 Hz, 1H), 7.50 (dd, J = 7.5, 1.5 Hz, 1H), 7.04 (s, 1H), 5.63 (s, 1H), 3.18 (s, 3H), 3.03-2.98 (m, 2H), 2.68 (s, 3H), 2.16-2.06 (m, 1H), 1.44-1.33 (m, 1H), 0.99-0.84 (m, 2H). |
| 391 | $CF_3$ | 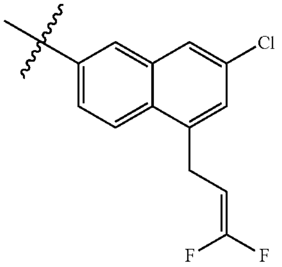 [SMILES: *c1ccc2c(CC=C(F)F)cc(Cl)cc2c1] | |
| 392 | $CF_3$ | 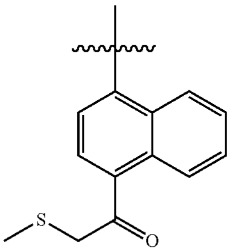 [SMILES: *c1ccc(C(=O)CSC)c2ccccc12] | (500 MHz, Chloroform-d) δ 8.31 (d, J = 7.5 Hz, 1H), 8.10 (d, J = 7.5 Hz, 1H), 7.84-7.70 (m, 3H), 7.54-7.42 (m, 1H), 7.09 (s, 1H), 5.63 (s, 1H), 3.70 (s, 2H), 2.27 (s, 3H). |
| 393 | $CF_3$ | 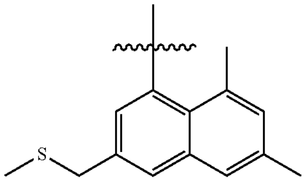 | (500 MHz, Chloroform-d) δ 7.82-7.73 (m, 1H), 7.67-7.60 (m, 2H), 7.19 (d, J = 1.5 Hz, 1H), 7.07 (s, 1H), 5.40 (s, 1H), 3.81 (s, 2H), 2.52 (s, 3H), 2.35 (s, 3H), 2.27 (s, 3H). |
| 394 | $CF_3$ | 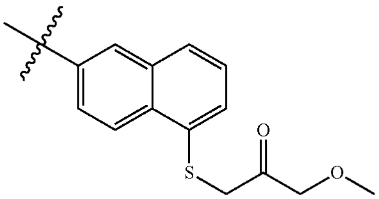 [SMILES: *c1ccc2c(SCC(=O)COC)cccc2c1] | (500 MHz, Chloroform-d) δ 8.30-8.13 (m, 2H), 7.85-7.76 (m, 2H), 7.69-7.62 (m, 2H), 7.09 (s, 1H), 5.43 (s, 1H), 4.53 (s, 2H), 3.95 (s, 2H), 3.28 (s, 3H). |
| 395 | $CF_3$ | 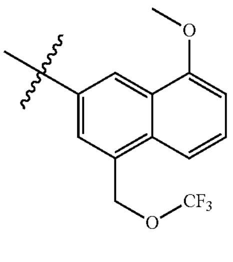 [SMILES: *c1cc(COC(F)(F)F)c2cccc(OC)c2c1] | (500 MHz, Chloroform-d) δ 8.42-8.37 (m, 1H), 7.54 (d, J = 1.5 Hz, 1H), 7.47-7.36 (m, 2H), 7.04 (s, 1H), 6.88-6.69 (m, 1H), 5.71 (s, 1H), 4.96 (s, 2H), 3.90 (s, 3H). |

TABLE 1-continued
Structure and $^1$HNMR data of Compound I
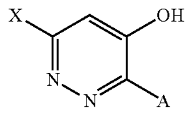
I
| No. | X | A | $^1$H NMR |
| --- | --- | --- | --- |
| 396 | $CF_3$ | 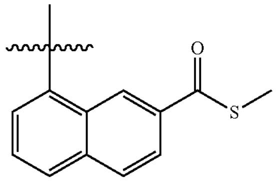 [SMILES: *c1cccc2ccc(C(=O)SC)cc12] | (500 MHz, Chloroform-d) δ 8.38 (d, J = 1.5 Hz, 1H), 8.18 (dd, J = 7.5, 1.5 Hz, 1H), 8.12-8.01 (m, 2H), 7.88-7.62 (m, 2H), 7.07 (s, 1H), 5.55 (s, 1H), 2.42 (s, 3H). |
| 397 | $CF_3$ | 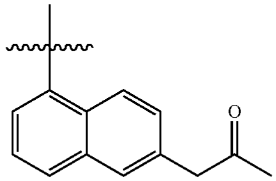 [SMILES: *c1cccc2cc(CC(C)=O)ccc12] | (500 MHz, Chloroform-d) δ 8.05-7.97 (m, 1H), 8.00-7.91 (m, 2H), 7.76-7.68 (m, 2H), 7.58-7.42 (m, 1H), 7.08 (s, 1H), 5.57 (s, 1H), 3.82 (s, 2H), 1.85 (s, 3H). |
| 398 | $CF_3$ | 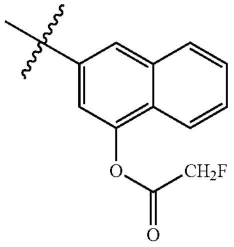 | (500 MHz, Chloroform-d) δ 7.99-7.93 (m, 2H), 7.83-7.53 (m, 2H), 7.40-7.24 (m, 2H), 7.09 (s, 1H), 5.49 (d, J = 73.5 Hz, 1H), 5.20 (s, 1H). |
| 399 | $CF_3$ | 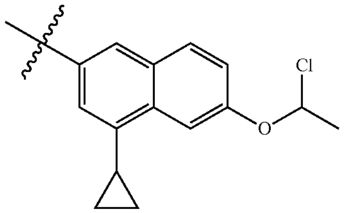 [SMILES: *c1cc(C2CC2)c2cc(OC(C)Cl)ccc2c1] | |
| 400 | $CF_3$ | 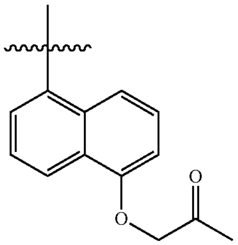 [SMILES: *c1cccc2c(OCC(C)=O)cccc12] | (500 MHz, Chloroform-d) δ 8.43-8.34 (m, 2H), 7.99-7.82 (m, 2H), 7.73-7.66 (m, 1H), 7.09 (s, 1H), 6.24-6.12 (m, 1H), 5.57 (s, 1H), 5.10 (s, 2H), 2.20 (s, 3H). |
| 401 | $CF_3$ | 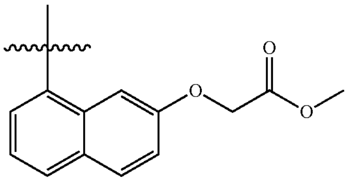 [SMILES: *c1cccc2ccc(OCC(=O)OC)cc12] | (500 MHz, Chloroform-d) δ 8.00-7.88 (m, 2H), 7.91-7.70 (m, 2H), 7.51-7.39 (m, 1H), 7.11-7.05 (m, 2H), 5.62 (s, 1H), 4.93 (s, 2H), 3.73 (s, 3H). |

TABLE 1-continued
Structure and ¹HNMR data of Compound I
I
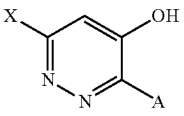
| No. | X | A | ¹H NMR |
|---|---|---|---|
| 402 | $CF_3$ | 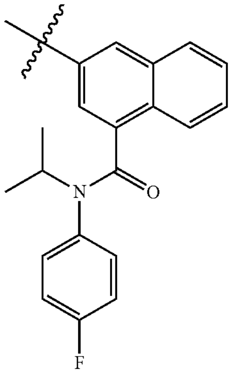 [SMILES: *c1cc(C(=O)N(c2ccc(F)cc2)C(C)C)c2ccccc2c1] | (500 MHz, Chloroform-d) δ 8.69-8.42 (m, 2H), 8.11-8.00 (m, 2H), 7.78-7.53 (m, 2H), 7.50-7.42 (m, 2H), 7.12-7.03 (m, 3H), 5.71 (s, 1H), 3.94 (hept, J = 6.5 Hz, 1H), 1.52 (d, J = 6.5 Hz, 6H). |
| 403 | $CF_3$ | 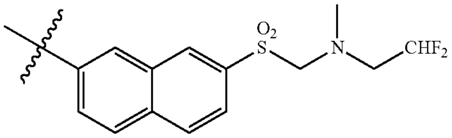 [SMILES: *c1ccc2ccc(S(=O)(=O)CN(C)CC(F)F)cc2c1] | (500 MHz, Chloroform-d) δ 8.71-8.63 (m, 1H), 8.34-8.20 (m, 2H), 8.13-8.04 (m, 2H), 7.88-7.79 (m, 1H), 7.10 (s, 1H), 5.72-5.50 (m, 1H), 5.44 (s, 1H), 4.48 (s, 2H), 2.72-2.50 (m, 2H), 2.39 (s, 3H). |
| 404 | $CF_3$ | 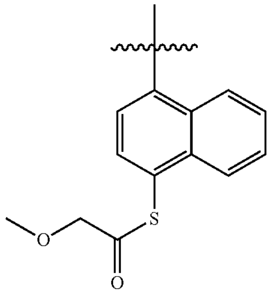 [SMILES: *c1ccc(SC(=O)COC)c2ccccc12] | (500 MHz, Chloroform-d) δ 8.11-8.06 (m, 2H), 7.73-7.64 (m, 2H), 7.51-7.37 (m, 2H), 7.09 (s, 1H), 5.61 (s, 1H), 4.48 (s, 2H), 3.34 (s, 3H). |
| 405 | $CF_3$ | 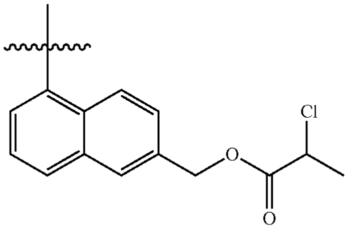 [SMILES: *c1cccc2cc(COC(=O)C(C)Cl)ccc12] | |
| 406 | $CF_3$ | 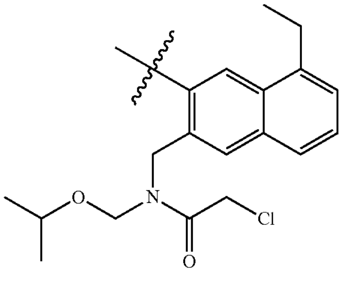 [SMILES: *c1cc2c(CC)cccc2cc1CN(COC(C)C)C(=O)CCl] | (500 MHz, Chloroform-d) δ 8.06 (s, 1H), 7.74-7.64 (m, 2H), 7.42-7.29 (m, 2H), 7.09 (s, 1H), 5.64 (s, 1H), 5.24 (s, 2H), 5.00 (s, 2H), 4.27 (s, 2H), 3.70 (hept, J = 6.5 Hz, 1H), 3.10 (q, J = 8.0 Hz, 2H), 1.35 (t, J = 8.0 Hz, 3H), 1.02 (d, J = 6.5 Hz, 6H). |

TABLE 1-continued
Structure and $^1$HNMR data of Compound I
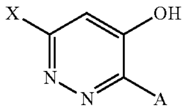
I
| No. | X | A | $^1$H NMR |
|---|---|---|---|
| 407 | $CF_3$ | 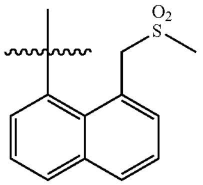 [SMILES: *c1cccc2cccc(CS(C)(=O)=O)c12] | (500 MHz, Chloroform-d) δ 8.05-7.98 (m, 2H), 7.79-7.72 (m, 2H), 7.50-7.43 (m, 2H), 7.31 (s, 1H), 5.41 (s, 1H), 5.11 (s, 2H), 2.86 (s, 3H). |
| 408 | $CF_3$ | 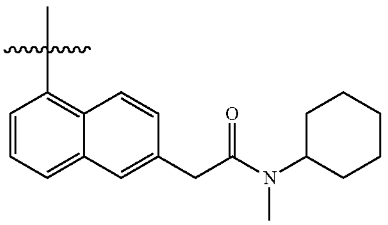 [SMILES: *c1cccc2cc(CC(=O)N(C)C3CCCCC3)ccc12] | (500 MHz, Chloroform-d) δ 7.88 (d, J = 7.5 Hz, 1H), 7.72-7.64 (m, 2H), 7.63 (d, J = 7.5 Hz, 1H), 7.56 (d, J = 7.5 Hz, 1H), 7.09 (s, 1H), 5.51 (s, 1H), 3.81 (s, 2H), 3.64-3.47 (m, 1H), 2.94 (s, 3H), 1.83-1.71 (m, 3H), 1.71-1.57 (m, 2H), 1.57-1.37 (m, 5H). |
| 409 | $CF_3$ | 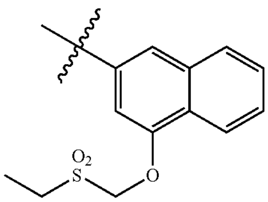 [SMILES: *c1cc(OCS(=O)(=O)CC)c2ccccc2c1] | (500 MHz, Chloroform-d) δ 7.68-7.55 (m, 2H), 7.41-7.31 (m, 3H), 7.28-7.19 (m, 1H), 7.09 (s, 1H), 6.06 (s, 2H), 5.55 (s, 1H), 3.45 (q, J = 8.0 Hz, 2H), 1.22 (t, J = 8.0 Hz, 3H). |
| 410 | $CF_3$ | 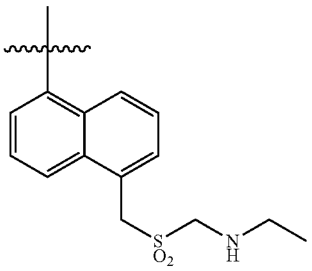 [SMILES: *c1cccc2c(CS(=O)(=O)CNCC)cccc12] | (500 MHz, Chloroform-d) δ 8.10-8.00 (m, 2H), 7.94-7.81 (m, 1H), 7.79-7.65 (m, 2H), 7.49-7.33 (m, 1H), 7.09 (s, 1H), 5.56 (s, 1H), 5.11 (s, 2H), 4.67 (s, 2H), 2.59 (q, J = 8.0 Hz, 2H), 1.29 (s, 1H), 1.02 (t, J = 8.0 Hz, 3H). |
| 411 | $CF_3$ | 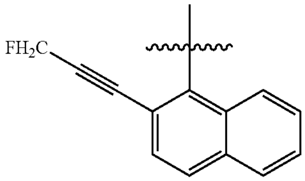 | |
| 412 | $CF_3$ | 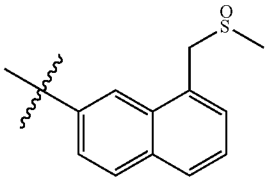 | (500 MHz, Chloroform-d) δ 8.18 (d, J = 1.5 Hz, 1H), 8.02 (dd, J = 7.5, 1.5 Hz, 1H), 7.85-7.77 (m, 2H), 7.53-7.43 (m, 2H), 7.10 (s, 1H), 5.41 (s, 1H), 4.27 (s, 2H), 2.56 (s, 3H). |

TABLE 1-continued

Structure and $^1$HNMR data of Compound I

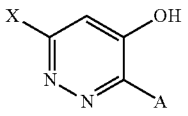

I

| No. | X | A | $^1$H NMR |
|---|---|---|---|
| 413 | $CF_3$ | 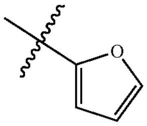 [SMILES: *c1ccco1] | (500 MHz, Chloroform-d) δ 7.83 (dd, J = 2.5 Hz, 1H), 7.17 (d, J = 2.0 Hz, 2H), 6.80 (dd, J = 2.5, 2.0 Hz, 1H). |
| 414 | $CF_3$ | 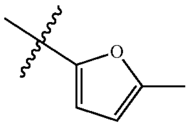 [SMILES: *c1ccc(C)o1] | (500 MHz, Chloroform-d) δ 7.18 (s, 1H), 6.90 (d, J = 2.5 Hz, 1H), 6.11 (d, J = 2.5 Hz, 1H), 2.36 (s, 3H). |
| 415 | $CF_3$ | 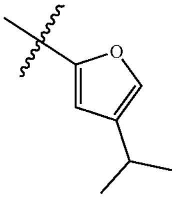 [SMILES: *c1cc(C(C)C)co1] | (500 MHz, Chloroform-d) δ 7.40 (s, 1H), 7.20 (s, 1H), 6.30 (s, 1H), 6.00 (s, 1H), 2.94 (hept, J = 6.5 Hz, 1H), 1.52 (d, J = 6.5 Hz, 6H). |
| 416 | $CF_3$ | 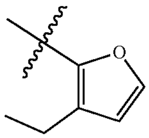 [SMILES: *c1occc1CC] | (500 MHz, Chloroform-d) δ 7.35 (d, J = 2.5 Hz, 1H), 7.18 (s, 1H), 6.45 (d, J = 2.5 Hz, 1H), 2.66 (q, J = 8.0 Hz, 2H), 1.30 (t, J = 8.0 Hz, 3H). |
| 417 | $CF_3$ | 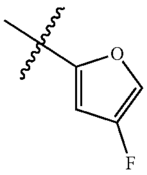 [SMILES: *c1cc(F)co1] | (500 MHz, Chloroform-d) δ 7.40 (d, J = 9.0 Hz, 1H), 7.20 (s, 1H), 6.30 (d, J = 8.5 Hz, 1H), 6.00 (s, 1H). |
| 418 | $CF_3$ | 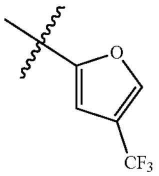 [SMILES: *c1cc(C(F)(F)F)co1] | (500 MHz, Chloroform-d) δ 7.50 (s, 1H), 7.18 (s, 1H), 6.67 (s, 1H), 5.64 (s, 1H). |
| 419 | $CF_3$ | 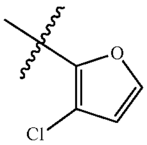 [SMILES: *c1occc1Cl] | (500 MHz, Chloroform-d) δ 7.45 (d, J = 2.5 Hz, 1H), 7.15 (s, 1H), 6.76 (d, J = 2.5 Hz, 1H), 5.84 (s, 1H). |
| 420 | $CF_3$ | 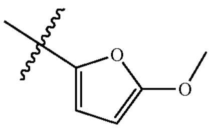 [SMILES: *c1ccc(OC)o1] | (500 MHz, Chloroform-d) δ 7.18 (s, 1H), 6.85 (d, J = 2.5 Hz, 1H), 5.80 (d, J = 2.5 Hz, 1H), 3.85 (s, 3H). |

TABLE 1-continued

Structure and $^1$HNMR data of Compound I

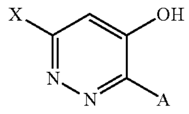

I

| No. | X | A | $^1$H NMR |
|---|---|---|---|
| 421 | $CF_3$ | 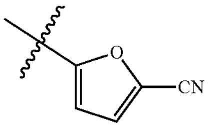 [SMILES: *c1ccc(C#N)o1] | (500 MHz, Chloroform-d) δ 7.29 (d, J = 2.5 Hz, 1H), 7.20 (s, 1H), 7.06 (d, J = 2.5 Hz, 1H), 5.67 (s, 1H). |
| 422 | $CF_3$ | 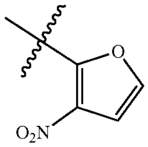 [SMILES: *c1occc1[N+](=O)[O-]] | (500 MHz, Chloroform-d) δ 7.43 (d, J = 2.5 Hz, 1H), 7.30 (d, J = 2.5 Hz, 1H), 7.17 (s, 1H), 5.77 (s, 1H). |
| 423 | $CF_3$ | 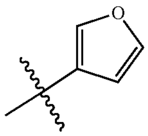 [SMILES: *c1ccoc1] | $^1$H NMR (500 MHz, DMSO-$d_6$) δ 10.38 (s, 1H), 7.71 (d, J = 1.5 Hz, 1H), 7.47 (d, J = 1.5 Hz, 1H), 7.13 (s, 1H), 6.43 (s, 1H). |
| 424 | $CF_3$ | 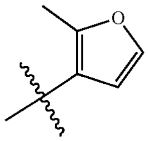 [SMILES: *c1ccoc1C] | (500 MHz, Chloroform-d) δ 7.20 (d, J = 2.5 Hz, 1H), 7.15 (s, 1H), 6.42 (d, J = 2.5 Hz, 1H), 5.81 (s, 1H), 2.37 (s, 3H). |
| 425 | $CF_3$ | 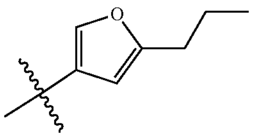 [SMILES: *c1coc(CCC)c1] | (500 MHz, Chloroform-d) δ 7.63 (s, 1H), 7.15 (s, 1H), 6.09 (s, 1H), 5.87 (s, 1H), 2.38 (t, J = 6.5 Hz, 2H), 1.86-1.71 (m, 2H), 1.00 (t, J = 8.0 Hz, 3H). |
| 426 | $CF_3$ | 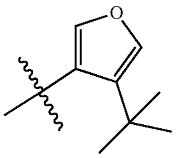 [SMILES: *c1cocc1C(C)(C)C] | (500 MHz, Chloroform-d) δ 7.34 (s, 1H), 7.27 (s, 1H), 7.20 (s, 1H), 6.07 (s, 1H), 1.30 (s, 9H). |
| 427 | $CF_3$ | 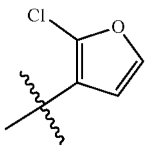 [SMILES: *c1ccoc1Cl] | (500 MHz, Chloroform-d) δ 7.30 (d, J = 2.5 Hz, 1H), 7.16 (s, 1H), 6.32 (d, J = 2.5 Hz, 1H), 5.74 (s, 1H). |
| 428 | $CF_3$ | 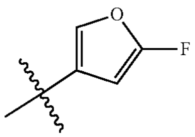 [SMILES: *c1coc(F)c1] | (500 MHz, Chloroform-d) δ 7.40 (s, 1H), 7.20 (s, 1H), 6.30 (d, J = 8.0 Hz, 1H), 6.00 (s, 1H). |
| 429 | $CF_3$ | 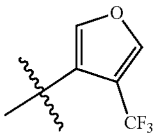 [SMILES: *c1cocc1C(F)(F)F] | (500 MHz, Chloroform-d) δ 7.60 (s, 1H), 7.53 (s, 1H), 7.24 (s, 1H), 5.52 (s, 1H). |

TABLE 1-continued

Structure and $^1$HNMR data of Compound I

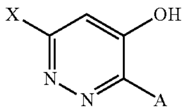

I

| No. | X | A | $^1$H NMR |
| --- | --- | --- | --- |
| 430 | $CF_3$ | 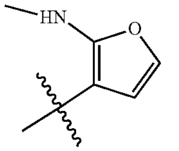 [SMILES: *c1ccoc1NC] | (500 MHz, Chloroform-d) δ 8.99 (s, 1H), 8.25 (s, 1H), 7.20 (s, 1H), 6.90 (d, J = 7.5 Hz, 1H), 6.11 (d, J = 7.5 Hz, 1H), 2.87 (s, 3H). |
| 431 | $CF_3$ | 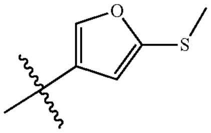 [SMILES: *c1coc(SC)c1] | (500 MHz, Chloroform-d) δ 7.59 (s, 1H), 7.15 (s, 1H), 6.40 (s, 1H), 5.88 (s, 1H), 2.43 (s, 3H). |
| 432 | $CF_3$ | 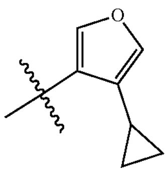 [SMILES: *c1cocc1C1CC1] | (500 MHz, Chloroform-d) δ 7.24 (s, 1H), 7.20 (s, 1H), 7.10 (s, 1H), 6.00 (s, 1H), 1.50-1.37 (m, 1H), 1.12-1.02 (m, 2H), 0.82-0.72 (m, 2H). |
| 433 | $CF_3$ | 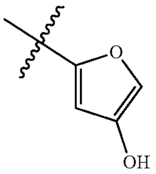 [SMILES: *c1cc(O)co1] | (500 MHz, Chloroform-d) δ 7.18 (s, 1H), 6.70 (s, 1H), 6.44 (s, 1H), 5.87 (s, 1H), 5.66 (s, 1H). |
| 434 | $CF_3$ | 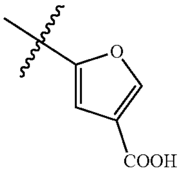 [SMILES: *c1cc(C(=O)O)co1] | (500 MHz, Chloroform-d) δ 8.40 (s, 1H), 7.73 (s, 1H), 7.19 (s, 1H). |
| 435 | $CF_3$ | 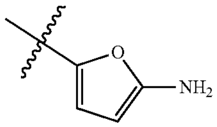 [SMILES: *c1ccc(N)o1] | (500 MHz, Chloroform-d) δ 7.15 (s, 1H), 6.86 (d, J = 2.5 Hz, 1H), 6.17 (d, J = 2.5 Hz, 1H). |
| 436 | $CF_3$ | 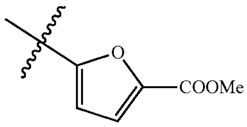 [SMILES: *c1ccc(C(=O)OC)o1] | (500 MHz, Chloroform-d) δ 7.29 (d, J = 2.5 Hz, 1H), 7.23-7.18 (m, 2H), 3.91 (s, 3H). |
| 437 | $CF_3$ | 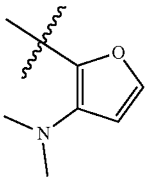 [SMILES: *c1occc1N(C)C] | (500 MHz, Chloroform-d) δ 7.47 (d, J = 2.5 Hz, 1H), 7.16 (s, 1H), 6.49 (d, J = 2.5 Hz, 1H), 2.99 (s, 6H). |

TABLE 1-continued
Structure and $^1$HNMR data of Compound I
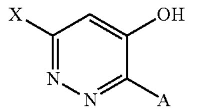
I
| No. | X | A | $^1H$ NMR |
| --- | --- | --- | --- |
| 438 | $CF_3$ | 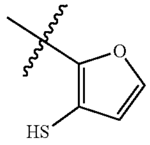 | |
| 439 | $CF_3$ | 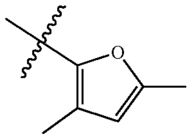 [SMILES: *c1oc(C)cc1C] | (500 MHz, Chloroform-d) δ 7.17 (s, 1H), 6.04 (s, 1H), 2.36 (s, 3H), 2.26 (s, 3H). |
| 440 | $CF_3$ | 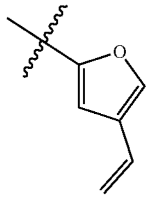 [SMILES: *c1cc(C=C)co1] | (500 MHz, Chloroform-d) δ 7.56 (s, 1H), 7.18 (s, 1H), 7.06 (s, 1H), 6.83-6.67 (m, 1H), 5.67-5.46 (m, 2H). |
| 441 | $CF_3$ | 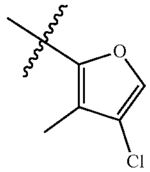 [SMILES: *c1occ(Cl)c1C] | $^1H$ NMR (500 MHz, Chloroform-d) δ 7.17 (s, 1H), 6.57 (s, 1H), 5.32 (s, 1H), 2.19 (s, 3H). |
| 442 | $CF_3$ | 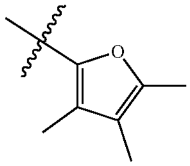 [SMILES: *c1oc(C)c(C)c1C] | (500 MHz, Chloroform-d) δ 7.17 (s, 1H), 2.32 (s, 3H), 2.19 (s, 3H), 2.05 (s, 3H). |
| 443 | $CF_3$ | 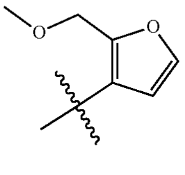 [SMILES: *c1ccoc1COC] | (500 MHz, Chloroform-d) δ 7.27 (d, J = 2.5 Hz, 1H), 7.15 (s, 1H), 6.37 (d, J = 2.5 Hz, 1H), 5.78 (s, 1H), 4.48 (s, 2H), 3.38 (s, 3H). |
| 444 | $CF_3$ | 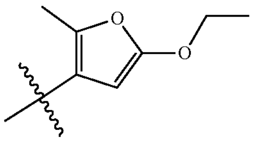 [SMILES: *c1cc(OCC)oc1C] | (500 MHz, Chloroform-d) δ 7.27 (s, 1H), 7.15 (s, 1H), 5.78 (s, 1H), 3.88 (q, J = 8.0 Hz, 2H), 3.08 (s, 3H), 1.48 (t, J = 8.0 Hz, 3H). |
| 445 | $CF_3$ | 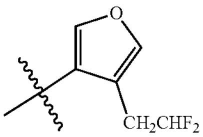 | (500 MHz, Chloroform-d) δ 7.64 (s, 1H), 7.26 (s, 1H), 7.19 (s, 1H), 6.09-6.00 (m, 1H), 5.74 (s, 1H), 2.95-2.89 (m, 2H). |

TABLE 1-continued

Structure and $^{1}$HNMR data of Compound I

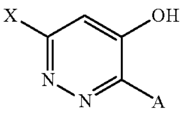

I

| No. | X | A | $^{1}$H NMR |
|---|---|---|---|
| 446 | $CF_3$ | 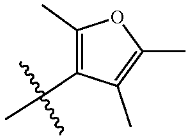 [SMILES: *c1c(C)oc(C)c1C] | (500 MHz, Chloroform-d) δ 7.16 (s, 1H), 5.73 (s, 1H), 2.30 (s, 3H), 2.24 (s, 3H), 2.05 (s, 3H). |
| 447 | $CF_3$ | 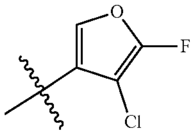 [SMILES: *c1coc(F)c1Cl] | (500 MHz, Chloroform-d) δ 7.40 (s, 1H), 7.20 (s, 1H), 6.00 (s, 1H). |
| 448 | $CF_3$ | 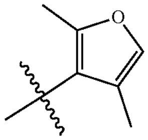 [SMILES: *c1c(C)coc1C] | (500 MHz, Chloroform-d) δ 7.21 (s, 2H), 5.97 (s, 1H), 2.31 (s, 3H), 2.05 (s, 3H). |
| 449 | $CF_3$ | 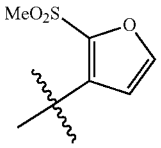 [SMILES: *c1ccoc1S(C)(=O)=O] | (500 MHz, Chloroform-d) δ 9.78 (s, 1H), 7.64 (d, J = 2.5 Hz, 1H), 7.43 (s, 1H), 6.56 (d, J = 2.5 Hz, 1H), 3.16 (s, 3H). |
| 450 | $CF_3$ | 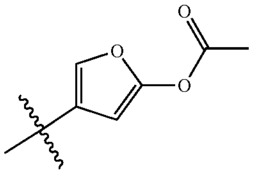 [SMILES: *c1coc(OC(C)=O)c1] | (500 MHz, Chloroform-d) δ 7.17 (s, 1H), 7.05 (s, 1H), 5.74 (s, 1H), 5.39 (s, 1H), 2.34 (s, 3H). |
| 451 | $CF_3$ | 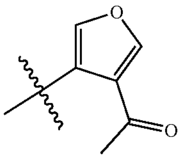 [SMILES: *c1cocc1C(C)=O] | (500 MHz, Chloroform-d) δ 8.50 (s, 1H), 8.34 (s, 1H), 7.66 (s, 1H), 7.44 (s, 1H), 2.55 (s, 3H). |
| 452 | $CF_3$ | 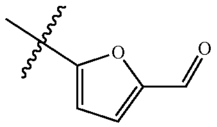 | (500 MHz, Chloroform-d) δ 8.69 (s, 1H), 7.25-7.17 (m, 2H), 7.09 (d, J = 2.5 Hz, 1H). |
| 453 | $CF_3$ | 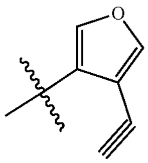 [SMILES: *c1cocc1C#C] | (500 MHz, Chloroform-d) δ 7.99 (s, 1H), 7.50 (s, 1H), 7.21 (s, 1H), 6.41 (s, 1H), 3.01 (s, 1H). |
| 454 | $CF_3$ | 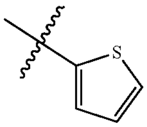 | (500 MHz, Chloroform-d) δ 7.56-7.44 (m, 2H), 7.24-7.17 (m, 2H). |

TABLE 1-continued

Structure and $^{1}$HNMR data of Compound I

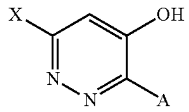

I

| No. | X | A | $^{1}$H NMR |
|---|---|---|---|
| 455 | $CF_3$ | 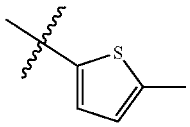 [SMILES: *c1ccc(C)s1] | $^{1}$H NMR (500 MHz, DMSO-$d_6$) δ 13.05 (s, 1H), 7.66 (d, J = 2.5 Hz, 1H), 7.12 (d, J = 2.5 Hz, 1H), 6.88 (s, 1H), 2.40 (s, 3H). |
| 456 | $CF_3$ | 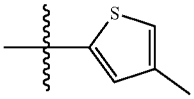 [SMILES: *c1cc(C)cs1] | (500 MHz, Chloroform-d) δ 7.46 (s, 1H), 7.20 (s, 2H), 7.09 (s, 1H), 2.30 (s, 3H). |
| 457 | $CF_3$ | 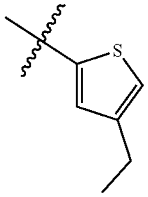 [SMILES: *c1cc(CC)cs1] | (500 MHz, Chloroform-d) δ 7.46 (s, 1H), 7.19 (s, 1H), 7.09 (s, 1H), 2.71 (q, J = 8.0 Hz, 2H), 1.26 (t, J = 8.0 Hz, 3H). |
| 458 | $CF_3$ | 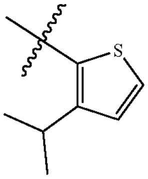 [SMILES: *c1sccc1C(C)C] | (500 MHz, Chloroform-d) δ 7.46 (d, J = 2.5 Hz, 1H), 7.19 (s, 1H), 7.09 (d, J = 2.5 Hz, 1H), 2.71 (hept, J = 8.0 Hz, 1H), 1.26 (d, J = 8.0 Hz, 6H). |
| 459 | $CF_3$ | 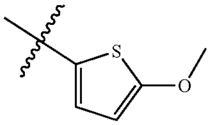 [SMILES: *c1ccc(OC)s1] | (500 MHz, Chloroform-d) δ 7.24 (d, J = 2.5 Hz, 1H), 7.15 (s, 1H), 6.29 (d, J = 2.5 Hz, 1H), 5.74 (s, 1H), 3.85 (s, 3H). |
| 460 | $CF_3$ | 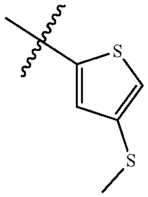 | (500 MHz, Chloroform-d) δ 7.60 (s, 1H), 7.34 (s, 1H), 7.09 (s, 1H), 2.41 (s, 3H). |
| 461 | $CF_3$ | 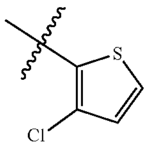 [SMILES: *c1sccc1Cl] | (500 MHz, Chloroform-d) δ 7.52 (d, J = 2.5 Hz, 1H), 7.33 (d, J = 2.5 Hz, 1H), 7.17 (s, 1H), 5.75 (s, 1H). |
| 462 | $CF_3$ | 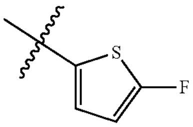 [SMILES: *c1ccc(F)s1] | (500 MHz, Chloroform-d) δ 7.22-7.13 (m, 2H), 6.72-6.57 (m, 1H), 6.00 (s, 1H). |

TABLE 1-continued

Structure and ¹HNMR data of Compound I

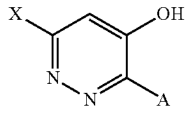

I

| No. | X | A | ¹H NMR |
| --- | --- | --- | --- |
| 463 | $CF_3$ | 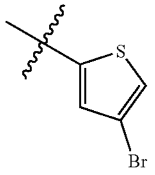 [SMILES: *c1cc(Br)cs1] | (500 MHz, Chloroform-d) δ 7.94 (s, 1H), 7.38 (s, 1H), 7.20 (s, 1H), 7.10 (s, 1H). |
| 464 | $CF_3$ | 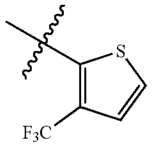 [SMILES: *c1sccc1C(F)(F)F] | (500 MHz, Chloroform-d) δ 7.61 (d, J = 2.5 Hz, 1H), 7.46 (d, J = 2.5 Hz, 1H), 7.18 (s, 1H), 5.85 (s, 1H). |
| 465 | $CF_3$ | 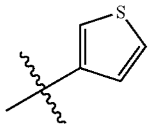 [SMILES: *c1ccsc1] | (500 MHz, Chloroform-d) δ 7.42 (d, J = 2.5 Hz, 1H), 7.36 (s, 1H), 7.20 (d, J = 2.5 Hz, 1H), 7.19 (s, 1H), 5.74 (s, 1H). |
| 466 | $CF_3$ | 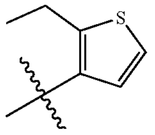 [SMILES: *c1ccsc1CC] | (500 MHz, Chloroform-d) δ 7.33 (d, J = 2.5 Hz, 1H), 7.16 (s, 1H), 7.08 (d, J = 2.5 Hz, 1H), 6.00 (s, 1H), 2.86 (q, J = 8.0 Hz, 2H), 1.32 (t, J = 8.0 Hz, 3H). |
| 467 | $CF_3$ | 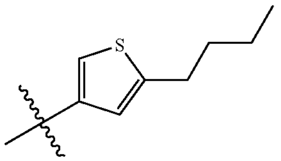 [SMILES: *c1csc(CCCC)c1] | (500 MHz, Chloroform-d) δ 7.56 (s, 1H), 7.18 (s, 1H), 6.92 (s, 1H), 5.74 (s, 1H), 2.61 (t, J = 7.5 Hz, 2H), 1.51-1.37 (m, 4H), 0.96 (t, J = 7.5 Hz, 3H). |
| 468 | $CF_3$ | 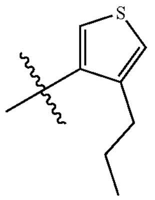 [SMILES: *c1cscc1CCC] | (500 MHz, Chloroform-d) δ 7.41 (s, 1H), 7.13 (s, 1H), 7.03 (s, 1H), 5.74 (s, 1H), 2.65 (t, J = 7.5 Hz, 2H), 1.74-1.61 (m, 2H), 0.99 (t, J = 8.0 Hz, 3H). |
| 469 | $CF_3$ | 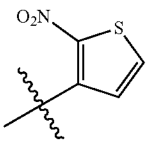 [SMILES: *c1ccsc1[N+](=O)[O-]] | (500 MHz, Chloroform-d) δ 7.93 (d, J = 2.5 Hz, 1H), 7.33 (d, J = 2.5 Hz, 1H), 7.11 (s, 1H), 5.65 (s, 1H). |
| 470 | $CF_3$ | 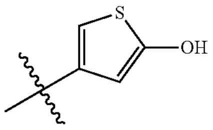 [SMILES: *c1csc(O)c1] | (500 MHz, Chloroform-d) δ 7.18 (s, 1H), 6.32 (s, 1H), 6.27 (s, 1H), 5.95 (s, 1H), 5.84 (s, 1H). |

TABLE 1-continued

Structure and $^1$HNMR data of Compound I

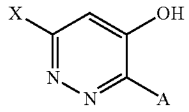

I

| No. | X | A | $^1$H NMR |
|---|---|---|---|
| 471 | $CF_3$ | 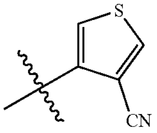 [SMILES: *c1cscc1C#N] | (500 MHz, Chloroform-d) δ 7.85 (s, 1H), 7.56 (s, 1H), 7.17 (s, 1H), 5.69 (s, 1H). |
| 472 | $CF_3$ | 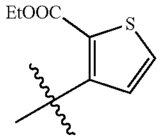 [SMILES: *c1ccsc1C(=O)OCC] | (500 MHz, Chloroform-d) δ 7.68 (d, J = 2.5 Hz, 1H), 7.31 (d, J = 2.5 Hz, 1H), 7.15 (s, 1H), 5.75 (s, 1H), 4.31 (q, J = 7.0 Hz, 2H), 1.33 (t, J = 7.0 Hz, 3H). |
| 473 | $CF_3$ | 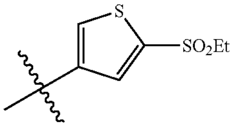 | (500 MHz, Chloroform-d) δ 9.16 (s, 1H), 8.50 (s, 1H), 7.13 (s, 1H), 5.86 (s, 1H), 3.45 (q, J = 6.5 Hz, 2H), 1.43 (t, J = 6.5 Hz, 3H). |
| 474 | $CF_3$ | 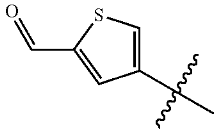 [SMILES: *c1csc(C=O)c1] | (500 MHz, Chloroform-d) δ 9.87 (s, 1H), 8.30 (s, 1H), 7.84 (s, 1H), 7.14 (s, 1H), 5.93 (s, 1H). |
| 475 | $CF_3$ | 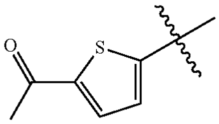 [SMILES: *c1ccc(C(C)=O)s1] | (500 MHz, Chloroform-d) δ 7.80 (d, J = 2.5 Hz, 1H), 7.73 (d, J = 2.5 Hz, 1H), 7.17 (s, 1H), 5.90 (s, 1H), 2.51 (s, 3H). |
| 476 | $CF_3$ | 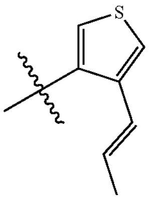 [SMILES: *c1cscc1/C=C/C] | (500 MHz, Chloroform-d) δ 7.69 (s, 1H), 7.17 (s, 1H), 6.30-6.23 (m, 1H), 6.19 (s, 1H), 6.10-6.01 (m, 1H), 1.70 (d, J = 6.5 Hz, 3H). |
| 477 | $CF_3$ | 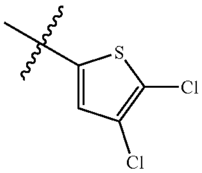 [SMILES: *c1cc(Cl)c(Cl)s1] | (500 MHz, Chloroform-d) δ 7.50 (s, 1H), 7.20 (s, 1H), 7.07 (s, 1H). |
| 478 | $CF_3$ | 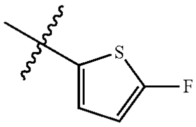 | (500 MHz, Chloroform-d) δ 7.20 (s, 1H), 6.63 (d, J = 7.5 Hz, 1H), 6.00 (s, 1H), 2.23 (s, 3H). |

TABLE 1-continued

Structure and $^1$HNMR data of Compound I

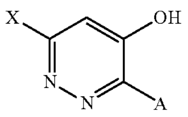

I

| No. | X | A | $^1$H NMR |
|---|---|---|---|
| 479 | $CF_3$ | 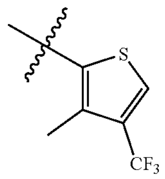 [SMILES: *c1scc(C(F)(F)F)c1C] | (500 MHz, Chloroform-d) δ 7.92 (s, 1H), 7.20 (s, 1H), 6.64 (s, 1H), 2.40 (s, 3H). |
| 480 | $CF_3$ | 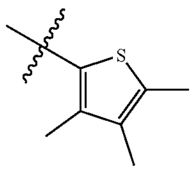 [SMILES: *c1sc(C)c(C)c1C] | (500 MHz, Chloroform-d) δ 7.19 (s, 1H), 6.70 (s, 1H), 2.46 (s, 3H), 2.36 (s, 3H), 2.30 (s, 3H). |
| 481 | $CF_3$ | 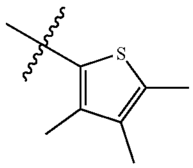 [SMILES: *c1sc(C)c(C)c1C] | (500 MHz, Chloroform-d) δ 7.20 (s, 1H), 6.00 (s, 1H), 2.44 (s, 3H), 2.24 (s, 3H). |
| 482 | $CF_3$ | 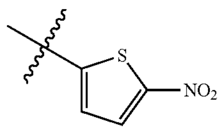 [SMILES: *c1ccc([N+](=O)[O-])s1] | (500 MHz, Chloroform-d) δ 8.22 (d, J = 2.5 Hz, 1H), 7.71 (d, J = 2.5 Hz, 1H), 7.21 (s, 1H), 7.15 (s, 1H). |
| 483 | $CF_3$ | 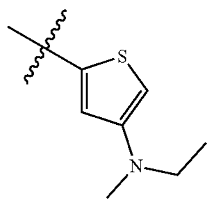 [SMILES: *c1cc(N(C)CC)cs1] | (500 MHz, Chloroform-d) δ 7.20 (s, 1H), 7.10 (s, 1H), 6.86 (s, 1H), 6.05 (s, 1H), 3.26 (q, J = 8.0 Hz, 2H), 2.98 (s, 3H), 1.19 (t, J = 8.0 Hz, 3H). |
| 484 | $CF_3$ | 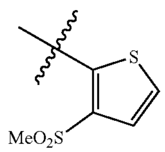 | (500 MHz, Chloroform-d) δ 8.60 (s, 1H), 7.85 (d, J = 2.5 Hz, 1H), 7.76 (d, J = 2.5 Hz, 1H), 7.37 (s, 1H), 3.15 (s, 3H). |
| 485 | $CF_3$ | 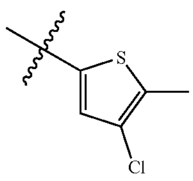 [SMILES: *c1cc(Cl)c(C)s1] | (500 MHz, Chloroform-d) δ 7.50 (s, 1H), 7.20 (s, 1H), 7.15 (s, 1H), 2.52 (s, 3H). |
| 486 | $CF_3$ | 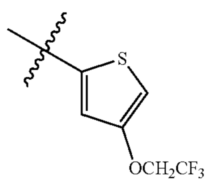 | (500 MHz, Chloroform-d) δ 7.25 (s, 1H), 7.22-7.16 (m, 2H), 6.55 (s, 1H), 4.46 (q, J = 9.5 Hz, 2H). |

TABLE 1-continued

Structure and $^1$HNMR data of Compound I

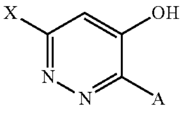

I

| No. | X | A | $^1$H NMR |
| --- | --- | --- | --- |
| 487 | $CF_3$ | 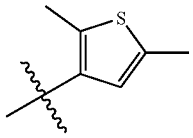 [SMILES: *c1cc(C)sc1C] | (500 MHz, Chloroform-d) δ 7.25 (s, 1H), 7.22 (s, 1H), 6.55 (s, 1H), 2.31 (s, 3H), 2.21 (s, 3H). |
| 488 | $CF_3$ | 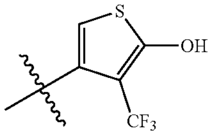 [SMILES: *c1csc(O)c1C(F)(F)F] | (500 MHz, Chloroform-d) δ 7.13 (s, 1H), 6.19 (s, 1H), 5.72 (s, 1H), 3.52 (s, 1H). |
| 489 | $CF_3$ | 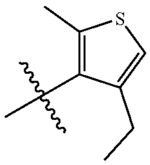 [SMILES: *c1c(CC)csc1C] | (500 MHz, Chloroform-d) δ 7.13 (s, 1H), 6.84 (s, 1H), 5.65 (s, 1H), 2.71 (q, J = 8.0 Hz, 2H), 2.41 (s, 3H), 1.26 (t, J = 8.0 Hz, 3H). |
| 490 | $CF_3$ | 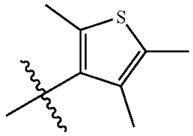 [SMILES: *c1c(C)sc(C)c1C] | (500 MHz, Chloroform-d) δ 7.13 (s, 1H), 5.68 (s, 1H), 3.52 (s, 1H), 2.40 (s, 3H), 2.30 (s, 3H), 2.26 (s, 3H). |
| 491 | $CF_3$ | 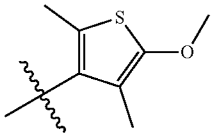 [SMILES: *c1c(C)sc(OC)c1C] | (500 MHz, Chloroform-d) δ 7.13 (s, 1H), 5.68 (s, 1H), 2.40 (d, J = 7.1 Hz, 6H), 2.26 (s, 3H). |
| 492 | $CF_3$ | 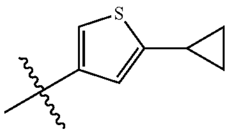 [SMILES: *c1csc(C2CC2)c1] | (500 MHz, Chloroform-d) δ 8.03 (s, 1H), 7.21 (s, 1H), 7.13 (s, 1H), 6.00 (s, 1H), 1.50-1.41 (m, 1H), 0.91-0.79 (m, 4H). |
| 493 | $CF_3$ | 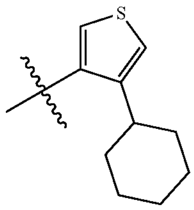 [SMILES: *c1cscc1C1CCCCC1] | (500 MHz, Chloroform-d) δ 7.33 (s, 1H), 7.24 (s, 1H), 7.14 (s, 1H), 6.00 (s, 1H), 2.32-2.22 (m, 1H), 2.04-1.91 (m, 4H), 1.78-1.62 (m, 6H). |
| 494 | $CF_3$ | 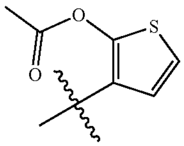 [SMILES: *c1ccsc1OC(C)=O] | (500 MHz, Chloroform-d) δ 7.38 (d, J = 2.5 Hz, 1H), 7.18 (s, 1H), 5.47 (d, J = 2.5 Hz, 1H), 5.30 (s, 1H), 2.21 (s, 3H). |

TABLE 1-continued

Structure and $^{1}$HNMR data of Compound I

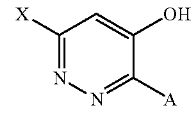

I

| No. | X | A | $^{1}$H NMR |
|---|---|---|---|
| 495 | $CF_3$ | 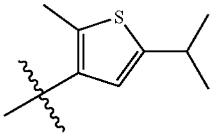 [SMILES: *c1cc(C(C)C)sc1C] | (500 MHz, Chloroform-d) δ 7.16 (s, 1H), 6.88 (s, 1H), 5.97 (s, 1H), 3.31 (hept, J = 6.5 Hz, 1H), 2.37 (s, 3H), 1.30 (d, J = 6.5 Hz, 6H). |
| 496 | $CF_3$ | 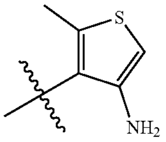 [SMILES: *c1c(N)csc1C] | (500 MHz, Chloroform-d) δ 7.18 (s, 1H), 7.06 (s, 1H), 5.88 (s, 1H), 3.50 (s, 2H), 2.46 (s, 3H). |
| 497 | $CF_3$ | 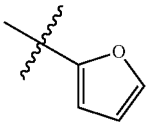 [SMILES: *c1ccco1] | $^{1}$H NMR (500 MHz, DMSO-$d_6$) δ11.71 (s, 1H), 8.13 (s, 1H), 7.76 (s, 1H), 6.88 (s, 1H). |
| 498 | $CF_3$ | 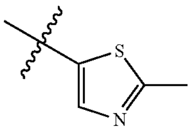 [SMILES: *c1cnc(C)s1] | (500 MHz, Chloroform-d) δ 8.35 (s, 1H), 7.20 (s, 1H), 6.98 (s, 1H), 2.77 (s, 3H). |
| 499 | $CF_3$ | 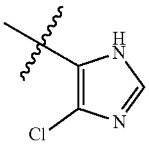 [SMILES: *c1[nH]cnc1Cl] | (500 MHz, Chloroform-d) δ 7.98 (s, 1H), 7.35 (s, 1H), 7.20 (s, 1H). |
| 500 | $CF_3$ | 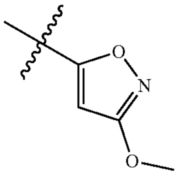 [SMILES: *c1cc(OC)no1] | (500 MHz, Chloroform-d) δ 9.43 (s, 1H), 7.20 (s, 1H), 6.82 (s, 1H), 4.00 (s, 3H). |
| 501 | $CF_3$ | 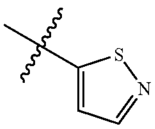 [SMILES: *c1ccns1] | $^{1}$H NMR (500 MHz, DMSO-$d_6$) δ 10.60 (s, 1H), 8.11 (d, J = 2.5 Hz, 1H), 7.37 (d, J = 2.5 Hz, 1H), 6.89 (s, 1H). |
| 502 | $CF_3$ | 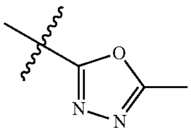 [SMILES: *c1nnc(C)o1] | (500 MHz, Chloroform-d) δ 7.12 (s, 1H), 5.79 (s, 1H), 2.46 (s, 3H). |
| 503 | $CF_3$ | 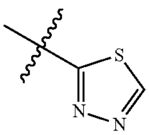 [SMILES: *c1nncs1] | $^{1}$H NMR (500 MHz, DMSO-$d_6$) δ11.73 (s, 1H), 9.42 (s, 1H), 6.84 (s, 1H). |

TABLE 1-continued
Structure and $^{1}$HNMR data of Compound I
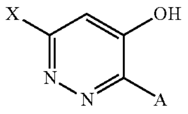
I
| No. | X | A | $^{1}$H NMR |
|---|---|---|---|
| 504 | $CF_3$ | 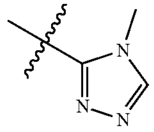 [SMILES: *c1nncn1C] | $^{1}$H NMR (500 MHz, DMSO-$d_6$) δ 12.25 (s, 1H), 9.12 (s, 1H), 6.89 (s, 1H), 3.79 (s, 3H). |
| 505 | $CF_3$ | 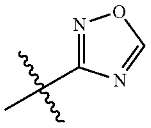 [SMILES: *c1ncon1] | (500 MHz, Chloroform-d) δ 7.12 (s, 1H), 5.71 (s, 1H). |
| 506 | $CF_3$ | 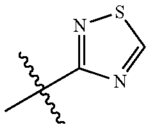 [SMILES: *c1ncsn1] | (500 MHz, Chloroform-d) δ 9.35 (s, 1H), 7.10 (s, 1H). |
| 507 | $CF_3$ | 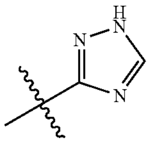 [SMILES: *c1nc[nH]n1] | (500 MHz, Chloroform-d) δ 8.11 (s, 1H), 7.18 (s, 1H). |
| 508 | $CF_3$ | 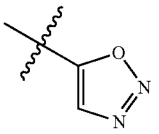 [SMILES: *c1cnno1] | $^{1}$H NMR (500 MHz, DMSO-$d_6$) δ 13.34 (s, 1H), 8.23 (s, 1H), 6.82 (s, 1H). |
| 509 | $CF_3$ | 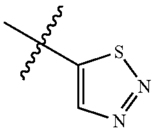 | $^{1}$H NMR (500 MHz, DMSO-$d_6$) δ 13.19 (s, 1H), 8.30 (s, 1H), 6.79 (s, 1H). |
| 510 | $CF_3$ | 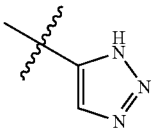 [SMILES: *c1cnn[nH]1] | (500 MHz, Chloroform-d) δ 8.44 (s, 1H), 7.17 (s, 1H). |
| 511 | $CF_3$ | 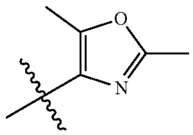 [SMILES: *c1nc(C)oc1C] | (500 MHz, Chloroform-d) δ 7.15 (s, 1H), 5.75 (s, 1H), 2.54 (s, 3H), 2.49 (s, 3H). |
| 512 | $CF_3$ | 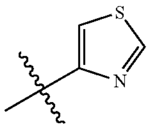 [SMILES: *c1cscn1] | $^{1}$H NMR (500 MHz, DMSO-$d_6$) δ 12.67 (s, 1H), 9.20 (s, 1H), 8.10 (s, 1H), 6.88 (s, 1H). |

TABLE 1-continued

Structure and $^1$HNMR data of Compound I

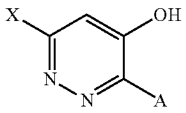

I

| No. | X | A | $^1$H NMR |
|---|---|---|---|
| 513 | $CF_3$ | 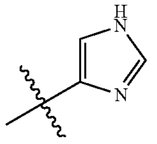 [SMILES: *c1c[nH]cn1] | (500 MHz, Chloroform-d) δ 7.85 (s, 1H), 7.30 (s, 1H), 7.18 (s, 1H). |
| 514 | $CF_3$ | 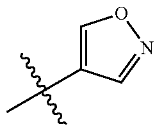 [SMILES: *c1cnoc1] | $^1$H NMR (500 MHz, DMSO-$d_6$) δ 13.38 1H), 8.18 (s, 1H), 8.10 (s, 1H), 7.12, 1H). |
| 515 | $CF_3$ | 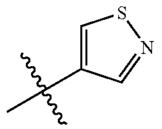 [SMILES: *c1cnsc1] | $^1$H NMR (500 MHz, DMSO-$d_6$) δ 13.01 (s, 1H), 8.72 (s, 1H), 7.89 (s, 1H), 6.94 (s, 1H). |
| 516 | $CF_3$ | 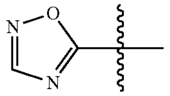 | (500 MHz, Chloroform-d) δ 9.14 (s, 1H), 7.08 (s, 1H). |
| 517 | $CF_3$ | 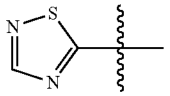 [SMILES: *c1ncns1] | (500 MHz, Chloroform-d) δ 9.32 (s, 1H), 7.11 (s, 1H), 5.77 (s, 1H). |
| 518 | $CF_3$ | 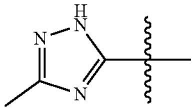 [SMILES: *c1nc(C)n[nH]1] | (500 MHz, Chloroform-d) δ 7.19 (s, 1H), 2.54 (s, 3H). |
| 519 | $CF_3$ | 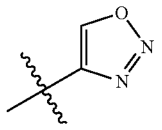 [SMILES: *c1conn1] | $^1$H NMR (500 MHz, DMSO-$d_6$) δ 12.59 (s, 1H), 8.19 (s, 1H), 6.84 (s, 1H). |
| 520 | $CF_3$ | 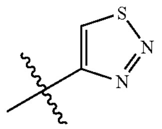 [SMILES: *c1csnn1] | $^1$H NMR (500 MHz, DMSO-$d_6$) δ 12.73 (s, 1H), 9.49 (s, 1H), 6.82 (s, 1H). |
| 521 | $CF_3$ | 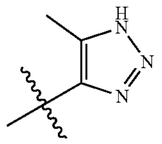 [SMILES: *c1nn[nH]c1C] | (500 MHz, Chloroform-d) δ 7.16 (s, 1H), 2.68 (s, 3H). |
| 522 | $CF_3$ | 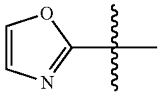 [SMILES: *c1ncco1] | $^1$H NMR (500 MHz, DMSO-$d_6$) δ 12.88 (s, 1H), 7.92 (d, J = 2.5 Hz, 1H), 7.37 (d, J = 2.5 Hz, 1H), 6.87 (s, 1H). |

TABLE 1-continued

Structure and $^{1}$HNMR data of Compound I

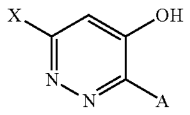

I

| No. | X | A | $^{1}$H NMR |
|---|---|---|---|
| 523 | $CF_3$ | 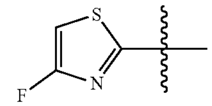 [SMILES: *c1nc(F)cs1] | (500 MHz, Chloroform-d) δ 7.20 (s, 1H), 6.89 (d, J = 7.5 Hz, 1H), 6.00 (s, 1H). |
| 524 | $CF_3$ | 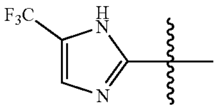 [SMILES: *c1ncc(C(F)(F)F)[nH]1] | (500 MHz, Chloroform-d) δ 7.31 (s, 1H), 7.19 (s, 1H). |
| 525 | $CF_3$ | 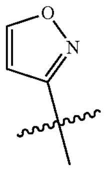 [SMILES: *c1ccon1] | $^{1}$H NMR (500 MHz, DMSO-$d_6$) δ 12.11 (s, 1H), 8.74 (d, J = 2.5 Hz, 1H), 7.26 (d, J = 2.5 Hz, 1H), 6.88 (s, 1H). |
| 526 | $CF_3$ | 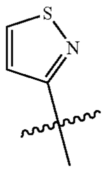 [SMILES: *c1ccsn1] | $^{1}$H NMR (500 MHz, DMSO-$d_6$) δ 12.47 (s, 1H), 8.72 (d, J = 2.0 Hz, 1H), 7.40 (d, J = 2.0 Hz, 1H), 6.85 (s, 1H). |
| 527 | $CF_3$ | 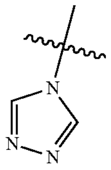 [SMILES: *n1cnnc1] | (500 MHz, Chloroform-d) δ 9.48 (s, 2H), 7.07 (s, 1H), 5.93 (s, 1H). |
| 528 | $CF_3$ | 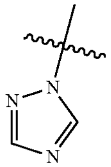 [SMILES: *n1cncn1] | (500 MHz, Chloroform-d) δ 8.58 (s, 1H), 8.37 (s, 1H), 7.10 (s, 1H), 5.93 (s, 1H). |
| 529 | $CF_3$ | 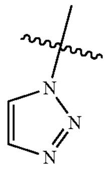 [SMILES: *n1ccnn1] | (500 MHz, Chloroform-d) δ 7.75 (d, J = 2.5 Hz, 1H), 7.15 (s, 1H), 6.76 (d, J = 2.5 Hz, 1H), 5.95 (s, 1H). |
| 530 | $CF_3$ | 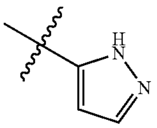 [SMILES: *c1ccn[nH]1] | $^{1}$H NMR (500 MHz, DMSO-d6) δ 13.41 (s, 1H), 8.81 (d, J = 2.5 Hz, 1H), 8.04 (s, 1H), 7.69 (d, J = 2.5 Hz, 1H), 6.74 (s, 1H). |

TABLE 1-continued
Structure and $^1$HNMR data of Compound I
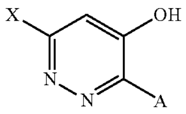
I
| No. | X | A | $^1$H NMR |
|---|---|---|---|
| 531 | $CF_3$ | 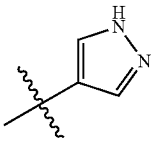 [SMILES: *c1cn[nH]c1] | (500 MHz, Chloroform-d) δ 7.29 (s, 2H), 7.22 (s, 1H). |
| 532 | $CF_3$ | 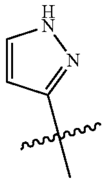 [SMILES: *c1cc[nH]n1] | (500 MHz, Chloroform-d) δ 7.33 (d, J = 2.5 Hz, 1H), 7.18 (s, 1H), 6.77 (d, J = 2.5 Hz, 1H). |
| 533 | $CF_3$ | 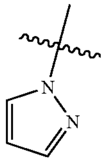 [SMILES: *n1cccn1] | (500 MHz, Chloroform-d) δ 7.88 (d, J = 2.5 Hz, 1H), 7.53 (d, J = 2.0 Hz, 1H), 7.26 (s, 1H), 6.62 (dd, J = 2.5, 2.0 Hz, 1H), 5.93 (s, 1H). |
| 534 | $CF_3$ | 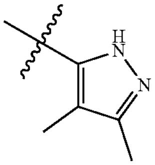 [SMILES: *c1[nH]nc(C)c1C] | (500 MHz, Chloroform-d) δ 7.15 (s, 1H), 2.34 (s, 3H), 2.28 (s, 3H). |
| 535 | $CF_3$ | 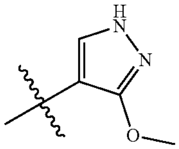 [SMILES: *c1c[nH]nc1OC] | (500 MHz, Chloroform-d) δ 7.55 (s, 1H), 7.17 (s, 1H), 4.01 (s, 3H). |
| 536 | $CF_3$ | 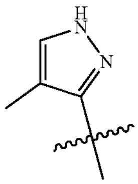 [SMILES: *c1n[nH]cc1C] | (500 MHz, Chloroform-d) δ 7.19 (s, 1H), 7.15 (s, 1H), 2.17 (s, 3H). |
| 537 | $CF_3$ | 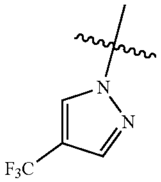 [SMILES: *n1cc(C(F)(F)F)cn1] | (500 MHz, Chloroform-d) δ 7.44 (s, 1H), 7.36 (s, 1H), 7.27 (s, 1H), 5.93 (s, 1H). |

TABLE 1-continued
Structure and $^1$HNMR data of Compound I
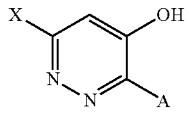
I
| No. | X | A | $^1$H NMR |
|---|---|---|---|
| 538 | $CF_3$ | 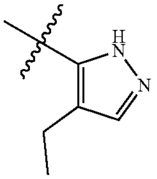 [SMILES: *c1[nH]ncc1CC] | (500 MHz, Chloroform-d) δ 7.48 (s, 1H), 7.15 (s, 1H), 2.66 (q, J = 8.0 Hz, 2H), 1.30 (t, J = 8.0 Hz, 3H). |
| 539 | $CF_3$ | 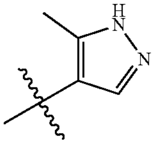 [SMILES: *c1cn[nH]c1C] | (500 MHz, Chloroform-d) δ 7.47 (s, 1H), 7.15 (s, 1H), 2.60 (s, 3H). |
| 540 | $CF_3$ | 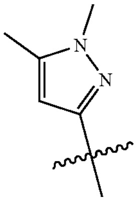 [SMILES: *c1cc(C)n(C)n1] | (500 MHz, Chloroform-d) δ 7.18 (s, 1H), 6.42 (s, 1H), 3.86 (s, 3H), 2.35 (s, 3H). |
| 541 | $CF_3$ | 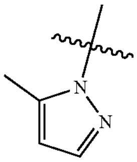 [SMILES: *n1nccc1C] | (500 MHz, Chloroform-d) δ 7.51 (d, J = 2.5 Hz, 1H), 7.26 (s, 1H), 6.13 (d, J = 2.5 Hz, 1H), 5.93 (s, 1H), 2.38 (s, 3H). |
| 542 | $CF_3$ | 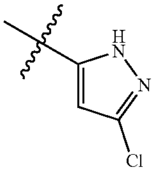 [SMILES: *c1cc(Cl)n[nH]1] | (500 MHz, Chloroform-d) δ 7.16 (s, 1H), 7.05 (s, 1H). |
| 543 | $CF_3$ | 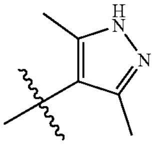 [SMILES: *c1c(C)n[nH]c1C] | (500 MHz, Chloroform-d) δ 7.21 (s, 1H), 2.56 (s, 6H). |
| 544 | $CF_3$ | 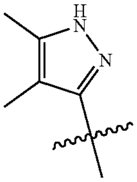 [SMILES: *c1n[nH]c(C)c1C] | (500 MHz, Chloroform-d) δ 7.18 (s, 1H), 2.22 (s, 3H), 2.12 (s, 3H). |

TABLE 1-continued

Structure and $^1$HNMR data of Compound I

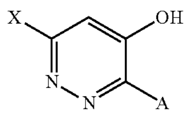

I

| No. | X | A | $^1$H NMR |
|---|---|---|---|
| 545 | $CF_3$ | 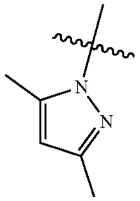 [SMILES: *n1nc(C)cc1C] | (500 MHz, Chloroform-d) δ 7.26 (s, 1H), 6.07 (s, 1H), 5.93 (s, 1H), 2.40 (s, 3H), 1.75 (s, 3H). |
| 546 | $CF_3$ | 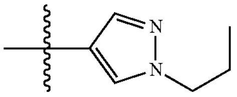 [SMILES: *c1cnn(CCC)c1] | $^1$H NMR (500 MHz, DMSO-d6) δ 13.03 (s, 1H), 8.55 (s, 1H), 8.23 (s, 1H), 7.47 (s, 1H), 4.17 (t, J = 6.5 Hz, 2H), 1.83-1.66 (m, 2H), 0.85 (t, J = 7.5 Hz, 3H). |
| 547 | $CF_3$ | 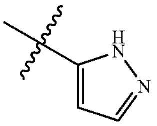 [SMILES: *c1ccn[nH]1] | (500 MHz, Chloroform-d) δ 7.15 (s, 1H), 7.01-6.81 (m, 2H), 6.37-6.23 (m, 1H), 5.92 (s, 1H). |
| 548 | $CF_3$ | 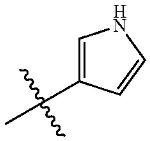 [SMILES: *c1cc[nH]c1] | (500 MHz, Chloroform-d) δ 8.18 (s, 1H), 7.15 (s, 1H), 7.07 (s, 1H), 6.88 (d, J = 2.5 Hz, 1H), 6.33 (d, J = 2.5 Hz, 1H), 5.81 (s, 1H). |
| 549 | $CF_3$ | 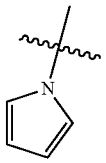 [SMILES: *n1cccc1] | (500 MHz, Chloroform-d) δ 7.33-7.21 (m, 2H), 7.13 (s, 1H), 6.33-6.21 (m, 2H), 5.93 (s, 1H). |
| 550 | $CF_3$ | 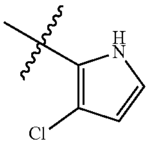 [SMILES: *c1[nH]ccc1Cl] | (500 MHz, Chloroform-d) δ 8.80 (s, 1H), 7.19 (s, 1H), 7.05 (d, J = 2.5 Hz, 1H), 6.55 (d, J = 2.5 Hz, 1H), 5.39 (s, 1H). |
| 551 | $CF_3$ | 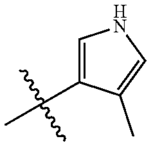 [SMILES: *c1c[nH]cc1C] | (500 MHz, Chloroform-d) δ 8.07 (s, 1H), 7.20 (s, 1H), 6.74 (s, 1H), 6.66 (s, 1H), 6.00 (s, 1H), 2.15 (s, 3H). |
| 552 | $CF_3$ | 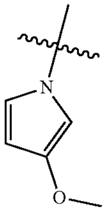 [SMILES: *n1ccc(OC)c1] | (500 MHz, Chloroform-d) δ 7.37 (d, J = 2.5 Hz, 1H), 7.13 (s, 1H), 6.43 (s, 1H), 5.93 (s, 1H), 5.82 (d, J = 2.5 Hz, 1H), 3.85 (s, 3H). |

TABLE 1-continued

Structure and $^1$HNMR data of Compound I

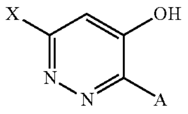

I

| No. | X | A | $^1$H NMR |
|---|---|---|---|
| 553 | $CF_3$ | 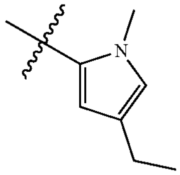 [SMILES: *c1cc(CC)cn1C] | (500 MHz, Chloroform-d) δ 7.19 (s, 1H), 6.45 (s, 1H), 6.32-6.26 (m, 2H), 3.71 (s, 3H), 2.63 (q, J = 8.0 Hz, 2H), 1.25 (t, J = 8.0 Hz, 3H). |
| 554 | $CF_3$ | 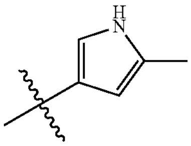 [SMILES: *c1c[nH]c(C)c1] | (500 MHz, Chloroform-d) δ 7.92 (s, 1H), 7.21 (s, 1H), 6.58 (s, 1H), 5.94 (s, 1H), 5.86 (s, 1H), 2.30 (s, 3H). |
| 555 | $CF_3$ | 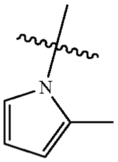 [SMILES: *n1cccc1C] | (500 MHz, Chloroform-d) δ 7.24 (s, 1H), 6.94 (d, J = 2.5 Hz, 1H), 6.24 (dd, J = 2.5, 2.0 Hz, 1H), 6.09 (d, J = 2.0 Hz, 1H), 5.93 (s, 1H), 2.21 (s, 3H). |
| 556 | $CF_3$ | 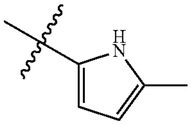 [SMILES: *c1ccc(C)[nH]1] | (500 MHz, Chloroform-d) δ 8.50 (s, 1H), 7.22 (s, 1H), 6.54 (d, J = 2.5 Hz, 1H), 6.00 (d, J = 2.5 Hz, 1H), 5.74 (s, 1H), 2.33 (s, 3H). |
| 557 | $CF_3$ | 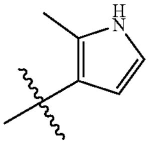 [SMILES: *c1cc[nH]c1C] | (500 MHz, Chloroform-d) δ 7.87 (s, 1H), 7.19 (s, 1H), 6.67 (d, J = 2.5 Hz, 1H), 6.18 (s, 1H), 6.05 (d, J = 2.5 Hz, 1H), 2.42 (s, 3H). |
| 558 | $CF_3$ | 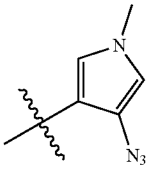 [SMILES: *c1cn(C)cc1N=[N+]=[N-]] | |
| 559 | $CF_3$ | 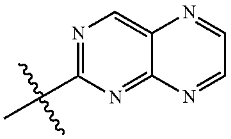 [SMILES: *c1ncc2nccnc2n1] | (500 MHz, Chloroform-d) δ 9.53 (s, 1H), 8.99-8.88 (m, 2H), 7.29 (s, 1H). |
| 560 | $CF_3$ | 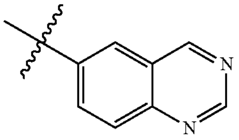 [SMILES: *c1ccc2ncncc2c1] | (500 MHz, Chloroform-d) δ 9.61 (s, 1H), 9.55 (s, 1H), 9.41 (s, 1H), 7.28 (s, 1H), 5.74 (s, 1H). |

TABLE 1-continued

Structure and $^1$HNMR data of Compound I

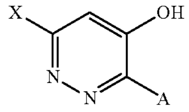

I

| No. | X | A | $^1$H NMR |
|---|---|---|---|
| 561 | $CF_3$ | 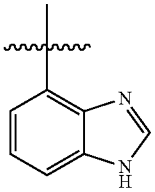 [SMILES: *c1cccc2[nH]cnc12] | (500 MHz, Chloroform-d) δ 9.55 (s, 1H), 8.63 (s, 1H), 7.36 (s, 1H). |
| 562 | $CF_3$ | 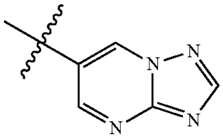 [SMILES: *c1cnc2ncnn2c1] | (500 MHz, Chloroform-d) δ 9.39 (d, J = 1.5 Hz, 1H), 9.23 (d, J = 1.5 Hz, 1H), 8.57 (s, 1H), 7.28 (s, 1H), 5.94 (s, 1H). |
| 563 | $CF_3$ | 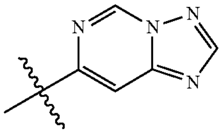 [SMILES: *c1cc2ncnn2cn1] | (500 MHz, Chloroform-d) δ 9.99 (s, 1H), 8.78 (s, 1H), 7.87 (s, 1H), 7.29 (s, 1H), 5.54 (s, 1H). |
| 564 | $CF_3$ | 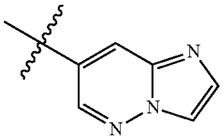 [SMILES: *c1cnn2ccnc2c1] | (500 MHz, Chloroform-d) δ 9.23 (d, J = 1.5 Hz, 1H), 7.84 (d, J = 1.5 Hz, 1H), 7.53 (d, J = 2.5 Hz, 1H), 7.28 (s, 1H), 7.22 (d, J = 2.5 Hz, 1H), 5.92 (s, 1H). |
| 565 | $CF_3$ | 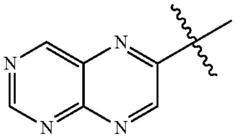 [SMILES: *c1cnc2ncncc2n1] | (500 MHz, Chloroform-d) δ 9.61 (s, 1H), 9.55 (s, 1H), 9.42 (s, 1H), 7.28 (s, 1H), 5.74 (s, 1H). |
| 566 | $CF_3$ | 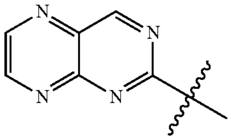 [SMILES: *c1ncc2nccnc2n1] | (500 MHz, Chloroform-d) δ 9.53 (s, 1H), 8.99-8.88 (m, 2H), 7.29 (s, 1H), 5.34 (s, 1H). |
| 567 | $CF_3$ | 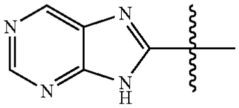 [SMILES: *c1nc2cncnc2[nH]1] | (500 MHz, Chloroform-d) δ 9.35 (s, 1H), 8.25 (s, 1H), 7.25 (s, 1H). |
| 568 | $CF_3$ | 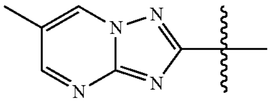 [SMILES: *c1nc2ncc(C)cn2n1] | (500 MHz, Chloroform-d) δ 8.75 (q, J = 1.5 Hz, 1H), 8.35 (q, J = 1.5 Hz, 1H), 7.28 (s, 1H), 2.39 (s, 3H). |
| 569 | $CF_3$ | 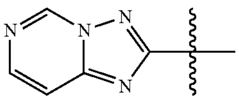 [SMILES: *c1nc2ccncn2n1] | (500 MHz, Chloroform-d) δ 9.84 (s, 1H), 8.75 (d, J = 5.5 Hz, 1H), 7.56 (d, J = 5.5 Hz, 1H), 7.28 (s, 1H). |
| 570 | $CF_3$ | 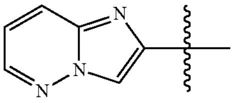 [SMILES: *c1cn2ncccc2n1] | (500 MHz, Chloroform-d) δ 8.91 (dd, J = 5.5, 1.5 Hz, 1H), 7.70 (dd, J = 7.5, 5.5 Hz, 1H), 7.49 (dd, J = 7.5, 1.5 Hz, 1H), 7.43 (s, 1H), 7.28 (s, 1H). |

TABLE 1-continued
Structure and $^1$HNMR data of Compound I
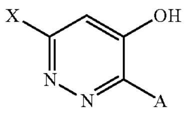
I
| No. | X | A | $^1$H NMR |
|---|---|---|---|
| 571 | $CF_3$ | 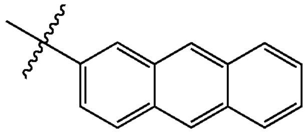 [SMILES: *c1ccc2cc3ccccc3cc2c1] | (500 MHz, Chloroform-d) δ 8.45-8.36 (m, 3H), 8.24-8.01 (m, 3H), 7.89-7.79 (m, 1H), 7.54-7.45 (m, 2H), 7.10 (s, 1H), 5.56 (s, 1H). |
| 572 | $CF_3$ | 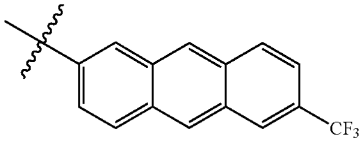 [SMILES: *c1ccc2cc3cc(C(F)(F)F)ccc3cc2c1] | (500 MHz, Chloroform-d) δ 8.95-8.91 (m, 1H), 8.59-8.55 (m, 1H), 8.37-8.30 (m, 1H), 8.22-8.12 (m, 2H), 7.92-7.74 (m, 3H), 7.11 (s, 1H), 5.55 (s, 1H). |
| 573 | $CF_3$ | 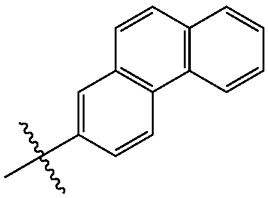 [SMILES: *c1ccc2c(ccc3ccccc32)c1] | (500 MHz, Chloroform-d) δ 8.86-8.31 (m, 3H), 8.04-7.90 (m, 3H), 7.75-7.68 (m, 2H), 7.63-7.55 (m, 1H), 7.10 (s, 1H), 5.52 (s, 1H). |
| 574 | $CF_3$ | 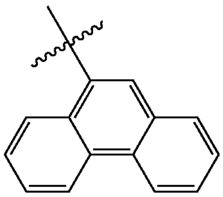 [SMILES: *c1cc2ccccc2c2ccccc12] | (500 MHz, Chloroform-d) δ 9.08-8.84 (m, 1H), 8.12-7.91 (m, 4H), 7.74-7.58 (m, 4H), 7.10 (s, 1H), 5.66 (s, 1H). |
| 575 | $CF_3$ | 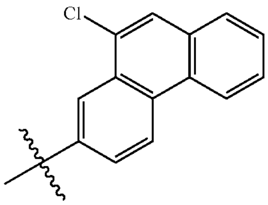 [SMILES: *c1ccc2c(c1)c(Cl)cc1ccccc12] | (500 MHz, Chloroform-d) δ 8.90-8.84 (m, 2H), 8.58-8.37 (m, 2H), 7.91-7.80 (m, 2H), 7.68-7.63 (m, 2H), 7.10 (s, 1H), 5.61 (s, 1H). |
| 576 | $CF_3$ | 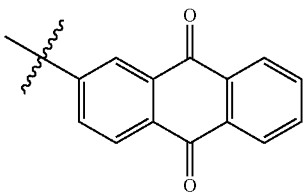 [SMILES: *c1ccc2c(c1)C(=O)c1ccccc1C2=O] | (500 MHz, Chloroform-d) δ 8.51 (d, J = 2.0 Hz, 1H), 8.32-8.26 (m, 3H), 7.89-7.80 (m, 3H), 7.03 (s, 1H), 5.87 (s, 1H). |
| 577 | $CF_3$ | 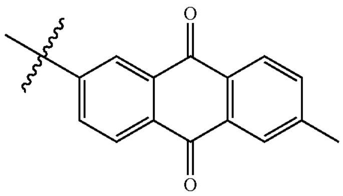 [SMILES: *c1ccc2c(c1)C(=O)c1ccc(C)cc1C2=O] | (500 MHz, Chloroform-d) δ 8.43 (d, J = 2.0 Hz, 1H), 8.26-8.06 (m, 2H), 7.95-7.90 (m, 1H), 7.45-7.39 (m, 2H), 7.08 (s, 1H), 5.71 (s, 1H), 2.30 (s, 3H). |

TABLE 1-continued

Structure and $^{1}$HNMR data of Compound I

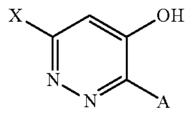

I

| No. | X | A | $^{1}$H NMR |
| --- | --- | --- | --- |
| 578 | $CF_3$ | 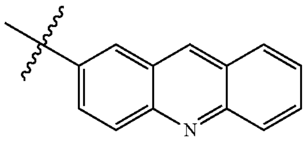 [SMILES: *c1ccc2nc3ccccc3cc2c1] | (500 MHz, Chloroform-d) δ 8.55-8.45 (m, 2H), 8.27-8.20 (m, 2H), 8.11-7.97 (m, 2H), 7.72-7.54 (m, 2H), 7.10 (s, 1H), 5.50 (s, 1H). |
| 579 | $CF_3$ | 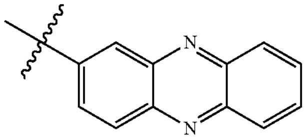 [SMILES: *c1ccc2nc3ccccc3nc2c1] | (500 MHz, Chloroform-d) δ 8.61 (d, J = 1.5 Hz, 1H), 8.39 (d, J = 7.5 Hz, 1H), 8.14-8.10 (m, 3H), 7.80-7.67 (m, 2H), 7.05 (s, 1H), 5.75 (s, 1H). |
| 580 | $CF_3$ | 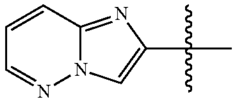 [SMILES: *c1cn2ncccc2n1] | (500 MHz, Chloroform-d) δ 9.42-9.13 (m, 2H), 8.59-8.49 (m, 2H), 7.97-7.88 (m, 2H), 7.68-7.56 (m, 1H), 7.28 (s, 1H), 5.76 (s, 1H). |
| 581 | $CF_3$ | 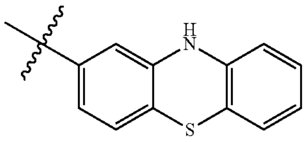 [SMILES: *c1ccc2c(c1)Nc1ccccc1S2] | (500 MHz, Chloroform-d) δ 9.08 (s, 1H), 7.50-7.23 (m, 2H), 7.16-7.11 (m, 2H), 7.05-6.91 (m, 2H), 6.89-6.77 (m, 2H), 5.48 (s, 1H). |
| 582 | $CF_3$ | 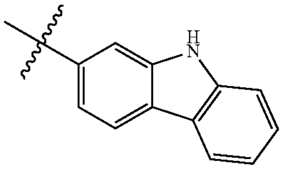 [SMILES: *c1ccc2c(c1)[nH]c1ccccc12] | (500 MHz, Chloroform-d) δ 8.28-8.12 (m, 2H), 7.83 (d, J = 1.5 Hz, 1H), 7.59-7.51 (m, 2H), 7.55 (s, 1H), 7.34-7.26 (m, 2H), 7.09 (s, 1H), 5.72 (s, 1H). |
| 583 | $CF_3$ | 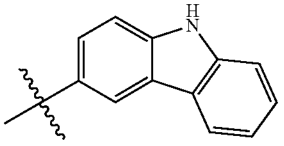 [SMILES: *c1ccc2[nH]c3ccccc3c2c1] | (500 MHz, Chloroform-d) δ 8.33-8.27 (m, 2H), 7.70-7.62 (m, 2H), 7.60-7.53 (m, 2H), 7.34-7.26 (m, 2H), 7.03 (s, 1H), 5.84 (s, 1H). |
| 584 | $CF_3$ | 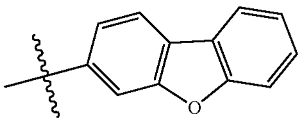 [SMILES: *c1ccc2c(c1)oc1ccccc12] | (500 MHz, Chloroform-d) δ 8.05-7.95 (m, 2H), 7.86-7.65 (m, 2H), 7.54-7.44 (m, 2H), 7.35-7.23 (m, 1H), 7.09 (s, 1H), 5.76 (s, 1H). |
| 585 | $CF_3$ | 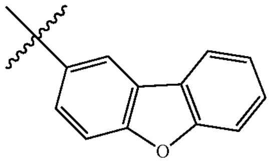 [SMILES: *c1ccc2oc3ccccc3c2c1] | (500 MHz, Chloroform-d) δ 8.14 (d, J = 1.5 Hz, 1H), 8.05 (dd, J = 7.5, 1.5 Hz, 1H), 7.79-7.73 (m, 2H), 7.54-7.44 (m, 2H), 7.35-7.28 (m, 1H), 7.04 (s, 1H), 5.89 (s, 1H). |
| 586 | $CF_3$ | 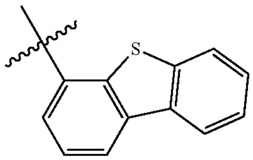 [SMILES: *c1cccc2c1sc1ccccc12] | (500 MHz, Chloroform-d) δ 8.52 (dd, J = 7.5, 1.5 Hz, 1H), 8.42 (dd, J = 7.0, 1.5 Hz, 1H), 7.96-7.81 (m, 2H), 7.60-7.51 (m, 2H), 7.31-7.20 (m, 1H), 7.06 (s, 1H), 5.76 (s, 1H). |

TABLE 1-continued

Structure and $^1$HNMR data of Compound I

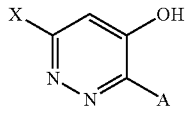

I

| No. | X | A | $^1$H NMR |
| --- | --- | --- | --- |
| 587 | $CF_3$ | 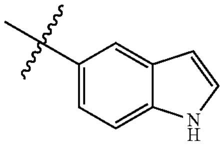 [SMILES: *c1ccc2[nH]ccc2c1] | (500 MHz, Chloroform-d) δ 8.23 (s, 1H), 7.96-7.51 (m, 3H), 7.18 (d, J = 2.5 Hz, 1H), 7.08 (s, 1H), 6.68-6.51 (m, 1H), 5.75 (s, 1H). |
| 588 | $CF_3$ | 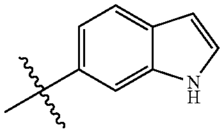 [SMILES: *c1ccc2cc[nH]c2c1] | (500 MHz, Chloroform-d) δ 8.06 (s, 1H), 7.90-7.80 (m, 2H), 7.58 (dd, J = 7.5, 1.5 Hz, 1H), 7.18 (d, J = 7.5 Hz, 1H), 7.02 (s, 1H), 6.56-6.47 (m, 1H), 5.82 (s, 1H). |
| 589 | $CF_3$ | 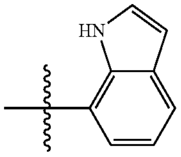 [SMILES: *c1cccc2cc[nH]c12] | (500 MHz, Chloroform-d) δ 8.06 (s, 1H), 7.90-7.80 (m, 2H), 7.58 (dd, J = 7.5, 1.5 Hz, 1H), 7.18 (d, J = 7.5 Hz, 1H), 7.02 (s, 1H), 6.56-6.45 (m, 1H), 5.82 (s, 1H). |
| 590 | $CF_3$ | 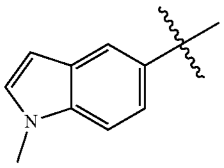 [SMILES: *c1ccc2c(ccn2C)c1] | (500 MHz, Chloroform-d) δ 7.77 (d, J = 1.5 Hz, 1H), 7.65 (d, J = 1.0 Hz, 1H), 7.14-7.05 (m, 3H), 6.62 (dd, J = 7.5, 1.5 Hz, 1H), 5.72 (s, 1H), 3.74 (s, 3H). |
| 591 | $CF_3$ | 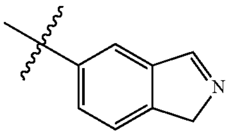 [SMILES: *c1ccc2c(c1)C=NC2] | |
| 592 | $CF_3$ | 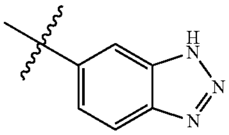 [SMILES: *c1ccc2nn[nH]c2c1] | (500 MHz, Chloroform-d) δ 8.02-7.93 (m, 2H), 7.65 (dd, J = 7.5, 1.5 Hz, 1H), 7.09 (s, 1H). |
| 593 | $CF_3$ | 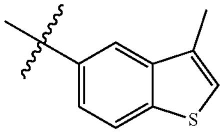 [SMILES: *c1ccc2scc(C)c2c1] | (500 MHz, Chloroform-d) δ 8.11-8.03 (m, 2H), 7.67 (dd, J = 7.5, 1.5 Hz, 1H), 7.17 (s, 1H), 7.09 (s, 1H), 5.68 (s, 1H), 2.50 (s, 3H). |
| 594 | $CF_3$ | 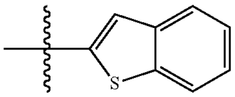 [SMILES: *c1cc2ccccc2s1] | $^1$H NMR (500 MHz, DMSO-d6) δ 13.86 (s, 1H), 8.57 (s, 1H), 7.99-7.81 (m, 2H), 7.48-7.36 (m, 2H), 7.29 (s, 1H). |
| 595 | $CF_3$ | 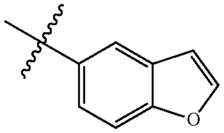 [SMILES: *c1ccc2occc2c1] | (500 MHz, Chloroform-d) δ 7.83 (d, J = 1.5 Hz, 1H), 7.66-7.58 (m, 3H), 7.08 (s, 1H), 6.76 (dd, J = 7.5, 1.5 Hz, 1H), 5.63 (s, 1H). |

TABLE 1-continued

Structure and $^1$HNMR data of Compound I

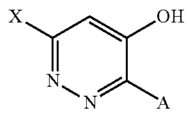

I

| No. | X | A | $^1$H NMR |
|---|---|---|---|
| 596 | $CF_3$ | 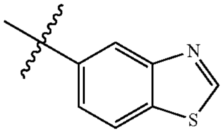 [SMILES: *c1ccc2scnc2c1] | (500 MHz, Chloroform-d) δ 9.33 (s, 1H), 8.31 (d, J = 1.5 Hz, 1H), 8.16 (d, J = 7.5 Hz, 1H), 7.81 (dd, J = 7.5, 1.5 Hz, 1H), 7.08 (s, 1H), 5.81 (s, 1H). |
| 597 | $CF_3$ | 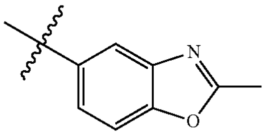 [SMILES: *c1ccc2oc(C)nc2c1] | (500 MHz, Chloroform-d) δ 7.85 (d, J = 1.5 Hz, 1H), 7.79 (d, J = 7.5 Hz, 1H), 7.67 (dd, J = 7.5, 1.5 Hz, 1H), 7.03 (s, 1H), 5.84 (s, 1H), 2.61 (s, 3H). |
| 598 | $CF_3$ | 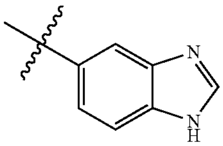 [SMILES: *c1ccc2[nH]cnc2c1] | (500 MHz, Chloroform-d) δ 8.25 (s, 1H), 7.99 (d, J = 1.5 Hz, 1H), 7.71 (d, J = 7.5 Hz, 1H), 7.59 (dd, J = 7.5, 1.5 Hz, 1H), 7.07 (s, 1H), 5.84 (s, 1H). |
| 599 | $CF_3$ | 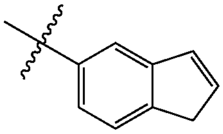 [SMILES: *c1ccc2c(c1)C=CC2] | (500 MHz, Chloroform-d) δ 7.66 (d, J = 1.5 Hz, 1H), 7.58 (d, J = 7.5 Hz, 1H), 7.46 (dd, J = 7.5, 1.5 Hz, 1H), 7.06 (s, 6.75-6.69 (m, 1H), 6.45-6.33 (m, 1H), 5.60 (s, 1H), 3.22-3.12 (m, 2H). |
| 600 | $CF_3$ | 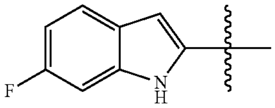 | (500 MHz, Chloroform-d) δ 9.18 (s, 1H), 8.09-8.00 (m, 1H), 7.31-7.25 (m, 2H), 7.21-7.15 (m, 2H), 5.98 (s, 1H). |
| 601 | $CF_3$ | 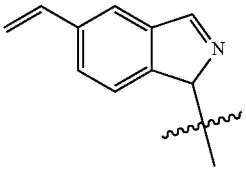 [SMILES: *C1N=Cc2cc(C=C)ccc21] | |
| 602 | $CF_3$ | 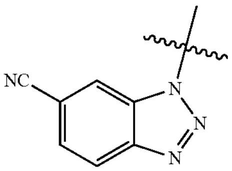 [SMILES: *n1nnc2ccc(C#N)cc21] | (500 MHz, Chloroform-d) δ 8.36 (d, J = 1.5 Hz, 1H), 8.06 (d, J = 7.5 Hz, 1H), 7.73 (dd, J = 7.5, 1.5 Hz, 1H), 7.15 (s, 1H), 5.93 (s, 1H). |
| 603 | $CF_3$ | 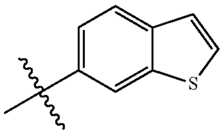 [SMILES: *c1ccc2ccsc2c1] | (500 MHz, Chloroform-d) δ 8.22 (d, J = 1.5 Hz, 1H), 8.05 (d, J = 7.5 Hz, 1H), 7.66 (dd, J = 7.5, 1.5 Hz, 1H), 7.42 (d, J = 2.5 Hz, 1H), 7.32 (dd, J = 2.5, 1.6 Hz, 1H), 7.08 (s, 1H), 5.67 (s, 1H). |
| 604 | $CF_3$ | 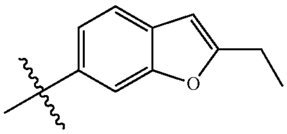 [SMILES: *c1ccc2cc(CC)oc2c1] | (500 MHz, Chloroform-d) δ 7.76 (d, J = 1.5 Hz, 1H), 7.69 (d, J = 7.5 Hz, 1H), 7.58 (dd, J = 7.5, 1.5 Hz, 1H), 7.08 (s, 1H), 6.28 (s, 1H), 5.71 (s, 1H), 2.86 (q, J = 8.0 Hz, 2H), 1.32 (t, J = 8.0 Hz, 3H). |

TABLE 1-continued

Structure and $^1$HNMR data of Compound I

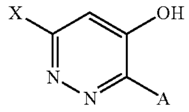

I

| No. | X | A | $^1$H NMR |
|---|---|---|---|
| 605 | $CF_3$ | 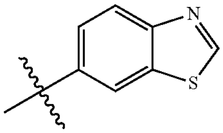 [SMILES: *c1ccc2ncsc2c1] | (500 MHz, Chloroform-d) δ 9.34 (s, 1H), 8.38 (d, J = 1.5 Hz, 1H), 7.86 (d, J = 7.5 Hz, 1H), 7.78 (dd, J = 7.5, 1.5 Hz, 1H), 7.08 (s, 1H), 5.64 (s, 1H). |
| 606 | $CF_3$ | 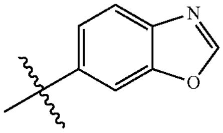 | (500 MHz, Chloroform-d) δ 8.30 (s, 1H), 7.79-7.70 (m, 2H), 7.49 (dd, J = 7.5, 1.5 Hz, 1H), 7.02 (s, 1H), 5.82 (s, 1H). |
| 607 | $CF_3$ | 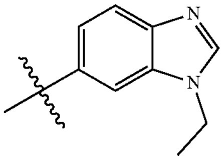 [SMILES: *c1ccc2ncn(CC)c2c1] | (500 MHz, Chloroform-d) δ 8.41 (s, 1H), 7.95 (d, J = 1.5 Hz, 1H), 7.79 (d, J = 7.5 Hz, 1H), 7.60 (dd, J = 7.5, 1.5 Hz, 1H), 7.08 (s, 1H), 5.64 (s, 1H), 4.55 (q, J = 8.0 Hz, 2H), 1.63 (t, J = 8.0 Hz, 3H). |
| 608 | $CF_3$ | 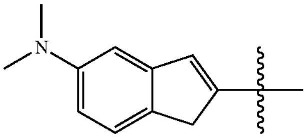 [SMILES: *C1=Cc2cc(N(C)C)ccc2C1] | (500 MHz, Chloroform-d) δ 7.23 (d, J = 7.5 Hz, 1H), 7.15-7.07 (m, 2H), 6.59 (dd, J = 7.5, 1.5 Hz, 1H), 6.49 (d, J = 1.5 Hz, 1H), 5.87 (s, 1H), 3.10 (s, 2H), 2.90 (s, 6H). |
| 609 | $CF_3$ | 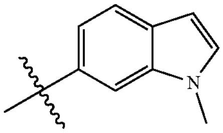 [SMILES: *c1ccc2ccn(C)c2c1] | (500 MHz, Chloroform-d) δ 7.82-7.74 (m, 2H), 7.73 (d, J = 1.5 Hz, 1H), 7.11 (d, J = 2.5 Hz, 1H), 7.02 (s, 1H), 6.50 (d, J = 2.5 Hz, 1H), 5.82 (s, 1H), 3.80 (s, 3H). |
| 610 | $CF_3$ | 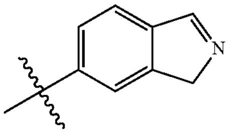 [SMILES: *c1ccc2c(c1)CN=C2] | |
| 611 | $CF_3$ | 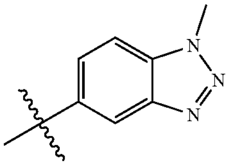 [SMILES: *c1ccc2c(c1)nnn2C] | (500 MHz, Chloroform-d) δ 8.30 (d, J = 1.5 Hz, 1H), 7.82-7.72 (m, 2H), 7.02 (s, 1H), 5.79 (s, 1H), 4.30 (s, 3H). |
| 612 | $CF_3$ | 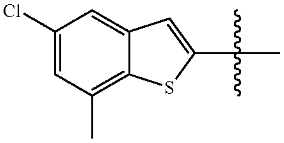 [SMILES: *c1cc2cc(Cl)cc(C)c2s1] | (500 MHz, Chloroform-d) δ 7.80-7.71 (m, 2H), 7.33-7.25 (m, 2H), 6.17 (s, 1H), 2.49 (s, 3H). |
| 613 | $CF_3$ | 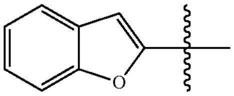 [SMILES: *c1cc2ccccc2o1] | (500 MHz, Chloroform-d) δ 7.66-7.55 (m, 2H), 7.32-7.24 (m, 2H), 7.26-7.18 (m, 2H), 6.04 (s, 1H). |

TABLE 1-continued
Structure and $^1$HNMR data of Compound I
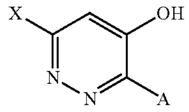
I
| No. | X | A | $^1$H NMR |
| --- | --- | --- | --- |
| 614 | $CF_3$ | 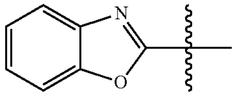 | (500 MHz, Chloroform-d) δ 8.18-8.08 (m, 2H), 7.58-7.50 (m, 2H), 7.29 (s, 1H). |
| 615 | $CF_3$ | 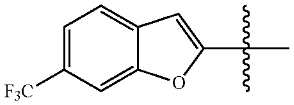 | (500 MHz, Chloroform-d) δ 7.72-7.58 (m, 3H), 7.29 (s, 1H). |
| 616 | $CF_3$ | 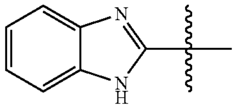 [SMILES: *c1nc2ccccc2[nH]1] | (500 MHz, Chloroform-d) δ 7.66-7.52 (m, 2H), 7.30-7.20 (m, 2H), 7.09 (s, 1H). |
| 617 | $CF_3$ | 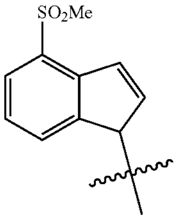 [SMILES: *C1C=Cc2c1cccc2S(C)(=O)=O] | |
| 618 | $CF_3$ | 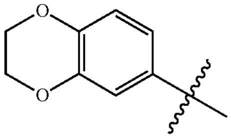 [SMILES: *c1ccc2c(c1)OCCO2] | (500 MHz, Chloroform-d) δ 7.86 (s, 1H), 7.16 (d, J = 2.0 Hz, 1H), 7.08 (dd, J = 7.5, 2.0 Hz, 1H), 6.99 (d, J = 7.5 Hz, 1H), 5.34 (s, 1H), 4.32-4.25 (m, 4H). |
| 619 | $CF_3$ | 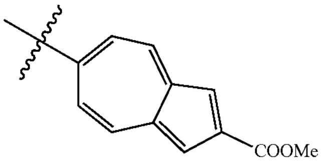 [SMILES: *c1ccc2cc(C(=O)OC)cc-2cc1] | |
| 620 | $CF_3$ | 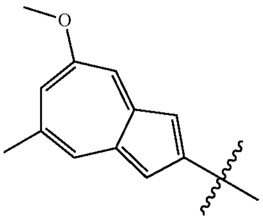 [SMILES: *c1cc2cc(C)cc(OC)cc-2c1] | |
| 621 | $CF_3$ | 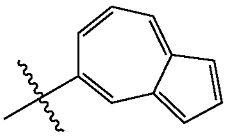 [SMILES: *c1cccc2cccc-2c1] | |

TABLE 1-continued

Structure and $^{1}$HNMR data of Compound I

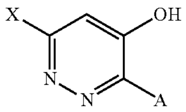

I

| No. | X | A | $^{1}$H NMR |
| --- | --- | --- | --- |
| 622 | $CF_3$ | 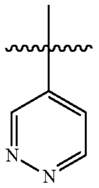 [SMILES: *c1ccnnc1] | (500 MHz, Chloroform-d) δ 9.72 (d, J = 1.5 Hz, 1H), 9.43 (d, J = 7.5 Hz, 1H), 8.03 (dd, J = 7.5, 1.5 Hz, 1H), 7.24 (s, 1H), 5.86 (s, 1H). |
| 623 | $CF_3$ | 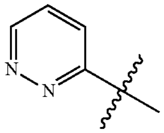 [SMILES: *c1cccnn1] | (500 MHz, Chloroform-d) δ 9.50 (dd, J = 7.5, 1.5 Hz, 1H), 8.01 (dd, J = 7.0, 1.5 Hz, 1H), 7.82 (dd, J = 7.5, 7.0 Hz, 1H), 7.23 (s, 1H), 5.77 (s, 1H). |
| 624 | $CF_3$ | 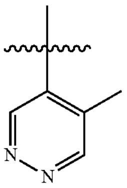 | (500 MHz, Chloroform-d) δ 9.50 (s, 1H), 9.42 (s, 1H), 7.28 (s, 1H), 5.44 (s, 1H), 2.38 (s, 3H). |
| 625 | $CF_3$ | 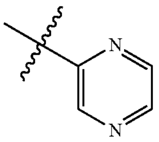 [SMILES: *c1cnccn1] | (500 MHz, Chloroform-d) δ 9.26 (s, 1H), 8.82 (d, J = 5.5 Hz, 1H), 8.75 (d, J = 5.5 Hz, 1H), 7.26 (s, 1H), 5.59 (s, 1H). |
| 626 | $CF_3$ | 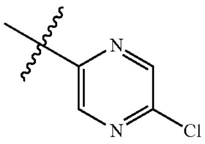 [SMILES: *c1cnc(Cl)cn1] | (500 MHz, Chloroform-d) δ 9.19 (s, 1H), 8.88 (s, 1H), 7.28 (s, 1H). |
| 627 | $CF_3$ | 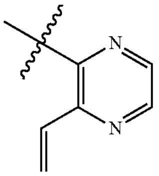 [SMILES: *c1nccnc1C=C] | (500 MHz, Chloroform-d) δ 8.82-8.66 (m, 2H), 7.31 (s, 1H), 6.92-6.81 (m, 1H), 5.93-5.84 (m, 2H). |
| 628 | $CF_3$ | 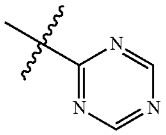 [SMILES: *c1ncncn1] | (500 MHz, Chloroform-d) δ 9.45 (s, 2H), 7.29 (s, 1H), 5.39 (s, 1H). |
| 629 | $CF_3$ | 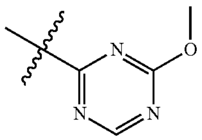 [SMILES: *c1ncnc(OC)n1] | (500 MHz, Chloroform-d) δ 9.46 (s, 1H), 7.25 (s, 1H), 5.85 (s, 1H), 3.93 (s, 3H). |

TABLE 1-continued
Structure and $^1$HNMR data of Compound I
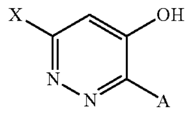
I
| No. | X | A | $^1$H NMR |
|---|---|---|---|
| 630 | $CF_3$ | 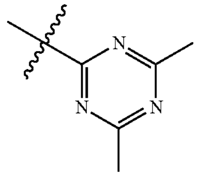 [SMILES: *c1nc(C)nc(C)n1] | (500 MHz, Chloroform-d) δ 7.05 (s, 1H), 5.87 (s, 1H), 2.82 (s, 6H). |
| 631 | $CF_3$ | 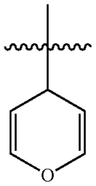 [SMILES: *C1C=COC=C1] | |
| 632 | $CF_3$ | 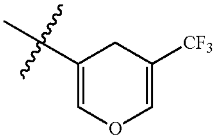 [SMILES: *C1=COC=C(C(F)(F)F)C1] | |
| 633 | $CF_3$ | 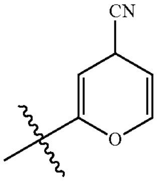 [SMILES: *C1=CC(C#N)C=CO1] | |
| 634 | $CF_3$ | 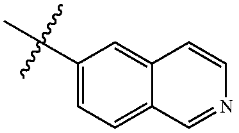 [SMILES: *c1ccc2cnccc2c1] | (500 MHz, Chloroform-d) δ 9.25 (d, J = 1.5 Hz, 1H), 8.53 (d, J = 7.5 Hz, 1H), 8.11-8.04 (m, 2H), 7.91-7.82 (m, 3H), 5.50 (s, 1H). |
| 635 | $CF_3$ | 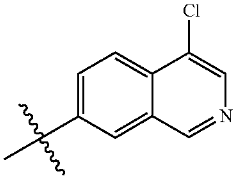 [SMILES: *c1ccc2c(Cl)cncc2c1] | (500 MHz, Chloroform-d) δ 9.13 (s, 1H), 8.64-8.51 (m, 2H), 8.39 (d, J = 7.5 Hz, 1H), 8.05-7.96 (m, 2H), 6.86 (s, 1H). |
| 636 | $CF_3$ | 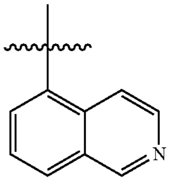 [SMILES: *c1cccc2cnccc12] | (500 MHz, Chloroform-d) δ 9.08 (d, J = 1.5 Hz, 1H), 8.61 (d, J = 7.5 Hz, 1H), 8.06 (dd, J = 7.5, 1.5 Hz, 1H), 7.91-7.83 (m, 2H), 7.78-7.69 (m, 2H), 5.36 (s, 1H). |

TABLE 1-continued

Structure and $^1$HNMR data of Compound I

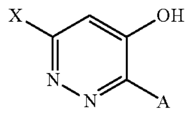

I

| No. | X | A | $^1$H NMR |
|---|---|---|---|
| 637 | $CF_3$ | 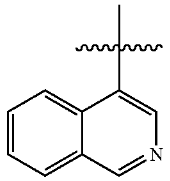 [SMILES: *c1cncc2ccccc12] | (500 MHz, Chloroform-d) δ 9.34 (d, J = 1.4 Hz, 1H), 8.78 (s, 1H), 8.10 (s, 1H), 8.00 (dt, J = 7.5, 1.6 Hz, 1H), 7.81 (dd, J = 7.3, 1.6 Hz, 1H), 7.65-7.53 (m, 2H), 5.49 (s, 1H). |
| 638 | $CF_3$ | 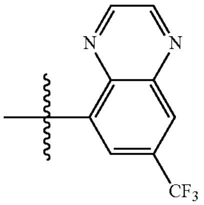 [SMILES: *c1cc(C(F)(F)F)cc2nccnc12] | (500 MHz, Chloroform-d) δ 9.00 (d, J = 7.5 Hz, 1H), 8.78 (d, J = 7.5 Hz, 1H), 8.37 (d, J = 1.5 Hz, 1H), 8.12 (d, J = 1.5 Hz, 1H), 7.86 (s, 1H), 5.16 (s, 1H). |
| 639 | $CF_3$ | 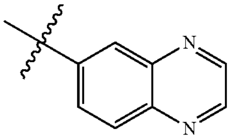 [SMILES: *c1ccc2nccnc2c1] | (500 MHz, Chloroform-d) δ 8.78-8.60 (m, 2H), 8.40 (d, J = 1.5 Hz, 1H), 8.27 (d, J = 7.5 Hz, 1H), 7.94 (dd, J = 7.5, 1.5 Hz, 1H), 7.89 (s, 1H), 5.46 (s, 1H). |
| 640 | $CF_3$ | 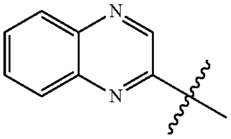 [SMILES: *c1cnc2ccccc2n1] | (500 MHz, Chloroform-d) δ 9.68 (s, 1H), 8.25 (dd, J = 7.5, 1.5 Hz, 1H), 8.18-8.11 (m, 3H), 7.74 (s, 1H). |
| 641 | $CF_3$ | 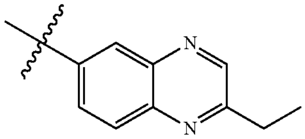 [SMILES: *c1ccc2nc(CC)cnc2c1] | (500 MHz, Chloroform-d) δ 8.92 (s, 1H), 8.40 (d, J = 1.5 Hz, 1H), 8.25 (d, J = 7.5 Hz, 1H), 7.92 (dd, J = 7.5, 1.5 Hz, 1H), 7.89 (s, 1H), 5.43 (s, 1H), 2.93 (q, J = 8.0 Hz, 2H), 1.27 (t, J = 8.0 Hz, 3H). |
| 642 | $CF_3$ | 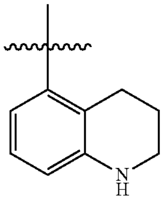 [SMILES: *c1cccc2c1CCCN2] | (500 MHz, Chloroform-d) δ 7.84 (s, 1H), 6.81 (dd, J = 7.5, 7.0 Hz, 1H), 6.66 (dd, J = 7.5, 2.0 Hz, 1H), 6.44 (dd, J = 7.0, 2.0 Hz, 1H), 5.20 (s, 1H), 4.24 (s, 1H), 3.04-2.89 (m, 4H), 2.15-2.07 (m, 2H). |
| 643 | $CF_3$ | 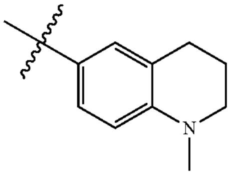 [SMILES: *c1ccc2c(c1)CCCN2C] | (500 MHz, Chloroform-d) δ 7.85 (s, 1H), 7.14 (dd, J = 7.5, 2.0 Hz, 1H), 6.83 (d, J = 2.0 Hz, 1H), 6.67 (d, J = 7.5 Hz, 1H), 5.34 (s, 1H), 3.33-3.17 (m, 2H), 2.95-2.87 (m, 5H), 2.10-2.02 (m, 2H). |
| 644 | $CF_3$ | 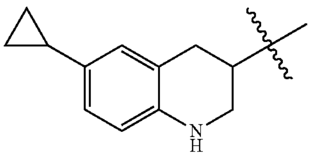 [SMILES: *C1CNc2ccc(C3CC3)cc2C1] | (500 MHz, Chloroform-d) δ 7.83 (s, 1H), 6.55-6.44 (m, 3H), 5.87 (s, 1H), 3.95 (s, 1H), 3.72-3.58 (m, 2H), 3.41-3.25 (m, 2H), 2.99-2.87 (m, 1H), 1.88-1.79 (m, 1H), 1.19-1.09 (m, 2H), 0.91-0.82 (m, 2H). |

TABLE 1-continued
Structure and $^{1}$HNMR data of Compound I
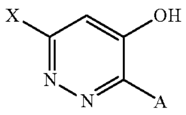
I
| No. | X | A | $^{1}$H NMR |
|---|---|---|---|
| 645 | $CF_3$ | 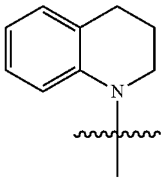 [SMILES: *N1CCCc2ccccc21] | (500 MHz, Chloroform-d) δ 7.23-7.16 (m, 2H), 7.08-6.88 (m, 2H), 6.77 (s, 1H), 5.87 (s, 1H), 3.52-3.39 (m, 2H), 2.90-2.77 (m, 2H), 2.11-2.03 (m, 2H). |
| 646 | $CF_3$ | 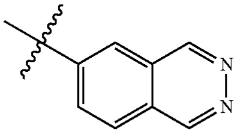 [SMILES: *c1ccc2cnncc2c1] | (500 MHz, Chloroform-d) δ 9.95-9.86 (m, 2H), 8.29 (dd, J = 2.5, 1.5 Hz, 1H), 8.15 (dd, J = 7.5, 1.5 Hz, 1H), 8.10 (d, J = 7.5 Hz, 1H), 7.86 (s, 1H), 5.70 (s, 1H). |
| 647 | $CF_3$ | 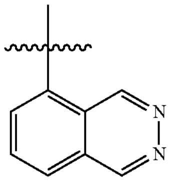 [SMILES: *c1cccc2cnncc12] | (500 MHz, Chloroform-d) δ 9.95 (d, J = 1.5 Hz, 1H), 9.69 (s, 1H), 8.08-7.99 (m, 2H), 7.94 (d, J = 7.5 Hz, 1H), 7.89 (s, 1H), 5.46 (s, 1H). |
| 648 | $CF_3$ | 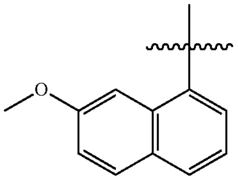 [SMILES: *c1cccc2ccc(OC)cc12] | (500 MHz, Chloroform-d) δ 8.10 (s, 1H), 8.05 (dd, J = 7.5, 1.5 Hz, 1H), 7.59 (d, J = 7.5 Hz, 1H), 6.74 (d, J = 1.5 Hz, 1H), 5.35 (s, 1H), 3.87 (s, 3H). |
| 649 | $CF_3$ | 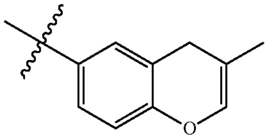 [SMILES: *c1ccc2c(c1)CC(C)=CO2] | |
| 650 | $CF_3$ | 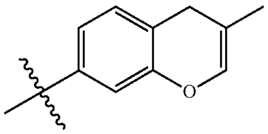 [SMILES: *c1ccc2c(c1)OC=C(C)C2] | |
| 651 | $CF_3$ | 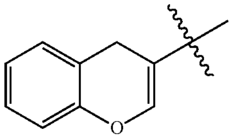 [SMILES: *C1=COc2ccccc2C1] | |
| 652 | $CF_3$ | 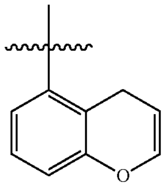 [SMILES: *c1cccc2c1CC=CO2] | |

TABLE 1-continued

Structure and $^1$HNMR data of Compound I

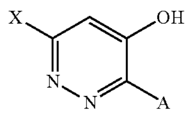

I

| No. | X | A | $^1H$ NMR |
| --- | --- | --- | --- |
| 653 | $CF_3$ | 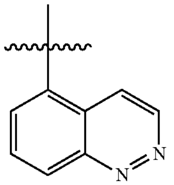 [SMILES: *c1cccc2nnccc12] | (500 MHz, Chloroform-d) δ 9.31 (d, J = 5.5 Hz, 1H), 8.28 (dd, J = 7.5, 1.5 Hz, 1H), 8.00 (d, J = 7.5 Hz, 1H), 7.90 (s, 1H), 7.87-7.76 (m, 2H), 5.50 (s, 1H). |
| 654 | $CF_3$ | 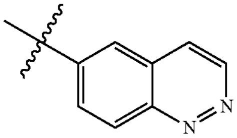 [SMILES: *c1ccc2nnccc2c1] | (500 MHz, Chloroform-d) δ 9.33 (d, J = 7.5 Hz, 1H), 8.41 (d, J = 7.5 Hz, 1H), 8.10 (dd, J = 7.5, 1.5 Hz, 1H), 8.02 (d, J = 1.5 Hz, 1H), 7.94 (d, J = 7.5 Hz, 1H), 7.90 (s, 1H), 5.59 (s, 1H). |
| 655 | $CF_3$ | 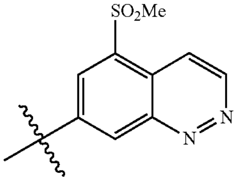 [SMILES: *c1cc(S(C)(=O)=O)c2ccnnc2c1] | (500 MHz, Chloroform-d) δ 9.39 (d, J = 7.5 Hz, 1H), 9.01 (d, J = 1.5 Hz, 1H), 8.85 (s, 1H), 8.75 (d, J = 1.5 Hz, 1H), 8.62 (d, J = 7.5 Hz, 1H), 6.80 (s, 1H), 3.17 (s, 3H). |
| 656 | $CF_3$ | 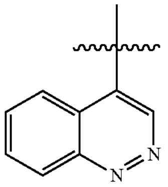 [SMILES: *c1cnnc2ccccc12] | (500 MHz, Chloroform-d) δ 9.39 (s, 1H), 8.01-7.85 (m, 2H), 8.75-8.62 (m, 2H), 6.80 (s, 1H). |
| 657 | $CF_3$ | 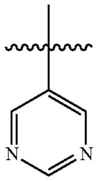 [SMILES: *c1cncnc1] | (500 MHz, Chloroform-d) δ 9.11 (s, 2H), 7.24 (s, 1H), 5.84 (s, 1H). |
| 658 | $CF_3$ | 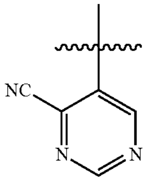 [SMILES: *c1cncnc1C#N] | (500 MHz, Chloroform-d) δ 9.77 (s, 1H), 9.32 (s, 1H), 7.30 (s, 1H), 5.30 (s, 1H). |
| 659 | $CF_3$ | 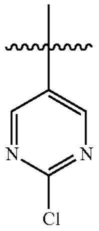 | (500 MHz, Chloroform-d) δ 9.00 (s, 2H), 7.25 (s, 1H), 5.76 (s, 1H). |

TABLE 1-continued
Structure and $^1$HNMR data of Compound I
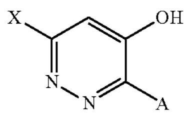
I
| No. | X | A | $^1$H NMR |
|---|---|---|---|
| 660 | $CF_3$ | 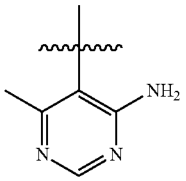 [SMILES: *c1c(C)ncnc1N] | (500 MHz, Chloroform-d) δ 9.19 (s, 1H), 7.37 (s, 1H), 7.08 (s, 2H), 5.32 (s, 1H), 2.82 (s, 3H). |
| 661 | $CF_3$ | 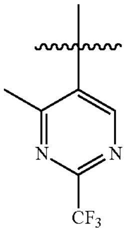 [SMILES: *c1cnc(C(F)(F)F)nc1C] | (500 MHz, Chloroform-d) δ 9.05 (s, 1H), 7.26 (s, 1H), 5.59 (s, 1H), 2.84 (s, 3H). |
| 662 | $CF_3$ | 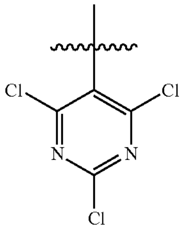 [SMILES: *c1c(Cl)nc(Cl)nc1Cl] | (500 MHz, Chloroform-d) δ 7.25 (s, 1H), 5.68 (s, 1H). |
| 663 | $CF_3$ | 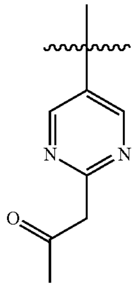 [SMILES: *c1cnc(CC(C)=O)nc1] | (500 MHz, Chloroform-d) δ 9.25 (s, 2H), 8.30 (s, 1H), 7.34 (s, 1H), 4.98 (s, 1H), 2.11 (s, 3H). |
| 664 | $CF_3$ | 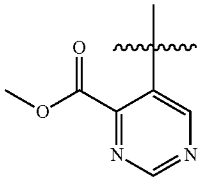 [SMILES: *c1cncnc1C(=O)OC] | (500 MHz, Chloroform-d) δ 9.83 (s, 1H), 9.34 (s, 1H), 7.49 (s, 1H), 6.57 (s, 1H), 3.96 (s, 3H). |
| 665 | $CF_3$ | 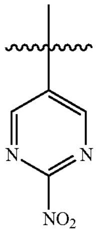 [SMILES: *c1cnc([N+](=O)[O-])nc1] | (500 MHz, Chloroform-d) δ 9.57 (s, 2H), 7.25 (s, 1H), 5.91 (s, 1H). |

TABLE 1-continued

Structure and $^1$HNMR data of Compound I

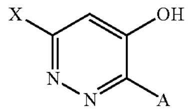

I

| No. | X | A | $^1$H NMR |
|---|---|---|---|
| 666 | $CF_3$ | 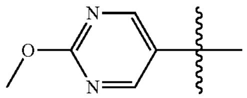 | (500 MHz, Chloroform-d) δ 9.21 (s, 2H), 7.24 (s, 1H), 5.84 (s, 1H), 3.83 (s, 3H). |
| 667 | $CF_3$ | 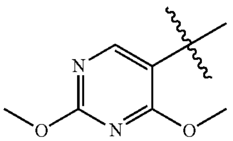 | (500 MHz, Chloroform-d) δ 9.23 (s, 1H), 9.05 (s, 1H), 7.34 (s, 1H), 3.99 (s, 3H), 3.83 (s, 3H). |
| 668 | $CF_3$ | 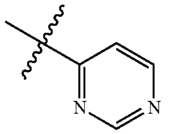 | (500 MHz, Chloroform-d) δ 9.60 (s, 1H), 9.15 (d, J = 5.0 Hz, 1H), 7.86 (d, J = 5.0 Hz, 1H), 7.27 (s, 1H). |
| 669 | $CF_3$ | 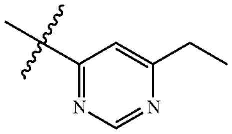 [SMILES: *c1cc(CC)ncn1] | (500 MHz, Chloroform-d) δ 9.60 (s, 1H), 7.71 (s, 1H), 7.27 (s, 1H), 2.27 (q, J = 8.0 Hz, 2H), 1.19 (t, J = 8.0 Hz, 3H). |
| 670 | $CF_3$ | 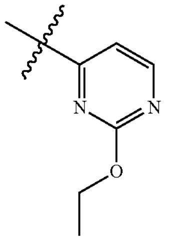 [SMILES: *c1ccnc(OCC)n1] | (500 MHz, Chloroform-d) δ 8.86 (d, J = 5.0 Hz, 1H), 7.52 (d, J = 5.0 Hz, 1H), 7.28 (s, 1H), 4.29 (q, J = 8.0 Hz, 2H), 1.29 (t, J = 8.0 Hz, 3H). |
| 671 | $CF_3$ | 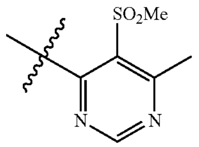 [SMILES: *c1ncnc(C)c1S(C)(=O)=O] | (500 MHz, Chloroform-d) δ 9.87 (s, 1H), 8.82 (s, 1H), 7.35 (s, 1H), 3.00 (s, 3H), 2.68 (s, 3H). |
| 672 | $CF_3$ | 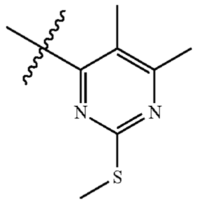 [SMILES: *c1nc(SC)nc(C)c1C] | (500 MHz, Chloroform-d) δ 8.73 (s, 1H), 7.27 (s, 1H), 2.60 (s, 3H), 2.45 (s, 3H). |
| 673 | $CF_3$ | 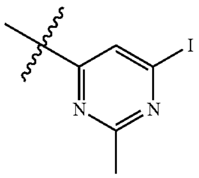 [SMILES: *c1cc(I)nc(C)n1] | (500 MHz, Chloroform-d) δ 8.06 (s, 1H), 7.27 (s, 1H), 2.35 (s, 3H). |

TABLE 1-continued
Structure and $^1$HNMR data of Compound I
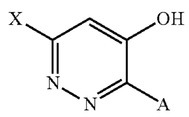
I
| No. | X | A | $^1H$ NMR |
|---|---|---|---|
| 674 | $CF_3$ | 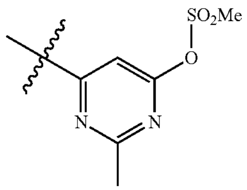 [SMILES: *c1cc(OS(C)(=O)=O)nc(C)n1] | (500 MHz, Chloroform-d) δ 7.27 (s, 1H), 3.19 (s, 3H), 2.49 (s, 3H), 2.39 (s, 3H). |
| 675 | $CF_3$ | 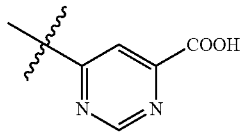 [SMILES: *c1cc(C(=O)O)ncn1] | (500 MHz, Chloroform-d) δ 9.96 (s, 1H), 8.63 (s, 1H), 7.28 (s, 1H). |
| 676 | $CF_3$ | 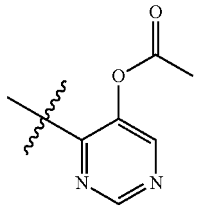 [SMILES: *c1ncncc1OC(C)=O] | (500 MHz, Chloroform-d) δ 9.30 (s, 1H), 8.59 (s, 1H), 7.20 (s, 1H), 2.49 (s, 3H). |
| 677 | $CF_3$ | 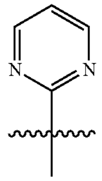 [SMILES: *c1ncccn1] | (500 MHz, Chloroform-d) δ 9.02 (d, J = 5.0 Hz, 2H), 7.47 (t, J = 5.0 Hz, 1H), 7.26 (s, 1H). |
| 678 | $CF_3$ | 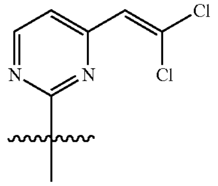 [SMILES: *c1nccc(C=C(Cl)Cl)n1] | |
| 679 | $CF_3$ | 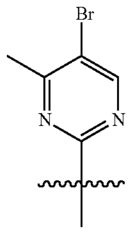 [SMILES: *c1ncc(Br)c(C)n1] | (500 MHz, Chloroform-d) δ 7.26 (s, 1H), 6.51 (s, 1H), 2.67 (s, 3H). |

TABLE 1-continued
Structure and $^1$HNMR data of Compound I
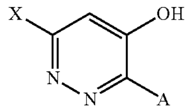
I
| No. | X | A | $^1$H NMR |
|---|---|---|---|
| 680 | $CF_3$ | 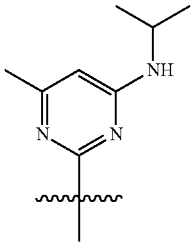 [SMILES: *c1nc(C)cc(NC(C)C)n1] | (500 MHz, Chloroform-d) δ 8.05 (s, 1H), 7.26 (s, 1H), 3.47 (hept, J = 8.0 Hz, 1H), 2.66 (s, 3H), 1.47 (d, J = 8.0 Hz, 1H). |
| 681 | $CF_3$ | 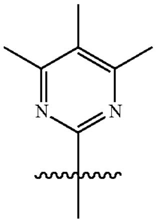 | (500 MHz, Chloroform-d) δ 7.22 (s, 1H), 5.71 (s, 1H), 2.70 (s, 6H), 2.34 (s, 3H). |
| 682 | $CF_3$ | 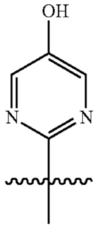 [SMILES: *c1ncc(O)cn1] | (500 MHz, Chloroform-d) δ 8.72 (s, 2H), 7.25 (s, 1H), 6.80 (s, 1H), 5.87 (s, 1H). |
| 683 | $CF_3$ | 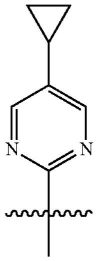 [SMILES: *c1ncc(C2CC2)cn1] | (500 MHz, Chloroform-d) δ 8.72 (s, 2H), 7.25 (s, 1H), 1.70-1.56 (m, 1H), 1.06-0.97 (m, 2H), 0.78-0.69 (m, 2H). |
| 684 | $CF_3$ | 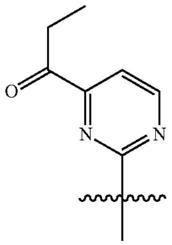 [SMILES: *c1nccc(C(=O)CC)n1] | (500 MHz, Chloroform-d) δ 9.17 (d, J = 5.0 Hz, 1H), 8.06 (d, J = 5.0 Hz, 1H), 7.27 (s, 1H), 2.73 (q, J = 8.0 Hz, 2H), 1.34 (t, J = 8.0 Hz, 3H). |

TABLE 1-continued
Structure and $^1$HNMR data of Compound I
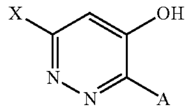
I
| No. | X | A | $^1$H NMR |
|---|---|---|---|
| 685 | $CF_3$ | 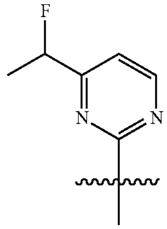 [SMILES: *c1nccc(C(C)F)n1] | (500 MHz, Chloroform-d) δ 8.88 (d, J = 5.0 Hz, 1H), 7.88 (d, J = 5.0 Hz, 1H), 7.26 (s, 1H), 5.62-5.52 (m, 2H), 1.73-1.44 (m, 3H). |
| 686 | $CF_3$ | 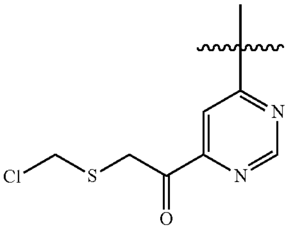 [SMILES: *c1cc(C(=O)CSCCl)ncn1] | |
| 687 | $CF_3$ | 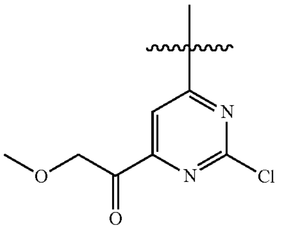 [SMILES: *c1cc(C(=O)COC)nc(Cl)n1] | (500 MHz, Chloroform-d) δ 8.24 (s, 1H), 7.25 (s, 1H), 5.64 (s, 1H), 4.48 (s, 2H), 3.40 (s, 3H). |
| 688 | $CF_3$ | 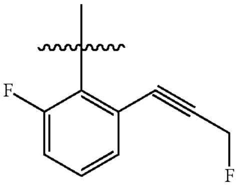 [SMILES: *c1c(F)cccc1C#CCF] | |
| 689 | $CF_3$ | 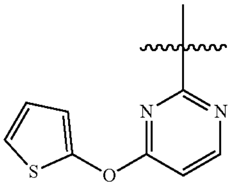 [SMILES: *c1nccc(Oc2cccs2)n1] | (500 MHz, Chloroform-d) δ 8.96 (d, J = 5.0 Hz, 1H), 7.36-7.28 (m, 2H), 7.21 (d, J = 5.0 Hz, 1H), 6.90 (s, 1H), 6.45 (d, J = 2.5 Hz, 1H), 5.61 (dd, J = 2.5, 1.5 Hz, 1H). |
| 690 | $CF_3$ | 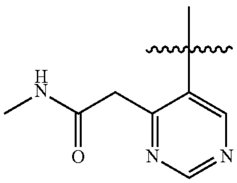 [SMILES: *c1cncnc1CC(=O)NC] | (500 MHz, Chloroform-d) δ 9.94 (s, 1H), 9.47 (s, 1H), 8.95 (s, 1H), 7.45 (s, 1H), 5.98 (s, 1H), 3.44 (s, 2H), 2.78 (s, 3H). |

TABLE 1-continued
Structure and $^1$HNMR data of Compound I
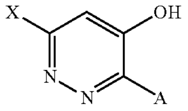
I
| No. | X | A | $^1$H NMR |
| --- | --- | --- | --- |
| 691 | $CF_3$ | 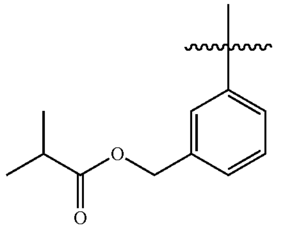 [SMILES: *c1cccc(COC(=O)C(C)C)c1] | (500 MHz, Chloroform-d) δ 9.49 (s, 1H), 7.39 (s, 1H), 7.24 (s, 1H), 5.77 (s, 1H), 5.10 (s, 2H), 2.66 (hept, J = 7.0 Hz, 1H), 1.18 (d, J = 7.0 Hz, 6H). |
| 692 | $CF_3$ | 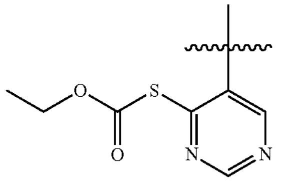 [SMILES: *c1cncnc1SC(=O)OCC] | (500 MHz, Chloroform-d) δ 9.38 (s, 1H), 9.05 (s, 1H), 8.40 (s, 1H), 7.49 (s, 1H), 4.48 (s, 2H), 3.34 (s, 3H). |
| 693 | $CF_3$ | 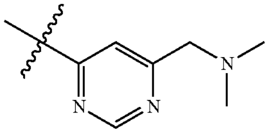 [SMILES: *c1cc(CN(C)C)ncn1] | (500 MHz, Chloroform-d) δ 9.60 (d, J = 1.5 Hz, 1H), 7.71 (s, 1H), 7.24 (s, 1H), 5.72 (s, 1H), 3.62 (s, 2H), 2.68 (s, 6H). |
| 694 | $CF_3$ | 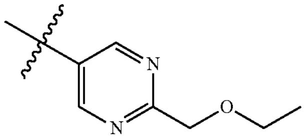 [SMILES: *c1cnc(COCC)nc1] | (500 MHz, Chloroform-d) δ 9.19 (s, 2H), 7.29 (s, 1H), 5.40 (s, 1H), 4.66 (s, 2H), 3.60 (q, J = 8.0 Hz, 2H), 1.15 (t, J = 8.0 Hz, 3H). |
| 695 | $CF_3$ | 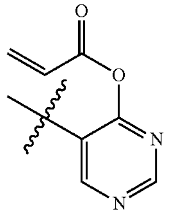 [SMILES: *c1cncnc1OC(=O)C=C] | (500 MHz, Chloroform-d) δ 9.12 (s, 1H), 9.05 (s, 1H), 7.26 (s, 1H), 6.48-6.33 (m, 1H), 6.21 (s, 1H), 5.91-5.78 (m, 2H). |
| 696 | $CF_3$ | 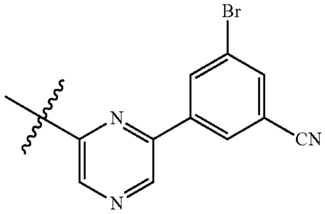 [SMILES: *c1cncc(-c2cc(Br)cc(C#N)c2)n1] | (500 MHz, Chloroform-d) δ 8.90 (d, J = 5.0 Hz, 1H), 8.11 (dd, J = 2.5, 2.0 Hz, 1H), 8.06-7.96 (m, 2H), 7.92 (t, J = 2.0 Hz, 1H), 7.28 (s, 1H). |
| 697 | $CF_3$ | 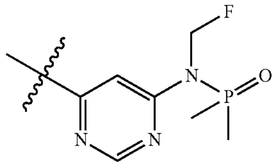 [SMILES: *c1cc(N(CF)P(C)(C)=O)ncn1] | |

TABLE 1-continued
Structure and ¹HNMR data of Compound I
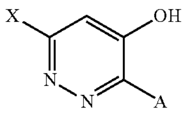
I
| No. | X | A | ¹H NMR |
|---|---|---|---|
| 698 | $CF_3$ | 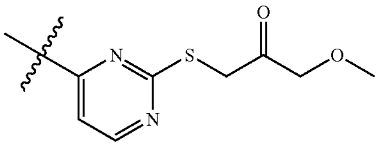 [SMILES: *c1ccnc(SCC(=O)COC)n1] | (500 MHz, Chloroform-d) δ 8.89 (d, J = 5.0 Hz, 1H), 7.59 (d, J = 5.0 Hz, 1H), 7.24 (s, 1H), 5.83 (s, 1H), 4.53 (s, 2H), 4.09 (s, 2H), 3.43 (s, 3H). |
| 699 | $CF_3$ | 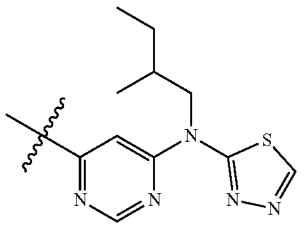 [SMILES: *c1cc(N(CC(C)CC)c2nncs2)ncn1] | (500 MHz, Chloroform-d) δ 9.16 (s, 1H), 8.95 (s, 1H), 7.27 (s, 1H), 6.78 (s, 1H), 4.02-3.94 (m, 2H), 1.84-1.71 (m, 1H), 1.49-1.38 (m, 1H), 1.18-1.00 (d, J = 6.8 Hz, 3H), 0.97-0.82 (m, 4H). |
| 700 | $CF_3$ | 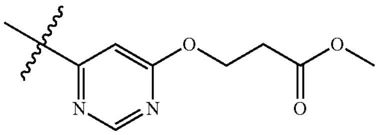 [SMILES: *c1cc(OCCC(=O)OC)ncn1] | (500 MHz, Chloroform-d) δ 9.48 (s, 1H), 7.34 (s, 1H), 7.21 (s, 1H), 4.33 (t, J = 7.5 Hz, 2H), 3.64 (s, 3H), 2.67 (t, J = 7.5 Hz, 2H). |
| 701 | $CF_3$ | 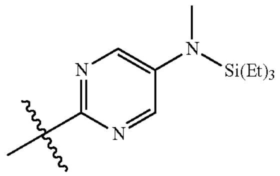 | |
| 702 | $CF_3$ | 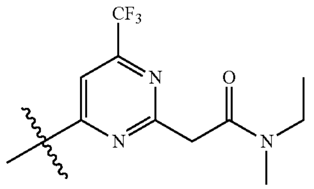 | (500 MHz, Chloroform-d) δ 7.77 (s, 1H), 7.25 (s, 1H), 5.89 (s, 1H), 3.72 (q, J = 8.0 Hz, 2H), 3.44 (s, 2H), 3.08 (s, 3H), 1.23 (t, J = 8.0 Hz, 3H). |
| 703 | $CF_3$ | 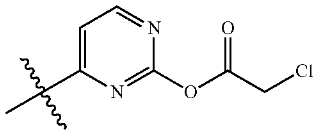 [SMILES: *c1ccnc(OC(=O)CCl)n1] | (500 MHz, Chloroform-d) δ 8.98 (d, J = 5.0 Hz, 1H), 7.24-7.19 (m, 2H), 4.32 (s, 2H). |
| 704 | $CF_3$ | 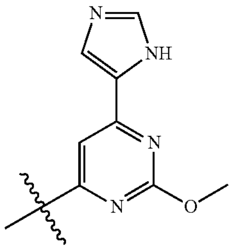 [SMILES: *c1cc(-c2cnc[nH]2)nc(OC)n1] | (500 MHz, Chloroform-d) δ 7.97 (s, 1H), 7.88 (s, 1H), 7.83 (s, 1H), 7.29 (s, 1H), 3.89 (s, 3H). |

TABLE 1-continued
Structure and $^1$HNMR data of Compound I
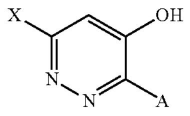
I
| No. | X | A | $^1$H NMR |
| --- | --- | --- | --- |
| 705 | $CF_3$ | 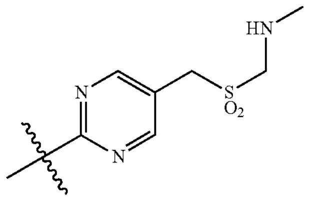 [SMILES: *c1ncc(CS(=O)(=O)CNC)cn1] | (500 MHz, Chloroform-d) δ 8.96 (s, 2H), 7.26 (s, 1H), 4.67 (s, 2H), 4.37 (s, 2H) 2.41 (s, 3H). |
| 706 | $CF_3$ | 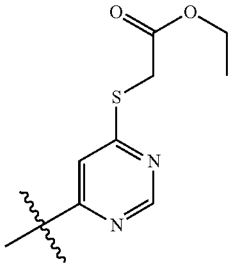 [SMILES: *c1cc(SCC(=O)OCC)ncn1] | (500 MHz, Chloroform-d) δ 9.34 (s, 1H), 7.79 (s, 1H), 7.26 (s, 1H), 4.53 (s, 2H), 4.09 (s, 2H), 3.34 (s, 3H). |
| 707 | $CF_3$ | 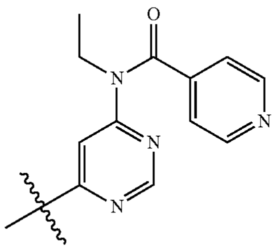 [SMILES: *c1cc(N(CC)C(=O)c2ccncc2)ncn1] | (500 MHz, Chloroform-d) δ 9.09 (s, 1H), 8.70 (d, J = 5.0 Hz, 2H), 7.64 (d, J = 5.0 Hz, 2H), 7.28 (s, 1H), 7.18 (s, 1H), 3.67 (q, J = 8.0 Hz, 2H), 1.34 (t, J = 8.0 Hz, 3H). |
| 708 | $CF_3$ | 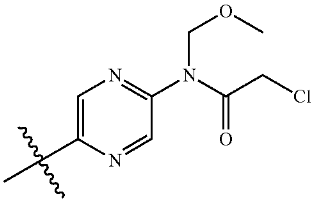 [SMILES: *c1cnc(N(COC)C(=O)CCl)cn1] | (500 MHz, Chloroform-d) δ 9.24 (s, 2H), 7.35 (s, 1H), 5.71 (s, 2H), 3.63 (s, 2H), 3.43 (s, 3H). |
| 709 | $CF_3$ | 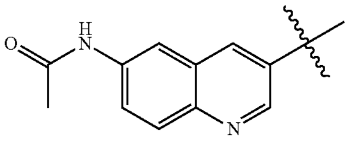 [SMILES: *c1cnc2ccc(NC(C)=O)cc2c1] | (500 MHz, Chloroform-d) δ 9.26 (d, J = 1.5 Hz, 1H), 8.43 (t, J = 1.5 Hz, 1H), 8.27-8.18 (m, 2H), 8.10 (s, 1H), 7.62-7.48 (m, 2H), 5.74 (s, 1H), 2.10 (s, 3H). |
| 710 | $CF_3$ | 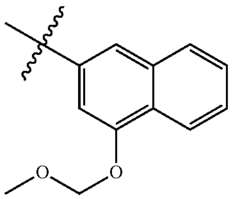 [SMILES: *c1cc(OCOC)c2ccccc2c1] | (500 MHz, Chloroform-d) δ 9.06 (dd, J = 7.5, 1.5 Hz, 1H), 7.53-7.41 (m, 1H), 7.30-7.23 (m, 2H), 7.06 (s, 1H), 6.97 (d, J = 1.5 Hz, 1H), 6.02 (s, 2H), 5.53 (s, 1H), 3.30 (s, 3H). |

TABLE 1-continued

Structure and $^1$HNMR data of Compound I

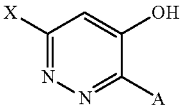

I

| No. | X | A | $^1$H NMR |
|---|---|---|---|
| 711 | $CF_3$ | 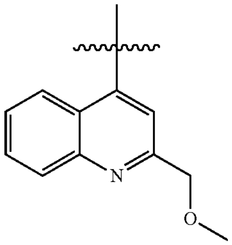 [SMILES: *c1cc(COC)nc2ccccc12] | (500 MHz, Chloroform-d) δ 8.17-8.14 (m, 2H), 7.78-7.68 (m, 3H), 7.55-7.39 (m, 1H), 5.41 (s, 1H), 4.78 (s, 2H), 3.40 (s, 3H). |
| 712 | $CF_3$ | 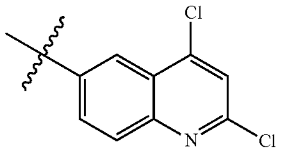 [SMILES: *c1ccc2nc(Cl)cc(Cl)c2c1] | (500 MHz, Chloroform-d) δ 8.58 (d, J = 1.5 Hz, 1H), 8.34 (d, J = 7.5 Hz, 1H), 8.10 (dd, J = 7.5, 1.5 Hz, 1H), 7.56 (s, 1H), 7.04 (s, 1H), 5.72 (s, 1H). |
| 713 | $CF_3$ | 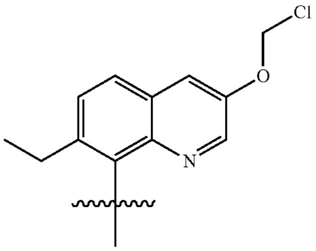 [SMILES: *c1c(CC)ccc2cc(OCCl)cnc12] | |
| 714 | $CF_3$ | 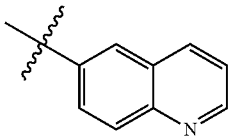 [SMILES: *c1ccc2ncccc2c1] | (500 MHz, Chloroform-d) δ 8.90 (dd, J = 7.5, 1.5 Hz, 1H), 8.36 (d, J = 7.5 Hz, 1H), 8.25-8.16 (m, 3H), 7.39-7.26 (m, 1H), 7.03 (s, 1H), 5.72 (s, 1H). |
| 715 | $CF_3$ | 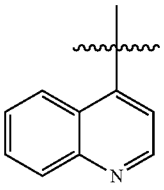 [SMILES: *c1ccnc2ccccc12] | (500 MHz, Chloroform-d) δ 9.14 (d, J = 7.5 Hz, 1H), 8.17-8.14 (m, 2H), 7.76-7.68 (m, 3H), 7.57-7.41 (m, 1H), 5.48 (s, 1H). |
| 716 | $CF_3$ | 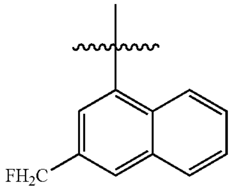 | (500 MHz, Chloroform-d) δ 8.81 (dd, J = 7.5, 1.5 Hz, 1H), 8.19-8.10 (m, 2H), 7.93 (d, J = 1.5 Hz, 1H), 7.87 (s, 1H), 7.51 (dd, J = 7.5, 5.0 Hz, 1H), 5.47 (s, 1H), 5.30 (d, J = 73.5 Hz, 1H). |
| 717 | $CF_3$ | 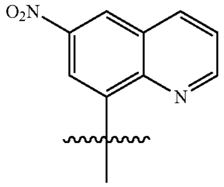 [SMILES: *c1cc([N+](=O)[O-])cc2cccnc12] | (500 MHz, Chloroform-d) δ 9.15 (dd, J = 7.5, 1.7 Hz, 1H), 8.88 (d, J = 1.5 Hz, 1H), 8.45-8.37 (m, 2H), 7.58 (dd, J = 7.5, 5.5 Hz, 1H), 6.99 (s, 1H). |

TABLE 1-continued

Structure and $^1$HNMR data of Compound I

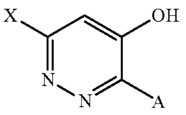

I

| No. | X | A | $^1H$ NMR |
|---|---|---|---|
| 718 | $CF_3$ | 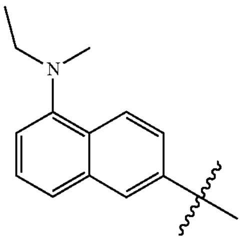 [SMILES: *c1ccc2c(N(C)CC)cccc2c1] | (500 MHz, Chloroform-d) δ 8.84 (d, J = 7.5 Hz, 1H), 7.97-7.88 (m, 2H), 7.73 (dd, J = 7.5, 1.5 Hz, 1H), 7.51 (dd, J = 7.5, 7.0 Hz, 1H), 6.94 (dd, J = 7.5, 1.5 Hz, 1H), 5.70 (s, 1H), 3.29 (q, J = 8.0 Hz, 2H), 2.98 (s, 3H), 1.20 (t, J = 8.0 Hz, 3H). |
| 719 | $CF_3$ | 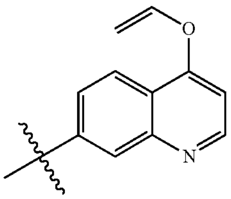 [SMILES: *c1ccc2c(OC=C)ccnc2c1] | |
| 720 | $CF_3$ | 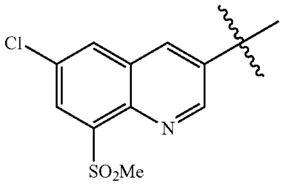 [SMILES: *c1cnc2c(S(C)(=O)=O)cc(Cl)cc2c1] | (500 MHz, Chloroform-d) δ 9.33 (d, J = 1.5 Hz, 1H), 8.50 (dd, J = 2.5, 1.5 Hz, 1H), 8.19 (d, J = 1.5 Hz, 1H), 8.04-7.90 (m, 2H), 5.08 (s, 1H), 3.27 (s, 3H). |
| 721 | $CF_3$ | 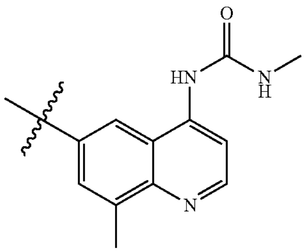 [SMILES: *c1cc(C)c2nccc(NC(=O)NC)c2c1] | (500 MHz, Chloroform-d) δ 8.89 (d, J = 5.5 Hz, 1H), 8.15 (s, 1H), 7.87 (d, J = 1.5 Hz, 1H), 7.77 (d, J = 1.5 Hz, 1H), 7.12 (s, 1H), 6.85 (d, J = 5.5 Hz, 1H), 5.27-5.14 (m, 2H), 2.64 (s, 3H), 2.46 (s, 3H). |
| 722 | $CF_3$ | 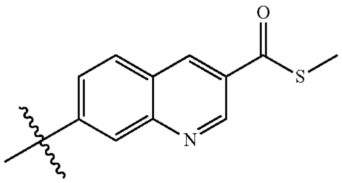 [SMILES: *c1ccc2cc(C(=O)SC)cnc2c1] | (500 MHz, Chloroform-d) δ 9.29 (d, J = 1.5 Hz, 1H), 8.99 (s, 1H), 8.74 (q, J = 1.5 Hz, 1H), 7.86-7.79 (m, 2H), 6.82 (s, 1H), 2.49 (s, 3H), 2.44 (s, 3H). |
| 723 | $CF_3$ | 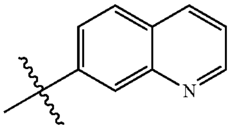 [SMILES: *c1ccc2cccnc2c1] | (500 MHz, Chloroform-d) δ 8.90 (d, J = 6.5 Hz, 1H), 8.35 (d, J = 1.5 Hz, 1H), 8.14 (dd, J = 6.5, 1.5 Hz, 1H), 7.94 (dd, J = 7.5, 1.5 Hz, 1H), 7.84 (dd, J = 7.5, 1.5 Hz, 1H), 7.38 (d, J = 7.5 Hz, 1H), 6.85 (s, 1H). |
| 724 | $CF_3$ | 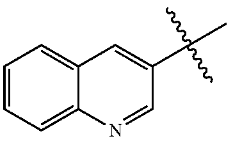 [SMILES: *c1cnc2ccccc2c1] | (500 MHz, Chloroform-d) δ 9.29 (d, J = 1.5 Hz, 1H), 8.38 (dd, J = 2.0, 1.5 Hz, 1H), 8.15 (dd, J = 7.5, 1.5 Hz, 1H), 8.13 (s, 1H), 7.88-7.70 (m, 2H), 7.54-7.41 (m, 1H), 5.43 (s, 1H). |

TABLE 1-continued

Structure and $^1$HNMR data of Compound I

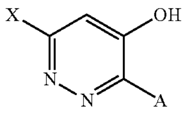

I

| No. | X | A | $^1$H NMR |
|---|---|---|---|
| 725 | $CF_3$ | 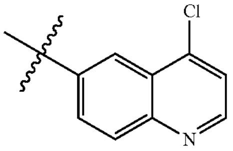 | (500 MHz, Chloroform-d) δ 8.92 (d, J = 5.5 Hz, 1H), 8.52 (d, J = 1.5 Hz, 1H), 8.35 (d, J = 5.5 Hz, 1H), 8.08 (dd, J = 7.5, 1.5 Hz, 1H), 7.50 (d, J = 7.5 Hz, 1H), 7.09 (s, 1H), 5.46 (s, 1H). |
| 726 | $CF_3$ | 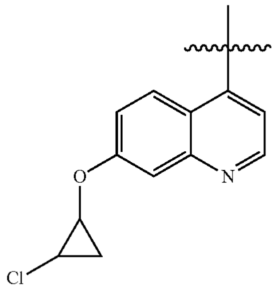 [SMILES: *c1ccnc2cc(OC3CC3Cl)ccc12] | |
| 727 | $CF_3$ | 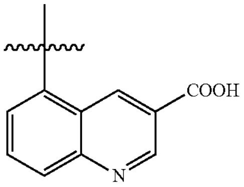 [SMILES: *c1cccc2ncc(C(=O)O)cc12] | (500 MHz, Chloroform-d) δ 9.42 (d, J = 1.5 Hz, 1H), 8.72 (d, J = 1.5 Hz, 1H), 8.37 (dd, J = 7.5, 1.5 Hz, 1H), 8.04 (dd, J = 7.5, 7.0 Hz, 1H), 7.94 (dd, J = 7.0, 1.5 Hz, 1H), 7.90 (s, 1H), 5.37 (s, 1H). |
| 728 | $CF_3$ | 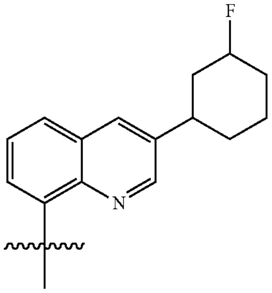 [SMILES: *c1cccc2cc(C3CCCC(F)C3)cnc12] | (500 MHz, Chloroform-d) δ 9.00 (s, 1H), 8.16-8.09 (m, 2H), 7.93 (d, J = 7.5 Hz, 1H), 7.66 (dd, J = 7.5, 7.0 Hz, 1H), 6.96 (s, 1H), 2.73-2.56 (m, 1H), 2.29-2.14 (m, 1H), 2.18-2.01 (m, 3H), 1.98-1.84 (m, 2H), 1.62-1.45 (m, 3H). |
| 729 | $CF_3$ | 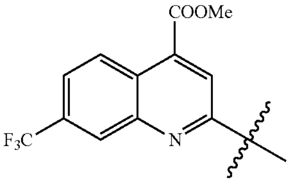 [SMILES: *c1cc(C(=O)OC)c2ccc(C(F)(F)F)cc2n1] | (500 MHz, Chloroform-d) δ 8.70 (d, J = 7.5 Hz, 1H), 8.44 (d, J = 1.5 Hz, 1H), 8.38 (s, 1H), 8.04 (s, 1H), 7.63 (dd, J = 7.5, 1.5 Hz, 1H), 3.95 (s, 3H). |
| 730 | $CF_3$ | 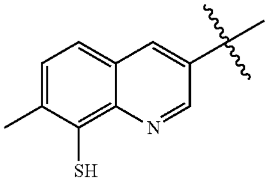 [SMILES: *c1cnc2c(S)c(C)ccc2c1] | (500 MHz, Chloroform-d) δ 8.70 (d, J = 1.5 Hz, 1H), 8.44-8.38 (m, 2H), 8.04 (s, 1H), 7.63 (dd, J = 7.5, 1.7 Hz, 1H), 3.95 (s, 3H). |

TABLE 1-continued

Structure and $^1$HNMR data of Compound I

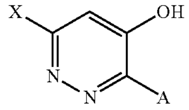

I

| No. | X | A | $^1$H NMR |
| --- | --- | --- | --- |
| 731 | $CF_3$ | 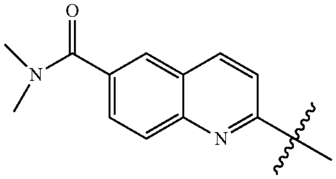 [SMILES: *c1ccc2cc(C(=O)N(C)C)ccc2n1] | (500 MHz, Chloroform-d) δ 8.52 (d, J = 7.5 Hz, 1H), 8.44 (dd, J = 7.5, 1.5 Hz, 1H), 8.14-8.08 (m, 2H), 8.03 (s, 1H), 7.69 (dd, J = 7.5, 1.5 Hz, 1H), 3.03 (s, 3H), 2.85 (s, 3H). |
| 732 | $CF_3$ | 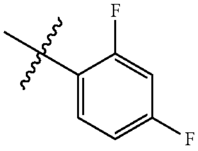 [SMILES: *c1ccc(F)cc1F] | (500 MHz, Chloroform-d) δ 7.54-7.31 (m, 1H), 7.04-6.94 (m, 2H), 6.92-6.71 (m, 1H), 5.50 (s, 1H). |
| 733 | $CF_3$ | 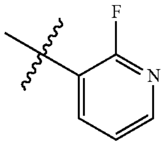 [SMILES: *c1cccnc1F] | $^1$H NMR (500 MHz, DMSO-d6) δ 8.39-8.31 (m, 1H), 8.21-8.18 (m, 1H), 7.55-7.52 (m, 1H), 7.35 (s, 1H). |
| 734 | $CF_3$ | 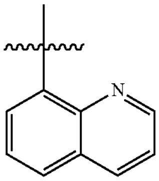 [SMILES: *c1cccc2cccnc12] | (500 MHz, Chloroform-d) δ 9.10 (dd, J = 7.5, 1.5 Hz, 1H), 8.29-8.16 (m, 2H), 7.99-7.72 (m, 2H), 7.52-7.39 (m, 1H), 7.17 (s, 1H). |
| 735 | $CF_3$ | 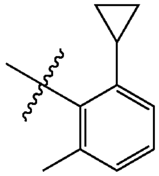 [SMILES: *c1c(C)cccc1C1CC1] | (500 MHz, Chloroform-d) δ 7.35 (dd, J = 7.5, 7.0 Hz, 1H), 7.16 (dd, J = 7.5, 1.5 Hz, 1H), 7.09 (dd, J = 7.0, 1.5 Hz, 1H), 7.04 (s, 1H), 5.76 (s, 1H), 2.31 (s, 3H), 1.95-1.85 (m, 1H), 1.07-0.98 (m, 2H), 0.89-0.80 (m, 2H). |
| 736 | $CF_3$ | 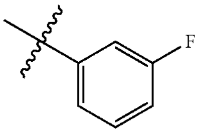 | (500 MHz, Chloroform-d) δ 7.52 (dd, J = 11.0, 2.0 Hz, 1H), 7.44-7.21 (m, 1H), 7.30-7.25 (m, 2H), 7.07 (s, 1H), 5.50 (s, 1H). |
| 737 | $CF_3$ | 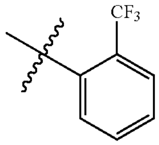 [SMILES: *c1ccccc1C(F)(F)F] | (500 MHz, Chloroform-d) δ 7.61-7.52 (m, 2H), 7.48-7.40 (m, 2H), 7.04 (s, 1H), 5.69 (s, 1H). |
| 738 | $CF_3$ | 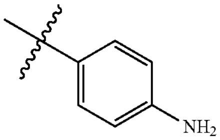 [SMILES: *c1ccc(N)cc1] | (500 MHz, Chloroform-d) δ 7.68-7.61 (m, 2H), 7.00 (s, 1H), 6.75-6.68 (m, 2H), 5.76 (s, 1H), 4.56 (s, 2H). |

TABLE 1-continued

Structure and $^1$HNMR data of Compound I

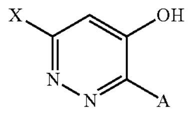

I

| No. | X | A | $^1$H NMR |
|---|---|---|---|
| 739 | $CF_3$ | 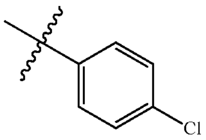 [SMILES: *c1ccc(Cl)cc1] | (500 MHz, Chloroform-d) δ 7.47-7.37 (m, 4H), 7.07 (s, 1H), 5.48 (s, 1H). |
| 740 | $CF_3$ | 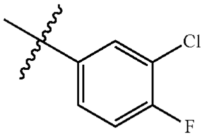 [SMILES: *c1ccc(F)c(Cl)c1] | (500 MHz, Chloroform-d) δ 7.62 (dd, J = 5.5, 2.0 Hz, 1H), 7.36-7.25 (m, 1H), 7.16 (dd, J = 11.0, 7.5 Hz, 1H), 7.01 (s, 1H), 5.81 (s, 1H). |
| 741 | $CF_3$ | 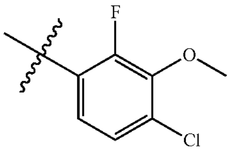 [SMILES: *c1ccc(Cl)c(OC)c1F] | (500 MHz, Chloroform-d) δ 7.30-7.23 (m, 2H), 7.10 (s, 1H), 5.62 (s, 1H), 3.89 (s, 3H). |
| 742 | $CF_3$ | 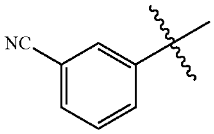 [SMILES: *c1cccc(C#N)c1] | (500 MHz, Chloroform-d) δ 7.94-7.74 (m, 2H), 7.67-7.55 (m, 2H), 7.07 (s, 1H), 5.49 (s, 1H). |
| 743 | $CF_3$ | 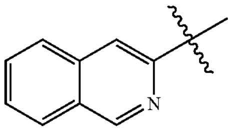 [SMILES: *c1cc2ccccc2cn1] | (500 MHz, Chloroform-d) δ 9.38 (d, J = 1.5 Hz, 1H), 8.16 (d, J = 1.5 Hz, 1H), 7.98-7.92 (m, 2H), 7.64-7.51 (m, 2H), 7.15 (s, 1H). |
| 744 | $CF_3$ | 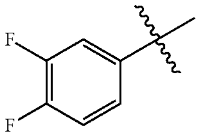 [SMILES: *c1ccc(F)c(F)c1] | (500 MHz, Chloroform-d) δ 7.45-7.25 (m, 2H), 7.18-7.05 (m, 1H), 7.01 (s, 1H), 5.81 (s, 1H). |
| 745 | $CF_3$ | 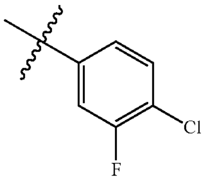 [SMILES: *c1ccc(Cl)c(F)c1] | (500 MHz, Chloroform-d) δ 7.50 (dd, J = 7.5, 5.5 Hz, 1H), 7.45 (dd, J = 11.0, 2.0 Hz, 1H), 7.24-7.11 (m, 1H), 7.01 (s, 1H), 5.80 (s, 1H). |
| 746 | $CF_3$ | 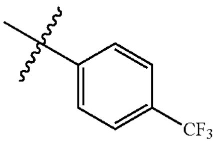 | (500 MHz, Chloroform-d) δ 7.73 (d, J = 7.5 Hz, 2H), 7.54 (d, J = 7.5 Hz, 2H), 7.07 (s, 1H), 5.48 (s, 1H). |

TABLE 1-continued

Structure and $^1$HNMR data of Compound I

I

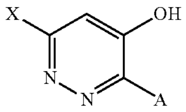

| No. | X | A | $^1H$ NMR |
|---|---|---|---|
| 747 | $CF_3$ | 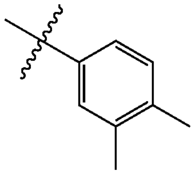 [SMILES: *c1ccc(C)c(C)c1] | (500 MHz, Chloroform-d) δ 7.37-7.33 (m, 1H), 7.25 (dd, J = 7.5, 1.5 Hz, 1H), 7.14 (d, J = 7.5 Hz, 1H), 7.06 (s, 1H), 5.57 (s, 1H), 2.30 (s, 3H), 2.20 (s, 3H). |
| 748 | $CF_3$ | 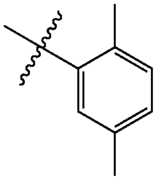 [SMILES: *c1cc(C)ccc1C] | (500 MHz, Chloroform-d) δ 7.32 (d, J = 1.5 Hz, 1H), 7.26-7.17 (m, 2H), 7.03 (s, 1H), 5.67 (s, 1H), 2.50 (s, 3H), 2.35 (s, 3H). |
| 749 | $CF_3$ | 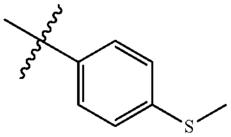 [SMILES: *c1ccc(SC)cc1] | (500 MHz, Chloroform-d) δ 7.53 (d, J = 7.5 Hz, 2H), 7.42 (d, J = 7.5 Hz, 2H), 7.06 (s, 1H), 5.49 (s, 1H), 2.45 (s, 3H). |
| 750 | $CF_3$ | 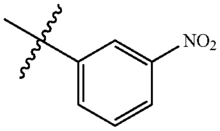 [SMILES: *c1cccc([N+](=O)[O-])c1] | (500 MHz, Chloroform-d) δ 8.57 (dd, J = 2.0, 1.5 Hz, 1H), 8.27-8.16 (m, 1H), 7.95-7.71 (m, 2H), 7.03 (s, 1H), 5.85 (s, 1H). |
| 751 | $CF_3$ | 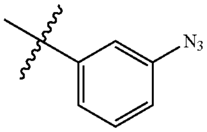 [SMILES: *c1cccc(N=[N+]=[N-])c1] | (500 MHz, Chloroform-d) δ 7.76 (dd, J = 2.0, 1.5 Hz, 1H), 7.61-7.52 (m, 1H), 7.50-7.41 (m, 2H), 7.01 (s, 1H), 5.78 (s, 1H). |
| 752 | $CF_3$ | 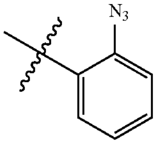 [SMILES: *c1ccccc1N=[N+]=[N-]] | (500 MHz, Chloroform-d) δ 7.56-7.47 (m, 3H), 7.42-7.30 (m, 1H), 7.00 (s, 1H), 5.61 (s, 1H). |
| 753 | $CF_3$ | 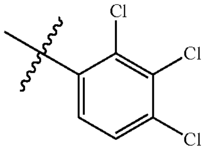 | (500 MHz, Chloroform-d) δ 7.35 (d, J = 7.5 Hz, 1H), 7.20 (d, J = 7.5 Hz, 1H), 7.03 (s, 1H), 5.66 (s, 1H). |
| 754 | $CF_3$ | 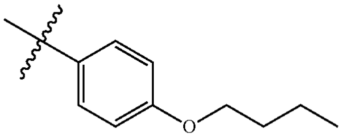 [SMILES: *c1ccc(OCCCC)cc1] | (500 MHz, Chloroform-d) δ 7.47 (d, J = 7.5 Hz, 2H), 7.09-7.03 (m, 3H), 5.49 (s, 1H), 4.00 (t, J = 7.5 Hz, 2H), 1.74-1.50 (m, 4H), 1.04 (t, J = 8.0 Hz, 3H). |

TABLE 1-continued

Structure and $^1$HNMR data of Compound I

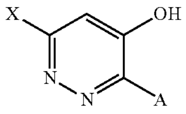

I

| No. | X | A | $^1$H NMR |
|---|---|---|---|
| 755 | $CF_3$ | 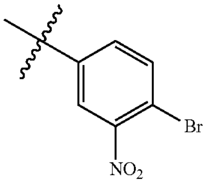 | (500 MHz, Chloroform-d) δ 8.09 (d, J = 2.0 Hz, 1H), 7.92 (dd, J = 7.5, 2.0 Hz, 1H), 7.83 (d, J = 7.5 Hz, 1H), 7.05 (s, 1H), 5.49 (s, 1H). |
| 756 | $CF_3$ | 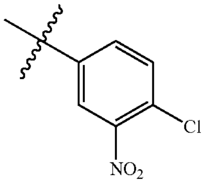 | (500 MHz, Chloroform-d) δ 8.13 (d, J = 1.5 Hz, 1H), 7.78-7.70 (m, 2H), 7.05 (s, 1H), 5.54 (s, 1H). |
| 757 | $CF_3$ | 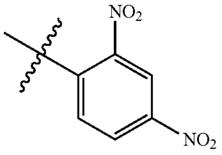 [SMILES: *c1ccc([N+](=O)[O-])cc1[N+](=O)[O-]] | (500 MHz, Chloroform-d) δ 8.80 (d, J = 2.0 Hz, 1H), 8.62 (dd, J = 7.5, 2.0 Hz, 1H), 8.11 (d, J = 7.5 Hz, 1H), 7.01 (s, 1H), 5.69 (s, 1H). |
| 758 | $CF_3$ | 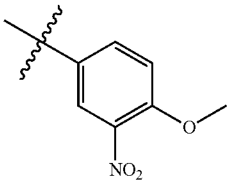 [SMILES: *c1ccc(OC)c([N+](=O)[O-])c1] | (500 MHz, Chloroform-d) δ 8.06 (d, J = 2.0 Hz, 1H), 7.75 (dd, J = 7.5, 2.0 Hz, 1H), 7.17 (d, J = 7.5 Hz, 1H), 7.08 (s, 1H), 5.29 (s, 1H), 4.02 (s, 3H). |
| 759 | $CF_3$ | 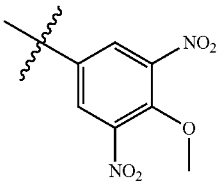 [SMILES: *c1cc([N+](=O)[O-])c(OC)c([N+](=O)[O-])c1] | (500 MHz, Chloroform-d) δ 8.48 (s, 2H), 7.02 (s, 1H), 5.86 (s, 1H), 3.97 (s, 3H). |
| 760 | $CF_3$ | 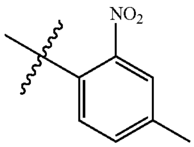 [SMILES: *c1ccc(C)cc1[N+](=O)[O-]] | (500 MHz, Chloroform-d) δ 7.87 (d, J = 1.5 Hz, 1H), 7.56-7.50 (m, 2H), 6.99 (s, 1H), 5.62 (s, 1H), 2.48 (s, 3H). |
| 761 | $CF_3$ | 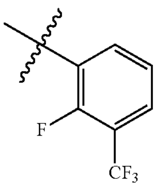 [SMILES: *c1cccc(C(F)(F)F)c1F] | (500 MHz, Chloroform-d) δ 7.70-7.63 (m, 2H), 7.20-7.07 (m, 2H), 5.43 (s, 1H). |

TABLE 1-continued

Structure and $^{1}$HNMR data of Compound I

I

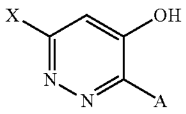

| No. | X | A | $^{1}$H NMR |
|---|---|---|---|
| 762 | $CF_3$ | 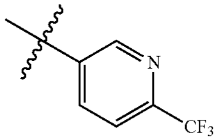 | $^{1}$H NMR (500 MHz, DMSO-$d_6$) δ 13.75 (s, 1H), 9.34 (d, J = 2.0 Hz, 1H), 8.69 (dd, J = 8.0, 2.0 Hz, 1H), 8.09 (d, J = 8.0 Hz, 1H), 7.38 (s, 1H). |
| 763 | $CF_3$ | 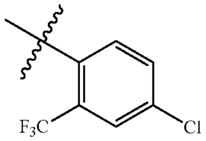 | (500 MHz, Chloroform-d) δ 7.77 (d, J = 2.0 Hz, 1H), 7.49 (d, J = 7.5 Hz, 1H), 7.43 (dd, J = 7.5, 2.0 Hz, 1H), 7.04 (s, 1H), 5.65 (s, 1H). |
| 764 | $CF_3$ | 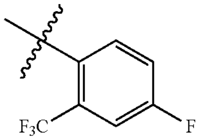 | (500 MHz, Chloroform-d) δ 7.43-7.36 (m, 1H), 7.35-7.23 (m, 2H), 7.01 (s, 1H), 5.69 (s, 1H). |
| 765 | $CF_3$ | 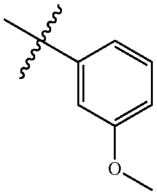 [SMILES: *c1cccc(OC)c1] | (500 MHz, Chloroform-d) δ 7.33-7.22 (m, 3H), 7.01 (s, 1H), 6.85-6.69 (m, 1H), 5.79 (s, 1H), 3.87 (s, 3H). |
| 766 | $CF_3$ | 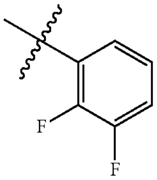 [SMILES: *c1cccc(F)c1F] | (500 MHz, Chloroform-d) δ 7.37-7.23 (m, 1H), 7.22-7.11 (m, 2H), 7.12 (s, 1H), 5.50 (s, 1H). |
| 767 | $CF_3$ | 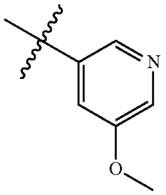 [SMILES: *c1cncc(OC)c1] | $^{1}$H NMR (500 MHz, DMSO-$d_6$) δ 13.44 (s, 1H), 8.78 (s, 1H), 8.47-8.35 (m, 1H), 7.99-7.87 (m, 1H), 7.30 (s, 1H), 3.88 (s, 3H). |
| 768 | $CF_3$ | 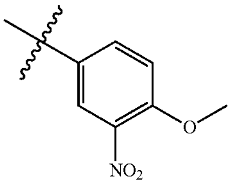 [SMILES: *c1ccc(OC)c([N+](=O)[O-])c1] | $^{1}$H NMR (500 MHz, DMSO-$d_6$) δ 12.27 (s, 1H), 8.99 (d, J = 2.0 Hz, 1H), 8.42 (dd, J = 8.5, 2.0 Hz, 1H), 7.61 (d, J = 8.5 Hz, 1H), 7.25 (s, 1H). |

TABLE 1-continued

Structure and ¹HNMR data of Compound I

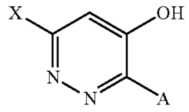

I

| No. | X | A | ¹H NMR |
|---|---|---|---|
| 769 | $CF_3$ | 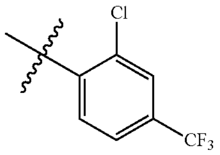 [SMILES: *c1ccc(C(F)(F)F)cc1Cl] | (500 MHz, Chloroform-d) δ 7.80 (d, J = 2.5 Hz, 1H), 7.61 (dd, J = 7.5, 2.5 Hz, 1H), 7.53 (d, J = 7.5 Hz, 1H), 7.01 (s, 1H), 5.66 (s, 1H). |
| 770 | $CF_3$ | 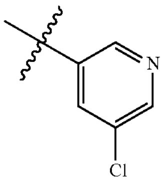 [SMILES: *c1cncc(Cl)c1] | ¹H NMR (500 MHz, DMSO-$d_6$) δ 12.25 (s, 1H), 9.07 (d, J = 2.0 Hz, 1H), 8.67 (d, J = 2.5 Hz, 1H), 8.41 (dd, J = 2.5, 2.0 Hz, 1H), 7.24 (s, 1H). |
| 771 | $CF_3$ | 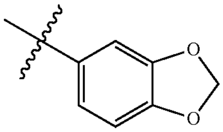 [SMILES: *c1ccc2c(c1)OCO2] | (500 MHz, Chloroform-d) δ 7.30 (d, J = 2.0 Hz, 1H), 7.22 (dd, J = 7.5, 2.0 Hz, 1H), 7.06-6.98 (m, 2H), 6.07 (s, 2H), 5.78 (s, 1H). |
| 772 | $CF_3$ | 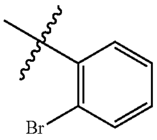 [SMILES: *c1ccccc1Br] | (500 MHz, Chloroform-d) δ 7.65 (dd, J = 7.5, 2.0 Hz, 1H), 7.46-7.29 (m, 3H), 7.05 (s, 1H), 5.66 (s, 1H). |
| 773 | $CF_3$ | 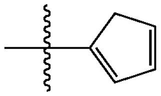 [SMILES: *C1=CC=CC1] | |
| 774 | $CF_3$ | 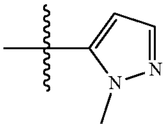 [SMILES: *c1ccnn1C] | ¹H NMR (500 MHz, DMSO-d6) δ 13.27 (br, 1H), 5 7.61 (d, J = 1.5 Hz, 1H), 7.38 (s, 1H), 6.99 (d, J = 1.5 Hz, 1H), 4.09 (s, 3H). |
| 775 | $CF_3$ | 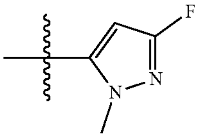 [SMILES: *c1cc(F)nn1C] | ¹H NMR (500 MHz, DMSO-$d_6$) δ 13.38 (s, 1H), 7.07 (s, 1H), 6.70 (s, 1H), 3.86 (s, 3H). |
| 776 | $CF_3$ | 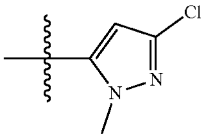 [SMILES: *c1cc(Cl)nn1C] | ¹H NMR (500 MHz, DMSO-$d_6$) δ 13.19 (s, 1H), 7.15 (s, 1H), 6.87 (s, 1H), 3.90 (s, 3H). |
| 777 | $CF_3$ | 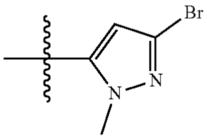 | ¹H NMR (500 MHz, DMSO-$d_6$) δ 13.40 (s, 1H), 7.34 (s, 1H), 6.97 (s, 1H), 3.87 (s, 3H). |

TABLE 1-continued

Structure and $^1$HNMR data of Compound I

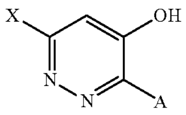

I

| No. | X | A | $^1$H NMR |
|---|---|---|---|
| 778 | $CF_3$ | 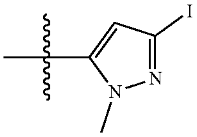 [SMILES: *c1cc(I)nn1C] | $^1$H NMR (500 MHz, DMSO-$d_6$) δ 13.38 (s, 1H), 7.37 (s, 1H), 6.80 (s, 1H), 3.76 (s, 3H). |
| 779 | $CF_3$ | 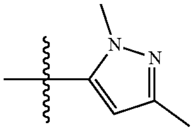 | $^1$H NMR (500 MHz, DMSO-d6) δ 13.27 (br, 1H), 5 7.32 (s, 1H), 6.68 (s, 1H), 3.91 (s, 3H), 2.19 (s, 3H). |
| 780 | $CF_3$ | 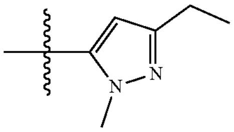 [SMILES: *c1cc(CC)nn1C] | $^1$H NMR (500 MHz, DMSO-$d_6$) δ 12.64 (s, 1H), 6.90 (s, 1H), 6.60 (s, 1H), 3.88 (s, 3H), 2.60 (q, J = 8.0 Hz, 2H), 1.19 (t, J = 8.0 Hz, 3H). |
| 781 | $CF_3$ | 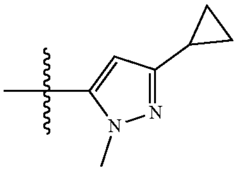 [SMILES: *c1cc(C2CC2)nn1C] | $^1$H NMR (500 MHz, DMSO-$d_6$) δ 13.48 (s, 1H), 6.93 (s, 1H), 6.37 (s, 1H), 3.76 (s, 3H), 1.87-1.73 (m, 1H), 1.20-0.91 (m, 2H), 0.75-0.68 (m, 2H). |
| 782 | $CF_3$ | 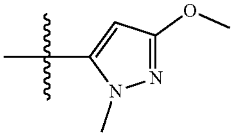 [SMILES: *c1cc(OC)nn1C] | $^1$H NMR (500 MHz, DMSO-$d_6$) δ 13.25 (s, 1H), 6.85 (s, 1H), 5.96 (s, 1H), 3.92 (s, 3H), 3.84 (s, 3H). |
| 783 | $CF_3$ | 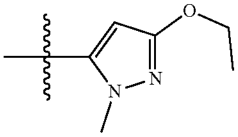 [SMILES: *c1cc(OCC)nn1C] | $^1$H NMR (500 MHz, DMSO-$d_6$) δ 13.26 (s, 1H), 6.90 (s, 1H), 5.86 (s, 1H), 4.39 (q, J = 8.0 Hz, 2H), 3.89 (s, 3H), 1.36 (t, J = 8.0 Hz, 3H). |
| 784 | $CF_3$ | 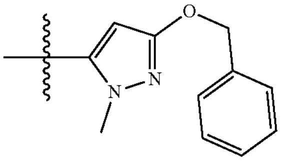 [SMILES: *c1cc(OCc2ccccc2)nn1C] | $^1$H NMR (500 MHz, DMSO-$d_6$) δ 12.64 (s, 1H), 7.47-7.39 (m, 2H), 7.18-7.11 (m, 2H), 7.03-6.94 (m, 2H), 6.06 (s, 1H), 4.65 (s, 2 H), 3.83 (s, 3H). |
| 785 | $CF_3$ | 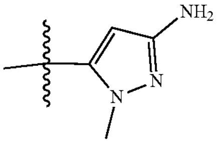 [SMILES: *c1cc(N)nn1C] | $^1$H NMR (500 MHz, DMSO-$d_6$) δ 13.23 (s, 1H), 7.21 (s, 1H), 6.86 (s, 1H), 3.88 (s, 3H), 3.55 (br, 2 H). |
| 786 | $CF_3$ | 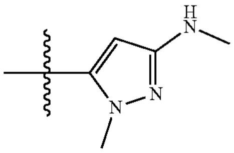 [SMILES: *c1cc(NC)nn1C] | $^1$H NMR (500 MHz, DMSO-$d_6$) δ 12.66 (s, 1H), 8.17 (s, 1H), 6.95 (s, 1H), 6.26 (s, 1H), 3.91 (s, 3H), 3.03 (s, 3H). |

TABLE 1-continued

Structure and $^1$HNMR data of Compound I

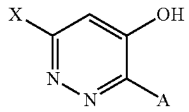

I

| No. | X | A | $^1$H NMR |
|---|---|---|---|
| 787 | $CF_3$ | 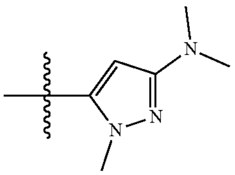 [SMILES: *c1cc(N(C)C)nn1C] | $^1$H NMR (500 MHz, DMSO-$d_6$) δ 13.45 (s, 1H), 6.85 (s, 1H), 6.36 (s, 1H), 3.94 (s, 3H), 3.19 (s, 6H). |
| 788 | $CF_3$ | 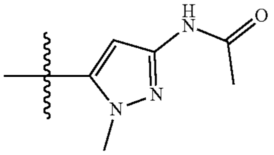 [SMILES: *c1cc(NC(C)=O)nn1C] | $^1$H NMR (500 MHz, DMSO-$d_6$) δ 13.52 (s, 1H), 7.38 (s, 1H), 6.94 (s, 1H), 5.56 (s, 1H), 3.88 (s, 3H), 2.13 (s, 3H). |
| 789 | $CF_3$ | 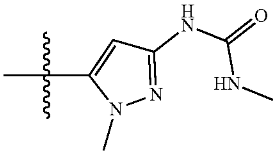 [SMILES: *c1cc(NC(=O)NC)nn1C] | $^1$H NMR (500 MHz, DMSO-$d_6$) δ 13.06 (s, 1H), 8.56 (s, 1H), 7.85 (s, 1H), 6.95 (s, 1H), 5.56 (s, 1H), 3.90 (s, 3H), 2.71 (s, 3H). |
| 790 | $CF_3$ | 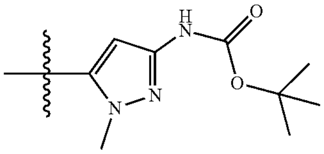 [SMILES: *c1cc(NC(=O)OC(C)(C)C)nn1C] | $^1$H NMR (500 MHz, DMSO-$d_6$) δ13.18 (s, 1H), 10.14 (s, 1H), 6.94 (s, 1H), 5.56 (s, 1H), 3.95 (s, 3H), 1.29 (s, 9H). |
| 791 | $CF_3$ | 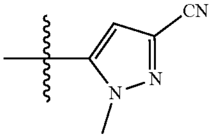 [SMILES: *c1cc(C#N)nn1C] | $^1$H NMR (500 MHz, DMSO-$d_6$) δ 12.72 (s, 1H), 6.99 (s, 1H), 6.92 (s, 1H), 3.91 (s, 3H). |
| 792 | $CF_3$ | 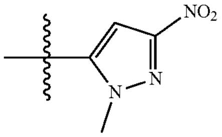 [SMILES: *c1cc([N+](=O)[O-])nn1C] | $^1$H NMR (500 MHz, DMSO-$d_6$) δ 13.58 (s, 1H), 7.50 (s, 1H), 6.91 (s, 1H), 3.87 (s, 3H). |
| 793 | $CF_3$ | 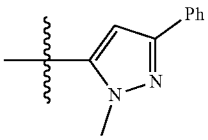 [SMILES: *c1cc(-c2ccccc2)nn1C] | $^1$H NMR (500 MHz, DMSO-$d_6$) δ 13.25 (s, 1H), 7.92-7.85 (m, 2H), 7.51-7.41 (m, 3H), 7.25 (s, 1H), 6.99 (s, 1H), 3.92 (s, 3H). |
| 794 | $CF_3$ | 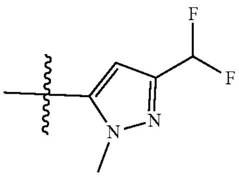 [SMILES: *c1cc(C(F)F)nn1C] | $^1$H NMR (500 MHz, DMSO-$d_6$) δ 13.25 (s, 1H), 6.94 (t, J = 73.5 Hz, 1 H), 6.90 (s, 1H), 6.84 (s, 1H), 3.89 (s, 3H). |

TABLE 1-continued
Structure and $^{1}$HNMR data of Compound I
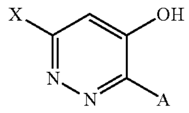
I
| No. | X | A | $^{1}$H NMR |
|---|---|---|---|
| 795 | $CF_3$ | 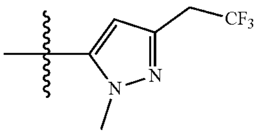 [SMILES: *c1cc(CC(F)(F)F)nn1C] | $^{1}$H NMR (500 MHz, DMSO-$d_6$) δ13.51 (s, 1H), 6.91 (s, 1H), 6.71 (s, 1H), 3.89 (s, 3H), 3.07 (s, 2H). |
| 796 | $CF_3$ | 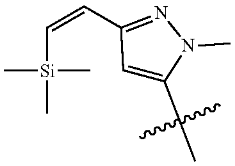 | |
| 797 | $CF_3$ | 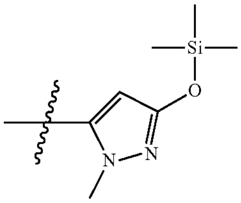 [SMILES: *c1cc(O[Si](C)(C)C)nn1C] | |
| 798 | $CF_3$ | 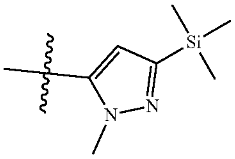 [SMILES: *c1cc([Si](C)(C)C)nn1C] | |
| 799 | $CF_3$ | 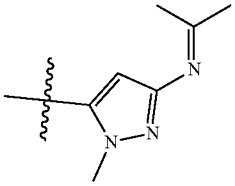 [SMILES: *c1cc(N=C(C)C)nn1C] | |
| 800 | $CF_3$ | 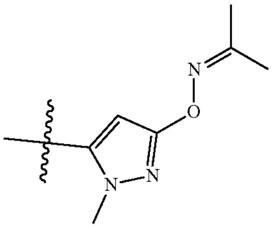 [SMILES: *c1cc(ON=C(C)C)nn1C] | |
| 801 | $CF_3$ | 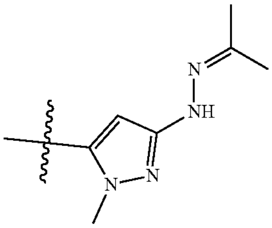 [SMILES: *c1cc(NN=C(C)C)nn1C] | |

TABLE 1-continued
Structure and $^1$HNMR data of Compound I
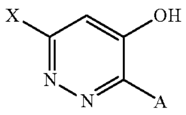
I
| No. | X | A | $^1$H NMR |
|---|---|---|---|
| 802 | $CF_3$ | 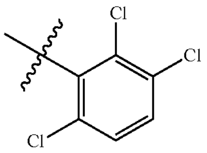 | |
| 803 | $CF_3$ | 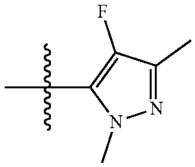 [SMILES: *c1c(F)c(C)nn1C] | $^1$H NMR (500 MHz, DMSO-$d_6$) δ 12.78 (s, 1H), 7.37 (s, 1H), 3.76 (s, 3H), 2.70 (s, 3H). |
| 804 | $CF_3$ | 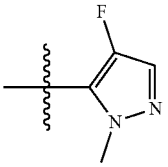 [SMILES: *c1c(F)cnn1C] | $^1$H NMR (500 MHz, DMSO-$d_6$) δ 13.48 (s, 1H), 7.50 (s, 1H), 6.37 (s, 1H), 3.76 (s, 3H). |
| 805 | $CF_3$ | 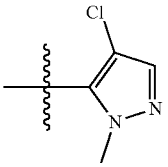 [SMILES: *c1c(Cl)cnn1C] | $^1$H NMR (500 MHz, DMSO-$d_6$) δ 12.59 (s, 1H), 7.87 (s, 1H), 6.89 (s, 1H), 3.88 (s, 3H). |
| 806 | $CF_3$ | 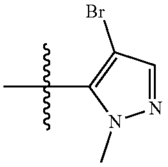 | $^1$H NMR (500 MHz, DMSO-$d_6$) δ 13.42 (s, 1H), 8.12 (s, 1H), 6.90 (s, 1H), 3.86 (s, 3H). |
| 807 | $CF_3$ | 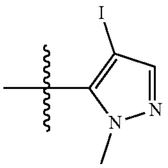 [SMILES: *c1c(I)cnn1C] | $^1$H NMR (500 MHz, DMSO-$d_6$) δ 13.38 (s, 1H), 7.60 (s, 1H), 6.37 (s, 1H), 3.76 (s, 3H). |
| 808 | $CF_3$ | 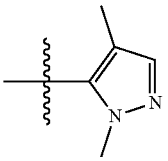 [SMILES: *c1c(C)cnn1C] | $^1$H NMR (500 MHz, DMSO-$d_6$) δ 13.40 (s, 1H), 7.56 (s, 1H), 6.88 (s, 1H), 3.85 (s, 3H), 2.08 (s, 3H). |
| 809 | $CF_3$ | 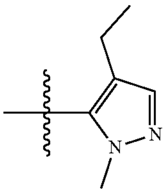 [SMILES: *c1c(CC)cnn1C] | $^1$H NMR (500 MHz, DMSO-$d_6$) δ 13.38 (s, 1H), 7.67 (s, 1H), 6.89 (s, 1H), 3.84 (s, 3H), 2.70 (q, J = 8.0 Hz, 2H), 1.17 (t, J = 8.0 Hz, 3H). |

TABLE 1-continued
Structure and $^1$HNMR data of Compound I
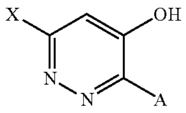
I
| No. | X | A | $^1H$ NMR |
| --- | --- | --- | --- |
| 810 | $CF_3$ | 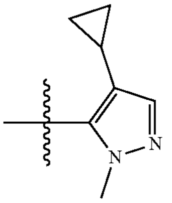 [SMILES: *c1c(C2CC2)cnn1C] | $^1H$ NMR (500 MHz, DMSO-$d_6$) δ 12.68 (s, 1H), 7.76 (s, 1H), 6.37 (s, 1H), 3.76 (s, 3H), 2.41-2.28 (m, 1H), 1.12-1.02 (m, 2H), 0.82-0.72 (m, 2H). |
| 811 | $CF_3$ | 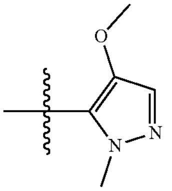 [SMILES: *c1c(OC)cnn1C] | $^1H$ NMR (500 MHz, DMSO-$d_6$) δ 12.78 (s, 1H), 7.19 (s, 1H), 6.90 (s, 1H), 3.90 (s, 3H), 3.80 (s, 3H). |
| 812 | $CF_3$ | 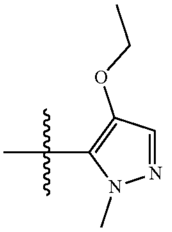 [SMILES: *c1c(OCC)cnn1C] | $^1H$ NMR (500 MHz, DMSO-$d_6$) δ 12.87 (s, 1H), 7.19 (s, 1H), 6.90 (s, 1H), 4.10 (q, J = 8.0 Hz, 2H), 3.90 (s, 3H), 1.34 (t, J = 8.0 Hz, 3H). |
| 813 | $CF_3$ | 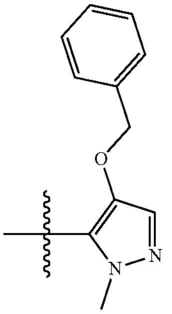 [SMILES: *c1c(OCc2ccccc2)cnn1C] | $^1H$ NMR (500 MHz, DMSO-$d_6$) δ 12.78 (s, 1H), 7.50-7.44 (m, 2H), 7.41-7.27 (m, 4H), 6.95 (s, 1H), 5.15 (s, 2H), 3.91 (s, 3H). |
| 814 | $CF_3$ | 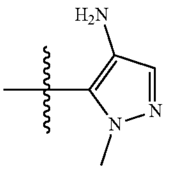 [SMILES: *c1c(N)cnn1C] | $^1H$ NMR (500 MHz, DMSO-$d_6$) δ 13.03 (s, 1H), 7.70 (s, 1H), 6.86 (s, 1H), 5.83 (s, 2H), 3.89 (s, 3H). |
| 815 | $CF_3$ | 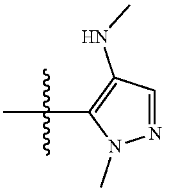 [SMILES: *c1c(NC)cnn1C] | |

TABLE 1-continued
Structure and $^1$HNMR data of Compound I
I
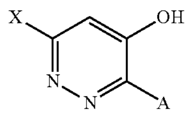
| No. | X | A | $^1$H NMR |
|---|---|---|---|
| 816 | $CF_3$ | 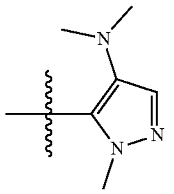 [SMILES: *c1c(N(C)C)cnn1C] | $^1$H NMR (500 MHz, DMSO-$d_6$) δ 13.35 (s, 1H), 7.71 (s, 1H), 6.90 (s, 1H), 3.89 (s, 3H), 2.86 (s, 6H). |
| 817 | $CF_3$ | 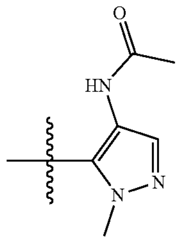 [SMILES: *c1c(NC(C)=O)cnn1C] | $^1$H NMR (500 MHz, DMSO-$d_6$) δ 13.03 (s, 1 H) 9.96 (s, 1H), 7.87 (s, 1H), 6.95 (s, 1H), 3.92 (s, 3H), 2.07 (s, 3H). |
| 818 | $CF_3$ | 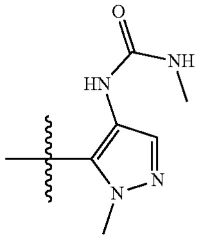 [SMILES: *c1c(NC(=O)NC)cnn1C] | $^1$H NMR (500 MHz, DMSO-$d_6$) δ 12.66 (s, 1H), 8.60 (s, 1H), 7.87 (s, 1H), 6.97 (s, 1H), 6.16 (s, 1H), 3.93 (s, 3H), 2.68 (s, 3H). |
| 819 | $CF_3$ | 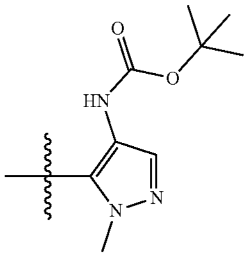 [SMILES: *c1c(NC(=O)OC(C)(C)C)cnn1C] | $^1$H NMR (500 MHz, DMSO-$d_6$) δ 13.35 (s, 1H), 9.78 (s, 1H), 7.87 (s, 1H), 6.95 (s, 1H), 3.92 (s, 3H), 1.49 (s, 9H). |
| 820 | $CF_3$ | 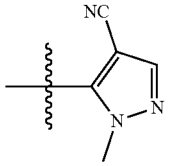 [SMILES: *c1c(C#N)cnn1C] | $^1$H NMR (500 MHz, DMSO-$d_6$) δ 13.21 (s, 1H), 7.92 (s, 1H), 6.92 (s, 1H), 3.87 (s, 3H). |
| 821 | $CF_3$ | 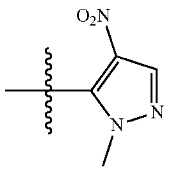 | $^1$H NMR (500 MHz, DMSO-$d_6$) δ 13.45 (s, 1H), 8.27 (s, 1H), 6.89 (s, 1H), 3.89 (s, 3H). |

TABLE 1-continued

Structure and $^1$HNMR data of Compound I

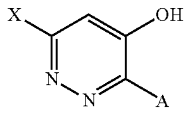

I

| No. | X | A | $^1$H NMR |
|---|---|---|---|
| 822 | $CF_3$ | 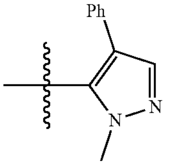 [SMILES: *c1c(-c2ccccc2)cnn1C] | |
| 823 | $CF_3$ | 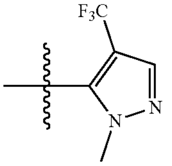 | $^1$H NMR (500 MHz, DMSO-$d_6$) δ 13.10 (s, 1H), 7.82 (s, 1H), 6.92 (s, 1H), 3.85 (s, 3H). |
| 824 | $CF_3$ | 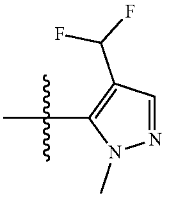 [SMILES: *c1c(C(F)F)cnn1C] | $^1$H NMR (500 MHz, DMSO-$d_6$) δ 13.36 (s, 1H), 7.91 (s, 1H), 6.95 (s, 1H), 6.67 (t, J = 73.5 Hz, 1H), 3.83 (s, 3H). |
| 825 | $CF_3$ | 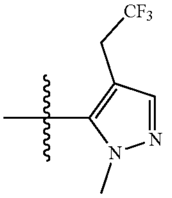 [SMILES: *c1c(CC(F)(F)F)cnn1C] | $^1$H NMR (500 MHz, DMSO-$d_6$) δ 13.16 (s, 1H), 7.77 (s, 1H), 6.93 (s, 1H), 3.83 (s, 3H), 3.07 (s, 2H). |
| 826 | $CF_3$ | 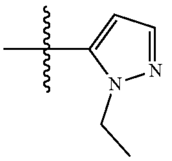 [SMILES: *c1ccnn1CC] | $^1$H NMR (500 MHz, DMSO-$d_6$) δ 12.89 (s, 1H), 7.61 (d, J = 2.5 Hz, 1H), 7.15 (s, 1H), 6.84 (d, J = 2.5 Hz, 1H), 3.68 (q, J = 8.0 Hz, 2H), 1.53 (t, J = 8.0 Hz, 3H). |
| 827 | $CF_3$ | 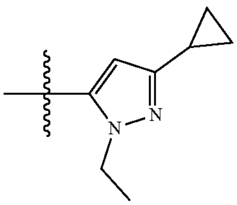 [SMILES: *c1cc(C2CC2)nn1CC] | $^1$H NMR (500 MHz, DMSO-$d_6$) δ 12.78 (s, 1H), 7.16 (s, 1H), 6.37 (s, 1H), 4.08 (q, J = 8.0 Hz, 2H), 1.87-1.76 (m, 1H), 1.30 (t, J = 8.0 Hz, 3H), 1.12-0.88 (m, 2H), 0.71-0.63 (m, 2H). |
| 828 | $CF_3$ | 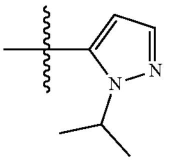 [SMILES: *c1ccnn1C(C)C] | $^1$H NMR (500 MHz, DMSO-$d_6$) δ 12.57 (s, 1H), 7.60 (d, J = 2.0 Hz, 1H), 7.03 (s, 1H), 6.73 (d, J = 2.0 Hz, 1H), 4.15-3.82 (m, 1H), 1.26 (d, J = 6.5 Hz, 6H). |

TABLE 1-continued

Structure and $^1$HNMR data of Compound I

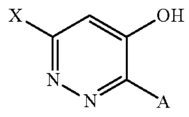

I

| No. | X | A | $^1$H NMR |
|---|---|---|---|
| 829 | $CF_3$ | 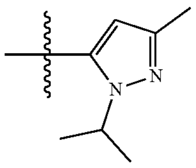 [SMILES: *c1cc(C)nn1C(C)C] | $^1$H NMR (500 MHz, DMSO-$d_6$) δ 12.76 (s, 1H), 7.06 (s, 1H), 6.78 (s, 1H), 4.56-4.23 (m, 1H), 2.39 (s, 3H), 1.26 (d, J = 4.5 Hz, 6H). |
| 830 | $CF_3$ | 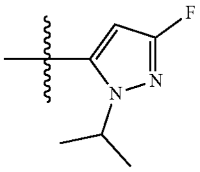 [SMILES: *c1cc(F)nn1C(C)C] | $^1$H NMR (500 MHz, DMSO-$d_6$) δ 13.08 (s, 1H), 7.17 (d, J = 8.5 Hz, 1H), 6.50 (s, 1H), 4.46-4.09 (m, 1H), 1.40 (d, J = 4.5 Hz, 6H). |
| 831 | $CF_3$ | 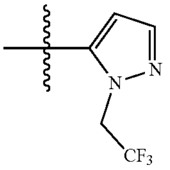 | $^1$H NMR (500 MHz, DMSO-$d_6$) δ13.51 (s, 1H), 7.64 (d, J = 2.5 Hz, 1H), 6.91 (s, 1H), 6.68 (d, J = 2.5 Hz, 1H), 5.32 (s, 2H). |
| 832 | $CF_3$ | 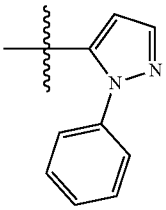 [SMILES: *c1ccnn1-c1ccccc1] | $^1$H NMR (500 MHz, DMSO-$d_6$) δ13.11 (s, 1H), 7.96 (d, J = 2.5 Hz, 1H), 7.65-7.51 (m, 2H), 7.46-7.24 (m, 2H), 7.12-7.01 (m, 2H), 6.83 (s, 1H). |
| 833 | $CF_3$ | 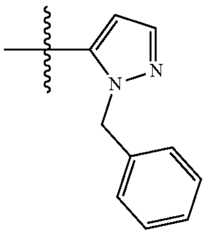 [SMILES: *c1ccnn1Cc1ccccc1] | $^1$H NMR (500 MHz, DMSO-$d_6$) δ 12.63 (s, 1H), 7.64 (d, J = 2.0 Hz, 1H), 7.55-7.15 (m, 2H), 7.32-7.24 (m, 1H), 7.22-7.16 (m, 2H), 6.90 (s, 1H), 6.62 (d, J = 2.0 Hz, 1H), 5.46 (s, 2H). |
| 834 | $CF_3$ | 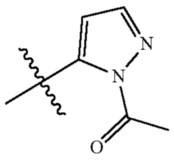 [SMILES: *c1ccnn1C(C)=O] | $^1$H NMR (500 MHz, Chloroform-d) δ 7.84 (d, J = 2.5 Hz, 1H), 7.21 (s, 1H), 6.68 (d, J = 2.5 Hz, 1H), 5.49 (s, 1H), 2.54 (s, 3H). |
| 835 | $CF_3$ | 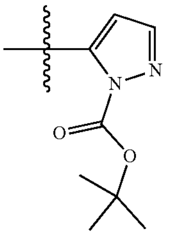 [SMILES: *c1ccnn1C(=O)OC(C)(C)C] | $^1$H NMR (500 MHz, DMSO-$d_6$) δ13.13 (s, 1H), 8.11 (d, J = 2.5 Hz, 1H), 6.97 (d, J = 2.5 Hz, 1H), 6.9O (s, 1H), 1.61 (s, 9H). |

TABLE 1-continued
| Structure and ¹HNMR data of Compound I | | | |
|---|---|---|---|
| 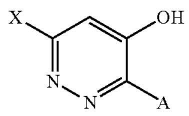 | | | I |
| No. | X | A | ¹H NMR |
| 836 | $CF_3$ | 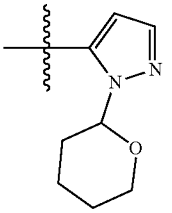 [SMILES: *c1ccnn1C1CCCCO1] | |
| 837 | $CF_3$ | 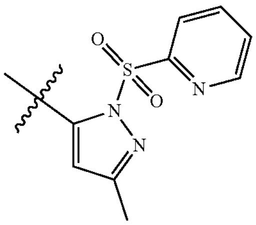 [SMILES: *c1cc(C)nn1S(=O)(=O)c1ccccn1] | |
| 838 | $CF_3$ | 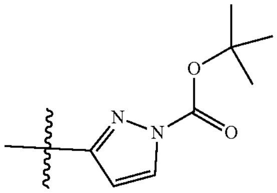 [SMILES: *c1ccn(C(=O)OC(C)(C)C)n1] | |
| 839 | $CF_3$ | 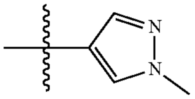 [SMILES: *c1cnn(C)c1] | ¹H NMR (500 MHz, DMSO-d6) δ 13.25 (s, 1H), 8.53 (s, 1H), 8.18 (s, 1H), 7.23 (s, 1H), 3.92 (s, 3H). |
| 840 | $CF_3$ | 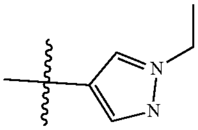 | ¹H NMR (500 MHz, DMSO-d6) δ 12.83 (s, 1H), 8.56 (s, 1H), 8.20 (s, 1H), 7.20 (s, 1H), 4.22 (q, J = 7.2 Hz, 2H), 1.40 (t, J = 7.2 Hz, 3H). |
| 841 | $CF_3$ | 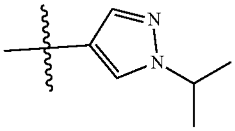 [SMILES: *c1cnn(C(C)C)c1] | |
| 842 | $CF_3$ | 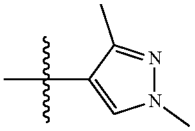 [SMILES: *c1cn(C)nc1C] | ¹H NMR (500 MHz, DMSO-d6) δ 12.66 (s, 1H), 8.44 (s, 1H), 7.22 (s, 1H), 3.83 (s, 3H), 3.31 (s, 3H). |
| 843 | $CF_3$ | 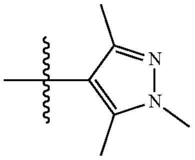 [SMILES: *c1c(C)nn(C)c1C] | |

TABLE 1-continued
Structure and $^1$HNMR data of Compound I
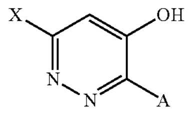
I
| No. | X | A | $^1$H NMR |
| --- | --- | --- | --- |
| 844 | $CF_3$ | 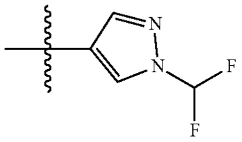 [SMILES: *c1cnn(C(F)F)c1] | $^1$H NMR (500 MHz, DMSO-d6) 13.52 (s, 1H), 8.99 (s, 1H), 8.50 (s, 1H), 7.92 (t, J = 58.5 Hz, 1H), 7.23 (s, 1H). |
| 845 | $CF_3$ | 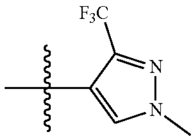 [SMILES: *c1cn(C)nc1C(F)(F)F] | |
| 846 | $CF_3$ | 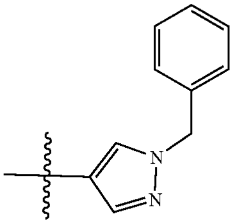 [SMILES: *c1cnn(Cc2ccccc2)c1] | $^1$H NMR (500 MHz, DMSO-d6) δ 13.27 (br, 1H), 8.68 (s, 1H), 8.24 (s, 1H), 7.72-6.70 (m, 6H), 5.43 (s, 2H). |
| 847 | $CF_3$ | 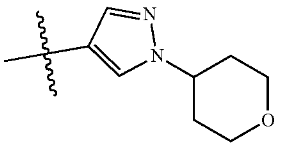 [SMILES: *c1cnn(C2CCOCC2)c1] | |
| 848 | $CF_3$ | 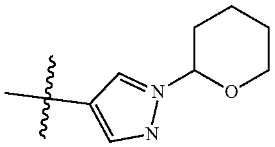 | $^1$H NMR (500 MHz, DMSO-$d_6$) δ 12.87 (s, 1H), 7.81 (s, 1H), 7.19 (s, 1H), 6.97 (s, 1H), 5.36 (t, J = 6.8 Hz, 1H), 3.90-3.77 (m, 2H), 2.13-2.01 (m, 2H), 1.85-1.68 (m, 2H), 1.67-1.50 (m, 2H). |
| 849 | $CF_3$ | 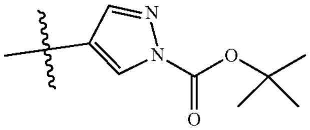 [SMILES: *c1cnn(C(=O)OC(C)(C)C)c1] | |
| 850 | $CF_3$ | 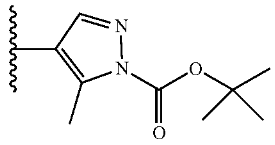 [SMILES: *c1cnn(C(=O)OC(C)(C)C)c1C] | |
| 851 | $CF_3$ | 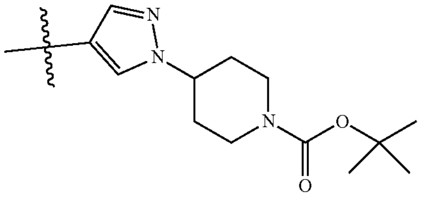 [SMILES: *c1cnn(C2CCN(C(=O)OC(C)(C)C)CC2)c1] | |

TABLE 1-continued
Structure and $^1$HNMR data of Compound I
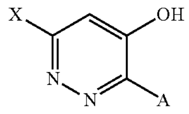
I
| No. | X | A | $^1$H NMR |
| --- | --- | --- | --- |
| 852 | $CF_3$ | 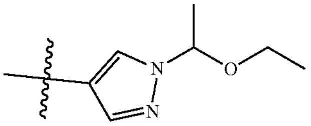 [SMILES: *c1cnn(C(C)OCC)c1] | $^1$H NMR (500 MHz, DMSO-d) δ 12.84 (s, 1H), 8.68 (s, 1H), 8.27 (s, 1H), 7.22 (s, 1H), 5.67 (q, J = 6.0 Hz, 1H), 3.45 (q, J = 7.0 Hz, 1H), 3.21 (dq, J = 14.2, 7.0 Hz, 1H), 1.62 (d, J = 6.0 Hz, 3H), 1.03 (t, J = 7.0 Hz, 3H). |
| 853 | $CF_3$ | 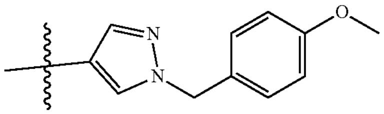 [SMILES: *c1cnn(Cc2ccc(OC)cc2)c1] | |
| 854 | $CF_3$ | 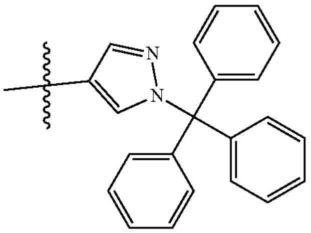 [SMILES: *c1cnn(C(c2ccccc2)(c2ccccc2)c2ccccc2)c1] | |
| 855 | $CF_3$ | 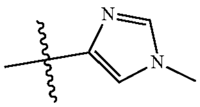 [SMILES: *c1cn(C)cn1] | $^1$H NMR (500 MHz, DMSO-$d_6$) δ 12.54 (s, 1H), 7.72 (s, 1H), 7.45 (s, 1H), 6.87 (s, 1H), 3.68 (s, 3H). |
| 856 | $CF_3$ | 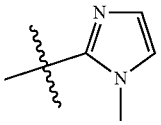 [SMILES: *c1nccn1C] | $^1$H NMR (500 MHz, DMSO-$d_6$) δ 12.93 (s, 1H), 7.40 (d, J = 2.5 Hz, 1H), 7.10 (d, J = 2.5 Hz, 1H), 6.87 (s, 1H), 3.94 (s, 3H). |
| 857 | $CF_3$ | 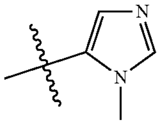 [SMILES: *c1cncn1C] | $^1$H NMR (500 MHz, DMSO-$d_6$) δ 13.24 (s, 1H), 7.75 (s, 1H), 7.58 (s, 1H), 6.91 (s, 1H), 3.79 (s, 3H). |
| 858 | $CF_3$ | 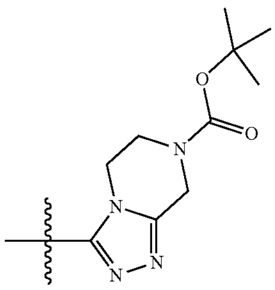 [SMILES: *c1nnc2n1CCN(C(=O)OC(C)(C)C)C2] | |
| 859 | $CF_3$ | 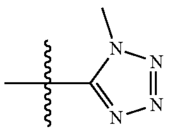 [SMILES: *c1nnnn1C] | $^1$H NMR (500 MHz, DMSO-$d_6$) δ 13.00 (s, 1H), 6.89 (s, 1H), 4.19 (s, 3H). |

TABLE 1-continued
Structure and $^1$HNMR data of Compound I
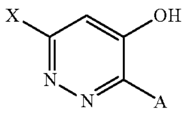
I
| No. | X | A | $^1$H NMR |
|---|---|---|---|
| 860 | $CF_3$ | 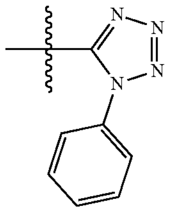 [SMILES: *c1nnnn1-c1ccccc1] | |
| 861 | $CF_3$ | 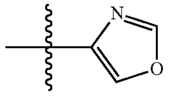 [SMILES: *c1cocn1] | $^1$H NMR (500 MHz, DMSO-$d_6$) δ13.13 (s, 1H), 8.26 (s, 1H), 8.00 (s, 1H), 6.88 (s, 1H). |
| 862 | $CF_3$ | 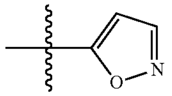 [SMILES: *c1ccno1] | $^1$H NMR (500 MHz, DMSO-$d_6$) δ 12.60 (s, 1H), 8.23 (d, J = 2.0 Hz, 1H), 7.41 (d, J = 2.0 Hz, 1H), 6.89 (s, 1H). |
| 863 | $CF_3$ | 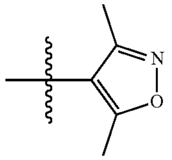 [SMILES: *c1c(C)noc1C] | $^1$H NMR (500 MHz, DMSO-d6) δ 12.86 (br, 1H), 7.26 (s, 1H), 2.38 (s, 3H), 2.20 (s, 3H). |
| 864 | $CF_3$ | 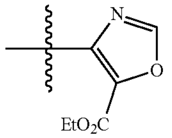 | |
| 865 | $CF_3$ | 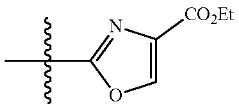 [SMILES: *c1nc(C(=O)OCC)co1] | |
| 866 | $CF_3$ | 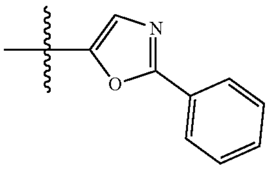 [SMILES: *c1cnc(-c2ccccc2)o1] | |
| 867 | $CF_3$ | 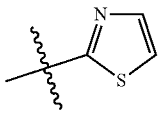 [SMILES: *c1nccs1] | $^1$H NMR (500 MHz, DMSO-$d_6$) δ 12.66 (s, 1H), 8.05 (d, J = 2.5 Hz, 1H), 7.56 (d, J = 2.5 Hz, 1H), 6.88 (s, 1H). |
| 868 | $CF_3$ | 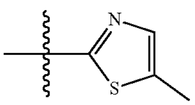 [SMILES: *c1ncc(C)s1] | |
| 869 | $CF_3$ | 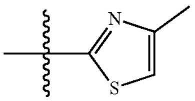 [SMILES: *c1nc(C)cs1] | |

TABLE 1-continued
Structure and $^1$HNMR data of Compound I
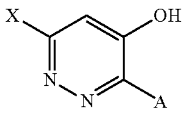
I
| No. | X | A | $^1H$ NMR |
|---|---|---|---|
| 870 | $CF_3$ | 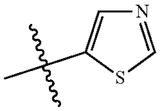 [SMILES: *c1cncs1] | $^1H$ NMR (500 MHz, DMSO-$d_6$) δ 12.83 (s, 1H), 9.24 (s, 1H), 8.24 (s, 1H), 6.89 (s, 1H). |
| 871 | $CF_3$ | 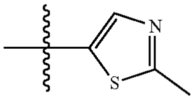 [SMILES: *c1cnc(C)s1] | |
| 872 | $CF_3$ | 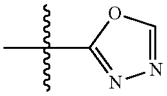 | $^1H$ NMR (500 MHz, DMSO-$d_6$) δ 12.70 (s, 1H), 7.94 (s, 1H), 6.84 (s, 1H). |
| 873 | $CF_3$ | 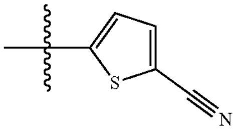 [SMILES: *c1ccc(C#N)s1] | $^1H$ NMR (500 MHz, DMSO-d6) δ 13.26 (br, 1H), 7.35 (s, 1H), 7.29 (s, 1H), 4.08 (s, 3H). |
| 874 | $CF_3$ | 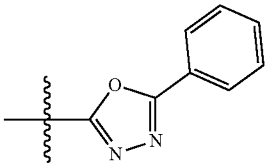 [SMILES: *c1nnc(-c2ccccc2)o1] | |
| 875 | $CF_3$ | 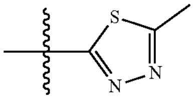 [SMILES: *c1nnc(C)s1] | |
| 876 | $CF_3$ | 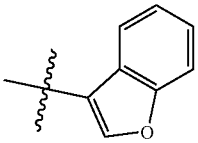 [SMILES: *c1coc2ccccc12] | $^1H$ NMR (500 MHz, DMSO-d6) δ 13.86 (s, 1H), 9.07 (s, 1H), 8.50 (d, J = 6.5 Hz, 1H), 7.70 (d, J = 7.5 Hz, 1H), 7.50-7.34 (m, 2H), 7.21 (s, 1H). |
| 877 | $CF_3$ | 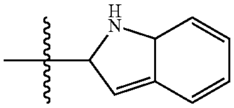 | $^1H$ NMR (500 MHz, DMSO-d6) δ 12.91 (s, 1H), 7.63 (d, J = 8.0 Hz, 1H), 7.54 (s, 1H), 7.51 (d, J = 8.0 Hz, 1H), 7.25 (s, 1H), 7.17 (m, 1H), 7.00 (m, 1H). |
| 878 | $CF_3$ | 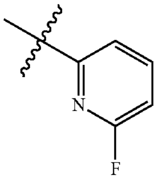 [SMILES: *c1cccc(F)n1] | |
| 879 | $CF_3$ | 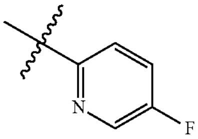 [SMILES: *c1ccc(F)cn1] | |

TABLE 1-continued
Structure and $^1$HNMR data of Compound I
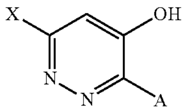
I
| No. | X | A | $^1$H NMR |
|---|---|---|---|
| 880 | $CF_3$ | 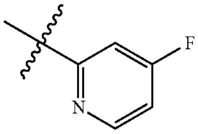 | |
| 881 | $CF_3$ | 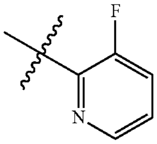 [SMILES: *c1ncccc1F] | |
| 882 | $CF_3$ | 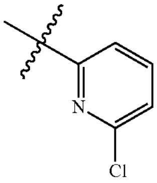 | |
| 883 | $CF_3$ | 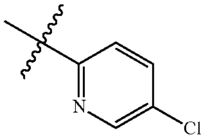 [SMILES: *c1ccc(Cl)cn1] | |
| 884 | $CF_3$ | 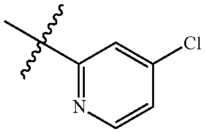 [SMILES: *c1cc(Cl)ccn1] | |
| 885 | $CF_3$ | 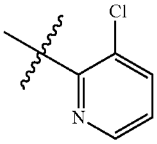 [SMILES: *c1ncccc1Cl] | |
| 886 | $CF_3$ | 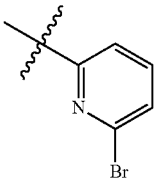 [SMILES: *c1cccc(Br)n1] | |
| 887 | $CF_3$ | 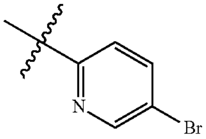 [SMILES: *c1ccc(Br)cn1] | |

TABLE 1-continued
Structure and $^1$HNMR data of Compound I
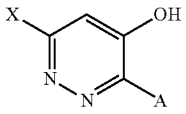
I
| No. | X | A | $^1H$ NMR |
|---|---|---|---|
| 888 | $CF_3$ | 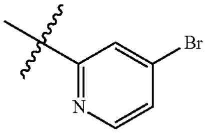 [SMILES: *c1cc(Br)ccn1] | |
| 889 | $CF_3$ | 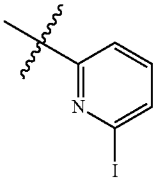 [SMILES: *c1cccc(I)n1] | |
| 890 | $CF_3$ | 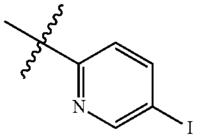 [SMILES: *c1ccc(I)cn1] | |
| 891 | $CF_3$ | 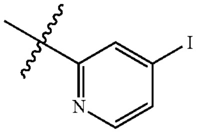 [SMILES: *c1cc(I)ccn1] | |
| 892 | $CF_3$ | 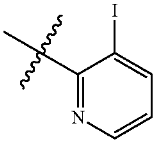 | |
| 893 | $CF_3$ | 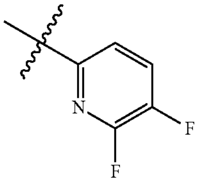 [SMILES: *c1ccc(F)c(F)n1] | |
| 894 | $CF_3$ | 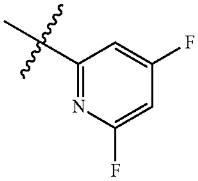 [SMILES: *c1cc(F)cc(F)n1] | |
| 895 | $CF_3$ | 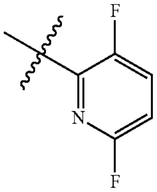 [SMILES: *c1nc(F)ccc1F] | |

TABLE 1-continued
Structure and $^1$HNMR data of Compound I
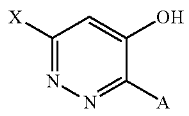
I
| No. | X | A | $^1H$ NMR |
|---|---|---|---|
| 896 | $CF_3$ | 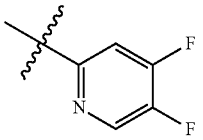 | |
| 897 | $CF_3$ | 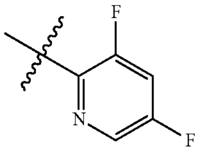 [SMILES: *c1ncc(F)cc1F] | |
| 898 | $CF_3$ | 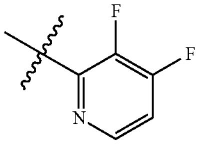 [SMILES: *c1nccc(F)c1F] | |
| 899 | $CF_3$ | 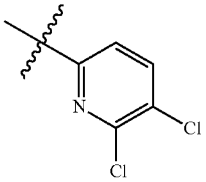 [SMILES: *c1ccc(Cl)c(Cl)n1] | |
| 900 | $CF_3$ | 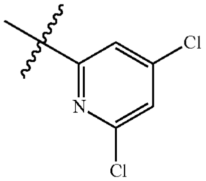 [SMILES: *c1cc(Cl)cc(Cl)n1] | |
| 901 | $CF_3$ | 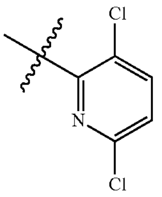 [SMILES: *c1nc(Cl)ccc1Cl] | |
| 902 | $CF_3$ | 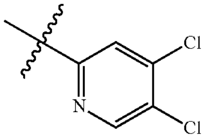 | |
| 903 | $CF_3$ | 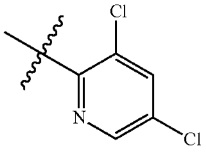 | |

TABLE 1-continued
Structure and $^1$HNMR data of Compound I
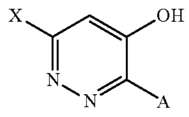
I
| No. | X | A | $^1H$ NMR |
|---|---|---|---|
| 904 | $CF_3$ | 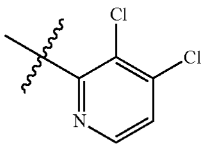 | |
| 905 | $CF_3$ | 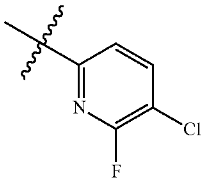 [SMILES: *c1ccc(Cl)c(F)n1] | |
| 906 | $CF_3$ | 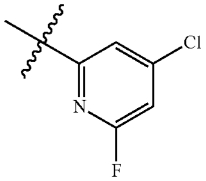 [SMILES: *c1cc(Cl)cc(F)n1] | |
| 907 | $CF_3$ | 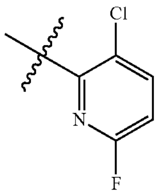 [SMILES: *c1nc(F)ccc1Cl] | |
| 908 | $CF_3$ | 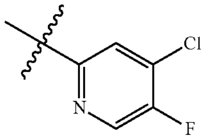 | |
| 909 | $CF_3$ | 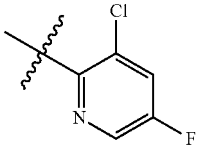 [SMILES: *c1ncc(F)cc1Cl] | |
| 910 | $CF_3$ | 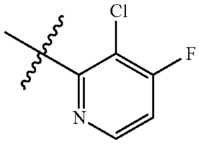 [SMILES: *c1nccc(F)c1Cl] | |
| 911 | $CF_3$ | 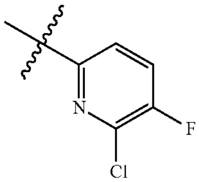 [SMILES: *c1ccc(F)c(Cl)n1] | |

TABLE 1-continued
Structure and $^1$HNMR data of Compound I
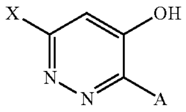
I
| No. | X | A | $^1$H NMR |
| --- | --- | --- | --- |
| 912 | $CF_3$ | 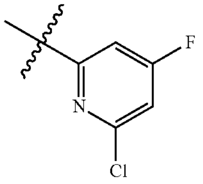 [SMILES: *c1cc(F)cc(Cl)n1] | |
| 913 | $CF_3$ | 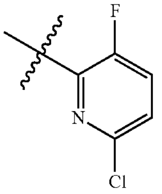 [SMILES: *c1nc(Cl)ccc1F] | |
| 914 | $CF_3$ | 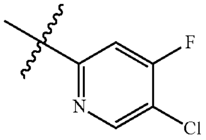 [SMILES: *c1cc(F)c(Cl)cn1] | |
| 915 | $CF_3$ | 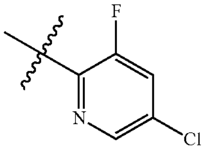 [SMILES: *c1ncc(Cl)cc1F] | |
| 916 | $CF_3$ | 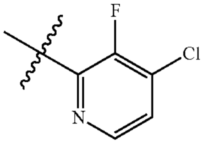 [SMILES: *c1nccc(Cl)c1F] | |
| 917 | $CF_3$ | 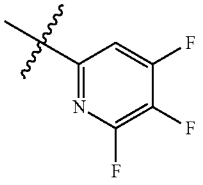 [SMILES: *c1cc(F)c(F)c(F)n1] | |
| 918 | $CF_3$ | 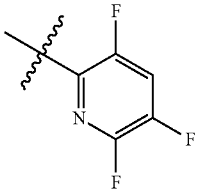 [SMILES: *c1nc(F)c(F)cc1F] | |

TABLE 1-continued
Structure and ¹HNMR data of Compound I
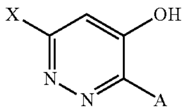
I
| No. | X | A | ¹H NMR |
|---|---|---|---|
| 919 | $CF_3$ | 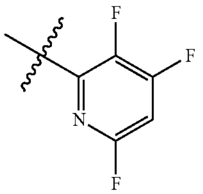 [SMILES: *c1nc(F)cc(F)c1F] | |
| 920 | $CF_3$ | 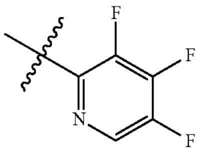 [SMILES: *c1ncc(F)c(F)c1F] | |
| 921 | $CF_3$ | 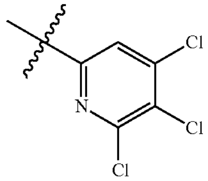 [SMILES: *c1cc(Cl)c(Cl)c(Cl)n1] | |
| 922 | $CF_3$ | 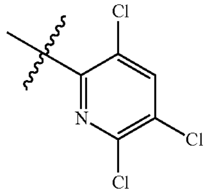 [SMILES: *c1nc(Cl)c(Cl)cc1Cl] | |
| 923 | $CF_3$ | 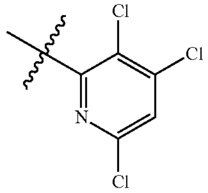 [SMILES: *c1nc(Cl)cc(Cl)c1Cl] | |
| 924 | $CF_3$ | 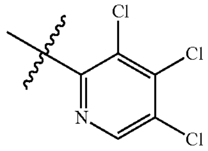 [SMILES: *c1ncc(Cl)c(Cl)c1Cl] | |
| 925 | $CF_3$ | 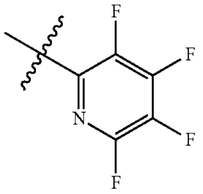 [SMILES: *c1nc(F)c(F)c(F)c1F] | |

TABLE 1-continued
Structure and $^1$HNMR data of Compound I
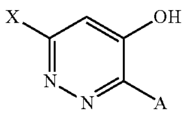
I
| No. | X | A | $^1$H NMR |
|---|---|---|---|
| 926 | $CF_3$ | 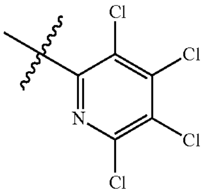 [SMILES: *c1nc(Cl)c(Cl)c(Cl)c1Cl] | |
| 927 | $CF_3$ | 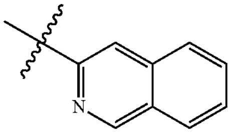 | |
| 928 | $CF_3$ | 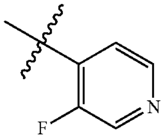 [SMILES: *c1ccncc1F] | |
| 929 | $CF_3$ | 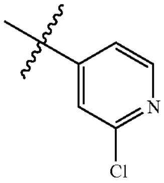 | |
| 930 | $CF_3$ | 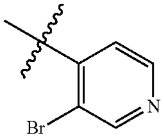 [SMILES: *c1ccncc1Br] | |
| 931 | $CF_3$ | 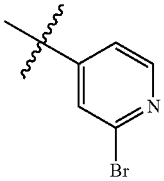 [SMILES: *c1ccnc(Br)c1] | |
| 932 | $CF_3$ | 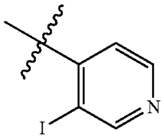 [SMILES: *c1ccncc1I] | |
| 933 | $CF_3$ | 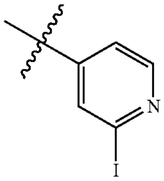 [SMILES: *c1ccnc(I)c1] | |

TABLE 1-continued
Structure and $^1$HNMR data of Compound I
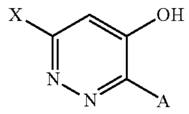
I
| No. | X | A | $^1$H NMR |
|---|---|---|---|
| 934 | $CF_3$ | 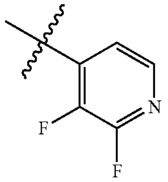 [SMILES: *c1ccnc(F)c1F] | |
| 935 | $CF_3$ | 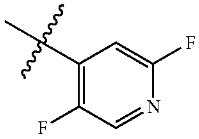 [SMILES: *c1cc(F)ncc1F] | |
| 936 | $CF_3$ | 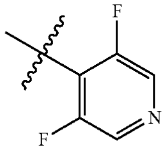 [SMILES: *c1c(F)cncc1F] | |
| 937 | $CF_3$ | 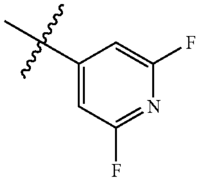 [SMILES: *c1cc(F)nc(F)c1] | |
| 938 | $CF_3$ | 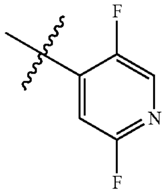 [SMILES: *c1cc(F)ncc1F] | |
| 939 | $CF_3$ | 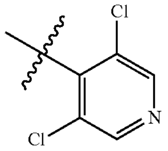 [SMILES: *c1c(Cl)cncc1Cl] | |
| 940 | $CF_3$ | 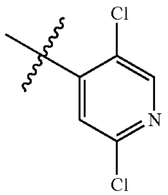 [SMILES: *c1cc(Cl)ncc1Cl] | |

TABLE 1-continued
Structure and ¹HNMR data of Compound I
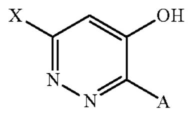
I
| No. | X | A | $^1$H NMR |
|---|---|---|---|
| 941 | $CF_3$ | 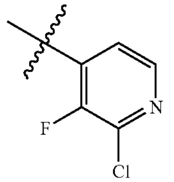 [SMILES: *c1ccnc(Cl)c1F] | |
| 942 | $CF_3$ | 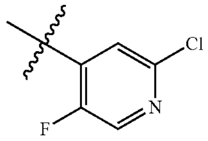 [SMILES: *c1cc(Cl)ncc1F] | |
| 943 | $CF_3$ | 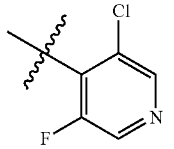 | |
| 944 | $CF_3$ | 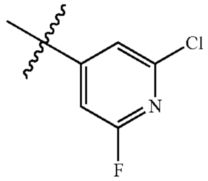 [SMILES: *c1cc(F)nc(Cl)c1] | |
| 945 | $CF_3$ | 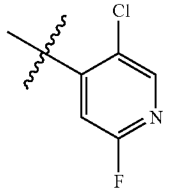 [SMILES: *c1cc(F)ncc1Cl] | |
| 946 | $CF_3$ | 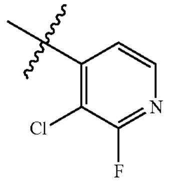 [SMILES: *c1ccnc(F)c1Cl] | |
| 947 | $CF_3$ | 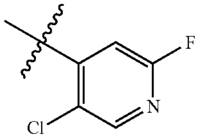 [SMILES: *c1cc(F)ncc1Cl] | |
| 948 | $CF_3$ | 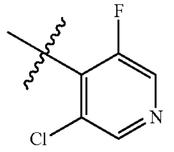 [SMILES: *c1c(F)cncc1Cl] | |

TABLE 1-continued
Structure and $^1$HNMR data of Compound I
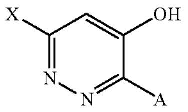
I
| No. | X | A | $^1$H NMR |
|---|---|---|---|
| 949 | $CF_3$ | 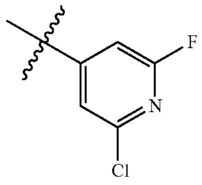 [SMILES: *c1cc(F)nc(Cl)c1] | |
| 950 | $CF_3$ | 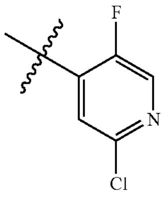 [SMILES: *c1cc(Cl)ncc1F] | |
| 951 | $CF_3$ | 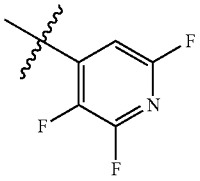 [SMILES: *c1cc(F)nc(F)c1F] | |
| 952 | $CF_3$ | 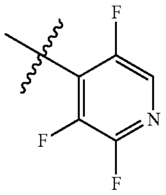 [SMILES: *c1c(F)cnc(F)c1F] | |
| 953 | $CF_3$ | 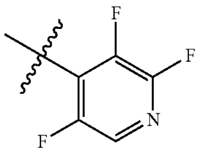 [SMILES: *c1c(F)cnc(F)c1F] | |
| 954 | $CF_3$ | 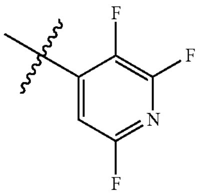 [SMILES: *c1cc(F)nc(F)c1F] | |
| 955 | $CF_3$ | 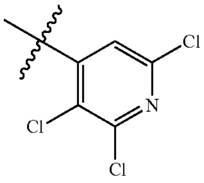 [SMILES: *c1cc(Cl)nc(Cl)c1Cl] | |

TABLE 1-continued
Structure and $^1$HNMR data of Compound I
I
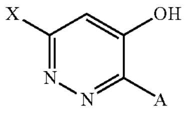
| No. | X | A | $^1$H NMR |
| --- | --- | --- | --- |
| 956 | $CF_3$ | 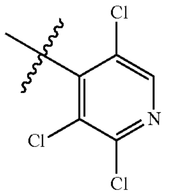 [SMILES: *c1c(Cl)cnc(Cl)c1Cl] | |
| 957 | $CF_3$ | 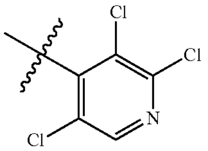 [SMILES: *c1c(Cl)cnc(Cl)c1Cl] | |
| 958 | $CF_3$ | 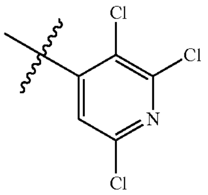 [SMILES: *c1cc(Cl)nc(Cl)c1Cl] | |
| 959 | $CF_3$ | 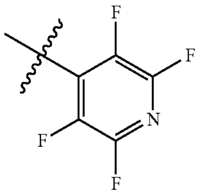 [SMILES: *c1c(F)c(F)nc(F)c1F] | |
| 960 | $CF_3$ | 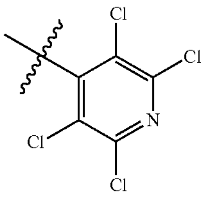 [SMILES: *c1c(Cl)c(Cl)nc(Cl)c1Cl] | |
| 961 | $CF_3$ | 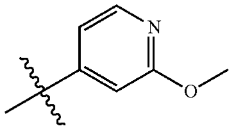 [SMILES: *c1ccnc(OC)c1] | |
| 962 | $CF_3$ | 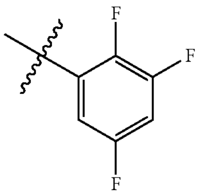 [SMILES: *c1cc(F)cc(F)c1F] | |

TABLE 1-continued

Structure and ¹HNMR data of Compound I

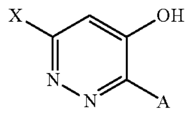

I

| No. | X | A | ¹H NMR |
| --- | --- | --- | --- |
| 963 | $CF_3$ | 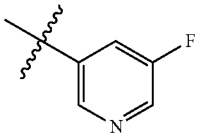 [SMILES: *c1cncc(F)c1] | ¹H NMR (500 MHz, DMSO-d6) δ 12.59 (s, 1H), 8.66 (d, J = 1.5 Hz, 1H), 8.36 (dd, J = 8.0, 1.5 Hz, 1H), 7.66 (m, 1H), 7.24 (s, 1H). |
| 964 | $CF_3$ | 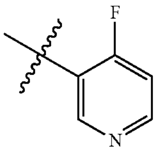 [SMILES: *c1cnccc1F] | ¹H NMR (500 MHz, DMSO-d6) δ 12.67 (s, 1H), 8.84 (d, J = 5.0 Hz, 1H), 8.58 (m, 1H), 7.23 (s, 1H), 7.17 (dd, J = 8.0, 5.0 Hz, 1H). |
| 965 | $CF_3$ | 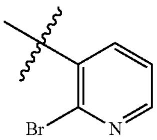 [SMILES: *c1cccnc1Br] | ¹H NMR (500 MHz, DMSO-d6) δ 12.98 (s, 1H), 8.46 (dd, J = 5.0, 1.5 Hz, 1H), 7.99 (dd, J = 8.0, 1.5 Hz, 1H), 7.61 (dd, J = 8.1, 5.0 Hz, 1H), 7.28 (s, 1H). |
| 966 | $CF_3$ | 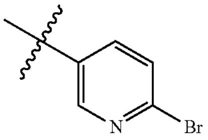 [SMILES: *c1ccc(Br)nc1] | ¹H NMR (500 MHz, DMSO-$d_6$) δ 13.62 (s, 1H), 8.99 (d, J = 2.5 Hz, 1H), 8.34 (dd, J = 8.5, 2.5 Hz, 1H), 7.81 (d, J = 8.5 Hz, 1H), 7.3O (s, 1H). |
| 967 | $CF_3$ | 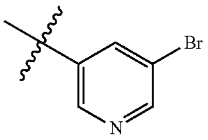 [SMILES: *c1cncc(Br)c1] | ¹H NMR (500 MHz, DMSO-$d_6$) δ 13.73 (s, 1H), 9.14 (s, 1H), 8.82 (s, 1H), 8.59 (s, 1H), 7.32 (s, 1H). |
| 968 | $CF_3$ | 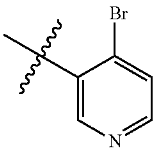 [SMILES: *c1cnccc1Br] | ¹H NMR (500 MHz, DMSO-d6) δ 12.66 (s, 1H), 8.82 (s, 1H), 8.56 (d, J = 5.0 Hz, 1H), 7.68 (d, J = 5.0 Hz, 1H), 7.28 (s, 1H) |
| 969 | $CF_3$ | 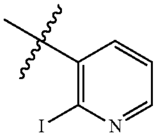 | ¹H NMR (500 MHz, DMSO-d6) δ 13.12 (s, 1H), 8.26 (dd, J = 5.0, 1.5 Hz, 1H), 7.77 (dd, J = 8.0, 1.5 Hz, 1H), 7.50 (dd, J = 8.0, 5.0 Hz, 1H), 7.26 (s, 1H). |
| 970 | $CF_3$ | 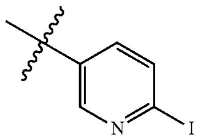 [SMILES: *c1ccc(I)nc1] | ¹H NMR (500 MHz, DMSO-d6) δ 12.87 (s, 1H), 8.59 (d, J = 1.0 Hz, 1H), 7.82 (d, J = 7.5 Hz, 1H), 7.70 (dd, J = 7.5, 1.0 Hz, 1H), 7.28 (s, 1H) |
| 971 | $CF_3$ | 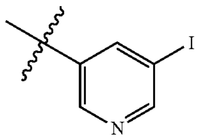 [SMILES: *c1cncc(I)c1] | ¹H NMR (500 MHz, DMSO-d6) δ 13.17 (s, 1H), 8.99 (d, J = 1.0 Hz, 1H), 8.87 (d, J = 1.0 Hz, 1H), 8.31 (s, 1H), 7.23 (s, 1H). |

TABLE 1-continued

Structure and $^1$HNMR data of Compound I

I

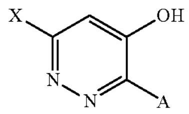

| No. | X | A | $^1$H NMR |
|---|---|---|---|
| 972 | $CF_3$ | 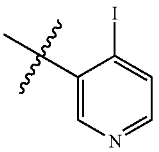 [SMILES: *c1cnccc1I] | $^1$H NMR (500 MHz, DMSO-d6) δ 12.97 (s, 1H), 8.61 (s, 1H), 8.32 (d, J = 5.0 Hz, 1H), 7.80 (d, J = 5.0 Hz, 1H), 7.29 (s, 1H). |
| 973 | $CF_3$ | 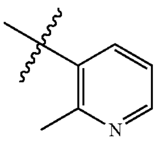 [SMILES: *c1cccnc1C] | $^1$H NMR (500 MHz, DMSO-$d_6$) δ13.62 (s, 1H), 8.55 (dd, J = 5.0, 1.5 Hz, 1H), 7.76 (dd, J = 7.5, 1.5 Hz, 1H), 7.35 (dd, J = 7.5, 5.0 Hz, 1H), 7.30 (s, 1H), 2.32 (s, 3H). |
| 974 | $CF_3$ | 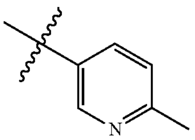 [SMILES: *c1ccc(C)nc1] | $^1$H NMR (500 MHz, DMSO-$d_6$) δ 13.41 (s, 1H), 9.07 (d, J = 2.0 Hz, 1H), 8.30 (dd, J = 8.0, 2.0 Hz, 1H), 7.41 (d, J = 8.0 Hz, 1H), 7.26 (s, 1H), 2.54 (s, 3H). |
| 975 | $CF_3$ | 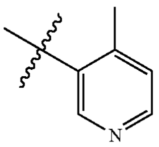 [SMILES: *c1cnccc1C] | $^1$H NMR (500 MHz, Chloroform-d) δ 8.73 (s, 1H), 8.61 (d, J = 5.0 Hz, 1H), 7.26 (d, J = 5.0 Hz, 1H), 6.94 (s, 1H), 5.64 (s, 1H), 2.36 (s, 3H). |
| 976 | $CF_3$ | 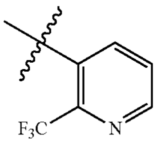 [SMILES: *c1cccnc1C(F)(F)F] | $^1$H NMR (500 MHz, DMSO-$d_6$) δ 13.78 (s, 1H), 8.93-8.92 (m, 1H), 8.49-8.45 (m, 1H), 8.34-8.33 (m, 1H), 7.35 (s, 1H). |
| 977 | $CF_3$ | 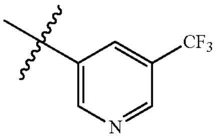 [SMILES: *c1cncc(C(F)(F)F)c1] | $^1$H NMR (500 MHz, DMSO-$d_6$) δ 13.65 (s, 1H), 9.44 (s, 1H), 9.10 (s, 1H), 8.75 (s, 1H), 7.33 (s, 1H). |
| 978 | $CF_3$ | 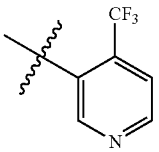 [SMILES: *c1cnccc1C(F)(F)F] | $^1$H NMR (500 MHz, DMSO-d6) δ 12.88 (s, 1H), 8.85 (s, 1H), 8.70 (d, J = 5.0 Hz, 1H), 7.58-7.53 (m, 1H), 7.28 (s, 1H). |
| 979 | $CF_3$ | 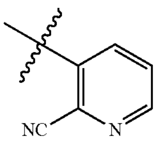 [SMILES: *c1cccnc1C#N] | $^1$H NMR (500 MHz, DMSO-d6) δ 13.37 (s, 1H), 8.85 (dd, J = 5.0, 1.5 Hz, 1H), 8.22 (dd, J = 8.1, 1.5 Hz, 1H), 7.92 (dd, J = 7.9, 5.0 Hz, 1H), 7.28 (s, 1H). |
| 980 | $CF_3$ | 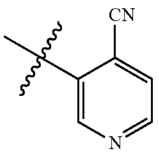 [SMILES: *c1cnccc1C#N] | $^1$H NMR (500 MHz, DMSO-d6) δ 13.27 (s, 1H), 9.09 (s, 1H), 8.88 (d, J = 5.0 Hz, 1H), 7.86 (d, J = 5.0 Hz, 1H), 7.25 (s, 1H). |

TABLE 1-continued

Structure and $^{1}$HNMR data of Compound I

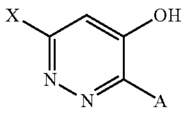

I

| No. | X | A | $^{1}$H NMR |
| --- | --- | --- | --- |
| 981 | $CF_3$ | 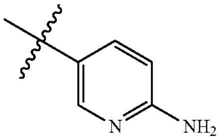 | $^{1}$H NMR (500 MHz, DMSO-$d_6$) δ 8.84 (d, J = 2.5 Hz, 1H), 8.22 (dd, J = 8.5, 2.5 Hz, 1H), 7.16 (s, 1H), 6.76 (s, 2H), 6.62 (d, J = 8.5 Hz, 1H). |
| 982 | $CF_3$ | 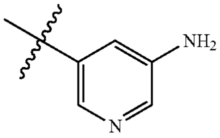 [SMILES: *c1cncc(N)c1] | $^{1}$H NMR (500 MHz, DMSO-$d_6$) δ 8.47 (s, 1H), 7.99 (s, 1H), 7.75 (s, 1H), 7.15 (s, 1H). |
| 983 | $CF_3$ | 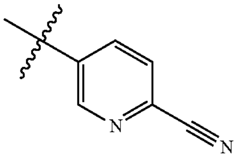 [SMILES: *c1ccc(C#N)nc1] | $^{1}$H NMR (500 MHz, DMSO-$d_6$) δ 13.53 (s, 1H), 9.31 (d, J = 2.0 Hz, 1H), 8.63 (dd, J = 8.0, 2.0 Hz, 1H), 8.18 (d, J = 8.0 Hz, 1H), 7.33 (s, 1H). |
| 984 | $CF_3$ | 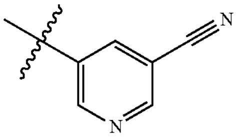 [SMILES: *c1cncc(C#N)c1] | $^{1}$H NMR (500 MHz, DMSO-$d_6$) δ 13.84 (s, 1H), 9.40 (s, 1H), 9.14 (s, 1H), 8.84 (s, 1H), 7.34 (s, 1H). |
| 985 | $CF_3$ | 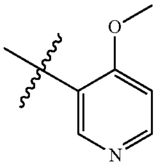 [SMILES: *c1cnccc1OC] | |
| 986 | $CF_3$ | 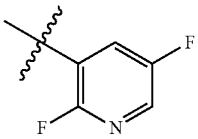 [SMILES: *c1cc(F)cnc1F] | $^{1}$H NMR (500 MHz, DMSO-d6) δ 13.02 (s, 1H), 8.43-8.35 (dd, J = 8.0, 1.0 Hz, 1H), 7.84-7.81 (m, 1H), 7.24 (s, 1H). |
| 987 | $CF_3$ | 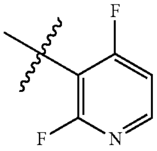 | $^{1}$H NMR (500 MHz, DMSO-d6) δ 13.22 (s, 1H), 8.45-8.41 (m, 1H), 7.25-7.18 (m, 2H). |
| 988 | $CF_3$ | 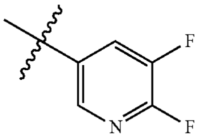 [SMILES: *c1cnc(F)c(F)c1] | $^{1}$H NMR (500 MHz, DMSO-d6) δ 13.14 (s, 1H), 8.58-8.43 (m, 1H), 7.91-7.88 (m, 1H), 7.24 (s, 1H). |

TABLE 1-continued

Structure and $^1$HNMR data of Compound I

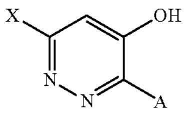

I

| No. | X | A | $^1$H NMR |
|---|---|---|---|
| 989 | $CF_3$ | 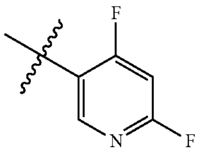 [SMILES: *c1cnc(F)cc1F] | $^1$H NMR (500 MHz, DMSO-d6) δ 13.02 (s, 1H), 8.76-8.63 (m, 1H), 7.24 (s, 1H), 7.01 (m, 1H). |
| 990 | $CF_3$ | 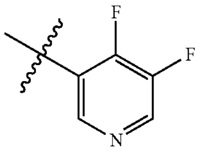 [SMILES: *c1cncc(F)c1F] | $^1$H NMR (500 MHz, DMSO-d6) δ 13.22 (s, 1H), 8.66-8.42 (m, 1H), 8.35-8.23 (m, 1H), 7.36 (s, 1H). |
| 991 | $CF_3$ | 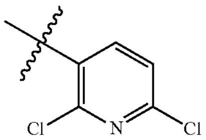 [SMILES: *c1ccc(Cl)nc1Cl] | $^1$H NMR (500 MHz, DMSO-d6) δ 13.15 (s, 1H), 8.16 (d, J = 8.0 Hz, 1H), 7.43 (d, J = 8.0 Hz, 1H), 7.24 (s, 1H). |
| 992 | $CF_3$ | 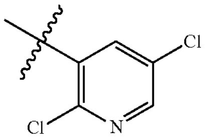 [SMILES: *c1cc(Cl)cnc1Cl] | $^1$H NMR (500 MHz, DMSO-d6) δ 13.01 (s, 1H), 8.60 (d, J = 1.5 Hz, 1H), 8.12 (d, J = 1.5 Hz, 1H), 7.24 (s, 1H). |
| 993 | $CF_3$ | 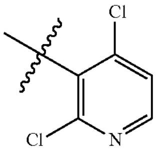 [SMILES: *c1c(Cl)ccnc1Cl] | $^1$H NMR (500 MHz, DMSO-d6) δ 13.08 (s, 1H), 8.59 (d, J = 5.0 Hz, 1H), 7.59 (d, J = 5.0 Hz, 1H), 7.24 (s, 1H). |
| 994 | $CF_3$ | 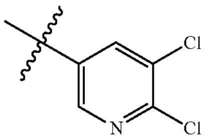 [SMILES: *c1cnc(Cl)c(Cl)c1] | $^1$H NMR (500 MHz, DMSO-d6) δ 12.99 (s, 1H), 8.95 (d, J = 1.5 Hz, 1H), 8.23 (d, J = 1.5 Hz, 1H), 7.24 (s, 1H). |
| 995 | $CF_3$ | 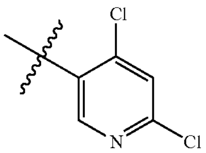 [SMILES: *c1cnc(Cl)cc1Cl] | $^1$H NMR (500 MHz, DMSO-d6) δ 13.41 (s, 1H), 8.88 (s, 1H), 7.68 (s, 1H), 7.24 (s, 1H). |
| 996 | $CF_3$ | 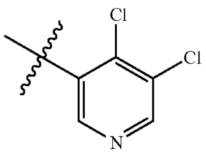 | $^1$H NMR (500 MHz, DMSO-d6) δ 13.25 (s, 1H), 8.77 (d, J = 1.5 Hz, 1H), 8.49 (d, J = 1.5 Hz, 1H), 7.24 (s, 1H). |
| 997 | $CF_3$ | 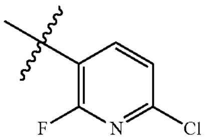 [SMILES: *c1ccc(Cl)nc1F] | $^1$H NMR (500 MHz, DMSO-$d_6$) δ 13.38 (s, 1H), 8.29 (dd, J = 8.5, 7.5 Hz, 1H), 7.71 (d, J = 7.5 Hz, 1H), 7.36 (s, 1H). |

TABLE 1-continued

Structure and $^{1}$HNMR data of Compound I

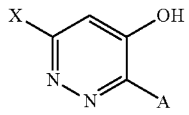

I

| No. | X | A | $^{1}$H NMR |
|---|---|---|---|
| 998 | $CF_3$ | 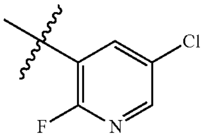 [SMILES: *c1cc(Cl)cnc1F] | $^{1}$H NMR (500 MHz, DMSO-d6) δ 13.31 (s, 1H), 8.43 (dd, J = 7.5, 1.0 Hz, 1H), 8.21 (dd, J = 5.0, 1.0 Hz, 1H), 7.24 (s, 1H). |
| 999 | $CF_3$ | 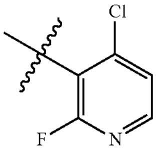 [SMILES: *c1c(Cl)ccnc1F] | $^{1}$H NMR (500 MHz, DMSO-d6) δ 13.22 (s, 1H), 8.42 (dd, J = 6.0, 5.0 Hz, 1H), 7.50 (d, J = 5.0 Hz, 1H), 7.23 (s, 1H). |
| 1000 | $CF_3$ | 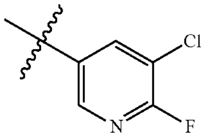 [SMILES: *c1cnc(F)c(Cl)c1] | $^{1}$H NMR (500 MHz, DMSO-d6) δ 13.45 (s, 1H), 8.79 (dd, J = 6.5, 1.0 Hz, 1H), 8.30 (dd, J = 5.0, 1.0 Hz, 1H), 7.24 (s, 1H). |
| 1001 | $CF_3$ | 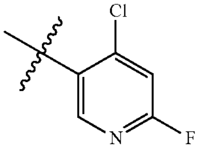 [SMILES: *c1cnc(F)cc1Cl] | $^{1}$H NMR (500 MHz, DMSO-d6) δ 12.88 (s, 1H), 8.71 (d, J = 5.5 Hz, 1H), 7.31 (d, J = 7.5 Hz, 1H), 7.24 (s, 1H). |
| 1002 | $CF_3$ | 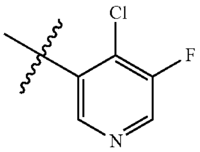 [SMILES: *c1cncc(F)c1Cl] | $^{1}$H NMR (500 MHz, DMSO-d6) δ 13.13 (s, 1H), 8.55 (s, 1H), 8.36 (d, J = 8.0 Hz, 1H), 7.24 (s, 1H). |
| 1003 | $CF_3$ | 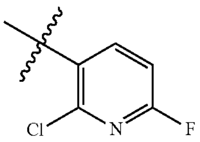 [SMILES: *c1ccc(F)nc1Cl] | $^{1}$H NMR (500 MHz, DMSO-d6) δ 13.17 (s, 1H), 8.27 (dd, J = 8.0, 5.0 Hz, 1H), 7.24 (s, 1H), 7.07 (dd, J = 9.5, 8.0 Hz, 1H). |
| 1004 | $CF_3$ | 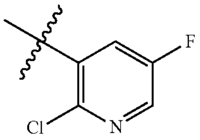 [SMILES: *c1cc(F)cnc1Cl] | $^{1}$H NMR (500 MHz, DMSO-d6) δ 13.05 (s, 1H), 8.60 (dd, J = 8.0, 1.0 Hz, 1H), 7.74 (dd, J = 5.5, 1.0 Hz, 1H), 7.24 (s, 1H). |
| 1005 | $CF_3$ | 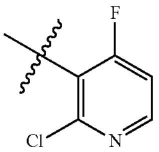 [SMILES: *c1c(F)ccnc1Cl] | $^{1}$H NMR (500 MHz, DMSO-d6) δ 13.09 (s, 1H), 8.62 (dd, J = 6.5, 5.0 Hz, 1H), 7.30 (dd, J = 8.0, 5.0 Hz, 1H), 7.23 (s, 1H). |
| 1006 | $CF_3$ | 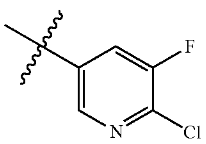 [SMILES: *c1cnc(Cl)c(F)c1] | $^{1}$H NMR (500 MHz, DMSO-d6) δ 13.18 (s, 1H), 8.75 (d, J = 1.0 Hz, 1H), 7.83 (dd, J = 8.0, 1.0 Hz, 1H), 7.24 (s, 1H). |

TABLE 1-continued
Structure and 1HNMR data of Compound I
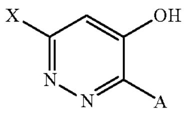
I
| No. | X | A | 1H NMR |
|---|---|---|---|
| 1007 | $CF_3$ | 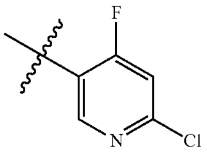 [SMILES: *c1cnc(Cl)cc1F] | 1H NMR (500 MHz, DMSO-d6) δ 13.27 (s, 1H), 8.93 (d, J = 5.0 Hz, 1H), 7.38 (d, J = 8.0 Hz, 1H), 7.23 (s, 1H). |
| 1008 | $CF_3$ | 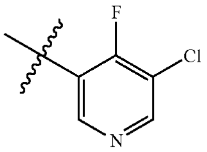 [SMILES: *c1cncc(Cl)c1F] | 1H NMR (500 MHz, DMSO-d6) δ 12.57 (s, 1H), 8.88 (d, J = 5.0 Hz, 1H), 8.47 (d, J = 4.0 Hz, 1H), 7.36 (s, 1H). |
| 1009 | $CF_3$ | 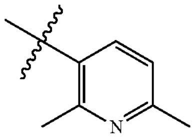 [SMILES: *c1ccc(C)nc1C] | |
| 1010 | $CF_3$ | 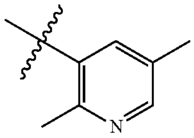 | |
| 1011 | $CF_3$ | 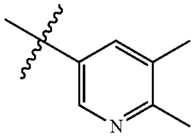 [SMILES: *c1cnc(C)c(C)c1] | |
| 1012 | $CF_3$ | 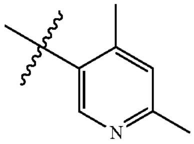 [SMILES: *c1cnc(C)cc1C] | |
| 1013 | $CF_3$ | 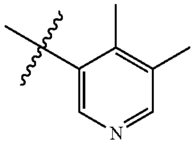 [SMILES: *c1cncc(C)c1C] | |
| 1014 | $CF_3$ | 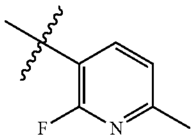 | |
| 1015 | $CF_3$ | 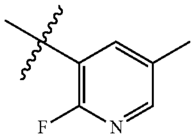 | |

TABLE 1-continued
Structure and $^{1}$HNMR data of Compound I
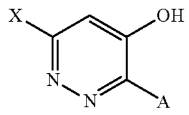
I
| No. | X | A | $^{1}$H NMR |
| --- | --- | --- | --- |
| 1016 | $CF_3$ | 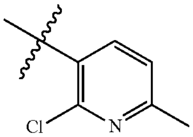 [SMILES: *c1ccc(C)nc1Cl] | |
| 1017 | $CF_3$ | 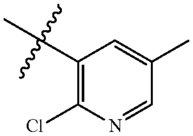 [SMILES: *c1cc(C)cnc1Cl] | |
| 1018 | $CF_3$ | 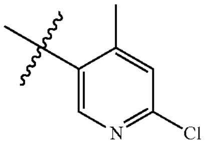 [SMILES: *c1cnc(Cl)cc1C] | $^{1}$H NMR (500 MHz, DMSO-$d_6$) δ 13.15 (s, 1H), 8.36 (s, 1H), 7.57 (s, 1H), 7.34 (s, 1H), 2.20 (s, 3H). |
| 1019 | $CF_3$ | 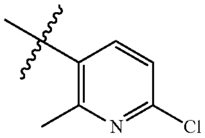 [SMILES: *c1ccc(Cl)nc1C] | |
| 1020 | $CF_3$ | 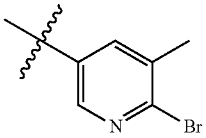 [SMILES: *c1cnc(Br)c(C)c1] | |
| 1021 | $CF_3$ | 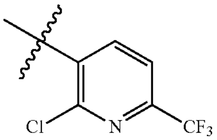 | |
| 1022 | $CF_3$ | 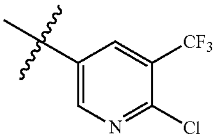 [SMILES: *c1cnc(Cl)c(C(F)(F)F)c1] | |
| 1023 | $CF_3$ | 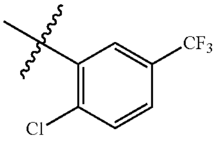 [SMILES: *c1cc(C(F)(F)F)ccc1Cl] | |
| 1024 | $CF_3$ | 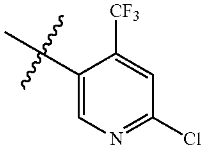 | |

TABLE 1-continued
Structure and $^1$HNMR data of Compound I
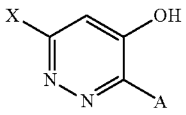
I
| No. | X | A | $^1H$ NMR |
|---|---|---|---|
| 1025 | $CF_3$ | 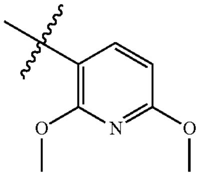 | |
| 1026 | $CF_3$ | 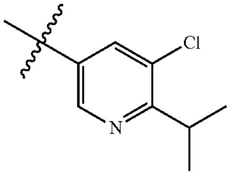 [SMILES: *c1cnc(C(C)C)c(Cl)c1] | |
| 1027 | $CF_3$ | 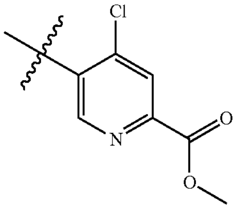 [SMILES: *c1cnc(C(=O)OC)cc1Cl] | |
| 1028 | $CF_3$ | 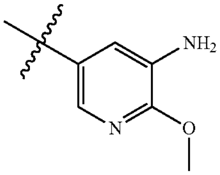 [SMILES: *c1cnc(OC)c(N)c1] | $^1H$ NMR (500 MHz, DMSO-$d_6$) δ 12.70 (s, 1H), 8.14 (d, J = 2.0 Hz, 1H), 7.58 (d, J = 2.0 Hz, 1H), 7.24 (s, 1H), 5.18 (s, 2H), 3.91 (s, 3H). |
| 1029 | $CF_3$ | 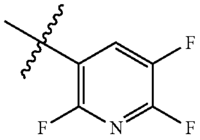 [SMILES: *c1cc(F)c(F)nc1F] | |
| 1030 | $CF_3$ | 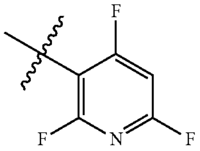 [SMILES: *c1c(F)cc(F)nc1F] | |
| 1031 | $CF_3$ | 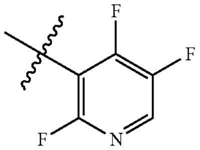 [SMILES: *c1c(F)ncc(F)c1F] | |
| 1032 | $CF_3$ | 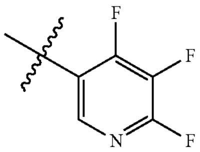 [SMILES: *c1cnc(F)c(F)c1F] | |

TABLE 1-continued
Structure and $^1$HNMR data of Compound I
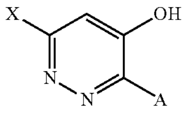
I
| No. | X | A | $^1$H NMR |
|---|---|---|---|
| 1033 | $CF_3$ | 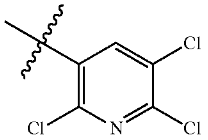 [SMILES: *c1cc(Cl)c(Cl)nc1Cl] | |
| 1034 | $CF_3$ | 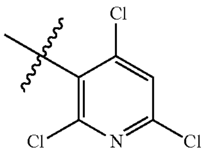 [SMILES: *c1c(Cl)cc(Cl)nc1Cl] | |
| 1035 | $CF_3$ | 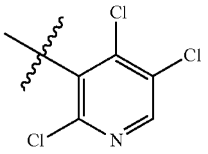 [SMILES: *c1c(Cl)ncc(Cl)c1Cl] | |
| 1036 | $CF_3$ | 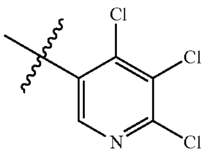 [SMILES: *c1cnc(Cl)c(Cl)c1Cl] | |
| 1037 | $CF_3$ | 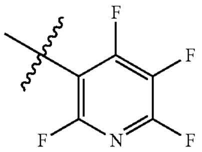 [SMILES: *c1c(F)nc(F)c(F)c1F] | |
| 1038 | $CF_3$ | 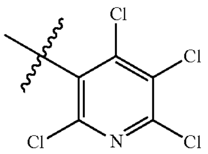 [SMILES: *c1c(Cl)nc(Cl)c(Cl)c1Cl] | |
| 1039 | $CF_3$ | 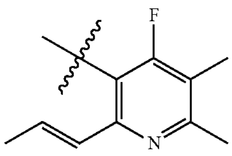 [SMILES: *c1c(/C=C/C)nc(C)c(C)c1F] | |
| 1040 | $CF_3$ | 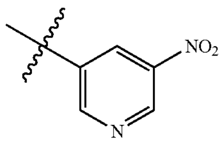 [SMILES: *c1cncc([N+](=O)[O-])c1] | |

TABLE 1-continued
Structure and $^1$HNMR data of Compound I
I
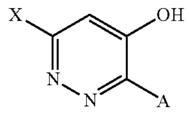
| No. | X | A | $^1$H NMR |
|---|---|---|---|
| 1041 | $CF_3$ | 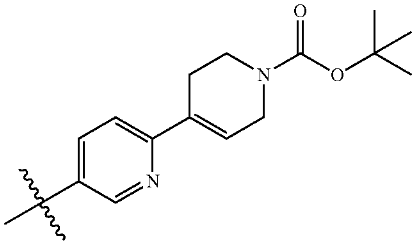 [SMILES: *c1ccc(C2=CCN(C(=O)OC(C)(C)C)CC2)nc1] | $^1$H NMR (500 MHz, DMSO-$d_6$) δ 13.13 (s, 1H), 8.89 (d, J = 2.5 Hz, 1H), 8.24 (dd, J = 9.0, 2.5 Hz, 1H), 7.19 (s, 1H), 6.94 (d, J = 9.0 Hz, 1H), 3.65-3.55 (m, 4H), 3.42 (s, 4H), 1.41 (s, 9H). |
| 1042 | $CF_3$ | 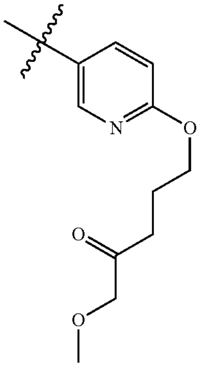 | |
| 1043 | $CF_3$ | 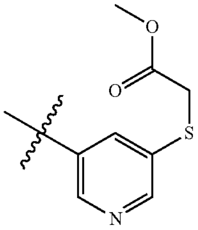 [SMILES: *c1cncc(SCC(=O)OC)c1] | |
| 1044 | $CF_3$ | 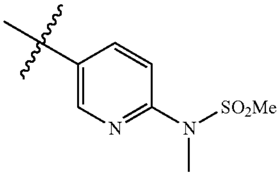 [SMILES: *c1ccc(N(C)S(C)(=O)=O)nc1] | |
| 1045 | $CF_3$ | 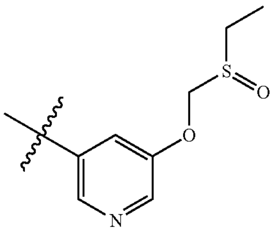 [SMILES: *c1cncc(OCS(=O)CC)c1] | |

TABLE 1-continued
Structure and ¹HNMR data of Compound I
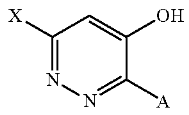
I
| No. | X | A | $^1H$ NMR |
|---|---|---|---|
| 1046 | $CF_3$ | 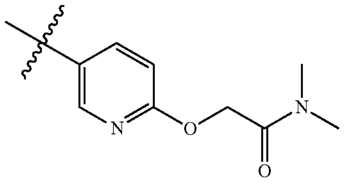 [SMILES: *c1ccc(OCC(=O)N(C)C)nc1] | |
| 1047 | $CF_3$ | 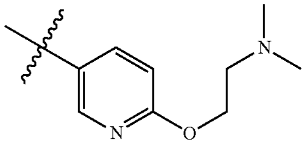 [SMILES: *c1ccc(OCCN(C)C)nc1] | |
| 1048 | $CF_3$ | 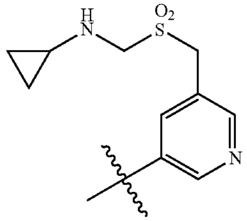 [SMILES: *c1cncc(CS(=O)(=O)CNC2CC2)c1] | |
| 1049 | $CF_3$ | 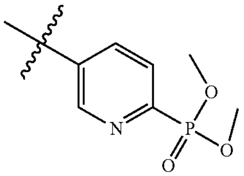 [SMILES: *c1ccc(P(=O)(OC)OC)nc1] | |
| 1050 | $CF_3$ | 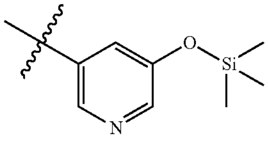 [SMILES: *c1cncc(O[Si](C)(C)C)c1] | |
| 1051 | $CF_3$ | 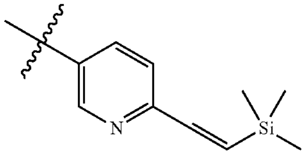 [SMILES: *c1ccc(C=C[Si](C)(C)C)nc1] | |
| 1052 | $CF_3$ | 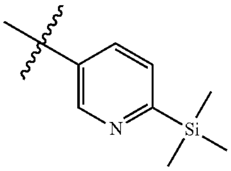 [SMILES: *c1ccc([Si](C)(C)C)nc1] | |
| 1053 | $CF_3$ | 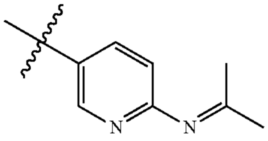 [SMILES: *c1ccc(N=C(C)C)nc1] | |

TABLE 1-continued
Structure and $^{1}$HNMR data of Compound I
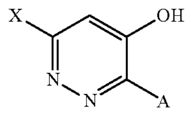
I
| No. | X | A | $^{1}$H NMR |
|---|---|---|---|
| 1054 | $CF_3$ | 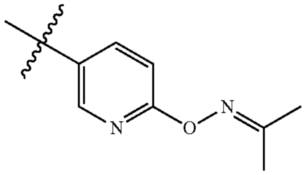 [SMILES: *c1ccc(ON=C(C)C)nc1] | |
| 1055 | $CF_3$ | 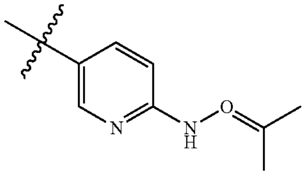 | |
| 1056 | $CF_3$ | 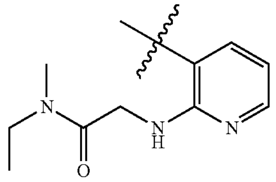 [SMILES: *c1cccnc1NCC(=O)N(C)CC] | |
| 1057 | $CF_3$ | 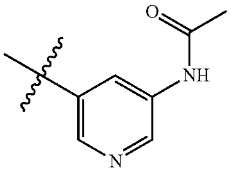 [SMILES: *c1cncc(NC(C)=O)c1] | |
| 1058 | $CF_3$ | 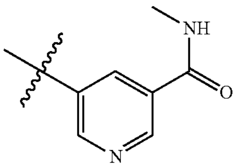 [SMILES: *c1cncc(C(=O)NC)c1] | |
| 1059 | $CF_3$ | 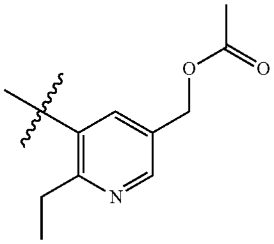 [SMILES: *c1cc(COC(C)=O)cnc1CC] | |

TABLE 1-continued
Structure and $^1$HNMR data of Compound I
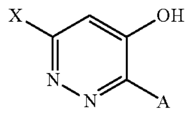
I
| No. | X | A | $^1$H NMR |
| --- | --- | --- | --- |
| 1060 | $CF_3$ | 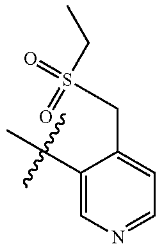 [SMILES: *c1cnccc1CS(=O)(=O)CC] | |
| 1061 | $CF_3$ | 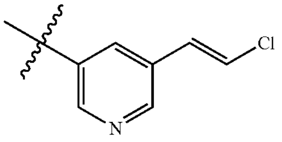 [SMILES: *c1cncc(/C=C/Cl)c1] | |
| 1062 | $CF_3$ | 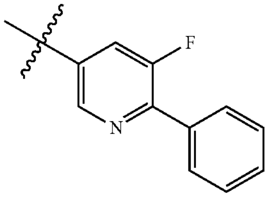 [SMILES: *c1cnc(-c2ccccc2)c(F)c1] | |
| 1063 | $CF_3$ | 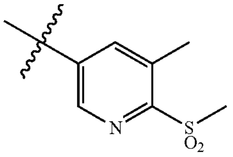 [SMILES: *c1cnc(S(C)(=O)=O)c(C)c1] | |
| 1064 | $CF_3$ | 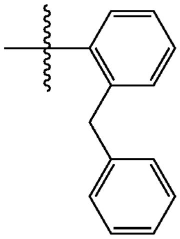 [SMILES: *c1ccccc1Cc1ccccc1] | |
| 1065 | $CF_3$ | 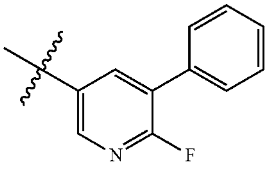 [SMILES: *c1cnc(F)c(-c2ccccc2)c1] | |
| 1066 | $CF_3$ | 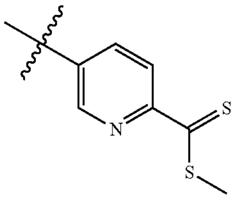 [SMILES: *c1ccc(C(=S)SC)nc1] | |

TABLE 1-continued
Structure and 1HNMR data of Compound I
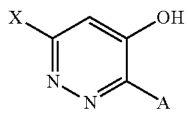
I
| No. | X | A | $^1$H NMR |
|---|---|---|---|
| 1067 | $CF_3$ | 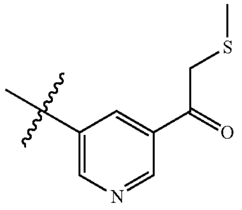 [SMILES: *c1cncc(C(=O)CSC)c1] | |
| 1068 | $CF_3$ | 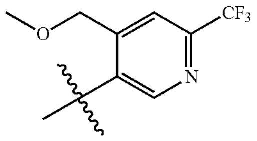 [SMILES: *c1cnc(C(F)(F)F)cc1COC] | |
| 1069 | $CF_3$ | 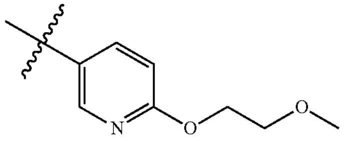 [SMILES: *c1ccc(OCCOC)nc1] | |
| 1070 | $CF_2CF_3$ | 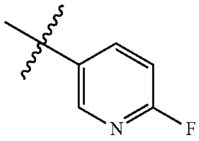 | |
| 1071 | $CF_2CF_3$ | 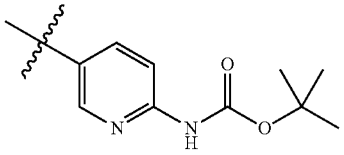 [SMILES: *c1ccc(NC(=O)OC(C)(C)C)nc1] | |
| 1072 | $CF_2CF_3$ | 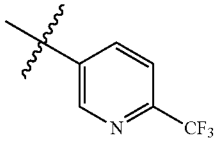 [SMILES: *c1ccc(C(F)(F)F)nc1] | |
| 1073 | $CH_2F$ | 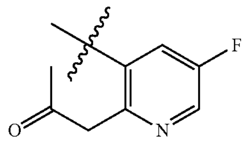 [SMILES: *c1cc(F)cnc1CC(C)=O] | |
| 1074 | $CH_2F$ | 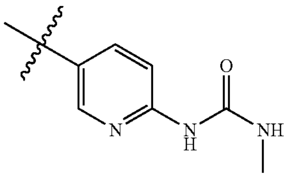 [SMILES: *c1ccc(NC(=O)NC)nc1] | |

TABLE 1-continued

Structure and $^1$HNMR data of Compound I

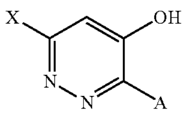

I

| No. | X | A | $^1$H NMR |
| --- | --- | --- | --- |
| 1075 | $CH_2F$ | 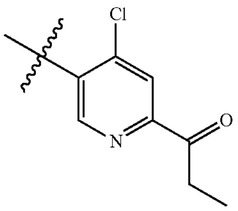 [SMILES: *c1cnc(C(=O)CC)cc1Cl] | |
| 1076 | $CH_2F$ | 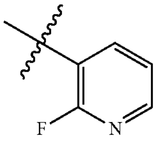 [SMILES: *c1cccnc1F] | $^1$H NMR (500 MHz, DMSO-$d_6$) δ 13.15 (s, 1H), 8.43-8.33 (m, 1H), 7.99-7.80 (m, 1H), 7.74-7.55 (m, 1H), 6.95 (s, 1H), 5.40 (d, J = 65.0 Hz, 2H). |
| 1077 | $CH_2F$ | 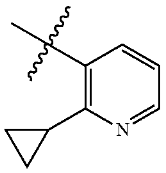 [SMILES: *c1cccnc1C1CC1] | $^1$H NMR (500 MHz, DMSO-$d_6$) δ 13.18 (s, 1H), 8.73 (dd, J = 4.5, 1.5 Hz, 1H), 7.80-7.71 (m, 2H), 6.96 (s, 1H), 5.40 (d, J = 65.0 Hz, 2H), 1.87-1.81 (m, 1H), 0.77-0.65 (m, 2H), 0.62-0.55 (m, 2H). |
| 1078 | $CH_2F$ | 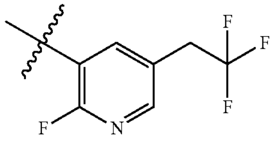 [SMILES: *c1cc(CC(F)(F)F)cnc1F] | $^1$H NMR (500 MHz, DMSO-$d_6$) δ 13.00 (s, 1H), 8.47 (dd, J = 5.5, 1.0 Hz, 1H), 8.14 (dd, J = 7.0, 1.0 Hz, 1H), 7.04 (s, 1H), 5.40 (d, J = 65.0 Hz, 2H), 3.07 (q, J = 9.0 Hz, 2H). |
| 1079 | $CH_2F$ | 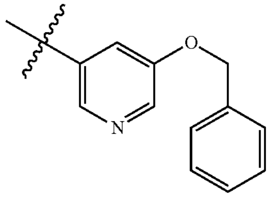 [SMILES: *c1cncc(OCc2ccccc2)c1] | |
| 1080 | $CH_2F$ | 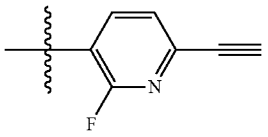 [SMILES: *c1ccc(C#C)nc1F] | $^1$H NMR (500 MHz, DMSO-$d_6$) δ 13.18 (s, 1H), 8.26 (dd, J = 8.0, 5.0 Hz, 1H), 7.82 (d, J = 8.0 Hz, 1H), 6.96 (s, 1H), 6.60 (t, J = 73.5 Hz, 1H), 5.30 (s, 1H). |
| 1081 | $CF_2CF_3$ | 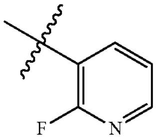 [SMILES: *c1cccnc1F] | $^1$H NMR (500 MHz, DMSO-$d_6$) δ 13.05 (s, 1H), 8.43-8.35 (m, 1H), 8.04-7.90 (m, 1H), 7.75-7.61 (m, 1H), 7.00 (s, 1H). |
| 1082 | $CF_2CF_3$ | 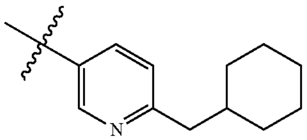 [SMILES: *c1ccc(CC2CCCCC2)nc1] | $^1$H NMR (500 MHz, DMSO-$d_6$) δ 12.97 (s, 1H), 9.16 (d, J = 1.5 Hz, 1H), 8.18 (dd, J = 8.0, 1.5 Hz, 1H), 7.74 (d, J = 8.0 Hz, 1H), 6.96 (s, 1H), 3.00 (d, J = 7.0 Hz, 2H), 1.73-1.52 (m, 4H), 1.56-1.37 (m, 2H), 1.33-1.14 (m, 5H). |

TABLE 1-continued
Structure and $^1$HNMR data of Compound I
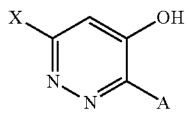
I
| No. | X | A | $^1H$ NMR |
|---|---|---|---|
| 1083 | $CF_2CF_3$ | 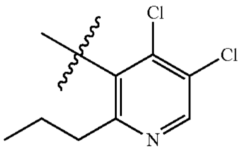 [SMILES: *c1c(CCC)ncc(Cl)c1Cl] | $^1H$ NMR (500 MHz, DMSO-$d_6$) δ 13.14 (s, 1H), 8.81 (s, 1H), 6.89 (s, 1H), 2.98 (t, J = 7.5 Hz, 2H), 1.70-1.55 (m, 2H), 0.92 (t, J = 8.0 Hz, 3H). |
| 1084 | $CH_2F$ | 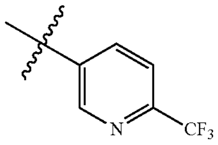 | |
| 1085 | $CHF_2$ | 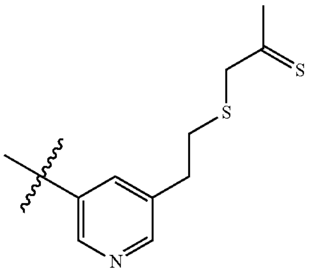 [SMILES: *c1cncc(CCSCC(C)=S)c1] | |
| 1086 | $CHF_2$ | 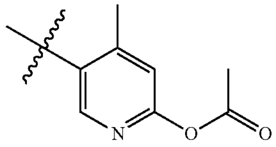 [SMILES: *c1cnc(OC(C)=O)cc1C] | |
| 1087 | $CH_2F$ | 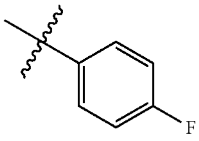 | |
| 1088 | $CH_2F$ | 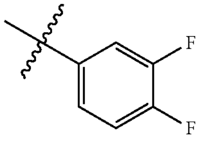 | |
| 1089 | $CHF_2$ | 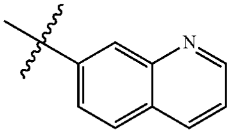 [SMILES: *c1ccc2cccnc2c1] | |
| 1090 | $CHF_2$ | 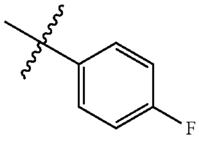 [SMILES: *c1ccc(F)cc1] | |

TABLE 1-continued
Structure and $^1$HNMR data of Compound I
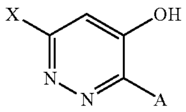
I
| No. | X | A | $^1$H NMR |
|---|---|---|---|
| 1091 | $CHF_2$ | 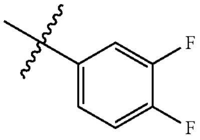 [SMILES: *c1ccc(F)c(F)c1] | |
| 1092 | $CF_2CF_3$ | 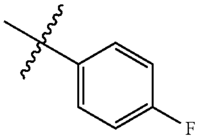 | |
| 1093 | $CF_2CF_3$ | 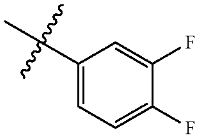 | |
| 1094 | $CF_2CF_3$ | 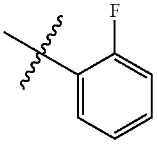 [SMILES: *c1ccccc1F] | |
| 1095 | $CF_2CF_3$ | 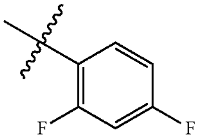 [SMILES: *c1ccc(F)cc1F] | |
| 1096 | $CF_2CF_3$ | 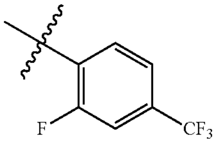 | |
| 1097 | $CF_2CF_3$ | 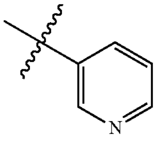 [SMILES: *c1cccnc1] | |
| 1098 | $CF_3$ | 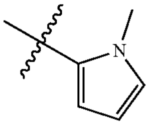 [SMILES: *c1cccn1C] | |
| 1099 | $CF_3$ | 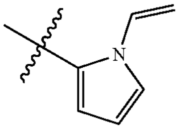 [SMILES: *c1cccn1C=C] | |

TABLE 1-continued
Structure and $^1$HNMR data of Compound I
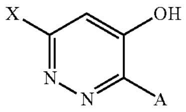
I
| No. | X | A | $^1H$ NMR |
| --- | --- | --- | --- |
| 1100 | $CF_3$ | 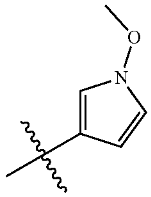 [SMILES: *c1ccn(OC)c1] | |
| 1101 | $CF_3$ | 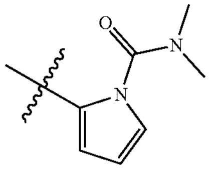 [SMILES: *c1cccn1C(=O)N(C)C] | |
| 1102 | $CF_3$ | 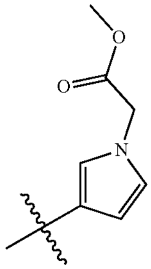 [SMILES: *c1ccn(CC(=O)OC)c1] | |
| 1103 | $CF_3$ | 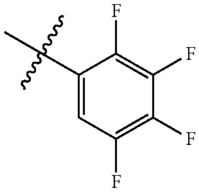 [SMILES: *c1cc(F)c(F)c(F)c1F] | |
| 1104 | $CF_3$ | 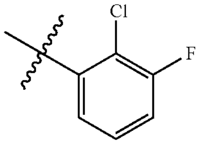 | |
| 1105 | $CF_3$ | 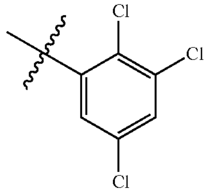 [SMILES: *c1cc(Cl)cc(Cl)c1Cl] | |

TABLE 1-continued
Structure and $^1$HNMR data of Compound I
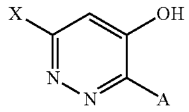
I
| No. | X | A | $^1$H NMR |
|---|---|---|---|
| 1106 | $CF_3$ | 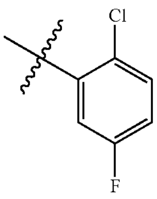 [SMILES: *c1cc(F)ccc1Cl] | |
| 1107 | $CF_3$ | 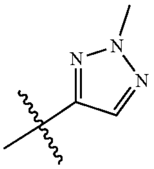 [SMILES: *c1cnn(C)n1] | |
| 1108 | $CF_3$ | 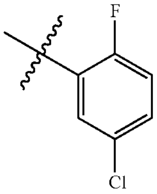 [SMILES: *c1cc(Cl)ccc1F] | |
| 1109 | $CF_3$ | 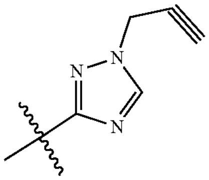 [SMILES: *c1ncn(CC#C)n1] | |
| 1110 | $CF_3$ | 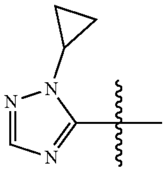 [SMILES: *c1ncnn1C1CC1] | |
| 1111 | $CF_3$ | 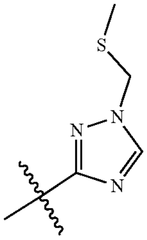 [SMILES: *c1ncn(CSC)n1] | |

TABLE 1-continued
Structure and $^1$HNMR data of Compound I
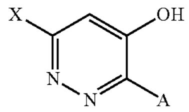
I
| No. | X | A | $^{1}H$ NMR |
| --- | --- | --- | --- |
| 1112 | $CF_3$ | 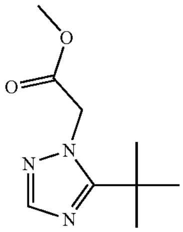 | |
| 1113 | $CF_3$ | 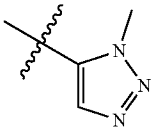 [SMILES: *c1cnnn1C] | |
| 1114 | $CF_3$ | 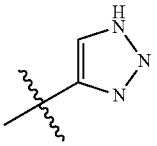 [SMILES: *C1=CNNN1] | |
| 1115 | $CF_3$ | 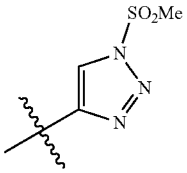 [SMILES: *c1cn(S(C)(=O)=O)nn1] | |
| 1116 | $CF_3$ | 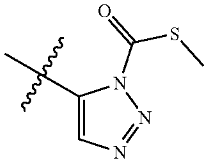 [SMILES: *c1cnnn1C(=O)SC] | |
| 1117 | $CF_3$ | 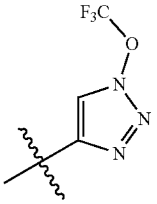 [SMILES: *c1cn(OC(F)(F)F)nn1] | |
| 1118 | $CF_3$ | 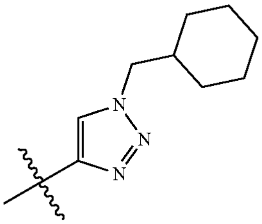 [SMILES: *c1cn(CC2CCCCC2)nn1] | |

TABLE 1-continued
Structure and $^1$HNMR data of Compound I
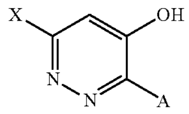
I
| No. | X | A | $^1$H NMR |
|---|---|---|---|
| 1119 | $CF_3$ | 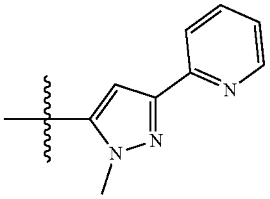 [SMILES: *c1cc(-c2ccccn2)nn1C] | |
| 1120 | $CF_3$ | 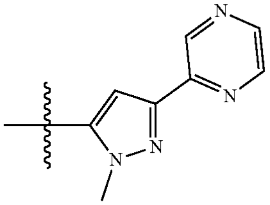 [SMILES: *c1cc(-c2cnccn2)nn1C] | |
| 1121 | $CF_3$ | 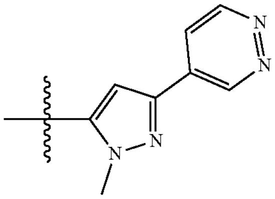 [SMILES: *c1cc(-c2ccnnc2)nn1C] | |
| 1122 | $CF_3$ | 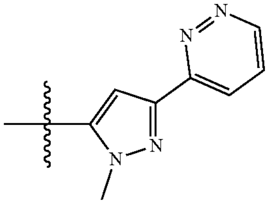 [SMILES: *c1cc(-c2cccnn2)nn1C] | |
| 1123 | $CF_3$ | 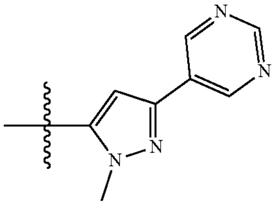 [SMILES: *c1cc(-c2cncnc2)nn1C] | |
| 1124 | $CF_3$ | 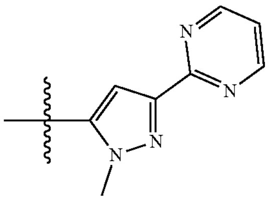 [SMILES: *c1cc(-c2ncccn2)nn1C] | |

TABLE 1-continued
Structure and $^1$HNMR data of Compound I
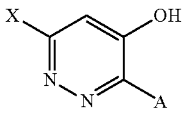
I
| No. | X | A | $^1$H NMR |
| --- | --- | --- | --- |
| 1125 | $CF_3$ | 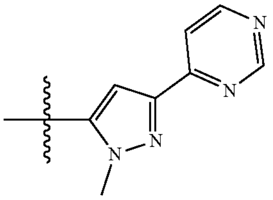 [SMILES: *c1cc(-c2ccncn2)nn1C] | |
| 1126 | $CF_3$ | 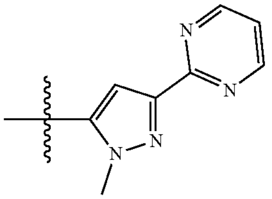 [SMILES: *c1cc(-c2ncccn2)nn1C] | |
| 1127 | $CF_3$ | 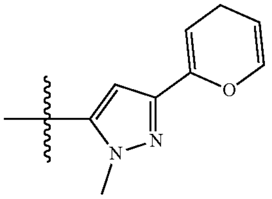 [SMILES: *c1cc(C2=CCC=CO2)nn1C] | |
| 1128 | $CF_3$ | 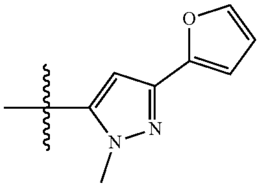 [SMILES: *c1cc(-c2ccco2)nn1C] | |
| 1129 | $CF_3$ | 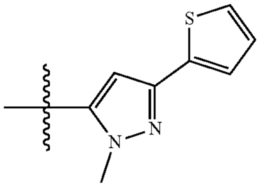 | |
| 1130 | $CF_3$ | 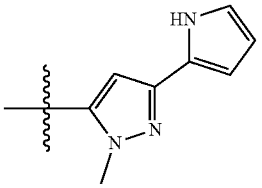 [SMILES: *c1cc(-c2ccc[nH]2)nn1C] | |
| 1131 | $CF_3$ | 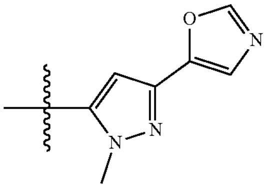 | |

TABLE 1-continued
Structure and ¹HNMR data of Compound I
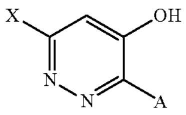
I
| No. | X | A | ¹H NMR |
|---|---|---|---|
| 1132 | $CF_3$ | 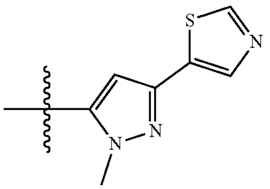 [SMILES: *c1cc(-c2cncs2)nn1C] | |
| 1133 | $CF_3$ | 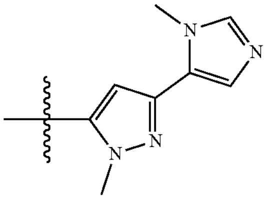 [SMILES: *c1cc(-c2cncn2C)nn1C] | |
| 1134 | $CF_3$ | 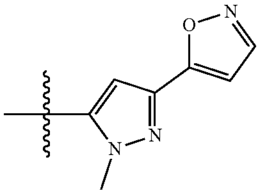 [SMILES: *c1cc(-c2ccno2)nn1C] | |
| 1135 | $CF_3$ | 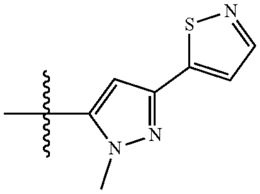 [SMILES: *c1cc(-c2ccns2)nn1C] | |
| 1136 | $CF_3$ | 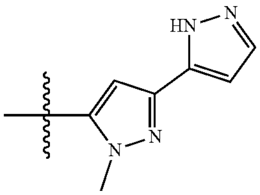 [SMILES: *c1cc(-c2ccn[nH]2)nn1C] | |
| 1137 | $CF_3$ | 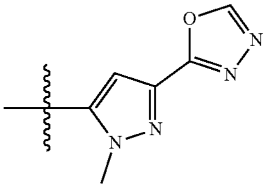 [SMILES: *c1cc(-c2nnco2)nn1C] | |
| 1138 | $CF_3$ | 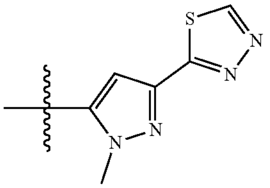 | |

TABLE 1-continued
Structure and $^1$HNMR data of Compound I
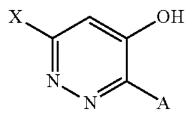
I
| No. | X | A | $^1$H NMR |
|---|---|---|---|
| 1139 | $CF_3$ | 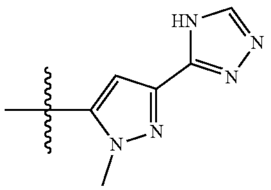 [SMILES: *c1cc(-c2nnc[nH]2)nn1C] | |
| 1140 | $CF_3$ | 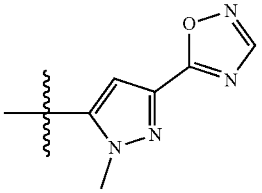 [SMILES: *c1cc(-c2ncno2)nn1C] | |
| 1141 | $CF_3$ | 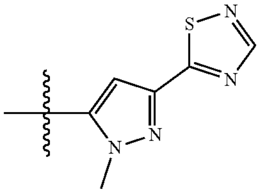 | |
| 1142 | $CF_3$ | 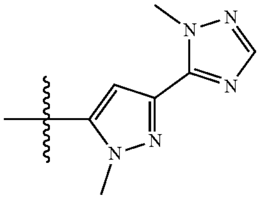 [SMILES: *c1cc(-c2ncnn2C)nn1C] | |
| 1143 | $CF_3$ | 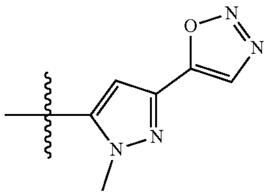 [SMILES: *c1cc(-c2cnno2)nn1C] | |
| 1144 | $CF_3$ | 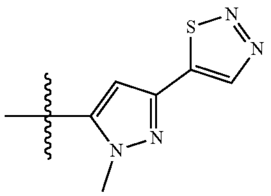 [SMILES: *c1cc(-c2cnns2)nn1C] | |

TABLE 1-continued
Structure and $^1$HNMR data of Compound I
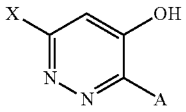
I
| No. | X | A | $^1H$ NMR |
|---|---|---|---|
| 1145 | $CF_3$ | 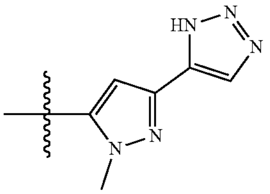 | |
| 1146 | $CF_3$ | 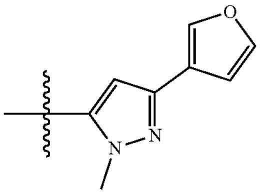 [SMILES: *c1cc(-c2ccoc2)nn1C] | |
| 1147 | $CF_3$ | 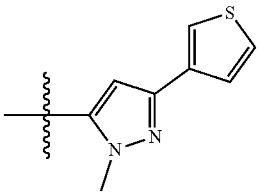 [SMILES: *c1cc(-c2ccsc2)nn1C] | |
| 1148 | $CF_3$ | 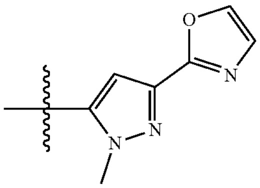 [SMILES: *c1cc(-c2ncco2)nn1C] | |
| 1149 | $CF_3$ | 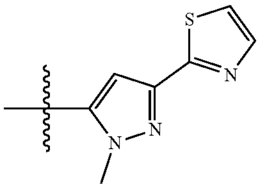 [SMILES: *c1cc(-c2nccs2)nn1C] | |
| 1150 | $CF_3$ | 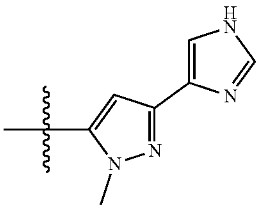 [SMILES: *c1cc(-c2c[nH]cn2)nn1C] | |

TABLE 1-continued
Structure and $^1$HNMR data of Compound I
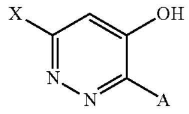
I
| No. | X | A | $^1$H NMR |
|---|---|---|---|
| 1151 | $CF_3$ | 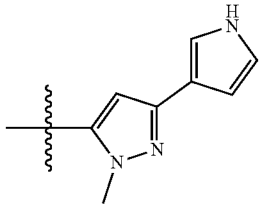 [SMILES: *c1cc(-c2cc[nH]c2)nn1C] | |
| 1152 | $CF_3$ | 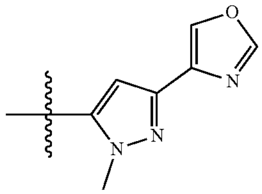 [SMILES: *c1cc(-c2cocn2)nn1C] | |
| 1153 | $CF_3$ | 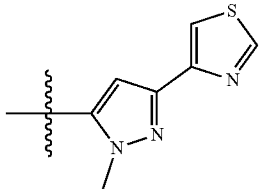 [SMILES: *c1cc(-c2cscn2)nn1C] | |
| 1154 | $CF_3$ | 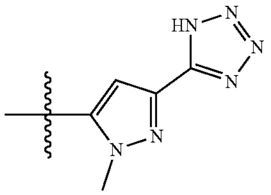 [SMILES: *c1cc(-c2nnn[nH]2)nn1C] | |
| 1155 | $CF_3$ | 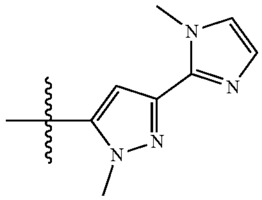 [SMILES: *c1cc(-c2nccn2C)nn1C] | |
| 1156 | $CF_3$ | 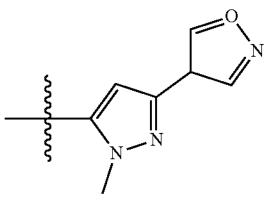 | |

TABLE 1-continued
| Structure and $^1$HNMR data of Compound I | | | |
|---|---|---|---|
| 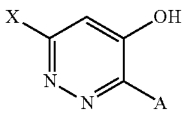 I | | | |
| No. | X | A | $^1$H NMR |
| 1157 | $CF_3$ | 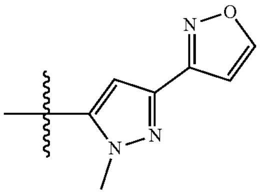 [SMILES: *c1cc(-c2ccon2)nn1C] | |
| 1158 | $CF_3$ | 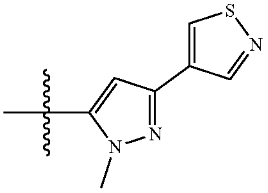 [SMILES: *c1cc(-c2cnsc2)nn1C] | |
| 1159 | $CF_3$ | 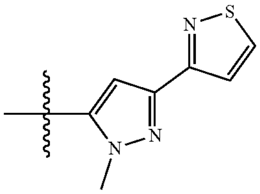 [SMILES: *c1cc(-c2ccsn2)nn1C] | |
| 1160 | $CF_3$ | 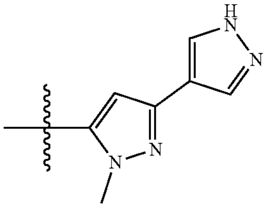 [SMILES: *c1cc(-c2cn[nH]c2)nn1C] | |
| 1161 | $CF_3$ | 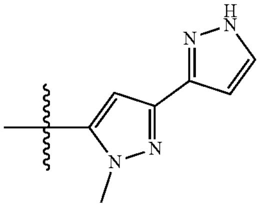 [SMILES: *c1cc(-c2cc[nH]n2)nn1C] | |
| 1162 | $CF_3$ | 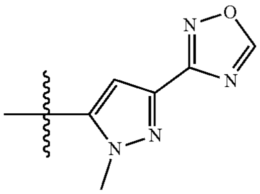 [SMILES: *c1cc(-c2ncon2)nn1C] | |

TABLE 1-continued
Structure and $^1$HNMR data of Compound I
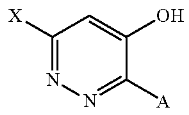
I
| No. | X | A | $^1$H NMR |
|---|---|---|---|
| 1163 | $CF_3$ | 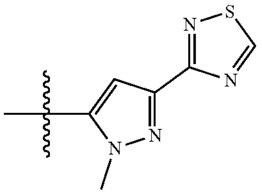 | |
| 1164 | $CF_3$ | 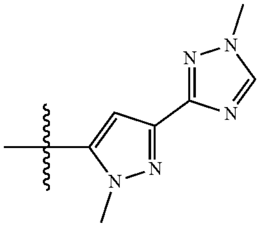 [SMILES: *c1cc(-c2ncn(C)n2)nn1C] | |
| 1165 | $CF_3$ | 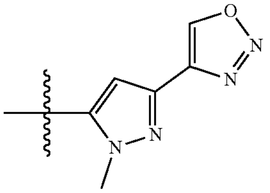 | |
| 1166 | $CF_3$ | 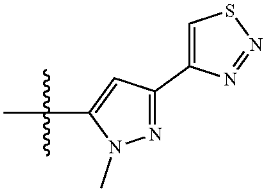 [SMILES: *c1cc(-c2csnn2)nn1C] | |
| 1167 | $CF_3$ | 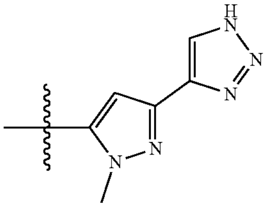 [SMILES: *c1cc(-c2c[nH]nn2)nn1C] | |
| 1168 | $CF_3$ | 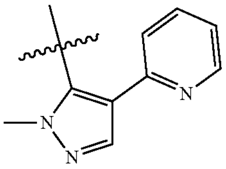 [SMILES: *c1c(-c2ccccn2)cnn1C] | |
| 1169 | $CF_3$ | 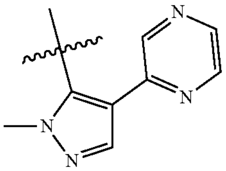 [SMILES: *c1c(-c2cnccn2)cnn1C] | |

TABLE 1-continued
Structure and $^1$HNMR data of Compound I
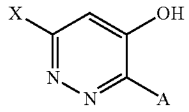
I
| No. | X | A | $^1$H NMR |
|---|---|---|---|
| 1170 | $CF_3$ | 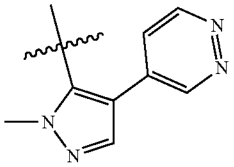 [SMILES: *c1c(-c2ccnnc2)cnn1C] | |
| 1171 | $CF_3$ | 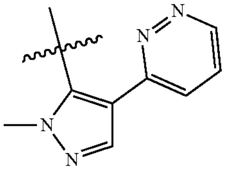 [SMILES: *c1c(-c2cccnn2)cnn1C] | |
| 1172 | $CF_3$ | 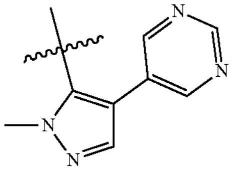 [SMILES: *c1c(-c2cncnc2)cnn1C] | |
| 1173 | $CF_3$ | 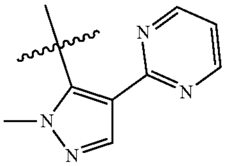 [SMILES: *c1c(-c2ncccn2)cnn1C] | |
| 1174 | $CF_3$ | 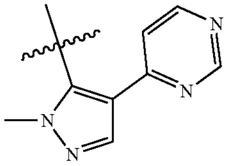 [SMILES: *c1c(-c2ccncn2)cnn1C] | |
| 1175 | $CF_3$ | 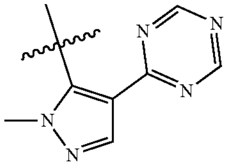 [SMILES: *c1c(-c2ncncn2)cnn1C] | |
| 1176 | $CF_3$ | 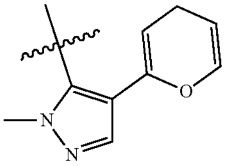 [SMILES: *c1c(C2=CCC=CO2)cnn1C] | |

TABLE 1-continued
Structure and $^1$HNMR data of Compound I
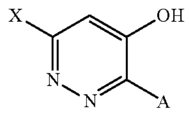
I
| No. | X | A | $^1$H NMR |
| --- | --- | --- | --- |
| 1177 | $CF_3$ | 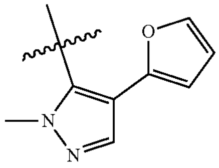 [SMILES: *c1c(-c2ccco2)cnn1C] | |
| 1178 | $CF_3$ | 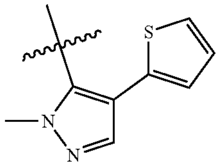 | |
| 1179 | $CF_3$ | 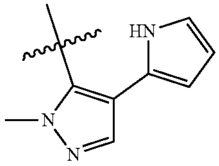 [SMILES: *c1c(-c2ccc[nH]2)cnn1C] | |
| 1180 | $CF_3$ | 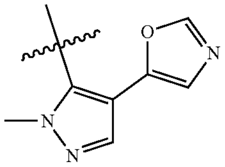 [SMILES: *c1c(-c2cnco2)cnn1C] | |
| 1181 | $CF_3$ | 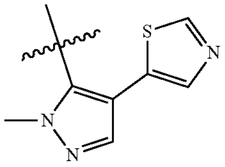 [SMILES: *c1c(-c2cncs2)cnn1C] | |
| 1182 | $CF_3$ | 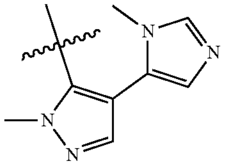 [SMILES: *c1c(-c2cncn2C)cnn1C] | |
| 1183 | $CF_3$ | 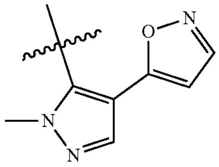 [SMILES: *c1c(-c2ccno2)cnn1C] | |
| 1184 | $CF_3$ | 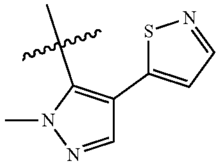 [SMILES: *c1c(-c2ccns2)cnn1C] | |

TABLE 1-continued
Structure and $^1$HNMR data of Compound I
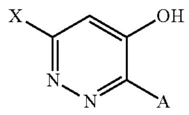
I
| No. | X | A | $^1$H NMR |
| --- | --- | --- | --- |
| 1185 | $CF_3$ | 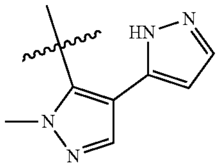 [SMILES: *c1c(-c2ccn[nH]2)cnn1C] | |
| 1186 | $CF_3$ | 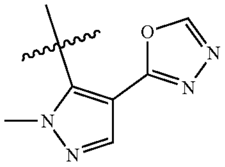 | |
| 1187 | $CF_3$ | 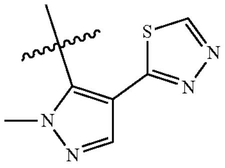 [SMILES: *c1c(-c2nncs2)cnn1C] | |
| 1188 | $CF_3$ | 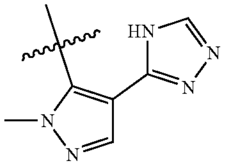 | |
| 1189 | $CF_3$ | 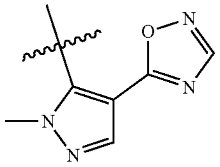 [SMILES: *c1c(-c2ncno2)cnn1C] | |
| 1190 | $CF_3$ | 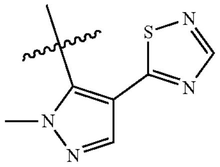 [SMILES: *c1c(-c2ncns2)cnn1C] | |
| 1191 | $CF_3$ | 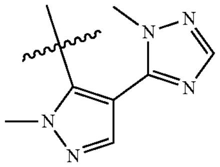 [SMILES: *c1c(-c2ncnn2C)cnn1C] | |

TABLE 1-continued
Structure and $^1$HNMR data of Compound I
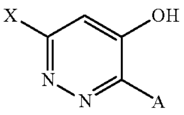
I
| No. | X | A | $^1$H NMR |
|---|---|---|---|
| 1192 | $CF_3$ | 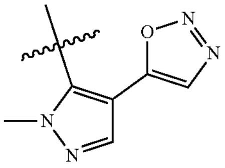 [SMILES: *c1c(-c2cnns2)cnn1C] | |
| 1193 | $CF_3$ | 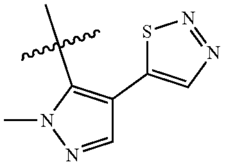 | |
| 1194 | $CF_3$ | 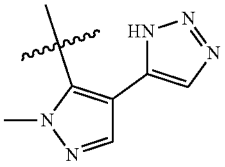 [SMILES: *c1c(-c2cnn[nH]2)cnn1C] | |
| 1195 | $CF_3$ | 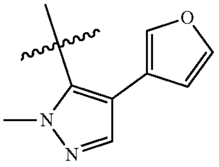 [SMILES: *c1c(-c2ccoc2)cnn1C] | |
| 1196 | $CF_3$ | 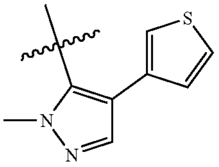 [SMILES: *c1c(-c2ccsc2)cnn1C] | |
| 1197 | $CF_3$ | 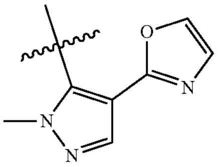 [SMILES: *c1c(-c2ncco2)cnn1C] | |
| 1198 | $CF_3$ | 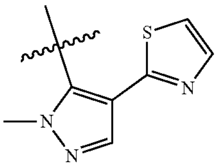 [SMILES: *c1c(-c2nccs2)cnn1C] | |
| 1199 | $CF_3$ | 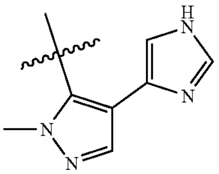 | |

TABLE 1-continued
Structure and $^1$HNMR data of Compound I
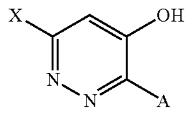
I
| No. | X | A | $^1H$ NMR |
|---|---|---|---|
| 1200 | $CF_3$ | 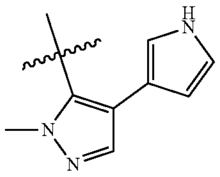 [SMILES: *c1c(-c2cc[nH]c2)cnn1C] | |
| 1201 | $CF_3$ | 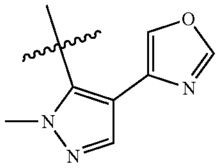 | |
| 1202 | $CF_3$ | 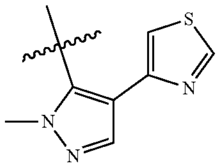 [SMILES: *c1c(-c2cocn2)cnn1C] | |
| 1203 | $CF_3$ | 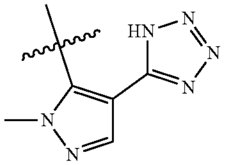 [SMILES: *c1c(-c2nnn[nH]2)cnn1C] | |
| 1204 | $CF_3$ | 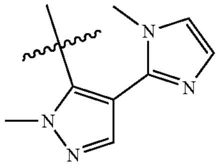 [SMILES: *c1c(-c2nccn2C)cnn1C] | |
| 1205 | $CF_3$ | 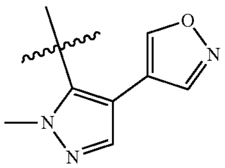 [SMILES: *c1c(-c2cnoc2)cnn1C] | |
| 1206 | $CF_3$ | 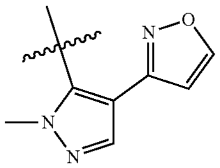 | |

TABLE 1-continued
Structure and $^1$HNMR data of Compound I
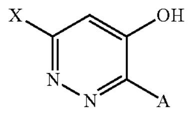
I
| No. | X | A | $^1$H NMR |
| --- | --- | --- | --- |
| 1207 | $CF_3$ | 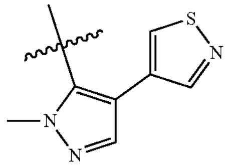 [SMILES: *c1c(-c2cnsc2)cnn1C] | |
| 1208 | $CF_3$ | 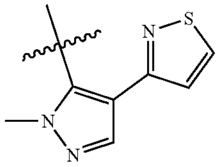 | |
| 1209 | $CF_3$ | 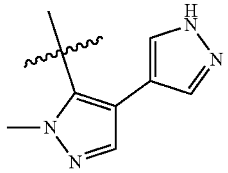 [SMILES: *c1c(-c2cn[nH]c2)cnn1C] | |
| 1210 | $CF_3$ | 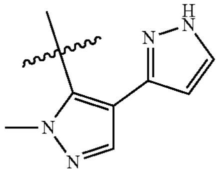 [SMILES: *c1c(-c2cc[nH]n2)cnn1C] | |
| 1211 | $CF_3$ | 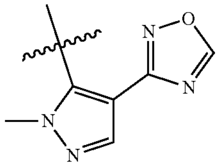 [SMILES: *c1c(-c2ncsn2)cnn1C] | |
| 1212 | $CF_3$ | 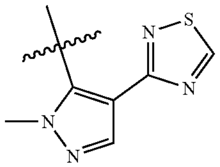 | |
| 1213 | $CF_3$ | 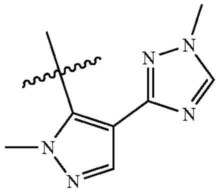 [SMILES: *c1c(-c2ncn(C)n2)cnn1C] | |

TABLE 1-continued
Structure and $^1$HNMR data of Compound I
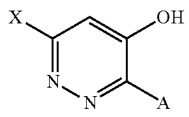
I
| No. | X | A | $^1$H NMR |
| --- | --- | --- | --- |
| 1214 | $CF_3$ | 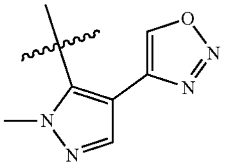 | |
| 1215 | $CF_3$ | 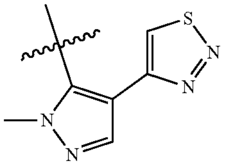 [SMILES: *c1c(-c2conn2)cnn1C] | |
| 1216 | $CF_3$ | 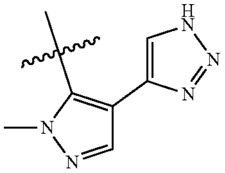 [SMILES: *c1c(-c2c[nH]nn2)cnn1C] | |
| 1217 | $CF_3$ | 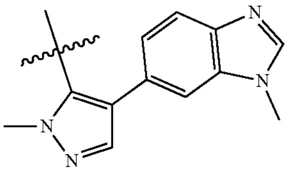 [SMILES: *c1c(-c2ccc3ncn(C)c3c2)cnn1C] | |
| 1218 | $CF_3$ | 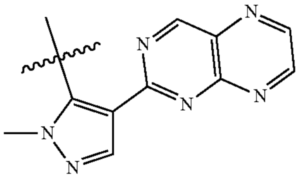 [SMILES: *c1c(-c2ncc3nccnc3n2)cnn1C] | |
| 1219 | $CF_3$ | 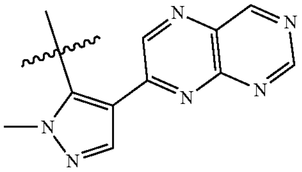 [SMILES: *c1c(-c2cnc3cncnc3n2)cnn1C] | |
| 1220 | $CF_3$ | 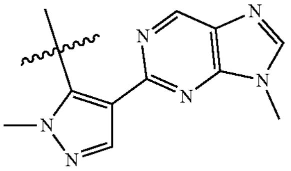 [SMILES: *c1c(-c2ncc3ncn(C)c3n2)cnn1C] | |

TABLE 1-continued
| Structure and 1HNMR data of Compound I | | | |
|---|---|---|---|
| 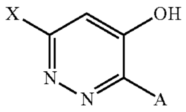 | | | I |
| No. | X | A | $^1$H NMR |
| 1221 | $CF_3$ | 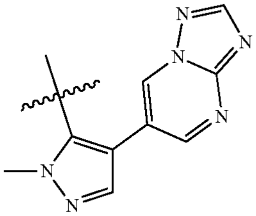 [SMILES: *c1c(-c2cnc3ncnn3c2)cnn1C] | |
| 1222 | $CF_3$ | 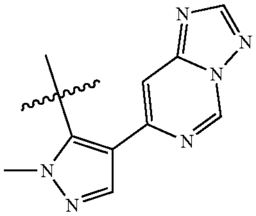 [SMILES: *c1c(-c2cc3ncnn3cn2)cnn1C] | |
| 1223 | $CF_3$ | 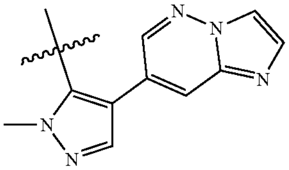 [SMILES: *c1c(-c2cnn3ccnc3c2)cnn1C] | |
| 1224 | $CF_3$ | 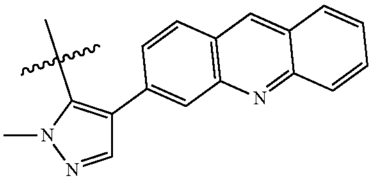 [SMILES: *c1c(-c2ccc3cc4ccccc4nc3c2)cnn1C] | |
| 1225 | $CF_3$ | 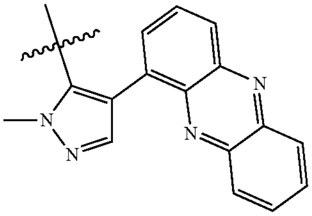 [SMILES: *c1c(-c2cccc3nc4ccccc4nc23)cnn1C] | |
| 1226 | $CF_3$ | 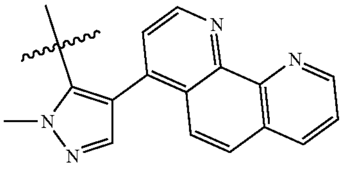 [SMILES: *c1c(-c2ccnc3c2ccc2cccnc23)cnn1C] | |

TABLE 1-continued
Structure and $^1$HNMR data of Compound I
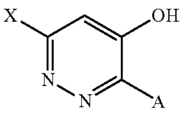
I
| No. | X | A | $^{1}$H NMR |
| --- | --- | --- | --- |
| 1227 | $CF_3$ | 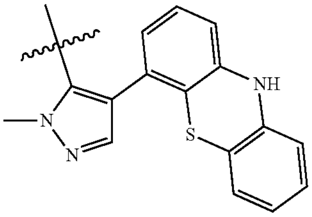 [SMILES: *c1c(-c2cccc3c2Sc2ccccc2N3)cnn1C] | |
| 1228 | $CF_3$ | 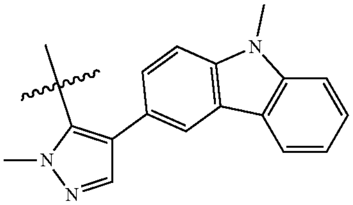 [SMILES: *c1c(-c2ccc3c(c2)c2ccccc2n3C)cnn1C] | |
| 1229 | $CF_3$ | 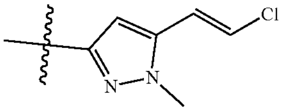 [SMILES: *c1cc(/C=C/Cl)n(C)n1] | |
| 1030 | $CF_3$ | 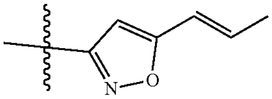 [SMILES: *c1cc(/C=C/C)on1] | |
| 1231 | $CF_3$ | 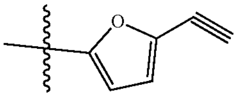 [SMILES: *c1ccc(C#C)o1] | |
| 1232 | $CF_3$ | 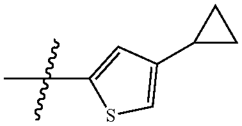 [SMILES: *c1cc(C2CC2)cs1] | |
| 1233 | $CF_3$ | 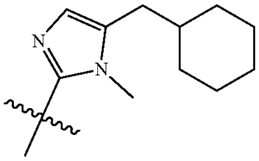 [SMILES: *c1ncc(CC2CCCCC2)n1C] | |
| 1234 | $CF_3$ | 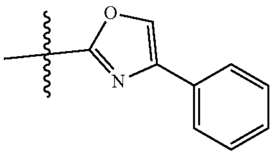 [SMILES: *c1nc(-c2ccccc2)co1] | |
| 1235 | $CF_3$ | 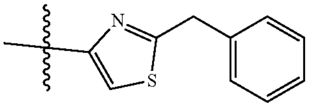 [SMILES: *c1csc(Cc2ccccc2)n1] | |

TABLE 1-continued
Structure and $^1$HNMR data of Compound I
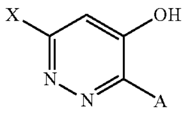
I
| No. | X | A | $^1$H NMR |
|---|---|---|---|
| 1236 | $CF_3$ | 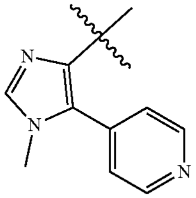 [SMILES: *c1ncn(C)c1-c1ccncc1] | |
| 1237 | $CF_3$ | 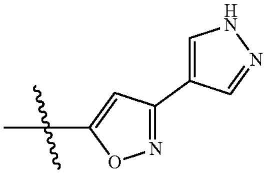 [SMILES: *c1cc(-c2cn[nH]c2)no1] | |
| 1238 | $CF_3$ | 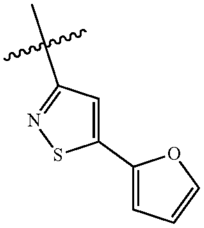 [SMILES: *c1cc(-c2ccco2)sn1] | |
| 1239 | $CF_3$ | 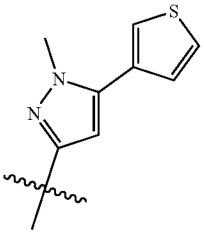 [SMILES: *c1cc(-c2ccsc2)n(C)n1] | |
| 1240 | $CF_3$ | 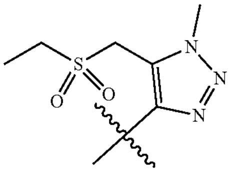 [SMILES: *c1nnn(C)c1CS(=O)(=O)CC] | |
| 1241 | $CF_3$ | 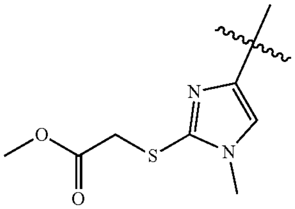 [SMILES: *c1cn(C)c(SCC(=O)OC)n1] | |

TABLE 1-continued
Structure and $^1$HNMR data of Compound I
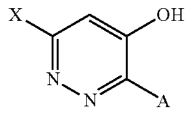
I
| No. | X | A | $^1H$ NMR |
| --- | --- | --- | --- |
| 1242 | $CF_3$ | 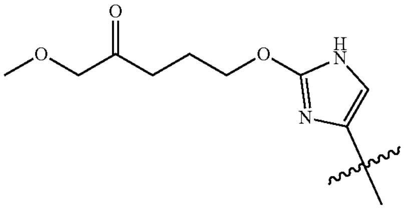 [SMILES: *c1c[nH]c(OCCCC(=O)COC)n1] | |
| 1243 | $CF_3$ | 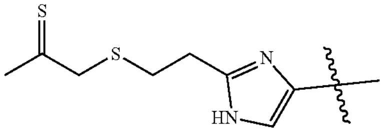 [SMILES: *c1c[nH]c(CCSCC(C)=S)n1] | |
| 1244 | $CF_3$ | 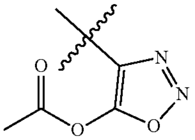 [SMILES: *c1nnoc1OC(C)=O] | |
| 1245 | $CF_3$ | 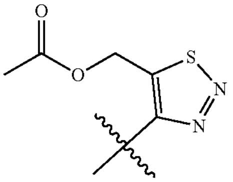 [SMILES: *c1nnsc1COC(C)=O] | |
| 1246 | $CF_3$ | 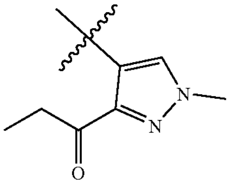 [SMILES: *c1cn(C)nc1C(=O)CC] | |
| 1247 | $CF_3$ | 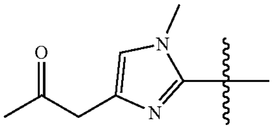 [SMILES: *c1nc(CC(C)=O)cn1C] | |
| 1248 | $CF_3$ | 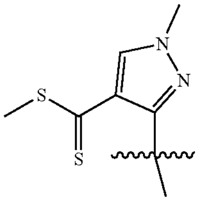 [SMILES: *c1nn(C)cc1C(=S)SC] | |

TABLE 1-continued
Structure and $^1$HNMR data of Compound I
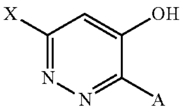
I
| No. | X | A | $^1$H NMR |
|---|---|---|---|
| 1249 | $CF_3$ | 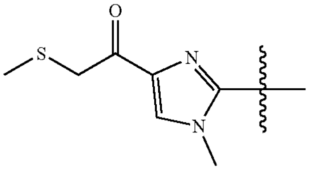 [SMILES: *c1nc(C(=O)CSC)cn1C] | |
| 1250 | $CF_3$ | 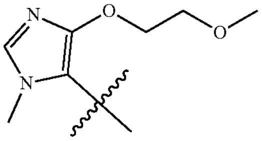 [SMILES: *c1c(OCCOC)ncn1C] | |
| 1251 | $CF_3$ | 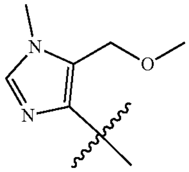 [SMILES: *c1ncn(C)c1COC] | |
| 1252 | $CF_3$ | 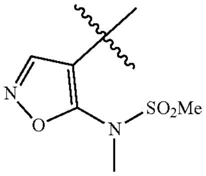 [SMILES: *c1cnoc1N(C)S(C)(=O)=O] | |
| 1253 | $CF_3$ | 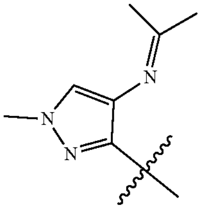 [SMILES: *c1nn(C)cc1N=C(C)C] | |
| 1254 | $CF_3$ | 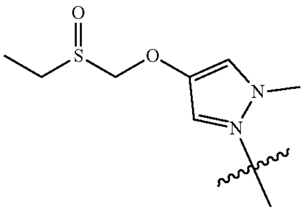 | |
| 1255 | $CF_3$ | 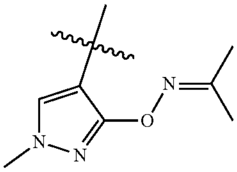 [SMILES: *c1cn(C)nc1ON=C(C)C] | |

TABLE 1-continued
Structure and 1HNMR data of Compound I
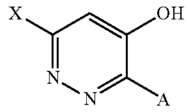
I
| No. | X | A | $^1$H NMR |
|---|---|---|---|
| 1256 | $CF_3$ | 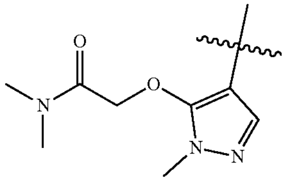 [SMILES: *c1cnn(C)c1OCC(=O)N(C)C] | |
| 1257 | $CF_3$ | 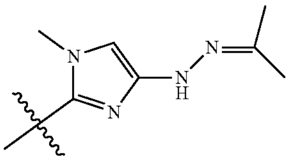 [SMILES: *c1nc(NN=C(C)C)cn1C] | |
| 1258 | $CF_3$ | 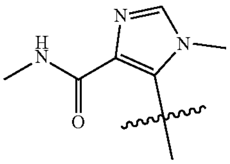 | |
| 1259 | $CF_3$ | 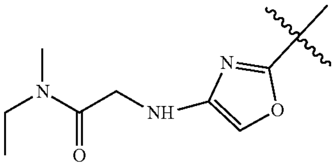 [SMILES: *c1nc(NCC(=O)N(C)CC)co1] | |
| 1260 | $CF_3$ | 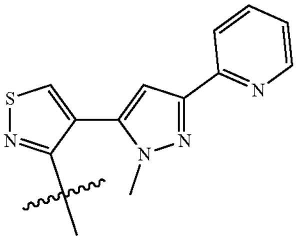 [SMILES: *c1nscc1-c1cc(-c2ccccn2)nn1C] | |
| 1261 | $CF_3$ | 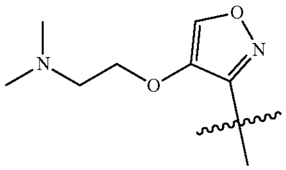 [SMILES: *c1nocc1OCCN(C)C] | |
| 1262 | $CF_3$ | 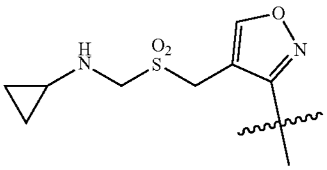 [SMILES: *c1nocc1CS(=O)(=O)CNC1CC1] | |

TABLE 1-continued
Structure and $^1$HNMR data of Compound I
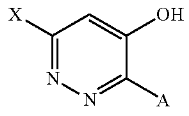
I
| No. | X | A | $^1$H NMR |
|---|---|---|---|
| 1263 | $CF_3$ | 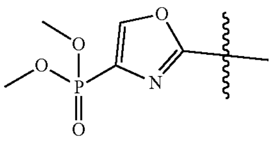 [SMILES: *c1nc(P(=O)(OC)OC)co1] | |
| 1264 | $CF_3$ | 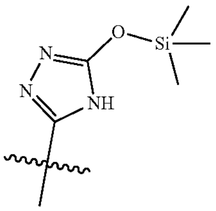 [SMILES: *c1nnc(O[Si](C)(C)C)[nH]1] | |
| 1265 | $CF_3$ | 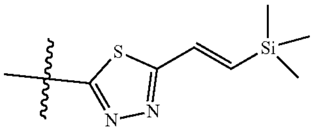 [SMILES: *c1nnc(/C=C/[Si](C)(C)C)s1] | |
| 1266 | $CF_3$ | 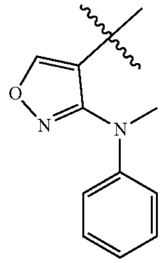 [SMILES: *c1conc1N(C)c1ccccc1] | |
| 1267 | $CF_3$ | 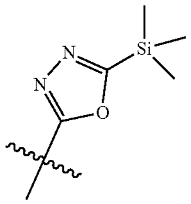 [SMILES: *c1nnc([Si](C)(C)C)o1] | |
| 1268 | $CF_3$ | 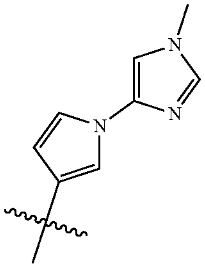 [SMILES: *c1ccn(-c2cn(C)cn2)c1] | |

TABLE 1-continued
Structure and $^1$HNMR data of Compound I
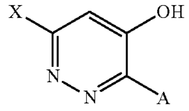
I
| No. | X | A | $^1$H NMR |
|---|---|---|---|
| 1269 | $CF_3$ | 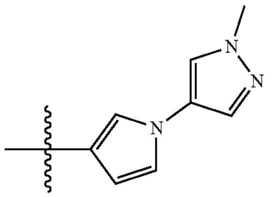 [SMILES: *c1ccn(-c2cnn(C)c2)c1] | |
| 1270 | $CF_3$ | 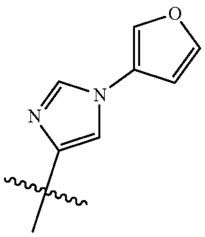 [SMILES: *c1cn(-c2ccoc2)cn1] | |
| 1271 | $CF_3$ | 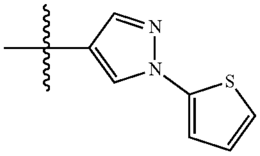 [SMILES: *c1cnn(-c2cccs2)c1] | |
| 1272 | $CF_3$ | 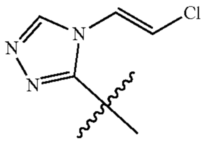 [SMILES: *c1nncn1/C=C/Cl] | |
| 1273 | $CF_3$ | 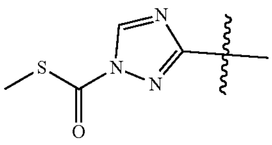 [SMILES: *c1ncn(C(=O)SC)n1] | |
| 1274 | $CF_3$ | 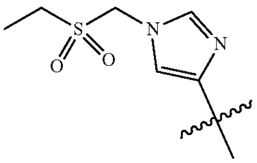 [SMILES: *c1cn(CS(=O)(=O)CC)cn1] | |
| 1275 | $CF_3$ | 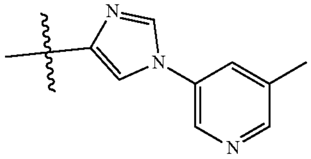 [SMILES: *c1cn(-c2cncc(C)c2)cn1] | |

TABLE 1-continued
Structure and $^1$HNMR data of Compound I
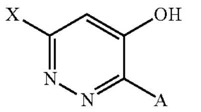
I
| No. | X | A | $^1H$ NMR |
| --- | --- | --- | --- |
| 1276 | $CF_3$ | 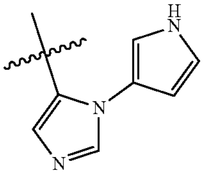 [SMILES: *c1cncn1-c1cc[nH]c1] | |
| 1277 | $CF_3$ | 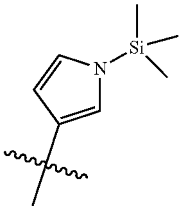 [SMILES: *c1ccn([Si](C)(C)C)c1] | |
| 1278 | $CF_3$ | 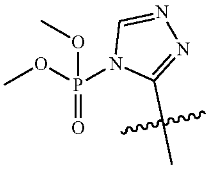 [SMILES: *c1nncn1P(=O)(OC)OC] | |
| 1279 | $CF_3$ | 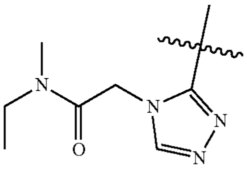 [SMILES: *c1nncn1CC(=O)N(C)CC] | |
| 1280 | $CF_3$ | 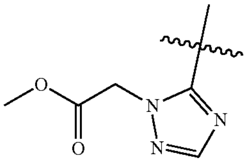 [SMILES: *c1ncnn1CC(=O)OC] | |
| 1281 | $CF_3$ | 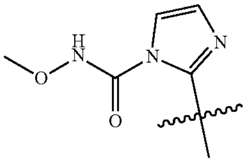 [SMILES: *c1nccn1C(=O)NOC] | |
| 1282 | $CF_3$ | 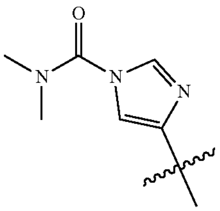 [SMILES: *c1cn(C(=O)N(C)C)cn1] | |

TABLE 1-continued
Structure and $^1$HNMR data of Compound I
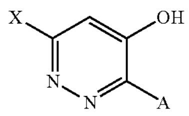
I
| No. | X | A | $^1$H NMR |
|---|---|---|---|
| 1283 | $CF_3$ | 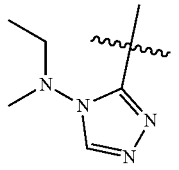 [SMILES: *c1nncn1N(C)CC] | |
| 1284 | $CF_3$ | 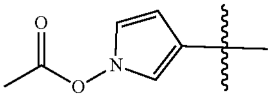 [SMILES: *c1ccn(OC(C)=O)c1] | |
| 1285 | $CF_3$ | 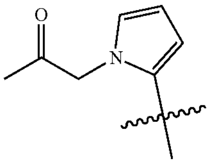 [SMILES: *c1cccn1CC(C)=O] | |
| 1286 | $CF_3$ | 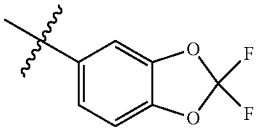 [SMILES: *c1ccc2c(c1)OC(F)(F)O2] | $^1$H NMR (500 MHz, Chloroform-d) 7.25 (d, J = 2.0 Hz, 1H), 7.19 (dd, J = 7.5, 2.0 Hz, 1H), 7.06-6.91 (m, 2H), 5.52 (s, 1H). |
| 1287 | $CF_3$ | 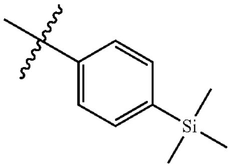 [SMILES: *c1ccc([Si](C)(C)C)cc1] | $^1$H NMR (500 MHz, Chloroform-d) 7.83 (d, J = 7.5 Hz, 2H), 7.59 (d, J = 7.5 Hz, 2H), 7.10 (s, 1H), 5.88 (s, 1H), 0.25 (s, 9H). |
| 1288 | $CF_3$ | 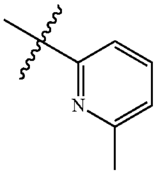 [SMILES: *c1cccc(C)n1] | |
| 1289 | $CF_3$ | 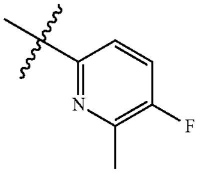 [SMILES: *c1ccc(F)c(C)n1] | |
| 1290 | $CF_3$ | 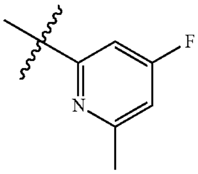 [SMILES: *c1cc(F)cc(C)n1] | |

TABLE 1-continued
Structure and $^1$HNMR data of Compound I
I
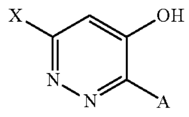
| No. | X | A | $^1$H NMR |
|---|---|---|---|
| 1291 | $CF_3$ | 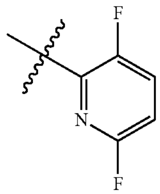 [SMILES: *c1nc(F)ccc1F] | |
| 1292 | $CF_3$ | 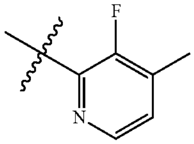 | |
| 1293 | $CF_3$ | 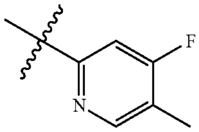 [SMILES: *c1cc(F)c(C)cn1] | |
| 1294 | $CF_3$ | 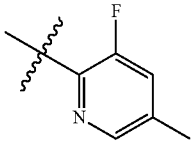 [SMILES: *c1ncc(C)cc1F] | |
| 1295 | $CF_3$ | 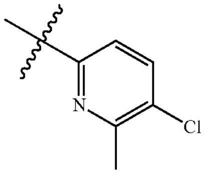 [SMILES: *c1ccc(Cl)c(C)n1] | |
| 1296 | $CF_3$ | 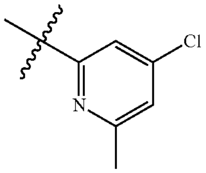 [SMILES: *c1cc(Cl)cc(C)n1] | |
| 1297 | $CF_3$ | 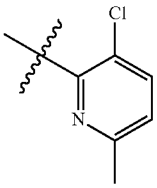 [SMILES: *c1nc(C)ccc1Cl] | |
| 1298 | $CF_3$ | 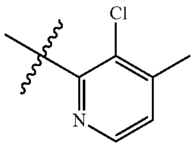 [SMILES: *c1nccc(C)c1Cl] | |

TABLE 1-continued
Structure and ¹HNMR data of Compound I
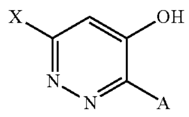
I
| No. | X | A | ¹H NMR |
|---|---|---|---|
| 1299 | $CF_3$ | 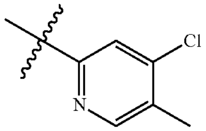 [SMILES: *c1cc(Cl)c(C)cn1] | |
| 1300 | $CF_3$ | 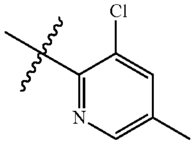 [SMILES: *c1ncc(C)cc1Cl] | |
| 1301 | $CF_3$ | 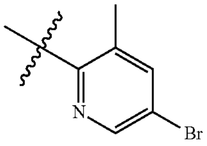 [SMILES: *c1ncc(Br)cc1C] | |
| 1302 | $CF_3$ | 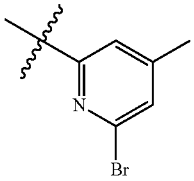 [SMILES: *c1cc(C)cc(Br)n1] | |
| 1303 | $CF_3$ | 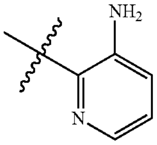 [SMILES: *c1ncccc1N] | |
| 1304 | $CF_3$ | 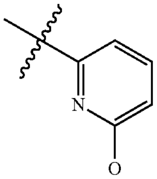 [SMILES: *c1cccc(O)n1] | |
| 1305 | $CF_3$ | 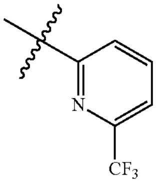 [SMILES: *c1cccc(C(F)(F)F)n1] | |
| 1306 | $CF_3$ | 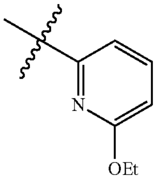 [SMILES: *c1cccc(OCC)n1] | |

TABLE 1-continued
Structure and $^1$HNMR data of Compound I
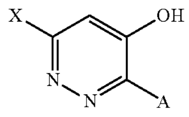
I
| No. | X | A | $^1H$ NMR |
|---|---|---|---|
| 1307 | $CF_3$ | 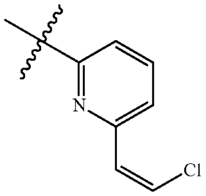 [SMILES: *c1cccc(/C=C\Cl)n1] | |
| 1308 | $CF_3$ | 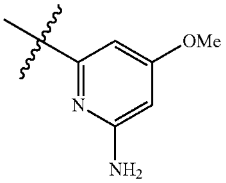 [SMILES: *c1cc(OC)cc(N)n1] | |
| 1309 | $CF_3$ | 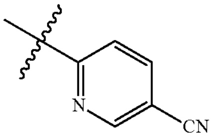 [SMILES: *c1ccc(C#N)cn1] | |
| 1310 | $CF_3$ | 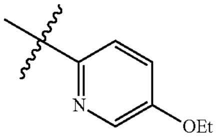 [SMILES: *c1ccc(OCC)cn1] | |
| 1311 | $CF_3$ | 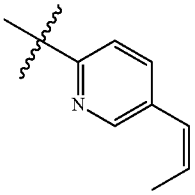 [SMILES: *c1ccc(/C=C\C)cn1] | |
| 1312 | $CF_3$ | 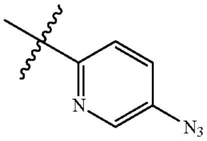 | |
| 1313 | $CF_3$ | 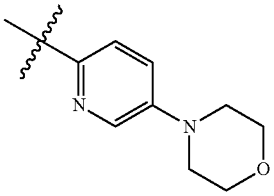 [SMILES: *c1ccc(N2CCOCC2)cn1] | |
| 1314 | $CF_3$ | 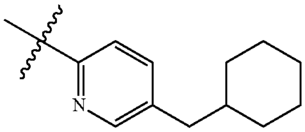 [SMILES: *c1ccc(CC2CCCCC2)cn1] | |

TABLE 1-continued
Structure and $^1$HNMR data of Compound I
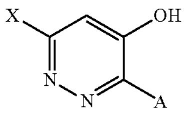
I
| No. | X | A | $^1$H NMR |
|---|---|---|---|
| 1315 | $CF_3$ | 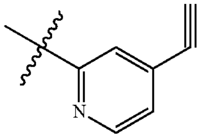 [SMILES: *c1cc(C#C)ccn1] | |
| 1316 | $CF_3$ | 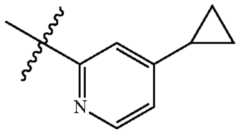 | |
| 1317 | $CF_3$ | 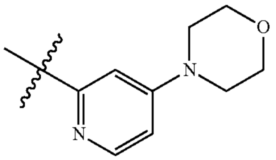 [SMILES: *c1cc(N2CCOCC2)ccn1] | |
| 1318 | $CF_3$ | 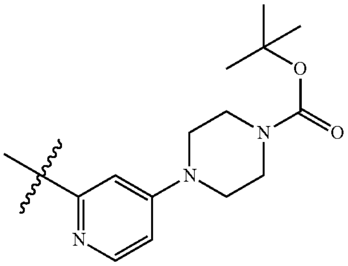 [SMILES: *c1cc(N2CCN(C(=O)OC(C)(C)C)CC2)ccn1] | |
| 1319 | $CF_3$ | 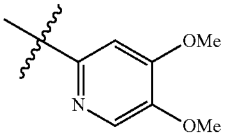 [SMILES: *c1cc(OC)c(OC)cn1] | |
| 1320 | $CF_3$ | 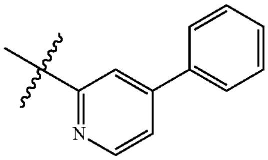 [SMILES: *c1cc(-c2ccccc2)ccn1] | |
| 1321 | $CF_3$ | 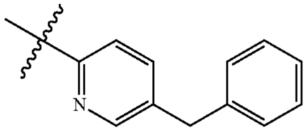 [SMILES: *c1ccc(Cc2ccccc2)cn1] | |
| 1322 | $CF_3$ | 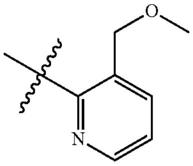 [SMILES: *c1ncccc1COC] | |

TABLE 1-continued
Structure and $^1$HNMR data of Compound I
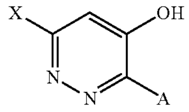
I
| No. | X | A | $^1$H NMR |
|---|---|---|---|
| 1323 | $CF_3$ | 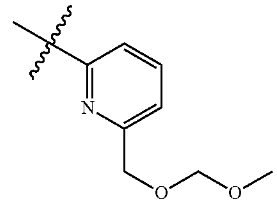 [SMILES: *c1cccc(COCOC)n1] | |
| 1324 | $CF_3$ | 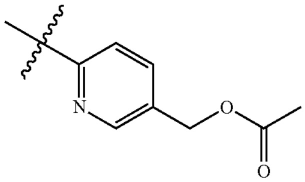 [SMILES: *c1ccc(COC(C)=O)cn1] | |
| 1325 | $CF_3$ | 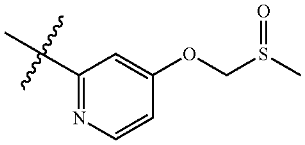 [SMILES: *c1cc(OCS(C)=O)ccn1] | |
| 1326 | $CF_3$ | 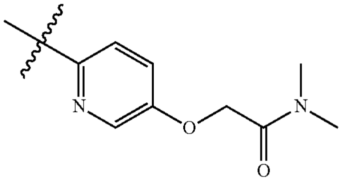 [SMILES: *c1ccc(OCC(=O)N(C)C)cn1] | |
| 1327 | $CF_3$ | 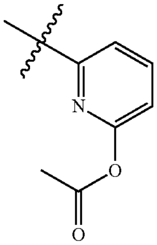 [SMILES: *c1cccc(OC(C)=O)n1] | |
| 1328 | $CF_3$ | 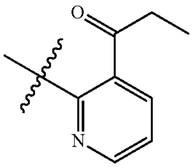 [SMILES: *c1ncccc1C(=O)CC] | |
| 1329 | $CF_3$ | 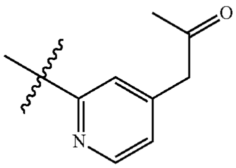 [SMILES: *c1cc(CC(C)=O)ccn1] | |

TABLE 1-continued
Structure and $^1$HNMR data of Compound I
I
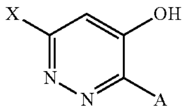
| No. | X | A | $^1$H NMR |
|---|---|---|---|
| 1330 | $CF_3$ | 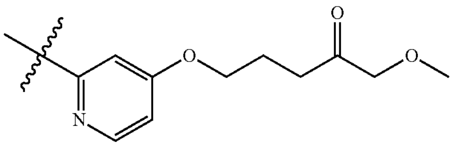 [SMILES: *c1cc(OCCCC(=O)COC)ccn1] | |
| 1331 | $CF_3$ | 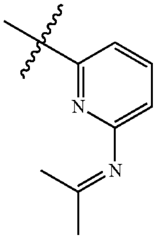 [SMILES: *c1cccc(N=C(C)C)n1] | |
| 1332 | $CF_3$ | 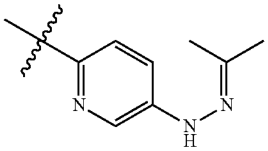 [SMILES: *c1ccc(NN=C(C)C)cn1] | |
| 1333 | $CF_3$ | 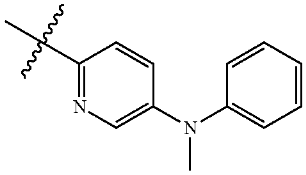 [SMILES: *c1ccc(N(C)c2ccccc2)cn1] | |
| 1334 | $CF_3$ | 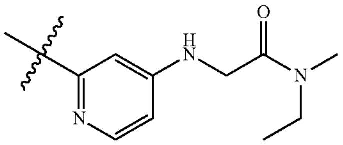 [SMILES: *c1cc(NCC(=O)N(C)CC)ccn1] | |
| 1335 | $CF_3$ | 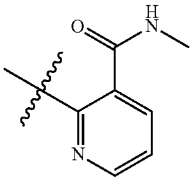 [SMILES: *c1ncccc1C(=O)NC] | |
| 1336 | $CF_3$ | 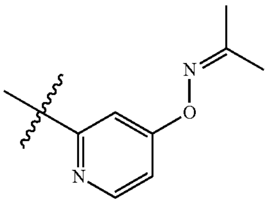 [SMILES: *c1cc(ON=C(C)C)ccn1] | |

TABLE 1-continued
Structure and $^1$HNMR data of Compound I
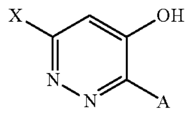
I
| No. | X | A | $^1$H NMR |
|---|---|---|---|
| 1337 | $CF_3$ | 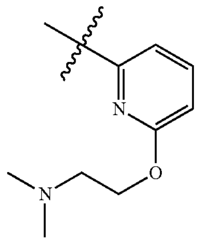 [SMILES: *c1cccc(OCCN(C)C)n1] | |
| 1338 | $CF_3$ | 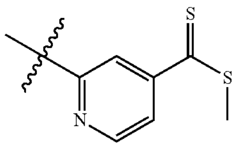 [SMILES: *c1cc(C(=S)SC)ccn1] | |
| 1339 | $CF_3$ | 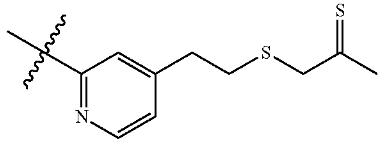 [SMILES: *c1cc(CCSCC(C)=S)ccn1] | |
| 1340 | $CF_3$ | 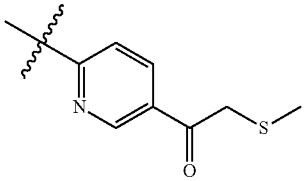 [SMILES: *c1ccc(C(=O)CSC)cn1] | |
| 1341 | $CF_3$ | 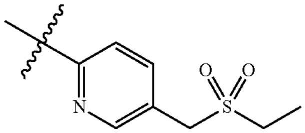 [SMILES: *c1ccc(CS(=O)(=O)CC)cn1] | |
| 1342 | $CF_3$ | 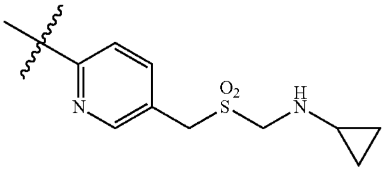 [SMILES: *c1ccc(CS(=O)(=O)CNC2CC2)cn1] | |
| 1343 | $CF_3$ | 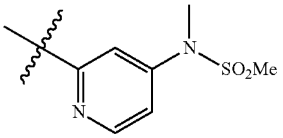 [SMILES: *c1cc(N(C)S(C)(=O)=O)ccn1] | |
| 1344 | $CF_3$ | 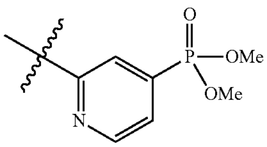 [SMILES: *c1cc(P(=O)(OC)OC)ccn1] | |

TABLE 1-continued
Structure and $^1$HNMR data of Compound I
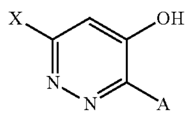
I
| No. | X | A | $^1$H NMR |
|---|---|---|---|
| 1345 | $CF_3$ | 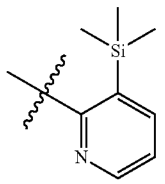 [SMILES: *c1ncccc1[Si](C)(C)C] | |
| 1346 | $CF_3$ | 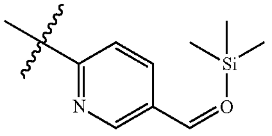 | |
| 1347 | $CF_3$ | 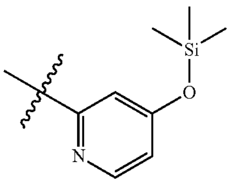 [SMILES: *c1cc(O[Si](C)(C)C)ccn1] | |
| 1348 | $CF_3$ | 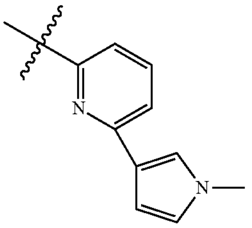 [SMILES: *c1cccc(-c2ccn(C)c2)n1] | |
| 1349 | $CF_3$ | 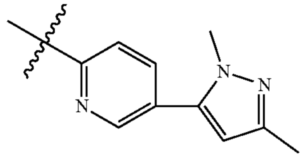 [SMILES: *c1ccc(-c2cc(C)nn2C)cn1] | |
| 1350 | $CF_3$ | 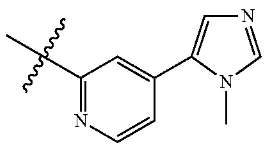 [SMILES: *c1cc(-c2cncn2C)ccn1] | |
| 1351 | $CF_3$ | 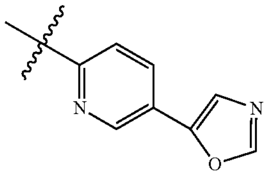 [SMILES: *c1ccc(-c2cnco2)cn1] | |

TABLE 1-continued
Structure and ¹HNMR data of Compound I
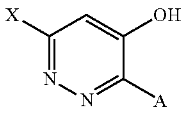
I
| No. | X | A | ¹H NMR |
| --- | --- | --- | --- |
| 1352 | $CF_3$ | 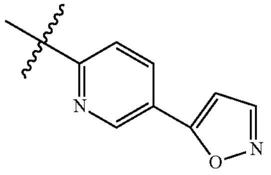 [SMILES: *c1ccc(-c2ccno2)cn1] | |
| 1353 | $CF_3$ | 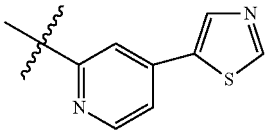 [SMILES: *c1cc(-c2cncs2)ccn1] | |
| 1354 | $CF_3$ | 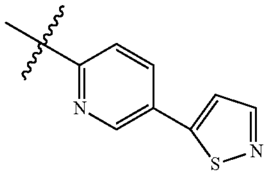 [SMILES: *c1ccc(-c2ccns2)cn1] | |
| 1355 | $CF_3$ | 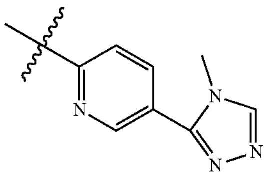 [SMILES: *c1ccc(-c2nncn2C)cn1] | |
| 1356 | $CF_3$ | 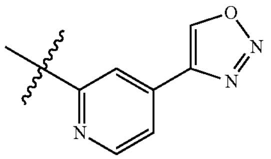 [SMILES: *c1cc(-c2conn2)ccn1] | |
| 1357 | $CF_3$ | 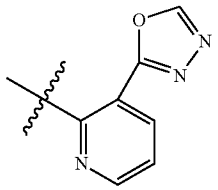 [SMILES: *c1ncccc1-c1nnco1] | |
| 1358 | $CF_3$ | 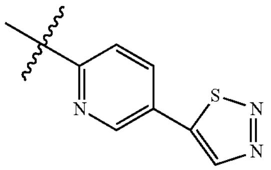 [SMILES: *c1ccc(-c2cnns2)cn1] | |

TABLE 1-continued
Structure and $^1$HNMR data of Compound I
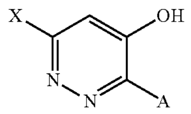
I
| No. | X | A | $^1H$ NMR |
| --- | --- | --- | --- |
| 1359 | $CF_3$ | 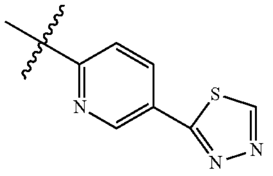 [SMILES: *c1ccc(-c2nncs2)cn1] | |
| 1360 | $CF_3$ | 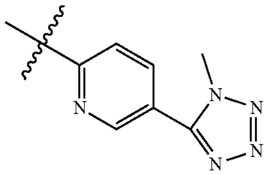 [SMILES: *c1ccc(-c2nnnn2C)cn1] | |
| 1361 | $CF_3$ | 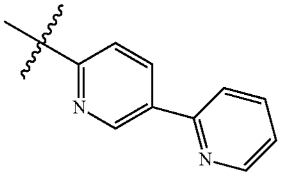 [SMILES: *c1ccc(-c2ccccn2)cn1] | |
| 1362 | $CF_3$ | 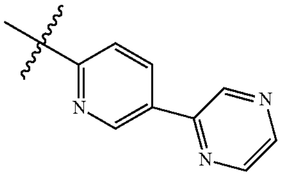 [SMILES: *c1ccc(-c2cnccn2)cn1] | |
| 1363 | $CF_3$ | 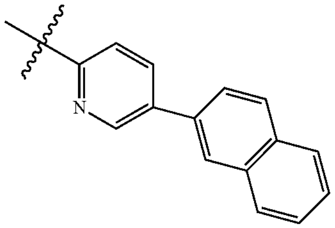 [SMILES: *c1ccc(-c2ccc3ccccc3c2)cn1] | |
| 1364 | $CF_3$ | 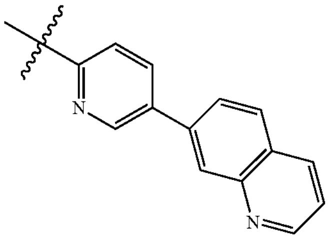 [SMILES: *c1ccc(-c2ccc3cccnc3c2)cn1] | |

TABLE 1-continued
Structure and $^1$HNMR data of Compound I
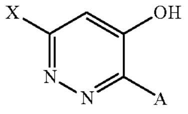
I
| No. | X | A | $^1$H NMR |
|---|---|---|---|
| 1365 | $CF_3$ | 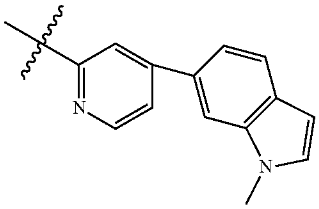 [SMILES: *c1cc(-c2ccc3ccn(C)c3c2)ccn1] | |
| 1366 | $CF_3$ | 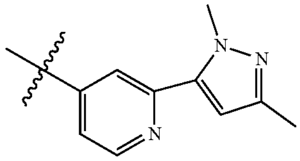 [SMILES: *c1ccnc(-c2cc(C)nn2C)c1] | |
| 1367 | $CF_3$ | 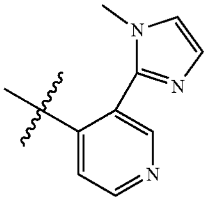 [SMILES: *c1ccncc1-c1nccn1C] | |
| 1368 | $CF_3$ | 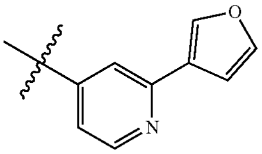 [SMILES: *c1ccnc(-c2ccoc2)c1] | |
| 1369 | $CF_3$ | 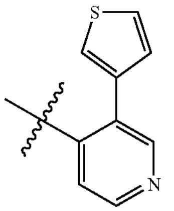 [SMILES: *c1ccncc1-c1ccsc1] | |
| 1370 | $CF_3$ | 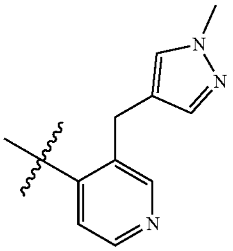 [SMILES: *c1ccncc1Cc1cnn(C)c1] | |
| 1371 | $CF_3$ | 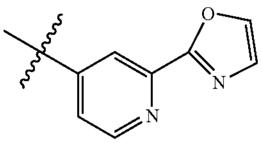 [SMILES: *c1ccnc(-c2ncco2)c1] | |

TABLE 1-continued
| Structure and ¹HNMR data of Compound I | | | |
|---|---|---|---|
| 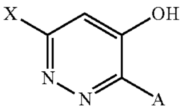 I | | | |
| No. | X | A | ¹H NMR |
| 1372 | $CF_3$ | 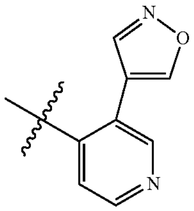 [SMILES: *c1ccncc1-c1cnoc1] | |
| 1373 | $CF_3$ | 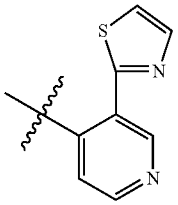 [SMILES: *c1ccncc1-c1nccs1] | |
| 1374 | $CF_3$ | 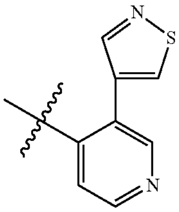 [SMILES: *c1ccncc1-c1cnsc1] | |
| 1375 | $CF_3$ | 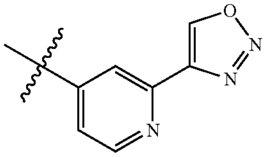 [SMILES: *c1ccnc(-c2conn2)c1] | |
| 1376 | $CF_3$ | 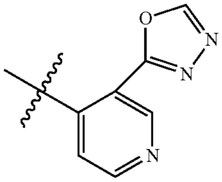 [SMILES: *c1ccncc1-c1nnco1] | |
| 1377 | $CF_3$ | 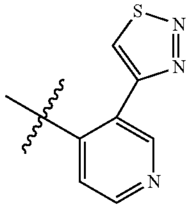 [SMILES: *c1ccncc1-c1csnn1] | |

TABLE 1-continued
Structure and $^1$HNMR data of Compound I
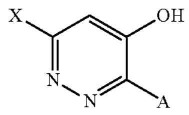
I
| No. | X | A | $^{1}H$ NMR |
| --- | --- | --- | --- |
| 1378 | $CF_3$ | 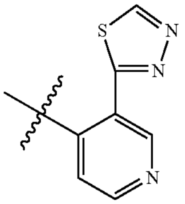 [SMILES: *c1ccncc1-c1nncs1] | |
| 1379 | $CF_3$ | 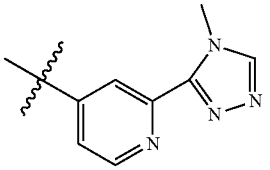 [SMILES: *c1ccnc(-c2nncn2C)c1] | |
| 1380 | $CF_3$ | 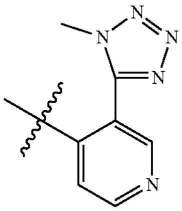 [SMILES: *c1ccncc1-c1nnnn1C] | |
| 1381 | $CF_3$ | 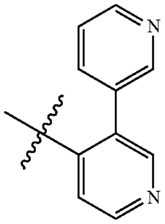 [SMILES: *c1ccncc1-c1cccnc1] | |
| 1382 | $CF_3$ | 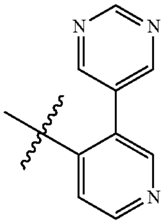 [SMILES: *c1ccncc1-c1cncnc1] | |
| 1383 | $CF_3$ | 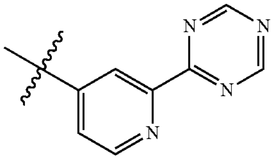 [SMILES: *c1ccnc(-c2ncncn2)c1] | |
| 1384 | $CF_3$ | 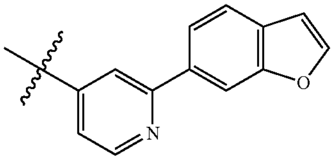 [SMILES: *c1ccnc(-c2ccc3ccoc3c2)c1] | |

TABLE 1-continued
Structure and $^1$HNMR data of Compound I
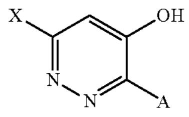
I
| No. | X | A | $^1$H NMR |
|---|---|---|---|
| 1385 | $CF_3$ | 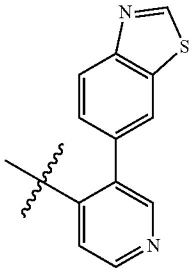 [SMILES: *c1ccncc1-c1ccc2ncsc2c1] | |
| 1386 | $CF_3$ | 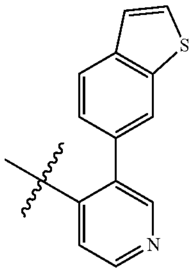 [SMILES: *c1ccncc1-c1ccc2ccsc2c1] | |
| 1387 | $CF_3$ | 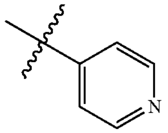 [SMILES: *c1ccncc1] | |
| 1388 | $CF_3$ | 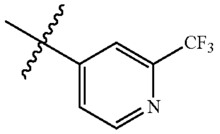 [SMILES: *c1ccnc(C(F)(F)F)c1] | |
| 1389 | $CF_3$ | 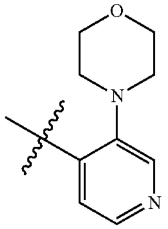 [SMILES: *c1ccncc1N1CCOCC1] | |
| 1390 | $CF_3$ | 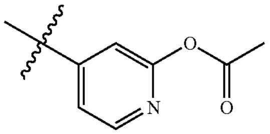 [SMILES: *c1ccnc(OC(C)=O)c1] | |
| 1391 | $CF_3$ | 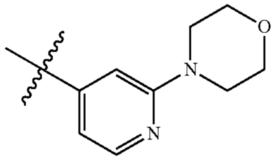 [SMILES: *c1ccnc(N2CCOCC2)c1] | |

TABLE 1-continued
Structure and $^1$HNMR data of Compound I
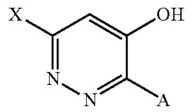
I
| No. | X | A | $^1$H NMR |
|---|---|---|---|
| 1392 | $CF_3$ | 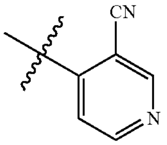 [SMILES: *c1ccncc1C#N] | |
| 1393 | $CF_3$ | 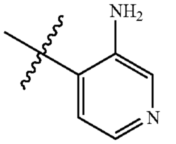 [SMILES: *c1ccncc1N] | |
| 1394 | $CF_3$ | 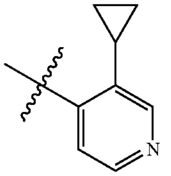 [SMILES: *c1ccncc1C1CC1] | |
| 1395 | $CF_3$ | 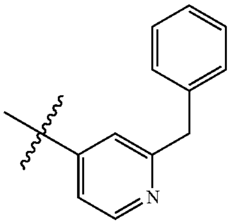 [SMILES: *c1ccnc(Cc2ccccc2)c1] | |
| 1396 | $CF_3$ | 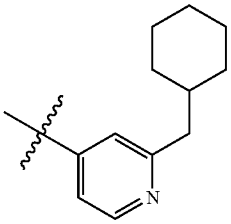 [SMILES: *c1ccnc(CC2CCCCC2)c1] | |
| 1397 | $CF_3$ | 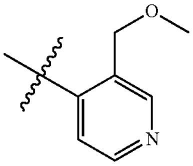 [SMILES: *c1ccncc1COC] | |
| 1398 | $CF_3$ | 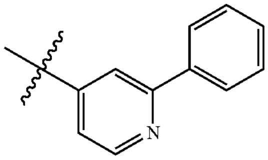 [SMILES: *c1ccnc(-c2ccccc2)c1] | |

TABLE 1-continued
Structure and $^{1}$HNMR data of Compound I
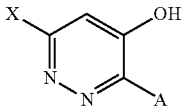
I
| No. | X | A | $^{1}$H NMR |
|---|---|---|---|
| 1399 | $CF_3$ | 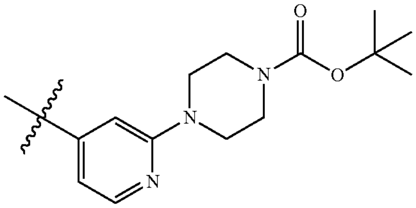 [SMILES: *c1ccnc(N2CCN(C(=O)OC(C)(C)C)CC2)c1] | |
| 1400 | $CF_3$ | 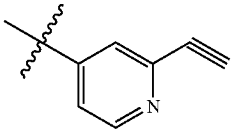 [SMILES: *c1ccnc(C#C)c1] | |
| 1401 | $CF_3$ | 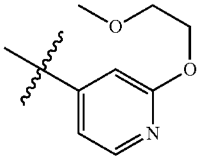 [SMILES: *c1ccnc(OCCOC)c1] | |
| 1402 | $CF_3$ | 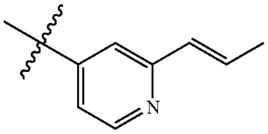 [SMILES: *c1ccnc(/C=C/C)c1] | |
| 1403 | $CF_3$ | 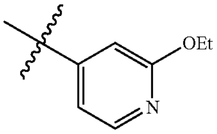 [SMILES: *c1ccnc(OCC)c1] | |
| 1404 | $CF_3$ | 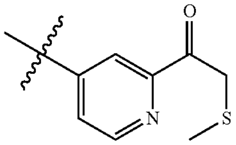 [SMILES: *c1ccnc(C(=O)CSC)c1] | |
| 1405 | $CF_3$ | 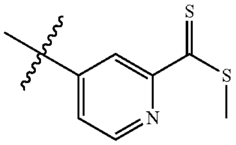 [SMILES: *c1ccnc(C(=S)SC)c1] | |
| 1406 | $CF_3$ | 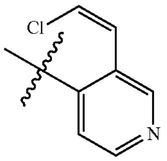 [SMILES: *c1ccncc1/C=C\Cl] | |

TABLE 1-continued
Structure and $^1$HNMR data of Compound I
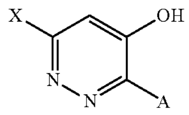
I
| No. | X | A | $^{1}H$ NMR |
|---|---|---|---|
| 1407 | $CF_3$ | 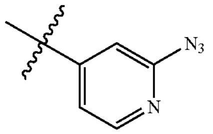 [SMILES: *c1ccnc(N=[N+]=[N-])c1] | |
| 1408 | $CF_3$ | 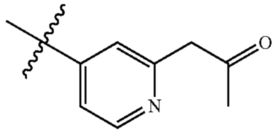 [SMILES: *c1ccnc(CC(C)=O)c1] | |
| 1409 | $CF_3$ | 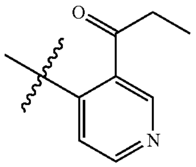 [SMILES: *c1ccncc1C(=O)CC] | |
| 1410 | $CF_3$ | 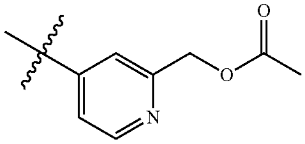 [SMILES: *c1ccnc(COC(C)=O)c1] | |
| 1411 | $CF_3$ | 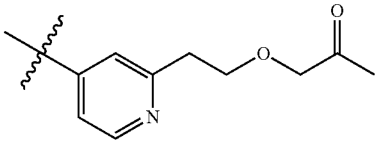 [SMILES: *c1ccnc(CCOCC(C)=O)c1] | |
| 1412 | $CF_3$ | 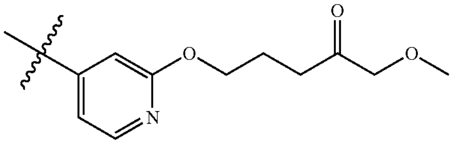 [SMILES: *c1ccnc(OCCCC(=O)COC)c1] | |
| 1413 | $CF_3$ | 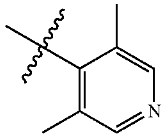 [SMILES: *c1c(C)cncc1C] | |
| 1414 | $CF_3$ | 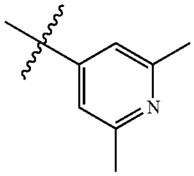 [SMILES: *c1cc(C)nc(C)c1] | |
| 1415 | $CF_3$ | 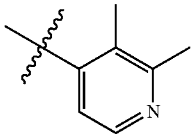 [SMILES: *c1ccnc(C)c1C] | |

TABLE 1-continued
Structure and $^1$HNMR data of Compound I
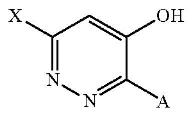
I
| No. | X | A | $^1$H NMR |
| --- | --- | --- | --- |
| 1416 | $CF_3$ | 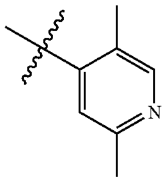 [SMILES: *c1cc(C)ncc1C] | |
| 1417 | $CF_3$ | 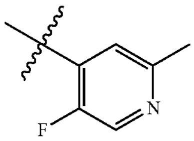 [SMILES: *c1cc(C)ncc1F] | |
| 1418 | $CF_3$ | 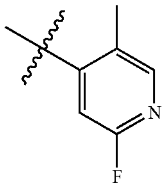 [SMILES: *c1cc(F)ncc1C] | |
| 1419 | $CF_3$ | 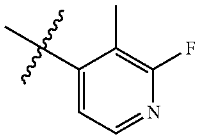 [SMILES: *c1ccnc(F)c1C] | |
| 1420 | $CF_3$ | 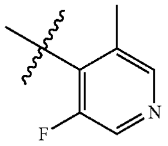 | |
| 1421 | $CF_3$ | 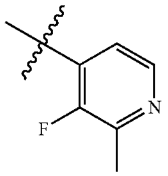 [SMILES: *c1ccnc(C)c1F] | |
| 1422 | $CF_3$ | 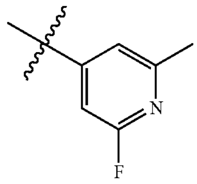 [SMILES: *c1cc(C)nc(F)c1] | |
| 1423 | $CF_3$ | 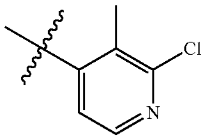 [SMILES: *c1ccnc(Cl)c1C] | |

TABLE 1-continued
Structure and $^1$HNMR data of Compound I
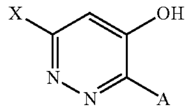
I
| No. | X | A | $^1$H NMR |
|---|---|---|---|
| 1424 | $CF_3$ | 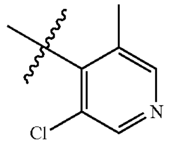 [SMILES: *c1c(C)cncc1Cl] | |
| 1425 | $CF_3$ | 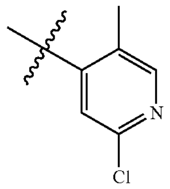 [SMILES: *c1cc(Cl)ncc1C] | |
| 1426 | $CF_3$ | 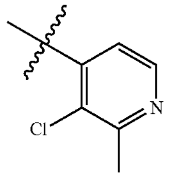 [SMILES: *c1ccnc(C)c1Cl] | |
| 1427 | $CF_3$ | 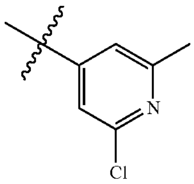 [SMILES: *c1cc(C)nc(Cl)c1] | |
| 1428 | $CF_3$ | 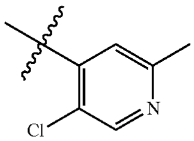 [SMILES: *c1cc(C)ncc1Cl] | |
| 1429 | $CF_3$ | 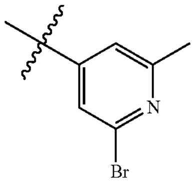 [SMILES: *c1cc(C)nc(Br)c1] | |
| 1430 | $CF_3$ | 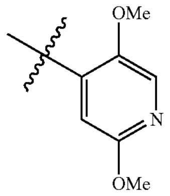 [SMILES: *c1cc(OC)ncc1OC] | |

TABLE 1-continued
Structure and $^1$HNMR data of Compound I
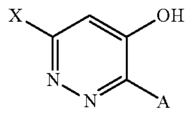
I
| No. | X | A | $^1$H NMR |
|---|---|---|---|
| 1431 | $CF_3$ | 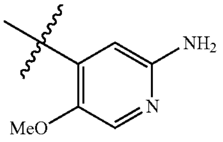 [SMILES: *c1cc(N)ncc1OC] | |
| 1432 | $CF_3$ | 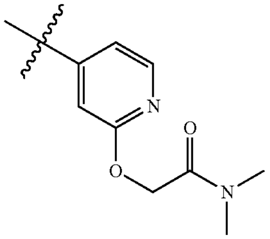 [SMILES: *c1ccnc(OCC(=O)N(C)C)c1] | |
| 1433 | $CF_3$ | 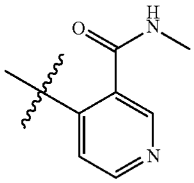 [SMILES: *c1ccncc1C(=O)NC] | |
| 1434 | $CF_3$ | 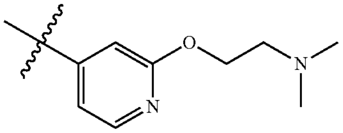 [SMILES: *c1ccnc(OCCN(C)C)c1] | |
| 1435 | $CF_3$ | 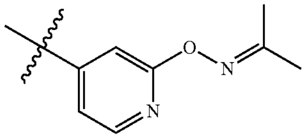 [SMILES: *c1ccnc(ON=C(C)C)c1] | |
| 1436 | $CF_3$ | 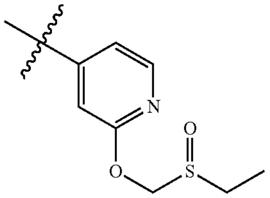 [SMILES: *c1ccnc(OCS(=O)CC)c1] | |
| 1437 | $CF_3$ | 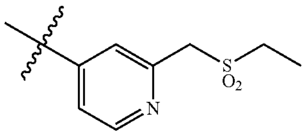 [SMILES: *c1ccnc(CS(=O)(=O)CC)c1] | |
| 1438 | $CF_3$ | 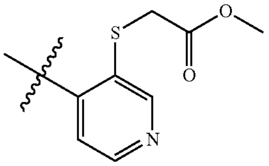 [SMILES: *c1ccncc1SCC(=O)OC] | |

TABLE 1-continued
| Structure and $^1$HNMR data of Compound I | | | |
|---|---|---|---|
| 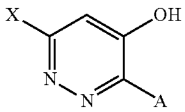 I | | | |
| No. | X | A | $^1$H NMR |
| 1439 | $CF_3$ | 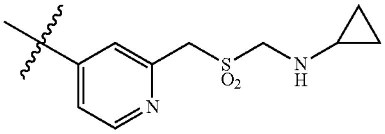 [SMILES: *c1ccnc(CS(=O)(=O)CNC2CC2)c1] | |
| 1440 | $CF_3$ | 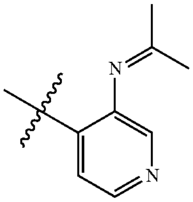 [SMILES: *c1ccncc1N=C(C)C] | |
| 1441 | $CF_3$ | 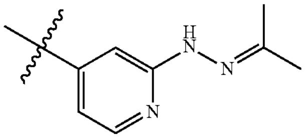 [SMILES: *c1ccnc(NN=C(C)C)c1] | |
| 1442 | $CF_3$ | 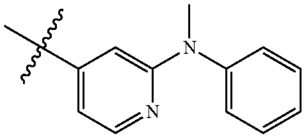 [SMILES: *c1ccnc(N(C)c2ccccc2)c1] | |
| 1443 | $CF_3$ | 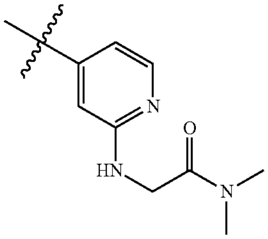 [SMILES: *c1ccnc(NCC(=O)N(C)C)c1] | |
| 1444 | $CF_3$ | 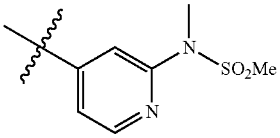 [SMILES: *c1ccnc(N(C)S(C)(=O)=O)c1] | |
| 1445 | $CF_3$ | 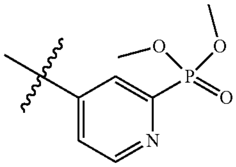 [SMILES: *c1ccnc(P(=O)(OC)OC)c1] | |

TABLE 1-continued
Structure and $^1$HNMR data of Compound I
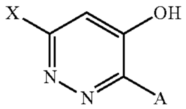
I
| No. | X | A | $^1$H NMR |
|---|---|---|---|
| 1446 | $CF_3$ | 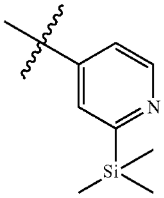 [SMILES: *c1ccnc([Si](C)(C)C)c1] | |
| 1447 | $CF_3$ | 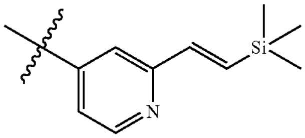 [SMILES: *c1ccnc(/C=C/[Si](C)(C)C)c1] | |
| 1448 | $CF_3$ | 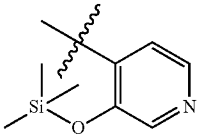 [SMILES: *c1ccncc1O[Si](C)(C)C] | |
| 1449 | $CF_3$ | 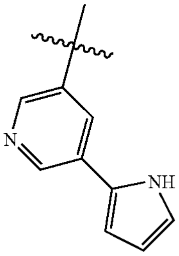 [SMILES: *c1cncc(-c2ccc[nH]2)c1] | |
| 1450 | $CF_3$ | 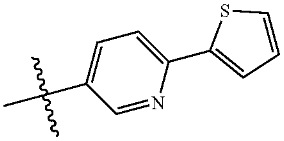 [SMILES: *c1ccc(-c2cccs2)nc1] | |
| 1451 | $CF_3$ | 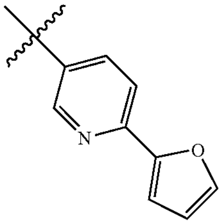 [SMILES: *c1ccc(-c2ccco2)nc1] | |
| 1452 | $CF_3$ | 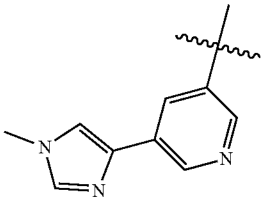 [SMILES: *c1cncc(-c2cn(C)cn2)c1] | |

TABLE 1-continued
Structure and $^1$HNMR data of Compound I
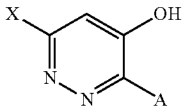
I
| No. | X | A | $^1$H NMR |
|---|---|---|---|
| 1453 | $CF_3$ | 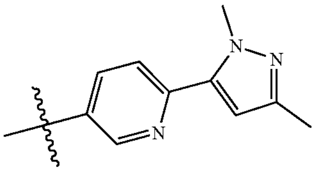 [SMILES: *c1ccc(-c2cc(C)nn2C)nc1] | |
| 1454 | $CF_3$ | 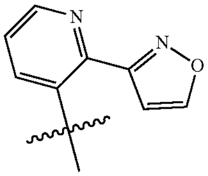 [SMILES: *c1cccnc1-c1ccon1] | |
| 1455 | $CF_3$ | 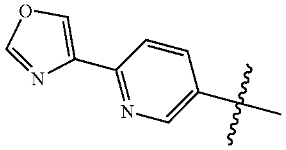 [SMILES: *c1ccc(-c2cocn2)nc1] | |
| 1456 | $CF_3$ | 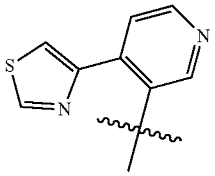 [SMILES: *c1cnccc1-c1cscn1] | |
| 1457 | $CF_3$ | 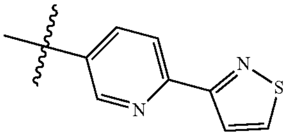 [SMILES: *c1ccc(-c2ccsn2)nc1] | |
| 1458 | $CF_3$ | 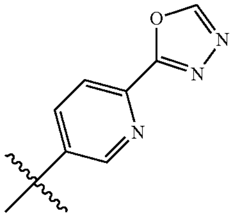 [SMILES: *c1ccc(-c2nnco2)nc1] | |
| 1459 | $CF_3$ | 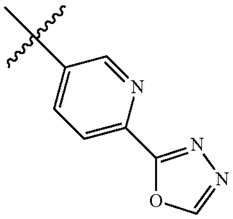 [SMILES: *c1ccc(-c2nnco2)nc1] | |

TABLE 1-continued
Structure and ¹HNMR data of Compound I
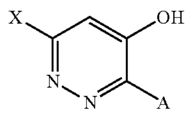
I
| No. | X | A | ¹H NMR |
|---|---|---|---|
| 1460 | $CF_3$ | 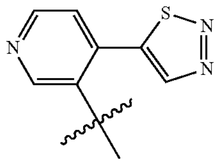 [SMILES: *c1cnccc1-c1cnns1] | |
| 1461 | $CF_3$ | 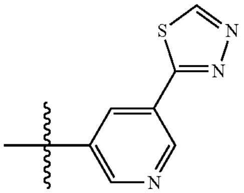 [SMILES: *c1cncc(-c2nncs2)c1] | |
| 1462 | $CF_3$ | 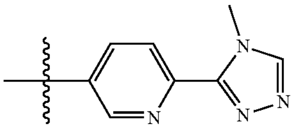 [SMILES: *c1ccc(-c2nncn2C)nc1] | |
| 1463 | $CF_3$ | 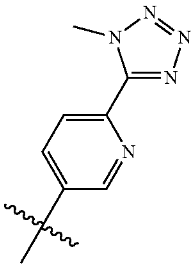 [SMILES: *c1ccc(-c2nnnn2C)nc1] | |
| 1464 | $CF_3$ | 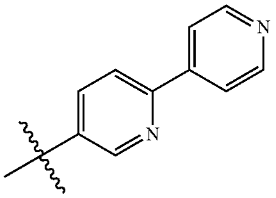 [SMILES: *c1ccc(-c2ccncc2)nc1] | |
| 1465 | $CF_3$ | 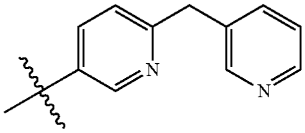 [SMILES: *c1ccc(Cc2cccnc2)nc1] | |
| 1466 | $CF_3$ | 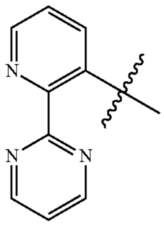 [SMILES: *c1cccnc1-c1ncccn1] | |

TABLE 1-continued
Structure and 1HNMR data of Compound I
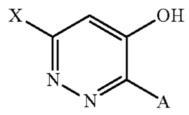
I
| No. | X | A | $^1$H NMR |
|---|---|---|---|
| 1467 | $CF_3$ | 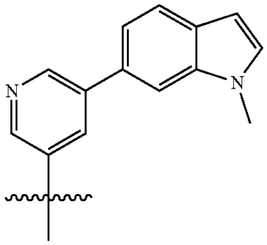 [SMILES: *c1cncc(-c2ccc3ccn(C)c3c2)c1] | |
| 1468 | $CF_3$ | 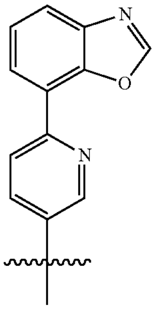 [SMILES: *c1ccc(-c2cccc3ncoc23)nc1] | |
| 1469 | $CF_3$ | 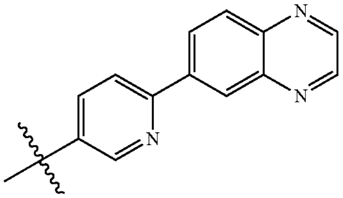 [SMILES: *c1ccc(-c2ccc3nccnc3c2)nc1] | |
| 1470 | $CF_2CF_3$ | 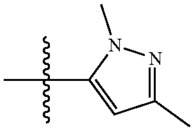 [SMILES: *c1cc(C)nn1C] | |
| 1471 | $CH_2F$ | 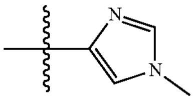 [SMILES: *c1cn(C)cn1] | |
| 1472 | $CHF_2$ | 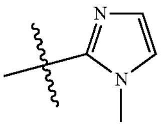 [SMILES: *c1nccn1C] | |
| 1473 | $CF_2CF_3$ | 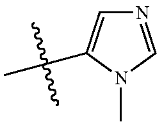 [SMILES: *c1cncn1C] | |
| 1474 | $CHF_2$ | 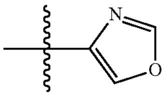 | |

TABLE 1-continued
Structure and ¹HNMR data of Compound I
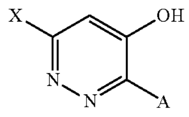
I
| No. | X | A | ¹H NMR |
|---|---|---|---|
| 1475 | $CHF_2$ | 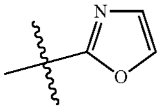 [SMILES: *c1ncco1] | |
| 1476 | $CF_2CF_3$ | 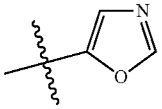 [SMILES: *c1cnco1] | |
| 1477 | $CH_2F$ | 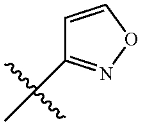 [SMILES: *c1ccon1] | |
| 1478 | $OCHF_2$ | 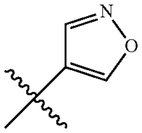 [SMILES: *c1cnoc1] | |
| 1479 | $CF_2CF_3$ | 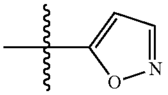 | |
| 1480 | $CF_2CF_3$ | 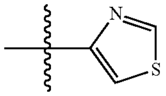 [SMILES: *c1cscn1] | |
| 1481 | $CF_2CF_3$ | 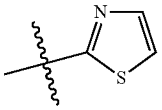 [SMILES: *c1nccs1] | |
| 1482 | $CF_2CF_3$ | 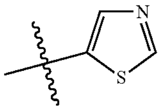 [SMILES: *c1cncs1] | |
| 1483 | Ph | 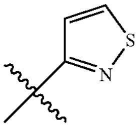 [SMILES: *c1ccsn1] | |
| 1484 | $CF_2CF_3$ | 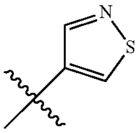 [SMILES: *c1cnsc1] | |
| 1485 | $CF_2CF_3$ | 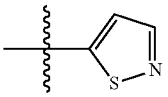 | |

TABLE 1-continued
Structure and $^{1}$HNMR data of Compound I
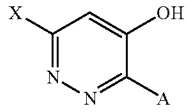
I
| No. | X | A | $^{1}$H NMR |
|---|---|---|---|
| 1486 | $CF_2CF_3$ | 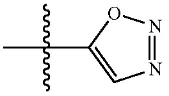 | |
| 1487 | CN | 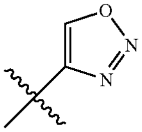 [SMILES: *c1conn1] | |
| 1488 | $CF_2CF_3$ | 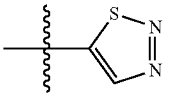 [SMILES: *c1cnns1] | |
| 1489 | $CF_2CF_3$ | 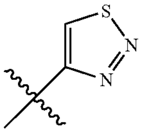 [SMILES: *c1csnn1] | |
| 1490 | $CF_2CF_3$ | 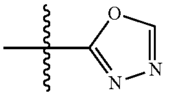 [SMILES: *c1nnco1] | |
| 1491 | $CF_2CF_3$ | 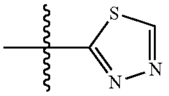 | |
| 1492 | $CF_2CF_3$ | 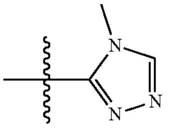 [SMILES: *c1nncn1C] | |
| 1493 | $CF_3$ | 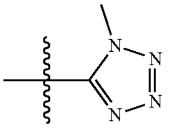 [SMILES: *c1nnnn1C] | $^{1}$H NMR (500 MHz, Chloroform-d) 7.16 (s, 1H), 5.85 (s, 1H), 4.27 (s, 3H). |
| 1494 | $CF_3$ | 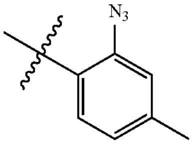 [SMILES: *c1ccc(C)cc1N=[N+]=[N-]] | |
| 1495 | $CF_3$ | 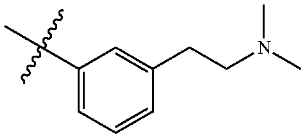 [SMILES: *c1cccc(CCN(C)C)c1] | |

TABLE 1-continued
Structure and $^1$HNMR data of Compound I
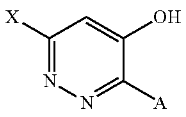
I
| No. | X | A | $^1$H NMR |
|---|---|---|---|
| 1496 | $CF_3$ | 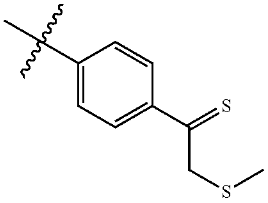 [SMILES: *c1ccc(C(=S)CSC)cc1] | |
| 1497 | $CF_3$ | 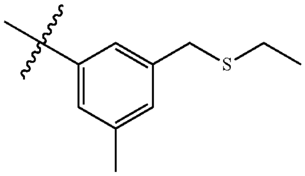 [SMILES: *c1cc(C)cc(CSCC)c1] | |
| 1498 | $CF_3$ | 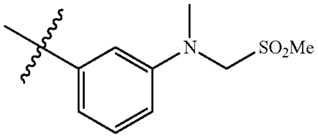 [SMILES: *c1cccc(N(C)CS(C)(=O)=O)c1] | |
| 1499 | $CF_3$ | 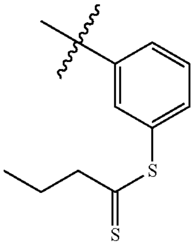 [SMILES: *c1cccc(SC(=S)CCC)c1] | |
| 1500 | $CF_3$ | 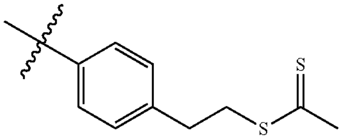 [SMILES: *c1ccc(CCSC(C)=S)cc1] | |
| 1501 | $CF_3$ | 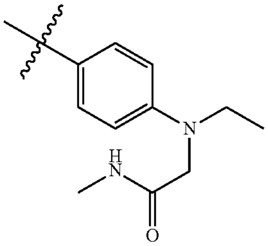 [SMILES: *c1ccc(N(CC)CC(=O)NC)cc1] | |
| 1502 | $CF_3$ | 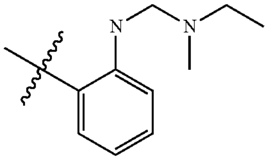 | |

TABLE 1-continued
Structure and $^{1}$HNMR data of Compound I
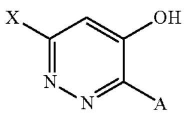
I
| No. | X | A | $^{1}$H NMR |
|---|---|---|---|
| 1503 | $CF_3$ | 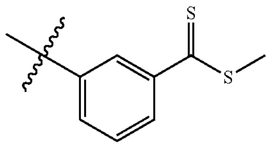 [SMILES: *c1cccc(C(=S)SC)c1] | |
| 1504 | $CF_3$ | 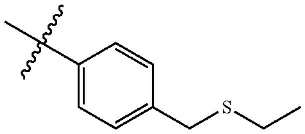 [SMILES: *c1ccc(CSCC)cc1] | |
| 1505 | $CF_3$ | 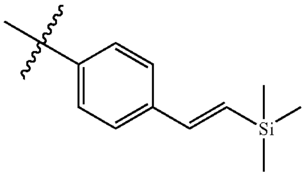 [SMILES: *c1ccc(/C=C/[Si](C)(C)C)cc1] | |
| 1506 | $CF_3$ | 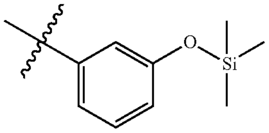 [SMILES: *c1cccc(O[Si](C)(C)C)c1] | |
| 1507 | $CONH_2$ | 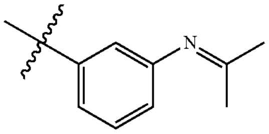 [SMILES: *c1cccc(N=C(C)C)c1] | |
| 1508 | $CF_3$ | 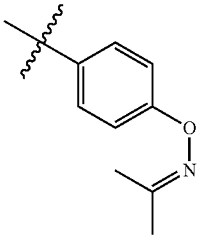 [SMILES: *c1ccc(ON=C(C)C)cc1] | |
| 1509 | $CF_3$ | 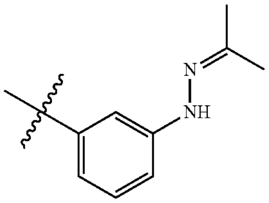 [SMILES: *c1cccc(NN=C(C)C)c1] | |
| 1510 | $CF_3$ | 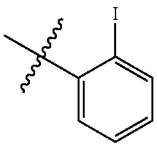 [SMILES: *c1ccccc1I] | |

TABLE 1-continued
Structure and $^1$HNMR data of Compound I
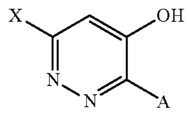
I
| No. | X | A | $^1$H NMR |
|---|---|---|---|
| 1511 | $CF_3$ | 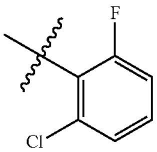 [SMILES: *c1c(F)cccc1Cl] | |
| 1512 | $CF_3$ | 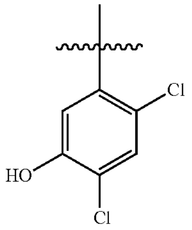 [SMILES: *c1cc(O)c(Cl)cc1Cl] | $^1$H NMR (500 MHz, Chloroform-d) 7.34 (s, 1H), 7.08 (s, 1H), 7.04 (s, 1H), 5.78 (s, 1H), 5.53 (s, 1H). |
| 1513 | Ph | 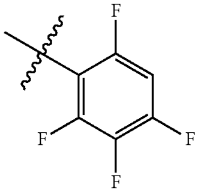 [SMILES: *c1c(F)cc(F)c(F)c1F] | |
| 1514 | $CF_3$ | 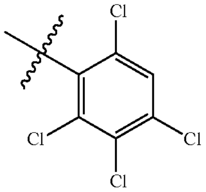 [SMILES: *c1c(Cl)cc(Cl)c(Cl)c1Cl] | |
| 1515 | $CF_3$ | 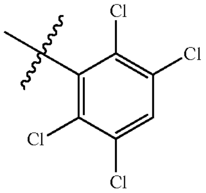 [SMILES: *c1c(Cl)c(Cl)cc(Cl)c1Cl] | |
| 1516 | $NH_2$ | 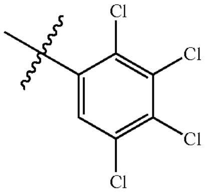 [SMILES: *c1cc(Cl)c(Cl)c(Cl)c1Cl] | |
| 1517 | $CF_3$ | 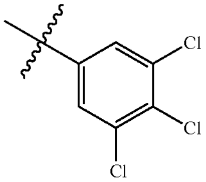 [SMILES: *c1cc(Cl)c(Cl)c(Cl)c1] | |

TABLE 1-continued
Structure and $^{1}$HNMR data of Compound I
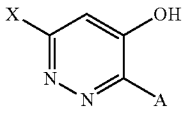
I
| No. | X | A | $^{1}$H NMR |
|---|---|---|---|
| 1518 | $CF_3$ | 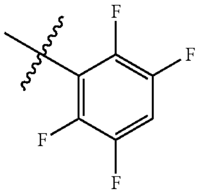 [SMILES: *c1c(F)c(F)cc(F)c1F] | |
| 1519 | $CF_3$ | 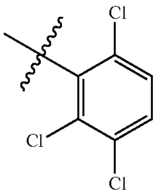 [SMILES: *c1c(Cl)ccc(Cl)c1Cl] | |
| 1520 | $CF_3$ | 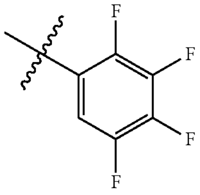 [SMILES: *c1cc(F)c(F)c(F)c1F] | |
| 1521 | $CF_3$ | 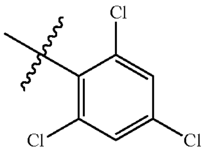 [SMILES: *c1c(Cl)cc(Cl)cc1Cl] | |
| 1522 | $CF_3$ | 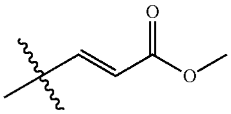 [SMILES: */C=C/C(=O)OC] | $^{1}$H NMR (500 MHz, Chloroform-d) δ 7.74 (d, J = 15.0 Hz, 1H), 7.00 (s, 1H), 6.50 (d, J = 15.0 Hz, 1H), 5.87 (s, 1H), 4.24 (q, J = 8.0 Hz, 2H), 1.31 (t, J = 8.0 Hz, 3H). |
| 1523 | $CF_3$ | 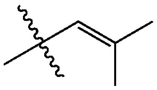 [SMILES: *C=C(C)C] | $^{1}$H NMR (500 MHz, Chloroform-d) δ 6.99 (s, 1H), 6.25 (s, 1H), 5.87 (s, 1H), 1.78 (s, 6H). |
| 1524 | $CF_3$ | 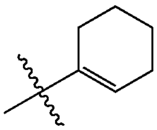 [SMILES: *C1=CCCCC1] | $^{1}$H NMR (500 MHz, Chloroform-d) δ 7.07 (s, 1H), 6.07-5.96 (m, 1H), 5.87 (s, 1H), 2.03-1.93 (m, 4H), 1.66-1.56 (m, 4H). |
| 1525 | $CF_3$ | Me | (500 MHz, Chloroform-7) 5 6.96 (s, 1H), 5.87 (s, 1H), 2.10 (s, 3H). |
| 1526 | $CF_3$ | 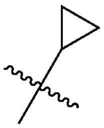 [SMILES: *C1CC1] | |

TABLE 1-continued
Structure and $^1$HNMR data of Compound I
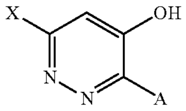
I
| No. | X | A | $^1$H NMR |
|---|---|---|---|
| 1527 | OH | 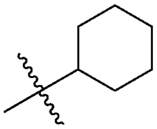 [SMILES: *C1CCCCC1] | |
| 1528 | $CF_3$ | 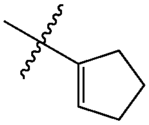 [SMILES: *C1=CCCC1] | (500 MHz, Chloroform-d) δ 6.95 (s, 1H), 6.38-6.31 (m, 1H), 5.87 (s, 1H), 2.35-2.24 (m, 4H), 1.82-1.70 (m, 2H). |
| 1529 | $CF_3$ | 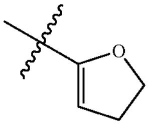 [SMILES: *C1=CCCO1] | (500 MHz, Chloroform-d) δ 6.99 (s, 1H), 5.87 (s, 1H), 5.65-5.42 (m, 1H), 4.31-4.22 (m, 2H), 2.62-2.54 (m, 2H). |
| 1530 | $CF_3$ | 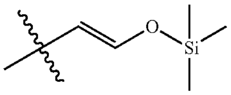 [SMILES: */C=C/O[Si](C)(C)C] | (500 MHz, Chloroform-d) δ 7.03 (s, 1H), 6.22 (d, J = 15.0 Hz, 1H), 5.93-5.85 (m, 2H), 0.08 (s, 9H). |
| 1531 | $CF_3$ | 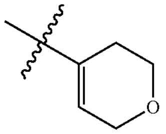 [SMILES: *C1=CCOCC1] | (500 MHz, Chloroform-d) δ 7.09 (s, 1H), 5.87 (s, 1H), 5.81-5.74 (m, 1H), 4.20-4.04 (m, 2H), 3.79-3.66 (m, 2H), 2.13-2.01 (m, 2H). |
| 1532 | $CF_3$ | 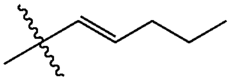 [SMILES: */C=C/CCC] | (500 MHz, Chloroform-d) δ 7.03 (s, 1H), 6.40-6.26 (m, 2H), 5.87 (s, 1H), 2.07-1.97 (m, 2H), 1.46-1.32 (m, 2H), 0.95 (t, J = 8.0 Hz, 3H). |
| 1533 | $CF_3$ | Et | (500 MHz, Chloroform-d) δ 6.96 (s, 1H), 5.87 (s, 1H), 2.41 (q, J = 8.0 Hz, 2H), 1.16 (t, J = 8.0 Hz, 3H). |
| 1534 | $OCF_3$ | 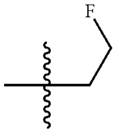 | |
| 1535 | $CF_3$ | 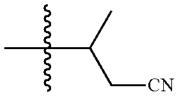 [SMILES: *C(C)CC#N] | |
| 1536 | CN | 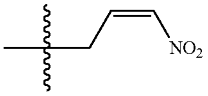 [SMILES: *C/C=C\[N+](=O)[O-]] | |
| 1537 | $CF_3$ | 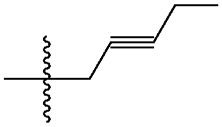 [SMILES: *CC#CCC] | |

TABLE 1-continued
Structure and $^1$HNMR data of Compound I
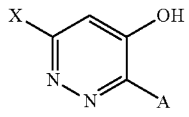
I
| No. | X | A | $^1H$ NMR |
| --- | --- | --- | --- |
| 1538 | $CF_3$ | 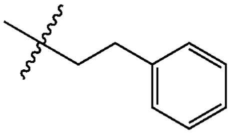 [SMILES: *CCc1ccccc1] | |
| 1539 | $CF_3$ | 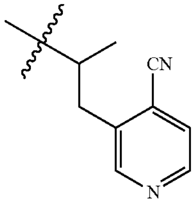 [SMILES: *C(C)Cc1cnccc1C#N] | |
| 1540 | $CF_3$ | 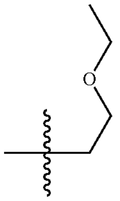 [SMILES: *CCOCC] | |
| 1541 | $CF_3$ | 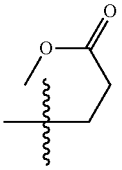 [SMILES: *CCC(=O)OC] | |
| 1542 | $CF_3$ | 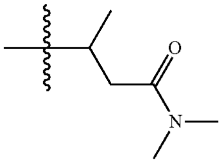 [SMILES: *C(C)CC(=O)N(C)C] | |
| 1543 | $CF_2CF_3$ | 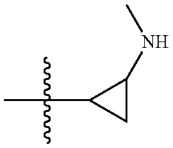 [SMILES: *C1CC1NC] | |
| 1544 | $CF_3$ | 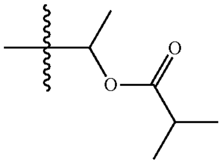 [SMILES: *C(C)OC(=O)C(C)C] | |
| 1545 | $CF_3$ | 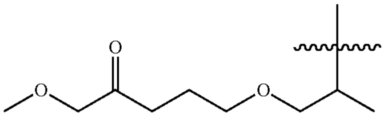 [SMILES: *C(C)COCCCC(=O)COC] | |

TABLE 1-continued
Structure and $^{1}$HNMR data of Compound I
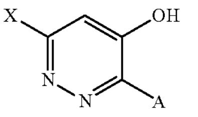
I
| No. | X | A | $^{1}$H NMR |
|---|---|---|---|
| 1546 | $CF_3$ | 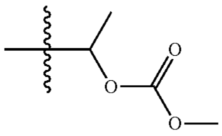 [SMILES: *C(C)OC(=O)OC] | |
| 1547 | $CHF_2$ | 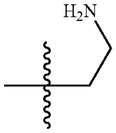 [SMILES: *CCN] | |
| 1548 | $CF_3$ | 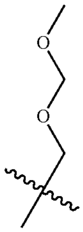 [SMILES: *COCOC] | |
| 1549 | $CF_3$ | 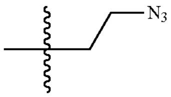 [SMILES: *CCN=[N+]=[N-]] | |
TABLE 2
Structure and $^{1}$HNMR data of the derivative Compound I-1
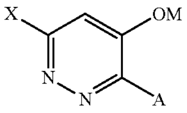
I-1
| No. | X | M | A | $^{1}$HNMR |
|---|---|---|---|---|
| 1-1 | $CF_3$ | 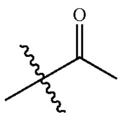 [SMILES: *C(C)=O] | 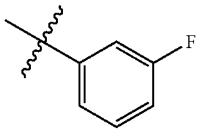 [SMILES: *c1cccc(F)c1] | (500 MHz, Chloroform-d) δ 7.43-7.27 (m, 3H), 7.15-7.02 (m, 2H), 2.47 (s, 3H). |
| 1-2 | $CF_3$ | 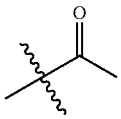 [SMILES: *C(C)=O] | 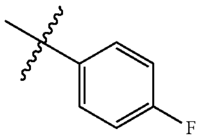 [SMILES: *c1ccc(F)cc1] | (500 MHz, Chloroform-d) δ 7.47-7.39 (m, 2H), 7.18 (s, 1H), 7.11-7.03 (m, 2H), 2.47 (s, 3H). |
| 1-3 | $CF_3$ | 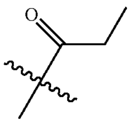 [SMILES: *C(=O)CC] | 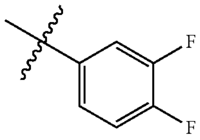 [SMILES: *c1ccc(F)c(F)c1] | (500 MHz, Chloroform-d) δ 7.45-7.33 (m, 2H), 7.20-7.11 (m, 2H), 2.27 (q, 7 = 8.0 Hz, 1H), 1.12 (t, J = 8.0 Hz, 2H). |

TABLE 2-continued

Structure and $^1$HNMR data of the derivative Compound I-1

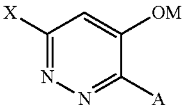

I-1

| No. | X | M | A | $^1$HNMR |
|---|---|---|---|---|
| 1-4 | $CF_3$ | 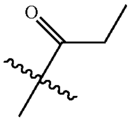 [SMILES: *C(=O)CC] | 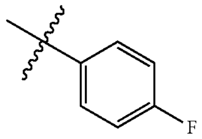 [SMILES: *c1ccc(F)cc1] | (500 MHz, Chloroform-d) δ 7.45-7.37 (m, 2H), 7.18 (s, 1H), 7.11-7.03 (m, 2H), 2.27 (q, J = 8.0 Hz, 2H), 1.03 (t, J = 8.0 Hz, 3H). |
| 1-5 | $CF_3$ | 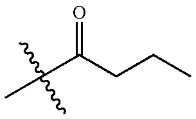 [SMILES: *C(=O)CCC] | 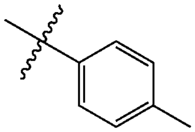 [SMILES: *c1ccc(C)cc1] | (500 MHz, Chloroform-d) δ 7.37-7.31 (m,2H),7.17(s, 1H), 6.84-6.78 (m, 2H), 2.78 (t, J = 8.0 Hz, 2H), 2.27 (s, 3H), 1.73- 1.62 (m, 2H), 1.38 (t, J = 8.0 Hz, 3H). |
| 1-6 | $CF_3$ | 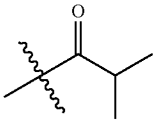 [SMILES: *C(=O)C(C)C] | 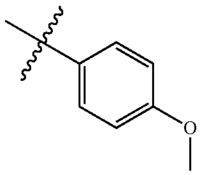 [SMILES: *c1ccc(OC)cc1] | (500 MHz, Chloroform-d) δ 7.43-7.36 (m, 2H), 7.17 (s, 1H), 6.80-6.74 (m, 2H), 3.80 (s, 3H), 2.70 (hept, J = 6.5 Hz, 1H), 1.17 (d, J = 6.5 Hz, 6H). |
| 1-7 | $CF_3$ | 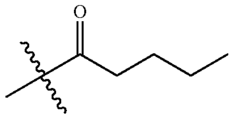 [SMILES: *C(=O)CCCC] | 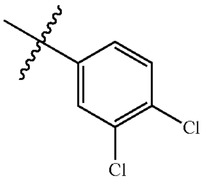 | (500 MHz, Chloroform-d) δ 7.63 (d, J = 2.0 Hz, 1H), 7.31 (dd, J = 7.5, 2.0 Hz, 1H), 7.26 (d, J = 7.5 Hz, 1H), 7.18 (s, 1H), 2.33 (t, J = 8.0 Hz, 2H), 1.53-1.41 (m, 4H), 0.92 (t, J = 8.0 Hz, 3H). |
| 1-8 | $CF_3$ | 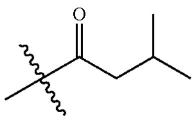 [SMILES: *C(=O)CC(C)C] | 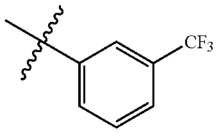 [SMILES: *c1cccc(C(F)(F)F)c1] | (500 MHz, Chloroform-d) δ 7.98-7.89 (m, 2H), 7.75-7.63 (m, 2H),7.19(s, 1H), 4.08 (d, J = 7.0 Hz, 2H), 2.19-2.02 (m, 1H), 0.97 (d,7 = 7.0 Hz, 6H). |
| 1-9 | $CF_3$ | 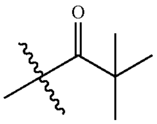 [SMILES: *C(=O)C(C)(C)C] | 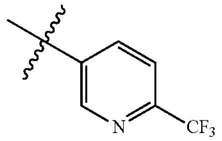 | (500 MHz, Chloroform-d) δ 9.13 (d, J = 1.5 Hz, 1H), 8.09 (dd, J = 8.0,1.5 Hz, 1H), 7.41 (d, J = 7.0 Hz, 2H), 1.16 (s, 9H). |
| 1-10 | $CF_3$ | 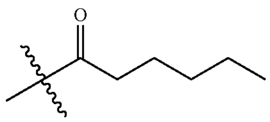 [SMILES: *C(=O)CCCCC] | 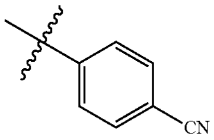 [SMILES: *c1ccc(C#N)cc1] | (500 MHz, Chloroform-d) δ 7.92 (d, J = 7.5 Hz, 2H), 7.70 (d,7 = 7.5 Hz, 2H),7.18 (s, 1H), 2.33 (t, J = 8.0 Hz, 2H), 1.50-1.23 (m, 6H), 0.92 (t, J = 8.0 Hz, 3H). |
| 1-11 | $CF_3$ | 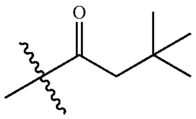 [SMILES: *C(=O)CC(C)(C)C] | 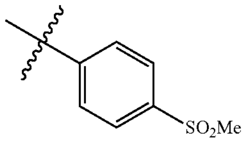 [SMILES: *c1ccc(S(C)(=O)=O)cc1] | (500 MHz, Chloroform-d) δ 7.96-7.90 (m, 2H), 7.90-7.84 (m, 2H), 7.26 (s, 1H), 3.30 (s, 3H), 2.09 (s, 2H), 0.93 (s, 9H). |

TABLE 2-continued

Structure and $^1$HNMR data of the derivative Compound I-1

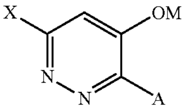

I-1

| No. | X | M | A | $^1$HNMR |
|---|---|---|---|---|
| 1-12 | $CF_3$ | 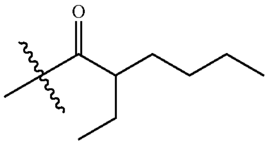 [SMILES: *C(=O)C(CC)CCCC] | 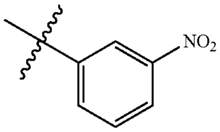 [SMILES: *c1cccc([N+](=O)[O-])c1] | (500 MHz, Chloroform-d) δ 8.41-8.21 (m, 2H), 7.91-7.60 (m, 2H),7.19(s, 1H), 2.14-1.77 (m, 3H), 1.75-1.53 (m, 2H), 1.45-1.24 (m, 4H), 0.90 (t, J = 7.5 Hz, 3H), 0.79 (t, J = 8.0 Hz, 3H). |
| 1-13 | $CF_3$ | 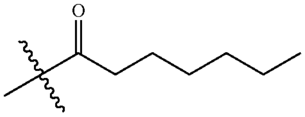 [SMILES: *C(=O)CCCCCC] | 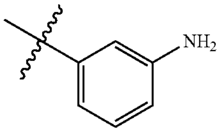 | (500 MHz, Chloroform-d) δ 7.18-7.08 (m, 2H), 6.93-6.68 (m, 2H), 6.62-6.47 (m, 1H), 4.13(s, 2H), 2.33 (t, J = 6.0 Hz, 2H), 1.51-1.22 (m, 8H), 0.93 (t, J = 8.0 Hz, 3H). |
| 1-14 | $CF_3$ | 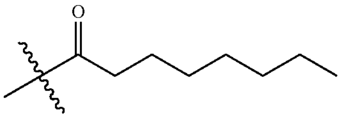 [SMILES: *C(=O)CCCCCCC] | 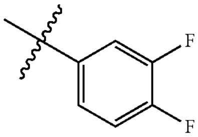 [SMILES: *c1ccc(F)c(F)c1] | (500 MHz, Chloroform-d) δ 7.41-7.19 (m, 2H), 7.23-7.10 (m, 2H), 2.33 (t, J = 8.0 Hz, 2H), 1.51-1.36 (m, 2H), 1.34-1.22 (m, 8H), 0.94 (t, J = 8.0 Hz, 3H). |
| 1-15 | $CF_3$ | 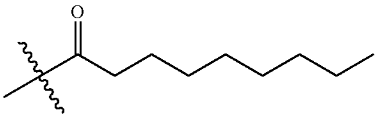 [SMILES: *C(=O)CCCCCCCC] | 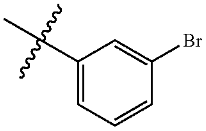 | (500 MHz, Chloroform-d) δ 7.62-7.52 (m, 2H), 7.46-7.29 (m, 2H),7.14(s, 1H), 2.33 (t, J = 8.0 Hz, 2H), 1.51-1.22 (m, 12H), 0.93 (t, J = 8.0 Hz, 3H). |
| 1-16 | $CF_3$ | 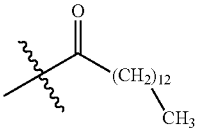 | 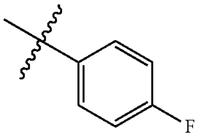 [SMILES: *c1ccc(F)cc1] | (500 MHz, Chloroform-d) δ 7.47-7.39 (m, 2H), 7.11-7.03 (m, 2H), 2.33 (t, J = 7.5 Hz, 2H), 1.51-1.22 (m, 22H), 0.89 (t, J = 8.0 Hz, 3H). |
| 1-17 | $CF_3$ | 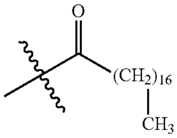 | 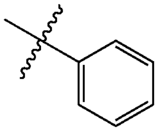 [SMILES: *c1ccccc1] | (500 MHz, Chloroform-d) δ 7.59-7.52 (m, 2H), 7.41-7.31 (m, 3H), 2.33 (t, J = 7.5 Hz, 2H), 1.51-1.22 (m, 30H), 0.87 (t, J = 8.0 Hz, 3H). |
| 1-18 | $CF_3$ | 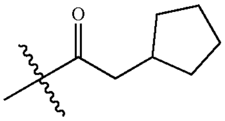 [SMILES: *C(=O)CC1CCCC1] | 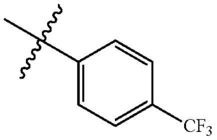 [SMILES: *c1ccc(C(F)(F)F)cc1] | (500 MHz, Chloroform-d) δ 7.70 (d, J = 7.5 Hz, 2H), 7.43 (d, J = 7.5 Hz, 2H), 7.13 (s, 1H), 4.08 (d, J = 7.0 Hz, 2H), 1.71-1.52 (m, 7H), 1.28-1.17 (m, 2H). |
| 1-19 | $CF_3$ | 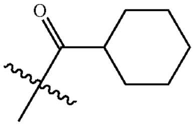 [SMILES: *C(=O)C1CCCCC1] | 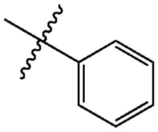 [SMILES: *c1ccccc1] | (500 MHz, Chloroform-d) δ 7.53-7.45 (m, 2H), 7.46-7.37 (m, 3H), 7.18 (s, 1H), 2.37-2.29 (m, 1H), 2.25-2.14 (m, 2H), 1.82-1.63 (m, 5H), 1.53-1.40 (m,3H). |
| 1-20 | $CF_3$ | 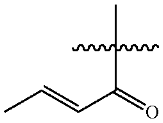 [SMILES: *C(=O)/C=C/C] | 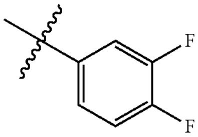 [SMILES: *c1ccc(F)c(F)c1] | (500 MHz, Chloroform-d) δ 7.47-7.27 (m, 2H), 7.22-7.14 (m, 1H), 7.17-7.00 (m, 2H), 5.54-5.42 (m, 1H), 1.87 -1.72(m, 3H). |

TABLE 2-continued

Structure and $^1$HNMR data of the derivative Compound I-1

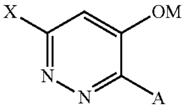

I-1

| No. | X | M | A | $^1$HNMR |
|---|---|---|---|---|
| 1-21 | $CF_3$ | 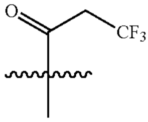 [SMILES: *C(=O)CC(F)(F)F] | 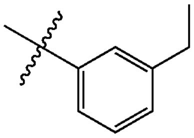 [SMILES: *c1cccc(CC)c1] | (500 MHz, Chloroform-d) δ 7.39-7.32 (m, 2H), 7.32-7.26 (m, 2H),7.14 (s, 1H), 2.75 (q, J = 8.0 Hz, 2H), 2.71-2.61 (m, 2H), 1.21 (t, J = 8.0 Hz, 3H). |
| 1-22 | $CF_3$ | 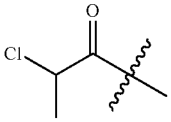 [SMILES: *C(=O)C(C)Cl] | 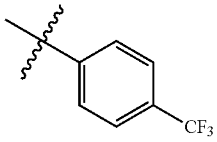 [SMILES: *c1ccc(C(F)(F)F)cc1] | (500 MHz, Chloroform-d) δ 7.72-7.67 (m, 2H), 7.59-7.52 (m, 2H),7.17 (s, 1H), 4.49 (q, J = 6.5 Hz, 1H), 1.72 (d, J = 6.5 Hz, 3H). |
| 1-23 | $CF_3$ | 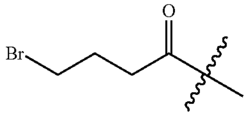 [SMILES: *C(=O)CCCBr] | 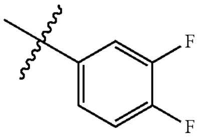 [SMILES: *c1ccc(F)c(F)c1] | (500 MHz, Chloroform-d) δ 7.44-7.30 (m, 2H), 7.25-7.17 (m, 2H), 3.28(t, J = 7.0 Hz, 2H), 2.33 (t, J = 7.5 Hz, 2H), 2.06-1.98 (m, 2H). |
| 1-24 | $CF_3$ | 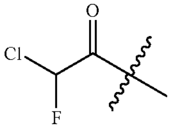 [SMILES: *C(=O)C(F)Cl] | 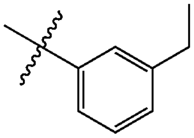 [SMILES: *c1cccc(CC)c1] | |
| 1-25 | $CF_3$ | 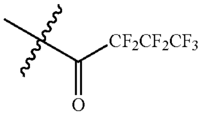 | 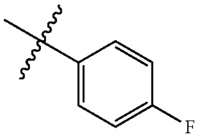 [SMILES: *c1ccc(F)cc1] | (500 MHz, Chloroform-d) δ 7.48-7.40 (m, 2H), 7.24 (s, 1H), 7.11-7.03 (m, 2H). |
| 1-26 | $CF_3$ | 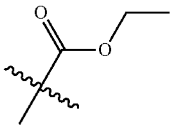 [SMILES: *C(=O)OCC] | 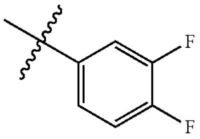 [SMILES: *c1ccc(F)c(F)c1] | (500 MHz, Chloroform-d) δ 7.43-7.22 (m, 2H), 7.20-7.11 (m,2H), 4.25 (q, J = 8.0 Hz, 2H), 1.26 (t, J = 8.0 Hz, 3H). |
| 1-27 | $CF_3$ | 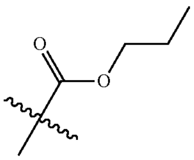 [SMILES: *C(=O)OCCC] | 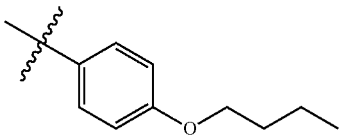 [SMILES: *c1ccc(OCCCC)cc1] | (500 MHz, Chloroform-d) δ 7.51-7.45 (m, 2H), 7.09-7.03 (m, 2H), 4.23 (t, J = 7.5 Hz, 2H), 4.00 (t, J = 7.5 Hz, 2H), 1.87-1.50 (m, 6H), 1.02 (t, J = 8.0 Hz, 3H), 0.92 (t, J = 8.0 Hz, 3H). |
| 1-28 | $CF_3$ | 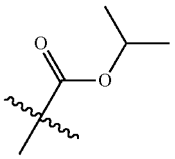 [SMILES: *C(=O)OC(C)C] | 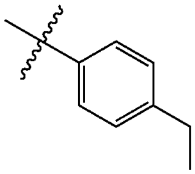 [SMILES: *c1ccc(CC)cc1] | (500 MHz, Chloroform-d) δ 7.50(d, J = 7.5Hz, 2H), 7.21 (s, 1H), 7.10 (d, J = 7.5 Hz, 2H), 5.15 (hept, J = 6.5 Hz, 1H), 2.77 (q, J = 7.5 Hz, 2H), 1.26-1.15 (m, 9H). |
| 1-29 | $CF_3$ | 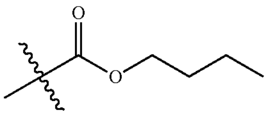 [SMILES: *C(=O)OCCCC] | 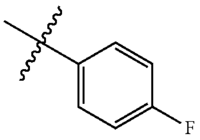 [SMILES: *c1ccc(F)cc1] | (500 MHz, Chloroform-d) δ 7.48-7.40 (m, 2H), 7.21 (s, 1H), 7.11-7.03 (m, 2H), 4.23 (t, J = 7.5 Hz, 2H), 1.60-1.40 (m, 4H), 0.98 (t, J = 8.0 Hz, 3H). |

TABLE 2-continued

Structure and $^1$HNMR data of the derivative Compound I-1

I-1

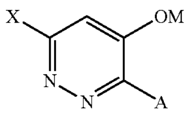

| No. | X | M | A | $^1$HNMR |
|---|---|---|---|---|
| 1-30 | $CF_3$ | 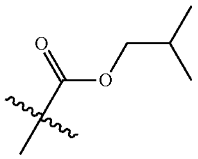 [SMILES: *C(=O)OCC(C)C] | 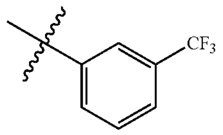 [SMILES: *c1cccc(C(F)(F)F)c1] | (500 MHz, Chloroform-d) δ 7.99-7.90 (m, 2H), 7.75-7.69-7.61 (m, 2H), 7.22 (s, 1H), 4.05 (d, J = 7.0 Hz, 2H), 1.95- 1.80 (m, 1H), 0.95 (d, J = 6.5 Hz, 6H). |
| 1-31 | $CF_3$ | 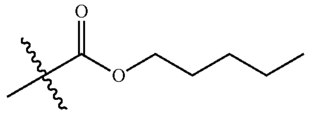 [SMILES: *C(=O)OCCCCC] | 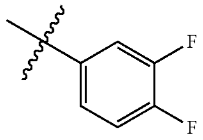 [SMILES: *c1ccc(F)c(F)c1] | (500 MHz, Chloroform-d) δ 7.43-7.22 (m, 2H), 7.21-7.11 (m, 2H), 4.23 (t, J = 7.5 Hz, 2H), 1.79-1.39 (m, 6H), 0.95 (t, J = 8.0 Hz, 3H). |
| 1-32 | $CF_3$ | 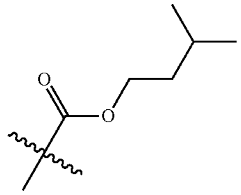 | 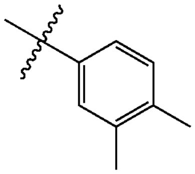 [SMILES: *c1ccc(C)c(C)c1] | (500 MHz, Chloroform-d) δ 7.36-7.28 (m, 2H), 7.20 (s, 1H), 7.13 (dd, J = 7.5, 1.0 Hz, 1H), 4.23 (t, J = 7.5 Hz, 2H), 2.30 (s, 3H), 2.20 (s, 3H), 1.78 -1.52 (m, 3H), 0.97 (d, J = 7.0 Hz, 6H). |
| 1-33 | $CF_3$ | 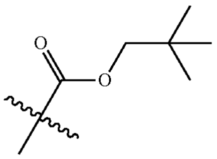 | 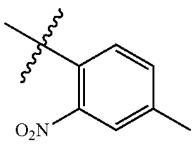 [SMILES: *c1ccc(C)cc1[N+](=O)[O-]] | (500 MHz, Chloroform-d) δ 7.96 (d, J = 2.5 Hz, 1H), 7.83 (dd, J = 7.5, 2.5 Hz, 1H), 7.48 (d, J = 7.5 Hz, 1H),7.22(s, 1H), 4.02 (s, 2H), 2.50 (s, 3H), 0.95 (s, 9H). |
| 1-34 | $CF_3$ | 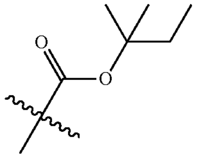 [SMILES: *C(=O)OC(C)(C)CC] | 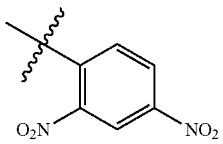 | (500 MHz, Chloroform-d) δ 8.77 (d, J = 2.0 Hz, 1H), 8.57 (dd, J = 7.5, 2.0 Hz, 1H), 8.25 (d, J = 7.5 Hz, 1H),7.24(s, 1H), 1.61 (s, 6H), 1.49 (q, J = 8.0 Hz, 2H), 0.90 (t, J = 8.0 Hz, 3H). |
| 1-35 | $CF_3$ | 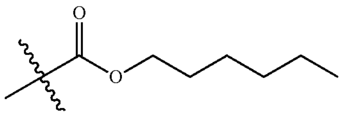 [SMILES: *C(=O)OCCCCCC] | 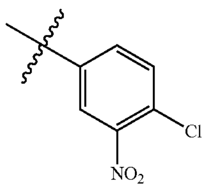 [SMILES: *c1ccc(Cl)c([N+](=O)[O-])c1] | (500 MHz, Chloroform-d) δ 8.05 (d, J = 2.0 Hz, 1H),7.80-7.70 (m, 2H), 7.22 (s, 1H), 4.23 (t, J = 7.5 Hz, 2H), 1.72-1.31 (m, 8H), 0.93 (t, J = 7.5 Hz, 3H). |
| 1-36 | $CF_3$ | 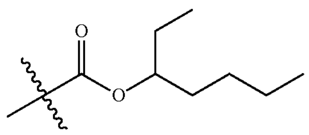 [SMILES: *C(=O)OC(CC)CCCC] | 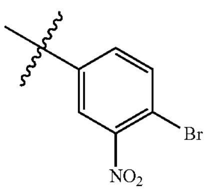 | (500 MHz, Chloroform-d) δ 8.08 (d, J = 2.0 Hz, 1H), 7.93 (dd, J = 7.5, 2.0 Hz, 1H), 7.82 (d, J = 7.5 Hz, 1H), 7.20 (s, 1H), 4.79-4.53 (m, 1H), 2.06 -1.88 (m, 2H), 1.71-1.57 (m, 4H), 1.30-1.19 (m, 2H), 0.89 (t, J = 8.0 Hz, 3H), 0.78 (t, J = 8.0 Hz, 3H). |

TABLE 2-continued

Structure and $^1$HNMR data of the derivative Compound I-1

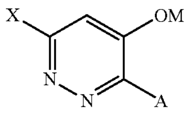

I-1

| No. | X | M | A | $^1$HNMR |
|---|---|---|---|---|
| 1-37 | $CF_3$ | 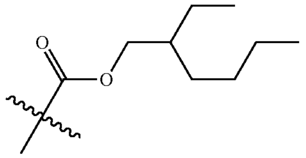 [SMILES: *C(=O)OCC(CC)CCCC] | 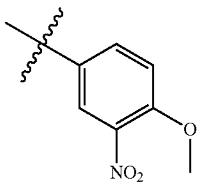 | (500 MHz, Chloroform-d) δ 8.04 (d, J = 2.0 Hz, 1H), 7.82 (dd, 7 = 7.5, 2.0 Hz, 1H), 7.20 (s, 1H), 7.15 (d, J = 7.5 Hz, 1H), 4.27-4.19 (m, 2H), 4.04 (s, 3H), 1.85- 1.75 (m, 2H), 1.79-1.71 (m, 1H), 1.65-1.51 (m, 2H), 1.40-1.20 (m, 2H), 1.18-1.05 (m,2H), 0.89 (t, J = 8.0 Hz, 3H), 0.83 (t, J = 8.0 Hz, 3H). |
| 1-38 | $CF_3$ | 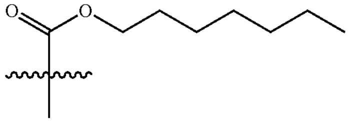 [SMILES: *C(=O)OCCCCCCC] | 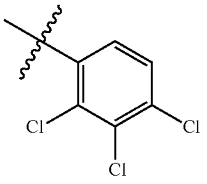 [SMILES: *c1ccc(Cl)c(Cl)c1Cl] | (500 MHz, Chloroform-d) δ 7.38 (d, J = 7.5 Hz, 1H), 7.23-7.16 (m,2H), 4.23 (t, J = 7.5 Hz, 2H), 1.72-1.61 (m, 2H), 1.47- 1.28 (m, 8H), 0.93 (t, J = 8.0 Hz, 3H). |
| 1-39 | $CF_3$ | 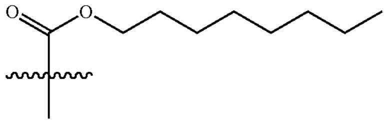 | 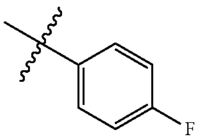 [SMILES: *c1ccc(F)cc1] | (500 MHz, Chloroform-d) δ 7.41-7.34 (m, 2H), 7.21-7.03 (m, 3H), 4.23 (t, J = 7.5 Hz, 2H), 1.72-1.35 (m, 12H), 0.93 (t, J = 8.0 Hz, 3H). |
| 1-40 | $CF_3$ | 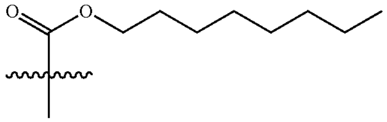 | 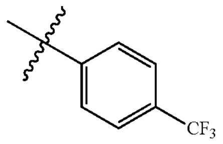 [SMILES: *c1ccc(C(F)(F)F)cc1] | (500 MHz, Chloroform-d) δ 7.69 (d, J = 7.5 Hz, 2H), 7.57-7.31 (d, J = 7.5 Hz, 2H), 7.10 (s, 1H), 4.23 (t, J = 7.5 Hz, 1H), 1.72-1.35 (m, 12H), 0.93 (t, J = 8.0 Hz, 3H). |
| 1-41 | $CF_3$ | 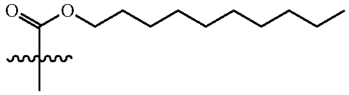 | 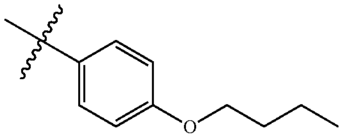 [SMILES: *c1ccc(OCCCC)cc1] | (500 MHz, Chloroform-d) δ 7.49 (d, J = 7.5 Hz, 2H), 7.09 (d, J = 7.5 Hz, 2H), 7.02 (s, 1H), 4.23 (t, J = 7.5 Hz, 1H), 4.00 (t, J = 7.5 Hz, 1H), 1.73-1.49 (m, 4H), 1.35-1.04 (m, 16H), 0.93-0.85 (m, 6H). |
| 1-42 | $CF_3$ | 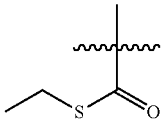 [SMILES: *C(=O)SCC] | 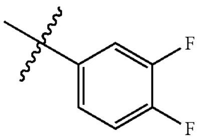 [SMILES: *c1ccc(F)c(F)c1] | (500 MHz, Chloroform-d) δ 7.47-7.35 (m, 2H), 7.23-7.11 (m, 2H), 2.91 (q, J = 7.0 Hz, 2H), 1.26 (t, J = 7.0 Hz, 3H). |
| 1-43 | $CF_3$ | 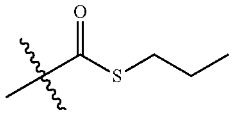 [SMILES: *C(=O)SCCC] | 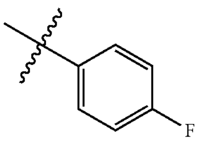 [SMILES: *c1ccc(F)cc1] | (500 MHz, Chloroform-d) δ 7.48-7.40 (m, 2H), 7.21 (s, 1H), 7.11-7.03 (m, 2H), 2.85 (t, J = 8.0 Hz, 2H), 1.66-1.50 (m, 2H), 0.90 (t, J = 8.0 Hz, 3H). |
| 1-44 | $CF_3$ | 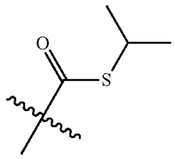 [SMILES: *C(=O)SC(C)C] | 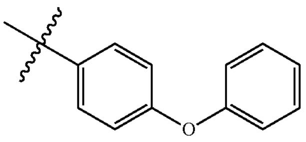 [SMILES: *c1ccc(Oc2ccccc2)cc1] | (500 MHz, Chloroform-d) δ 7.57-7.51 (m, 2H), 7.38-7.30 (m, 3H), 7.17-7.08 (m, 3H), 7.02-6.96 (m, 2H), 3.29 (hept, J = 6.5 Hz, 1H), 1.46 (d, J = 6.5 Hz, 6H). |

TABLE 2-continued

Structure and $^{1}$HNMR data of the derivative Compound I-1

I-1

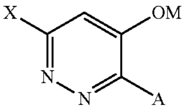

| No. | X | M | A | $^{1}$HNMR |
|---|---|---|---|---|
| 1-45 | $CF_3$ | 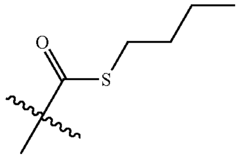 [SMILES: *C(=O)SCCCC] | 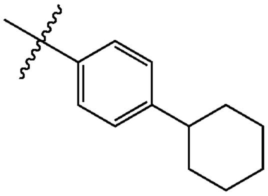 [SMILES: *c1ccc(C2CCCCC2)cc1] | (500 MHz, Chloroform-d) δ 7.49 (d, J = 7.5 Hz, 2H), 7.38 (d, J = 7.5 Hz, 2H), 7.33 (s, 1H), 2.85 (t, J = 8.0 Hz, 2H), 2.55-2.42 (m, 1H), 2.15-2.07 (m, 2H), 1.82-1.70 (m, 6H), 1.43- 1.38 (m, 4H), 1.37 -1.26(m, 2H), 0.87 (t, J = 8.0 Hz, 3H). |
| 1-46 | $CF_3$ | 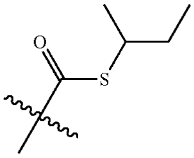 [SMILES: *C(=O)SC(C)CC] | 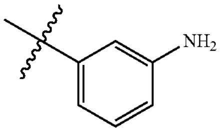 | (500 MHz, Chloroform-d) δ 7.31 (s, 1H), 7.13-6.97 (m, 2H), 6.76-6.67 (m, 2H), 4.13 (s, 2H), 3.26-3.18 (m, 1H), 1.73-1.60 (m, 2H), 1.36 (d, J = 6.5 Hz, 3H), 0.90 (t, J = 8.0 Hz, 3H). |
| 1-47 | $CF_3$ | 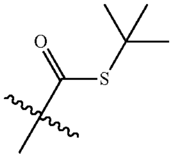 [SMILES: *C(=O)SC(C)(C)C] | 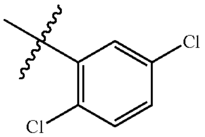 [SMILES: *c1cc(Cl)ccc1Cl] | (500 MHz, Chloroform-d) δ 7.52-7.43 (m, 3H), 7.29 (s, 1H), 1.26 (s, 9H). |
| 1-48 | $CF_3$ | 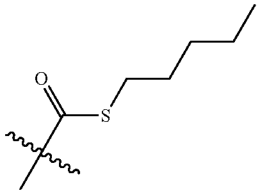 [SMILES: *C(=O)SCCCCC] | 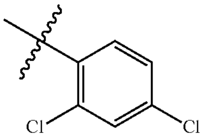 [SMILES: *c1ccc(Cl)cc1Cl] | (500 MHz, Chloroform-d) δ 7.52 (d, J = 2.0 Hz, 1H), 7.45 (d, J = 7.5 Hz, 1H), 7.35-7.27 (m, 2H), 2.85 (t, J = 7.5 Hz, 2H), 1.56- 1.23 (m, 6H), 0.94 (t, J = 8.0 Hz, 3H). |
| 1-49 | $CF_3$ | 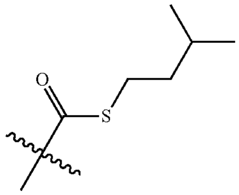 | 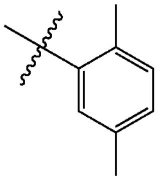 [SMILES: *c1cc(C)ccc1C] | (500 MHz, Chloroform-d) δ 7.42-7.37 (m, 1H), 7.23-7.14 (m, 3H), 2.85 (t, J = 8.0 Hz, 2H), 2.50 (s, 3H), 2.40 (s, 3H), 1.68-1.47 (m,3H), 0.88 (d, J = 6.5 Hz, 6H). |
| 1-50 | $CF_3$ | 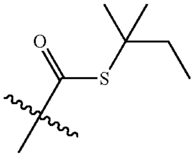 [SMILES: *C(=O)SC(C)(C)CC] | 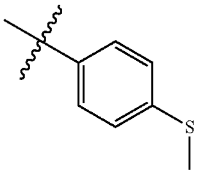 [SMILES: *c1ccc(SC)cc1] | (500 MHz, Chloroform-d) δ 7.55 (d, J = 7.5 Hz, 2H), 7.41 (d, J = 7.5 Hz, 2H), 7.17 (s, 1H), 2.45 (s, 3H), 1.88 (q, J = 8.0 Hz, 1H), 1.24 (s, 6H), 0.85 (t, J = 8.0 Hz, 3H). |
| 1-51 | $CF_3$ | 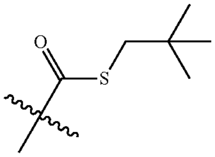 | 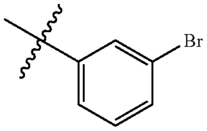 | (500 MHz, Chloroform-d) δ 7.81-7.61 (m, 1H), 7.49-7.28 (m, 2H), 7.22 (s, 1H), 2.73 (s, 2H), 0.95 (s, 9H). |

TABLE 2-continued

Structure and $^{1}$HNMR data of the derivative Compound I-1

I-1

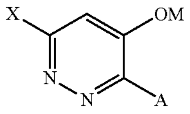

| No. | X | M | A | $^{1}$HNMR |
|---|---|---|---|---|
| 1-52 | $CF_3$ | 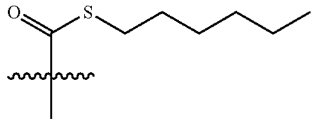 [SMILES: *C(=O)SCCCCCC] | 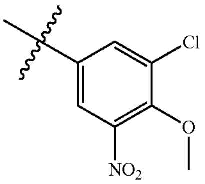 [SMILES: *c1cc(Cl)c(OC)c([N+](=O)[O-])c1] | (500 MHz, Chloroform-d) δ 8.41 (s, 2H), 7.23 (s, 1H), 3.97 (s, 3H), 2.85 (t, J = 8.0 Hz, 2H), 1.94-1.78 (m, 2H), 1.37 -1.24(m, 6H), 0.93 (t, J = 8.0 Hz, 3H). |
| 1-53 | $CF_3$ | 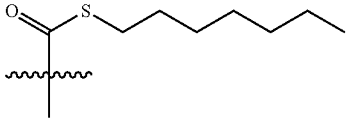 [SMILES: *C(=O)SCCCCCCC] | 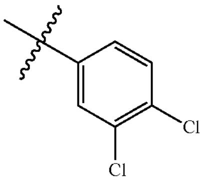 [SMILES: *c1ccc(Cl)c(Cl)c1] | (500 MHz, Chloroform-d) δ 7.67 (d, J = 2.0 Hz, 1H), 7.34-7.23 (m, 2H), 7.21 (s, 1H), 2.85 (t, J = 8.0 Hz, 2H), 1.94-1.80 (m, 2H), 1.38-1.22 (m, 8H), 0.93 (t, J = 8.0 Hz, 3H). |
| 1-54 | $CF_3$ | 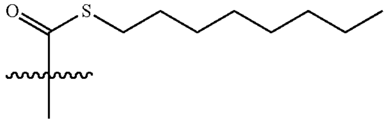 [SMILES: *C(=O)SCCCCCCCC] | 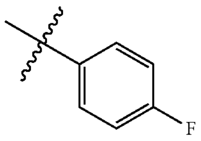 [SMILES: *c1ccc(F)cc1] | (500 MHz, Chloroform-d) δ 7.48-7.32 (m, 2H), 7.11-6.93 (m, 3H), 2.85 (t, J = 8.0 Hz, 2H), 1.94-1.81 (m, 2H), 1.37- 1.20 (m, 10H), 0.94 (t, J = 8.0 Hz, 3H). |
| 1-55 | $CF_3$ | 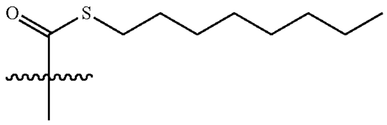 | 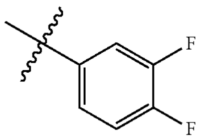 [SMILES: *c1ccc(F)c(F)c1] | (500 MHz, Chloroform-d) δ 7.26 (s, 1H), 7.21-7.11 (m, 3H), 2.85 (t, J = 8.0 Hz, 2H), 1.94-1.81 (m, 2H), 1.38-1.20 (m, 10H), 0.93 (t, J = 8.0 Hz, 3H). |
| 1-56 | $CF_3$ | 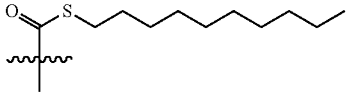 [SMILES: *C(=O)SCCCCCCCCCC] | 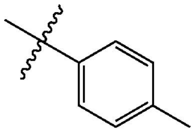 [SMILES: *c1ccc(C)cc1] | (500 MHz, Chloroform-d) δ 7.47 (d, J = 7.5 Hz, 2H), 7.23 (d, J = 7.5 Hz, 2H), 2.85 (t, J = 8.0 Hz, 2H), 2.33 (s, 3H), 1.94 -1.81 (m, 2H), 1.38-1.20 (m, 14H), 0.93 (t, J = 8.0 Hz, 3H). |
| 1-57 | $CF_3$ | 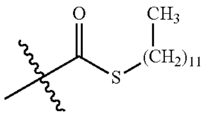 | 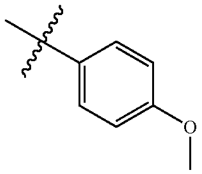 [SMILES: *c1ccc(OC)cc1] | (500 MHz, Chloroform-d) δ 7.61 (d, J = 7.5 Hz, 2H), 7.41 (d, J = 7.5 Hz, 2H), 7.11 (s, 1H), 3.11 (s, 3H), 2.85 (t, J = 8.0 Hz, 1H), 1.94-1.81 (m, 2H), 1.47-1.20 (m, 18H), 0.92 (t, J = 8.0 Hz, 3H). |
| 1-58 | $CF_3$ | 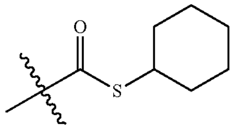 [SMILES: *C(=O)SC1CCCCC1] | 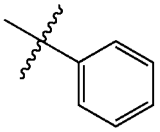 [SMILES: *c1ccccc1] | (500 MHz, Chloroform-d) δ 7.57-7.50 (m, 2H), 7.46-7.37 (m, 3H), 7.32 (s, 1H), 2.93-2.81 (m, 1H), 1.79-1.62 (m, 4H), 1.42-1.15 (m, 6H). |
| 1-59 | $CF_3$ | 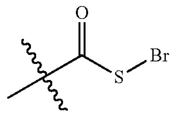 [SMILES: *C(=O)SBr] | 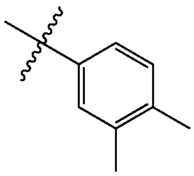 [SMILES: *c1ccc(C)c(C)c1] | |

TABLE 2-continued

Structure and $^{1}$HNMR data of the derivative Compound I-1

I-1

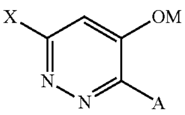

| No. | X | M | A | $^{1}$HNMR |
|---|---|---|---|---|
| 1-60 | $CF_3$ | 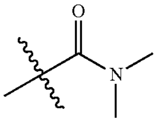 [SMILES: *C(=O)N(C)C] | 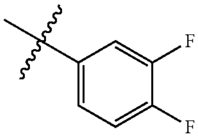 [SMILES: *c1ccc(F)c(F)c1] | (500 MHz, Chloroform-d) δ 7.37-7.21 (m, 2H), 7.18 (s, 1H), 7.13-7.01 (m, 1H), 3.14 (s, 3H), 3.04 (s, 3H). |
| 1-61 | $CF_3$ | 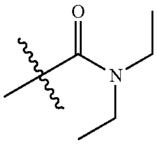 [SMILES: *C(=O)N(CC)CC] | 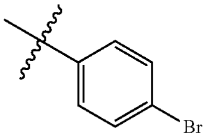 [SMILES: *c1ccc(Br)cc1] | (500 MHz, Chloroform-d) δ 7.60 (d, J = 7.5 Hz, 2H), 7.53 (d, J = 7.5 Hz, 2H), 7.15 (s, 1H), 3.48 (q, 7 = 8.0 Hz, 4H), 1.23 (t, J = 8.0 Hz, 6H). |
| 1-62 | $CF_3$ | 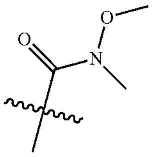 [SMILES: *C(=O)N(C)OC] | 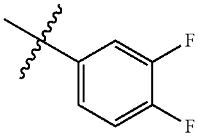 [SMILES: *c1ccc(F)c(F)c1] | (500 MHz, Chloroform-d) δ 7.33-7.21 (m, 1H), 7.17-7.04 (m, 2H), 3.58 (s, 3H), 3.44 (s, 3H). |
| 1-63 | $CF_3$ | 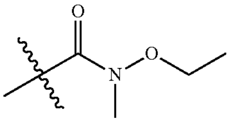 [SMILES: *C(=O)N(C)OCC] | 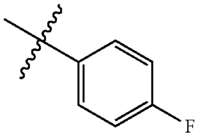 [SMILES: *c1ccc(F)cc1] | (500 MHz, Chloroform-d) δ 7.42-7.34 (m, 2H), 7.16 (s, 1H), 7.11-7.03 (m, 2H), 3.57 (q, J = 8.0 Hz, 2H), 3.44 (s, 3H), 1.21 (t, J = 8.0 Hz, 3H). |
| 1-64 | $CF_3$ | 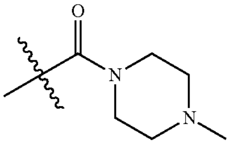 [SMILES: *C(=O)N1CCN(C)CC1] | 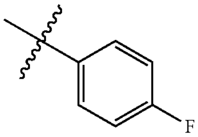 [SMILES: *c1ccc(F)cc1] | (500 MHz, Chloroform-d) δ 7.46-7.38 (m, 2H), 7.17 (s, 1H), 7.11-7.03 (m, 2H), 3.47 -3.30 (m,4H), 3.19-3.04 (m, 4H), 2.32 (s, 3H). |
| 1-65 | $CF_3$ | 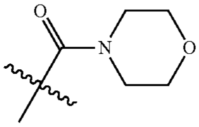 [SMILES: *C(=O)N1CCOCC1] | 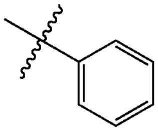 [SMILES: *c1ccccc1] | (500 MHz, Chloroform-d) δ 7.53-7.45 (m, 2H), 7.41-7.22 (m, 3H),7.16(s, 1H), 3.64-3.49 (m, 4H), 3.47-3.32 (m, 4H). |
| 1-66 | $CF_3$ | 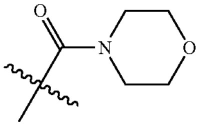 [SMILES: *C(=O)N1CCOCC1] | 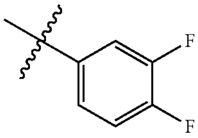 [SMILES: *c1ccc(F)c(F)c1] | (500 MHz, Chloroform-d) δ 7.38-7.24 (m, 1H), 7.23-7.13 (m, 3H), 3.84-3.66 (m, 4H), 3.47-3.33 (m, 4H). |
| 1-67 | $CF_3$ | 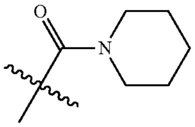 [SMILES: *C(=O)N1CCCCC1] | 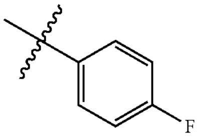 [SMILES: *c1ccc(F)cc1] | (500 MHz, Chloroform-d) δ 7.44-7.37 (m, 2H), 7.17 (s, 1H), 7.11-7.03 (m, 2H), 3.90 -3.77 (m,4H), 1.79- 1.65 (m, 6H). |
| 1-68 | $CF_3$ | 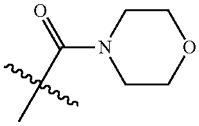 [SMILES: *C(=O)N1CCOCC1] | 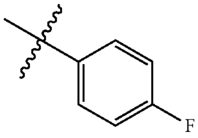 [SMILES: *c1ccc(F)cc1] | (500 MHz, Chloroform-d) δ 7.57-7.43 (m, 2H), 7.46-7.37 (m, 2H), 7.32 (s, 1H), 3.84-3.66 (m, 4H), 3.47-3.33 (m, 4H) |

TABLE 2-continued

Structure and $^1$HNMR data of the derivative Compound I-1

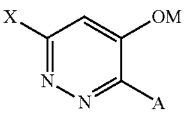

I-1

| No. | X | M | A | $^1$HNMR |
|---|---|---|---|---|
| 1-69 | $CF_3$ | 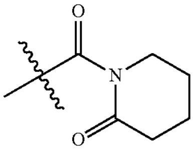 [SMILES: *C(=O)N1CCCCC1=O] | 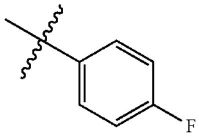 [SMILES: *c1ccc(F)cc1] | (500 MHz, Chloroform-d) δ 7.52-7.44 (m, 2H), 7.18 (s, 1H), 7.11-7.03 (m, 2H), 3.46 -3.23 (m, 2H), 2.16 v 2.02 (m, 2H), 1.92-1.77 (m, 4H). |
| 1-70 | $CF_3$ | 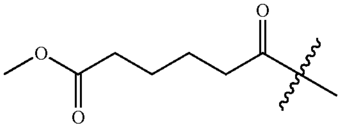 [SMILES: *C(=O)CCCCC(=O)OC] | 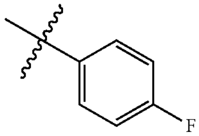 [SMILES: *c1ccc(F)cc1] | (500 MHz, Chloroform-d) δ 7.51-7.44 (m, 2H), 7.27 (s, 1H), 7.11-7.03 (m, 2H), 3.64 (s, 3H), 2.34-2.22 (m, 4H), 1.77-1.67 (m, 2H), 1.65-1.55 (m, 2H). |
| 1-71 | $CF_3$ | 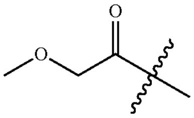 [SMILES: *C(=O)COC] | 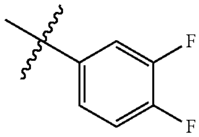 [SMILES: *c1ccc(F)c(F)c1] | (500 MHz, Chloroform-d) δ 7.43-7.28 (m, 2H), 7.23-7.16 (m, 1H), 7.14 (s, 1H), 4.31 (s, 2H), 3.30 (s, 3H). |
| 1-72 | $CF_3$ | 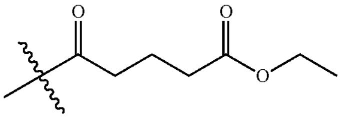 [SMILES: *C(=O)CCCC(=O)OCC] | 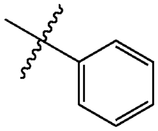 [SMILES: *c1ccccc1] | (500 MHz, Chloroform-d) δ 7.57-7.41 (m, 2H), 4.07 (q, J = 8.0 Hz, 1H), 2.34 (t, J = 7.5 Hz, 2H), 2.05 (d, J = 8.0 Hz, 2H), 1.17-1.05 (m, 2H). |
| 1-73 | $CF_3$ | 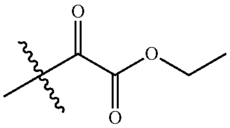 [SMILES: *C(=O)C(=O)OCC] | 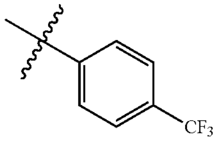 | (500 MHz, Chloroform-d) δ 7.68 (d, J = 7.5 Hz, 2H), 7.57 (d, J = 7.5 Hz, 2H), 7.22 (s, 1H), 4.22 (q, J = 8.0 Hz, 2H), 1.31 (t, J = 8.0 Hz, 3H). |
| 1-74 | $CF_3$ | 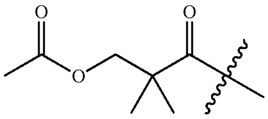 [SMILES: *C(=O)C(C)(C)COC(C)=O] | 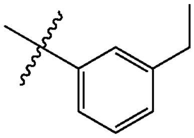 [SMILES: *c1cccc(CC)c1] | (500 MHz, Chloroform-d) δ 7.53-7.48 (m, 1H), 7.47-7.40 (m, 2H), 7.31-7.18 (m, 2H), 4.23 (s, 2H), 2.71 (d, J = 8.0 Hz, 2H), 2.02 (s, 3H), 1.21 (t, J = 8.0 Hz, 3H), 1.19 (s, 6H). |
| 1-75 | $CF_3$ | 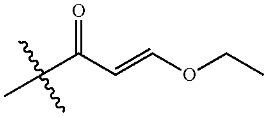 [SMILES: *C(=O)/C=C/OCC] | 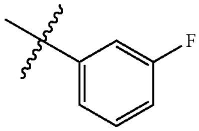 [SMILES: *c1cccc(F)c1] | (500 MHz, Chloroform-d) δ 7.48-7.40 (m, 1H), 7.32-7.21 (m, 3H), 7.03-6.90 (m, 1H), 4.79-4.66 (m, 1H), 4.06 (q, J = 8.0 Hz, 2H), 1.21 (t, J = 8.0 Hz, 3H). |
| 1-76 | $CF_3$ | 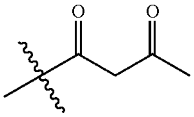 [SMILES: *C(=O)CC(C)=O] | 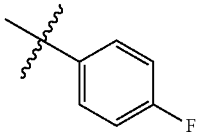 [SMILES: *c1ccc(F)cc1] | (500 MHz, Chloroform-d) δ 7.48-7.40 (m, 2H), 7.20 (s, 1H), 7.11-7.03 (m, 2H), 3.39 (s, 2H), 2.05 (s, 3H). |
| 1-77 | $CF_3$ | 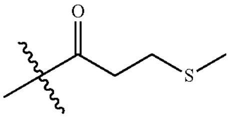 [SMILES: *C(=O)CCSC] | 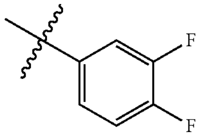 [SMILES: *c1ccc(F)c(F)c1] | (500 MHz, Chloroform-d) δ 7.40-7.29 (2, 1H), 7.23-7.10 (m, 2H), 2.71 (t, J = 8.0 Hz, 2H), 2.60 (t, J = 8.0 Hz, 2H), 2.14 (s, 3H). |

TABLE 2-continued

Structure and $^{1}$HNMR data of the derivative Compound I-1

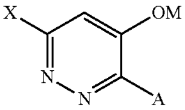

I-1

| No. | X | M | A | $^{1}$HNMR |
|---|---|---|---|---|
| 1-78 | $CF_3$ | 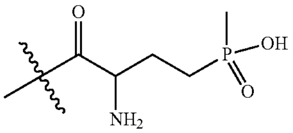 [SMILES: *C(=O)C(N)CCP(C)(=O)O] | 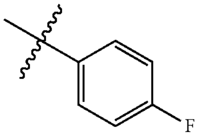 [SMILES: *c1ccc(F)cc1] | (500 MHz, Chloroform-d) δ 7.42-7.34 (m, 2H), 7.16 (s, 1H), 7.11-7.03 (m, 2H), 3.46 -3.30 (m, 2H), 2.73-2,66 (m, 2H), 2.19-2.09 (m, 1H), 1.79 (s, 2H), 1.26 (s, 3H). |
| 1-79 | $CF_3$ | 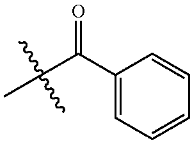 [SMILES: *C(=O)c1ccccc1] | 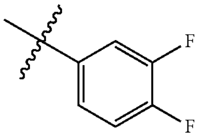 [SMILES: *c1ccc(F)c(F)c1] | (500 MHz, Chloroform-d) δ 8.16-8.09 (m, 2H), 7.67-7.55 (m, 3H), 7.37-7.18 (m, 2H), 7.14-7.00 (m, 3H). |
| 1-80 | $CF_3$ | 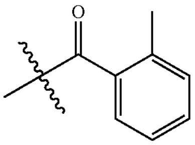 [SMILES: *C(=O)c1ccccc1C] | 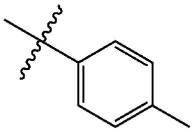 [SMILES: *c1ccc(C)cc1] | (500 MHz, Chloroform-d) δ 7.49-7.35 (m, 4H), 7.36-7.26 (m, 2H), 7.26-7.18 (m, 3H), 2.52 (s, 3H), 2.33 (s, 3H). |
| 1-81 | $CF_3$ | 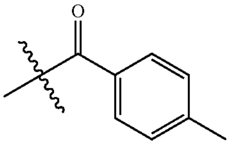 [SMILES: *C(=O)c1ccc(C)cc1] | 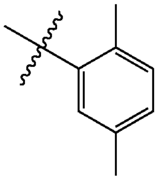 [SMILES: *c1cc(C)ccc1C] | (500 MHz, Chloroform-d) δ 8.05-7.99 (m, 2H), 7.51-7.41 (m, 3H), 7.24 (s, 1H), 7.21-7.13 (m, 2H), 2.50 (s, 3H), 2.41 (s, 3H), 2.30 (s, 3H). |
| 1-82 | $CF_3$ | 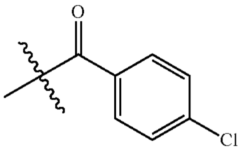 [SMILES: *C(=O)c1ccc(Cl)cc1] | 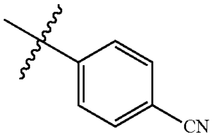 [SMILES: *c1ccc(C#N)cc1] | (500 MHz, Chloroform-d) δ 8.05-7.89 (m, 4H), 7.76-7.59 (m, 4H), 7.25 (s, 1H). |
| 1-83 | $CF_3$ | 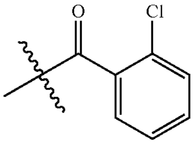 [SMILES: *C(=O)c1ccccc1Cl] | 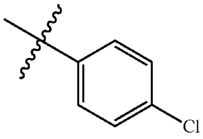 [SMILES: *c1ccc(Cl)cc1] | (500 MHz, Chloroform-d) δ 7.59-7.52 (m, 2H), 7.49-7.40 (m, 5H), 7.33 (s, 1H), 7.32-7.28 (m, 1H). |
| 1-84 | $CF_3$ | 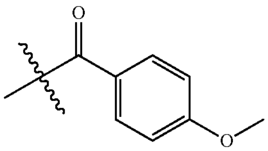 [SMILES: *C(=O)c1ccc(OC)cc1] | 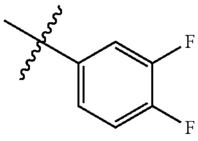 [SMILES: *c1ccc(F)c(F)c1] | (500 MHz, Chloroform-d) δ 8.12-8.06 (m, 2H), 7.37-7.19 (m, 3H), 7.15-7.03 (m, 3H), 3.80 (s, 3H). |
| 1-85 | $CF_3$ | 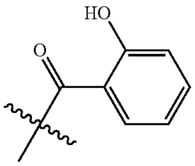 [SMILES: *C(=O)c1ccccc1O] | 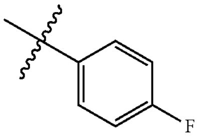 [SMILES: *c1ccc(F)cc1] | (500 MHz, Chloroform-d) δ 7.93-7.58 (m, 2H), 7.46-7.39 (m, 2H), 7.23 (s, 1H),7.11 -7.03 (m, 4H),5.19(s, 1H). |

TABLE 2-continued

Structure and $^1$HNMR data of the derivative Compound I-1

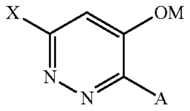

I-1

| No. | X | M | A | $^1$HNMR |
| --- | --- | --- | --- | --- |
| 1-86 | $CF_3$ | 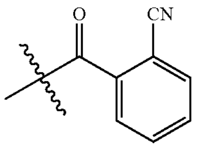 [SMILES: *C(=O)c1ccccc1C#N] | 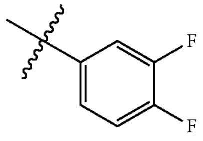 [SMILES: *c1ccc(F)c(F)c1] | (500 MHz, Chloroform-d) δ 7.90 (dd, J = 7.5, 2.0 Hz, 1H), 7.81-7.73 (m, 2H), 7.75-7.68 (m, 1H), 7.44 (s, 1H), 7.39-7.16(m, 3H). |
| 1-87 | $CF_3$ | 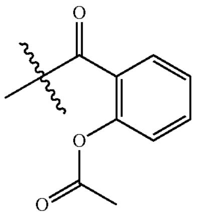 [SMILES: *C(=O)c1ccccc1OC(C)=O] | 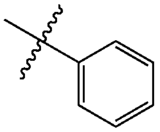 [SMILES: *c1ccccc1] | (500 MHz, Chloroform-d) δ 8.10 (dd, J = 7.5, 2.0 Hz, 1H), 7.60-7.43 (m, 3H), 7.46-7.37 (m, 3H), 7.25-7.15 (m, 2H), 2.39 (s, 3H). |
| 1-88 | $CF_3$ | 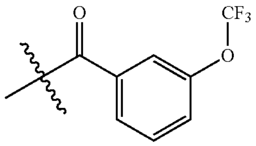 [SMILES: *C(=O)c1cccc(OC(F)(F)F)c1] | 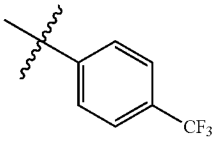 [SMILES: *c1ccc(C(F)(F)F)cc1] | (500 MHz, Chloroform-d) δ 7.83-7.68 (m, 2H), 7.52-7.33 (m, 4H), 7.27-7.21 (m, 3H). |
| 1-89 | $CF_3$ | 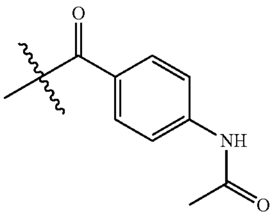 [SMILES: *C(=O)c1ccc(NC(C)=O)cc1] | 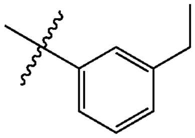 [SMILES: *c1cccc(CC)c1] | (500 MHz, Chloroform-d) δ 7.96-7.89 (m, 2H), 7.85-7.79 (m, 2H), 7.73 (s, 1H), 7.46-7.38 (m, 2H), 7.33-7.26 (m, 2H), 7.22 (s, 1H), 2.71 (q, J = 8.0 Hz, 2H), 2.10 (s, 3H), 1.21 (t, J = 8.0 Hz, 3H). |
| 1-90 | $CF_3$ | 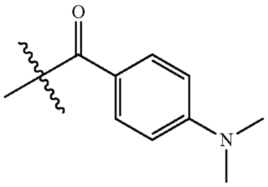 [SMILES: *C(=O)c1ccc(N(C)C)cc1] | 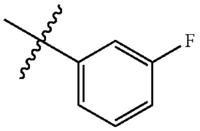 [SMILES: *c1cccc(F)c1] | (500 MHz, Chloroform-d) δ 7.71-7.65 (m, 2H), 7.48-7.34 (m, 2H), 7.25-7.20 (m, 3H), 6.82-6.75 (m, 2H), 3.02 (s, 6H). |
| 1-91 | $CF_3$ | 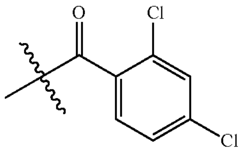 [SMILES: *C(=O)c1ccc(Cl)cc1Cl] | 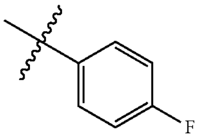 [SMILES: *c1ccc(F)cc1] | (500 MHz, Chloroform-d) δ 7.57 (d, J = 2.0 Hz, 1H), 7.50-7.36 (m, 4H), 7.33 (s, 1H),7.11 -7.03 (m, 2H). |
| 1-92 | $CF_3$ | 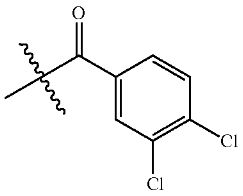 [SMILES: *C(=O)c1ccc(Cl)c(Cl)c1] | 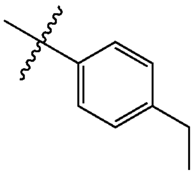 [SMILES: *c1ccc(CC)cc1] | (500 MHz, Chloroform-d) δ 8.24 (d, J = 2.0 Hz, 1H), 7.73 (dd, J = 7.5, 2.0 Hz, 1H), 7.54 (d, J = 7.5 Hz, 1H), 7.52 (d, J = 7.5 Hz, 2H), 7.25 (s, 1H), 7.13 (d, J = 7.5 Hz, 2H), 2.77 (d, J = 8.0 Hz, 2H), 1.19 (t, J = 8.0 Hz, 3H). |

TABLE 2-continued

Structure and $^1$HNMR data of the derivative Compound I-1

I-1

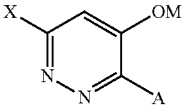

| No. | X | M | A | $^1$HNMR |
|---|---|---|---|---|
| 1-93 | $CF_3$ | 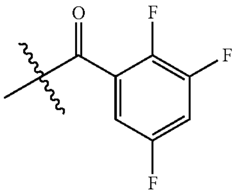 [SMILES: *C(=O)c1cc(F)cc(F)c1F] | 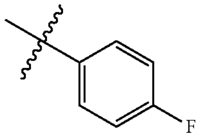 [SMILES: *c1ccc(F)cc1] | (500 MHz, Chloroform-d) δ 7.53-7.45 (m, 2H), 7.41-7.32 (m, 2H), 7.25 (s, 1H), 7.15-7.03 (m, 2H). |
| 1-94 | $CF_3$ | 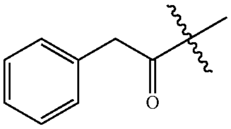 [SMILES: *C(=O)Cc1ccccc1] | 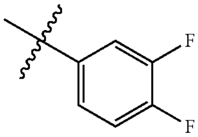 | (500 MHz, Chloroform-d) δ 7.31-7.27 (m, 3H), 7.31-7.24 (m, 1H), 7.27-7.18 (m, 3H), 7.17-7.08 (m, 2H), 3.92 (s, 2H). |
| 1-95 | $CF_3$ | 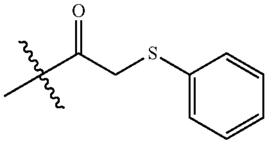 [SMILES: *C(=O)CSc1ccccc1] | 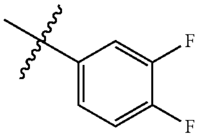 [SMILES: *c1ccc(F)c(F)c1] | (500 MHz, Chloroform-d) δ 7.53-7.46 (m, 3H), 7.43-7.31 (m, 3H), 7.25-7.15 (m, 3H), 3.54 (s, 2H). |
| 1-96 | $CF_3$ | 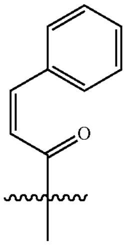 [SMILES: *C(=O)/C=C\c1ccccc1] | 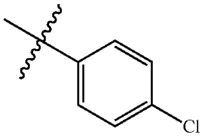 [SMILES: *c1ccc(Cl)cc1] | (500 MHz, Chloroform-d) δ 7.59-7.41 (m, 5H), 7.39-7.27 (m, 5H), 7.16 (s, 1H), 5.90 (d, J = 10.5 Hz, 1H). |
| 1-97 | $CF_3$ | 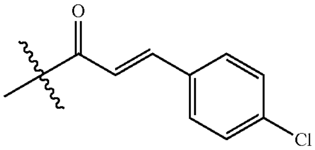 [SMILES: *C(=O)/C=C/c1ccc(Cl)cc1] | 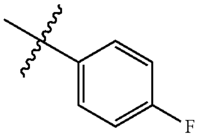 [SMILES: *c1ccc(F)cc1] | (500 MHz, Chloroform-d) δ 7.50-7.42 (m, 4H), 7.45-7.35 (m, 5H), 7.11-7.00 (d, J = 11.0 Hz, 1H),5.87 (d, J = 11.0 Hz, 1H). |
| 1-98 | $CF_3$ | 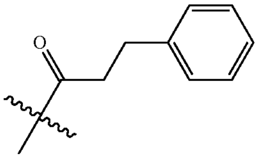 [SMILES: *C(=O)CCc1ccccc1] | 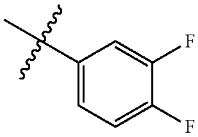 [SMILES: *c1ccc(F)c(F)c1] | (500 MHz, Chloroform-d) δ 7.62-7.55 (m, 2H), 7.47-7.38 (m, 4H), 7.34 (s, 1H), 7.11 -7.03 (m, 2H),5.99 (s, 2H). |
| 1-99 | $CF_3$ | 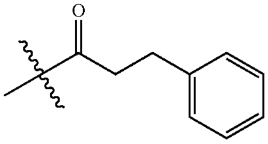 [SMILES: *C(=O)CCc1ccccc1] | 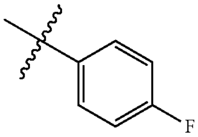 [SMILES: *c1ccc(F)cc1] | (500 MHz, Chloroform-d) δ 7.40-7.30 (m, 3H), 7.29-7.18 (m, 3H), 7.21 (s, 1H), 6.99-6.87 (m, 3H), 3.10 (t, J = 8.0 Hz, 2H), 3.00 (t, J = 8.0 Hz, 2H). |
| 1-100 | $CF_3$ | 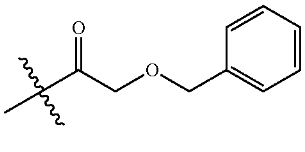 [SMILES: *C(=O)COCc1ccccc1] | 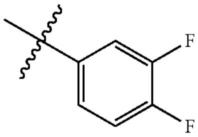 [SMILES: *c1ccc(F)c(F)c1] | (500 MHz, Chloroform-d) δ 7.48-7.40 (m, 3H), 7.24-7.16 (m, 3H), 7.11-7.03 (m, 3H), 5.69 (s, 2H), 5.56 (s, 2H). |

TABLE 2-continued

Structure and $^1$HNMR data of the derivative Compound I-1

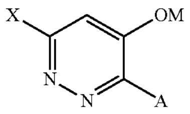

I-1

| No. | X | M | A | $^1$HNMR |
| --- | --- | --- | --- | --- |
| 1-101 | $CF_3$ | 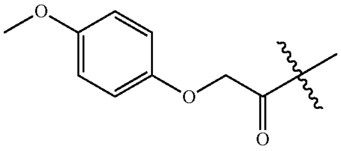 [SMILES: *C(=O)COc1ccc(OC)cc1] | 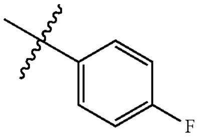 [SMILES: *c1ccc(F)cc1] | (500 MHz, Chloroform-d) δ 7.51-7.38 (m, 3H), 7.25-7.14 (m, 3H),7.17(s, 1H), 7.08-7.00 (m, 2H), 4.52 (s, 2H), 4.31 (s, 3H). |
| 1-102 | $CF_3$ | 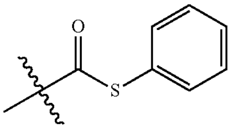 [SMILES: *C(=O)Sc1ccccc1] | 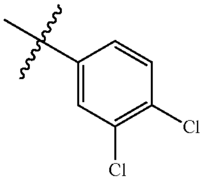 [SMILES: *c1ccc(Cl)c(Cl)c1] | (500 MHz, Chloroform-d) δ 7.49-7.41 (m, 3H), 7.21 (s, 1H), 7.11-7.03 (m, 2H), 6.89 -6.81 (m, 4H). |
| 1-103 | $CF_3$ | 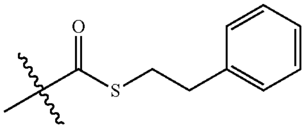 [SMILES: *C(=O)SCCc1ccccc1] | 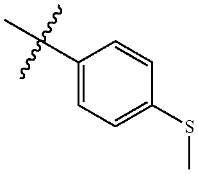 [SMILES: *c1ccc(SC)cc1] | (500 MHz, Chloroform-d) δ 7.58-7.46 (m, 3H), 7.32-7.20 (m, 5H), 7.19-7.07 (m, 2H), 3.70 (t, J = 8.0 Hz, 2H), 2.90 (t, J = 8.0 Hz, 2H), 2.70 (s, 3H). |
| 1-104 | $CF_3$ | 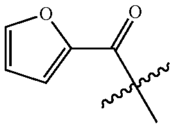 [SMILES: *C(=O)c1ccco1] | 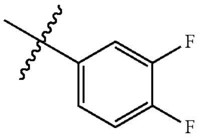 [SMILES: *c1ccc(F)c(F)c1] | (500 MHz, Chloroform-d) δ 7.57-7.51 (m, 2H), 7.52-7.45 (m, 2H), 7.33 (s, 1H), 7.27 (s, 1H), 7.28-7.16 (m, 1H). |
| 1-105 | $CF_3$ | 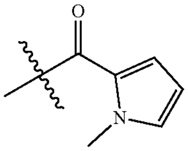 [SMILES: *C(=O)c1cccn1C] | 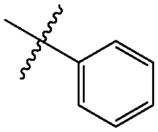 [SMILES: *c1ccccc1] | (500 MHz, Chloroform-d) δ 7.55 (dd, J = 7.5, 1.5 Hz, 1H), 7.42-7.33 (m, 3H), 7.24 (s, 1H), 7.28-7.16 (m, 3H), 6.48 (t, J = 7.5 Hz, 1H), 3.68 (s, 3H). |
| 1-106 | $CF_3$ | 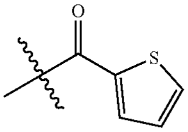 [SMILES: *C(=O)c1cccs1] | 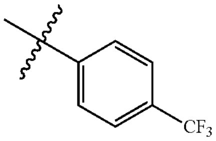 [SMILES: *c1ccc(C(F)(F)F)cc1] | (500 MHz, Chloroform-d) δ 7.63 (d, J = 7.5 Hz, 2H), 7.41-7.34 (m, 2H), 7.24 (s, 1H), 7.15-7.02 (m, 2H), 6.47-6.38 (m, 1H). |
| 1-107 | $CF_3$ | 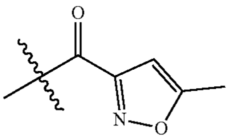 [SMILES: *C(=O)c1cc(C)on1] | 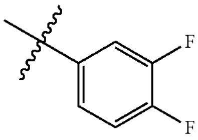 [SMILES: *c1ccc(F)c(F)c1] | (500 MHz, Chloroform-d) δ 8.11-8.06 (m, 1H), 7.57-7.50 (m, 2H), 7.33-7.27 (m, 1H), 7.25 (s, 1H), 2.62 (s, 3H). |
| 1-108 | $CF_3$ | 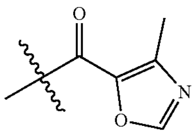 [SMILES: *C(=O)c1ocnc1C] | 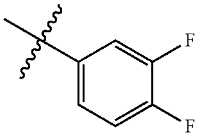 [SMILES: *c1ccc(F)c(F)c1] | (500 MHz, Chloroform-d) δ 7.42-7.28 (m, 2H), 7.24 (s, 1H), 7.20-7.09 (m, 1H), 6.58 (s, 1H), 2.42 (s, 3H). |

TABLE 2-continued

Structure and $^1$HNMR data of the derivative Compound I-1

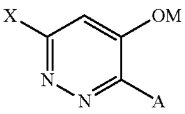

I-1

| No. | X | M | A | $^1$HNMR |
|---|---|---|---|---|
| 1-109 | $CF_3$ | 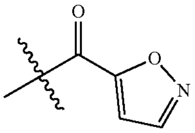 [SMILES: *C(=O)c1ccno1] | 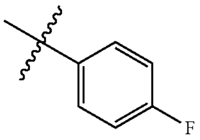 [SMILES: *c1ccc(F)cc1] | (500 MHz, Chloroform-d) δ 8.19-8.07 (m, 1H), 7.43-7.27 (m, 3H), 7.24 (s, 1H), 7.20-7.06 (m, 2H). |
| 1-110 | $CF_3$ | 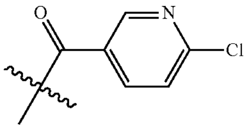 [SMILES: *C(=O)c1ccc(Cl)nc1] | 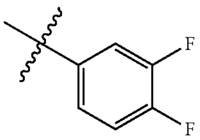 [SMILES: *c1ccc(F)c(F)c1] | (500 MHz, Chloroform-d) δ 8.37 (d, J = 2.5 Hz, 1H), 7.36-7.28 (m, 2H), 7.22 (s, 1H),7.11 -7.03 (m, 2H), 6.80 (d, J = 7.5 Hz, 1H). |
| 1-111 | $CF_3$ | 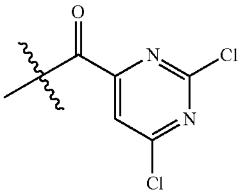 [SMILES: *C(=O)c1cc(Cl)nc(Cl)n1] | 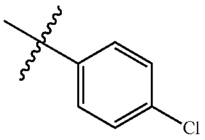 [SMILES: *c1ccc(Cl)cc1] | (500 MHz, Chloroform-d) δ 8.75 (d, J = 1.3 Hz, 1H), 7.70 (d, J = 8.0 Hz, 2H), 7.38 (d, J = 8.0 Hz, 2H). |
| 1-112 | $CF_3$ | 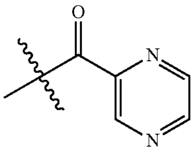 [SMILES: *C(=O)c1cnccn1] | 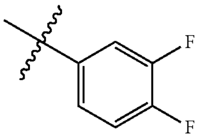 [SMILES: *c1ccc(F)c(F)c1] | (500 MHz, Chloroform-d) δ 9.21 (s, 1H), 8.79 (d, J = 5.5 Hz, 1H), 8.73 (d, J = 5.5 Hz, 1H), 7.24-7.13 (m, 4H). |
| 1-113 | $CF_3$ | 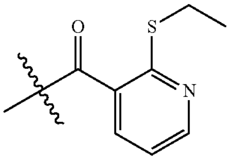 [SMILES: *C(=O)c1cccnc1SCC] | 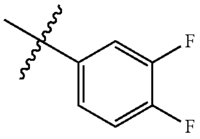 [SMILES: *c1ccc(F)c(F)c1] | (500 MHz, Chloroform-d) δ 8.56 (dd, J = 5.0, 1.0 Hz, 1H), 7.80 (dd, J = 8.0, 1.0 Hz, 1H), 7.37 (dd, J = 8.0, 5.0 Hz, 1H), 7.30-7.23 (m, 2H), 7.18-7.13 (m, 2H), 2.97 (q, J = 8.0 Hz, 2H), 1.39 (t, J = 8.0 Hz, 3H) |
| 1-114 | $CF_3$ | 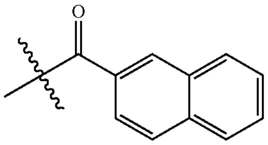 [SMILES: *C(=O)c1ccc2ccccc2c1] | 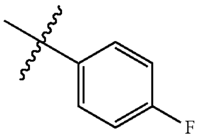 [SMILES: *c1ccc(F)cc1] | (500 MHz, Chloroform-d) δ 8.12-8.02 (m, 2H), 8.08-7.99 (m, 2H), 8.00-7.94 (m, 1H), 7.73-7.64 (m, 2H), 7.49 -7.41 (m, 2H),7.26 (s, 1H), 7.11-7.03 (m, 2H) |
| 1-115 | $CF_3$ | 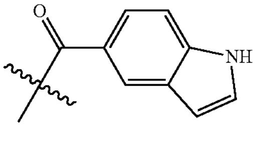 [SMILES: *C(=O)c1ccc2[nH]ccc2c1] | 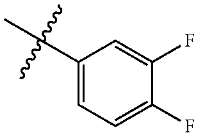 [SMILES: *c1ccc(F)c(F)c1] | (500 MHz, Chloroform-d) δ 8.66-8.59 (m, 2H), 7.97 (dd, J = 7.5, 1.5 Hz, 1H), 7.62 (d, J = 7.5 Hz, 1H), 7.46-7.40 (m, 1H), 7.32-7.25 (m,2H), 7.26 -7.15 (m, 2H), 6.66-6.52 (m, 1H). |
| 1-116 | $CF_3$ | 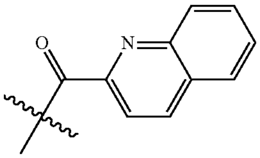 [SMILES: *C(=O)c1ccc2ccccc2n1] | 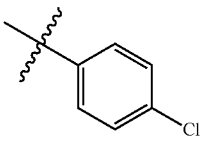 [SMILES: *c1ccc(Cl)cc1] | (500 MHz, Chloroform-d) δ 8.33-8.05 (m, 3H), 7.92 (d, J = 7.5, 1.5 Hz, 1H), 7.77-7.67 (m, 2H), 7.54-7.48 (m, 2H), 7.45-7.39 (m, 2H), 7.27 (s, 1H). |

TABLE 2-continued

Structure and $^1$HNMR data of the derivative Compound I-1

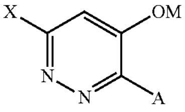

I-1

| No. | X | M | A | $^1$HNMR |
|---|---|---|---|---|
| 1-117 | $CF_3$ | 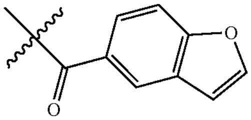 [SMILES: *C(=O)c1ccc2occc2c1] | 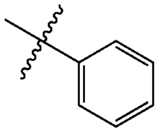 [SMILES: *c1ccccc1] | (500 MHz, Chloroform-d) δ 8.23-8.04 (m, 2H), 7.92 (d, J = 7.5 Hz, 1H), 7.75 (d, J = 7.5 Hz, 1H), 7.56-7.48 (m, 2H), 7.41-7.30 (m, 3H), 7.25 (s, 1H), 6.86 (dd, J = 7.5, 1.5 Hz, 1H). |
| 1-118 | $CF_3$ | 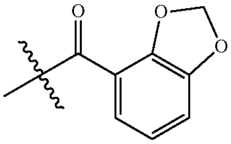 [SMILES: *C(=O)c1cccc2c1OCO2] | 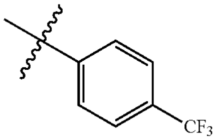 | (500 MHz, Chloroform-d) δ 7.77 (dd, J = 7.0, 2.5 Hz, 1H), 7.72 (d, J = 7.5 Hz, 2H), 7.62-7.56 (m, 2H), 7.24 (s, 1H), 7.19-7.10 (m, 2H), 5.99 (s, 2H). |
| 1-119 | $CF_3$ | 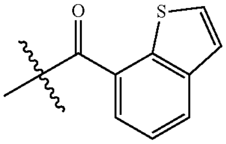 [SMILES: *C(=O)c1cccc2ccsc12] | 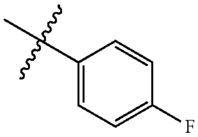 [SMILES: *c1ccc(F)cc1] | (500 MHz, Chloroform-d) δ 8.11-8.02 (m,2H), 7.59-7.41 (m, 1H), 7.50-7.40 (m, 3H), 7.36-7.30 (m, 2H), 7.11 -7.03 (m, 2H). |
| 1-120 | $CF_3$ | 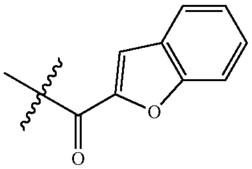 [SMILES: *C(=O)c1cc2ccccc2o1] | 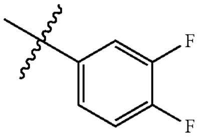 [SMILES: *c1ccc(F)c(F)c1] | (500 MHz, Chloroform-d) δ 7.65-7.58 (m, 2H), 7.54 (d, J = 1.5 Hz, 1H), 7.44-7.33 (m, 2H), 7.32-7.24 (m, 1H), 7.28 (s, 1H), 7.26-7.15 (m, 2H). |
| 1-121 | $CF_3$ | 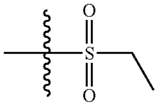 [SMILES: *S(=O)(=O)CC] | 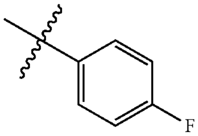 [SMILES: *c1ccc(F)cc1] | (500 MHz, Chloroform-d) δ 7.62 (s, 1H), 7.51-7.44 (m, 2H), 7.11-7.03 (m, 2H), 3.07 (q, J = 8.0 Hz, 2H), 1.50 (t, J = 8.0 Hz, 3H). |
| 1-122 | $CF_3$ | 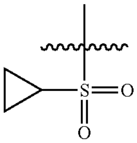 [SMILES: *S(=O)(=O)C1CC1] | 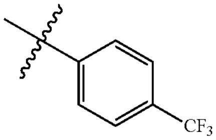 [SMILES: *c1ccc(C(F)(F)F)cc1] | (500 MHz, Chloroform-d) δ 7.77 (d, J = 7.5 Hz, 2H), 7.57-7.50 (m, 3H), 1.72-1.61 (m, 1H), 0.81-0.73 (m, 2H), 0.58 -0.51 (m,2H). |
| 1-123 | $CF_3$ | 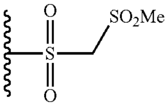 [SMILES: *S(=O)(=O)CS(C)(=O)=O] | 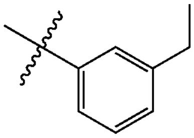 [SMILES: *c1cccc(CC)c1] | (500 MHz, Chloroform-d) δ 7.66-7.52 (m, 2H), 7.46-7.39 (m, 2H), 7.34-7.29 (m, 1H), 5.15 (s, 2H), 3.05 (s, 3H), 2.71 (d, J = 8.0 Hz,2H), 1.21 (t, J = 8.0 Hz, 3H). |
| 1-124 | $CF_3$ | 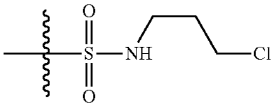 [SMILES: *S(=O)(=O)NCCCCl] | 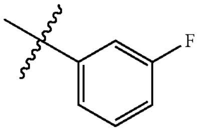 [SMILES: *c1cccc(F)c1] | (500 MHz, Chloroform-d) δ 7.63-7.59 (m, 2H), 7.45-7.33 (m, 2H), 7.25-7.18 (m, 1H), 4.45 (s, lH),3.75 (t, J = 7.5 Hz, 2H), 2.63 (t, J = 7.5 Hz, 2H), 1.83- 1.68 (m, 2H). |
| 1-125 | $CF_3$ | 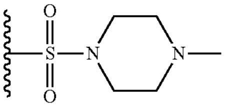 [SMILES: *S(=O)(=O)N1CCN(C)CC1] | 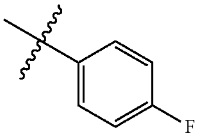 [SMILES: *c1ccc(F)cc1] | (500 MHz, Chloroform-d) δ 7.57 (s, 1H), 7.45-7.37 (m, 2H), 7.11-7.03 (m, 2H), 2.50 -2.38 (m, 8H), 2.27 (s, 3H). |

TABLE 2-continued

Structure and $^{1}$HNMR data of the derivative Compound I-1

I-1

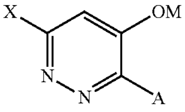

| No. | X | M | A | $^{1}$HNMR |
|---|---|---|---|---|
| 1-126 | $CF_3$ | 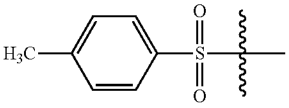 | 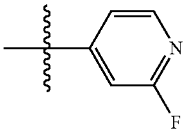 [SMILES: *c1ccnc(F)c1] | (500 MHz, Chloroform-d) δ 7.76-7.70(m, 2H), 7.61 (s, 1H), 7.49-7.43 (m, 2H), 7.41 -7.30 (m, 1H), 7.20-7.10 (m, 2H), 2.42 (s, 3H). |
| 1-127 | $CF_3$ | 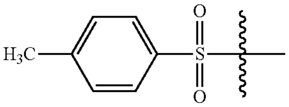 [SMILES: *S(=O)(=O)c1ccc(C)cc1] | 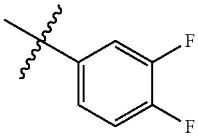 [SMILES: *c1ccc(F)c(F)c1] | (500 MHz, Chloroform-d) δ 7.78 (d, J = 7.5 Hz, 2H), 7.64 (s, 1H), 7.56-7.41 (m, 1H), 7.51-7.42 (m,2H), 7.19-7.10 (m, 2H). |
| 1-128 | $CF_3$ | 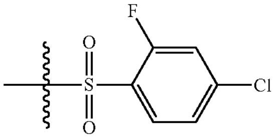 [SMILES: *S(=O)(=O)c1ccc(Cl)cc1F] | 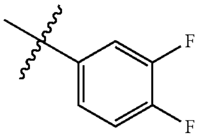 [SMILES: *c1ccc(F)c(F)c1] | (500 MHz, Chloroform-d) δ 7.78-7.64 (m, 2H), 7.56-7.41 (m, 1H), 7.51-7.42 (m, 2H), 7.19-7.10 (m,2H). |
| 1-129 | $CF_3$ | 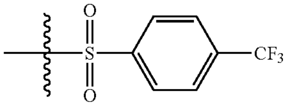 [SMILES: *S(=O)(=O)c1ccc(C(F)(F)F)cc1] | 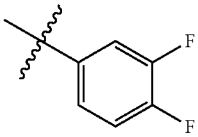 [SMILES: *c1ccc(F)c(F)c1] | (500 MHz, Chloroform-d) δ 7.86 (d, J = 7.5 Hz, 2H), 7.76 (d, J = 7.5 Hz, 2H), 7.59 (s, 1H), 7.42-7.34 (m, 1H),7.16 -7.07 (m, 2H). |
| 1-130 | $CF_3$ | 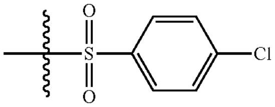 [SMILES: *S(=O)(=O)c1ccc(Cl)cc1] | 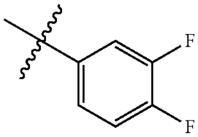 [SMILES: *c1ccc(F)c(F)c1] | (500 MHz, Chloroform-d) δ 7.91 (d, J = 7.5 Hz, 2H), 7.78 (d, J = 7.5 Hz, 2H), 7.59 (s, 1H), 7.45-7.38 (m, 1H), 7.26 -7.17 (m, 2H). |
| 1-131 | $CF_3$ | 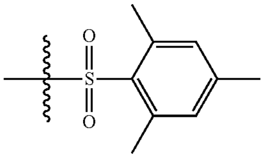 [SMILES: *S(=O)(=O)c1c(C)cc(C)cc1C] | 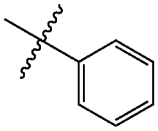 [SMILES: *c1ccccc1] | (500 MHz, Chloroform-d) δ 7.70 (s, 1H), 7.64-7.57 (m, 2H), 7.41-7.31 (m, 3H), 7.08 (s, 2H), 2.55 (s, 6H), 2.13 (s, 3H). |
| 1-132 | $CF_3$ | 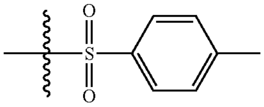 [SMILES: *S(=O)(=O)c1ccc(C)cc1] | 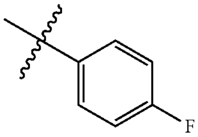 [SMILES: *c1ccc(F)cc1] | (500 MHz, Chloroform-d) δ 7.76-7.70 (m, 2H), 7.58 (s, 1H), 7.45 (ddd, J = 7.6, 6.2, 2.1 Hz, 4H), 7.11-7.03 (m, 2H), 2.42 (d, J = 1.5 Hz, 2H). |
| 1-133 | $CF_3$ | 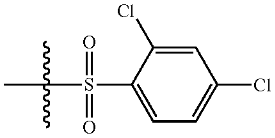 | 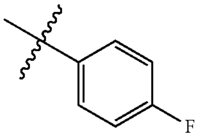 [SMILES: *c1ccc(F)cc1] | (500 MHz, Chloroform-d) δ 7.83 (d, J = 2.0 Hz, 1H), 7.71-7.63 (m, 2H), 7.55-7.47 (m, 3H), 7.11-7.03 (m, 2H). |
| 1-134 | $CF_3$ | 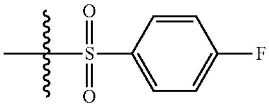 [SMILES: *S(=O)(=O)c1ccc(F)cc1] | 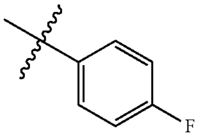 [SMILES: *c1ccc(F)cc1] | (500 MHz, Chloroform-d) δ 7.84-7.76 (m, 2H), 7.59 (s, 1H), 7.49-7.41 (m, 2H),7.33 -7.24 (m, 2H), 7.11-7.03 (m, 2H). |

TABLE 2-continued

Structure and $^{1}$HNMR data of the derivative Compound I-1

I-1

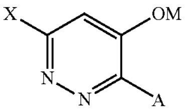

| No. | X | M | A | $^{1}$HNMR |
|---|---|---|---|---|
| 1-135 | $CF_3$ | 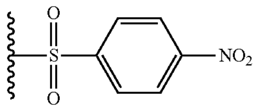 [SMILES: *S(=O)(=O)c1ccc([N+](=O)[O-])cc1] | 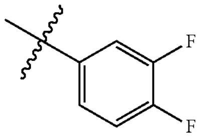 [SMILES: *c1ccc(F)c(F)c1] | (500 MHz, Chloroform-d) δ 8.46(d, J = 7.5Hz, 2H), 8.07 (d, J = 7.5 Hz, 2H), 7.58 (s, 1H), 7.32-7.22 (m, 3H). |
| 1-136 | $CF_3$ | 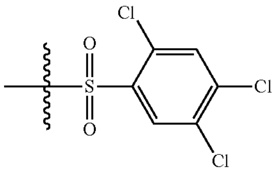 [SMILES: *S(=O)(=O)c1cc(Cl)c(Cl)cc1Cl] | 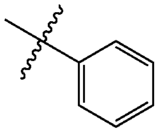 [SMILES: *c1ccccc1] | (500 MHz, Chloroform-d) δ 8.32 (s, 1H), 8.08 (s, 1H), 7.60 -7.50 (m, 3H), 7.41-7.30 (m, 3H). |
| 1-137 | $CF_3$ | 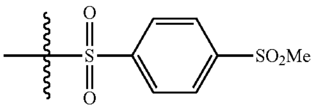 [SMILES: *S(=O)(=O)c1ccc(S(C)(=O)=O)cc1] | 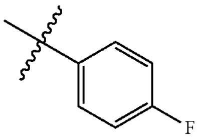 [SMILES: *c1ccc(F)cc1] | (500 MHz, Chloroform-d) δ 8.17-8.11 (m, 2H), 8.12-8.05 (m, 2H), 7.53 (s, 1H), 7.46-7.38 (m,2H), 7.11-7.03 (m, 2H), 3.30 (s, 3H). |
| 1-138 | $CF_3$ | 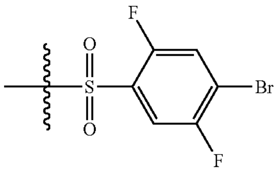 | 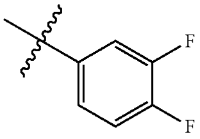 [SMILES: *c1ccc(F)c(F)c1] | (500 MHz, Chloroform-d) δ 7.61 (s, 1H), 7.64-7.57 (m, 1H), 7.52-7.39 (m, 2H), 7.28 -7.17 (m, 2H). |
| 1-139 | $CF_3$ | 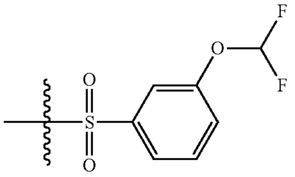 [SMILES: *S(=O)(=O)c1cccc(OC(F)F)c1] | 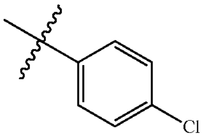 [SMILES: *c1ccc(Cl)cc1] | (500 MHz, Chloroform-d) δ 7.60-7.50 (m, 3H), 7.43 (d, J = 7.5 Hz, 2H), 7.40 (dd, J = 2.5, 1.5 Hz, 1H), 7.32-7.26 (m, 2H), 7.18 (s, 1H), 7.43 (t, J = 73.5 Hz, 1H). |
| 1-140 | $CF_3$ | 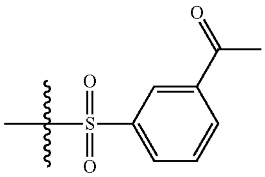 [SMILES: *S(=O)(=O)c1cccc(C(C)=O)c1] | 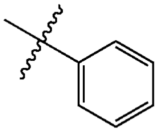 [SMILES: *c1ccccc1] | (500 MHz, Chloroform-d) δ 8.33-8.28 (m, 2H), 8.17-8.06 (m, 1H), 7.73-6.65 (m, 1H), 7.60-7.51 (m, 3H), 7.41 -7.30 (m, 3H), 2.60 (s, 3H). |
| 1-141 | $CF_3$ | 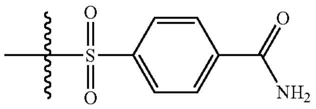 [SMILES: *S(=O)(=O)c1ccc(C(N)=O)cc1] | 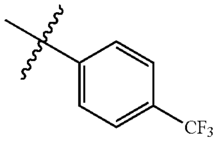 | (500 MHz, Chloroform-d) δ 8.10 (d, J = 7.5 Hz, 2H), 8.04 (d, J = 7.5 Hz, 2H), 7.69 (d, J = 7.5 Hz, 2H), 7.57 (d, J = 7.5 Hz, 2H), 7.17 (s, 1H), 6.41 (s, 2H). |
| 1-142 | $CF_3$ | 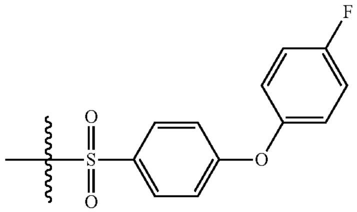 [SMILES: *S(=O)(=O)c1ccc(Oc2ccc(F)cc2)cc1] | 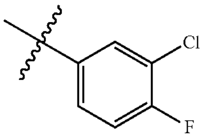 [SMILES: *c1ccc(F)c(Cl)c1] | (500 MHz, Chloroform-d) δ 7.79-7.70 (m, 3H), 7.45-7.38 (m, 2H), 7.31-7.19 (m, 3H), 7.18-7.12 (m, 2H), 7.12 -7.04 (m, 2H). |

TABLE 2-continued

Structure and $^1$HNMR data of the derivative Compound I-1

I-1

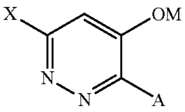

| No. | X | M | A | $^1$HNMR |
| --- | --- | --- | --- | --- |
| 1-143 | $CF_3$ | 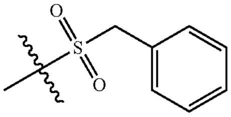 [SMILES: *S(=O)(=O)Cc1ccccc1] | 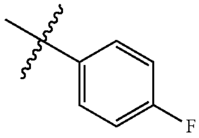 [SMILES: *c1ccc(F)cc1] | (500 MHz, Chloroform-d) δ 7.60 (s, 1H), 7.53-7.45 (m, 2H), 7.30-7.20 (m, 5H), 7.11 -7.03 (m, 2H), 4.29 (s, 2H). |
| 1-144 | $CF_3$ | 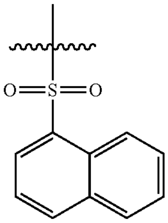 [SMILES: *S(=O)(=O)c1cccc2ccccc12] | 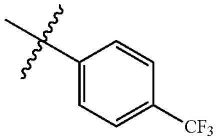 | (500 MHz, Chloroform-d) δ 8.80 (dd, J = 7.5, 1.5 Hz, 1H), 8.26-8.15 (m, 2H), 8.01-7.78 (m, 2H), 7.58-7.50 (m, 4H), 7.51-7.40 (m, 3H). |
| 1-145 | $CF_3$ | 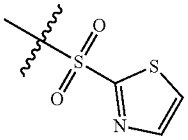 [SMILES: *S(=O)(=O)c1nccs1] | 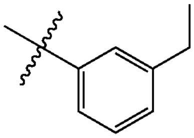 [SMILES: *c1cccc(CC)c1] | (500 MHz, Chloroform-d) δ 8.16 (d, J = 2.5 Hz, 1H), 7.75-7.69 (m, 2H), 7.47-7.36 (m, 3H), 7.33-7.24 (m, 1H), 2.71 -2.61 (d, J = 8.0 Hz, 2H), 1.21 (t, J = 8.0 Hz, 3H). |
| 1-146 | $CF_3$ | 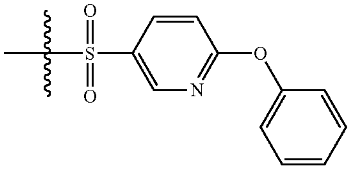 [SMILES: *S(=O)(=O)c1ccc(Oc2ccccc2)nc1] | 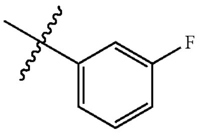 [SMILES: *c1cccc(F)c1] | (500 MHz, Chloroform-d) δ 8.41 (d, J = 1.5 Hz, 1H),7.99 (dd, J = 8.0, 1.5 Hz, 1H), 7.63 (s, 1H), 7.50-7.39 (m, 4H), 7.32-7.21 (m, 2H), 7.18-7.08 (m, 3H), 6.96(dd, J = 7.5, 2.0 Hz, 1H). |
| 1-147 | $CF_3$ | 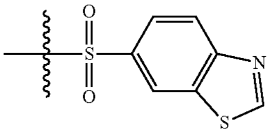 [SMILES: *S(=O)(=O)c1ccc2ncsc2c1] | 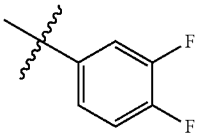 [SMILES: *c1ccc(F)c(F)c1] | (500 MHz, Chloroform-d) δ 9.38 (s, 1H), 8.81 (d, J = 1.5 Hz, 1H), 7.99-7.91 (m, 2H), 7.63 (s, 1H), 7.48-7.25 (m, 3H). |
| 1-148 | $CF_3$ | 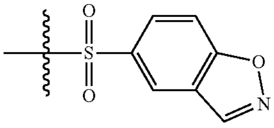 [SMILES: *S(=O)(=O)c1ccc2oncc2c1] | 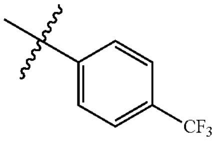 [SMILES: *c1ccc(C(F)(F)F)cc1] | (500 MHz, Chloroform-d) δ 8.43 (d, J = 1.5 Hz, 1H), 8.15 (dd, J = 2.5,1.5 Hz, 1H), 7.85 (dd, J = 7.5,1.5 Hz, 1H), 7.77 -7.60 (m, 3H), 7.56-7.49 (m, 3H). |
| 1-149 | $CF_3$ | 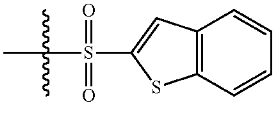 [SMILES: *S(=O)(=O)c1cc2ccccc2s1] | 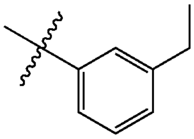 [SMILES: *c1cccc(CC)c1] | (500 MHz, Chloroform-d) δ 7.97 (dd, J = 6.5, 2.0 Hz, 1H), 7.70-7.65 (m, 2H), 7.61 (d, J = 1.5 Hz, 1H), 7.53-7.43 (m, 3H), 7.37-7.27 (m, 3H), 2.71 -2.62 (d, J = 8.0 Hz, 2H), 1.21 (t, J = 8.0 Hz, 3H). |
| 1-150 | $CF_3$ | 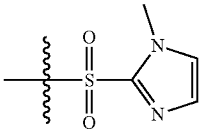 [SMILES: *S(=O)(=O)c1nccn1C] | 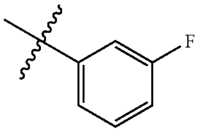 [SMILES: *c1cccc(F)c1] | (500 MHz, Chloroform-d) δ 7.73 (s, 1H), 7.59-7.49 (m, 2H), 7.36 (d, J = 2.5 Hz, 1H), 7.31-7.25 (m, 3H), 3.66 (s, 3H). |

TABLE 2-continued

Structure and $^1$HNMR data of the derivative Compound I-1

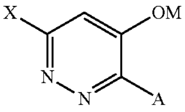

I-1

| No. | X | M | A | $^1$HNMR |
| --- | --- | --- | --- | --- |
| 1-151 | $CF_3$ | 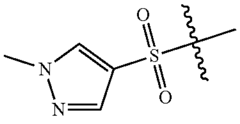 [SMILES: *S(=O)(=O)c1cnn(C)c1] | 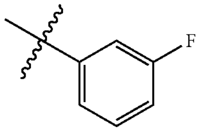 [SMILES: *c1cccc(F)c1] | (500 MHz, Chloroform-d) δ 7.73-7.65 (m, 2H), 7.62 (s, 1H), 7.57-7.42 (m, 2H), 7.25 -7.19 (m,2H), 3.92 (s, 3H). |
| 1-152 | $CF_3$ | 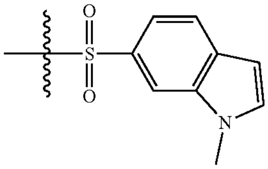 [SMILES: *S(=O)(=O)c1ccc2ccn(C)c2c1] | 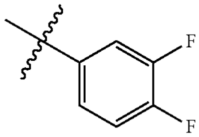 [SMILES: *c1ccc(F)c(F)c1] | (500 MHz, Chloroform-d) δ 7.93-7.85 (m, 2H), 7.80 (dd, J = 7.5, 1.5 Hz, 1H), 7.72 (s, lH),7.33-7.19(m, 3H),7.11 (d, J = 7.5 Hz, 1H), 6.50 (dd, J = 7.5, 1.5 Hz, 1H), 3.80 (s, 3H). |
| 1-153 | $CF_3$ | 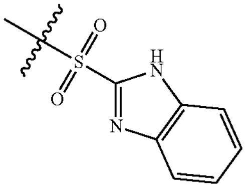 [SMILES: *S(=O)(=O)c1nc2ccccc2[nH]1] | 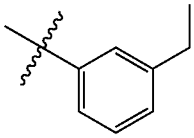 [SMILES: *c1cccc(CC)c1] | (500 MHz, Chloroform-d) δ 7.76-7.60 (m, 4H), 7.56-7.44 (,,,, 4H), 7.26-7.14 (m, 2H), 2.66 (q, J = 8.0 Hz, 1H), 1.21 (t, J = 8.0 Hz, 1H). |
| 1-154 | $CF_3$ | 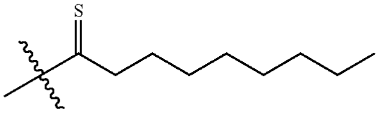 [SMILES: *C(=S)CCCCCCCC] | 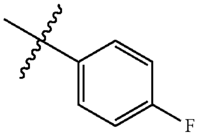 [SMILES: *c1ccc(F)cc1] | (500 MHz, Chloroform-d) δ 7.45 (dd, J = 7.5, 5.5 Hz, 2H), 7.28 (s, 1H),7.07(dd, J = 9.0, 7.5 Hz, 2H), 1.41 (t, J = 8.0 Hz, 2H), 1.36-1.22 (m, 12H), 0.93 (t, J = 8.0 Hz, 3H). |
| 1-155 | $CF_3$ | 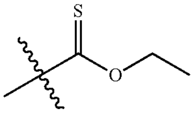 [SMILES: *C(=S)OCC] | 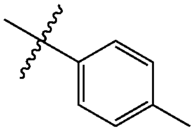 [SMILES: *c1ccc(C)cc1] | (500 MHz, Chloroform-d) δ 7.44 (d, J = 7.5 Hz, 2H), 7.22-7.13 (m,3H), 3.62 (q,7 = 8.0 Hz, 2H), 2.33 (s, 3H), 1.36 (t, J = 8.0 Hz, 3H). |
| 1-156 | $CF_3$ | 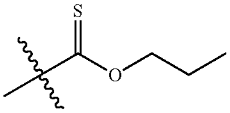 [SMILES: *C(=S)OCCC] | 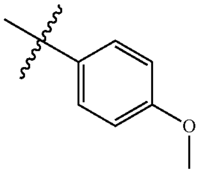 [SMILES: *c1ccc(OC)cc1] | (500 MHz, Chloroform-d) δ 7.50(d, J = 7.5 Hz, 2H), 7.21 (s, 1H), 6.80 (d, J = 7.5 Hz, 2H), 3.80 (s, 3H),3.60(t, J = 7.5 Hz, 2H), 1.78-1.66 (m, 2H), 1.01 (t, J = 8.0 Hz, 3H). |
| 1-157 | $CF_3$ | 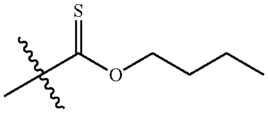 [SMILES: *C(=S)OCCCC] | 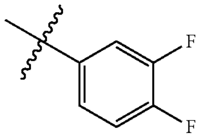 [SMILES: *c1ccc(F)c(F)c1] | (500 MHz, Chloroform-d) δ 7.30-7.22 (m, 2H), 7.20 (s, 1H), 7.15-7.05 (m, 1H), 3.65 (t, J = 8.0 Hz, 2H), 1.46-1.36 (m, 4H), 1.03 (t, J = 8.0 Hz, 3H). |
| 1-158 | $CF_3$ | 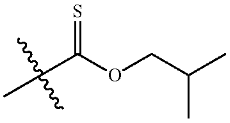 [SMILES: *C(=S)OCC(C)C] | 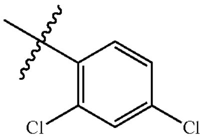 [SMILES: *c1ccc(Cl)cc1Cl] | (500 MHz, Chloroform-d) δ 7.52-7.43 (m, 2H), 7.34 (s, 1H), 7.27 (dd, J = 7.5, 2.0 Hz, 1H), 3.45 (d, J = 7.0 Hz, 2H), 1.49-1.38 (m, 1H), 0.92 (d, J = 7.5 Hz, 6H). |

TABLE 2-continued

Structure and 1HNMR data of the derivative Compound I-1

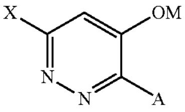

I-1

| No. | X | M | A | $^1$HNMR |
| --- | --- | --- | --- | --- |
| 1-159 | $CF_3$ | 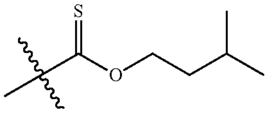 [SMILES: *C(=S)OCCC(C)C] | 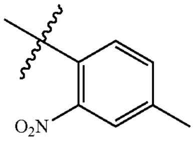 [SMILES: *c1ccc(C)cc1[N+](=O)[O-]] | (500 MHz, Chloroform-d) δ 7.84 (dd, J = 2.0 Hz, 1H), 7.62 (d, J = 7.5 Hz, 1H), 7.43-7.33 (m, 1H), 7.19 (s, 1H), 3.60 (t, J = 7.5 Hz, 2H), 2.50 (s, 3H), 1.67-1.60 (m, 1H), 1.43-1.31 (m, 2H), 0.97 (d, J = 6.5 Hz, 6H). |
| 1-160 | $CF_3$ | 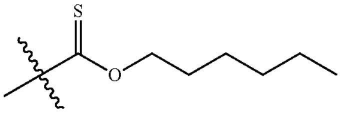 | 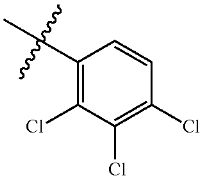 [SMILES: *c1ccc(Cl)c(Cl)c1Cl] | (500 MHz, Chloroform-d) δ 7.31 (d, J = 7.5 Hz, 1H), 7.22 (s, 1H), 7.14 (d, J = 7.5 Hz, 1H), 3.60 (t, J = 7.0 Hz, 2H), 1.65-1.55 (m, 2H), 1.43-1.31 (m, 6H), 0.89 (t, J = 7.5 Hz, 3H). |
| 1-161 | $CF_3$ | 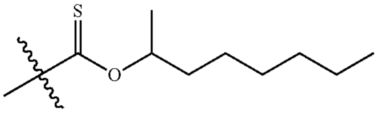 [SMILES: *C(=S)OC(C)CCCCCC] | 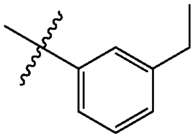 [SMILES: *c1cccc(CC)c1] | (500 MHz, Chloroform-d) δ 7.40-7.35 (m, 2H), 7.33-7.15 (m, 3H), 3.88-3.73 (m, 1H), 2.65-2.55 (m, 2H), 1.69 -1.55 (m, 2H), 1.59-1.39 (m, 3H), 1.28-1.07 (m, 11H), 0.89 (t, J = 7.5 Hz, 3H). |
| 1-162 | $CF_3$ | 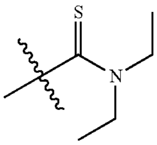 [SMILES: *C(=S)N(CC)CC] | 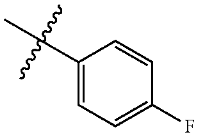 [SMILES: *c1ccc(F)cc1] | (500 MHz, Chloroform-d) δ 7.45-7.37(m, 2H), 7.20 (s, 1H), 7.11-7.03 (m, 2H), 3.65 (q, J = 8.0 Hz, 4H), 1.17 (t, J = 8.0 Hz, 6H). |
| 1-163 | $CF_3$ | 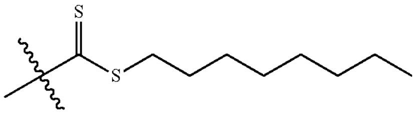 [SMILES: *C(=S)SCCCCCCCC] | 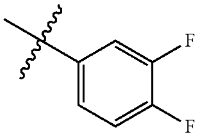 [SMILES: *c1ccc(F)c(F)c1] | (500 MHz, Chloroform-d) δ 7.45-7.37 (m, 2H), 7.24-7.11 (m, 2H), 2.85 (t, J = 8.0 Hz, 2H), 1.94-1.81 (m, 2H), 1.38-1.29 (m, 2H), 1.32-1.20 (m, 8H), 0.93-0.85 (t, J = 8.0 Hz, 3H). |
| 1-164 | $CF_3$ | 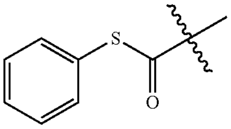 | 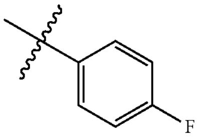 [SMILES: *c1ccc(F)cc1] | (500 MHz, Chloroform-d) δ 7.53-7.47 (m, 2H), 7.48-7.40 (m, 2H), 7.28-7.20 (m, 3H), 7.11-7.03 (m, 3H). |
| 1-165 | $CF_3$ | 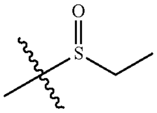 [SMILES: *S(=O)CC] | 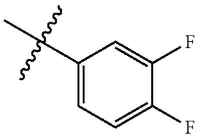 [SMILES: *c1ccc(F)c(F)c1] | (500 MHz, Chloroform-d) δ 7.40-7.28 (m, 2H), 7.19-7.14 (m, 2H), 2.61 (q, J = 8.0 Hz, 2H), 1.35 (t, J = 8.0 Hz, 3H). |
| 1-166 | $CF_3$ | 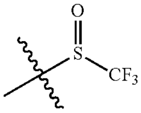 [SMILES: *S(=O)C(F)(F)F] | 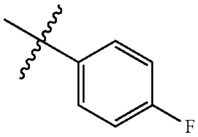 [SMILES: *c1ccc(F)cc1] | (500 MHz, Chloroform-d) δ 7.45-7.37(m, 2H), 7.28 (s, 1H), 7.11-7.03 (m, 2H). |

TABLE 2-continued

Structure and $^1$HNMR data of the derivative Compound I-1

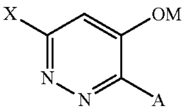

I-1

| No. | X | M | A | $^1$HNMR |
|---|---|---|---|---|
| 1-167 | $CF_3$ | 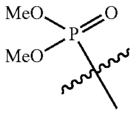 [SMILES: *P(=O)(OC)OC] | 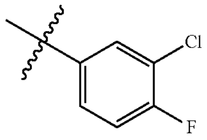 [SMILES: *c1ccc(F)c(Cl)c1] | (500 MHz, Chloroform-d) δ 7.58 (dd, J = 5.5, 2.0 Hz, 1H), 7.36-7.29 (m, 1H), 7.32 (s, lH),7.16(dd, J = 10.5, 7.5 Hz, 1H), 3.78 (s, 6H). |
| 1-168 | $CF_3$ | 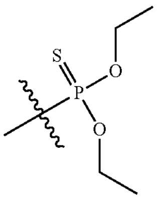 [SMILES: *P(=S)(OCC)OCC] | 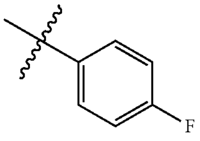 [SMILES: *c1ccc(F)cc1] | |
| 1-169 | $CF_3$ | 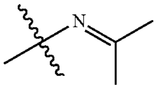 [SMILES: *N=C(C)C] | 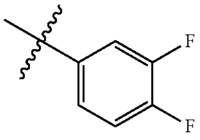 [SMILES: *c1ccc(F)c(F)c1] | (500 MHz, Chloroform-d) δ 7.38-7.30 (m, 1H), 7.25-7.13 (m, 2H), 7.08 (s, 1H), 2.65 (s, 6H). |
| 1-170 | $CF_3$ | 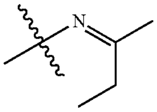 [SMILES: */N=C(/C)CC] | 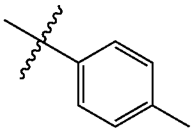 [SMILES: *c1ccc(C)cc1] | (500 MHz, Chloroform-d) δ 7.46 (d, J = 7.0 Hz, 2H), 7.20 (d, J = 7.0 Hz,2H),7.15(s, 1H), 2.59 (s, 3H), 2.33 (s, 3H), 2.17 (q, J = 8.0 Hz, 2H), 0.92 (t, J = 8.0 Hz, 3H). |
| 1-171 | $CF_3$ | 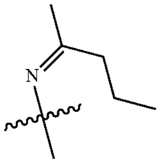 [SMILES: */N=C(/C)CCC] | 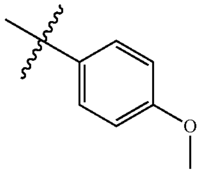 [SMILES: *c1ccc(OC)cc1] | (500 MHz, Chloroform-d) δ 7.49 (d, J = 7.5 Hz, 2H), 6.80-6.74 (m, 3H), 3.80 (s, 3H), 2.58 (s, 3H), 2.11 (t, J = 7.5 Hz, 2H), 1.54-1.44 (m, 2H), 0.76 (t, J = 8.0 Hz, 3H). |
| 1-172 | $CF_3$ | 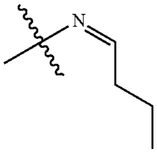 [SMILES: */N=C\CCC] | 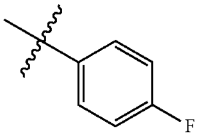 [SMILES: *c1ccc(F)cc1] | (500 MHz, Chloroform-d) δ 7.47-7.40 (m, 2H), 7.15 (s, 1H), 7.11-7.03 (m, 2H), 6.87 (t, J = 7.0 Hz, 1H), 2.11-2.00 (m, 2H), 1.54-1.42 (m, 2H), 0.81 (t, J = 8.0 Hz, 3H). |
| 1-173 | $CF_3$ | 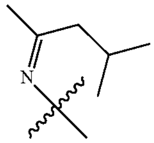 [SMILES: */N=C(/C)CC(C)C] | 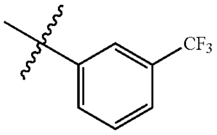 [SMILES: *c1cccc(C(F)(F)F)c1] | (500 MHz, Chloroform-d) δ 7.95-7.89 (m, 2H), 7.72-7.66 (m, 2H), 7.09 (s, 1H), 2.62 (s, 3H), 2.05 (d, J = 7.0 Hz, 2H), 1.77- 1.68 (m, 1H), 0.97 (d, J = 6.5 Hz, 6H). |
| 1-174 | $CF_3$ | 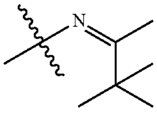 [SMILES: */N=C(/C)C(C)(C)C] | 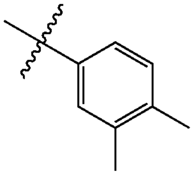 [SMILES: *c1ccc(C)c(C)c1] | (500 MHz, Chloroform-d) δ 7.41 (d, J = 2.0 Hz, 1H), 7.32 (dd, J = 7.5, 2.0 Hz, 1H), 7.15 (d, J = 7.5 Hz, 1H), 7.08 (s, 1H), 2.66 (s, 3H), 2.30 (s, 3H), 2.20 (s, 3H), 1.16 (s, 9H). |

TABLE 2-continued

Structure and $^1$HNMR data of the derivative Compound I-1

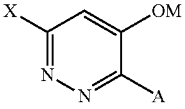

I-1

| No. | X | M | A | $^1$HNMR |
| --- | --- | --- | --- | --- |
| 1-175 | $CF_3$ | 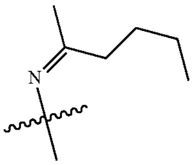 [SMILES: */N=C(/C)CCCC] | 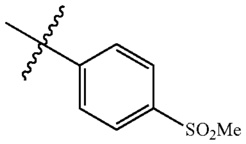 [SMILES: *c1ccc(S(C)(=O)=O)cc1] | (500 MHz, Chloroform-d) δ 7.99 (d, J = 7.0 Hz, 2H), 7.87-7.81 (m, 3H), 3.30 (s, 3H), 2.59 (s, 3H), 2.11 (t, J = 8.0 Hz, 2H), 1.55- 1.40 (m, 4H), 0.95 (t, J = 8.0 Hz, 3H). |
| 1-176 | $CF_3$ | 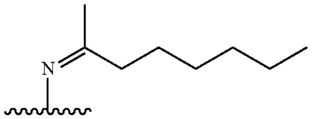 [SMILES: */N=C(/C)CCCCCC] | 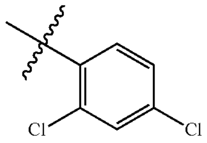 [SMILES: *c1ccc(Cl)cc1Cl] | (500 MHz, Chloroform-d) δ 7.54 (d, J = 2.0 Hz, 1H), 7.49 (d, J = 7.5 Hz, 1H), 7.34 (dd, J = 7.5, 2.0 Hz, 1H), 7.14 (s, 1H), 2.57 (s, 3H), 2.11 (t, J = 8.0 Hz, 2H), 1.55-1.47 (m, 2H), 1.34-1.23 (m, 6H), 0.93 (t, J = 8.0 Hz, 3H). |
| 1-177 | $CF_3$ | 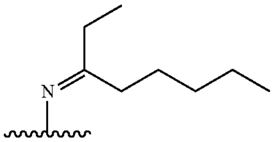 [SMILES: */N=C(/CC)CCCCC] | 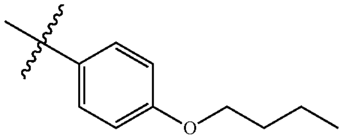 [SMILES: *c1ccc(OCCCC)cc1] | (500 MHz, Chloroform-d) δ 7.50 (d, J = 7.5 Hz, 2H), 7.19-7.03 (m, 3H), 4.00 (t, J = 7.5 Hz, 2H), 2.21-2.07 (m, 4H), 1.60-1.44 (m, 8H), 1.36-1.23 (m,5H), 1.04 (t, J = 8.0 Hz, 3H), 0.92 (t, J = 8.0 Hz, 3H). |
| 1-178 | $CF_3$ | 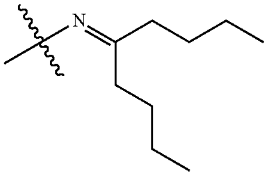 [SMILES: *N=C(CCCC)CCCC] | 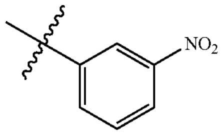 [SMILES: *c1cccc([N+](=O)[O-])c1] | (500 MHz, Chloroform-d) δ 8.43-8.25 (m, 2H), 7.91-7.80 (m, 1H), 7.63-7.55 (m, 1H), 7.16 (s, 1H), 2.11 (t, J = 7.5 Hz, 4H), 1.55-1.40 (m, 8H), 0.95 (t, J = 8.0 Hz, 6H). |
| 1-179 | $CF_3$ | 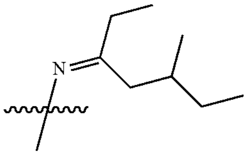 [SMILES: */N=C(/CC)CC(C)CC] | 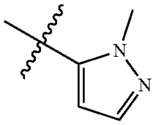 [SMILES: *c1ccnn1C] | (500 MHz, Chloroform-d) δ 7.62 (d, J = 2.5 Hz, 1H), 7.30 (s, 1H), 6.45 (d, J = 2.5 Hz, 1H), 4.00 (s, 3H), 2.55-2.41 (m, 2H), 2.32-2.02 (m, 2H), 1.68- 1.57 (m, 1H), 1.37-1.19 (m, 2H), 1.02-0.88 (m, 9H). |
| 1-180 | $CF_3$ | 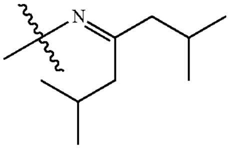 [SMILES: *N=C(CC(C)C)CC(C)C] | 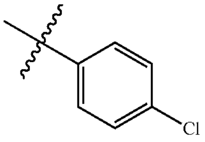 [SMILES: *c1ccc(Cl)cc1] | (500 MHz, Chloroform-d) δ 7.47 (d, J = 7.0 Hz, 2H), 7.17-7.03 (m, 3H), 2.05 (d, J = 7.0 Hz, 4H), 1.72-1.60 (m, 2H), 0.96 (d, J = 6.5 Hz, 12H). |
| 1-181 | $CF_3$ | 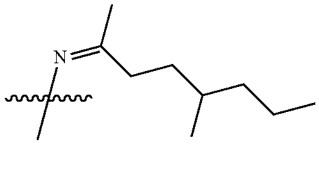 [SMILES: */N=C(/C)CCC(C)CCC] | 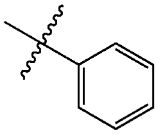 [SMILES: *c1ccccc1] | (500 MHz, Chloroform-d) δ 7.59-7.51 (m, 2H), 7.41-7.33 (m, 3H), 7.16 (s, 1H), 2.59 (s, 3H), 2.40 (t, J = 7.5 Hz, 2H), 1.61-1.55 (m, 3H), 1.31-1.15 (m, 2H), 1.17-1.09 (m, 1H), 1.12-1.02 (m, 2H), 0.85 (t, J = 7.5 Hz, 2H), 0.74 (d, J = 6.5 Hz, 3H). |

TABLE 2-continued

Structure and $^1$HNMR data of the derivative Compound I-1

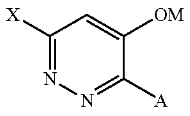

I-1

| No. | X | M | A | $^1$HNMR |
| --- | --- | --- | --- | --- |
| 1-182 | $CF_3$ | 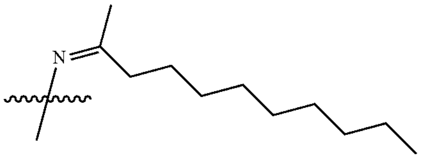 [SMILES: */N=C(/C)CCCCCCCCC] | 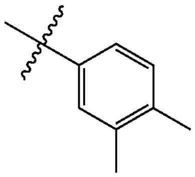 [SMILES: *c1ccc(C)c(C)c1] | (500 MHz, Chloroform-d) δ 7.35-7.27 (m, 2H),7.16(dd, J = 7.5, 1.0 Hz, 1H), 7.13 (s, 1H), 2.57 (s, 3H), 2.30 (s, 3H), 2.20 (s, 3H), 2.11 (t, J = 8.0 Hz, 2H), 1.55-1.22 (m, 14H), 0.89 (t, J = 8.0 Hz, 3H). |
| 1-183 | $CF_3$ | 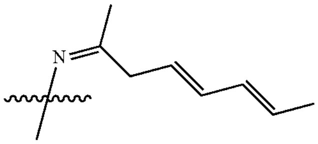 [SMILES: */N=C(/C)C/C=C/C=C/C] | 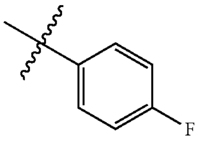 [SMILES: *c1ccc(F)cc1] | |
| 1-184 | $CF_3$ | 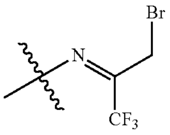 | 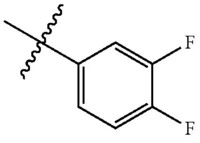 [SMILES: *c1ccc(F)c(F)c1] | |
| 1-185 | $CF_3$ | 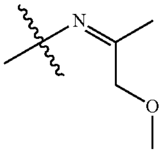 [SMILES: */N=C(/C)COC] | 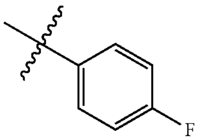 [SMILES: *c1ccc(F)cc1] | (500 MHz, Chloroform-d) δ 7.47-7.40 (m, 2H), 7.16 (s, 1H), 7.11-7.03 (m, 2H), 4.21 (s, 2H), 3.19(s, 3H), 2.57 (s, 3H). |
| 1-186 | $CF_3$ | 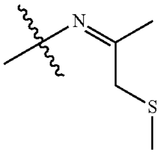 | 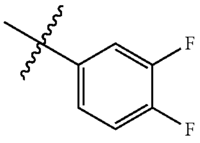 [SMILES: *c1ccc(F)c(F)c1] | (500 MHz, Chloroform-d) δ 7.44-7.37 (m, 1H), 7.25-7.16 (m, 2H),7.16(s, 1H), 3.28 (s, 2H), 2.60 (s, 3H), 2.00 (s, 3H). |
| 1-187 | $CF_3$ | 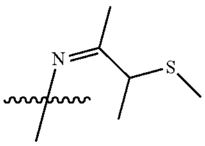 [SMILES: */N=C(/C)C(C)SC] | 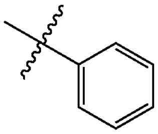 [SMILES: *c1ccccc1] | (500 MHz, Chloroform-d) δ 7.59-7.51 (m, 2H), 7.41-7.27 (m, 3H),7.14(s, 1H), 2.73 (q, J = 6.5 Hz, 1H), 2.59 (s, 3H), 2.10 (s,3H), 1.31 (d, J = 6.5 Hz, 3H). |
| 1-188 | $CF_3$ | 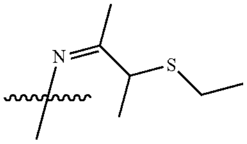 [SMILES: */N=C(/C)C(C)SCC] | 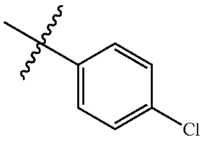 [SMILES: *c1ccc(Cl)cc1] | (500 MHz, Chloroform-d) δ 7.45 (d, J = 7.5 Hz, 2H), 7.25 (d, J = 7.5 Hz, 2H), 7.11 (s, 1H), 2.73 (q, J = 6.5 Hz, 1H), 2.59 (s, 3H), 2.19 (d, J = 8.0 Hz, 2H), 1.31 (d, J = 6.5 Hz, 3H) 1.24 (t, J = 8.0 Hz, 3H). |
| 1-189 | $CF_3$ | 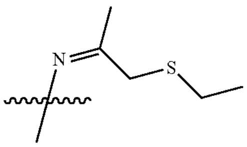 [SMILES: */N=C(/C)CSCC] | 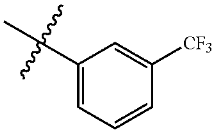 [SMILES: *c1cccc(C(F)(F)F)c1] | (500 MHz, Chloroform-d) δ 8.01-7.91 (m, 2H), 7.70-7.53 (m, 2H), 7.19 (s, 1H), 3.28 (s, 2H), 2.60 (s, 3H), 2.48 (q, J = 8.0 Hz, 2H), 1.21 (t, J = 8.0 Hz, 3H). |

TABLE 2-continued

Structure and ¹HNMR data of the derivative Compound I-1

I-1

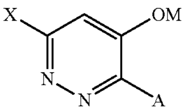

| No. | X | M | A | ¹HNMR |
|---|---|---|---|---|
| 1-190 | $CF_3$ | 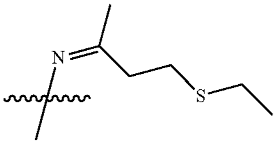 [SMILES: */N=C(/C)CCSCC] | 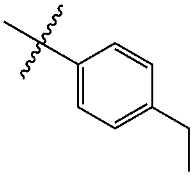 [SMILES: *c1ccc(CC)cc1] | (500 MHz, Chloroform-d) δ 7.46 (d, J = 7.0 Hz, 1H), 7.17-7.10 (m, 3H), 2.75-2.63 (m, 4H), 2.59 (s, 3H), 2.49 (q, J = 8.0 Hz, 2H), 1.21 (t, J = 8.0 Hz, 3H). |
| 1-191 | $CF_3$ | 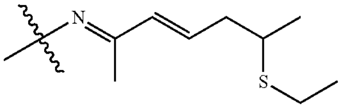 [SMILES: */N=C(C)/C=C/CC(C)SCC] | 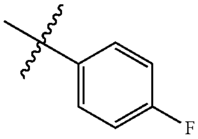 [SMILES: *c1ccc(F)cc1] | |
| 1-192 | $CF_3$ | 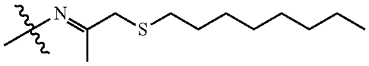 [SMILES: */N=C(\C)CSCCCCCCCC] | 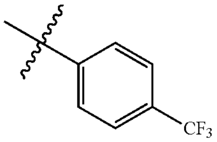 | (500 MHz, Chloroform-d) δ 7.73 (d, J = 7.5 Hz, 1H), 7.60-7.53 (m, 3H), 3.28 (s, 2H), 2.71 (t, J = 8.0 Hz, 1H), 2.58 (s, 3H), 1.38-1.20 (m, 12H), 0.93 (t, J = 8.0 Hz, 3H). |
| 1-193 | $CF_3$ | 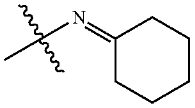 [SMILES: *N=C1CCCCC1] | 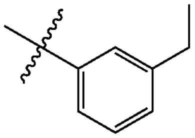 [SMILES: *c1cccc(CC)c1] | (500 MHz, Chloroform-d) δ 7.50-7.40 (m, 1H), 7.37-7.28 (m, 2H), 7.22-7.17 (m, 1H), 7.11 (s, 1H), 2.71-2.62 (m, 4H), 2.17 (q, J = 8.0 Hz, 2H), 1.60-1.50 (m, 6H), 1.21 (t, J = 8.0 Hz, 3H). |
| 1-194 | $CF_3$ | 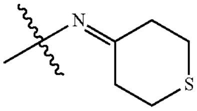 [SMILES: *N=C1CCSCC1] | 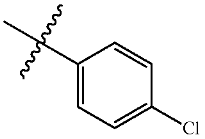 [SMILES: *c1ccc(Cl)cc1] | (500 MHz, Chloroform-d) δ 7.53 (t, J = 7.0 Hz, 2H), 7.44 (t, J = 7.0 Hz, 2H), 7.15 (s, 1H), 2.66-2.53 (m, 4H), 2.50 -2.36 (m, 4H). |
| 1-195 | $CF_3$ | 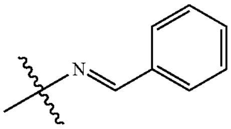 [SMILES: */N=C/c1ccccc1] | 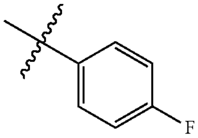 [SMILES: *c1ccc(F)cc1] | (500 MHz, Chloroform-d) δ 7.58-7.50 (m, 2H), 7.52-7.39 (m, 4H), 7.33-7.26 (m, 2H),7.17(s, 1H), 7.11-7.03 (m, 2H). |
| 1-196 | $CF_3$ | 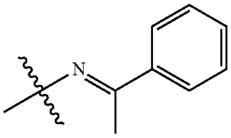 [SMILES: */N=C(\C)c1ccccc1] | 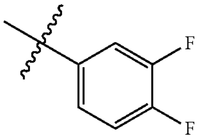 [SMILES: *c1ccc(F)c(F)c1] | (500 MHz, Chloroform-d) δ 7.50 (s, 5H), 7.53-7.40 (m, 1H), 7.28-7.19 (m, 2H), 7.15 (s, 1H), 3.08 (s, 3H). |
| 1-197 | $CF_3$ | 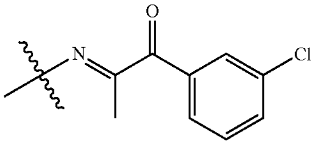 [SMILES: */N=C(\C)C(=O)c1cccc(Cl)c1] | 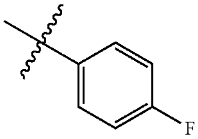 [SMILES: *c1ccc(F)cc1] | |

TABLE 2-continued
Structure and $^1$HNMR data of the derivative Compound I-1
I-1
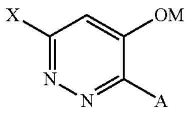
| No. | X | M | A | $^1$HNMR |
| --- | --- | --- | --- | --- |
| 1-198 | $CF_3$ | 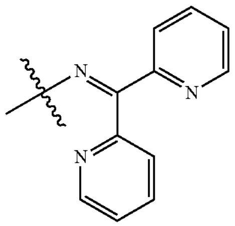 [SMILES: *N=C(c1ccccn1)c1ccccn1] | 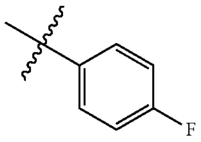 [SMILES: *c1ccc(F)cc1] | (500 MHz, Chloroform-d) δ 8.59-8.37 (m, 2H), 7.72-7.49 (m, 4H), 7.41-7.33 (m, 4H),7.19(s, 1H), 7.11-7.03 (m, 2H). |
| 1-199 | $CF_3$ | 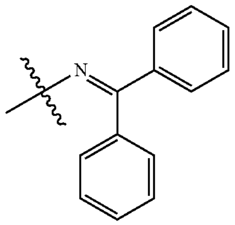 [SMILES: *N=C(c1ccccc1)c1ccccc1] | 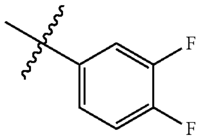 [SMILES: *c1ccc(F)c(F)c1] | (500 MHz, Chloroform-d) δ 7.52-7.44 (m, 2H), 7.38-7.23 (m, 7H), 7.26-7.16 (m, 4H), 7.09 (s, 1H). |
| 1-200 | $CF_3$ | 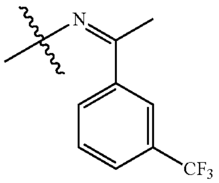 [SMILES: */N=C(/C)c1cccc(C(F)(F)F)c1] | 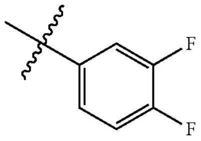 [SMILES: *c1ccc(F)c(F)c1] | (500 MHz, Chloroform-d) δ 7.62-7.52 (m, 2H), 7.45-7.37 (m, 1H), 7.32-7.19 (m, 4H), 7.13 (s, 1H), 2.36 (s, 3H). |
| 1-201 | $CF_3$ | 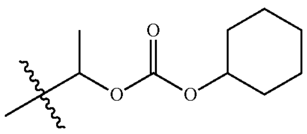 [SMILES: *C(C)OC(=O)OC1CCCCC1] | 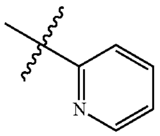 [SMILES: *c1ccccn1] | |
| 1-202 | $CF_3$ | OEt | 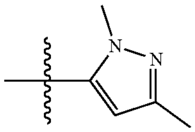 [SMILES: *c1cc(C)nn1C] | |
| 1-203 | $CF_3$ | 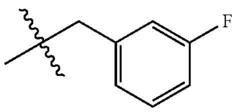 [SMILES: *Cc1cccc(F)c1] | 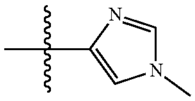 [SMILES: *c1cn(C)cn1] | |
| 1-204 | $CF_3$ | 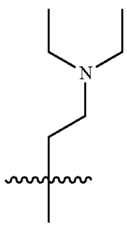 [SMILES: *CCN(CC)CC] | 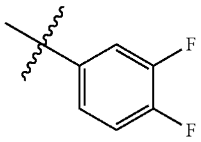 [SMILES: *c1ccc(F)c(F)c1] | |

TABLE 2-continued
Structure and $^{1}$HNMR data of the derivative Compound I-1
I-1
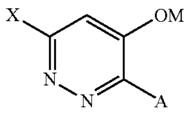
| No. | X | M | A | $^{1}$HNMR |
| --- | --- | --- | --- | --- |
| 1-205 | $CF_3$ | 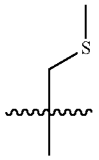 [SMILES: *CSC] | 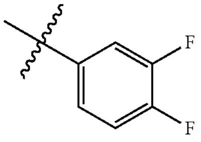 [SMILES: *c1ccc(F)c(F)c1] | |
| 1-206 | $CF_3$ | 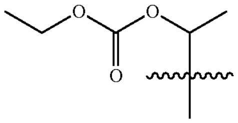 [SMILES: *C(C)OC(=O)OCC] | 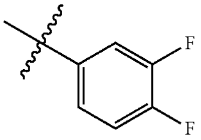 [SMILES: *c1ccc(F)c(F)c1] | |
| 1-207 | $CF_3$ | 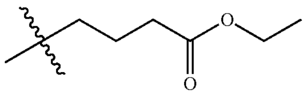 [SMILES: *CCCC(=O)OCC] | 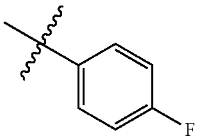 [SMILES: *c1ccc(F)cc1] | (500 MHz, Chloroform-d) δ 7.50-7.43 (m, 2H), 7.35 (s, 1H), 7.11-7.03 (m, 2H), 4.07 (q, J = 8.0 Hz, 2H), 3.95 (t, J = 7.5 Hz, 2H), 2.48 (t, J = 7.0 Hz, 2H), 2.11-2.00 (m, 2H), 1.17 (t, J = 8.0 Hz, 3H). |
| 1-208 | $CF_3$ | 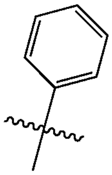 [SMILES: *c1ccccc1] | 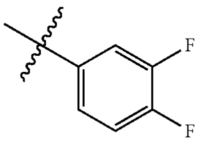 [SMILES: *c1ccc(F)c(F)c1] | (500 MHz, Chloroform-d) δ 7.45-7.32 (m, 3H), 7.26-7.14 (m, 4H), 6.83-6.76 (m, 2H). |
| 1-209 | $CF_3$ | 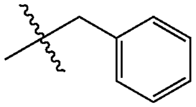 [SMILES: *Cc1ccccc1] | 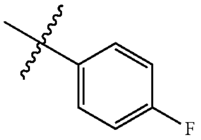 [SMILES: *c1ccc(F)cc1] | (500 MHz, Chloroform-d) δ 7.53-7.45 (m, 3H), 7.44-7.27 (m, 3H), 7.11-7.03 (m, 4H), 4.98 (s, 2H). |
| 1-210 | $CF_3$ | 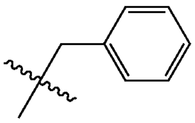 [SMILES: *Cc1ccccc1] | 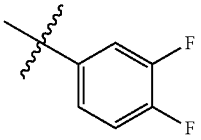 [SMILES: *c1ccc(F)c(F)c1] | (500 MHz, Chloroform-d) δ 7.44-7.27 (m, 4H), 7.13-7.07 (m, 5H), 4.98 (s, 2H). |
| 1-211 | $CF_3$ | 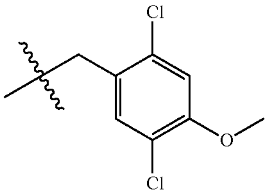 [SMILES: *Cc1cc(Cl)c(OC)cc1Cl] | 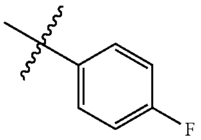 [SMILES: *c1ccc(F)cc1] | (500 MHz, Chloroform-d) δ 7.50-7.42 (m, 3H), 7.35 (s, 1H), 7.14-7.03 (m, 3H), 5.12 (s, 2H), 3.86 (s, 3H). |
| 1-212 | $CF_3$ | 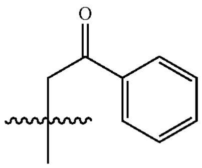 [SMILES: *CC(=O)c1ccccc1] | 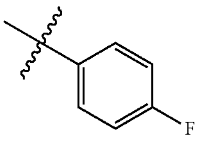 [SMILES: *c1ccc(F)cc1] | (500 MHz, Chloroform-d) δ 8.07-8.00 (m, 3H), 7.64-7.56 (m, 3H), 7.54-7.42 (m, 2H),7.31 (s, 1H), 7.11-7.03 (m, 2H), 5.70 (s, 2H). |

TABLE 2-continued
Structure and $^1$HNMR data of the derivative Compound I-1
I-1
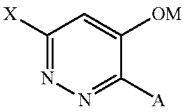
| No. | X | M | A | $^1$HNMR |
|---|---|---|---|---|
| 1-213 | $CF_3$ | 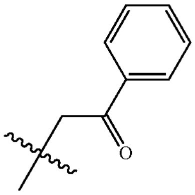 [SMILES: *CC(=O)c1ccccc1] | 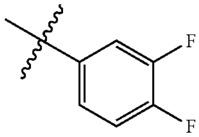 [SMILES: *c1ccc(F)c(F)c1] | (500 MHz, Chloroform-d) δ 8.03-7.89 (m, 2H), 7.64-7.56 (m, 2H), 7.54-7.34 (m, 1H), 7.28-7.18 (m, 3H), 5.70 (s, 2H). |
| 1-214 | $CF_3$ | 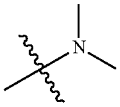 [SMILES: *N(C)C] | 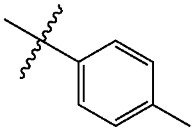 [SMILES: *c1ccc(C)cc1] | (500 MHz, Chloroform-d) δ 7.42 (d, J = 7.0 Hz, 2H), 7.22 (d, J = 7.0 Hz, 2H), 7.12 (s, 1H), 2.47 (s, 6H), 2.33 (s, 3H). |
| 1-215 | $CF_3$ | 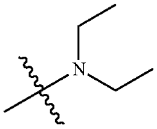 | 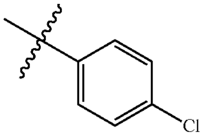 [SMILES: *c1ccc(Cl)cc1] | (500 MHz, Chloroform-d) δ 7.47 (d, J = 7.5 Hz, 2H), 7.39 (d, J = 7.5 Hz, 2H), 7.12 (s, 1H), 2.59 (q, J = 8.0 Hz, 4H), 1.04 (t, J = 8.0 Hz, 6H). |
| 1-216 | CF | 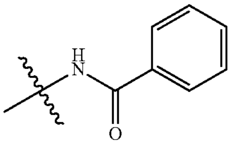 [SMILES: *NC(=O)c1ccccc1] | 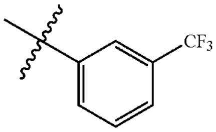 [SMILES: *c1cccc(C(F)(F)F)c1] | |
| 1-217 | $CF_3$ | 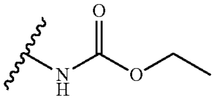 [SMILES: *NC(=O)OCC] | 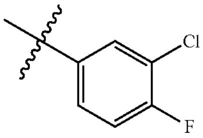 [SMILES: *c1ccc(F)c(Cl)c1] | |
| 1-218 | $CH_2F$ | 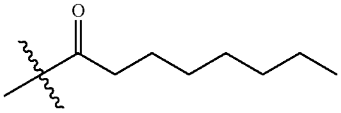 [SMILES: *C(=O)CCCCCCC] | 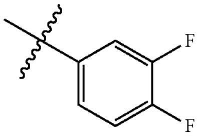 [SMILES: *c1ccc(F)c(F)c1] | |
| 1-219 | $CH_2F$ | 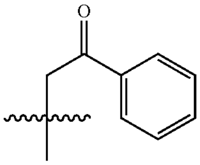 [SMILES: *CC(=O)c1ccccc1] | 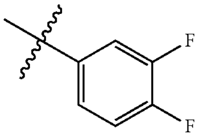 [SMILES: *c1ccc(F)c(F)c1] | |
| 1-220 | $CH_2F$ | 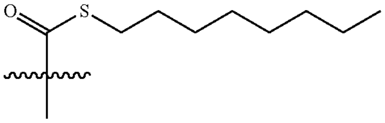 | 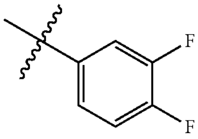 [SMILES: *c1ccc(F)c(F)c1] | |

TABLE 2-continued
Structure and $^1$HNMR data of the derivative Compound I-1
I-1
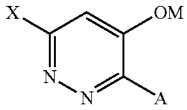
| No. | X | M | A | $^1$HNMR |
|---|---|---|---|---|
| 1-221 | $CHF_2$ | 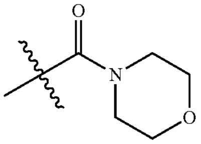 [SMILES: *C(=O)N1CCOCC1] | 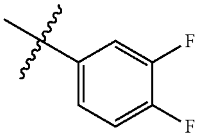 [SMILES: *c1ccc(F)c(F)c1] | |
| 1-222 | $CHF_2$ | 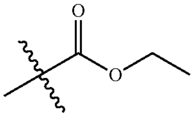 [SMILES: *C(=O)OCC] | 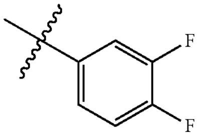 [SMILES: *c1ccc(F)c(F)c1] | |
| 1-223 | $CFCF_3$ | 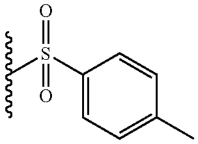 [SMILES: *S(=O)(=O)c1ccc(C)cc1] | 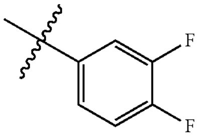 [SMILES: *c1ccc(F)c(F)c1] | |
| 1-224 | $CFCF_3$ | 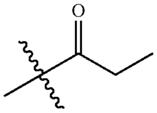 [SMILES: *C(=O)CC] | 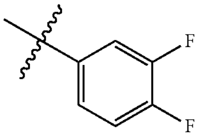 | |
| 1-225 | $CFCF_3$ | 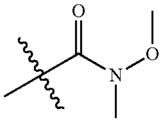 [SMILES: *C(=O)N(C)OC] | 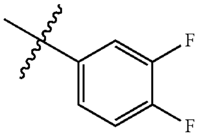 [SMILES: *c1ccc(F)c(F)c1] | |
| 1-226 | $CF_3$ | 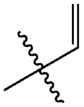 [SMILES: *C=C] | 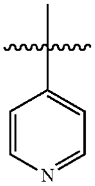 [SMILES: *c1ccncc1] | |
| 1-227 | $CF_3$ | 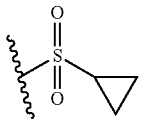 [SMILES: *S(=O)(=O)C1CC1] | 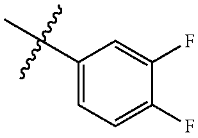 [SMILES: *c1ccc(F)c(F)c1] | |
| 1-228 | $CF_3$ | 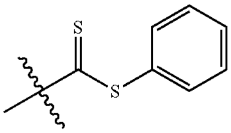 [SMILES: *C(=S)Sc1ccccc1] | 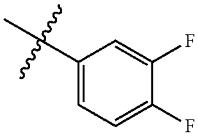 [SMILES: *c1ccc(F)c(F)c1] | |

TABLE 2-continued
Structure and ¹HNMR data of the derivative Compound I-1
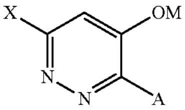
I-1
| No. | X | M | A | ¹HNMR |
|---|---|---|---|---|
| 1-229 | $CF_3$ | 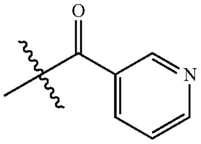 [SMILES: *C(=O)c1cccnc1] | 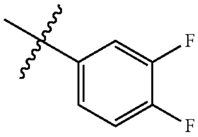 [SMILES: *c1ccc(F)c(F)c1] | |
| 1-230 | $CF_3$ | 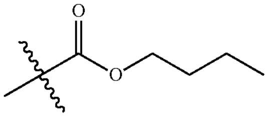 [SMILES: *C(=O)OCCCC] | 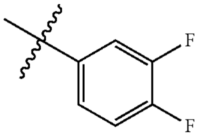 [SMILES: *c1ccc(F)c(F)c1] | |
| 1-231 | $CF_3$ | 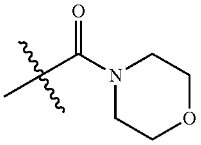 [SMILES: *C(=O)N1CCOCC1] | 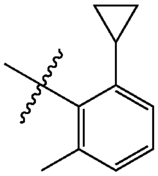 [SMILES: *c1c(C)cccc1C1CC1] | |
| 1-232 | $CF_3$ | 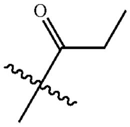 [SMILES: *C(=O)CC] | 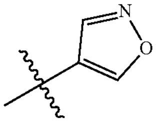 [SMILES: *c1cnoc1] | |
| 1-233 | $CF_3$ | 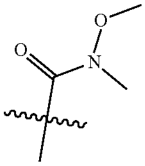 [SMILES: *C(=O)N(C)OC] | 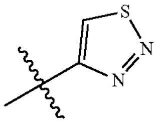 [SMILES: *c1csnn1] | |
| 1-234 | $CF_3$ | 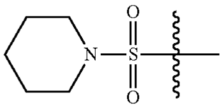 [SMILES: *S(=O)(=O)N1CCCCC1] | 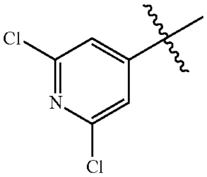 [SMILES: *c1cc(Cl)nc(Cl)c1] | |
| 1-235 | $CF_3$ | 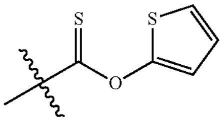 [SMILES: *C(=S)Oc1cccs1] | 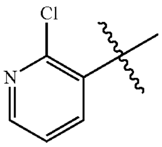 | |
| 1-236 | $CF_3$ | 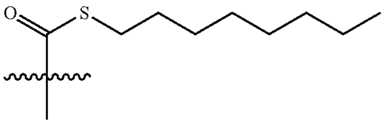 [SMILES: *C(=O)SCCCCCCCC] | 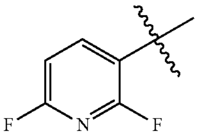 [SMILES: *c1ccc(F)nc1F] | |

TABLE 2-continued
Structure and $^{1}$HNMR data of the derivative Compound I-1
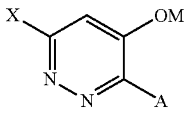
I-1
| No. | X | M | A | $^{1}$HNMR |
|---|---|---|---|---|
| 1-237 | $CF_3$ | 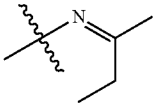 [SMILES: */N=C(/C)CC] | 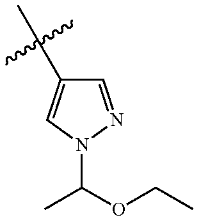 [SMILES: *c1cnn(C(C)OCC)c1] | |
| 1-238 | $CF_3$ | 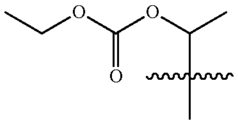 [SMILES: *C(C)OC(=O)OCC] | 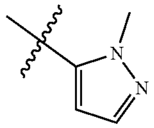 [SMILES: *c1ccnn1C] | |
| 1-239 | $CF_3$ | 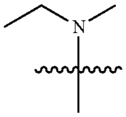 | 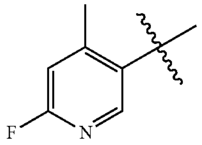 [SMILES: *c1cnc(F)cc1C] | |
| 1-240 | $CF_3$ | 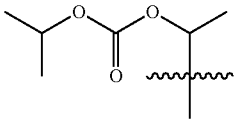 [SMILES: *C(C)OC(=O)OC(C)C] | 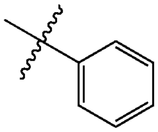 [SMILES: *c1ccccc1] | $^{1}$H NMR (500 MHz, Chloroform-d) 7.56-7.48 (m, 2H), 7.41-7.33 (m, 3H), 7.00-6.91 (m, 2H), 5.27 (hept, J = 6.5 Hz, 1H), 1.73 (d, J = 7.0 Hz, 3H), 1.31 (d,J = 6.5 Hz, 6H). |
| 1-241 | $CF_3$ | CN | 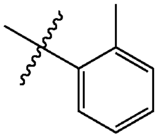 [SMILES: *c1ccccc1C] | |
| 1-242 | $CF_3$ | 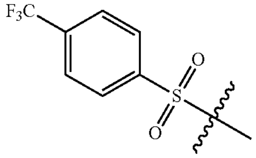 [SMILES: *S(=O)(=O)c1ccc(C(F)(F)F)cc1] | 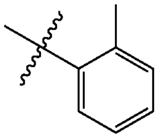 [SMILES: *c1ccccc1C] | $^{1}$H NMR (500MHz, Chloroform-d) δ 7.77-7.66 (m, 4H), 7.60-7.53 (m, 2H), 7.41-7.22 (m, 3H). |
| 1-243 | $CF_3$ | 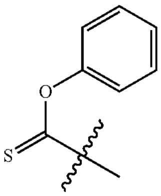 [SMILES: *C(=S)Oc1ccccc1] | 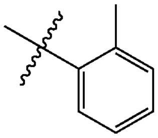 [SMILES: *c1ccccc1C] | $^{1}$H NMR (500MHz, Chloroform-d) δ 7.51-7.44 (m, 2H), 7.42-7.33 (m, 4H), 7.20 (s, 1H), 7.07-7.00 (m, 3H). |
| 1-244 | $CF_3$ | 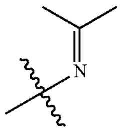 [SMILES: *N=C(C)C] | 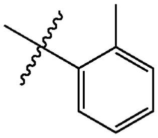 [SMILES: *c1ccccc1C] | $^{1}$H NMR (500MHz, Chloroform-d) δ 7.59-7.51 (m, 2H), 7.41-7.33 (m, 2H), 7.15 (s, 1H), 2.59 (s, 3H), 2.51 (s, 3H), 2.30 (s, 3H). |

TABLE 2-continued

Structure and $^1$HNMR data of the derivative Compound I-1

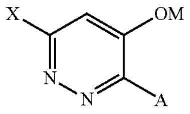

I-1

| No. | X | M | A | $^1$HNMR |
| --- | --- | --- | --- | --- |
| 1-245 | $CF_3$ | 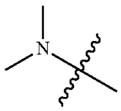 [SMILES: *N(C)C] | 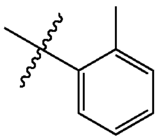 [SMILES: *c1ccccc1C] | $^1H$ NMR (500 MHz, Chloroform-d) δ 7.55-7.47 (m, 2H), 7.41-7.30 (m, 2H), 7.11 (s, 1H), 2.47 (s, 6H), 2.32 (s, 3H). |
| 1-246 | $CF_3$ | 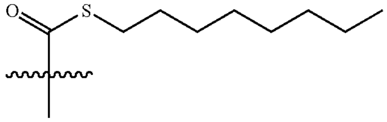 [SMILES: *C(=O)SCCCCCCCC] | 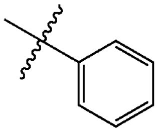 [SMILES: *c1ccccc1] | $^1H$ NMR (500 MHz, Chloroform-d) 7.58-7.42 (m, 3H), 7.31-7.12(m, 3H), 2.85 (t, J = 7.5 Hz, 2H), 1.38-1.26 (m, 12H), 0.89 (t, J = 7.0 Hz, 1H). |
| 1-247 | $CF_3$ | 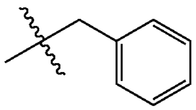 [SMILES: *Cc1ccccc1] | 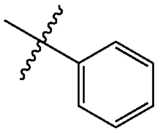 [SMILES: *c1ccccc1] | $^1H$ NMR (500 MHz, Chloroform-d) 7.65-7.49 (m, 6H), 7.42-7.27 (m, 4H), 7.11 (s, 1H), 4.98 (s, 2H). |
| 1-248 | $CF_3$ | 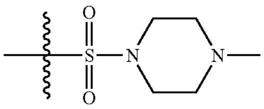 [SMILES: *S(=O)(=O)N1CCN(C)CC1] | 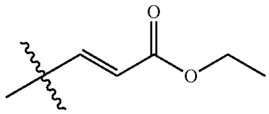 [SMILES: */C=C/C(=O)OCC] | |
| 1-249 | $CF_3$ | 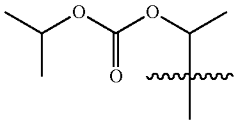 [SMILES: *C(C)OC(=O)OC(C)C] | 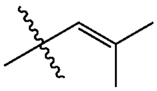 | |
| 1-250 | $CF_3$ | 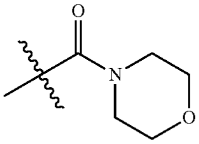 [SMILES: *C(=O)N1CCOCC1] | 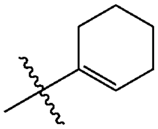 [SMILES: *C1=CCCCC1] | |
| 1-251 | $CF_3$ | 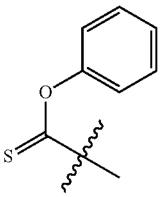 [SMILES: *C(=S)Oc1ccccc1] | Me | |

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route. Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art, for example, protection of suitable group in the process of the reaction, etc.

The following method of application can be used to improve further understanding of the preparation method of the present invention. The specific material, class and condition have been determined to be further explication of the present invention, not to be any limit of the reasonable scope thereof. Reagents of the following synthetic compound showed in the table can either be purchased from the market or easily prepared by those skilled in the art.

Examples of representative compounds are as follows:

1. Synthesis of Compound 1

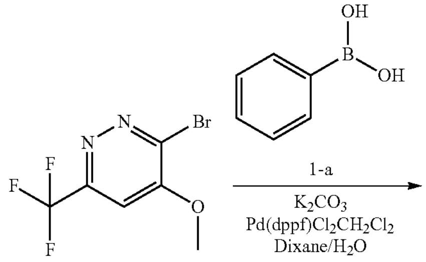

II

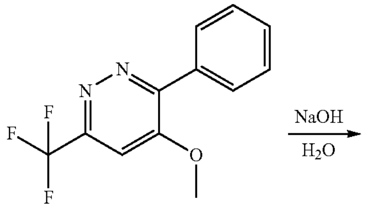

1-b

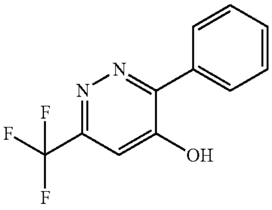

1

(1) experimental apparatus: a 50 mL round bottom single-necked flask, a magnetic stirrer, and a thermostatic magnetic stirrer.

Compound II (1 g, 3.9 mmol), Compound 1-a (0.72 g, 5.9 mmol), and potassium carbonate (1.62 g, 11.7 mmol) were placed in the round bottom flask, added with 1,4-dioxane (10 mL)/water (2 mL) and then subjected to replacement of nitrogen gas three times, followed by the quickly addition of $Pd(dppf)Cl_2CH_2Cl_2$ (0.16 g), and subjected to replacement of nitrogen gas three times, then the reaction solution was subjected to replacement of nitrogen gas three times once again, and finally the reaction was carried out at 100° C. for 36 hours. The reaction was complete detected by HPLC, the reaction system was concentrated, and separated by column chromatography to give 0.8 g (3.1 mmol, yield: 79%) of Compound 1-b (white solid).

(2) experimental apparatus: 50 mL round bottom single-necked flask, magnetic stirrer, thermostatic magnetic stirrer, and spherical condenser.

Compound 1-b (0.8 g, 3.1 mmol) was placed in the round bottom flask, 8 mL of water and sodium hydroxide (0.37 g, 9.3 mmol) were added, the resulting mixture was reacted at 80° C. for 12 h. After the reaction was completed, the reaction solution was extracted with 30 mL of dichloromethane three times. The aqueous phase was adjusted to pH 2 with 1N HCl solution, and a white solid was precipitated. The filter cake was obtained by filtration, and then dried to give 0.65 g (2.7 mmol, yield 87%) of Compound 1.

2. Synthesis of Compound 27

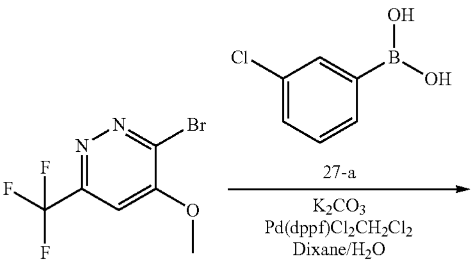

II

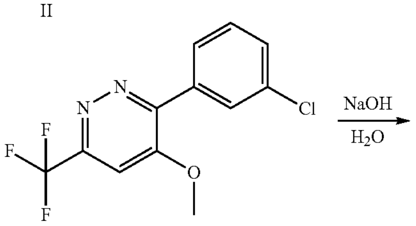

27-b

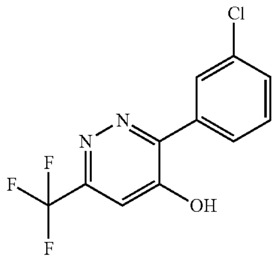

27

(1) Compound 11 (1 g, 3.9 mmol), Compound 27-a (0.92 g, 5.9 mmol), and potassium carbonate (1.62 g, 11.7 mmol) were placed in a round bottom flask, added with 1,4-dioxane (10 mL)/water (2 mL) and then subjected to replacement of nitrogen gas three times, followed by the quickly addition of Pd(dppf) $Cl_2CH_2Cl_2$ (0.16 g) and subjected to replacement of nitrogen gas three times, the reaction solution was then subjected to replacement of nitrogen gas three times once again, and finally the reaction was carried out at 120° C. for 36 hours. The reaction was complete detected by HPLC, the reaction system was concentrated and purified by concentration column chromatography (PE:EA=5:1) to give 0.71 g (2.4 mmol, yield 61%) of Compound 27-b (white solid).

(2) Compound 27-b (0.71 g, 2.4 mmol) was placed in a round bottom flask, 8 mL of water and sodium hydroxide (0.096 g, 2.4 mmol) were added, the resulting mixture was reacted at 120° C. for 12 h. The reaction was complete detected by TLC, then the reaction solution was cooled and extracted three times with 30 mL of dichloromethane. The aqueous phase was adjusted to pH=2 with IN HCl solution, and a white solid was precipitated, which was filtered to give a filter cake, and dried to give 0.35 g (1.3 mmol, yield 87%) of Compound 27.

3. Synthesis of Compound 32

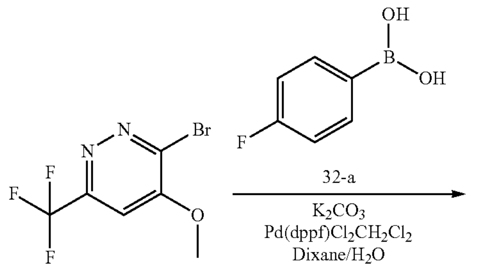

II

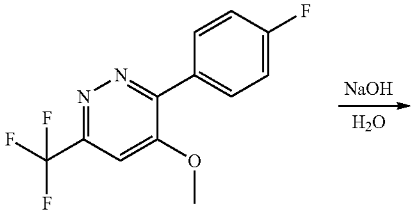

32-b

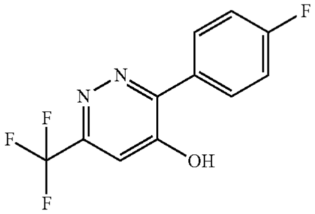

32

(1) Compound II (1 g, 3.9 mmol), Compound 32-a (0.82 g, 5.9 mmol), and potassium carbonate (1.62 g, 11.7 mmol) were placed in a round bottom flask, added with 1,4-dioxane (10 mL)/water (1 mL) and then subjected to replacement of nitrogen gas three times, followed by the quickly addition of $Pd(dppf)Cl_2CH_2Cl_2$ (0.16 g), and subjected to replacement of nitrogen gas three times, the reaction solution was then subjected to replacement of nitrogen gas three times once again, and finally the reaction was carried out 110° C. for 36 hours. After the reaction was complete detected by HPLC, the reaction solution was concentrated and purified by column chromatography (PE:EA=5:1) to give 0.8 g (3.1 mmol, yield 79%) of Compound 32-b (white solid).

(2) Compound 32-b (0.8 g, 3.1 mmol) was placed in a round bottom flask, added with 8 mL of water and sodium hydroxide (0.37 g, 9.3 mmol), and then reacted at 120° C. for 12 h. After the reaction was complete detected by TLC, the reaction solution was extracted three times with 30 mL of dichloromethane. The aqueous phase was adjusted to pH 2 with 1N HCl solution, and a white solid was precipitated, which was filtered to give a filter cake, and dried to give 0.65 g (2.7 mmol, yield 87%) of Compound 32.

4. Synthesis of Compound 207

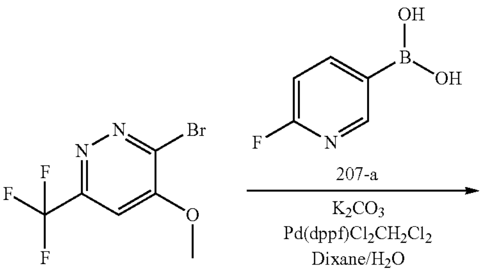

II

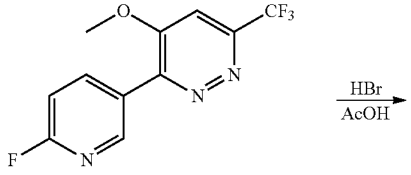

207-b

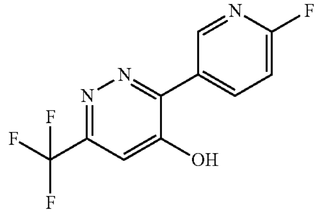

207

(1) Compound II (1 g, 3.9 mmol), Compound 207-a (0.83 g, 5.9 mmol), and potassium carbonate (1.61 g, 11.7 mmol) were placed in a round bottom flask, added with 1,4-dioxane (10 mL)/water (1 mL) and then subjected to replacement of nitrogen gas three times, followed by the quickly addition of $Pd(dppf)Cl_2CH_2Cl_2$ (0.16 g), and then subjected to replacement of nitrogen gas three times, the reaction solution was then subjected to replacement of nitrogen gas three times once again, and finally the reaction was carried out at 110° C. for 36 hours. After the reaction was complete detected by HPLC, the reaction solution was concentrated and purified by column chromatography (PE:EA=3:1) to give 0.57 g (2.1 mmol, yield 53%) of Compound 207-b (white solid).

(2) Compound 207-b (0.57 g, 2.1 mmol) was placed in a round bottom flask, added with 6 mL of HBr (30%, AcOH) and reacted at 50° C. for 12 h. After the reaction was complete detected by HPLC, the reaction solution was cooled to room temperature, added with water to precipitate, and filtered to obtain a white solid, which was dried to give 0.25 g (1.0 mmol, yield 47%) of Compound 5. Synthesis of Compound 211

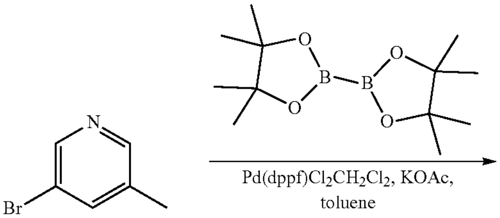

-continued

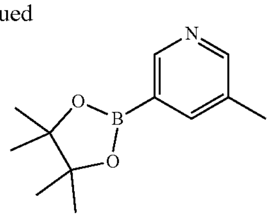

211-a

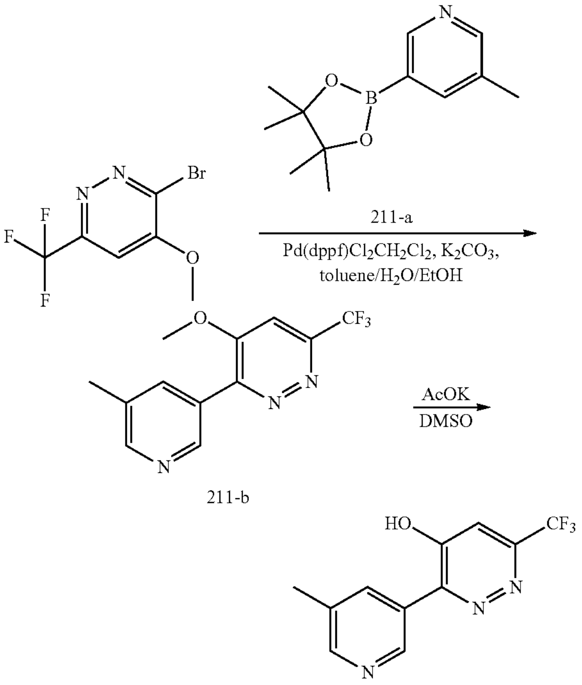

211-b

211

(1) Compound

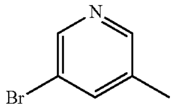

(1.0 g, 5.8 mmol, 1.0 eq), bis-boronic acid pinacol ester (1.6 g, 6.38 mmol, 1.1 eq), and potassium acetate (1.1 g, 11.6 mmol, 2.0 eq) were placed in a 100 mL round bottom flask, added with toluene (40 mL) and then subjected to replacement of nitrogen gas once, followed by the quickly addition of $Pd(dppf)Cl_2CH_2Cl_2$ (237 mg, 0.29 mmol, 0.05 eq), and then subjected to replacement of nitrogen gas three times, and then heated to 120° C. and reacted for 16 h. The system was cooled to room temperature, and Compound II (1.48 g, 5.8 mmol, 1.0 eq), $K_2CO_3$ (1.6 g, 11.6 mmol, 2.0 eq), 95% ethanol (8 mL) and $Pd(dppf)Cl_2CH_2Cl_2$ (237 mg, 0.29 mmol, 0.05 eq) were added, and then subjected to replacement of nitrogen gas three times, and heated to 120° C. (reflux) and reacted for 4 h. After the reaction was complete detected by LCMS, the reaction mixture was concentrated and then added with silica gel and purified by column chromatography to give obtain Compound 211-b (560 mg, Y: 36%).

(2) Compound 211-b (0.56 g, 2.0 mmol) was placed in a round bottom flask, added with AcOK (0.98 g, 10 mmol) and DMSO (5.6 mL) and then reacted at 125° C. for 3 h. After the reaction was complete, the temperature was lowered. The reaction solution was added with 20 mL of water, extracted three times with 30 mL of dichloromethane, and the aqueous phase was adjusted to pH 6 with 1N HCl solution, and a white solid was precipitated, which was filtered to obtain a filter cake, and dried to give 0.26 g of Compound 211 (1.6 mmol, yield 50%).

6. Synthesis of Compound 733

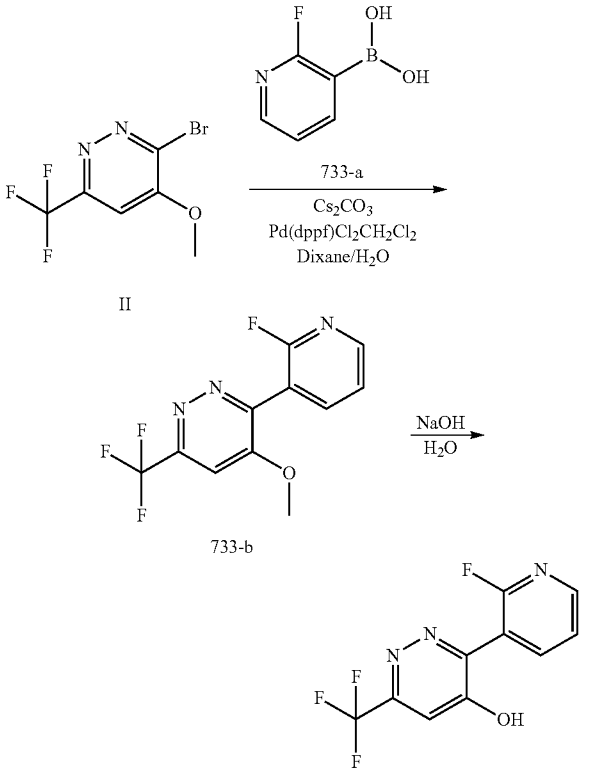

II 733-b

733

(1) experimental apparatus: a 50 mL round bottom single-necked flask, a magnetic stirrer, and a thermostatic magnetic stirrer.

Compound II (1 g, 3.9 mmol), Compound 733-a (0.83 g, 5.9 mmol), and cesium carbonate (3.81 g, 11.7 mmol) were placed in the round bottom flask, added with 1,4-dioxane (20 mL)/water (5 mL) and then subjected to replacement of nitrogen gas three times, followed by the quickly addition of $Pd(dppf)Cl_2CH_2Cl_2$ (0.16 g), and then subjected to replacement of nitrogen gas three times, and then the reaction solution was subjected to replacement of nitrogen gas three times once again, and finally the reaction was carried out at 100° C. for 36 hours. After the reaction was complete detected by HPLC, the reaction system was concentrated and purified by column chromatography to give 0.6 g (2.2 mmol, yield: 56%) of Compound 733-b (white solid).

(2) experimental apparatus: a 50 mL round bottom single-necked flask, a magnetic stirrer, a thermostatic magnetic stirrer, and a spherical condenser.

Compound 733-b (0.6 g, 2.2 mmol) was placed in the round bottom flask, added with 8 mL of water and sodium hydroxide (0.26 g, 6.6 mmol) and reacted at 80° C. for 12 h. After the reaction was complete, the reaction solution was extracted three times with 30 mL of dichloromethane, the aqueous phase was adjusted to pH 2 with 1N HCl solution, and a white solid was precipitated, a filter cake was obtained by filtration, and the filter cake was dried to give 0.41 g (1.6 mmol, yield 73%) of Compound 733.

7. Synthesis of Compound 734

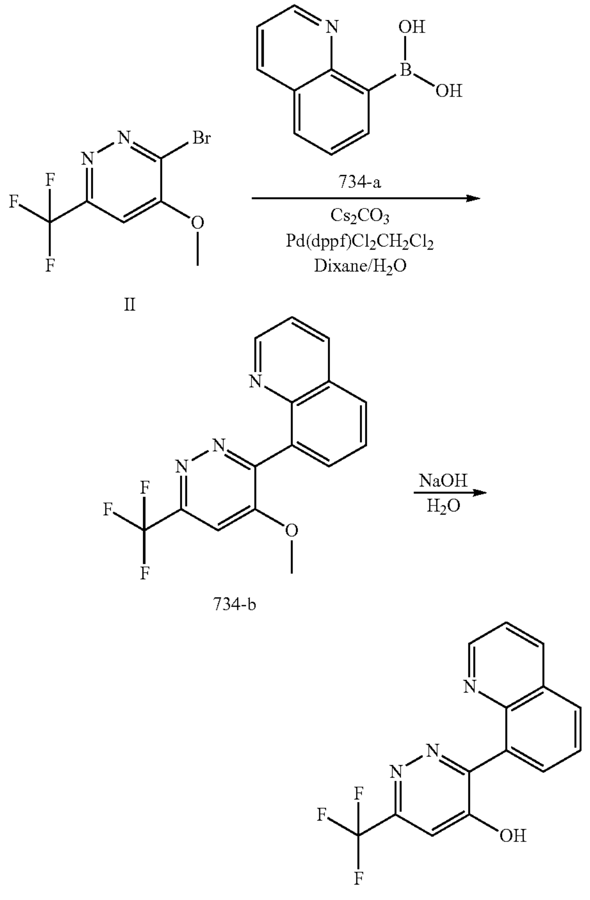

734

(1) experimental apparatus: a 50 mL round bottom single-necked flask, a magnetic stirrer, and a thermostatic magnetic stirrer.

Compound II (1 g, 3.9 mmol), Compound 734-a (1.0 g, 5.9 mmol), and cesium carbonate (3.81 g, 11.7 mmol) were placed in the round bottom flask, added with 1,4-dioxane (20 mL)/water (5 mL) and then subjected to replacement of nitrogen three times, followed by the quickly addition of $Pd(dppf)Cl_2CH_2Cl_2$ (0.16 g), and subjected to replacement of nitrogen gas three times, then the reaction solution was subjected to replacement of nitrogen gas three times once again, and finally the reaction was carried out at 110° C. for 36 hours. After the reaction was complete detected by HPLC, the reaction system was concentrated and purified by column chromatography to give 0.7 g (2.3 mmol, yield 57%) of Compound 734-b (white solid).

(2) experimental apparatus: a 50 mL round bottom single-necked flask, a magnetic stirrer, a thermostatic magnetic stirrer, and a spherical condenser.

Compound 734-b (0.7 g, 2.3 mmol) was placed in the round bottom flask, added with 15 mL of water, sodium hydroxide (0.27 g, 6.9 mmol), and then reacted at 90° C. for 12 h. After the reaction was complete, the reaction solution was extracted three time with 30 mL of dichloromethane, the aqueous phase was adjusted to pH 2 with 1N HCl solution, and a white solid was precipitated, which was filtered to obtain a filter cake, and dried to give 0.41 g (1.6 mmol, yield 73%) of Compound 734.

8. Synthesis of Compound 744

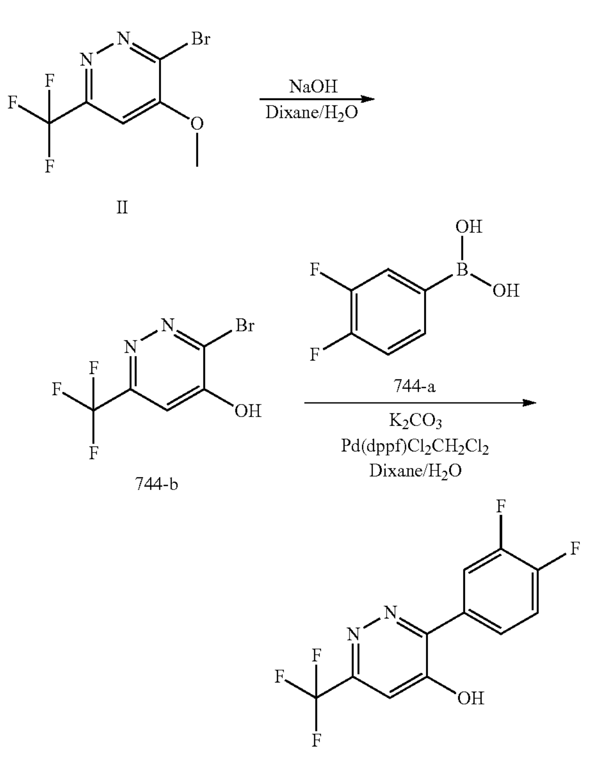

744

(1) Compound II (1 g, 3.9 mmol) was placed in a round bottom flask, added with dioxane:$H_2O$=3:1 (10 mL), sodium hydroxide (0.23 g, 5.8 mmol), and then reacted at 120° C. for 5 h. After the reaction was complete detected by TLC, the reaction solution was subjected to rotary evaporation to remove the solvent, added with 20 mL of water, and then extracted three times with 20 mL of dichloromethane. The aqueous phase was adjusted to pH 2 with 1N HCl solution, and a white solid was precipitated, which was dried to give 0.6 g (2.5 mmol, yield 65%) of Compound 744-b.

(2) Compound 744-b (1 g, 4.1 mmol), Compound 744-a (0.96 g, 6.1 mmol), and potassium carbonate (1.69 g, 12.3 mmol) were placed in a round bottom flask, added with 1,4-dioxane (10 mL)/water (1 mL) and then subjected to replacement of nitrogen gas three times, followed by the quickly addition of $Pd(dppf)Cl_2CH_2Cl_2$ (0.16 g), and then subjected to replacement of nitrogen gas three times, and then the reaction solution was subjected to replacement of nitrogen gas three times once again, and finally the reaction was carried out at 110° C. for 36 hours. After the reaction was complete detected by HPLC, the reaction mixture was concentrated, then added with 20 mL of water, and extracted three times with 30 mL of dichloromethane. The aqueous phase was adjusted to pH 4 with 1N HCl solution, and a white solid was precipitated, which was filtered to obtain a filter cake, and then dried to give 0.51 g of Compound 744 (1.85 mmol, yield 45%).

9. Synthesis of Compound 770

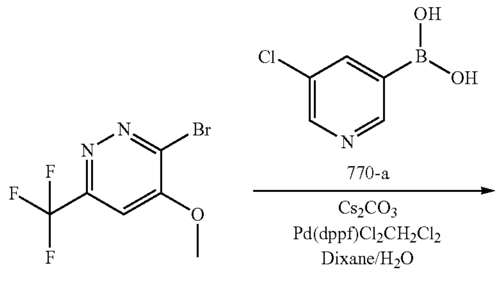

II

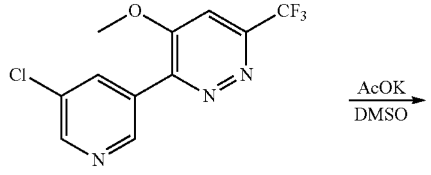

770-b

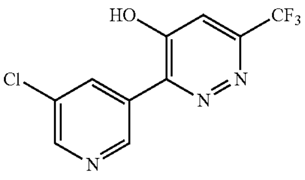

770

(1) Compound II (1 g, 3.9 mmol), Compound 770-a (0.92 g, 5.9 mmol), and cesium carbonate (3.81 g, 11.7 mmol) were placed in a round bottom flask, added with 1,4-dioxane (10 mL)/water (1 mL) and then subjected to replacement of nitrogen gas three times, followed by the quickly addition of $Pd(dppf)Cl_2CH_2Cl_2$ (0.16 g) and then subjected to replacement of nitrogen gas three times, then the reaction solution was subjected to replacement of nitrogen gas three times once again, and finally the reaction was carried out at 110° C. for 36 hours. After the reaction was complete detected by HPLC, the reaction solution was directly concentrated and purified by column chromatography (PE:EA=3:1) to give 0.63 g (2.3 mmol, yield 58.9%) of Compound 770-b (white solid).

(2) Compound 770-b (0.63 g, 2.3 mmol) was placed in a round bottom flask, added with AcOK (1.12 g, 11.5 mmol) and DMSO (6.3 mL) and reacted at 125° C. for 3 h. After the reaction was complete, the temperature was lowered. The reaction solution was added with 20 mL of water, and extracted three times with 30 mL of dichloromethane. The aqueous phase was adjusted to pH 6 with 1N HCl solution, and a white solid was precipitated, which was filtered to obtain a filter cake, and dried to give 0.41 g of Compound 770 (1.6 mmol, yield 73%).

10. Synthesis of Compound 774

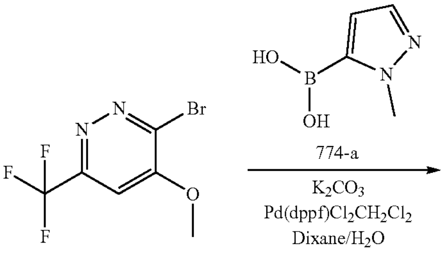

II

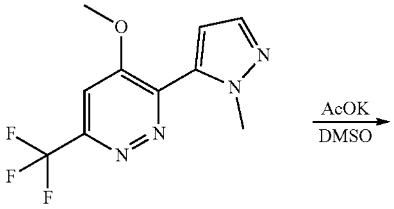

774-b

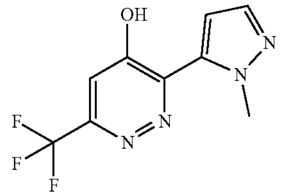

774

(1) Compound II (1 g, 3.9 mmol), Compound 774-a (0.737 g, 5.9 mmol), and potassium carbonate (1.62 g, 11.7 mmol) were placed in a round bottom flask, added with 1,4-dioxane (10 mL)/water (1 mL) and then subjected to replacement of nitrogen gas three times, then followed by the quickly addition of Pd(dppf) $Cl_2CH_2Cl_2$ (0.16 g), and then subjected to replacement of nitrogen gas three times, then the reaction solution was subjected to replacement of nitrogen gas three times once again, and finally the reaction was carried out at 110° C. for 36 hours. After the reaction was complete detected by HPLC, the reaction solution was concentrated and purified by column chromatography (PE:EA=5:1) to give 0.82 g (3.2 mmol, yield 83%) of Compound 774-b (white solid).

(2) Compound 774-b (0.82 g, 3.2 mmol) was placed in a round bottom flask, added with AcOK (1.56 g, 16 mmol) and DMSO (8.3 mL) and reacted at 120° C. for 3 h. After the reaction was complete, the temperature was lowered. The reaction solution was added with 20 mL of water, and extracted with three time with 30 mL of dichloromethane. The aqueous phase was adjusted to pH 4 with 1N HCl solution, and a white solid was precipitated, which was filtered to obtain a filter cake, and then dried to give 0.50 g of Compound 774 (2.08 mmol, Yield 65%).

11. Synthesis of Compound 1-39

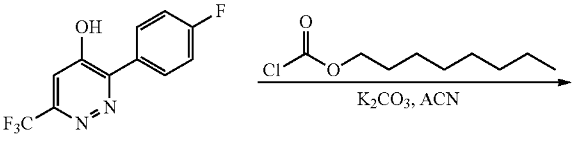

32

-continued

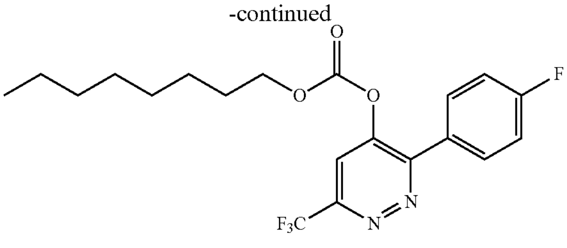

1-39

Compound 32 (1 eq.),

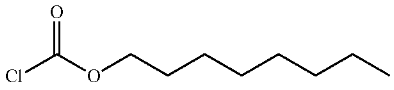

(1.1 eq.), potassium carbonate (1.5 eq.) and acetonitrile (5 V, V represents per gram of substrate corresponding to 1 mL of acetonitrile, similarly hereinafter) were added at room temperature into a 50 mL single-mouth eggplant-shaped bottle, stirred for 1 h at a controlled temperature of 20° C. After the reaction was complete detected by TLC, the reaction system was subjected to a rotary evaporator to remove acetonitrile, added with water-ethyl acetate for extraction, the residue was separated by column chromatography with silica gel (100 mesh to 200 mesh) to give the product in a yield of 79%.

12. Synthesis of Compound 1-127

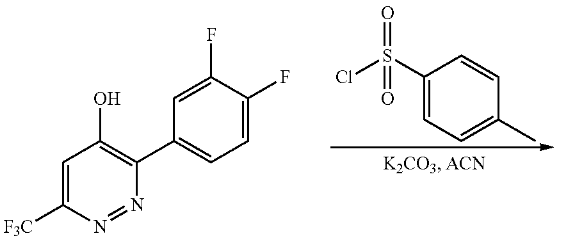

744

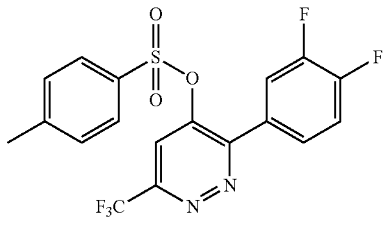

1-127

Compound 744 (1 eq.),

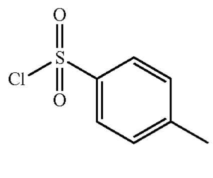

(2 eq.), potassium carbonate (3 eq.) and acetonitrile (10 V) were added into a 50 mL single-mouth eggplant-shaped flask at room temperature, and stirred at a controlled temperature of 80° C. for 12 h. After the reaction was complete detected by TLC, the reaction system was subjected to a rotary evaporator to remove acetonitrile, added with water-ethyl acetate for extraction. The residue was separated by column chromatography with silica gel (100 mesh to 200 mesh) to give a product in yield of 83%.

13. Synthesis of Compound 1-170

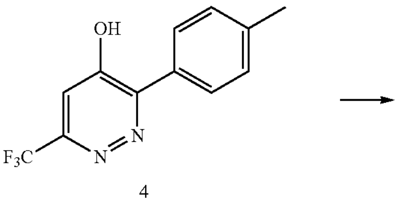

4

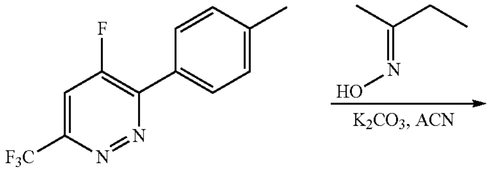

4-1

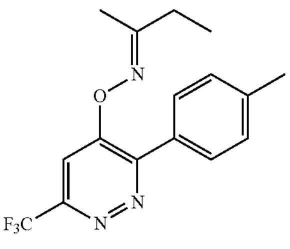

1-170

Referring to the synthesis method of Compound 1, Compound 4 was prepared, and then Compound 4-1 was prepared according to the synthesis method disclosed in WO2012142162A2. Finally, Compound 4-1 (1 eq.).),

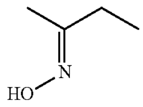

(1.1 eq.), potassium carbonate (3 eq.) and acetonitrile (10 V) were added into a 50 mL single-mouth eggplant-shaped bottle at room temperature, hearted to 80° C., and stirred for 12 h. After the reaction was complete detected by TLC, the reaction system was subjected to a rotary evaporator to remove acetonitrile, and the residue was separated by column chromatography with silica gel (100 mesh to 200 mesh) to give a product in yield of 68%.

14. Synthesis of Compound 1-213

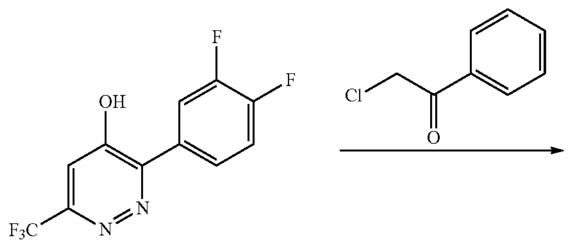

744

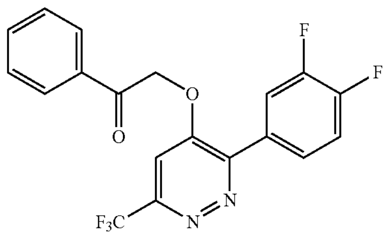

1-213

Compound 744 (1 eq.),

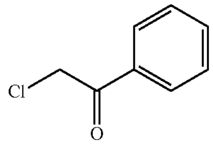

(1.5 eq.), triethylamine (3 eq.) and dichloromethane (10 V) were added into a 50 mL single-mouth eggplant-shaped flask at room temperature, and stirred at a controlled temperature of 40° C. for 1 h. After the reaction was complete detected by TLC, the reaction system was subjected to a rotary evaporator to remove dichloromethane, and added with water-ethyl acetate for extraction. The residue was separated by column chromatography with silica gel (100 mesh to 200 mesh) to give a product in yield of 72%.

15. Synthesis of Compound 1-242

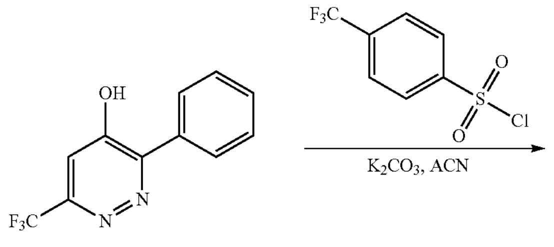

1

-continued

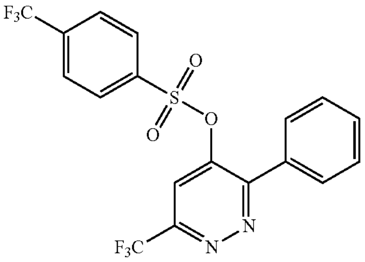

1-242

Compound 1 (1 eq.),

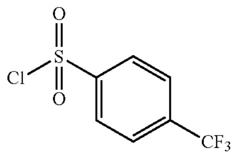

(1.1 eq.), potassium carbonate (3 eq.) and acetonitrile (10 V) were added into a 50 mL single-mouth eggplant-shaped bottle at room temperature, and stirred at room temperature for 30 min. After the reaction was complete detected by TLC, the reaction system was subjected to distillation under reduced pressure to remove acetonitrile, then added with water (5V) for dissolution and extracted with ethyl acetate (5V*3). The ethyl acetate was removed by evaporation under reduced pressure, and the residue was purified by column chromatography with silica gel (100 mesh to 200 mesh) to give a product as Compound 1-242 in yield of 85%, 16. Synthesis of Compound 1-243

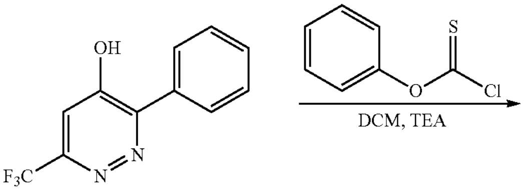

1

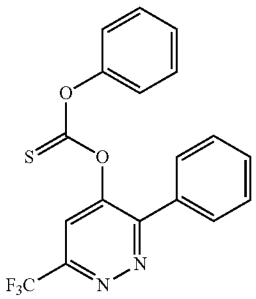

1-243

Compound 1 (1 eq.), triethylamine (3 eq.) and dichloromethane (5 V) were added into a 50 mL single-mouth eggplant-shaped flask under ice bath, and added dropwise with

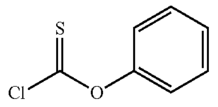

(1.2 eq.) under ice bath, then stirred at room temperature for 30 min. After the reaction was complete detected by TLC, the reaction system was added with water (5V) and extracted with dichloromethane (5V*3). The dichloromethane was removed by distillation under reduced pressure, and the residue was separated by column chromatography with silica gel (100 mesh to 200 mesh) to give a product as Compound 1-243 in yield of 78%.

17. Synthesis of Compound 1-244

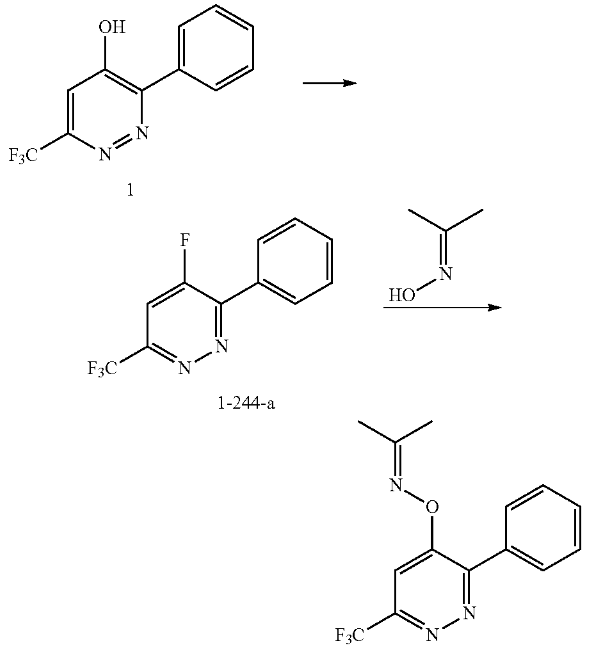

1

1-244-a 1-244

Compound 1 (1 equivalent), Phenofluor™ (1.5 equivalent), cesium fluoride (3 equivalents), and toluene (10 V) were added into a 50 mL single-mouth eggplant-shaped bottle at room temperature, heated to 80° C. and stirred for 18 h. After the reaction was complete detected by TLC, intermediate Compound 1-244-a was obtained after workup. Compound 1-244-a (1 eq.),

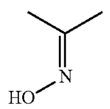

(1.2 eq.), potassium carbonate (3 eq.) and acetonitrile (10 V) were added to another 50 mL single-mouth eggplant-shaped bottle, heated to 80° C. and stirred for 18 h. After the reaction was complete detected by TLC, the reaction system was subjected to evaporation under reduced pressure to remove acetonitrile, then added with water (5V) for dissolution and extracted with ethyl acetate (5V*3). The ethyl acetate was removed by evaporation under reduced pressure, and the residue was purified by column chromatography with silica gel (100 mesh to 200 mesh) to give a product as Compound 1-244 in yield of 69%.

18. Synthesis of Compound 1-245

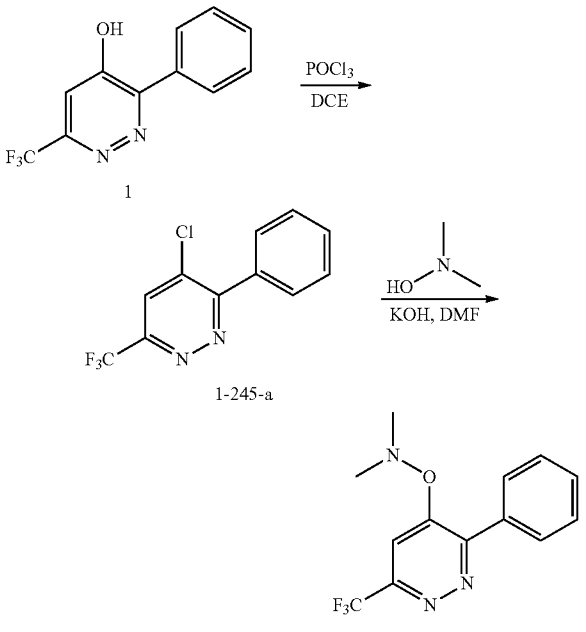

1

1-245-a 1-245

Compound 1 (1 eq.), $POCl_3$ (1.5 eq.), 1,2-dichloroethane (10 V), and 5% N,N-dimethylformamide were added into a 50 mL single-mouth eggplant-shaped bottle at room temperature, heated to 80° C. and stirred for 6 h. After the reaction was complete detected by TLC, water (5V) was added for dissolution, and then extraction was carried out with 1,2-dichloroethane (5V*3). The 1,2-dichloroethane was removed by distillation under reduced pressure to give Compound 1-245-a. Compound 1-245-a (1 eq.),

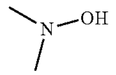

(1.2 eq.), potassium hydroxide (3 eq.) and N,N-dimethylformamide (10 V) were added at room temperature into another 50 mL single-mouth eggplant-shaped bottle, heated to 100° C., and stirred for 18 h. After the reaction was complete detected by TLC, water (5 V) was added for dissolution, and then extraction was carried out with ethyl acetate (5V*3). The ethyl acetate was removed by distillation under reduced pressure, and the residue was separated by column chromatography with silica gel (100 mesh to 200 mesh) to give a product as Compound 1-245 in a yield of 52%.

The compounds in Table 1 and Table 2 are prepared by the methods described above.

Evaluation of Biological Activity:

The activity level standard of harmful plant destruction (i.e. growth inhibition rate) is as follows:

Level 10: completely dead;

Level 9: above 90% growth inhibition rate;

Level 8: above 80% growth inhibition rate;

Level 7: above 70% growth inhibition rate;
Level 6: above 60% growth inhibition rate;
Level 5: above 50% growth inhibition rate;
Level 4: above 40% growth inhibition rate;
Level 3: above 30% growth inhibition rate;
Level 2: above 20% growth inhibition rate;
Level 1: below 20% growth inhibition rate;
Level 0: no effect.

The above described growth inhibition rates are fresh weight inhibition rates.

Experiment of post-emergence test: monocotyledonous and dicotyledonous weed seeds as well as main crop seeds (i.e., wheat, corn, rice, soybean, cotton, oilseed rape, millet and sorghum) were put into a plastic pot loaded with soil, then covered with 0.5-2 cm of soil, and the seeds were allowed to grow in good greenhouse environment. The test plants were treated at 2-3 leaf stage 2-3 weeks after sowing. The test compounds of the invention were dissolved in acetone respectively, then added with Tween-80 and diluted by a certain amount of water to give solutions with certain concentrations, and added with 80% vegetable oil methyl ester synergist at 1500 g/ha. The solution was sprayed to the plants with a sprayer. The plants were cultured for 3 weeks in the greenhouse. The experiment results of weed controlling effect after 3 weeks were listed in Table 3 and Table 4.

TABLE 3

Experiment on weed control effect of compounds of Formula I in Post-emergence stage

| Compound No. | *Amaranthus retroflexus* | *Rorippa indica* | *Veronica polita* | Chenopodiaceae | Dose |
|---|---|---|---|---|---|
| 1 | 10 | 10 | 10 | 8 | 2000 g/ha |
| 4 | 10 | 10 | 10 | 8 | 2000 g/ha |
| 8 | 10 | 10 | 10 | 8 | 2000 g/ha |
| 24 | 10 | 10 | 10 | 10 | 2000 g/ha |
| 26 | 10 | 10 | 10 | 10 | 1000 g/ha |
| 27 | 10 | 10 | 10 | 10 | 1000 g/ha |
| 28 | 10 | 10 | 10 | 10 | 1000 g/ha |
| 29 | 10 | 10 | 10 | 10 | 1000 g/ha |
| 30 | 10 | 10 | 10 | 10 | 1000 g/ha |
| 31 | 10 | 10 | 10 | 10 | 1000 g/ha |
| 32 | 10 | 10 | 10 | 10 | 1000 g/ha |
| 33 | 10 | 10 | 10 | 10 | 1000 g/ha |
| 34 | 10 | 10 | 10 | 10 | 1000 g/ha |
| 35 | 10 | 10 | 10 | 10 | 1000 g/ha |
| 36 | 10 | 10 | 10 | 10 | 1000 g/ha |
| 37 | 10 | 10 | 10 | 10 | 1000 g/ha |
| 38 | 10 | 10 | 10 | 10 | 1000 g/ha |
| 39 | 10 | 10 | 10 | 10 | 1000 g/ha |
| 40 | 10 | 10 | 10 | 10 | 1000 g/ha |
| 41 | 10 | 10 | 10 | 10 | 1000 g/ha |
| 42 | 10 | 10 | 10 | 10 | 1000 g/ha |
| 43 | 10 | 10 | 10 | 10 | 1000 g/ha |
| 44 | 10 | 10 | 10 | 10 | 1000 g/ha |
| 45 | 10 | 10 | 10 | 10 | 1000 g/ha |
| 46 | 10 | 10 | 10 | 10 | 1000 g/ha |
| 47 | 10 | 10 | 10 | 10 | 1000 g/ha |
| 48 | 10 | 10 | 10 | 10 | 1000 g/ha |
| 49 | 10 | 10 | 10 | 10 | 1000 g/ha |
| 50 | 10 | 10 | 10 | 10 | 1000 g/ha |
| 51 | 10 | 10 | 10 | 10 | 1000 g/ha |
| 52 | 10 | 10 | 10 | 10 | 1000 g/ha |
| 53 | 10 | 10 | 10 | 10 | 1000 g/ha |
| 54 | 10 | 10 | 10 | 10 | 1000 g/ha |
| 55 | 10 | 10 | 10 | 10 | 1000 g/ha |
| 56 | 10 | 10 | 10 | 10 | 1000 g/ha |
| 57 | 10 | 10 | 10 | 10 | 1000 g/ha |
| 58 | 10 | 10 | 10 | 10 | 1000 g/ha |
| 59 | 10 | 10 | 10 | 10 | 1000 g/ha |
| 60 | 10 | 10 | 10 | 10 | 1000 g/ha |
| 61 | 10 | 10 | 10 | 10 | 1000 g/ha |
| 62 | 10 | 10 | 10 | 10 | 1000 g/ha |

TABLE 3-continued

Experiment on weed control effect of compounds of Formula I in Post-emergence stage

| Compound No. | *Amaranthus retroflexus* | *Rorippa indica* | *Veronica polita* | Chenopodiaceae | Dose |
|---|---|---|---|---|---|
| 63 | 10 | 10 | 10 | 10 | 1000 g/ha |
| 64 | 10 | 10 | 10 | 10 | 1000 g/ha |
| 65 | 10 | 10 | 10 | 10 | 1000 g/ha |
| 66 | 10 | 10 | 10 | 10 | 1000 g/ha |
| 67 | 10 | 10 | 10 | 10 | 1000 g/ha |
| 68 | 10 | 10 | 10 | 10 | 1000 g/ha |
| 69 | 10 | 10 | 10 | 10 | 1000 g/ha |
| 70 | 10 | 10 | 10 | 10 | 1000 g/ha |
| 71 | 10 | 10 | 10 | 10 | 1000 g/ha |
| 72 | 10 | 10 | 10 | 10 | 1000 g/ha |
| 77 | 10 | 10 | 10 | 10 | 2000 g/ha |
| 81 | 10 | 10 | 10 | 10 | 1000 g/ha |
| 82 | 10 | 10 | 10 | 10 | 1000 g/ha |
| 83 | 10 | 10 | 10 | 10 | 1000 g/ha |
| 92 | 10 | 10 | 10 | 10 | 1000 g/ha |
| 93 | 10 | 10 | 10 | 10 | 1000 g/ha |
| 94 | 10 | 10 | 10 | 10 | 1000 g/ha |
| 95 | 10 | 10 | 10 | 10 | 1000 g/ha |
| 96 | 10 | 10 | 10 | 10 | 1000 g/ha |
| 97 | 10 | 10 | 10 | 10 | 1000 g/ha |
| 111 | 10 | 10 | 10 | 10 | 1000 g/ha |
| 114 | 10 | 10 | 10 | 10 | 1000 g/ha |
| 128 | 10 | 10 | 10 | 10 | 1000 g/ha |
| 163 | 10 | 10 | 10 | 10 | 2000 g/ha |
| 165 | 10 | 10 | 10 | 10 | 2000 g/ha |
| 166 | 10 | 10 | 10 | 10 | 2000 g/ha |
| 168 | 10 | 10 | 10 | 10 | 2000 g/ha |
| 169 | 10 | 10 | 10 | 10 | 2000 g/ha |
| 173 | 10 | 10 | 10 | 10 | 2000 g/ha |
| 179 | 10 | 10 | 10 | 10 | 2000 g/ha |
| 202 | 10 | 10 | 10 | 10 | 2000 g/ha |
| 204 | 10 | 10 | 10 | 10 | 2000 g/ha |
| 205 | 10 | 10 | 10 | 10 | 2000 g/ha |
| 206 | 10 | 10 | 10 | 10 | 2000 g/ha |
| 207 | 10 | 10 | 10 | 10 | 2000 g/ha |
| 211 | 10 | 10 | 10 | 10 | 2000 g/ha |
| 212 | 10 | 10 | 10 | 10 | 2000 g/ha |
| 214 | 10 | 10 | 10 | 10 | 2000 g/ha |
| 218 | 10 | 10 | 10 | 10 | 2000 g/ha |
| 219 | 10 | 10 | 10 | 10 | 2000 g/ha |
| 220 | 10 | 10 | 10 | 10 | 2000 g/ha |
| 221 | 10 | 10 | 10 | 10 | 2000 g/ha |
| 222 | 10 | 10 | 10 | 10 | 2000 g/ha |
| 223 | 10 | 10 | 10 | 10 | 2000 g/ha |
| 224 | 10 | 10 | 10 | 10 | 2000 g/ha |
| 225 | 10 | 10 | 10 | 10 | 2000 g/ha |
| 226 | 10 | 10 | 10 | 10 | 2000 g/ha |
| 227 | 10 | 10 | 10 | 10 | 2000 g/ha |
| 231 | 10 | 10 | 10 | 10 | 2000 g/ha |
| 236 | 10 | 10 | 10 | 10 | 2000 g/ha |
| 263 | 10 | 10 | 10 | 10 | 2000 g/ha |
| 279 | 10 | 10 | 10 | 10 | 2000 g/ha |
| 323 | 10 | 10 | 10 | 10 | 2000 g/ha |
| 349 | 10 | 10 | 10 | 10 | 2000 g/ha |
| 370 | 10 | 10 | 10 | 10 | 2000 g/ha |
| 371 | 10 | 10 | 10 | 10 | 2000 g/ha |
| 380 | 10 | 10 | 10 | 10 | 2000 g/ha |
| 414 | 10 | 10 | 10 | 10 | 3000 g/ha |
| 418 | 10 | 10 | 10 | 10 | 3000 g/ha |
| 439 | 10 | 10 | 10 | 10 | 3000 g/ha |
| 540 | 10 | 10 | 10 | 10 | 3000 g/ha |
| 543 | 10 | 10 | 10 | 10 | 3000 g/ha |
| 544 | 10 | 10 | 10 | 10 | 3000 g/ha |
| 546 | 10 | 10 | 10 | 10 | 3000 g/ha |
| 570 | 10 | 10 | 10 | 10 | 3000 g/ha |
| 588 | 10 | 10 | 10 | 10 | 3000 g/ha |
| 589 | 10 | 10 | 10 | 10 | 3000 g/ha |
| 594 | 10 | 10 | 10 | 10 | 3000 g/ha |
| 595 | 10 | 10 | 10 | 10 | 3000 g/ha |
| 597 | 10 | 10 | 10 | 10 | 3000 g/ha |
| 613 | 10 | 10 | 10 | 10 | 3000 g/ha |
| 634 | 10 | 10 | 10 | 10 | 3000 g/ha |
| 636 | 10 | 10 | 10 | 10 | 3000 g/ha |
| 637 | 10 | 10 | 10 | 10 | 3000 g/ha |

TABLE 3-continued

Experiment on weed control effect of compounds of Formula I in Post-emergence stage

| Compound No. | *Amaranthus retroflexus* | *Rorippa indica* | *Veronica polita* | Chenopo-diaceae | Dose |
|---|---|---|---|---|---|
| 714 | 10 | 10 | 10 | 10 | 3000 g/ha |
| 723 | 10 | 10 | 10 | 10 | 3000 g/ha |
| 732 | 10 | 10 | 10 | 10 | 1000 g/ha |
| 733 | 10 | 10 | 10 | 10 | 1000 g/ha |
| 734 | 10 | 10 | 10 | 10 | 1000 g/ha |
| 735 | 10 | 10 | 10 | 10 | 1000 g/ha |
| 736 | 10 | 10 | 10 | 10 | 1000 g/ha |
| 737 | 10 | 10 | 10 | 10 | 3000 g/ha |
| 739 | 10 | 10 | 10 | 10 | 3000 g/ha |
| 740 | 10 | 10 | 10 | 10 | 3000 g/ha |
| 741 | 10 | 10 | 10 | 10 | 3000 g/ha |
| 742 | 10 | 10 | 10 | 10 | 3000 g/ha |
| 743 | 10 | 10 | 10 | 10 | 3000 g/ha |
| 744 | 10 | 10 | 10 | 10 | 3000 g/ha |
| 745 | 10 | 10 | 10 | 10 | 3000 g/ha |
| 746 | 10 | 10 | 10 | 10 | 3000 g/ha |
| 753 | 10 | 10 | 10 | 10 | 3000 g/ha |
| 755 | 10 | 10 | 10 | 10 | 3000 g/ha |
| 761 | 10 | 10 | 10 | 10 | 3000 g/ha |
| 762 | 10 | 10 | 10 | 10 | 3000 g/ha |
| 763 | 10 | 10 | 10 | 10 | 3000 g/ha |
| 764 | 10 | 10 | 10 | 10 | 3000 g/ha |
| 766 | 10 | 10 | 10 | 10 | 3000 g/ha |
| 768 | 10 | 10 | 10 | 10 | 3000 g/ha |
| 769 | 10 | 10 | 10 | 10 | 3000 g/ha |
| 770 | 10 | 10 | 10 | 10 | 3000 g/ha |
| 771 | 10 | 10 | 10 | 10 | 3000 g/ha |
| 772 | 10 | 10 | 10 | 10 | 3000 g/ha |
| 774 | 10 | 10 | 10 | 10 | 3000 g/ha |
| 775 | 10 | 10 | 10 | 10 | 3000 g/ha |
| 776 | 10 | 10 | 10 | 10 | 3000 g/ha |
| 777 | 10 | 10 | 10 | 10 | 3000 g/ha |
| 778 | 10 | 10 | 10 | 10 | 3000 g/ha |
| 779 | 10 | 10 | 10 | 10 | 3000 g/ha |
| 780 | 10 | 10 | 10 | 10 | 3000 g/ha |
| 781 | 10 | 10 | 10 | 10 | 3000 g/ha |
| 782 | 10 | 10 | 10 | 10 | 3000 g/ha |
| 783 | 10 | 10 | 10 | 10 | 3000 g/ha |
| 784 | 10 | 10 | 10 | 10 | 3000 g/ha |
| 787 | 10 | 10 | 10 | 10 | 3000 g/ha |
| 791 | 10 | 10 | 10 | 10 | 3000 g/ha |
| 794 | 10 | 10 | 10 | 10 | 3000 g/ha |
| 803 | 10 | 10 | 10 | 10 | 3000 g/ha |
| 804 | 10 | 10 | 10 | 10 | 3000 g/ha |
| 805 | 10 | 10 | 10 | 10 | 3000 g/ha |
| 806 | 10 | 10 | 10 | 10 | 3000 g/ha |
| 807 | 10 | 10 | 10 | 10 | 3000 g/ha |
| 808 | 10 | 10 | 10 | 10 | 3000 g/ha |
| 809 | 10 | 10 | 10 | 10 | 3000 g/ha |
| 810 | 10 | 10 | 10 | 10 | 3000 g/ha |
| 811 | 10 | 10 | 10 | 10 | 3000 g/ha |
| 812 | 10 | 10 | 10 | 10 | 3000 g/ha |
| 813 | 10 | 10 | 10 | 10 | 3000 g/ha |
| 816 | 10 | 10 | 10 | 10 | 3000 g/ha |
| 820 | 10 | 10 | 10 | 10 | 3000 g/ha |
| 823 | 10 | 10 | 10 | 10 | 3000 g/ha |
| 824 | 10 | 10 | 10 | 10 | 3000 g/ha |
| 825 | 10 | 10 | 10 | 10 | 3000 g/ha |
| 826 | 10 | 10 | 10 | 10 | 3000 g/ha |
| 827 | 10 | 10 | 10 | 10 | 3000 g/ha |
| 828 | 10 | 10 | 10 | 10 | 3000 g/ha |
| 829 | 10 | 10 | 10 | 10 | 3000 g/ha |
| 830 | 10 | 10 | 10 | 10 | 3000 g/ha |
| 831 | 10 | 10 | 10 | 10 | 3000 g/ha |
| 832 | 10 | 10 | 10 | 10 | 3000 g/ha |
| 833 | 10 | 10 | 10 | 10 | 3000 g/ha |
| 834 | 10 | 10 | 10 | 10 | 3000 g/ha |
| 839 | 10 | 10 | 10 | 10 | 3000 g/ha |
| 844 | 10 | 10 | 10 | 10 | 2000 g/ha |
| 857 | 10 | 10 | 10 | 10 | 3000 g/ha |
| 873 | 10 | 10 | 10 | 10 | 3000 g/ha |
| 877 | 10 | 10 | 10 | 10 | 3000 g/ha |
| 963 | 10 | 10 | 10 | 10 | 3000 g/ha |
| 964 | 10 | 10 | 10 | 10 | 3000 g/ha |

TABLE 3-continued

Experiment on weed control effect of compounds of Formula I in Post-emergence stage

| Compound No. | *Amaranthus retroflexus* | *Rorippa indica* | *Veronica polita* | Chenopo-diaceae | Dose |
|---|---|---|---|---|---|
| 965 | 10 | 10 | 10 | 10 | 3000 g/ha |
| 966 | 10 | 10 | 10 | 10 | 3000 g/ha |
| 967 | 10 | 10 | 10 | 10 | 3000 g/ha |
| 968 | 10 | 10 | 10 | 10 | 3000 g/ha |
| 969 | 10 | 10 | 10 | 10 | 3000 g/ha |
| 970 | 10 | 10 | 10 | 10 | 3000 g/ha |
| 971 | 10 | 10 | 10 | 10 | 3000 g/ha |
| 972 | 10 | 10 | 10 | 10 | 3000 g/ha |
| 973 | 10 | 10 | 10 | 10 | 3000 g/ha |
| 974 | 10 | 10 | 10 | 10 | 3000 g/ha |
| 975 | 10 | 10 | 10 | 10 | 3000 g/ha |
| 976 | 10 | 10 | 10 | 10 | 3000 g/ha |
| 977 | 10 | 10 | 10 | 10 | 3000 g/ha |
| 978 | 10 | 10 | 10 | 10 | 3000 g/ha |
| 979 | 10 | 10 | 10 | 10 | 3000 g/ha |
| 980 | 10 | 10 | 10 | 10 | 3000 g/ha |
| 983 | 10 | 10 | 10 | 10 | 3000 g/ha |
| 984 | 10 | 10 | 10 | 10 | 3000 g/ha |
| 986 | 10 | 10 | 10 | 10 | 3000 g/ha |
| 987 | 10 | 10 | 10 | 10 | 3000 g/ha |
| 988 | 10 | 10 | 10 | 10 | 3000 g/ha |
| 989 | 10 | 10 | 10 | 10 | 3000 g/ha |
| 990 | 10 | 10 | 10 | 10 | 3000 g/ha |
| 991 | 10 | 10 | 10 | 10 | 3000 g/ha |
| 992 | 10 | 10 | 10 | 10 | 3000 g/ha |
| 993 | 10 | 10 | 10 | 10 | 3000 g/ha |
| 994 | 10 | 10 | 10 | 10 | 3000 g/ha |
| 995 | 10 | 10 | 10 | 10 | 3000 g/ha |
| 996 | 10 | 10 | 10 | 10 | 3000 g/ha |
| 997 | 10 | 10 | 10 | 10 | 3000 g/ha |
| 998 | 10 | 10 | 10 | 10 | 3000 g/ha |
| 999 | 10 | 10 | 10 | 10 | 3000 g/ha |
| 1000 | 10 | 10 | 10 | 10 | 3000 g/ha |
| 1001 | 10 | 10 | 10 | 10 | 3000 g/ha |
| 1002 | 10 | 10 | 10 | 10 | 3000 g/ha |
| 1003 | 10 | 10 | 10 | 10 | 3000 g/ha |
| 1004 | 10 | 10 | 10 | 10 | 3000 g/ha |
| 1005 | 10 | 10 | 10 | 10 | 3000 g/ha |
| 1006 | 10 | 10 | 10 | 10 | 3000 g/ha |
| 1007 | 10 | 10 | 10 | 10 | 3000 g/ha |
| 1008 | 10 | 10 | 10 | 10 | 3000 g/ha |
| 1018 | 10 | 10 | 10 | 10 | 3000 g/ha |
| 1076 | 10 | 10 | 10 | 10 | 3000 g/ha |
| 1081 | 10 | 10 | 10 | 10 | 3000 g/ha |
| 1286 | 10 | 10 | 10 | 10 | 3000 g/ha |
| 1522 | 10 | N | N | 10 | 3000 g/ha |
| 1523 | 10 | 10 | 10 | 10 | 3000 g/ha |
| 1524 | 10 | 10 | 10 | 10 | 3000 g/ha |

Note:
N means no data.

TABLE 4

Experiment on weed control effect of derivatives of Formula I-1 in Post-emergence stage

| Compound No. | *Amaranthus retroflexus* | *Rorippa indica* | *Veronica polita* | Chenopo-diaceae | Dose |
|---|---|---|---|---|---|
| 1-1 | 10 | 10 | 10 | 10 | 3000 g/ha |
| 1-2 | 10 | 10 | 10 | 10 | 3000 g/ha |
| 1-3 | 10 | 10 | 10 | 10 | 3000 g/ha |
| 1-4 | 10 | 10 | 10 | 10 | 3000 g/ha |
| 1-7 | 10 | 10 | 10 | 10 | 3000 g/ha |
| 1-8 | 10 | 10 | 10 | 10 | 3000 g/ha |
| 1-9 | 10 | 10 | 10 | 10 | 3000 g/ha |
| 1-10 | 10 | 10 | 10 | 10 | 3000 g/ha |
| 1-14 | 10 | 10 | 10 | 10 | 3000 g/ha |
| 1-15 | 10 | 10 | 10 | 10 | 3000 g/ha |
| 1-16 | 10 | 10 | 10 | 10 | 3000 g/ha |
| 1-17 | 10 | 10 | 10 | 10 | 3000 g/ha |

TABLE 4-continued

Experiment on weed control effect of derivatives of Formula I-1 in Post-emergence stage

| Compound No. | *Amaranthus retroflexus* | *Rorippa indica* | *Veronica polita* | Chenopodiaceae | Dose |
|---|---|---|---|---|---|
| 1-18 | 10 | 10 | 10 | 10 | 3000 g/ha |
| 1-19 | 10 | 10 | 10 | 10 | 3000 g/ha |
| 1-22 | 10 | 10 | 10 | 10 | 3000 g/ha |
| 1-23 | 10 | 10 | 10 | 10 | 3000 g/ha |
| 1-25 | 10 | 10 | 10 | 10 | 3000 g/ha |
| 1-26 | 10 | 10 | 10 | 10 | 3000 g/ha |
| 1-29 | 10 | 10 | 10 | 10 | 3000 g/ha |
| 1-30 | 10 | 10 | 10 | 10 | 3000 g/ha |
| 1-31 | 10 | 10 | 10 | 10 | 3000 g/ha |
| 1-33 | 10 | 10 | 10 | 10 | 3000 g/ha |
| 1-35 | 10 | 10 | 10 | 10 | 3000 g/ha |
| 1-36 | 10 | 10 | 10 | 10 | 3000 g/ha |
| 1-38 | 10 | 10 | 10 | 10 | 3000 g/ha |
| 1-39 | 10 | 10 | 10 | 10 | 3000 g/ha |
| 1-40 | 10 | 10 | 10 | 10 | 3000 g/ha |
| 1-42 | 10 | 10 | 10 | 10 | 3000 g/ha |
| 1-43 | 10 | 10 | 10 | 10 | 3000 g/ha |
| 1-47 | 10 | 10 | 10 | 10 | 3000 g/ha |
| 1-51 | 10 | 10 | 10 | 10 | 3000 g/ha |
| 1-53 | 10 | 10 | 10 | 10 | 3000 g/ha |
| 1-54 | 10 | 10 | 10 | 10 | 3000 g/ha |
| 1-55 | 10 | 10 | 10 | 10 | 3000 g/ha |
| 1-58 | 10 | 10 | 10 | 10 | 3000 g/ha |
| 1-60 | 10 | 10 | 10 | 10 | 3000 g/ha |
| 1-63 | 10 | 10 | 10 | 10 | 3000 g/ha |
| 1-64 | 10 | 10 | 10 | 10 | 3000 g/ha |
| 1-65 | 10 | 10 | 10 | 10 | 3000 g/ha |
| 1-66 | 10 | 10 | 10 | 10 | 3000 g/ha |
| 1-67 | 10 | 10 | 10 | 10 | 3000 g/ha |
| 1-68 | 10 | 10 | 10 | 10 | 3000 g/ha |
| 1-69 | 10 | 10 | 10 | 10 | 3000 g/ha |
| 1-70 | 10 | 10 | 10 | 10 | 3000 g/ha |
| 1-71 | 10 | 10 | 10 | 10 | 3000 g/ha |
| 1-75 | 10 | 10 | 10 | 10 | 3000 g/ha |
| 1-76 | 10 | 10 | 10 | 10 | 3000 g/ha |
| 1-77 | 10 | 10 | 10 | 10 | 3000 g/ha |
| 1-78 | 10 | 10 | 10 | 10 | 3000 g/ha |
| 1-79 | 10 | 10 | 10 | 10 | 3000 g/ha |
| 1-80 | 10 | 10 | 10 | 10 | 3000 g/ha |
| 1-82 | 10 | 10 | 10 | 10 | 3000 g/ha |
| 1-83 | 10 | 10 | 10 | 10 | 3000 g/ha |
| 1-84 | 10 | 10 | 10 | 10 | 3000 g/ha |
| 1-85 | 10 | 10 | 10 | 10 | 3000 g/ha |
| 1-86 | 10 | 10 | 10 | 10 | 3000 g/ha |
| 1-87 | 10 | 10 | 10 | 10 | 3000 g/ha |
| 1-88 | 10 | 10 | 10 | 10 | 3000 g/ha |
| 1-90 | 10 | 10 | 10 | 10 | 3000 g/ha |
| 1-91 | 10 | 10 | 10 | 10 | 3000 g/ha |
| 1-93 | 10 | 10 | 10 | 10 | 3000 g/ha |
| 1-94 | 10 | 10 | 10 | 10 | 3000 g/ha |
| 1-95 | 10 | 10 | 10 | 10 | 3000 g/ha |
| 1-96 | 10 | 10 | 10 | 10 | 3000 g/ha |
| 1-97 | 10 | 10 | 10 | 10 | 3000 g/ha |
| 1-98 | 10 | 10 | 10 | 10 | 3000 g/ha |
| 1-99 | 10 | 10 | 10 | 10 | 3000 g/ha |
| 1-100 | 10 | 10 | 10 | 10 | 3000 g/ha |
| 1-101 | 10 | 10 | 10 | 10 | 3000 g/ha |
| 1-102 | 10 | 10 | 10 | 10 | 3000 g/ha |
| 1-103 | 10 | 10 | 10 | 10 | 3000 g/ha |
| 1-104 | 10 | 10 | 10 | 10 | 3000 g/ha |
| 1-105 | 10 | 10 | 10 | 10 | 3000 g/ha |
| 1-106 | 10 | 10 | 10 | 10 | 3000 g/ha |
| 1-107 | 10 | 10 | 10 | 10 | 3000 g/ha |
| 1-108 | 10 | 10 | 10 | 10 | 3000 g/ha |
| 1-109 | 10 | 10 | 10 | 10 | 3000 g/ha |
| 1-110 | 10 | 10 | 10 | 10 | 3000 g/ha |
| 1-111 | 10 | 10 | 10 | 10 | 3000 g/ha |
| 1-112 | 10 | 10 | 10 | 10 | 3000 g/ha |
| 1-113 | 10 | 10 | 10 | 10 | 3000 g/ha |
| 1-114 | 10 | 10 | 10 | 10 | 3000 g/ha |
| 1-115 | 10 | 10 | 10 | 10 | 3000 g/ha |
| 1-116 | 10 | 10 | 10 | 10 | 3000 g/ha |
| 1-117 | 10 | 10 | 10 | 10 | 3000 g/ha |
| 1-118 | 10 | 10 | 10 | 10 | 3000 g/ha |

TABLE 4-continued

Experiment on weed control effect of derivatives of Formula I-1 in Post-emergence stage

| Compound No. | *Amaranthus retroflexus* | *Rorippa indica* | *Veronica polita* | Chenopodiaceae | Dose |
|---|---|---|---|---|---|
| 1-119 | 10 | 10 | 10 | 10 | 3000 g/ha |
| 1-120 | 10 | 10 | 10 | 10 | 3000 g/ha |
| 1-121 | 10 | 10 | 10 | 10 | 3000 g/ha |
| 1-122 | 10 | 10 | 10 | 10 | 3000 g/ha |
| 1-123 | 10 | 10 | 10 | 10 | 3000 g/ha |
| 1-124 | 10 | 10 | 10 | 10 | 3000 g/ha |
| 1-125 | 10 | 10 | 10 | 10 | 3000 g/ha |
| 1-126 | 10 | 10 | 10 | 10 | 3000 g/ha |
| 1-127 | 10 | 10 | 10 | 10 | 3000 g/ha |
| 1-128 | 10 | 10 | 10 | 10 | 3000 g/ha |
| 1-129 | 10 | 10 | 10 | 10 | 3000 g/ha |
| 1-130 | 10 | 10 | 10 | 10 | 3000 g/ha |
| 1-131 | 10 | 10 | 10 | 10 | 3000 g/ha |
| 1-132 | 10 | 10 | 10 | 10 | 3000 g/ha |
| 1-133 | 10 | 10 | 10 | 10 | 3000 g/ha |
| 1-134 | 10 | 10 | 10 | 10 | 3000 g/ha |
| 1-135 | 10 | 10 | 10 | 10 | 3000 g/ha |
| 1-136 | 10 | 10 | 10 | 10 | 3000 g/ha |
| 1-137 | 10 | 10 | 10 | 10 | 3000 g/ha |
| 1-138 | 10 | 10 | 10 | 10 | 3000 g/ha |
| 1-139 | 10 | 10 | 10 | 10 | 3000 g/ha |
| 1-140 | 10 | 10 | 10 | 10 | 3000 g/ha |
| 1-141 | 10 | 10 | 10 | 10 | 3000 g/ha |
| 1-142 | 10 | 10 | 10 | 10 | 3000 g/ha |
| 1-143 | 10 | 10 | 10 | 10 | 3000 g/ha |
| 1-144 | 10 | 10 | 10 | 10 | 3000 g/ha |
| 1-145 | 10 | 10 | 10 | 10 | 3000 g/ha |
| 1-146 | 10 | 10 | 10 | 10 | 3000 g/ha |
| 1-147 | 10 | 10 | 10 | 10 | 3000 g/ha |
| 1-148 | 10 | 10 | 10 | 10 | 3000 g/ha |
| 1-149 | 10 | 10 | 10 | 10 | 3000 g/ha |
| 1-150 | 10 | 10 | 10 | 10 | 3000 g/ha |
| 1-151 | 10 | 10 | 10 | 10 | 3000 g/ha |
| 1-152 | 10 | 10 | 10 | 10 | 3000 g/ha |
| 1-153 | 10 | 10 | 10 | 10 | 3000 g/ha |
| 1-154 | 10 | 10 | 10 | 10 | 3000 g/ha |
| 1-155 | 10 | 10 | 10 | 10 | 3000 g/ha |
| 1-156 | 10 | 10 | 10 | 10 | 3000 g/ha |
| 1-157 | 10 | 10 | 10 | 10 | 3000 g/ha |
| 1-158 | 10 | 10 | 10 | 10 | 3000 g/ha |
| 1-159 | 10 | 10 | 10 | 10 | 3000 g/ha |
| 1-160 | 10 | 10 | 10 | 10 | 3000 g/ha |
| 1-162 | 10 | 10 | 10 | 10 | 3000 g/ha |
| 1-163 | 10 | 10 | 10 | 10 | 3000 g/ha |
| 1-164 | 10 | 10 | 10 | 10 | 3000 g/ha |
| 1-165 | 10 | 10 | 10 | 10 | 3000 g/ha |
| 1-166 | 10 | 10 | 10 | 10 | 3000 g/ha |
| 1-167 | 10 | 10 | 10 | 10 | 3000 g/ha |
| 1-169 | 10 | 10 | 10 | 10 | 3000 g/ha |
| 1-170 | 10 | 10 | 10 | 10 | 3000 g/ha |
| 1-171 | 10 | 10 | 10 | 10 | 3000 g/ha |
| 1-172 | 10 | 10 | 10 | 10 | 3000 g/ha |
| 1-173 | 10 | 10 | 10 | 10 | 3000 g/ha |
| 1-174 | 10 | 10 | 10 | 10 | 3000 g/ha |
| 1-175 | 10 | 10 | 10 | 10 | 3000 g/ha |
| 1-176 | 10 | 10 | 10 | 10 | 3000 g/ha |
| 1-178 | 10 | 10 | 10 | 10 | 3000 g/ha |
| 1-179 | 10 | 10 | 10 | 10 | 3000 g/ha |
| 1-180 | 10 | 10 | 10 | 10 | 3000 g/ha |
| 1-181 | 10 | 10 | 10 | 10 | 3000 g/ha |
| 1-207 | 10 | 10 | 10 | 10 | 3000 g/ha |
| 1-208 | 10 | 10 | 10 | 10 | 3000 g/ha |
| 1-209 | 10 | 10 | 10 | 10 | 3000 g/ha |
| 1-210 | 10 | 10 | 10 | 10 | 3000 g/ha |
| 1-211 | 10 | 10 | 10 | 10 | 3000 g/ha |
| 1-212 | 10 | 10 | 10 | 10 | 3000 g/ha |
| 1-213 | 10 | 10 | 10 | 10 | 3000 g/ha |
| 1-240 | 10 | 10 | 10 | 10 | 3000 g/ha |

Comparative Experiment:

The post-emergence test conditions were the same as above, and the results are shown in Table Control Compound A:

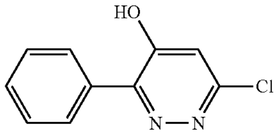 [SMILES: Oc1cc(Cl)nnc1-c1ccccc1]

Control Compound B:

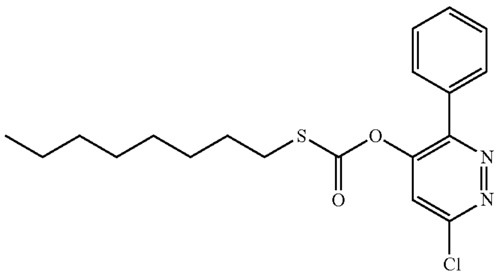 [SMILES: CCCCCCCCSC(=O)Oc1cc(Cl)nnc1-c1ccccc1]

Control Compound C:

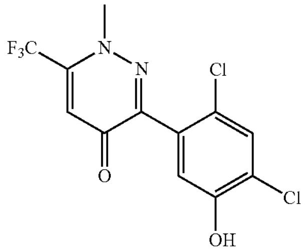 [SMILES: Cn1nc(-c2cc(O)c(Cl)cc2Cl)c(=O)cc1C(F)(F)F]

(from patent CN106316962A)

Control Compound D:

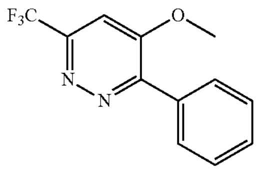 [SMILES: COc1cc(C(F)(F)F)nnc1-c1ccccc1]

Control Compound E:

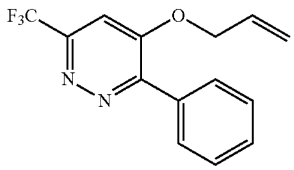 [SMILES: C=CCOc1cc(C(F)(F)F)nnc1-c1ccccc1]

TABLE 5

Results of comparison experiment

| Compound | *Echinochloa crus-galli* | *Setaria viridis* | Chenopodiaceae | *Rorippa indica* | *Galium aparine* | *Veronica polita* | Dose |
|---|---|---|---|---|---|---|---|
| 32 | 10 | 10 | 10 | 10 | 10 | 10 | 300 g/ha |
| 35 | 10 | 10 | 10 | 10 | 9 | 10 | 300 g/ha |
| 51 | 6 | 9 | 10 | 10 | 8 | 9 | 300 g/ha |
| 202 | 7 | 10 | 10 | 10 | 10 | 8 | 300 g/ha |
| 206 | 10 | 10 | 10 | 10 | 10 | 10 | 300 g/ha |
| 207 | 10 | 10 | 10 | 10 | 10 | 10 | 300 g/ha |
| 220 | 10 | 10 | 10 | 10 | 10 | 10 | 300 g/ha |
| 733 | 10 | 10 | 10 | 10 | 10 | 10 | 300 g/ha |
| 739 | 10 | 10 | 10 | 10 | 8 | 10 | 300 g/ha |
| 740 | 10 | 10 | 10 | 10 | 10 | 10 | 300 g/ha |
| 744 | 10 | 10 | 10 | 10 | 10 | 10 | 300 g/ha |
| 779 | 10 | 10 | 10 | 10 | 10 | 10 | 300 g/ha |
| 844 | 10 | 10 | 10 | 10 | 10 | 10 | 150 g/ha |
| 1000 | 10 | 10 | 10 | 10 | 10 | 10 | 300 g/ha |
| 1524 | N | 10 | 10 | 10 | 9 | 9 | 300 g/ha |
| 1-39 | 10 | 10 | 10 | 10 | 10 | 10 | 150 g/ha |
| 1-43 | 10 | 10 | 10 | 10 | 10 | 10 | 150 g/ha |
| 1-55 | 10 | 10 | 10 | 10 | 10 | 10 | 150 g/ha |
| 1-82 | 7 | 10 | 10 | 10 | 7 | 8 | 150 g/ha |
| 1-86 | 10 | 10 | 10 | 10 | 10 | 10 | 150 g/ha |
| A | 0 | 3 | 5 | 2 | 5 | 3 | 300 g/ha |
| B | 0 | 3 | 3 | 3 | 4 | 3 | 300 g/ha |
| C | 0 | 0 | 3 | 3 | 2 | 2 | 300 g/ha |
| D | 0 | 0 | 1 | 1 | 0 | 0 | 300 g/ha |
| E | 0 | 0 | 1 | 1 | 0 | 0 | 300 g/ha |

Note:
N means no data.

It can be seen from the above table, the compounds of the present invention have superior herbicidal activity compared with the control compounds.

In addition, after testing, the compounds of the present invention have good selectivity for crops when being applied preemergence or postemergence, especially for wheat, rice, soybean, cotton, corn, sorghum, millet and other crops.

Experiment of Pre-Emergence Test:

Seeds of monocotyledonous and dicotyledonous weeds and main crops (e.g. wheat, corn, rice, soybean, cotton, oilseed rape, millet and sorghum) were put into a plastic pot loaded with soil and covered with 0.5-2 cm of soil. The test compounds of the present invention was dissolved with acetone, then added with Tween-80, diluted by a certain amount of water to reach a certain concentration, and sprayed immediately after sowing. The obtained seeds were incubated for 4 weeks in the greenhouse after spraying. The test results were observed 3 weeks later. It was observed that the herbicides of the present invention mostly had excellent effect at dose of 250 g/ha, especially to weeds such as *Echinochloa crusgalli, Digitaria sanguinalis* and *Abutilon theophrasti*, etc., and many compounds had good selectivity for corn, wheat, rice, soybean, oilseed rape, etc.

It is found in the experiment that the compounds of the present invention generally have good weed control efficacy, especially for major broadleaf weeds such as *Abutilon theophrasti* and *Bidens bipinnata*, etc., which are widely occurred in corn, rice and wheat fields, and have excellent commercial value. Above all, it is noted that the compound of the invention have extremely high activity to broadleaf weeds, which are resistant to ALS inhibitor, like corn gromwell, cleavers and chickweed, etc.

Transplanted rice safety evaluation and weed control effect evaluation in rice field:

Rice field soil was loaded into a 1/1,000,000 ha pot. The seeds of *Echinochloa crusgalli, Scirpus juncoides, Bidens* tripartite and *Sagittaria trifolia* L. were sowed and gently covered with soil, then left to stand still in greenhouse in the state of 0.5-1 cm of water storage. The tuber of *Sagittaria trifolia* L. was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa crusgalli, Scirpus* juncoides and *Bidens* tripartite reached 0.5 leaf stage and *Sagittaria trifolia* L. reached the time point of primary leaf stage.

In addition, the rice field soil that loaded into the 1/1,000,000 ha pot was leveled to keep water storage at 3-4 cm depth. The 3 leaf stage rice (japonica rice) was transplanted at 3 cm of transplanting depth the next day. The compound of the present invention was treated by the same way after 5 days of transplantation.

The fertility condition of *Echinochloa crusgalli, Scirpus juncoides, Bidens* tripartite and *Sagittaria trifolia* L. 14 days after the treatment of the compound of the invention and the fertility condition of rice 21 days after the treatment of the compound of the invention respectively with the naked eye. Evaluate the weed control effect with 1-10 activity standard level. It has been found that many of the compounds of the present invention have excellent activity and selectivity, especially for *Sagittaria trifolia* L. and *Echinochloa crusgalli.*

Note: The seeds of *Echinochloa crusgalli, Scirpus juncoides, Sagittaria trifolia* L. and *Bidens* tripartite were collected from Heilongjiang Province of China. Tests indicated that the weeds were resistant to common rate of pyrazosulfuron-ethyl.

Further, the present invention also relates to a herbicidal composition comprising component (i) (such as the compound of Formula I) and component (ii), and some of the compositions are as follows:

1 (Compound No. as shown in Table 1, similarly hereinafter)+Sulcotrione, 1+Mesotrione, 1+Topramezone, 1+Tembotrione, 1+Bicyclopyrone, 1+Tefuryltrione, 1+Benzobicyclon, 1+Lancotrione, 1+Shuangzuocaotong, 1+Huanbifucaotong, 1+Sanzuohuangcaotong, 1+Benzuofucaotong, 1+Pyrasulfotole, 1+Pyrazolate, 1+Benzofenap, 1+Tolpyralate, 1+Fenquinotrione, 1+Isoxaflutole, 1+Fluroxypyr or esters thereof, 1+Halauxifen-methyl, 1+Florpyrauxifen-benzyl, 1+Quinclorac, 1+Quinmerac, 1+Chipton or salts/esters thereof, 1+2-methyl 4-chlorophenoxypropionic acid or salts/esters thereof, 1+MCPB or salts/esters thereof, 1+2,4-D or salts/esters thereof, 1+Dichlorprop or salts/esters thereof, 1+2,4-DB or salts/esters thereof, 1+Dicamba, 1+Picloram, 1+Trichlopyr, 1+Clopyralid, 1+Triclopyr, 1+Flurochloridone, 1+Flurtamone, 1+Diflufenican, 1+Picolinafen, 1+Beflubutamid, 1+Norflurazon, 1+Fluridone.

2+Sulcotrione, 2+Mesotrione, 2+Topramezone, 2+Tembotrione, 2+Bicyclopyrone, 2+Tefuryltrione, 2+Benzobicyclon, 2+Lancotrione, 2+Shuangzuocaotong, 2+Huanbifucaotong, 2+Sanzuohuangcaotong, 2+Benzuofucaotong, 2+Pyrasulfotole, 2+Pyrazolate, 2+Benzofenap, 2+Tolpyralate, 2+Fenquinotrione, 2+Isoxaflutole, 2+Fluroxypyr or esters thereof, 2+Halauxifen-methyl, 2+Florpyrauxifen-benzyl, 2+Quinclorac, 2+Quinmerac, 2+Chipton or salts/esters thereof, 2+2-methyl 4-chlorophenoxypropionic acid or salts/esters thereof, 2+MCPB or salts/esters thereof, 2+2,4-D or salts/esters thereof, 2+Dichlorprop or salts/esters thereof, 2+2,4-DB or salts/esters thereof, 2+Dicamba, 2+Picloram, 2+Trichlopyr, 2+Clopyralid, 2+Triclopyr, 2+Flurochloridone, 2+Flurtamone, 2+Diflufenican, 2+Picolinafen, 2+Beflubutamid, 2+Norflurazon, 2+Fluridone.

3+Sulcotrione, 3+Mesotrione, 3+Topramezone, 3+Tembotrione, 3+Bicyclopyrone, 3+Tefuryltrione, 3+Benzobicyclon, 3+Lancotrione, 3+Shuangzuocaotong, 3+Huanbifucaotong, 3+Sanzuohuangcaotong, 3+Benzuofucaotong, 3+Pyrasulfotole, 3+Pyrazolate, 3+Benzofenap, 3+Tolpyralate, 3+Fenquinotrione, 3+Isoxaflutole, 3+Fluroxypyr or esters thereof, 3+Halauxifen-methyl, 3+Florpyrauxifen-benzyl, 3+Quinclorac, 3+Quinmerac, 3+Chipton or salts/esters thereof, 3+2-methyl 4-chlorophenoxypropionic acid or salts/esters thereof, 3+MCPB or salts/esters thereof, 3+2,4-D or salts/esters thereof, 3+Dichlorprop or salts/esters thereof, 3+2,4-DB or salts/esters thereof, 3+Dicamba, 3+Picloram, 3+Trichlopyr, 3+Clopyralid, 3+Triclopyr, 3+Flurochloridone, 3+Flurtamone, 3+Diflufenican, 3+Picolinafen, 3+Beflubutamid, 3+Norflurazon, 3+Fluridone.

4+Sulcotrione, 4+Mesotrione, 4+Topramezone, 4+Tembotrione, 4+Bicyclopyrone, 4+Tefuryltrione, 4+Benzobicyclon, 4+Lancotrione, 4+Shuangzuocaotong, 4+Huanbifucaotong, 4+Sanzuohuangcaotong, 4+Benzuofucaotong, 4+Pyrasulfotole, 4+Pyrazolate, 4+Benzofenap, 4+Tolpyralate, 4+Fenquinotrione, 4+Isoxaflutole, 4+Fluroxypyr or esters thereof, 4+Halauxifen-methyl, 4+Florpyrauxifen-benzyl, 4+Quinclorac, 4+Quinmerac, 4+Chipton or salts/esters thereof, 4+2-methyl 4-chlorophenoxypropionic acid or salts/esters thereof, 4+MCPB or salts/esters thereof, 4+2,4-D or salts/esters thereof, 4+Dichlorprop or salts/esters thereof, 4+2,4-DB or salts/esters thereof, 4+Dicamba, 4+Picloram, 4+Trichlopyr, 4+Clopyralid, 4+Triclopyr, 4+Flurochloridone, 4+Flurtamone, 4+Diflufenican, 4+Picolinafen, 4+Beflubutamid, 4+Norflurazon, 4+Fluridone.

7+Sulcotrione, 7+Mesotrione, 7+Topramezone, 7+Tembotrione, 7+Bicyclopyrone, 7+Tefuryltrione, 7+Benzobicyclon, 7+Lancotrione, 7+Shuangzuocaotong, 7+Huanbifucaotong, 7+Sanzuohuangcaotong, 7+Benzuofucaotong, 7+Pyrasulfotole, 7+Pyrazolate, 7+Benzofenap, 7+Tolpyralate, 7+Fenquinotrione, 7+Isoxaflutole, 7+Fluroxypyr or esters thereof, 7+Halauxifen-methyl, 7+Florpyrauxifen-benzyl, 7+Quinclorac, 7+Quinmerac, 7+Chipton or salts/esters thereof, 7+2-methyl 4-chlorophenoxypropionic acid or salts/esters thereof, 7+MCPB or salts/esters thereof, 7+2,4-D or salts/esters thereof, 7+Dichlorprop or salts/esters thereof, 7+2,4-DB or salts/esters thereof, 7+Dicamba, 7+Picloram, 7+Trichlopyr, 7+Clopyralid, 7+Triclopyr, 7+Flurochloridone, 7+Flurtamone, 7+Diflufenican, 7+Picolinafen, 7+Beflubutamid, 7+Norflurazon, 7+Fluridone.

8+Sulcotrione, 8+Mesotrione, 8+Topramezone, 8+Tembotrione, 8+Bicyclopyrone, 8+Tefuryltrione, 8+Benzobicyclon, 8+Lancotrione, 8+Shuangzuocaotong, 8+Huanbifucaotong, 8+Sanzuohuangcaotong, 8+Benzuofucaotong, 8+Pyrasulfotole, 8+Pyrazolate, 8+Benzofenap, 8+Tolpyralate, 8+Fenquinotrione, 8+Isoxaflutole, 8+Fluroxypyr or esters thereof, 8+Halauxifen-methyl, 8+Florpyrauxifen-benzyl, 8+Quinclorac, 8+Quinmerac, 8+Chipton or salts/esters thereof, 8+2-methyl 4-chlorophenoxypropionic acid or salts/esters thereof, 8+MCPB or salts/esters thereof, 8+2,4-D or salts/esters thereof, 8+Dichlorprop or salts/esters thereof, 8+2,4-DB or salts/esters thereof, 8+Dicamba, 8+Picloram, 8+Trichlopyr, 8+Clopyralid, 8+Triclopyr, 8+Flurochloridone, 8+Flurtamone, 8+Diflufenican, 8+Picolinafen, 8+Beflubutamid, 8+Norflurazon, 8+Fluridone.

22+Sulcotrione, 22+Mesotrione, 22+Topramezone, 22+Tembotrione, 22+Bicyclopyrone, 22+Tefuryltrione, 22+Benzobicyclon, 22+Lancotrione, 22+Shuangzuocaotong, 22+Huanbifucaotong, 22+Sanzuohuangcaotong, 22+Benzuofucaotong, 22+Pyrasulfotole, 22+Pyrazolate, 22+Benzofenap, 22+Tolpyralate, 22+Fenquinotrione, 22+Isoxaflutole, 22+Fluroxypyr or esters thereof, 22+Halauxifen-methyl, 22+Florpyrauxifen-benzyl, 22+Quinclorac, 22+Quinmerac, 22+Chipton or salts/esters thereof, 22+2-methyl 4-chlorophenoxypropionic acid or salts/esters thereof, 22+MCPB or salts/esters thereof, 22+2,4-D or salts/esters thereof, 22+Dichlorprop or salts/esters thereof, 22+2,4-DB or salts/esters thereof, 22+Dicamba, 22+Picloram, 22+Trichlopyr, 22+Clopyralid, 22+Triclopyr, 22+Flurochloridone, 22+Flurtamone, 22+Diflufenican, 22+Picolinafen, 22+Beflubutamid, 22+Norflurazon, 22+Fluridone.

26+Sulcotrione, 26+Mesotrione, 26+Topramezone, 26+Tembotrione, 26+Bicyclopyrone, 26+Tefuryltrione, 26+Benzobicyclon, 26+Lancotrione, 26+Shuangzuocaotong, 26+Huanbifucaotong, 26+Sanzuohuangcaotong, 26+Benzuofucaotong, 26+Pyrasulfotole, 26+Pyrazolate, 26+Benzofenap, 26+Tolpyralate, 26+Fenquinotrione, 26+Isoxaflutole, 26+Fluroxypyr or esters thereof, 26+Halauxifen-methyl, 26+Florpyrauxifen-benzyl, 26+Quinclorac, 26+Quinmerac, 26+Chipton or salts/esters thereof, 26+2-methyl 4-chlorophenoxypropionic acid or salts/esters thereof, 26+MCPB or salts/esters thereof, 26+2,4-D or salts/esters thereof, 26+Dichlorprop or salts/esters thereof, 26+2,4-DB or salts/esters thereof, 26+Dicamba, 26+Picloram, 26+Trichlopyr, 26+Clopyralid, 26+Triclopyr, 26+Flurochloridone, 26+Flurtamone, 26+Diflufenican, 26+Picolinafen, 26+Beflubutamid, 26+Norflurazon, 26+Fluridone.

27+Sulcotrione, 27+Mesotrione, 27+Topramezone, 27+Tembotrione, 27+Bicyclopyrone, 27+Tefuryltrione, 27+Benzobicyclon, 27+Lancotrione, 27+Shuangzuocaotong, 27+Huanbifucaotong, 27+Sanzuohuangcaotong, 27+Benzuofucaotong, 27+Pyrasulfotole, 27+Pyrazolate, 27+Benzofenap, 27+Tolpyralate, 27+Fenquinotrione, 27+Isoxaflutole, 27+Fluroxypyr or esters thereof, 27+Halauxifen-methyl, 27+Florpyrauxifen-benzyl, 27+Quinclorac, 27+Quinmerac, 27+Chipton or salts/esters thereof, 27+2-methyl 4-chlorophenoxypropionic acid or salts/esters thereof, 27+MCPB or salts/esters thereof, 27+2,4-D or salts/esters thereof, 27+Dichlorprop or salts/esters thereof, 27+2,4-DB or salts/esters thereof, 27+Dicamba, 27+Picloram, 27+Trichlopyr, 27+Clopyralid, 27+Triclopyr, 27+Flurochloridone, 27+Flurtamone, 27+Diflufenican, 27+Picolinafen, 27+Beflubutamid, 27+Norflurazon, 27+Fluridone.

32+Sulcotrione, 32+Mesotrione, 32+Topramezone, 32+Tembotrione, 32+Bicyclopyrone, 32+Tefuryltrione, 32+Benzobicyclon, 32+Lancotrione, 32+Shuangzuocaotong, 32+Huanbifucaotong, 32+Sanzuohuangcaotong, 32+Benzuofucaotong, 32+Pyrasulfotole, 32+Pyrazolate, 32+Benzofenap, 32+Tolpyralate, 32+Fenquinotrione, 32+Isoxaflutole, 32+Fluroxypyr or esters thereof, 32+Halauxifen-methyl, 32+Florpyrauxifen-benzyl, 32+Quinclorac, 32+Quinmerac, 32+Chipton or salts/esters thereof, 32+2-methyl 4-chlorophenoxypropionic acid or salts/esters thereof, 32+MCPB or salts/esters thereof, 32+2,4-D or salts/esters thereof, 32+Dichlorprop or salts/esters thereof, 32+2,4-DB or salts/esters thereof, 32+Dicamba, 32+Picloram, 32+Trichlopyr, 32+Clopyralid, 32+Triclopyr, 32+Flurochloridone, 32+Flurtamone, 32+Diflufenican, 32+Picolinafen, 32+Beflubutamid, 32+Norflurazon, 32+Fluridone.

34+Sulcotrione, 34+Mesotrione, 34+Topramezone, 34+Tembotrione, 34+Bicyclopyrone, 34+Tefuryltrione, 34+Benzobicyclon, 34+Lancotrione, 34+Shuangzuocaotong, 34+Huanbifucaotong, 34+Sanzuohuangcaotong, 34+Benzuofucaotong, 34+Pyrasulfotole, 34+Pyrazolate, 34+Benzofenap, 34+Tolpyralate, 34+Fenquinotrione, 34+Isoxaflutole, 34+Fluroxypyr or esters thereof, 34+Halauxifen-methyl, 34+Florpyrauxifen-benzyl, 34+Quinclorac, 34+Quinmerac, 34+Chipton or salts/esters thereof, 34+2-methyl 4-chlorophenoxypropionic acid or salts/esters thereof, 34+MCPB or salts/esters thereof, 34+2,4-D or salts/esters thereof, 34+Dichlorprop or salts/esters thereof, 34+2,4-DB or salts/esters thereof, 34+Dicamba, 34+Picloram, 34+Trichlopyr, 34+Clopyralid, 34+Triclopyr, 34+Flurochloridone, 34+Flurtamone, 34+Diflufenican, 34+Picolinafen, 34+Beflubutamid, 34+Norflurazon, 34+Fluridone.

35+Sulcotrione, 35+Mesotrione, 35+Topramezone, 35+Tembotrione, 35+Bicyclopyrone, 35+Tefuryltrione, 35+Benzobicyclon, 35+Lancotrione, 35+Shuangzuocaotong, 35+Huanbifucaotong, 35+Sanzuohuangcaotong, 35+Benzuofucaotong, 35+Pyrasulfotole, 35+Pyrazolate, 35+Benzofenap, 35+Tolpyralate, 35+Fenquinotrione, 35+Isoxaflutole, 35+Fluroxypyr or esters thereof, 35+Halauxifen-methyl, 35+Florpyrauxifen-benzyl, 35+Quinclorac, 35+Quinmerac, 35+Chipton or salts/esters thereof, 35+2-methyl 4-chlorophenoxypropionic acid or salts/esters thereof, 35+MCPB or salts/esters thereof, 35+2,4-D or salts/esters thereof, 35+Dichlorprop or salts/esters thereof, 35+2,4-DB or salts/esters thereof, 35+Dicamba, 35+Picloram, 35+Trichlopyr, 35+Clopyralid, 35+Triclopyr, 35+Flurochloridone, 35+Flurtamone, 35+Diflufenican, 35+Picolinafen, 35+Beflubutamid, 35+Norflurazon, 35+Fluridone.

37+Sulcotrione, 37+Mesotrione, 37+Topramezone, 37+Tembotrione, 37+Bicyclopyrone, 37+Tefuryltrione, 37+Benzobicyclon, 37+Lancotrione, 37+Shuangzuocaotong, 37+Huanbifucaotong, 37+Sanzuohuangcaotong, 37+Benzuofucaotong, 37+Pyrasulfotole, 37+Pyrazolate, 37+Benzofenap, 37+Tolpyralate, 37+Fenquinotrione, 37+Isoxaflutole, 37+Fluroxypyr or esters thereof, 37+Halauxifen-methyl, 37+Florpyrauxifen-benzyl, 37+Quinclorac, 37+Quinmerac, 37+Chipton or salts/esters thereof, 37+2-methyl 4-chlorophenoxypropionic acid or salts/esters thereof, 37+MCPB or salts/esters thereof, 37+2,4-D or salts/esters thereof, 37+Dichlorprop or salts/esters thereof, 37+2,4-DB or salts/esters thereof, 37+Dicamba, 37+Picloram, 37+Trichlopyr, 37+Clopyralid, 37+Triclopyr, 37+Flurochloridone, 37+Flurtamone, 37+Diflufenican, 37+Picolinafen, 37+Beflubutamid, 37+Norflurazon, 37+Fluridone.

38+Sulcotrione, 38+Mesotrione, 38+Topramezone, 38+Tembotrione, 38+Bicyclopyrone, 38+Tefuryltrione, 38+Benzobicyclon, 38+Lancotrione, 38+Shuangzuocaotong, 38+Huanbifucaotong, 38+Sanzuohuangcaotong, 38+Benzuofucaotong, 38+Pyrasulfotole, 38+Pyrazolate, 38+Benzofenap, 38+Tolpyralate, 38+Fenquinotrione, 38+Isoxaflutole, 38+Fluroxypyr or esters thereof, 38+Halauxifen-methyl, 38+Florpyrauxifen-benzyl, 38+Quinclorac, 38+Quinmerac, 38+Chipton or salts/esters thereof, 38+2-methyl 4-chlorophenoxypropionic acid or salts/esters thereof, 38+MCPB or salts/esters thereof, 38+2,4-D or salts/esters thereof, 38+Dichlorprop or salts/esters thereof, 38+2,4-DB or salts/esters thereof, 38+Dicamba, 38+Picloram, 38+Trichlopyr, 38+Clopyralid, 38+Triclopyr, 38+Flurochloridone, 38+Flurtamone, 38+Diflufenican, 38+Picolinafen, 38+Beflubutamid, 38+Norflurazon, 38+Fluridone.

39+Sulcotrione, 39+Mesotrione, 39+Topramezone, 39+Tembotrione, 39+Bicyclopyrone, 39+Tefuryltrione, 39+Benzobicyclon, 39+Lancotrione, 39+Shuangzuocaotong, 39+Huanbifucaotong, 39+Sanzuohuangcaotong, 39+Benzuofucaotong, 39+Pyrasulfotole, 39+Pyrazolate, 39+Benzofenap, 39+Tolpyralate, 39+Fenquinotrione, 39+Isoxaflutole, 39+Fluroxypyr or esters thereof, 39+Halauxifen-methyl, 39+Florpyrauxifen-benzyl, 39+Quinclorac, 39+Quinmerac, 39+Chipton or salts/esters thereof, 39+2-methyl 4-chlorophenoxypropionic acid or salts/esters thereof, 39+MCPB or salts/esters thereof, 39+2,4-D or salts/esters thereof, 39+Dichlorprop or salts/esters thereof, 39+2,4-DB or salts/esters thereof, 39+Dicamba, 39+Picloram, 39+Trichlopyr, 39+Clopyralid, 39+Triclopyr, 39+Flurochloridone, 39+Flurtamone, 39+Diflufenican, 39+Picolinafen, 39+Beflubutamid, 39+Norflurazon, 39+Fluridone.

40+Sulcotrione, 40+Mesotrione, 40+Topramezone, 40+Tembotrione, 40+Bicyclopyrone, 40+Tefuryltrione, 40+Benzobicyclon, 40+Lancotrione, 40+Shuangzuocaotong, 40+Huanbifucaotong, 40+Sanzuohuangcaotong, 40+Benzuofucaotong, 40+Pyrasulfotole, 40+Pyrazolate, 40+Benzofenap, 40+Tolpyralate, 40+Fenquinotrione, 40+Isoxaflutole, 40+Fluroxypyr or esters thereof, 40+Halauxifen-methyl, 40+Florpyrauxifen-benzyl, 40+Quinclorac, 40+Quinmerac, 40+Chipton or salts/esters thereof, 40+2-methyl 4-chlorophenoxypropionic acid or salts/esters thereof, 40+MCPB or salts/esters thereof, 40+2,4-D or salts/esters thereof, 40+Dichlorprop or salts/esters thereof, 40+2,4-DB or salts/esters thereof, 40+Dicamba, 40+Picloram, 40+Trichlopyr, 40+Clopyralid, 40+Triclopyr, 40+Flurochloridone, 40+Flurtamone, 40+Diflufenican, 40+Picolinafen, 40+Beflubutamid, 40+Norflurazon, 40+Fluridone.

42+Sulcotrione, 42+Mesotrione, 42+Topramezone, 42+Tembotrione, 42+Bicyclopyrone, 42+Tefuryltrione, 42+Benzobicyclon, 42+Lancotrione, 42+Shuangzuocaotong, 42+Huanbifucaotong, 42+Sanzuohuangcaotong, 42+Benzuofucaotong, 42+Pyrasulfotole, 42+Pyrazolate, 0.42+Benzofenap, 42+Tolpyralate, 42+Fenquinotrione, 42+Isoxaflutole, 42+Fluroxypyr or esters thereof, 42+Halauxifen-methyl, 42+Florpyrauxifen-benzyl, 42+Quinclorac, 42+Quinmerac, 42+Chipton or salts/esters thereof, 42+2-methyl 4-chlorophenoxypropionic acid or salts/esters thereof, 42+MCPB or salts/esters thereof, 42+2,4-D or salts/esters thereof, 42+Dichlorprop or salts/esters thereof, 42+2,4-DB or salts/esters thereof, 42+Dicamba, 42+Picloram, 42+Trichlopyr, 42+Clopyralid, 42+Triclopyr, 42+Flurochloridone, 42+Flurtamone, 42+Diflufenican, 42+Picolinafen, 42+Beflubutamid, 42+Norflurazon, 42+Fluridone.

43+Sulcotrione, 43+Mesotrione, 43+Topramezone, 43+Tembotrione, 43+Bicyclopyrone, 43+Tefuryltrione, 43+Benzobicyclon, 43+Lancotrione, 43+Shuangzuocaotong, 43+Huanbifucaotong, 43+Sanzuohuangcaotong, 43+Benzuofucaotong, 43+Pyrasulfotole, 43+Pyrazolate, 43+Benzofenap, 43+Tolpyralate, 43+Fenquinotrione, 43+Isoxaflutole, 43+Fluroxypyr or esters thereof, 43+Halauxifen-methyl, 43+Florpyrauxifen-benzyl, 43+Quinclorac, 43+Quinmerac, 43+Chipton or salts/esters thereof, 43+2-methyl 4-chlorophenoxypropionic acid or salts/esters thereof, 43+MCPB or salts/esters thereof, 43+2,4-D or salts/esters thereof, 43+Dichlorprop or salts/esters thereof, 43+2,4-DB or salts/esters thereof, 43+Dicamba, 43+Picloram, 43+Trichlopyr, 43+Clopyralid, 43+Triclopyr, 43+Flurochloridone, 43+Flurtamone, 43+Diflufenican, 43+Picolinafen, 43+Beflubutamid, 43+Norflurazon, 43+Fluridone.

44+Sulcotrione, 44+Mesotrione, 44+Topramezone, 44+Tembotrione, 44+Bicyclopyrone, 44+Tefuryltrione, 44+Benzobicyclon, 44+Lancotrione, 44+Shuangzuocaotong, 44+Huanbifucaotong, 44+Sanzuohuangcaotong, 44+Benzuofucaotong, 44+Pyrasulfotole, 44+Pyrazolate, 44+Benzofenap, 44+Tolpyralate, 44+Fenquinotrione, 44+Isoxaflutole, 44+Fluroxypyr or esters thereof, 44+Halauxifen-methyl, 44+Florpyrauxifen-benzyl, 44+Quinclorac, 44+Quinmerac, 44+Chipton or salts/esters thereof, 44+2-methyl 4-chlorophenoxypropionic acid or salts/esters thereof, 44+MCPB or salts/esters thereof, 44+2,4-D or salts/esters thereof, 44+Dichlorprop or salts/esters thereof, 44+2,4-DB or salts/esters thereof, 44+Dicamba, 44+Picloram, 44+Trichlopyr, 44+Clopyralid, 44+Triclopyr, 44+Flurochloridone, 44+Flurtamone, 44+Diflufenican, 44+Picolinafen, 44+Beflubutamid, 44+Norflurazon, 44+Fluridone.

50+Sulcotrione, 50+Mesotrione, 50+Topramezone, 50+Tembotrione, 50+Bicyclopyrone, 50+Tefuryltrione, 50+Benzobicyclon, 50+Lancotrione, 50+Shuangzuocaotong, 50+Huanbifucaotong, 50+Sanzuohuangcaotong, 50+Benzuofucaotong, 50+Pyrasulfotole, 50+Pyrazolate, 50+Benzofenap, 50+Tolpyralate, 50+Fenquinotrione, 50+Isoxaflutole, 50+Fluroxypyr or esters thereof, 50+Halauxifen-methyl, 50+Florpyrauxifen-benzyl, 50+Quinclorac, 50+Quinmerac, 50+Chipton or salts/esters thereof, 50+2-methyl 4-chlorophenoxypropionic acid or salts/esters thereof, 50+MCPB or salts/esters thereof, 50+2,4-D or salts/esters thereof, 50+Dichlorprop or salts/esters thereof, 50+2,4-DB or salts/esters thereof, 50+Dicamba, 50+Picloram, 50+Trichlopyr, 50+Clopyralid, 50+Triclopyr, 50+Flurochloridone, 50+Flurtamone, 50+Diflufenican, 50+Picolinafen, 50+Beflubutamid, 50+Norflurazon, 50+Fluridone.

51+Sulcotrione, 51+Mesotrione, 51+Topramezone, 51+Tembotrione, 51+Bicyclopyrone, 51+Tefuryltrione, 51+Benzobicyclon, 51+Lancotrione, 51+Shuangzuocaotong, 51+Huanbifucaotong, 51+Sanzuohuangcaotong, 51+Benzuofucaotong, 51+Pyrasulfotole, 51+Pyrazolate, 51+Benzofenap, 51+Tolpyralate, 51+Fenquinotrione, 51+Isoxaflutole, 51+Fluroxypyr or esters thereof, 51+Halauxifen-methyl, 51+Florpyrauxifen-benzyl, 51+Quinclorac, 51+Quinmerac, 51+Chipton or salts/esters thereof, 51+2-methyl 4-chlorophenoxypropionic acid or salts/esters thereof, 51+MCPB or salts/esters thereof, 51+2,4-D or salts/esters thereof, 51+Dichlorprop or salts/esters thereof, 51+2,4-DB or salts/esters thereof, 51+Dicamba, 51+Picloram, 51+Trichlopyr, 51+Clopyralid, 51+Triclopyr, 51+Flurochloridone, 51+Flurtamone, 51+Diflufenican, 51+Picolinafen, 51+Beflubutamid, 51+Norflurazon, 51+Fluridone.

53+Sulcotrione, 53+Mesotrione, 53+Topramezone, 53+Tembotrione, 53+Bicyclopyrone, 53+Tefuryltrione, 53+Benzobicyclon, 53+Lancotrione, 53+Shuangzuocaotong, 53+Huanbifucaotong, 53+Sanzuohuangcaotong, 53+Benzuofucaotong, 53+Pyrasulfotole, 53+Pyrazolate, 53+Benzofenap, 53+Tolpyralate, 53+Fenquinotrione, 53+Isoxaflutole, 53+Fluroxypyr or esters thereof, 53+Halauxifen-methyl, 53+Florpyrauxifen-benzyl, 53+Quinclorac, 53+Quinmerac, 53+Chipton or salts/esters thereof, 53+2-methyl 4-chlorophenoxypropionic acid or salts/esters thereof, 53+MCPB or salts/esters thereof, 53+2,4-D or salts/esters thereof, 53+Dichlorprop or salts/esters thereof, 53+2,4-DB or salts/esters thereof, 53+Dicamba, 53+Picloram, 53+Trichlopyr, 53+Clopyralid, 53+Triclopyr, 53+Flurochloridone, 53+Flurtamone, 53+Diflufenican, 53+Picolinafen, 53+Beflubutamid, 53+Norflurazon, 53+Fluridone.

56+Sulcotrione, 56+Mesotrione, 56+Topramezone, 56+Tembotrione, 56+Bicyclopyrone, 56+Tefuryltrione, 56+Benzobicyclon, 56+Lancotrione, 56+Shuangzuocaotong, 56+Huanbifucaotong, 56+Sanzuohuangcaotong, 56+Benzuofucaotong, 56+Pyrasulfotole, 56+Pyrazolate, 56+Benzofenap, 56+Tolpyralate, 56+Fenquinotrione, 56+Isoxaflutole, 56+Fluroxypyr or esters thereof, 56+Halauxifen-methyl, 56+Florpyrauxifen-benzyl, 56+Quinclorac, 56+Quinmerac, 56+Chipton or salts/esters thereof, 56+2-methyl 4-chlorophenoxypropionic acid or salts/esters thereof, 56+MCPB or salts/esters thereof, 56+2,4-D or salts/esters thereof, 56+Dichlorprop or salts/esters thereof, 56+2,4-DB or salts/esters thereof, 56+Dicamba, 56+Picloram, 56+Trichlopyr, 56+Clopyralid, 56+Triclopyr, 56+Flurochloridone, 56+Flurtamone, 56+Diflufenican, 56+Picolinafen, 56+Beflubutamid, 56+Norflurazon, 56+Fluridone.

57+Sulcotrione, 57+Mesotrione, 57+Topramezone, 57+Tembotrione, 57+Bicyclopyrone, 57+Tefuryltrione, 57+Benzobicyclon, 57+Lancotrione, 57+Shuangzuocaotong, 57+Huanbifucaotong, 57+Sanzuohuangcaotong, 57+Benzuofucaotong, 57+Pyrasulfotole, 57+Pyrazolate, 57+Benzofenap, 57+Tolpyralate, 57+Fenquinotrione, 57+Isoxaflutole, 57+Fluroxypyr or esters thereof, 57+Halauxifen-methyl, 57+Florpyrauxifen-benzyl, 57+Quinclorac, 57+Quinmerac, 57+Chipton or salts/esters thereof, 57+2-methyl 4-chlorophenoxypropionic acid or salts/esters thereof, 57+MCPB or salts/esters thereof, 57+2,4-D or salts/esters thereof, 57+Dichlorprop or salts/esters thereof, 57+2,4-DB or salts/esters thereof, 57+Dicamba, 57+Picloram, 57+Trichlopyr, 57+Clopyralid, 57+Triclopyr, 57+Flurochloridone, 57+Flurtamone, 57+Diflufenican, 57+Picolinafen, 57+Beflubutamid, 57+Norflurazon, 57+Fluridone.

58+Sulcotrione, 58+Mesotrione, 58+Topramezone, 58+Tembotrione, 58+Bicyclopyrone, 58+Tefuryltrione, 58+Benzobicyclon, 58+Lancotrione, 58+Shuangzuocaotong, 58+Huanbifucaotong, 58+Sanzuohuangcaotong, 58+Benzuofucaotong, 58+Pyrasulfotole, 58+Pyrazolate, 58+Benzofenap, 58+Tolpyralate, 58+Fenquinotrione, 58+Isoxaflutole, 58+Fluroxypyr or esters thereof, 58+Halauxifen-methyl, 58+Florpyrauxifen-benzyl, 58+Quinclorac, 58+Quinmerac, 58+Chipton or salts/esters thereof, 58+2-methyl 4-chlorophenoxypropionic acid or salts/esters thereof, 58+MCPB or salts/esters thereof, 58+2,4-D or salts/esters thereof, 58+Dichlorprop or salts/esters thereof, 58+2,4-DB or salts/esters thereof, 58+Dicamba, 58+Picloram, 58+Trichlopyr, 58+Clopyralid, 58+Triclopyr, 58+Flurochloridone, 58+Flurtamone, 58+Diflufenican, 58+Picolinafen, 58+Beflubutamid, 58+Norflurazon, 58+Fluridone.

59+Sulcotrione, 59+Mesotrione, 59+Topramezone, 59+Tembotrione, 59+Bicyclopyrone, 59+Tefuryltrione, 59+Benzobicyclon, 59+Lancotrione, 59+Shuangzuocaotong, 59+Huanbifucaotong, 59+Sanzuohuangcaotong, 59+Benzuofucaotong, 59+Pyrasulfotole, 59+Pyrazolate, 59+Benzofenap, 59+Tolpyralate, 59+Fenquinotrione, 59+Isoxaflutole, 59+Fluroxypyr or esters thereof, 59+Halauxifen-methyl, 59+Florpyrauxifen-benzyl, 59+Quinclorac, 59+Quinmerac, 59+Chipton or salts/esters thereof, 59+2-methyl 4-chlorophenoxypropionic acid or salts/esters thereof, 59+MCPB or salts/esters thereof, 59+2,4-D or salts/esters thereof, 59+Dichlorprop or salts/esters thereof, 59+2,4-DB or salts/esters thereof, 59+Dicamba, 59+Picloram, 59+Trichlopyr, 59+Clopyralid, 59+Triclopyr, 59+Flurochloridone, 59+Flurtamone, 59+Diflufenican, 59+Picolinafen, 59+Beflubutamid, 59+Norflurazon, 59+Fluridone.

60+Sulcotrione, 60+Mesotrione, 60+Topramezone, 60+Tembotrione, 60+Bicyclopyrone, 60+Tefuryltrione, 60+Benzobicyclon, 60+Lancotrione, 60+Shuangzuocaotong, 60+Huanbifucaotong, 60+Sanzuohuangcaotong, 60+Benzuofucaotong, 60+Pyrasulfotole, 60+Pyrazolate, 60+Benzofenap, 60+Tolpyralate, 60+Fenquinotrione, 60+Isoxaflutole, 60+Fluroxypyr or esters thereof, 60+Halauxifen-methyl, 60+Florpyrauxifen-benzyl, 60+Quinclorac, 60+Quinmerac, 60+Chipton or salts/esters thereof, 60+2-methyl 4-chlorophenoxypropionic acid or salts/esters thereof, 60+MCPB or salts/esters thereof, 60+2,4-D or salts/esters thereof, 60+Dichlorprop or salts/esters thereof, 60+2,4-DB or salts/esters thereof, 60+Dicamba, 60+Picloram, 60+Trichlopyr, 60+Clopyralid, 60+Triclopyr, 60+Flurochloridone, 60+Flurtamone, 60+Diflufenican, 60+Picolinafen, 60+Beflubutamid, 60+Norflurazon, 60+Fluridone.

66+Sulcotrione, 66+Mesotrione, 66+Topramezone, 66+Tembotrione, 66+Bicyclopyrone, 66+Tefuryltrione, 66+Benzobicyclon, 66+Lancotrione, 66+Shuangzuocaotong, 66+Huanbifucaotong, 66+Sanzuohuangcaotong, 66+Benzuofucaotong, 66+Pyrasulfotole, 66+Pyrazolate, 66+Benzofenap, 66+Tolpyralate, 66+Fenquinotrione, 66+Isoxaflutole, 66+Fluroxypyr or esters thereof, 66+Halauxifen-methyl, 66+Florpyrauxifen-benzyl, 66+Quinclorac, 66+Quinmerac, 66+Chipton or salts/esters thereof, 66+2-methyl 4-chlorophenoxypropionic acid or salts/esters thereof, 66+MCPB or salts/esters thereof, 66+2,4-D or salts/esters thereof, 66+Dichlorprop or salts/esters thereof, 66+2,4-DB or salts/esters thereof, 66+Dicamba, 66+Picloram, 66+Trichlopyr, 66+Clopyralid, 66+Triclopyr, 66+Flurochloridone, 66+Flurtamone, 66+Diflufenican, 66+Picolinafen, 66+Beflubutamid, 66+Norflurazon, 66+Fluridone.

68+Sulcotrione, 68+Mesotrione, 68+Topramezone, 68+Tembotrione, 68+Bicyclopyrone, 68+Tefuryltrione, 68+Benzobicyclon, 68+Lancotrione, 68+Shuangzuocaotong, 68+Huanbifucaotong, 68+Sanzuohuangcaotong, 68+Benzuofucaotong, 68+Pyrasulfotole, 68+Pyrazolate, 68+Benzofenap, 68+Tolpyralate, 68+Fenquinotrione, 68+Isoxaflutole, 68+Fluroxypyr or esters thereof, 68+Halauxifen-methyl, 68+Florpyrauxifen-benzyl, 68+Quinclorac, 68+Quinmerac, 68+Chipton or salts/esters thereof, 68+2-methyl 4-chlorophenoxypropionic acid or salts/esters thereof, 68+MCPB or salts/esters thereof, 68+2,4-D or salts/esters thereof, 68+Dichlorprop or salts/esters thereof, 68+2,4-DB or salts/esters thereof, 68+Dicamba, 68+Picloram, 68+Trichlopyr, 68+Clopyralid, 68+Triclopyr, 68+Flurochloridone, 68+Flurtamone, 68+Diflufenican, 68+Picolinafen, 68+Beflubutamid, 68+Norflurazon, 68+Fluridone.

77+Sulcotrione, 77+Mesotrione, 77+Topramezone, 77+Tembotrione, 77+Bicyclopyrone, 77+Tefuryltrione, 77+Benzobicyclon, 77+Lancotrione, 77+Shuangzuocaotong, 77+Huanbifucaotong, 77+Sanzuohuangcaotong, 77+Benzuofucaotong, 77+Pyrasulfotole, 77+Pyrazolate, 77+Benzofenap, 77+Tolpyralate, 77+Fenquinotrione, 77+Isoxaflutole, 77+Fluroxypyr or esters thereof, 77+Halauxifen-methyl, 77+Florpyrauxifen-benzyl, 77+Quinclorac, 77+Quinmerac, 77+Chipton or salts/esters thereof, 77+2-methyl 4-chlorophenoxypropionic acid or salts/esters thereof, 77+MCPB or salts/esters thereof, 77+2,4-D or salts/esters thereof, 77+Dichlorprop or salts/esters thereof, 77+2,4-DB or salts/esters thereof, 77+Dicamba, 77+Picloram, 77+Trichlopyr, 77+Clopyralid, 77+Triclopyr, 77+Flurochloridone, 77+Flurtamone, 77+Diflufenican, 77+Picolinafen, 77+Beflubutamid, 77+Norflurazon, 77+Fluridone.

79+Sulcotrione, 79+Mesotrione, 79+Topramezone, 79+Tembotrione, 79+Bicyclopyrone, 79+Tefuryltrione, 79+Benzobicyclon, 79+Lancotrione, 79+Shuangzuocaotong, 79+Huanbifucaotong, 79+Sanzuohuangcaotong, 79+Benzuofucaotong, 79+Pyrasulfotole, 79+Pyrazolate, 79+Benzofenap, 79+Tolpyralate, 79+Fenquinotrione, 79+Isoxaflutole, 79+Fluroxypyr or esters thereof, 79+Halauxifen-methyl, 79+Florpyrauxifen-benzyl, 79+Quinclorac, 79+Quinmerac, 79+Chipton or salts/esters thereof, 79+2-methyl 4-chlorophenoxypropionic acid or salts/esters thereof, 79+MCPB or salts/esters thereof, 79+2,4-D or salts/esters thereof, 79+Dichlorprop or salts/esters thereof, 79+2,4-DB or salts/esters thereof, 79+Dicamba, 79+Picloram, 79+Trichlopyr, 79+Clopyralid, 79+Triclopyr, 79+Flurochloridone, 79+Flurtamone, 79+Diflufenican, 79+Picolinafen, 79+Beflubutamid, 79+Norflurazon, 79+Fluridone.

87+Sulcotrione, 87+Mesotrione, 87+Topramezone, 87+Tembotrione, 87+Bicyclopyrone, 87+Tefuryltrione, 87+Benzobicyclon, 87+Lancotrione, 87+Shuangzuocaotong, 87+Huanbifucaotong, 87+Sanzuohuangcaotong, 87+Benzuofucaotong, 87+Pyrasulfotole, 87+Pyrazolate, 87+Benzofenap, 87+Tolpyralate, 87+Fenquinotrione, 87+Isoxaflutole, 87+Fluroxypyr or esters thereof, 87+Halauxifen-methyl, 87+Florpyrauxifen-benzyl, 87+Quinclorac, 87+Quinmerac, 87+Chipton or salts/esters thereof, 87+2-methyl 4-chlorophenoxypropionic acid or salts/esters thereof, 87+MCPB or salts/esters thereof, 87+2,4-D or salts/esters thereof, 87+Dichlorprop or salts/esters thereof, 87+2,4-DB or salts/esters thereof, 87+Dicamba, 87+Picloram, 87+Trichlopyr, 87+Clopyralid, 87+Triclopyr, 87+Flurochloridone, 87+Flurtamone, 87+Diflufenican, 87+Picolinafen, 87+Beflubutamid, 87+Norflurazon, 87+Fluridone.

92+Sulcotrione, 92+Mesotrione, 92+Topramezone, 92+Tembotrione, 92+Bicyclopyrone, 92+Tefuryltrione, 92+Benzobicyclon, 92+Lancotrione, 92+Shuangzuocaotong, 92+Huanbifucaotong, 92+Sanzuohuangcaotong, 92+Benzuofucaotong, 92+Pyrasulfotole, 92+Pyrazolate, 92+Benzofenap, 92+Tolpyralate, 92+Fenquinotrione, 92+Isoxaflutole, 92+Fluroxypyr or esters thereof, 92+Halauxifen-methyl, 92+Florpyrauxifen-benzyl, 92+Quinclorac, 92+Quinmerac, 92+Chipton or salts/esters thereof, 92+2-methyl 4-chlorophenoxypropionic acid or salts/esters thereof, 92+MCPB or salts/esters thereof, 92+2,4-D or salts/esters thereof, 92+Dichlorprop or salts/esters thereof, 92+2,4-DB or salts/esters thereof, 92+Dicamba, 92+Picloram, 92+Trichlopyr, 92+Clopyralid, 92+Triclopyr, 92+Flurochloridone, 92+Flurtamone, 92+Diflufenican, 92+Picolinafen, 92+Beflubutamid, 92+Norflurazon, 92+Fluridone.

191+Sulcotrione, 191+Mesotrione, 191+Topramezone, 191+Tembotrione, 191+Bicyclopyrone, 191+Tefuryltrione, 191+Benzobicyclon, 191+Lancotrione, 191+Shuangzuocaotong, 191+Huanbifucaotong, 191+Sanzuohuangcaotong, 191+Benzuofucaotong, 191+Pyrasulfotole, 191+Pyrazolate, 191+Benzofenap, 191+

Tolpyralate, 191+Fenquinotrione, 191+Isoxaflutole, 191+Fluroxypyr or esters thereof, 191+Halauxifen-methyl, 191+Florpyrauxifen-benzyl, 191+Quinclorac, 191+Quinmerac, 191+Chipton or salts/esters thereof, 191+2-methyl 4-chlorophenoxypropionic acid or salts/esters thereof, 191+MCPB or salts/esters thereof, 191+2,4-D or salts/esters thereof, 191+Dichlorprop or salts/esters thereof, 191+2,4-DB or salts/esters thereof, 191+Dicamba, 191+Picloram, 191+Trichlopyr, 191+Clopyralid, 191+Triclopyr, 191+Flurochloridone, 191+Flurtamone, 191+Diflufenican, 191+Picolinafen, 191+Beflubutamid, 191+Norflurazon, 191+Fluridone.

202+Sulcotrione, 202+Mesotrione, 202+Topramezone, 202+Tembotrione, 202+Bicyclopyrone, 202+Tefuryltrione, 202+Benzobicyclon, 202+Lancotrione, 202+Shuangzuocaotong, 202+Huanbifucaotong, 202+Sanzuohuangcaotong, 202+Benzuofucaotong, 202+Pyrasulfotole, 202+Pyrazolate, 202+Benzofenap, 202+Tolpyralate, 202+Fenquinotrione, 202+Isoxaflutole, 202+Fluroxypyr or esters thereof, 202+Halauxifen-methyl, 202+Florpyrauxifen-benzyl, 202+Quinclorac, 202+Quinmerac, 202+Chipton or salts/esters thereof, 202+2-methyl 4-chlorophenoxypropionic acid or salts/esters thereof, 202+MCPB or salts/esters thereof, 202+2,4-D or salts/esters thereof, 202+Dichlorprop or salts/esters thereof, 202+2,4-DB or salts/esters thereof, 202+Dicamba, 202+Picloram, 202+Trichlopyr, 202+Clopyralid, 202+Triclopyr, 202+Flurochloridone, 202+Flurtamone, 202+Diflufenican, 202+Picolinafen, 202+Beflubutamid, 202+Norflurazon, 202+Fluridone.

206+Sulcotrione, 206+Mesotrione, 206+Topramezone, 206+Tembotrione, 206+Bicyclopyrone, 206+Tefuryltrione, 206+Benzobicyclon, 206+Lancotrione, 206+Shuangzuocaotong, 206+Huanbifucaotong, 206+Sanzuohuangcaotong, 206+Benzuofucaotong, 206+Pyrasulfotole, 206+Pyrazolate, 206+Benzofenap, 206+Tolpyralate, 206+Fenquinotrione, 206+Isoxaflutole, 206+Fluroxypyr or esters thereof, 206+Halauxifen-methyl, 206+Florpyrauxifen-benzyl, 206+Quinclorac, 206+Quinmerac, 206+Chipton or salts/esters thereof, 206+2-methyl 4-chlorophenoxypropionic acid or salts/esters thereof, 206+MCPB or salts/esters thereof, 206+2,4-D or salts/esters thereof, 206+Dichlorprop or salts/esters thereof, 206+2,4-DB or salts/esters thereof, 206+Dicamba, 206+Picloram, 206+Trichlopyr, 206+Clopyralid, 206+Triclopyr, 206+Flurochloridone, 206+Flurtamone, 206+Diflufenican, 206+Picolinafen, 206+Beflubutamid, 206+Norflurazon, 206+Fluridone.

207+Sulcotrione, 207+Mesotrione, 207+Topramezone, 207+Tembotrione, 207+Bicyclopyrone, 207+Tefuryltrione, 207+Benzobicyclon, 207+Lancotrione, 207+Shuangzuocaotong, 207+Huanbifucaotong, 207+Sanzuohuangcaotong, 207+Benzuofucaotong, 207+Pyrasulfotole, 207+Pyrazolate, 207+Benzofenap, 207+Tolpyralate, 207+Fenquinotrione, 207+Isoxaflutole, 207+Fluroxypyr or esters thereof, 207+Halauxifen-methyl, 207+Florpyrauxifen-benzyl, 207+Quinclorac, 207+Quinmerac, 207+Chipton or salts/esters thereof, 207+2-methyl 4-chlorophenoxypropionic acid or salts/esters thereof, 207+MCPB or salts/esters thereof, 207+2,4-D or salts/esters thereof, 207+Dichlorprop or salts/esters thereof, 207+2,4-DB or salts/esters thereof, 207+Dicamba, 207+Picloram, 207+Trichlopyr, 207+Clopyralid, 207+Triclopyr, 207+Flurochloridone, 207+Flurtamone, 207+Diflufenican, 207+Picolinafen, 207+Beflubutamid, 207+Norflurazon, 207+Fluridone.

220+Sulcotrione, 220+Mesotrione, 220+Topramezone, 220+Tembotrione, 220+Bicyclopyrone, 220+Tefuryltrione, 220+Benzobicyclon, 220+Lancotrione, 220+Shuangzuocaotong, 220+Huanbifucaotong, 220+Sanzuohuangcaotong, 220+Benzuofucaotong, 220+Pyrasulfotole, 220+Pyrazolate, 220+Benzofenap, 220+-Tolpyralate, 220+Fenquinotrione, 220+Isoxaflutole, 220+Fluroxypyr or esters thereof, 220+Halauxifen-methyl, 220+Florpyrauxifen-benzyl, 220+Quinclorac, 220+Quinmerac, 220+Chipton or salts/esters thereof, 220+2-methyl 4-chlorophenoxypropionic acid or salts/esters thereof, 220+MCPB or salts/esters thereof, 220+2,4-D or salts/esters thereof, 220+Dichlorprop or salts/esters thereof, 220+2,4-DB or salts/esters thereof, 220+Dicamba, 220+Picloram, 220+Trichlopyr, 220+Clopyralid, 220+Triclopyr, 220+Flurochloridone, 220+Flurtamone, 220+Diflufenican, 220+Picolinafen, 220+Beflubutamid, 220+Norflurazon, 220+Fluridone.

278+Sulcotrione, 278+Mesotrione, 278+Topramezone, 278+Tembotrione, 278+Bicyclopyrone, 278+Tefuryltrione, 278+Benzobicyclon, 278+Lancotrione, 278+Shuangzuocaotong, 278+Huanbifucaotong, 278+Sanzuohuangcaotong, 278+Benzuofucaotong, 278+Pyrasulfotole, 278+Pyrazolate, 278+Benzofenap, 278+Tolpyralate, 278+Fenquinotrione, 278+Isoxaflutole, 278+Fluroxypyr or esters thereof, 278+Halauxifen-methyl, 278+Florpyrauxifen-benzyl, 278+Quinclorac, 278+Quinmerac, 278+Chipton or salts/esters thereof, 278+2-methyl 4-chlorophenoxypropionic acid or salts/esters thereof, 278+MCPB or salts/esters thereof, 278+2,4-D or salts/esters thereof, 278+Dichlorprop or salts/esters thereof, 278+2,4-DB or salts/esters thereof, 278+Dicamba, 278+Picloram, 278+Trichlopyr, 278+Clopyralid, 278+Triclopyr, 278+Flurochloridone, 278+Flurtamone, 278+Diflufenican, 278+Picolinafen, 278+Beflubutamid, 278+Norflurazon, 278+Fluridone.

341+Sulcotrione, 341+Mesotrione, 341+Topramezone, 341+Tembotrione, 341+Bicyclopyrone, 341+Tefuryltrione, 341+Benzobicyclon, 341+Lancotrione, 341+Shuangzuocaotong, 341+Huanbifucaotong, 341+Sanzuohuangcaotong, 341+Benzuofucaotong, 341+Pyrasulfotole, 341+Pyrazolate, 341+Benzofenap, 341+Tolpyralate, 341+Fenquinotrione, 341+Isoxaflutole, 341+Fluroxypyr or esters thereof, 341+Halauxifen-methyl, 341+Florpyrauxifen-benzyl, 341+Quinclorac, 341+Quinmerac, 341+Chipton or salts/esters thereof, 341+2-methyl 4-chlorophenoxypropionic acid or salts/esters thereof, 341+MCPB or salts/esters thereof, 341+2,4-D or salts/esters thereof, 341+Dichlorprop or salts/esters thereof, 341+2,4-DB or salts/esters thereof, 341+Dicamba, 341+Picloram, 341+Trichlopyr, 341+Clopyralid, 341+Triclopyr, 341+Flurochloridone, 341+Flurtamone, 341+Diflufenican, 341+Picolinafen, 341+Beflubutamid, 341+Norflurazon, 341+Fluridone.

732+Sulcotrione, 732+Mesotrione, 732+Topramezone, 732+Tembotrione, 732+Bicyclopyrone, 732+Tefuryltrione, 732+Benzobicyclon, 732+Lancotrione, 732+Shuangzuocaotong, 732+Huanbifucaotong, 732+Sanzuohuangcaotong, 732+Benzuofucaotong, 732+Pyrasulfotole, 732+Pyrazolate, 732+Benzofenap, 732+Tolpyralate, 732+Fenquinotrione, 732+Isoxaflutole, 732+Fluroxypyr or esters thereof, 732+Halauxifen-methyl, 732+Florpyrauxifen-benzyl, 732+Quinclorac, 732+Quinmerac, 732+Chipton or salts/esters thereof, 732+2-methyl 4-chlorophenoxypropionic acid or salts/esters thereof, 732+MCPB or salts/esters thereof, 732+

2,4-D or salts/esters thereof, 732+Dichlorprop or salts/esters thereof, 732+2,4-DB or salts/esters thereof, 732+Dicamba, 732+Picloram, 732+Trichlopyr, 732+Clopyralid, 732+Triclopyr, 732+Flurochloridone, 732+Flurtamone, 732+Diflufenican, 732+Picolinafen, 732+Beflubutamid, 732+Norflurazon, 732+Fluridone.

733+Sulcotrione, 733+Mesotrione, 733+Topramezone, 733+Tembotrione, 733+Bicyclopyrone, 733+Tefuryltrione, 733+Benzobicyclon, 733+Lancotrione, 733+Shuangzuocaotong, 733+Huanbifucaotong, 733+Sanzuohuangcaotong, 733+Benzuofucaotong, 733+Pyrasulfotole, 733+Pyrazolate, 733+Benzofenap, 733+Tolpyralate, 733+Fenquinotrione, 733+Isoxaflutole, 733+Fluroxypyr or esters thereof, 733+Halauxifen-methyl, 733+Florpyrauxifen-benzyl, 733+Quinclorac, 733+Quinmerac, 733+Chipton or salts/esters thereof, 733+2-methyl 4-chlorophenoxypropionic acid or salts/esters thereof, 733+MCPB or salts/esters thereof, 733+2,4-D or salts/esters thereof, 733+Dichlorprop or salts/esters thereof, 733+2,4-DB or salts/esters thereof, 733+Dicamba, 733+Picloram, 733+Trichlopyr, 733+Clopyralid, 733+Triclopyr, 733+Flurochloridone, 733+Flurtamone, 733+Diflufenican, 733+Picolinafen, 733+Beflubutamid, 733+Norflurazon, 733+Fluridone.

734+Sulcotrione, 734+Mesotrione, 734+Topramezone, 734+Tembotrione, 734+Bicyclopyrone, 734+Tefuryltrione, 734+Benzobicyclon, 734+Lancotrione, 734+Shuangzuocaotong, 734+Huanbifucaotong, 734+Sanzuohuangcaotong, 734+Benzuofucaotong, 734+Pyrasulfotole, 734+Pyrazolate, 734+Benzofenap, 734+Tolpyralate, 734+Fenquinotrione, 734+Isoxaflutole, 734+Fluroxypyr or esters thereof, 734+Halauxifen-methyl, 734+Florpyrauxifen-benzyl, 734+Quinclorac, 734+Quinmerac, 734+Chipton or salts/esters thereof, 734+2-methyl 4-chlorophenoxypropionic acid or salts/esters thereof, 734+MCPB or salts/esters thereof, 734+2,4-D or salts/esters thereof, 734+Dichlorprop or salts/esters thereof, 734+2,4-DB or salts/esters thereof, 734+Dicamba, 734+Picloram, 734+Trichlopyr, 734+Clopyralid, 734+Triclopyr, 734+Flurochloridone, 734+Flurtamone, 734+Diflufenican, 734+Picolinafen, 734+Beflubutamid, 734+Norflurazon, 734+Fluridone.

735+Sulcotrione, 735+Mesotrione, 735+Topramezone, 735+Tembotrione, 735+Bicyclopyrone, 735+Tefuryltrione, 735+Benzobicyclon, 735+Lancotrione, 735+Shuangzuocaotong, 735+Huanbifucaotong, 735+Sanzuohuangcaotong, 735+Benzuofucaotong, 735+Pyrasulfotole, 735+Pyrazolate, 735+Benzofenap, 735+Tolpyralate, 735+Fenquinotrione, 735+Isoxaflutole, 735+Fluroxypyr or esters thereof, 735+Halauxifen-methyl, 735+Florpyrauxifen-benzyl, 735+Quinclorac, 735+Quinmerac, 735+Chipton or salts/esters thereof, 735+2-methyl 4-chlorophenoxypropionic acid or salts/esters thereof, 735+MCPB or salts/esters thereof, 735+2,4-D or salts/esters thereof, 735+Dichlorprop or salts/esters thereof, 735+2,4-DB or salts/esters thereof, 735+Dicamba, 735+Picloram, 735+Trichlopyr, 735+Clopyralid, 735+Triclopyr, 735+Flurochloridone, 735+Flurtamone, 735+Diflufenican, 735+Picolinafen, 735+Beflubutamid, 735+Norflurazon, 735+Fluridone.

736+Sulcotrione, 736+Mesotrione, 736+Topramezone, 736+Tembotrione, 736+Bicyclopyrone, 736+Tefuryltrione, 736+Benzobicyclon, 736+Lancotrione, 736+Shuangzuocaotong, 736+Huanbifucaotong, 736+Sanzuohuangcaotong, 736+Benzuofucaotong, 736+Pyrasulfotole, 736+Pyrazolate, 736+Benzofenap, 736+Tolpyralate, 736+Fenquinotrione, 736+Isoxaflutole, 736+Fluroxypyr or esters thereof, 736+Halauxifen-methyl, 736+Florpyrauxifen-benzyl, 736+Quinclorac, 736+Quinmerac, 736+Chipton or salts/esters thereof, 736+2-methyl 4-chlorophenoxypropionic acid or salts/esters thereof, 736+MCPB or salts/esters thereof, 736+2,4-D or salts/esters thereof, 736+Dichlorprop or salts/esters thereof, 736+2,4-DB or salts/esters thereof, 736+Dicamba, 736+Picloram, 736+Trichlopyr, 736+Clopyralid, 736+Triclopyr, 736+Flurochloridone, 736+Flurtamone, 736+Diflufenican, 736+Picolinafen, 736+Beflubutamid, 736+Norflurazon, 736+Fluridone.

737+Sulcotrione, 737+Mesotrione, 737+Topramezone, 737+Tembotrione, 737+Bicyclopyrone, 737+Tefuryltrione, 737+Benzobicyclon, 737+Lancotrione, 737+Shuangzuocaotong, 737+Huanbifucaotong, 737+Sanzuohuangcaotong, 737+Benzuofucaotong, 737+Pyrasulfotole, 737+Pyrazolate, 737+Benzofenap, 737+Tolpyralate, 737+Fenquinotrione, 737+Isoxaflutole, 737+Fluroxypyr or esters thereof, 737+Halauxifen-methyl, 737+Florpyrauxifen-benzyl, 737+Quinclorac, 737+Quinmerac, 737+Chipton or salts/esters thereof, 737+2-methyl 4-chlorophenoxypropionic acid or salts/esters thereof, 737+MCPB or salts/esters thereof, 737+2,4-D or salts/esters thereof, 737+Dichlorprop or salts/esters thereof, 737+2,4-DB or salts/esters thereof, 737+Dicamba, 737+Picloram, 737+Trichlopyr, 737+Clopyralid, 737+Triclopyr, 737+Flurochloridone, 737+Flurtamone, 737+Diflufenican, 737+Picolinafen, 737+Beflubutamid, 737+Norflurazon, 737+Fluridone.

738+Sulcotrione, 738+Mesotrione, 738+Topramezone, 738+Tembotrione, 738+Bicyclopyrone, 738+Tefuryltrione, 738+Benzobicyclon, 738+Lancotrione, 738+Shuangzuocaotong, 738+Huanbifucaotong, 738+Sanzuohuangcaotong, 738+Benzuofucaotong, 738+Pyrasulfotole, 738+Pyrazolate, 738+Benzofenap, 738+Tolpyralate, 738+Fenquinotrione, 738+Isoxaflutole, 738+Fluroxypyr or esters thereof, 738+Halauxifen-methyl, 738+Florpyrauxifen-benzyl, 738+Quinclorac, 738+Quinmerac, 738+Chipton or salts/esters thereof, 738+2-methyl 4-chlorophenoxypropionic acid or salts/esters thereof, 738+MCPB or salts/esters thereof, 738+2,4-D or salts/esters thereof, 738+Dichlorprop or salts/esters thereof, 738+2,4-DB or salts/esters thereof, 738+Dicamba, 738+Picloram, 738+Trichlopyr, 738+Clopyralid, 738+Triclopyr, 738+Flurochloridone, 738+Flurtamone, 738+Diflufenican, 738+Picolinafen, 738+Beflubutamid, 738+Norflurazon, 738+Fluridone.

739+Sulcotrione, 739+Mesotrione, 739+Topramezone, 739+Tembotrione, 739+Bicyclopyrone, 739+Tefuryltrione, 739+Benzobicyclon, 739+Lancotrione, 739+Shuangzuocaotong, 739+Huanbifucaotong, 739+Sanzuohuangcaotong, 739+Benzuofucaotong, 739+Pyrasulfotole, 739+Pyrazolate, 739+Benzofenap, 739+Tolpyralate, 739+Fenquinotrione, 739+Isoxaflutole, 739+Fluroxypyr or esters thereof, 739+Halauxifen-methyl, 739+Florpyrauxifen-benzyl, 739+Quinclorac, 739+Quinmerac, 739+Chipton or salts/esters thereof, 739+2-methyl 4-chlorophenoxypropionic acid or salts/esters thereof, 739+MCPB or salts/esters thereof, 739+2,4-D or salts/esters thereof, 739+Dichlorprop or salts/esters thereof, 739+2,4-DB or salts/esters thereof, 739+Dicamba, 739+Picloram, 739+Trichlopyr, 739+Clopyralid, 739+Triclopyr, 739+Flurochloridone, 739+Flurtamone, 739+Diflufenican, 739+Picolinafen, 739+Beflubutamid, 739+Norflurazon, 739+Fluridone.

740+Sulcotrione, 740+Mesotrione, 740+Topramezone, 740+Tembotrione, 740+Bicyclopyrone, 740+Tefuryltrione, 740+Benzobicyclon, 740+Lancotrione, 740+Shuangzuocaotong, 740+Huanbifucaotong, 740+Sanzuohuangcaotong, 740+Benzuofucaotong, 740+Pyrasulfotole, 740+Pyrazolate, 740+Benzofenap, 740+Tolpyralate, 740+Fenquinotrione, 740+Isoxaflutole, 740+Fluroxypyr or esters thereof, 740+Halauxifen-methyl, 740+Florpyrauxifen-benzyl, 740+Quinclorac, 740+Quinmerac, 740+Chipton or salts/esters thereof, 740+2-methyl 4-chlorophenoxypropionic acid or salts/esters thereof, 740+MCPB or salts/esters thereof, 740+2,4-D or salts/esters thereof, 740+Dichlorprop or salts/esters thereof, 740+2,4-DB or salts/esters thereof, 740+Dicamba, 740+Picloram, 740+Trichlopyr, 740+Clopyralid, 740+Triclopyr, 740+Flurochloridone, 740+Flurtamone, 740+Diflufenican, 740+Picolinafen, 740+Beflubutamid, 740+Norflurazon, 740+Fluridone.

741+Sulcotrione, 741+Mesotrione, 741+Topramezone, 741+Tembotrione, 741+Bicyclopyrone, 741+Tefuryltrione, 741+Benzobicyclon, 741+Lancotrione, 741+Shuangzuocaotong, 741+Huanbifucaotong, 741+Sanzuohuangcaotong, 741+Benzuofucaotong, 741+Pyrasulfotole, 741+Pyrazolate, 741+Benzofenap, 741+Tolpyralate, 741+Fenquinotrione, 741+Isoxaflutole, 741+Fluroxypyr or esters thereof, 741+Halauxifen-methyl, 741+Florpyrauxifen-benzyl, 741+Quinclorac, 741+Quinmerac, 741+Chipton or salts/esters thereof, 741+2-methyl 4-chlorophenoxypropionic acid or salts/esters thereof, 741+MCPB or salts/esters thereof, 741+2,4-D or salts/esters thereof, 741+Dichlorprop or salts/esters thereof, 741+2,4-DB or salts/esters thereof, 741+Dicamba, 741+Picloram, 741+Trichlopyr, 741+Clopyralid, 741+Triclopyr, 741+Flurochloridone, 741+Flurtamone, 741+Diflufenican, 741+Picolinafen, 741+Beflubutamid, 741+Norflurazon, 741+Fluridone.

742+Sulcotrione, 742+Mesotrione, 742+Topramezone, 742+Tembotrione, 742+Bicyclopyrone, 742+Tefuryltrione, 742+Benzobicyclon, 742+Lancotrione, 742+Shuangzuocaotong, 742+Huanbifucaotong, 742+Sanzuohuangcaotong, 742+Benzuofucaotong, 742+Pyrasulfotole, 742+Pyrazolate, 742+Benzofenap, 742+Tolpyralate, 742+Fenquinotrione, 742+Isoxaflutole, 742+Fluroxypyr or esters thereof, 742+Halauxifen-methyl, 742+Florpyrauxifen-benzyl, 742+Quinclorac, 742+Quinmerac, 742+Chipton or salts/esters thereof, 742+2-methyl 4-chlorophenoxypropionic acid or salts/esters thereof, 742+MCPB or salts/esters thereof, 742+2,4-D or salts/esters thereof, 742+Dichlorprop or salts/esters thereof, 742+2,4-DB or salts/esters thereof, 742+Dicamba, 742+Picloram, 742+Trichlopyr, 742+Clopyralid, 742+Triclopyr, 742+Flurochloridone, 742+Flurtamone, 742+Diflufenican, 742+Picolinafen, 742+Beflubutamid, 742+Norflurazon, 742+Fluridone.

743+Sulcotrione, 743+Mesotrione, 743+Topramezone, 743+Tembotrione, 743+Bicyclopyrone, 743+Tefuryltrione, 743+Benzobicyclon, 743+Lancotrione, 743+Shuangzuocaotong, 743+Huanbifucaotong, 743+Sanzuohuangcaotong, 743+Benzuofucaotong, 743+Pyrasulfotole, 743+Pyrazolate, 743+Benzofenap, 743+Tolpyralate, 743+Fenquinotrione, 743+Isoxaflutole, 743+Fluroxypyr or esters thereof, 743+Halauxifen-methyl, 743+Florpyrauxifen-benzyl, 743+Quinclorac, 743+Quinmerac, 743+Chipton or salts/esters thereof, 743+2-methyl 4-chlorophenoxypropionic acid or salts/esters thereof, 743+MCPB or salts/esters thereof, 743+2,4-D or salts/esters thereof, 743+Dichlorprop or salts/esters thereof, 743+2,4-DB or salts/esters thereof, 743+Dicamba, 743+Picloram, 743+Trichlopyr, 743+Clopyralid, 743+Triclopyr, 743+Flurochloridone, 743+Flurtamone, 743+Diflufenican, 743+Picolinafen, 743+Beflubutamid, 743+Norflurazon, 743+Fluridone.

744+Sulcotrione, 744+Mesotrione, 744+Topramezone, 744+Tembotrione, 744+Bicyclopyrone, 744+Tefuryltrione, 744+Benzobicyclon, 744+Lancotrione, 744+Shuangzuocaotong, 744+Huanbifucaotong, 744+Sanzuohuangcaotong, 744+Benzuofucaotong, 744+Pyrasulfotole, 744+Pyrazolate, 744+Benzofenap, 744+Tolpyralate, 744+Fenquinotrione, 744+Isoxaflutole, 744+Fluroxypyr or esters thereof, 744+Halauxifen-methyl, 744+Florpyrauxifen-benzyl, 744+Quinclorac, 744+Quinmerac, 744+Chipton or salts/esters thereof, 744+2-methyl 4-chlorophenoxypropionic acid or salts/esters thereof, 744+MCPB or salts/esters thereof, 744+2,4-D or salts/esters thereof, 744+Dichlorprop or salts/esters thereof, 744+2,4-DB or salts/esters thereof, 744+Dicamba, 744+Picloram, 744+Trichlopyr, 744+Clopyralid, 744+Triclopyr, 744+Flurochloridone, 744+Flurtamone, 744+Diflufenican, 744+Picolinafen, 744+Beflubutamid, 744+Norflurazon, 744+Fluridone.

745+Sulcotrione, 745+Mesotrione, 745+Topramezone, 745+Tembotrione, 745+Bicyclopyrone, 745+Tefuryltrione, 745+Benzobicyclon, 745+Lancotrione, 745+Shuangzuocaotong, 745+Huanbifucaotong, 745+Sanzuohuangcaotong, 745+Benzuofucaotong, 745+Pyrasulfotole, 745+Pyrazolate, 745+Benzofenap, 745+Tolpyralate, 745+Fenquinotrione, 745+Isoxaflutole, 745+Fluroxypyr or esters thereof, 745+Halauxifen-methyl, 745+Florpyrauxifen-benzyl, 745+Quinclorac, 745+Quinmerac, 745+Chipton or salts/esters thereof, 745+2-methyl 4-chlorophenoxypropionic acid or salts/esters thereof, 745+MCPB or salts/esters thereof, 745+2,4-D or salts/esters thereof, 745+Dichlorprop or salts/esters thereof, 745+2,4-DB or salts/esters thereof, 745+Dicamba, 745+Picloram, 745+Trichlopyr, 745+Clopyralid, 745+Triclopyr, 745+Flurochloridone, 745+Flurtamone, 745+Diflufenican, 745+Picolinafen, 745+Beflubutamid, 745+Norflurazon, 745+Fluridone.

746+Sulcotrione, 746+Mesotrione, 746+Topramezone, 746+Tembotrione, 746+Bicyclopyrone, 746+Tefuryltrione, 746+Benzobicyclon, 746+Lancotrione, 746+Shuangzuocaotong, 746+Huanbifucaotong, 746+Sanzuohuangcaotong, 746+Benzuofucaotong, 746+Pyrasulfotole, 746+Pyrazolate, 746+Benzofenap, 746+Tolpyralate, 746+Fenquinotrione, 746+Isoxaflutole, 746+Fluroxypyr or esters thereof, 746+Halauxifen-methyl, 746+Florpyrauxifen-benzyl, 746+Quinclorac, 746+Quinmerac, 746+Chipton or salts/esters thereof, 746+2-methyl 4-chlorophenoxypropionic acid or salts/esters thereof, 746+MCPB or salts/esters thereof, 746+2,4-D or salts/esters thereof, 746+Dichlorprop or salts/esters thereof, 746+2,4-DB or salts/esters thereof, 746+Dicamba, 746+Picloram, 746+Trichlopyr, 746+Clopyralid, 746+Triclopyr, 746+Flurochloridone, 746+Flurtamone, 746+Diflufenican, 746+Picolinafen, 746+Beflubutamid, 746+Norflurazon, 746+Fluridone.

779+Sulcotrione, 779+Mesotrione, 779+Topramezone, 779+Tembotrione, 779+Bicyclopyrone, 779+Tefuryltrione, 779+Benzobicyclon, 779+Lancotrione, 779+Shuangzuocaotong, 779+Huanbifucaotong, 779+Sanzuohuangcaotong, 779+Benzuofucaotong, 779+Pyrasulfotole, 779+Pyrazolate, 779+Benzofenap, 779+Tolpyralate, 779+Fenquinotrione, 779+Isoxaflutole, 779+Fluroxypyr or esters thereof, 779+Halauxifen-methyl, 779+Florpyrauxifen-benzyl, 779+Quinclorac, 779+Quinmerac, 779+Chipton or salts/esters thereof, 779+2-methyl 4-chlorophenoxypropionic acid or salts/esters thereof, 779+MCPB or salts/esters thereof, 779+2,4-D or salts/esters thereof, 779+Dichlorprop or salts/esters thereof, 779+2,4-DB or salts/esters thereof, 779+Dicamba, 779+Picloram, 779+Trichlopyr, 779+Clopyralid, 779+Triclopyr, 779+Flurochloridone, 779+Flurtamone, 779+Diflufenican, 779+Picolinafen, 779+Beflubutamid, 779+Norflurazon, 779+Fluridone.

963+Sulcotrione, 963+Mesotrione, 963+Topramezone, 963+Tembotrione, 963+Bicyclopyrone, 963+Tefuryltrione, 963+Benzobicyclon, 963+Lancotrione, 963+Shuangzuocaotong, 963+Huanbifucaotong, 963+Sanzuohuangcaotong, 963+Benzuofucaotong, 963+Pyrasulfotole, 963+Pyrazolate, 963+Benzofenap, 963+Tolpyralate, 963+Fenquinotrione, 963+Isoxaflutole, 963+Fluroxypyr or esters thereof, 963+Halauxifen-methyl, 963+Florpyrauxifen-benzyl, 963+Quinclorac, 963+Quinmerac, 963+Chipton or salts/esters thereof, 963+2-methyl 4-chlorophenoxypropionic acid or salts/esters thereof, 963+MCPB or salts/esters thereof, 963+2,4-D or salts/esters thereof, 963+Dichlorprop or salts/esters thereof, 963+2,4-DB or salts/esters thereof, 963+Dicamba, 963+Picloram, 963+Trichlopyr, 963+Clopyralid, 963+Triclopyr, 963+Flurochloridone, 963+Flurtamone, 963+Diflufenican, 963+Picolinafen, 963+Beflubutamid, 963+Norflurazon, 963+Fluridone.

1000+Sulcotrione, 1000+Mesotrione, 1000+Topramezone, 1000+Tembotrione, 1000+Bicyclopyrone, 1000+Tefuryltrione, 1000+Benzobicyclon, 1000+Lancotrione, 1000+Shuangzuocaotong, 1000+Huanbifucaotong, 1000+Sanzuohuangcaotong, 1000+Benzuofucaotong, 1000+Pyrasulfotole, 1000+Pyrazolate, 1000+Benzofenap, 1000+Tolpyralate, 1000+Fenquinotrione, 1000+Isoxaflutole, 1000+Fluroxypyr or esters thereof, 1000+Halauxifen-methyl, 1000+Florpyrauxifen-benzyl, 1000+Quinclorac, 1000+Quinmerac, 1000+Chipton or salts/esters thereof, 1000+2-methyl 4-chlorophenoxypropionic acid or salts/esters thereof, 1000+MCPB or salts/esters thereof, 1000+2,4-D or salts/esters thereof, 1000+Dichlorprop or salts/esters thereof, 1000+2,4-DB or salts/esters thereof, 1000+Dicamba, 1000+Picloram, 1000+Trichlopyr, 1000+Clopyralid, 1000+Triclopyr, 1000+Flurochloridone, 1000+Flurtamone, 1000+Diflufenican, 1000+Picolinafen, 1000+Beflubutamid, 1000+Norflurazon, 1000+Fluridone.

1-3+Sulcotrione, 1-3+Mesotrione, 1-3+Topramezone, 1-3+Tembotrione, 1-3+Bicyclopyrone, 1-3+Tefuryltrione, 1-3+Benzobicyclon, 1-3+Lancotrione, 1-3+Shuangzuocaotong, 1-3+Huanbifucaotong, 1-3+Sanzuohuangcaotong, 1-3+Benzuofucaotong, 1-3+Pyrasulfotole, 1-3+Pyrazolate, 1-3+Benzofenap, 1-3+Tolpyralate, 1-3+Fenquinotrione, 1-3+Isoxaflutole, 1-3+Fluroxypyr or esters thereof, 1-3+Halauxifen-methyl, 1-3+Florpyrauxifen-benzyl, 1-3+Quinclorac, 1-3+Quinmerac, 1-3+Chipton or salts/esters thereof, 1-3+2-methyl 4-chlorophenoxypropionic acid or salts/esters thereof, 1-3+MCPB or salts/esters thereof, 1-3+2,4-D or salts/esters thereof, 1-3+Dichlorprop or salts/esters thereof, 1-3+2,4-DB or salts/esters thereof, 1-3+Dicamba, 1-3+Picloram, 1-3+Trichlopyr, 1-3+Clopyralid, 1-3+Triclopyr, 1-3+Flurochloridone, 1-3+Flurtamone, 1-3+Diflufenican, 1-3+Picolinafen, 1-3+Beflubutamid, 1-3+Norflurazon, 1-3+Fluridone.

1-39+Sulcotrione, 1-39+Mesotrione, 1-39+Topramezone, 1-39+Tembotrione, 1-39+Bicyclopyrone, 1-39+Tefuryltrione, 1-39+Benzobicyclon, 1-39+Lancotrione, 1-39+Shuangzuocaotong, 1-39+Huanbifucaotong, 1-39+Sanzuohuangcaotong, 1-39+Benzuofucaotong, 1-39+Pyrasulfotole, 1-39+Pyrazolate, 1-39+Benzofenap, 1-39+Tolpyralate, 1-39+Fenquinotrione, 1-39+Isoxaflutole, 1-39+Fluroxypyr or esters thereof, 1-39+Halauxifen-methyl, 1-39+Florpyrauxifen-benzyl, 1-39+Quinclorac, 1-39+Quinmerac, 1-39+Chipton or salts/esters thereof, 1-39+2-methyl 4-chlorophenoxypropionic acid or salts/esters thereof, 1-39+MCPB or salts/esters thereof, 1-39+2,4-D or salts/esters thereof, 1-39+Dichlorprop or salts/esters thereof, 1-39+2,4-DB or salts/esters thereof, 1-39+Dicamba, 1-39+Picloram, 1-39+Trichlopyr, 1-39+Clopyralid, 1-39+Triclopyr, 1-39+Flurochloridone, 1-39+Flurtamone, 1-39+Diflufenican, 1-39+Picolinafen, 1-39+Beflubutamid, 1-39+Norflurazon, 1-39+Fluridone.

1-43+Sulcotrione, 1-43+Mesotrione, 1-43+Topramezone, 1-43+Tembotrione, 1-43+Bicyclopyrone, 1-43+Tefuryltrione, 1-43+Benzobicyclon, 1-43+Lancotrione, 1-43+Shuangzuocaotong, 1-43+Huanbifucaotong, 1-43+Sanzuohuangcaotong, 1-43+Benzuofucaotong, 1-43+Pyrasulfotole, 1-43+Pyrazolate, 1-43+Benzofenap, 1-43+Tolpyralate, 1-43+Fenquinotrione, 1-43+Isoxaflutole, 1-43+Fluroxypyr or esters thereof, 1-43+Halauxifen-methyl, 1-43+Florpyrauxifen-benzyl, 1-43+Quinclorac, 1-43+Quinmerac, 1-43+Chipton or salts/esters thereof, 1-43+2-methyl 4-chlorophenoxypropionic acid or salts/esters thereof, 1-43+MCPB or salts/esters thereof, 1-43+2,4-D or salts/esters thereof, 1-43+Dichlorprop or salts/esters thereof, 1-43+2,4-DB or salts/esters thereof, 1-43+Dicamba, 1-43+Picloram, 1-43+Trichlopyr, 1-43+Clopyralid, 1-43+Triclopyr, 1-43+Flurochloridone, 1-43+Flurtamone, 1-43+Diflufenican, 1-43+Picolinafen, 1-43+Beflubutamid, 1-43+Norflurazon, 1-43+Fluridone.

1-55+Sulcotrione, 1-55+Mesotrione, 1-55+Topramezone, 1-55+Tembotrione, 1-55+Bicyclopyrone, 1-55+Tefuryltrione, 1-55+Benzobicyclon, 1-55+Lancotrione, 1-55+Shuangzuocaotong, 1-55+Huanbifucaotong, 1-55+Sanzuohuangcaotong, 1-55+Benzuofucaotong, 1-55+Pyrasulfotole, 1-55+Pyrazolate, 1-55+Benzofenap, 1-55+Tolpyralate, 1-55+Fenquinotrione, 1-55+Isoxaflutole, 1-55+Fluroxypyr or esters thereof, 1-55+Halauxifen-methyl, 1-55+Florpyrauxifen-benzyl, 1-55+Quinclorac, 1-55+Quinmerac, 1-55+Chipton or salts/esters thereof, 1-55+2-methyl 4-chlorophenoxypropionic acid or salts/esters thereof, 1-55+MCPB or salts/esters thereof, 1-55+2,4-D or salts/esters thereof, 1-55+Dichlorprop or salts/esters thereof, 1-55+2,4-DB or salts/esters thereof, 1-55+Dicamba, 1-55+Picloram, 1-55+Trichlopyr, 1-55+Clopyralid, 1-55+Triclopyr, 1-55+Flurochloridone, 1-55+Flurtamone, 1-55+Diflufenican, 1-55+Picolinafen, 1-55+Beflubutamid, 1-55+Norflurazon, 1-55+Fluridone.

1-82+Sulcotrione, 1-82+Mesotrione, 1-82+Topramezone, 1-82+Tembotrione, 1-82+Bicyclopyrone, 1-82+Tefuryltrione, 1-82+Benzobicyclon, 1-82+Lancotrione, 1-82+Shuangzuocaotong, 1-82+Huanbifucaotong, 1-82+Sanzuohuangcaotong, 1-82+Benzuofucaotong, 1-82+Pyrasulfotole, 1-82+Pyrazolate, 1-82+Benzofenap, 1-82+Tolpyralate, 1-82+Fenquinotrione, 1-82+Isoxaflutole, 1-82+Fluroxypyr or esters thereof, 1-82+Halauxifen-methyl, 1-82+Florpyrauxifen-benzyl, 1-82+Quinclorac, 1-82+Quinmerac, 1-82+Chipton or salts/esters thereof, 1-82+2-methyl 4-chlorophenoxypropionic acid or salts/esters thereof, 1-82+MCPB or salts/esters thereof, 1-82+2,4-D or salts/esters thereof, 1-82+Dichlorprop or salts/esters thereof, 1-82+2,4-DB or salts/esters thereof, 1-82+Dicamba, 1-82+Picloram, 1-82+Trichlopyr, 1-82+Clopyralid, 1-82+Triclopyr, 1-82+Flurochloridone, 1-82+Flurtamone, 1-82+Diflufenican, 1-82+Picolinafen, 1-82+Beflubutamid, 1-82+Norflurazon, 1-82+Fluridone.

1-86+Sulcotrione, 1-86+Mesotrione, 1-86+Topramezone, 1-86+Tembotrione, 1-86+Bicyclopyrone, 1-86+Tefuryltrione, 1-86+Benzobicyclon, 1-86+Lancotrione, 1-86+Shuangzuocaotong, 1-86+Huanbifucaotong, 1-86+Sanzuohuangcaotong, 1-86+Benzuofucaotong, 1-86+Pyrasulfotole, 1-86+Pyrazolate, 1-86+Benzofenap, 1-86+Tolpyralate, 1-86+Fenquinotrione, 1-86+Isoxaflutole, 1-86+Fluroxypyr or esters thereof, 1-86+Halauxifen-methyl, 1-86+Florpyrauxifen-benzyl, 1-86+Quinclorac, 1-86+Quinmerac, 1-86+Chipton or salts/esters thereof, 1-86+2-methyl 4-chlorophenoxypropionic acid or salts/esters thereof, 1-86+MCPB or salts/esters thereof, 1-86+2,4-D or salts/esters thereof, 1-86+Dichlorprop or salts/esters thereof, 1-86+2,4-DB or salts/esters thereof, 1-86+Dicamba, 1-86+Picloram, 1-86+Trichlopyr, 1-86+Clopyralid, 1-86+Triclopyr, 1-86+Flurochloridone, 1-86+Flurtamone, 1-86+Diflufenican, 1-86+Picolinafen, 1-86+Beflubutamid, 1-86+Norflurazon, 1-86+Fluridone.

1-226+Sulcotrione, 1-226+Mesotrione, 1-226+Topramezone, 1-226+Tembotrione, 1-226+Bicyclopyrone, 1-226+Tefuryltrione, 1-226+Benzobicyclon, 1-226+Lancotrione, 1-226+Shuangzuocaotong, 1-226+Huanbifucaotong, 1-226+Sanzuohuangcaotong, 1-226+Benzuofucaotong, 1-226+Pyrasulfotole, 1-226+Pyrazolate, 1-226+Benzofenap, 1-226+Tolpyralate, 1-226+Fenquinotrione, 1-226+Isoxaflutole, 1-226+Fluroxypyr or esters thereof, 1-226+Halauxifen-methyl, 1-226+Florpyrauxifen-benzyl, 1-226+Quinclorac, 1-226+Quinmerac, 1-226+Chipton or salts/esters thereof, 1-226+2-methyl 4-chlorophenoxypropionic acid or salts/esters thereof, 1-226+MCPB or salts/esters thereof, 1-226+2,4-D or salts/esters thereof, 1-226+Dichlorprop or salts/esters thereof, 1-226+2,4-DB or salts/esters thereof, 1-226+Dicamba, 1-226+Picloram, 1-226+Trichlopyr, 1-226+Clopyralid, 1-226+Triclopyr, 1-226+Flurochloridone, 1-226+Flurtamone, 1-226+Diflufenican, 1-226+Picolinafen, 1-226+Beflubutamid, 1-226+Norflurazon, 1-226+Fluridone.

1-227+Sulcotrione, 1-227+Mesotrione, 1-227+Topramezone, 1-227+Tembotrione, 1-227+Bicyclopyrone, 1-227+Tefuryltrione, 1-227+Benzobicyclon, 1-227+Lancotrione, 1-227+Shuangzuocaotong, 1-227+Huanbifucaotong, 1-227+Sanzuohuangcaotong, 1-227+Benzuofucaotong, 1-227+Pyrasulfotole, 1-227+Pyrazolate, 1-227+Benzofenap, 1-227+Tolpyralate, 1-227+Fenquinotrione, 1-227+Isoxaflutole, 1-227+Fluroxypyr or esters thereof, 1-227+Halauxifen-methyl, 1-227+Florpyrauxifen-benzyl, 1-227+Quinclorac, 1-227+Quinmerac, 1-227+Chipton or salts/esters thereof, 1-227+2-methyl 4-chlorophenoxypropionic acid or salts/esters thereof, 1-227+MCPB or salts/esters thereof, 1-227+2,4-D or salts/esters thereof, 1-227+Dichlorprop or salts/esters thereof, 1-227+2,4-DB or salts/esters thereof, 1-227+Dicamba, 1-227+Picloram, 1-227+Trichlopyr, 1-227+Clopyralid, 1-227+Triclopyr, 1-227+Flurochloridone, 1-227+Flurtamone, 1-227+Diflufenican, 1-227+Picolinafen, 1-227+Beflubutamid, 1-227+Norflurazon, 1-227+Fluridone.

1-228+Sulcotrione, 1-228+Mesotrione, 1-228+Topramezone, 1-228+Tembotrione, 1-228+Bicyclopyrone, 1-228+Tefuryltrione, 1-228+Benzobicyclon, 1-228+Lancotrione, 1-228+Shuangzuocaotong, 1-228+Huanbifucaotong, 1-228+Sanzuohuangcaotong, 1-228+Benzuofucaotong, 1-228+Pyrasulfotole, 1-228+Pyrazolate, 1-228+Benzofenap, 1-228+Tolpyralate, 1-228+Fenquinotrione, 1-228+Isoxaflutole, 1-228+Fluroxypyr or esters thereof, 1-228+Halauxifen-methyl, 1-228+Florpyrauxifen-benzyl, 1-228+Quinclorac, 1-228+Quinmerac, 1-228+Chipton or salts/esters thereof, 1-228+2-methyl 4-chlorophenoxypropionic acid or salts/esters thereof, 1-228+MCPB or salts/esters thereof, 1-228+2,4-D or salts/esters thereof, 1-228+Dichlorprop or salts/esters thereof, 1-228+2,4-DB or salts/esters thereof, 1-228+Dicamba, 1-228+Picloram, 1-228+Trichlopyr, 1-228+Clopyralid, 1-228+Triclopyr, 1-228+Flurochloridone, 1-228+Flurtamone, 1-228+Diflufenican, 1-228+Picolinafen, 1-228+Beflubutamid, 1-228+Norflurazon, 1-228+Fluridone.

1-229+Sulcotrione, 1-229+Mesotrione, 1-229+Topramezone, 1-229+Tembotrione, 1-229+Bicyclopyrone, 1-229+Tefuryltrione, 1-229+Benzobicyclon, 1-229+Lancotrione, 1-229+Shuangzuocaotong, 1-229+Huanbifucaotong, 1-229+Sanzuohuangcaotong, 1-229+Benzuofucaotong, 1-229+Pyrasulfotole, 1-229+Pyrazolate, 1-229+Benzofenap, 1-229+Tolpyralate, 1-229+Fenquinotrione, 1-229+Isoxaflutole, 1-229+Fluroxypyr or esters thereof, 1-229+Halauxifen-methyl, 1-229+Florpyrauxifen-benzyl, 1-229+Quinclorac, 1-229+Quinmerac, 1-229+Chipton or salts/esters thereof, 1-229+2-methyl 4-chlorophenoxypropionic acid or salts/esters thereof, 1-229+MCPB or salts/esters thereof, 1-229+2,4-D or salts/esters thereof, 1-229+Dichlorprop or salts/esters thereof, 1-229+2,4-DB or salts/esters thereof, 1-229+Dicamba, 1-229+Picloram, 1-229+Trichlopyr, 1-229+Clopyralid, 1-229+Triclopyr, 1-229+Flurochloridone, 1-229+Flurtamone, 1-229+Diflufenican, 1-229+Picolinafen, 1-229+Beflubutamid, 1-229+Norflurazon, 1-229+Fluridone.

1-230+Sulcotrione, 1-230+Mesotrione, 1-230+Topramezone, 1-230+Tembotrione, 1-230+Bicyclopyrone, 1-230+Tefuryltrione, 1-230+Benzobicyclon, 1-230+Lancotrione, 1-230+Shuangzuocaotong, 1-230+Huanbifucaotong, 1-230+Sanzuohuangcaotong, 1-230+Benzuofucaotong, 1-230+Pyrasulfotole, 1-230+Pyrazolate, 1-230+Benzofenap, 1-230+Tolpyralate, 1-230+Fenquinotrione, 1-230+Isoxaflutole, 1-230+Fluroxypyr or esters thereof, 1-230+Halauxifen-methyl, 1-230+Florpyrauxifen-benzyl, 1-230+Quinclorac, 1-230+Quinmerac, 1-230+Chipton or salts/esters thereof, 1-230+2-methyl 4-chlorophenoxypropionic acid or salts/esters thereof, 1-230+MCPB or salts/esters thereof, 1-230+2,4-D or salts/esters thereof, 1-230+Dichlorprop or salts/esters thereof, 1-230+2,4-DB or salts/esters thereof, 1-230+Dicamba, 1-230+Picloram, 1-230+Trichlopyr, 1-230+Clopyralid, 1-230+Triclopyr, 1-230+Flurochloridone, 1-230+Flurtamone, 1-230+Diflufenican, 1-230+Picolinafen, 1-230+Beflubutamid, 1-230+Norflurazon, 1-230+Fluridone.

Wherein, the actual control effect of the combination of the above components (i) and (ii) on weeds were tested with postemergence applications, that is, when the weeds were in the 3-4 leaf stage, the combination mentioned above diluted with 30 kg/667 $m^2$ water were sprayed uniformly to the stems and leaves of the weed by the hand sprayer. 20 days after treatment, Theoretical fresh weight inhibition rate of a combination of two active ingredients in each group was calculated by the Gowing method ($E0=X+Y-X*Y/100$), and then compared with an actually measured inhibition rate (E), thereby effect of the combination (hereafter referred to as combined effect) on weeds was evaluated: the value of E−E0, which was greater than 10%, corresponded to a synergistic effect, the value of E−E0, which was less than −10%, corresponded to an antagonistic effect, and the value of E−E0, which was from −10% to 10%, corresponded to an additional effect. An optimum ratio of the two active ingredients was determined by the actual control effect, characteristics of herbicides, and balance of a corresponding formula. Wherein, in the formula, X represented the fresh weight inhibition rate of the active ingredient A in a dosage of P, and Y represented the fresh weight inhibition rate of the active ingredient B in a dosage of Q. The statistic results are shown in Table 6.

TABLE 6

Actual control effect and synergistic effect of the mixture of (i) and (ii) in weeds (Gowing method)

| Component (i)/ Compound No. | Component (ii) | (i) + (ii) g a.i./ha | Weed species | Inhibitory effect of component (i) when applied alone at same dose | Inhibitory effect of component (ii) when applied alone at same dose (%) | E (%) | E0 (%) | E − E0 (%) |
|---|---|---|---|---|---|---|---|---|
| 1 | Sulcotrione | 30 + 50 | *Abutilon theophrasti* | 20 | 30 | 100 | 44 | 56 |
| 1 | Mesotrione | 30 + 30 | *Abutilon theophrasti* | 20 | 40 | 100 | 52 | 48 |
| 1 | Topramezone | 30 + 5 | *Abutilon theophrasti* | 20 | 40 | 100 | 52 | 48 |
| 1 | Tembotrione | 30 + 15 | *Abutilon theophrasti* | 20 | 30 | 100 | 44 | 56 |
| 1 | Bicyclopyrone | 30 + 15 | *Abutilon theophrasti* | 20 | 40 | 100 | 52 | 48 |
| 1 | Tefuryltrione | 30 + 50 | *Abutilon theophrasti* | 20 | 40 | 80 | 52 | 28 |
| 1 | Benzobicyclon | 30 + 150 | *Abutilon theophrasti* | 20 | 50 | 100 | 60 | 40 |
| 1 | Lancotrione | 30 + 50 | *Abutilon theophrasti* | 20 | 40 | 100 | 52 | 48 |
| 1 | Shuangzuocaotong | 30 + 5 | *Sisymbrium sophia* | 20 | 40 | 100 | 52 | 48 |
| 1 | Huanbifucaotong | 30 + 30 | *Abutilon theophrasti* | 20 | 30 | 100 | 44 | 56 |
| 1 | Sanzuohuangcaotong | 30 + 30 | *Abutilon theophrasti* | 20 | 30 | 100 | 44 | 56 |
| 1 | Benzuofucaotong | 30 + 15 | *Abutilon theophrasti* | 20 | 40 | 100 | 52 | 48 |
| 1 | Pyrasulfotole | 30 + 15 | *Abutilon theophrasti* | 20 | 50 | 100 | 60 | 40 |
| 1 | Benzofenap | 30 + 150 | *Abutilon theophrasti* | 20 | 40 | 100 | 52 | 48 |
| 1 | Tolpyralate | 30 + 5 | *Abutilon theophrasti* | 20 | 50 | 100 | 60 | 40 |
| 1 | Isoxaflutole | 30 + 30 | *Abutilon theophrasti* | 20 | 30 | 100 | 44 | 56 |
| 1 | Fluroxypyr | 30 + 30 | *Galium aparine* | 20 | 40 | 80 | 52 | 28 |
| 1 | Halauxifen-methyl | 30 + 2 | *Abutilon theophrasti* | 20 | 40 | 100 | 52 | 48 |
| 1 | Florpyrauxifen-benzyl | 30 + 2 | *Abutilon theophrasti* | 20 | 45 | 100 | 56 | 44 |
| 1 | Quinclorac | 30 + 50 | *Galium aparine* | 20 | 50 | 80 | 60 | 20 |
| 1 | Chipton sodium salt | 30 + 60 | *Sisymbrium sophia* | 20 | 40 | 80 | 52 | 28 |
| 1 | 2-methyl 4-chlorophenoxy propionic acid | 30 + 100 | *Sisymbrium sophia* | 20 | 30 | 75 | 44 | 31 |
| 1 | MCPB | 30 + 200 | *Sisymbrium sophia* | 20 | 40 | 85 | 52 | 33 |
| 1 | 2,4-D iso-octyl ester | 30 + 50 | *Sisymbrium sophia* | 20 | 40 | 85 | 52 | 33 |
| 1 | Dichlorprop | 30 + 100 | *Sisymbrium sophia* | 20 | 40 | 100 | 52 | 48 |
| 1 | 2,4-DB | 30 + 200 | *Sisymbrium sophia* | 20 | 50 | 90 | 60 | 30 |
| 1 | Dicamba | 30 + 10 | *Sisymbrium sophia* | 20 | 30 | 75 | 44 | 31 |
| 1 | Picloram | 30 + 50 | *Abutilon theophrasti* | 20 | 40 | 80 | 52 | 28 |
| 1 | Trichlopyr | 30 + 50 | *Abutilon theophrasti* | 20 | 40 | 70 | 52 | 18 |

TABLE 6-continued

Actual control effect and synergistic effect of the mixture of (i) and (ii) in weeds (Gowing method)

| Component (i)/ Compound No. | Component (ii) | (i) + (ii) g a.i./ha | Weed species | Inhibitory effect of component (i) when applied alone at same dose | Inhibitory effect of component (ii) when applied alone at same dose (%) | E (%) | E0 (%) | E − E0 (%) |
|---|---|---|---|---|---|---|---|---|
| 1 | Clopyralid | 30 + 50 | *Galinsoga parviflora* | 30 | 40 | 85 | 58 | 27 |
| 1 | Triclopyr | 30 + 50 | *Abutilon theophrasti* | 20 | 35 | 75 | 48 | 27 |
| 1 | Flurochloridone | 30 + 100 | *Galium aparine* | 20 | 40 | 90 | 52 | 38 |
| 1 | Flurtamone | 30 + 100 | *Galium aparine* | 20 | 35 | 85 | 48 | 37 |
| 1 | Diflufenican | 30 + 100 | *Veronica polita* | 30 | 45 | 90 | 61.5 | 28.5 |
| 1 | Picolinafen | 30 + 50 | *Abutilon theophrasti* | 20 | 30 | 85 | 44 | 41 |
| 1 | Beflubutamid | 30 + 200 | *Abutilon theophrasti* | 20 | 40 | 100 | 52 | 48 |
| 1 | Norflurazon | 30 + 300 | *Abutilon theophrasti* | 20 | 50 | 85 | 60 | 25 |
| 1 | Fluridone | 30 + 100 | *Abutilon theophrasti* | 20 | 45 | 85 | 56 | 29 |

At the same time, it is found after several tests that similar herbicidal effects were achieved when other components (i) of the present invention were combined with the component (ii). In addition, the compound and the composition of the present invention have good selectivity to many gramineae grasses such as *Zoysia japonica*, bermuda grass, tall fescue, bluegrass, ryegrass and seashore *Paspalum* etc, and are able to control many important grass weeds and broadleaf weeds. The compounds also show excellent selectivity and commercial value in the tests on wheat, corn, rice, sugarcane, soybean, cotton, oil sunflower, potato, orchards and vegetables in different herbicide application methods.

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route. Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art, for example, protection of suitable group in the process of the reaction, etc.

The following method of application can be used to improve further understanding of the preparation method of the present invention. The specific material, class and condition have been determined to be further explication of the present invention, not to be any limit of the reasonable scope thereof. Reagents of the following synthetic compound showed in the table can either be purchased from the market or easily prepared by those skilled in the art.

Examples of representative compounds are as follows:

1. Synthesis of Compound 1

What is claimed is:

1. A herbicidally active pyridazinol compound of Formula I or a derivative thereof:

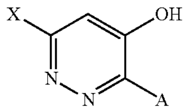

1 wherein, X is halogenated alkyl;

A is selected from unsubstituted or substituted C2-C8 alkenyl, unsubstituted or substituted C2-C8 alkynyl, unsubstituted or substituted C3-C8 cycloalkyl, unsubstituted or substituted C3-C8 cycloalkenyl, unsubstituted or substituted C3-C8 cycloalkyl-C1-C8 alkyl, unsubstituted or substituted

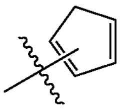

, unsubstituted or substituted 5- to 14-membered heteroaryl, and unsubstituted or substituted 5- to 14-membered aliphatic heterocyclyl; wherein, when being substituted, said C2-C8 alkenyl, C2-C8 alkynyl, C3-C8 cycloalkyl, C3-C8 cycloalkenyl, or C3-C8 cycloalkyl-C1-C8 alkyl is substituted with one or more substituents independently selected from halogen, cyano, nitro, azido, aryl, and heteroaryl, said aryl or heteroaryl is unsubstituted or independently substituted with 1-5 groups selected from halogen, cyano, nitro, hydroxy, carboxyl, sulfhydryl, amino, and a halogen-containing or not containing group selected from C1-C8 alkyl, C3-C8 cycloalkyl, C3-C8 cycloalkenyl, C3-C8 cycloalkyl-C1-C8 alkyl, C2-C8 alkenyl, C2-C8 alkynyl, C1-C8 alkoxy, C1-C8 alkylcarbonyl, C1-C8 alkoxycarbonyl, C1-C8 alkylsulfonyl, C1-C8 alkylamino, and C1-C8 alkylcarbonyloxy, —(CH2)n-O—(CH2)p-, —(CH2)n-S—(CH2)p-, —(CH2)n-NR3-(CH2)p-, R—O—, R—O—(CH2)p-O—, R—O—(CH2)p-S—, R—S—, R—S—(CH2)p-O—, R—S—(CH2)p-S—, R—O—(C═O)—(CH2)q-(O)m-, R—O—(CH2)n-(C═O)—(O)m-, R—O—(CH2)n-(C═O)—, R—S—(C═S)—(CH2)q-(S)m-, R—S—(CH2)n-(C═S)—(S)m-, R—S—(CH2)n-(C═S)—, R—O—(C═O)—(CH2)q-(S)m-, R—O—(CH2)n-(C═O)—(S)m-, R—O—(C═S)—(CH2)q-(O)m-, R—O—(CH2)n-(C═S)—(O)m-, R—O—(CH2)n-(C═S)—, R—S—(C═O)—(CH2)q-(O)m-, R—S—(CH2)n-(C═O)—(O)m-, R—S—(CH2)n-(C═O)—, R—O—(C═S)—(CH2)q-(S)m-, R—O—(CH2)n-(C═S)—(S)m-, R—S—(C═O)—(CH2)q-(S)m-, R—S—(CH2)n-(C═O)—(S)m-, R—S—(C═S)—(CH2)q-(O)m-, R—S—(CH2)n-(C═S)—(O)m-, R—(C═O)—, R—(C═S)—, R—(C═O)—O—, R—(C═S)—S—, R—(C═O)—S—, R—(C═S)—O—, R—SO—(O)m-, R—SO—(S)m-, R—SO—(NR3)m-, R—SO2-(O)m-, R—SO2-(S)m-, R—SO2 (NR3)m-, R1 R2N—, R1 R2N—O—(CH2)q-(O)m-, R1 R2N—(CH2)n-O—, R1 R2N—O—(CH2)q-(S)m-, R1 R2N—O—(CH2)q-(NR3)m-, R1 R2N—(C═O)—(CH2)q-(O)m-, R1 R2N—(CH2)n-(C═O)—(O)m-, R1 R2N—(CH2)n-(C═O)—, R1 R2N—(C═O)—(CH2)q-(S)m-, R1 R2N—(CH2)n-(C═O)—(S)m-, R1 R2N—(C═O)—(CH2)q-(NR3)m-, R1 R2N—(CH2) n-(C═O)—(NR3)m-, R1 R2N—SO2-(CH2)q-(O)m-, R1 R2N—(CH2)n-SO2-(O)m-, R1 R2N—(CH2)n-SO2-, R1 R2N—SO2-(CH2)q-(S)m-, R1 R2N—(CH2) n-SO2-(S)m-, R1 R2N—SO2-(CH2)q-(NR3)m-, R1 R2N—(CH2)n-SO2-(NR3)m-, R1 R2P(O)—, R1 R2R3SiO—, R1 R2R3Si—(CH═CH)m-, R1 R2C═N—(O)m-, and R1 R2C═N—NH—;

when being substituted, each of said

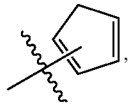

5- to 14-membered heteroaryl or 5- to 14-membered aliphatic heterocyclyl is independently substituted with one or more substituents selected from halogen, cyano, nitro, azido, a halogen-containing or not containing group selected from C1-C8 alkyl, C2-C8 alkenyl, C2-C8 alkynyl, C3-C8 cycloalkyl, C3-C8 cycloalkenyl, and C3-C8 cycloalkyl-C1-C8 alkyl, aryl, aryl-C1-C8 alkyl, heteroaryl, heteroaryl-C1-C8 alkyl, aliphatic heterocyclyl, and aliphatic heterocyclyl-C1-C8 alkyl, each of said aryl, aryl-C1-C8 alkyl, heteroaryl, heteroaryl-C1-C8 alkyl, aliphatic heterocyclyl, or aliphatic heterocyclyl-C1-C8 alkyl is unsubstituted or substituted with 1-5 groups independently selected from halogen, cyano, nitro, hydroxy, carboxyl, sulfhydryl, amino, and a halogen-containing or not containing group selected from C1-C8 alkyl, C3-C8 cycloalkyl, C3-C8 cycloalkenyl, C3-C8 cycloalkyl-C1-C8 alkyl, C2-C8 alkenyl, C2-C8 alkynyl, C1-C8 alkoxy, C1-C8 alkylcarbonyl, C1-C8 alkoxycarbonyl, C1-C8 alkylsulfonyl, C1-C8 alkylamino, and C1-C8 alkylcarbonyloxy, R—O—(CH2)n-, R—O—(CH2)p-O—(CH2)q-, R—O—(CH2)p-S—(CH2)q-, R—S—(CH2) n-, R—S—(CH2)p-O—(CH2)q-, R—S—(CH2)p-S—(CH2)q-, R—O—(CH2)n-(C═O)—(CH2)q-(O)m-, R—S—(CH2)n-(C═S)—(CH2)q-, R—O—(CH2)n-(C═S)—(CH2)q-, R—S—(CH2)n-(C═O)—(CH2) q-, R—S—(C═S)—(CH2)q-(S)m-, R—O—(CH2)n-(C═O)—(CH2)q-(S)m-, R—O—(C═S)—(CH2)q-(O)m-, R—S—(C═O)—(CH2)q-(O)m-, R—O—(C═S)—(CH2)q-(S)m-, R—S—(C═O)—(CH2)q-(S) m-, R—S—(C═S)—(CH2)q-(O)m-, R—S—(CH2)n-(C═S)—(S)m-, R—O—(CH2)n-(C═S)—(O)m-, R—S—(CH2)n-(C═O)—(O)m-, R—O—(CH2)n-(C═S)—(S)m-, R—S—(CH2)n-(C═O)—(S)m-, R—S—(CH2)n-(C═S)—(O)m-, R—(C═O)—(CH2) n-, R—(C═S)—, R—(C═O)—(CH2)n-O—(CH2)q-, R—(C═S)—(CH2)n-S—, R—(C═O)—(CH2)n-S—, R—(C═S)—(CH2)n-O—, R—(C═S)—S—(CH2)q-, R—(C═O)—S—(CH2)q-, R—(C═S)—O—(CH2) q-, R—SO—(O)m-, R—SO—(S)m-, R—SO—(NR3) m-, R—SO2-(CH2)n-(O)m-, R—SO2-(S)m-, R—SO2-(CH2)n-(NR3)m-, R—SO—(CH2)n-, R1 R2N—(CH2)n-, R1 R2N—(CH2)n-O—(CH2)q-, R1 R2N—(C═O)—(CH2)q-(O)m-, R1 R2N—(CH2)n-(C═O)—(CH2)q-, R1 R2N—(CH2)n-(C═O)—(O) m-, R1 R2N—(CH2)n-(C═O)—(S)m-, R1 R2N—(CH2)n-(C═O)—(NR3)m-, R1 R2N—(CH2)n-SO2-(CH2)q-(O)m-, R1 R2N—(CH2)n-SO2-(S)m-, R1 R2N—(CH2)n-SO2-(NR3)m-, R1 R2N—(C═O)—(CH2)n-(O)m-, R1 R2N—(C═O)—(CH2)n-(S)m-, R1 R2N—(C═O)—(CH2)n-(NR3)m-, R1 R2N—SO2-(CH2)q-(S)m-, R1 R2N—SO2-(CH2)q-(NR3)m-, R1 R2N—(CH2)n-O—, R1 R2N—O—(CH2)q-, R1 R2P (O)—(O)m-, R1 R2R3SiO—, R1 R2R3Si—(CH═CH)m-, R1 R2C═N—(O)m-, and R1 R2C═N—NH—;

m is 0 or 1, n and q are independently an integer from 0 to 6, p is an integer from 1 to 6;

R is hydrogen, a halogen-containing or not containing group selected from C1-C8 alkyl, C2-C8 alkenyl, C2-C8 alkynyl, C3-C8 cycloalkyl, C3-C8 cycloalkenyl, and C3-C8 cycloalkyl-C1-C8 alkyl, aryl, aryl-C1-C8 alkyl, heteroaryl, or heteroaryl-C1-C8 alkyl, each of said aryl, aryl-C1-C8 alkyl, heteroaryl, or heteroaryl-C1-C8 alkyl is unsubstituted or substituted with 1-5 groups substituents independently selected from halogen, cyano, nitro, hydroxy, carboxyl, sulfhydryl, amino, and a halogen-containing or not containing group selected from C1-C8 alkyl, C3-C8 cycloalkyl, C3-C8 cycloalkenyl, C3-C8 cycloalkyl-C1-C8 alkyl, C2-C8 alkenyl, C2-C8 alkynyl, C1-C8 alkoxy, C1-C8 alkylcarbonyl, C1-C8 alkoxycarbonyl, C1-C8 alkylsulfonyl, C1-C8 alkylamino, and C1-C8 alkylcarbonyloxy;

R1, R2, R3 are each independently hydrogen, nitro, hydroxy, amino, a halogen-containing or not containing group selected from C1-C8 alkyl, C2-C8 alkenyl, C2-C8 alkynyl, C3-C8 cycloalkyl, C3-C8 cycloalkenyl, C3-C8 cycloalkyl-C1-C8 alkyl, C1-C8 alkoxy, C2-C8 alkenyloxy, C2-C8 alkynyloxy, C3-C8 cycloalkyloxy, C1-C8 alkoxy-C1-C8 alkyl, C1-C8 alkoxycarbonyl, C1-C8 alkylcarbonyl-C1-C8 alkyl, C1-C8 alkylsulfanylcarbonyl, C1-C8 alkylsulfonyl, C1-C8 alkylsulfonyl-C1-C8 alkyl, C1-C8 alkylcarbonyl, C1-C8 alkylcarbonyloxy, C1-C8 alkylamino, C1-C8 alkylaminocarbonyl, C1-C8 alkoxyaminocarbonyl, C1-C8 alkoxycarbonyl-C1-C8 alkyl, C1-C8 alkylaminocarbonyl-C1-C8 alkyl, triC1-C8 alkylsilyl, and diC1-C8 alkylphosphonyl, aryl, aryl-C1-C8 alkyl, aryloxy, aryl-C1-C8 alkyloxy, aryloxy-C1-C8 alkyl, arylcarbonyl, arylsulfonyl, heteroaryl, heteroaryl-C1-C8 alkyl, heteroaryloxy, heteroaryl-C1-C8 alkyloxy, heteroaryloxy-C1-C8 alkyl, heteroarylcarbonyl, heteroarylsulfonyl, aliphatic heterocyclyl, aliphatic heterocyclyl-C1-C8 alkyl, aliphatic heterocyclyloxy, aliphatic heterocyclyl-C1-C8 alkyloxy, aliphatic heterocyclyloxy-C1-C8 alkyl, aliphatic heterocyclylcarbonyl, or aliphatic heterocyclylsulfonyl, each of said aryl, aryl-C1-C8 alkyl, aryloxy, aryl-C1-C8 alkyloxy, aryloxy-C1-C8 alkyl, arylcarbonyl, arylsulfonyl, heteroaryl, heteroaryl-C1-C8 alkyl, heteroaryloxy, heteroaryl-C1-C8 alkyloxy, heteroaryloxy-C1-C8 alkyl, heteroarylcarbonyl, heteroarylsulfonyl, aliphatic heterocyclyl, aliphatic heterocyclyl-C1-C8 alkyl, aliphatic heterocyclyloxy, aliphatic heterocyclyl-C1-C8 alkyloxy, aliphatic heterocyclyloxy-C1-C8 alkyl, aliphatic heterocyclylcarbonyl, or aliphatic heterocyclylsulfonyl is unsubstituted or substituted with 1-5 groups independently selected from halogen, cyano, nitro, hydroxy, carboxyl, sulfhydryl, amino, and a halogen-containing or not containing group selected from C1-C8 alkyl, C3-C8 cycloalkyl, C3-C8 cycloalkenyl, C3-C8 cycloalkyl-C1-C8 alkyl, C2-C8 alkenyl, C2-C8 alkynyl, C1-C8 alkoxy, C1-C8 alkylcarbonyl, C1-C8 alkoxycarbonyl, C1-C8 alkylsulfonyl, C1-C8 alkylamino, and C1-C8 alkylcarbonyloxy; or R1 R2N— forms a 5- to 6-membered heterocyclyl; or wherein A is phenyl or 7- to 14-membered aryl, which is substituted with one or more substituents independently selected from azido, halogenated C1-C8 alkyl, a halogen-containing aryl, a halogen-containing aryl-C1-C8 alkyl, a halogen-containing or not containing group selected from C2-C8 alkenyl, C2-C8 alkynyl, C3-C8 cycloalkyl, C3-C8 cycloalkenyl, and C3-C8 cycloalkyl-C1-C8 alkyl, heteroaryl, heteroaryl-C1-C8 alkyl, aliphatic heterocyclyl, and aliphatic heterocyclyl-C1-C8 alkyl, each of said heteroaryl, heteroaryl-C1-C8 alkyl, aliphatic heterocyclyl, or aliphatic heterocyclyl-C1-C8 alkyl is unsubstituted or substituted with 1-5 groups independently selected from halogen, cyano, nitro, hydroxy, carboxyl, sulfhydryl, amino, and a halogen-containing or not containing group selected from C1-C8 alkyl, C3-C8 cycloalkyl, C3-C8 cycloalkenyl, C3-C8 cycloalkyl-C1-C8 alkyl, C2-C8 alkenyl, C2-C8 alkynyl, C1-C8 alkoxy, C1-C8 alkylcarbonyl, C1-C8 alkoxycarbonyl, C1-C8 alkylsulfonyl, C1-C8 alkylamino, and C1-C8 alkylcarbonyloxy, R—O—(CH2)n-, R—O—(CH2)p-O—(CH2)q-, R—O—(CH2)p-S—(CH2)q-, R—S—(CH2)n-, R—S—(CH2)p-O—(CH2)q-, R—S—(CH2)p-S—(CH2)q-, R—O—(CH2)n-(C═O)—(CH2)q-(O)m-, R—S—(CH2)n-(C═S)—(CH2)q-, R—O—(CH2)n-(C═S)—(CH2)q-, R—S—(CH2)n-(C═O)—(CH2)q-, R—S—(C═S)—(CH2)q-(S)m-, R—O—(CH2)n-(C═O)—(CH2)q-(S)m-, R—O—(C═S)—(CH2)q-(O)m-, R—S—(C═O)—(CH2)q-(O)m-, R—O—(C═S)—(CH2)q-(S)m-, R—S—(C═O)—(CH2)q-(S)m-, R—S—(C═S)—(CH2)q-(O)m-, R—S—(CH2)n-(C═S)—(S)m-, R—O—(CH2)n-(C═S)—(O)m-, R—S—(CH2)n-(C═O)—(O)m-, R—O—(CH2)n-(C═S)—(S)m-, R—S—(CH2)n-(C═O)—(S)m-, R—S—(CH2)n-(C═S)—(O)m-, R—(C═O)—(CH2)n-, R—(C═S)—, R—(C═O)—(CH2)n-O—(CH2)q-, R—(C═S)—(CH2)n-S—, R—(C═O)—(CH2)n-S—, R—(C═S)—(CH2)n-O—, R—(C═S)—S—(CH2)q-, R—(C═O)—S—(CH2)q-, R—(C═S)—O—(CH2)q-, R—SO—(O)m-, R—SO—(S)m-, R—SO—(NR3)m-, R—SO2-(CH2)n-(O)m-, R—SO2-(S)m-, R—SO2-(CH2)n-(NR3)m-, R—SO—(CH2)n-, R1 R2N—(CH2)n-, R1 R2N—(CH2)n-O—(CH2)q-, R1 R2N—(C═O)—(CH2)q-(O)m-, R1 R2N—(CH2)n-(C═O)—(CH2)q-, R1 R2N—(CH2)n-(C═O)—(O)m-, R1 R2N—(CH2)n-(C═O)—(S)m-, R1 R2N—(CH2)n-(C═O)—(NR3)m-, R1 R2N—(CH2)n-SO2-(CH2)q-(O)m-, R1 R2N—(CH2)n-SO2-(S)m-, R1 R2N—(CH2)n-SO2-(NR3)m-, R1 R2N—(C═O)—(CH2)n-(O)m-, R1 R2N—(C═O)—(CH2)n-(S)m-, R1 R2N—(C═O)—(CH2)n-(NR3)m-, R1 R2N—SO2-(CH2)q-(S)m-, R1 R2N—SO2-(CH2)q-(NR3)m-, R1 R2N—(CH2)n-O—, R1 R2N—O—(CH2)q-, R1 R2P(O)—(O)m-, R1 R2R3SiO—, R1 R2R3Si—(CH═CH)m-, R1 R2C═N—(O)m-, and R1 R2C═N—NH—;

wherein the derivative is an agriculturally acceptable salt or a compound derivatized from 4-hydroxy of the pyridazine ring of the Formula I, further wherein the compound derivatized from 4-hydroxy of the pyridazine ring of the Formula I is selected from an ester, an oxime, and a hydroxylamine thereof.

2. The herbicidally active pyridazinol compound or a derivative thereof according to claim 1, wherein, X is halogenated C1-C8 alkyl;

wherein the derivative is an agriculturally acceptable salt or a compound derivatized from the 4-hydroxy of the pyridazine ring of the Formula I, further wherein the compound derivatized from 4-hydroxy of the pyridazine ring of the Formula I is selected from an ester, an oxime, and a hydroxylamine thereof.

3. The herbicidally active pyridazinol compound or a derivative thereof according to claim 1, wherein, X is halogenated C1-C6 alkyl;

A is selected from unsubstituted or substituted C2-C6 alkenyl, unsubstituted or substituted C2-C6 alkynyl, unsubstituted or substituted C3-C6 cycloalkyl, unsubstituted or substituted C3-C6 cycloalkenyl, unsubstituted or substituted C3-C6 cycloalkyl-C1-C6 alkyl, unsubstituted or substituted

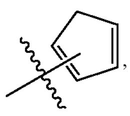, unsubstituted or substituted 5- to 14-membered heteroaryl, and unsubstituted or substituted 5- to 14-membered aliphatic heterocyclyl; wherein, when being substituted, each of said C2-C6 alkenyl, C2-C6 alkynyl, C3-C6 cycloalkyl, C3-C6 cycloalkenyl, or C3-C6 cycloalkyl-C1-C6 alkyl is substituted with one or more substituents independently selected from halogen, cyano, nitro, azido, aryl, heteroaryl, said aryl or heteroaryl is unsubstituted or substituted with 1-3 groups independently selected from halogen, cyano, nitro, hydroxy, carboxyl, sulfhydryl, amino, and a halogen-containing or not containing group selected from C1-C6 alkyl, C3-C6 cycloalkyl, C3-C6 cycloalkenyl, C3-C6 cycloalkyl-C1-C6 alkyl, C2-C6 alkenyl, C2-C6 alkynyl, C1-C6 alkoxy, C1-C6 alkylcarbonyl, C1-C6 alkoxycarbonyl, C1-C6 alkylsulfonyl, C1-C6 alkylamino, and C1-C6 alkylcarbonyloxy, $-(CH_2)_n-O-$, $-(CH_2)_n-S-$, $-(CH_2)_n-NR_3-$, R—O—, R—O—$(CH_2)_p$—O—, R—O—$(CH_2)_p$—S—, R—S—, R—S—$(CH_2)_p$—O—, R—S—$(CH_2)_p$—S—, R—O—$(CH_2)_n$—(C═O)—, R—S—(C═S)—, R—O—(C═S)—, R—S—(C═O)—, R—(C═O)—, R—(C═S)—, R—(C═O)—O—, R—(C═S)—S—, R—(C═O)—S—, R—(C═S)—O—, R—SO—, R—$SO_2$—, $R_1R_2N$—, $R_1R_2N$—O—, $R_1R_2N$—(C═O)—, $R_1R_2N$—$SO_2$—, $R_1R_2P(O)$—, $R_1R_2R_3SiO$—, $R_1R_2R_3Si$—(CH═CH)—, $R_1R_2R_3Si$—, $R_1R_2C$═N—(O)—, $R_1R_2C$═N—, and $R_1R_2C$═N—NH—;

when being substituted, each of said

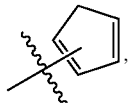, 5- to 14-membered heteroaryl or 5- to 14-membered aliphatic heterocyclyl is substituted with one or more substituents independently selected from halogen, cyano, nitro, azido, a halogen-containing or not containing group selected from C1-C6 alkyl, C2-C6 alkenyl, C2-C6 alkynyl, C3-C6 cycloalkyl, C3-C6 cycloalkenyl, and C3-C6 cycloalkyl-C1-C6 alkyl, aryl, aryl-C1-C6 alkyl, heteroaryl, heteroaryl-C1-C6 alkyl, aliphatic heterocyclyl, aliphatic heterocyclyl-C1-C6 alkyl, each of said aryl, aryl-C1-C6 alkyl, heteroaryl, heteroaryl-C1-C6 alkyl, aliphatic heterocyclyl, or aliphatic heterocyclyl-C1-C6 alkyl is unsubstituted or substituted with 1-5 groups independently selected from halogen, cyano, nitro, hydroxy, carboxyl, sulfhydryl, amino, and a halogen-containing or not containing group selected from C1-C6 alkyl, C3-C6 cycloalkyl, C3-C6 cycloalkenyl, C3-C6 cycloalkyl-C1-C6 alkyl, C2-C6 alkenyl, C2-C6 alkynyl, C1-C6 alkoxy, C1-C6 alkylcarbonyl, C1-C6 alkoxycarbonyl, C1-C6 alkylsulfonyl, C1-C6 alkylamino, and C1-C6 alkylcarbonyloxy, R—O—$(CH_2)_n$—, R—O—$(CH_2)_p$—O—, R—O—$(CH_2)_p$—S—, R—S—$(CH_2)_n$—, R—O—$(CH_2)_n$—(C═O)—$(CH_2)_q$—$(O)_m$—, R—O—$(CH_2)_n$—(C═O)—$(CH_2)_q$—$(S)_m$—, R—S—$(CH_2)_p$—O—, R—S—$(CH_2)_p$—S—, R—S—(C═S)—$(S)_m$—, R—O—(C═S)—$(O)_m$—, R—S—$(CH_2)_n$—(C═O)—$(O)_m$—, R—O—(C═S)—$(S)_m$—, R—S—(C═O)—$(S)_m$—, R—S—(C═S)—$(O)_m$—, R—S—(C═S)—$(CH_2)_q$—, R—O—(C═S)—$(CH_2)_q$—, R—S—(C═O)—$(CH_2)_q$—, R—S—$(CH_2)_n$—(C═S)—, R—O—$(CH_2)_n$—(C═S)—, R—S—$(CH_2)_n$—(C═O)—, R—(C═O)—$(CH_2)_n$—, R—(C═S)—, R—(C═O)—$(CH_2)_n$—O—$(CH_2)_q$—, R—(C═S)—S—, R—(C═O)—S—, R—(C═S)—O—, R—SO—$(CH_2)_n$—, R—$SO_2$—$(CH_2)_n$—$(O)_m$—, R—$SO_2$—$(CH_2)_n$—$(NR_3)_m$—, $R_1R_2N$—$(CH_2)_n$—, $R_1R_2N$—O—, $R_1R_2N$—(C═O)—$(CH_2)_q$—$(O)_m$—, $R_1R_2N$—(C═O)—$(S)_m$—, $R_1R_2N$—(C═O)—$(NR_3)_m$—, $R_1R_2N$—$(CH_2)_n$—$SO_2$—$(CH_2)_q$—$(O)_m$—, $R_1R_2N$—$(CH_2)_p$—(C═O)—, $R_1R_2N$—$(CH_2)_p$—O—, $R_1R_2N$—O—$(CH_2)_p$—, $R_1R_2P(O)$—, $R_1R_2R_3SiO$—, $R_1R_2R_3Si$—, $R_1R_2R_3Si$—CH═CH—, $R_1R_2C$═N—, $R_1R_2C$═N—O—, and $R_1R_2C$═N—NH—;

m is 0 or 1, n and q are each independently an integer from 0 to 4, p is an integer from 1 to 4;

R is hydrogen, a halogen-containing or not containing group selected from C1-C6 alkyl, C2-C6 alkenyl, C2-C6 alkynyl, C3-C6 cycloalkyl, C3-C6 cycloalkenyl, and C3-C6 cycloalkyl-C1-C6 alkyl, aryl, aryl-C1-C6 alkyl, heteroaryl, or heteroaryl-C1-C6 alkyl, each of said aryl, aryl-C1-C6 alkyl, heteroaryl, or heteroaryl-C1-C6 alkyl is unsubstituted or substituted with 1-3 groups independently selected from halogen, cyano, nitro, hydroxy, carboxyl, sulfhydryl, amino, and a halogen-containing or not containing group selected from C1-C6 alkyl, C3-C6 cycloalkyl, C3-C6 cycloalkenyl, C3-C6 cycloalkyl-C1-C6 alkyl, C2-C6 alkenyl, C2-C6 alkynyl, C1-C6 alkoxy, C1-C6 alkylcarbonyl, C1-C6 alkoxycarbonyl, C1-C6 alkylsulfonyl, C1-C6 alkylamino, and C1-C6 alkylcarbonyloxy;

$R_1$, $R_2$, $R_3$ are each independently is hydrogen, nitro, hydroxy, amino, a halogen-containing or not containing group selected from C1-C6 alkyl, C2-C6 alkenyl, C2-C6 alkynyl, C3-C6 cycloalkyl, C3-C6 cycloalkenyl, C3-C6 cycloalkyl-C1-C6 alkyl, C1-C6 alkoxy, C2-C6 alkenyloxy, C2-C6 alkynyloxy, C3-C6 cycloalkyloxy, C1-C6 alkoxy-C1-C6 alkyl, C1-C6 alkoxycarbonyl, C1-C6 alkylsulfanylcarbonyl, C1-C6 alkylsulfonyl, C1-C6 alkylsulfonyl-C1-C6 alkyl, C1-C6 alkylcarbonyl, C1-C6 alkylcarbonyl-C1-C6 alkyl, C1-C6 alkylcarbonyloxy, C1-C6 alkylamino, C1-C6 alkylaminocarbonyl, C1-C6 alkoxyaminocarbonyl, C1-C6 alkoxycarbonyl-C1-C6 alkyl, C1-C6 alkylaminocarbonyl-C1-C6 alkyl, triC1-C6 alkylsilyl, and diC1-C6 alkylphosphonyl, aryl, aryl-C1-C6 alkyl, aryloxy, aryl-C1-C6 alkyloxy, aryloxy-C1-C6 alkyl, arylcarbonyl, arylsulfonyl, heteroaryl, heteroaryl-C1-C6 alkyl, heteroaryloxy, heteroaryl-C1-C6 alkyloxy, heteroaryloxy-C1-C6 alkyl, heteroarylcarbonyl, heteroarylsulfonyl, aliphatic heterocyclyl, aliphatic heterocyclyl-C1-C6 alkyl, aliphatic heterocyclyloxy, aliphatic heterocyclyl-C1-C6 alkyloxy, aliphatic heterocyclyloxy-C1-C6 alkyl, aliphatic heterocyclylcarbonyl, or aliphatic heterocyclylsulfonyl, each of said aryl, aryl-C1-C6 alkyl, aryloxy, aryl-C1-C6 alkyloxy, aryloxy-C1-C6 alkyl, arylcarbonyl, arylsulfonyl, heteroaryl, heteroaryl-C1-C6 alkyl, heteroaryloxy, heteroaryl-C1-C6 alkyloxy, heteroaryloxy-C1-C6 alkyl, heteroarylcarbonyl, heteroarylsulfonyl, aliphatic heterocyclyl, aliphatic heterocyclyl-C1-C6 alkyl, aliphatic heterocyclyloxy, aliphatic heterocyclyl-C1-C6 alkyloxy, aliphatic heterocyclyloxy-C1-C6 alkyl, aliphatic heterocyclylcarbonyl, or aliphatic heterocyclylsulfonyl is unsubstituted or substituted with 1-3 groups independently selected from halogen, cyano, nitro, hydroxy, carboxyl, sulfhydryl, amino, and a halogen-containing or not containing group selected from C1-C6 alkyl, C3-C6 cycloalkyl, C3-C6 cycloalkenyl, C3-C6 cycloalkyl-C1-C6 alkyl, C2-C6 alkenyl, C2-C6 alkynyl, C1-C6 alkoxy, C1-C6 alkylcarbonyl, C1-C6 alkoxycarbonyl, C1-C6 alkylsulfonyl, C1-C6 alkylamino, and C1-C6 alkylcarbonyloxy; or $R_1R_2N$— is

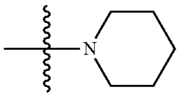, 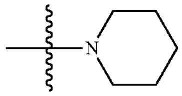 or

-continued
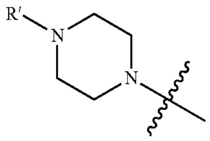
;
the aryl is selected from
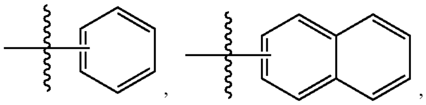
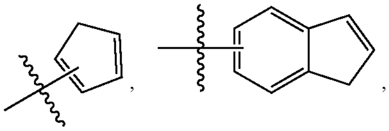
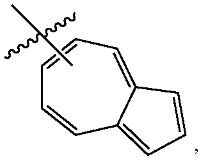 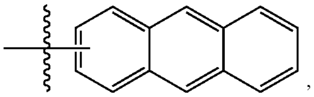
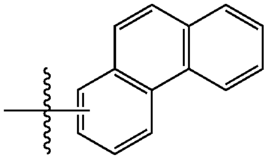
, and
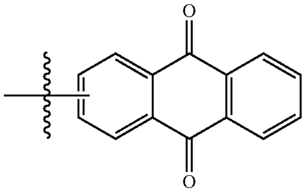
;
the heteroaryl is selected from
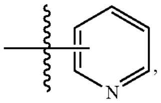 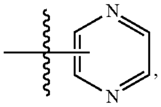 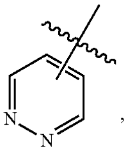
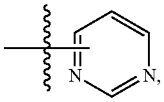 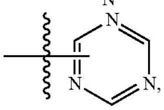 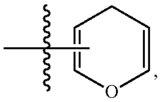
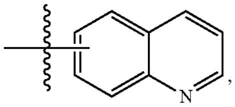 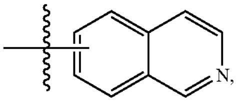
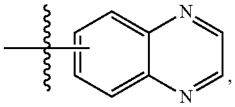 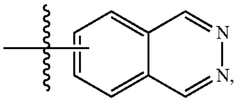
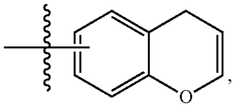 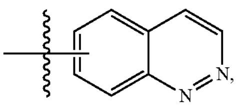
-continued
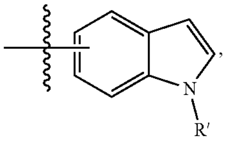 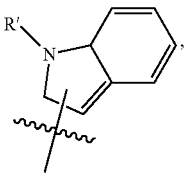
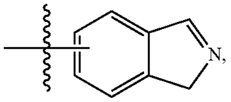 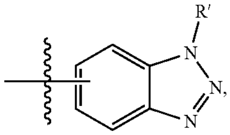
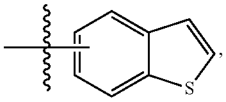 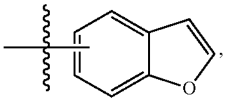
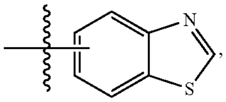 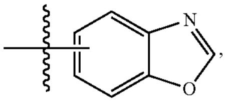
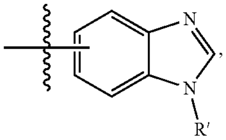 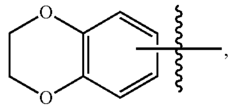
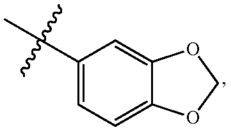 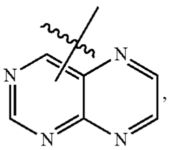
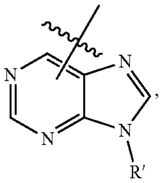 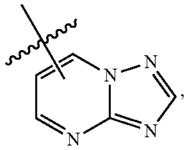
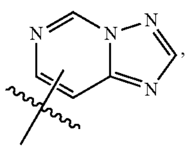 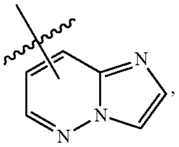
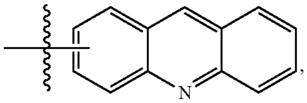
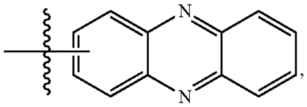
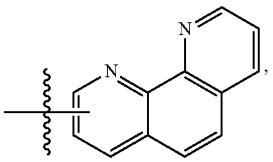
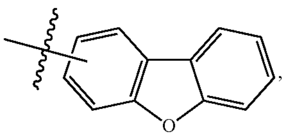 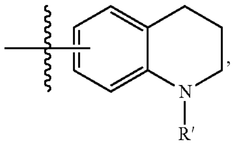

-continued

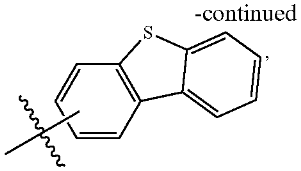

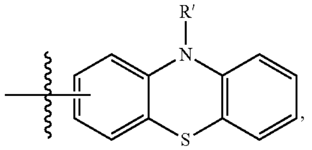

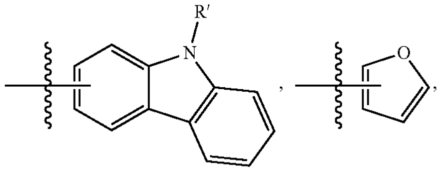

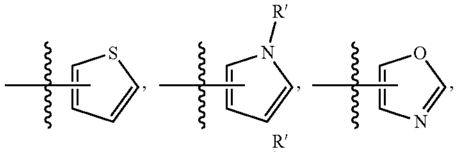

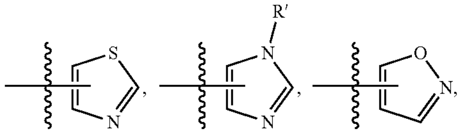

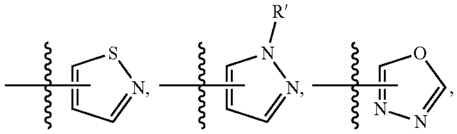

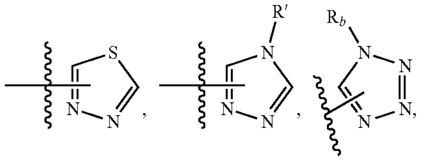

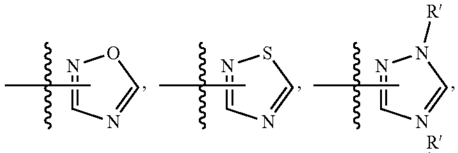

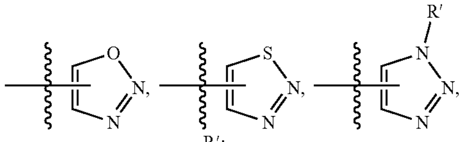

and

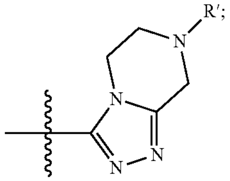

R' is hydrogen, nitro, hydroxy, amino, a fluoro-, chloro-, or bromo-containing or not containing group selected from C1-C6 alkyl, C2-C6 alkenyl, C2-C6 alkynyl, C3-C6 cycloalkyl, C3-C6 cycloalkenyl, C3-C6 cycloalkyl-C1-C6 alkyl, C1-C6 alkoxy, C2-C6 alkenyloxy, C2-C6 alkynyloxy, C3-C6 cycloalkyloxy, C1-C6 alkoxy-C1-C6 alkyl, C1-C6 alkoxycarbonyl, C1-C6 alkylsulfanylcarbonyl, C1-C6 alkylsulfonyl, C1-C6 alkylsulfonyl-C1-C6 alkyl, C1-C6 alkylcarbonyl, C1-C6 alkylcarbonyl-C1-C6 alkyl, C1-C6 alkylcarbonyloxy, C1-C6 alkylamino, C1-C6 alkylaminocarbonyl, C1-C6 alkoxyaminocarbonyl, C1-C6 alkoxycarbonyl-C1-C6 alkyl, C1-C6 alkylaminocarbonyl-C1—C6 alkyl, triC1-C6 alkylsilyl, and diC1-C6 alkylphosphonyl, aryl, aryl-C1-C6 alkyl, aryloxy, aryl-C1-C6 alkyloxy, aryloxy-C1-C6 alkyl, arylcarbonyl, arylsulfonyl, heteroaryl, heteroaryl-C1-C6 alkyl, heteroaryloxy, heteroaryl-C1-C6 alkyloxy, heteroaryloxy-C1-C6 alkyl, heteroarylcarbonyl, heteroarylsulfonyl, aliphatic heterocyclyl, aliphatic heterocyclyl-C1-C6 alkyl, aliphatic heterocyclyloxy, aliphatic heterocyclyl-C1-C6 alkyloxy, aliphatic heterocyclyloxy-C1-C6 alkyl, aliphatic heterocyclylcarbonyl, or aliphatic heterocyclylsulfonyl, each of said aryl, aryl-C1-C6 alkyl, aryloxy, aryl-C1-C6 alkyloxy, aryloxy-C1-C6 alkyl, arylcarbonyl, arylsulfonyl, heteroaryl, heteroaryl-C1-C6 alkyl, heteroaryloxy, heteroaryl-C1-C6 alkyloxy, heteroaryloxy-C1-C6 alkyl, heteroarylcarbonyl, heteroarylsulfonyl, aliphatic heterocyclyl, aliphatic heterocyclyl-C1-C6 alkyl, aliphatic heterocyclyloxy, aliphatic heterocyclyl-C1-C6 alkyloxy, aliphatic heterocyclyloxy-C1-C6 alkyl, aliphatic heterocyclylcarbonyl, or aliphatic heterocyclylsulfonyl is unsubstituted or substituted with 1-3 groups independently selected from fluorine, chlorine, bromine, cyano, nitro, hydroxy, carboxyl, sulfhydryl, amino, and a fluoro-, chloro-, bromo-containing or not containing group selected from C1-C6 alkyl, C3-C6 cycloalkyl, C3-C6 cycloalkenyl, C3-C6 cycloalkyl-C1-C6 alkyl, C2-C6 alkenyl, C2-C6 alkynyl, C1-C6 alkoxy, C1-C6 alkylcarbonyl, C1-C6 alkoxycarbonyl, C1-C6 alkylsulfonyl, C1-C6 alkylamino, and C1-C6 alkylcarbonyloxy;

the aliphatic heterocyclyl is selected from

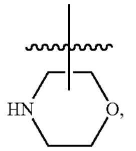

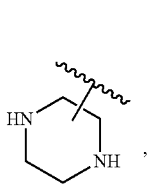

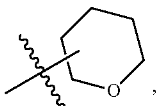

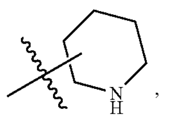

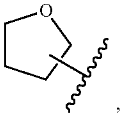

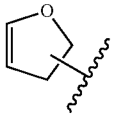

and

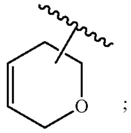

;

or wherein A is phenyl or 7- to 14-membered aryl, which is substituted with one or more substituents independently selected from azido, halogenated C1-C6 alkyl, a halogen-containing aryl, a halogen-containing aryl-C1-C6 alkyl, a halogen-containing or not containing group selected from C2-C6 alkenyl, C2-C6 alkynyl, C3-C6 cycloalkyl, C3-C6 cycloalkenyl, and C3-C6 cycloalkyl-C1-C6 alkyl, heteroaryl, heteroaryl-C1-C6 alkyl, aliphatic heterocyclyl, and aliphatic heterocyclyl-C1-C6 alkyl, each of said heteroaryl, heteroaryl-C1-C6 alkyl, aliphatic heterocyclyl, or aliphatic heterocyclyl-C1-C6 alkyl is unsubstituted or substituted with 1-5 groups independently selected from halogen, cyano, nitro, hydroxy, carboxyl, sulfhydryl, amino, and a halogen-containing or not containing group selected from C1-C6 alkyl, C3-C6 cycloalkyl, C3-C6 cycloalkenyl, C3-C6 cycloalkyl-C1-C6 alkyl, C2-C6 alkenyl, C2-C6 alkynyl, C1-C6 alkoxy, C1-C6 alkylcarbonyl, C1-C6 alkoxycarbonyl, C1-C6 alkylsulfonyl, C1-C6 alkylamino, and C1-C6 alkylcarbonyloxy, R—O—$(CH_2)_n$—, R—O—$(CH_2)_p$—O—, R—O—$(CH_2)_p$—S—, R—S—$(CH_2)_n$—, R—O—$(CH_2)_n$—(C═O)—$(CH_2)_q$—$(O)_m$—, R—O—$(CH_2)_n$—(C═O)—$(CH_2)_q$—$(S)_m$—, R—S—$(CH_2)_p$—O—, R—S—$(CH_2)_p$—S—, R—S—(C═S)—$(S)_m$—, R—O—(C═S)—$(O)_m$—, R—S—$(CH_2)_n$—(C═O)—$(O)_m$—, R—O—(C═S)—$(S)_m$—, R—S—(C═O)—$(S)_m$—, R—S—(C═S)—$(O)_m$—, R—S—(C═S)—$(CH_2)_q$—, R—O—(C═S)—$(CH_2)_q$—, R—S—(C═O)—$(CH_2)_q$—, R—S—$(CH_2)_n$—(C═S)—, R—O—$(CH_2)_n$—(C═S)—, R—S—$(CH_2)_n$—(C═O)—, R—(C═O)—$(CH_2)_n$—, R—(C═S)—, R—(C═O)—$(CH_2)_n$—O—$(CH_2)_q$—, R—(C═S)—S—, R—(C═O)—S—, R—(C═S)—O—, R—SO—$(CH_2)_n$—, R—$SO_2$—$(CH_2)_n$—$(O)_m$—, R—$SO_2$—$(CH_2)_n$—$(NR_3)_m$—, $R_1R_2N$—$(CH_2)_n$—, $R_1R_2N$—O—, $R_1R_2N$—(C═O)—$(CH_2)_q$—$(O)_m$—, $R_1R_2N$—(C═O)—$(S)_m$—, $R_1R_2N$—(C═O)—$(NR_3)_m$—, $R_1R_2N$—$(CH_2)_n$—$SO_2$—$(CH_2)_q$—$(O)_m$—, $R_1R_2N$—$(CH_2)_p$—(C═O)—, $R_1R_2N$—$(CH_2)_p$—O—, $R_1R_2N$—O—$(CH_2)_p$—, $R_1R_2P(O)$—, $R_1R_2R_3SiO$—, $R_1R_2R_3Si$—, $R_1R_2R_3Si$—CH═CH—, $R_1R_2C$═N—, $R_1R_2C$═N—O—, and $R_1R_2C$═N—NH—;

wherein the derivative is an agriculturally acceptable salt or a compound derivatized from 4-hydroxy of the pyridazine ring of the Formula I, further wherein the compound derivatized from 4-hydroxy of the pyridazine ring of the Formula I is selected from an ester, an oxime, and a hydroxylamine thereof.

4. The herbicidally active pyridazinol compound or a derivative thereof according to claim 1, wherein, X is halogenated C1-C6 alkyl;

A is selected from unsubstituted or substituted C2-C6 alkenyl, unsubstituted or substituted C3-C6 cycloalkyl, unsubstituted or substituted C3-C6 cycloalkenyl, unsubstituted or substituted

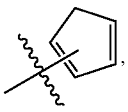, unsubstituted or substituted 5- to 14-membered heteroaryl, and unsubstituted or substituted 5- to 14-membered aliphatic heterocyclyl; wherein, when being substituted, said C2-C6 alkenyl, C3-C6 cycloalkyl, or C3-C6 cycloalkenyl is substituted with one or more substituents independently selected from R—O—$(CH_2)_n$—(C═O)— and $R_1R_2R_3SiO$—;

when being substituted, said

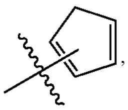, 5- to 14-membered heteroaryl or 5- to 14-membered aliphatic heterocyclyl is substituted with one or more substituents independently selected from halogen, cyano, nitro, azido, a halogen-containing or not containing group selected from C1-C6 alkyl, C2-C6 alkenyl, C2-C6 alkynyl, C3-C6 cycloalkyl, and C3-C6 cycloalkyl-C1-C6 alkyl, aryl, aryl-C1-C6 alkyl, heteroaryl, heteroaryl-C1-C6 alkyl, aliphatic heterocyclyl, aliphatic heterocyclyl-C1-C6 alkyl, each of said aryl, aryl-C1-C6 alkyl, heteroaryl, heteroaryl-C1-C6 alkyl, aliphatic heterocyclyl, or aliphatic heterocyclyl-C1-C6 alkyl is unsubstituted or substituted with 1-5 groups independently selected from halogen, cyano, nitro, hydroxy, carboxyl, sulfhydryl, amino, and a halogen-containing or not containing group selected from C1-C6 alkyl, C3-C6 cycloalkyl, C3-C6 cycloalkyl-C1-C6 alkyl, C2-C6 alkenyl, C2-C6 alkynyl, C1-C6 alkoxy, C1-C6 alkylcarbonyl, C1-C6 alkoxycarbonyl, C1-C6 alkylsulfonyl, C1-C6 alkylamino, and C1-C6 alkylcarbonyloxy, R—O—$(CH_2)_n$—, R—O—$(CH_2)_p$—O—, R—S—$(CH_2)_n$—, R—O—$(CH_2)_n$—(C═O)—$(CH_2)_q$—$(O)_m$—, R—O—$(CH_2)_n$—(C═O)—$(CH_2)_q$—$(S)_m$—, R—S—$(CH_2)_n$—(C═O)—, R—(C═O)—$(CH_2)_n$—, R—(C═O)—$(CH_2)_n$—O—$(CH_2)_q$—, R—SO—$(CH_2)_n$—, R—$SO_2$—$(CH_2)_n$—$(O)_m$—, R—$SO_2$—$(CH_2)_n$—$(NR_3)_m$—, $R_1R_2N$—(C═O)—$(CH_2)_q$—$(O)_m$—, $R_1R_2N$—(C═O)—$(NR_3)_m$—, $R_1R_2N$—$(CH_2)_n$—, $R_1R_2N$—$(CH_2)_n$—$SO_2$—$(CH_2)_q$—, $R_1R_2P(O)$—, and $R_1R_2R_3Si$—;

m is 0 or 1, n and q are each independently an integer from 0 to 4, p is an integer from 1 to 4;

R is hydrogen, a halogen-containing or not containing group selected from C1-C6 alkyl, C2-C6 alkenyl, C2-C6 alkynyl, C3-C6 cycloalkyl, and C3-C6 cycloalkyl-C1-C6 alkyl, 5- to 14-membered aryl, 5- to 14-membered aryl-C1-C4 alkyl, or 5- to 14-membered heteroaryl, each of said 5- to 14-membered aryl, 5- to 14-membered aryl-C1-C4 alkyl, or 5- to 14-membered heteroaryl is unsubstituted or substituted with 1-3 groups independently selected from halogens;

$R_1$, $R_2$, $R_3$ are each independently hydrogen, nitro, hydroxy, amino, a halogen-containing or not containing group selected from C1-C6 alkyl, C2-C6 alkenyl, C2-C6 alkynyl, C3-C6 cycloalkyl, C1-C6 alkoxy, C1-C6 alkoxy-C1-C6 alkyl, C1-C6 alkoxycarbonyl, C1-C6 alkylcarbonyl, C1-C6 alkylcarbonyl-C1-C6 alkyl, and C1-C6 alkylcarbonyloxy, 5- to 14-membered aryl, 5- to 14-membered aryl-C1-C6 alkyl, 5- to 14-membered aryloxy, 5- to 14-membered arylcarbonyl, 5- to 14-membered heteroaryl, 5- to 14-membered heteroaryl-C1-C6 alkyl, 5- to 14-membered heteroaryloxy, 5- to 14-membered heteroarylcarbonyl, or 5- to 14-membered aliphatic heterocyclylcarbonyl, each of said 5- to 14-membered aryl, 5- to 14-membered aryl-C1-C6 alkyl, 5- to 14-membered aryloxy, 5- to 14-membered arylcarbonyl, 5- to 14-membered heteroaryl, 5- to 14-membered heteroaryl-C1-C6 alkyl, 5- to 14-membered heteroaryloxy, 5- to 14-membered heteroarylcarbonyl, or 5- to 14-membered aliphatic heterocyclylcarbonyl is unsubstituted or substituted with 1-3 groups independently selected from halogen, cyano, nitro, hydroxy, carboxyl, sulfhydryl, amino, and a halogen-containing or not containing group selected from C1-C6 alkyl, C3-C6 cycloalkyl, C3-C6 cycloalkyl-C1-C6 alkyl, C2-C6 alkenyl, C2-C6 alkynyl, C1-C6 alkoxy, C1-C6 alkylcarbonyl, C1-C6 alkoxycarbonyl, C1-C6 alkylsulfonyl, C1-C6 alkylamino, and C1-C6 alkylcarbonyloxy; or $R_1R_2N$— is
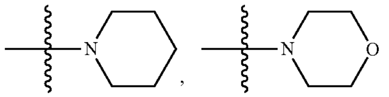
or
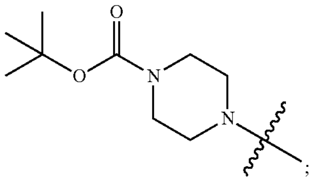
;
the aryl is selected from
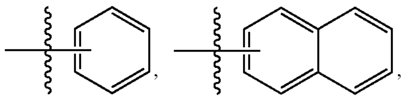
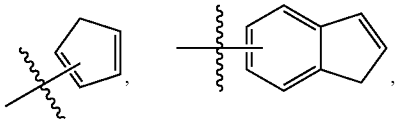
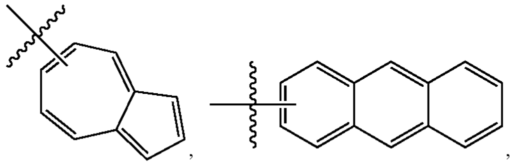
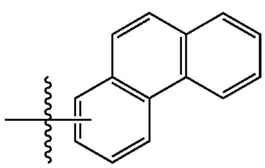
and
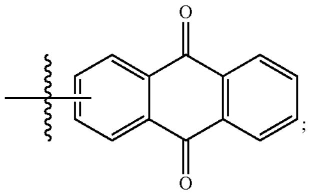
;
the heteroaryl is selected from
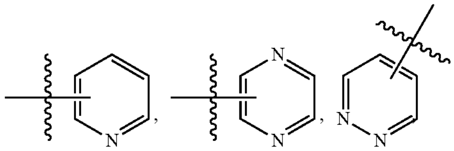
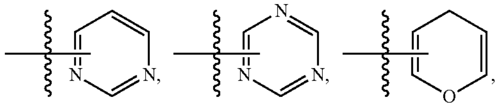
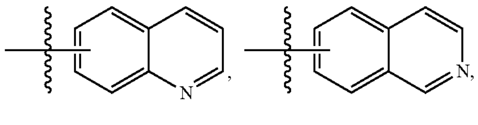
-continued
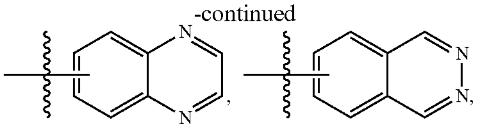
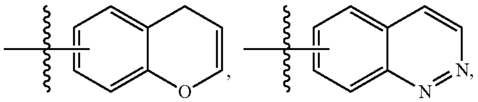
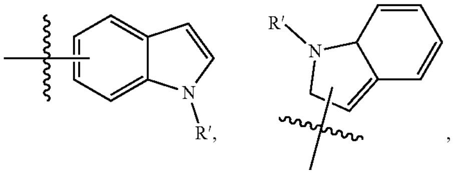
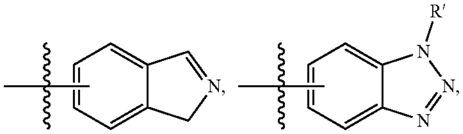
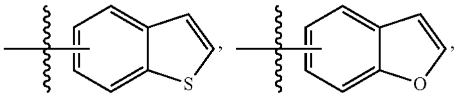
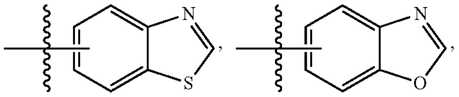
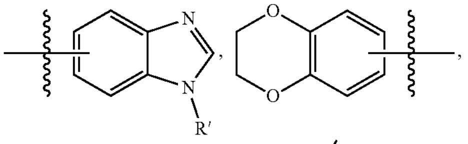
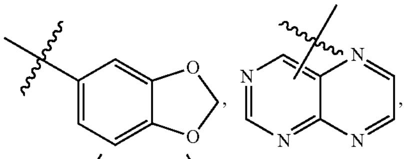
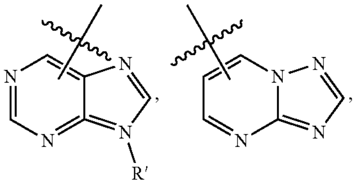
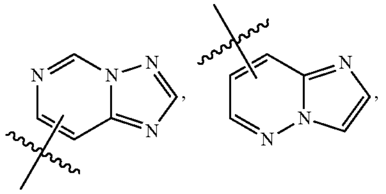
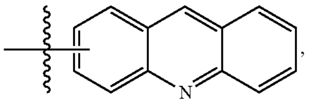
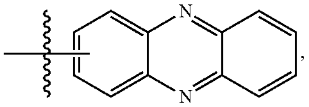
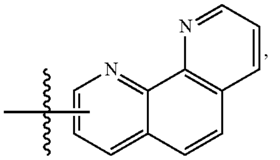

-continued

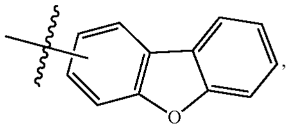, 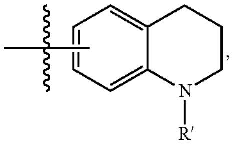,

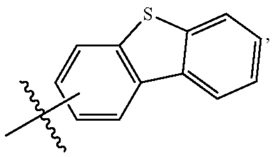,

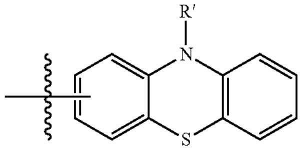,

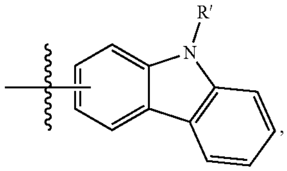, 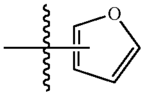,

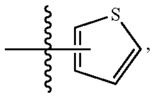, 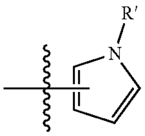, 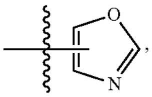,

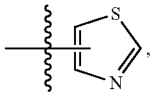, 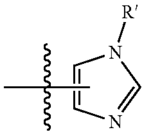, 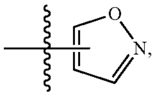

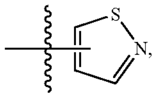 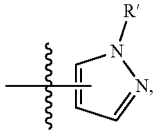 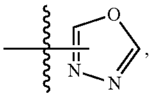,

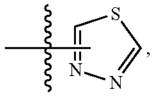, 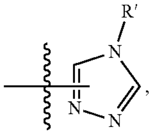, 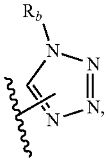

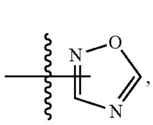, 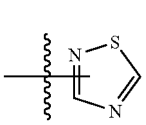, 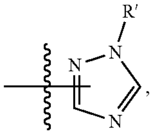,

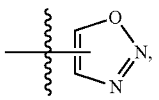 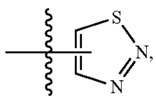 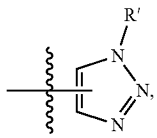 and

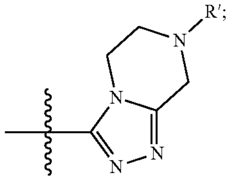

R' is hydrogen, a fluoro-, chloro-, or bromo-containing or not containing group selected from C1-C6 alkyl, C1-C6 alkoxy-C1-C6 alkyl, C1-C6 alkoxycarbonyl, and C1-C6 alkylcarbonyl, aliphatic heterocyclyl, phenyl, or benzyl;

the aliphatic heterocyclyl is selected from

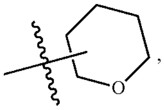, 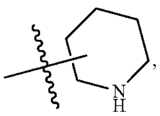, 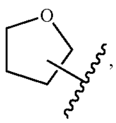,

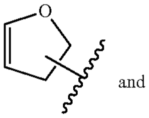 and 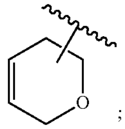 ;

or wherein A is phenyl or 7- to 14-membered aryl, which is substituted with one or more substituents independently selected from azido, halogenated C1-C6 alkyl, a halogen-containing aryl, a halogen-containing aryl-C1-C6 alkyl, a halogen-containing or not containing group selected from C2-C6 alkenyl, C2-C6 alkynyl, C3-C6 cycloalkyl, and C3-C6 cycloalkyl-C1-C6 alkyl, heteroaryl, heteroaryl-C1-C6 alkyl, aliphatic heterocyclyl, and aliphatic heterocyclyl-C1-C6 alkyl, each of said heteroaryl, heteroaryl-C1-C6 alkyl, aliphatic heterocyclyl, or aliphatic heterocyclyl-C1-C6 alkyl is unsubstituted or substituted with 1-5 groups independently selected from halogen, cyano, nitro, hydroxy, carboxyl, sulfhydryl, amino, and a halogen-containing or not containing group selected from C1-C6 alkyl, C3-C6 cycloalkyl, C3-C6 cycloalkyl-C1-C6 alkyl, C2-C6 alkenyl, C2-C6 alkynyl, C1-C6 alkoxy, C1-C6 alkylcarbonyl, C1-C6 alkoxycarbonyl, C1-C6 alkylsulfonyl, C1-C6 alkylamino, and C1-C6 alkylcarbonyloxy, $R—O—(CH_2)_n—$, $R—O—(CH_2)_p—O—$, $R—S—(CH_2)_n—$, $R—O—(CH_2)_n—(C{=}O)—(CH_2)_q—(O)_m—$, $R—O—(CH_2)_n—(C{=}O)—(CH_2)_q—(S)_m—$, $R—S—(CH_2)_n—(C{=}O)—$, $R—(C{=}O)—(CH_2)_n—$, $R—(C{=}O)—(CH_2)_n—O—(CH_2)_q—$, $R—SO—(CH_2)_n—$, $R—SO_2—(CH_2)_n—(O)_m—$, $R—SO_2—(CH_2)_n—(NR_3)_m—$, $R_1R_2N—(C{=}O)—(CH_2)_q—(O)_m—$, $R_1R_2N—(C{=}O)—(NR_3)_m—$, $R_1R_2N—(CH_2)_n—$, $R_1R_2N—(CH_2)_n—SO_2—(CH_2)_q—$, $R_1R_2P(O)—$, and $R_1R_2R_3Si—$;

wherein the derivative is an agriculturally acceptable salt or a compound derivatized from 4-hydroxy of the pyridazine ring of the Formula I, further wherein the compound derivatized from 4-hydroxy of the pyridazine ring of the Formula I is selected from an ester, an oxime, and a hydroxylamine thereof.

5. The herbicidally active pyridazinol compound or a derivative thereof according to claim 1, wherein, X is halogenated C1-C4 alkyl;

A is selected from unsubstituted or substituted C2-C4 alkenyl, unsubstituted or substituted C3-C6 cycloalkyl, unsubstituted or substituted C3-C6 cycloalkenyl, unsubstituted or substituted

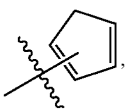, unsubstituted or substituted 5- to 14-membered heteroaryl, and unsubstituted or substituted 5- to 14-membered aliphatic heterocyclyl; wherein, when being substituted, C2-C4 alkenyl, C3-C6 cycloalkyl, or C3-C6 cycloalkenyl is substituted with one or more substituents independently selected from R—O—(C═O)— and $R_1R_2R_3SiO$—;

when being substituted, said

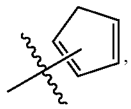, 5- to 14-membered heteroaryl or 5- to 14-membered aliphatic heterocyclyl is substituted with one or more substituents independently selected from fluorine, chlorine, bromine, iodine, cyano, nitro, azido, a fluoro-, chloro- or bromo-containing or not containing group selected from C1-C4 alkyl, C2-C4 alkenyl, C2-C4 alkynyl, C3-C6 cycloalkyl, and C3-C6 cycloalkyl-C1-C4 alkyl, aryl, aryl-C1-C4 alkyl, heteroaryl, heteroaryl-C1-C4 alkyl, and, aliphatic heterocyclyl, each of said aryl, aryl-C1-C4 alkyl, heteroaryl, heteroaryl-C1-C4 alkyl, or aliphatic heterocyclyl is unsubstituted or substituted with 1-3 groups independently selected from fluorine, chlorine, bromine, cyano, hydroxy, and a fluoro-, chloro- or bromo-containing or not containing group selected from C1-C4 alkyl, C1-C4 alkoxy, C1-C4 alkoxycarbonyl, C1-C4 alkylsulfonyl, and C1-C4 alkylamino, R—O—$(CH_2)_n$—, R—O—$CH_2$—O—, R—S—$(CH_2)_n$—, R—O—$(CH_2)_n$—(C═O)—, R—O—$(CH_2)_n$—(C═O)—O—, R—O—(C═O)—$(CH_2)_q$—O—, R—O—$(CH_2)_n$—(C═O)—$(CH_2)_q$—S—, R—S—$(CH_2)_n$—(C═O)—, R—(C═O)—$(CH_2)_n$—, R—(C═O)—O—$(CH_2)_q$—, R—(C═O)—$(CH_2)_n$—O—, R—SO—$(CH_2)_n$—, R—$SO_2$—$(CH_2)_n$—$(O)_m$—, R—$SO_2$—$(CH_2)_n$—$NR_3$—, $R_1R_2N$—(C═O)—$(CH_2)_q$—, $R_1R_2N$—(C═O)—$(CH_2)_q$—O—, $R_1R_2N$—(C═O)—$(NR_3)_m$—, $R_1R_2N$—$(CH_2)_n$—, $R_1R_2N$—$(CH_2)_n$—$SO_2$—$(CH_2)_q$—, $R_1R_2P(O)$—, and $R_1R_2R_3Si$—;

m is 0 or 1, n and q are each independently an integer from 0, 1, 2 and 3, p is an integer from 1, 2 and 3;

R is hydrogen, a halogen-containing or not containing group selected from C1-C4 alkyl, C2-C4 alkenyl, C2-C6 alkynyl, C3-C6 cycloalkyl, and C3-C6 cycloalkyl-C1-C4 alkyl, 5- to 14-membered aryl, 5- to 14-membered aryl-C1-C2 alkyl, or 5- to 6-membered heteroaryl, each of said 5- to 14-membered aryl, 5- to 14-membered aryl-C1-C2 alkyl, or 5- to 6-membered heteroaryl is unsubstituted or substituted with 1-3 groups independently selected from fluorine, chlorine, and bromine;

$R_1$, $R_2$, $R_3$ are each independently hydrogen, a fluoro-, chloro- or bromo-containing or not containing group selected from C1-C4 alkyl, C2-C4 alkenyl, C2-C4 alkynyl, C3-C6 cycloalkyl, C1-C4 alkoxy, C1-C4 alkoxyC1-C4 alkyl, C1-C4 alkoxycarbonyl, C1-C4 alkylcarbonyl, C1-C4 alkylcarbonyl-C1-C4 alkyl, and C1-C4 alkylcarbonyloxy, 5- to 14-membered aryl, 5- to 14-membered aryloxy, 5- to 14-membered arylcarbonyl, 5- to 6-membered heteroaryl, 5- to 6-membered heteroaryl-C1-C4 alkyl, or 5- to 6-membered heteroarylcarbonyl, each of said 5- to 14-membered aryl, 5- to 14-membered aryloxy, 5- to 14-membered arylcarbonyl, 5- to 6-membered heteroaryl, 5- to 6-membered heteroaryl-C1-C4 alkyl, or 5- to 6-membered heteroarylcarbonyl is unsubstituted or substituted with 1-3 groups independently selected from fluorine, chlorine, bromine, C1-C4 alkyl, C1-C4 alkoxy, C1-C4 alkylamino, and C3-C6 cycloalkyl; or $R_1R_2N$— is

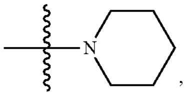, 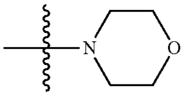 or

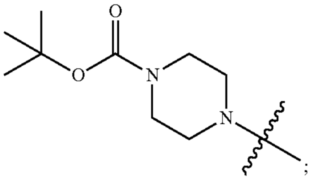;

the aryl is selected from

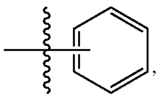, 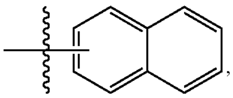,

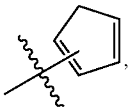, 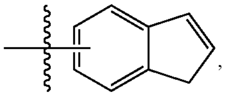,

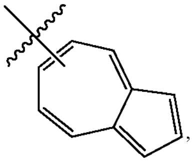, 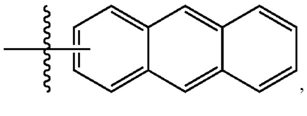,

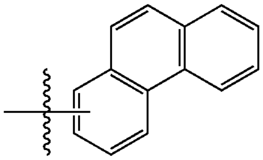 and

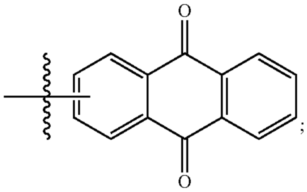;

the heteroaryl is selected from

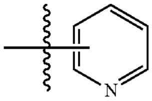, 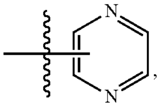, 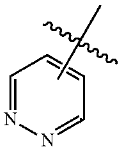

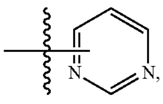, 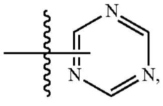, 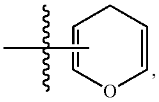,

-continued
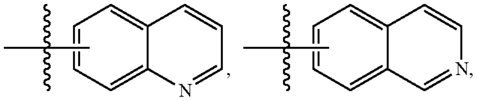
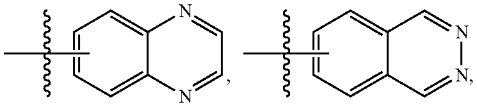
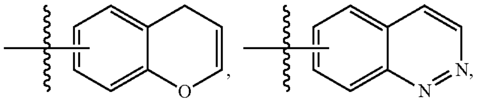
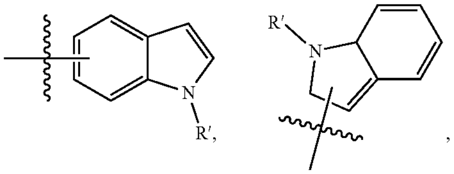
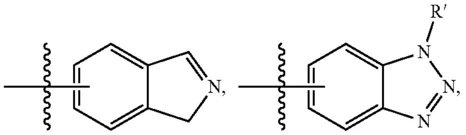
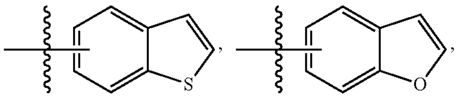
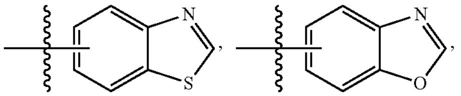
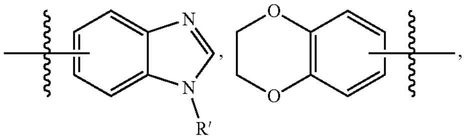
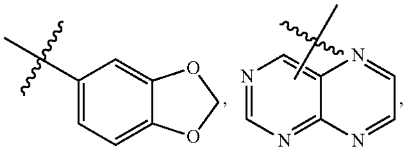
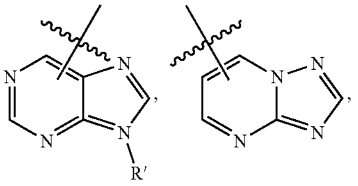
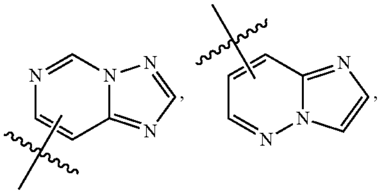
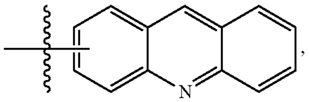
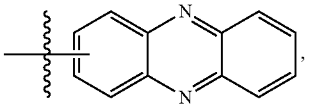
-continued
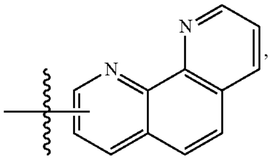
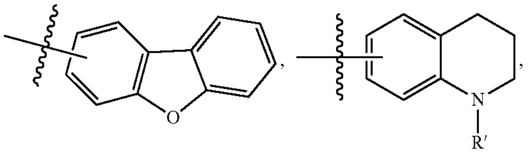
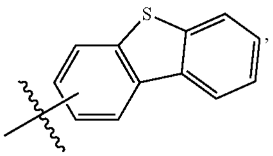
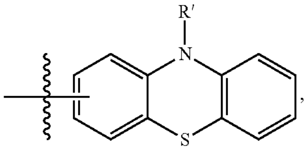
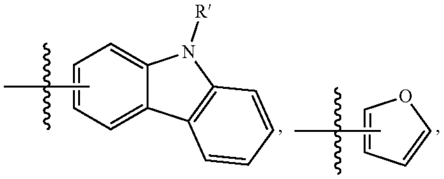
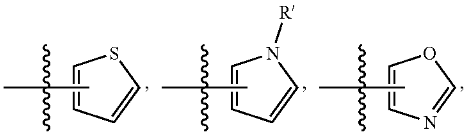
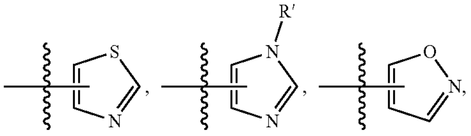
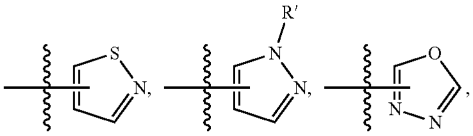
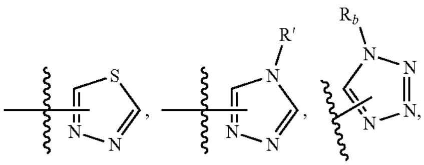
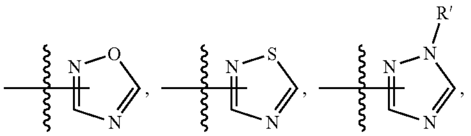
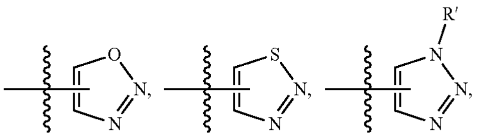
and -continued

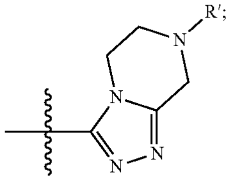

R' is hydrogen, a fluoro-, chloro-, or bromo-containing or not containing group selected from C1-C4 alkyl, C1-C4 alkoxy-1-04 alkyl, C1-C4 alkoxycarbonyl, and C1-C4 alkylcarbonyl,

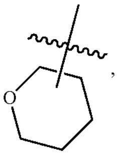

phenyl, or benzyl;

the aliphatic heterocyclyl is selected from

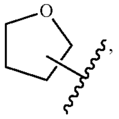
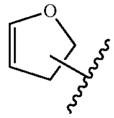
and
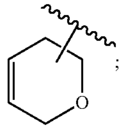
;

or wherein A is phenyl phenyl or 7- to 14-membered aryl, which is substituted with one or more substituents independently selected from azido, halogenated C1-C4 alkyl, a fluoro-, chloro- or bromo-containing aryl, a fluoro-, chloro- or bromo-containing aryl-C1-C4 alkyl, a fluoro-, chloro- or bromo-containing or not containing group selected from C2-C4 alkenyl, C2-C4 alkynyl, C3-C6 cycloalkyl, and C3-C6 cycloalkyl-C1-C4 alkyl, heteroaryl, heteroaryl-C1-C4 alkyl, and aliphatic heterocyclyl, each of said heteroaryl, heteroaryl-C1-C4 alkyl, or aliphatic heterocyclyl is unsubstituted or substituted with 1-3 groups independently selected from fluorine, chlorine, bromine, cyano, hydroxy, and a fluoro-, chloro- or bromo-containing or not containing group selected from C1-C4 alkyl, C1-C4 alkoxy, C1-C4 alkoxycarbonyl, C1-C4 alkylsulfonyl, and C1-C4 alkylamino, $R—O—(CH_2)_n—$, $R—O—CH_2—O—$, $R—S—(CH_2)_n—$, $R—O—(CH_2)_n—(C{=}O)—$, $R—O—(CH_2)_n—(C{=}O)—O—$, $R—O—(C{=}O)—(CH_2)_q—O—$, $R—O—(CH_2)_n—(C{=}O)—(CH_2)_q—S—$, $R—S—(CH_2)_n—(C{=}O)—$, $R—(C{=}O)—(CH_2)_n—$, $R—(C{=}O)—O—(CH_2)_q—$, $R—(C{=}O)—(CH_2)_n—O—$, $R—SO—(CH_2)_n—$, $R—SO_2—(CH_2)_n—(O)_m—$, $R—SO_2—(CH_2)_n—NR_3—$, $R_1R_2N—(C{=}O)—(CH_2)_q—$, $R_1R_2N—(C{=}O)—(CH_2)_q—O—$, $R_1R_2N—(C{=}O)—(NR_3)_m—$, $R_1R_2N—(CH_2)_n—$, $R_1R_2N—(CH_2)_n—SO_2—(CH_2)_q—$, $R_1R_2P(O)—$, and $R_1R_2R_3Si—$;

wherein the derivative is an agriculturally acceptable salt or a compound derivatized from 4-hydroxy of the pyridazine ring of the Formula I, further wherein the compound derivatized from 4-hydroxy of the pyridazine ring of the Formula I is selected from an ester, an oxime, and a hydroxylamine thereof.

6. The herbicidally active pyridazinol compound or a derivative thereof according to claim 1, wherein, X is $CH_2F$, $CHF_2$, $CF_3$, or $CF_2CF_3$;

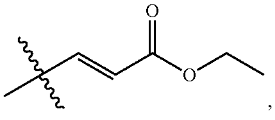
,
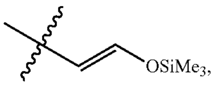
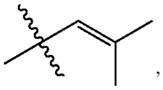
,
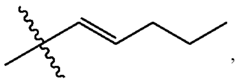
,
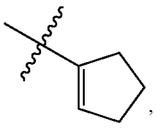
,
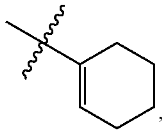
, unsubstituted or substituted

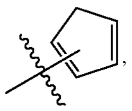
, unsubstituted or substituted 5- to 14-membered heteroaryl, or unsubstituted or substituted 5- to 14-membered aliphatic heterocyclyl; wherein, said substituted

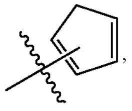
, substituted 5- to 14-membered heteroaryl or substituted 5- to 14-membered aliphatic heterocyclyl is the

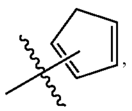
, 5- to 14-membered heteroaryl, or 5- to 14-membered aliphatic heterocyclyl, which is substituted with one or more substituents independently selected from fluorine, chlorine, bromine, iodine, cyano, nitro, azido, a fluoro-, chloro-, or bromo-containing or not containing group selected from C1-C4 alkyl, C2-C4 alkenyl, C2-C4 alkynyl, C3-C6 cycloalkyl, and C3-C6 cycloalkyl-C1-C2 alkyl, phenyl, pyrrolyl, furyl, imidazolyl, pyrazolyl, oxazolyl, isoxazolyl, thiazolyl, oxadiazolyl, thiadiazolyl, triazolyl, pyridyl, pyrazinyl, pyrimidinyl, benzyl, tetrahydropyranyl, thienylmethyl, each of said phenyl, pyrrolyl, furyl, imidazolyl, pyrazolyl, oxazolyl, isoxazolyl, thiazolyl, oxadiazolyl, thiadiazolyl, triazolyl, pyridyl, pyrazinyl, pyrimidinyl, benzyl, tetrahydropyranyl, thienylmethyl is unsubstituted or substituted with 1-3 groups independently selected from fluorine, chlorine, bromine, cyano, hydroxy, and a fluoro-, chloro-, or bromo-containing or not containing group selected from C1-C4 alkyl, C1-C4 alkoxy, C1-C4 alkoxycarbonyl, C1-C4 alkylsulfonyl, and C1-C4 alkylamino, R—O—, R—O—$CH_2$—, R—O—$CH_2CH_2$—, R—O—$CH_2$—O—, R—O—(C═O)—, R—O—$CH_2$—(C═O)—, R—O—$CH_2$—(C═O)—O—, R—O—(C═O)—$CH_2$—O—, R—O—(C═O)—$CH_2CH_2$—O—, R—O—(C═O)—$CH_2$—S—, R—O—$CH_2$—(C═O)—S—, R—O—$CH_2$—(C═O)—$CH_2$—S—, R—S—$CH_2$—, R—S—, R—S—(C═O)—, R—S—$CH_2$—(C═O)—, R—(C═O)—$CH_2$—, R—(C═O)—, R—(C═O)—O—$CH_2$—, R—(C═O)—$CH_2$—O—, R—(C═O)—$CH_2CH_2$—O—, R—(C═O)—O—, R—SO—$CH_2$—, R—SO—, R—$SO_2$—$CH_2$—O—, R—$SO_2$—$CH_2$—, R—$SO_2$—O—, R—$SO_2$—, R—$SO_2$—$CH_2$—$NR_3$—, R—$SO_2$—$NR_3$—, $R_1R_2N$—$CH_2$—, $R_1R_2N$—, $R_1R_2N$—(C═O)—$CH_2$—, $R_1R_2N$—(C═O)—$CH_2$—O—, $R_1R_2N$—(C═O)—, $R_1R_2N$—(C═O)—$NR_3$—, $R_1R_2N$—$CH_2$—$SO_2$—, $R_1R_2N$—$CH_2$—$SO_2$—$CH_2$—, $R_1R_2N$—$SO_2$—$CH_2$—, $R_1R_2N$—$SO_2$—, $R_1R_2P(O)$—, and $R_1R_2R_3Si$—;

R is hydrogen, a fluoro-, chloro-, or bromo-containing or not containing group selected from C1-C4 alkyl, C2-C4 alkenyl, C2-C4 alkynyl, C3-C6 cycloalkyl, and C3-C6 cycloalkyl-C1-C2 alkyl, phenyl, benzyl, or thienyl, each of said phenyl, benzyl, or thienyl is unsubstituted or substituted with 1-3 groups independently selected from fluorine, chlorine, and bromine;

$R_1$, $R_2$, $R_3$ are each independently is hydrogen, a fluoro-, chloro-, or bromo-containing or not containing group selected from C1-C4 alkyl, C2-C4 alkenyl, C2-C4 alkynyl, C3-C6 cycloalkyl, C1-C4 alkoxy, C1-C4 alkoxy-C1-C2 alkyl, C1-C4 alkoxycarbonyl, C1-C4 alkylcarbonyl, C1-C4 alkylcarbonyl-C1-C2 alkyl, and C1-C4 alkylcarbonyloxy, phenyl, naphthyl, phenoxy, furyl, thienyl, thiadiazolyl, thienylmethyl, pyrazolylmethyl, benzoyl, or pyridinylformyl, each of said phenyl, naphthyl, phenoxy, furyl, thienyl, thiadiazolyl, thienylmethyl, pyrazolylmethyl, benzoyl, or pyridinylformyl is unsubstituted or substituted with 1-3 groups independently selected from fluorine, chlorine, bromine, C1-C4 alkyl, C3-C6 cycloalkyl, C1-C4 alkoxy, and C1-C4 alkylamino; or $R_1R_2N$— is

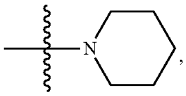, 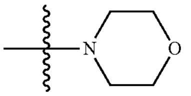 or

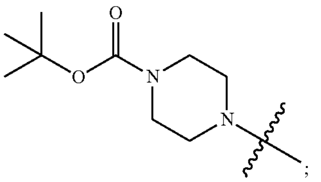;

the 5- to 14-membered aryl is selected from

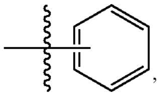, 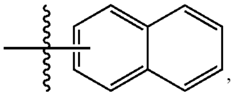,

-continued

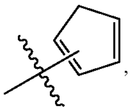, 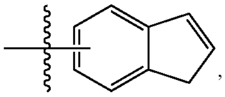,

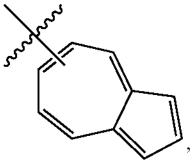, 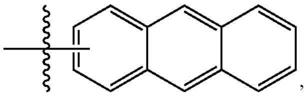,

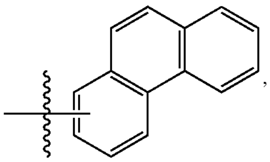, and

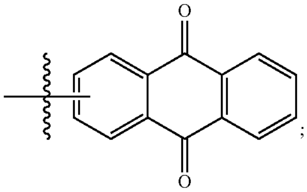;

the heteroaryl is selected from

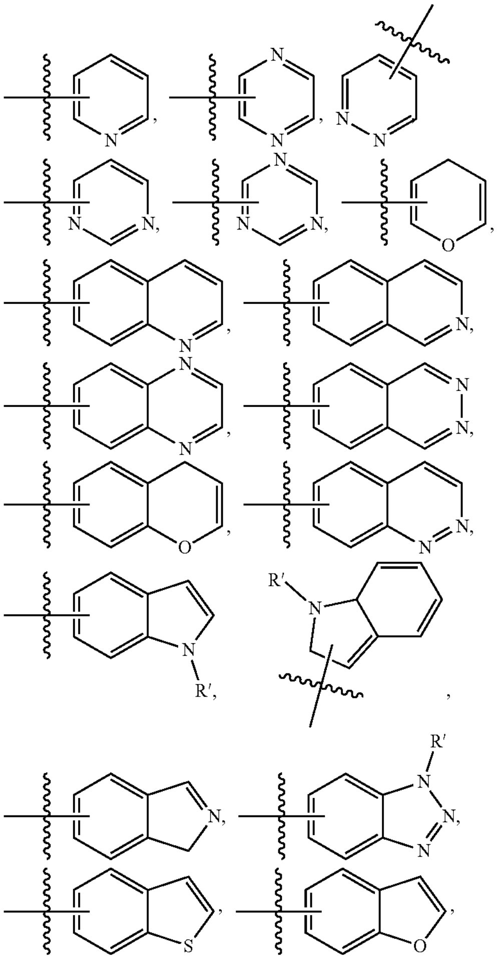

-continued
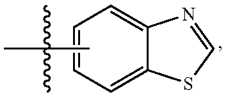, 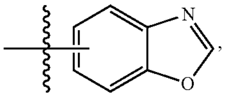,
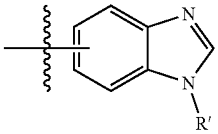, 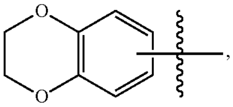,
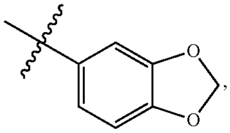, 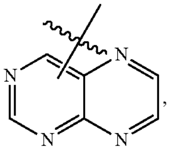,
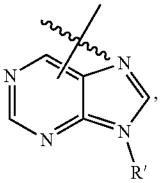, 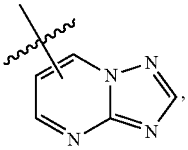,
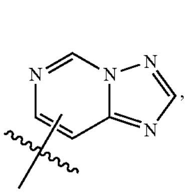, 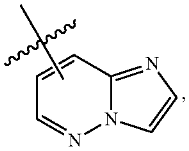,
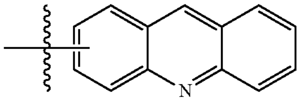,
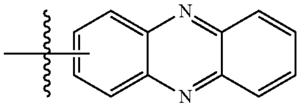,
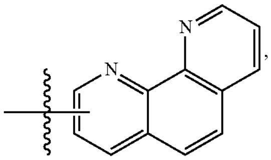,
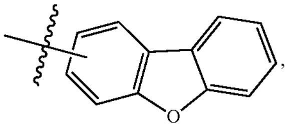, 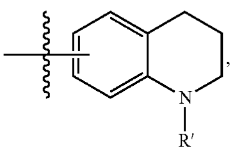,
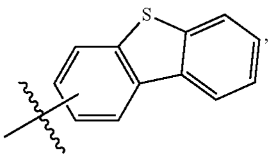,
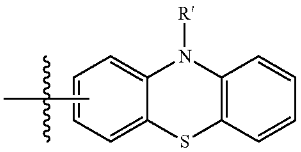,
-continued
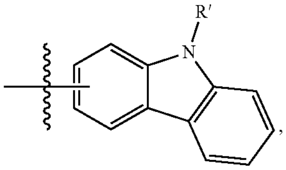, 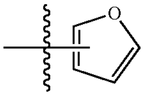,
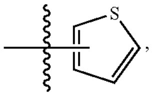, 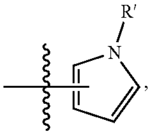, 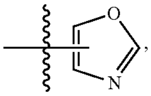,
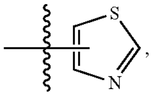, 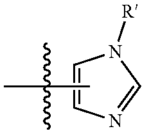, 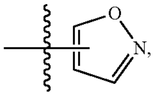,
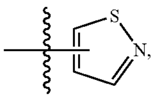, 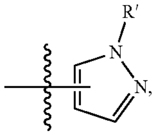, 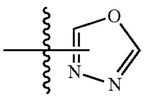,
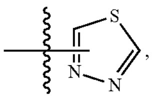, 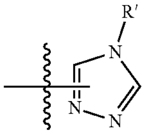, 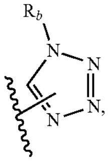,
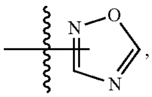, 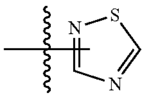, 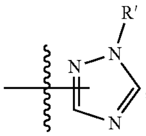,
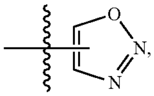, 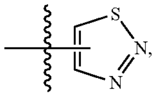, 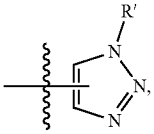 and
R';
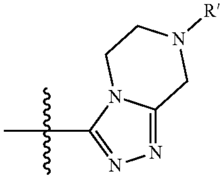
R' is hydrogen, a fluoro-, chloro-, or bromo-containing or not containing group selected from C1-C4 alkyl, C1-C4 alkoxy-C1-C2 alkyl, C1-C4 alkoxycarbonyl, and C1-C4 alkylcarbonyl,
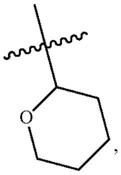 [SMILES: *C1CCCCO1], phenyl, or benzyl;

the aliphatic heterocyclyl is

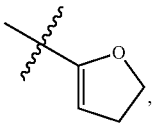, or 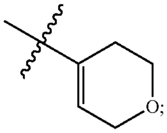

or wherein A is phenyl or 7- to 14-membered aryl, which is substituted with one or more substituents independently selected from azido, halogenated C1-C4 alkyl, a fluoro-, chloro- or bromo-containing phenyl, a fluoro-, chloro- or bromo-containing benzyl, a fluoro-, chloro-, or bromo-containing or not containing group selected from, C2-C4 alkenyl, C2-C4 alkynyl, C3-C6 cycloalkyl, and C3-C6 cycloalkyl-C1-C2 alkyl, pyrrolyl, furyl, imidazolyl, pyrazolyl, oxazolyl, isoxazolyl, thiazolyl, oxadiazolyl, thiadiazolyl, triazolyl, pyridyl, pyrazinyl, pyrimidinyl, tetrahydropyranyl, and thienylmethyl, each of said pyrrolyl, furyl, imidazolyl, pyrazolyl, oxazolyl, isoxazolyl, thiazolyl, oxadiazolyl, thiadiazolyl, triazolyl, pyridyl, pyrazinyl, pyrimidinyl, tetrahydropyranyl, or thienylmethyl is unsubstituted or substituted with 1-3 groups independently selected from fluorine, chlorine, bromine, cyano, hydroxy, and a fluoro-, chloro-, or bromo-containing or not containing group selected from C1-C4 alkyl, C1-C4 alkoxy, C1-C4 alkoxycarbonyl, C1-C4 alkylsulfonyl, and C1-C4 alkylamino, R—O—, R—O—$CH_2$—, R—O—$CH_2CH_2$—, R—O—$CH_2$—O—, R—O—(C═O)—, R—O—$CH_2$—(C═O)—, R—O—$CH_2$—(C═O)—O—, R—O—(C═O)—$CH_2$—O—, R—O—(C═O)—$CH_2CH_2$—O—, R—O—(C═O)—$CH_2$—S—, R—O—$CH_2$—(C═O)—S—, R—O—$CH_2$—(C═O)—$CH_2$—S—, R—S—$CH_2$—, R—S—, R—S—(C═O)—, R—S—$CH_2$—(C═O)—, R—(C═O)—$CH_2$—, R—(C═O)—, R—(C═O)—O—$CH_2$—, R—(C═O)—$CH_2$—O—, R—(C═O)—$CH_2CH_2$—O—, R—(C═O)—O—, R—SO—$CH_2$—, R—SO—, R—$SO_2$—$CH_2$—O—, R—$SO_2$—$CH_2$—, R—$SO_2$—O—, R—$SO_2$—, R—$SO_2$—$CH_2$—$NR_3$—, R—$SO_2$—$NR_3$—, $R_1R_2N$—$CH_2$—, $R_1R_2N$—, $R_1R_2N$—(C═O)—$CH_2$—, $R_1R_2N$—(C═O)—$CH_2$—O—, $R_1R_2N$—(C═O)—, $R_1R_2N$—(C═O)—$NR_3$—, $R_1R_2N$—$CH_2$—$SO_2$—, $R_1R_2N$—$CH_2$—$SO_2$—$CH_2$—, $R_1R_2N$—$SO_2$—$CH_2$—, $R_1R_2N$—$SO_2$—, $R_1R_2P(O)$—, and $R_1R_2R_3Si$—;

wherein the derivative is an agriculturally acceptable salt or a compound derivatized from 4-hydroxy of the pyridazine ring of the Formula I, further wherein the compound derivatized from 4-hydroxy of the pyridazine ring of the Formula I is selected from an ester, an oxime, and a hydroxylamine thereof.

7. A herbicidally active pyridazinol compound of Formula I or a derivative thereof,

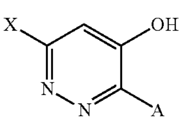

I wherein X and A are shown below:

| No. | X | A |
| --- | --- | --- |
| 20 | $CF_3$ | 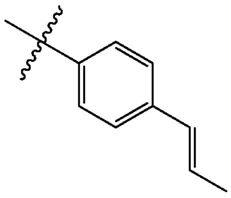 [SMILES: *c1ccc(/C=C/C)cc1] |
| 21 | $CF_3$ | 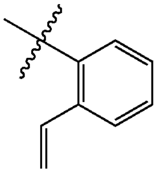 [SMILES: *c1ccccc1C=C] |
| 22 | $CF_3$ | 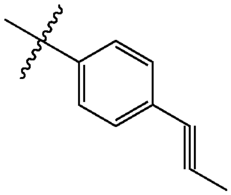 [SMILES: *c1ccc(C#CC)cc1] |
| 23 | $CF_3$ | 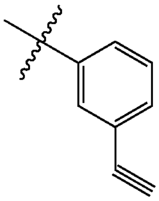 [SMILES: *c1cccc(C#C)c1] |
| 24 | $CF_3$ | 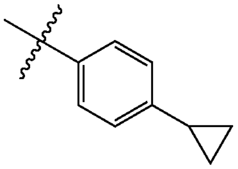 [SMILES: *c1ccc(C2CC2)cc1] |
| 25 | $CF_3$ | 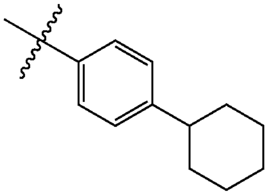 [SMILES: *c1ccc(C2CCCCC2)cc1] |
| 50 | $CF_3$ | 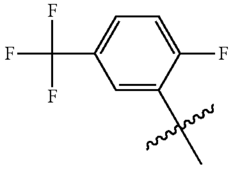 [SMILES: *c1cc(C(F)(F)F)ccc1F] |
| 51 | $CF_3$ | 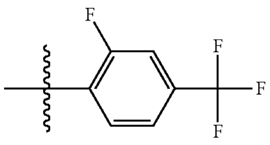 [SMILES: *c1ccc(C(F)(F)F)cc1F] |

-continued
| No. | X | A |
|---|---|---|
| 63 | $CF_3$ | 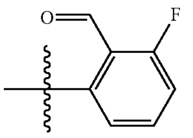 [SMILES: *c1cccc(F)c1C=O] |
| 64 | $CF_3$ | 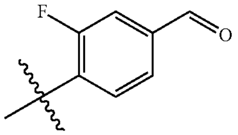 [SMILES: *c1ccc(C=O)cc1F] |
| 65 | $CF_3$ | 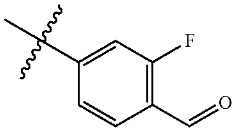 [SMILES: *c1ccc(C=O)c(F)c1] |
| 67 | $CF_3$ | 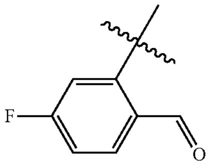 [SMILES: *c1cc(F)ccc1C=O] |
| 84 | $CF_3$ | 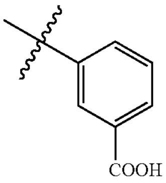 [SMILES: *c1cccc(C(=O)O)c1] |
| 85 | $CF_3$ | 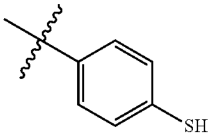 [SMILES: *c1ccc(S)cc1] |
| 86 | $CF_3$ | 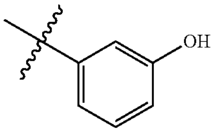 [SMILES: *c1cccc(O)c1] |
| 87 | $CF_3$ | 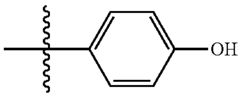 |
| 88 | $CF_3$ | 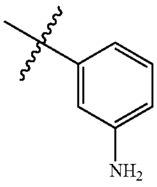 [SMILES: *c1cccc(N)c1] |
-continued
| No. | X | A |
|---|---|---|
| 92 | $CF_3$ | 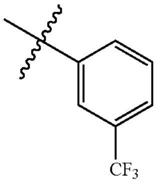 |
| 95 | $CF_3$ | 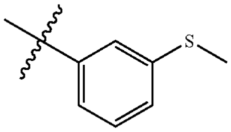 [SMILES: *c1cccc(SC)c1] |
| 96 | $CF_3$ | 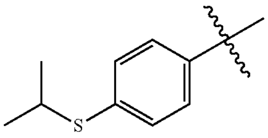 [SMILES: *c1ccc(SC(C)C)cc1] |
| 97 | $CF_3$ | 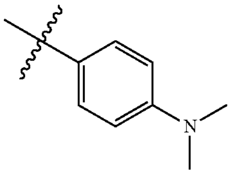 [SMILES: *c1ccc(N(C)C)cc1] |
| 98 | $CF_3$ | 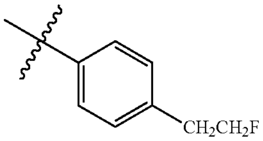 |
| 99 | $CF_3$ | 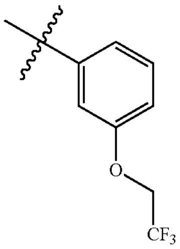 [SMILES: *c1cccc(OCC(F)(F)F)c1] |
| 100 | $CF_3$ | 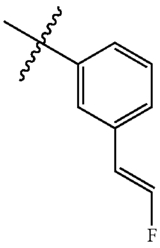 [SMILES: *c1cccc(/C=C/F)c1] |
| 102 | $CF_3$ | 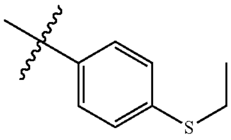 [SMILES: *c1ccc(SCC)cc1] |

-continued
| No. | X | A |
| --- | --- | --- |
| 103 | $CF_3$ | 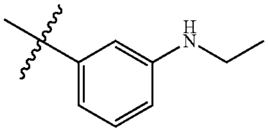 [SMILES: *c1cccc(NCC)c1] |
| 104 | $CF_3$ | 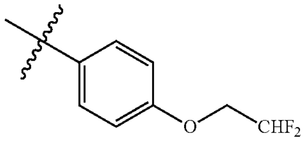 [SMILES: *c1ccc(OCC(F)F)cc1] |
| 106 | $CF_3$ | 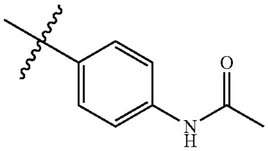 [SMILES: *c1ccc(NC(C)=O)cc1] |
| 107 | $CF_3$ | 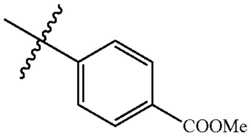 [SMILES: *c1ccc(C(=O)OC)cc1] |
| 108 | $CF_3$ | 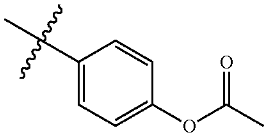 [SMILES: *c1ccc(OC(C)=O)cc1] |
| 109 | $CF_3$ | 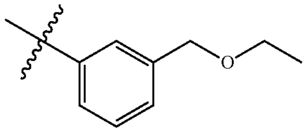 [SMILES: *c1cccc(COCC)c1] |
| 110 | $CF_3$ | 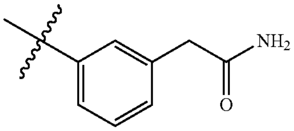 [SMILES: *c1cccc(CC(N)=O)c1] |
| 111 | $CF_3$ | 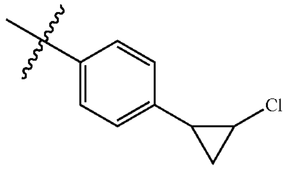 [SMILES: *c1ccc(C2CC2Cl)cc1] |
| 112 | $CF_3$ | 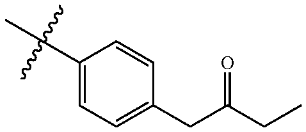 [SMILES: *c1ccc(CC(=O)CC)cc1] |
| 113 | $CF_3$ | 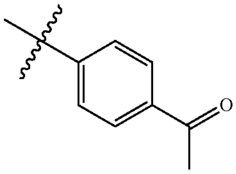 [SMILES: *c1ccc(C(C)=O)cc1] |
-continued
| No. | X | A |
| --- | --- | --- |
| 114 | $CF_3$ | 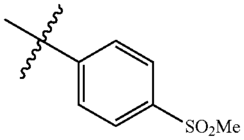 [SMILES: *c1ccc(S(C)(=O)=O)cc1] |
| 115 | $CF_3$ | 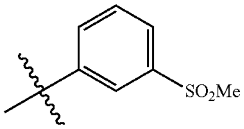 [SMILES: *c1cccc(S(C)(=O)=O)c1] |
| 116 | $CF_3$ | 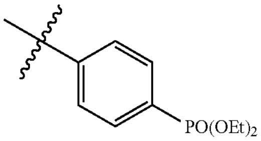 |
| 119 | $CF_3$ | 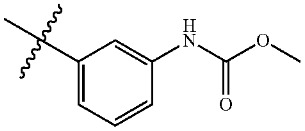 [SMILES: *c1cccc(NC(=O)OC)c1] |
| 120 | $CF_3$ | 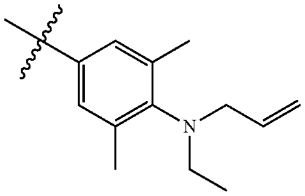 [SMILES: *c1cc(C)c(N(CC)CC=C)c(C)c1] |
| 121 | $CF_3$ | 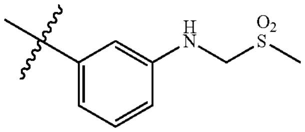 [SMILES: *c1cccc(NCS(C)(=O)=O)c1] |
| 122 | $CF_3$ | 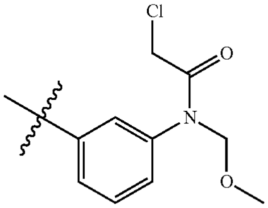 [SMILES: *c1cccc(N(COC)C(=O)CCl)c1] |
| 123 | $CF_3$ | 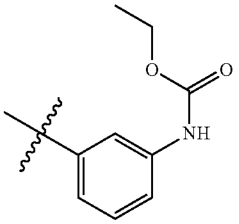 [SMILES: *c1cccc(NC(=O)OCC)c1] |
| 124 | $CF_3$ | 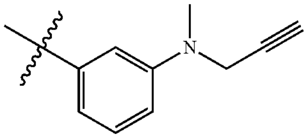 [SMILES: *c1cccc(N(C)CC#C)c1] |

-continued
| No. | X | A |
|---|---|---|
| 125 | $CF_3$ | 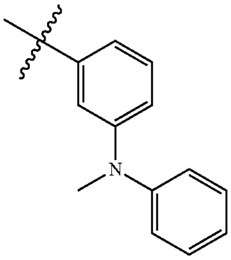 [SMILES: *c1cccc(N(C)c2ccccc2)c1] |
| 126 | $CF_3$ | 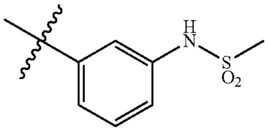 [SMILES: *c1cccc(NS(C)(=O)=O)c1] |
| 127 | $CF_3$ | 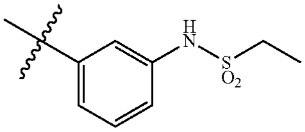 [SMILES: *c1cccc(NS(=O)(=O)CC)c1] |
| 128 | $CF_3$ | 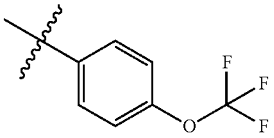 [SMILES: *c1ccc(OC(F)(F)F)cc1] |
| 129 | $CF_3$ | 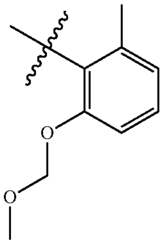 [SMILES: *c1c(C)cccc1OCOC] |
| 130 | $CF_3$ | 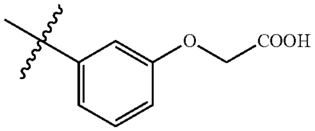 [SMILES: *c1cccc(OCC(=O)O)c1] |
| 131 | $CF_3$ | 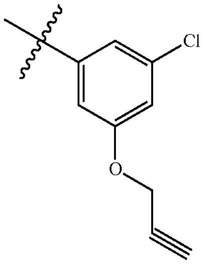 [SMILES: *c1cc(Cl)cc(OCC#C)c1] |
| 132 | $CF_3$ | 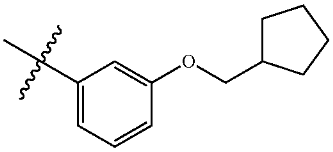 [SMILES: *c1cccc(OCC2CCCC2)c1] |
-continued
| No. | X | A |
|---|---|---|
| 133 | $CF_3$ | 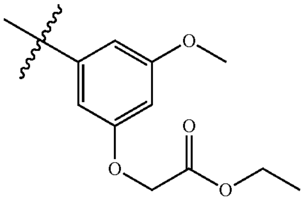 [SMILES: *c1cc(OC)cc(OCC(=O)OCC)c1] |
| 134 | $CF_3$ | 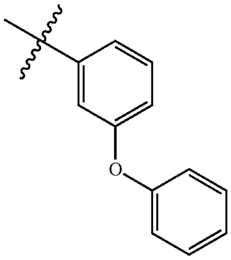 [SMILES: *c1cccc(Oc2ccccc2)c1] |
| 135 | $CF_3$ | 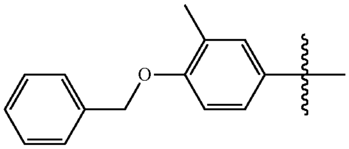 [SMILES: *c1ccc(OCc2ccccc2)c(C)c1] |
| 136 | $CF_3$ | 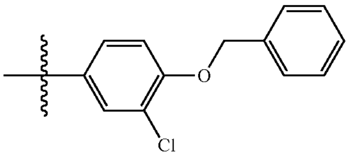 [SMILES: *c1ccc(OCc2ccccc2)c(Cl)c1] |
| 137 | $CF_3$ | 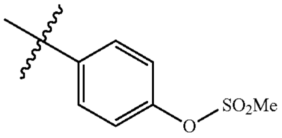 [SMILES: *c1ccc(OS(C)(=O)=O)cc1] |
| 138 | $CF_3$ | 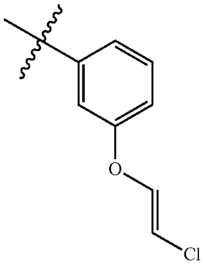 [SMILES: *c1cccc(O/C=C/Cl)c1] |
| 139 | $CF_3$ | 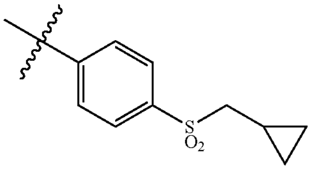 [SMILES: *c1ccc(S(=O)(=O)CC2CC2)cc1] |
| 140 | $CF_3$ | 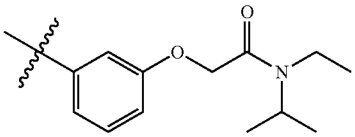 [SMILES: *c1cccc(OCC(=O)N(CC)C(C)C)c1] |

-continued
| No. | X | A |
|---|---|---|
| 141 | $CF_3$ | 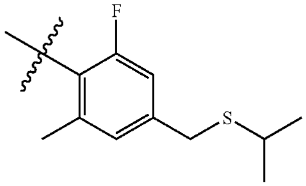 [SMILES: *c1c(C)cc(CSC(C)C)cc1F] |
| 142 | $CF_3$ | 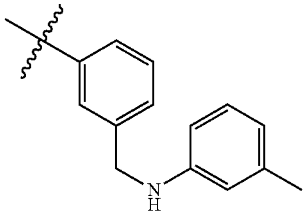 [SMILES: *c1cccc(CNc2cccc(C)c2)c1] |
| 143 | $CF_3$ | 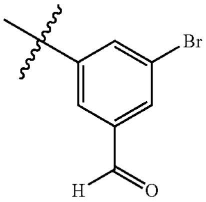 [SMILES: *c1cc(Br)cc(C=O)c1] |
| 144 | $CF_3$ | 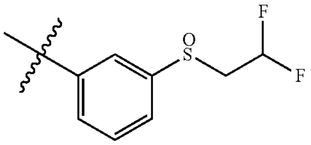 |
| 145 | $CF_3$ | 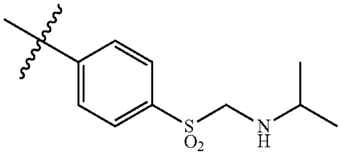 [SMILES: *c1ccc(S(=O)(=O)CNC(C)C)cc1] |
| 146 | $CF_3$ | 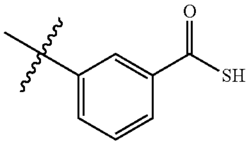 [SMILES: *c1cccc(C(=O)S)c1] |
| 147 | $CF_3$ | 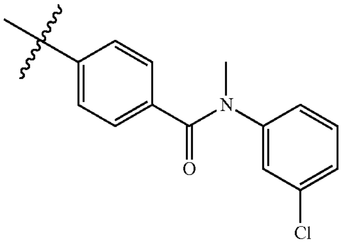 [SMILES: *c1ccc(C(=O)N(C)c2cccc(Cl)c2)cc1] |
| 148 | $CF_3$ | 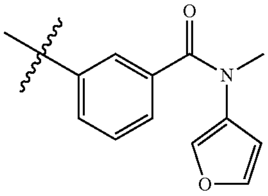 [SMILES: *c1cccc(C(=O)N(C)c2ccoc2)c1] |
-continued
| No. | X | A |
|---|---|---|
| 149 | $CF_3$ | 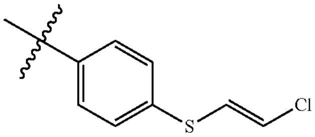 [SMILES: *c1ccc(S/C=C/Cl)cc1] |
| 150 | $CF_3$ | 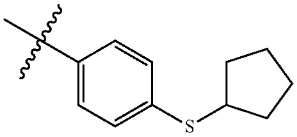 [SMILES: *c1ccc(SC2CCCC2)cc1] |
| 151 | $CF_3$ | 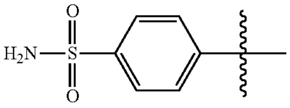 [SMILES: *c1ccc(S(N)(=O)=O)cc1] |
| 152 | $CF_3$ | 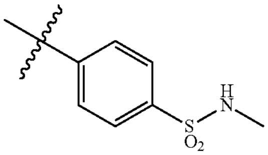 [SMILES: *c1ccc(S(=O)(=O)NC)cc1] |
| 155 | $CF_3$ | 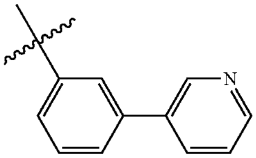 [SMILES: *c1cccc(-c2cccnc2)c1] |
| 156 | $CF_3$ | 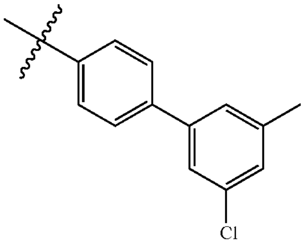 [SMILES: *c1ccc(-c2cc(C)cc(Cl)c2)cc1] |
| 159 | $CF_3$ | 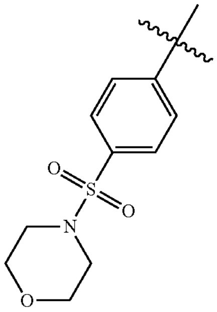 [SMILES: *c1ccc(S(=O)(=O)N2CCOCC2)cc1] |
| 160 | $CF_3$ | 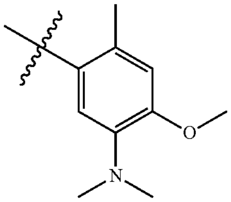 [SMILES: *c1cc(N(C)C)c(OC)cc1C] |

-continued
| No. | X | A |
| --- | --- | --- |
| 164 | $CF_3$ | 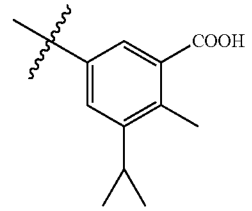 [SMILES: *c1cc(C(=O)O)c(C)c(C(C)C)c1] |
| 165 | $CF_3$ | 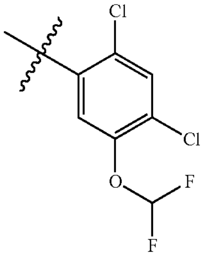 [SMILES: *c1cc(OC(F)F)c(Cl)cc1Cl] |
| 166 | $CF_3$ | 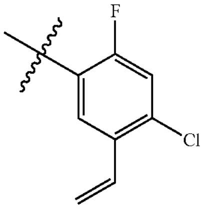 [SMILES: *c1cc(C=C)c(Cl)cc1F] |
| 167 | $CF_3$ | 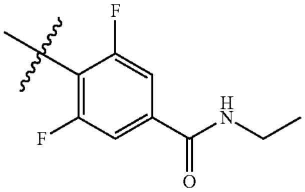 [SMILES: *c1c(F)cc(C(=O)NCC)cc1F] |
| 168 | $CF_3$ | 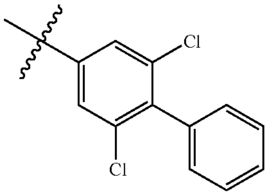 [SMILES: *c1cc(Cl)c(-c2ccccc2)c(Cl)c1] |
| 169 | $CF_3$ | 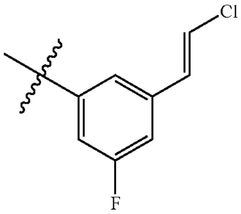 [SMILES: *c1cc(F)cc(/C=C/Cl)c1] |
| 170 | $CF_3$ | 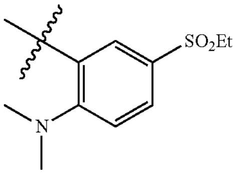 |
-continued
| No. | X | A |
| --- | --- | --- |
| 171 | $CF_3$ | 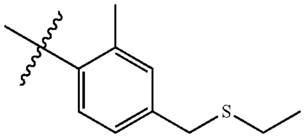 [SMILES: *c1ccc(CSCC)cc1C] |
| 172 | $CF_3$ | 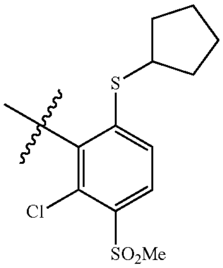 [SMILES: *c1c(SC2CCCC2)ccc(S(C)(=O)=O)c1Cl] |
| 173 | $CF_3$ | 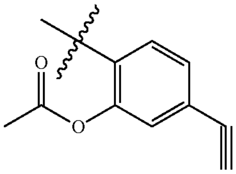 [SMILES: *c1ccc(C#C)cc1OC(C)=O] |
| 174 | $CF_3$ | 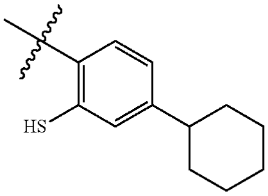 [SMILES: *c1ccc(C2CCCCC2)cc1S] |
| 175 | $CF_3$ | 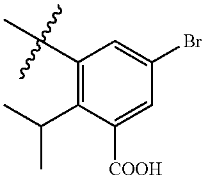 [SMILES: *c1cc(Br)cc(C(=O)O)c1C(C)C] |
| 176 | $CF_3$ | 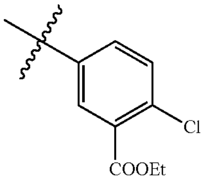 [SMILES: *c1ccc(Cl)c(C(=O)OCC)c1] |
| 177 | $CF_3$ | 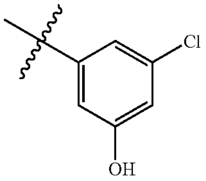 [SMILES: *c1cc(O)cc(Cl)c1] |

-continued
| No. | X | A |
| --- | --- | --- |
| 178 | $CF_3$ | 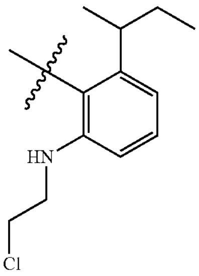 [SMILES: *c1c(NCCCl)cccc1C(C)CC] |
| 180 | $CF_3$ | 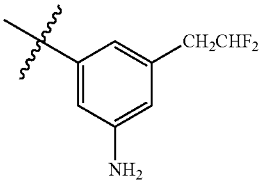 |
| 181 | $CF_3$ | 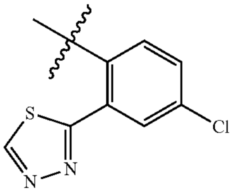 [SMILES: *c1ccc(Cl)cc1-c1nncs1] |
| 182 | $CF_3$ | 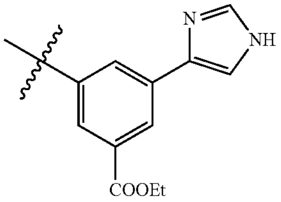 [SMILES: *c1cc(C(=O)OCC)cc(-c2c[nH]cn2)c1] |
| 183 | $CF_3$ | 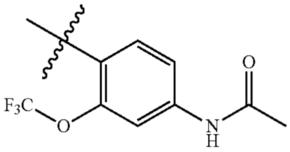 [SMILES: *c1ccc(NC(C)=O)cc1OC(F)(F)F] |
| 184 | $CF_3$ | 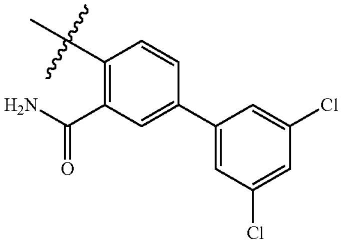 [SMILES: *c1ccc(-c2cc(Cl)cc(Cl)c2)cc1C(N)=O] |
| 185 | $CF_3$ | 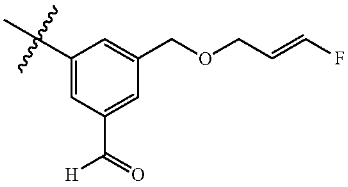 [SMILES: *c1cc(C=O)cc(COC/C=C/F)c1] |
| 186 | $CF_3$ | 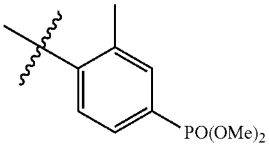 |
| 187 | $CF_3$ | 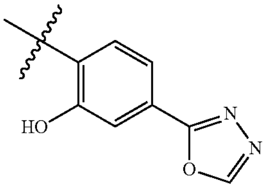 [SMILES: *c1ccc(-c2nnco2)cc1O] |
| 188 | $CF_3$ | 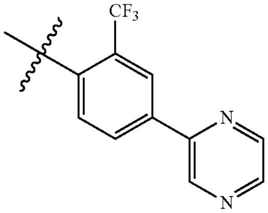 [SMILES: *c1ccc(-c2cnccn2)cc1C(F)(F)F] |
| 189 | $CF_3$ | 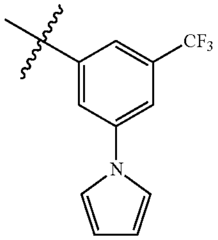 [SMILES: *c1cc(-n2cccc2)cc(C(F)(F)F)c1] |
| 190 | $CF_3$ | 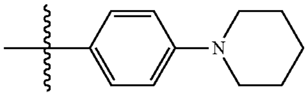 [SMILES: *c1ccc(N2CCCCC2)cc1] |
| 191 | $CF_3$ | 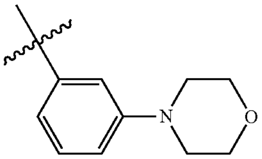 [SMILES: *c1cccc(N2CCOCC2)c1] |
| 192 | $CF_3$ | 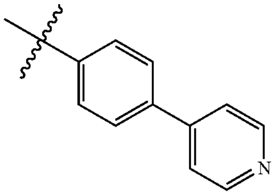 [SMILES: *c1ccc(-c2ccncc2)cc1] |
| 193 | $CF_3$ | 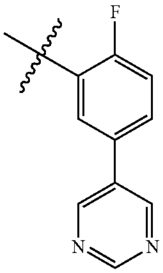 [SMILES: *c1cc(-c2cncnc2)ccc1F] |

-continued
| No. | X | A |
|---|---|---|
| 194 | $CF_3$ | 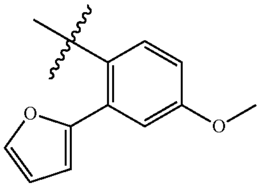 [SMILES: *c1ccc(OC)cc1-c1ccco1] |
| 195 | $CF_3$ | 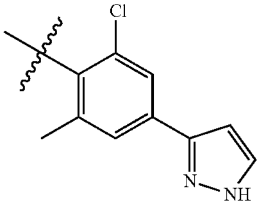 [SMILES: *c1c(C)cc(-c2cc[nH]n2)cc1Cl] |
| 196 | $CF_3$ | 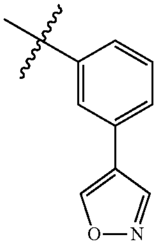 [SMILES: *c1cccc(-c2cnoc2)c1] |
| 197 | $CF_3$ | 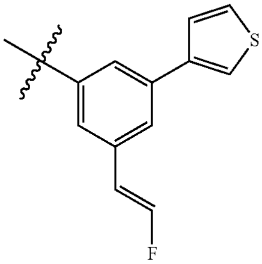 [SMILES: *c1cc(/C=C/F)cc(-c2ccsc2)c1] |
| 198 | $CF_3$ | 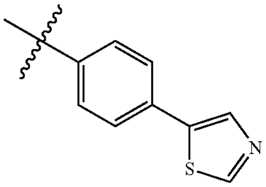 [SMILES: *c1ccc(-c2cncs2)cc1] |
| 199 | $CF_3$ | 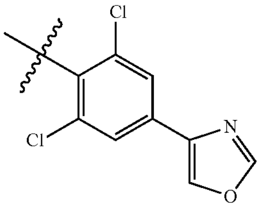 [SMILES: *c1c(Cl)cc(-c2cocn2)cc1Cl] |
-continued
| No. | X | A |
|---|---|---|
| 200 | $CF_3$ | 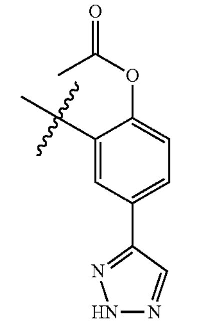 [SMILES: *c1cc(-c2cn[nH]n2)ccc1OC(C)=O] |
| 201 | $CF_3$ | 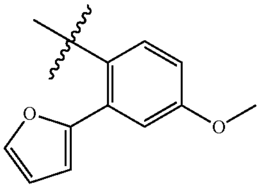 [SMILES: *c1ccc(OC)cc1-c1ccco1] |
| 202 | $CF_3$ | 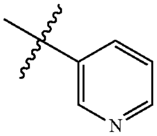 [SMILES: *c1cccnc1] |
| 203 | $CF_3$ | 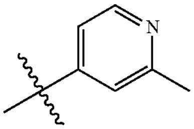 [SMILES: *c1ccnc(C)c1] |
| 204 | $CF_3$ | 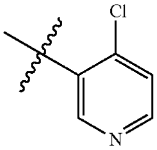 |
| 205 | $CF_3$ | 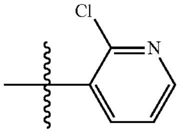 [SMILES: *c1cccnc1Cl] |
| 206 | $CF_3$ | 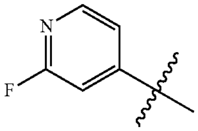 [SMILES: *c1ccnc(F)c1] |
| 207 | $CF_3$ | 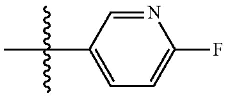 [SMILES: *c1ccc(F)nc1] |
| 208 | $CF_3$ | 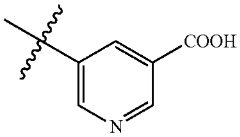 [SMILES: *c1cncc(C(=O)O)c1] |

-continued
| No. | X | A |
|---|---|---|
| 209 | $CF_3$ | 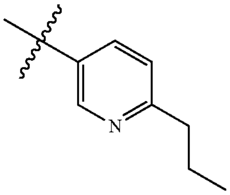 [SMILES: *c1ccc(CCC)nc1] |
| 210 | $CF_3$ | 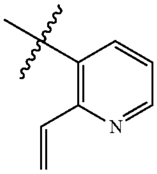 [SMILES: *c1cccnc1C=C] |
| 211 | $CF_3$ | 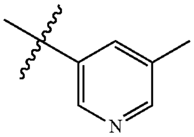 [SMILES: *c1cncc(C)c1] |
| 212 | $CF_3$ | 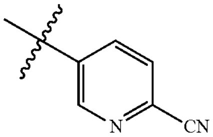 [SMILES: *c1ccc(C#N)nc1] |
| 213 | $CF_3$ | 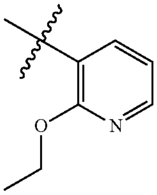 [SMILES: *c1cccnc1OCC] |
| 214 | $CF_3$ | 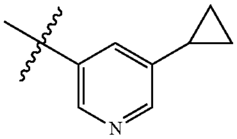 [SMILES: *c1cncc(C2CC2)c1] |
| 215 | $CF_3$ | 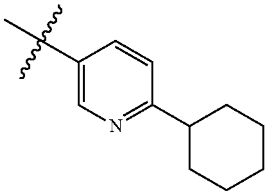 [SMILES: *c1ccc(C2CCCCC2)nc1] |
| 216 | $CF_3$ | 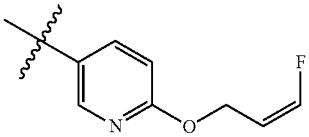 [SMILES: *c1ccc(OC/C=C\F)nc1] |
| 217 | $CF_3$ | 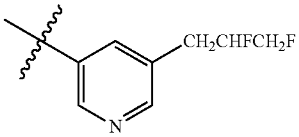 |
| 218 | $CF_3$ | 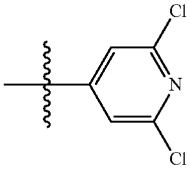 [SMILES: *c1cc(Cl)nc(Cl)c1] |
| 219 | $CF_3$ | 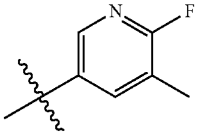 [SMILES: *c1cnc(F)c(C)c1] |
| 220 | $CF_3$ | 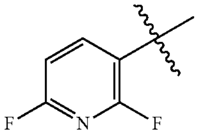 [SMILES: *c1ccc(F)nc1F] |
| 221 | $CF_3$ | 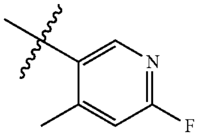 [SMILES: *c1cnc(F)cc1C] |
| 222 | $CF_3$ | 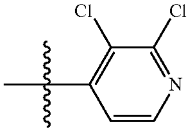 [SMILES: *c1ccnc(Cl)c1Cl] |
| 223 | $CF_3$ | 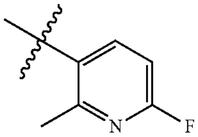 [SMILES: *c1ccc(F)nc1C] |
| 224 | $CF_3$ | 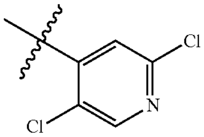 [SMILES: *c1cc(Cl)ncc1Cl] |
| 225 | $CF_3$ | 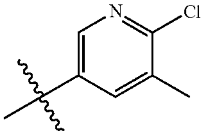 [SMILES: *c1cnc(Cl)c(C)c1] |
| 226 | $CF_3$ | 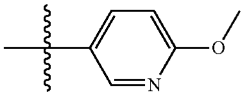 [SMILES: *c1ccc(OC)nc1] |
| 227 | $CF_3$ | 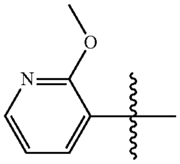 [SMILES: *c1cccnc1OC] |

-continued
| No. | X | A |
|---|---|---|
| 228 | $CF_3$ | 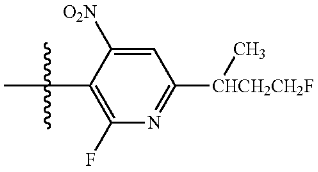 |
| 229 | $CF_3$ | 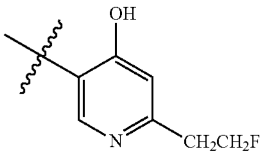 |
| 230 | $CF_3$ | 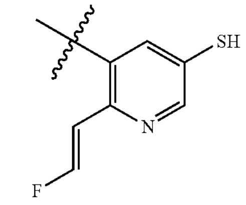 [SMILES: *c1cc(S)cnc1/C=C/F] |
| 231 | $CF_3$ | 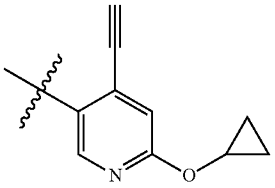 [SMILES: *c1cnc(OC2CC2)cc1C#C] |
| 232 | $CF_3$ | 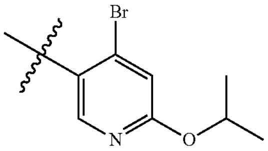 [SMILES: *c1cnc(OC(C)C)cc1Br] |
| 233 | $CF_3$ | 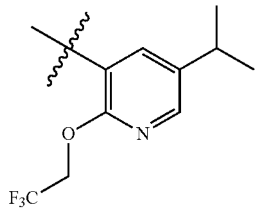 |
| 234 | $CF_3$ | 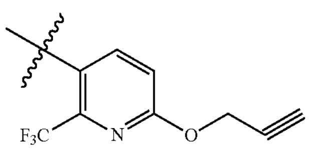 [SMILES: *c1ccc(OCC#C)nc1C(F)(F)F] |
| 235 | $CF_3$ | 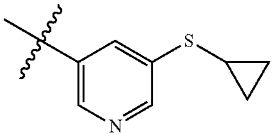 [SMILES: *c1cncc(SC2CC2)c1] |
| 236 | $CF_3$ | 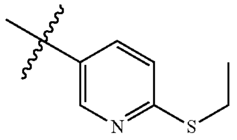 [SMILES: *c1ccc(SCC)nc1] |
-continued
| No. | X | A |
|---|---|---|
| 237 | $CF_3$ | 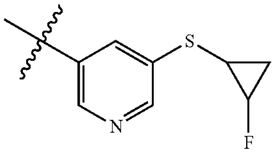 [SMILES: *c1cncc(SC2CC2F)c1] |
| 238 | $CF_3$ | 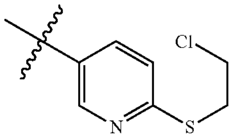 [SMILES: *c1ccc(SCCCl)nc1] |
| 239 | $CF_3$ | 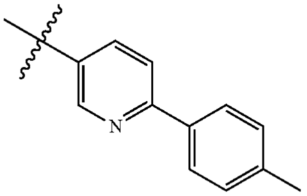 [SMILES: *c1ccc(-c2ccc(C)cc2)nc1] |
| 240 | $CF_3$ | 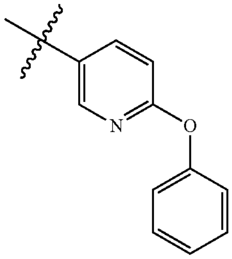 [SMILES: *c1ccc(Oc2ccccc2)nc1] |
| 241 | $CF_3$ | 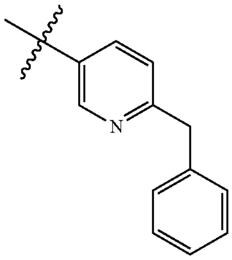 [SMILES: *c1ccc(Cc2ccccc2)nc1] |
| 242 | $CF_3$ | 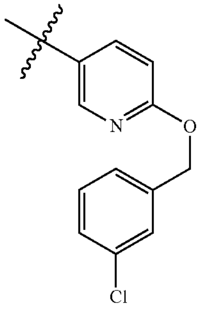 [SMILES: *c1ccc(OCc2cccc(Cl)c2)nc1] |
| 243 | $CF_3$ | 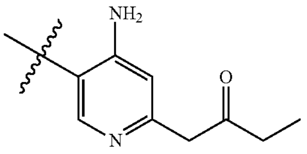 [SMILES: *c1cnc(CC(=O)CC)cc1N] |

-continued
| No. | X | A |
|---|---|---|
| 244 | $CF_3$ | 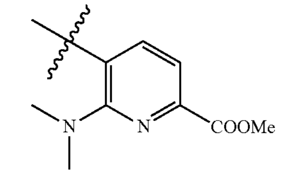 [SMILES: *c1ccc(C(=O)OC)nc1N(C)C] |
| 245 | $CF_3$ | 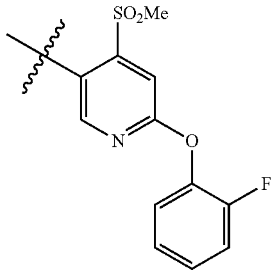 [SMILES: *c1cnc(Oc2ccccc2F)cc1S(C)(=O)=O] |
| 246 | $CF_3$ | 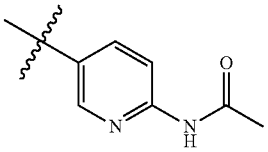 [SMILES: *c1ccc(NC(C)=O)nc1] |
| 247 | $CF_3$ | 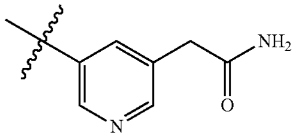 [SMILES: *c1cncc(CC(N)=O)c1] |
| 248 | $CF_3$ | 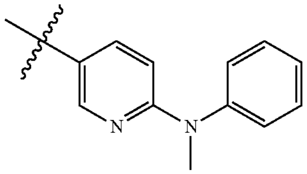 [SMILES: *c1ccc(N(C)c2ccccc2)nc1] |
| 249 | $CF_3$ | 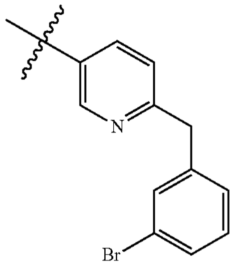 [SMILES: *c1ccc(Cc2cccc(Br)c2)nc1] |
| 250 | $CF_3$ | 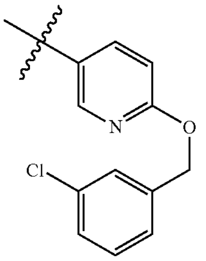 [SMILES: *c1ccc(OCc2cccc(Cl)c2)nc1] |
| 251 | $CF_3$ | 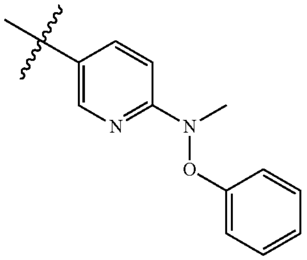 [SMILES: *c1ccc(N(C)Oc2ccccc2)nc1] |
| 252 | $CF_3$ | 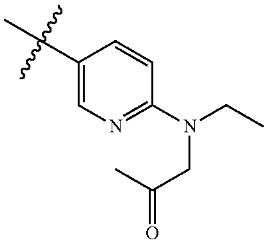 [SMILES: *c1ccc(N(CC)CC(C)=O)nc1] |
| 253 | $CF_3$ | 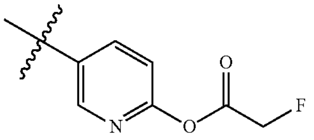 [SMILES: *c1ccc(OC(=O)CF)nc1] |
| 254 | $CF_3$ | 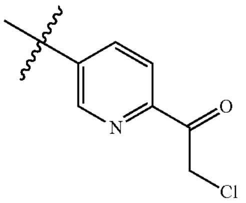 [SMILES: *c1ccc(C(=O)CCl)nc1] |
| 255 | $CF_3$ | 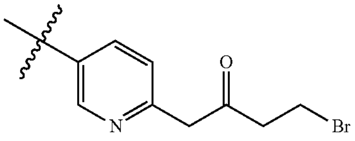 [SMILES: *c1ccc(CC(=O)CCBr)nc1] |
| 256 | $CF_3$ | 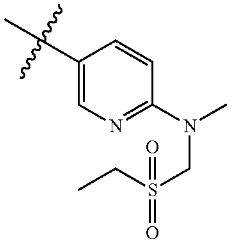 [SMILES: *c1ccc(N(C)CS(=O)(=O)CC)nc1] |
| 257 | $CF_3$ | 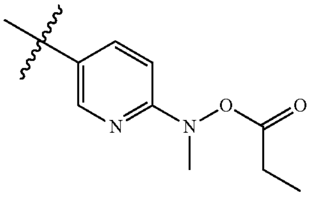 [SMILES: *c1ccc(N(C)OC(=O)CC)nc1] |

-continued
| No. | X | A |
|---|---|---|
| 258 | $CF_3$ | 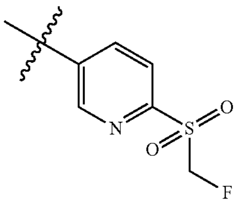 [SMILES: *c1ccc(S(=O)(=O)CF)nc1] |
| 259 | $CF_3$ | 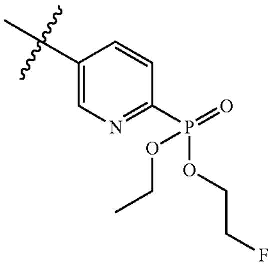 |
| 260 | $CF_3$ | 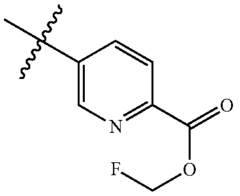 [SMILES: *c1ccc(C(=O)OCF)nc1] |
| 261 | $CF_3$ | 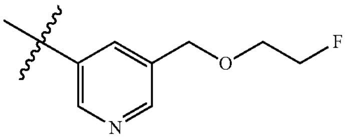 [SMILES: *c1cncc(COCCF)c1] |
| 262 | $CF_3$ | 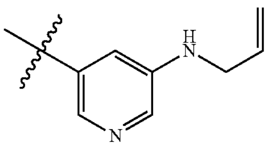 [SMILES: *c1cncc(NCC=C)c1] |
| 263 | $CF_3$ | 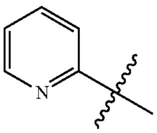 [SMILES: *c1ccccn1] |
| 264 | $CF_3$ | 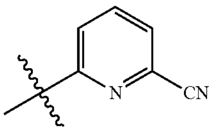 [SMILES: *c1cccc(C#N)n1] |
| 265 | $CF_3$ | 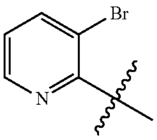 [SMILES: *c1ncccc1Br] |
-continued
| No. | X | A |
|---|---|---|
| 266 | $CF_3$ | 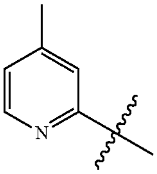 [SMILES: *c1cc(C)ccn1] |
| 267 | $CF_3$ | 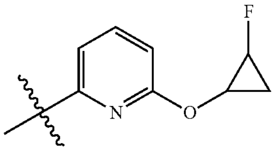 [SMILES: *c1cccc(OC2CC2F)n1] |
| 268 | $CF_3$ | 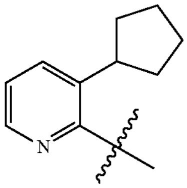 [SMILES: *c1ncccc1C1CCCC1] |
| 269 | $CF_3$ | 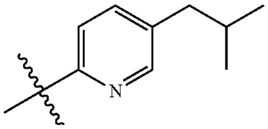 [SMILES: *c1ccc(CC(C)C)cn1] |
| 270 | $CF_3$ | 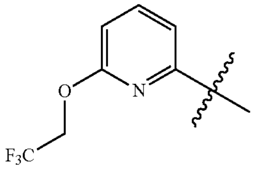 [SMILES: *c1cccc(OCC(F)(F)F)n1] |
| 271 | $CF_3$ | 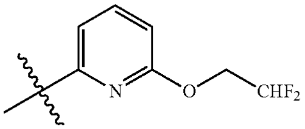 [SMILES: *c1cccc(OCC(F)F)n1] |
| 272 | $CF_3$ | 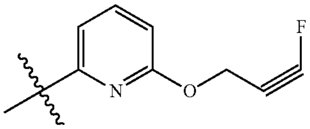 [SMILES: *c1cccc(OCC#CF)n1] |
| 273 | $CF_3$ | 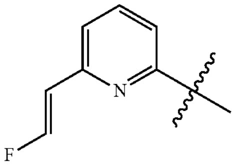 [SMILES: *c1cccc(/C=C/F)n1] |
| 274 | $CF_3$ | 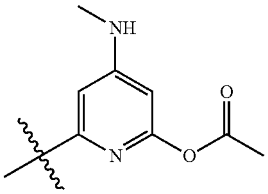 [SMILES: *c1cc(NC)cc(OC(C)=O)n1] |

-continued
| No. | X | A |
|---|---|---|
| 275 | $CF_3$ | 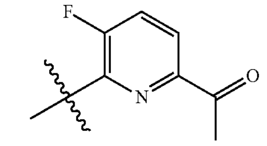 [SMILES: *c1nc(C(C)=O)ccc1F] |
| 276 | $CF_3$ | 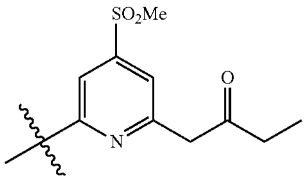 [SMILES: *c1cc(S(C)(=O)=O)cc(CC(=O)CC)n1] |
| 277 | $CF_3$ | 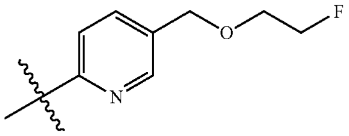 [SMILES: *c1ccc(COCCF)cn1] |
| 278 | $CF_3$ | 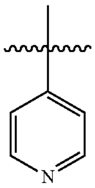 [SMILES: *c1ccncc1] |
| 279 | $CF_3$ | 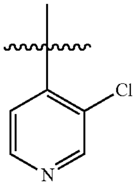 [SMILES: *c1ccncc1Cl] |
| 280 | $CF_3$ | 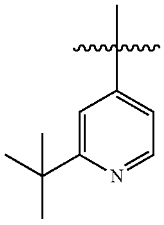 [SMILES: *c1ccnc(C(C)(C)C)c1] |
| 281 | $CF_3$ | 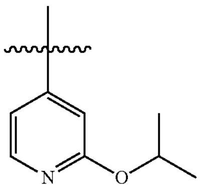 [SMILES: *c1ccnc(OC(C)C)c1] |
| 282 | $CF_3$ | 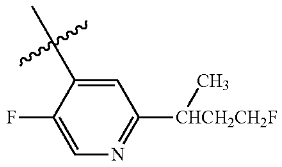 |
-continued
| No. | X | A |
|---|---|---|
| 283 | $CF_3$ | 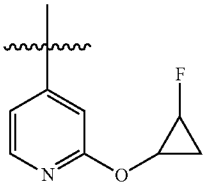 [SMILES: *c1ccnc(OC2CC2F)c1] |
| 284 | $CF_3$ | 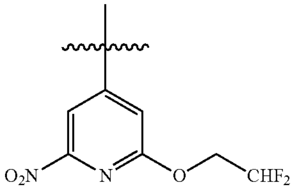 [SMILES: *c1cc(OCC(F)F)nc([N+](=O)[O-])c1] |
| 285 | $CF_3$ | 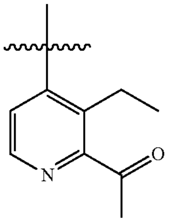 [SMILES: *c1ccnc(C(C)=O)c1CC] |
| 286 | $CF_3$ | 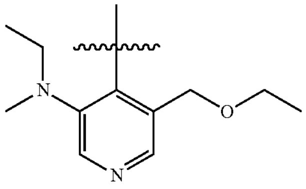 [SMILES: *c1c(COCC)cncc1N(C)CC] |
| 287 | $CF_3$ | 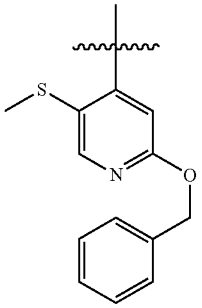 [SMILES: *c1cc(OCc2ccccc2)ncc1SC] |
| 288 | $CF_3$ | 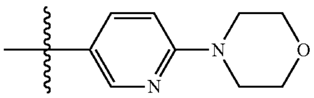 [SMILES: *c1ccc(N2CCOCC2)nc1] |
| 289 | $CF_3$ | 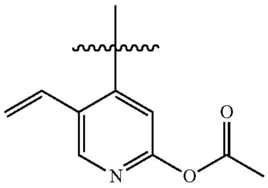 [SMILES: *c1cc(OC(C)=O)ncc1C=C] |

-continued
| No. | X | A |
|---|---|---|
| 290 | $CF_3$ | 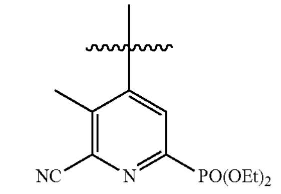 |
| 291 | $CF_3$ | 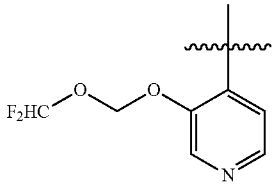 [SMILES: *c1ccncc1OCOC(F)F] |
| 292 | $CF_3$ | 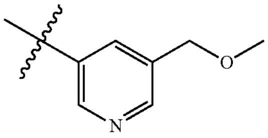 [SMILES: *c1cncc(COC)c1] |
| 293 | $CF_3$ | 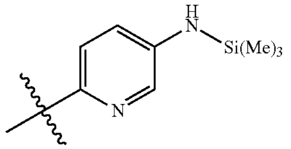 |
| 294 | $CF_3$ | 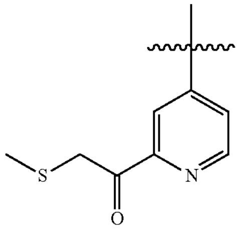 [SMILES: *c1ccnc(C(=O)CSC)c1] |
| 295 | $CF_3$ | 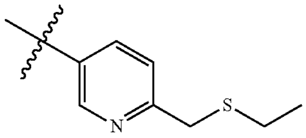 [SMILES: *c1ccc(CSCC)nc1] |
| 296 | $CF_3$ | 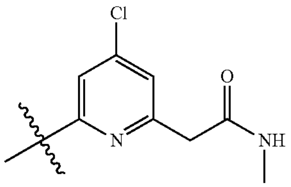 [SMILES: *c1cc(Cl)cc(CC(=O)NC)n1] |
| 297 | $CF_3$ | 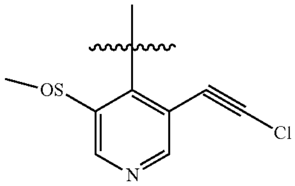 |
| 298 | $CF_3$ | 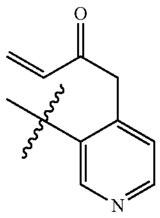 [SMILES: *c1cnccc1CC(=O)C=C] |
| 299 | $CF_3$ | 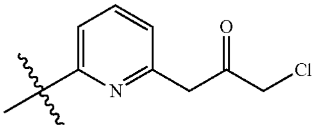 [SMILES: *c1cccc(CC(=O)CCl)n1] |
| 300 | $CF_3$ | 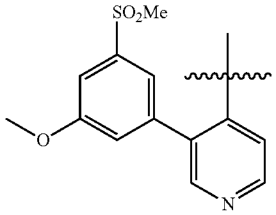 [SMILES: *c1ccncc1-c1cc(OC)cc(S(C)(=O)=O)c1] |
| 301 | $CF_3$ | 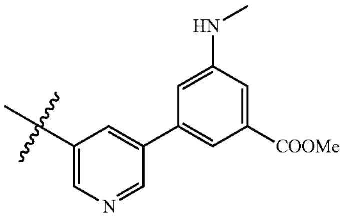 [SMILES: *c1cncc(-c2cc(NC)cc(C(=O)OC)c2)c1] |
| 302 | $CF_3$ | 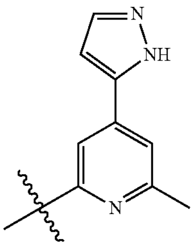 [SMILES: *c1cc(-c2ccn[nH]2)cc(C)n1] |
| 303 | $CF_3$ | 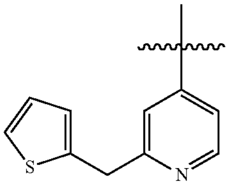 [SMILES: *c1ccnc(Cc2cccs2)c1] |
| 304 | $CF_3$ | 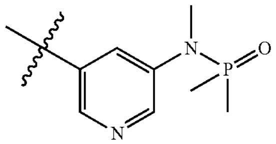 [SMILES: *c1cncc(N(C)P(C)(C)=O)c1] |

-continued
| No. | X | A |
| --- | --- | --- |
| 305 | $CF_3$ | 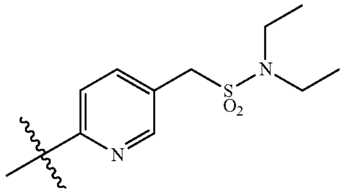 [SMILES: *c1ccc(CS(=O)(=O)N(CC)CC)cn1] |
| 306 | $CF_3$ | 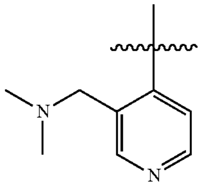 [SMILES: *c1ccncc1CN(C)C] |
| 307 | $CF_3$ | 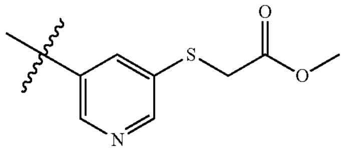 [SMILES: *c1cncc(SCC(=O)OC)c1] |
| 308 | $CF_3$ | 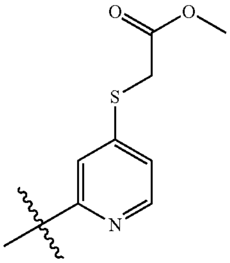 [SMILES: *c1cc(SCC(=O)OC)ccn1] |
| 309 | $CF_3$ | 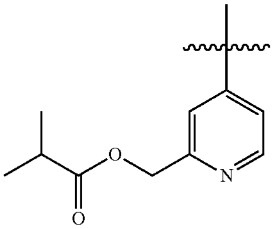 [SMILES: *c1ccnc(COC(=O)C(C)C)c1] |
| 310 | $CF_3$ | 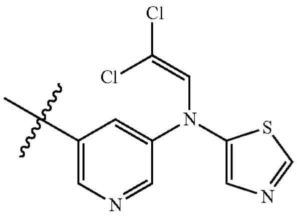 [SMILES: *c1cncc(N(C=C(Cl)Cl)c2cncs2)c1] |
| 311 | $CF_3$ | 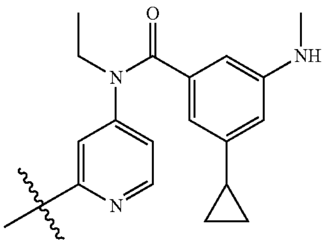 [SMILES: *c1cc(N(CC)C(=O)c2cc(NC)cc(C3CC3)c2)ccn1] |
-continued
| No. | X | A |
| --- | --- | --- |
| 312 | $CF_3$ | 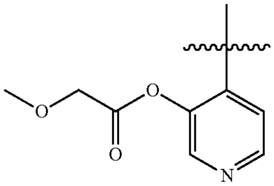 [SMILES: *c1ccncc1OC(=O)COC] |
| 313 | $CF_3$ | 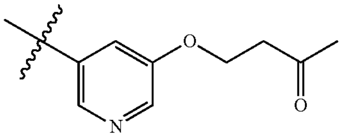 [SMILES: *c1cncc(OCCC(C)=O)c1] |
| 314 | $CF_3$ | 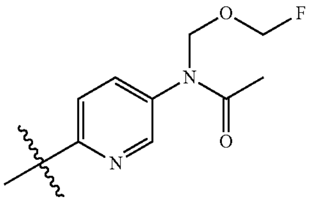 [SMILES: *c1ccc(N(COCF)C(C)=O)cn1] |
| 315 | $CF_3$ | 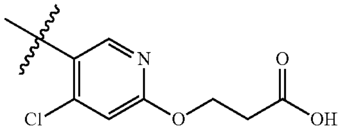 [SMILES: *c1cnc(OCCC(=O)O)cc1Cl] |
| 316 | $CF_3$ | 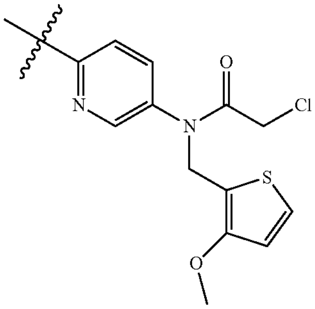 [SMILES: *c1ccc(N(Cc2sccc2OC)C(=O)CCl)cn1] |
| 317 | $CF_3$ | 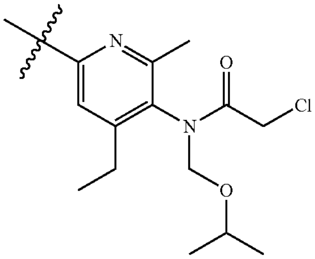 [SMILES: *c1cc(CC)c(N(COC(C)C)C(=O)CCl)c(C)n1] |
| 318 | $CF_3$ | 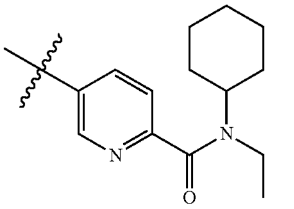 [SMILES: *c1ccc(C(=O)N(CC)C2CCCCC2)nc1] |

-continued
| No. | X | A |
| --- | --- | --- |
| 319 | $CF_3$ | 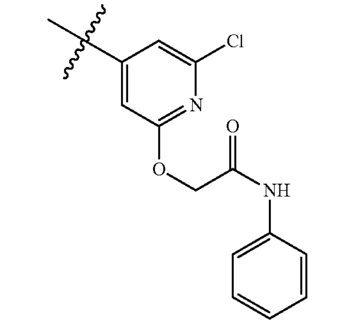 [SMILES: *c1cc(Cl)nc(OCC(=O)Nc2ccccc2)c1] |
| 320 | $CF_3$ | 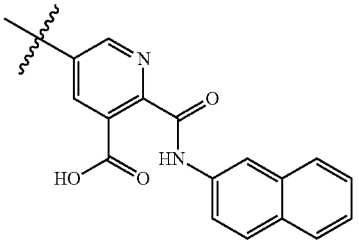 [SMILES: *c1cnc(C(=O)Nc2ccc3ccccc3c2)c(C(=O)O)c1] |
| 321 | $CF_3$ | 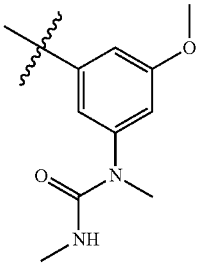 [SMILES: *c1cc(OC)cc(N(C)C(=O)NC)c1] |
| 322 | $CF_3$ | 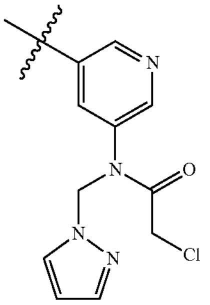 [SMILES: *c1cncc(N(Cn2cccn2)C(=O)CCl)c1] |
| 323 | $CF_3$ | 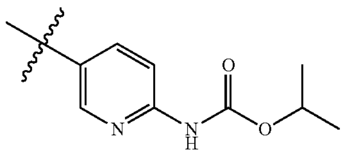 [SMILES: *c1ccc(NC(=O)OC(C)C)nc1] |
| 324 | $CF_3$ | 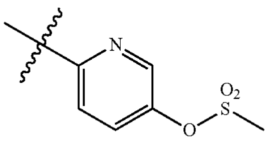 [SMILES: *c1ccc(OS(C)(=O)=O)cn1] |
| 325 | $CF_3$ | 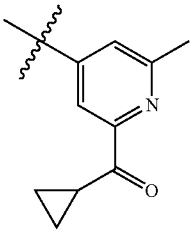 [SMILES: *c1cc(C)nc(C(=O)C2CC2)c1] |
| 326 | $CF_3$ | 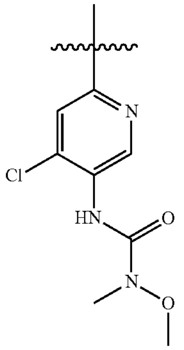 [SMILES: *c1cc(Cl)c(NC(=O)N(C)OC)cn1] |
| 327 | $CF_3$ | 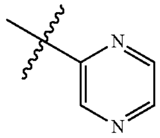 [SMILES: *c1cnccn1] |
| 328 | $CF_3$ | 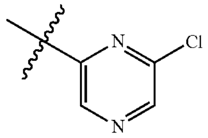 [SMILES: *c1cncc(Cl)n1] |
| 329 | $CF_3$ | 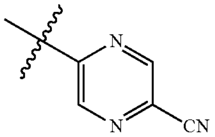 [SMILES: *c1cnc(C#N)cn1] |
| 330 | $CF_3$ | 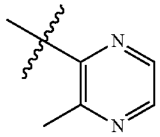 [SMILES: *c1nccnc1C] |
| 331 | $CF_3$ | 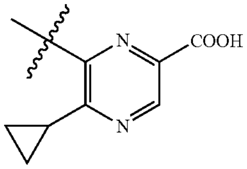 [SMILES: *c1nc(C(=O)O)cnc1C1CC1] |
| 332 | $CF_3$ | 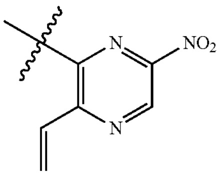 [SMILES: *c1nc([N+](=O)[O-])cnc1C=C] |

-continued
| No. | X | A |
|---|---|---|
| 333 | $CF_3$ | 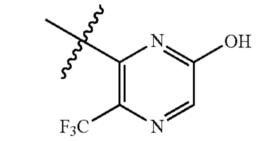 |
| 334 | $CF_3$ | 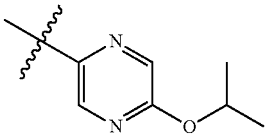 [SMILES: *c1cnc(OC(C)C)cn1] |
| 335 | $CF_3$ | 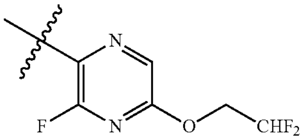 [SMILES: *c1ncc(OCC(F)F)nc1F] |
| 336 | $CF_3$ | 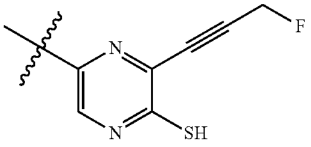 [SMILES: *c1cnc(S)c(C#CCF)n1] |
| 337 | $CF_3$ | 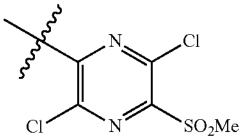 [SMILES: *c1nc(Cl)c(S(C)(=O)=O)nc1Cl] |
| 338 | $CF_3$ | 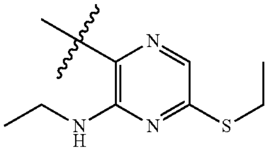 [SMILES: *c1ncc(SCC)nc1NCC] |
| 339 | $CF_3$ | 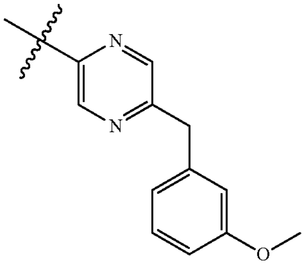 [SMILES: *c1cnc(Cc2cccc(OC)c2)cn1] |
| 340 | $CF_3$ | 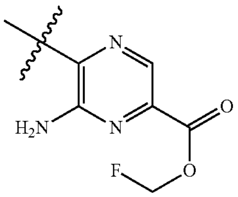 [SMILES: *c1ncc(C(=O)OCF)nc1N] |
| 341 | $CF_3$ | 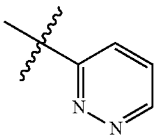 [SMILES: *c1cccnn1] |
-continued
| No. | X | A |
|---|---|---|
| 342 | $CF_3$ | 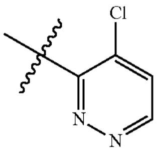 [SMILES: *c1nnccc1Cl] |
| 343 | $CF_3$ | 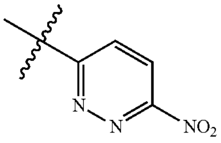 [SMILES: *c1ccc([N+](=O)[O-])nn1] |
| 344 | $CF_3$ | 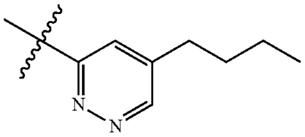 [SMILES: *c1cc(CCCC)cnn1] |
| 345 | $CF_3$ | 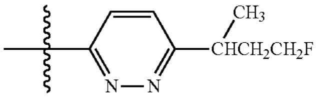 |
| 346 | $CF_3$ | 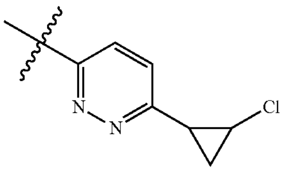 [SMILES: *c1ccc(C2CC2Cl)nn1] |
| 347 | $CF_3$ | 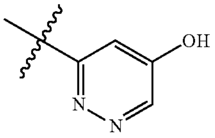 [SMILES: *c1cc(O)cnn1] |
| 348 | $CF_3$ | 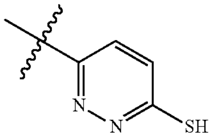 |
| 349 | $CF_3$ | 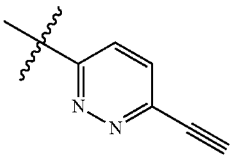 [SMILES: *c1ccc(C#C)nn1] |
| 350 | $CF_3$ | 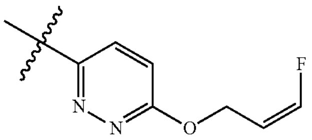 [SMILES: *c1ccc(OC/C=C\F)nn1] |
| 351 | $CF_3$ | 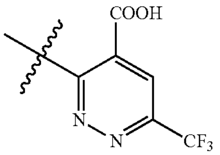 [SMILES: *c1nnc(C(F)(F)F)cc1C(=O)O] |

-continued
| No. | X | A |
| --- | --- | --- |
| 352 | $CF_3$ | 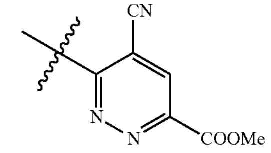 [SMILES: *c1nnc(C(=O)OC)cc1C#N] |
| 353 | $CF_3$ | 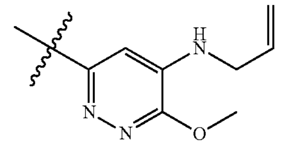 [SMILES: *c1cc(NCC=C)c(OC)nn1] |
| 354 | $CF_3$ | 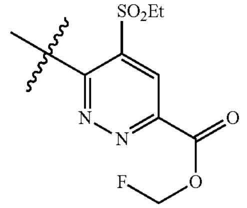 |
| 355 | $CF_3$ | 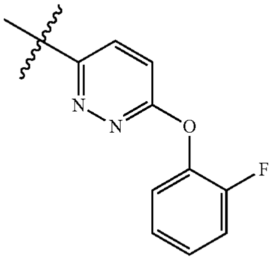 [SMILES: *c1ccc(Oc2ccccc2F)nn1] |
| 356 | $CF_3$ | 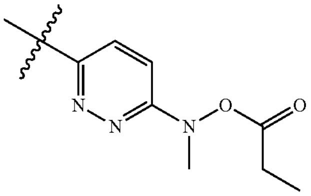 [SMILES: *c1ccc(N(C)OC(=O)CC)nn1] |
| 357 | $CF_3$ | 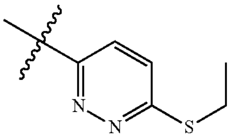 |
| 358 | $CF_3$ | 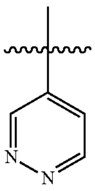 |
| 359 | $CF_3$ | 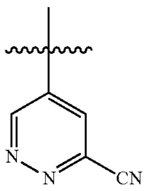 [SMILES: *c1cnnc(C#N)c1] |
-continued
| No. | X | A |
| --- | --- | --- |
| 360 | $CF_3$ | 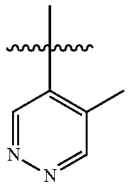 [SMILES: *c1cnncc1C] |
| 361 | $CF_3$ | 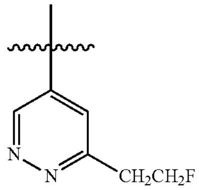 |
| 362 | $CF_3$ | 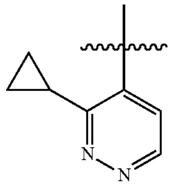 [SMILES: *c1ccnnc1C1CC1] |
| 363 | $CF_3$ | 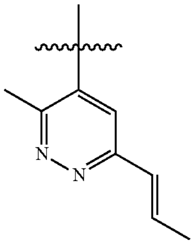 [SMILES: *c1cc(/C=C/C)nnc1C] |
| 364 | $CF_3$ | 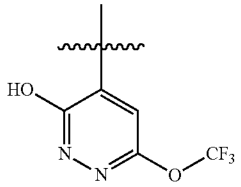 [SMILES: *c1cc(OC(F)(F)F)nnc1O] |
| 365 | $CF_3$ | 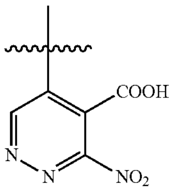 |
| 366 | $CF_3$ | 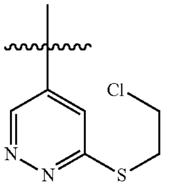 [SMILES: *c1cnnc(SCCCl)c1] |

-continued
| No. | X | A |
| --- | --- | --- |
| 367 | $CF_3$ | 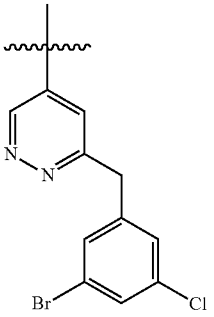 [SMILES: *c1cnnc(Cc2cc(Cl)cc(Br)c2)c1] |
| 368 | $CF_3$ | 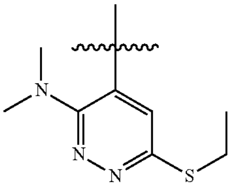 [SMILES: *c1cc(SCC)nnc1N(C)C] |
| 369 | $CF_3$ | 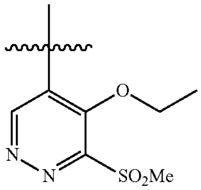 [SMILES: *c1cnnc(S(C)(=O)=O)c1OCC] |
| 374 | $CF_3$ | 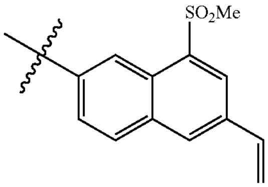 [SMILES: *c1ccc2cc(C=C)cc(S(C)(=O)=O)c2c1] |
| 375 | $CF_3$ | 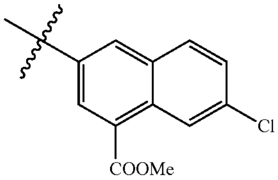 [SMILES: *c1cc(C(=O)OC)c2cc(Cl)ccc2c1] |
| 376 | $CF_3$ | 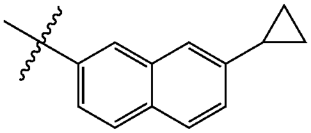 [SMILES: *c1ccc2ccc(C3CC3)cc2c1] |
| 377 | $CF_3$ | 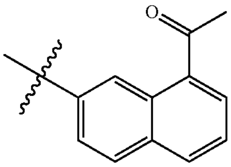 [SMILES: *c1ccc2cccc(C(C)=O)c2c1] |
-continued
| No. | X | A |
| --- | --- | --- |
| 378 | $CF_3$ | 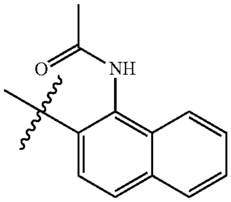 [SMILES: *c1ccc2ccccc2c1NC(C)=O] |
| 379 | $CF_3$ | 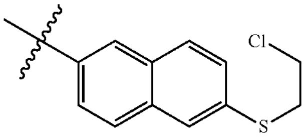 [SMILES: *c1ccc2cc(SCCCl)ccc2c1] |
| 381 | $CF_3$ | 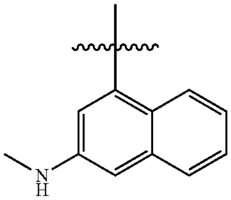 [SMILES: *c1cc(NC)cc2ccccc12] |
| 382 | $CF_3$ | 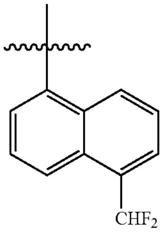 [SMILES: *c1cccc2c(C(F)F)cccc12] |
| 383 | $CF_3$ | 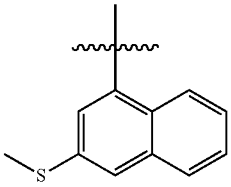 [SMILES: *c1cc(SC)cc2ccccc12] |
| 386 | $CF_3$ | 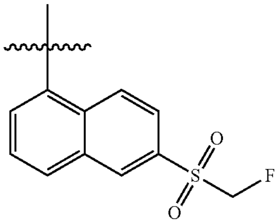 [SMILES: *c1cccc2cc(S(=O)(=O)CF)ccc12] |
| 387 | $CF_3$ | 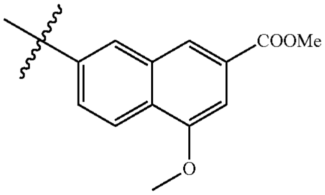 [SMILES: *c1ccc2c(OC)cc(C(=O)OC)cc2c1] |

-continued
| No. | X | A |
|---|---|---|
| 388 | $CF_3$ | 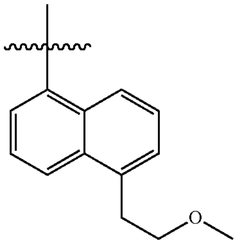 [SMILES: *c1cccc2c(CCOC)cccc12] |
| 389 | $CF_3$ | 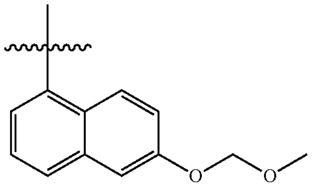 [SMILES: *c1cccc2cc(OCOC)ccc12] |
| 390 | $CF_3$ | 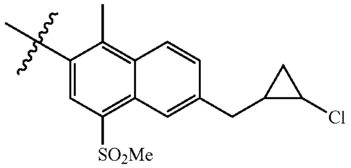 |
| 391 | $CF_3$ | 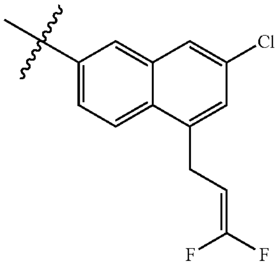 [SMILES: *c1ccc2c(CC=C(F)F)cc(Cl)cc2c1] |
| 392 | $CF_3$ | 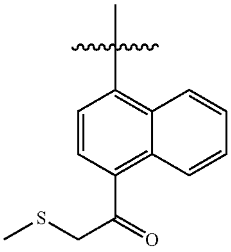 [SMILES: *c1ccc(C(=O)CSC)c2ccccc12] |
| 393 | $CF_3$ | 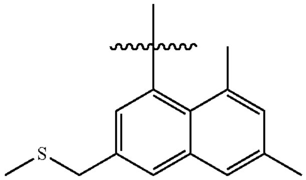 |
| 394 | $CF_3$ | 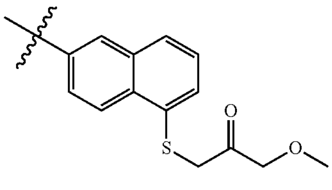 [SMILES: *c1ccc2c(SCC(=O)COC)cccc2c1] |
-continued
| No. | X | A |
|---|---|---|
| 395 | $CF_3$ | 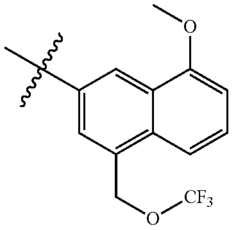 [SMILES: *c1cc(COC(F)(F)F)c2cccc(OC)c2c1] |
| 396 | $CF_3$ | 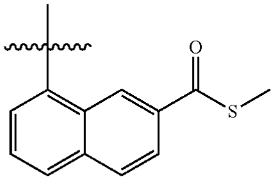 [SMILES: *c1cccc2ccc(C(=O)SC)cc12] |
| 397 | $CF_3$ | 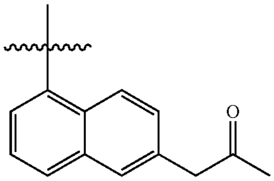 [SMILES: *c1cccc2cc(CC(C)=O)ccc12] |
| 398 | $CF_3$ | 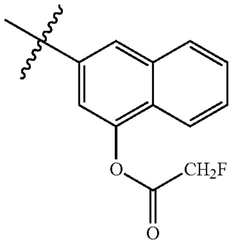 |
| 399 | $CF_3$ | 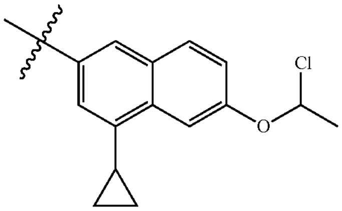 [SMILES: *c1cc(C2CC2)c2cc(OC(C)Cl)ccc2c1] |
| 400 | $CF_3$ | 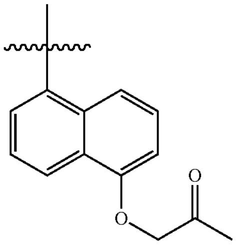 [SMILES: *c1cccc2c(OCC(C)=O)cccc12] |
| 401 | $CF_3$ | 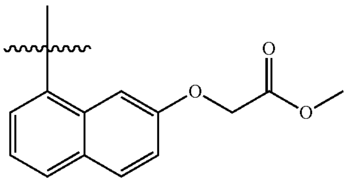 [SMILES: *c1cccc2ccc(OCC(=O)OC)cc12] |

-continued
| No. | X | A |
|---|---|---|
| 402 | $CF_3$ | 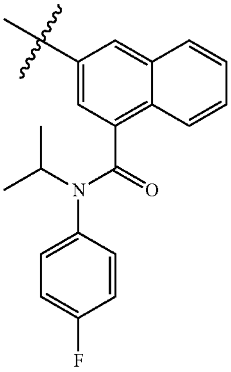 [SMILES: *c1cc(C(=O)N(c2ccc(F)cc2)C(C)C)c2ccccc2c1] |
| 403 | $CF_3$ | 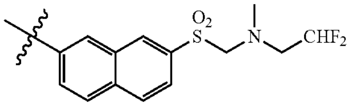 [SMILES: *c1ccc2ccc(S(=O)(=O)CN(C)CC(F)F)cc2c1] |
| 404 | $CF_3$ | 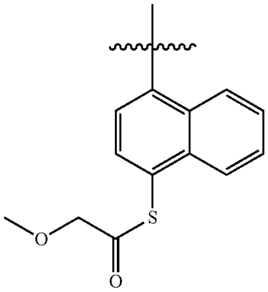 [SMILES: *c1ccc(SC(=O)COC)c2ccccc12] |
| 405 | $CF_3$ | 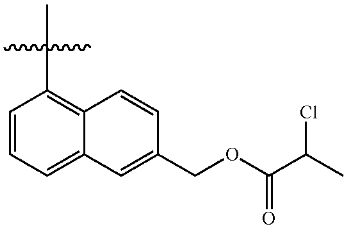 [SMILES: *c1cccc2cc(COC(=O)C(C)Cl)ccc12] |
| 406 | $CF_3$ | 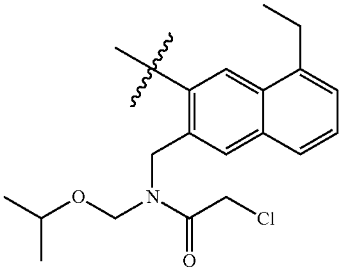 [SMILES: *c1cc2c(CC)cccc2cc1CN(COC(C)C)C(=O)CCl] |
| 407 | $CF_3$ | 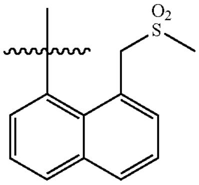 [SMILES: *c1cccc2cccc(CS(C)(=O)=O)c12] |
-continued
| No. | X | A |
|---|---|---|
| 408 | $CF_3$ | 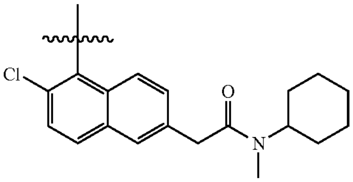 [SMILES: *c1c(Cl)ccc2cc(CC(=O)N(C)C3CCCCC3)ccc12] |
| 409 | $CF_3$ | 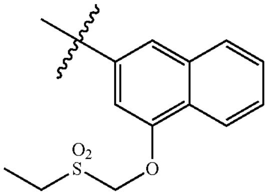 [SMILES: *c1cc(OCS(=O)(=O)CC)c2ccccc2c1] |
| 410 | $CF_3$ | 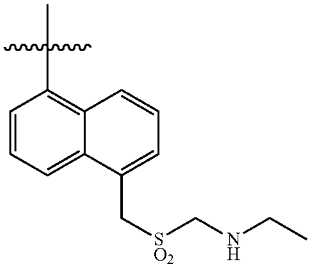 [SMILES: *c1cccc2c(CS(=O)(=O)CNCC)cccc12] |
| 411 | $CF_3$ | 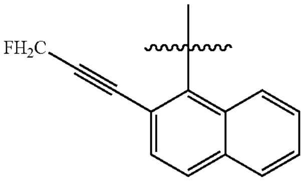 |
| 412 | $CF_3$ | 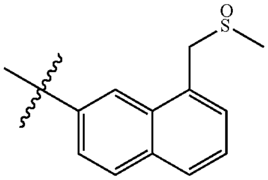 |
| 413 | $CF_3$ | 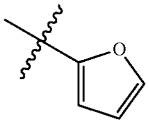 [SMILES: *c1ccco1] |
| 414 | $CF_3$ | 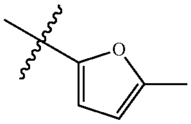 [SMILES: *c1ccc(C)o1] |
| 415 | $CF_3$ | 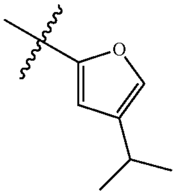 [SMILES: *c1cc(C(C)C)co1] |

-continued
| No. | X | A |
|---|---|---|
| 416 | $CF_3$ | 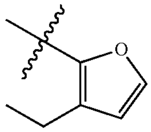 [SMILES: *c1occc1CC] |
| 417 | $CF_3$ | 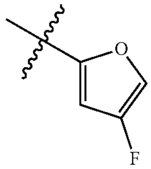 [SMILES: *c1cc(F)co1] |
| 418 | $CF_3$ | 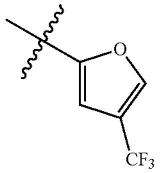 [SMILES: *c1cc(C(F)(F)F)co1] |
| 419 | $CF_3$ | 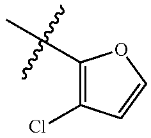 [SMILES: *c1occc1Cl] |
| 420 | $CF_3$ | 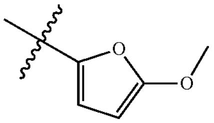 [SMILES: *c1ccc(OC)o1] |
| 421 | $CF_3$ | 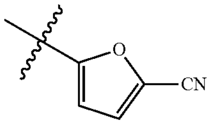 [SMILES: *c1ccc(C#N)o1] |
| 422 | $CF_3$ | 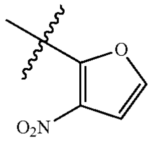 |
| 423 | $CF_3$ | 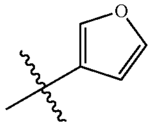 [SMILES: *c1ccoc1] |
| 424 | $CF_3$ | 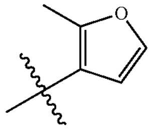 [SMILES: *c1ccoc1C] |
| 425 | $CF_3$ | 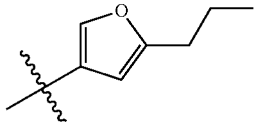 [SMILES: *c1coc(CCC)c1] |
-continued
| No. | X | A |
|---|---|---|
| 426 | $CF_3$ | 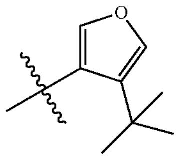 [SMILES: *c1cocc1C(C)(C)C] |
| 427 | $CF_3$ | 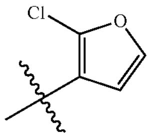 [SMILES: *c1ccoc1Cl] |
| 428 | $CF_3$ | 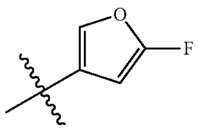 [SMILES: *c1coc(F)c1] |
| 429 | $CF_3$ | 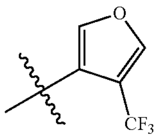 [SMILES: *c1cocc1C(F)(F)F] |
| 430 | $CF_3$ | 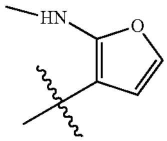 [SMILES: *c1ccoc1NC] |
| 431 | $CF_3$ | 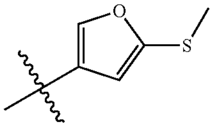 [SMILES: *c1coc(SC)c1] |
| 432 | $CF_3$ | 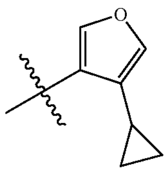 [SMILES: *c1cocc1C1CC1] |
| 433 | $CF_3$ | 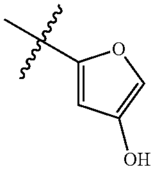 [SMILES: *c1cc(O)co1] |
| 434 | $CF_3$ | 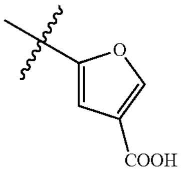 [SMILES: *c1cc(C(=O)O)co1] |

-continued
| No. | X | A |
| --- | --- | --- |
| 435 | $CF_3$ | 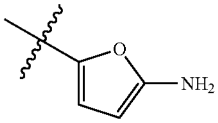 [SMILES: *c1ccc(N)o1] |
| 436 | $CF_3$ | 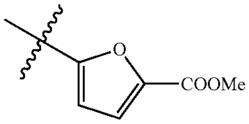 [SMILES: *c1ccc(C(=O)OC)o1] |
| 437 | $CF_3$ | 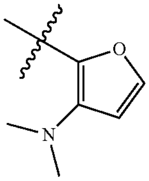 [SMILES: *c1occc1N(C)C] |
| 438 | $CF_3$ | 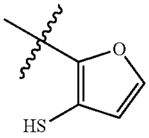 [SMILES: *c1occc1S] |
| 439 | $CF_3$ | 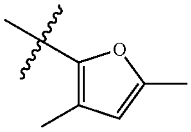 [SMILES: *c1oc(C)cc1C] |
| 440 | $CF_3$ | 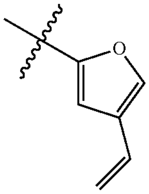 [SMILES: *c1cc(C=C)co1] |
| 441 | $CF_3$ | 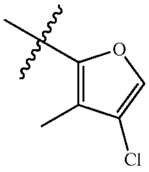 [SMILES: *c1occ(Cl)c1C] |
| 442 | $CF_3$ | 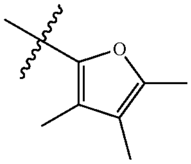 [SMILES: *c1oc(C)c(C)c1C] |
| 443 | $CF_3$ | 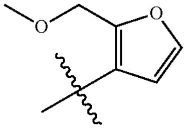 [SMILES: *c1ccoc1COC] |
-continued
| No. | X | A |
| --- | --- | --- |
| 444 | $CF_3$ | 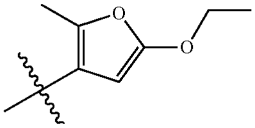 [SMILES: *c1cc(OCC)oc1C] |
| 445 | $CF_3$ | 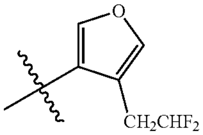 |
| 446 | $CF_3$ | 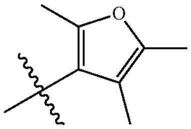 [SMILES: *c1c(C)oc(C)c1C] |
| 447 | $CF_3$ | 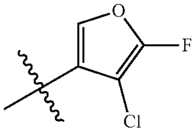 [SMILES: *c1coc(F)c1Cl] |
| 448 | $CF_3$ | 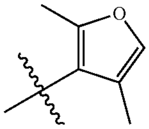 [SMILES: *c1c(C)coc1C] |
| 449 | $CF_3$ | 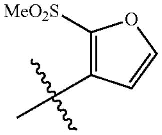 [SMILES: *c1ccoc1S(C)(=O)=O] |
| 450 | $CF_3$ | 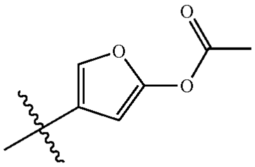 [SMILES: *c1coc(OC(C)=O)c1] |
| 451 | $CF_3$ | 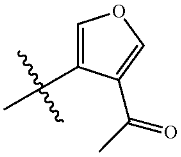 [SMILES: *c1cocc1C(C)=O] |
| 452 | $CF_3$ | 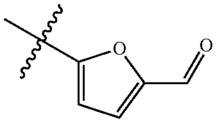 [SMILES: *c1ccc(C=O)o1] |
| 453 | $CF_3$ | 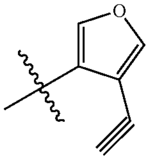 [SMILES: *c1cocc1C#C] |

-continued
| No. | X | A |
|---|---|---|
| 454 | $CF_3$ | 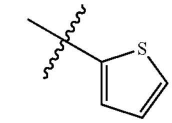 [SMILES: *c1cccs1] |
| 455 | $CF_3$ | 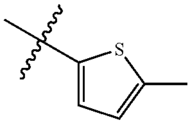 [SMILES: *c1ccc(C)s1] |
| 456 | $CF_3$ | 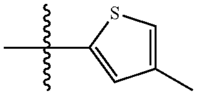 [SMILES: *c1cc(C)cs1] |
| 457 | $CF_3$ | 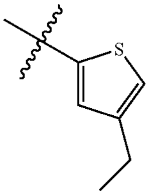 [SMILES: *c1cc(CC)cs1] |
| 458 | $CF_3$ | 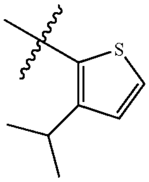 [SMILES: *c1sccc1C(C)C] |
| 459 | $CF_3$ | 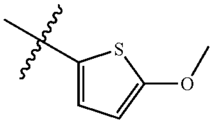 [SMILES: *c1ccc(OC)s1] |
| 460 | $CF_3$ | 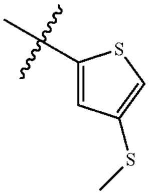 [SMILES: *c1cc(SC)cs1] |
| 461 | $CF_3$ | 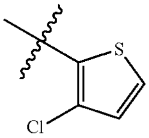 [SMILES: *c1sccc1Cl] |
| 462 | $CF_3$ | 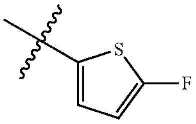 [SMILES: *c1ccc(F)s1] |
-continued
| No. | X | A |
|---|---|---|
| 463 | $CF_3$ | 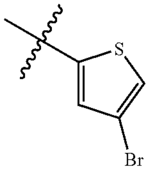 [SMILES: *c1cc(Br)cs1] |
| 464 | $CF_3$ | 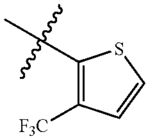 |
| 465 | $CF_3$ | 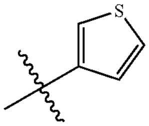 [SMILES: *c1ccsc1] |
| 466 | $CF_3$ | 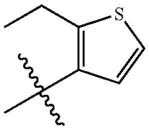 [SMILES: *c1ccsc1CC] |
| 467 | $CF_3$ | 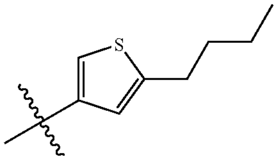 [SMILES: *c1csc(CCCC)c1] |
| 468 | $CF_3$ | 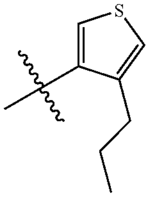 [SMILES: *c1cscc1CCC] |
| 469 | $CF_3$ | 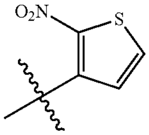 [SMILES: *c1ccsc1[N+](=O)[O-]] |
| 470 | $CF_3$ | 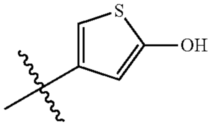 [SMILES: *c1csc(O)c1] |
| 471 | $CF_3$ | 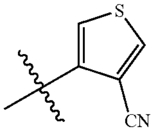 [SMILES: *c1cscc1C#N] |

-continued
| No. | X | A |
|---|---|---|
| 472 | $CF_3$ | 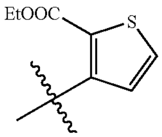 [SMILES: *c1ccsc1C(=O)OCC] |
| 473 | $CF_3$ | 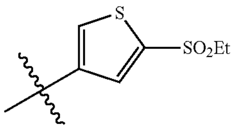 |
| 474 | $CF_3$ | 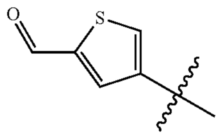 [SMILES: *c1csc(C=O)c1] |
| 475 | $CF_3$ | 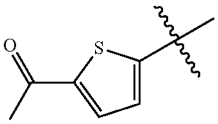 [SMILES: *c1ccc(C(C)=O)s1] |
| 476 | $CF_3$ | 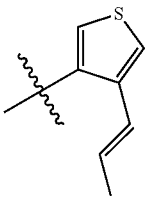 [SMILES: *c1cscc1/C=C/C] |
| 477 | $CF_3$ | 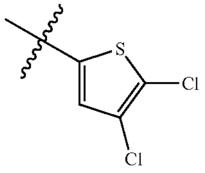 [SMILES: *c1cc(Cl)c(Cl)s1] |
| 478 | $CF_3$ | 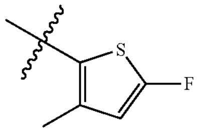 [SMILES: *c1sc(F)cc1C] |
| 479 | $CF_3$ | 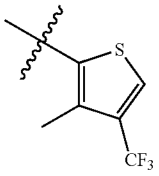 [SMILES: *c1scc(C(F)(F)F)c1C] |
| 480 | $CF_3$ | 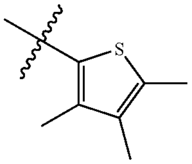 [SMILES: *c1sc(C)c(C)c1C] |
-continued
| No. | X | A |
|---|---|---|
| 481 | $CF_3$ | 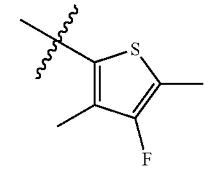 [SMILES: *c1sc(C)c(F)c1C] |
| 482 | $CF_3$ | 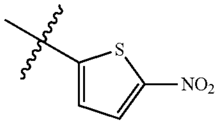 [SMILES: *c1ccc([N+](=O)[O-])s1] |
| 483 | $CF_3$ | 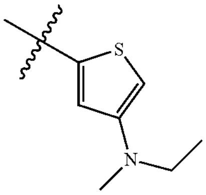 [SMILES: *c1cc(N(C)CC)cs1] |
| 484 | $CF_3$ | 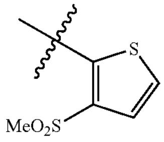 [SMILES: *c1sccc1S(C)(=O)=O] |
| 485 | $CF_3$ | 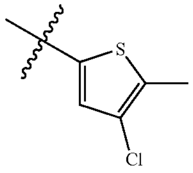 [SMILES: *c1cc(Cl)c(C)s1] |
| 486 | $CF_3$ | 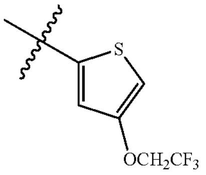 |
| 487 | $CF_3$ | 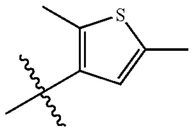 [SMILES: *c1cc(C)sc1C] |
| 488 | $CF_3$ | 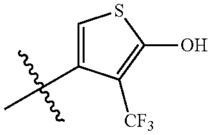 |
| 489 | $CF_3$ | 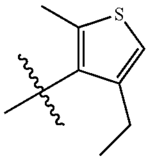 [SMILES: *c1c(CC)csc1C] |

-continued
| No. | X | A |
|---|---|---|
| 490 | $CF_3$ | 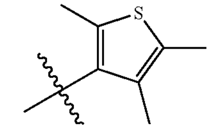 [SMILES: *c1c(C)sc(C)c1C] |
| 491 | $CF_3$ | 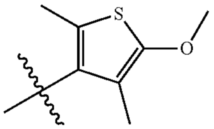 [SMILES: *c1c(C)sc(OC)c1C] |
| 492 | $CF_3$ | 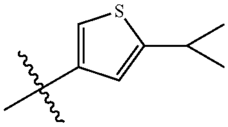 [SMILES: *c1csc(C(C)C)c1] |
| 493 | $CF_3$ | 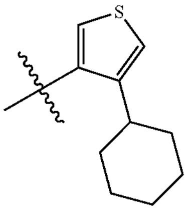 [SMILES: *c1cscc1C1CCCCC1] |
| 494 | $CF_3$ | 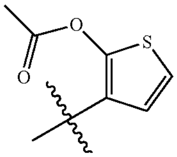 [SMILES: *c1ccsc1OC(C)=O] |
| 495 | $CF_3$ | 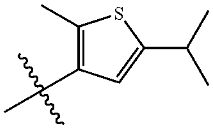 [SMILES: *c1cc(C(C)C)sc1C] |
| 496 | $CF_3$ | 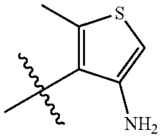 [SMILES: *c1c(N)csc1C] |
| 497 | $CF_3$ | 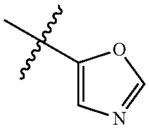 [SMILES: *c1cnco1] |
| 498 | $CF_3$ | 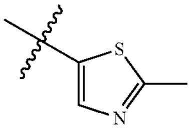 [SMILES: *c1cnc(C)s1] |
| 499 | $CF_3$ | 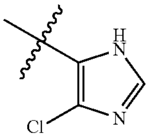 [SMILES: *c1[nH]cnc1Cl] |
-continued
| No. | X | A |
|---|---|---|
| 500 | $CF_3$ | 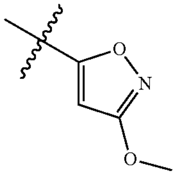 [SMILES: *c1cc(OC)no1] |
| 501 | $CF_3$ | 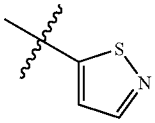 [SMILES: *c1ccns1] |
| 502 | $CF_3$ | 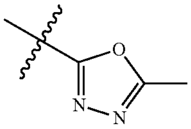 [SMILES: *c1nnc(C)o1] |
| 503 | $CF_3$ | 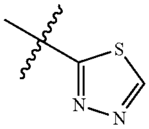 [SMILES: *c1nncs1] |
| 504 | $CF_3$ | 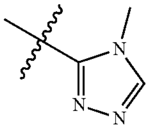 [SMILES: *c1nncn1C] |
| 505 | $CF_3$ | 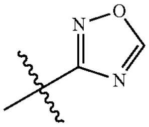 [SMILES: *c1ncon1] |
| 506 | $CF_3$ | 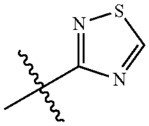 [SMILES: *c1ncsn1] |
| 507 | $CF_3$ | 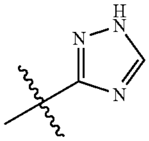 [SMILES: *c1nc[nH]n1] |
| 508 | $CF_3$ | 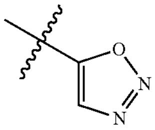 [SMILES: *c1cnno1] |
| 509 | $CF_3$ | 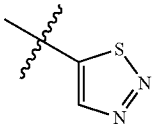 [SMILES: *c1cnns1] |

-continued
| No. | X | A |
|---|---|---|
| 510 | $CF_3$ | 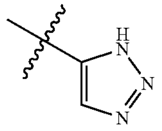 [SMILES: *c1cnn[nH]1] |
| 511 | $CF_3$ | 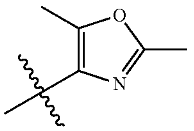 [SMILES: *c1nc(C)oc1C] |
| 512 | $CF_3$ | 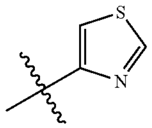 [SMILES: *c1cscn1] |
| 513 | $CF_3$ | 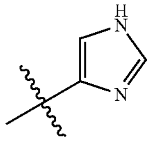 [SMILES: *c1c[nH]cn1] |
| 514 | $CF_3$ | 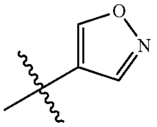 [SMILES: *c1cnoc1] |
| 515 | $CF_3$ | 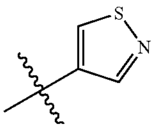 [SMILES: *c1cnsc1] |
| 516 | $CF_3$ | 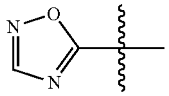 |
| 517 | $CF_3$ | 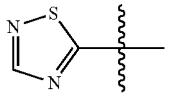 [SMILES: *c1ncns1] |
| 518 | $CF_3$ | 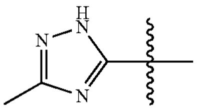 [SMILES: *c1nc(C)n[nH]1] |
| 519 | $CF_3$ | 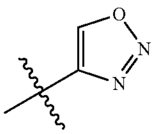 [SMILES: *c1conn1] |
| 520 | $CF_3$ | 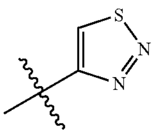 [SMILES: *c1csnn1] |
-continued
| No. | X | A |
|---|---|---|
| 521 | $CF_3$ | 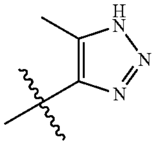 [SMILES: *c1nn[nH]c1C] |
| 522 | $CF_3$ | 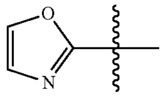 [SMILES: *c1ncco1] |
| 523 | $CF_3$ | 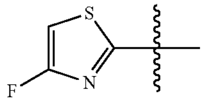 [SMILES: *c1nc(F)cs1] |
| 524 | $CF_3$ | 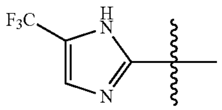 |
| 525 | $CF_3$ | 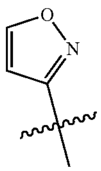 [SMILES: *c1ccon1] |
| 526 | $CF_3$ | 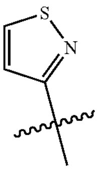 [SMILES: *c1ccsn1] |
| 527 | $CF_3$ | 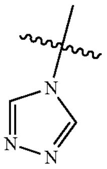 |
| 528 | $CF_3$ | 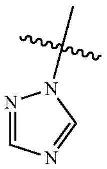 |
| 529 | $CF_3$ | 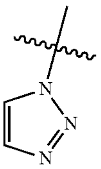 [SMILES: *n1ccnn1] |
| 530 | $CF_3$ | 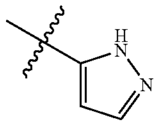 [SMILES: *c1ccn[nH]1] |

-continued
| No. | X | A |
|---|---|---|
| 531 | $CF_3$ | 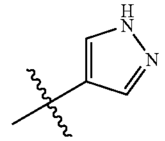 [SMILES: *c1cn[nH]c1] |
| 532 | $CF_3$ | 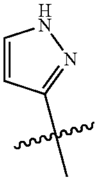 [SMILES: *c1cc[nH]n1] |
| 533 | $CF_3$ | 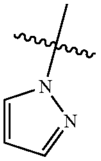 [SMILES: *n1cccn1] |
| 534 | $CF_3$ | 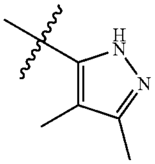 [SMILES: *c1[nH]nc(C)c1C] |
| 535 | $CF_3$ | 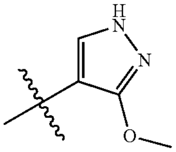 [SMILES: *c1c[nH]nc1OC] |
| 536 | $CF_3$ | 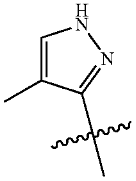 [SMILES: *c1n[nH]cc1C] |
| 537 | $CF_3$ | 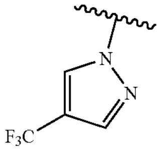 |
| 538 | $CF_3$ | 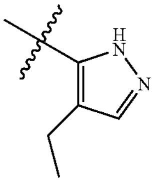 [SMILES: *c1[nH]ncc1CC] |
| 539 | $CF_3$ | 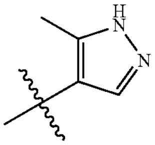 [SMILES: *c1cn[nH]c1C] |
| 540 | $CF_3$ | 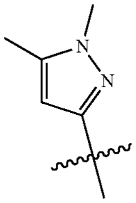 [SMILES: *c1cc(C)n(C)n1] |
| 541 | $CF_3$ | 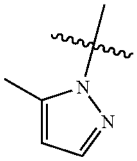 [SMILES: *n1nccc1C] |
| 542 | $CF_3$ | 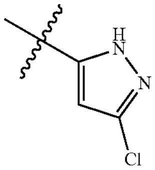 [SMILES: *c1cc(Cl)n[nH]1] |
| 543 | $CF_3$ | 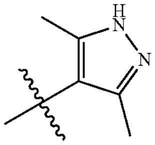 [SMILES: *c1c(C)n[nH]c1C] |
| 544 | $CF_3$ | 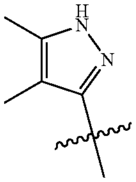 [SMILES: *c1n[nH]c(C)c1C] |
| 545 | $CF_3$ | 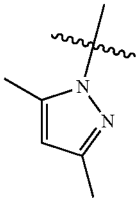 [SMILES: *n1nc(C)cc1C] |
| 546 | $CF_3$ | 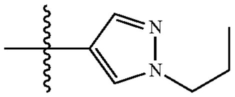 [SMILES: *c1cnn(CCC)c1] |
| 547 | $CF_3$ | 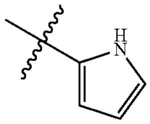 [SMILES: *c1ccc[nH]1] |
| 548 | $CF_3$ | 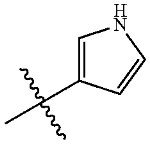 [SMILES: *c1cc[nH]c1] |

-continued
| No. | X | A |
| --- | --- | --- |
| 549 | $CF_3$ | 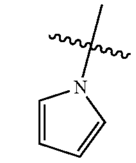 [SMILES: *n1cccc1] |
| 550 | $CF_3$ | 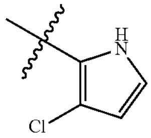 [SMILES: *c1[nH]ccc1Cl] |
| 551 | $CF_3$ | 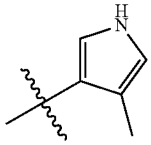 [SMILES: *c1c[nH]cc1C] |
| 552 | $CF_3$ | 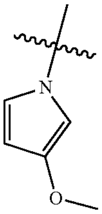 [SMILES: *n1ccc(OC)c1] |
| 553 | $CF_3$ | 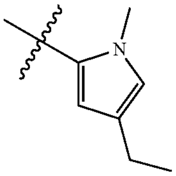 [SMILES: *c1cc(CC)cn1C] |
| 554 | $CF_3$ | 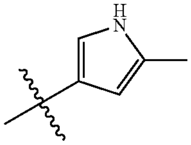 [SMILES: *c1c[nH]c(C)c1] |
| 555 | $CF_3$ | 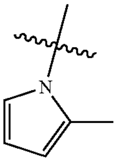 [SMILES: *n1cccc1C] |
| 556 | $CF_3$ | 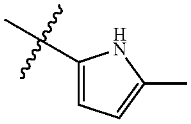 [SMILES: *c1ccc(C)[nH]1] |
| 557 | $CF_3$ | 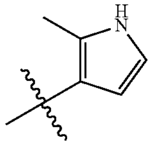 [SMILES: *c1cc[nH]c1C] |
| 558 | $CF_3$ | 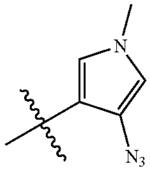 [SMILES: *c1cn(C)cc1N=[N+]=[N-]] |
| 559 | $CF_3$ | 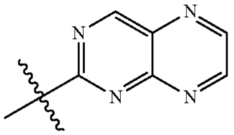 [SMILES: *c1ncc2nccnc2n1] |
| 560 | $CF_3$ | 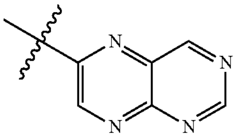 [SMILES: *c1cnc2ncncc2n1] |
| 561 | $CF_3$ | 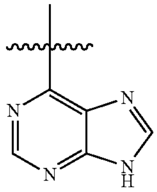 [SMILES: *c1ncnc2[nH]cnc12] |
| 562 | $CF_3$ | 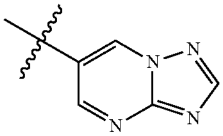 [SMILES: *c1cnc2ncnn2c1] |
| 563 | $CF_3$ | 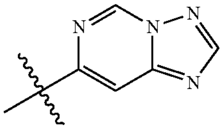 [SMILES: *c1cc2ncnn2cn1] |
| 564 | $CF_3$ | 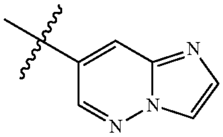 [SMILES: *c1cnn2ccnc2c1] |
| 565 | $CF_3$ | 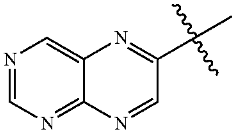 [SMILES: *c1cnc2ncncc2n1] |
| 566 | $CF_3$ | 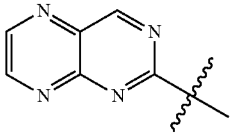 [SMILES: *c1ncc2nccnc2n1] |
| 567 | $CF_3$ | 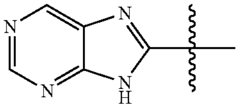 [SMILES: *c1nc2cncnc2[nH]1] |

-continued
| No. | X | A |
|---|---|---|
| 568 | $CF_3$ | 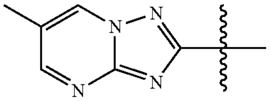 [SMILES: *c1nc2ncc(C)cn2n1] |
| 569 | $CF_3$ | 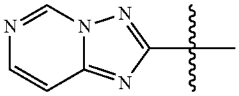 [SMILES: *c1nc2ccncn2n1] |
| 570 | $CF_3$ | 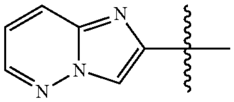 [SMILES: *c1cn2ncccc2n1] |
| 572 | $CF_3$ | 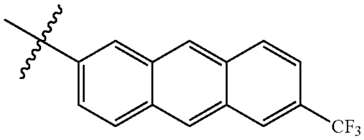 [SMILES: *c1ccc2cc3cc(C(F)(F)F)ccc3cc2c1] |
| 578 | $CF_3$ | 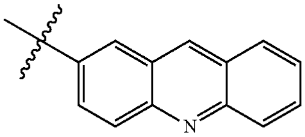 [SMILES: *c1ccc2nc3ccccc3cc2c1] |
| 579 | $CF_3$ | 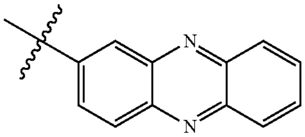 [SMILES: *c1ccc2nc3ccccc3nc2c1] |
| 580 | $CF_3$ | 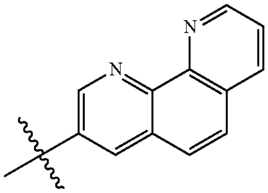 [SMILES: *c1cnc2c(ccc3cccnc32)c1] |
| 581 | $CF_3$ | 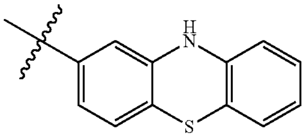 [SMILES: *c1ccc2c(c1)Nc1ccccc1S2] |
| 582 | $CF_3$ | 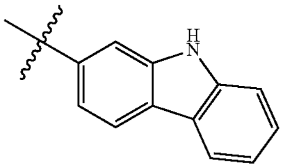 [SMILES: *c1ccc2c(c1)[nH]c1ccccc12] |
| 583 | $CF_3$ | 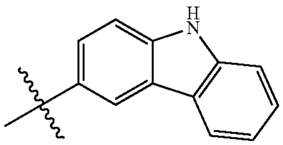 [SMILES: *c1ccc2[nH]c3ccccc3c2c1] |
-continued
| No. | X | A |
|---|---|---|
| 584 | $CF_3$ | 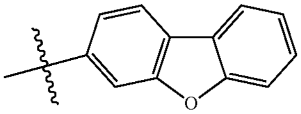 [SMILES: *c1ccc2c(c1)oc1ccccc12] |
| 585 | $CF_3$ | 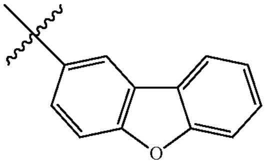 [SMILES: *c1ccc2oc3ccccc3c2c1] |
| 586 | $CF_3$ | 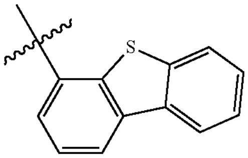 [SMILES: *c1cccc2c1sc1ccccc12] |
| 587 | $CF_3$ | 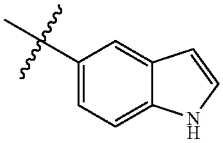 [SMILES: *c1ccc2[nH]ccc2c1] |
| 588 | $CF_3$ | 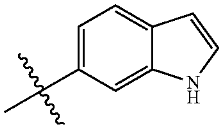 [SMILES: *c1ccc2cc[nH]c2c1] |
| 589 | $CF_3$ | 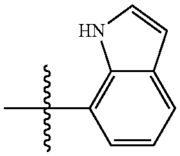 [SMILES: *c1cccc2cc[nH]c12] |
| 590 | $CF_3$ | 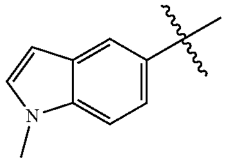 [SMILES: *c1ccc2c(ccn2C)c1] |
| 591 | $CF_3$ | 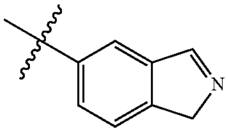 [SMILES: *c1ccc2c(c1)C=NC2] |
| 592 | $CF_3$ | 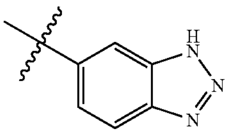 [SMILES: *c1ccc2nn[nH]c2c1] |
| 593 | $CF_3$ | 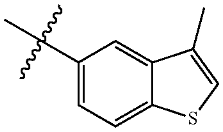 [SMILES: *c1ccc2scc(C)c2c1] |

-continued
| No. | X | A |
|---|---|---|
| 594 | $CF_3$ | 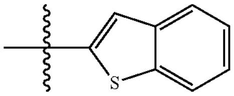 [SMILES: *c1cc2ccccc2s1] |
| 595 | $CF_3$ | 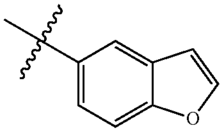 [SMILES: *c1ccc2occc2c1] |
| 596 | $CF_3$ | 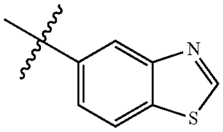 [SMILES: *c1ccc2scnc2c1] |
| 597 | $CF_3$ | 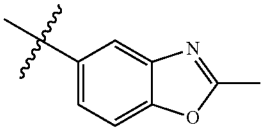 [SMILES: *c1ccc2oc(C)nc2c1] |
| 598 | $CF_3$ | 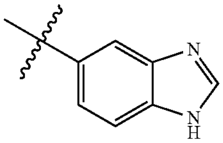 [SMILES: *c1ccc2[nH]cnc2c1] |
| 599 | $CF_3$ | 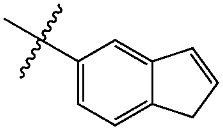 [SMILES: *c1ccc2c(c1)C=CC2] |
| 600 | $CF_3$ | 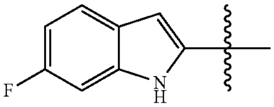 [SMILES: *c1cc2ccc(F)cc2[nH]1] |
| 601 | $CF_3$ | 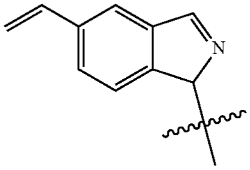 [SMILES: *C1N=Cc2cc(C=C)ccc21] |
| 602 | $CF_3$ | 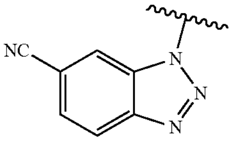 [SMILES: *n1nnc2ccc(C#N)cc21] |
| 603 | $CF_3$ | 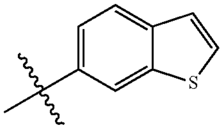 [SMILES: *c1ccc2ccsc2c1] |
| 604 | $CF_3$ | 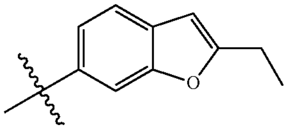 [SMILES: *c1ccc2cc(CC)oc2c1] |
-continued
| No. | X | A |
|---|---|---|
| 605 | $CF_3$ | 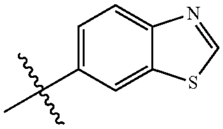 [SMILES: *c1ccc2ncsc2c1] |
| 606 | $CF_3$ | 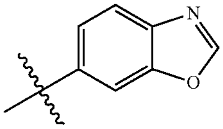 [SMILES: *c1ccc2ncoc2c1] |
| 607 | $CF_3$ | 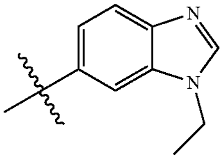 [SMILES: *c1ccc2ncn(CC)c2c1] |
| 608 | $CF_3$ | 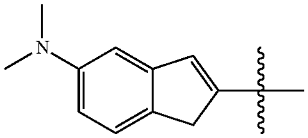 [SMILES: *C1=Cc2cc(N(C)C)ccc2C1] |
| 609 | $CF_3$ | 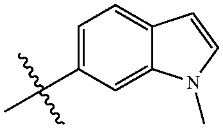 [SMILES: *c1ccc2ccn(C)c2c1] |
| 610 | $CF_3$ | 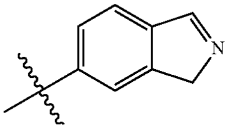 [SMILES: *c1ccc2c(c1)CN=C2] |
| 611 | $CF_3$ | 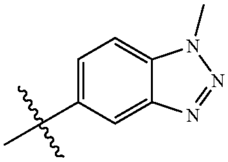 [SMILES: *c1ccc2c(c1)nnn2C] |
| 612 | $CF_3$ | 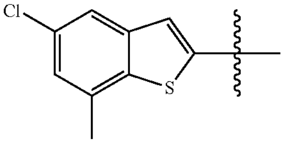 [SMILES: *c1cc2cc(Cl)cc(C)c2s1] |
| 613 | $CF_3$ | 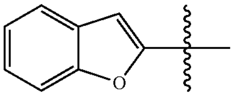 [SMILES: *c1cc2ccccc2o1] |
| 614 | $CF_3$ | 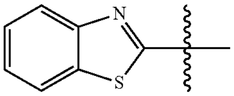 [SMILES: *c1nc2ccccc2s1] |
| 615 | $CF_3$ | 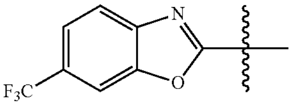 [SMILES: *c1nc2ccc(C(F)(F)F)cc2o1] |

-continued
| No. | X | A |
|---|---|---|
| 616 | $CF_3$ | 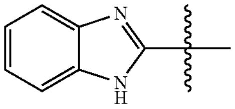 [SMILES: *c1nc2ccccc2[nH]1] |
| 617 | $CF_3$ | 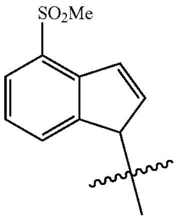 [SMILES: *C1C=Cc2c1cccc2S(C)(=O)=O] |
| 618 | $CF_3$ | 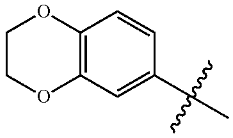 [SMILES: *c1ccc2c(c1)OCCO2] |
| 619 | $CF_3$ | 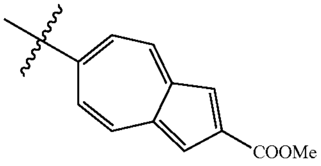 [SMILES: *c1ccc2cc(C(=O)OC)cc-2cc1] |
| 620 | $CF_3$ | 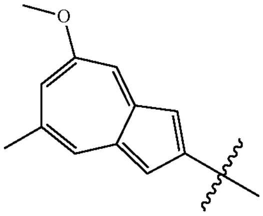 [SMILES: *c1cc2cc(C)cc(OC)cc-2c1] |
| 622 | $CF_3$ | 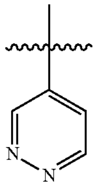 |
| 623 | $CF_3$ | 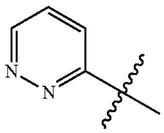 [SMILES: *c1cccnn1] |
| 624 | $CF_3$ | 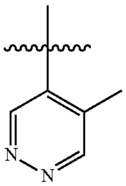 [SMILES: *c1cnncc1C] |
-continued
| No. | X | A |
|---|---|---|
| 625 | $CF_3$ | 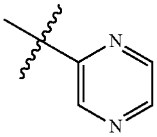 [SMILES: *c1cnccn1] |
| 626 | $CF_3$ | 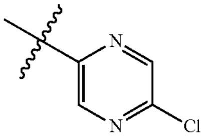 [SMILES: *c1cnc(Cl)cn1] |
| 627 | $CF_3$ | 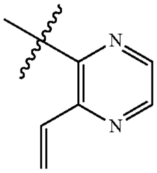 [SMILES: *c1nccnc1C=C] |
| 628 | $CF_3$ | 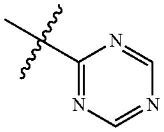 [SMILES: *c1ncncn1] |
| 629 | $CF_3$ | 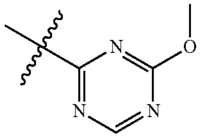 [SMILES: *c1ncnc(OC)n1] |
| 630 | $CF_3$ | 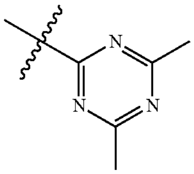 [SMILES: *c1nc(C)nc(C)n1] |
| 631 | $CF_3$ | 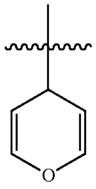 |
| 632 | $CF_3$ | 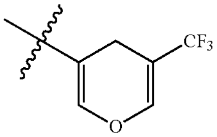 [SMILES: *C1=COC=C(C(F)(F)F)C1] |
| 633 | $CF_3$ | 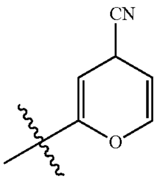 [SMILES: *C1=CC(C#N)C=CO1] |

-continued
| No. | X | A |
|---|---|---|
| 634 | $CF_3$ | 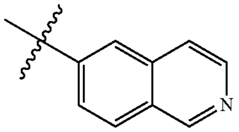 [SMILES: *c1ccc2cnccc2c1] |
| 635 | $CF_3$ | 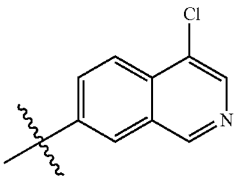 [SMILES: *c1ccc2c(Cl)cncc2c1] |
| 636 | $CF_3$ | 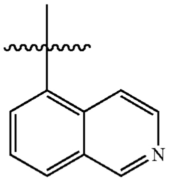 [SMILES: *c1cccc2cnccc12] |
| 637 | $CF_3$ | 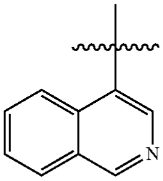 [SMILES: *c1cncc2ccccc12] |
| 638 | $CF_3$ | 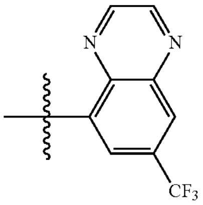 [SMILES: *c1cc(C(F)(F)F)cc2nccnc12] |
| 639 | $CF_3$ | 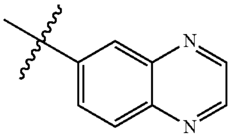 [SMILES: *c1ccc2nccnc2c1] |
| 640 | $CF_3$ | 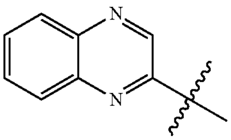 [SMILES: *c1cnc2ccccc2n1] |
| 641 | $CF_3$ | 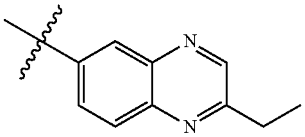 [SMILES: *c1ccc2nc(CC)cnc2c1] |
| 642 | $CF_3$ | 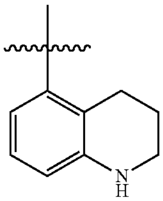 [SMILES: *c1cccc2c1CCCN2] |
-continued
| No. | X | A |
|---|---|---|
| 643 | $CF_3$ | 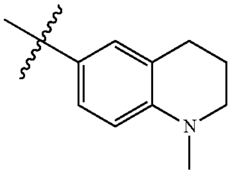 [SMILES: *c1ccc2c(c1)CCCN2C] |
| 644 | $CF_3$ | 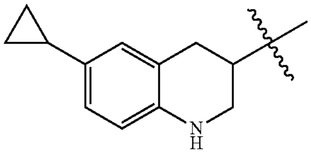 [SMILES: *C1CNc2ccc(C3CC3)cc2C1] |
| 645 | $CF_3$ | 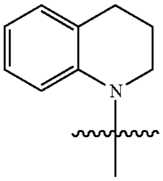 |
| 646 | $CF_3$ | 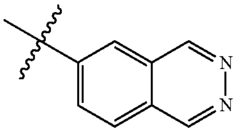 [SMILES: *c1ccc2cnncc2c1] |
| 647 | $CF_3$ | 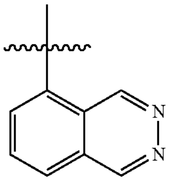 [SMILES: *c1cccc2cnncc12] |
| 648 | $CF_3$ | 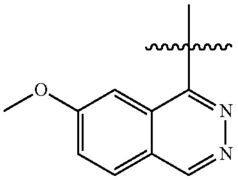 [SMILES: *c1nncc2ccc(OC)cc12] |
| 649 | $CF_3$ | 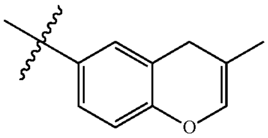 [SMILES: *c1ccc2c(c1)CC(C)=CO2] |
| 650 | $CF_3$ | 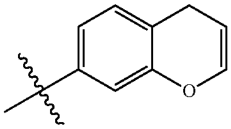 [SMILES: *c1ccc2c(c1)OC=CC2] |
| 651 | $CF_3$ | 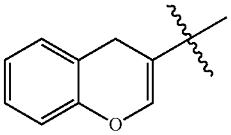 [SMILES: *C1=COc2ccccc2C1] |

-continued
| No. | X | A |
|---|---|---|
| 652 | $CF_3$ | 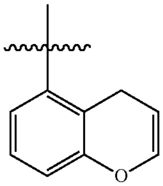 [SMILES: *c1cccc2c1CC=CO2] |
| 653 | $CF_3$ | 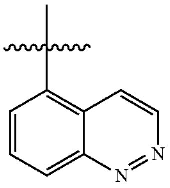 [SMILES: *c1cccc2nnccc12] |
| 654 | $CF_3$ | 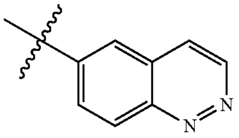 [SMILES: *c1ccc2nnccc2c1] |
| 655 | $CF_3$ | 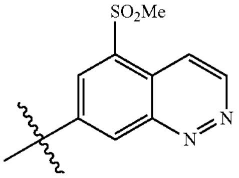 [SMILES: *c1cc(S(C)(=O)=O)c2ccnnc2c1] |
| 656 | $CF_3$ | 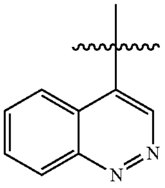 [SMILES: *c1cnnc2ccccc12] |
| 657 | $CF_3$ | 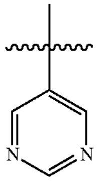 [SMILES: *c1cncnc1] |
| 658 | $CF_3$ | 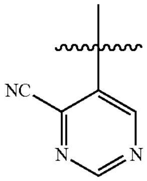 [SMILES: *c1cncnc1C#N] |
| 659 | $CF_3$ | 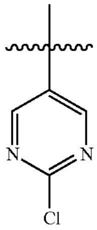 [SMILES: *c1cnc(Cl)nc1] |
| 660 | $CF_3$ | 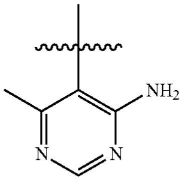 [SMILES: *c1c(C)ncnc1N] |
| 661 | $CF_3$ | 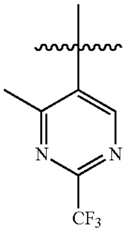 |
| 662 | $CF_3$ | 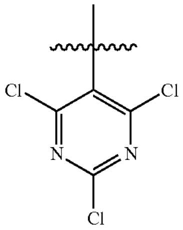 [SMILES: *c1c(Cl)nc(Cl)nc1Cl] |
| 663 | $CF_3$ | 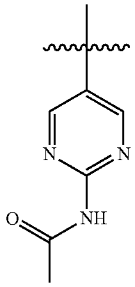 [SMILES: *c1cnc(NC(C)=O)nc1] |
| 664 | $CF_3$ | 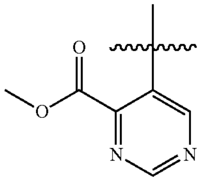 [SMILES: *c1cncnc1C(=O)OC] |
| 665 | $CF_3$ | 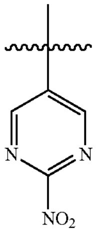 |
| 666 | $CF_3$ | 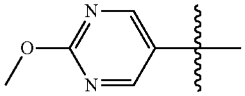 [SMILES: *c1cnc(OC)nc1] |

-continued
| No. | X | A |
| --- | --- | --- |
| 667 | $CF_3$ | 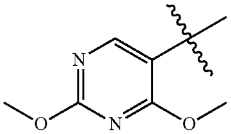 |
| 668 | $CF_3$ | 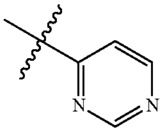 [SMILES: *c1ccncn1] |
| 669 | $CF_3$ | 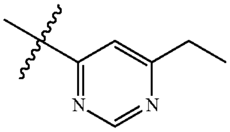 [SMILES: *c1cc(CC)ncn1] |
| 670 | $CF_3$ | 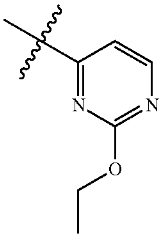 [SMILES: *c1ccnc(OCC)n1] |
| 671 | $CF_3$ | 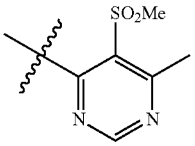 [SMILES: *c1ncnc(C)c1S(C)(=O)=O] |
| 672 | $CF_3$ | 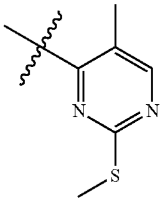 [SMILES: *c1nc(SC)ncc1C] |
| 673 | $CF_3$ | 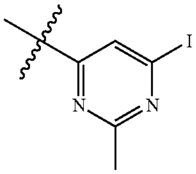 [SMILES: *c1cc(I)nc(C)n1] |
| 674 | $CF_3$ | 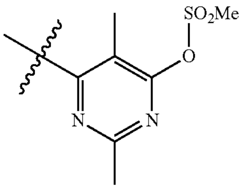 [SMILES: *c1nc(C)nc(OS(C)(=O)=O)c1C] |
| 675 | $CF_3$ | 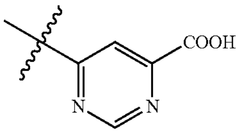 [SMILES: *c1cc(C(=O)O)ncn1] |
-continued
| No. | X | A |
| --- | --- | --- |
| 676 | $CF_3$ | 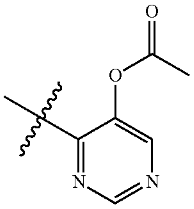 |
| 677 | $CF_3$ | 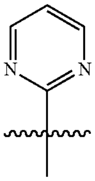 |
| 678 | $CF_3$ | 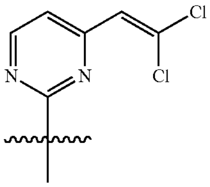 [SMILES: *c1nccc(C=C(Cl)Cl)n1] |
| 679 | $CF_3$ | 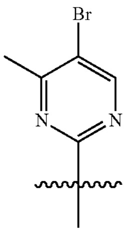 [SMILES: *c1ncc(Br)c(C)n1] |
| 680 | $CF_3$ | 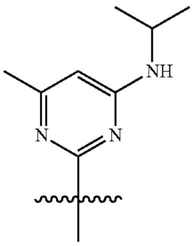 [SMILES: *c1nc(C)cc(NC(C)C)n1] |
| 681 | $CF_3$ | 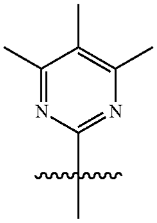 |
| 682 | $CF_3$ | 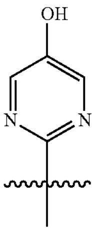 |

-continued
| No. | X | A |
| --- | --- | --- |
| 683 | $CF_3$ | 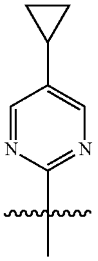 [SMILES: *c1ncc(C2CC2)cn1] |
| 684 | $CF_3$ | 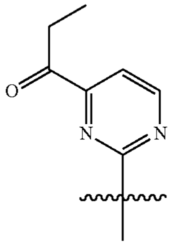 [SMILES: *c1nccc(C(=O)CC)n1] |
| 685 | $CF_3$ | 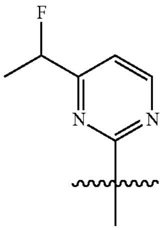 [SMILES: *c1nccc(C(C)F)n1] |
| 686 | $CF_3$ | 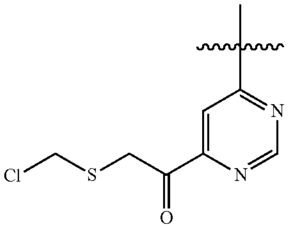 [SMILES: *c1cc(C(=O)CSCCl)ncn1] |
| 687 | $CF_3$ | 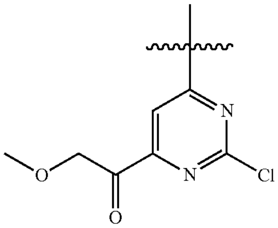 [SMILES: *c1cc(C(=O)COC)nc(Cl)n1] |
| 688 | $CF_3$ | 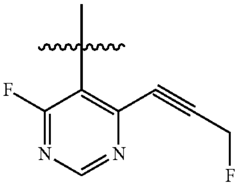 [SMILES: *c1c(F)ncnc1C#CCF] |
-continued
| No. | X | A |
| --- | --- | --- |
| 689 | $CF_3$ | 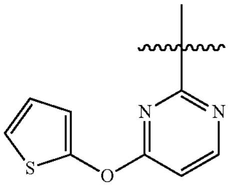 [SMILES: *c1nccc(Oc2cccs2)n1] |
| 690 | $CF_3$ | 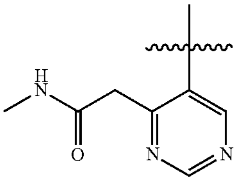 [SMILES: *c1cncnc1CC(=O)NC] |
| 691 | $CF_3$ | 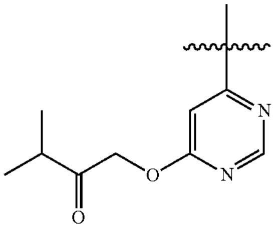 [SMILES: *c1cc(OCC(=O)C(C)C)ncn1] |
| 692 | $CF_3$ | 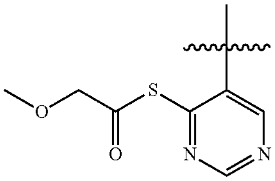 [SMILES: *c1cncnc1SC(=O)COC] |
| 693 | $CF_3$ | 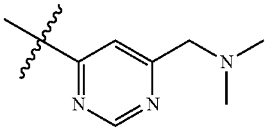 [SMILES: *c1cc(CN(C)C)ncn1] |
| 694 | $CF_3$ | 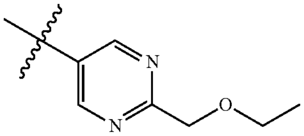 [SMILES: *c1cnc(COCC)nc1] |
| 695 | $CF_3$ | 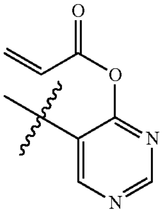 [SMILES: *c1cncnc1OC(=O)C=C] |
| 696 | $CF_3$ | 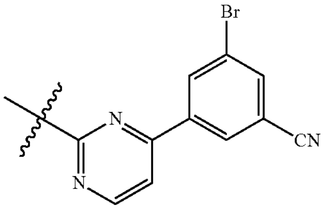 [SMILES: *c1nccc(-c2cc(Br)cc(C#N)c2)n1] |

-continued
| No. | X | A |
|---|---|---|
| 697 | $CF_3$ | 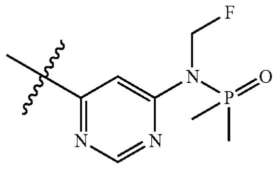 [SMILES: *c1cc(N(CF)P(C)(C)=O)ncn1] |
| 698 | $CF_3$ | 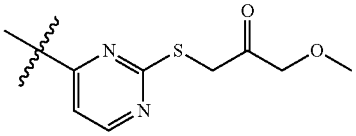 [SMILES: *c1ccnc(SCC(=O)COC)n1] |
| 699 | $CF_3$ | 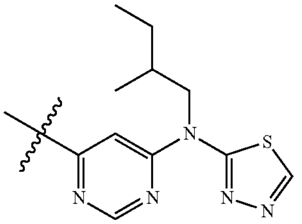 [SMILES: *c1cc(N(CC(C)CC)c2nncs2)ncn1] |
| 700 | $CF_3$ | 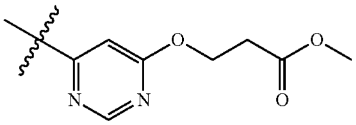 [SMILES: *c1cc(OCCC(=O)OC)ncn1] |
| 701 | $CF_3$ | 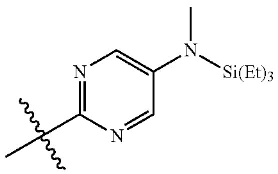 |
| 702 | $CF_3$ | 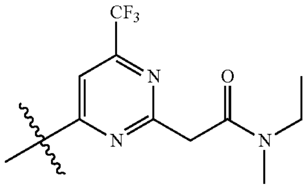 [SMILES: *c1cc(C(F)(F)F)nc(CC(=O)N(C)CC)n1] |
| 703 | $CF_3$ | 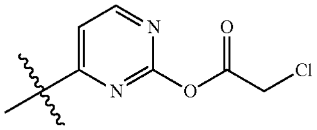 [SMILES: *c1ccnc(OC(=O)CCl)n1] |
| 704 | $CF_3$ | 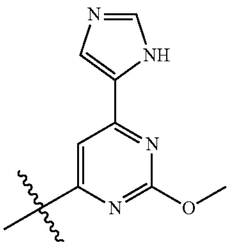 [SMILES: *c1cc(-c2cnc[nH]2)nc(OC)n1] |
-continued
| No. | X | A |
|---|---|---|
| 705 | $CF_3$ | 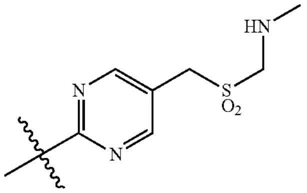 [SMILES: *c1ncc(CS(=O)(=O)CNC)cn1] |
| 706 | $CF_3$ | 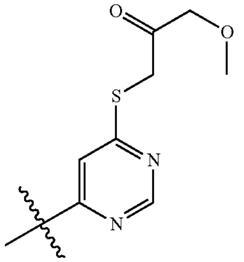 [SMILES: *c1cc(SCC(=O)COC)ncn1] |
| 707 | $CF_3$ | 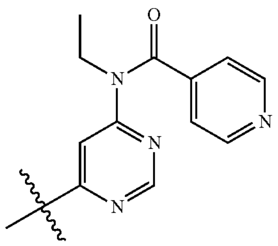 [SMILES: *c1cc(N(CC)C(=O)c2ccncc2)ncn1] |
| 708 | $CF_3$ | 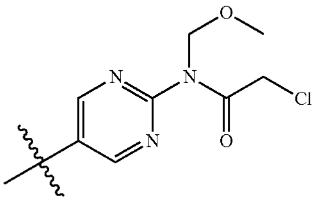 [SMILES: *c1cnc(N(COC)C(=O)CCl)nc1] |
| 709 | $CF_3$ | 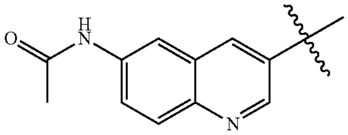 [SMILES: *c1cnc2ccc(NC(C)=O)cc2c1] |
| 710 | $CF_3$ | 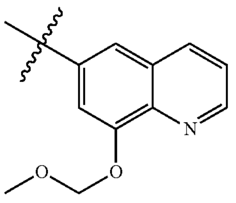 [SMILES: *c1cc(OCOC)c2ncccc2c1] |
| 711 | $CF_3$ | 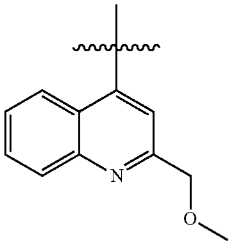 |

-continued
| No. | X | A |
|---|---|---|
| 712 | $CF_3$ | 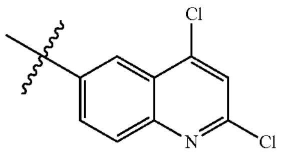 [SMILES: *c1ccc2nc(Cl)cc(Cl)c2c1] |
| 713 | $CF_3$ | 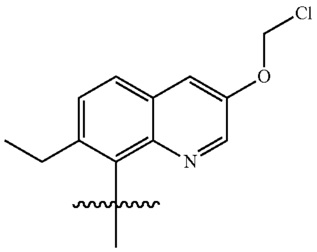 [SMILES: *c1c(CC)ccc2cc(OCCl)cnc12] |
| 714 | $CF_3$ | 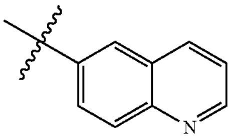 [SMILES: *c1ccc2ncccc2c1] |
| 715 | $CF_3$ | 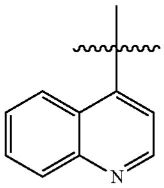 |
| 716 | $CF_3$ | 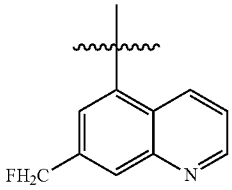 |
| 717 | $CF_3$ | 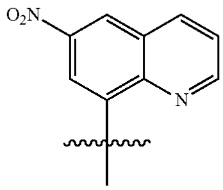 [SMILES: *c1cc([N+](=O)[O-])cc2cccnc12] |
| 718 | $CF_3$ | 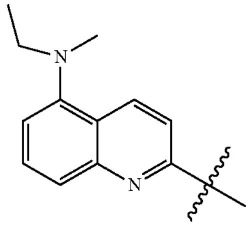 [SMILES: *c1ccc2c(N(C)CC)cccc2n1] |
| 719 | $CF_3$ | 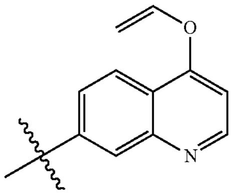 [SMILES: *c1ccc2c(OC=C)ccnc2c1] |
| 720 | $CF_3$ | 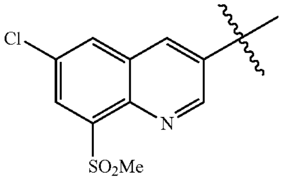 [SMILES: *c1cnc2c(S(C)(=O)=O)cc(Cl)cc2c1] |
| 721 | $CF_3$ | 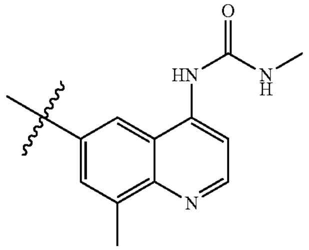 [SMILES: *c1cc(C)c2nccc(NC(=O)NC)c2c1] |
| 722 | $CF_3$ | 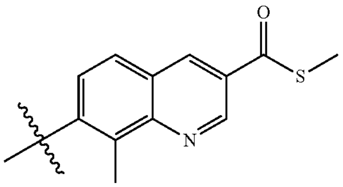 [SMILES: *c1ccc2cc(C(=O)SC)cnc2c1C] |
| 723 | $CF_3$ | 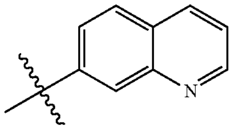 [SMILES: *c1ccc2cccnc2c1] |
| 724 | $CF_3$ | 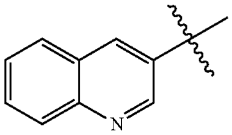 [SMILES: *c1cnc2ccccc2c1] |
| 725 | $CF_3$ | 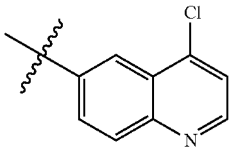 [SMILES: *c1ccc2nccc(Cl)c2c1] |
| 726 | $CF_3$ | 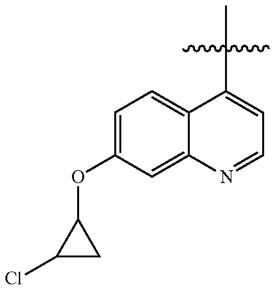 [SMILES: *c1ccnc2cc(OC3CC3Cl)ccc12] |

-continued
| No. | X | A |
|---|---|---|
| 727 | $CF_3$ | 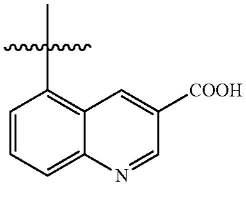 [SMILES: *c1cccc2ncc(C(=O)O)cc12] |
| 728 | $CF_3$ | 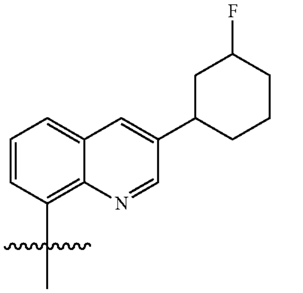 [SMILES: *c1cccc2cc(C3CCCC(F)C3)cnc12] |
| 729 | $CF_3$ | 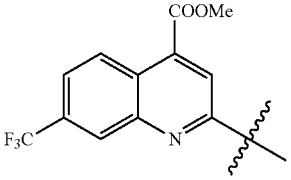 [SMILES: *c1cc(C(=O)OC)c2ccc(C(F)(F)F)cc2n1] |
| 730 | $CF_3$ | 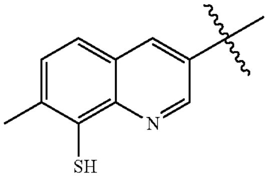 [SMILES: *c1cnc2c(S)c(C)ccc2c1] |
| 731 | $CF_3$ | 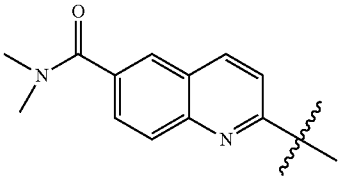 [SMILES: *c1ccc2cc(C(=O)N(C)C)ccc2n1] |
| 733 | $CF_3$ | 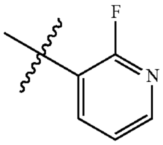 [SMILES: *c1cccnc1F] |
| 734 | $CF_3$ | 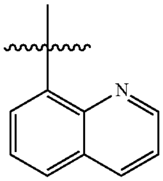 |
-continued
| No. | X | A |
|---|---|---|
| 735 | $CF_3$ | 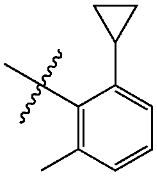 [SMILES: *c1c(C)cccc1C1CC1] |
| 737 | $CF_3$ | 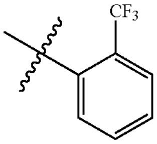 |
| 738 | $CF_3$ | 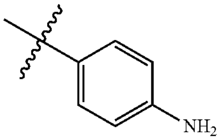 |
| 743 | $CF_3$ | 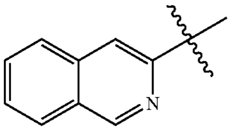 [SMILES: *c1cc2ccccc2cn1] |
| 746 | $CF_3$ | 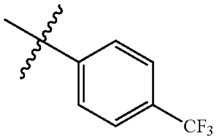 |
| 749 | $CF_3$ | 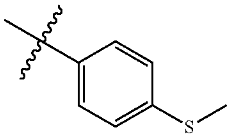 [SMILES: *c1ccc(SC)cc1] |
| 751 | $CF_3$ | 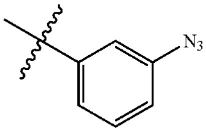 |
| 752 | $CF_3$ | 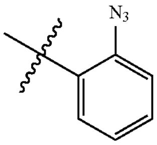 [SMILES: *c1ccccc1N=[N+]=[N-]] |
| 761 | $CF_3$ | 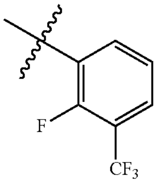 [SMILES: *c1cccc(C(F)(F)F)c1F] |
| 762 | $CF_3$ | 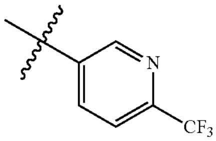 [SMILES: *c1ccc(C(F)(F)F)nc1] |

-continued
| No. | X | A |
|---|---|---|
| 763 | $CF_3$ | 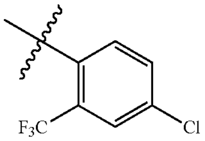 |
| 764 | $CF_3$ | 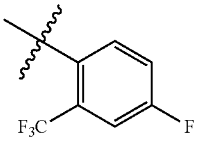 [SMILES: *c1ccc(F)cc1C(F)(F)F] |
| 767 | $CF_3$ | 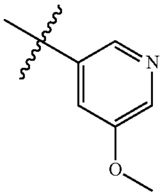 [SMILES: *c1cncc(OC)c1] |
| 768 | $CF_3$ | 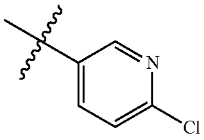 [SMILES: *c1ccc(Cl)nc1] |
| 769 | $CF_3$ | 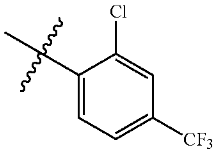 [SMILES: *c1ccc(C(F)(F)F)cc1Cl] |
| 770 | $CF_3$ | 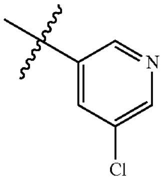 [SMILES: *c1cncc(Cl)c1] |
| 771 | $CF_3$ | 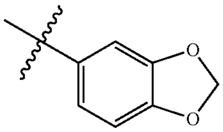 [SMILES: *c1ccc2c(c1)OCO2] |
| 773 | $CF_3$ | 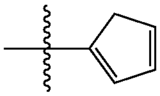 [SMILES: *C1=CC=CC1] |
| 774 | $CF_3$ | 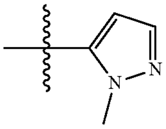 [SMILES: *c1ccnn1C] |
| 775 | $CF_3$ | 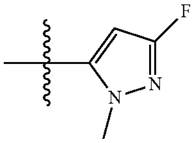 [SMILES: *c1cc(F)nn1C] |
-continued
| No. | X | A |
|---|---|---|
| 776 | $CF_3$ | 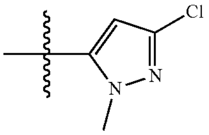 [SMILES: *c1cc(Cl)nn1C] |
| 777 | $CF_3$ | 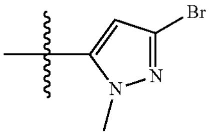 [SMILES: *c1cc(Br)nn1C] |
| 778 | $CF_3$ | 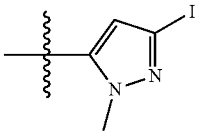 [SMILES: *c1cc(I)nn1C] |
| 779 | $CF_3$ | 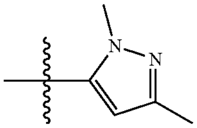 [SMILES: *c1cc(C)nn1C] |
| 780 | $CF_3$ | 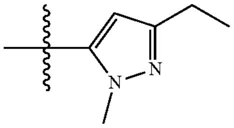 [SMILES: *c1cc(CC)nn1C] |
| 781 | $CF_3$ | 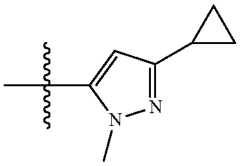 [SMILES: *c1cc(C2CC2)nn1C] |
| 782 | $CF_3$ | 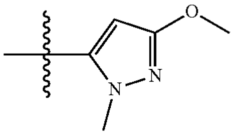 [SMILES: *c1cc(OC)nn1C] |
| 783 | $CF_3$ | 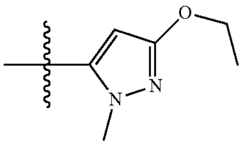 [SMILES: *c1cc(OCC)nn1C] |
| 784 | $CF_3$ | 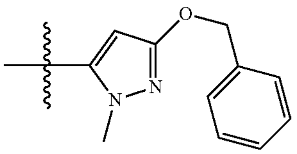 [SMILES: *c1cc(OCc2ccccc2)nn1C] |
| 785 | $CF_3$ | 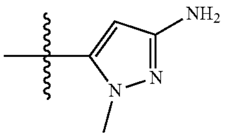 [SMILES: *c1cc(N)nn1C] |

-continued
| No. | X | A |
| --- | --- | --- |
| 786 | $CF_3$ | 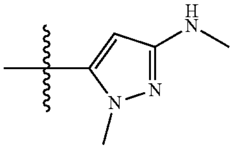 [SMILES: *c1cc(NC)nn1C] |
| 787 | $CF_3$ | 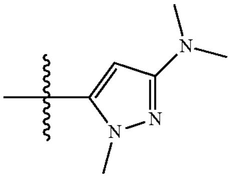 [SMILES: *c1cc(N(C)C)nn1C] |
| 788 | $CF_3$ | 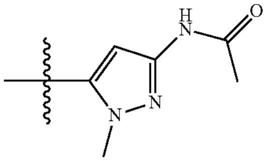 [SMILES: *c1cc(NC(C)=O)nn1C] |
| 789 | $CF_3$ | 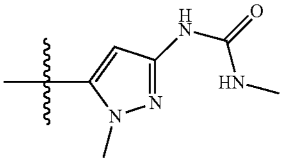 [SMILES: *c1cc(NC(=O)NC)nn1C] |
| 790 | $CF_3$ | 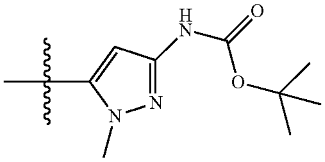 [SMILES: *c1cc(NC(=O)OC(C)(C)C)nn1C] |
| 791 | $CF_3$ | 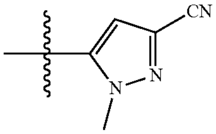 [SMILES: *c1cc(C#N)nn1C] |
| 792 | $CF_3$ | 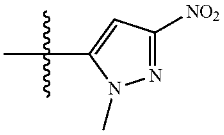 [SMILES: *c1cc([N+](=O)[O-])nn1C] |
| 793 | $CF_3$ | 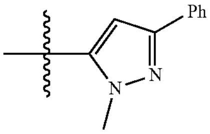 [SMILES: *c1cc(-c2ccccc2)nn1C] |
| 794 | $CF_3$ | 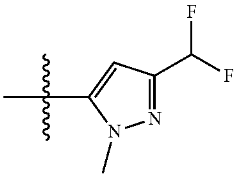 [SMILES: *c1cc(C(F)F)nn1C] |
-continued
| No. | X | A |
| --- | --- | --- |
| 795 | $CF_3$ | 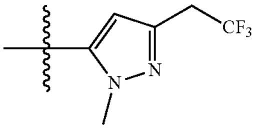 [SMILES: *c1cc(CC(F)(F)F)nn1C] |
| 796 | $CF_3$ | 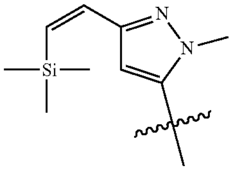 |
| 797 | $CF_3$ | 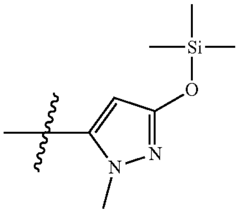 [SMILES: *c1cc(O[Si](C)(C)C)nn1C] |
| 798 | $CF_3$ | 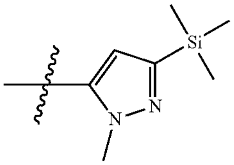 [SMILES: *c1cc([Si](C)(C)C)nn1C] |
| 799 | $CF_3$ | 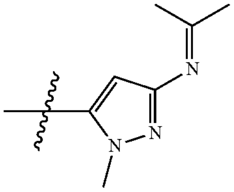 [SMILES: *c1cc(N=C(C)C)nn1C] |
| 800 | $CF_3$ | 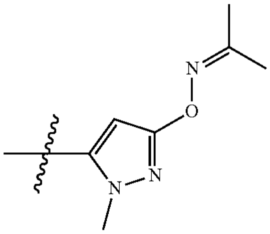 [SMILES: *c1cc(ON=C(C)C)nn1C] |
| 801 | $CF_3$ | 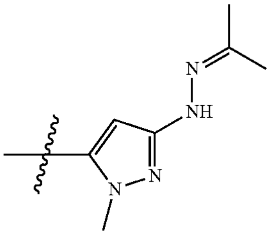 [SMILES: *c1cc(NN=C(C)C)nn1C] |
| 802 | $CF_3$ | 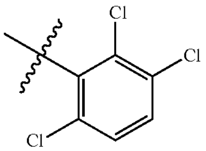 |

-continued
| No. | X | A |
| --- | --- | --- |
| 803 | $CF_3$ | 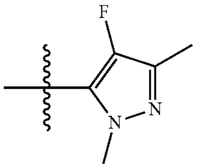 [SMILES: *c1c(F)c(C)nn1C] |
| 804 | $CF_3$ | 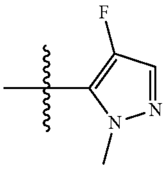 [SMILES: *c1c(F)cnn1C] |
| 805 | $CF_3$ | 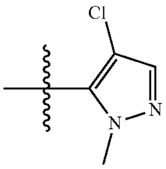 [SMILES: *c1c(Cl)cnn1C] |
| 806 | $CF_3$ | 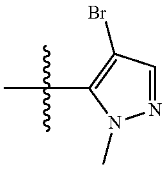 |
| 807 | $CF_3$ | 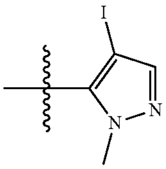 [SMILES: *c1c(I)cnn1C] |
| 808 | $CF_3$ | 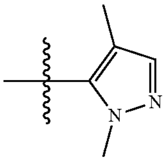 [SMILES: *c1c(C)cnn1C] |
| 809 | $CF_3$ | 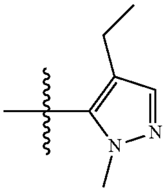 [SMILES: *c1c(CC)cnn1C] |
| 810 | $CF_3$ | 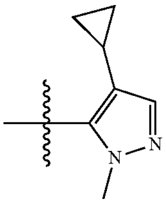 [SMILES: *c1c(C2CC2)cnn1C] |
| 811 | $CF_3$ | 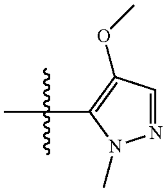 [SMILES: *c1c(OC)cnn1C] |
| 812 | $CF_3$ | 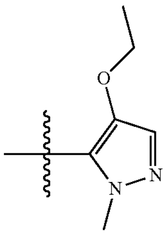 [SMILES: *c1c(OCC)cnn1C] |
| 813 | $CF_3$ | 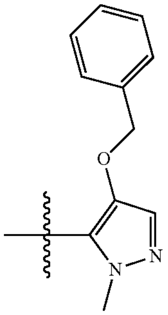 [SMILES: *c1c(OCc2ccccc2)cnn1C] |
| 814 | $CF_3$ | 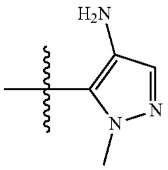 |
| 815 | $CF_3$ | 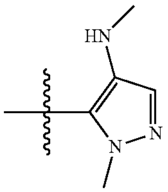 [SMILES: *c1c(NC)cnn1C] |
| 816 | $CF_3$ | 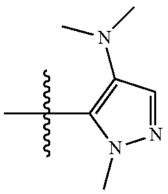 [SMILES: *c1c(N(C)C)cnn1C] |
| 817 | $CF_3$ | 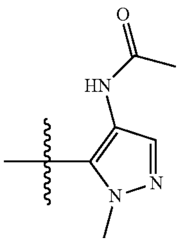 [SMILES: *c1c(NC(C)=O)cnn1C] |

-continued
| No. | X | A |
|---|---|---|
| 818 | $CF_3$ | 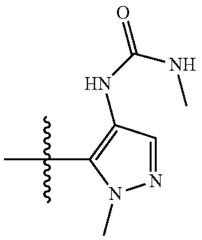 [SMILES: *c1c(NC(=O)NC)cnn1C] |
| 819 | $CF_3$ | 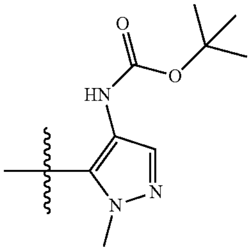 [SMILES: *c1c(NC(=O)OC(C)(C)C)cnn1C] |
| 820 | $CF_3$ | 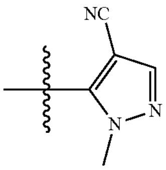 [SMILES: *c1c(C#N)cnn1C] |
| 821 | $CF_3$ | 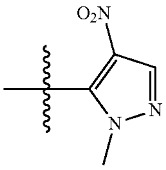 [SMILES: *c1c([N+](=O)[O-])cnn1C] |
| 822 | $CF_3$ | 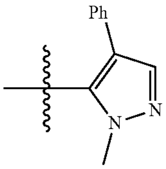 [SMILES: *c1c(-c2ccccc2)cnn1C] |
| 823 | $CF_3$ | 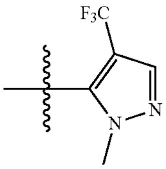 [SMILES: *c1c(C(F)(F)F)cnn1C] |
| 824 | $CF_3$ | 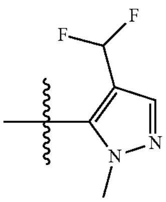 [SMILES: *c1c(C(F)F)cnn1C] |
-continued
| No. | X | A |
|---|---|---|
| 825 | $CF_3$ | 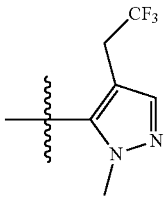 [SMILES: *c1c(CC(F)(F)F)cnn1C] |
| 826 | $CF_3$ | 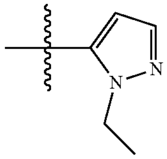 [SMILES: *c1ccnn1CC] |
| 827 | $CF_3$ | 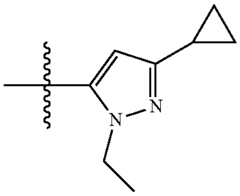 [SMILES: *c1cc(C2CC2)nn1CC] |
| 828 | $CF_3$ | 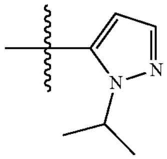 [SMILES: *c1ccnn1C(C)C] |
| 829 | $CF_3$ | 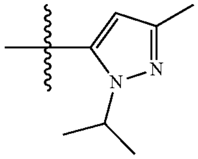 [SMILES: *c1cc(C)nn1C(C)C] |
| 830 | $CF_3$ | 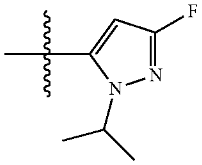 [SMILES: *c1cc(F)nn1C(C)C] |
| 831 | $CF_3$ | 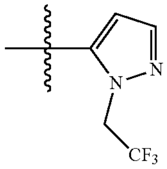 |
| 832 | $CF_3$ | 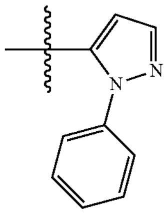 [SMILES: *c1ccnn1-c1ccccc1] |

-continued
| No. | X | A |
|---|---|---|
| 833 | $CF_3$ | 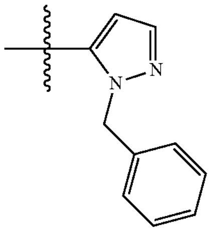 [SMILES: *c1ccnn1Cc1ccccc1] |
| 834 | $CF_3$ | 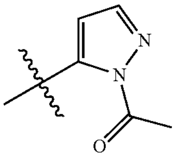 [SMILES: *c1ccnn1C(C)=O] |
| 835 | $CF_3$ | 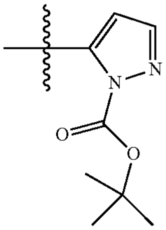 [SMILES: *c1ccnn1C(=O)OC(C)(C)C] |
| 836 | $CF_3$ | 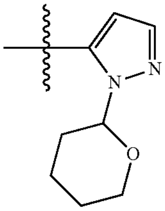 [SMILES: *c1ccnn1C1CCCCO1] |
| 837 | $CF_3$ | 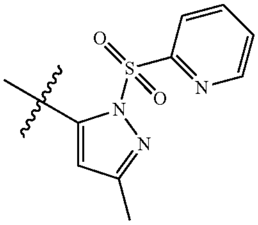 [SMILES: *c1cc(C)nn1S(=O)(=O)c1ccccn1] |
| 838 | $CF_3$ | 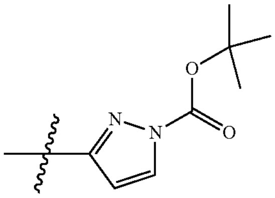 [SMILES: *c1ccn(C(=O)OC(C)(C)C)n1] |
| 839 | $CF_3$ | 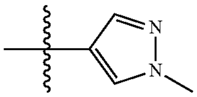 |
| 840 | $CF_3$ | 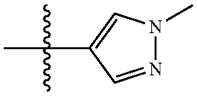 [SMILES: *c1cnn(C)c1] |
-continued
| No. | X | A |
|---|---|---|
| 841 | $CF_3$ | 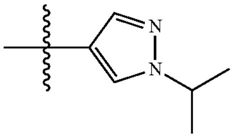 [SMILES: *c1cnn(C(C)C)c1] |
| 842 | $CF_3$ | 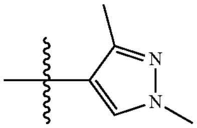 [SMILES: *c1cn(C)nc1C] |
| 843 | $CF_3$ | 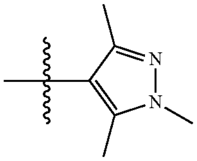 [SMILES: *c1c(C)nn(C)c1C] |
| 844 | $CF_3$ | 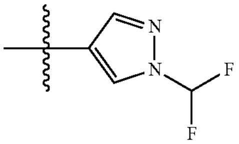 [SMILES: *c1cnn(C(F)F)c1] |
| 845 | $CF_3$ | 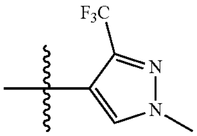 [SMILES: *c1cn(C)nc1C(F)(F)F] |
| 846 | $CF_3$ | 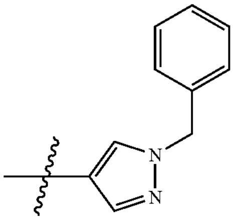 [SMILES: *c1cnn(Cc2ccccc2)c1] |
| 847 | $CF_3$ | 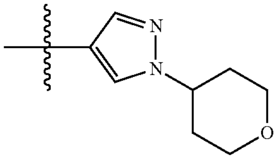 [SMILES: *c1cnn(C2CCOCC2)c1] |
| 848 | $CF_3$ | 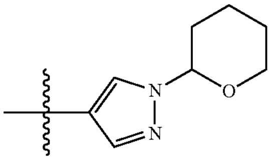 [SMILES: *c1cnn(C2CCCCO2)c1] |
| 849 | $CF_3$ | 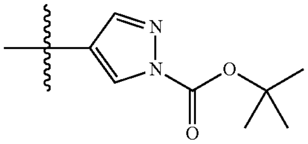 |

-continued
| No. | X | A |
| --- | --- | --- |
| 850 | $CF_3$ | 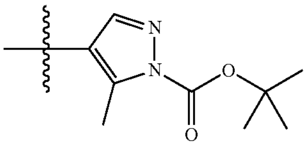 [SMILES: *c1cnn(C(=O)OC(C)(C)C)c1C] |
| 851 | $CF_3$ | 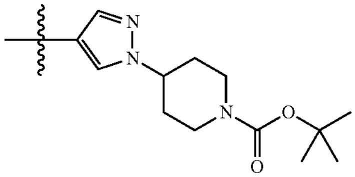 [SMILES: *c1cnn(C2CCN(C(=O)OC(C)(C)C)CC2)c1] |
| 852 | $CF_3$ | 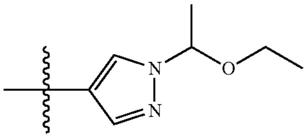 [SMILES: *c1cnn(C(C)OCC)c1] |
| 853 | $CF_3$ | 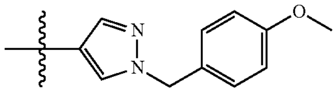 [SMILES: *c1cnn(Cc2ccc(OC)cc2)c1] |
| 854 | $CF_3$ | 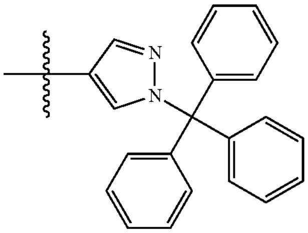 [SMILES: *c1cnn(C(c2ccccc2)(c2ccccc2)c2ccccc2)c1] |
| 855 | $CF_3$ | 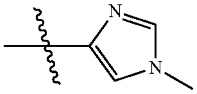 [SMILES: *c1cn(C)cn1] |
| 856 | $CF_3$ | 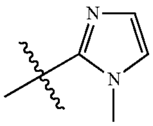 [SMILES: *c1nccn1C] |
| 857 | $CF_3$ | 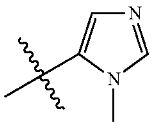 |
| 858 | $CF_3$ | 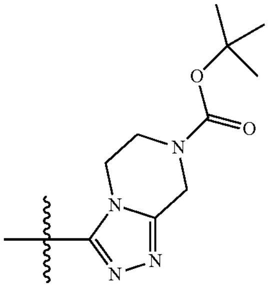 [SMILES: *c1nnc2n1CCN(C(=O)OC(C)(C)C)C2] |
| 859 | $CF_3$ | 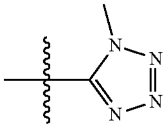 [SMILES: *c1nnnn1C] |
| 860 | $CF_3$ | 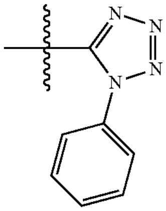 [SMILES: *c1nnnn1-c1ccccc1] |
| 861 | $CF_3$ | 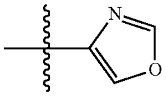 |
| 862 | $CF_3$ | 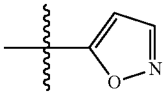 |
| 863 | $CF_3$ | 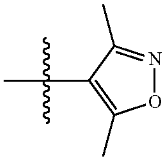 [SMILES: *c1c(C)noc1C] |
| 864 | $CF_3$ | 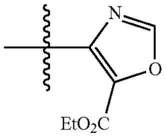 |
| 865 | $CF_3$ | 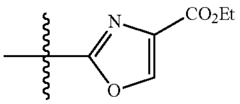 [SMILES: *c1nc(C(=O)OCC)co1] |
| 866 | $CF_3$ | 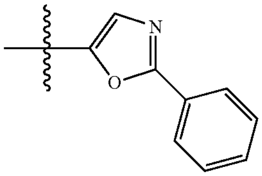 [SMILES: *c1cnc(-c2ccccc2)o1] |
| 867 | $CF_3$ | 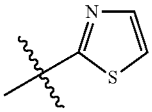 [SMILES: *c1nccs1] |
| 868 | $CF_3$ | 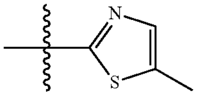 [SMILES: *c1ncc(C)s1] |
| 869 | $CF_3$ | 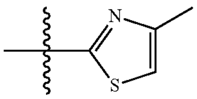 [SMILES: *c1nc(C)cs1] |

-continued
| No. | X | A |
|---|---|---|
| 870 | $CF_3$ | 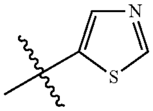 [SMILES: *c1cncs1] |
| 871 | $CF_3$ | 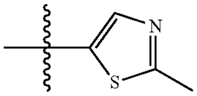 [SMILES: *c1cnc(C)s1] |
| 872 | $CF_3$ | 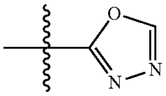 [SMILES: *c1nnco1] |
| 873 | $CF_3$ | 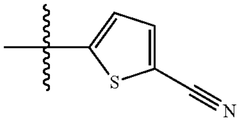 [SMILES: *c1ccc(C#N)s1] |
| 874 | $CF_3$ | 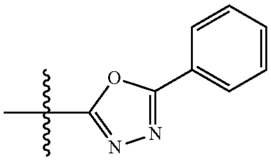 [SMILES: *c1nnc(-c2ccccc2)o1] |
| 875 | $CF_3$ | 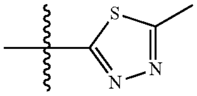 [SMILES: *c1nnc(C)s1] |
| 876 | $CF_3$ | 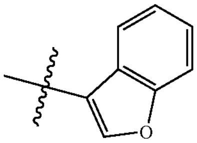 [SMILES: *c1coc2ccccc12] |
| 877 | $CF_3$ | 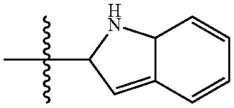 [SMILES: *C1C=C2C=CC=CC2N1] |
| 878 | $CF_3$ | 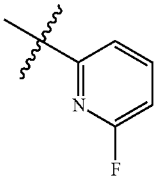 [SMILES: *c1cccc(F)n1] |
| 879 | $CF_3$ | 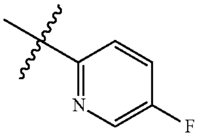 |
| 880 | $CF_3$ | 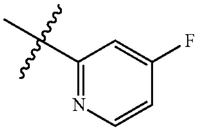 [SMILES: *c1cc(F)ccn1] |
-continued
| No. | X | A |
|---|---|---|
| 881 | $CF_3$ | 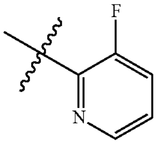 |
| 882 | $CF_3$ | 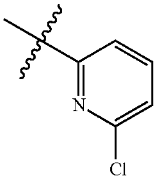 [SMILES: *c1cccc(Cl)n1] |
| 883 | $CF_3$ | 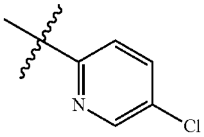 [SMILES: *c1ccc(Cl)cn1] |
| 884 | $CF_3$ | 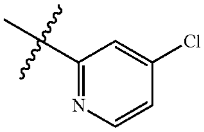 [SMILES: *c1cc(Cl)ccn1] |
| 885 | $CF_3$ | 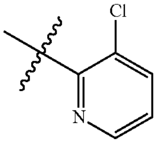 |
| 886 | $CF_3$ | 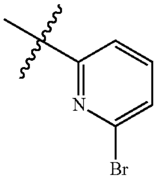 [SMILES: *c1cccc(Br)n1] |
| 887 | $CF_3$ | 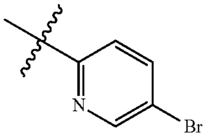 |
| 888 | $CF_3$ | 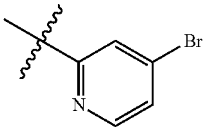 [SMILES: *c1cc(Br)ccn1] |
| 889 | $CF_3$ | 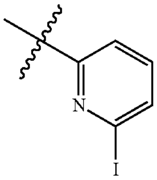 [SMILES: *c1cccc(I)n1] |

-continued
| No. | X | A |
|---|---|---|
| 890 | $CF_3$ | 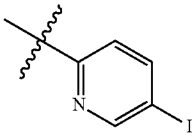 [SMILES: *c1ccc(I)cn1] |
| 891 | $CF_3$ | 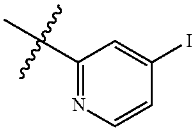 [SMILES: *c1cc(I)ccn1] |
| 892 | $CF_3$ | 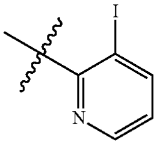 [SMILES: *c1ncccc1I] |
| 893 | $CF_3$ | 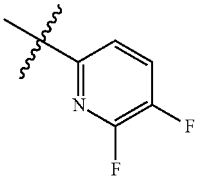 [SMILES: *c1ccc(F)c(F)n1] |
| 894 | $CF_3$ | 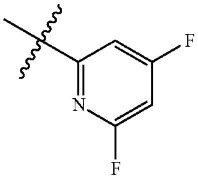 [SMILES: *c1cc(F)cc(F)n1] |
| 895 | $CF_3$ | 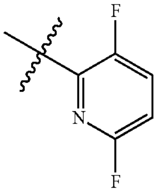 [SMILES: *c1nc(F)ccc1F] |
| 896 | $CF_3$ | 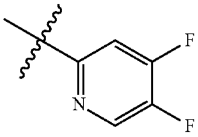 |
| 897 | $CF_3$ | 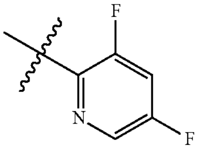 [SMILES: *c1ncc(F)cc1F] |
| 898 | $CF_3$ | 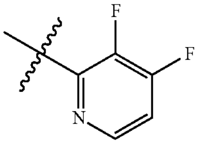 [SMILES: *c1nccc(F)c1F] |
-continued
| No. | X | A |
|---|---|---|
| 899 | $CF_3$ | 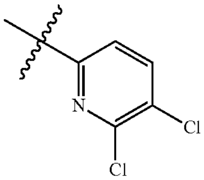 [SMILES: *c1ccc(Cl)c(Cl)n1] |
| 900 | $CF_3$ | 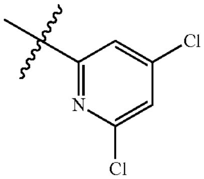 [SMILES: *c1cc(Cl)cc(Cl)n1] |
| 901 | $CF_3$ | 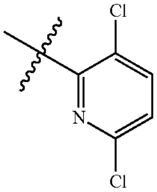 |
| 902 | $CF_3$ | 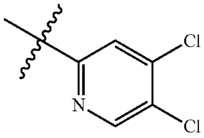 [SMILES: *c1cc(Cl)c(Cl)cn1] |
| 903 | $CF_3$ | 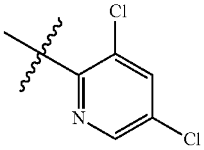 |
| 904 | $CF_3$ | 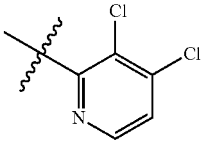 [SMILES: *c1nccc(Cl)c1Cl] |
| 905 | $CF_3$ | 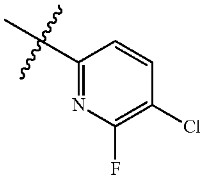 [SMILES: *c1ccc(Cl)c(F)n1] |
| 906 | $CF_3$ | 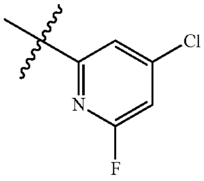 [SMILES: *c1cc(Cl)cc(F)n1] |

-continued
| No. | X | A |
| --- | --- | --- |
| 907 | $CF_3$ | 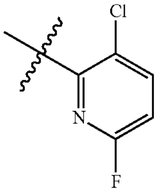 [SMILES: *c1nc(F)ccc1Cl] |
| 908 | $CF_3$ | 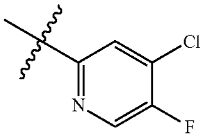 [SMILES: *c1cc(Cl)c(F)cn1] |
| 909 | $CF_3$ | 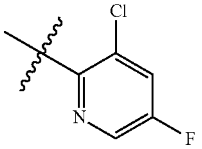 |
| 910 | $CF_3$ | 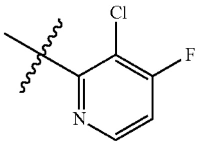 |
| 911 | $CF_3$ | 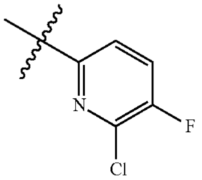 [SMILES: *c1ccc(F)c(Cl)n1] |
| 912 | $CF_3$ | 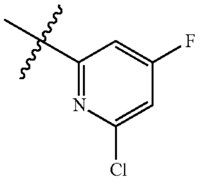 [SMILES: *c1cc(F)cc(Cl)n1] |
| 913 | $CF_3$ | 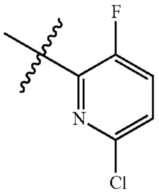 [SMILES: *c1nc(Cl)ccc1F] |
| 914 | $CF_3$ | 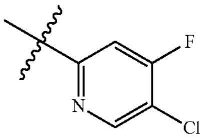 [SMILES: *c1cc(F)c(Cl)cn1] |
| 915 | $CF_3$ | 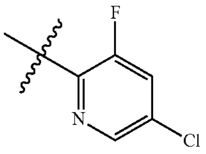 [SMILES: *c1ncc(Cl)cc1F] |
-continued
| No. | X | A |
| --- | --- | --- |
| 916 | $CF_3$ | 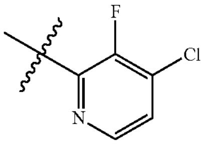 [SMILES: *c1nccc(Cl)c1F] |
| 917 | $CF_3$ | 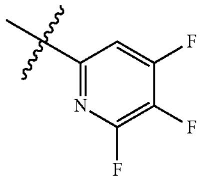 [SMILES: *c1cc(F)c(F)c(F)n1] |
| 918 | $CF_3$ | 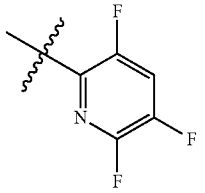 [SMILES: *c1nc(F)c(F)cc1F] |
| 919 | $CF_3$ | 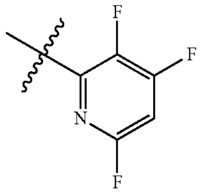 [SMILES: *c1nc(F)cc(F)c1F] |
| 920 | $CF_3$ | 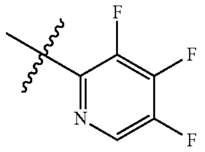 [SMILES: *c1ncc(F)c(F)c1F] |
| 921 | $CF_3$ | 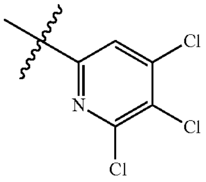 [SMILES: *c1cc(Cl)c(Cl)c(Cl)n1] |
| 922 | $CF_3$ | 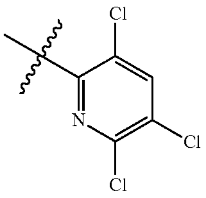 [SMILES: *c1nc(Cl)c(Cl)cc1Cl] |
| 923 | $CF_3$ | 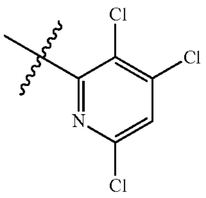 [SMILES: *c1nc(Cl)cc(Cl)c1Cl] |

-continued
| No. | X | A |
|---|---|---|
| 924 | $CF_3$ | 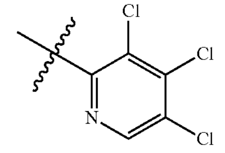 |
| 925 | $CF_3$ | 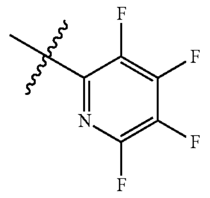 [SMILES: *c1nc(F)c(F)c(F)c1F] |
| 926 | $CF_3$ | 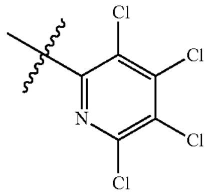 [SMILES: *c1nc(Cl)c(Cl)c(Cl)c1Cl] |
| 927 | $CF_3$ | 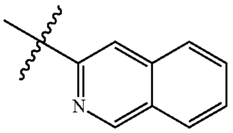 [SMILES: *c1cc2ccccc2cn1] |
| 928 | $CF_3$ | 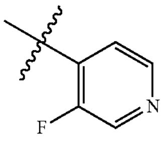 |
| 929 | $CF_3$ | 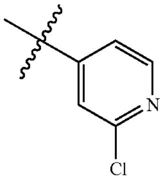 [SMILES: *c1ccnc(Cl)c1] |
| 930 | $CF_3$ | 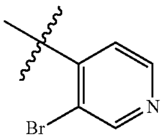 |
| 931 | $CF_3$ | 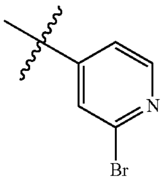 [SMILES: *c1ccnc(Br)c1] |
| 932 | $CF_3$ | 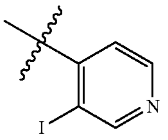 [SMILES: *c1ccncc1I] |
-continued
| No. | X | A |
|---|---|---|
| 933 | $CF_3$ | 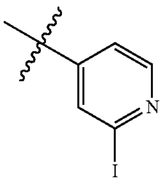 [SMILES: *c1ccnc(I)c1] |
| 934 | $CF_3$ | 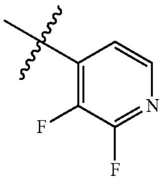 [SMILES: *c1ccnc(F)c1F] |
| 935 | $CF_3$ | 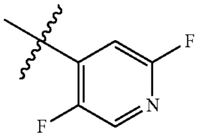 [SMILES: *c1cc(F)ncc1F] |
| 936 | $CF_3$ | 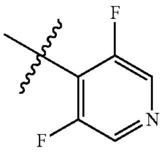 |
| 937 | $CF_3$ | 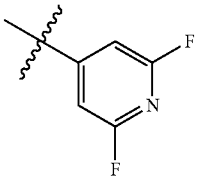 [SMILES: *c1cc(F)nc(F)c1] |
| 938 | $CF_3$ | 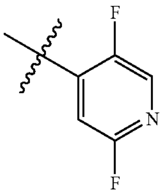 |
| 939 | $CF_3$ | 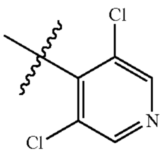 |
| 940 | $CF_3$ | 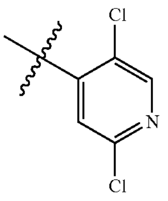 |

-continued
| No. | X | A |
|---|---|---|
| 941 | $CF_3$ | 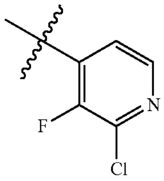 [SMILES: *c1ccnc(Cl)c1F] |
| 942 | $CF_3$ | 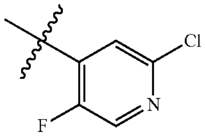 [SMILES: *c1cc(Cl)ncc1F] |
| 943 | $CF_3$ | 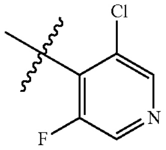 |
| 944 | $CF_3$ | 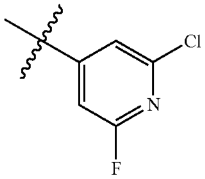 [SMILES: *c1cc(F)nc(Cl)c1] |
| 945 | $CF_3$ | 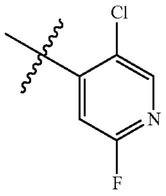 |
| 946 | $CF_3$ | 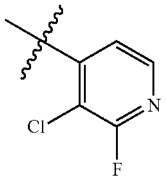 [SMILES: *c1ccnc(F)c1Cl] |
| 947 | $CF_3$ | 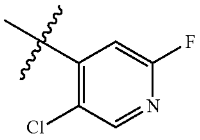 [SMILES: *c1cc(F)ncc1Cl] |
| 948 | $CF_3$ | 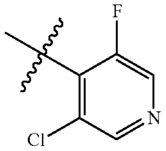 [SMILES: *c1c(F)cncc1Cl] |
| 949 | $CF_3$ | 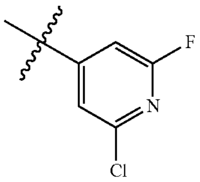 [SMILES: *c1cc(F)nc(Cl)c1] |
-continued
| No. | X | A |
|---|---|---|
| 950 | $CF_3$ | 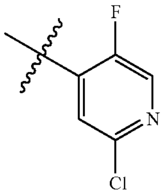 |
| 951 | $CF_3$ | 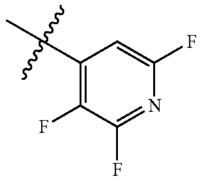 [SMILES: *c1cc(F)nc(F)c1F] |
| 952 | $CF_3$ | 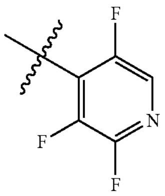 |
| 953 | $CF_3$ | 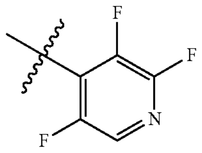 [SMILES: *c1c(F)cnc(F)c1F] |
| 954 | $CF_3$ | 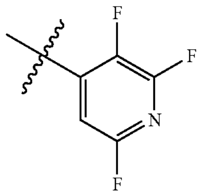 [SMILES: *c1cc(F)nc(F)c1F] |
| 955 | $CF_3$ | 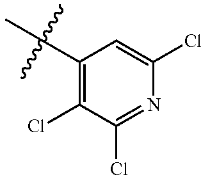 [SMILES: *c1cc(Cl)nc(Cl)c1Cl] |
| 956 | $CF_3$ | 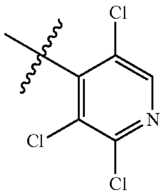 |
| 957 | $CF_3$ | 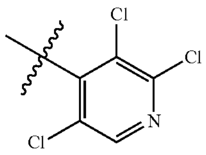 [SMILES: *c1c(Cl)cnc(Cl)c1Cl] |

-continued
| No. | X | A |
|---|---|---|
| 958 | $CF_3$ | 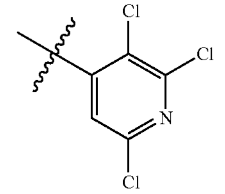 [SMILES: *c1cc(Cl)nc(Cl)c1Cl] |
| 959 | $CF_3$ | 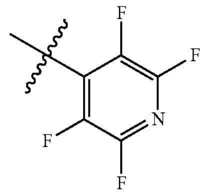 [SMILES: *c1c(F)c(F)nc(F)c1F] |
| 960 | $CF_3$ | 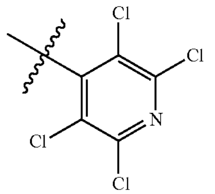 [SMILES: *c1c(Cl)c(Cl)nc(Cl)c1Cl] |
| 961 | $CF_3$ | 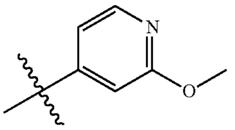 [SMILES: *c1ccnc(OC)c1] |
| 962 | $CF_3$ | 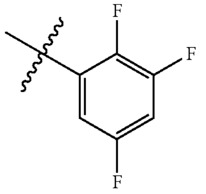 [SMILES: *c1cc(F)cc(F)c1F] |
| 963 | $CF_3$ | 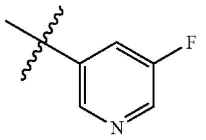 [SMILES: *c1cncc(F)c1] |
| 964 | $CF_3$ | 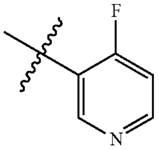 [SMILES: *c1cnccc1F] |
| 965 | $CF_3$ | 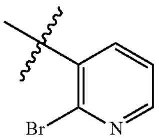 [SMILES: *c1cccnc1Br] |
| 966 | $CF_3$ | 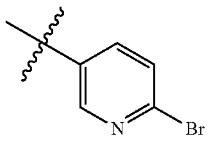 [SMILES: *c1ccc(Br)nc1] |
| 967 | $CF_3$ | 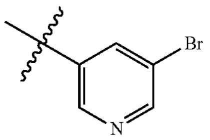 [SMILES: *c1cncc(Br)c1] |
| 968 | $CF_3$ | 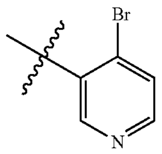 [SMILES: *c1cnccc1Br] |
| 969 | $CF_3$ | 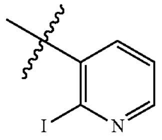 [SMILES: *c1cccnc1I] |
| 970 | $CF_3$ | 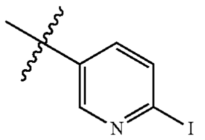 [SMILES: *c1ccc(I)nc1] |
| 971 | $CF_3$ | 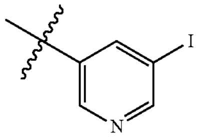 [SMILES: *c1cncc(I)c1] |
| 972 | $CF_3$ | 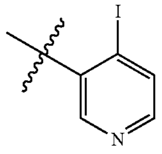 [SMILES: *c1cnccc1I] |
| 973 | $CF_3$ | 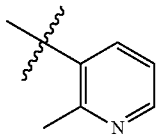 [SMILES: *c1cccnc1C] |
| 974 | $CF_3$ | 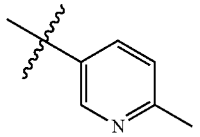 [SMILES: *c1ccc(C)nc1] |
| 975 | $CF_3$ | 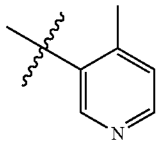 [SMILES: *c1cnccc1C] |
| 976 | $CF_3$ | 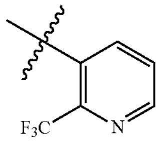 |

-continued
| No. | X | A |
| --- | --- | --- |
| 977 | $CF_3$ | 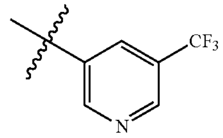 [SMILES: *c1cncc(C(F)(F)F)c1] |
| 978 | $CF_3$ | 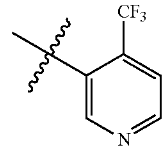 [SMILES: *c1cnccc1C(F)(F)F] |
| 979 | $CF_3$ | 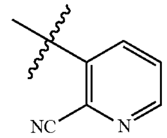 [SMILES: *c1cccnc1C#N] |
| 980 | $CF_3$ | 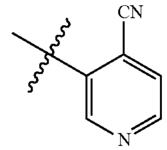 [SMILES: *c1cnccc1C#N] |
| 981 | $CF_3$ | 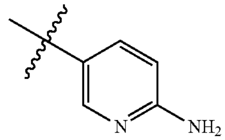 [SMILES: *c1ccc(N)nc1] |
| 982 | $CF_3$ | 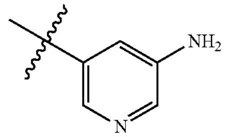 [SMILES: *c1cncc(N)c1] |
| 983 | $CF_3$ | 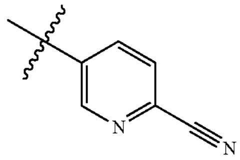 [SMILES: *c1ccc(C#N)nc1] |
| 984 | $CF_3$ | 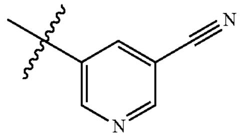 [SMILES: *c1cncc(C#N)c1] |
| 985 | $CF_3$ | 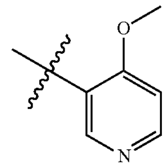 [SMILES: *c1cnccc1OC] |
| 986 | $CF_3$ | 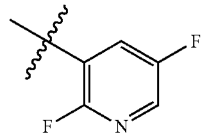 [SMILES: *c1cc(F)cnc1F] |
-continued
| No. | X | A |
| --- | --- | --- |
| 987 | $CF_3$ | 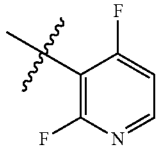 [SMILES: *c1c(F)ccnc1F] |
| 988 | $CF_3$ | 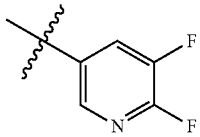 [SMILES: *c1cnc(F)c(F)c1] |
| 989 | $CF_3$ | 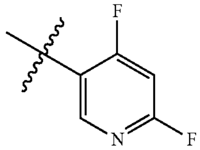 [SMILES: *c1cnc(F)cc1F] |
| 990 | $CF_3$ | 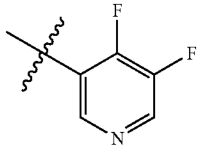 [SMILES: *c1cncc(F)c1F] |
| 991 | $CF_3$ | 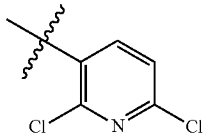 [SMILES: *c1ccc(Cl)nc1Cl] |
| 992 | $CF_3$ | 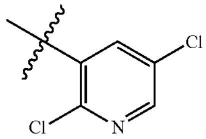 [SMILES: *c1cc(Cl)cnc1Cl] |
| 993 | $CF_3$ | 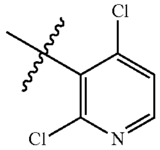 [SMILES: *c1c(Cl)ccnc1Cl] |
| 994 | $CF_3$ | 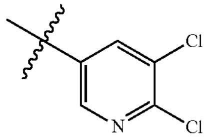 [SMILES: *c1cnc(Cl)c(Cl)c1] |
| 995 | $CF_3$ | 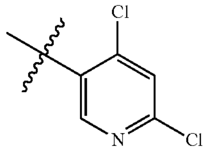 |
| 996 | $CF_3$ | 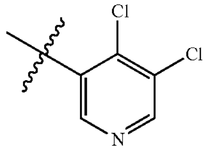 |

-continued
| No. | X | A |
|---|---|---|
| 997 | $CF_3$ | 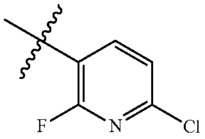 [SMILES: *c1ccc(Cl)nc1F] |
| 998 | $CF_3$ | 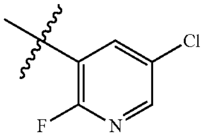 [SMILES: *c1cc(Cl)cnc1F] |
| 999 | $CF_3$ | 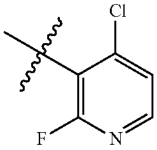 [SMILES: *c1c(Cl)ccnc1F] |
| 1000 | $CF_3$ | 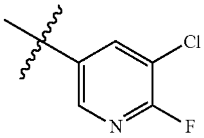 [SMILES: *c1cnc(F)c(Cl)c1] |
| 1001 | $CF_3$ | 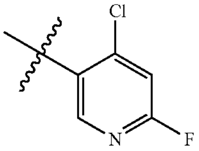 |
| 1002 | $CF_3$ | 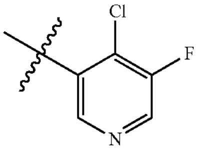 |
| 1003 | $CF_3$ | 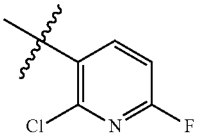 [SMILES: *c1ccc(F)nc1Cl] |
| 1004 | $CF_3$ | 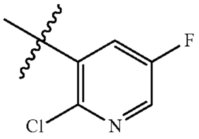 [SMILES: *c1cc(F)cnc1Cl] |
| 1005 | $CF_3$ | 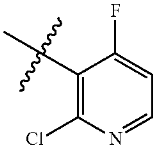 [SMILES: *c1c(F)ccnc1Cl] |
| 1006 | $CF_3$ | 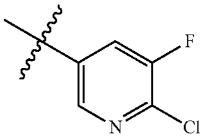 [SMILES: *c1cnc(Cl)c(F)c1] |
-continued
| No. | X | A |
|---|---|---|
| 1007 | $CF_3$ | 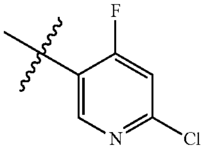 [SMILES: *c1cnc(Cl)cc1F] |
| 1008 | $CF_3$ | 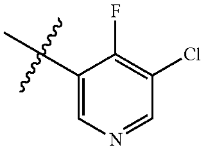 [SMILES: *c1cncc(Cl)c1F] |
| 1009 | $CF_3$ | 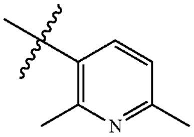 [SMILES: *c1ccc(C)nc1C] |
| 1010 | $CF_3$ | 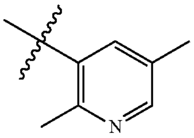 [SMILES: *c1cc(C)cnc1C] |
| 1011 | $CF_3$ | 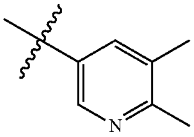 [SMILES: *c1cnc(C)c(C)c1] |
| 1012 | $CF_3$ | 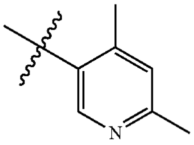 [SMILES: *c1cnc(C)cc1C] |
| 1013 | $CF_3$ | 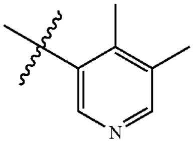 [SMILES: *c1cncc(C)c1C] |
| 1014 | $CF_3$ | 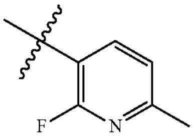 [SMILES: *c1ccc(C)nc1F] |
| 1015 | $CF_3$ | 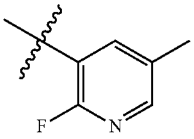 [SMILES: *c1cc(C)cnc1F] |
| 1016 | $CF_3$ | 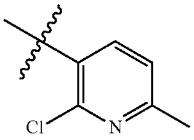 [SMILES: *c1ccc(C)nc1Cl] |

-continued
| No. | X | A |
| --- | --- | --- |
| 1017 | $CF_3$ | 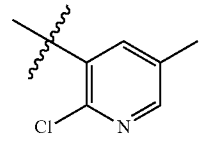 [SMILES: *c1cc(C)cnc1Cl] |
| 1018 | $CF_3$ | 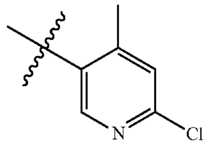 [SMILES: *c1cnc(Cl)cc1C] |
| 1019 | $CF_3$ | 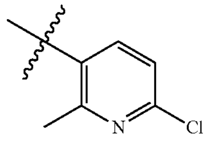 [SMILES: *c1ccc(Cl)nc1C] |
| 1020 | $CF_3$ | 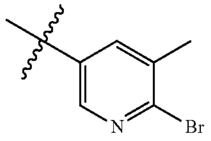 [SMILES: *c1cnc(Br)c(C)c1] |
| 1021 | $CF_3$ | 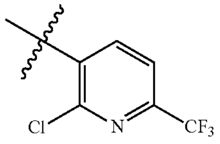 [SMILES: *c1ccc(C(F)(F)F)nc1Cl] |
| 1022 | $CF_3$ | 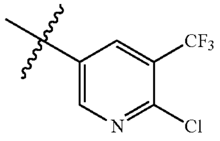 [SMILES: *c1cnc(Cl)c(C(F)(F)F)c1] |
| 1023 | $CF_3$ | 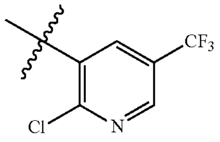 [SMILES: *c1cc(C(F)(F)F)cnc1Cl] |
| 1024 | $CF_3$ | 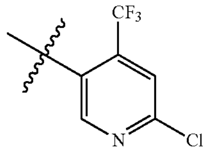 |
| 1025 | $CF_3$ | 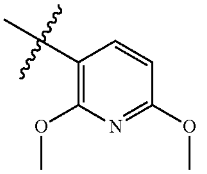 [SMILES: *c1ccc(OC)nc1OC] |
-continued
| No. | X | A |
| --- | --- | --- |
| 1026 | $CF_3$ | 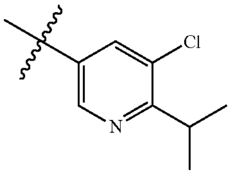 [SMILES: *c1cnc(C(C)C)c(Cl)c1] |
| 1027 | $CF_3$ | 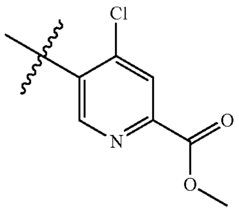 [SMILES: *c1cnc(C(=O)OC)cc1Cl] |
| 1028 | $CF_3$ | 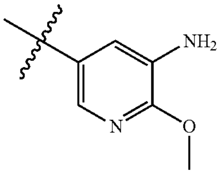 [SMILES: *c1cnc(OC)c(N)c1] |
| 1029 | $CF_3$ | 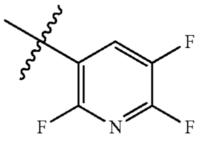 [SMILES: *c1cc(F)c(F)nc1F] |
| 1030 | $CF_3$ | 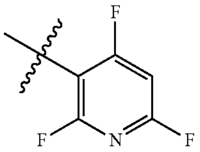 [SMILES: *c1c(F)cc(F)nc1F] |
| 1031 | $CF_3$ | 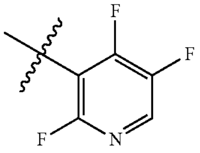 [SMILES: *c1c(F)ncc(F)c1F] |
| 1032 | $CF_3$ | 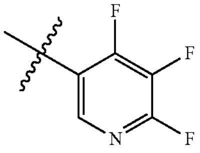 [SMILES: *c1cnc(F)c(F)c1F] |
| 1033 | $CF_3$ | 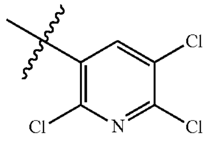 [SMILES: *c1cc(Cl)c(Cl)nc1Cl] |
| 1034 | $CF_3$ | 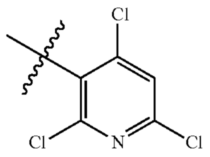 |

-continued
| No. | X | A |
|---|---|---|
| 1035 | $CF_3$ | 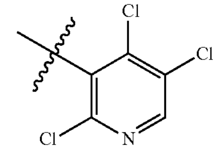 [SMILES: *c1c(Cl)ncc(Cl)c1Cl] |
| 1036 | $CF_3$ | 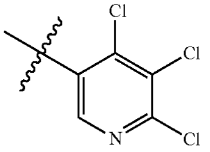 |
| 1037 | $CF_3$ | 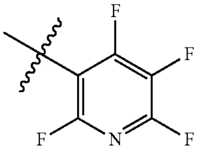 [SMILES: *c1c(F)nc(F)c(F)c1F] |
| 1038 | $CF_3$ | 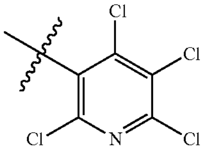 [SMILES: *c1c(Cl)nc(Cl)c(Cl)c1Cl] |
| 1039 | $CF_3$ | 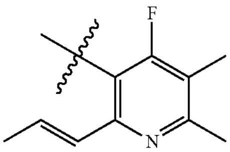 [SMILES: *c1c(/C=C/C)nc(C)c(C)c1F] |
| 1040 | $CF_3$ | 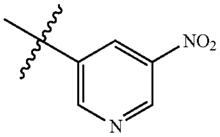 [SMILES: *c1cncc([N+](=O)[O-])c1] |
| 1041 | $CF_3$ | 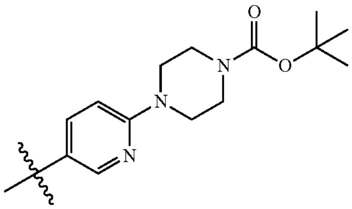 [SMILES: *c1ccc(N2CCN(C(=O)OC(C)(C)C)CC2)nc1] |
| 1042 | $CF_3$ | 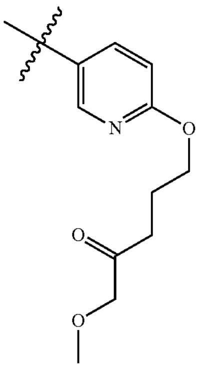 [SMILES: *c1ccc(OCCCC(=O)COC)nc1] |
| 1043 | $CF_3$ | 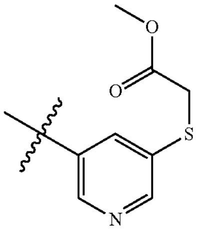 [SMILES: *c1cncc(SCC(=O)OC)c1] |
| 1044 | $CF_3$ | 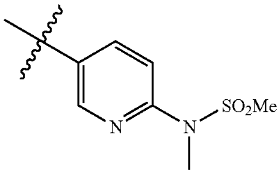 [SMILES: *c1ccc(N(C)S(C)(=O)=O)nc1] |
| 1045 | $CF_3$ | 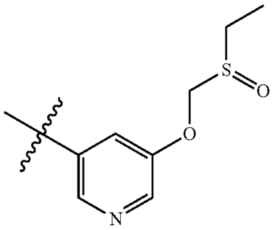 [SMILES: *c1cncc(OCS(=O)CC)c1] |
| 1046 | $CF_3$ | 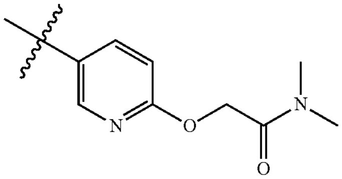 [SMILES: *c1ccc(OCC(=O)N(C)C)nc1] |
| 1047 | $CF_3$ | 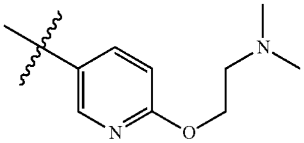 [SMILES: *c1ccc(OCCN(C)C)nc1] |
| 1048 | $CF_3$ | 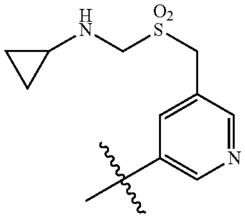 [SMILES: *c1cncc(CS(=O)(=O)CNC2CC2)c1] |
| 1049 | $CF_3$ | 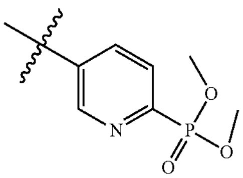 [SMILES: *c1ccc(P(=O)(OC)OC)nc1] |
| 1050 | $CF_3$ | 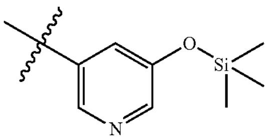 [SMILES: *c1cncc(O[Si](C)(C)C)c1] |

-continued
| No. | X | A |
|---|---|---|
| 1051 | $CF_3$ | 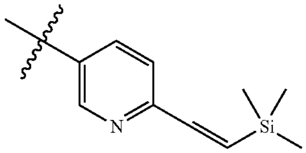 [SMILES: *c1ccc(C=C[Si](C)(C)C)nc1] |
| 1052 | $CF_3$ | 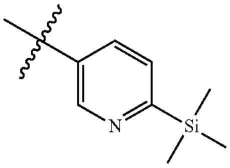 [SMILES: *c1ccc([Si](C)(C)C)nc1] |
| 1053 | $CF_3$ | 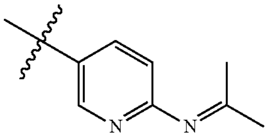 [SMILES: *c1ccc(N=C(C)C)nc1] |
| 1054 | $CF_3$ | 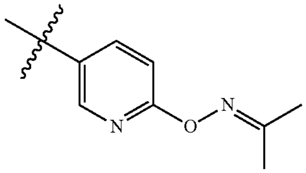 [SMILES: *c1ccc(ON=C(C)C)nc1] |
| 1055 | $CF_3$ | 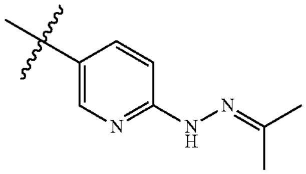 [SMILES: *c1ccc(NN=C(C)C)nc1] |
| 1056 | $CF_3$ | 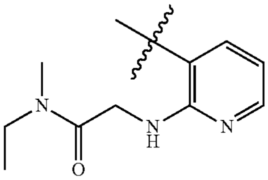 [SMILES: *c1cccnc1NCC(=O)N(C)CC] |
| 1057 | $CF_3$ | 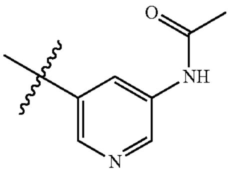 [SMILES: *c1cncc(NC(C)=O)c1] |
| 1058 | $CF_3$ | 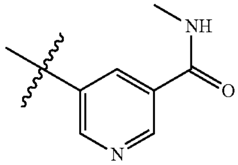 [SMILES: *c1cncc(C(=O)NC)c1] |
-continued
| No. | X | A |
|---|---|---|
| 1059 | $CF_3$ | 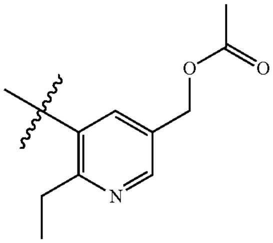 [SMILES: *c1cc(COC(C)=O)cnc1CC] |
| 1060 | $CF_3$ | 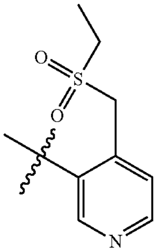 [SMILES: *c1cnccc1CS(=O)(=O)CC] |
| 1061 | $CF_3$ | 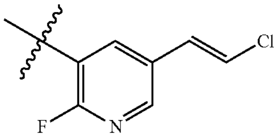 [SMILES: *c1cc(/C=C/Cl)cnc1F] |
| 1062 | $CF_3$ | 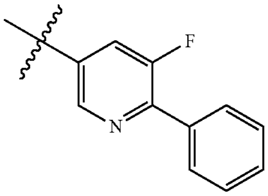 [SMILES: *c1cnc(-c2ccccc2)c(F)c1] |
| 1063 | $CF_3$ | 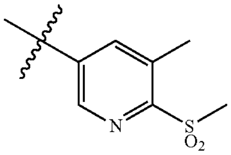 |
| 1064 | $CF_3$ | 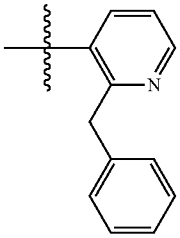 |
| 1065 | $CF_3$ | 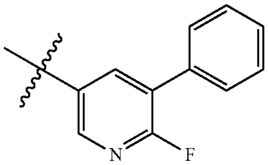 [SMILES: *c1cnc(F)c(-c2ccccc2)c1] |

-continued
| No. | X | A |
| --- | --- | --- |
| 1066 | $CF_3$ | 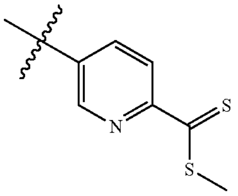 [SMILES: *c1ccc(C(=S)SC)nc1] |
| 1067 | $CF_3$ | 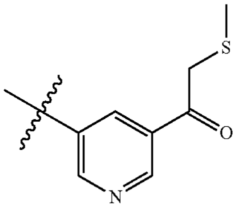 [SMILES: *c1cncc(C(=O)CSC)c1] |
| 1068 | $CF_3$ | 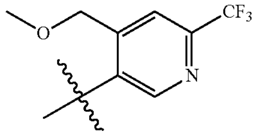 [SMILES: *c1cnc(C(F)(F)F)cc1COC] |
| 1069 | $CF_3$ | 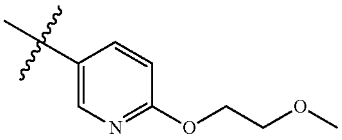 [SMILES: *c1ccc(OCCOC)nc1] |
| 1070 | $CF_2CF_3$ | 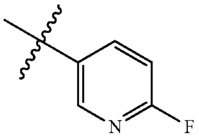 [SMILES: *c1ccc(F)nc1] |
| 1071 | $CF_2CF_3$ | 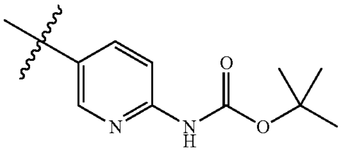 [SMILES: *c1ccc(NC(=O)OC(C)(C)C)nc1] |
| 1072 | $CF_2CF_3$ | 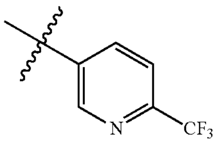 |
| 1073 | $CH_2F$ | 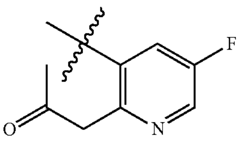 [SMILES: *c1cc(F)cnc1CC(C)=O] |
| 1074 | $CH_2F$ | 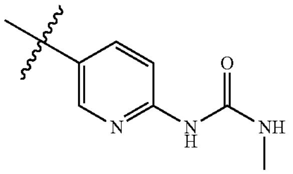 [SMILES: *c1ccc(NC(=O)NC)nc1] |
-continued
| No. | X | A |
| --- | --- | --- |
| 1075 | $CH_2F$ | 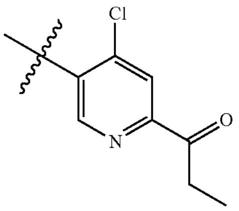 [SMILES: *c1cnc(C(=O)CC)cc1Cl] |
| 1076 | $CH_2F$ | 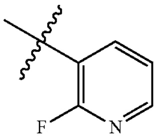 [SMILES: *c1cccnc1F] |
| 1077 | $CH_2F$ | 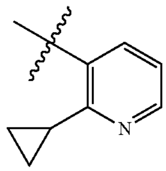 [SMILES: *c1cccnc1C1CC1] |
| 1078 | $CH_2F$ | 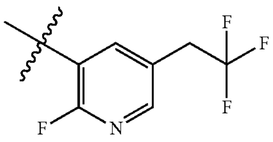 [SMILES: *c1cc(CC(F)(F)F)cnc1F] |
| 1079 | $CHF_2$ | 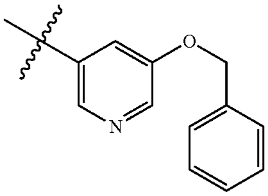 [SMILES: *c1cncc(OCc2ccccc2)c1] |
| 1080 | $CHF_2$ | 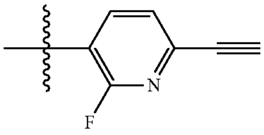 [SMILES: *c1ccc(C#C)nc1F] |
| 1081 | $CF_2CF_3$ | 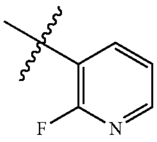 |
| 1082 | $CF_2CF_3$ | 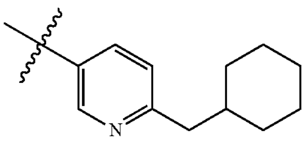 [SMILES: *c1ccc(CC2CCCCC2)nc1] |
| 1083 | $CF_2CF_3$ | 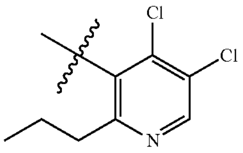 [SMILES: *c1c(CCC)ncc(Cl)c1Cl] |

-continued
| No. | X | A |
|---|---|---|
| 1084 | $CH_2F$ | 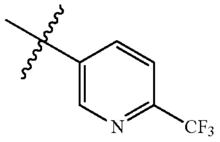 |
| 1085 | $CHF_2$ | 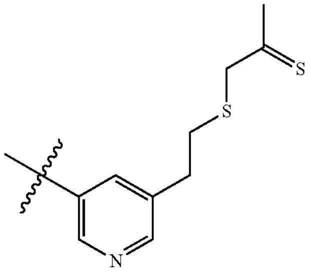 [SMILES: *c1cncc(CCSCC(C)=S)c1] |
| 1086 | $CHF_2$ | 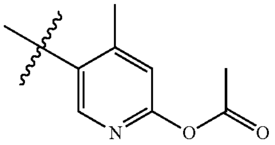 [SMILES: *c1cnc(OC(C)=O)cc1C] |
| 1089 | $CHF_2$ | 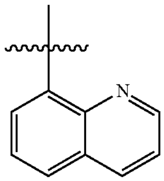 |
| 1096 | $CF_2CF_3$ | 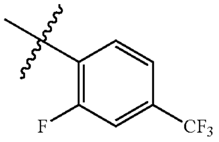 |
| 1097 | $CF_2CF_3$ | 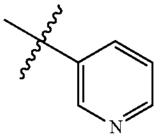 [SMILES: *c1cccnc1] |
| 1098 | $CF_3$ | 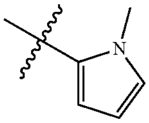 [SMILES: *c1cccn1C] |
| 1099 | $CF_3$ | 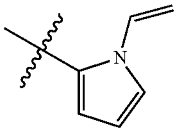 [SMILES: *c1cccn1C=C] |
| 1100 | $CF_3$ | 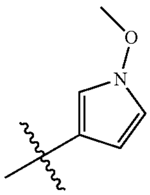 [SMILES: *c1ccn(OC)c1] |
-continued
| No. | X | A |
|---|---|---|
| 1101 | $CF_3$ | 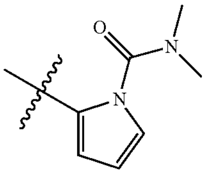 [SMILES: *c1cccn1C(=O)N(C)C] |
| 1102 | $CF_3$ | 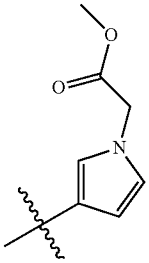 [SMILES: *c1ccn(CC(=O)OC)c1] |
| 1107 | $CF_3$ | 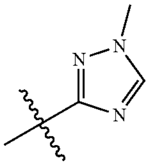 [SMILES: *c1ncn(C)n1] |
| 1109 | $CF_3$ | 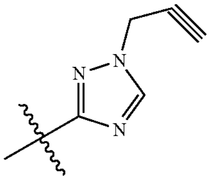 [SMILES: *c1ncn(CC#C)n1] |
| 1110 | $CF_3$ | 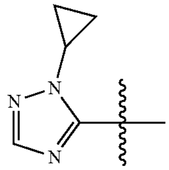 [SMILES: *c1ncnn1C1CC1] |
| 1111 | $CF_3$ | 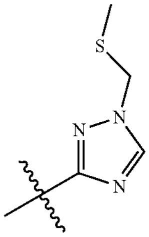 [SMILES: *c1ncn(CSC)n1] |
| 1112 | $CF_3$ | 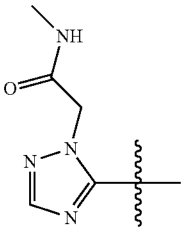 [SMILES: *c1ncnn1CC(=O)NC] |

-continued
| No. | X | A |
| --- | --- | --- |
| 1113 | $CF_3$ | 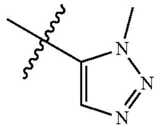 [SMILES: *c1cnnn1C] |
| 1114 | $CF_3$ | 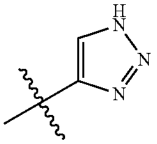 [SMILES: *c1c[nH]nn1] |
| 1115 | $CF_3$ | 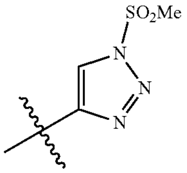 [SMILES: *c1cn(S(C)(=O)=O)nn1] |
| 1116 | $CF_3$ | 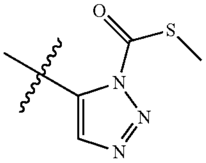 [SMILES: *c1cnnn1C(=O)SC] |
| 1117 | $CF_3$ | 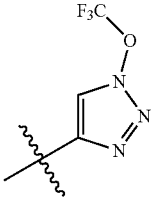 [SMILES: *c1cn(OC(F)(F)F)nn1] |
| 1118 | $CF_3$ | 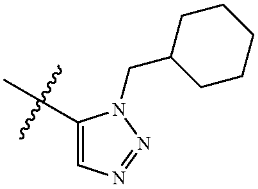 [SMILES: *c1cnnn1CC1CCCCC1] |
| 1119 | $CF_3$ | 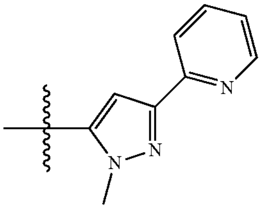 [SMILES: *c1cc(-c2ccccn2)nn1C] |
| 1120 | $CF_3$ | 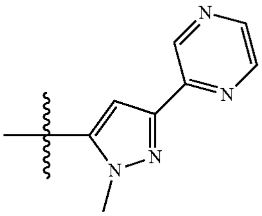 [SMILES: *c1cc(-c2cnccn2)nn1C] |
-continued
| No. | X | A |
| --- | --- | --- |
| 1121 | $CF_3$ | 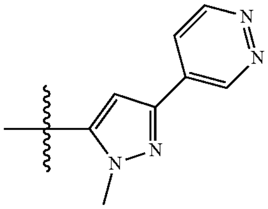 [SMILES: *c1cc(-c2ccnnc2)nn1C] |
| 1122 | $CF_3$ | 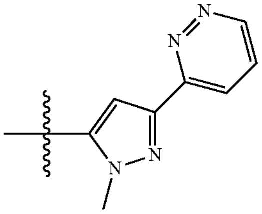 [SMILES: *c1cc(-c2cccnn2)nn1C] |
| 1123 | $CF_3$ | 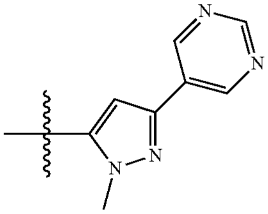 [SMILES: *c1cc(-c2cncnc2)nn1C] |
| 1124 | $CF_3$ | 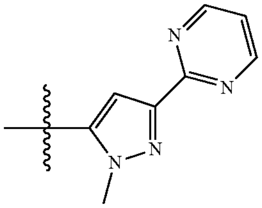 [SMILES: *c1cc(-c2ncccn2)nn1C] |
| 1125 | $CF_3$ | 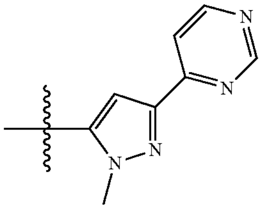 [SMILES: *c1cc(-c2ccncn2)nn1C] |
| 1126 | $CF_3$ | 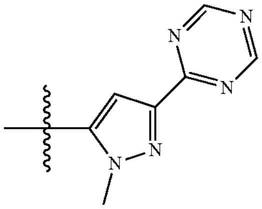 [SMILES: *c1cc(-c2ncncn2)nn1C] |
| 1127 | $CF_3$ | 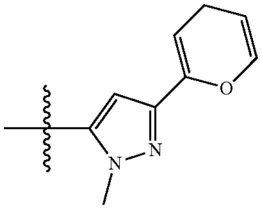 [SMILES: *c1cc(C2=CCC=CO2)nn1C] |

-continued
| No. | X | A |
|---|---|---|
| 1128 | $CF_3$ | 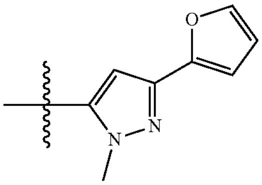 [SMILES: *c1cc(-c2ccco2)nn1C] |
| 1129 | $CF_3$ | 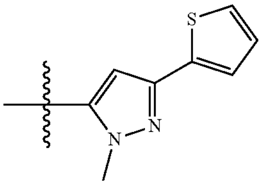 [SMILES: *c1cc(-c2cccs2)nn1C] |
| 1130 | $CF_3$ | 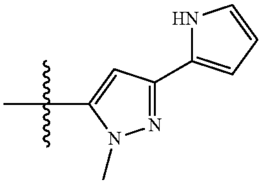 [SMILES: *c1cc(-c2ccc[nH]2)nn1C] |
| 1131 | $CF_3$ | 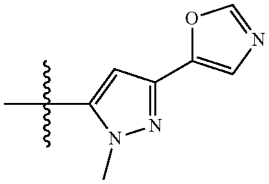 [SMILES: *c1cc(-c2cnco2)nn1C] |
| 1132 | $CF_3$ | 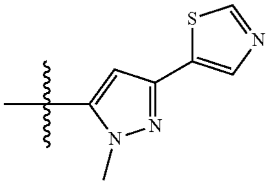 [SMILES: *c1cc(-c2cncs2)nn1C] |
| 1133 | $CF_3$ | 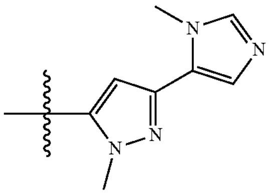 [SMILES: *c1cc(-c2cncn2C)nn1C] |
| 1134 | $CF_3$ | 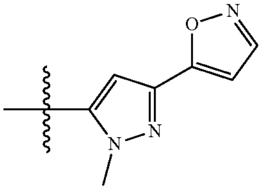 [SMILES: *c1cc(-c2ccno2)nn1C] |
| 1135 | $CF_3$ | 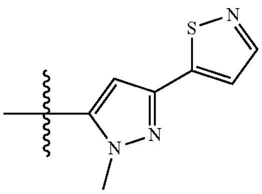 [SMILES: *c1cc(-c2ccns2)nn1C] |
| 1136 | $CF_3$ | 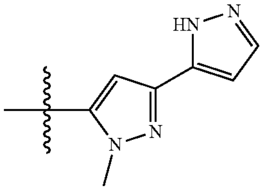 [SMILES: *c1cc(-c2ccn[nH]2)nn1C] |
| 1137 | $CF_3$ | 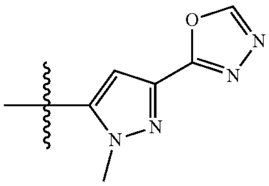 [SMILES: *c1cc(-c2nnco2)nn1C] |
| 1138 | $CF_3$ | 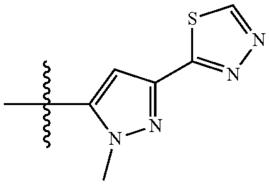 [SMILES: *c1cc(-c2nncs2)nn1C] |
| 1139 | $CF_3$ | 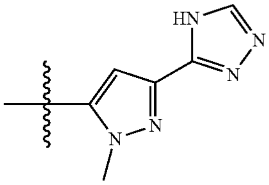 [SMILES: *c1cc(-c2nnc[nH]2)nn1C] |
| 1140 | $CF_3$ | 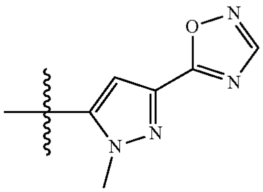 [SMILES: *c1cc(-c2ncno2)nn1C] |
| 1141 | $CF_3$ | 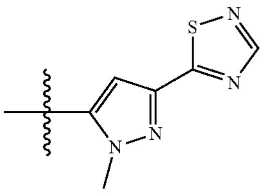 [SMILES: *c1cc(-c2ncns2)nn1C] |
| 1142 | $CF_3$ | 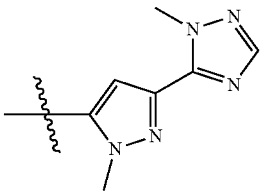 [SMILES: *c1cc(-c2ncnn2C)nn1C] |
| 1143 | $CF_3$ | 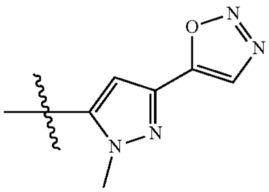 [SMILES: *c1cc(-c2cnno2)nn1C] |

-continued
| No. | X | A |
| --- | --- | --- |
| 1144 | $CF_3$ | 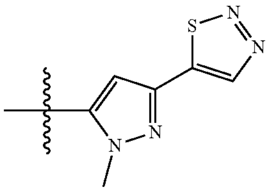 [SMILES: *c1cc(-c2cnns2)nn1C] |
| 1145 | $CF_3$ | 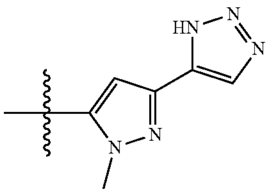 [SMILES: *c1cc(-c2cnn[nH]2)nn1C] |
| 1146 | $CF_3$ | 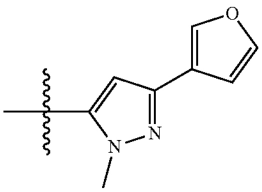 [SMILES: *c1cc(-c2ccoc2)nn1C] |
| 1147 | $CF_3$ | 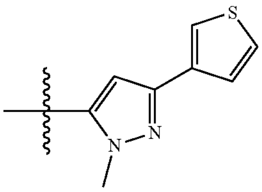 [SMILES: *c1cc(-c2ccsc2)nn1C] |
| 1148 | $CF_3$ | 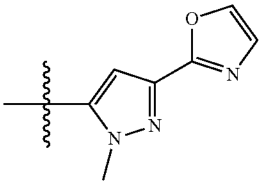 [SMILES: *c1cc(-c2ncco2)nn1C] |
| 1149 | $CF_3$ | 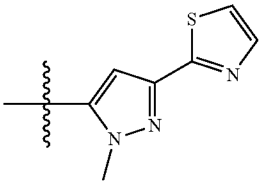 [SMILES: *c1cc(-c2nccs2)nn1C] |
| 1150 | $CF_3$ | 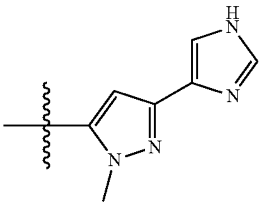 [SMILES: *c1cc(-c2c[nH]cn2)nn1C] |
-continued
| No. | X | A |
| --- | --- | --- |
| 1151 | $CF_3$ | 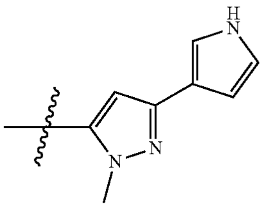 [SMILES: *c1cc(-c2cc[nH]c2)nn1C] |
| 1152 | $CF_3$ | 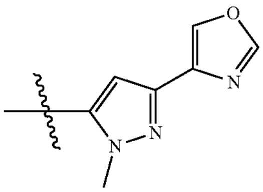 [SMILES: *c1cc(-c2cocn2)nn1C] |
| 1153 | $CF_3$ | 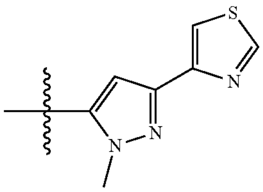 [SMILES: *c1cc(-c2cscn2)nn1C] |
| 1154 | $CF_3$ | 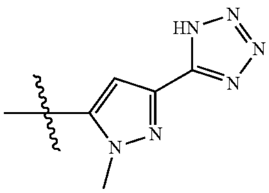 [SMILES: *c1cc(-c2nnn[nH]2)nn1C] |
| 1155 | $CF_3$ | 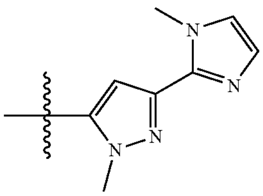 [SMILES: *c1cc(-c2nccn2C)nn1C] |
| 1156 | $CF_3$ | 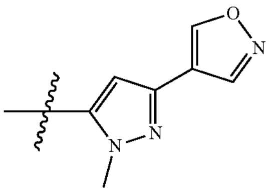 [SMILES: *c1cc(-c2cnoc2)nn1C] |
| 1157 | $CF_3$ | 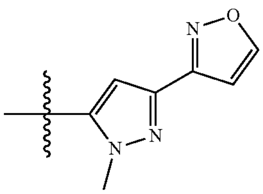 [SMILES: *c1cc(-c2ccon2)nn1C] |

-continued
| No. | X | A |
|---|---|---|
| 1158 | $CF_3$ | 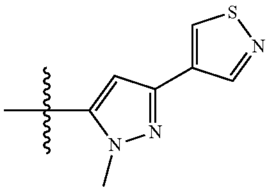 [SMILES: *c1cc(-c2cnsc2)nn1C] |
| 1159 | $CF_3$ | 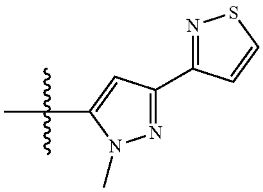 [SMILES: *c1cc(-c2ccsn2)nn1C] |
| 1160 | $CF_3$ | 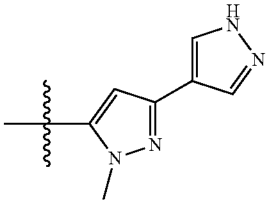 [SMILES: *c1cc(-c2cn[nH]c2)nn1C] |
| 1161 | $CF_3$ | 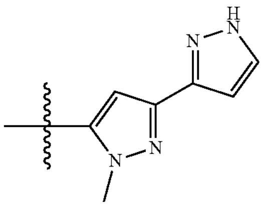 [SMILES: *c1cc(-c2cc[nH]n2)nn1C] |
| 1162 | $CF_3$ | 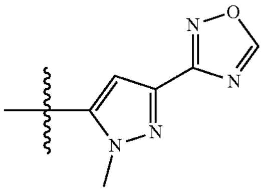 [SMILES: *c1cc(-c2ncon2)nn1C] |
| 1163 | $CF_3$ | 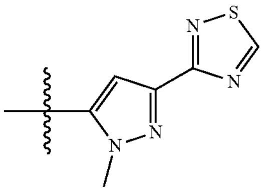 [SMILES: *c1cc(-c2ncsn2)nn1C] |
| 1164 | $CF_3$ | 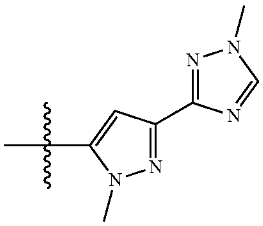 [SMILES: *c1cc(-c2ncn(C)n2)nn1C] |
-continued
| No. | X | A |
|---|---|---|
| 1165 | $CF_3$ | 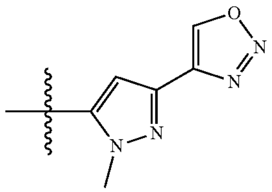 [SMILES: *c1cc(-c2conn2)nn1C] |
| 1166 | $CF_3$ | 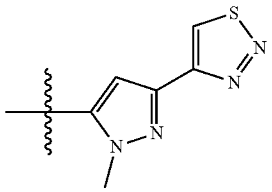 [SMILES: *c1cc(-c2csnn2)nn1C] |
| 1167 | $CF_3$ | 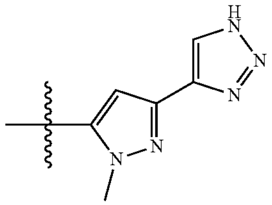 [SMILES: *c1cc(-c2c[nH]nn2)nn1C] |
| 1168 | $CF_3$ | 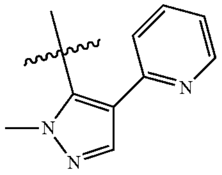 [SMILES: *c1c(-c2ccccn2)cnn1C] |
| 1169 | $CF_3$ | 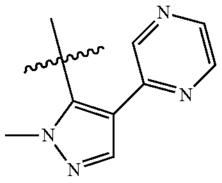 [SMILES: *c1c(-c2cnccn2)cnn1C] |
| 1170 | $CF_3$ | 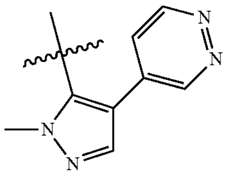 [SMILES: *c1c(-c2ccnnc2)cnn1C] |
| 1171 | $CF_3$ | 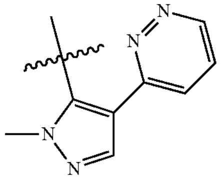 [SMILES: *c1c(-c2cccnn2)cnn1C] |
| 1172 | $CF_3$ | 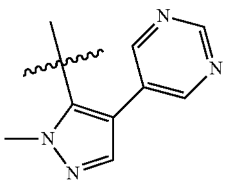 [SMILES: *c1c(-c2cncnc2)cnn1C] |

-continued
| No. | X | A |
|---|---|---|
| 1173 | $CF_3$ | 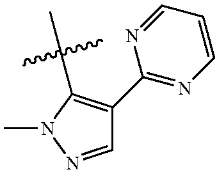 [SMILES: *c1c(-c2ncccn2)cnn1C] |
| 1174 | $CF_3$ | 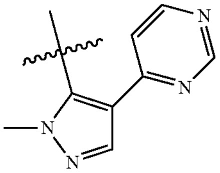 [SMILES: *c1c(-c2ccncn2)cnn1C] |
| 1175 | $CF_3$ | 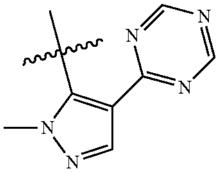 [SMILES: *c1c(-c2ncncn2)cnn1C] |
| 1176 | $CF_3$ | 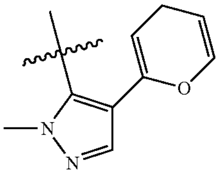 [SMILES: *c1c(C2=CCC=CO2)cnn1C] |
| 1177 | $CF_3$ | 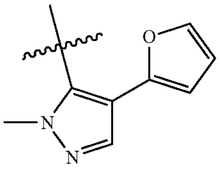 [SMILES: *c1c(-c2ccco2)cnn1C] |
| 1178 | $CF_3$ | 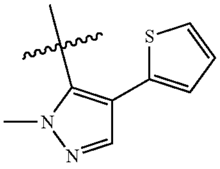 [SMILES: *c1c(-c2cccs2)cnn1C] |
| 1179 | $CF_3$ | 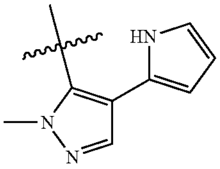 [SMILES: *c1c(-c2ccc[nH]2)cnn1C] |
| 1180 | $CF_3$ | 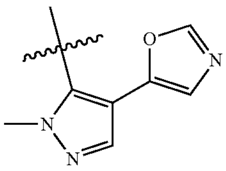 [SMILES: *c1c(-c2cnco2)cnn1C] |
| 1181 | $CF_3$ | 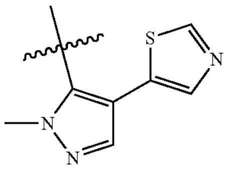 [SMILES: *c1c(-c2cncs2)cnn1C] |
| 1182 | $CF_3$ | 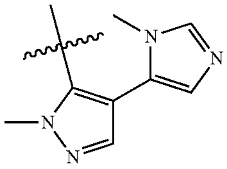 [SMILES: *c1c(-c2cncn2C)cnn1C] |
| 1183 | $CF_3$ | 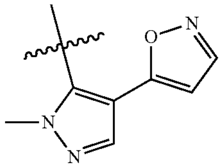 [SMILES: *c1c(-c2ccno2)cnn1C] |
| 1184 | $CF_3$ | 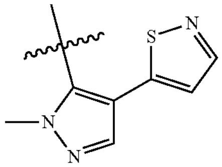 [SMILES: *c1c(-c2ccns2)cnn1C] |
| 1185 | $CF_3$ | 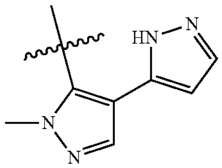 [SMILES: *c1c(-c2ccn[nH]2)cnn1C] |
| 1186 | $CF_3$ | 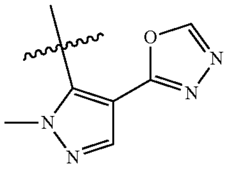 [SMILES: *c1c(-c2nnco2)cnn1C] |
| 1187 | $CF_3$ | 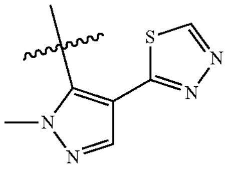 [SMILES: *c1c(-c2nncs2)cnn1C] |
| 1188 | $CF_3$ | 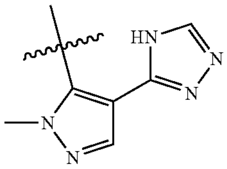 [SMILES: *c1c(-c2nnc[nH]2)cnn1C] |

-continued
| No. | X | A |
|---|---|---|
| 1189 | $CF_3$ | 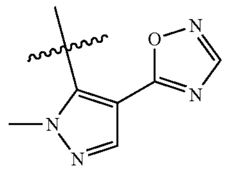 [SMILES: *c1c(-c2ncno2)cnn1C] |
| 1190 | $CF_3$ | 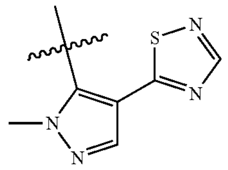 [SMILES: *c1c(-c2ncns2)cnn1C] |
| 1191 | $CF_3$ | 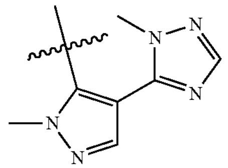 [SMILES: *c1c(-c2ncnn2C)cnn1C] |
| 1192 | $CF_3$ | 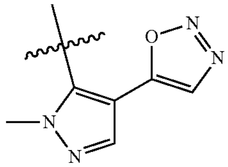 [SMILES: *c1c(-c2cnno2)cnn1C] |
| 1193 | $CF_3$ | 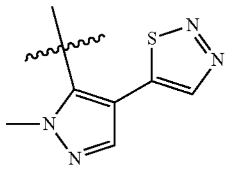 [SMILES: *c1c(-c2cnns2)cnn1C] |
| 1194 | $CF_3$ | 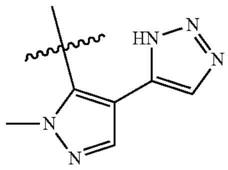 [SMILES: *c1c(-c2cnn[nH]2)cnn1C] |
| 1195 | $CF_3$ | 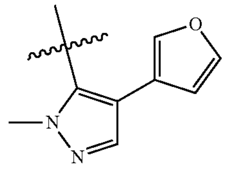 [SMILES: *c1c(-c2ccoc2)cnn1C] |
| 1196 | $CF_3$ | 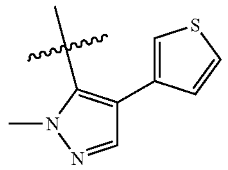 [SMILES: *c1c(-c2ccsc2)cnn1C] |
-continued
| No. | X | A |
|---|---|---|
| 1197 | $CF_3$ | 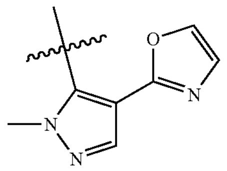 [SMILES: *c1c(-c2ncco2)cnn1C] |
| 1198 | $CF_3$ | 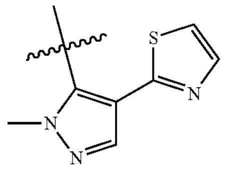 [SMILES: *c1c(-c2nccs2)cnn1C] |
| 1199 | $CF_3$ | 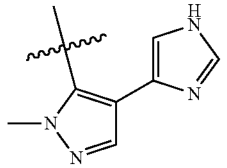 [SMILES: *c1c(-c2c[nH]cn2)cnn1C] |
| 1200 | $CF_3$ | 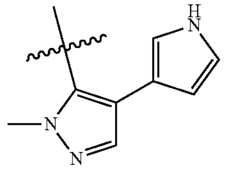 [SMILES: *c1c(-c2cc[nH]c2)cnn1C] |
| 1201 | $CF_3$ | 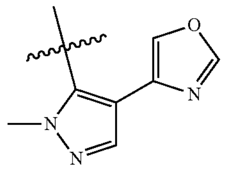 [SMILES: *c1c(-c2cocn2)cnn1C] |
| 1202 | $CF_3$ | 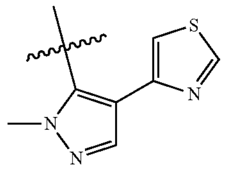 [SMILES: *c1c(-c2cscn2)cnn1C] |
| 1203 | $CF_3$ | 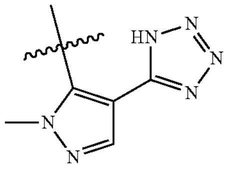 [SMILES: *c1c(-c2nnn[nH]2)cnn1C] |
| 1204 | $CF_3$ | 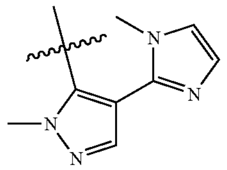 [SMILES: *c1c(-c2nccn2C)cnn1C] |

-continued
| No. | X | A |
|---|---|---|
| 1205 | $CF_3$ | 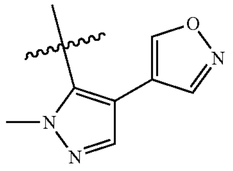 [SMILES: *c1c(-c2cnoc2)cnn1C] |
| 1206 | $CF_3$ | 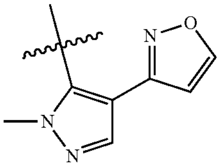 [SMILES: *c1c(-c2ccon2)cnn1C] |
| 1207 | $CF_3$ | 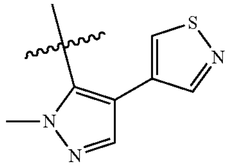 [SMILES: *c1c(-c2cnsc2)cnn1C] |
| 1208 | $CF_3$ | 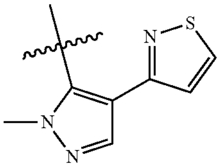 [SMILES: *c1c(-c2ccsn2)cnn1C] |
| 1209 | $CF_3$ | 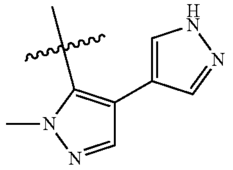 [SMILES: *c1c(-c2cn[nH]c2)cnn1C] |
| 1210 | $CF_3$ | 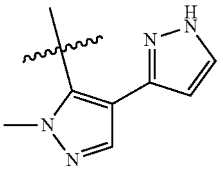 [SMILES: *c1c(-c2cc[nH]n2)cnn1C] |
| 1211 | $CF_3$ | 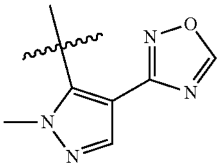 [SMILES: *c1c(-c2ncon2)cnn1C] |
| 1212 | $CF_3$ | 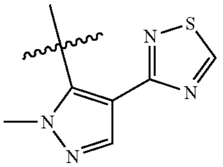 [SMILES: *c1c(-c2ncsn2)cnn1C] |
-continued
| No. | X | A |
|---|---|---|
| 1213 | $CF_3$ | 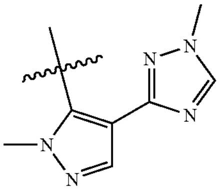 [SMILES: *c1c(-c2ncn(C)n2)cnn1C] |
| 1214 | $CF_3$ | 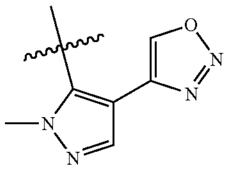 [SMILES: *c1c(-c2conn2)cnn1C] |
| 1215 | $CF_3$ | 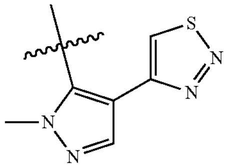 [SMILES: *c1c(-c2csnn2)cnn1C] |
| 1216 | $CF_3$ | 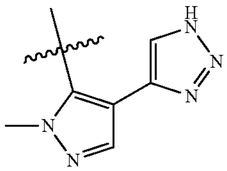 [SMILES: *c1c(-c2c[nH]nn2)cnn1C] |
| 1217 | $CF_3$ | 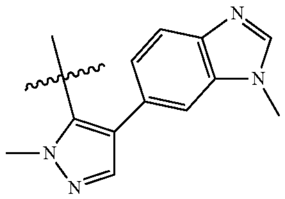 |
| 1218 | $CF_3$ | 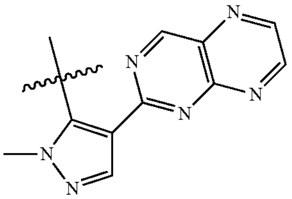 [SMILES: *c1c(-c2ncc3nccnc3n2)cnn1C] |
| 1219 | $CF_3$ | 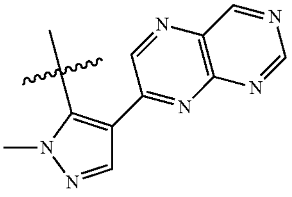 [SMILES: *c1c(-c2cnc3cncnc3n2)cnn1C] |
| 1220 | $CF_3$ | 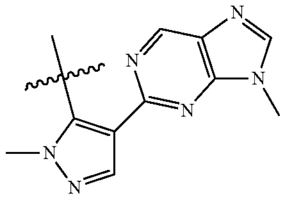 |

-continued
| No. | X | A |
|---|---|---|
| 1221 | $CF_3$ | 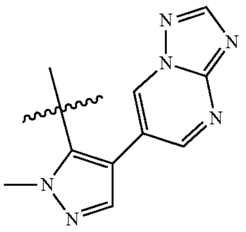 [SMILES: *c1c(-c2cnc3ncnn3c2)cnn1C] |
| 1222 | $CF_3$ | 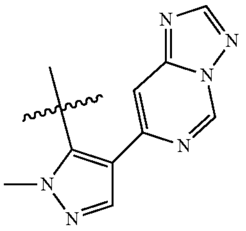 [SMILES: *c1c(-c2cc3ncnn3cn2)cnn1C] |
| 1223 | $CF_3$ | 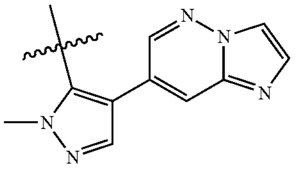 [SMILES: *c1c(-c2cnn3ccnc3c2)cnn1C] |
| 1224 | $CF_3$ | 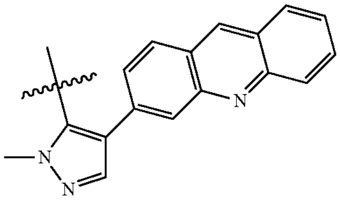 [SMILES: *c1c(-c2ccc3cc4ccccc4nc3c2)cnn1C] |
| 1225 | $CF_3$ | 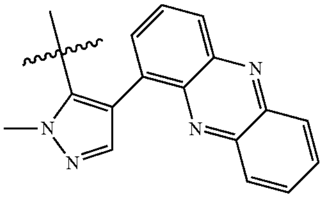 [SMILES: *c1c(-c2cccc3nc4ccccc4nc23)cnn1C] |
| 1226 | $CF_3$ | 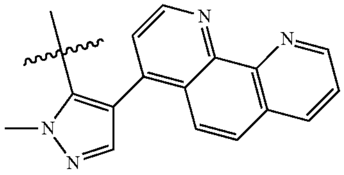 [SMILES: *c1c(-c2ccnc3c2ccc2cccnc23)cnn1C] |
| 1227 | $CF_3$ | 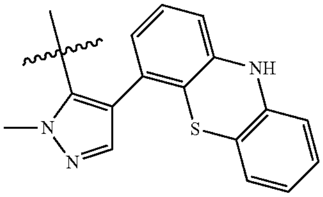 [SMILES: *c1c(-c2cccc3c2Sc2ccccc2N3)cnn1C] |
-continued
| No. | X | A |
|---|---|---|
| 1228 | $CF_3$ | 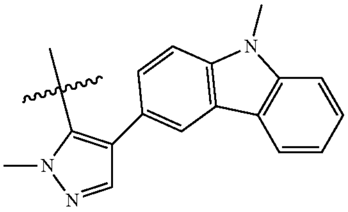 [SMILES: *c1c(-c2ccc3c(c2)c2ccccc2n3C)cnn1C] |
| 1229 | $CF_3$ | 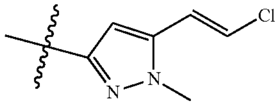 [SMILES: *c1cc(/C=C/Cl)n(C)n1] |
| 1230 | $CF_3$ | 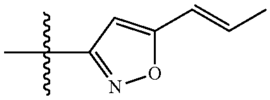 [SMILES: *c1cc(/C=C/C)on1] |
| 1231 | $CF_3$ | 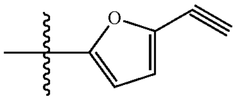 [SMILES: *c1ccc(C#C)o1] |
| 1232 | $CF_3$ | 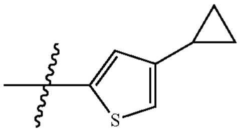 [SMILES: *c1cc(C2CC2)cs1] |
| 1233 | $CF_3$ | 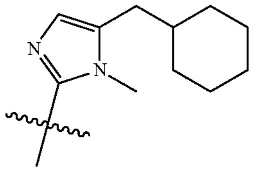 [SMILES: *c1ncc(CC2CCCCC2)n1C] |
| 1234 | $CF_3$ | 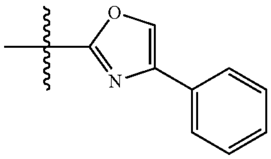 [SMILES: *c1nc(-c2ccccc2)co1] |
| 1235 | $CF_3$ | 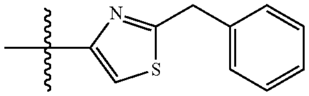 [SMILES: *c1csc(Cc2ccccc2)n1] |
| 1236 | $CF_3$ | 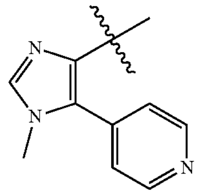 [SMILES: *c1ncn(C)c1-c1ccncc1] |
| 1237 | $CF_3$ | 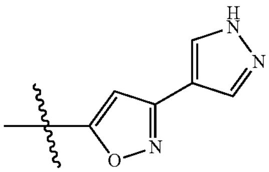 [SMILES: *c1cc(-c2cn[nH]c2)no1] |

-continued
| No. | X | A |
|---|---|---|
| 1238 | $CF_3$ | 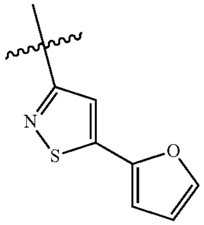 [SMILES: *c1cc(-c2ccco2)sn1] |
| 1239 | $CF_3$ | 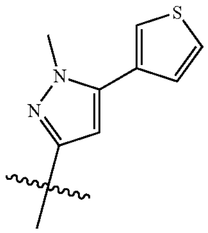 [SMILES: *c1cc(-c2ccsc2)n(C)n1] |
| 1240 | $CF_3$ | 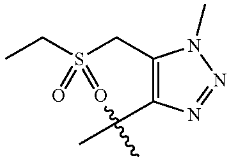 [SMILES: *c1nnn(C)c1CS(=O)(=O)CC] |
| 1241 | $CF_3$ | 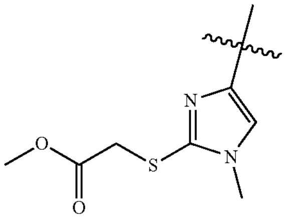 [SMILES: *c1cn(C)c(SCC(=O)OC)n1] |
| 1242 | $CF_3$ | 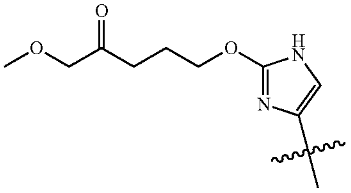 [SMILES: *c1c[nH]c(OCCCC(=O)COC)n1] |
| 1243 | $CF_3$ | 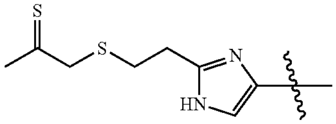 [SMILES: *c1c[nH]c(CCSCC(C)=S)n1] |
| 1244 | $CF_3$ | 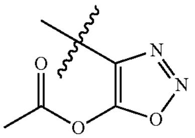 [SMILES: *c1nnoc1OC(C)=O] |
| 1245 | $CF_3$ | 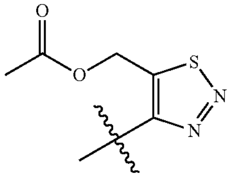 [SMILES: *c1nnsc1COC(C)=O] |
-continued
| No. | X | A |
|---|---|---|
| 1246 | $CF_3$ | 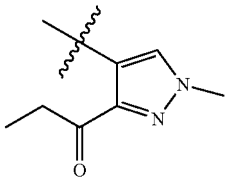 [SMILES: *c1cn(C)nc1C(=O)CC] |
| 1247 | $CF_3$ | 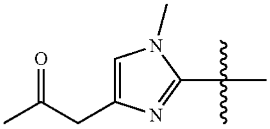 [SMILES: *c1nc(CC(C)=O)cn1C] |
| 1248 | $CF_3$ | 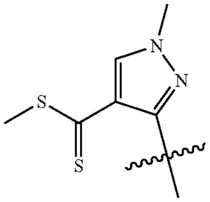 [SMILES: *c1nn(C)cc1C(=S)SC] |
| 1249 | $CF_3$ | 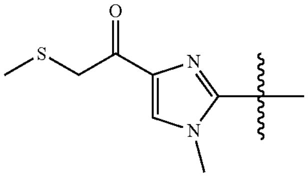 [SMILES: *c1nc(C(=O)CSC)cn1C] |
| 1250 | $CF_3$ | 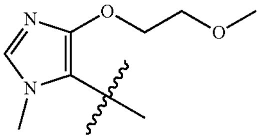 [SMILES: *c1c(OCCOC)ncn1C] |
| 1251 | $CF_3$ | 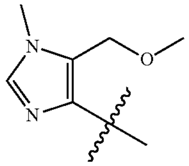 [SMILES: *c1ncn(C)c1COC] |
| 1252 | $CF_3$ | 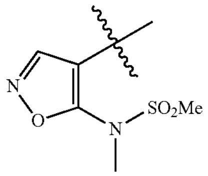 [SMILES: *c1cnoc1N(C)S(C)(=O)=O] |
| 1253 | $CF_3$ | 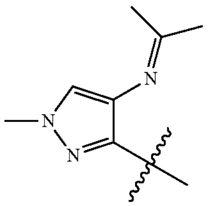 [SMILES: *c1nn(C)cc1N=C(C)C] |

-continued
| No. | X | A |
|---|---|---|
| 1254 | $CF_3$ | 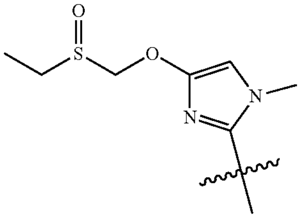 [SMILES: *c1nc(OCS(=O)CC)cn1C] |
| 1255 | $CF_3$ | 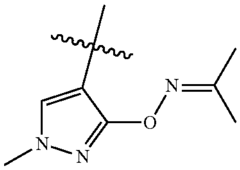 [SMILES: *c1cn(C)nc1ON=C(C)C] |
| 1256 | $CF_3$ | 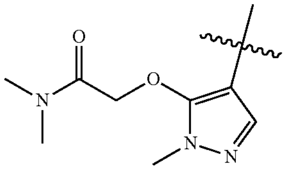 [SMILES: *c1cnn(C)c1OCC(=O)N(C)C] |
| 1257 | $CF_3$ | 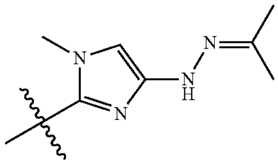 [SMILES: *c1nc(NN=C(C)C)cn1C] |
| 1258 | $CF_3$ | 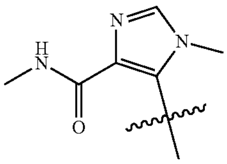 |
| 1259 | $CF_3$ | 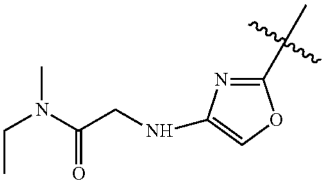 [SMILES: *c1nc(NCC(=O)N(C)CC)co1] |
| 1260 | $CF_3$ | 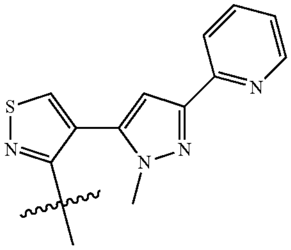 [SMILES: *c1nscc1-c1cc(-c2ccccn2)nn1C] |
| 1261 | $CF_3$ | 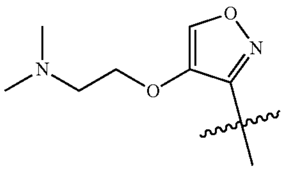 [SMILES: *c1nocc1OCCN(C)C] |
-continued
| No. | X | A |
|---|---|---|
| 1262 | $CF_3$ | 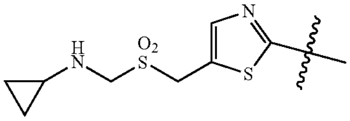 [SMILES: *c1ncc(CS(=O)(=O)CNC2CC2)s1] |
| 1263 | $CF_3$ | 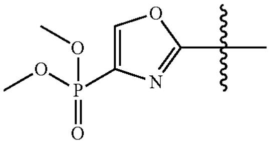 [SMILES: *c1nc(P(=O)(OC)OC)co1] |
| 1264 | $CF_3$ | 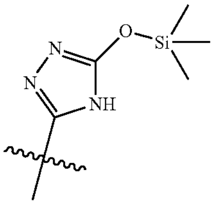 [SMILES: *c1nnc(O[Si](C)(C)C)[nH]1] |
| 1265 | $CF_3$ | 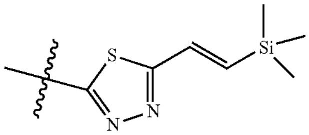 [SMILES: *c1nnc(/C=C/[Si](C)(C)C)s1] |
| 1266 | $CF_3$ | 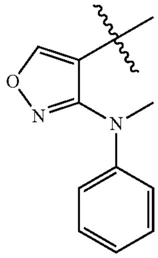 [SMILES: *c1conc1N(C)c1ccccc1] |
| 1267 | $CF_3$ | 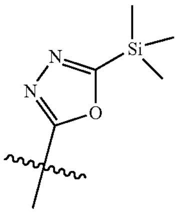 [SMILES: *c1nnc([Si](C)(C)C)o1] |
| 1268 | $CF_3$ | 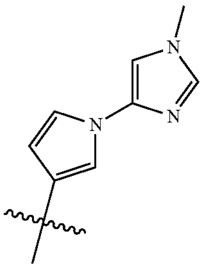 [SMILES: *c1ccn(-c2cn(C)cn2)c1] |

-continued
| No. | X | A |
|---|---|---|
| 1269 | $CF_3$ | 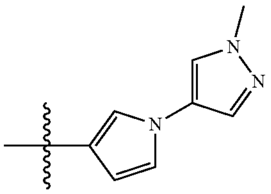 [SMILES: *c1ccn(-c2cnn(C)c2)c1] |
| 1270 | $CF_3$ | 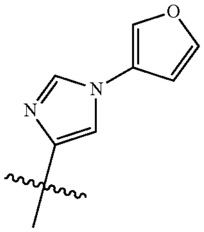 [SMILES: *c1cn(-c2ccoc2)cn1] |
| 1271 | $CF_3$ | 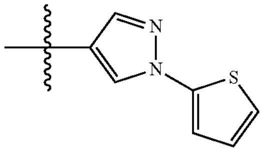 [SMILES: *c1cnn(-c2cccs2)c1] |
| 1272 | $CF_3$ | 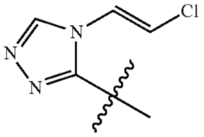 [SMILES: *c1nncn1/C=C/Cl] |
| 1273 | $CF_3$ | 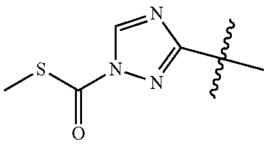 [SMILES: *c1ncn(C(=O)SC)n1] |
| 1274 | $CF_3$ | 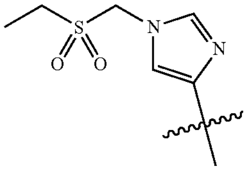 [SMILES: *c1cn(CS(=O)(=O)CC)cn1] |
| 1275 | $CF_3$ | 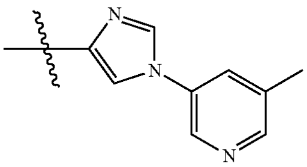 [SMILES: *c1cn(-c2cncc(C)c2)cn1] |
| 1276 | $CF_3$ | 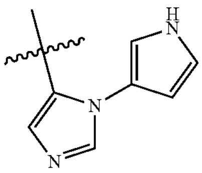 [SMILES: *c1cncn1-c1cc[nH]c1] |
| 1277 | $CF_3$ | 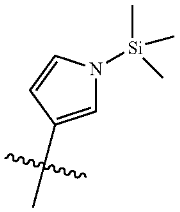 [SMILES: *c1ccn([Si](C)(C)C)c1] |
| 1278 | $CF_3$ | 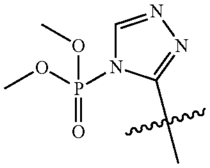 [SMILES: *c1nncn1P(=O)(OC)OC] |
| 1279 | $CF_3$ | 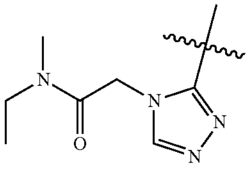 [SMILES: *c1nncn1CC(=O)N(C)CC] |
| 1280 | $CF_3$ | 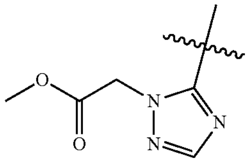 [SMILES: *c1ncnn1CC(=O)OC] |
| 1281 | $CF_3$ | 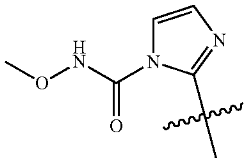 [SMILES: *c1nccn1C(=O)NOC] |
| 1282 | $CF_3$ | 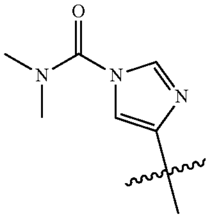 [SMILES: *c1cn(C(=O)N(C)C)cn1] |
| 1283 | $CF_3$ | 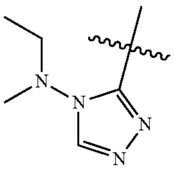 [SMILES: *c1nncn1N(C)CC] |
| 1284 | $CF_3$ | 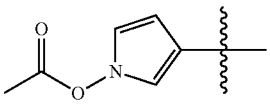 [SMILES: *c1ccn(OC(C)=O)c1] |

-continued
| No. | X | A |
|---|---|---|
| 1285 | $CF_3$ | 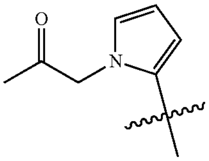 [SMILES: *c1cccn1CC(C)=O] |
| 1286 | $CF_3$ | 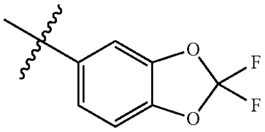 [SMILES: *c1ccc2c(c1)OC(F)(F)O2] |
| 1287 | $CF_3$ | 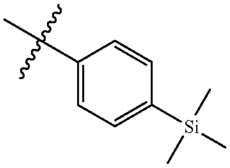 [SMILES: *c1ccc([Si](C)(C)C)cc1] |
| 1288 | $CF_3$ | 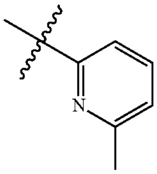 [SMILES: *c1cccc(C)n1] |
| 1289 | $CF_3$ | 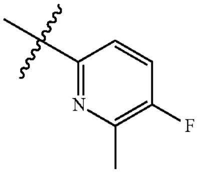 [SMILES: *c1ccc(F)c(C)n1] |
| 1290 | $CF_3$ | 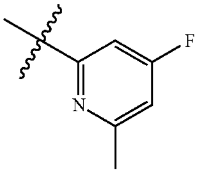 [SMILES: *c1cc(F)cc(C)n1] |
| 1291 | $CF_3$ | 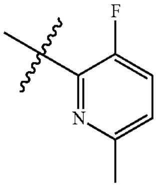 [SMILES: *c1nc(C)ccc1F] |
| 1292 | $CF_3$ | 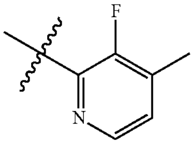 [SMILES: *c1nccc(C)c1F] |
| 1293 | $CF_3$ | 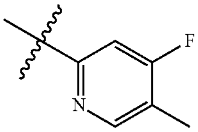 [SMILES: *c1cc(F)c(C)cn1] |
| 1294 | $CF_3$ | 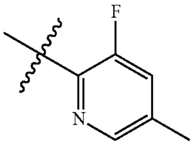 [SMILES: *c1ncc(C)cc1F] |
| 1295 | $CF_3$ | 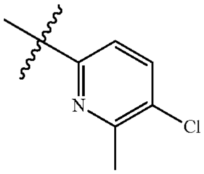 [SMILES: *c1ccc(Cl)c(C)n1] |
| 1296 | $CF_3$ | 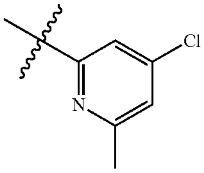 [SMILES: *c1cc(Cl)cc(C)n1] |
| 1297 | $CF_3$ | 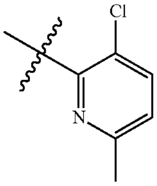 |
| 1298 | $CF_3$ | 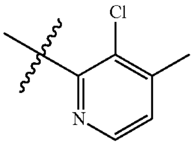 [SMILES: *c1nccc(C)c1Cl] |
| 1299 | $CF_3$ | 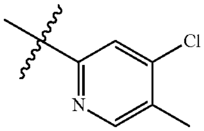 [SMILES: *c1cc(Cl)c(C)cn1] |
| 1300 | $CF_3$ | 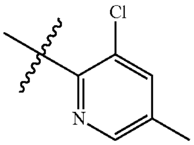 [SMILES: *c1ncc(C)cc1Cl] |
| 1301 | $CF_3$ | 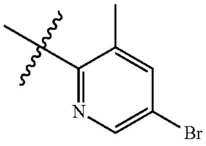 [SMILES: *c1ncc(Br)cc1C] |
| 1302 | $CF_3$ | 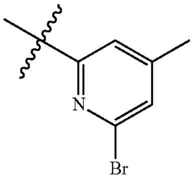 [SMILES: *c1cc(C)cc(Br)n1] |

-continued
| No. | X | A |
|---|---|---|
| 1303 | $CF_3$ | 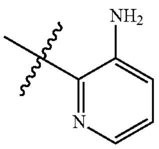 [SMILES: *c1ncccc1N] |
| 1304 | $CF_3$ | 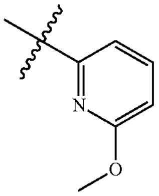 [SMILES: *c1cccc(OC)n1] |
| 1305 | $CF_3$ | 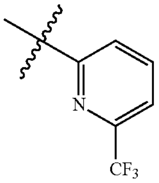 [SMILES: *c1cccc(C(F)(F)F)n1] |
| 1306 | $CF_3$ | 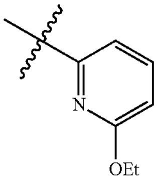 [SMILES: *c1cccc(OCC)n1] |
| 1307 | $CF_3$ | 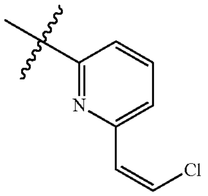 [SMILES: *c1cccc(/C=C\Cl)n1] |
| 1308 | $CF_3$ | 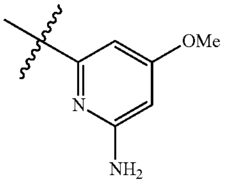 [SMILES: *c1cc(OC)cc(N)n1] |
| 1309 | $CF_3$ | 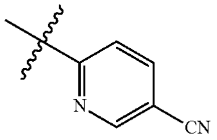 [SMILES: *c1ccc(C#N)cn1] |
| 1310 | $CF_3$ | 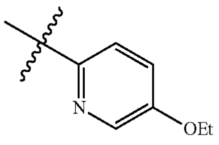 [SMILES: *c1ccc(OCC)cn1] |
-continued
| No. | X | A |
|---|---|---|
| 1311 | $CF_3$ | 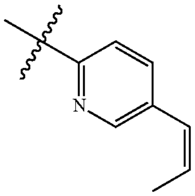 [SMILES: *c1ccc(/C=C\C)cn1] |
| 1312 | $CF_3$ | 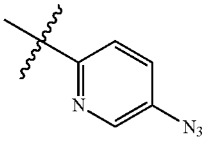 |
| 1313 | $CF_3$ | 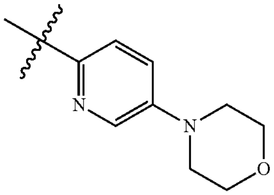 [SMILES: *c1ccc(N2CCOCC2)cn1] |
| 1314 | $CF_3$ | 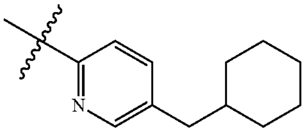 [SMILES: *c1ccc(CC2CCCCC2)cn1] |
| 1315 | $CF_3$ | 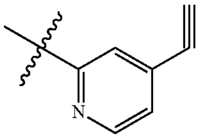 [SMILES: *c1cc(C#C)ccn1] |
| 1316 | $CF_3$ | 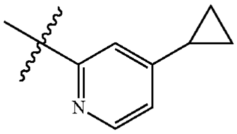 [SMILES: *c1cc(C2CC2)ccn1] |
| 1317 | $CF_3$ | 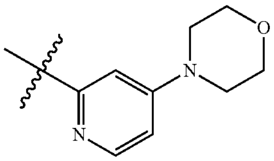 [SMILES: *c1cc(N2CCOCC2)ccn1] |
| 1318 | $CF_3$ | 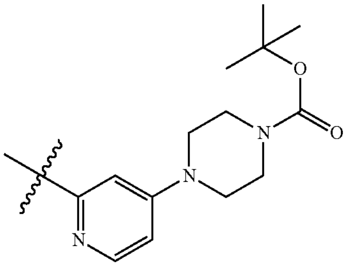 [SMILES: *c1cc(N2CCN(C(=O)OC(C)(C)C)CC2)ccn1] |
| 1319 | $CF_3$ | 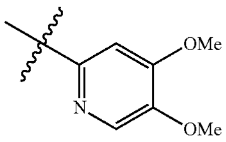 [SMILES: *c1cc(OC)c(OC)cn1] |

-continued
| No. | X | A |
| --- | --- | --- |
| 1320 | $CF_3$ | 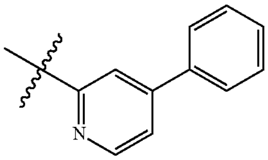 [SMILES: *c1cc(-c2ccccc2)ccn1] |
| 1321 | $CF_3$ | 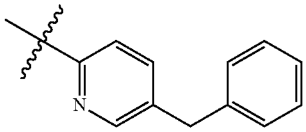 [SMILES: *c1ccc(Cc2ccccc2)cn1] |
| 1322 | $CF_3$ | 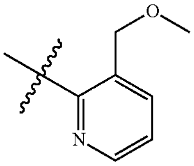 [SMILES: *c1ncccc1COC] |
| 1323 | $CF_3$ | 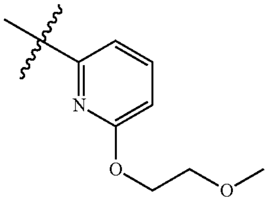 [SMILES: *c1cccc(OCCOC)n1] |
| 1324 | $CF_3$ | 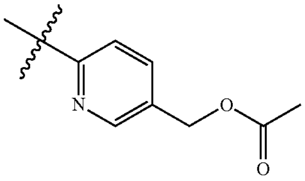 [SMILES: *c1ccc(COC(C)=O)cn1] |
| 1325 | $CF_3$ | 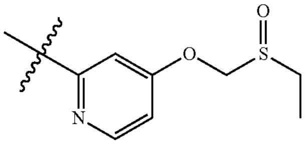 [SMILES: *c1cc(OCS(=O)CC)ccn1] |
| 1326 | $CF_3$ | 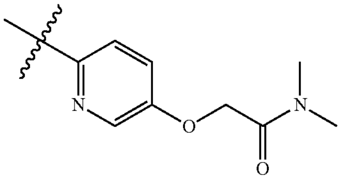 [SMILES: *c1ccc(OCC(=O)N(C)C)cn1] |
| 1327 | $CF_3$ | 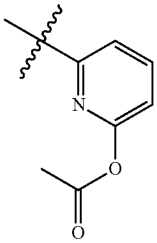 [SMILES: *c1cccc(OC(C)=O)n1] |
| 1328 | $CF_3$ | 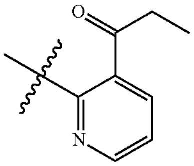 [SMILES: *c1ncccc1C(=O)CC] |
| 1329 | $CF_3$ | 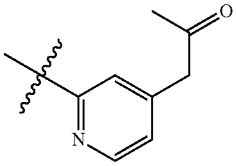 [SMILES: *c1cc(CC(C)=O)ccn1] |
| 1330 | $CF_3$ | 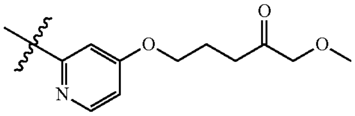 [SMILES: *c1cc(OCCCC(=O)COC)ccn1] |
| 1331 | $CF_3$ | 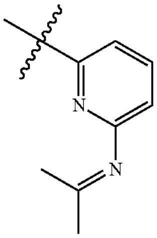 [SMILES: *c1cccc(N=C(C)C)n1] |
| 1332 | $CF_3$ | 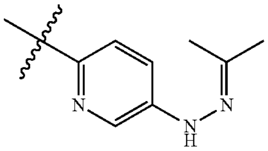 [SMILES: *c1ccc(NN=C(C)C)cn1] |
| 1333 | $CF_3$ | 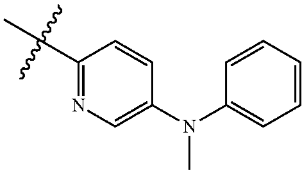 [SMILES: *c1ccc(N(C)c2ccccc2)cn1] |
| 1334 | $CF_3$ | 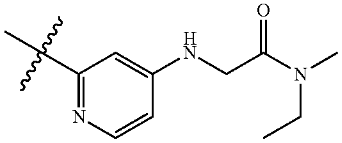 [SMILES: *c1cc(NCC(=O)N(C)CC)ccn1] |
| 1335 | $CF_3$ | 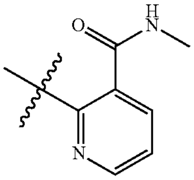 [SMILES: *c1ncccc1C(=O)NC] |

-continued
| No. | X | A |
|---|---|---|
| 1336 | $CF_3$ | 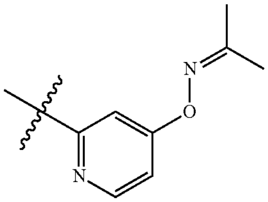 [SMILES: *c1cc(ON=C(C)C)ccn1] |
| 1337 | $CF_3$ | 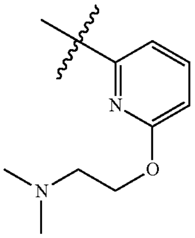 [SMILES: *c1cccc(OCCN(C)C)n1] |
| 1338 | $CF_3$ | 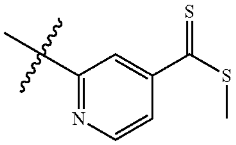 [SMILES: *c1cc(C(=S)SC)ccn1] |
| 1339 | $CF_3$ | 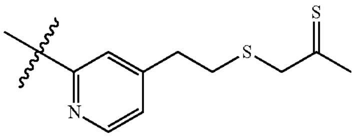 [SMILES: *c1cc(CCSCC(C)=S)ccn1] |
| 1340 | $CF_3$ | 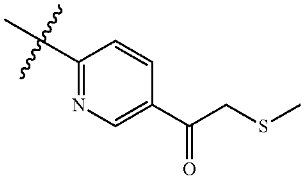 [SMILES: *c1ccc(C(=O)CSC)cn1] |
| 1341 | $CF_3$ | 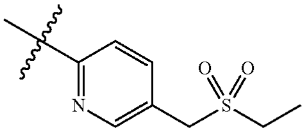 [SMILES: *c1ccc(CS(=O)(=O)CC)cn1] |
| 1342 | $CF_3$ | 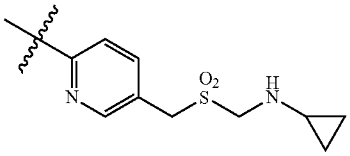 [SMILES: *c1ccc(CS(=O)(=O)CNC2CC2)cn1] |
| 1343 | $CF_3$ | 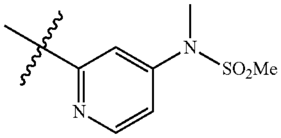 [SMILES: *c1cc(N(C)S(C)(=O)=O)ccn1] |
| 1344 | $CF_3$ | 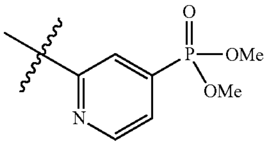 |
-continued
| No. | X | A |
|---|---|---|
| 1345 | $CF_3$ | 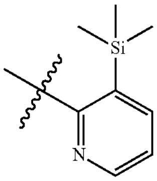 [SMILES: *c1ncccc1[Si](C)(C)C] |
| 1346 | $CF_3$ | 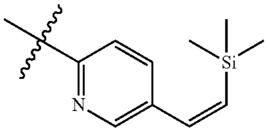 [SMILES: *c1ccc(/C=C\[Si](C)(C)C)cn1] |
| 1347 | $CF_3$ | 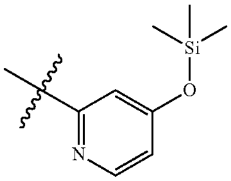 [SMILES: *c1cc(O[Si](C)(C)C)ccn1] |
| 1348 | $CF_3$ | 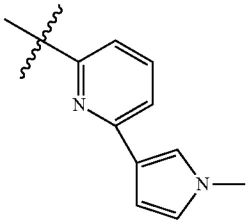 [SMILES: *c1cccc(-c2ccn(C)c2)n1] |
| 1349 | $CF_3$ | 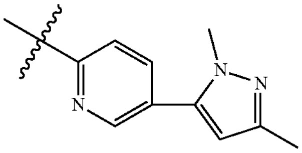 [SMILES: *c1ccc(-c2cc(C)nn2C)cn1] |
| 1350 | $CF_3$ | 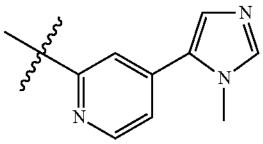 [SMILES: *c1cc(-c2cncn2C)ccn1] |
| 1351 | $CF_3$ | 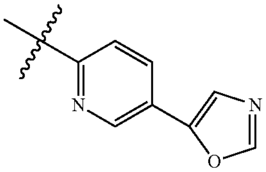 [SMILES: *c1ccc(-c2cnco2)cn1] |
| 1352 | $CF_3$ | 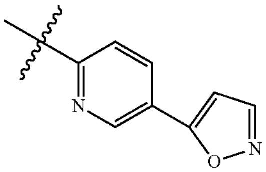 [SMILES: *c1ccc(-c2ccno2)cn1] |

-continued
| No. | X | A |
|---|---|---|
| 1353 | $CF_3$ | 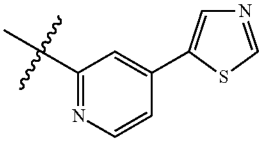 [SMILES: *c1cc(-c2cncs2)ccn1] |
| 1354 | $CF_3$ | 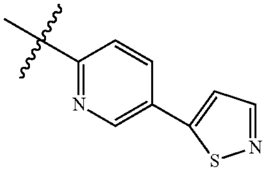 [SMILES: *c1ccc(-c2ccns2)cn1] |
| 1355 | $CF_3$ | 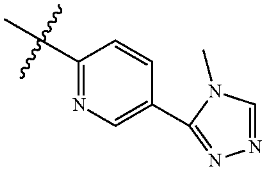 [SMILES: *c1ccc(-c2nncn2C)cn1] |
| 1356 | $CF_3$ | 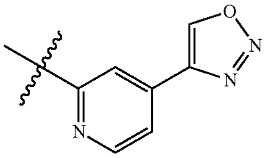 [SMILES: *c1cc(-c2conn2)ccn1] |
| 1357 | $CF_3$ | 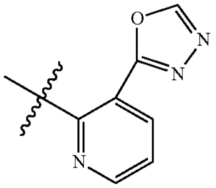 [SMILES: *c1ncccc1-c1nnco1] |
| 1358 | $CF_3$ | 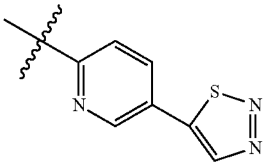 [SMILES: *c1ccc(-c2cnns2)cn1] |
| 1359 | $CF_3$ | 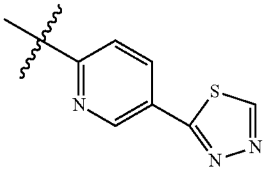 [SMILES: *c1ccc(-c2nncs2)cn1] |
| 1360 | $CF_3$ | 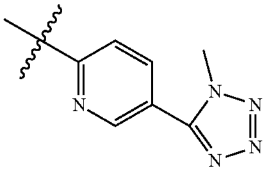 [SMILES: *c1ccc(-c2nnnn2C)cn1] |
| 1361 | $CF_3$ | 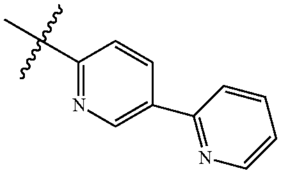 [SMILES: *c1ccc(-c2ccccn2)cn1] |
| 1362 | $CF_3$ | 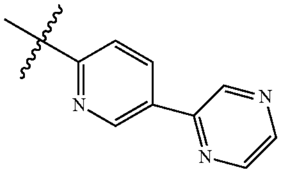 [SMILES: *c1ccc(-c2cnccn2)cn1] |
| 1363 | $CF_3$ | 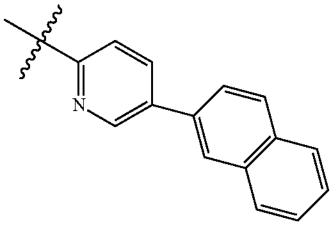 [SMILES: *c1ccc(-c2ccc3ccccc3c2)cn1] |
| 1364 | $CF_3$ | 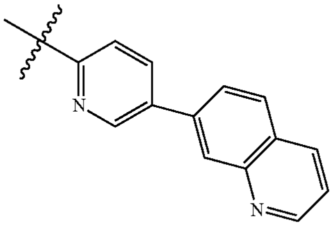 [SMILES: *c1ccc(-c2ccc3cccnc3c2)cn1] |
| 1365 | $CF_3$ | 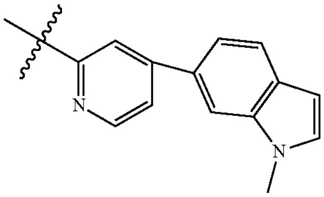 [SMILES: *c1cc(-c2ccc3ccn(C)c3c2)ccn1] |
| 1366 | $CF_3$ | 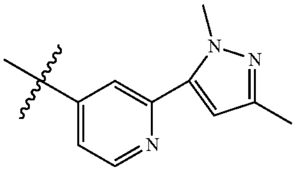 [SMILES: *c1ccnc(-c2cc(C)nn2C)c1] |
| 1367 | $CF_3$ | 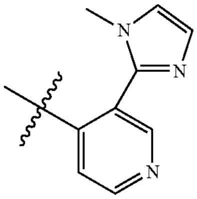 [SMILES: *c1ccncc1-c1nccn1C] |

-continued
| No. | X | A |
|---|---|---|
| 1368 | $CF_3$ | 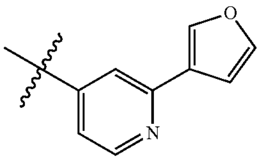 [SMILES: *c1ccnc(-c2ccoc2)c1] |
| 1369 | $CF_3$ | 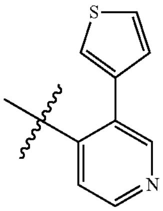 [SMILES: *c1ccncc1-c1ccsc1] |
| 1370 | $CF_3$ | 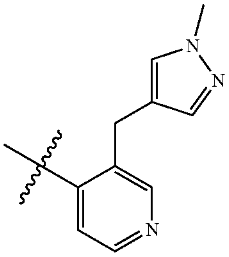 [SMILES: *c1ccncc1Cc1cnn(C)c1] |
| 1371 | $CF_3$ | 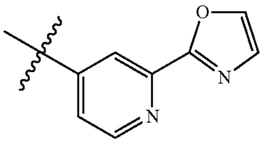 [SMILES: *c1ccnc(-c2ncco2)c1] |
| 1372 | $CF_3$ | 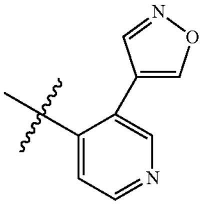 [SMILES: *c1ccncc1-c1cnoc1] |
| 1373 | $CF_3$ | 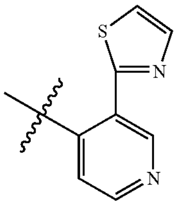 [SMILES: *c1ccncc1-c1nccs1] |
| 1374 | $CF_3$ | 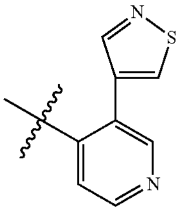 [SMILES: *c1ccncc1-c1cnsc1] |
| 1375 | $CF_3$ | 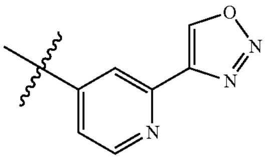 [SMILES: *c1ccnc(-c2conn2)c1] |
| 1376 | $CF_3$ | 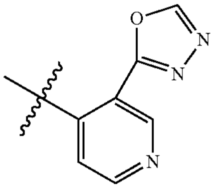 [SMILES: *c1ccncc1-c1nnco1] |
| 1377 | $CF_3$ | 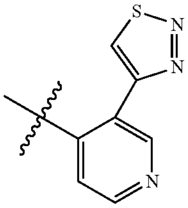 [SMILES: *c1ccncc1-c1csnn1] |
| 1378 | $CF_3$ | 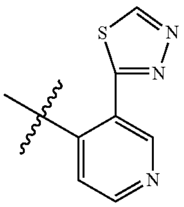 [SMILES: *c1ccncc1-c1nncs1] |
| 1379 | $CF_3$ | 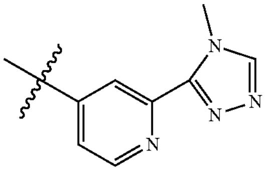 [SMILES: *c1ccnc(-c2nncn2C)c1] |
| 1380 | $CF_3$ | 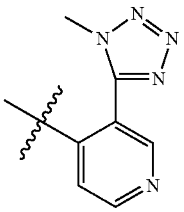 [SMILES: *c1ccncc1-c1nnnn1C] |
| 1381 | $CF_3$ | 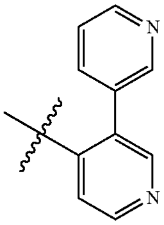 [SMILES: *c1ccncc1-c1cccnc1] |

-continued
| No. | X | A |
|---|---|---|
| 1382 | $CF_3$ | 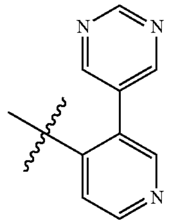 [SMILES: *c1ccncc1-c1cncnc1] |
| 1383 | $CF_3$ | 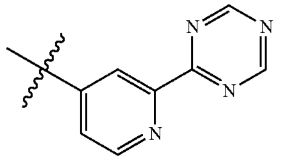 [SMILES: *c1ccnc(-c2ncncn2)c1] |
| 1384 | $CF_3$ | 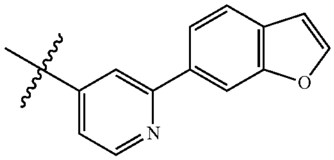 [SMILES: *c1ccnc(-c2ccc3ccoc3c2)c1] |
| 1385 | $CF_3$ | 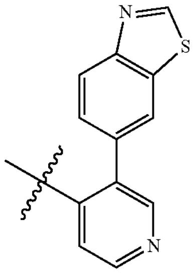 [SMILES: *c1ccncc1-c1ccc2ncsc2c1] |
| 1386 | $CF_3$ | 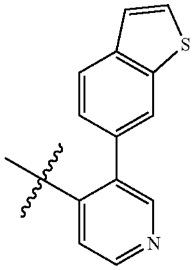 [SMILES: *c1ccncc1-c1ccc2ccsc2c1] |
| 1387 | $CF_3$ | 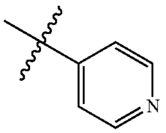 [SMILES: *c1ccncc1] |
| 1388 | $CF_3$ | 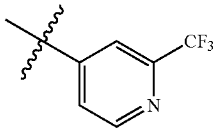 [SMILES: *c1ccnc(C(F)(F)F)c1] |
-continued
| No. | X | A |
|---|---|---|
| 1389 | $CF_3$ | 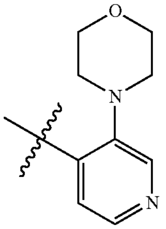 |
| 1390 | $CF_3$ | 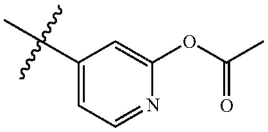 [SMILES: *c1ccnc(OC(C)=O)c1] |
| 1391 | $CF_3$ | 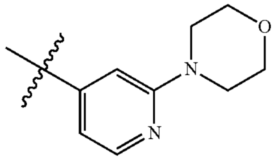 [SMILES: *c1ccnc(N2CCOCC2)c1] |
| 1392 | $CF_3$ | 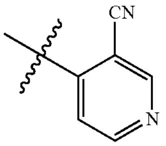 [SMILES: *c1ccncc1C#N] |
| 1393 | $CF_3$ | 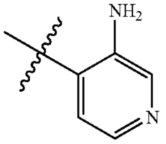 [SMILES: *c1ccncc1N] |
| 1394 | $CF_3$ | 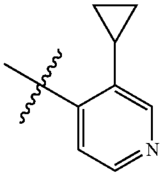 [SMILES: *c1ccncc1C1CC1] |
| 1395 | $CF_3$ | 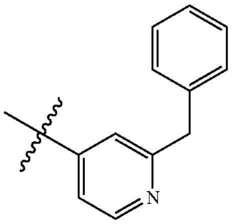 [SMILES: *c1ccnc(Cc2ccccc2)c1] |
| 1396 | $CF_3$ | 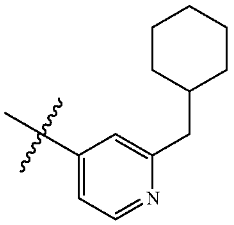 [SMILES: *c1ccnc(CC2CCCCC2)c1] |

-continued
| No. | X | A |
|---|---|---|
| 1397 | $CF_3$ | 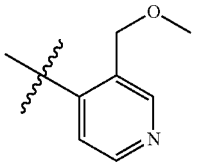 [SMILES: *c1ccncc1COC] |
| 1398 | $CF_3$ | 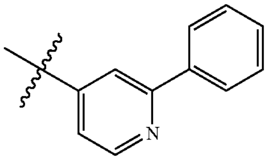 [SMILES: *c1ccnc(-c2ccccc2)c1] |
| 1399 | $CF_3$ | 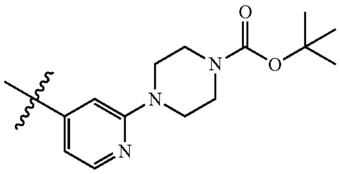 [SMILES: *c1ccnc(N2CCN(C(=O)OC(C)(C)C)CC2)c1] |
| 1400 | $CF_3$ | 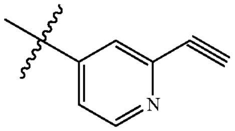 [SMILES: *c1ccnc(C#C)c1] |
| 1401 | $CF_3$ | 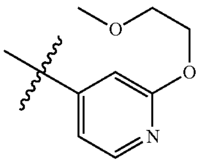 [SMILES: *c1ccnc(OCCOC)c1] |
| 1402 | $CF_3$ | 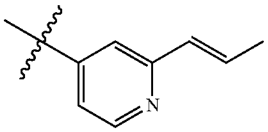 [SMILES: *c1ccnc(/C=C/C)c1] |
| 1403 | $CF_3$ | 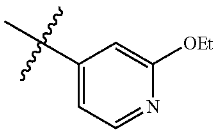 [SMILES: *c1ccnc(OCC)c1] |
| 1404 | $CF_3$ | 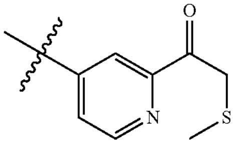 [SMILES: *c1ccnc(C(=O)CSC)c1] |
| 1405 | $CF_3$ | 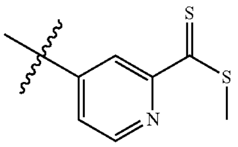 [SMILES: *c1ccnc(C(=S)SC)c1] |
| 1406 | $CF_3$ | 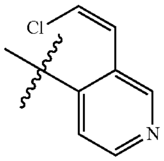 [SMILES: *c1ccncc1/C=C\Cl] |
| 1407 | $CF_3$ | 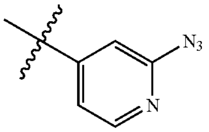 [SMILES: *c1ccnc(N=[N+]=[N-])c1] |
| 1408 | $CF_3$ | 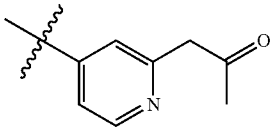 [SMILES: *c1ccnc(CC(C)=O)c1] |
| 1409 | $CF_3$ | 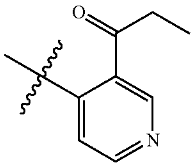 [SMILES: *c1ccncc1C(=O)CC] |
| 1410 | $CF_3$ | 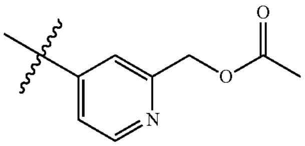 [SMILES: *c1ccnc(COC(C)=O)c1] |
| 1411 | $CF_3$ | 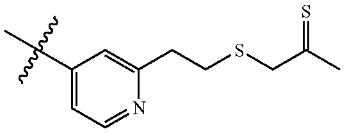 [SMILES: *c1ccnc(CCSCC(C)=S)c1] |
| 1412 | $CF_3$ | 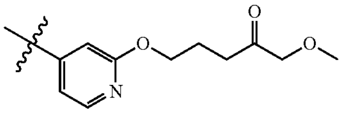 [SMILES: *c1ccnc(OCCCC(=O)COC)c1] |
| 1413 | $CF_3$ | 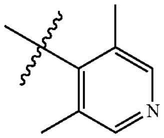 [SMILES: *c1c(C)cncc1C] |
| 1414 | $CF_3$ | 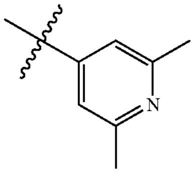 [SMILES: *c1cc(C)nc(C)c1] |
| 1415 | $CF_3$ | 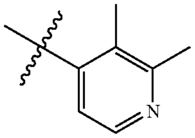 [SMILES: *c1ccnc(C)c1C] |

-continued
| No. | X | A |
| --- | --- | --- |
| 1416 | $CF_3$ | 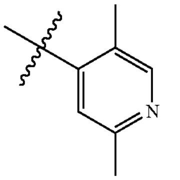 [SMILES: *c1cc(C)ncc1C] |
| 1417 | $CF_3$ | 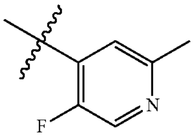 [SMILES: *c1cc(C)ncc1F] |
| 1418 | $CF_3$ | 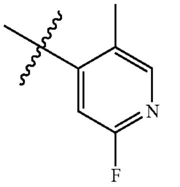 [SMILES: *c1cc(F)ncc1C] |
| 1419 | $CF_3$ | 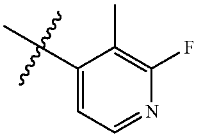 [SMILES: *c1ccnc(F)c1C] |
| 1420 | $CF_3$ | 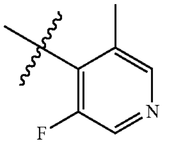 |
| 1421 | $CF_3$ | 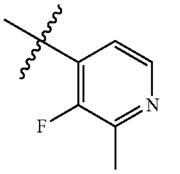 [SMILES: *c1ccnc(C)c1F] |
| 1422 | $CF_3$ | 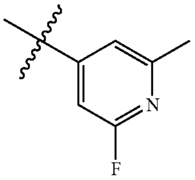 [SMILES: *c1cc(C)nc(F)c1] |
| 1423 | $CF_3$ | 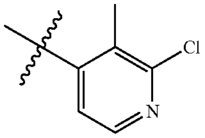 [SMILES: *c1ccnc(Cl)c1C] |
| 1424 | $CF_3$ | 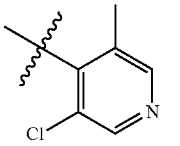 [SMILES: *c1c(C)cncc1Cl] |
-continued
| No. | X | A |
| --- | --- | --- |
| 1425 | $CF_3$ | 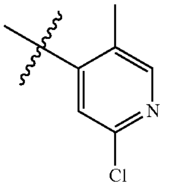 |
| 1426 | $CF_3$ | 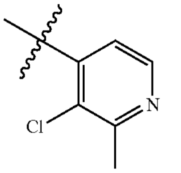 [SMILES: *c1ccnc(C)c1Cl] |
| 1427 | $CF_3$ | 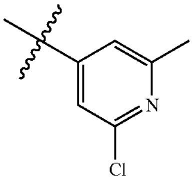 [SMILES: *c1cc(C)nc(Cl)c1] |
| 1428 | $CF_3$ | 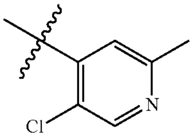 [SMILES: *c1cc(C)ncc1Cl] |
| 1429 | $CF_3$ | 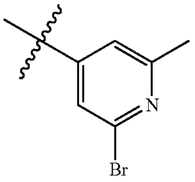 [SMILES: *c1cc(C)nc(Br)c1] |
| 1430 | $CF_3$ | 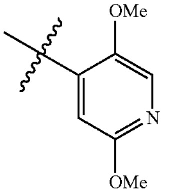 [SMILES: *c1cc(OC)ncc1OC] |
| 1431 | $CF_3$ | 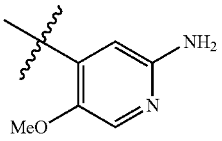 [SMILES: *c1cc(N)ncc1OC] |
| 1432 | $CF_3$ | 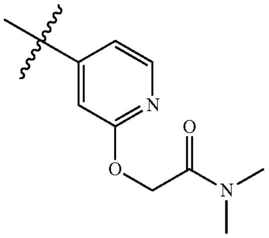 [SMILES: *c1ccnc(OCC(=O)N(C)C)c1] |

-continued
| No. | X | A |
|---|---|---|
| 1433 | $CF_3$ | 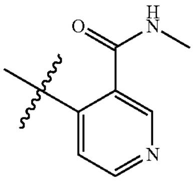 [SMILES: *c1ccncc1C(=O)NC] |
| 1434 | $CF_3$ | 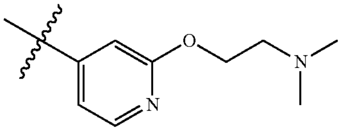 [SMILES: *c1ccnc(OCCN(C)C)c1] |
| 1435 | $CF_3$ | 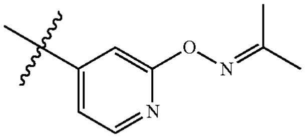 [SMILES: *c1ccnc(ON=C(C)C)c1] |
| 1436 | $CF_3$ | 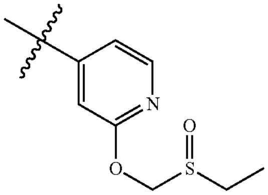 [SMILES: *c1ccnc(OCS(=O)CC)c1] |
| 1437 | $CF_3$ | 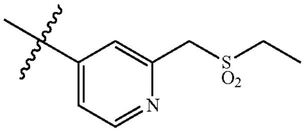 [SMILES: *c1ccnc(CS(=O)(=O)CC)c1] |
| 1438 | $CF_3$ | 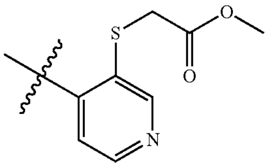 [SMILES: *c1ccncc1SCC(=O)OC] |
| 1439 | $CF_3$ | 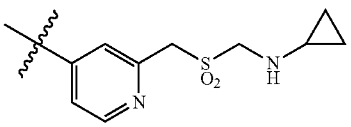 [SMILES: *c1ccnc(CS(=O)(=O)CNC2CC2)c1] |
| 1440 | $CF_3$ | 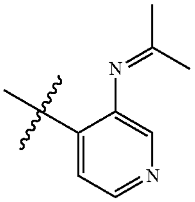 [SMILES: *c1ccncc1N=C(C)C] |
| 1441 | $CF_3$ | 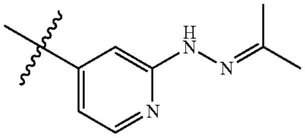 [SMILES: *c1ccnc(NN=C(C)C)c1] |
-continued
| No. | X | A |
|---|---|---|
| 1442 | $CF_3$ | 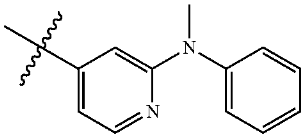 [SMILES: *c1ccnc(N(C)c2ccccc2)c1] |
| 1443 | $CF_3$ | 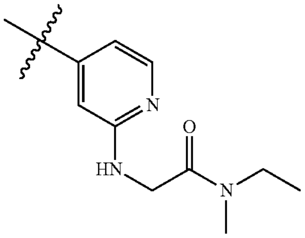 [SMILES: *c1ccnc(NCC(=O)N(C)CC)c1] |
| 1444 | $CF_3$ | 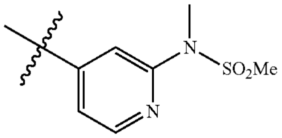 [SMILES: *c1ccnc(N(C)S(C)(=O)=O)c1] |
| 1445 | $CF_3$ | 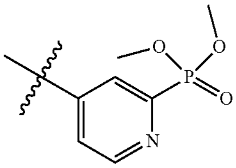 [SMILES: *c1ccnc(P(=O)(OC)OC)c1] |
| 1446 | $CF_3$ | 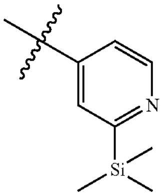 [SMILES: *c1ccnc([Si](C)(C)C)c1] |
| 1447 | $CF_3$ | 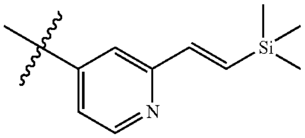 [SMILES: *c1ccnc(/C=C/[Si](C)(C)C)c1] |
| 1448 | $CF_3$ | 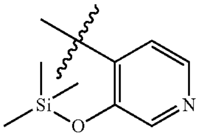 [SMILES: *c1ccncc1O[Si](C)(C)C] |
| 1449 | $CF_3$ | 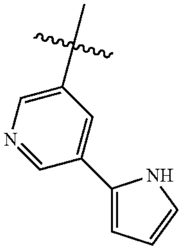 [SMILES: *c1cncc(-c2ccc[nH]2)c1] |

-continued
| No. | X | A |
|---|---|---|
| 1450 | $CF_3$ | 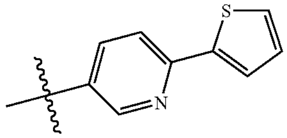 [SMILES: *c1ccc(-c2cccs2)nc1] |
| 1451 | $CF_3$ | 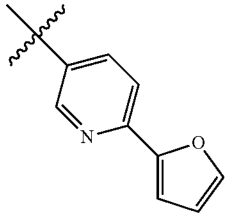 [SMILES: *c1ccc(-c2ccco2)nc1] |
| 1452 | $CF_3$ | 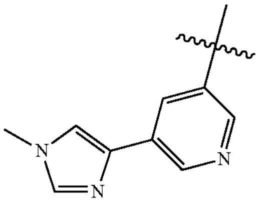 [SMILES: *c1cncc(-c2cn(C)cn2)c1] |
| 1453 | $CF_3$ | 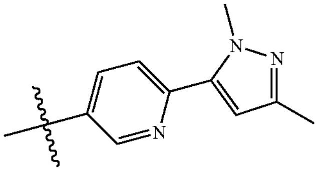 [SMILES: *c1ccc(-c2cc(C)nn2C)nc1] |
| 1454 | $CF_3$ | 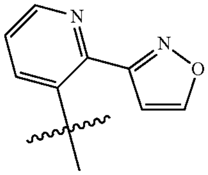 [SMILES: *c1cccnc1-c1ccon1] |
| 1455 | $CF_3$ | 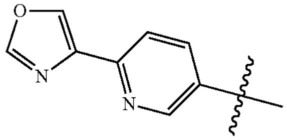 [SMILES: *c1ccc(-c2cocn2)nc1] |
| 1456 | $CF_3$ | 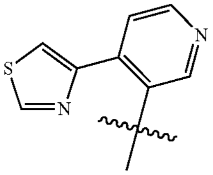 [SMILES: *c1cnccc1-c1cscn1] |
| 1457 | $CF_3$ | 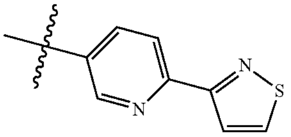 [SMILES: *c1ccc(-c2ccsn2)nc1] |
-continued
| No. | X | A |
|---|---|---|
| 1458 | $CF_3$ | 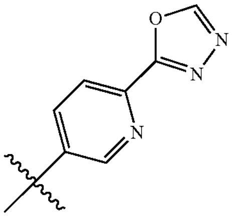 [SMILES: *c1ccc(-c2nnco2)nc1] |
| 1459 | $CF_3$ | 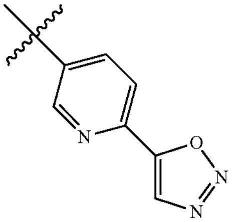 [SMILES: *c1ccc(-c2cnno2)nc1] |
| 1460 | $CF_3$ | 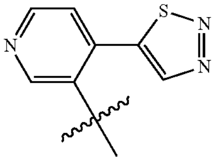 [SMILES: *c1cnccc1-c1cnns1] |
| 1461 | $CF_3$ | 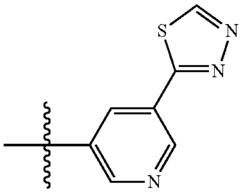 [SMILES: *c1cncc(-c2nncs2)c1] |
| 1462 | $CF_3$ | 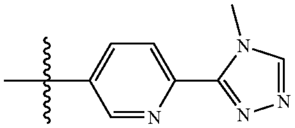 [SMILES: *c1ccc(-c2nncn2C)nc1] |
| 1463 | $CF_3$ | 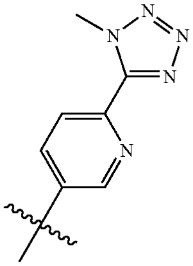 [SMILES: *c1ccc(-c2nnnn2C)nc1] |
| 1464 | $CF_3$ | 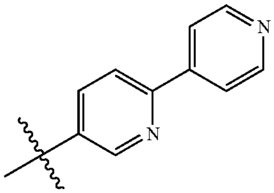 [SMILES: *c1ccc(-c2ccncc2)nc1] |
| 1465 | $CF_3$ | 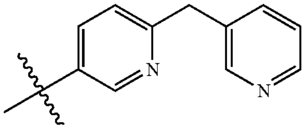 [SMILES: *c1ccc(Cc2cccnc2)nc1] |

-continued
| No. | X | A |
|---|---|---|
| 1466 | $CF_3$ | 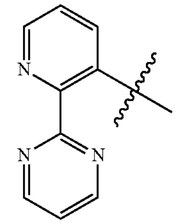 [SMILES: *c1cccnc1-c1ncccn1] |
| 1467 | $OCH_3$ | 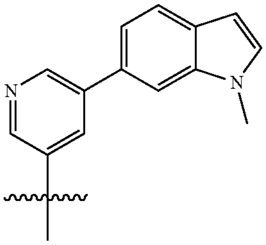 [SMILES: *c1cncc(-c2ccc3ccn(C)c3c2)c1] |
| 1468 | $CF_3$ | 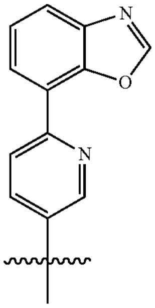 [SMILES: *c1ccc(-c2cccc3ncoc23)nc1] |
| 1469 | $CF_3$ | 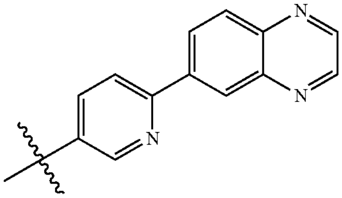 [SMILES: *c1ccc(-c2ccc3nccnc3c2)nc1] |
| 1470 | $CF_2CF_3$ | 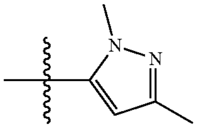 [SMILES: *c1cc(C)nn1C] |
| 1471 | $CH_2F$ | 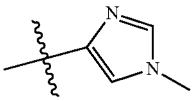 [SMILES: *c1cn(C)cn1] |
| 1472 | $CHF_2$ | 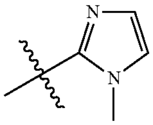 [SMILES: *c1nccn1C] |
| 1473 | $CF_2CF_3$ | 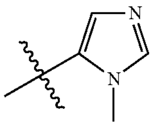 [SMILES: *c1cncn1C] |
-continued
| No. | X | A |
|---|---|---|
| 1474 | $CH_2F$ | 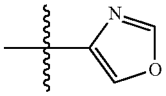 |
| 1475 | $CHF_2$ | 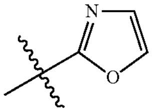 [SMILES: *c1ncco1] |
| 1476 | $CF_2CF_3$ | 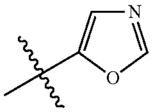 [SMILES: *c1cnco1] |
| 1477 | $CH_2F$ | 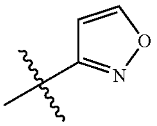 [SMILES: *c1ccon1] |
| 1478 | $OCHF_2$ | 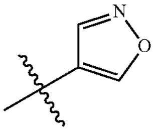 [SMILES: *c1cnoc1] |
| 1479 | $CF_2CF_3$ | 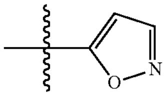 [SMILES: *c1ccno1] |
| 1480 | $CF_2CF_3$ | 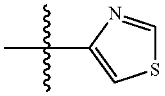 [SMILES: *c1cscn1] |
| 1481 | $CF_2CF_3$ | 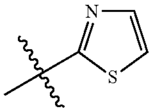 [SMILES: *c1nccs1] |
| 1482 | $CF_2CF_3$ | 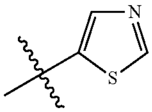 [SMILES: *c1cncs1] |
| 1483 | Ph | 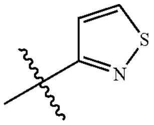 [SMILES: *c1ccsn1] |
| 1484 | $CF_2CF_3$ | 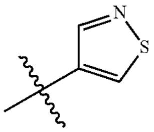 [SMILES: *c1cnsc1] |
| 1485 | $CF_2CF_3$ | 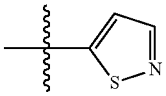 [SMILES: *c1ccns1] |

-continued
| No. | X | A |
| --- | --- | --- |
| 1486 | $CF_2CF_3$ | 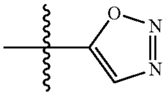 [SMILES: *c1cnno1] |
| 1487 | CN | 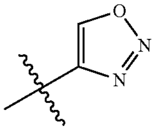 [SMILES: *c1conn1] |
| 1488 | $CF_2CF_3$ | 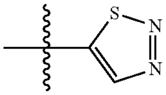 |
| 1489 | $CF_2CF_3$ | 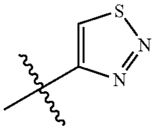 [SMILES: *c1csnn1] |
| 1490 | $CF_2CF_3$ | 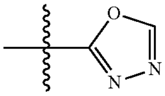 |
| 1491 | $CF_2CF_3$ | 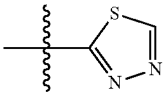 |
| 1492 | $CF_2CF_3$ | 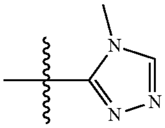 [SMILES: *c1nncn1C] |
| 1493 | $CF_3$ | 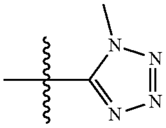 [SMILES: *c1nnnn1C] |
| 1494 | $CF_3$ | 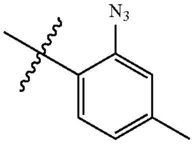 [SMILES: *c1ccc(C)cc1N=[N+]=[N-]] |
| 1495 | $CF_3$ | 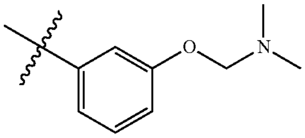 [SMILES: *c1cccc(OCN(C)C)c1] |
| 1496 | $CF_3$ | 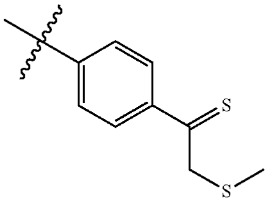 [SMILES: *c1ccc(C(=S)CSC)cc1] |
-continued
| No. | X | A |
| --- | --- | --- |
| 1497 | $CF_3$ | 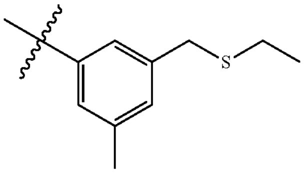 [SMILES: *c1cc(C)cc(CSCC)c1] |
| 1498 | $CF_3$ | 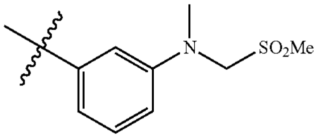 [SMILES: *c1cccc(N(C)CS(C)(=O)=O)c1] |
| 1499 | $CF_3$ | 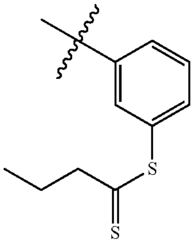 [SMILES: *c1cccc(SC(=S)CCC)c1] |
| 1500 | $CF_3$ | 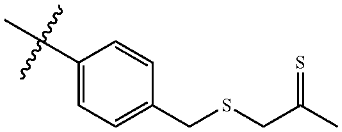 [SMILES: *c1ccc(CSCC(C)=S)cc1] |
| 1501 | $OCF_3$ | 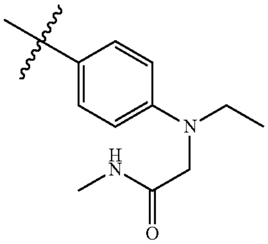 [SMILES: *c1ccc(N(CC)CC(=O)NC)cc1] |
| 1502 | $CF_3$ | 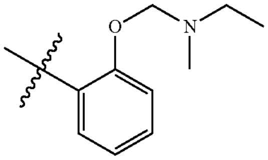 [SMILES: *c1ccccc1OCN(C)CC] |
| 1503 | $CF_3$ | 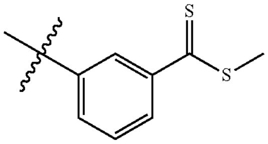 [SMILES: *c1cccc(C(=S)SC)c1] |
| 1504 | $CF_3$ | 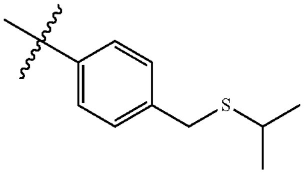 [SMILES: *c1ccc(CSC(C)C)cc1] |

-continued
| No. | X | A |
|---|---|---|
| 1505 | $CF_3$ | 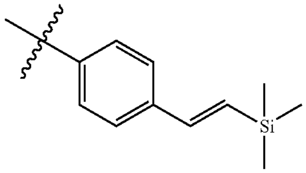 [SMILES: *c1ccc(/C=C/[Si](C)(C)C)cc1] |
| 1506 | $CF_3$ | 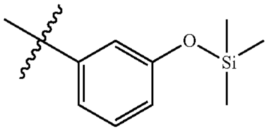 [SMILES: *c1cccc(O[Si](C)(C)C)c1] |
| 1507 | $CONH_2$ | 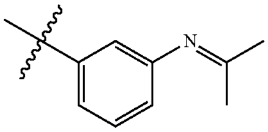 [SMILES: *c1cccc(N=C(C)C)c1] |
| 1508 | $CF_3$ | 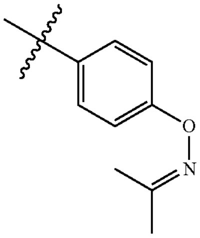 [SMILES: *c1ccc(ON=C(C)C)cc1] |
| 1509 | $CF_3$ | 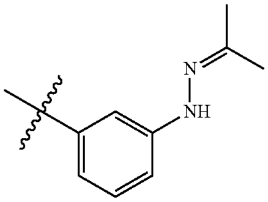 [SMILES: *c1cccc(NN=C(C)C)c1] |
| 1512 | $CF_3$ | 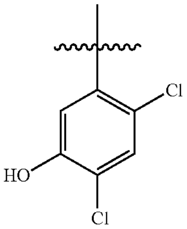 [SMILES: *c1cc(O)c(Cl)cc1Cl] |
| 1522 | $CF_3$ | 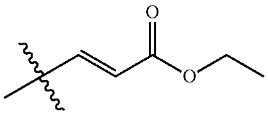 [SMILES: */C=C/C(=O)OCC] |
| 1523 | $CF_3$ | 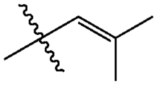 [SMILES: *C=C(C)C] |
| 1524 | $CF_3$ | 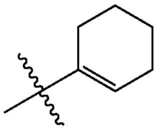 [SMILES: *C1=CCCCC1] |
-continued
| No. | X | A |
|---|---|---|
| 1526 | $CF_3$ | 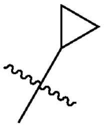 [SMILES: *C1CC1] |
| 1527 | OH | 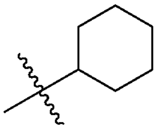 [SMILES: *C1CCCCC1] |
| 1528 | $CF_3$ | 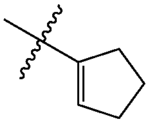 [SMILES: *C1=CCCC1] |
| 1529 | $CF_3$ | 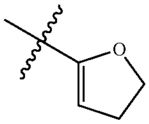 [SMILES: *C1=CCCO1] |
| 1530 | $CF_3$ | 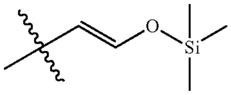 [SMILES: */C=C/O[Si](C)(C)C] |
| 1531 | $CF_3$ | 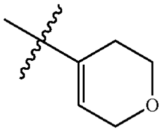 [SMILES: *C1=CCOCC1] |
| 1532 | $CF_3$ | 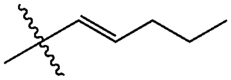 [SMILES: */C=C/CCC] |
| 1534 | $OCF_3$ | 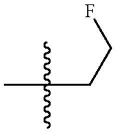 [SMILES: *CCF] |
| 1535 | $CF_3$ | 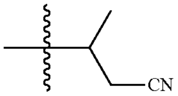 |
| 1536 | CN | 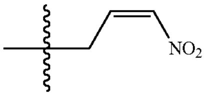 [SMILES: *C/C=C\[N+](=O)[O-]] |
| 1537 | $CF_3$ | 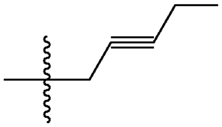 [SMILES: *CC#CCC] |
| 1538 | $CF_3$ | 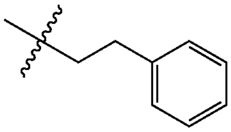 [SMILES: *CCc1ccccc1] |

-continued

| No. | X | A |
|---|---|---|
| 1539 | $CF_3$ | 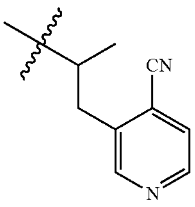 [SMILES: *C(C)Cc1cnccc1C#N] |
| 1540 | $CF_3$ | 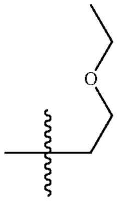 [SMILES: *CCOCC] |
| 1541 | $CF_3$ | 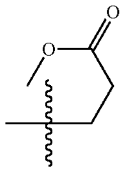 |
| 1542 | $CF_3$ | 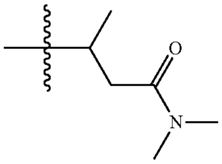 [SMILES: *C(C)CC(=O)N(C)C] |
| 1543 | $CF_2CF_3$ | 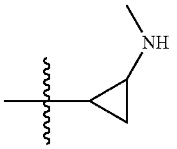 |
| 1544 | $CF_3$ | 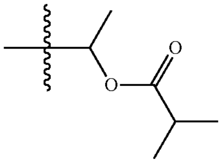 [SMILES: *C(C)OC(=O)C(C)C] |
| 1545 | $CF_3$ | 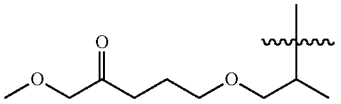 [SMILES: *C(C)COCCCC(=O)COC] |
| 1546 | $CF_3$ | 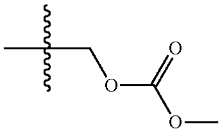 [SMILES: *COC(=O)OC] |
| 1547 | $CHF_2$ | 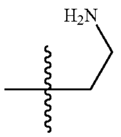 [SMILES: *CCN] |

-continued

| No. | X | A |
|---|---|---|
| 1548 | $CF_3$ | 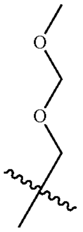 [SMILES: *COCOC] |
| 1549 | $CF_3$ | 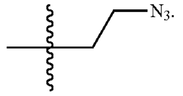 [SMILES: *CCN=[N+]=[N-]] |

wherein the derivative is an agriculturally acceptable salt or a compound derivatized from 4-hydroxy of the pyridazine ring of the Formula I, further wherein the compound derivatized from 4-hydroxy of the pyridazine ring of the Formula I is selected from an ester, an oxime, and a hydroxylamine thereof.

8. A compound as shown in Formula I-1:

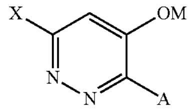

I-1 wherein, M is (thio)formyl, C1-C18 alkyl(thio)carbonyl, wherein said (thio)formyl or C1-C18 alkyl(thio)carbonyl is unsubstituted or substituted with a substituent independently selected from: halogen, amino, C3-C8 cycloalkyl, C1-C8 alkoxycarbonyl, C1-C8 alkylcarbonyloxy, C1-C8 alkylcarbonyl, hydroxy(methyl)phosphinyl, and an unsubstituted or halogenated or C1-C8 alkoxy substituted group selected from phenyl, phenylsulfanyl, phenyloxy, and benzyloxy; an unsubstituted or phenyl substituted group of C1-C18 alkoxy(thio)carbonyl or C1-C18 alkylsulfanyl(thio)carbonyl; C3-C8 cycloalkylsulfanyl(thio)carbonyl; phenyl-C1-C8 alkylsulfanyl(thio)carbonyl; C2-C8 alkenyl(thio)carbonyl, wherein said C2-C8 alkenyl(thio)carbonyl unsubstituted or substituted with a substituent selected from: C1-C8 alkoxy, phenyl and halogenated phenyl; (thio)benzoyl, wherein said (thio)benzoyl is unsubstituted or substituted with a substituent selected from: halogen, hydroxy, C1-C8 alkyl, C1-C8 alkoxy, cyano, halogenated C1-C8 alkoxy, C1-C8 alkylcarbonyloxy, C1-C8 alkylcarbonylamino, amino and amino substituted with 1 or 2 C1-C8 alkyl; halogenated sulfanyl formyl; 3- to 8-membered heterocyclyl(thio)carbonyl, wherein said 3- to 8-membered heterocyclyl(thio)carbonyl is unsubstituted or substituted with a substituent selected from C1-C8 alkyl, halogen, and C1-C8 alkylsulfanyl; fused 5- to 14-membered bicyclic or tricyclic heterocyclyl(thio)carbonyl; amino(thio)formyl, wherein said amino(thio)formyl is unsubstituted or substituted with a substituent selected from C1-C8 alkyl and C1-C8 alkoxy; an unsubstituted or halogen or C1-C8 alkylsulfonyl substituted group selected from C1-C8 alkylsulfoxide, C1-C8 alkylsulfonyl, and C3-C8 cycloalkylsulfonyl; phenylsulfonyl, benzylsulfonyl, naphthylsulfonyl, wherein each of said phenylsulfonyl, benzylsulfonyl or naphthylsulfonyl is unsubstituted or substituted with a substituent independently selected from: halogen, nitro, C1-C8 alkyl, halogenated C1-C8 alkyl, halogenated C1-C8 alkoxy, C1-C8 alkylcarbonyl, C1-C8 alkylsulfonyl, aminoformyl, phenoxy and halogenated phenoxy; 5- to 10-membered heteroarylsulfonyl, wherein said 5- to 10-membered heteroarylsulfonyl is unsubstituted or substituted with C1-C8 alkyl or phenoxy; C1-C8 alkylaminosulfonyl that is unsubstituted or substituted with halogen; di(C1-C8 alkyl) phosphoryl; C1-18alkyl substituted with a substituent independently selected from C1-C8 alkoxycarbonyl and C1-C8 alkoxycarbonyloxy; an unsubstituted or halogenated or C1-C8 alkoxy substituted group selected from phenyl, benzyl, and benzoyl-C1-C8 alkyl;

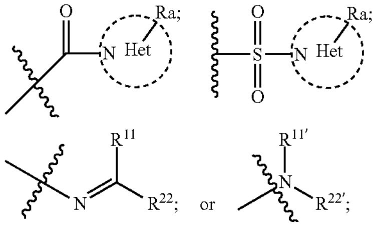

or wherein, $R_{11}$ and $R_{22}$ are independently selected from hydrogen, C1-C18 alkyl, wherein said C1-C18 alkyl is unsubstituted or substituted with a substituent selected from C1-C8 alkoxy and C1-C8 alkylsulfanyl, and an unsubstituted or halogenated C1-C8 alkyl substituted group selected from phenyl and 5- to 6-membered heteroaryl; or $R_{11}$ and $R_{12}$ forms a 5- to 6-membered saturated carbocyclic ring or a 5- to 6-membered saturated heterocyclic ring;

$R_{11}'$ and $R_{22}'$ independently is C1-C18 alkyl;

Het is selected from

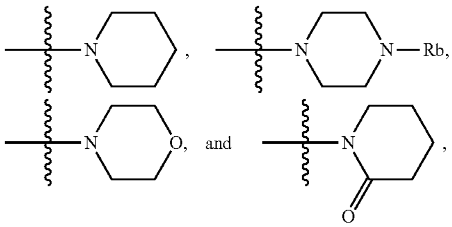

and

Ra and Rb independently are hydrogen or C1-C6 alkyl; wherein, X is halogenated alkyl;

A is selected from alkyl, alkenyl, alkynyl, cycloalkyl, cycloalkenyl, cycloalkylalkyl, aryl, heteroaryl, and aliphatic heterocyclyl, each of which is unsubstituted or substituted; wherein, when being substituted, each of said alkyl, alkenyl, alkynyl, cycloalkyl, cycloalkenyl, or cycloalkylalkyl is independently substituted with one or more substituents selected from halogen, cyano, nitro, azido, unsubstituted or substituted aryl, unsubstituted or substituted heteroaryl, —(CH2)n-O—(CH2)p-, —(CH2)n-S—(CH2)p-, —(CH2)n-NR3-(CH2)p-, R—O—, R—O—(CH2)p-O—, R—O—(CH2)p-S—, R—S—, R—S—(CH2)p-O—, R—S—(CH2)p-S—, R—O—(CH2)n-(C═O)—(CH2)q-(O)m-, R—S—(CH2)n-(C═S)—(CH2)q-(S)m-, R—O—(CH2)n-(C═O)—(CH2)q-(S)m-, R—O—(CH2)n-(C═S)—(CH2)q-(O)m-, R—S—(CH2)n-(C═O)—(CH2)q-(O)m-, R—O—(CH2)n-(C═S)—(CH2)q-(S)m-, R—S—(CH2)n-(C═O)—(CH2)q-(S)m-, R—S—(CH2)n-(C═S)—(CH2)q-(O)m-, R—(C═O)—, R—(C═S)—, R—(C═O)—(CH2)n-O—, R—(C═S)—(CH2)n-S—, R—(C═O)—(CH2)n-S—, R—(C═S)—(CH2)n-O—, R—SO—(CH2)n-(O)m-, R—SO—(CH2)n-(S)m-, R—SO—(CH2)n-(NR3)m-, R—SO2-(CH2)n-(O)m-, R—SO2-(CH2)n-(S)m-, R—SO2-(CH2)n-(NR3)m-SR1R2N—, R1 R2N—(CH2)n-O—(CH2)q-(O)m-, R1 R2N—(CH2)n-O—(CH2)q-(S)m-, R1 R2N—(CH2)n-O—(CH2)q-(NR3)m-, R1 R2N—(CH2)n-(C═O)—(CH2)q-(O)m-, R1 R2N—(CH2)n-(C═O)—(CH2)q-(S)m-, R1 R2N—(CH2)n-(C═O)—(CH2)q-(NR3)m-, R1 R2N—(CH2)n-SO2-(CH2)q-(O)m-, R1 R2N—(CH2)n-SO2-(CH2)q-(S)m-, R1 R2N—(CH2)n-SO2-(CH2)q-(NR3)m-, R1 R2P(O)—(O)m-, R1 R2R3SiO—, R1 R2R3Si—(CH═CH)m-, R1 R2C═N—(O)m-, and R1 R2C═N—NH—;

when being substituted, each of said aryl, heteroaryl, or aliphatic heterocyclyl is substituted with one or more substituents selected from halogen, cyano, nitro, azido, a halogen-containing or not containing group selected from alkyl, alkenyl, alkynyl, cycloalkyl, cycloalkenyl, and cycloalkylalkyl, a group selected from aryl, arylalkyl, heteroaryl, heteroarylalkyl, aliphatic heterocyclyl, and aliphatic heterocyclylalkyl, which is unsubstituted or substituted, R—O—(CH2)n-, R—O—(CH2)p-O—(CH2)q-, R—O—(CH2)p-S—(CH2)q-, R—S—(CH2)n-, R—S—(CH2)p-O—(CH2)q-, R—S—(CH2)p-S—(CH2)q-, R—O—(CH2)n-(C═O)—(CH2)q-(O)m-, R—S—(CH2)n-(C═S)—(CH2)q-(S)m-, R—O—(CH2)n-(C═O)—(CH2)q-(S)m-, R—O—(CH2)n-(C═S)—(CH2)q-(O)m-, R—S—(CH2)n-(C═O)—(CH2)q-(O)m-, R—O—(CH2)n-(C═S)—(CH2)q-(S)m-, R—S—(CH2)n-(C═O)—(CH2)q-(S)m-, R—S—(CH2)n-(C═S)—(CH2)q-(O)m-, R—(C═O)—(CH2)n-, R—(C═S)—(CH2)n-, R—(C═O)—(CH2)n-O—(CH2)q-, R—(C═S)—(CH2)n-S—(CH2)q-, R—(C═O)—(CH2)n-S—(CH2)q-, R—(C═S)—(CH2)n-O—(CH2)q-, R—SO—(CH2)n-(O)m-, R—SO—(CH2)n-(S)m-, R—SO—(CH2)n-(NR3)m-, R—SO2-(CH2)n-(O)m-, R—SO2-(CH2)n-(S)m-, R—SO2-(CH2)n-(NR3)m-, R1 R2N—(CH2)n-, R1 R2N—(CH2)n-O—(CH2)q-(O)m-, R1 R2N—(CH2)n-O—(CH2)q-(S)m-, R1 R2N—(CH2)n-O—(CH2)q-(NR3)m-, R1 R2N—(CH2)n-(C═O)—(CH2)q-(O)m-, R1 R2N—(CH2)n-(C═O)—(CH2)q-(S)m-, R1 R2N—(CH2)n-(C═O)—(CH2)q-(NR3)m-, R1 R2N—(CH2)n-SO2-(CH2)q-(O)m-, R1 R2N—(CH2)n-SO2-(CH2)q-(S)m-, R1 R2N—(CH2)n-SO2-(CH2)q-(NR3)m-, R1 R2PO3-(O)m-(CH2)q-, R1 R2R3SiO—(CH2)q-, R1 R2R3Si—(CH═CH)m-(CH2)q-, R1 R2C═N—(O)m-(CH2)n-, and R1 R2C═N—NH—(CH2)n-;

m is 0 or 1, n and q are independently an integer from 0 to 8, p is an integer from 1 to 8;

R is hydrogen, a halogen-containing or not containing group selected from alkyl, alkenyl, alkynyl, cycloalkyl, cycloalkenyl, and cycloalkylalkyl, or a group selected from aryl, arylalkyl, heteroaryl, and heteroarylalkyl, which is unsubstituted or substituted;

R1, R2, R3 are each independently hydrogen, nitro, hydroxy, amino, a halogen-containing or not containing group selected from alkyl, alkenyl, alkynyl, cycloalkyl, cycloalkenyl, cycloalkylalkyl, alkoxy, alkenyloxy, alkynyloxy, cycloalkyloxy, alkoxyalkyl, alkoxycarbonyl, alkylsulfanylcarbonyl, alkylsulfonyl, alkylsulfonylalkyl, alkylcarbonyl, alkylcarbonylalkyl, alkylcarbonyloxy, alkylamino, alkylaminocarbonyl, alkoxyaminocarbonyl, alkoxycarbonylalkyl, alkylaminocarbonylalkyl, trialkylsilyl, and dialkylphosphonyl, or a group selected from aryl, arylalkyl, aryloxy, arylalkyloxy, aryloxyalkyl, arylcarbonyl, arylsulfonyl, heteroaryl, heteroarylalkyl, heteroaryloxy, heteroarylalkyloxy, heteroaryloxyalkyl, heteroarylcarbonyl, heteroarylsulfonyl, aliphatic heterocyclyl, aliphatic heterocyclylalkyl, aliphatic heterocyclyloxy, aliphatic heterocyclylalkoxy, aliphatic heterocyclyloxyalkyl, aliphatic heterocyclylcarbonyl, and aliphatic heterocyclylsulfonyl, which is unsubstituted or substituted; or R1 R2N— forms a 5- to 6-membered heterocyclyl.

9. The compound according to claim 8,

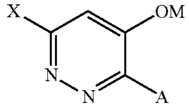

wherein X, M, and A are shown below:

| No. | X | M | A |
|---|---|---|---|
| 1-1 | $CF_3$ | 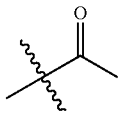 [SMILES: *C(C)=O] | 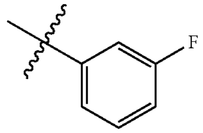 [SMILES: *c1cccc(F)c1] |
| 1-2 | $CF_3$ | 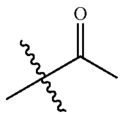 [SMILES: *C(C)=O] | 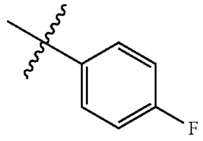 [SMILES: *c1ccc(F)cc1] |
| 1-3 | $CF_3$ | 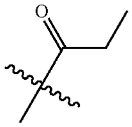 [SMILES: *C(=O)CC] | 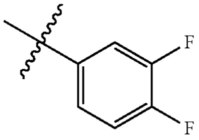 [SMILES: *c1ccc(F)c(F)c1] |
| 1-4 | $CF_3$ | 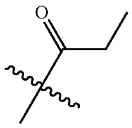 [SMILES: *C(=O)CC] | 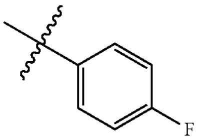 [SMILES: *c1ccc(F)cc1] |
| 1-5 | $CF_3$ | 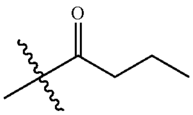 [SMILES: *C(=O)CCC] | 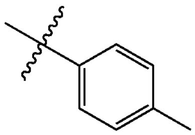 [SMILES: *c1ccc(C)cc1] |
| 1-6 | $CF_3$ | 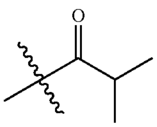 [SMILES: *C(=O)C(C)C] | 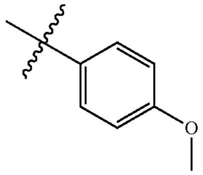 [SMILES: *c1ccc(OC)cc1] |
| 1-7 | $CF_3$ | 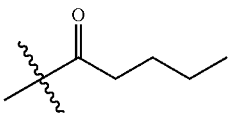 [SMILES: *C(=O)CCCC] | 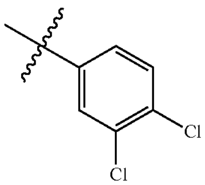 [SMILES: *c1ccc(Cl)c(Cl)c1] |

-continued
| No. | X | M | A |
| --- | --- | --- | --- |
| 1-8 | $CF_3$ | 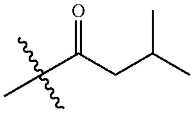 [SMILES: *C(=O)CC(C)C] | 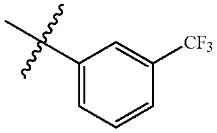 [SMILES: *c1cccc(C(F)(F)F)c1] |
| 1-9 | $CF_3$ | 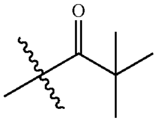 [SMILES: *C(=O)C(C)(C)C] | 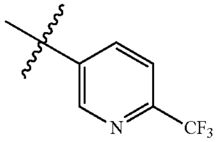 |
| 1-10 | $CF_3$ | 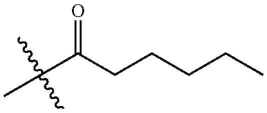 [SMILES: *C(=O)CCCCC] | 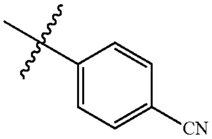 [SMILES: *c1ccc(C#N)cc1] |
| 1-11 | $CF_3$ | 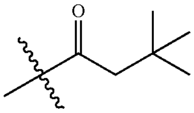 [SMILES: *C(=O)CC(C)(C)C] | 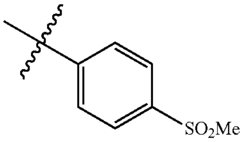 |
| 1-12 | $CF_3$ | 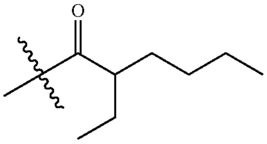 [SMILES: *C(=O)C(CC)CCCC] | 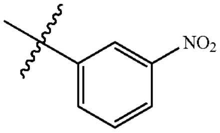 [SMILES: *c1cccc([N+](=O)[O-])c1] |
| 1-13 | $CF_3$ | 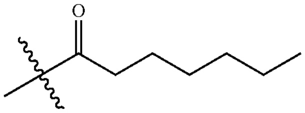 [SMILES: *C(=O)CCCCCC] | 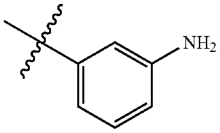 |
| 1-14 | $CF_3$ | 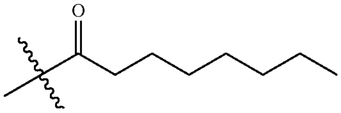 [SMILES: *C(=O)CCCCCCC] | 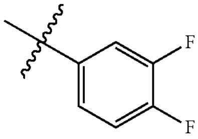 [SMILES: *c1ccc(F)c(F)c1] |
| 1-15 | $CF_3$ | 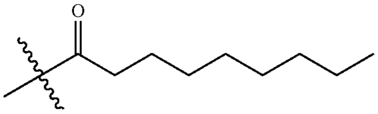 [SMILES: *C(=O)CCCCCCCC] | 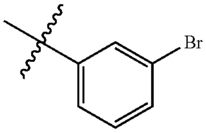 |
| 1-16 | $CF_3$ | 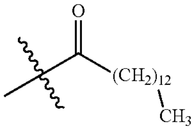 | 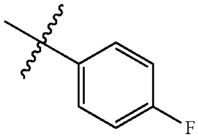 [SMILES: *c1ccc(F)cc1] |
| 1-17 | $CF_3$ | 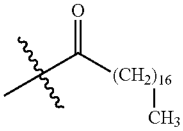 | 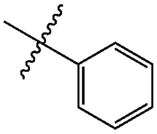 [SMILES: *c1ccccc1] |

-continued
| No. | X | M | A |
| --- | --- | --- | --- |
| 1-18 | $CF_3$ | 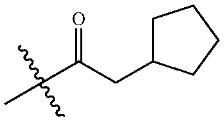 [SMILES: *C(=O)CC1CCCC1] | 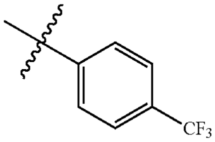 |
| 1-19 | $CF_3$ | 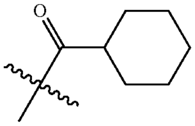 [SMILES: *C(=O)C1CCCCC1] | 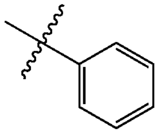 [SMILES: *c1ccccc1] |
| 1-20 | $CF_3$ | 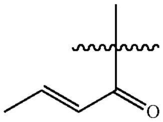 [SMILES: *C(=O)/C=C/C] | 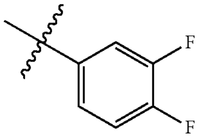 [SMILES: *c1ccc(F)c(F)c1] |
| 1-21 | $CF_3$ | 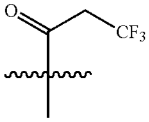 [SMILES: *C(=O)CC(F)(F)F] | 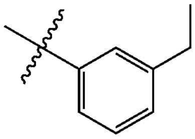 [SMILES: *c1cccc(CC)c1] |
| 1-22 | $CF_3$ | 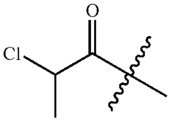 [SMILES: *C(=O)C(C)Cl] | 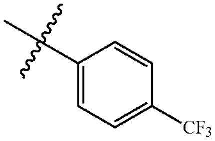 |
| 1-23 | $CF_3$ | 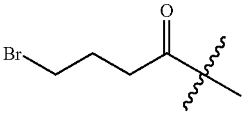 [SMILES: *C(=O)CCCBr] | 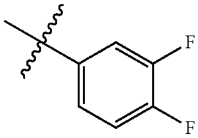 [SMILES: *c1ccc(F)c(F)c1] |
| 1-24 | $CF_3$ | 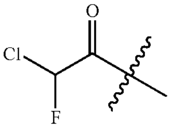 [SMILES: *C(=O)C(F)Cl] | 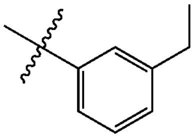 [SMILES: *c1cccc(CC)c1] |
| 1-25 | $CF_3$ | 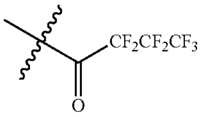 | 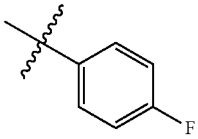 [SMILES: *c1ccc(F)cc1] |
| 1-26 | $CF_3$ | 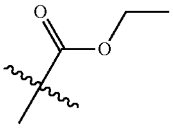 | 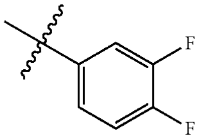 [SMILES: *c1ccc(F)c(F)c1] |
| 1-27 | $CF_3$ | 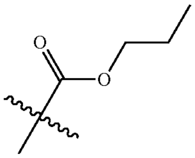 [SMILES: *C(=O)OCCC] | 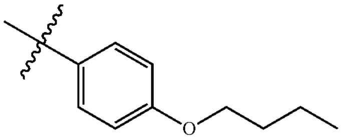 [SMILES: *c1ccc(OCCCC)cc1] |

-continued
| No. | X | M | A |
|---|---|---|---|
| 1-28 | $CF_3$ | 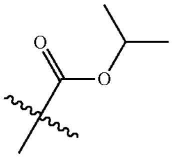 [SMILES: *C(=O)OC(C)C] | 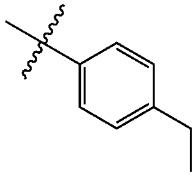 [SMILES: *c1ccc(CC)cc1] |
| 1-29 | $CF_3$ | 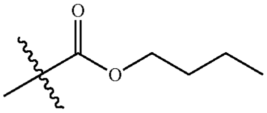 [SMILES: *C(=O)OCCCC] | 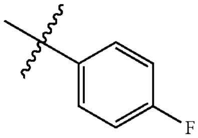 [SMILES: *c1ccc(F)cc1] |
| 1-30 | $CF_3$ | 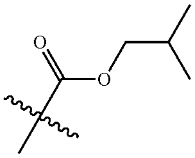 [SMILES: *C(=O)OCC(C)C] | 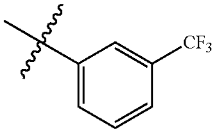 [SMILES: *c1cccc(C(F)(F)F)c1] |
| 1-31 | $CF_3$ | 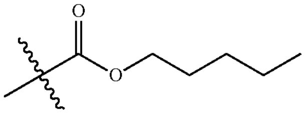 [SMILES: *C(=O)OCCCCC] | 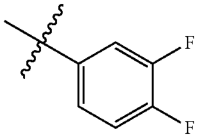 [SMILES: *c1ccc(F)c(F)c1] |
| 1-32 | $CF_3$ | 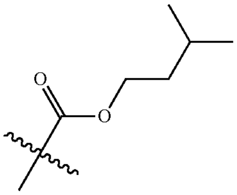 [SMILES: *C(=O)OCCC(C)C] | 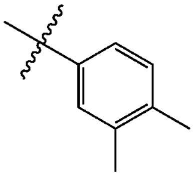 [SMILES: *c1ccc(C)c(C)c1] |
| 1-33 | $CF_3$ | 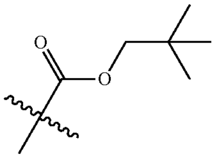 [SMILES: *C(=O)OCC(C)(C)C] | 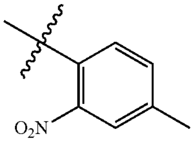 [SMILES: *c1ccc(C)cc1[N+](=O)[O-]] |
| 1-34 | $CF_3$ | 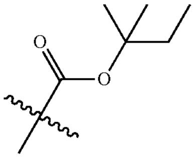 [SMILES: *C(=O)OC(C)(C)CC] | 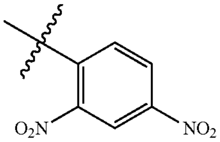 [SMILES: *c1ccc([N+](=O)[O-])cc1[N+](=O)[O-]] |
| 1-35 | $CF_3$ | 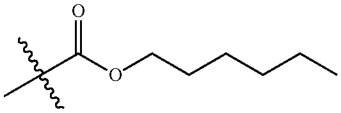 [SMILES: *C(=O)OCCCCCC] | 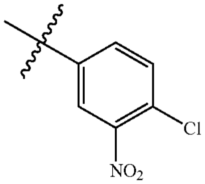 |
| 1-36 | $CF_3$ | 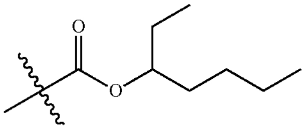 [SMILES: *C(=O)OC(CC)CCCC] | 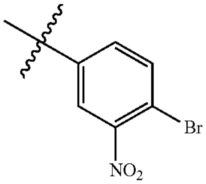 [SMILES: *c1ccc(Br)c([N+](=O)[O-])c1] |

-continued
| No. | X | M | A |
|---|---|---|---|
| 1-37 | $CF_3$ | 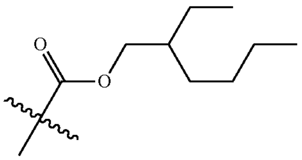 [SMILES: *C(=O)OCC(CC)CCCC] | 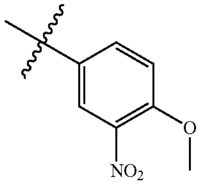 |
| 1-38 | $CF_3$ | 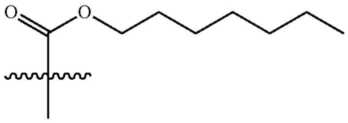 | 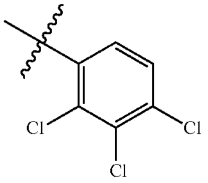 [SMILES: *c1ccc(Cl)c(Cl)c1Cl] |
| 1-39 | $CF_3$ | 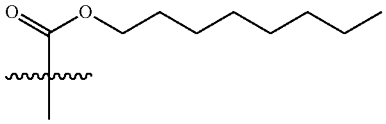 | 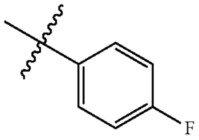 [SMILES: *c1ccc(F)cc1] |
| 1-40 | $CF_3$ | 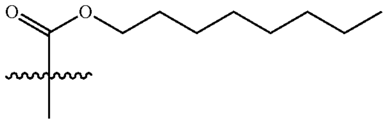 | 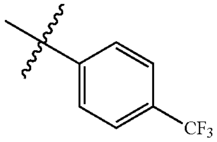 |
| 1-41 | $CF_3$ | 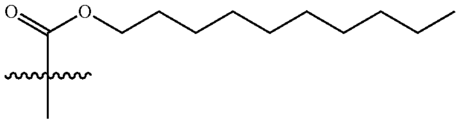 [SMILES: *C(=O)OCCCCCCCCCC] | 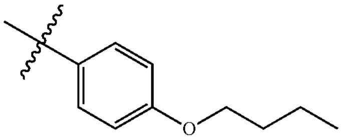 [SMILES: *c1ccc(OCCCC)cc1] |
| 1-42 | $CF_3$ | 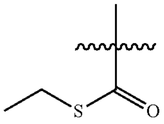 [SMILES: *C(=O)SCC] | 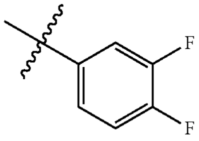 [SMILES: *c1ccc(F)c(F)c1] |
| 1-43 | $CF_3$ | 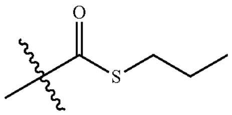 [SMILES: *C(=O)SCCC] | 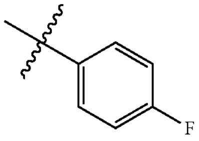 [SMILES: *c1ccc(F)cc1] |
| 1-44 | $CF_3$ | 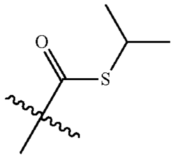 | 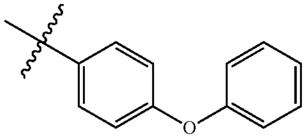 [SMILES: *c1ccc(Oc2ccccc2)cc1] |
| 1-45 | $CF_3$ | 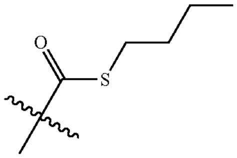 [SMILES: *C(=O)SCCCC] | 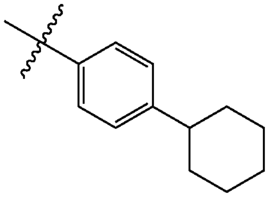 [SMILES: *c1ccc(C2CCCCC2)cc1] |

-continued
| No. | X | M | A |
|---|---|---|---|
| 1-46 | $CF_3$ | 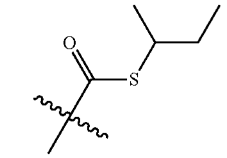 [SMILES: *C(=O)SC(C)CC] | 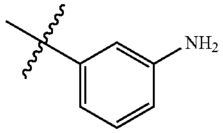 |
| 1-47 | $CF_3$ | 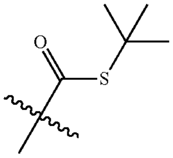 [SMILES: *C(=O)SC(C)(C)C] | 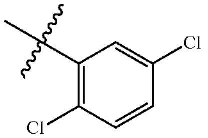 [SMILES: *c1cc(Cl)ccc1Cl] |
| 1-48 | $CF_3$ | 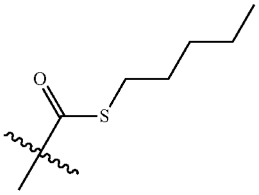 [SMILES: *C(=O)SCCCCC] | 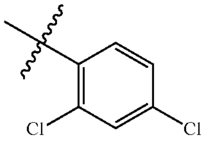 [SMILES: *c1ccc(Cl)cc1Cl] |
| 1-49 | $CF_3$ | 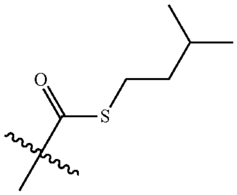 [SMILES: *C(=O)SCCC(C)C] | 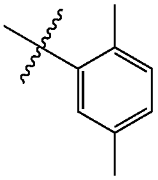 [SMILES: *c1cc(C)ccc1C] |
| 1-50 | $CF_3$ | 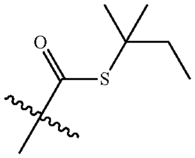 [SMILES: *C(=O)SC(C)(C)CC] | 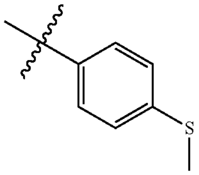 [SMILES: *c1ccc(SC)cc1] |
| 1-51 | $CF_3$ | 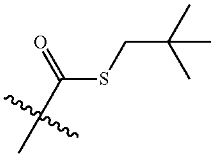 [SMILES: *C(=O)SCC(C)(C)C] | 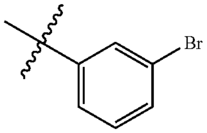 |
| 1-52 | $CF_3$ | 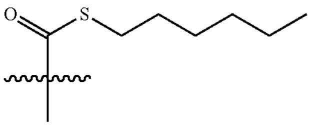 [SMILES: *C(=O)SCCCCCC] | 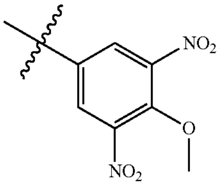 [SMILES: *c1cc([N+](=O)[O-])c(OC)c([N+](=O)[O-])c1] |
| 1-53 | $CF_3$ | 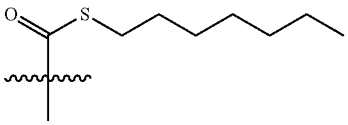 | 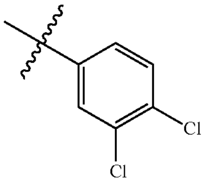 [SMILES: *c1ccc(Cl)c(Cl)c1] |

-continued
| No. | X | M | A |
|---|---|---|---|
| 1-54 | $CF_3$ | 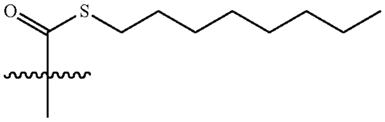 [SMILES: *C(=O)SCCCCCCCC] | 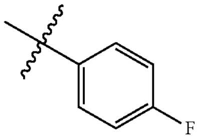 [SMILES: *c1ccc(F)cc1] |
| 1-55 | $CF_3$ | 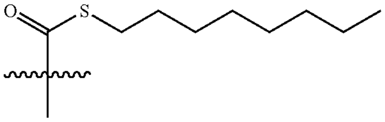 [SMILES: *C(=O)SCCCCCCCC] | 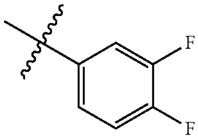 [SMILES: *c1ccc(F)c(F)c1] |
| 1-56 | $CF_3$ | 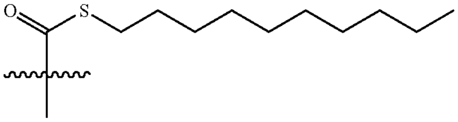 | 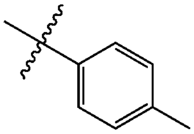 [SMILES: *c1ccc(C)cc1] |
| 1-57 | $CF_3$ | 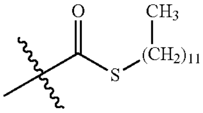 | 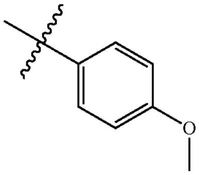 [SMILES: *c1ccc(OC)cc1] |
| 1-58 | $CF_3$ | 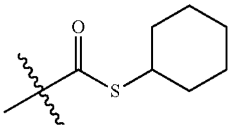 [SMILES: *C(=O)SC1CCCCC1] | 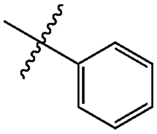 [SMILES: *c1ccccc1] |
| 1-59 | $CF_3$ | 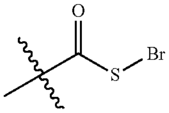 [SMILES: *C(=O)SBr] | 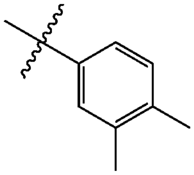 [SMILES: *c1ccc(C)c(C)c1] |
| 1-60 | $CF_3$ | 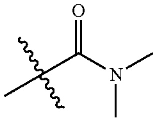 [SMILES: *C(=O)N(C)C] | 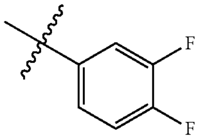 [SMILES: *c1ccc(F)c(F)c1] |
| 1-61 | $CF_3$ | 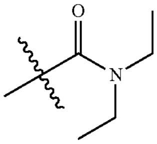 [SMILES: *C(=O)N(CC)CC] | 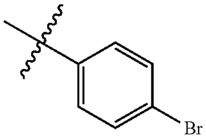 |
| 1-62 | $CF_3$ | 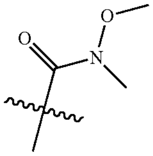 [SMILES: *C(=O)N(C)OC] | 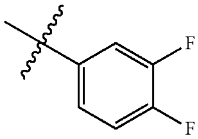 [SMILES: *c1ccc(F)c(F)c1] |
| 1-63 | $CF_3$ | 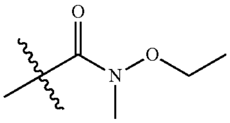 [SMILES: *C(=O)N(C)OCC] | 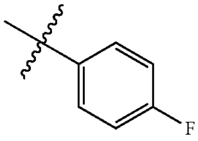 [SMILES: *c1ccc(F)cc1] |

-continued
| No. | X | M | A |
|---|---|---|---|
| 1-64 | $CF_3$ | 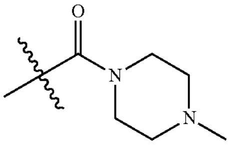 [SMILES: *C(=O)N1CCN(C)CC1] | 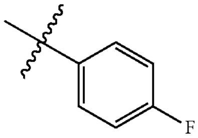 [SMILES: *c1ccc(F)cc1] |
| 1-65 | $CF_3$ | 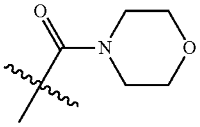 [SMILES: *C(=O)N1CCOCC1] | 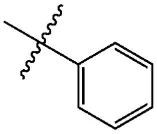 [SMILES: *c1ccccc1] |
| 1-66 | $CF_3$ | 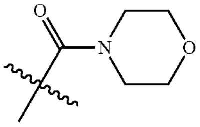 | 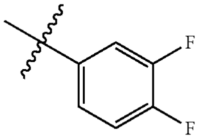 [SMILES: *c1ccc(F)c(F)c1] |
| 1-67 | $CF_3$ | 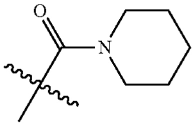 [SMILES: *C(=O)N1CCCCC1] | 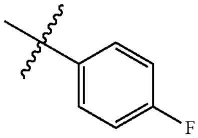 [SMILES: *c1ccc(F)cc1] |
| 1-68 | $CF_3$ | 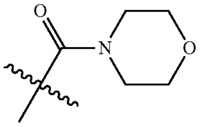 | 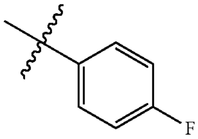 [SMILES: *c1ccc(F)cc1] |
| 1-69 | $CF_3$ | 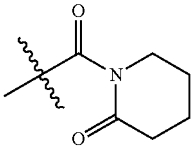 [SMILES: *C(=O)N1CCCCC1=O] | 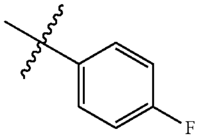 [SMILES: *c1ccc(F)cc1] |
| 1-70 | $CF_3$ | 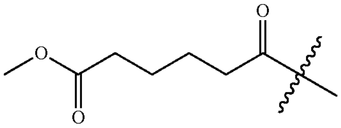 [SMILES: *C(=O)CCCCC(=O)OC] | 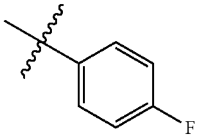 [SMILES: *c1ccc(F)cc1] |
| 1-71 | $CF_3$ | 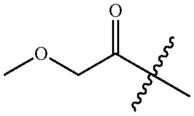 [SMILES: *C(=O)COC] | 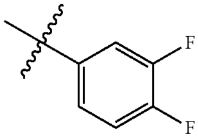 [SMILES: *c1ccc(F)c(F)c1] |
| 1-72 | $CF_3$ | 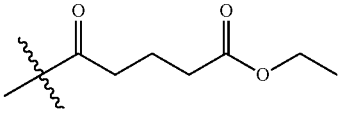 [SMILES: *C(=O)CCCC(=O)OCC] | 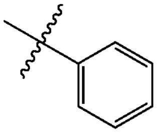 [SMILES: *c1ccccc1] |
| 1-73 | $CF_3$ | 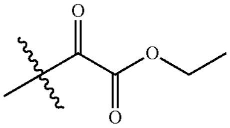 [SMILES: *C(=O)C(=O)OCC] | 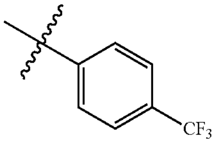 |

-continued
| No. | X | M | A |
|---|---|---|---|
| 1-74 | $CF_3$ | 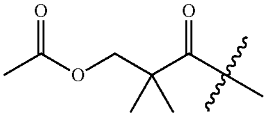 [SMILES: *C(=O)C(C)(C)COC(C)=O] | 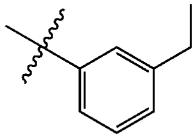 [SMILES: *c1cccc(CC)c1] |
| 1-75 | $CF_3$ | 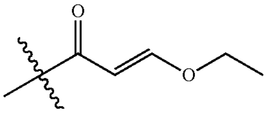 [SMILES: *C(=O)/C=C/OCC] | 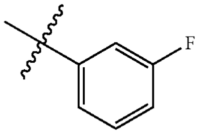 [SMILES: *c1cccc(F)c1] |
| 1-76 | $CF_3$ | 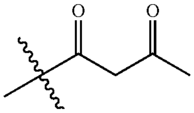 [SMILES: *C(=O)CC(C)=O] | 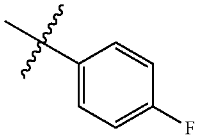 [SMILES: *c1ccc(F)cc1] |
| 1-77 | $CF_3$ | 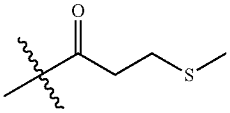 [SMILES: *C(=O)CCSC] | 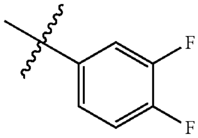 [SMILES: *c1ccc(F)c(F)c1] |
| 1-78 | $CF_3$ | 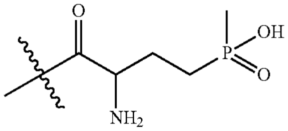 [SMILES: *C(=O)C(N)CCP(C)(=O)O] | 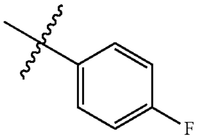 [SMILES: *c1ccc(F)cc1] |
| 1-79 | $CF_3$ | 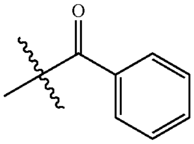 [SMILES: *C(=O)c1ccccc1] | 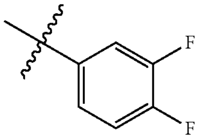 [SMILES: *c1ccc(F)c(F)c1] |
| 1-80 | $CF_3$ | 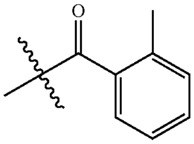 [SMILES: *C(=O)c1ccccc1C] | 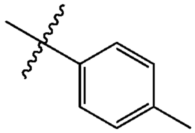 [SMILES: *c1ccc(C)cc1] |
| 1-81 | $CF_3$ | 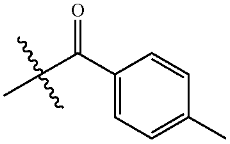 [SMILES: *C(=O)c1ccc(C)cc1] | 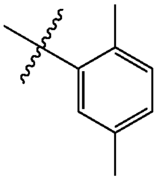 [SMILES: *c1cc(C)ccc1C] |
| 1-82 | $CF_3$ | 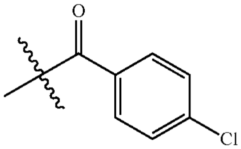 [SMILES: *C(=O)c1ccc(Cl)cc1] | 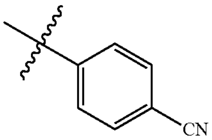 [SMILES: *c1ccc(C#N)cc1] |
| 1-83 | $CF_3$ | 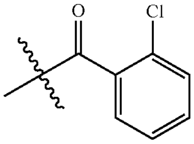 [SMILES: *C(=O)c1ccccc1Cl] | 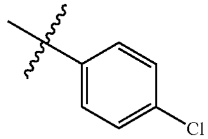 [SMILES: *c1ccc(Cl)cc1] |

-continued
| No. | X | M | A |
| --- | --- | --- | --- |
| 1-84 | $CF_3$ | 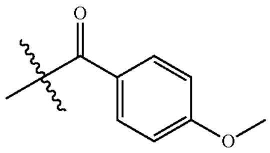 [SMILES: *C(=O)c1ccc(OC)cc1] | 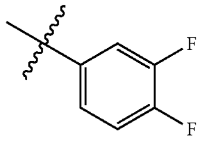 [SMILES: *c1ccc(F)c(F)c1] |
| 1-85 | $CF_3$ | 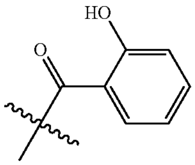 [SMILES: *C(=O)c1ccccc1O] | 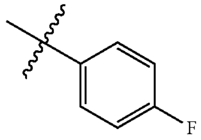 [SMILES: *c1ccc(F)cc1] |
| 1-86 | $CF_3$ | 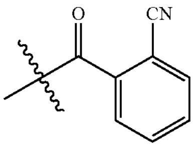 | 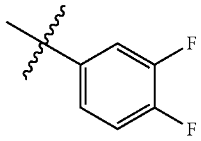 [SMILES: *c1ccc(F)c(F)c1] |
| 1-87 | $CF_3$ | 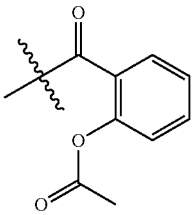 [SMILES: *C(=O)c1ccccc1OC(C)=O] | 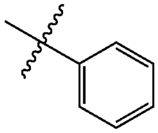 [SMILES: *c1ccccc1] |
| 1-88 | $CF_3$ | 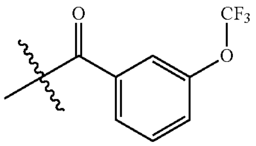 [SMILES: *C(=O)c1cccc(OC(F)(F)F)c1] | 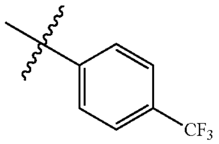 [SMILES: *c1ccc(C(F)(F)F)cc1] |
| 1-89 | $CF_3$ | 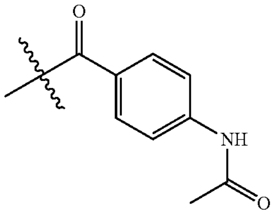 [SMILES: *C(=O)c1ccc(NC(C)=O)cc1] | 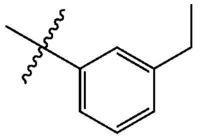 [SMILES: *c1cccc(CC)c1] |
| 1-90 | $CF_3$ | 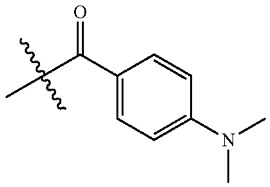 [SMILES: *C(=O)c1ccc(N(C)C)cc1] | 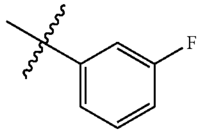 [SMILES: *c1cccc(F)c1] |
| 1-91 | $CF_3$ | 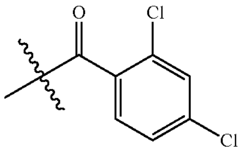 [SMILES: *C(=O)c1ccc(Cl)cc1Cl] | 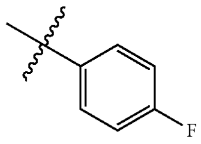 [SMILES: *c1ccc(F)cc1] |

-continued
| No. | X | M | A |
|---|---|---|---|
| 1-92 | $CF_3$ | 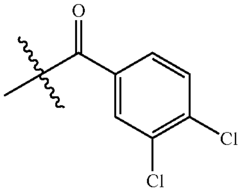 [SMILES: *C(=O)c1ccc(Cl)c(Cl)c1] | 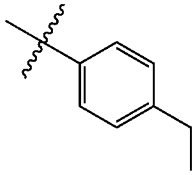 [SMILES: *c1ccc(CC)cc1] |
| 1-93 | $CF_3$ | 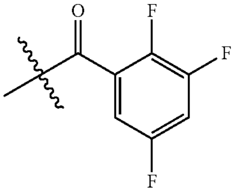 [SMILES: *C(=O)c1cc(F)cc(F)c1F] | 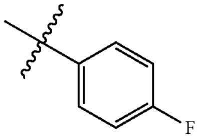 [SMILES: *c1ccc(F)cc1] |
| 1-94 | $CF_3$ | 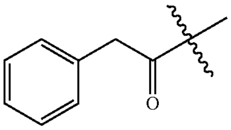 [SMILES: *C(=O)Cc1ccccc1] | 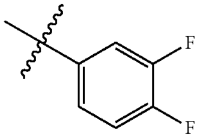 [SMILES: *c1ccc(F)c(F)c1] |
| 1-95 | $CF_3$ | 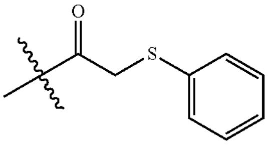 [SMILES: *C(=O)CSc1ccccc1] | 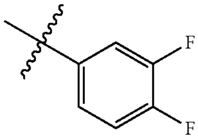 [SMILES: *c1ccc(F)c(F)c1] |
| 1-96 | $CF_3$ | 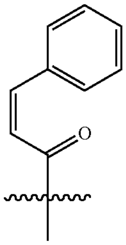 [SMILES: *C(=O)/C=C\c1ccccc1] | 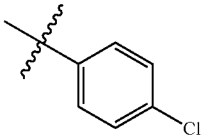 [SMILES: *c1ccc(Cl)cc1] |
| 1-97 | $CF_3$ | 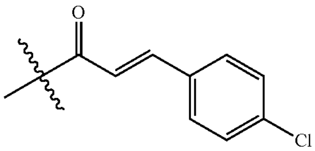 [SMILES: *C(=O)/C=C/c1ccc(Cl)cc1] | 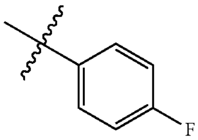 [SMILES: *c1ccc(F)cc1] |
| 1-98 | $CF_3$ | 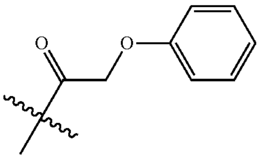 [SMILES: *C(=O)COc1ccccc1] | 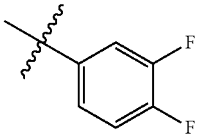 [SMILES: *c1ccc(F)c(F)c1] |
| 1-99 | $CF_3$ | 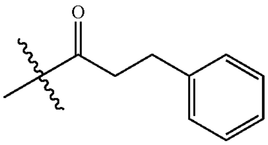 [SMILES: *C(=O)CCc1ccccc1] | 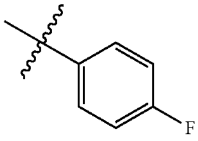 [SMILES: *c1ccc(F)cc1] |

-continued
| No. | X | M | A |
|---|---|---|---|
| 1-100 | $CF_3$ | 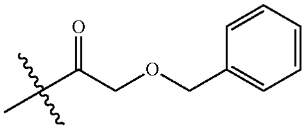 [SMILES: *C(=O)COCc1ccccc1] | 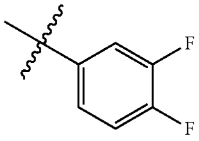 [SMILES: *c1ccc(F)c(F)c1] |
| 1-101 | $CF_3$ | 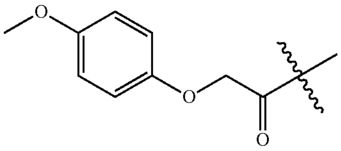 [SMILES: *C(=O)COc1ccc(OC)cc1] | 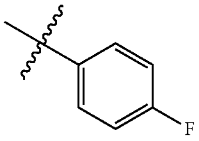 [SMILES: *c1ccc(F)cc1] |
| 1-102 | $CF_3$ | 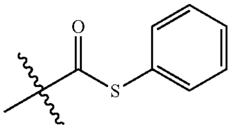 [SMILES: *C(=O)Sc1ccccc1] | 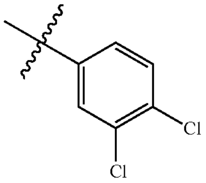 [SMILES: *c1ccc(Cl)c(Cl)c1] |
| 1-103 | $CF_3$ | 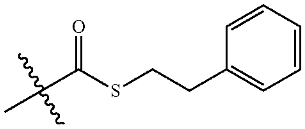 [SMILES: *C(=O)SCCc1ccccc1] | 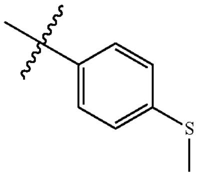 [SMILES: *c1ccc(SC)cc1] |
| 1-104 | $CF_3$ | 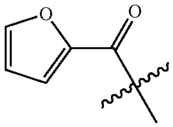 [SMILES: *C(=O)c1ccco1] | 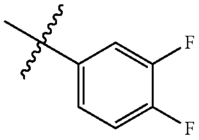 [SMILES: *c1ccc(F)c(F)c1] |
| 1-105 | $CF_3$ | 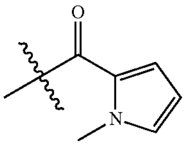 [SMILES: *C(=O)c1cccn1C] | 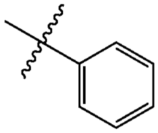 [SMILES: *c1ccccc1] |
| 1-106 | $CF_3$ | 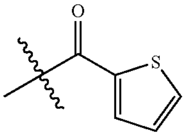 [SMILES: *C(=O)c1cccs1] | 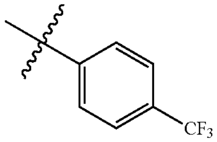 |
| 1-107 | $CF_3$ | 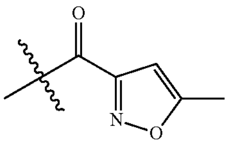 [SMILES: *C(=O)c1cc(C)on1] | 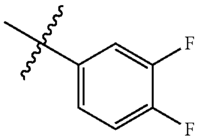 [SMILES: *c1ccc(F)c(F)c1] |
| 1-108 | $CF_3$ | 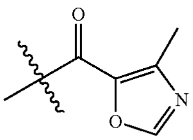 [SMILES: *C(=O)c1ocnc1C] | 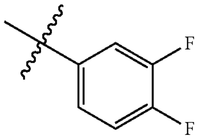 [SMILES: *c1ccc(F)c(F)c1] |

-continued
| No. | X | M | A |
|---|---|---|---|
| 1-109 | $CF_3$ | 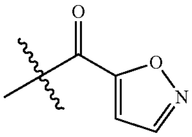 [SMILES: *C(=O)c1ccno1] | 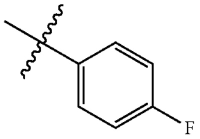 [SMILES: *c1ccc(F)cc1] |
| 1-110 | $CF_3$ | 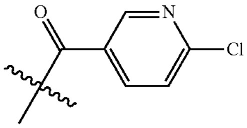 [SMILES: *C(=O)c1ccc(Cl)nc1] | 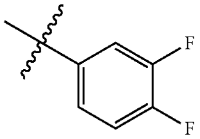 [SMILES: *c1ccc(F)c(F)c1] |
| 1-111 | $CF_3$ | 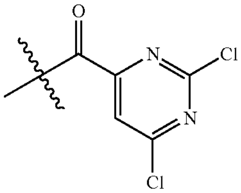 [SMILES: *C(=O)c1cc(Cl)nc(Cl)n1] | 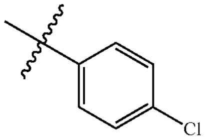 [SMILES: *c1ccc(Cl)cc1] |
| 1-112 | $CF_3$ | 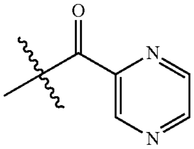 [SMILES: *C(=O)c1cnccn1] | 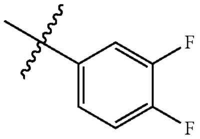 [SMILES: *c1ccc(F)c(F)c1] |
| 1-113 | $CF_3$ | 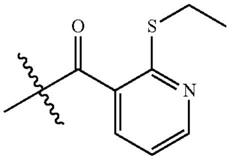 [SMILES: *C(=O)c1cccnc1SCC] | 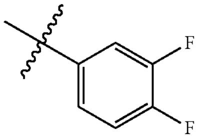 [SMILES: *c1ccc(F)c(F)c1] |
| 1-114 | $CF_3$ | 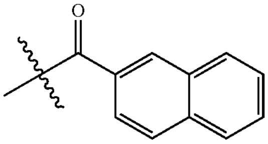 [SMILES: *C(=O)c1ccc2ccccc2c1] | 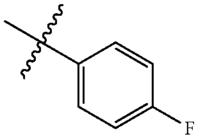 [SMILES: *c1ccc(F)cc1] |
| 1-115 | $CF_3$ | 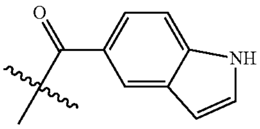 [SMILES: *C(=O)c1ccc2[nH]ccc2c1] | 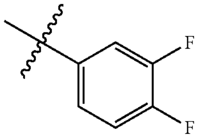 [SMILES: *c1ccc(F)c(F)c1] |
| 1-116 | $CF_3$ | 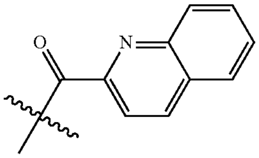 [SMILES: *C(=O)c1ccc2ccccc2n1] | 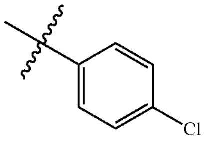 [SMILES: *c1ccc(Cl)cc1] |
| 1-117 | $CF_3$ | 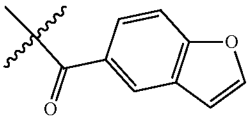 [SMILES: *C(=O)c1ccc2occc2c1] | 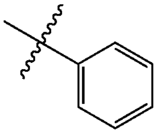 [SMILES: *c1ccccc1] |

-continued
| No. | X | M | A |
|---|---|---|---|
| 1-118 | $CF_3$ | 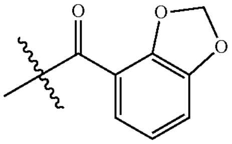 [SMILES: *C(=O)c1cccc2c1OCO2] | 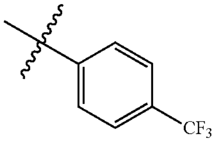 |
| 1-119 | $CF_3$ | 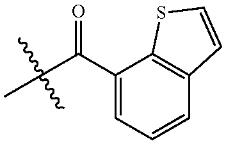 [SMILES: *C(=O)c1cccc2ccsc12] | 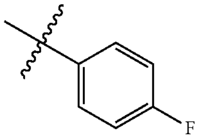 [SMILES: *c1ccc(F)cc1] |
| 1-120 | $CF_3$ | 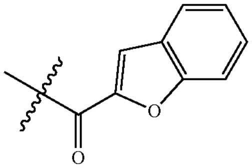 [SMILES: *C(=O)c1cc2ccccc2o1] | 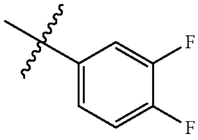 |
| 1-121 | $CF_3$ | 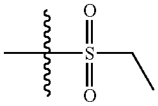 [SMILES: *S(=O)(=O)CC] | 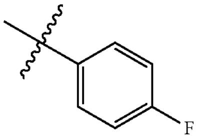 [SMILES: *c1ccc(F)cc1] |
| 1-122 | $CF_3$ | 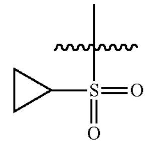 [SMILES: *S(=O)(=O)C1CC1] | 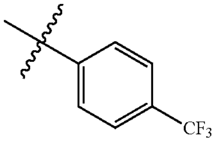 |
| 1-123 | $CF_3$ | 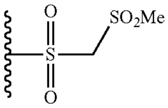 | 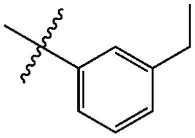 [SMILES: *c1cccc(CC)c1] |
| 1-124 | $CF_3$ | 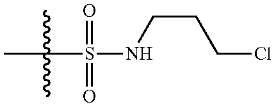 [SMILES: *S(=O)(=O)NCCCCl] | 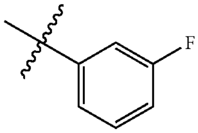 [SMILES: *c1cccc(F)c1] |
| 1-125 | $CF_3$ | 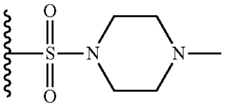 [SMILES: *S(=O)(=O)N1CCN(C)CC1] | 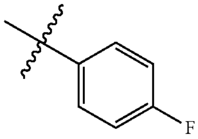 [SMILES: *c1ccc(F)cc1] |
| 1-126 | $CF_3$ | 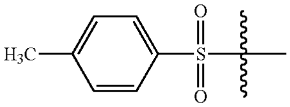 [SMILES: *S(=O)(=O)c1ccc(C)cc1] | 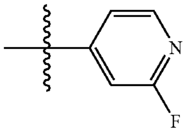 [SMILES: *c1ccnc(F)c1] |
| 1-127 | $CF_3$ | 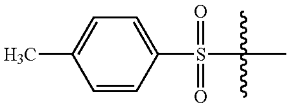 [SMILES: *S(=O)(=O)c1ccc(C)cc1] | 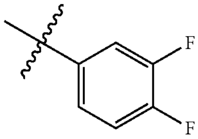 [SMILES: *c1ccc(F)c(F)c1] |

-continued
| No. | X | M | A |
|---|---|---|---|
| 1-128 | $CF_3$ | 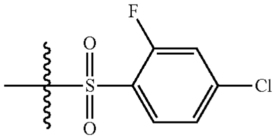 [SMILES: *S(=O)(=O)c1ccc(Cl)cc1F] | 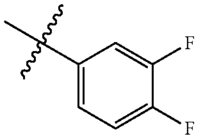 [SMILES: *c1ccc(F)c(F)c1] |
| 1-129 | $CF_3$ | 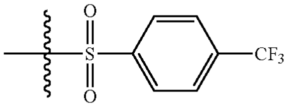 [SMILES: *S(=O)(=O)c1ccc(C(F)(F)F)cc1] | 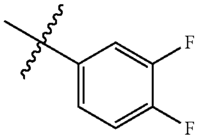 [SMILES: *c1ccc(F)c(F)c1] |
| 1-130 | $CF_3$ | 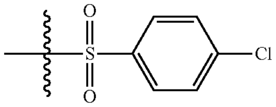 [SMILES: *S(=O)(=O)c1ccc(Cl)cc1] | 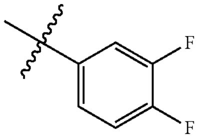 [SMILES: *c1ccc(F)c(F)c1] |
| 1-131 | $CF_3$ | 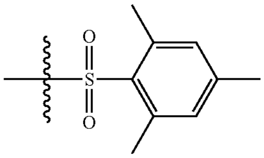 [SMILES: *S(=O)(=O)c1c(C)cc(C)cc1C] | 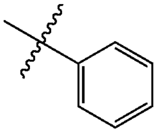 [SMILES: *c1ccccc1] |
| 1-132 | $CF_3$ | 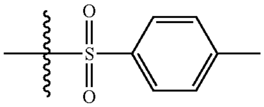 [SMILES: *S(=O)(=O)c1ccc(C)cc1] | 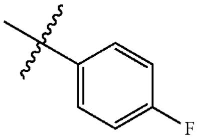 [SMILES: *c1ccc(F)cc1] |
| 1-133 | $CF_3$ | 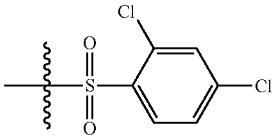 | 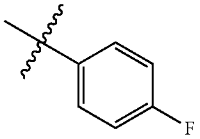 [SMILES: *c1ccc(F)cc1] |
| 1-134 | $CF_3$ | 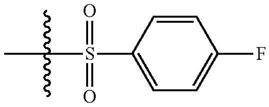 [SMILES: *S(=O)(=O)c1ccc(F)cc1] | 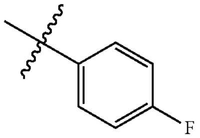 [SMILES: *c1ccc(F)cc1] |
| 1-135 | $CF_3$ | 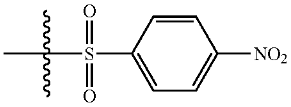 [SMILES: *S(=O)(=O)c1ccc([N+](=O)[O-])cc1] | 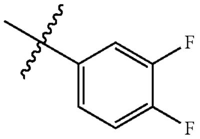 [SMILES: *c1ccc(F)c(F)c1] |
| 1-136 | $CF_3$ | 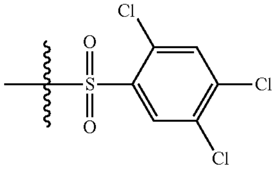 [SMILES: *S(=O)(=O)c1cc(Cl)c(Cl)cc1Cl] | 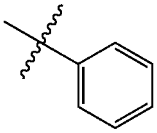 [SMILES: *c1ccccc1] |
| 1-137 | $CF_3$ | 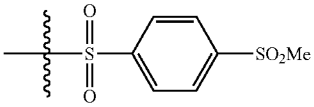 [SMILES: *S(=O)(=O)c1ccc(S(C)(=O)=O)cc1] | 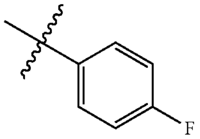 [SMILES: *c1ccc(F)cc1] |

-continued
| No. | X | M | A |
|---|---|---|---|
| 1-138 | $CF_3$ | 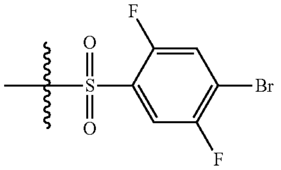 [SMILES: *S(=O)(=O)c1cc(F)c(Br)cc1F] | 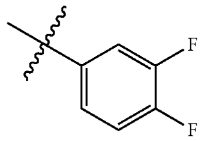 [SMILES: *c1ccc(F)c(F)c1] |
| 1-139 | $CF_3$ | 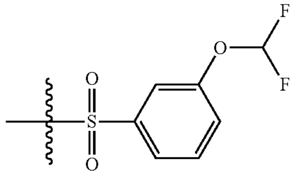 [SMILES: *S(=O)(=O)c1cccc(OC(F)F)c1] | 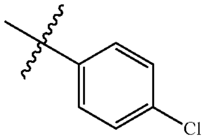 [SMILES: *c1ccc(Cl)cc1] |
| 1-140 | $CF_3$ | 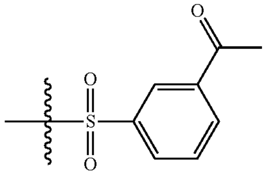 [SMILES: *S(=O)(=O)c1cccc(C(C)=O)c1] | 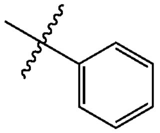 [SMILES: *c1ccccc1] |
| 1-141 | $CF_3$ | 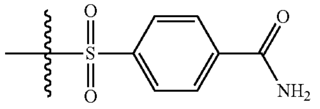 [SMILES: *S(=O)(=O)c1ccc(C(N)=O)cc1] | 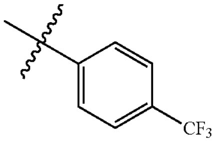 [SMILES: *c1ccc(C(F)(F)F)cc1] |
| 1-142 | $CF_3$ | 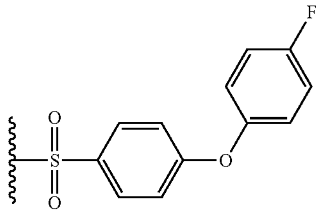 [SMILES: *S(=O)(=O)c1ccc(Oc2ccc(F)cc2)cc1] | 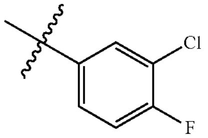 [SMILES: *c1ccc(F)c(Cl)c1] |
| 1-143 | $CF_3$ | 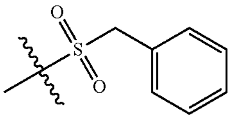 [SMILES: *S(=O)(=O)Cc1ccccc1] | 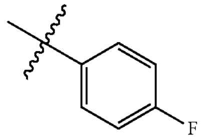 [SMILES: *c1ccc(F)cc1] |
| 1-144 | $CF_3$ | 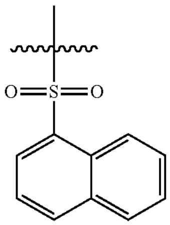 [SMILES: *S(=O)(=O)c1cccc2ccccc12] | 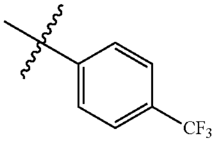 |
| 1-145 | $CF_3$ | 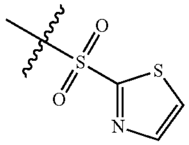 [SMILES: *S(=O)(=O)c1nccs1] | 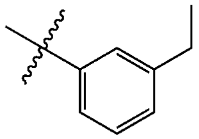 [SMILES: *c1cccc(CC)c1] |

-continued
| No. | X | M | A |
|---|---|---|---|
| 1-146 | $CF_3$ | 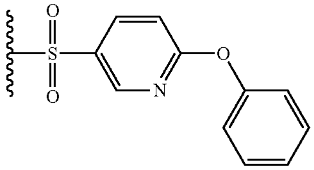 [SMILES: *S(=O)(=O)c1ccc(Oc2ccccc2)nc1] | 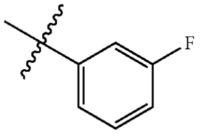 [SMILES: *c1cccc(F)c1] |
| 1-147 | $CF_3$ | 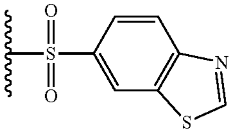 [SMILES: *S(=O)(=O)c1ccc2ncsc2c1] | 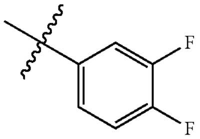 [SMILES: *c1ccc(F)c(F)c1] |
| 1-148 | $CF_3$ | 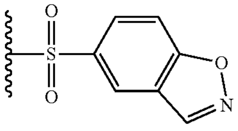 [SMILES: *S(=O)(=O)c1ccc2oncc2c1] | 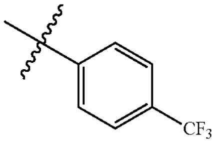 [SMILES: *c1ccc(C(F)(F)F)cc1] |
| 1-149 | $CF_3$ | 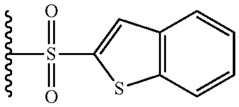 [SMILES: *S(=O)(=O)c1cc2ccccc2s1] | 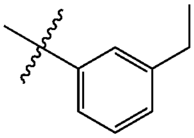 [SMILES: *c1cccc(CC)c1] |
| 1-150 | $CF_3$ | 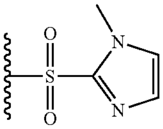 [SMILES: *S(=O)(=O)c1nccn1C] | 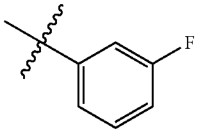 [SMILES: *c1cccc(F)c1] |
| 1-151 | $CF_3$ | 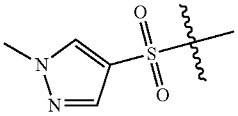 [SMILES: *S(=O)(=O)c1cnn(C)c1] | 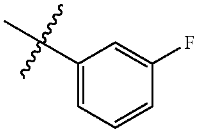 [SMILES: *c1cccc(F)c1] |
| 1-152 | $CF_3$ | 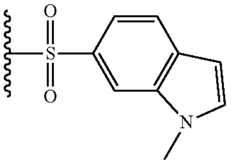 [SMILES: *S(=O)(=O)c1ccc2ccn(C)c2c1] | 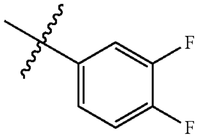 [SMILES: *c1ccc(F)c(F)c1] |
| 1-153 | $CF_3$ | 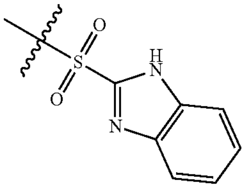 [SMILES: *S(=O)(=O)c1nc2ccccc2[nH]1] | 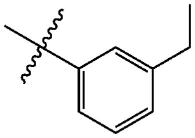 [SMILES: *c1cccc(CC)c1] |
| 1-154 | $CF_3$ | 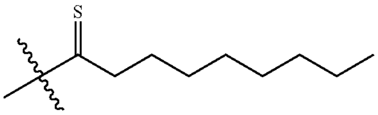 | 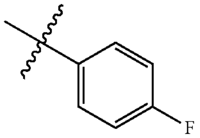 [SMILES: *c1ccc(F)cc1] |
| 1-155 | $CF_3$ | 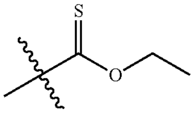 | 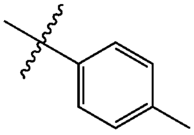 [SMILES: *c1ccc(C)cc1] |

-continued
| No. | X | M | A |
| --- | --- | --- | --- |
| 1-156 | $CF_3$ | 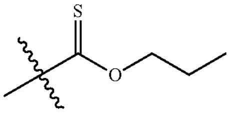 | 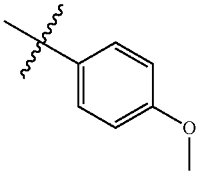 [SMILES: *c1ccc(OC)cc1] |
| 1-157 | $CF_3$ | 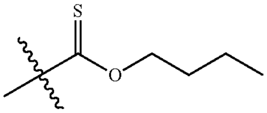 | 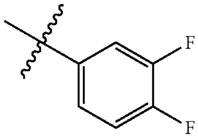 [SMILES: *c1ccc(F)c(F)c1] |
| 1-158 | $CF_3$ | 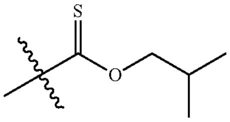 [SMILES: *C(=S)OCC(C)C] | 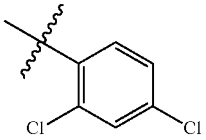 [SMILES: *c1ccc(Cl)cc1Cl] |
| 1-159 | $CF_3$ | 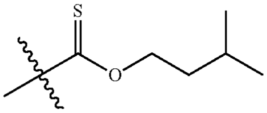 [SMILES: *C(=S)OCCC(C)C] | 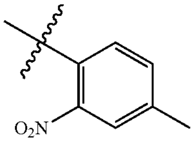 |
| 1-160 | $CF_3$ | 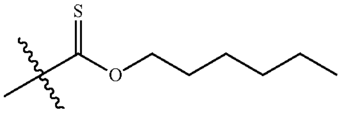 | 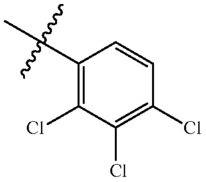 [SMILES: *c1ccc(Cl)c(Cl)c1Cl] |
| 1-161 | $CF_3$ | 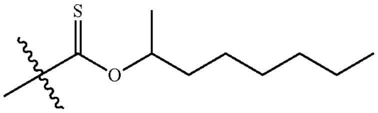 [SMILES: *C(=S)OC(C)CCCCCC] | 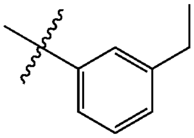 [SMILES: *c1cccc(CC)c1] |
| 1-162 | $CF_3$ | 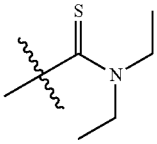 [SMILES: *C(=S)N(CC)CC] | 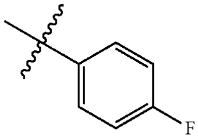 [SMILES: *c1ccc(F)cc1] |
| 1-163 | $CF_3$ | 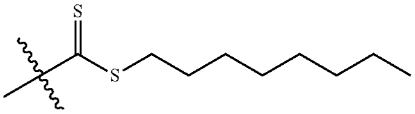 [SMILES: *C(=S)SCCCCCCCC] | 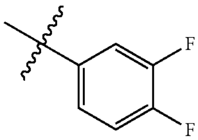 [SMILES: *c1ccc(F)c(F)c1] |
| 1-164 | $CF_3$ | 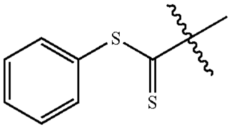 [SMILES: *C(=S)Sc1ccccc1] | 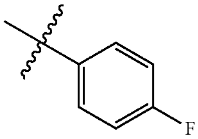 [SMILES: *c1ccc(F)cc1] |

-continued
| No. | X | M | A |
|---|---|---|---|
| 1-165 | $CF_3$ | 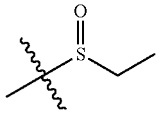 | 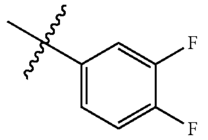 [SMILES: *c1ccc(F)c(F)c1] |
| 1-166 | $CF_3$ | 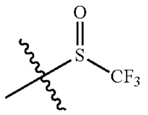 [SMILES: *S(=O)C(F)(F)F] | 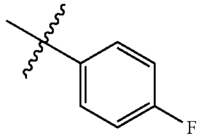 [SMILES: *c1ccc(F)cc1] |
| 1-167 | $CF_3$ | 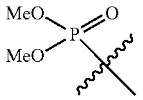 | 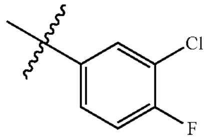 [SMILES: *c1ccc(F)c(Cl)c1] |
| 1-168 | $CF_3$ | 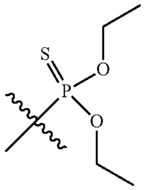 [SMILES: *P(=S)(OCC)OCC] | 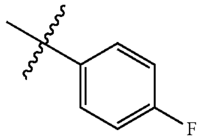 [SMILES: *c1ccc(F)cc1] |
| 1-169 | $CF_3$ | 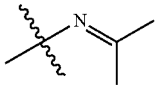 [SMILES: *N=C(C)C] | 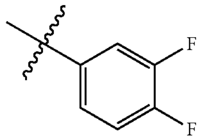 [SMILES: *c1ccc(F)c(F)c1] |
| 1-170 | $CF_3$ | 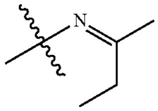 [SMILES: */N=C(/C)CC] | 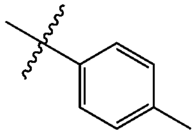 [SMILES: *c1ccc(C)cc1] |
| 1-171 | $CF_3$ | 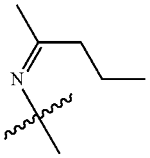 [SMILES: */N=C(/C)CCC] | 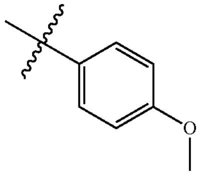 [SMILES: *c1ccc(OC)cc1] |
| 1-172 | $CF_3$ | 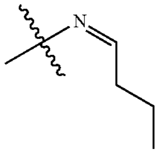 [SMILES: */N=C\CCC] | 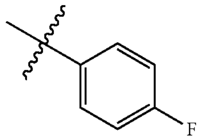 [SMILES: *c1ccc(F)cc1] |
| 1-173 | $CF_3$ | 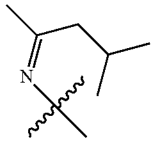 [SMILES: */N=C(/C)CC(C)C] | 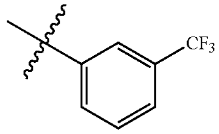 [SMILES: *c1cccc(C(F)(F)F)c1] |

-continued
| No. | X | M | A |
|---|---|---|---|
| 1-174 | $CF_3$ | 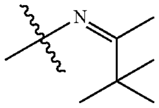 [SMILES: */N=C(/C)C(C)(C)C] | 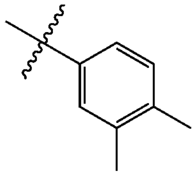 [SMILES: *c1ccc(C)c(C)c1] |
| 1-175 | $CF_3$ | 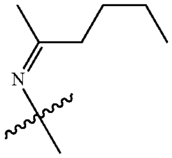 [SMILES: */N=C(/C)CCCC] | 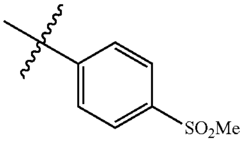 [SMILES: *c1ccc(S(C)(=O)=O)cc1] |
| 1-176 | $CF_3$ | 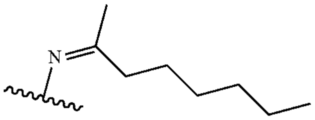 [SMILES: */N=C(/C)CCCCCC] | 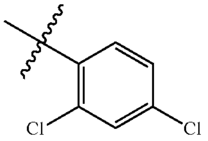 |
| 1-177 | $CF_3$ | 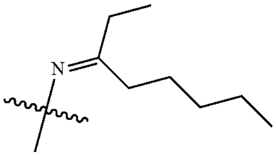 [SMILES: */N=C(/CC)CCCCC] | 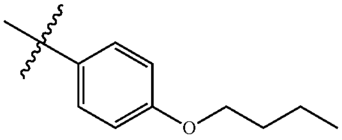 [SMILES: *c1ccc(OCCCC)cc1] |
| 1-178 | $CF_3$ | 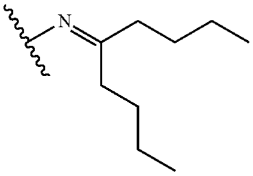 [SMILES: *N=C(CCCC)CCCC] | 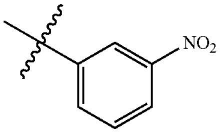 [SMILES: *c1cccc([N+](=O)[O-])c1] |
| 1-179 | $CF_3$ | 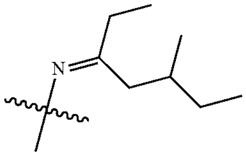 [SMILES: */N=C(/CC)CC(C)CC] | 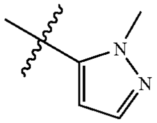 [SMILES: *c1ccnn1C] |
| 1-180 | $CF_3$ | 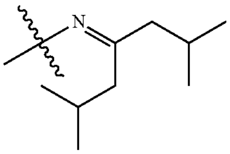 [SMILES: *N=C(CC(C)C)CC(C)C] | 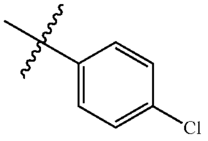 [SMILES: *c1ccc(Cl)cc1] |
| 1-181 | $CF_3$ | 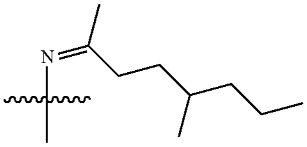 [SMILES: */N=C(/C)CCC(C)CCC] | 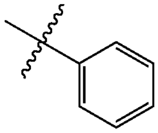 [SMILES: *c1ccccc1] |
| 1-182 | $CF_3$ | 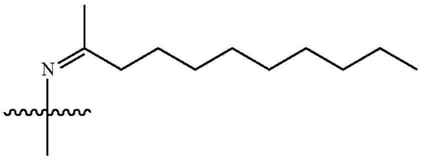 [SMILES: */N=C(/C)CCCCCCCCC] | 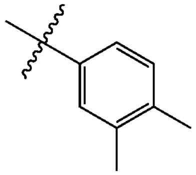 [SMILES: *c1ccc(C)c(C)c1] |

-continued
| No. | X | M | A |
|---|---|---|---|
| 1-183 | $CF_3$ | 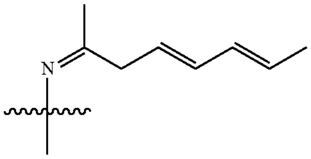 [SMILES: */N=C(/C)C/C=C/C=C/C] | 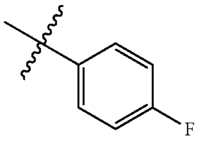 [SMILES: *c1ccc(F)cc1] |
| 1-184 | $CF_3$ | 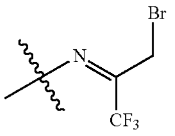 | 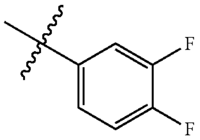 [SMILES: *c1ccc(F)c(F)c1] |
| 1-185 | $CF_3$ | 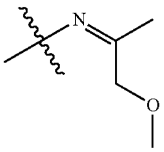 [SMILES: */N=C(/C)COC] | 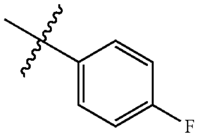 [SMILES: *c1ccc(F)cc1] |
| 1-186 | $CF_3$ | 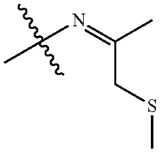 [SMILES: */N=C(/C)CSC] | 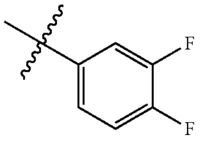 [SMILES: *c1ccc(F)c(F)c1] |
| 1-187 | $CF_3$ | 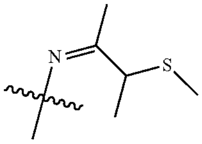 [SMILES: */N=C(/C)C(C)SC] | 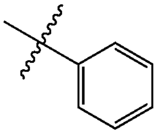 [SMILES: *c1ccccc1] |
| 1-188 | $CF_3$ | 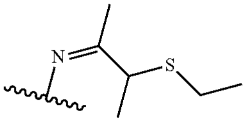 [SMILES: */N=C(/C)C(C)SCC] | 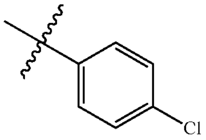 [SMILES: *c1ccc(Cl)cc1] |
| 1-189 | $CF_3$ | 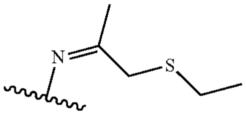 [SMILES: */N=C(/C)CSCC] | 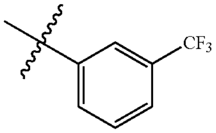 [SMILES: *c1cccc(C(F)(F)F)c1] |
| 1-190 | $CF_3$ | 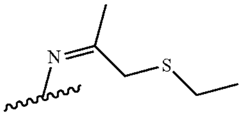 [SMILES: */N=C(/C)CSCC] | 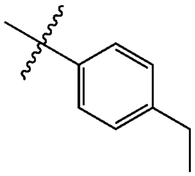 [SMILES: *c1ccc(CC)cc1] |
| 1-191 | $CF_3$ | 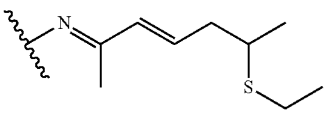 [SMILES: */N=C(C)/C=C/CC(C)SCC] | 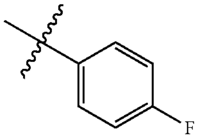 [SMILES: *c1ccc(F)cc1] |

-continued
| No. | X | M | A |
|---|---|---|---|
| 1-192 | $CF_3$ | 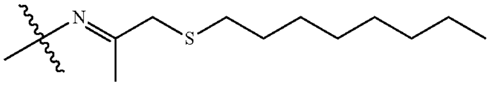 [SMILES: */N=C(\C)CSCCCCCCCC] | 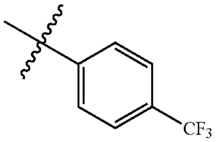 |
| 1-193 | $CF_3$ | 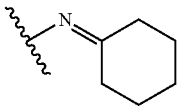 [SMILES: *N=C1CCCCC1] | 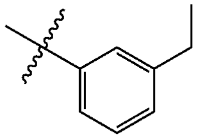 [SMILES: *c1cccc(CC)c1] |
| 1-194 | $CF_3$ | 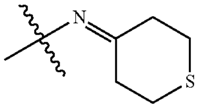 [SMILES: *N=C1CCSCC1] | 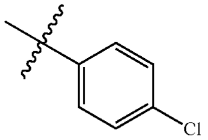 [SMILES: *c1ccc(Cl)cc1] |
| 1-195 | $CF_3$ | 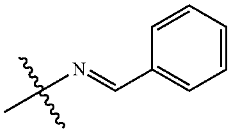 [SMILES: */N=C/c1ccccc1] | 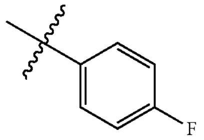 [SMILES: *c1ccc(F)cc1] |
| 1-196 | $CF_3$ | 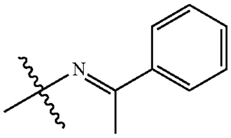 [SMILES: */N=C(\C)c1ccccc1] | 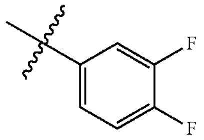 [SMILES: *c1ccc(F)c(F)c1] |
| 1-197 | $CF_3$ | 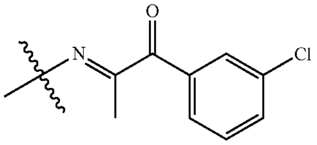 [SMILES: */N=C(\C)C(=O)c1cccc(Cl)c1] | 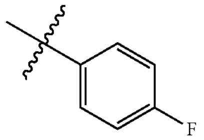 [SMILES: *c1ccc(F)cc1] |
| 1-198 | $CF_3$ | 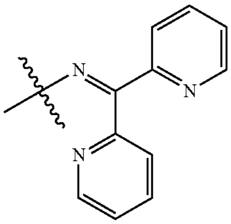 [SMILES: *N=C(c1ccccn1)c1ccccn1] | 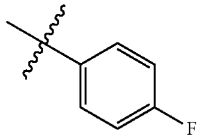 [SMILES: *c1ccc(F)cc1] |
| 1-199 | $CF_3$ | 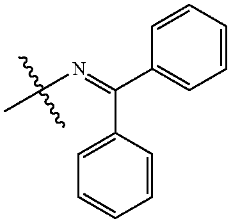 [SMILES: *N=C(c1ccccc1)c1ccccc1] | 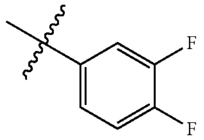 [SMILES: *c1ccc(F)c(F)c1] |
| 1-200 | $CF_3$ | 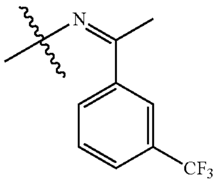 [SMILES: */N=C(/C)c1cccc(C(F)(F)F)c1] | 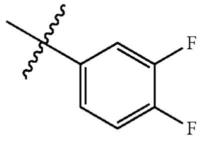 [SMILES: *c1ccc(F)c(F)c1] |

-continued
| No. | X | M | A |
|---|---|---|---|
| 1-201 | $CF_3$ | 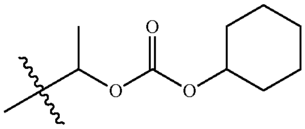 [SMILES: *C(C)OC(=O)OC1CCCCC1] | 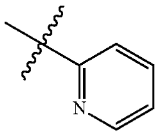 |
| 1-202 | $CF_3$ | OEt | 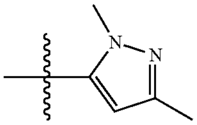 [SMILES: *c1cc(C)nn1C] |
| 1-203 | $CF_3$ | 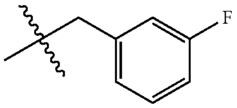 [SMILES: *Cc1cccc(F)c1] | 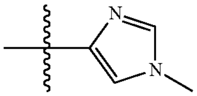 [SMILES: *c1cn(C)cn1] |
| 1-204 | $CF_3$ | 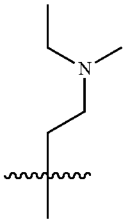 [SMILES: *CCN(C)CC] | 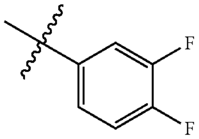 [SMILES: *c1ccc(F)c(F)c1] |
| 1-205 | $CF_3$ | 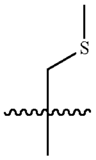 | 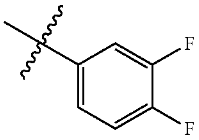 [SMILES: *c1ccc(F)c(F)c1] |
| 1-206 | $CF_3$ | 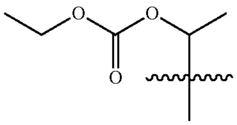 [SMILES: *C(C)OC(=O)OCC] | 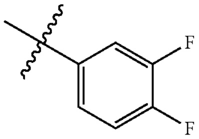 |
| 1-207 | $CF_3$ | 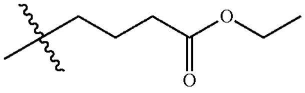 [SMILES: *CCCC(=O)OCC] | 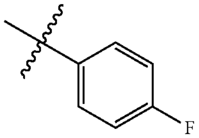 [SMILES: *c1ccc(F)cc1] |
| 1-208 | $CF_3$ | 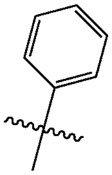 [SMILES: *c1ccccc1] | 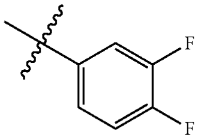 [SMILES: *c1ccc(F)c(F)c1] |
| 1-209 | $CF_3$ | 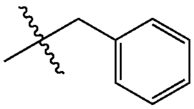 [SMILES: *Cc1ccccc1] | 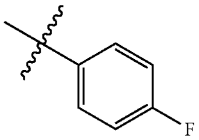 [SMILES: *c1ccc(F)cc1] |

-continued
| No. | X | M | A |
| --- | --- | --- | --- |
| 1-210 | $CF_3$ | 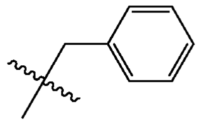 [SMILES: *Cc1ccccc1] | 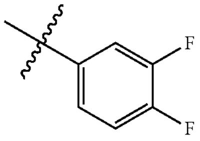 [SMILES: *c1ccc(F)c(F)c1] |
| 1-211 | $CF_3$ | 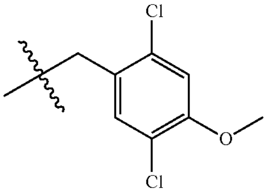 [SMILES: *Cc1cc(Cl)c(OC)cc1Cl] | 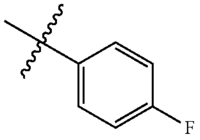 [SMILES: *c1ccc(F)cc1] |
| 1-212 | $CF_3$ | 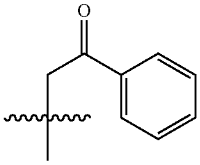 [SMILES: *CC(=O)c1ccccc1] | 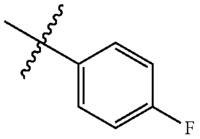 [SMILES: *c1ccc(F)cc1] |
| 1-213 | $CF_3$ | 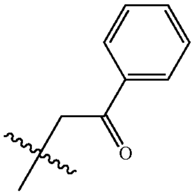 [SMILES: *CC(=O)c1ccccc1] | 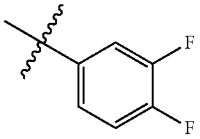 [SMILES: *c1ccc(F)c(F)c1] |
| 1-214 | $CF_3$ | 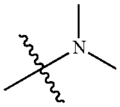 [SMILES: *N(C)C] | 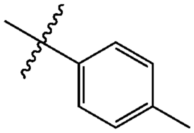 [SMILES: *c1ccc(C)cc1] |
| 1-215 | $CF_3$ | 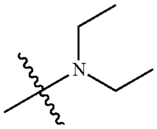 [SMILES: *N(CC)CC] | 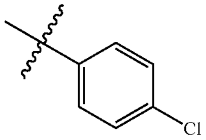 [SMILES: *c1ccc(Cl)cc1] |
| 1-216 | $CF_3$ | 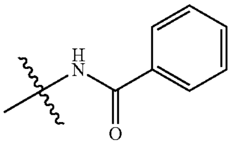 [SMILES: *NC(=O)c1ccccc1] | 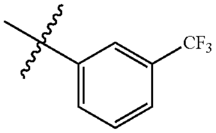 [SMILES: *c1cccc(C(F)(F)F)c1] |
| 1-217 | $CF_3$ | 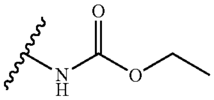 [SMILES: *NC(=O)OCC] | 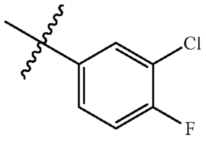 [SMILES: *c1ccc(F)c(Cl)c1] |
| 1-218 | $CH_2F$ | 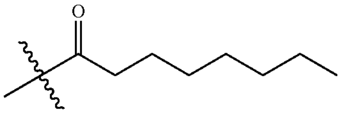 [SMILES: *C(=O)CCCCCCC] | 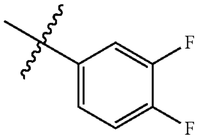 [SMILES: *c1ccc(F)c(F)c1] |

-continued
| No. | X | M | A |
|---|---|---|---|
| 1-219 | $CH_2F$ | 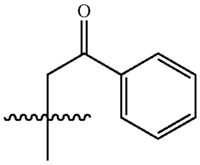 [SMILES: *CC(=O)c1ccccc1] | 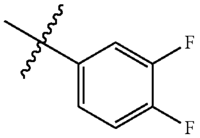 [SMILES: *c1ccc(F)c(F)c1] |
| 1-220 | $CH_2F$ | 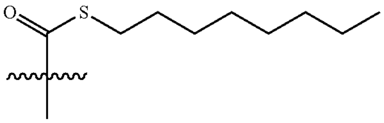 [SMILES: *C(=O)SCCCCCCCC] | 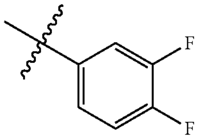 [SMILES: *c1ccc(F)c(F)c1] |
| 1-221 | $CHF_2$ | 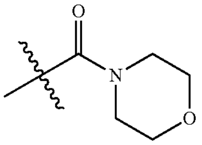 [SMILES: *C(=O)N1CCOCC1] | 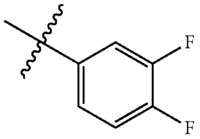 [SMILES: *c1ccc(F)c(F)c1] |
| 1-222 | $CHF_2$ | 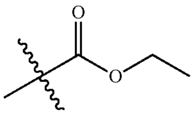 [SMILES: *C(=O)OCC] | 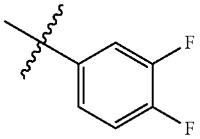 |
| 1-223 | $CF_2CF_3$ | 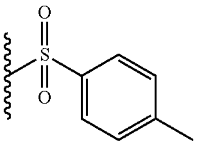 [SMILES: *S(=O)(=O)c1ccc(C)cc1] | 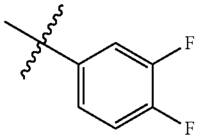 [SMILES: *c1ccc(F)c(F)c1] |
| 1-224 | $CF_2CF_3$ | 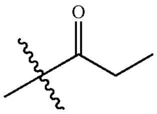 [SMILES: *C(=O)CC] | 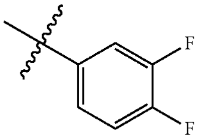 [SMILES: *c1ccc(F)c(F)c1] |
| 1-225 | $CF_2CF_3$ | 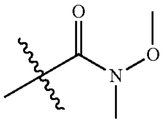 [SMILES: *C(=O)N(C)OC] | 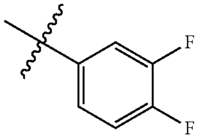 |
| 1-227 | $CF_3$ | 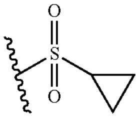 [SMILES: *S(=O)(=O)C1CC1] | 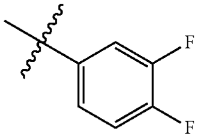 [SMILES: *c1ccc(F)c(F)c1] |
| 1-228 | $CF_3$ | 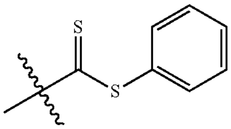 | 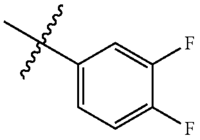 [SMILES: *c1ccc(F)c(F)c1] |
| 1-229 | $CF_3$ | 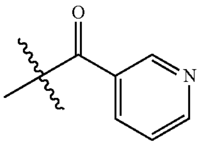 [SMILES: *C(=O)c1cccnc1] | 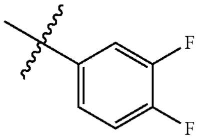 |

-continued
| No. | X | M | A |
|---|---|---|---|
| 1-230 | $CF_3$ | 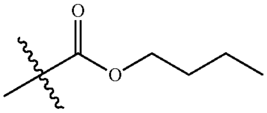 | 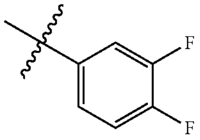 [SMILES: *c1ccc(F)c(F)c1] |
| 1-231 | $CF_3$ | 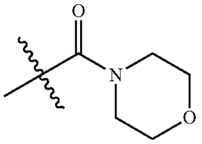 [SMILES: *C(=O)N1CCOCC1] | 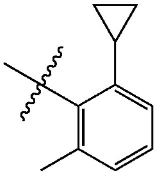 [SMILES: *c1c(C)cccc1C1CC1] |
| 1-232 | $CF_3$ | 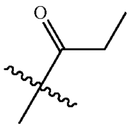 [SMILES: *C(=O)CC] | 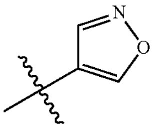 [SMILES: *c1cnoc1] |
| 1-233 | $CF_3$ | 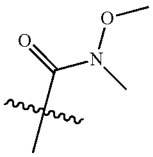 [SMILES: *C(=O)N(C)OC] | 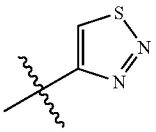 [SMILES: *c1csnn1] |
| 1-234 | $CF_3$ | 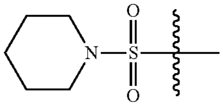 | 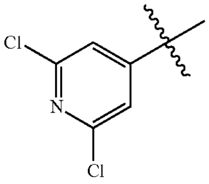 [SMILES: *c1cc(Cl)nc(Cl)c1] |
| 1-235 | $CF_3$ | 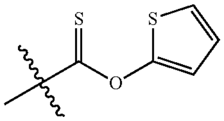 [SMILES: *C(=S)Oc1cccs1] | 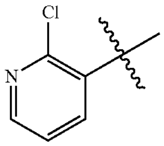 [SMILES: *c1cccnc1Cl] |
| 1-236 | $CF_3$ | 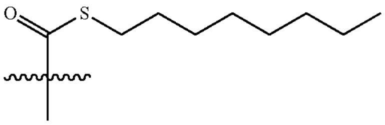 | 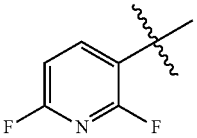 [SMILES: *c1ccc(F)nc1F] |
| 1-237 | $CF_3$ | 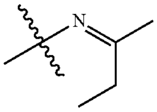 [SMILES: */N=C(/C)CC] | 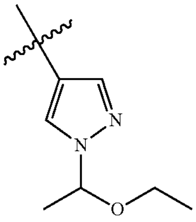 [SMILES: *c1cnn(C(C)OCC)c1] |
| 1-238 | $CF_3$ | 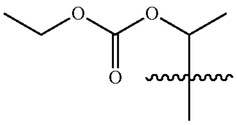 [SMILES: *C(C)OC(=O)OCC] | 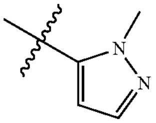 [SMILES: *c1ccnn1C] |

-continued
| No. | X | M | A |
|---|---|---|---|
| 1-239 | $CF_3$ | 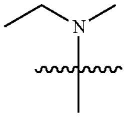 [SMILES: *N(C)CC] | 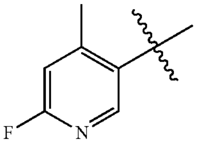 [SMILES: *c1cnc(F)cc1C] |
| 1-240 | $CF_3$ | 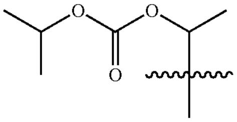 [SMILES: *C(C)OC(=O)OC(C)C] | 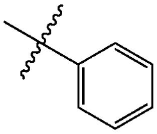 [SMILES: *c1ccccc1] |
| 1-241 | $CF_3$ | CN | 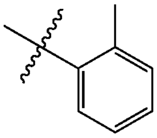 |
| 1-242 | $CF_3$ | 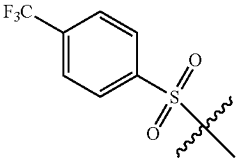 [SMILES: *S(=O)(=O)c1ccc(C(F)(F)F)cc1] | 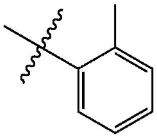 [SMILES: *c1ccccc1C] |
| 1-243 | $CF_3$ | 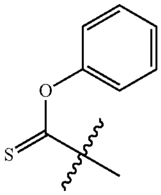 [SMILES: *C(=S)Oc1ccccc1] | 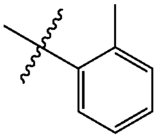 [SMILES: *c1ccccc1C] |
| 1-244 | $CF_3$ | 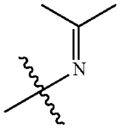 [SMILES: *N=C(C)C] | 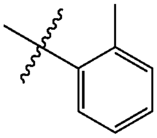 |
| 1-245 | $CF_3$ | 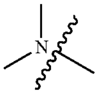 | 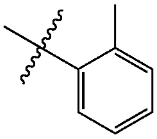 |
| 1-246 | $CF_3$ | 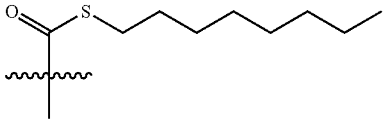 [SMILES: *C(=O)SCCCCCCCC] | 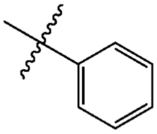 [SMILES: *c1ccccc1] |
| 1-247 | $CF_3$ | 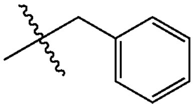 [SMILES: *Cc1ccccc1] | 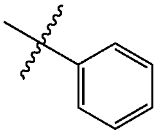 [SMILES: *c1ccccc1] |
| 1-248 | $CF_3$ | 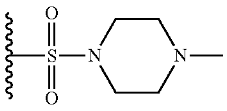 [SMILES: *S(=O)(=O)N1CCN(C)CC1] | 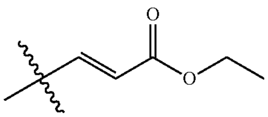 [SMILES: */C=C/C(=O)OCC] |

-continued

| No. | X | M | A |
| --- | --- | --- | --- |
| 1-249 | $CF_3$ | 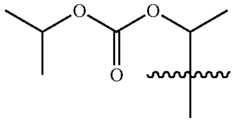 [SMILES: *C(C)OC(=O)OC(C)C] | 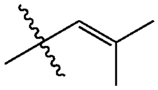 |
| 1-250 | $CF_3$ | 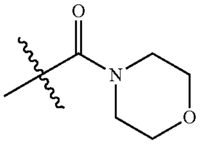 [SMILES: *C(=O)N1CCOCC1] | 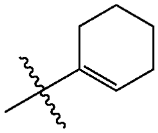 [SMILES: *C1=CCCCC1] |
| 1-251 | $CF_3$ | 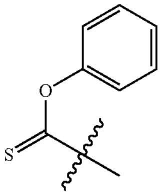 [SMILES: *C(=S)Oc1ccccc1] | Me. |

10. A herbicidal composition, comprising at least one compound chosen from the herbicidally active pyridazinol compound of Formula I and the derivative thereof according to claim 1.

11. A herbicidal composition, comprising at least one compound chosen from the derivative of the pyridazinol of Formula I-1 according to claim 8.

12. The herbicidal composition according to claim 10, further comprising at least one additional herbicide.

13. The herbicidal composition according to claim 11, further comprising at least one additional herbicide.

14. The herbicidal composition according to claim 12, wherein the at least one additional herbicide is selected from an HPPD inhibitor, a hormone herbicide, and a PDS inhibitor.

15. A method for preparing a pyridazinol compound or a derivative thereof according to claim 1, comprising:

(1) subjecting a compound of Formula II and a compound of Formula III to Suzuki reaction to obtain a compound of Formula IV;

(2) hydrolyzing the compound of Formula IV to obtain a compound of Formula I;

wherein the reaction route is as follows:

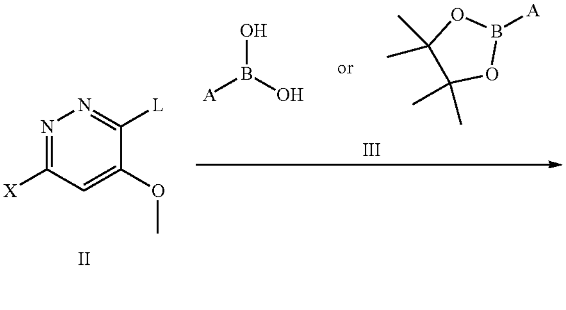

II

-continued

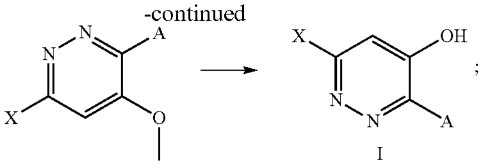
IV I;

or comprising:

(a) hydrolyzing a compound of Formula II to give a compound of Formula V;

(b) subjecting the compound of Formula V and a compound of Formula III to Suzuki reaction to obtain a compound of Formula I;

wherein the reaction route is as follows:

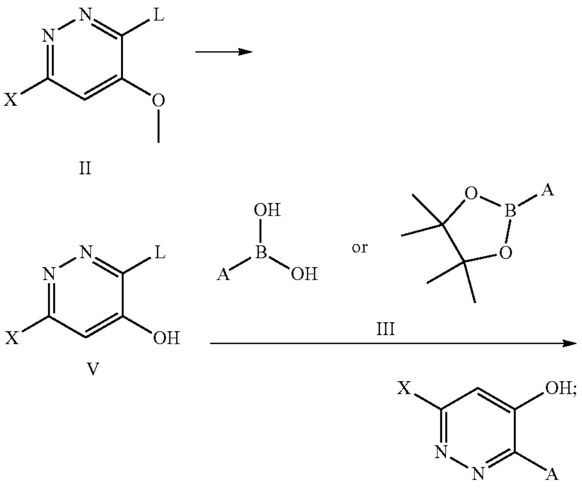

II V I;

wherein L is halogen, and other groups are as defined in claim 1.

16. The method according to claim 15, wherein, each of the steps independently is carried out at a temperature in the range from 20 to 150° C.;

wherein steps (1) and (b) are carried out in the presence of a catalyst, a base and a solvent, wherein the catalyst is $Pd(dppf)Cl_2CH_2Cl_2$, $Pd(dba)_2$, $Pd_2(dba)_3$, $Pd(PPh_3)_4$, $PdCl_2$, $Pd(OAc)_2$, $Pd(dppf)Cl_2$, $Pd(PPh_3)_2Cl_2$, or $Ni(dppf)Cl_2$, the base is one or more selected from $Et_3N$, $NaHCO_3$, KOAc, $K_2CO_3$, $K_3PO_4$, $Na_2CO_3$, CsF, $Cs_2CO_3$, t-BuONa, EtONa, KOH, and NaOH, and the solvent is THF/water, toluene/water, DMF/water, 1,4-dioxane/water, toluene/ethanol/water, acetonitrile/water, THF, toluene, 1,4-dioxane, acetonitrile, or DMF system;

steps (2) and (a) are carried out in the presence of a base and a solvent or in the presence of a solution of boron tribromide, a solution of hydrobromic acid in acetic acid, a solution of hydrochloric acid in methanol or a solution of hydrochloric acid in ethyl acetate, wherein the base is selected from NaOH, KOH, potassium acetate, and sodium acetate, and the solvent is water or DMSO.

17. A method for preparing a derivative of a pyridazinol compound according to claim 8, wherein, when the derivative is an ester or ether derivative, the reaction route is as follows:

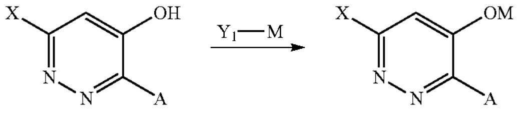

I I-1 wherein, $Y_1$ is a halogen;

when the derivative is an oxime or hydroxylamine derivative, the reaction route is as follows:

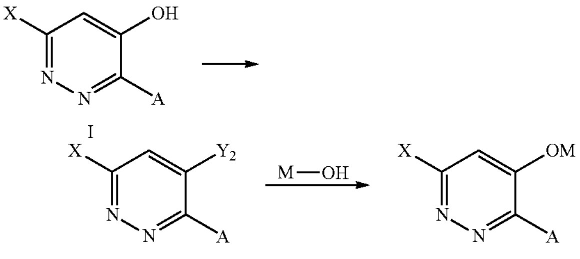

I I-2 I-1 wherein, $Y_2$ is a halogen; other groups are as defined in claim 8.

18. The method according to claim 17, wherein the reactions for preparing the ester and ether derivatives and the second step for preparing the oxime and hydroxylamine derivatives are carried out in the presence of a base and a solvent, wherein the base is one or more selected from sodium hydroxide, potassium hydroxide, sodium carbonate, potassium carbonate, sodium hydrogen carbonate, cesium carbonate, triethylamine and diisopropylethylamine; the solvent is THF, 1,4-dioxane, toluene, 1,2-dichloroethane, ethyl acetate, acetonitrile, DMF, acetone, dichloromethane, or chloroform;

the first step for preparing the oxime and hydroxylamine derivative is carried out in the presence of a halogenation reagent and a solvent, wherein the solvent is one or more selected from toluene, 1,2-dichloroethane, and DMF; and the reaction temperature is in the range of 0 to 120° C.

19. A method for controlling a harmful plant, comprising applying a herbicidally effective amount of at least one compound selected from the herbicidally active pyridazinol compound and the derivative thereof according to claim 1 to the harmful plant or an area with the harmful plant.

20. A method for controlling a harmful plant, comprising applying a herbicidally effective amount of at least one compound selected from the derivative of pyridazinol compound according to claim 8 to the harmful plant or an area with the harmful plant.

21. A method for controlling a harmful plant in a useful crop, comprising applying a herbicidally effective amount of at least one compound selected from the herbicidally active pyridazinol compound and the derivative thereof according to claim 1 to the harmful plant, wherein the useful crop is selected from wheat, corn, rice, soybean, cotton, oilseed rape, millet and sorghum.

22. A method for controlling a harmful plant in a useful crop, comprising applying a herbicidally effective amount of at least one compound selected from the derivative of pyridazinol compound according to claim 8 to the harmful plant, wherein the useful crop is selected from wheat, corn, rice, soybean, cotton, oilseed rape, millet and sorghum.

23. The method according to claim 20, wherein the harmful plant is a monocotyledonous or dicotyledonous harmful plant, selected from *Amaranthus retroflexus, Rorippa indica, Veronica polita*, Chenopodiaceae, *Echinochloa crus-galli, Setaria viridis, Galium aparine, Abutilon* mill, *Sisymbrium sophia* and *Galinsoga parviflora.*

24. The method according to claim 21, wherein the harmful plant is a monocotyledonous or dicotyledonous harmful plant, selected from *Amaranthus retroflexus, Rorippa indica, Veronica polita*, Chenopodiaceae, *Echinochloa crus-galli, Setaria viridis, Galium aparine, Abutilon* mill, *Sisymbrium sophia* and *Galinsoga parviflora.*

* * * * *